(12) United States Patent
Ljunggren et al.

(10) Patent No.: US 6,476,196 B1
(45) Date of Patent: Nov. 5, 2002

(54) ESTROGEN RECEPTOR LIGANDS

(75) Inventors: Jan Ljunggren, Solna; Ann-Gerd Thorsell, Stockholm; Owe Engstrom, Nacka; Tomas Bonn, Huddinge; Mats Carlquist, Spanga, all of (SE); Andrzeji Brzozowski, York (GB); Ashley Pike, York (GB); Roderick Hubbard, York (GB)

(73) Assignee: Kara Bio AB, Huddinge (SE)

( * ) Notice: Subject to any disclaimer, the term of this patent is extended or adjusted under 35 U.S.C. 154(b) by 0 days.

(21) Appl. No.: 09/844,132

(22) Filed: Apr. 27, 2001

Related U.S. Application Data

(63) Continuation-in-part of application No. 09/249,645, filed on Feb. 12, 1999, now Pat. No. 6,228,990.

(30) Foreign Application Priority Data

Feb. 13, 1998 (GB) .............................................. 9803062

(51) Int. Cl.$^7$ ................................................. C07K 1/00
(52) U.S. Cl. ........................ 530/350; 530/412; 530/418; 530/419
(58) Field of Search ................................. 530/350, 412, 530/418, 419

(56) References Cited

PUBLICATIONS

Pike et al., "Structure of the ligand–binding domain oestrogen receptor beta in the presence of a partial agonist and a full antagonist", EMBO, J. 18 (17), 4608–4618.
Shiau et al., "The structure bases of estrogen receptor/coactivator . . . ", Cell 95, 927–937 (1998).
Tananbaum et al., "Crystallographic comparison of estrogen and progestrone . . . ", Proc. Natl. Acad. Sci. USA, 95, 5998–6003.
Pike et al., "Structural Insights into the Mode of Action of a Pure Antiestrogen", Structure, vol. 9, Feb. 2001, 145–153.

*Primary Examiner*—Nashaat T. Nashed
(74) *Attorney, Agent, or Firm*—Todd E. Garabedian; Wiggin & Dana

(57) ABSTRACT

The present invention is directed to crystals of ERβ ligand binding domain complexed with (1) N-(n-butyl)-11-[3,17β-dihydroxyestra-1,3,5(10)-trien-7α-yl]N-methylundecanamide; estradiol and a peptide comprising the amino acid sequence LXXLL; or 17-epiestriol and a peptide comprising the amino acid sequence LXXLL.

9 Claims, 19 Drawing Sheets

ER–beta/genistein complex

ER–beta/genistein complex

ER-beta/genistein complex

ER-beta/raloxifene complex

ER-beta/raloxifene complex

ER-beta/KB-177complex

ER-beta/KB-177 complex

Affinity enhancing substituents marked by "R".

Covered by prior art:
hydrophobic substituents
α-face: 7α, 14α, 16α, and 17α
β-face: 11β

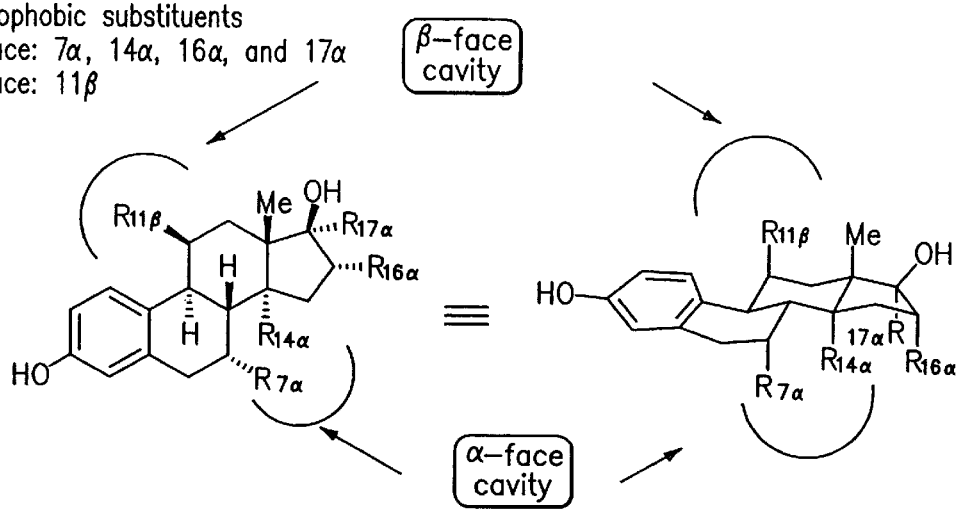

Prior art reviewed in "The estradiol pharmacophore: ligand structure–estrogen receptor binding affinity relationships" G.M. Anstead, K.E. Carlson, and J.A. Katzenellenbogen, Steroids, 62(3):268–303 (1997).

FIG. 5a

Affinity enhancing substituents marked by "R".

Not covered by prior art:
hydrophobic substituents
α-face: 9α and 12α
β-face: 8β, 15β, and 18

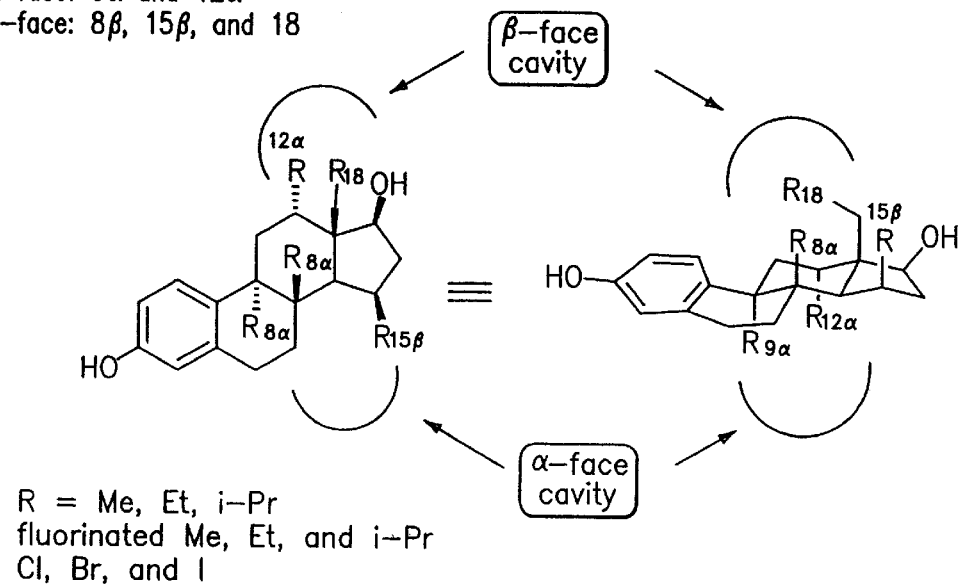

R = Me, Et, i-Pr
fluorinated Me, Et, and i-Pr
Cl, Br, and I

FIG. 5b

Affinity enhancing substituents marked by "R".

Affinity enhancing substituents. Replacement of 4'-OH group in raloxifene with 4'-$NH_2$ provides the opportunity of picking up an additional hydrogen bond to His-524.

Guanidino affinity enhancing substituent at position-3 of the steroid nucleus and position-6 of the benzothiophene nucleus.

Selectivity enhancing substituents $R_3$, $R_2'$, $R_3'$, and $R_6'$.

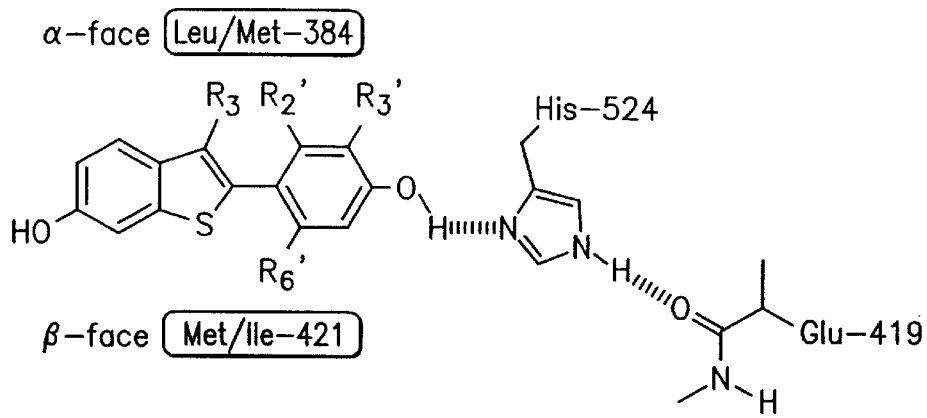

$R_3$, $R_2'$, $R_3'$, and $R_6'$ = Cl, Br, I, Me, Et, $i$-Pr, and perfluoro Me, Et, and $i$-Pr.

Selectivity enhancing substituents $R_3$, $R_2'$, $R_3'$, and $R_6'$. Movement of hydroxyl from position-4' to -5' biases binding orientation and therefore further enhances selectivity

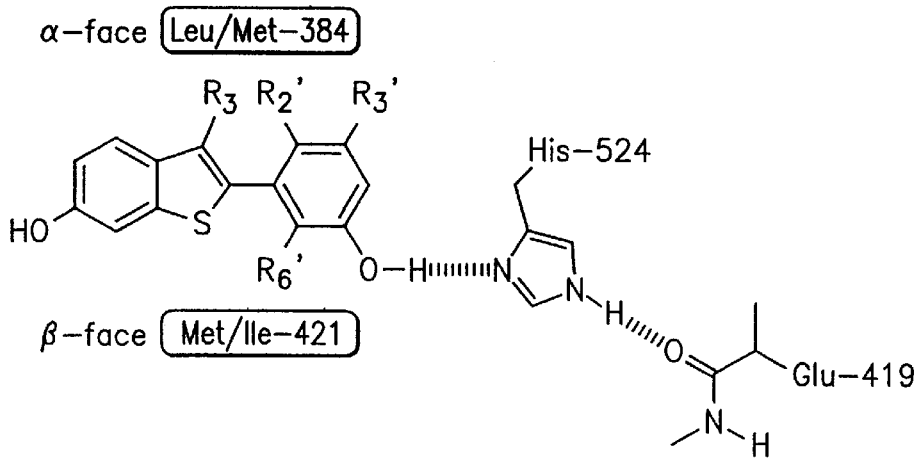

$R_3$, $R_2'$, $R_3'$, and $R_6'$ = Cl, Br, I, Me, Et, $i$-Pr, and perfluoro Me, Et, and $i$-Pr.

*FIG. 6b*

Selectivity enhancing substituents $R_3$.

modeling suggests that benzyl group of NRB–03855 may form a "π–teeing" interaction with Phe–445 and not with Tyr–445 which may account for the observed α–selectivity

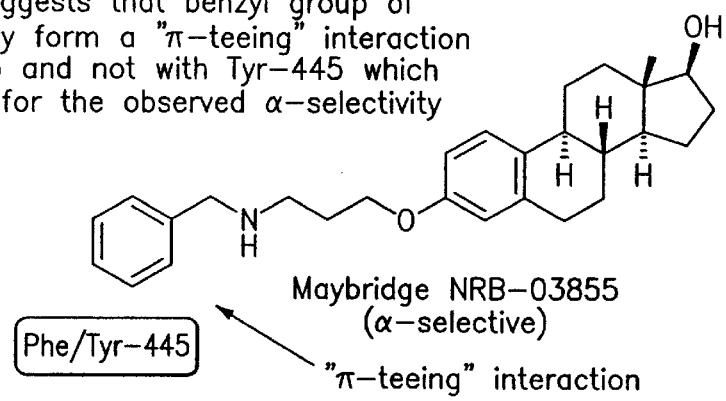

Maybridge NRB–03855 (α–selective)

Phe/Tyr–445

"π–teeing" interaction

*FIG. 6c*

Selectivity enhancing substituents $R_6$.

"water channel" may be reached from 6–position

Ile/Val–326 conserved Glu–323

Phe/Tyr–445

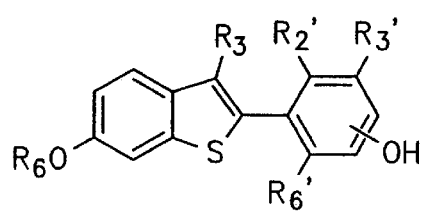

Phe/Tyr–445 may be reached with R–$(CH_2)_n$–chain where n=4, 5, or 6 and R=aromatic or heteroaromatic ring.

*FIG. 6d*

Selectivity enhancement reinforced by charged assisted hydrogen bond between substituent "R" in the ligand and either Glu-323 or Lys-449 in the receptor.

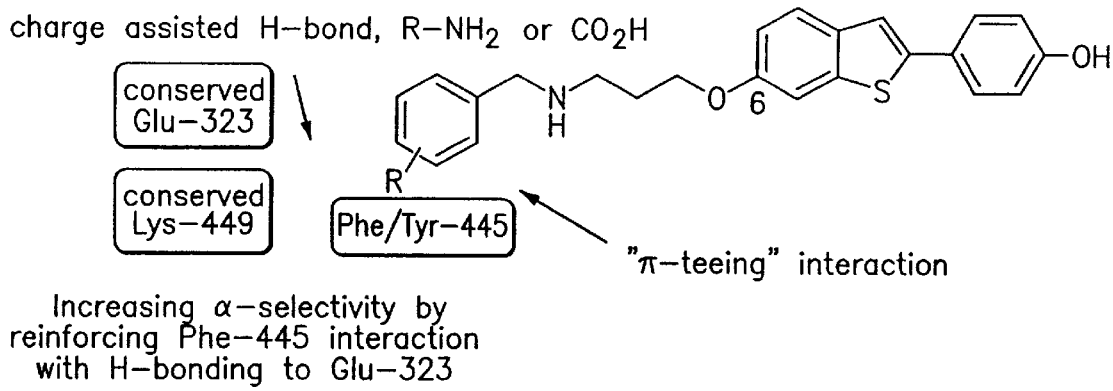

Increasing α-selectivity by reinforcing Phe-445 interaction with H-bonding to Glu-323

FIG. 6e

Selectivity enhancement reinforced by hydrogen bond network between pyridone ring in the ligand and residues Glu-323 and Lys-449 in the receptor

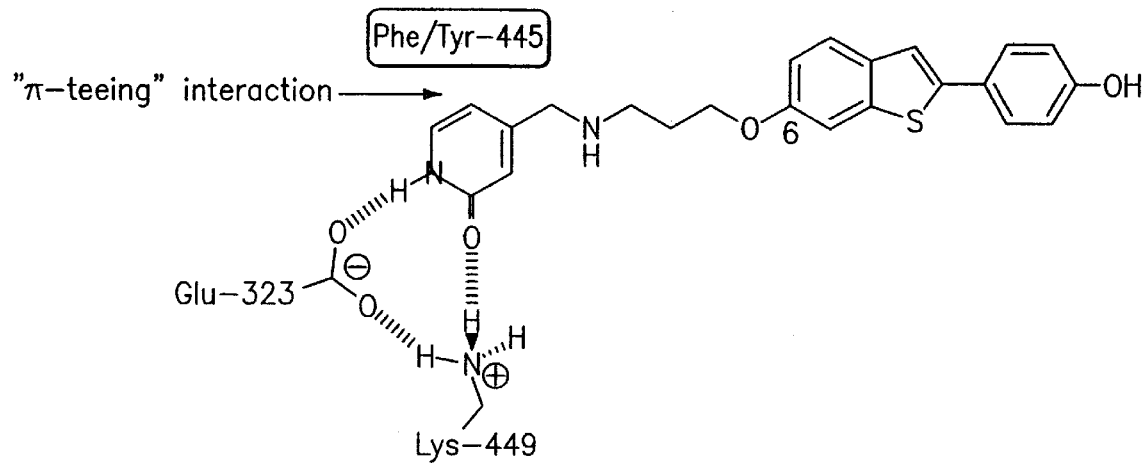

FIG. 6f

Figure 7A: ER-beta/ICI-164,384 complex
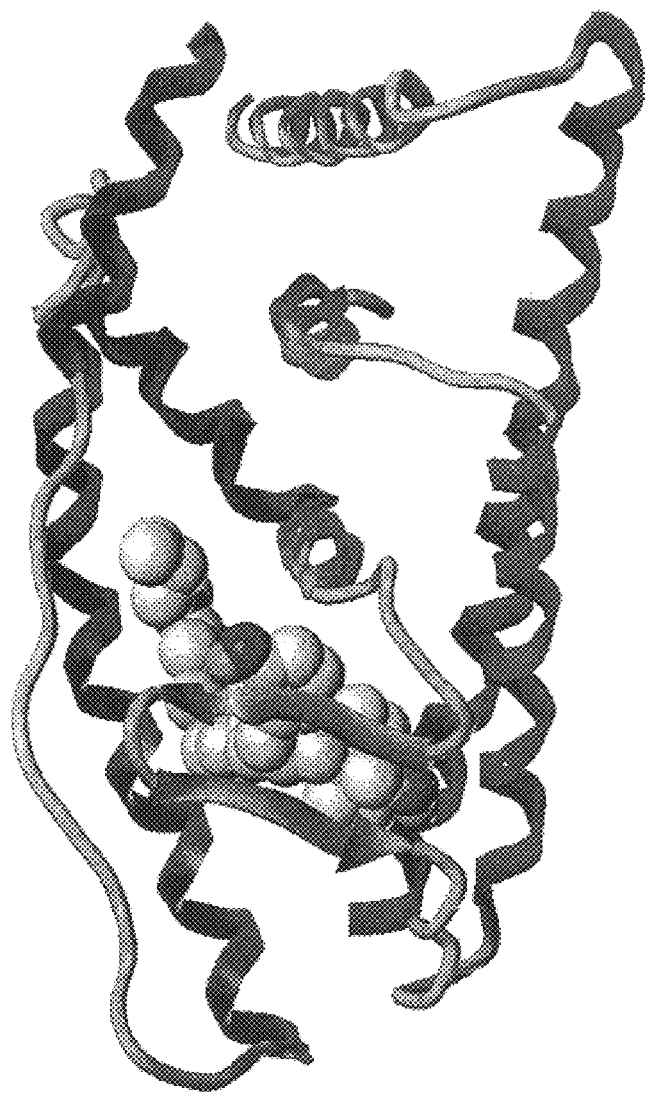

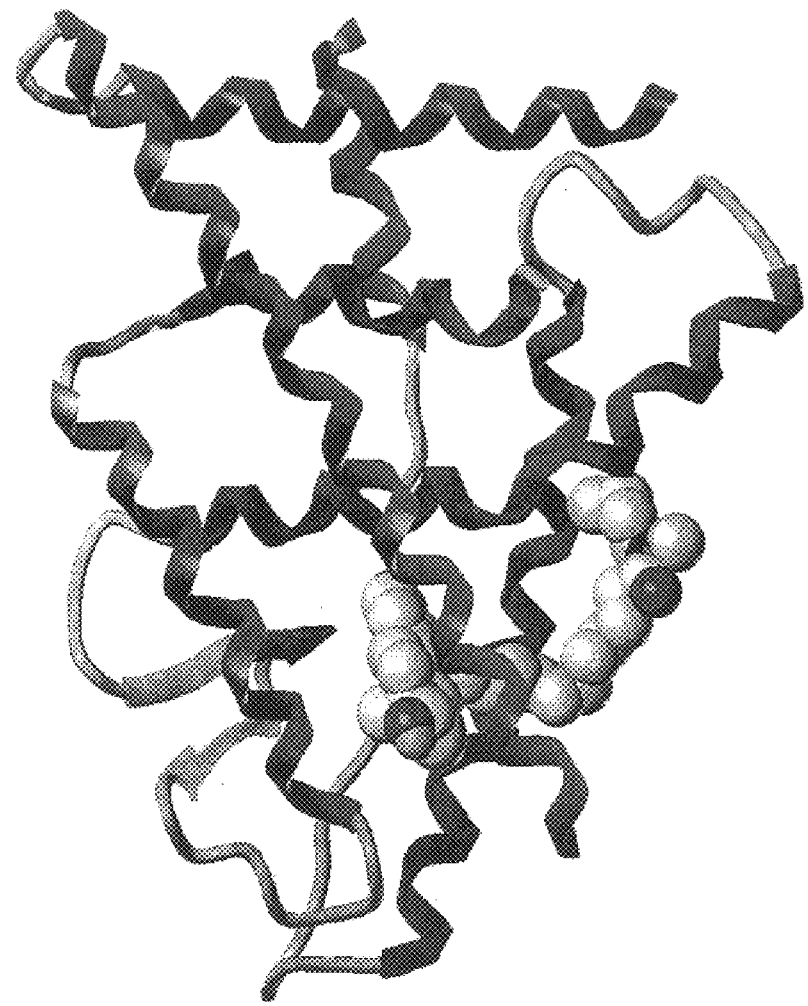
Figure 7B: ER-beta/ICI-164,384 complex

Figure 8A: ER-beta/estradiol complex
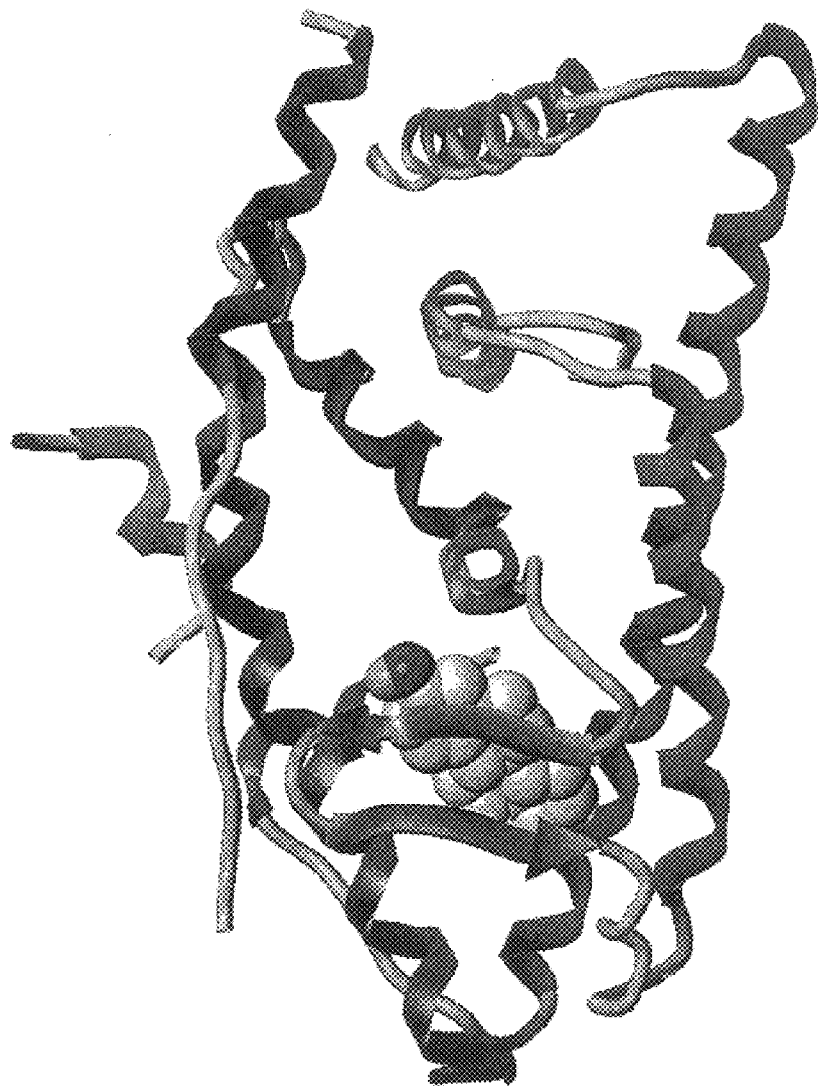

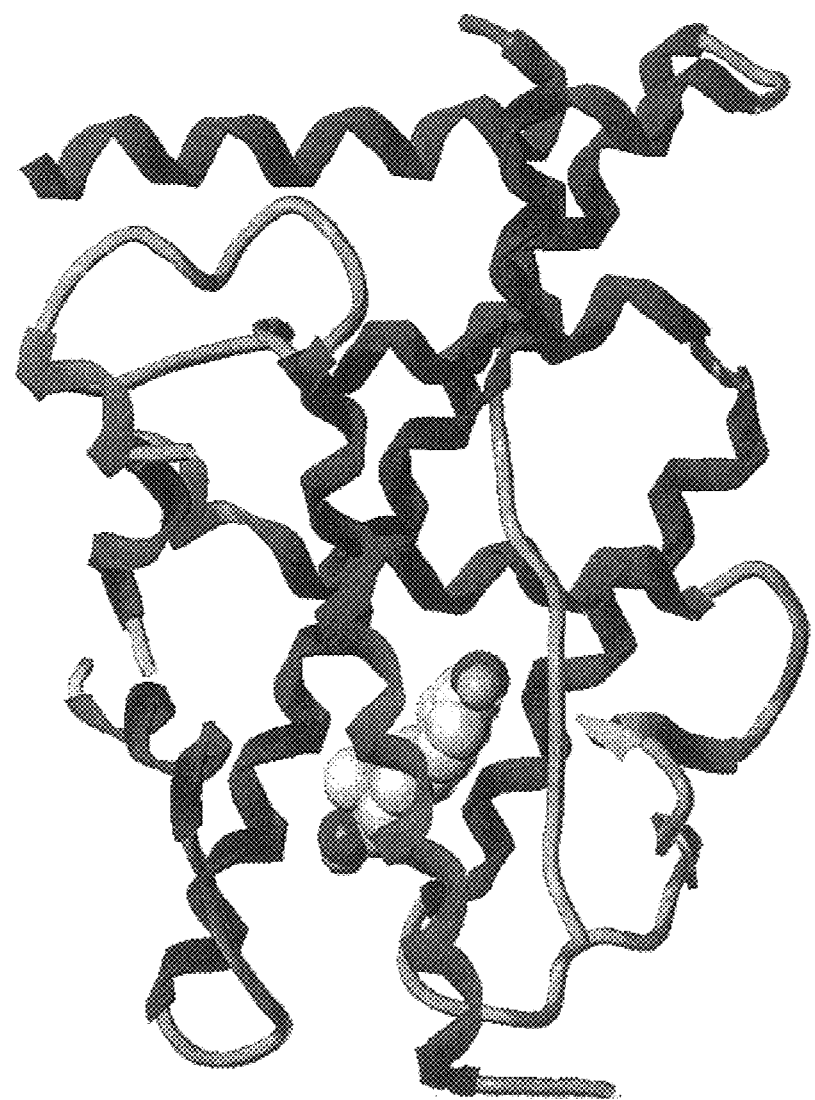
Figure 8B: ER-beta/estradiol complex

Figure 9A: ER-beta/17-epiestradiol complex
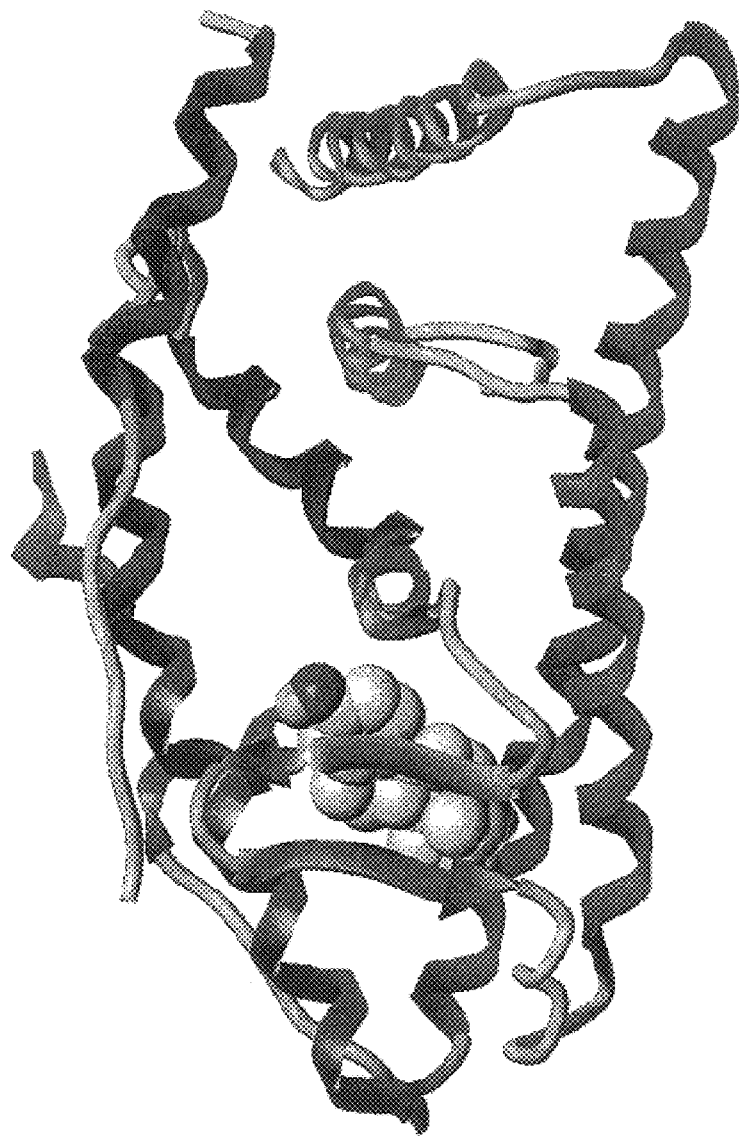

Figure 9B: ER-beta/17-epiestradiol complex
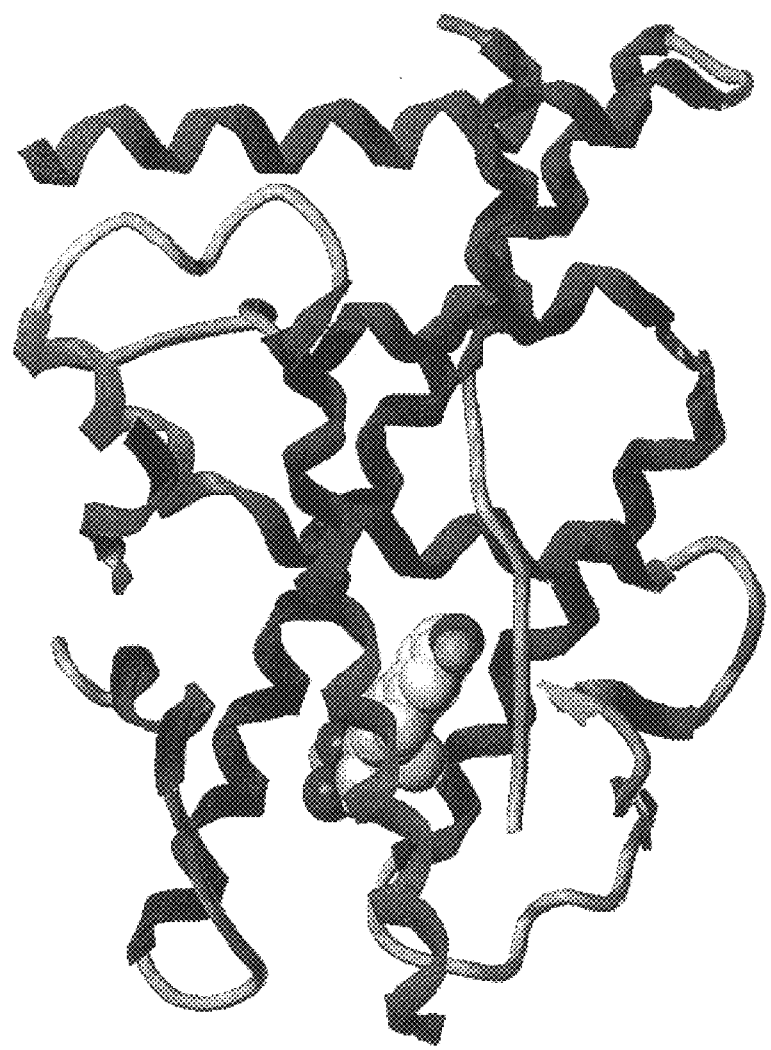

ESTROGEN RECEPTOR LIGANDS

CROSS-REFERENCE TO RELATED APPLICATIONS

This application is a Continuation-in-Part of U.S. Ser. No. 09/249,645 filed Feb. 12, 1999, now U.S. Pat. No. 6,228,990.

BACKGROUND OF THE INVENTION

1. Field of the Invention

This invention relates to estrogen receptors and ligands for them, and in particular to crystalline estrogen β receptor (ERβ) and to methods of identifying ligands utilizing crystalline ERβ.

2. Brief Description of the Art

The thyroid hormone receptor (TR) is known and its three-dimensional structure, and hence its ligand binding domain, has been determined. Knowledge of the three-dimensional structure has enabled a better understanding of the modes of ligand binding and the determination of the optimum conformation of ligand to bind to the receptor. It is generally believed in the art that the TR structure also provides a guide to the design of ER ligands.

Estrogen steroid hormone and thus the estrogen receptor (ER) is a member of the steroid hormone receptor family. Its primary natural ligand is estradiol (E2). However, it is known that a large number of structurally diverse non-steroidal compounds such as raloxifene, centchroman, coumestrol, diethylstilbesterol, esculin, tamoxifen, zearalenone, and zindoxifen also bind to the estrogen receptor (FIG. 4). The majority of these non-steroidal estrogen receptor ligands contain 2–4 carboxylic, aromatic, and/or heterocyclic rings connected by a 1–3 atom chain. One or more of the rings may be fused with the central atom chain or with each other.

It has been proposed that the receptor possesses a multifunctional modular structure potentially having discrete domains for DNA binding, ligand binding, and transactivation. The ligand binding domain (LBD) has been designated domain E and is the largest domain of the estrogen receptor. The ligand binding domain includes a ligand recognition site and regions for receptor dimerization interation with heat shock proteins, nuclear localization and ligand dependent transactivation.

A review of the structure and functioning of the estrogen receptor is provided in an article by Katzenellenbogen, J. et al., Steroids, (1997) 62(3):268–303.

It is known that compounds which bind to the estrogen receptor are potentially useful in the treatment of a wide range of disease states. These include estrogen agonists for treatment of disease linked to estrogen deficiency (e.g. osteoporosis, cardiovascular and neurodegenerative diseases in post menopausal women) and estrogen antagonists for treatment of breast and uterine cancer. Furthermore, it is known that certain ligands such as tamoxifen display mixed agonist/antagonist action (that is they are either estrogen agonists, estrogen antagonists, or a partial estrogen antagonists when binding to the estrogen receptors of different tissues) and such compounds may simultaneously prevent bone loss and reduce the risk of breast cancer. It is further known that benzothiophenes are usable as agonists or antagonists to steroid hormones, and that it is possible to modify their binding mechanics, for example the binding affinity, by changing the substituent groups at various positions on the molecule. Therefore, it would be desirable to be able to design ligands which are recognizable by and able to bind to the estrogen receptor. Additionally, it would be desirable to know the three dimensional structure of the estrogen receptor. Such knowledge would be useful for the design of compounds intended to bind to the estrogen receptor. The present inventors have been able to produce an estrogen receptor crystal and to determine from that the three dimensional structure of the estrogen receptor. Unexpectedly, the thus determined ER structure reveals that the TR structure does not provide a good model for binding of ligands to ER.

Our copending patent application No. PCT/GB98/01708 discloses inter alia, the crystal co-ordinates of crystalline estrogen receptor alpha (ERα).

SUMMARY OF THE INVENTION

We have now succeeded in crystallizing ERβ bound to a ligand which is an antagonist or partial agonist and determining its crystallographic co-ordinates. Therefore, in a first aspect the present invention provides a crystal comprising at least 150 amino acid residues of the ERβ ligand binding domain complexed with a ligand which is an antagonist or a partial agonist.

In a second aspect, the present invention provides ligands, particularly synthetic ligands, of ERβ identified by use of such a crystal.

In a third aspect of the invention, methods for designing ligands which will bind to ERβ are provided. Such methods use three dimensional models based on the crystals of the estrogen receptor ligand complex. Generally, such methods comprise determining compounds which are likely to bind to the receptor based on their three dimensional shape compared to that of the ERβ and in particular the ligand binding domain of the ERβ. Preferably, those compounds have a structure which is complementary to that of the ERβ. Such methods comprise the steps of determining which amino acid or amino acids of the ligand binding domain of the ERβ interacts with the binding ligand, and selecting compounds or modifying existing compounds, to improve the interaction. Preferably, improvements in the interaction are manifested as increases in the binding affinity but may also include increases receptor selectivity and/or modulation of efficacy.

Preferably the ligands bind to the ERβ with a high binding affinity, for example within the range of 20–2000 pmol.

The ligands may bind tightly to the ERβ yet not up-regulate gene expression thereby inhibiting the action of estradiol and estradiol mimetics. Thus, the invention also provides a method of inhibiting the activity of estradiol or estradiol mimetics by providing ligands which bind to ERβ with high affinity, blocking the activity of the estrogens. Alternatively, binding of the ligand to the ERβ may cause conformational changes to the ERβ inhibiting further binding thereto. The invention further provides a method of inhibiting estradiol activity in an animal, the method comprising administering to the animal a ligand which binds to at least the LBD, of the ERβ with high affinity and blocks binding of further ligands to at least the LBD of the ERβ. Such ligands are useful in, for example, the treatment of estrogen receptor mediated diseases in females.

BRIEF DESCRIPTION OF THE DRAWINGS

Embodiments of the invention will now be described in more detail, by way of example only, with reference to the accompanying drawings in which:

FIGS. 5a, 5b and 5c show modifications made to the steroid nucleus of ligands which bind to the estrogen receptor;

FIGS. 5d, 5e and 5f show how affinity of the ligand can be enhanced by adding substituents;

FIGS. 6a–6f show selectivity enhancement by using different substituents on the estrogen receptor ligand;

FIGS. 7A and 7B show orthogonal views of the crystallographic structure of the ligand binding domain of the estrogen receptor beta complexed with pure antagonist N-(n-butyl)-11-[3,17β-dihydroxyestra-1,3,5(10)-trien-7α-yl]N-methylundecanamide (ICI 164,384). The secondary structure of the receptor is represented by ribbons (alpha helices), ribbons with arrows (beta pleated sheets), and tubes (loops and random coils). The ligand N-(n-butyl)-11-[3,17β-dihydroxyestra-1,3,5(10)-trien-7α-yl]N-methylundecanamide is depicted as a space filling CPK model;

FIGS. 8A and 8B show orthogonal views of the crystallographic structure of the ligand binding domain of the estrogen receptor beta complexed with (17β)-Estra-1,3,5 (10)-triene-3,17-diol (estradiol) and LXXLL (SEQ ID NO:4) coactivator peptide. The secondary structure of the receptor is represented by ribbons (alpha helices), ribbons with arrows (beta pleated sheets), and tubes (loops and random coils). The estradiol ligand is depicted as a space filling CPK model; and FIGS. 9A and 9B show orthogonal views of the crystallographic structure of the ligand binding domain of the estrogen receptor beta complexed with (16α, 17α)-Estra-1, 3,5(10)-triene-3,16,17-triol (17-epiestriol) and LXXLL coactivator peptide. The secondary structure of the receptor is represented by ribbons (alpha helices), ribbons with arrows (beta pleated sheets), and tubes (loops and random coils). The epiestriol ligand is depicted as a space filling CPK model.

DETAILED DESCRIPTION OF THE INVENTION

Structure Based Design of ER Ligands

Figure 1A:
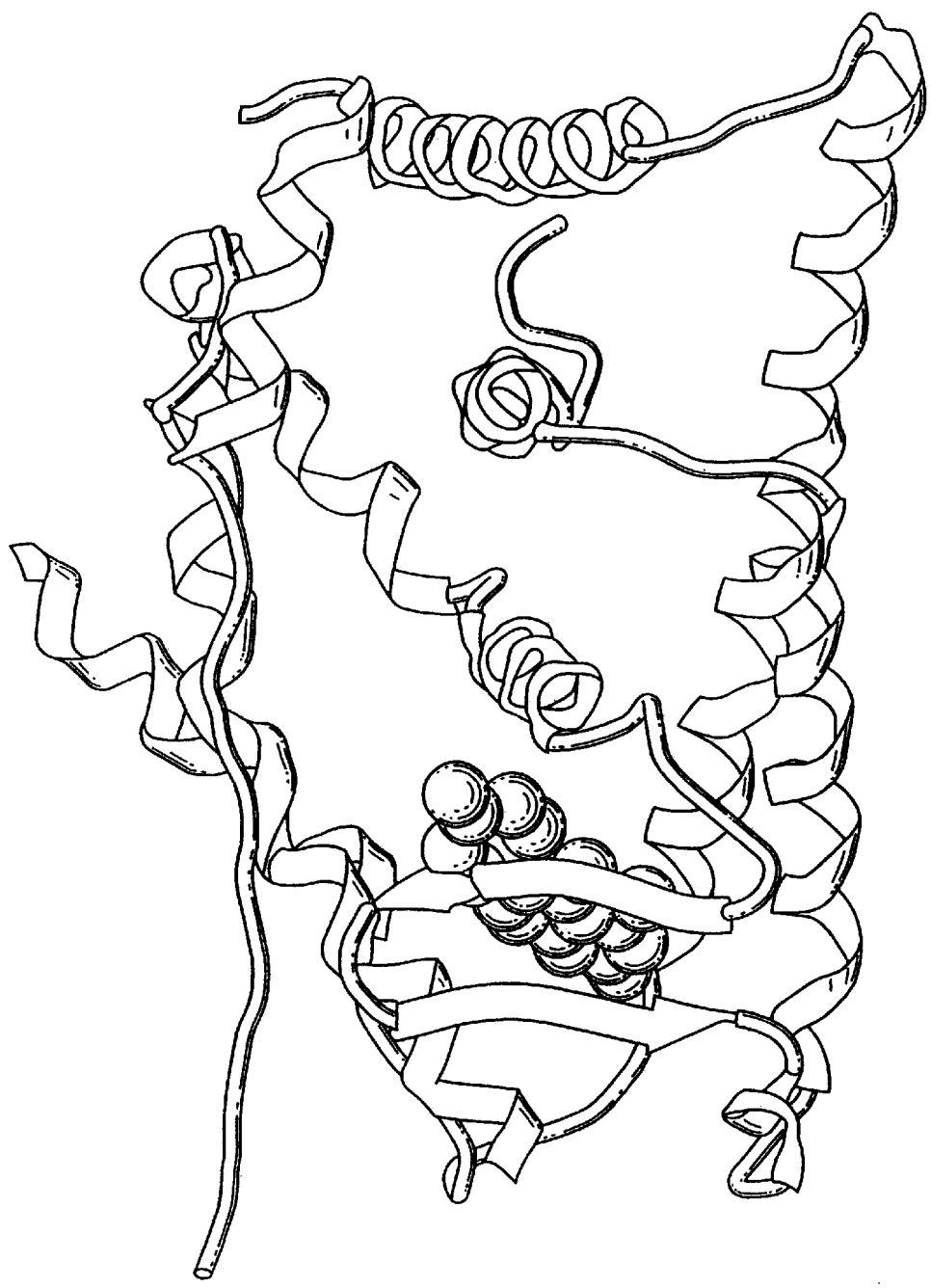
FIG. 1 shows orthogonal views (a and b) of the crystallographic structure of the ligand binding domain of the estrogen receptor beta isoform complexed with genistein. The secondary structure of the receptor is represented by ribbons (alpha helices), ribbons with arrows (beta pleated sheets), and tubes (loops and random coils). The ligand genistein is depicted as a space filling CPK model.
Figure 1B:
Figure 2A:
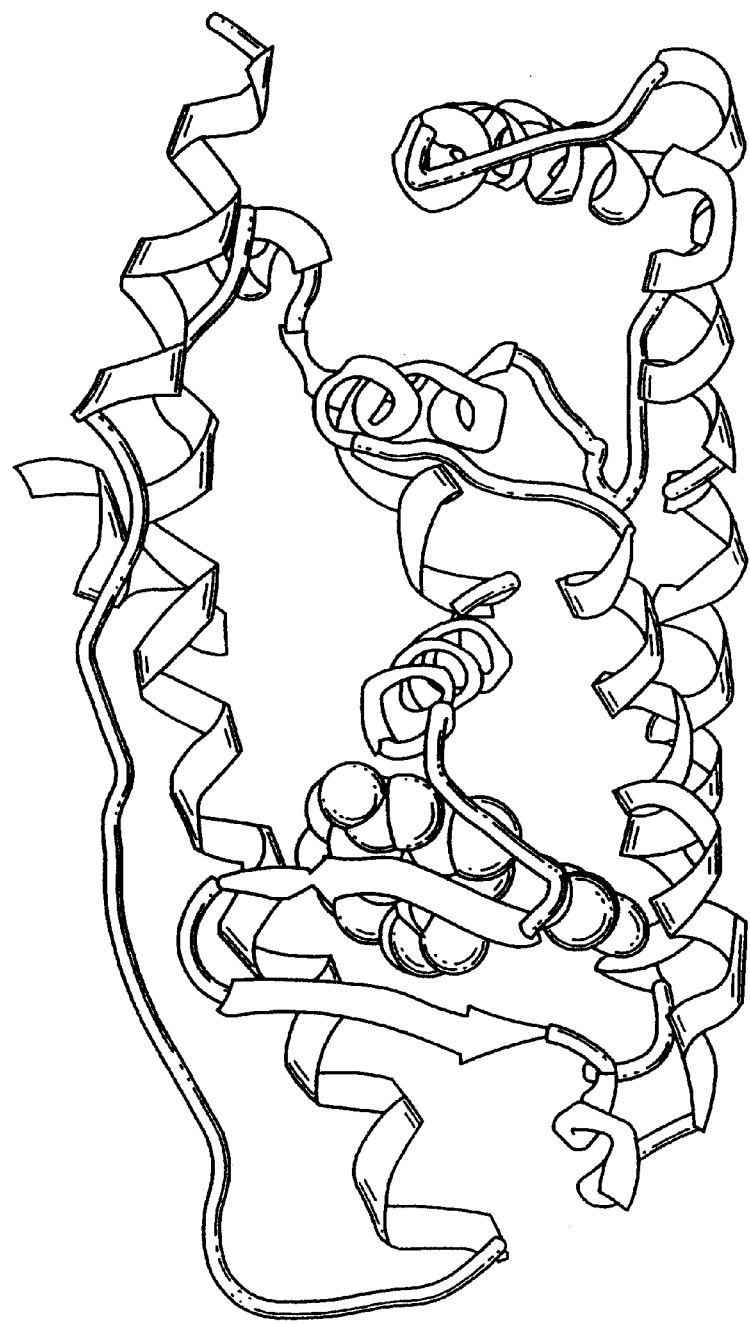
FIG. 2 shows orthogonal views (a and b) of the crystallographic structure of the ligand binding domain of the estrogen receptor beta isoform complexed with raloxifene. The structure of the receptor and ligand are depicted as in FIG. 1.
Figure 2B:
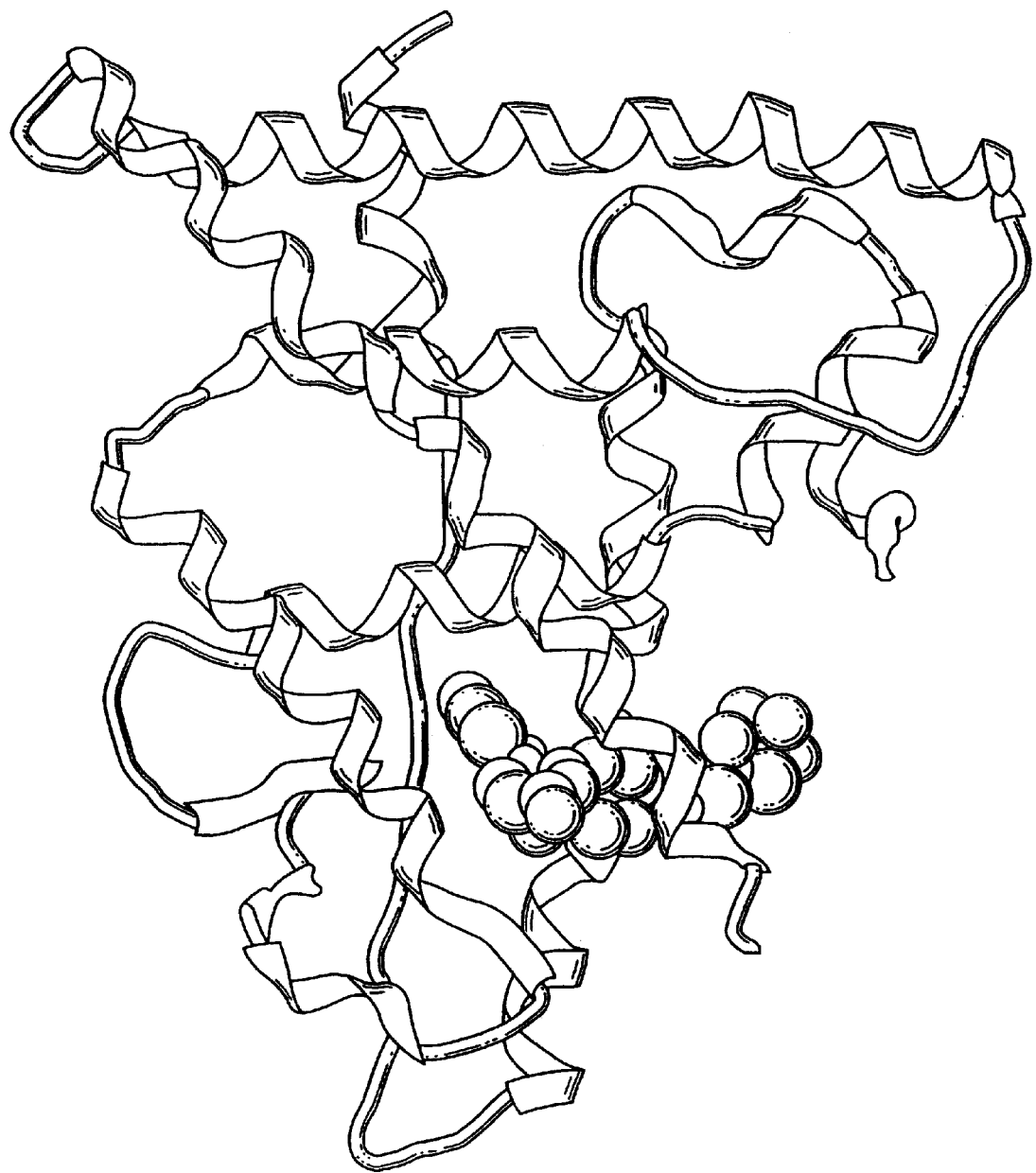
Figure 3A:
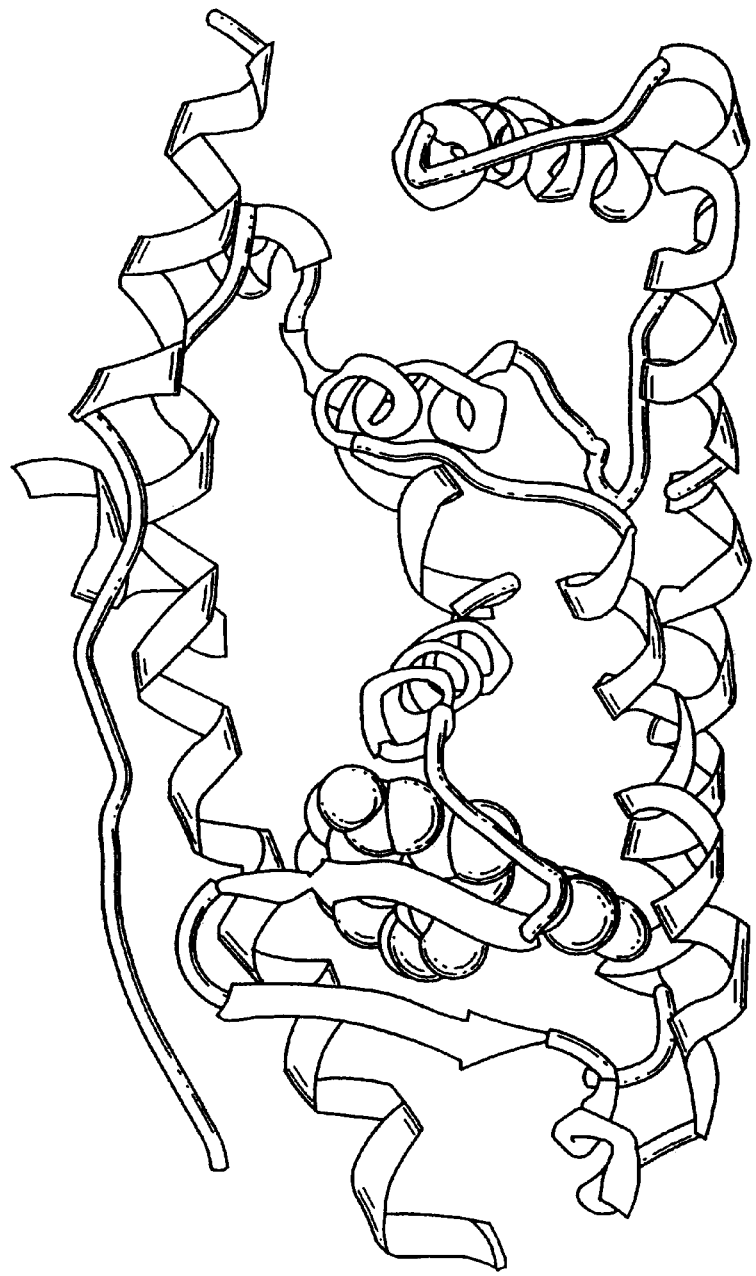
FIG. 3 shows orthogonal views (a and b) of the crystallographic structure of the ligand binding domain of the estrogen receptor beta isoform complexed with KB-177 ([2-(4-hydroxyphenyl)-6-hydroxybenzo[beta]thienyl-3-yl] [4-carboxyphenyl]methanone). The structure of the receptor and ligand are depicted as in FIG. 1.
Figure 3B:
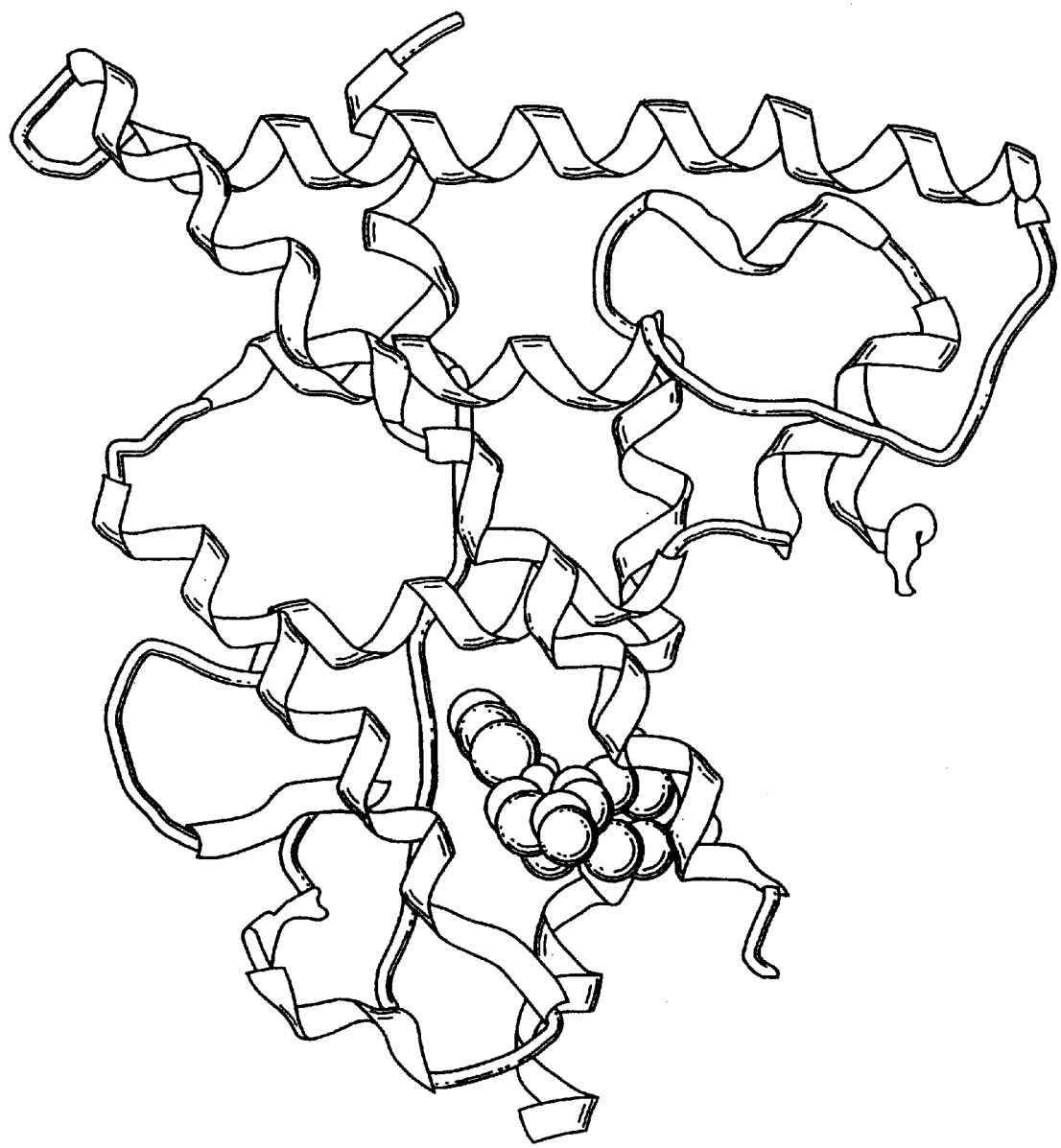
Figure 4:
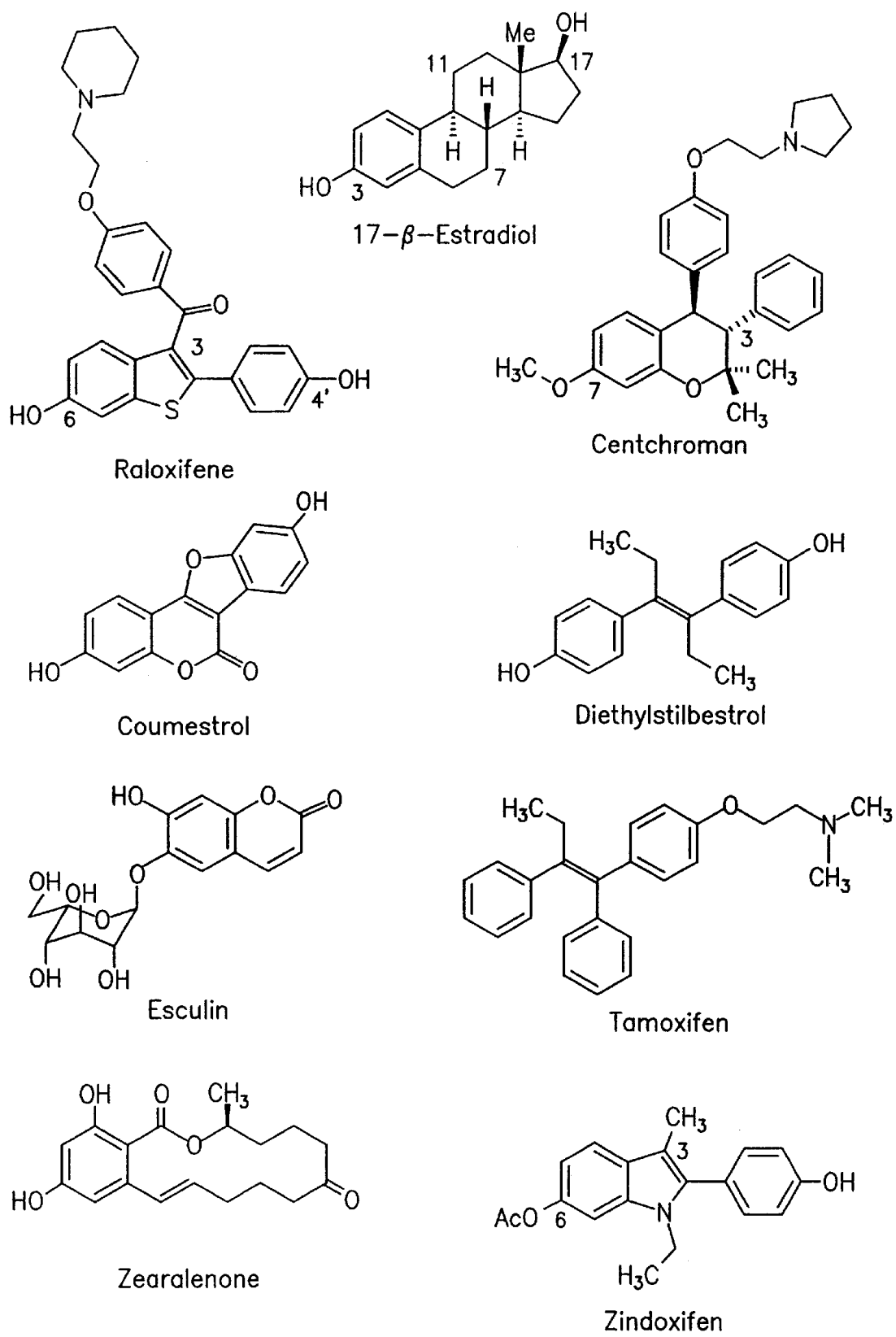
FIG. 4 shows the structure of several representative estrogen receptor ligands.

The present work has elucidated the structure of the ligand binding cavity of ERβ. Knowledge of the structure of this cavity has utility in the design of structurally novel ERβ ligands and in the design of non-obvious analogs of known ERβ ligands with improved properties. These enhanced properties include one or more of the following: (1) higher affinity, (2) improved selectivity for either the α- or β-isoform of the ER, and/or (3) a designed degree of efficacy (agonism vs. partial agonism vs. antagonism). Without knowledge of the EROS structure, modifications to produce ligands with enhanced properties and a reasonable likelihood of success would not be available to those skilled in the art. The ERβ structure also has utility in the discovery of new, structurally novel classes of ERβ ligands. Electronic screening of large, structurally diverse compound libraries such as the Available Chemical Directory (ACD) will identify new structural classes of ERβ ligands which will bind to the 3-dimensional structure of the estrogen receptor. Additionally the ERβ structure allows for "reverse-engineering" or "de novo design" of compounds to bind to ERβ.

This work is also described in copending British Application No. GB 9803062.0 which is herein incorporated by reference in its entirety.

(1) Enhanced Affinity

The present work has revealed the presence of estrogen receptor beta defined β- and α-face cavities centered respectively above and below the B- and C-rings of genistein.

The present invention provides new ligands which exploit this discovery by filling the α- and β-face cavities.

Preferably, the ligand fills at least one of the α- and β-face cavities so as to exclude water from the cavity or cavities.

The ligands produced in accordance with the invention bind more effectively to the ERβ than genistein. The ligand may bind with twice the binding affinity of genistein, preferably three times the affinity, and most preferably ten or more times the affinity.

Modifications to the steroid nucleus may be made at the positions marked in R in FIG. 8a and 8b (α-substitution at the 7-, 9-, 12-, 14-, 16-, and 17-positions; β-substitution at the 8-, 11-, 15-, and 18-positions). Preferably, those substituents are hydrophobic substituents, e.g., methyl, ethyl, iso-propyl, chlorine, bromine, or iodine.

Modifications to 2-aryl benzothiphenes may be made at the 2'-, 3'-, and 6'-positions (FIG. 5C) in order to fill the α- and β-face cavities of ER. Preferably substituents should be present in at least two of the following three positions; 3, 2', or 6' so that a perpendicular conformation between the B- and C-rings of the 2-aryl benzothiophene nucleus is enforced. This perpendicular conformation facilitates the positioning of the 2'-, 3'-, and 6'- substituents in the α- and β-face cavities of the ERβ.

In a manner analogous to the benzothiophene series, the affinity of other classes of non-steroidal ERβ ligands may be enhanced by substitution of small hydrophobic substituents at positions marked $R_2'$, $R_3'$, and/or $R_6'$ in FIG. 8C.

Preferably, the ligand produce in accordance with the invention fills at least one of the α- and β- cavities of the ERβ without perturbing the remainder of the ERβ structure.

Another aspect of this invention reveals an unfilled hydrophobic cavity in the raloxifene/ERβ complex. Filling this cavity with hydrophobic substituents so as to exclude water will enhance binding affinity. This cavity may be filled by positioning a hydrophobic substituent on the ethoxyphenyl sidechainα to the piperidinyl nitrogen atom of raloxifene. This hydrophobic substituent may be a linear alkyl or perfluoralkyl group ($—CH_3$ to $—C^{10}H_{21}$, $—CF_3$ to $—C_{10}F_{21}$), benzyl ($—CH_2Ph$), or methylene cyclohexyl ($—CH_2C_6H_{11}$).

In a third aspect of this invention, examination of the ERβ structure reveals that the hydroxyl group at position-3 of estradiol or position-6 of raloxifene form hydrogen bonding interactions with Glu-353 and Arg-394 (FIG. 5a and 5b). It is known that replacement of the hydroxyl group at position-3 of estrodiol or position-6 of raloxifene results in a decrease in affinity for the ERβ. The invention reveals the reason for this reduction in affinity: while one of the hydrogen atoms of the amino group forms a favourable hydrogen bonding interaction with Glu-353, the second hydrogen atom forms an unfavourable electrostatic interaction with Arg-394. Furthermore this invention reveals a method for enhancing the affinity of 3-amino analogs of estradiol and 6-amino analogs of raloxifene: replacement of one of the two hydrogen atoms of the amino group with an alkyl group to produce a secondary amino group. Alternatively, the group may be replaced with a guanidino group (FIG. 5e) which will pick up two additional hydrogen bonding interaction, the first is a salt bridge to Glu-353 and the second is a hydrogen bonding interaction with a backbone carbonyl group in residue Leu-387. Similar enhancement of affinity for the ERβ may be achieved by replacement of the guandino group with a fused 2-aminopyrrole (FIG. 5).

In a closely related aspect of this invention, an understanding is provided for the reduction in affinity for the ERβ seen in ether derivatives at either position-3 of estradiol or position-6 of raloxifene: electrostatic repulsion between the ether oxygen atom of the ligand and Glu-353 in the ERα. This invention reveals a way of increasing the affinity of estradiol position-3 or raloxifene position-6 ether derivatives: replacement of the ether oxygen atom with an amino (NH) group.

Figure 5C:
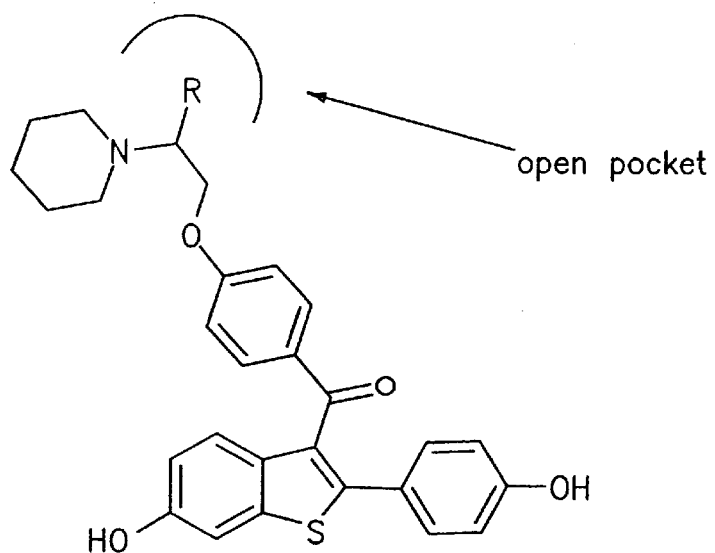
Figure 5D:
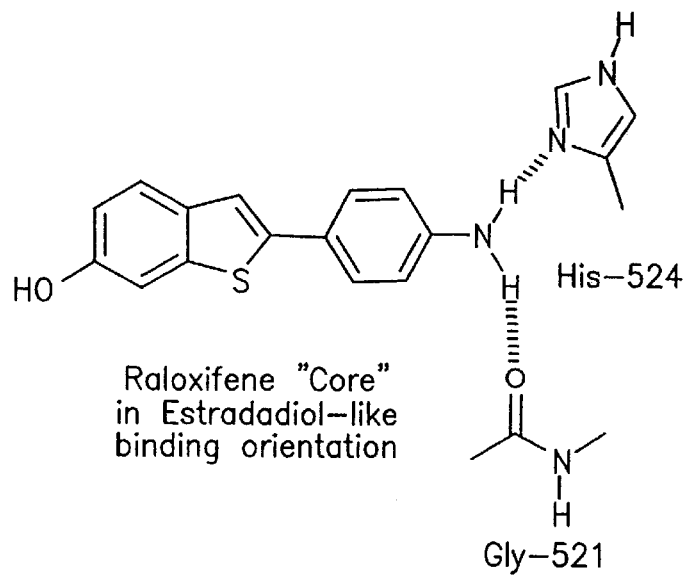
Figure 5E:
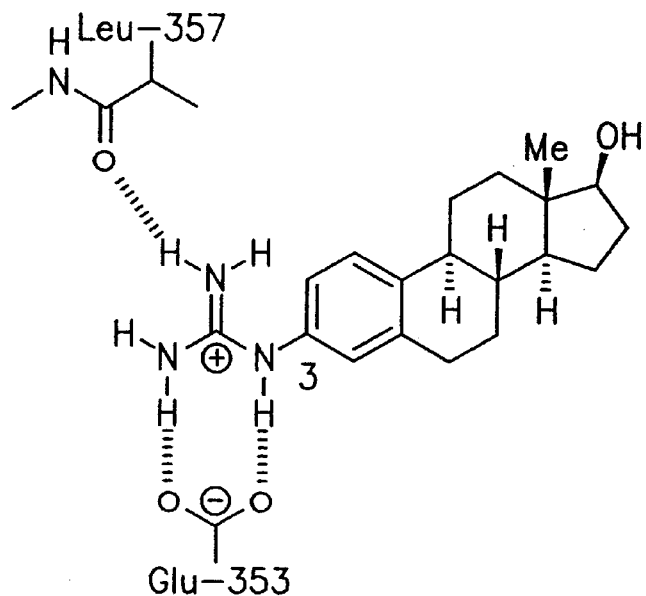
Figure 5E:
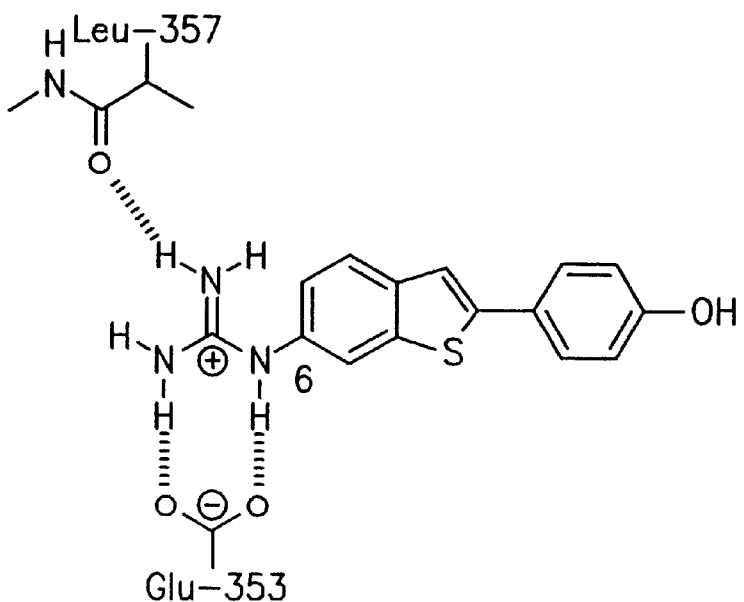

In a fourth aspect of this invention, replacement of the 4-hydroxyl group of raloxifene will enhance affinity by picking up a second hydrogen bonding interaction between the amino group and a backbone carbonyl group in Gly-521 of the ERβ (FIG. 5d).

(2) Improved Selectivity

The estrogen receptor has been found to have two discrete forms, known as ERα and ERβ. Furthermore the ratio of the α- to the β-forms of the ER may vary considerably in different cell and tissue types. Therefore it may be possible to dissociate desirable therapeutic effects from undesirable side effects of estrogen receptor ligands by designing ligands that selectively bind to one or the other isoforms of the estrogen receptor.

The α- and β-forms of the estrogen receptor differ significantly in their primary sequence and slightly in their tertiary structure. As a consequence of these receptor differences, ligands may bind with different affinity to the two isoforms.

The present inventors have been able to isolate, differentiate and produce crystals for both the ERα and ERβ. The present invention is confined however to ERβ. Further, the differences between the ERα and ERβ has been determined and using these differences, the ability of a ligand to bind to either the ERα and ERβ receptors or to both receptors can be predicted. Hence, if it is known that one tissue possesses solely one form of the estrogen receptor, then it is possible to confer a degree of tissue specificity to a ligand by designing the ligand to bind to that predominant form of the receptor. Advantageously, ligands. may be designed to specifically bind ERα or ERβ.

Furthermore, a detailed understanding of the different receptors enables the different behavior of a compound in different tissues to be understood. for example the estrogenic or anti-estrogenic behavior of raloxifen (RAL) dependence on the tissue in which it is active.

Thus, in a further aspect, the invention provides estrogen receptor ligand binding domain crystals for ERβ. Specificity of ligands for either the ERαto and ERβ or even to a specific ratio of ERα to ERβ is also provided. The advantage of this is that tissue specificity is conferred to the ligand. Thus, the invention also provides ligands, particularly synthetic ligands for ERβ together with methods for their design.

The present invention provides new ligands which exploit these differences by positioning ligand substituents in close proximity to one or more amino acid residue that differ between the α- and β-isoforms of the ER.

The ligands produced in accordance with the invention bind more effectively to either the α- or β-isoforms of the ER. The selectivity of the binding between the α- or β-isoforms may be ten-fold, more preferably one hundred-fold, and most preferably greater than one thousand-fold.

For example, in the β-face cavity of ER-α, the amino acid residue at position-384 is Leu (sidechain volume =76.6 Å$^3$) whereas in the corresponding position-293 of ER-β, the amino acid residue is Met (sidechain volume=79.3 Å$^3$). Therefore the β-face cavity of ER-β is smaller. Consequently ER-α selectivity may be enhanced by positioning substituents larger than a methyl group in the β-face cavity in close proximity to residue-384. Interaction between the ligand and residue-384 may be enhanced by introducing substituents at the β 8-, 15-, or 18-positions on the steroid nucleus.

In the α-face cavity of ER-α, the amino acid residue at position-421 is Met (sidechain volume=79.3 Å$^3$) whereas in ER-β, it is Ile-330 (sidechain volume=77.3 Å$^3$). Therefore the α-face cavity of ER-αis smaller. This difference may be exploited to produce β-selective compounds through substitutions larger than a methyl group at the α 14-, 16-, or 17-positions of the steroid nucleus.

Similarly, substitutions may be made from either the 2'- or 3'-positions of the 2-arylbenzothiophene nucleus to interact with residue-384 in the β-face cavity or from the 6'-position to interact with residue-421 in the α-face cavity (FIG. 6a and 6b). However free rotation about the C2—C1' bond will effectively interchange the substituents at the 2'- and 6'-positions thereby reducing selectivity. Moving the hydroxyl group from position (FIG. 6a) to position-5' (FIG. 6b) will bias the binding orientation such that the $R_2$' substituent will be positioned in the β-face pocket and the $R_6$' substituent in the α-face pocket. This bias results from the fact that only one of the two possible rotamers about the C2—C1' bond will allow hydrogen bond formation between the 5'-hydroxyl group and the receptor residue His-524.

This invention also provides a means of enhancing the selectivity of other classes of non-steroidal ER-β ligands. In a manner analogous to the benzothiophene series of ER-β ligands, substituents larger than methyl may be introduced at either the $R_2$' or $R_3$' positions to produced ER-α selective compounds or at $R_6$' to produce ER-β selective compounds (FIG. 5c).

Substitutions may be made from position-3 of the steroid nucleus or position-6 of the benzothiophene nucleus to exploit the differences between ER-α and ER-β at position-326 (Ile in ER-α and Val in ER-β) and at position-445 (Phe in ER-α and Tyr in ER-β).

(3) Modulation of Efficacy

This invention provides an understanding of the differences between estrogen and antiestrogen binding and therefore a means to design ER-β ligands with the desired degree of efficacy. An examination of the differences between the ER-β/genistein and ER-β/raloxifene complexes reveals a large movement in Helix-12 (H12). H12 adopts an "agonistic" conformation defined by the structure of the ER-β/genistein complex and an "antagonistic" conformation defined by the structure of the ER-β/raloxifene complex. These two conformation are in thermodynamic equilibrium. When the ER-β is complexed with a full agonist, such as genistein, the equilibrium lies far in the direction of the "agonistic" conformation. In contrast, while when complexed with an antagonist, the equilibrium is pushed in the direction of the "antagonistic" conformation. In the case of raloxifene, the large sidechain at position-3 sterically collides with H12 in it's agonistic conformation, thereby driving the equilibrium strongly in the antagonistic direction. By introduction of progressively shorter sidechains at position-3 of raloxifene, the equilibrium will be gradually shifted back towards the agonist conformation. Thus, this invention provides a means of developing ligands with the desired degree of efficacy (agonist, partial agonist, or antagonist).

In particular, the importance of H12 has been determined as playing a central role in determining the efficacy (agonism vs. antagonism) of a ligand. Thus, ligands which are able to bind to and/or alter the conformation of H12 are of particular importance when designing a ligand or assessing the binding of a ligand, for the estrogen receptor.

The present inventors have also found the reason why raloxifene has a different binding conformation to that of estradiol, the distinction lying in its active conformation but being unpredictable by virtue of it antagonistic action. The antagonism has been shown, by the present inventors, to be caused by a protruding portion on the raloxifene molecule which causes a large displacement of H12 relative to its conformation in the ER-β/estradiol complex.

Additionally, it has been found that at least the majority of such receptor proteins are in the form a dimer. Such dimerization leads to a potential route for disruption. Disruptions of this type can be used to predict antagonism or to produce antagonists. Disruptions may take the form of ligand binding which alters the conformation of the helices that comprise the dimerization interface or direct binding to the dimerization interface which then inhibits dimerization.

Further, the orientation of the ligand may be keyed to receptor, in the dimeric or monomeric form. Furthermore, using the crystals of the present invention, the influence of ligand binding to the LBD on the receptor conformations can now be shown to have influences on the behavior of the receptor since it may disrupt the binding of co-activator, co-repressor, or heat-shock proteins. Previously, such predictions could not be made.

Production of Estrogen Receptor Crystals and their Application.

The present inventors have been able to isolate, differentiate and produce crystals for both the ER-α and ER-β receptors. The present invention, however, is confined to ER-β. Further, the differences between the ER-α and ER-β receptors has been determined and, using these differences, the ability of a ligand to bind to either the ER-α and the ER-β receptor or to both receptors can be predicted. Hence. if it is known that one tissue possesses predominately one isoform of the estrogen receptor, then it is possible to confer a degree of tissue specificity to a ligand by designing the ligand to bind to that predominant isoform of the receptor.

Furthermore, a detailed understanding of the different receptors enables the different behavior of a compound in different tissues to be understood, for example the estrogenic or anti-estrogenic behavior of raloxifene (RAL) in dependence on the tissue in which it is active.

Preferably, the crystal is produced from a sequence comprising at least one hundred and fifty amino acids, and preferably at least two hundred amino acids of ER-β. Preferably, the sequence comprises at least a portion of the ligand binding domain of ER-β. More preferably, the sequence comprises the whole ligand binding domain of ER-β.

Preferably, the crystals used can withstand exposure to X-ray. Beams used to produce the diffraction pattern data necessary to solve the X-ray crystallographic structure. For example, crystals grown using estrogen receptor sequence bound to a various of ER-β ligands have been found to decompose during exposure to X-ray beams at room temperature, whereas crystals grown using estrogen receptor sequence bound to various ER-β ligands are freezable and are able to withstand exposure to X-ray beams.

Advantageously, the crystals have a resolution determined by X-ray crystallography of less than 3.5 Å and most preferably less than 2.8 Å. Preferably crystals grown using naturally occurring estradiol have an effective resolution of lower than 3.1 Å and crystals grown using raloxifene have an effective resolution of lower than 2.6 Å.

The production of such crystals has enabled the three dimensional structure of the ligand binding domain of ER-β to be mapped. Use of such crystals in conjunction with the map enables a better understanding of how estradiol and other estrogen bind to ER-β with precision. This technique can also enable the design of isoform selective estrogen agonists and antagonists since now the precise differences in the binding sites between ER-α and ER-β are now known.

For example, it was previously proposed that the amino acid residue Phe-425 in ER-α and the corresponding residue Phe-334 in ER-β which both line the ligand binding cavity adopt similar conformations and therefore ligands that probe this region of the receptor would not expected to be isoform selective. However a comparison of the human ER-α/raloxifene vs. rat ER-β/raloxifene complexes shows that the chi-1 sidechain torsion angle (the N-CA-CB-CG angle) differs markedly between the two structures (-156 vs. -87 resepectively). As a consequence, the ER-α binding cavity is effectively larger compared to the ER-β cavity when bound to antagonists. This suggests that raloxifene analogs which possess 2'- and 3'-substituents should be ER-α isoform selective.

Crystals of the ER-β binding domain can be used as models in methods for the design of synthetic compounds intended to bind to the receptor. Such models show why very slight difference in chemical moieties of a ligand potentially have widely varying binding affinities. Hence, the three dimensional structure of the ligand binding domain can be used a pharmaceutical model for compounds which bind to estrogen receptors.

EXAMPLE 1

Materials

Protein Purification and Crystallisation of the Estrogen Receptor (ER-β)

The rat or human ER-LBD-β (210–464) was cloned into the pLEX vector (Invitrogen), with an N-terminal FLAG-peptide (IBI), over expressed in *Escherichia coli* GI 724 under control of the inducible PL promoter. Fermentation was carried out in batch and fed batch (glucose limitation) mode in a defined glucose/salt medium at 30° C. Production of recombinant protein was induced by adding tryptophane to a concentration of 1.2 mM. After 3 hr of induction, cells were harvested by centrifugation, and frozen. Thawed cells, corresponding to 1200 mL fermentation volume were disrupted by a Bead Beater (Biospec, Bartlesville, Okla., USA) homogenizer (6×22 sec., with a 3 min resting time between bursts) in 250 mL 100 mM Tris-HCl (pH 8.0), 300 mM KCl, 10% glycerol, 5 mM EDTA, 4 mM DTT, 0.1 mM PMSF and 210 mL glass beads (212–300 micrones) at 0° C. After centrifugation, the supernatant was applied to a column of estradiol-Sepharose Fast Flow, 25 mL, (Greene G. et al Proc Natl Acad Sci USA (1980) 77, 5115–5119). (For the human ER-beta the KCl concentration was increased to 600 mM before the extract was loaded to the column.) The column was first washed with 100 mL 100 mM Tris-HCl (pH 8.0), 300 mM KCl (600 mM KCL for human ER-beta), 10% glycerol, 5 mM EDTA, 0.1 mM PMSF, 2 mM DTT, followed by 150 mL 10 mM Tris-HCl (pH 8.0), (300 mM KCl for the human ER-beta), 2 mM EDTA, 0.1 mM PMSF, 2 mM DTT. In the case of human ER-beta the KCl concentration was lowered to 100 mM prior Cys-modification. Reactive Cys residues were modified by washing the column with 100 mL 30 mM Tris-base, 15 mM iodoacetic acid (100 mM KCL for the human ER-beta) and pH 8.1. Excess reagents was washed out by 100 mL 20 mM Tris-HCl pH 8.0 (and 100 mM KCl for human ER-$\beta$) followed by 50 mL 20 mM Tris-HCl, pH 8.0, 10% dimethylformamide (and 100 mM KCl for human ER-beta). The ER-LBD-$\beta$ was eluted by including 50–75 $\mu$M of the desired ligand and 250 mM NaSCN to the last buffer, The fractions containing ER-LBD-$\beta$ was pooled and concentrated (Centriprep 30, Amicon) to 2 mL. Final purification was achieved using a Bio-Rad 491 preparative PAGE instrument according to the user manual. Using one dilution of the Ornstein/Davies buffer system. The stacking (0.5 cm) and resolving (5.5 cm) gels was 5.6% (acrylamide/bis). The elution buffer was 10 mM Tris-HCl pH 8.0 and the electrophoresis was carried out at 12 W. Fractions containing ER-LBD-$\beta$ was pooled and concentrated (Centriprep 30) to the desired protein concentration. All buffers contains 0.02% NaN$_3$.

Rat ER$\beta$-Raloxifene (rER$\beta$-R) Crystallization (Structure)

Crystals were grown by vapor diffusion using hanging drop technique at 19° C. Best crystals were obtained using 0.03 M Na acetate buffer pH 4.6, 9% (w/v) PEG 4000, 0.06 M ammonium acetate with the addition of 4% dimethylformamide on top. The optimum size of the drop was achieved by mixing 3.0 $\mu$L of protein solution (11 ]mg/mL) with 1.5 $\mu$L of the reservoir solution.

Upon analysis, the crystals were found to belong to the space group P4122 and have the unit cell dimensions a=67.9 Å, c=148.62 Å, and $\alpha=\beta=\gamma=90°$.

Upon analysis, the crystals were found to belong to the space group P4122 and have the unit cell dimensions a=67.9 Å, b=67.9 Å, c=148.62 Å, and $\alpha=\beta=\gamma=90°$.

Upon analysis, the crystals were found to belong to the space group P6122 and have the unit cell dimensions a=63.2 Å, b=63.2 Å, c=250.36 Å, $\alpha=\beta=90°$, and $\gamma=120°$.

Rat ER$\beta$-KB-000,177 (rER$\beta$-177) Crystallization (Structure)

Crystals were grown by vapor diffusion using hanging drop technique at 19° C. Best crystals were obtained using 0.03 M Na acetate buffer pH 4.6, 9% (w/v) PEG 4000, 0.06 M aimmonium acetate. The optimum size of the drop was achieved by mixing 3.0 $\mu$L of protein solution (9.5 mg/mL) with 1.5 $\mu$L of the reservoir solution.

Human ER$\beta$-genistein (hER $\beta$-gen) (Structure)

Crystals were grown by vapor diffusion using hanging drop technique at 19° C. Best crystals were obtained using 100 mM Tris-HCl buffer (pH 8.1), 7% (w/v) PEG 6000, 1.9 M NaCl with the addition of 2.7% iso-propanol on top. The optimum size of the drop was achieved by mixing 1.0 $\mu$L of protein solution (7 mg/mL) with 1.0 $\mu$L of the reservoir solution.

Rat ER$\beta$-genistein (rER$\beta$-gen) (Crystals)

Crystals were grown by vapor diffusion using hanging drop technique at 19° C. Best crystals were obtained using 100 mM Tris-HCl buffer (pH 8.1), 8–12% (w/v) PEG 6000, 1.2–2.1 M NaCl with the addition of 2.5% iso-propanol on top. The optimum size of the drop was achieved by mixing 1.0 $\mu$L of protein solution (9–12 mg/mL) with 1.0 $\mu$L of the reservoir solution.

EXAMPLE 2

Structure of Rat ER-$\beta$ Ligand-binding Domain (LBD) Complexed with the Pure Antiestrogen N-(n-Butyl)-11-[3,17$\beta$-dihydroxyestra-1,3,5(10)-trien-7$\alpha$-yl]N-methylundecanamide (ICI 164,384)

Crystallization, data collection, and processing:

Rat ER$\beta$-LBD was expressed, purified and carboxymethylated as described in Example 1, or by the procedure described in Pike, A.C.W., et al. & Carlquist, M. (1999) *EMBO J.*, 18, 4608–4618. N-(n-butyl)-11-[3,17$\beta$-dihydroxyestra- 1,3,5(10)-trien-7$\alpha$-yl]N-methylundecanamide (ICI 164,384; CA Registry number 98007-99-9] was prepared according to the procedure of Bowler et al. (Bowler, J.; Lilley, T. J.; Pittam, J. D.; Wakeling, A. E.; Steroids 1989, 54:71–99). Crystals were grown using the hanging-drop vapour diffusion technique at 18° C. Drops, comprising equal volumes of protein (10 mg/ml) and reservoir solution (7% (w/v) polyethylene glycol 2000 monomethyl ether, 3.5 mM nickel chloride, 10% (v/v) dioxane in 35 mM Tris HCl pH8.5), were equilibrated against the same reservoir solution. The resultant crystals belong to space group I2$_1$2$_1$2$_1$ with cell dimensions a=59.37 Å b=81.4 Å c=520.97 Å and contain five LBD monomers per asymmetric unit. The crystals were cryoprotected by slow sequential transfer from 2% to 30% ethylene glycol in 5% steps over 4 hrs. X-ray diffraction data were collected to a resolution of less than 2.5 Å, and more preferably about 2.3 Å, on station P7-11 (MAX-LAB, Lund). A total of 804099 observations were recorded on 576 images in two collection sweeps. These were then scaled and reduced to a final unique set of 42156 reflections (95.7% complete) with a R$_{merge}$(I) of 0.057 for data between 12–2.3 Å. The structure of ER$\beta$-LBD in complex with pure antagonist N-(n-butyl)-11-[3,17$\beta$-dihydroxyestra- 1,3,5(10)-trien-7$\alpha$-yl]N-methylundecanamide (ICI 164,384) is shown in FIGS. 7A (side view) and 7B (end-on view).

EXAMPLE 3

Structure of Rat ER-$\beta$ Ligand-binding Domain (LBD) Complexed with (17$\beta$)-Estra-1,3,5(10)-triene-3,17-diol (Estradiol) and LXXLL Coactivator Peptide Crystallization, data collection, and processing:

Rat ER$\beta$-LBD was expressed, purified, and carboxymethylated as described in Examples 1 and 2, or by the procedure described in Pike, A.C.W., et al., & Carlquist, N. (1999) EMBO J., 18, 4608–4618. (17$\beta$)-Estra-1,3,5(10)-triene-3,17-diol (Estradiol; CAS Registry No. 50-28-2) was obtained from Sigma-Aldrich. The LXXLL (SEQ ID NO:4)

coactivator peptide was obtained from MWG-Biotech AG. The LXXLL (SEQ ID NO:4) coactivator peptide was derived from the coactivator independent of AF2 function (CIA) described in Suave, F. et al. Mol. Cell. Biol. 21:343–353 (2001), and comprises residues 338–354 of that protein. The LXXLL peptide used in this experiment comprised 17 amino acids in length with the sequence HPPAIQSLINLLADNRY (SEQ ID NO:3).

Crystals were grown using the hanging-drop vapour diffusion technique at 18° C. Drops, comprising equal volumes of protein solution and reservoir solution (1 μL) were equilibrated against the same reservoir solution. The protein solution was prepared from 15 mg/ml ERβ LBD and LXXLL coactivator peptide (5 mM stock) mixed in a 1:5 molar ratio. The reservoir solution was prepared from 0.50–0.605 dilution of 10% (w/v) PEG8K, 10% (w/v) PEG1K, 0.2 M lithium sulphate, 100 mM Tris HCl (pH 8.0). Crystals were stored frozen in reservoir solution containing 25% (v:v) ethanediol. The resultant crystals belong to space group P4122 with cell dimensions a=62.55 Å, b=62.55 Å, c=171.70 Å. X-ray diffraction data were collected to a resolution of less than 2.5 Å, and preferably about 2.1 Å, on station ID14-4 (ESRF, Grenoble, France).

A total of 499631 observations were recorded on 320 images. These were then scaled and reduced to a final unique set of 20776 reflections (99.9% complete) with a Rmerge(I) of 0.061 for data between 40–2.1 Å. The structure of rat ER-β ligand-binding domain (LBD) complexed with estradiol and LXXLL coactivator peptide is shown in FIGS. 8A (side view) and 8B (end-on view).

EXAMPLE 4

Structure of Rat ER-β Ligand-binding Domain (LBD) Complexed with (16α,17α)-Estra-1,3,5(10)-triene-3,16,17-triol (17-epiestriol) and LXXLL Coactivator Peptide Crystallization, data collection, and processing:

Rat ERβ-LBD was expressed, purified and carboxymethylated as described in Examples 1 and 2, or by the procedure described in Pike, A.C.W., et al. & Carlquist, M. (1999) *EMBO J.*, 18, 4608–4618. 16α,17α)-Estra-1,3,5(10)-triene-3,16,17-triol (17-Epiestriol; CAS Registry No. 1228-72-4) was obtained from Sigma-Aldrich. The LXXLL coactivator peptide was obtained from MWG-Biotech AG. The LXXLL coactivator peptide was derived from the coactivator independent of AF2 function (CIA) described in Sauve, F. et al. Mol. Cell. Biol. 21:343–353 (2001), and comprises residues 338–354 of that protein. The LXXLL peptide used in this experiment comprised 17 amino acids in length with the sequence HPPAIQSLINLLADNRY (SEQ ID NO:3).

Crystals were grown using the hanging-drop vapour diffusion technique at 18° C. Drops, comprising equal volumes of protein solution and reservoir solution (1 μL) were equilibrated against the same reservoir solution. The protein solution was prepared from 15 mg/ml ERβ LBD and LXXLL coactivator peptide (5mM stock) mixed in a 1:5 molar ratio. The reservoir solution was prepared from 0.50–0.605 dilution of 10% (w/v) PEG8K, 10% (w/v) PEG1K, 0.2 M lithium sulphate, 100 mM Tris HCl (pH 8.0). Crystals were stored frozen in reservoir solution containing 25% (v:v) ethanediol. The resultant crystals belong to space group P4122 with cell dimensions a=62.64 Å, b=62.64 Å, c=171.64 Å. X-ray diffraction data were collected to a resolution of less than 2.0 Å, and preferable less than about 1.8 Å, on station ID14-4 (ESRF, Grenoble, France).

A total of 788988 observations were recorded on 400 images. These were then scaled and reduced to a final unique set of 32284 reflections (98.7% complete) with a Rmerge(I) of 0.039 for data between 30–1.8 Å. The structure of rat ER-b ligand-binding domain (LBD) complexed with epiestriol and LXXLL coactivator peptide is shown in FIGS. 9A (side view) and 9B (end-on view).

Experimental Description of ER Binding Assay

Affinity for the ER (by displacement of $^3$[H]-estradiol was measured using the scintistrip[1] assay. Human estrogen receptor (hER) alpha was extracted from the nuclei from SF9-cells infected with a recombinant baculovirus transfer vector containing the cloned hER genes.[2] The concentration of hER's in the extract was measured as specific $^3$[H]—E2 binding with the G25-assay.

1) Haggblad, J., Carlsson, B., Kivela, P., Siitari, H., (1995) *Biotechniques* 18, 146–151.
2) Barkhem, T., Carlsson, B., Simons, J., Moller, B., Berkenstam, A., Gustafsson, J. A., Nilsson, D. (1991) *J. Steroid Biochem. Molec. Biol.* 38,667–75.
3) Salononsson, M., Carlsson, B., Haggblad, J., (1994) *J. Steroid Biochem. Molec. Biol.* 50, 313–318.

The following pages give the crystal coordinates for:
(1) ERβ-LBD-genistein (SEQ ID NO:1);
(2) ERβ-LBD-Raloxifene(SEQ ID NO:2);
(3) ERβ-LBD-[2-(4-hydroxyphenyl)-6-hydroxybenzo[beta]thienyl-3-yl][4-carboxyphenyl]methanone (KB 177) (SEQ ID NO:2);
(4) ER-β LBD-N-(n-butyl)-11-[3,17β-dihydroxyestra-1,3,5(10)-trien-7α-yl]N-methylundecanamide (ICI 164,384) (SEQ ID NO:2);
(5) ER-β LBD-(17β)-Estradiol/LXXLL coactivator peptide (SEQ ID NO:2); and
(6) ER-β LBD-(17β)-Epiestriol/LXXLL coactivator peptide (SEQ ID NO:2).

```
TITLE     Human estrogen receptor beta LBD + genistein REMARK    Date: 28th August 1998
REMARK                                                                          REMARK
REMARK
REMARK    Ligand good and nice geometry                                         REMARK
 This file is herbgen_ref6_3.pdb
REMARK REMARK    Refined against data collected at LURE, France (22/07/98) REMARK
Rmerge(I): 0.074 Completeness: 99.4%
REMARK REMARK    Overall refinement statistics (25-2.3):
REMARK REMARK    refine_overall_R_factor         0.24398
REMARK    refine_ls_number_reflns              13359
REMARK    refine_ls_number_reflns_missing          6
REMARK    refine_free_R_factor             0.31669
REMARK    refine_ls_number_reflns_free           701
REMARK    refine_ls_number_reflns_free_missing     0
REMARK    refine_ls_WR_factor              0.22589
REMARK REMARK    Correlation_coefficients_Fo_to_Fc      0.90728
REMARK    Free_correlation_coeff_Fo_to_Fc    0.87115
REMARK REMARK    Overall_Coordinate_ESU_based_on_R_value(Cruickshanks DPI)    0.32670
REMARK    Overall_Coordinate_ESU_based_on_free_R_value     0.27902
REMARK AUTHOR    Ash Pike, Marek Brzozowski AUTHOR    Structural Biology Laboratory,
University of York, York YO10 5DD, UK
REMARK REMARK    Sequence is correct but not all sidechains may be present
REMARK    Incomplete residues: Asp218,Ser243,Lys257,Glu278,Arg286,Lys310,Glu328 REMARK
 Val371,Asp378,Lys437,Lys439
REMARK    Residues modelled as alt.confs: His236,Val237,Ser268,Arg343,Glu346, REMARK
 Gln407,Wat39,Wat41
REMARK    Ligand has residue name GEN    Residue A 600
REMARK CRYST1    63.200    63.200   250.360   90.00   90.00  120.00    P6122 SCALE1
0.01582    0.00914    0.00000       0.00000 SCALE2      0.00000    0.01827   0.00000
    0.00000 SCALE3      0.00000    0.00000    0.00399         0.00000
ATOM      1  N   ASP A 218      52.629  -9.066 105.176  1.00 77.86           N
ATOM      2  CA  ASP A 218      53.344  -8.241 104.155  1.00 77.56           C
ATOM      3  C   ASP A 218      52.628  -6.930 103.881  1.00 76.76           C
ATOM      4  O   ASP A 218      53.068  -5.825 104.207  1.00 78.71           O
ATOM      5  CB  ASP A 218      53.485  -9.010 102.848  1.00 78.27           C
ATOM      6  N   ALA A 219      51.413  -6.979 103.331  1.00 73.31           N
ATOM      7  CA  ALA A 219      50.547  -5.846 103.067  1.00 69.17           C
ATOM      8  C   ALA A 219      49.991  -5.244 104.375  1.00 66.79           C
ATOM      9  O   ALA A 219      49.313  -4.216 104.448  1.00 63.69           O
ATOM     10  CB  ALA A 219      49.384  -6.308 102.202  1.00 68.60           C
ATOM     11  N   LEU A 220      50.285  -5.907 105.487  1.00 62.30           N
ATOM     12  CA  LEU A 220      49.961  -5.593 106.837  1.00 58.79           C
ATOM     13  C   LEU A 220      51.154  -4.942 107.530  1.00 57.20           C
ATOM     14  O   LEU A 220      51.162  -4.863 108.763  1.00 58.18           O
ATOM     15  CB  LEU A 220      49.521  -6.849 107.588  1.00 59.55           C
ATOM     16  CG  LEU A 220      48.202  -7.520 107.173  1.00 58.34           C
ATOM     17  CD1 LEU A 220      48.059  -8.808 107.968  1.00 58.32           C
ATOM     18  CD2 LEU A 220      47.021  -6.585 107.367  1.00 56.37           C
ATOM     19  N   SER A 221      52.179  -4.512 106.800  1.00 53.19           N
ATOM     20  CA  SER A 221      53.313  -3.750 107.356  1.00 48.98           C
ATOM     21  C   SER A 221      52.773  -2.363 107.722  1.00 47.08           C
ATOM     22  O   SER A 221      51.932  -1.788 107.021  1.00 47.48           O
ATOM     23  CB  SER A 221      54.413  -3.742 106.302  1.00 47.88           C
ATOM     24  OG  SER A 221      55.098  -2.502 106.216  1.00 50.76           O
ATOM     25  N   PRO A 222      53.177  -1.779 108.830  1.00 45.19           N
ATOM     26  CA  PRO A 222      52.714  -0.517 109.380  1.00 41.25           C
ATOM     27  C   PRO A 222      52.449   0.614 108.407  1.00 36.75           C
ATOM     28  O   PRO A 222      51.327   1.064 108.134  1.00 27.94           O
ATOM     29  CB  PRO A 222      53.726  -0.088 110.472  1.00 41.92           C
ATOM     30  CG  PRO A 222      54.261  -1.437 110.887  1.00 44.17           C
ATOM     31  CD  PRO A 222      54.164  -2.410 109.736  1.00 44.11           C
ATOM     32  N   GLU A 223      53.534   1.110 107.856  1.00 36.09           N
ATOM     33  CA  GLU A 223      53.484   2.193 106.875  1.00 36.99           C
ATOM     34  C   GLU A 223      52.535   1.816 105.738  1.00 32.55           C
ATOM     35  O   GLU A 223      51.590   2.547 105.463  1.00 30.61           O
ATOM     36  CB  GLU A 223      54.894   2.454 106.344  1.00 40.35           C
ATOM     37  CG  GLU A 223      55.069   3.837 105.783  1.00 46.01           C
ATOM     38  CD  GLU A 223      56.462   4.384 106.046  1.00 52.28           C
ATOM     39  OE1 GLU A 223      56.709   4.890 107.175  1.00 55.58           O
ATOM     40  OE2 GLU A 223      57.342   4.323 105.150  1.00 52.83           O
ATOM     41  N   GLN A 224      52.737   0.698 105.085  1.00 29.61           N
ATOM     42  CA  GLN A 224      51.910   0.228 104.003  1.00 31.67           C
ATOM     43  C   GLN A 224      50.466   0.047 104.431  1.00 29.04           C
ATOM     44  O   GLN A 224      49.528   0.304 103.677  1.00 28.74           O
ATOM     45  CB  GLN A 224      52.465  -1.081 103.424  1.00 34.52           C
ATOM     46  CG  GLN A 224      51.523  -1.855 102.508  1.00 42.67           C
```

| | | | | | | | | | |
|---|---|---|---|---|---|---|---|---|---|
| ATOM | 1716 | CG1 | VAL A 441 | 13.010 | 4.323 | 111.283 | 1.00 | 64.20 | C |
| ATOM | 1717 | CG2 | VAL A 441 | 13.969 | 6.502 | 112.101 | 1.00 | 64.58 | C |
| ATOM | 1718 | N | VAL A 442 | 13.906 | 5.564 | 108.404 | 1.00 | 61.34 | N |
| ATOM | 1719 | CA | VAL A 442 | 14.265 | 4.628 | 107.333 | 1.00 | 61.05 | C |
| ATOM | 1720 | C | VAL A 442 | 14.721 | 3.381 | 108.093 | 1.00 | 58.22 | C |
| ATOM | 1721 | O | VAL A 442 | 15.402 | 3.467 | 109.116 | 1.00 | 57.91 | O |
| ATOM | 1722 | CB | VAL A 442 | 15.382 | 5.165 | 106.441 | 1.00 | 61.95 | C |
| ATOM | 1723 | CG1 | VAL A 442 | 16.187 | 4.051 | 105.781 | 1.00 | 63.15 | C |
| ATOM | 1724 | CG2 | VAL A 442 | 14.871 | 6.052 | 105.311 | 1.00 | 61.53 | C |
| ATOM | 1725 | N | PRO A 443 | 14.307 | 2.211 | 107.667 | 1.00 | 56.16 | N |
| ATOM | 1726 | CA | PRO A 443 | 14.671 | 0.944 | 108.290 | 1.00 | 53.73 | C |
| ATOM | 1727 | C | PRO A 443 | 16.107 | 0.566 | 107.933 | 1.00 | 52.37 | C |
| ATOM | 1728 | O | PRO A 443 | 16.398 | -0.353 | 107.164 | 1.00 | 53.06 | O |
| ATOM | 1729 | CB | PRO A 443 | 13.622 | -0.048 | 107.767 | 1.00 | 54.46 | C |
| ATOM | 1730 | CG | PRO A 443 | 13.177 | 0.557 | 106.461 | 1.00 | 53.93 | C |
| ATOM | 1731 | CD | PRO A 443 | 13.466 | 2.039 | 106.480 | 1.00 | 54.98 | C |
| ATOM | 1732 | N | VAL A 444 | 17.082 | 1.244 | 108.528 | 1.00 | 49.01 | N |
| ATOM | 1733 | CA | VAL A 444 | 18.492 | 1.055 | 108.262 | 1.00 | 47.38 | C |
| ATOM | 1734 | C | VAL A 444 | 18.933 | -0.388 | 108.430 | 1.00 | 44.92 | C |
| ATOM | 1735 | O | VAL A 444 | 19.560 | -0.987 | 107.551 | 1.00 | 42.10 | O |
| ATOM | 1736 | CB | VAL A 444 | 19.372 | 1.986 | 109.133 | 1.00 | 47.92 | C |
| ATOM | 1737 | CG1 | VAL A 444 | 20.829 | 1.959 | 108.685 | 1.00 | 47.16 | C |
| ATOM | 1738 | CG2 | VAL A 444 | 18.886 | 3.418 | 109.139 | 1.00 | 45.95 | C |
| ATOM | 1739 | N | TYR A 445 | 18.611 | -0.964 | 109.576 | 1.00 | 44.36 | N |
| ATOM | 1740 | CA | TYR A 445 | 18.986 | -2.337 | 109.885 | 1.00 | 45.72 | C |
| ATOM | 1741 | C | TYR A 445 | 18.472 | -3.353 | 108.883 | 1.00 | 45.56 | C |
| ATOM | 1742 | O | TYR A 445 | 19.277 | -4.211 | 108.435 | 1.00 | 44.98 | O |
| ATOM | 1743 | CB | TYR A 445 | 18.576 | -2.668 | 111.341 | 1.00 | 47.63 | C |
| ATOM | 1744 | CG | TYR A 445 | 19.126 | -4.024 | 111.709 | 1.00 | 48.50 | C |
| ATOM | 1745 | CD1 | TYR A 445 | 20.444 | -4.126 | 112.168 | 1.00 | 47.99 | C |
| ATOM | 1746 | CD2 | TYR A 445 | 18.348 | -5.178 | 111.562 | 1.00 | 47.75 | C |
| ATOM | 1747 | CE1 | TYR A 445 | 20.964 | -5.377 | 112.482 | 1.00 | 47.52 | C |
| ATOM | 1748 | CE2 | TYR A 445 | 18.876 | -6.417 | 111.884 | 1.00 | 47.19 | C |
| ATOM | 1749 | CZ | TYR A 445 | 20.177 | -6.505 | 112.346 | 1.00 | 47.14 | C |
| ATOM | 1750 | OH | TYR A 445 | 20.714 | -7.731 | 112.651 | 1.00 | 46.91 | O |
| ATOM | 1751 | N | ASP A 446 | 17.190 | -3.293 | 108.499 | 1.00 | 44.96 | N |
| ATOM | 1752 | CA | ASP A 446 | 16.718 | -4.273 | 107.498 | 1.00 | 46.39 | C |
| ATOM | 1753 | C | ASP A 446 | 17.390 | -3.946 | 106.166 | 1.00 | 43.51 | C |
| ATOM | 1754 | O | ASP A 446 | 17.835 | -4.873 | 105.477 | 1.00 | 41.91 | O |
| ATOM | 1755 | CB | ASP A 446 | 15.203 | -4.373 | 107.352 | 1.00 | 49.81 | C |
| ATOM | 1756 | CG | ASP A 446 | 14.514 | -4.779 | 108.637 | 1.00 | 53.40 | C |
| ATOM | 1757 | OD1 | ASP A 446 | 15.119 | -5.416 | 109.531 | 1.00 | 55.82 | O |
| ATOM | 1758 | OD2 | ASP A 446 | 13.319 | -4.464 | 108.805 | 1.00 | 55.69 | O |
| ATOM | 1759 | N | LEU A 447 | 17.619 | -2.668 | 105.841 | 1.00 | 42.43 | N |
| ATOM | 1760 | CA | LEU A 447 | 18.381 | -2.386 | 104.595 | 1.00 | 41.93 | C |
| ATOM | 1761 | C | LEU A 447 | 19.816 | -2.907 | 104.700 | 1.00 | 38.37 | C |
| ATOM | 1762 | O | LEU A 447 | 20.430 | -3.355 | 103.721 | 1.00 | 34.62 | O |
| ATOM | 1763 | CB | LEU A 447 | 18.253 | -0.923 | 104.189 | 1.00 | 41.35 | C |
| ATOM | 1764 | CG | LEU A 447 | 16.842 | -0.473 | 103.744 | 1.00 | 42.43 | C |
| ATOM | 1765 | CD1 | LEU A 447 | 16.675 | 1.017 | 103.973 | 1.00 | 41.30 | C |
| ATOM | 1766 | CD2 | LEU A 447 | 16.521 | -0.828 | 102.293 | 1.00 | 42.19 | C |
| ATOM | 1767 | N | LEU A 448 | 20.413 | -2.909 | 105.893 | 1.00 | 36.53 | N |
| ATOM | 1768 | CA | LEU A 448 | 21.779 | -3.401 | 106.060 | 1.00 | 37.37 | C |
| ATOM | 1769 | C | LEU A 448 | 21.859 | -4.906 | 105.774 | 1.00 | 37.36 | C |
| ATOM | 1770 | O | LEU A 448 | 22.826 | -5.402 | 105.168 | 1.00 | 33.46 | O |
| ATOM | 1771 | CB | LEU A 448 | 22.385 | -3.108 | 107.460 | 1.00 | 30.90 | C |
| ATOM | 1772 | CG | LEU A 448 | 23.713 | -3.816 | 107.751 | 1.00 | 31.80 | C |
| ATOM | 1773 | CD1 | LEU A 448 | 24.840 | -3.459 | 106.776 | 1.00 | 28.48 | C |
| ATOM | 1774 | CD2 | LEU A 448 | 24.159 | -3.586 | 109.186 | 1.00 | 29.44 | C |
| ATOM | 1775 | N | LEU A 449 | 20.849 | -5.617 | 106.299 | 1.00 | 39.62 | N |
| ATOM | 1776 | CA | LEU A 449 | 20.815 | -7.077 | 106.088 | 1.00 | 41.37 | C |
| ATOM | 1777 | C | LEU A 449 | 20.676 | -7.420 | 104.612 | 1.00 | 41.31 | C |
| ATOM | 1778 | O | LEU A 449 | 21.324 | -8.353 | 104.126 | 1.00 | 39.02 | O |
| ATOM | 1779 | CB | LEU A 449 | 19.733 | -7.726 | 106.952 | 1.00 | 41.56 | C |
| ATOM | 1780 | CG | LEU A 449 | 19.824 | -7.443 | 108.460 | 1.00 | 45.27 | C |
| ATOM | 1781 | CD1 | LEU A 449 | 18.862 | -8.351 | 109.213 | 1.00 | 45.52 | C |
| ATOM | 1782 | CD2 | LEU A 449 | 21.238 | -7.583 | 109.021 | 1.00 | 43.14 | C |
| ATOM | 1783 | N | GLU A 450 | 19.868 | -6.676 | 103.863 | 1.00 | 41.26 | N |
| ATOM | 1784 | CA | GLU A 450 | 19.717 | -6.912 | 102.431 | 1.00 | 43.88 | C |
| ATOM | 1785 | C | GLU A 450 | 21.057 | -6.709 | 101.737 | 1.00 | 43.38 | C |
| ATOM | 1786 | O | GLU A 450 | 21.428 | -7.512 | 100.880 | 1.00 | 45.22 | O |
| ATOM | 1787 | CB | GLU A 450 | 18.705 | -5.979 | 101.759 | 1.00 | 46.53 | C |
| ATOM | 1788 | CG | GLU A 450 | 17.315 | -6.197 | 102.361 | 1.00 | 54.14 | C |
| ATOM | 1789 | CD | GLU A 450 | 16.258 | -5.262 | 101.817 | 1.00 | 58.04 | C |
| ATOM | 1790 | OE1 | GLU A 450 | 16.428 | -4.722 | 100.688 | 1.00 | 60.56 | O |
| ATOM | 1791 | OE2 | GLU A 450 | 15.248 | -5.069 | 102.536 | 1.00 | 59.70 | O |
| ATOM | 1792 | N | MET A 451 | 21.795 | -5.664 | 102.117 | 1.00 | 42.15 | N |

| | | | | | | | | | |
|---|---|---|---|---|---|---|---|---|---|
| ATOM | 1639 | O | GLU | A | 431 | 16.265 | 2.394 | 121.005 | 1.00 33.36 | O |
| ATOM | 1640 | CB | GLU | A | 431 | 18.894 | 1.924 | 122.964 | 1.00 33.95 | C |
| ATOM | 1641 | CG | GLU | A | 431 | 17.797 | 1.754 | 123.986 | 1.00 35.52 | C |
| ATOM | 1642 | CD | GLU | A | 431 | 18.194 | 2.138 | 125.390 | 1.00 40.56 | C |
| ATOM | 1643 | OE1 | GLU | A | 431 | 19.322 | 2.559 | 125.745 | 1.00 39.99 | O |
| ATOM | 1644 | OE2 | GLU | A | 431 | 17.317 | 2.025 | 126.277 | 1.00 42.10 | O |
| ATOM | 1645 | N | HIS | A | 432 | 17.850 | 3.978 | 120.915 | 1.00 33.81 | N |
| ATOM | 1646 | CA | HIS | A | 432 | 16.954 | 5.074 | 120.541 | 1.00 34.48 | C |
| ATOM | 1647 | C | HIS | A | 432 | 16.269 | 4.825 | 119.194 | 1.00 36.85 | C |
| ATOM | 1648 | O | HIS | A | 432 | 15.084 | 5.079 | 118.929 | 1.00 36.92 | O |
| ATOM | 1649 | CB | HIS | A | 432 | 17.765 | 6.373 | 120.485 | 1.00 34.35 | C |
| ATOM | 1650 | CG | HIS | A | 432 | 16.915 | 7.557 | 120.165 | 1.00 36.73 | C |
| ATOM | 1651 | ND1 | HIS | A | 432 | 16.506 | 7.844 | 118.875 | 1.00 36.14 | N |
| ATOM | 1652 | CD2 | HIS | A | 432 | 16.380 | 8.511 | 120.970 | 1.00 36.31 | C |
| ATOM | 1653 | CE1 | HIS | A | 432 | 15.754 | 8.934 | 118.896 | 1.00 36.62 | C |
| ATOM | 1654 | NE2 | HIS | A | 432 | 15.665 | 9.349 | 120.155 | 1.00 36.71 | N |
| ATOM | 1655 | N | LEU | A | 433 | 17.035 | 4.280 | 118.243 | 1.00 35.35 | N |
| ATOM | 1656 | CA | LEU | A | 433 | 16.485 | 3.985 | 116.940 | 1.00 37.11 | C |
| ATOM | 1657 | C | LEU | A | 433 | 15.434 | 2.879 | 117.050 | 1.00 40.39 | C |
| ATOM | 1658 | O | LEU | A | 433 | 14.362 | 2.981 | 116.439 | 1.00 37.58 | O |
| ATOM | 1659 | CB | LEU | A | 433 | 17.596 | 3.559 | 115.995 | 1.00 35.74 | C |
| ATOM | 1660 | CG | LEU | A | 433 | 17.149 | 3.027 | 114.624 | 1.00 33.92 | C |
| ATOM | 1661 | CD1 | LEU | A | 433 | 16.100 | 3.947 | 114.007 | 1.00 32.94 | C |
| ATOM | 1662 | CD2 | LEU | A | 433 | 18.391 | 2.895 | 113.759 | 1.00 32.56 | C |
| ATOM | 1663 | N | LEU | A | 434 | 15.733 | 1.827 | 117.827 | 1.00 42.54 | N |
| ATOM | 1664 | CA | LEU | A | 434 | 14.768 | 0.735 | 117.972 | 1.00 46.96 | C |
| ATOM | 1665 | C | LEU | A | 434 | 13.475 | 1.231 | 118.619 | 1.00 47.13 | C |
| ATOM | 1666 | O | LEU | A | 434 | 12.437 | 0.680 | 118.296 | 1.00 43.63 | O |
| ATOM | 1667 | CB | LEU | A | 434 | 15.333 | -0.475 | 118.704 | 1.00 50.68 | C |
| ATOM | 1668 | CG | LEU | A | 434 | 16.284 | -1.302 | 117.835 | 1.00 54.39 | C |
| ATOM | 1669 | CD1 | LEU | A | 434 | 17.329 | -2.057 | 118.635 | 1.00 57.18 | C |
| ATOM | 1670 | CD2 | LEU | A | 434 | 15.472 | -2.287 | 117.004 | 1.00 56.91 | C |
| ATOM | 1671 | N | MET | A | 435 | 13.497 | 2.283 | 119.449 | 1.00 48.52 | N |
| ATOM | 1672 | CA | MET | A | 435 | 12.261 | 2.766 | 120.009 | 1.00 54.41 | C |
| ATOM | 1673 | C | MET | A | 435 | 11.574 | 3.794 | 119.111 | 1.00 56.88 | C |
| ATOM | 1674 | O | MET | A | 435 | 10.554 | 4.301 | 119.570 | 1.00 56.39 | O |
| ATOM | 1675 | CB | MET | A | 435 | 12.366 | 3.442 | 121.373 | 1.00 55.92 | C |
| ATOM | 1676 | CG | MET | A | 435 | 12.470 | 2.458 | 122.522 | 1.00 59.55 | C |
| ATOM | 1677 | SD | MET | A | 435 | 14.119 | 2.586 | 123.228 | 1.00 63.29 | S |
| ATOM | 1678 | CE | MET | A | 435 | 14.246 | 4.315 | 123.662 | 1.00 64.76 | C |
| ATOM | 1679 | N | MET | A | 436 | 12.091 | 4.091 | 117.939 | 1.00 60.46 | N |
| ATOM | 1680 | CA | MET | A | 436 | 11.484 | 5.050 | 117.048 | 1.00 63.65 | C |
| ATOM | 1681 | C | MET | A | 436 | 10.258 | 4.473 | 116.338 | 1.00 65.74 | C |
| ATOM | 1682 | O | MET | A | 436 | 10.138 | 3.292 | 116.064 | 1.00 63.98 | O |
| ATOM | 1683 | CB | MET | A | 436 | 12.441 | 5.480 | 115.918 | 1.00 63.56 | C |
| ATOM | 1684 | CG | MET | A | 436 | 13.417 | 6.556 | 116.356 | 1.00 62.30 | C |
| ATOM | 1685 | SD | MET | A | 436 | 12.599 | 8.137 | 116.492 | 1.00 62.81 | S |
| ATOM | 1686 | CE | MET | A | 436 | 12.320 | 8.367 | 118.222 | 1.00 62.26 | C |
| ATOM | 1687 | N | LYS | A | 437 | 9.366 | 5.393 | 116.010 | 1.00 70.64 | N |
| ATOM | 1688 | CA | LYS | A | 437 | 8.168 | 5.047 | 115.255 | 1.00 74.22 | C |
| ATOM | 1689 | C | LYS | A | 437 | 8.610 | 4.777 | 113.816 | 1.00 76.40 | C |
| ATOM | 1690 | O | LYS | A | 437 | 9.146 | 5.685 | 113.163 | 1.00 77.93 | O |
| ATOM | 1691 | CB | LYS | A | 437 | 7.184 | 6.204 | 115.280 | 1.00 74.58 | C |
| ATOM | 1692 | N | CYS | A | 438 | 8.366 | 3.598 | 113.295 | 1.00 77.32 | N |
| ATOM | 1693 | CA | CYS | A | 438 | 8.659 | 3.170 | 111.941 | 1.00 78.48 | C |
| ATOM | 1694 | C | CYS | A | 438 | 8.376 | 4.175 | 110.843 | 1.00 78.19 | C |
| ATOM | 1695 | O | CYS | A | 438 | 9.153 | 4.204 | 109.883 | 1.00 80.00 | O |
| ATOM | 1696 | CB | CYS | A | 438 | 7.865 | 1.874 | 111.692 | 1.00 81.14 | C |
| ATOM | 1697 | SG | CYS | A | 438 | 7.636 | 1.328 | 109.995 | 1.00 83.53 | S |
| ATOM | 1698 | N | LYS | A | 439 | 7.337 | 4.990 | 110.914 | 1.00 77.79 | N |
| ATOM | 1699 | CA | LYS | A | 439 | 6.985 | 5.983 | 109.922 | 1.00 75.66 | C |
| ATOM | 1700 | C | LYS | A | 439 | 7.957 | 7.145 | 109.845 | 1.00 73.95 | C |
| ATOM | 1701 | O | LYS | A | 439 | 8.205 | 7.690 | 108.759 | 1.00 74.95 | O |
| ATOM | 1702 | CB | LYS | A | 439 | 5.574 | 6.496 | 110.228 | 1.00 75.71 | C |
| ATOM | 1703 | N | ASN | A | 440 | 8.567 | 7.527 | 110.966 | 1.00 73.03 | N |
| ATOM | 1704 | CA | ASN | A | 440 | 9.504 | 8.652 | 110.981 | 1.00 72.76 | C |
| ATOM | 1705 | C | ASN | A | 440 | 10.949 | 8.211 | 110.832 | 1.00 70.05 | C |
| ATOM | 1706 | O | ASN | A | 440 | 11.902 | 8.920 | 111.163 | 1.00 69.49 | O |
| ATOM | 1707 | CB | ASN | A | 440 | 9.372 | 9.426 | 112.299 | 1.00 71.42 | C |
| ATOM | 1708 | CG | ASN | A | 440 | 7.970 | 10.015 | 112.368 | 1.00 72.63 | C |
| ATOM | 1709 | OD1 | ASN | A | 440 | 7.404 | 10.516 | 111.402 | 1.00 74.92 | O |
| ATOM | 1710 | ND2 | ASN | A | 440 | 7.430 | 9.926 | 113.569 | 1.00 73.51 | N |
| ATOM | 1711 | N | VAL | A | 441 | 11.122 | 7.029 | 110.242 | 1.00 66.49 | N |
| ATOM | 1712 | CA | VAL | A | 441 | 12.486 | 6.529 | 110.080 | 1.00 65.97 | C |
| ATOM | 1713 | C | VAL | A | 441 | 12.676 | 5.616 | 108.889 | 1.00 63.61 | C |
| ATOM | 1714 | O | VAL | A | 441 | 11.783 | 4.945 | 108.384 | 1.00 63.92 | O |
| ATOM | 1715 | CB | VAL | A | 441 | 12.802 | 5.815 | 111.419 | 1.00 65.51 | C |

| ATOM | 1562 | CB | HIS A 421 | 33.683 | 6.815 | 125.180 | 1.00 | 22.54 | C |
|------|------|------|-----------|--------|-------|---------|------|-------|---|
| ATOM | 1563 | CG | HIS A 421 | 33.935 | 6.952 | 126.649 | 1.00 | 30.57 | C |
| ATOM | 1564 | ND1 | HIS A 421 | 35.167 | 6.832 | 127.267 | 1.00 | 30.30 | N |
| ATOM | 1565 | CD2 | HIS A 421 | 33.052 | 7.186 | 127.667 | 1.00 | 32.44 | C |
| ATOM | 1566 | CE1 | HIS A 421 | 35.065 | 6.999 | 128.538 | 1.00 | 29.87 | C |
| ATOM | 1567 | NE2 | HIS A 421 | 33.798 | 7.209 | 128.820 | 1.00 | 33.72 | N |
| ATOM | 1568 | N | VAL A 422 | 32.892 | 5.140 | 122.463 | 1.00 | 22.32 | N |
| ATOM | 1569 | CA | VAL A 422 | 32.343 | 5.055 | 121.100 | 1.00 | 21.57 | C |
| ATOM | 1570 | C | VAL A 422 | 31.391 | 3.855 | 121.118 | 1.00 | 20.37 | C |
| ATOM | 1571 | O | VAL A 422 | 30.288 | 3.960 | 120.605 | 1.00 | 17.16 | O |
| ATOM | 1572 | CB | VAL A 422 | 33.378 | 4.853 | 119.964 | 1.00 | 21.33 | C |
| ATOM | 1573 | CG1 | VAL A 422 | 32.684 | 4.946 | 118.579 | 1.00 | 19.59 | C |
| ATOM | 1574 | CG2 | VAL A 422 | 34.525 | 5.868 | 120.016 | 1.00 | 16.45 | C |
| ATOM | 1575 | N | ARG A 423 | 31.771 | 2.755 | 121.791 | 1.00 | 21.34 | N |
| ATOM | 1576 | CA | ARG A 423 | 30.822 | 1.637 | 121.905 | 1.00 | 23.52 | C |
| ATOM | 1577 | C | ARG A 423 | 29.554 | 2.081 | 122.672 | 1.00 | 20.44 | C |
| ATOM | 1578 | O | ARG A 423 | 28.442 | 1.709 | 122.295 | 1.00 | 20.22 | O |
| ATOM | 1579 | CB | ARG A 423 | 31.403 | 0.405 | 122.612 | 1.00 | 23.79 | C |
| ATOM | 1580 | CG | ARG A 423 | 30.380 | -0.726 | 122.691 | 1.00 | 29.07 | C |
| ATOM | 1581 | CD | ARG A 423 | 30.324 | -1.586 | 121.434 | 1.00 | 31.23 | C |
| ATOM | 1582 | NE | ARG A 423 | 31.654 | -2.076 | 121.013 | 1.00 | 35.04 | N |
| ATOM | 1583 | CZ | ARG A 423 | 32.048 | -3.338 | 121.200 | 1.00 | 36.61 | C |
| ATOM | 1584 | NH1 | ARG A 423 | 31.230 | -4.187 | 121.804 | 1.00 | 35.25 | N |
| ATOM | 1585 | NH2 | ARG A 423 | 33.219 | -3.849 | 120.855 | 1.00 | 36.07 | N |
| ATOM | 1586 | N | HIS A 424 | 29.674 | 2.847 | 123.735 | 1.00 | 23.24 | N |
| ATOM | 1587 | CA | HIS A 424 | 28.552 | 3.340 | 124.546 | 1.00 | 24.81 | C |
| ATOM | 1588 | C | HIS A 424 | 27.637 | 4.225 | 123.683 | 1.00 | 25.21 | C |
| ATOM | 1589 | O | HIS A 424 | 26.437 | 3.945 | 123.601 | 1.00 | 23.78 | O |
| ATOM | 1590 | CB | HIS A 424 | 29.065 | 4.140 | 125.742 | 1.00 | 27.75 | C |
| ATOM | 1591 | CG | HIS A 424 | 28.121 | 4.266 | 126.882 | 1.00 | 34.47 | C |
| ATOM | 1592 | ND1 | HIS A 424 | 27.451 | 5.406 | 127.187 | 1.00 | 40.70 | N |
| ATOM | 1593 | CD2 | HIS A 424 | 27.678 | 3.431 | 127.831 | 1.00 | 38.87 | C |
| ATOM | 1594 | CE1 | HIS A 424 | 26.639 | 5.307 | 128.220 | 1.00 | 38.43 | C |
| ATOM | 1595 | NE2 | HIS A 424 | 26.767 | 4.087 | 128.652 | 1.00 | 38.19 | N |
| ATOM | 1596 | N | ALA A 425 | 28.197 | 5.224 | 122.961 | 1.00 | 21.82 | N |
| ATOM | 1597 | CA | ALA A 425 | 27.343 | 6.048 | 122.110 | 1.00 | 21.38 | C |
| ATOM | 1598 | C | ALA A 425 | 26.581 | 5.216 | 121.059 | 1.00 | 22.96 | C |
| ATOM | 1599 | O | ALA A 425 | 25.408 | 5.459 | 120.752 | 1.00 | 19.38 | O |
| ATOM | 1600 | CB | ALA A 425 | 28.157 | 7.143 | 121.435 | 1.00 | 20.28 | C |
| ATOM | 1601 | N | SER A 426 | 27.249 | 4.204 | 120.496 | 1.00 | 20.57 | N |
| ATOM | 1602 | CA | SER A 426 | 26.604 | 3.342 | 119.509 | 1.00 | 22.35 | C |
| ATOM | 1603 | C | SER A 426 | 25.439 | 2.543 | 120.096 | 1.00 | 24.19 | C |
| ATOM | 1604 | O | SER A 426 | 24.398 | 2.374 | 119.470 | 1.00 | 23.60 | O |
| ATOM | 1605 | CB | SER A 426 | 27.696 | 2.374 | 119.026 | 1.00 | 21.92 | C |
| ATOM | 1606 | OG | SER A 426 | 27.046 | 1.466 | 118.165 | 1.00 | 28.09 | O |
| ATOM | 1607 | N | ASN A 427 | 25.538 | 1.991 | 121.303 | 1.00 | 24.52 | N |
| ATOM | 1608 | CA | ASN A 427 | 24.466 | 1.271 | 121.977 | 1.00 | 25.04 | C |
| ATOM | 1609 | C | ASN A 427 | 23.347 | 2.256 | 122.335 | 1.00 | 25.68 | C |
| ATOM | 1610 | O | ASN A 427 | 22.189 | 1.885 | 122.193 | 1.00 | 27.61 | O |
| ATOM | 1611 | CB | ASN A 427 | 24.907 | 0.674 | 123.319 | 1.00 | 25.26 | C |
| ATOM | 1612 | CG | ASN A 427 | 25.978 | -0.386 | 123.167 | 1.00 | 28.45 | C |
| ATOM | 1613 | OD1 | ASN A 427 | 25.888 | -1.225 | 122.279 | 1.00 | 31.54 | O |
| ATOM | 1614 | ND2 | ASN A 427 | 26.986 | -0.373 | 124.010 | 1.00 | 29.07 | N |
| ATOM | 1615 | N | LYS A 428 | 23.639 | 3.467 | 122.775 | 1.00 | 24.44 | N |
| ATOM | 1616 | CA | LYS A 428 | 22.566 | 4.416 | 123.060 | 1.00 | 29.01 | C |
| ATOM | 1617 | C | LYS A 428 | 21.908 | 4.795 | 121.708 | 1.00 | 30.35 | C |
| ATOM | 1618 | O | LYS A 428 | 20.692 | 4.937 | 121.661 | 1.00 | 26.46 | O |
| ATOM | 1619 | CB | LYS A 428 | 22.958 | 5.684 | 123.777 | 1.00 | 31.63 | C |
| ATOM | 1620 | CG | LYS A 428 | 23.512 | 5.678 | 125.169 | 1.00 | 38.01 | C |
| ATOM | 1621 | CD | LYS A 428 | 22.776 | 4.806 | 126.158 | 1.00 | 42.22 | C |
| ATOM | 1622 | CE | LYS A 428 | 21.562 | 5.439 | 126.800 | 1.00 | 45.57 | C |
| ATOM | 1623 | NZ | LYS A 428 | 20.524 | 4.399 | 127.155 | 1.00 | 48.65 | N |
| ATOM | 1624 | N | GLY A 429 | 22.687 | 4.975 | 120.622 | 1.00 | 30.11 | N |
| ATOM | 1625 | CA | GLY A 429 | 22.051 | 5.316 | 119.346 | 1.00 | 30.05 | C |
| ATOM | 1626 | C | GLY A 429 | 21.166 | 4.151 | 118.890 | 1.00 | 31.61 | C |
| ATOM | 1627 | O | GLY A 429 | 20.054 | 4.406 | 118.451 | 1.00 | 30.01 | O |
| ATOM | 1628 | N | MET A 430 | 21.638 | 2.908 | 118.953 | 1.00 | 30.52 | N |
| ATOM | 1629 | CA | MET A 430 | 20.849 | 1.761 | 118.536 | 1.00 | 34.37 | C |
| ATOM | 1630 | C | MET A 430 | 19.531 | 1.591 | 119.311 | 1.00 | 34.13 | C |
| ATOM | 1631 | O | MET A 430 | 18.495 | 1.267 | 118.725 | 1.00 | 32.82 | O |
| ATOM | 1632 | CB | MET A 430 | 21.600 | 0.429 | 118.730 | 1.00 | 34.16 | C |
| ATOM | 1633 | CG | MET A 430 | 22.857 | 0.437 | 117.856 | 1.00 | 39.05 | C |
| ATOM | 1634 | SD | MET A 430 | 22.427 | -0.027 | 116.173 | 1.00 | 39.73 | S |
| ATOM | 1635 | CE | MET A 430 | 22.179 | -1.768 | 116.525 | 1.00 | 43.55 | C |
| ATOM | 1636 | N | GLU A 431 | 19.621 | 1.770 | 120.623 | 1.00 | 33.67 | N |
| ATOM | 1637 | CA | GLU A 431 | 18.475 | 1.676 | 121.508 | 1.00 | 35.10 | C |
| ATOM | 1638 | C | GLU A 431 | 17.437 | 2.733 | 121.122 | 1.00 | 33.77 | C |

```
ATOM   1485  CG  ARG A 411      48.714   8.495 122.192  1.00 27.89           C
ATOM   1486  CD  ARG A 411      49.483   9.497 121.345  1.00 26.01           C
ATOM   1487  NE  ARG A 411      48.543  10.145 120.411  1.00 26.96           N
ATOM   1488  CZ  ARG A 411      47.797  11.206 120.641  1.00 26.88           C
ATOM   1489  NH1 ARG A 411      47.778  11.880 121.786  1.00 23.51           N
ATOM   1490  NH2 ARG A 411      47.003  11.649 119.658  1.00 27.05           N
ATOM   1491  N   LEU A 412      48.559   5.016 123.888  1.00 22.69           N
ATOM   1492  CA  LEU A 412      47.867   3.810 123.447  1.00 23.35           C
ATOM   1493  C   LEU A 412      46.673   3.564 124.362  1.00 23.86           C
ATOM   1494  O   LEU A 412      45.532   3.469 123.925  1.00 24.06           O
ATOM   1495  CB  LEU A 412      48.819   2.605 123.445  1.00 21.40           C
ATOM   1496  CG  LEU A 412      48.182   1.263 123.068  1.00 22.94           C
ATOM   1497  CD1 LEU A 412      47.534   1.280 121.659  1.00 23.73           C
ATOM   1498  CD2 LEU A 412      49.225   0.166 123.081  1.00 19.68           C
ATOM   1499  N   ALA A 413      46.912   3.586 125.701  1.00 23.79           N
ATOM   1500  CA  ALA A 413      45.802   3.373 126.602  1.00 23.75           C
ATOM   1501  C   ALA A 413      44.766   4.505 126.533  1.00 23.55           C
ATOM   1502  O   ALA A 413      43.571   4.198 126.705  1.00 21.16           O
ATOM   1503  CB  ALA A 413      46.312   3.199 128.044  1.00 20.52           C
ATOM   1504  N   ASN A 414      45.116   5.775 126.362  1.00 23.66           N
ATOM   1505  CA  ASN A 414      44.136   6.853 126.302  1.00 27.21           C
ATOM   1506  C   ASN A 414      43.197   6.702 125.075  1.00 28.28           C
ATOM   1507  O   ASN A 414      41.996   6.962 125.193  1.00 29.75           O
ATOM   1508  CB  ASN A 414      44.798   8.221 126.253  1.00 29.46           C
ATOM   1509  CG  ASN A 414      45.513   8.688 127.490  1.00 36.32           C
ATOM   1510  OD1 ASN A 414      45.114   8.388 128.612  1.00 33.87           O
ATOM   1511  ND2 ASN A 414      46.603   9.465 127.291  1.00 39.24           N
ATOM   1512  N   LEU A 415      43.681   6.301 123.917  1.00 24.77           N
ATOM   1513  CA  LEU A 415      42.924   6.115 122.702  1.00 23.88           C
ATOM   1514  C   LEU A 415      42.000   4.915 122.830  1.00 22.80           C
ATOM   1515  O   LEU A 415      40.836   4.945 122.469  1.00 22.38           O
ATOM   1516  CB  LEU A 415      43.785   5.878 121.427  1.00 19.85           C
ATOM   1517  CG  LEU A 415      44.652   7.056 121.008  1.00 23.87           C
ATOM   1518  CD1 LEU A 415      45.736   6.788 119.959  1.00 24.70           C
ATOM   1519  CD2 LEU A 415      43.752   8.142 120.456  1.00 24.15           C
ATOM   1520  N   LEU A 416      42.562   3.808 123.301  1.00 22.94           N
ATOM   1521  CA  LEU A 416      41.837   2.562 123.435  1.00 22.49           C
ATOM   1522  C   LEU A 416      40.735   2.662 124.478  1.00 25.36           C
ATOM   1523  O   LEU A 416      39.630   2.152 124.176  1.00 20.70           O
ATOM   1524  CB  LEU A 416      42.828   1.434 123.702  1.00 26.48           C
ATOM   1525  CG  LEU A 416      43.203   0.587 122.479  1.00 30.93           C
ATOM   1526  CD1 LEU A 416      43.417   1.401 121.215  1.00 28.43           C
ATOM   1527  CD2 LEU A 416      44.364  -0.306 122.835  1.00 31.08           C
ATOM   1528  N   MET A 417      40.951   3.407 125.560  1.00 19.75           N
ATOM   1529  CA  MET A 417      39.932   3.646 126.574  1.00 23.76           C
ATOM   1530  C   MET A 417      38.756   4.377 125.959  1.00 23.62           C
ATOM   1531  O   MET A 417      37.569   4.143 126.283  1.00 25.06           O
ATOM   1532  CB  MET A 417      40.494   4.344 127.822  1.00 23.12           C
ATOM   1533  CG  MET A 417      41.059   3.276 128.807  1.00 30.43           C
ATOM   1534  SD  MET A 417      41.415   4.115 130.388  1.00 33.35           S
ATOM   1535  CE  MET A 417      43.077   4.709 130.009  1.00 33.01           C
ATOM   1536  N   LEU A 418      39.039   5.275 125.022  1.00 23.88           N
ATOM   1537  CA  LEU A 418      37.987   5.989 124.309  1.00 26.46           C
ATOM   1538  C   LEU A 418      37.141   5.024 123.485  1.00 26.92           C
ATOM   1539  O   LEU A 418      35.970   5.372 123.281  1.00 25.33           O
ATOM   1540  CB  LEU A 418      38.544   7.106 123.424  1.00 28.72           C
ATOM   1541  CG  LEU A 418      38.885   8.419 124.127  1.00 26.98           C
ATOM   1542  CD1 LEU A 418      39.472   9.436 123.156  1.00 30.27           C
ATOM   1543  CD2 LEU A 418      37.654   8.989 124.799  1.00 27.09           C
ATOM   1544  N   LEU A 419      37.605   3.840 123.051  1.00 25.98           N
ATOM   1545  CA  LEU A 419      36.762   2.920 122.316  1.00 25.67           C
ATOM   1546  C   LEU A 419      35.492   2.506 123.081  1.00 25.78           C
ATOM   1547  O   LEU A 419      34.409   2.345 122.437  1.00 21.03           O
ATOM   1548  CB  LEU A 419      37.465   1.634 121.880  1.00 28.32           C
ATOM   1549  CG  LEU A 419      38.698   1.736 120.992  1.00 34.00           C
ATOM   1550  CD1 LEU A 419      39.262   0.354 120.646  1.00 32.78           C
ATOM   1551  CD2 LEU A 419      38.460   2.443 119.670  1.00 34.96           C
ATOM   1552  N   SER A 420      35.611   2.378 124.420  1.00 21.58           N
ATOM   1553  CA  SER A 420      34.455   2.080 125.270  1.00 22.33           C
ATOM   1554  C   SER A 420      33.382   3.154 125.129  1.00 19.02           C
ATOM   1555  O   SER A 420      32.205   2.796 125.136  1.00 18.69           O
ATOM   1556  CB  SER A 420      34.733   2.085 126.821  1.00 21.14           C
ATOM   1557  OG  SER A 420      35.543   0.908 127.014  1.00 29.67           O
ATOM   1558  N   HIS A 421      33.837   4.400 125.034  1.00 18.79           N
ATOM   1559  CA  HIS A 421      32.922   5.537 124.876  1.00 24.11           C
ATOM   1560  C   HIS A 421      32.200   5.540 123.520  1.00 23.48           C
ATOM   1561  O   HIS A 421      30.999   5.863 123.470  1.00 20.51           O
```

```
ATOM  1408  O    SER A 401      56.747  12.568 118.713  1.00 48.03           O
ATOM  1409  CB   SER A 401      54.359  10.731 118.365  1.00 48.45           C
ATOM  1410  OG   SER A 401      54.827  10.434 119.670  1.00 49.27           O
ATOM  1411  N    GLY A 402      57.794  10.607 118.547  1.00 48.95           N
ATOM  1412  CA   GLY A 402      58.947  11.059 119.278  1.00 48.71           C
ATOM  1413  C    GLY A 402      58.924  10.911 120.780  1.00 49.06           C
ATOM  1414  O    GLY A 402      59.989  10.838 121.401  1.00 51.10           O
ATOM  1415  N    ILE A 403      57.752  10.835 121.376  1.00 46.33           N
ATOM  1416  CA   ILE A 403      57.566  10.728 122.813  1.00 42.91           C
ATOM  1417  C    ILE A 403      58.165   9.498 123.465  1.00 42.79           C
ATOM  1418  O    ILE A 403      58.521   8.445 122.949  1.00 38.67           O
ATOM  1419  CB   ILE A 403      56.062  10.920 123.113  1.00 41.27           C
ATOM  1420  CG1  ILE A 403      55.262   9.682 122.654  1.00 37.05           C
ATOM  1421  CG2  ILE A 403      55.603  12.210 122.421  1.00 38.00           C
ATOM  1422  CD1  ILE A 403      53.789   9.806 122.915  1.00 34.18           C
ATOM  1423  N    SER A 404      58.391   9.677 124.775  1.00 45.15           N
ATOM  1424  CA   SER A 404      59.003   8.653 125.610  1.00 45.00           C
ATOM  1425  C    SER A 404      58.151   7.403 125.622  1.00 44.70           C
ATOM  1426  O    SER A 404      56.953   7.456 125.301  1.00 44.93           O
ATOM  1427  CB   SER A 404      59.107   9.193 127.039  1.00 47.51           C
ATOM  1428  OG   SER A 404      57.817   9.223 127.655  1.00 52.08           O
ATOM  1429  N    SER A 405      58.771   6.311 126.031  1.00 43.19           N
ATOM  1430  CA   SER A 405      58.122   5.037 126.158  1.00 45.23           C
ATOM  1431  C    SER A 405      56.899   5.059 127.072  1.00 43.21           C
ATOM  1432  O    SER A 405      55.867   4.471 126.723  1.00 42.92           O
ATOM  1433  CB   SER A 405      59.067   3.983 126.765  1.00 46.88           C
ATOM  1434  OG   SER A 405      59.899   3.536 125.710  1.00 51.89           O
ATOM  1435  N    GLN A 406      57.011   5.727 128.204  1.00 40.47           N
ATOM  1436  CA   GLN A 406      55.886   5.781 129.129  1.00 41.98           C
ATOM  1437  C    GLN A 406      54.769   6.626 128.523  1.00 39.50           C
ATOM  1438  O    GLN A 406      53.596   6.276 128.743  1.00 37.37           O
ATOM  1439  CB   GLN A 406      56.307   6.195 130.520  1.00 45.16           C
ATOM  1440  CG   GLN A 406      55.668   7.446 131.086  1.00 51.44           C
ATOM  1441  CD   GLN A 406      54.476   7.143 131.953  1.00 55.45           C
ATOM  1442  OE1  GLN A 406      53.406   7.735 131.837  1.00 57.55           O
ATOM  1443  NE2  GLN A 406      54.697   6.193 132.860  1.00 59.95           N
ATOM  1444  N    GLN A 407      55.137   7.682 127.796  1.00 35.09           N
ATOM  1445  CA   GLN A 407      54.097   8.468 127.161  1.00 36.31           C
ATOM  1446  C    GLN A 407      53.469   7.654 126.024  1.00 34.75           C
ATOM  1447  O    GLN A 407      52.276   7.809 125.816  1.00 33.22           O
ATOM  1448  CB   GLN A 407      54.622   9.821 126.696  1.00 41.08           C
ATOM  1449  CG  AGLN A 407      54.952  10.735 127.864  0.50 40.59           C
ATOM  1450  CG  BGLN A 407      54.694  10.852 127.806  0.50 42.83           C
ATOM  1451  CD  AGLN A 407      53.702  11.307 128.504  0.50 42.07           C
ATOM  1452  CD  BGLN A 407      55.094  12.239 127.368  0.50 45.93           C
ATOM  1453  OE1 AGLN A 407      53.220  10.852 129.541  0.50 42.57           O
ATOM  1454  OE1 BGLN A 407      55.627  13.045 128.148  0.50 47.67           O
ATOM  1455  NE2 AGLN A 407      53.179  12.338 127.848  0.50 43.99           N
ATOM  1456  NE2 BGLN A 407      54.843  12.587 126.112  0.50 47.18           N
ATOM  1457  N    GLN A 408      54.200   6.798 125.324  1.00 31.34           N
ATOM  1458  CA   GLN A 408      53.628   5.987 124.280  1.00 31.26           C
ATOM  1459  C    GLN A 408      52.567   5.023 124.848  1.00 33.08           C
ATOM  1460  O    GLN A 408      51.450   4.942 124.303  1.00 27.12           O
ATOM  1461  CB   GLN A 408      54.733   5.176 123.578  1.00 30.57           C
ATOM  1462  CG   GLN A 408      55.599   6.140 122.780  1.00 32.80           C
ATOM  1463  CD   GLN A 408      56.811   5.512 122.166  1.00 34.55           C
ATOM  1464  OE1  GLN A 408      56.707   4.451 121.561  1.00 35.64           O
ATOM  1465  NE2  GLN A 408      57.985   6.131 122.323  1.00 34.81           N
ATOM  1466  N    SER A 409      52.926   4.306 125.930  1.00 31.51           N
ATOM  1467  CA   SER A 409      52.008   3.379 126.581  1.00 31.67           C
ATOM  1468  C    SER A 409      50.744   4.145 126.990  1.00 29.61           C
ATOM  1469  O    SER A 409      49.630   3.706 126.730  1.00 27.78           O
ATOM  1470  CB   SER A 409      52.659   2.737 127.830  1.00 35.14           C
ATOM  1471  OG   SER A 409      53.682   1.827 127.408  1.00 36.12           O
ATOM  1472  N    MET A 410      50.950   5.323 127.562  1.00 27.50           N
ATOM  1473  CA   MET A 410      49.840   6.166 127.941  1.00 32.03           C
ATOM  1474  C    MET A 410      48.977   6.583 126.743  1.00 30.10           C
ATOM  1475  O    MET A 410      47.748   6.545 126.880  1.00 29.01           O
ATOM  1476  CB   MET A 410      50.318   7.442 128.628  1.00 35.77           C
ATOM  1477  CG   MET A 410      49.265   8.143 129.459  1.00 41.11           C
ATOM  1478  SD   MET A 410      48.697   7.167 130.890  1.00 48.71           S
ATOM  1479  CE   MET A 410      50.244   6.619 131.597  1.00 41.81           C
ATOM  1480  N    ARG A 411      49.558   6.971 125.605  1.00 28.45           N
ATOM  1481  CA   ARG A 411      48.700   7.391 124.489  1.00 26.51           C
ATOM  1482  C    ARG A 411      47.932   6.189 123.967  1.00 25.73           C
ATOM  1483  O    ARG A 411      46.730   6.319 123.702  1.00 27.65           O
ATOM  1484  CB   ARG A 411      49.494   8.140 123.447  1.00 28.36           C
```

| | | | | | | | | | |
|---|---|---|---|---|---|---|---|---|---|
|ATOM|1331|CB|THR|A|391|47.137|-3.694|117.901|1.00 25.21|C|
|ATOM|1332|OG1|THR|A|391|45.754|-3.917|118.189|1.00 24.77|O|
|ATOM|1333|CG2|THR|A|391|47.844|-3.315|119.191|1.00 21.16|C|
|ATOM|1334|N|ASP|A|392|49.521|-3.270|115.978|1.00 26.23|N|
|ATOM|1335|CA|ASP|A|392|50.944|-2.968|115.752|1.00 30.36|C|
|ATOM|1336|C|ASP|A|392|51.148|-1.663|114.974|1.00 27.65|C|
|ATOM|1337|O|ASP|A|392|52.076|-0.931|115.281|1.00 27.69|O|
|ATOM|1338|CB|ASP|A|392|51.651|-4.048|114.890|1.00 34.98|C|
|ATOM|1339|CG|ASP|A|392|52.190|-5.135|115.796|1.00 40.59|C|
|ATOM|1340|OD1|ASP|A|392|52.512|-4.913|116.972|1.00 39.69|O|
|ATOM|1341|OD2|ASP|A|392|52.290|-6.289|115.351|1.00 46.09|O|
|ATOM|1342|N|ALA|A|393|50.307|-1.410|113.978|1.00 22.13|N|
|ATOM|1343|CA|ALA|A|393|50.348|-0.204|113.203|1.00 21.31|C|
|ATOM|1344|C|ALA|A|393|50.071|1.014|114.053|1.00 22.80|C|
|ATOM|1345|O|ALA|A|393|50.849|2.000|113.929|1.00 22.92|O|
|ATOM|1346|CB|ALA|A|393|49.397|-0.295|112.010|1.00 22.34|C|
|ATOM|1347|N|LEU|A|394|49.057|0.928|114.939|1.00 21.60|N|
|ATOM|1348|CA|LEU|A|394|48.802|2.079|115.823|1.00 21.27|C|
|ATOM|1349|C|LEU|A|394|50.020|2.334|116.717|1.00 23.05|C|
|ATOM|1350|O|LEU|A|394|50.414|3.498|116.897|1.00 21.37|O|
|ATOM|1351|CB|LEU|A|394|47.525|1.947|116.652|1.00 21.49|C|
|ATOM|1352|CG|LEU|A|394|47.210|3.076|117.652|1.00 21.20|C|
|ATOM|1353|CD1|LEU|A|394|47.010|4.417|116.942|1.00 16.54|C|
|ATOM|1354|CD2|LEU|A|394|45.932|2.759|118.440|1.00 19.78|C|
|ATOM|1355|N|VAL|A|395|50.698|1.290|117.167|1.00 23.07|N|
|ATOM|1356|CA|VAL|A|395|51.866|1.389|118.037|1.00 25.96|C|
|ATOM|1357|C|VAL|A|395|53.019|2.028|117.289|1.00 28.48|C|
|ATOM|1358|O|VAL|A|395|53.573|3.036|117.764|1.00 28.22|O|
|ATOM|1359|CB|VAL|A|395|52.228|0.024|118.663|1.00 26.03|C|
|ATOM|1360|CG1|VAL|A|395|53.565|-0.019|119.396|1.00 23.72|C|
|ATOM|1361|CG2|VAL|A|395|51.091|-0.409|119.588|1.00 22.05|C|
|ATOM|1362|N|TRP|A|396|53.236|1.574|116.068|1.00 29.78|N|
|ATOM|1363|CA|TRP|A|396|54.252|2.165|115.178|1.00 31.05|C|
|ATOM|1364|C|TRP|A|396|53.944|3.639|115.004|1.00 29.57|C|
|ATOM|1365|O|TRP|A|396|54.820|4.471|115.203|1.00 31.34|O|
|ATOM|1366|CB|TRP|A|396|54.208|1.466|113.804|1.00 35.99|C|
|ATOM|1367|CG|TRP|A|396|55.024|2.196|112.770|1.00 42.60|C|
|ATOM|1368|CD1|TRP|A|396|56.391|2.196|112.669|1.00 44.35|C|
|ATOM|1369|CD2|TRP|A|396|54.545|3.019|111.699|1.00 44.72|C|
|ATOM|1370|NE1|TRP|A|396|56.786|2.962|111.611|1.00 46.09|N|
|ATOM|1371|CE2|TRP|A|396|55.678|3.481|110.998|1.00 46.66|C|
|ATOM|1372|CE3|TRP|A|396|53.277|3.400|111.258|1.00 45.16|C|
|ATOM|1373|CZ2|TRP|A|396|55.575|4.309|109.881|1.00 47.31|C|
|ATOM|1374|CZ3|TRP|A|396|53.162|4.227|110.156|1.00 46.74|C|
|ATOM|1375|CH2|TRP|A|396|54.309|4.673|109.484|1.00 48.51|C|
|ATOM|1376|N|VAL|A|397|52.686|3.962|114.707|1.00 25.11|N|
|ATOM|1377|CA|VAL|A|397|52.299|5.354|114.555|1.00 30.60|C|
|ATOM|1378|C|VAL|A|397|52.630|6.170|115.804|1.00 30.37|C|
|ATOM|1379|O|VAL|A|397|53.171|7.290|115.710|1.00 30.89|O|
|ATOM|1380|CB|VAL|A|397|50.794|5.538|114.198|1.00 28.59|C|
|ATOM|1381|CG1|VAL|A|397|50.405|6.993|114.338|1.00 28.33|C|
|ATOM|1382|CG2|VAL|A|397|50.491|5.022|112.801|1.00 27.77|C|
|ATOM|1383|N|ILE|A|398|52.245|5.651|116.973|1.00 29.06|N|
|ATOM|1384|CA|ILE|A|398|52.546|6.424|118.189|1.00 27.97|C|
|ATOM|1385|C|ILE|A|398|54.040|6.577|118.379|1.00 28.45|C|
|ATOM|1386|O|ILE|A|398|54.459|7.640|118.813|1.00 25.87|O|
|ATOM|1387|CB|ILE|A|398|51.823|5.755|119.378|1.00 27.47|C|
|ATOM|1388|CG1|ILE|A|398|50.329|6.025|119.174|1.00 25.77|C|
|ATOM|1389|CG2|ILE|A|398|52.389|6.235|120.727|1.00 25.68|C|
|ATOM|1390|CD1|ILE|A|398|49.386|5.297|120.106|1.00 28.72|C|
|ATOM|1391|N|ALA|A|399|54.872|5.582|118.106|1.00 31.02|N|
|ATOM|1392|CA|ALA|A|399|56.325|5.714|118.288|1.00 37.21|C|
|ATOM|1393|C|ALA|A|399|56.934|6.824|117.439|1.00 41.85|C|
|ATOM|1394|O|ALA|A|399|57.683|7.679|117.973|1.00 42.40|O|
|ATOM|1395|CB|ALA|A|399|57.000|4.372|118.012|1.00 35.15|C|
|ATOM|1396|N|LYS|A|400|56.539|6.998|116.170|1.00 43.46|N|
|ATOM|1397|CA|LYS|A|400|57.018|8.068|115.317|1.00 47.35|C|
|ATOM|1398|C|LYS|A|400|56.754|9.460|115.877|1.00 47.44|C|
|ATOM|1399|O|LYS|A|400|57.379|10.445|115.470|1.00 46.88|O|
|ATOM|1400|CB|LYS|A|400|56.359|8.047|113.927|1.00 52.53|C|
|ATOM|1401|CG|LYS|A|400|56.955|7.129|112.891|1.00 58.31|C|
|ATOM|1402|CD|LYS|A|400|56.220|7.282|111.556|1.00 63.21|C|
|ATOM|1403|CE|LYS|A|400|57.194|7.059|110.395|1.00 65.66|C|
|ATOM|1404|NZ|LYS|A|400|56.543|7.124|109.041|1.00 67.45|N|
|ATOM|1405|N|SER|A|401|55.856|9.614|116.837|1.00 46.30|N|
|ATOM|1406|CA|SER|A|401|55.594|10.882|117.459|1.00 47.95|C|
|ATOM|1407|C|SER|A|401|56.770|11.414|118.267|1.00 48.19|C|

| ATOM | 1254 | CD | ARG A 381 | 45.160 | -20.751 | 113.851 | 1.00 | 89.16 | C |
|------|------|------|------------|--------|---------|---------|------|-------|---|
| ATOM | 1255 | NE | ARG A 381 | 46.529 | -20.292 | 113.652 | 1.00 | 92.45 | N |
| ATOM | 1256 | CZ | ARG A 381 | 47.175 | -20.217 | 112.494 | 1.00 | 94.33 | C |
| ATOM | 1257 | NH1 | ARG A 381 | 46.573 | -20.572 | 111.364 | 1.00 | 95.30 | N |
| ATOM | 1258 | NH2 | ARG A 381 | 48.427 | -19.768 | 112.434 | 1.00 | 95.23 | N |
| ATOM | 1259 | N | LYS A 382 | 42.757 | -16.104 | 112.260 | 1.00 | 66.05 | N |
| ATOM | 1260 | CA | LYS A 382 | 42.850 | -15.022 | 111.308 | 1.00 | 60.73 | C |
| ATOM | 1261 | C | LYS A 382 | 42.408 | -13.696 | 111.911 | 1.00 | 55.46 | C |
| ATOM | 1262 | O | LYS A 382 | 43.181 | -12.744 | 111.934 | 1.00 | 54.77 | O |
| ATOM | 1263 | CB | LYS A 382 | 42.032 | -15.419 | 110.081 | 1.00 | 60.54 | C |
| ATOM | 1264 | CG | LYS A 382 | 42.791 | -16.319 | 109.121 | 1.00 | 61.32 | C |
| ATOM | 1265 | CD | LYS A 382 | 41.983 | -16.557 | 107.850 | 1.00 | 61.35 | C |
| ATOM | 1266 | CE | LYS A 382 | 42.953 | -16.818 | 106.716 | 1.00 | 63.68 | C |
| ATOM | 1267 | NZ | LYS A 382 | 42.394 | -16.413 | 105.392 | 1.00 | 66.37 | N |
| ATOM | 1268 | N | LEU A 383 | 41.229 | -13.614 | 112.496 | 1.00 | 50.50 | N |
| ATOM | 1269 | CA | LEU A 383 | 40.732 | -12.371 | 113.057 | 1.00 | 48.60 | C |
| ATOM | 1270 | C | LEU A 383 | 41.694 | -11.722 | 114.042 | 1.00 | 45.59 | C |
| ATOM | 1271 | O | LEU A 383 | 42.021 | -10.547 | 113.904 | 1.00 | 40.40 | O |
| ATOM | 1272 | CB | LEU A 383 | 39.347 | -12.543 | 113.680 | 1.00 | 46.13 | C |
| ATOM | 1273 | CG | LEU A 383 | 38.678 | -11.262 | 114.169 | 1.00 | 44.82 | C |
| ATOM | 1274 | CD1 | LEU A 383 | 38.750 | -10.109 | 113.172 | 1.00 | 42.50 | C |
| ATOM | 1275 | CD2 | LEU A 383 | 37.263 | -11.643 | 114.544 | 1.00 | 43.21 | C |
| ATOM | 1276 | N | ALA A 384 | 42.209 | -12.522 | 114.955 | 1.00 | 45.01 | N |
| ATOM | 1277 | CA | ALA A 384 | 43.154 | -12.092 | 115.980 | 1.00 | 45.94 | C |
| ATOM | 1278 | C | ALA A 384 | 44.457 | -11.624 | 115.364 | 1.00 | 43.45 | C |
| ATOM | 1279 | O | ALA A 384 | 45.033 | -10.639 | 115.779 | 1.00 | 44.52 | O |
| ATOM | 1280 | CB | ALA A 384 | 43.404 | -13.233 | 116.963 | 1.00 | 46.89 | C |
| ATOM | 1281 | N | HIS A 385 | 44.898 | -12.252 | 114.311 | 1.00 | 43.47 | N |
| ATOM | 1282 | CA | HIS A 385 | 46.085 | -11.851 | 113.596 | 1.00 | 45.68 | C |
| ATOM | 1283 | C | HIS A 385 | 45.897 | -10.447 | 113.024 | 1.00 | 42.97 | C |
| ATOM | 1284 | O | HIS A 385 | 46.759 | -9.582 | 113.160 | 1.00 | 40.42 | O |
| ATOM | 1285 | CB | HIS A 385 | 46.328 | -12.831 | 112.453 | 1.00 | 49.88 | C |
| ATOM | 1286 | CG | HIS A 385 | 47.742 | -12.752 | 111.964 | 1.00 | 54.88 | C |
| ATOM | 1287 | ND1 | HIS A 385 | 48.803 | -13.079 | 112.803 | 1.00 | 57.34 | N |
| ATOM | 1288 | CD2 | HIS A 385 | 48.273 | -12.406 | 110.770 | 1.00 | 56.59 | C |
| ATOM | 1289 | CE1 | HIS A 385 | 49.923 | -12.933 | 112.109 | 1.00 | 57.33 | C |
| ATOM | 1290 | NE2 | HIS A 385 | 49.641 | -12.526 | 110.883 | 1.00 | 56.60 | N |
| ATOM | 1291 | N | LEU A 386 | 44.771 | -10.284 | 112.331 | 1.00 | 39.35 | N |
| ATOM | 1292 | CA | LEU A 386 | 44.392 | -9.018 | 111.745 | 1.00 | 36.87 | C |
| ATOM | 1293 | C | LEU A 386 | 44.301 | -7.905 | 112.781 | 1.00 | 34.04 | C |
| ATOM | 1294 | O | LEU A 386 | 44.914 | -6.824 | 112.612 | 1.00 | 33.31 | O |
| ATOM | 1295 | CB | LEU A 386 | 43.059 | -9.180 | 111.015 | 1.00 | 36.48 | C |
| ATOM | 1296 | CG | LEU A 386 | 43.079 | -9.015 | 109.509 | 1.00 | 36.23 | C |
| ATOM | 1297 | CD1 | LEU A 386 | 41.683 | -9.208 | 108.917 | 1.00 | 34.14 | C |
| ATOM | 1298 | CD2 | LEU A 386 | 43.621 | -7.625 | 109.183 | 1.00 | 37.05 | C |
| ATOM | 1299 | N | LEU A 387 | 43.642 | -8.169 | 113.910 | 1.00 | 33.99 | N |
| ATOM | 1300 | CA | LEU A 387 | 43.575 | -7.166 | 114.982 | 1.00 | 34.17 | C |
| ATOM | 1301 | C | LEU A 387 | 44.949 | -6.845 | 115.561 | 1.00 | 34.18 | C |
| ATOM | 1302 | O | LEU A 387 | 45.260 | -5.736 | 116.044 | 1.00 | 34.14 | O |
| ATOM | 1303 | CB | LEU A 387 | 42.649 | -7.639 | 116.103 | 1.00 | 36.42 | C |
| ATOM | 1304 | CG | LEU A 387 | 41.518 | -6.716 | 116.562 | 1.00 | 36.54 | C |
| ATOM | 1305 | CD1 | LEU A 387 | 40.736 | -7.422 | 117.646 | 1.00 | 35.95 | C |
| ATOM | 1306 | CD2 | LEU A 387 | 41.885 | -5.327 | 117.006 | 1.00 | 36.89 | C |
| ATOM | 1307 | N | ASN A 388 | 45.852 | -7.822 | 115.562 | 1.00 | 32.18 | N |
| ATOM | 1308 | CA | ASN A 388 | 47.193 | -7.682 | 116.063 | 1.00 | 33.27 | C |
| ATOM | 1309 | C | ASN A 388 | 47.999 | -6.801 | 115.117 | 1.00 | 32.74 | C |
| ATOM | 1310 | O | ASN A 388 | 48.658 | -5.846 | 115.586 | 1.00 | 34.25 | O |
| ATOM | 1311 | CB | ASN A 388 | 47.887 | -9.030 | 116.232 | 1.00 | 36.40 | C |
| ATOM | 1312 | CG | ASN A 388 | 47.535 | -9.766 | 117.508 | 1.00 | 39.74 | C |
| ATOM | 1313 | OD1 | ASN A 388 | 48.037 | -10.907 | 117.589 | 1.00 | 44.59 | O |
| ATOM | 1314 | ND2 | ASN A 388 | 46.762 | -9.258 | 118.460 | 1.00 | 36.73 | N |
| ATOM | 1315 | N | ALA A 389 | 47.805 | -7.073 | 113.831 | 1.00 | 27.57 | N |
| ATOM | 1316 | CA | ALA A 389 | 48.455 | -6.254 | 112.813 | 1.00 | 27.27 | C |
| ATOM | 1317 | C | ALA A 389 | 47.990 | -4.805 | 112.848 | 1.00 | 26.10 | C |
| ATOM | 1318 | O | ALA A 389 | 48.846 | -3.933 | 112.724 | 1.00 | 23.30 | O |
| ATOM | 1319 | CB | ALA A 389 | 48.152 | -6.829 | 111.438 | 1.00 | 30.38 | C |
| ATOM | 1320 | N | VAL A 390 | 46.694 | -4.520 | 113.072 | 1.00 | 26.58 | N |
| ATOM | 1321 | CA | VAL A 390 | 46.294 | -3.100 | 113.102 | 1.00 | 26.06 | C |
| ATOM | 1322 | C | VAL A 390 | 46.789 | -2.411 | 114.363 | 1.00 | 26.35 | C |
| ATOM | 1323 | O | VAL A 390 | 47.253 | -1.256 | 114.297 | 1.00 | 20.40 | O |
| ATOM | 1324 | CB | VAL A 390 | 44.786 | -2.904 | 112.910 | 1.00 | 27.42 | C |
| ATOM | 1325 | CG1 | VAL A 390 | 44.420 | -1.423 | 112.988 | 1.00 | 28.17 | C |
| ATOM | 1326 | CG2 | VAL A 390 | 44.378 | -3.483 | 111.557 | 1.00 | 24.55 | C |
| ATOM | 1327 | N | THR A 391 | 46.767 | -3.156 | 115.487 | 1.00 | 23.98 | N |
| ATOM | 1328 | CA | THR A 391 | 47.285 | -2.644 | 116.756 | 1.00 | 21.70 | C |
| ATOM | 1329 | C | THR A 391 | 48.761 | -2.345 | 116.589 | 1.00 | 24.38 | C |
| ATOM | 1330 | O | THR A 391 | 49.227 | -1.267 | 116.998 | 1.00 | 24.27 | O |

| | | | | | | | | |
|---|---|---|---|---|---|---|---|---|
| ATOM | 1177 | OD1 | ASN A 364 | 37.168 | -4.039 | 120.982 | 1.00 20.72 | O |
| ATOM | 1178 | ND2 | ASN A 364 | 37.747 | -6.039 | 120.373 | 1.00 16.89 | N |
| ATOM | 1179 | N | SER A 365 | 34.573 | -5.567 | 116.990 | 1.00 27.61 | N |
| ATOM | 1180 | CA | SER A 365 | 33.132 | -5.467 | 117.125 | 1.00 32.86 | C |
| ATOM | 1181 | C | SER A 365 | 32.433 | -6.649 | 117.788 | 1.00 33.07 | C |
| ATOM | 1182 | O | SER A 365 | 31.503 | -6.505 | 118.595 | 1.00 31.33 | O |
| ATOM | 1183 | CB | SER A 365 | 32.530 | -5.251 | 115.697 | 1.00 32.53 | C |
| ATOM | 1184 | OG | SER A 365 | 31.358 | -4.541 | 116.023 | 1.00 37.03 | O |
| ATOM | 1185 | N | SER A 366 | 32.802 | -7.866 | 117.418 | 1.00 35.53 | N |
| ATOM | 1186 | CA | SER A 366 | 32.055 | -8.964 | 118.047 | 1.00 44.38 | C |
| ATOM | 1187 | C | SER A 366 | 33.064 | -9.936 | 118.600 | 1.00 45.98 | C |
| ATOM | 1188 | O | SER A 366 | 33.995 | -10.296 | 117.892 | 1.00 48.34 | O |
| ATOM | 1189 | CB | SER A 366 | 31.004 | -9.499 | 117.096 | 1.00 47.02 | C |
| ATOM | 1190 | OG | SER A 366 | 30.619 | -10.847 | 117.342 | 1.00 49.79 | O |
| ATOM | 1191 | N | MET A 367 | 32.878 | -10.327 | 119.833 | 1.00 51.19 | N |
| ATOM | 1192 | CA | MET A 367 | 33.764 | -11.274 | 120.490 | 1.00 58.19 | C |
| ATOM | 1193 | C | MET A 367 | 33.608 | -12.711 | 119.972 | 1.00 59.71 | C |
| ATOM | 1194 | O | MET A 367 | 34.574 | -13.478 | 119.919 | 1.00 60.53 | O |
| ATOM | 1195 | CB | MET A 367 | 33.311 | -11.391 | 121.943 | 1.00 58.70 | C |
| ATOM | 1196 | CG | MET A 367 | 34.364 | -11.603 | 122.997 | 1.00 61.11 | C |
| ATOM | 1197 | SD | MET A 367 | 34.008 | -10.318 | 124.248 | 1.00 65.90 | S |
| ATOM | 1198 | CE | MET A 367 | 32.262 | -10.630 | 124.509 | 1.00 64.16 | C |
| ATOM | 1199 | N | TYR A 368 | 32.386 | -13.087 | 119.592 | 1.00 61.18 | N |
| ATOM | 1200 | CA | TYR A 368 | 32.131 | -14.441 | 119.125 | 1.00 65.20 | C |
| ATOM | 1201 | C | TYR A 368 | 33.157 | -15.007 | 118.176 | 1.00 65.27 | C |
| ATOM | 1202 | O | TYR A 368 | 33.778 | -16.050 | 118.413 | 1.00 62.84 | O |
| ATOM | 1203 | CB | TYR A 368 | 30.706 | -14.600 | 118.589 | 1.00 66.18 | C |
| ATOM | 1204 | CG | TYR A 368 | 29.720 | -14.281 | 119.699 | 1.00 69.98 | C |
| ATOM | 1205 | CD1 | TYR A 368 | 29.697 | -15.008 | 120.894 | 1.00 70.44 | C |
| ATOM | 1206 | CD2 | TYR A 368 | 28.818 | -13.242 | 119.523 | 1.00 69.95 | C |
| ATOM | 1207 | CE1 | TYR A 368 | 28.786 | -14.692 | 121.886 | 1.00 70.72 | C |
| ATOM | 1208 | CE2 | TYR A 368 | 27.909 | -12.928 | 120.515 | 1.00 70.96 | C |
| ATOM | 1209 | CZ | TYR A 368 | 27.900 | -13.652 | 121.691 | 1.00 71.09 | C |
| ATOM | 1210 | OH | TYR A 368 | 26.981 | -13.314 | 122.653 | 1.00 69.94 | O |
| ATOM | 1211 | N | PRO A 369 | 33.442 | -14.326 | 117.085 | 1.00 67.03 | N |
| ATOM | 1212 | CA | PRO A 369 | 34.408 | -14.741 | 116.083 | 1.00 69.40 | C |
| ATOM | 1213 | C | PRO A 369 | 35.792 | -15.058 | 116.621 | 1.00 71.08 | C |
| ATOM | 1214 | O | PRO A 369 | 36.590 | -15.664 | 115.892 | 1.00 71.77 | O |
| ATOM | 1215 | CB | PRO A 369 | 34.453 | -13.648 | 114.999 | 1.00 67.54 | C |
| ATOM | 1216 | CG | PRO A 369 | 33.169 | -12.908 | 115.238 | 1.00 67.30 | C |
| ATOM | 1217 | CD | PRO A 369 | 32.779 | -13.075 | 116.688 | 1.00 66.80 | C |
| ATOM | 1218 | N | LEU A 370 | 36.144 | -14.692 | 117.842 | 1.00 73.35 | N |
| ATOM | 1219 | CA | LEU A 370 | 37.441 | -14.992 | 118.417 | 1.00 75.50 | C |
| ATOM | 1220 | C | LEU A 370 | 37.302 | -16.129 | 119.427 | 1.00 74.90 | C |
| ATOM | 1221 | O | LEU A 370 | 38.286 | -16.713 | 119.868 | 1.00 75.19 | O |
| ATOM | 1222 | CB | LEU A 370 | 38.137 | -13.770 | 119.007 | 1.00 76.04 | C |
| ATOM | 1223 | CG | LEU A 370 | 38.773 | -12.844 | 117.958 | 1.00 76.73 | C |
| ATOM | 1224 | CD1 | LEU A 370 | 39.493 | -11.716 | 118.700 | 1.00 78.17 | C |
| ATOM | 1225 | CD2 | LEU A 370 | 39.718 | -13.589 | 117.027 | 1.00 76.69 | C |
| ATOM | 1226 | N | VAL A 371 | 36.063 | -16.483 | 119.762 | 1.00 75.98 | N |
| ATOM | 1227 | CA | VAL A 371 | 35.790 | -17.560 | 120.709 | 1.00 76.08 | C |
| ATOM | 1228 | C | VAL A 371 | 34.745 | -18.569 | 120.258 | 1.00 75.26 | C |
| ATOM | 1229 | O | VAL A 371 | 34.692 | -19.049 | 119.129 | 1.00 75.47 | O |
| ATOM | 1230 | CB | VAL A 371 | 35.323 | -16.908 | 122.017 | 1.00 75.19 | C |
| ATOM | 1231 | N | ASP A 378 | 40.792 | -21.144 | 112.549 | 1.00 87.02 | N |
| ATOM | 1232 | CA | ASP A 378 | 40.744 | -21.040 | 111.079 | 1.00 87.20 | C |
| ATOM | 1233 | C | ASP A 378 | 40.533 | -19.580 | 110.682 | 1.00 86.28 | C |
| ATOM | 1234 | O | ASP A 378 | 41.428 | -18.917 | 110.166 | 1.00 84.93 | O |
| ATOM | 1235 | CB | ASP A 378 | 39.673 | -21.980 | 110.547 | 1.00 87.38 | C |
| ATOM | 1236 | N | SER A 379 | 39.344 | -19.041 | 110.933 | 1.00 86.08 | N |
| ATOM | 1237 | CA | SER A 379 | 39.017 | -17.649 | 110.658 | 1.00 85.11 | C |
| ATOM | 1238 | C | SER A 379 | 39.174 | -16.902 | 111.990 | 1.00 84.91 | C |
| ATOM | 1239 | O | SER A 379 | 39.431 | -15.706 | 112.021 | 1.00 84.80 | O |
| ATOM | 1240 | CB | SER A 379 | 37.645 | -17.442 | 110.048 | 1.00 84.08 | C |
| ATOM | 1241 | OG | SER A 379 | 37.457 | -16.113 | 109.601 | 1.00 81.93 | O |
| ATOM | 1242 | N | SER A 380 | 39.125 | -17.644 | 113.099 | 1.00 84.74 | N |
| ATOM | 1243 | CA | SER A 380 | 39.349 | -17.079 | 114.423 | 1.00 84.46 | C |
| ATOM | 1244 | C | SER A 380 | 40.828 | -16.732 | 114.611 | 1.00 83.60 | C |
| ATOM | 1245 | O | SER A 380 | 41.191 | -15.694 | 115.154 | 1.00 83.26 | O |
| ATOM | 1246 | CB | SER A 380 | 38.971 | -18.023 | 115.551 | 1.00 85.10 | C |
| ATOM | 1247 | OG | SER A 380 | 37.668 | -17.824 | 116.051 | 1.00 86.43 | O |
| ATOM | 1248 | N | ARG A 381 | 41.695 | -17.629 | 114.126 | 1.00 81.43 | N |
| ATOM | 1249 | CA | ARG A 381 | 43.133 | -17.417 | 114.210 | 1.00 78.76 | C |
| ATOM | 1250 | C | ARG A 381 | 43.408 | -16.142 | 113.407 | 1.00 73.02 | C |
| ATOM | 1251 | O | ARG A 381 | 44.202 | -15.292 | 113.762 | 1.00 73.32 | O |
| ATOM | 1252 | CB | ARG A 381 | 43.959 | -18.550 | 113.599 | 1.00 81.56 | C |
| ATOM | 1253 | CG | ARG A 381 | 44.313 | -19.687 | 114.542 | 1.00 86.12 | C |

| | | | | | | | | | |
|---|---|---|---|---|---|---|---|---|---|
| ATOM | 1100 | CE1 | TYR A 354 | 37.921 | 8.417 | 111.689 | 1.00 | 22.14 | C |
| ATOM | 1101 | CE2 | TYR A 354 | 39.225 | 8.643 | 109.658 | 1.00 | 21.21 | C |
| ATOM | 1102 | CZ | TYR A 354 | 38.015 | 8.442 | 110.311 | 1.00 | 23.97 | C |
| ATOM | 1103 | OH | TYR A 354 | 36.844 | 8.266 | 109.605 | 1.00 | 27.78 | O |
| ATOM | 1104 | N | LEU A 355 | 42.803 | 6.477 | 111.270 | 1.00 | 18.57 | N |
| ATOM | 1105 | CA | LEU A 355 | 42.647 | 5.330 | 110.340 | 1.00 | 19.56 | C |
| ATOM | 1106 | C | LEU A 355 | 42.832 | 3.980 | 111.033 | 1.00 | 20.09 | C |
| ATOM | 1107 | O | LEU A 355 | 42.158 | 2.965 | 110.724 | 1.00 | 20.19 | O |
| ATOM | 1108 | CB | LEU A 355 | 43.622 | 5.429 | 109.158 | 1.00 | 16.13 | C |
| ATOM | 1109 | CG | LEU A 355 | 43.605 | 6.642 | 108.227 | 1.00 | 18.21 | C |
| ATOM | 1110 | CD1 | LEU A 355 | 44.849 | 6.800 | 107.317 | 1.00 | 14.15 | C |
| ATOM | 1111 | CD2 | LEU A 355 | 42.357 | 6.556 | 107.366 | 1.00 | 12.89 | C |
| ATOM | 1112 | N | CYS A 356 | 43.763 | 3.860 | 111.976 | 1.00 | 17.41 | N |
| ATOM | 1113 | CA | CYS A 356 | 43.917 | 2.555 | 112.656 | 1.00 | 18.85 | C |
| ATOM | 1114 | C | CYS A 356 | 42.746 | 2.295 | 113.598 | 1.00 | 18.37 | C |
| ATOM | 1115 | O | CYS A 356 | 42.127 | 1.219 | 113.636 | 1.00 | 17.27 | O |
| ATOM | 1116 | CB | CYS A 356 | 45.277 | 2.553 | 113.393 | 1.00 | 17.56 | C |
| ATOM | 1117 | SG | CYS A 356 | 46.785 | 2.623 | 112.395 | 1.00 | 18.97 | S |
| ATOM | 1118 | N | VAL A 357 | 42.336 | 3.314 | 114.368 | 1.00 | 20.20 | N |
| ATOM | 1119 | CA | VAL A 357 | 41.254 | 3.189 | 115.343 | 1.00 | 22.84 | C |
| ATOM | 1120 | C | VAL A 357 | 39.974 | 2.689 | 114.677 | 1.00 | 23.94 | C |
| ATOM | 1121 | O | VAL A 357 | 39.343 | 1.732 | 115.145 | 1.00 | 20.86 | O |
| ATOM | 1122 | CB | VAL A 357 | 41.065 | 4.497 | 116.154 | 1.00 | 23.60 | C |
| ATOM | 1123 | CG1 | VAL A 357 | 39.732 | 4.561 | 116.874 | 1.00 | 24.12 | C |
| ATOM | 1124 | CG2 | VAL A 357 | 42.208 | 4.614 | 117.177 | 1.00 | 23.09 | C |
| ATOM | 1125 | N | LYS A 358 | 39.586 | 3.353 | 113.579 | 1.00 | 23.03 | N |
| ATOM | 1126 | CA | LYS A 358 | 38.347 | 2.958 | 112.881 | 1.00 | 23.26 | C |
| ATOM | 1127 | C | LYS A 358 | 38.398 | 1.514 | 112.408 | 1.00 | 21.94 | C |
| ATOM | 1128 | O | LYS A 358 | 37.424 | 0.771 | 112.611 | 1.00 | 20.12 | O |
| ATOM | 1129 | CB | LYS A 358 | 37.982 | 3.948 | 111.757 | 1.00 | 19.75 | C |
| ATOM | 1130 | CG | LYS A 358 | 36.601 | 3.650 | 111.222 | 1.00 | 18.14 | C |
| ATOM | 1131 | CD | LYS A 358 | 36.099 | 4.629 | 110.151 | 1.00 | 20.88 | C |
| ATOM | 1132 | CE | LYS A 358 | 37.152 | 4.844 | 109.040 | 1.00 | 20.43 | C |
| ATOM | 1133 | NZ | LYS A 358 | 36.520 | 5.657 | 107.975 | 1.00 | 17.59 | N |
| ATOM | 1134 | N | ALA A 359 | 39.512 | 1.064 | 111.823 | 1.00 | 18.43 | N |
| ATOM | 1135 | CA | ALA A 359 | 39.691 | -0.336 | 111.464 | 1.00 | 20.22 | C |
| ATOM | 1136 | C | ALA A 359 | 39.571 | -1.223 | 112.716 | 1.00 | 21.57 | C |
| ATOM | 1137 | O | ALA A 359 | 38.986 | -2.315 | 112.692 | 1.00 | 20.36 | O |
| ATOM | 1138 | CB | ALA A 359 | 41.097 | -0.547 | 110.851 | 1.00 | 17.28 | C |
| ATOM | 1139 | N | MET A 360 | 40.165 | -0.796 | 113.837 | 1.00 | 21.90 | N |
| ATOM | 1140 | CA | MET A 360 | 40.054 | -1.556 | 115.085 | 1.00 | 24.64 | C |
| ATOM | 1141 | C | MET A 360 | 38.605 | -1.713 | 115.561 | 1.00 | 24.35 | C |
| ATOM | 1142 | O | MET A 360 | 38.204 | -2.814 | 116.002 | 1.00 | 22.34 | O |
| ATOM | 1143 | CB | MET A 360 | 40.938 | -0.960 | 116.201 | 1.00 | 25.26 | C |
| ATOM | 1144 | CG | MET A 360 | 42.409 | -1.115 | 115.875 | 1.00 | 30.32 | C |
| ATOM | 1145 | SD | MET A 360 | 43.645 | -0.353 | 116.971 | 1.00 | 34.28 | S |
| ATOM | 1146 | CE | MET A 360 | 42.844 | -0.643 | 118.552 | 1.00 | 31.82 | C |
| ATOM | 1147 | N | ILE A 361 | 37.804 | -0.653 | 115.435 | 1.00 | 21.38 | N |
| ATOM | 1148 | CA | ILE A 361 | 36.411 | -0.689 | 115.820 | 1.00 | 19.76 | C |
| ATOM | 1149 | C | ILE A 361 | 35.656 | -1.796 | 115.084 | 1.00 | 22.08 | C |
| ATOM | 1150 | O | ILE A 361 | 34.918 | -2.641 | 115.641 | 1.00 | 18.83 | O |
| ATOM | 1151 | CB | ILE A 361 | 35.763 | 0.680 | 115.604 | 1.00 | 19.21 | C |
| ATOM | 1152 | CG1 | ILE A 361 | 36.182 | 1.631 | 116.731 | 1.00 | 19.46 | C |
| ATOM | 1153 | CG2 | ILE A 361 | 34.239 | 0.587 | 115.552 | 1.00 | 19.38 | C |
| ATOM | 1154 | CD1 | ILE A 361 | 35.749 | 3.082 | 116.531 | 1.00 | 15.77 | C |
| ATOM | 1155 | N | LEU A 362 | 35.819 | -1.905 | 113.778 | 1.00 | 18.89 | N |
| ATOM | 1156 | CA | LEU A 362 | 35.231 | -2.954 | 112.981 | 1.00 | 20.99 | C |
| ATOM | 1157 | C | LEU A 362 | 35.718 | -4.328 | 113.477 | 1.00 | 20.42 | C |
| ATOM | 1158 | O | LEU A 362 | 34.927 | -5.215 | 113.757 | 1.00 | 22.14 | O |
| ATOM | 1159 | CB | LEU A 362 | 35.602 | -2.833 | 111.493 | 1.00 | 22.13 | C |
| ATOM | 1160 | CG | LEU A 362 | 35.431 | -4.110 | 110.647 | 1.00 | 22.51 | C |
| ATOM | 1161 | CD1 | LEU A 362 | 33.954 | -4.374 | 110.474 | 1.00 | 23.17 | C |
| ATOM | 1162 | CD2 | LEU A 362 | 36.098 | -3.954 | 109.283 | 1.00 | 27.08 | C |
| ATOM | 1163 | N | LEU A 363 | 37.009 | -4.547 | 113.527 | 1.00 | 17.85 | N |
| ATOM | 1164 | CA | LEU A 363 | 37.574 | -5.825 | 113.898 | 1.00 | 20.59 | C |
| ATOM | 1165 | C | LEU A 363 | 37.316 | -6.255 | 115.333 | 1.00 | 21.76 | C |
| ATOM | 1166 | O | LEU A 363 | 37.352 | -7.469 | 115.502 | 1.00 | 20.98 | O |
| ATOM | 1167 | CB | LEU A 363 | 39.079 | -5.912 | 113.591 | 1.00 | 17.44 | C |
| ATOM | 1168 | CG | LEU A 363 | 39.484 | -5.673 | 112.129 | 1.00 | 24.08 | C |
| ATOM | 1169 | CD1 | LEU A 363 | 40.998 | -5.433 | 111.995 | 1.00 | 21.49 | C |
| ATOM | 1170 | CD2 | LEU A 363 | 39.043 | -6.842 | 111.234 | 1.00 | 21.27 | C |
| ATOM | 1171 | N | ASN A 364 | 37.092 | -5.399 | 116.299 | 1.00 | 23.78 | N |
| ATOM | 1172 | CA | ASN A 364 | 36.859 | -5.718 | 117.714 | 1.00 | 25.70 | C |
| ATOM | 1173 | C | ASN A 364 | 35.365 | -5.692 | 118.042 | 1.00 | 26.96 | C |
| ATOM | 1174 | O | ASN A 364 | 34.853 | -5.744 | 119.165 | 1.00 | 26.18 | O |
| ATOM | 1175 | CB | ASN A 364 | 37.479 | -4.584 | 118.571 | 1.00 | 22.87 | C |
| ATOM | 1176 | CG | ASN A 364 | 37.444 | -4.822 | 120.072 | 1.00 | 22.38 | C |

| | | | | | | | | | |
|---|---|---|---|---|---|---|---|---|---|
|ATOM|1023|CG B|GLU|A 346|40.257|18.113|125.129|0.50 38.63|C|
|ATOM|1024|CD A|GLU|A 346|43.239|16.645|126.324|0.50 46.28|C|
|ATOM|1025|CD B|GLU|A 346|39.639|19.108|124.198|0.50 41.89|C|
|ATOM|1026|OE1A|GLU|A 346|43.181|15.445|125.983|0.50 49.07|O|
|ATOM|1027|OE1B|GLU|A 346|40.298|19.659|123.286|0.50 43.69|O|
|ATOM|1028|OE2A|GLU|A 346|44.170|17.060|127.050|0.50 49.44|O|
|ATOM|1029|OE2B|GLU|A 346|38.433|19.443|124.309|0.50 42.89|O|
|ATOM|1030|N|LEU|A 347|43.087|15.203|122.765|1.00 28.00|N|
|ATOM|1031|CA|LEU|A 347|44.272|14.342|122.604|1.00 24.74|C|
|ATOM|1032|C|LEU|A 347|45.008|14.660|121.310|1.00 23.19|C|
|ATOM|1033|O|LEU|A 347|46.093|14.126|121.039|1.00 16.02|O|
|ATOM|1034|CB|LEU|A 347|43.774|12.873|122.456|1.00 26.01|C|
|ATOM|1035|CG|LEU|A 347|43.402|12.263|123.821|1.00 30.44|C|
|ATOM|1036|CD1|LEU|A 347|42.843|10.868|123.715|1.00 28.78|C|
|ATOM|1037|CD2|LEU|A 347|44.629|12.318|124.727|1.00 31.20|C|
|ATOM|1038|N|LYS|A 348|44.393|15.521|120.464|1.00 23.51|N|
|ATOM|1039|CA|LYS|A 348|45.056|15.827|119.182|1.00 26.00|C|
|ATOM|1040|C|LYS|A 348|45.140|14.549|118.331|1.00 23.31|C|
|ATOM|1041|O|LYS|A 348|46.158|14.255|117.697|1.00 23.02|O|
|ATOM|1042|CB|LYS|A 348|46.408|16.485|119.398|1.00 28.63|C|
|ATOM|1043|CG|LYS|A 348|46.240|17.937|119.912|1.00 34.30|C|
|ATOM|1044|CD|LYS|A 348|47.617|18.501|120.267|1.00 38.43|C|
|ATOM|1045|CE|LYS|A 348|47.459|19.764|121.113|1.00 43.88|C|
|ATOM|1046|NZ|LYS|A 348|46.996|20.922|120.271|1.00 49.18|N|
|ATOM|1047|N|LEU|A 349|44.044|13.798|118.235|1.00 18.86|N|
|ATOM|1048|CA|LEU|A 349|44.071|12.613|117.376|1.00 23.61|C|
|ATOM|1049|C|LEU|A 349|44.676|12.876|116.000|1.00 22.65|C|
|ATOM|1050|O|LEU|A 349|44.290|13.801|115.299|1.00 23.16|O|
|ATOM|1051|CB|LEU|A 349|42.620|12.114|117.198|1.00 20.67|C|
|ATOM|1052|CG|LEU|A 349|42.450|10.816|116.426|1.00 19.76|C|
|ATOM|1053|CD1|LEU|A 349|43.072|9.595|117.135|1.00 22.59|C|
|ATOM|1054|CD2|LEU|A 349|40.942|10.609|116.217|1.00 19.16|C|
|ATOM|1055|N|GLN|A 350|45.601|12.099|115.515|1.00 22.68|N|
|ATOM|1056|CA|GLN|A 350|46.197|12.272|114.194|1.00 24.18|C|
|ATOM|1057|C|GLN|A 350|45.417|11.539|113.106|1.00 22.74|C|
|ATOM|1058|O|GLN|A 350|44.671|10.577|113.369|1.00 21.72|O|
|ATOM|1059|CB|GLN|A 350|47.623|11.702|114.251|1.00 26.25|C|
|ATOM|1060|CG|GLN|A 350|48.401|12.399|115.384|1.00 34.17|C|
|ATOM|1061|CD|GLN|A 350|48.659|13.833|114.906|1.00 39.01|C|
|ATOM|1062|OE1|GLN|A 350|49.554|13.923|114.046|1.00 41.52|O|
|ATOM|1063|NE2|GLN|A 350|47.884|14.785|115.430|1.00 39.18|N|
|ATOM|1064|N|HIS|A 351|45.646|11.924|111.858|1.00 23.54|N|
|ATOM|1065|CA|HIS|A 351|44.984|11.238|110.744|1.00 26.18|C|
|ATOM|1066|C|HIS|A 351|45.381|9.746|110.742|1.00 23.26|C|
|ATOM|1067|O|HIS|A 351|44.501|8.915|110.554|1.00 17.25|O|
|ATOM|1068|CB|HIS|A 351|45.453|11.759|109.381|1.00 31.47|C|
|ATOM|1069|CG|HIS|A 351|44.920|13.081|108.986|1.00 36.19|C|
|ATOM|1070|ND1|HIS|A 351|43.973|13.212|107.979|1.00 39.37|N|
|ATOM|1071|CD2|HIS|A 351|45.172|14.322|109.462|1.00 37.74|C|
|ATOM|1072|CE1|HIS|A 351|43.680|14.502|107.843|1.00 40.81|C|
|ATOM|1073|NE2|HIS|A 351|44.378|15.191|108.737|1.00 40.60|N|
|ATOM|1074|N|LYS|A 352|46.683|9.444|110.871|1.00 20.96|N|
|ATOM|1075|CA|LYS|A 352|47.111|8.053|110.846|1.00 23.22|C|
|ATOM|1076|C|LYS|A 352|46.507|7.257|112.031|1.00 24.92|C|
|ATOM|1077|O|LYS|A 352|46.216|6.078|111.823|1.00 21.55|O|
|ATOM|1078|CB|LYS|A 352|48.646|7.952|110.924|1.00 23.35|C|
|ATOM|1079|CG|LYS|A 352|49.325|8.594|109.753|1.00 24.96|C|
|ATOM|1080|CD|LYS|A 352|50.799|8.311|109.626|1.00 26.82|C|
|ATOM|1081|CE|LYS|A 352|51.604|8.872|110.782|1.00 25.58|C|
|ATOM|1082|NZ|LYS|A 352|51.300|10.338|110.883|1.00 25.65|N|
|ATOM|1083|N|GLU|A 353|46.327|7.891|113.213|1.00 20.65|N|
|ATOM|1084|CA|GLU|A 353|45.740|7.193|114.343|1.00 21.55|C|
|ATOM|1085|C|GLU|A 353|44.260|6.951|114.077|1.00 21.19|C|
|ATOM|1086|O|GLU|A 353|43.797|5.841|114.298|1.00 19.67|O|
|ATOM|1087|CB|GLU|A 353|45.895|7.965|115.679|1.00 21.42|C|
|ATOM|1088|CG|GLU|A 353|47.347|8.158|116.109|1.00 22.42|C|
|ATOM|1089|CD|GLU|A 353|47.504|9.190|117.207|1.00 23.41|C|
|ATOM|1090|OE1|GLU|A 353|46.721|10.162|117.273|1.00 22.59|O|
|ATOM|1091|OE2|GLU|A 353|48.417|9.096|118.049|1.00 24.08|O|
|ATOM|1092|N|TYR|A 354|43.495|7.940|113.592|1.00 19.95|N|
|ATOM|1093|CA|TYR|A 354|42.092|7.731|113.291|1.00 19.80|C|
|ATOM|1094|C|TYR|A 354|41.943|6.572|112.296|1.00 21.93|C|
|ATOM|1095|O|TYR|A 354|41.103|5.682|112.504|1.00 21.24|O|
|ATOM|1096|CB|TYR|A 354|41.546|9.013|112.630|1.00 22.88|C|
|ATOM|1097|CG|TYR|A 354|40.301|8.818|111.798|1.00 21.66|C|
|ATOM|1098|CD1|TYR|A 354|39.081|8.605|112.415|1.00 22.15|C|
|ATOM|1099|CD2|TYR|A 354|40.360|8.800|110.403|1.00 21.43|C|

```
ATOM    946  CA  LEU A 338      30.110  15.921 121.397  1.00 25.94           C
ATOM    947  C   LEU A 338      31.194  15.781 122.422  1.00 26.05           C
ATOM    948  O   LEU A 338      32.315  16.251 122.196  1.00 26.57           O
ATOM    949  CB  LEU A 338      29.175  17.107 121.731  1.00 26.94           C
ATOM    950  CG  LEU A 338      28.242  17.406 120.537  1.00 25.93           C
ATOM    951  CD1 LEU A 338      27.135  18.361 120.939  1.00 25.91           C
ATOM    952  CD2 LEU A 338      29.040  18.051 119.418  1.00 27.79           C
ATOM    953  N   ALA A 339      30.920  15.040 123.520  1.00 27.43           N
ATOM    954  CA  ALA A 339      31.930  14.885 124.571  1.00 25.26           C
ATOM    955  C   ALA A 339      33.017  13.919 124.116  1.00 27.53           C
ATOM    956  O   ALA A 339      34.192  14.238 124.327  1.00 26.99           O
ATOM    957  CB  ALA A 339      31.274  14.487 125.897  1.00 22.08           C
ATOM    958  N   THR A 340      32.665  12.802 123.447  1.00 26.89           N
ATOM    959  CA  THR A 340      33.730  11.891 122.982  1.00 25.56           C
ATOM    960  C   THR A 340      34.575  12.658 121.964  1.00 25.41           C
ATOM    961  O   THR A 340      35.800  12.601 122.031  1.00 20.92           O
ATOM    962  CB  THR A 340      33.163  10.630 122.327  1.00 28.53           C
ATOM    963  OG1 THR A 340      32.219  10.019 123.224  1.00 30.06           O
ATOM    964  CG2 THR A 340      34.167   9.526 121.981  1.00 25.87           C
ATOM    965  N   THR A 341      33.907  13.384 121.029  1.00 24.19           N
ATOM    966  CA  THR A 341      34.604  14.180 120.026  1.00 24.14           C
ATOM    967  C   THR A 341      35.554  15.176 120.684  1.00 24.75           C
ATOM    968  O   THR A 341      36.710  15.333 120.292  1.00 26.19           O
ATOM    969  CB  THR A 341      33.646  14.984 119.100  1.00 23.58           C
ATOM    970  OG1 THR A 341      32.799  14.013 118.480  1.00 19.97           O
ATOM    971  CG2 THR A 341      34.442  15.812 118.069  1.00 20.06           C
ATOM    972  N   SER A 342      35.121  15.872 121.735  1.00 27.28           N
ATOM    973  CA  SER A 342      36.073  16.767 122.423  1.00 26.73           C
ATOM    974  C   SER A 342      37.228  15.977 122.983  1.00 25.51           C
ATOM    975  O   SER A 342      38.308  16.531 123.018  1.00 28.14           O
ATOM    976  CB  SER A 342      35.363  17.533 123.565  1.00 26.44           C
ATOM    977  OG  SER A 342      34.248  18.190 122.921  1.00 28.06           O
ATOM    978  N   ARG A 343      37.104  14.761 123.500  1.00 26.43           N
ATOM    979  CA  ARG A 343      38.251  14.021 123.999  1.00 28.15           C
ATOM    980  C   ARG A 343      39.243  13.795 122.857  1.00 24.25           C
ATOM    981  O   ARG A 343      40.439  14.058 123.081  1.00 26.44           O
ATOM    982  CB  ARG A 343      37.915  12.666 124.629  1.00 30.03           C
ATOM    983  CG AARG A 343      36.750  12.691 125.600  0.50 33.36           C
ATOM    984  CG BARG A 343      37.863  12.680 126.148  0.50 33.69           C
ATOM    985  CD AARG A 343      37.202  13.207 126.977  0.50 36.57           C
ATOM    986  CD BARG A 343      39.150  13.089 126.812  0.50 34.95           C
ATOM    987  NE AARG A 343      37.536  14.618 126.848  0.50 39.93           N
ATOM    988  NE BARG A 343      40.050  12.025 127.269  0.50 36.61           N
ATOM    989  CZ AARG A 343      36.760  15.685 126.968  0.50 40.97           C
ATOM    990  CZ BARG A 343      41.340  12.288 127.459  0.50 39.09           C
ATOM    991  NH1AARG A 343      35.473  15.584 127.286  0.50 40.43           N
ATOM    992  NH1BARG A 343      41.735  13.535 127.197  0.50 40.99           N
ATOM    993  NH2AARG A 343      37.329  16.880 126.779  0.50 40.31           N
ATOM    994  NH2BARG A 343      42.201  11.379 127.877  0.50 38.95           N
ATOM    995  N   PHE A 344      38.798  13.321 121.697  1.00 20.53           N
ATOM    996  CA  PHE A 344      39.748  13.119 120.578  1.00 20.44           C
ATOM    997  C   PHE A 344      40.402  14.442 120.193  1.00 20.10           C
ATOM    998  O   PHE A 344      41.590  14.456 119.920  1.00 18.17           O
ATOM    999  CB  PHE A 344      39.008  12.577 119.334  1.00 20.52           C
ATOM   1000  CG  PHE A 344      38.663  11.124 119.489  1.00 18.56           C
ATOM   1001  CD1 PHE A 344      39.676  10.198 119.664  1.00 20.58           C
ATOM   1002  CD2 PHE A 344      37.372  10.669 119.445  1.00 18.69           C
ATOM   1003  CE1 PHE A 344      39.383   8.838 119.802  1.00 22.55           C
ATOM   1004  CE2 PHE A 344      37.061   9.337 119.572  1.00 18.73           C
ATOM   1005  CZ  PHE A 344      38.066   8.406 119.756  1.00 20.91           C
ATOM   1006  N   ARG A 345      39.661  15.570 120.211  1.00 22.44           N
ATOM   1007  CA  ARG A 345      40.245  16.866 119.917  1.00 24.78           C
ATOM   1008  C   ARG A 345      41.304  17.232 120.971  1.00 27.54           C
ATOM   1009  O   ARG A 345      42.420  17.603 120.584  1.00 26.66           O
ATOM   1010  CB  ARG A 345      39.232  18.012 119.876  1.00 25.33           C
ATOM   1011  CG  ARG A 345      39.911  19.403 119.789  1.00 25.77           C
ATOM   1012  CD  ARG A 345      38.841  20.465 119.432  1.00 26.69           C
ATOM   1013  NE  ARG A 345      37.784  20.481 120.427  1.00 28.82           N
ATOM   1014  CZ  ARG A 345      36.531  20.026 120.402  1.00 29.89           C
ATOM   1015  NH1 ARG A 345      35.965  19.456 119.340  1.00 27.42           N
ATOM   1016  NH2 ARG A 345      35.789  20.156 121.510  1.00 26.28           N
ATOM   1017  N   GLU A 346      41.023  17.027 122.246  1.00 26.63           N
ATOM   1018  CA  GLU A 346      41.967  17.312 123.319  1.00 31.74           C
ATOM   1019  C   GLU A 346      43.210  16.459 123.218  1.00 28.71           C
ATOM   1020  O   GLU A 346      44.307  16.919 123.516  1.00 26.71           O
ATOM   1021  CB  GLU A 346      41.294  17.123 124.694  1.00 36.03           C
ATOM   1022  CG AGLU A 346      42.177  17.594 125.841  0.50 42.65           C
```

| ATOM | 866 | C | GLU A 328 | 14.073 | 12.160 | 122.298 | 1.00 | 46.98 | C |
|---|---|---|---|---|---|---|---|---|---|
| ATOM | 867 | O | GLU A 328 | 14.179 | 11.327 | 121.399 | 1.00 | 44.72 | O |
| ATOM | 868 | CB | GLU A 328 | 11.625 | 12.581 | 122.652 | 1.00 | 49.47 | C |
| ATOM | 869 | CG | GLU A 328 | 11.425 | 12.375 | 124.143 | 1.00 | 51.33 | C |
| ATOM | 873 | N | GLY A 329 | 14.911 | 12.184 | 123.332 | 1.00 | 45.34 | N |
| ATOM | 874 | CA | GLY A 329 | 16.002 | 11.250 | 123.475 | 1.00 | 44.04 | C |
| ATOM | 875 | C | GLY A 329 | 17.290 | 11.564 | 122.722 | 1.00 | 41.89 | C |
| ATOM | 876 | O | GLY A 329 | 18.333 | 11.020 | 123.102 | 1.00 | 39.43 | O |
| ATOM | 877 | N | ILE A 330 | 17.276 | 12.412 | 121.715 | 1.00 | 39.86 | N |
| ATOM | 878 | CA | ILE A 330 | 18.445 | 12.727 | 120.923 | 1.00 | 38.95 | C |
| ATOM | 879 | C | ILE A 330 | 19.485 | 13.579 | 121.606 | 1.00 | 38.14 | C |
| ATOM | 880 | O | ILE A 330 | 20.705 | 13.399 | 121.444 | 1.00 | 35.81 | O |
| ATOM | 881 | CB | ILE A 330 | 17.984 | 13.362 | 119.590 | 1.00 | 41.34 | C |
| ATOM | 882 | CG1 | ILE A 330 | 17.625 | 12.225 | 118.627 | 1.00 | 42.13 | C |
| ATOM | 883 | CG2 | ILE A 330 | 18.991 | 14.343 | 119.012 | 1.00 | 39.18 | C |
| ATOM | 884 | CD1 | ILE A 330 | 18.751 | 11.459 | 117.962 | 1.00 | 40.79 | C |
| ATOM | 885 | N | LEU A 331 | 19.008 | 14.518 | 122.396 | 1.00 | 36.84 | N |
| ATOM | 886 | CA | LEU A 331 | 19.923 | 15.400 | 123.092 | 1.00 | 41.61 | C |
| ATOM | 887 | C | LEU A 331 | 20.971 | 14.624 | 123.889 | 1.00 | 42.65 | C |
| ATOM | 888 | O | LEU A 331 | 22.135 | 15.084 | 123.857 | 1.00 | 42.26 | O |
| ATOM | 889 | CB | LEU A 331 | 19.174 | 16.387 | 123.968 | 1.00 | 42.27 | C |
| ATOM | 890 | CG | LEU A 331 | 19.949 | 17.586 | 124.505 | 1.00 | 44.25 | C |
| ATOM | 891 | CD1 | LEU A 331 | 20.839 | 18.209 | 123.447 | 1.00 | 44.69 | C |
| ATOM | 892 | CD2 | LEU A 331 | 18.949 | 18.640 | 125.011 | 1.00 | 44.51 | C |
| ATOM | 893 | N | GLU A 332 | 20.614 | 13.500 | 124.530 | 1.00 | 39.71 | N |
| ATOM | 894 | CA | GLU A 332 | 21.646 | 12.799 | 125.270 | 1.00 | 40.51 | C |
| ATOM | 895 | C | GLU A 332 | 22.633 | 12.165 | 124.285 | 1.00 | 35.81 | C |
| ATOM | 896 | O | GLU A 332 | 23.815 | 12.200 | 124.616 | 1.00 | 33.18 | O |
| ATOM | 897 | CB | GLU A 332 | 21.166 | 11.815 | 126.338 | 1.00 | 44.11 | C |
| ATOM | 898 | CG | GLU A 332 | 20.059 | 10.884 | 125.967 | 1.00 | 50.80 | C |
| ATOM | 899 | CD | GLU A 332 | 20.038 | 9.472 | 126.539 | 1.00 | 54.61 | C |
| ATOM | 900 | OE1 | GLU A 332 | 20.513 | 9.183 | 127.661 | 1.00 | 50.05 | O |
| ATOM | 901 | OE2 | GLU A 332 | 19.479 | 8.633 | 125.750 | 1.00 | 58.18 | O |
| ATOM | 902 | N | ILE A 333 | 22.194 | 11.631 | 123.153 | 1.00 | 34.03 | N |
| ATOM | 903 | CA | ILE A 333 | 23.131 | 11.051 | 122.190 | 1.00 | 33.06 | C |
| ATOM | 904 | C | ILE A 333 | 24.073 | 12.146 | 121.716 | 1.00 | 29.61 | C |
| ATOM | 905 | O | ILE A 333 | 25.294 | 11.959 | 121.793 | 1.00 | 31.67 | O |
| ATOM | 906 | CB | ILE A 333 | 22.401 | 10.496 | 120.974 | 1.00 | 35.79 | C |
| ATOM | 907 | CG1 | ILE A 333 | 21.226 | 9.650 | 121.487 | 1.00 | 35.93 | C |
| ATOM | 908 | CG2 | ILE A 333 | 23.273 | 9.778 | 119.972 | 1.00 | 32.92 | C |
| ATOM | 909 | CD1 | ILE A 333 | 21.517 | 8.495 | 122.335 | 1.00 | 35.32 | C |
| ATOM | 910 | N | PHE A 334 | 23.530 | 13.285 | 121.317 | 1.00 | 27.71 | N |
| ATOM | 911 | CA | PHE A 334 | 24.364 | 14.403 | 120.875 | 1.00 | 29.44 | C |
| ATOM | 912 | C | PHE A 334 | 25.389 | 14.831 | 121.923 | 1.00 | 31.51 | C |
| ATOM | 913 | O | PHE A 334 | 26.548 | 15.076 | 121.532 | 1.00 | 31.48 | O |
| ATOM | 914 | CB | PHE A 334 | 23.569 | 15.612 | 120.423 | 1.00 | 27.17 | C |
| ATOM | 915 | CG | PHE A 334 | 22.868 | 15.477 | 119.091 | 1.00 | 28.60 | C |
| ATOM | 916 | CD1 | PHE A 334 | 22.767 | 14.290 | 118.418 | 1.00 | 25.27 | C |
| ATOM | 917 | CD2 | PHE A 334 | 22.270 | 16.599 | 118.524 | 1.00 | 28.49 | C |
| ATOM | 918 | CE1 | PHE A 334 | 22.104 | 14.203 | 117.220 | 1.00 | 27.88 | C |
| ATOM | 919 | CE2 | PHE A 334 | 21.605 | 16.514 | 117.318 | 1.00 | 30.43 | C |
| ATOM | 920 | CZ | PHE A 334 | 21.515 | 15.302 | 116.648 | 1.00 | 26.57 | C |
| ATOM | 921 | N | ASP A 335 | 24.990 | 14.878 | 123.197 | 1.00 | 31.11 | N |
| ATOM | 922 | CA | ASP A 335 | 25.913 | 15.245 | 124.242 | 1.00 | 32.16 | C |
| ATOM | 923 | C | ASP A 335 | 26.962 | 14.166 | 124.378 | 1.00 | 29.29 | C |
| ATOM | 924 | O | ASP A 335 | 28.134 | 14.552 | 124.511 | 1.00 | 33.27 | O |
| ATOM | 925 | CB | ASP A 335 | 25.289 | 15.607 | 125.600 | 1.00 | 34.43 | C |
| ATOM | 926 | CG | ASP A 335 | 24.545 | 16.930 | 125.503 | 1.00 | 36.37 | C |
| ATOM | 927 | OD1 | ASP A 335 | 24.907 | 17.822 | 124.700 | 1.00 | 36.70 | O |
| ATOM | 928 | OD2 | ASP A 335 | 23.543 | 17.113 | 126.229 | 1.00 | 39.54 | O |
| ATOM | 929 | N | MET A 336 | 26.640 | 12.905 | 124.251 | 1.00 | 26.61 | N |
| ATOM | 930 | CA | MET A 336 | 27.681 | 11.893 | 124.342 | 1.00 | 29.68 | C |
| ATOM | 931 | C | MET A 336 | 28.670 | 12.023 | 123.165 | 1.00 | 27.67 | C |
| ATOM | 932 | O | MET A 336 | 29.870 | 11.879 | 123.339 | 1.00 | 26.65 | O |
| ATOM | 933 | CB | MET A 336 | 27.048 | 10.495 | 124.268 | 1.00 | 32.01 | C |
| ATOM | 934 | CG | MET A 336 | 26.171 | 10.084 | 125.427 | 1.00 | 38.68 | C |
| ATOM | 935 | SD | MET A 336 | 25.380 | 8.463 | 125.064 | 1.00 | 42.98 | S |
| ATOM | 936 | CE | MET A 336 | 26.903 | 7.487 | 125.329 | 1.00 | 36.57 | C |
| ATOM | 937 | N | LEU A 337 | 28.140 | 12.224 | 121.954 | 1.00 | 26.36 | N |
| ATOM | 938 | CA | LEU A 337 | 28.945 | 12.335 | 120.742 | 1.00 | 25.14 | C |
| ATOM | 939 | C | LEU A 337 | 29.831 | 13.567 | 120.840 | 1.00 | 23.56 | C |
| ATOM | 940 | O | LEU A 337 | 31.033 | 13.458 | 120.630 | 1.00 | 21.31 | O |
| ATOM | 941 | CB | LEU A 337 | 28.059 | 12.386 | 119.491 | 1.00 | 22.91 | C |
| ATOM | 942 | CG | LEU A 337 | 27.264 | 11.099 | 119.186 | 1.00 | 23.00 | C |
| ATOM | 943 | CD1 | LEU A 337 | 26.167 | 11.422 | 118.172 | 1.00 | 22.22 | C |
| ATOM | 944 | CD2 | LEU A 337 | 28.173 | 9.999 | 118.656 | 1.00 | 20.73 | C |
| ATOM | 945 | N | LEU A 338 | 29.292 | 14.702 | 121.257 | 1.00 | 25.49 | N |

| | | | | | | | | | |
|---|---|---|---|---|---|---|---|---|---|
| ATOM | 789 | C | VAL | A | 318 | 24.483 | 20.438 | 111.015 | 1.00 34.90 | C |
| ATOM | 790 | O | VAL | A | 318 | 23.646 | 21.314 | 110.830 | 1.00 35.16 | O |
| ATOM | 791 | CB | VAL | A | 318 | 26.283 | 21.348 | 109.519 | 1.00 29.89 | C |
| ATOM | 792 | CG1 | VAL | A | 318 | 27.096 | 21.726 | 110.768 | 1.00 28.31 | C |
| ATOM | 793 | CG2 | VAL | A | 318 | 27.163 | 21.047 | 108.317 | 1.00 27.37 | C |
| ATOM | 794 | N | LEU | A | 319 | 24.591 | 19.736 | 112.133 | 1.00 36.83 | N |
| ATOM | 795 | CA | LEU | A | 319 | 23.671 | 19.964 | 113.241 | 1.00 40.24 | C |
| ATOM | 796 | C | LEU | A | 319 | 24.324 | 20.527 | 114.495 | 1.00 42.13 | C |
| ATOM | 797 | O | LEU | A | 319 | 25.352 | 20.018 | 114.916 | 1.00 39.77 | O |
| ATOM | 798 | CB | LEU | A | 319 | 22.966 | 18.645 | 113.600 | 1.00 38.94 | C |
| ATOM | 799 | CG | LEU | A | 319 | 22.092 | 17.912 | 112.604 | 1.00 37.12 | C |
| ATOM | 800 | CD1 | LEU | A | 319 | 21.521 | 16.625 | 113.199 | 1.00 36.00 | C |
| ATOM | 801 | CD2 | LEU | A | 319 | 20.902 | 18.756 | 112.136 | 1.00 37.44 | C |
| ATOM | 802 | N | ASP | A | 320 | 23.705 | 21.574 | 115.037 | 1.00 45.30 | N |
| ATOM | 803 | CA | ASP | A | 320 | 24.180 | 22.228 | 116.257 | 1.00 48.35 | C |
| ATOM | 804 | C | ASP | A | 320 | 23.742 | 21.406 | 117.466 | 1.00 46.10 | C |
| ATOM | 805 | O | ASP | A | 320 | 22.720 | 20.726 | 117.409 | 1.00 44.70 | O |
| ATOM | 806 | CB | ASP | A | 320 | 23.505 | 23.595 | 116.439 | 1.00 52.27 | C |
| ATOM | 807 | CG | ASP | A | 320 | 24.318 | 24.792 | 116.036 | 1.00 55.76 | C |
| ATOM | 808 | OD1 | ASP | A | 320 | 24.524 | 25.101 | 114.850 | 1.00 55.91 | O |
| ATOM | 809 | OD2 | ASP | A | 320 | 24.831 | 25.464 | 116.969 | 1.00 60.18 | O |
| ATOM | 810 | N | ARG | A | 321 | 24.427 | 21.503 | 118.575 | 1.00 46.50 | N |
| ATOM | 811 | CA | ARG | A | 321 | 23.995 | 20.803 | 119.786 | 1.00 48.41 | C |
| ATOM | 812 | C | ARG | A | 321 | 22.515 | 20.986 | 120.054 | 1.00 48.21 | C |
| ATOM | 813 | O | ARG | A | 321 | 21.796 | 19.998 | 120.124 | 1.00 48.20 | O |
| ATOM | 814 | CB | ARG | A | 321 | 24.892 | 21.318 | 120.915 | 1.00 49.79 | C |
| ATOM | 815 | CG | ARG | A | 321 | 24.756 | 20.575 | 122.237 | 1.00 50.69 | C |
| ATOM | 816 | CD | ARG | A | 321 | 23.645 | 21.102 | 123.114 | 1.00 49.10 | C |
| ATOM | 817 | NE | ARG | A | 321 | 23.674 | 20.421 | 124.412 | 1.00 51.19 | N |
| ATOM | 818 | CZ | ARG | A | 321 | 22.726 | 20.507 | 125.345 | 1.00 50.85 | C |
| ATOM | 819 | NH1 | ARG | A | 321 | 21.658 | 21.250 | 125.127 | 1.00 50.36 | N |
| ATOM | 820 | NH2 | ARG | A | 321 | 22.816 | 19.857 | 126.499 | 1.00 51.16 | N |
| ATOM | 821 | N | ASP | A | 322 | 21.963 | 22.184 | 120.177 | 1.00 49.80 | N |
| ATOM | 822 | CA | ASP | A | 322 | 20.588 | 22.532 | 120.443 | 1.00 50.85 | C |
| ATOM | 823 | C | ASP | A | 322 | 19.538 | 22.037 | 119.466 | 1.00 50.52 | C |
| ATOM | 824 | O | ASP | A | 322 | 18.349 | 22.094 | 119.818 | 1.00 51.42 | O |
| ATOM | 825 | CB | ASP | A | 322 | 20.329 | 24.048 | 120.573 | 1.00 52.13 | C |
| ATOM | 826 | CG | ASP | A | 322 | 21.027 | 24.725 | 121.728 | 1.00 54.56 | C |
| ATOM | 827 | OD1 | ASP | A | 322 | 21.412 | 24.078 | 122.735 | 1.00 52.98 | O |
| ATOM | 828 | OD2 | ASP | A | 322 | 21.221 | 25.971 | 121.595 | 1.00 56.37 | O |
| ATOM | 829 | N | GLU | A | 323 | 19.844 | 21.532 | 118.294 | 1.00 48.70 | N |
| ATOM | 830 | CA | GLU | A | 323 | 18.855 | 20.982 | 117.389 | 1.00 50.83 | C |
| ATOM | 831 | C | GLU | A | 323 | 18.422 | 19.605 | 117.892 | 1.00 51.12 | C |
| ATOM | 832 | O | GLU | A | 323 | 17.410 | 19.027 | 117.494 | 1.00 49.12 | O |
| ATOM | 833 | CB | GLU | A | 323 | 19.390 | 20.920 | 115.953 | 1.00 53.96 | C |
| ATOM | 834 | CG | GLU | A | 323 | 19.270 | 22.299 | 115.317 | 1.00 58.02 | C |
| ATOM | 835 | CD | GLU | A | 323 | 19.937 | 22.494 | 113.985 | 1.00 59.95 | C |
| ATOM | 836 | OE1 | GLU | A | 323 | 21.145 | 22.788 | 113.900 | 1.00 60.17 | O |
| ATOM | 837 | OE2 | GLU | A | 323 | 19.195 | 22.365 | 112.988 | 1.00 62.71 | O |
| ATOM | 838 | N | GLY | A | 324 | 19.187 | 19.048 | 118.840 | 1.00 50.69 | N |
| ATOM | 839 | CA | GLY | A | 324 | 18.910 | 17.793 | 119.481 | 1.00 52.58 | C |
| ATOM | 840 | C | GLY | A | 324 | 17.668 | 17.930 | 120.351 | 1.00 55.47 | C |
| ATOM | 841 | O | GLY | A | 324 | 16.865 | 17.008 | 120.447 | 1.00 55.54 | O |
| ATOM | 842 | N | LYS | A | 325 | 17.451 | 19.105 | 120.932 | 1.00 57.86 | N |
| ATOM | 843 | CA | LYS | A | 325 | 16.291 | 19.417 | 121.743 | 1.00 60.66 | C |
| ATOM | 844 | C | LYS | A | 325 | 14.966 | 19.124 | 121.044 | 1.00 60.70 | C |
| ATOM | 845 | O | LYS | A | 325 | 13.998 | 18.787 | 121.729 | 1.00 61.66 | O |
| ATOM | 846 | CB | LYS | A | 325 | 16.311 | 20.876 | 122.203 | 1.00 60.67 | C |
| ATOM | 847 | CG | LYS | A | 325 | 17.381 | 21.278 | 123.186 | 1.00 61.57 | C |
| ATOM | 848 | CD | LYS | A | 325 | 17.575 | 22.784 | 123.226 | 1.00 61.39 | C |
| ATOM | 849 | CE | LYS | A | 325 | 18.303 | 23.258 | 124.456 | 1.00 62.58 | C |
| ATOM | 850 | NZ | LYS | A | 325 | 18.330 | 24.759 | 124.513 | 1.00 64.75 | N |
| ATOM | 851 | N | CYS | A | 326 | 14.847 | 19.191 | 119.734 | 1.00 61.72 | N |
| ATOM | 852 | CA | CYS | A | 326 | 13.632 | 18.905 | 119.012 | 1.00 63.53 | C |
| ATOM | 853 | C | CYS | A | 326 | 13.193 | 17.441 | 119.018 | 1.00 62.28 | C |
| ATOM | 854 | O | CYS | A | 326 | 11.980 | 17.232 | 118.905 | 1.00 62.36 | O |
| ATOM | 855 | CB | CYS | A | 326 | 13.743 | 19.255 | 117.521 | 1.00 65.71 | C |
| ATOM | 856 | SG | CYS | A | 326 | 14.510 | 20.822 | 117.095 | 1.00 72.09 | S |
| ATOM | 857 | N | VAL | A | 327 | 14.107 | 16.465 | 119.050 | 1.00 58.35 | N |
| ATOM | 858 | CA | VAL | A | 327 | 13.637 | 15.080 | 119.021 | 1.00 54.82 | C |
| ATOM | 859 | C | VAL | A | 327 | 13.887 | 14.425 | 120.372 | 1.00 53.47 | C |
| ATOM | 860 | O | VAL | A | 327 | 15.014 | 14.408 | 120.858 | 1.00 52.44 | O |
| ATOM | 861 | CB | VAL | A | 327 | 14.284 | 14.263 | 117.894 | 1.00 54.60 | C |
| ATOM | 862 | CG1 | VAL | A | 327 | 13.678 | 12.865 | 117.855 | 1.00 53.26 | C |
| ATOM | 863 | CG2 | VAL | A | 327 | 14.187 | 14.964 | 116.548 | 1.00 52.73 | C |
| ATOM | 864 | N | GLU | A | 328 | 12.859 | 13.880 | 120.997 | 1.00 50.55 | N |
| ATOM | 865 | CA | GLU | A | 328 | 12.976 | 13.226 | 122.289 | 1.00 49.14 | C |

| | | | | | | | | | |
|---|---|---|---|---|---|---|---|---|---|
| ATOM | 710 | CE1 | HIS A 307 | 35.098 | 23.136 | 111.281 | 1.00 | 38.19 | C |
| ATOM | 711 | NE2 | HIS A 307 | 34.690 | 24.305 | 111.706 | 1.00 | 39.34 | N |
| ATOM | 712 | N | PRO A 308 | 33.781 | 22.458 | 117.881 | 1.00 | 34.63 | N |
| ATOM | 713 | CA | PRO A 308 | 33.042 | 22.406 | 119.126 | 1.00 | 35.50 | C |
| ATOM | 714 | C | PRO A 308 | 31.574 | 22.684 | 118.929 | 1.00 | 34.86 | C |
| ATOM | 715 | O | PRO A 308 | 31.214 | 23.536 | 118.107 | 1.00 | 34.92 | O |
| ATOM | 716 | CB | PRO A 308 | 33.654 | 23.543 | 120.001 | 1.00 | 37.48 | C |
| ATOM | 717 | CG | PRO A 308 | 35.086 | 23.557 | 119.481 | 1.00 | 36.81 | C |
| ATOM | 718 | CD | PRO A 308 | 35.056 | 23.197 | 118.022 | 1.00 | 35.14 | C |
| ATOM | 719 | N | GLY A 309 | 30.659 | 21.997 | 119.605 | 1.00 | 33.22 | N |
| ATOM | 720 | CA | GLY A 309 | 29.236 | 22.258 | 119.467 | 1.00 | 30.56 | C |
| ATOM | 721 | C | GLY A 309 | 28.564 | 21.821 | 118.192 | 1.00 | 32.45 | C |
| ATOM | 722 | O | GLY A 309 | 27.337 | 21.973 | 118.089 | 1.00 | 31.17 | O |
| ATOM | 723 | N | LYS A 310 | 29.265 | 21.292 | 117.177 | 1.00 | 30.62 | N |
| ATOM | 724 | CA | LYS A 310 | 28.558 | 20.906 | 115.982 | 1.00 | 30.60 | C |
| ATOM | 725 | C | LYS A 310 | 28.791 | 19.433 | 115.667 | 1.00 | 28.93 | C |
| ATOM | 726 | O | LYS A 310 | 29.830 | 18.888 | 115.981 | 1.00 | 28.43 | O |
| ATOM | 727 | CB | LYS A 310 | 29.040 | 21.656 | 114.734 | 1.00 | 33.04 | C |
| ATOM | 728 | CG | LYS A 310 | 29.486 | 23.078 | 114.889 | 1.00 | 36.29 | C |
| ATOM | 729 | CD | LYS A 310 | 28.343 | 24.029 | 115.193 | 1.00 | 38.31 | C |
| ATOM | 732 | N | LEU A 311 | 27.847 | 18.838 | 114.977 | 1.00 | 23.97 | N |
| ATOM | 733 | CA | LEU A 311 | 27.941 | 17.485 | 114.532 | 1.00 | 22.12 | C |
| ATOM | 734 | C | LEU A 311 | 27.892 | 17.582 | 113.004 | 1.00 | 23.06 | C |
| ATOM | 735 | O | LEU A 311 | 26.843 | 17.939 | 112.432 | 1.00 | 23.88 | O |
| ATOM | 736 | CB | LEU A 311 | 26.821 | 16.615 | 115.102 | 1.00 | 22.17 | C |
| ATOM | 737 | CG | LEU A 311 | 27.028 | 16.295 | 116.598 | 1.00 | 24.76 | C |
| ATOM | 738 | CD1 | LEU A 311 | 25.881 | 15.438 | 117.148 | 1.00 | 22.60 | C |
| ATOM | 739 | CD2 | LEU A 311 | 28.390 | 15.653 | 116.804 | 1.00 | 24.14 | C |
| ATOM | 740 | N | ILE A 312 | 29.000 | 17.284 | 112.352 | 1.00 | 21.46 | N |
| ATOM | 741 | CA | ILE A 312 | 28.993 | 17.361 | 110.866 | 1.00 | 21.24 | C |
| ATOM | 742 | C | ILE A 312 | 28.622 | 16.000 | 110.347 | 1.00 | 21.44 | C |
| ATOM | 743 | O | ILE A 312 | 29.460 | 15.196 | 109.924 | 1.00 | 20.99 | O |
| ATOM | 744 | CB | ILE A 312 | 30.361 | 17.864 | 110.336 | 1.00 | 22.62 | C |
| ATOM | 745 | CG1 | ILE A 312 | 30.619 | 19.256 | 110.943 | 1.00 | 23.20 | C |
| ATOM | 746 | CG2 | ILE A 312 | 30.410 | 18.002 | 108.816 | 1.00 | 22.05 | C |
| ATOM | 747 | CD1 | ILE A 312 | 31.973 | 19.857 | 110.635 | 1.00 | 27.58 | C |
| ATOM | 748 | N | PHE A 313 | 27.336 | 15.674 | 110.339 | 1.00 | 21.74 | N |
| ATOM | 749 | CA | PHE A 313 | 26.856 | 14.394 | 109.840 | 1.00 | 22.28 | C |
| ATOM | 750 | C | PHE A 313 | 27.231 | 14.201 | 108.390 | 1.00 | 22.59 | C |
| ATOM | 751 | O | PHE A 313 | 27.606 | 13.099 | 107.979 | 1.00 | 24.84 | O |
| ATOM | 752 | CB | PHE A 313 | 25.349 | 14.186 | 110.076 | 1.00 | 22.65 | C |
| ATOM | 753 | CG | PHE A 313 | 25.017 | 13.806 | 111.513 | 1.00 | 24.21 | C |
| ATOM | 754 | CD1 | PHE A 313 | 25.002 | 12.484 | 111.917 | 1.00 | 22.41 | C |
| ATOM | 755 | CD2 | PHE A 313 | 24.695 | 14.762 | 112.453 | 1.00 | 24.74 | C |
| ATOM | 756 | CE1 | PHE A 313 | 24.671 | 12.136 | 113.207 | 1.00 | 25.97 | C |
| ATOM | 757 | CE2 | PHE A 313 | 24.376 | 14.433 | 113.773 | 1.00 | 24.45 | C |
| ATOM | 758 | CZ | PHE A 313 | 24.379 | 13.103 | 114.169 | 1.00 | 24.29 | C |
| ATOM | 759 | N | ALA A 314 | 27.106 | 15.214 | 107.561 | 1.00 | 23.48 | N |
| ATOM | 760 | CA | ALA A 314 | 27.391 | 15.120 | 106.140 | 1.00 | 26.00 | C |
| ATOM | 761 | C | ALA A 314 | 27.512 | 16.551 | 105.627 | 1.00 | 25.27 | C |
| ATOM | 762 | O | ALA A 314 | 27.048 | 17.481 | 106.249 | 1.00 | 22.11 | O |
| ATOM | 763 | CB | ALA A 314 | 26.267 | 14.403 | 105.356 | 1.00 | 20.15 | C |
| ATOM | 764 | N | PRO A 315 | 28.045 | 16.663 | 104.441 | 1.00 | 28.32 | N |
| ATOM | 765 | CA | PRO A 315 | 28.135 | 17.957 | 103.757 | 1.00 | 31.55 | C |
| ATOM | 766 | C | PRO A 315 | 26.772 | 18.610 | 103.711 | 1.00 | 34.81 | C |
| ATOM | 767 | O | PRO A 315 | 26.824 | 19.824 | 103.982 | 1.00 | 34.26 | O |
| ATOM | 768 | CB | PRO A 315 | 28.786 | 17.688 | 102.420 | 1.00 | 30.21 | C |
| ATOM | 769 | CG | PRO A 315 | 29.518 | 16.376 | 102.699 | 1.00 | 28.22 | C |
| ATOM | 770 | CD | PRO A 315 | 28.578 | 15.592 | 103.596 | 1.00 | 25.78 | C |
| ATOM | 771 | N | ASP A 316 | 25.560 | 18.152 | 103.479 | 1.00 | 35.75 | N |
| ATOM | 772 | CA | ASP A 316 | 24.463 | 19.174 | 103.611 | 1.00 | 40.23 | C |
| ATOM | 773 | C | ASP A 316 | 23.660 | 18.869 | 104.875 | 1.00 | 37.14 | C |
| ATOM | 774 | O | ASP A 316 | 22.434 | 18.912 | 104.905 | 1.00 | 35.59 | O |
| ATOM | 775 | CB | ASP A 316 | 23.587 | 19.308 | 102.388 | 1.00 | 45.16 | C |
| ATOM | 776 | CG | ASP A 316 | 23.413 | 20.737 | 101.900 | 1.00 | 51.46 | C |
| ATOM | 777 | OD1 | ASP A 316 | 23.936 | 21.725 | 102.483 | 1.00 | 53.99 | O |
| ATOM | 778 | OD2 | ASP A 316 | 22.741 | 20.966 | 100.848 | 1.00 | 54.15 | O |
| ATOM | 779 | N | LEU A 317 | 24.338 | 18.484 | 105.947 | 1.00 | 35.29 | N |
| ATOM | 780 | CA | LEU A 317 | 23.637 | 18.149 | 107.185 | 1.00 | 32.38 | C |
| ATOM | 781 | C | LEU A 317 | 24.542 | 18.436 | 108.363 | 1.00 | 31.84 | C |
| ATOM | 782 | O | LEU A 317 | 25.238 | 17.563 | 108.898 | 1.00 | 32.48 | O |
| ATOM | 783 | CB | LEU A 317 | 23.190 | 16.692 | 107.154 | 1.00 | 33.55 | C |
| ATOM | 784 | CG | LEU A 317 | 22.529 | 16.152 | 108.428 | 1.00 | 37.02 | C |
| ATOM | 785 | CD1 | LEU A 317 | 21.383 | 17.059 | 108.865 | 1.00 | 38.32 | C |
| ATOM | 786 | CD2 | LEU A 317 | 22.009 | 14.726 | 108.232 | 1.00 | 37.75 | C |
| ATOM | 787 | N | VAL A 318 | 24.612 | 19.687 | 108.763 | 1.00 | 31.32 | N |
| ATOM | 788 | CA | VAL A 318 | 25.432 | 20.131 | 109.865 | 1.00 | 30.54 | C |

| | | | | | | | | | |
|---|---|---|---|---|---|---|---|---|---|
| ATOM | 633 | SD | MET A 298 | 36.331 | 6.909 | 116.348 | 1.00 | 20.52 | S |
| ATOM | 634 | CE | MET A 298 | 37.748 | 7.911 | 115.892 | 1.00 | 19.49 | C |
| ATOM | 635 | N | GLY A 299 | 33.288 | 7.965 | 112.307 | 1.00 | 18.33 | N |
| ATOM | 636 | CA | GLY A 299 | 33.481 | 8.886 | 111.204 | 1.00 | 16.45 | C |
| ATOM | 637 | C | GLY A 299 | 32.904 | 10.283 | 111.510 | 1.00 | 20.46 | C |
| ATOM | 638 | O | GLY A 299 | 33.554 | 11.317 | 111.249 | 1.00 | 18.84 | O |
| ATOM | 639 | N | LEU A 300 | 31.687 | 10.334 | 112.093 | 1.00 | 21.17 | N |
| ATOM | 640 | CA | LEU A 300 | 31.044 | 11.579 | 112.483 | 1.00 | 20.36 | C |
| ATOM | 641 | C | LEU A 300 | 31.968 | 12.356 | 113.442 | 1.00 | 22.15 | C |
| ATOM | 642 | O | LEU A 300 | 32.149 | 13.560 | 113.281 | 1.00 | 21.60 | O |
| ATOM | 643 | CB | LEU A 300 | 29.773 | 11.254 | 113.279 | 1.00 | 19.44 | C |
| ATOM | 644 | CG | LEU A 300 | 29.065 | 12.379 | 114.014 | 1.00 | 21.19 | C |
| ATOM | 645 | CD1 | LEU A 300 | 28.508 | 13.436 | 113.052 | 1.00 | 19.28 | C |
| ATOM | 646 | CD2 | LEU A 300 | 27.922 | 11.851 | 114.882 | 1.00 | 21.22 | C |
| ATOM | 647 | N | MET A 301 | 32.579 | 11.646 | 114.403 | 1.00 | 19.05 | N |
| ATOM | 648 | CA | MET A 301 | 33.416 | 12.290 | 115.390 | 1.00 | 19.82 | C |
| ATOM | 649 | C | MET A 301 | 34.669 | 12.857 | 114.723 | 1.00 | 19.63 | C |
| ATOM | 650 | O | MET A 301 | 35.129 | 13.929 | 115.120 | 1.00 | 21.94 | O |
| ATOM | 651 | CB | MET A 301 | 33.874 | 11.365 | 116.521 | 1.00 | 18.43 | C |
| ATOM | 652 | CG | MET A 301 | 32.737 | 10.955 | 117.457 | 1.00 | 22.68 | C |
| ATOM | 653 | SD | MET A 301 | 33.329 | 9.645 | 118.578 | 1.00 | 25.98 | S |
| ATOM | 654 | CE | MET A 301 | 31.818 | 8.925 | 119.128 | 1.00 | 22.42 | C |
| ATOM | 655 | N | TRP A 302 | 35.236 | 12.130 | 113.787 | 1.00 | 18.09 | N |
| ATOM | 656 | CA | TRP A 302 | 36.408 | 12.640 | 113.073 | 1.00 | 20.53 | C |
| ATOM | 657 | C | TRP A 302 | 35.971 | 13.825 | 112.210 | 1.00 | 19.43 | C |
| ATOM | 658 | O | TRP A 302 | 36.672 | 14.824 | 112.179 | 1.00 | 18.86 | O |
| ATOM | 659 | CB | TRP A 302 | 36.966 | 11.532 | 112.186 | 1.00 | 22.54 | C |
| ATOM | 660 | CG | TRP A 302 | 38.137 | 11.886 | 111.335 | 1.00 | 20.86 | C |
| ATOM | 661 | CD1 | TRP A 302 | 38.149 | 11.857 | 109.971 | 1.00 | 19.57 | C |
| ATOM | 662 | CD2 | TRP A 302 | 39.439 | 12.310 | 111.765 | 1.00 | 21.17 | C |
| ATOM | 663 | NE1 | TRP A 302 | 39.397 | 12.244 | 109.524 | 1.00 | 21.78 | N |
| ATOM | 664 | CE2 | TRP A 302 | 40.195 | 12.551 | 110.597 | 1.00 | 21.00 | C |
| ATOM | 665 | CE3 | TRP A 302 | 40.028 | 12.547 | 113.010 | 1.00 | 21.14 | C |
| ATOM | 666 | CZ2 | TRP A 302 | 41.526 | 12.969 | 110.626 | 1.00 | 21.36 | C |
| ATOM | 667 | CZ3 | TRP A 302 | 41.352 | 12.993 | 113.035 | 1.00 | 23.25 | C |
| ATOM | 668 | CH2 | TRP A 302 | 42.096 | 13.180 | 111.839 | 1.00 | 21.21 | C |
| ATOM | 669 | N | ARG A 303 | 34.811 | 13.744 | 111.534 | 1.00 | 18.15 | N |
| ATOM | 670 | CA | ARG A 303 | 34.396 | 14.904 | 110.725 | 1.00 | 20.16 | C |
| ATOM | 671 | C | ARG A 303 | 34.132 | 16.131 | 111.600 | 1.00 | 24.09 | C |
| ATOM | 672 | O | ARG A 303 | 34.244 | 17.242 | 111.080 | 1.00 | 21.31 | O |
| ATOM | 673 | CB | ARG A 303 | 33.115 | 14.652 | 109.944 | 1.00 | 18.84 | C |
| ATOM | 674 | CG | ARG A 303 | 33.351 | 13.626 | 108.813 | 1.00 | 23.11 | C |
| ATOM | 675 | CD | ARG A 303 | 32.180 | 13.496 | 107.859 | 1.00 | 20.12 | C |
| ATOM | 676 | NE | ARG A 303 | 30.961 | 12.991 | 108.496 | 1.00 | 19.15 | N |
| ATOM | 677 | CZ | ARG A 303 | 30.656 | 11.747 | 108.809 | 1.00 | 21.36 | C |
| ATOM | 678 | NH1 | ARG A 303 | 31.555 | 10.787 | 108.512 | 1.00 | 20.72 | N |
| ATOM | 679 | NH2 | ARG A 303 | 29.519 | 11.313 | 109.393 | 1.00 | 17.60 | N |
| ATOM | 680 | N | SER A 304 | 33.762 | 15.988 | 112.885 | 1.00 | 23.88 | N |
| ATOM | 681 | CA | SER A 304 | 33.417 | 17.125 | 113.707 | 1.00 | 22.87 | C |
| ATOM | 682 | C | SER A 304 | 34.487 | 17.529 | 114.716 | 1.00 | 22.08 | C |
| ATOM | 683 | O | SER A 304 | 34.248 | 18.458 | 115.482 | 1.00 | 24.18 | O |
| ATOM | 684 | CB | SER A 304 | 32.209 | 16.742 | 114.618 | 1.00 | 20.59 | C |
| ATOM | 685 | OG | SER A 304 | 31.295 | 16.081 | 113.761 | 1.00 | 20.75 | O |
| ATOM | 686 | N | ILE A 305 | 35.627 | 16.870 | 114.722 | 1.00 | 18.97 | N |
| ATOM | 687 | CA | ILE A 305 | 36.671 | 17.155 | 115.677 | 1.00 | 20.77 | C |
| ATOM | 688 | C | ILE A 305 | 37.078 | 18.592 | 115.803 | 1.00 | 25.23 | C |
| ATOM | 689 | O | ILE A 305 | 37.456 | 19.009 | 116.912 | 1.00 | 27.74 | O |
| ATOM | 690 | CB | ILE A 305 | 37.891 | 16.232 | 115.380 | 1.00 | 23.50 | C |
| ATOM | 691 | CG1 | ILE A 305 | 38.730 | 16.078 | 116.647 | 1.00 | 22.05 | C |
| ATOM | 692 | CG2 | ILE A 305 | 38.691 | 16.724 | 114.155 | 1.00 | 18.83 | C |
| ATOM | 693 | CD1 | ILE A 305 | 39.822 | 15.008 | 116.548 | 1.00 | 21.70 | C |
| ATOM | 694 | N | ASP A 306 | 37.184 | 19.358 | 114.714 | 1.00 | 27.08 | N |
| ATOM | 695 | CA | ASP A 306 | 37.676 | 20.726 | 114.883 | 1.00 | 31.62 | C |
| ATOM | 696 | C | ASP A 306 | 36.561 | 21.720 | 115.124 | 1.00 | 33.38 | C |
| ATOM | 697 | O | ASP A 306 | 36.864 | 22.910 | 115.129 | 1.00 | 34.90 | O |
| ATOM | 698 | CB | ASP A 306 | 38.515 | 21.126 | 113.666 | 1.00 | 30.90 | C |
| ATOM | 699 | CG | ASP A 306 | 39.786 | 20.290 | 113.656 | 1.00 | 30.70 | C |
| ATOM | 700 | OD1 | ASP A 306 | 40.430 | 20.266 | 114.716 | 1.00 | 32.47 | O |
| ATOM | 701 | OD2 | ASP A 306 | 40.130 | 19.675 | 112.640 | 1.00 | 29.66 | O |
| ATOM | 702 | N | HIS A 307 | 35.322 | 21.328 | 115.330 | 1.00 | 31.61 | N |
| ATOM | 703 | CA | HIS A 307 | 34.215 | 22.218 | 115.518 | 1.00 | 31.19 | C |
| ATOM | 704 | C | HIS A 307 | 33.353 | 21.986 | 116.726 | 1.00 | 32.66 | C |
| ATOM | 705 | O | HIS A 307 | 32.266 | 21.441 | 116.617 | 1.00 | 32.21 | O |
| ATOM | 706 | CB | HIS A 307 | 33.308 | 22.082 | 114.262 | 1.00 | 33.81 | C |
| ATOM | 707 | CG | HIS A 307 | 33.918 | 22.836 | 113.113 | 1.00 | 36.65 | C |
| ATOM | 708 | ND1 | HIS A 307 | 34.659 | 22.227 | 112.134 | 1.00 | 38.40 | N |
| ATOM | 709 | CD2 | HIS A 307 | 33.958 | 24.173 | 112.867 | 1.00 | 36.99 | C |

| | | | | | | | | | |
|---|---|---|---|---|---|---|---|---|---|
| ATOM | 556 | CB | GLU A 289 | 25.649 | -7.876 | 111.408 | 1.00 | 30.64 | C |
| ATOM | 557 | CG | GLU A 289 | 24.213 | -7.874 | 111.877 | 1.00 | 35.44 | C |
| ATOM | 558 | CD | GLU A 289 | 24.061 | -7.860 | 113.383 | 1.00 | 39.64 | C |
| ATOM | 559 | OE1 | GLU A 289 | 24.952 | -8.329 | 114.101 | 1.00 | 38.89 | O |
| ATOM | 560 | OE2 | GLU A 289 | 23.056 | -7.373 | 113.956 | 1.00 | 41.71 | O |
| ATOM | 561 | N | SER A 290 | 27.485 | -6.145 | 113.557 | 1.00 | 28.34 | N |
| ATOM | 562 | CA | SER A 290 | 27.527 | -5.516 | 114.875 | 1.00 | 30.56 | C |
| ATOM | 563 | C | SER A 290 | 28.282 | -4.189 | 114.896 | 1.00 | 26.61 | C |
| ATOM | 564 | O | SER A 290 | 27.885 | -3.460 | 115.778 | 1.00 | 22.62 | O |
| ATOM | 565 | CB | SER A 290 | 28.186 | -6.292 | 116.021 | 1.00 | 30.75 | C |
| ATOM | 566 | OG | SER A 290 | 29.182 | -7.131 | 115.520 | 1.00 | 36.14 | O |
| ATOM | 567 | N | CYS A 291 | 29.128 | -3.914 | 113.920 | 1.00 | 24.24 | N |
| ATOM | 568 | CA | CYS A 291 | 29.852 | -2.652 | 114.060 | 1.00 | 25.87 | C |
| ATOM | 569 | C | CYS A 291 | 29.249 | -1.416 | 113.442 | 1.00 | 22.70 | C |
| ATOM | 570 | O | CYS A 291 | 29.820 | -0.337 | 113.658 | 1.00 | 23.19 | O |
| ATOM | 571 | CB | CYS A 291 | 31.271 | -2.826 | 113.374 | 1.00 | 21.61 | C |
| ATOM | 572 | SG | CYS A 291 | 31.193 | -2.520 | 111.576 | 1.00 | 24.80 | S |
| ATOM | 573 | N | TRP A 292 | 28.246 | -1.538 | 112.607 | 1.00 | 24.57 | N |
| ATOM | 574 | CA | TRP A 292 | 27.847 | -0.425 | 111.744 | 1.00 | 25.71 | C |
| ATOM | 575 | C | TRP A 292 | 27.589 | 0.876 | 112.439 | 1.00 | 25.06 | C |
| ATOM | 576 | O | TRP A 292 | 28.164 | 1.818 | 111.890 | 1.00 | 25.15 | O |
| ATOM | 577 | CB | TRP A 292 | 26.714 | -0.818 | 110.769 | 1.00 | 27.44 | C |
| ATOM | 578 | CG | TRP A 292 | 25.414 | -1.005 | 111.454 | 1.00 | 28.89 | C |
| ATOM | 579 | CD1 | TRP A 292 | 24.945 | -2.173 | 112.008 | 1.00 | 29.92 | C |
| ATOM | 580 | CD2 | TRP A 292 | 24.422 | -0.007 | 111.709 | 1.00 | 30.56 | C |
| ATOM | 581 | NE1 | TRP A 292 | 23.704 | -1.953 | 112.583 | 1.00 | 30.37 | N |
| ATOM | 582 | CE2 | TRP A 292 | 23.359 | -0.642 | 112.407 | 1.00 | 30.38 | C |
| ATOM | 583 | CE3 | TRP A 292 | 24.321 | 1.352 | 111.407 | 1.00 | 29.69 | C |
| ATOM | 584 | CZ2 | TRP A 292 | 22.229 | 0.043 | 112.805 | 1.00 | 31.11 | C |
| ATOM | 585 | CZ3 | TRP A 292 | 23.191 | 2.037 | 111.801 | 1.00 | 29.63 | C |
| ATOM | 586 | CH2 | TRP A 292 | 22.170 | 1.389 | 112.492 | 1.00 | 32.64 | C |
| ATOM | 587 | N | MET A 293 | 26.824 | 0.982 | 113.520 | 1.00 | 24.13 | N |
| ATOM | 588 | CA | MET A 293 | 26.567 | 2.277 | 114.151 | 1.00 | 23.85 | C |
| ATOM | 589 | C | MET A 293 | 27.823 | 2.851 | 114.795 | 1.00 | 24.00 | C |
| ATOM | 590 | O | MET A 293 | 28.021 | 4.070 | 114.699 | 1.00 | 21.96 | O |
| ATOM | 591 | CB | MET A 293 | 25.411 | 2.197 | 115.145 | 1.00 | 24.17 | C |
| ATOM | 592 | CG | MET A 293 | 25.139 | 3.564 | 115.780 | 1.00 | 26.00 | C |
| ATOM | 593 | SD | MET A 293 | 24.338 | 4.689 | 114.620 | 1.00 | 29.32 | S |
| ATOM | 594 | CE | MET A 293 | 22.624 | 4.372 | 115.082 | 1.00 | 28.99 | C |
| ATOM | 595 | N | GLU A 294 | 28.687 | 2.005 | 115.373 | 1.00 | 22.15 | N |
| ATOM | 596 | CA | GLU A 294 | 29.960 | 2.477 | 115.881 | 1.00 | 22.71 | C |
| ATOM | 597 | C | GLU A 294 | 30.890 | 3.082 | 114.813 | 1.00 | 19.95 | C |
| ATOM | 598 | O | GLU A 294 | 31.649 | 4.035 | 115.048 | 1.00 | 14.72 | O |
| ATOM | 599 | CB | GLU A 294 | 30.774 | 1.305 | 116.453 | 1.00 | 24.27 | C |
| ATOM | 600 | CG | GLU A 294 | 30.290 | 0.705 | 117.746 | 1.00 | 27.51 | C |
| ATOM | 601 | CD | GLU A 294 | 31.093 | -0.568 | 118.101 | 1.00 | 28.87 | C |
| ATOM | 602 | OE1 | GLU A 294 | 30.757 | -1.678 | 117.627 | 1.00 | 27.32 | O |
| ATOM | 603 | OE2 | GLU A 294 | 32.061 | -0.332 | 118.839 | 1.00 | 22.15 | O |
| ATOM | 604 | N | VAL A 295 | 31.005 | 2.430 | 113.664 | 1.00 | 19.49 | N |
| ATOM | 605 | CA | VAL A 295 | 31.888 | 2.925 | 112.593 | 1.00 | 19.33 | C |
| ATOM | 606 | C | VAL A 295 | 31.308 | 4.221 | 112.072 | 1.00 | 21.07 | C |
| ATOM | 607 | O | VAL A 295 | 32.020 | 5.205 | 111.882 | 1.00 | 20.94 | O |
| ATOM | 608 | CB | VAL A 295 | 32.086 | 1.858 | 111.500 | 1.00 | 20.31 | C |
| ATOM | 609 | CG1 | VAL A 295 | 32.872 | 2.354 | 110.314 | 1.00 | 17.43 | C |
| ATOM | 610 | CG2 | VAL A 295 | 32.817 | 0.647 | 112.117 | 1.00 | 19.70 | C |
| ATOM | 611 | N | LEU A 296 | 29.992 | 4.330 | 111.870 | 1.00 | 21.83 | N |
| ATOM | 612 | CA | LEU A 296 | 29.356 | 5.554 | 111.440 | 1.00 | 20.43 | C |
| ATOM | 613 | C | LEU A 296 | 29.651 | 6.691 | 112.410 | 1.00 | 21.83 | C |
| ATOM | 614 | O | LEU A 296 | 30.069 | 7.788 | 112.007 | 1.00 | 19.76 | O |
| ATOM | 615 | CB | LEU A 296 | 27.825 | 5.383 | 111.302 | 1.00 | 19.34 | C |
| ATOM | 616 | CG | LEU A 296 | 27.305 | 4.609 | 110.089 | 1.00 | 20.72 | C |
| ATOM | 617 | CD1 | LEU A 296 | 25.812 | 4.834 | 109.856 | 1.00 | 18.60 | C |
| ATOM | 618 | CD2 | LEU A 296 | 28.018 | 4.945 | 108.779 | 1.00 | 21.67 | C |
| ATOM | 619 | N | MET A 297 | 29.468 | 6.433 | 113.717 | 1.00 | 21.58 | N |
| ATOM | 620 | CA | MET A 297 | 29.677 | 7.438 | 114.758 | 1.00 | 20.59 | C |
| ATOM | 621 | C | MET A 297 | 31.153 | 7.784 | 114.877 | 1.00 | 18.13 | C |
| ATOM | 622 | O | MET A 297 | 31.451 | 8.940 | 115.168 | 1.00 | 19.07 | O |
| ATOM | 623 | CB | MET A 297 | 29.081 | 7.040 | 116.123 | 1.00 | 19.88 | C |
| ATOM | 624 | CG | MET A 297 | 27.540 | 7.127 | 116.115 | 1.00 | 20.69 | C |
| ATOM | 625 | SD | MET A 297 | 26.942 | 6.460 | 117.718 | 1.00 | 18.06 | S |
| ATOM | 626 | CE | MET A 297 | 25.266 | 7.059 | 117.804 | 1.00 | 15.51 | C |
| ATOM | 627 | N | MET A 298 | 32.076 | 6.866 | 114.643 | 1.00 | 17.29 | N |
| ATOM | 628 | CA | MET A 298 | 33.495 | 7.250 | 114.689 | 1.00 | 18.54 | C |
| ATOM | 629 | C | MET A 298 | 33.835 | 8.193 | 113.521 | 1.00 | 20.06 | C |
| ATOM | 630 | O | MET A 298 | 34.520 | 9.216 | 113.699 | 1.00 | 18.27 | O |
| ATOM | 631 | CB | MET A 298 | 34.363 | 6.001 | 114.688 | 1.00 | 17.67 | C |
| ATOM | 632 | CG | MET A 298 | 35.837 | 6.347 | 114.700 | 1.00 | 19.24 | C |

| ATOM | 474 | CD1 | LEU A 279 | 37.648 | -11.119 | 109.419 | 1.00 | 29.53 | C |
| ATOM | 475 | CD2 | LEU A 279 | 39.587 | -12.743 | 109.379 | 1.00 | 24.65 | C |
| ATOM | 476 | N | SER A 280 | 36.423 | -15.871 | 107.119 | 1.00 | 34.24 | N |
| ATOM | 477 | CA | SER A 280 | 35.257 | -16.587 | 106.623 | 1.00 | 36.14 | C |
| ATOM | 478 | C | SER A 280 | 34.125 | -15.581 | 106.477 | 1.00 | 38.71 | C |
| ATOM | 479 | O | SER A 280 | 34.072 | -14.557 | 107.184 | 1.00 | 38.62 | O |
| ATOM | 480 | CB | SER A 280 | 34.766 | -17.616 | 107.636 | 1.00 | 35.56 | C |
| ATOM | 481 | OG | SER A 280 | 34.155 | -16.981 | 108.745 | 1.00 | 37.07 | O |
| ATOM | 482 | N | LEU A 281 | 33.187 | -15.926 | 105.611 | 1.00 | 41.27 | N |
| ATOM | 483 | CA | LEU A 281 | 32.017 | -15.100 | 105.346 | 1.00 | 43.17 | C |
| ATOM | 484 | C | LEU A 281 | 31.229 | -14.854 | 106.617 | 1.00 | 40.04 | C |
| ATOM | 485 | O | LEU A 281 | 30.712 | -13.763 | 106.850 | 1.00 | 39.57 | O |
| ATOM | 486 | CB | LEU A 281 | 31.077 | -15.701 | 104.298 | 1.00 | 47.74 | C |
| ATOM | 487 | CG | LEU A 281 | 30.981 | -15.036 | 102.922 | 1.00 | 51.84 | C |
| ATOM | 488 | CD1 | LEU A 281 | 30.789 | -13.523 | 102.988 | 1.00 | 50.83 | C |
| ATOM | 489 | CD2 | LEU A 281 | 32.208 | -15.354 | 102.077 | 1.00 | 52.08 | C |
| ATOM | 490 | N | PHE A 282 | 31.098 | -15.910 | 107.403 | 1.00 | 37.77 | N |
| ATOM | 491 | CA | PHE A 282 | 30.405 | -15.808 | 108.683 | 1.00 | 37.49 | C |
| ATOM | 492 | C | PHE A 282 | 31.041 | -14.700 | 109.511 | 1.00 | 35.36 | C |
| ATOM | 493 | O | PHE A 282 | 30.282 | -13.889 | 110.067 | 1.00 | 36.94 | O |
| ATOM | 494 | CB | PHE A 282 | 30.442 | -17.169 | 109.361 | 1.00 | 41.55 | C |
| ATOM | 495 | CG | PHE A 282 | 30.120 | -17.154 | 110.823 | 1.00 | 46.97 | C |
| ATOM | 496 | CD1 | PHE A 282 | 28.804 | -17.237 | 111.249 | 1.00 | 48.13 | C |
| ATOM | 497 | CD2 | PHE A 282 | 31.118 | -17.041 | 111.782 | 1.00 | 48.49 | C |
| ATOM | 498 | CE1 | PHE A 282 | 28.457 | -17.221 | 112.582 | 1.00 | 47.03 | C |
| ATOM | 499 | CE2 | PHE A 282 | 30.788 | -17.018 | 113.125 | 1.00 | 51.42 | C |
| ATOM | 500 | CZ | PHE A 282 | 29.457 | -17.116 | 113.522 | 1.00 | 49.60 | C |
| ATOM | 501 | N | ASP A 283 | 32.355 | -14.596 | 109.631 | 1.00 | 31.57 | N |
| ATOM | 502 | CA | ASP A 283 | 32.936 | -13.494 | 110.407 | 1.00 | 32.56 | C |
| ATOM | 503 | C | ASP A 283 | 32.782 | -12.114 | 109.754 | 1.00 | 29.94 | C |
| ATOM | 504 | O | ASP A 283 | 32.443 | -11.150 | 110.464 | 1.00 | 27.31 | O |
| ATOM | 505 | CB | ASP A 283 | 34.403 | -13.780 | 110.700 | 1.00 | 33.99 | C |
| ATOM | 506 | CG | ASP A 283 | 34.456 | -14.956 | 111.666 | 1.00 | 35.81 | C |
| ATOM | 507 | OD1 | ASP A 283 | 33.464 | -15.252 | 112.365 | 1.00 | 37.44 | O |
| ATOM | 508 | OD2 | ASP A 283 | 35.522 | -15.574 | 111.693 | 1.00 | 39.54 | O |
| ATOM | 509 | N | GLN A 284 | 32.877 | -12.041 | 108.444 | 1.00 | 25.34 | N |
| ATOM | 510 | CA | GLN A 284 | 32.677 | -10.765 | 107.749 | 1.00 | 28.85 | C |
| ATOM | 511 | C | GLN A 284 | 31.298 | -10.180 | 108.060 | 1.00 | 28.79 | C |
| ATOM | 512 | O | GLN A 284 | 31.189 | -9.017 | 108.452 | 1.00 | 26.78 | O |
| ATOM | 513 | CB | GLN A 284 | 32.810 | -10.889 | 106.217 | 1.00 | 26.15 | C |
| ATOM | 514 | CG | GLN A 284 | 34.170 | -11.460 | 105.825 | 1.00 | 28.32 | C |
| ATOM | 515 | CD | GLN A 284 | 34.331 | -11.567 | 104.312 | 1.00 | 31.89 | C |
| ATOM | 516 | OE1 | GLN A 284 | 33.892 | -10.686 | 103.553 | 1.00 | 32.16 | O |
| ATOM | 517 | NE2 | GLN A 284 | 34.983 | -12.633 | 103.858 | 1.00 | 31.37 | N |
| ATOM | 518 | N | VAL A 285 | 30.282 | -11.033 | 107.919 | 1.00 | 26.85 | N |
| ATOM | 519 | CA | VAL A 285 | 28.915 | -10.641 | 108.188 | 1.00 | 28.51 | C |
| ATOM | 520 | C | VAL A 285 | 28.673 | -10.279 | 109.645 | 1.00 | 28.58 | C |
| ATOM | 521 | O | VAL A 285 | 27.999 | -9.290 | 109.931 | 1.00 | 26.18 | O |
| ATOM | 522 | CB | VAL A 285 | 27.943 | -11.746 | 107.702 | 1.00 | 28.59 | C |
| ATOM | 523 | CG1 | VAL A 285 | 26.557 | -11.537 | 108.262 | 1.00 | 26.82 | C |
| ATOM | 524 | CG2 | VAL A 285 | 27.923 | -11.750 | 106.160 | 1.00 | 27.73 | C |
| ATOM | 525 | N | ARG A 286 | 29.203 | -11.066 | 110.570 | 1.00 | 29.36 | N |
| ATOM | 526 | CA | ARG A 286 | 29.052 | -10.819 | 111.996 | 1.00 | 29.97 | C |
| ATOM | 527 | C | ARG A 286 | 29.734 | -9.495 | 112.369 | 1.00 | 27.54 | C |
| ATOM | 528 | O | ARG A 286 | 29.144 | -8.689 | 113.057 | 1.00 | 25.10 | O |
| ATOM | 529 | CB | ARG A 286 | 29.766 | -11.920 | 112.790 | 1.00 | 31.41 | C |
| ATOM | 530 | CG | ARG A 286 | 29.009 | -13.200 | 112.978 | 1.00 | 35.09 | C |
| ATOM | 536 | N | LEU A 287 | 30.945 | -9.252 | 111.857 | 1.00 | 26.66 | N |
| ATOM | 537 | CA | LEU A 287 | 31.594 | -7.980 | 112.152 | 1.00 | 26.82 | C |
| ATOM | 538 | C | LEU A 287 | 30.767 | -6.836 | 111.564 | 1.00 | 28.02 | C |
| ATOM | 539 | O | LEU A 287 | 30.414 | -5.909 | 112.291 | 1.00 | 27.87 | O |
| ATOM | 540 | CB | LEU A 287 | 33.030 | -7.962 | 111.638 | 1.00 | 27.38 | C |
| ATOM | 541 | CG | LEU A 287 | 33.937 | -9.066 | 112.239 | 1.00 | 27.92 | C |
| ATOM | 542 | CD1 | LEU A 287 | 35.288 | -9.080 | 111.555 | 1.00 | 26.06 | C |
| ATOM | 543 | CD2 | LEU A 287 | 34.110 | -8.784 | 113.737 | 1.00 | 29.64 | C |
| ATOM | 544 | N | LEU A 288 | 30.389 | -6.899 | 110.295 | 1.00 | 26.29 | N |
| ATOM | 545 | CA | LEU A 288 | 29.638 | -5.830 | 109.678 | 1.00 | 27.56 | C |
| ATOM | 546 | C | LEU A 288 | 28.322 | -5.548 | 110.383 | 1.00 | 28.25 | C |
| ATOM | 547 | O | LEU A 288 | 27.991 | -4.389 | 110.658 | 1.00 | 25.84 | O |
| ATOM | 548 | CB | LEU A 288 | 29.448 | -6.082 | 108.170 | 1.00 | 22.24 | C |
| ATOM | 549 | CG | LEU A 288 | 30.785 | -5.971 | 107.399 | 1.00 | 24.44 | C |
| ATOM | 550 | CD1 | LEU A 288 | 30.669 | -6.498 | 105.981 | 1.00 | 22.80 | C |
| ATOM | 551 | CD2 | LEU A 288 | 31.313 | -4.538 | 107.280 | 1.00 | 22.93 | C |
| ATOM | 552 | N | GLU A 289 | 27.605 | -6.610 | 110.719 | 1.00 | 27.92 | N |
| ATOM | 553 | CA | GLU A 289 | 26.316 | -6.485 | 111.397 | 1.00 | 29.85 | C |
| ATOM | 554 | C | GLU A 289 | 26.445 | -5.883 | 112.770 | 1.00 | 28.05 | C |
| ATOM | 555 | O | GLU A 289 | 25.556 | -5.130 | 113.146 | 1.00 | 32.40 | O |

```
ATOM   394  CE2 TRP A 269      37.191   1.202 107.230  1.00 22.19           C
ATOM   395  CE3 TRP A 269      35.025   0.157 107.077  1.00 19.94           C
ATOM   396  CZ2 TRP A 269      37.337   0.890 108.603  1.00 21.87           C
ATOM   397  CZ3 TRP A 269      35.154  -0.120 108.436  1.00 20.46           C
ATOM   398  CH2 TRP A 269      36.288   0.217 109.189  1.00 20.17           C
ATOM   399  N   ALA A 270      35.444  -1.886 104.165  1.00 22.64           N
ATOM   400  CA  ALA A 270      35.890  -3.095 104.887  1.00 22.36           C
ATOM   401  C   ALA A 270      36.539  -4.109 103.956  1.00 24.63           C
ATOM   402  O   ALA A 270      37.577  -4.713 104.257  1.00 24.95           O
ATOM   403  CB  ALA A 270      34.730  -3.716 105.641  1.00 19.84           C
ATOM   404  N   LYS A 271      35.978  -4.285 102.765  1.00 28.59           N
ATOM   405  CA  LYS A 271      36.560  -5.223 101.789  1.00 32.04           C
ATOM   406  C   LYS A 271      37.969  -4.813 101.410  1.00 32.29           C
ATOM   407  O   LYS A 271      38.695  -5.696 100.950  1.00 29.65           O
ATOM   408  CB  LYS A 271      35.683  -5.307 100.545  1.00 35.53           C
ATOM   409  CG  LYS A 271      34.396  -6.125 100.790  1.00 39.05           C
ATOM   410  CD  LYS A 271      33.298  -5.382 100.013  1.00 44.27           C
ATOM   411  CE  LYS A 271      32.441  -6.307  99.179  1.00 46.36           C
ATOM   412  NZ  LYS A 271      33.241  -6.919  98.080  1.00 50.72           N
ATOM   413  N   LYS A 272      38.366  -3.546 101.558  1.00 30.13           N
ATOM   414  CA  LYS A 272      39.706  -3.095 101.285  1.00 27.83           C
ATOM   415  C   LYS A 272      40.646  -3.201 102.478  1.00 28.22           C
ATOM   416  O   LYS A 272      41.823  -2.858 102.327  1.00 29.46           O
ATOM   417  CB  LYS A 272      39.688  -1.632 100.817  1.00 29.77           C
ATOM   418  CG  LYS A 272      39.082  -1.487  99.413  1.00 26.08           C
ATOM   419  CD  LYS A 272      38.715  -0.057  99.155  1.00 28.90           C
ATOM   420  CE  LYS A 272      38.097   0.105  97.788  1.00 33.15           C
ATOM   421  NZ  LYS A 272      36.713   0.646  97.827  1.00 35.86           N
ATOM   422  N   ILE A 273      40.238  -3.559 103.682  1.00 27.70           N
ATOM   423  CA  ILE A 273      41.235  -3.667 104.773  1.00 27.85           C
ATOM   424  C   ILE A 273      41.979  -4.941 104.462  1.00 29.73           C
ATOM   425  O   ILE A 273      41.352  -5.980 104.323  1.00 30.78           O
ATOM   426  CB  ILE A 273      40.514  -3.764 106.133  1.00 26.29           C
ATOM   427  CG1 ILE A 273      39.862  -2.408 106.459  1.00 26.49           C
ATOM   428  CG2 ILE A 273      41.470  -4.151 107.231  1.00 23.14           C
ATOM   429  CD1 ILE A 273      38.764  -2.351 107.440  1.00 21.67           C
ATOM   430  N   PRO A 274      43.277  -4.949 104.299  1.00 33.33           N
ATOM   431  CA  PRO A 274      44.050  -6.145 104.000  1.00 33.20           C
ATOM   432  C   PRO A 274      43.656  -7.304 104.893  1.00 33.08           C
ATOM   433  O   PRO A 274      43.574  -7.140 106.092  1.00 31.65           O
ATOM   434  CB  PRO A 274      45.521  -5.770 104.295  1.00 35.52           C
ATOM   435  CG  PRO A 274      45.504  -4.274 104.226  1.00 35.16           C
ATOM   436  CD  PRO A 274      44.100  -3.740 104.456  1.00 33.78           C
ATOM   437  N   GLY A 275      43.274  -8.453 104.367  1.00 36.25           N
ATOM   438  CA  GLY A 275      42.925  -9.646 105.084  1.00 34.84           C
ATOM   439  C   GLY A 275      41.455  -9.827 105.387  1.00 36.21           C
ATOM   440  O   GLY A 275      40.989 -10.938 105.680  1.00 36.45           O
ATOM   441  N   PHE A 276      40.666  -8.747 105.354  1.00 35.82           N
ATOM   442  CA  PHE A 276      39.254  -8.862 105.714  1.00 32.38           C
ATOM   443  C   PHE A 276      38.537  -9.905 104.869  1.00 33.08           C
ATOM   444  O   PHE A 276      37.717 -10.593 105.463  1.00 28.64           O
ATOM   445  CB  PHE A 276      38.512  -7.520 105.669  1.00 28.57           C
ATOM   446  CG  PHE A 276      37.064  -7.549 106.128  1.00 23.73           C
ATOM   447  CD1 PHE A 276      36.735  -7.466 107.472  1.00 22.22           C
ATOM   448  CD2 PHE A 276      36.053  -7.656 105.223  1.00 22.93           C
ATOM   449  CE1 PHE A 276      35.427  -7.484 107.901  1.00 21.28           C
ATOM   450  CE2 PHE A 276      34.710  -7.689 105.616  1.00 25.71           C
ATOM   451  CZ  PHE A 276      34.405  -7.594 106.969  1.00 23.65           C
ATOM   452  N   VAL A 277      38.675  -9.877 103.538  1.00 34.14           N
ATOM   453  CA  VAL A 277      37.950 -10.786 102.689  1.00 37.01           C
ATOM   454  C   VAL A 277      38.429 -12.239 102.821  1.00 38.26           C
ATOM   455  O   VAL A 277      37.792 -13.163 102.348  1.00 39.54           O
ATOM   456  CB  VAL A 277      37.859 -10.379 101.193  1.00 36.40           C
ATOM   457  CG1 VAL A 277      37.045  -9.118 100.986  1.00 34.99           C
ATOM   458  CG2 VAL A 277      39.217 -10.233 100.527  1.00 33.87           C
ATOM   459  N   GLU A 278      39.513 -12.574 103.451  1.00 40.45           N
ATOM   460  CA  GLU A 278      40.119 -13.831 103.744  1.00 41.04           C
ATOM   461  C   GLU A 278      39.537 -14.452 105.015  1.00 40.91           C
ATOM   462  O   GLU A 278      39.803 -15.612 105.326  1.00 40.47           O
ATOM   463  CB  GLU A 278      41.635 -13.665 103.986  1.00 43.26           C
ATOM   464  CG  GLU A 278      42.311 -13.626 102.600  1.00 46.88           C
ATOM   468  N   LEU A 279      38.785 -13.633 105.747  1.00 36.14           N
ATOM   469  CA  LEU A 279      38.133 -14.136 106.940  1.00 34.62           C
ATOM   470  C   LEU A 279      36.988 -14.973 106.336  1.00 35.11           C
ATOM   471  O   LEU A 279      36.611 -14.686 105.189  1.00 34.70           O
ATOM   472  CB  LEU A 279      37.535 -13.044 107.828  1.00 28.05           C
ATOM   473  CG  LEU A 279      38.468 -12.096 108.561  1.00 29.33           C
```

```
ATOM  317  OD1 ASP A 260      20.183   1.611 103.247  1.00 32.98           O
ATOM  318  OD2 ASP A 260      19.619   3.438 102.200  1.00 35.25           O
ATOM  319  N   LYS A 261      22.796   5.321 103.190  1.00 28.20           N
ATOM  320  CA  LYS A 261      23.742   5.550 102.095  1.00 28.42           C
ATOM  321  C   LYS A 261      25.168   5.258 102.557  1.00 26.42           C
ATOM  322  O   LYS A 261      25.954   4.689 101.805  1.00 24.55           O
ATOM  323  CB  LYS A 261      23.700   6.983 101.598  1.00 31.20           C
ATOM  324  CG  LYS A 261      22.531   7.404 100.773  1.00 36.48           C
ATOM  325  CD  LYS A 261      22.274   8.901 100.922  1.00 38.59           C
ATOM  326  CE  LYS A 261      21.920   9.486  99.574  1.00 42.27           C
ATOM  327  NZ  LYS A 261      22.898   9.053  98.529  1.00 45.18           N
ATOM  328  N   GLU A 262      25.527   5.648 103.786  1.00 24.80           N
ATOM  329  CA  GLU A 262      26.889   5.377 104.265  1.00 23.48           C
ATOM  330  C   GLU A 262      27.177   3.891 104.369  1.00 24.10           C
ATOM  331  O   GLU A 262      28.295   3.453 104.093  1.00 22.13           O
ATOM  332  CB  GLU A 262      27.053   6.051 105.625  1.00 23.57           C
ATOM  333  CG  GLU A 262      27.259   7.559 105.500  1.00 23.49           C
ATOM  334  CD  GLU A 262      27.543   8.231 106.808  1.00 25.54           C
ATOM  335  OE1 GLU A 262      26.681   8.545 107.647  1.00 24.21           O
ATOM  336  OE2 GLU A 262      28.721   8.525 107.060  1.00 25.11           O
ATOM  337  N   LEU A 263      26.191   3.063 104.734  1.00 22.88           N
ATOM  338  CA  LEU A 263      26.421   1.631 104.875  1.00 23.57           C
ATOM  339  C   LEU A 263      26.914   1.054 103.574  1.00 24.52           C
ATOM  340  O   LEU A 263      27.843   0.230 103.571  1.00 25.61           O
ATOM  341  CB  LEU A 263      25.191   0.986 105.531  1.00 28.40           C
ATOM  342  CG  LEU A 263      25.093   1.377 107.018  1.00 31.82           C
ATOM  343  CD1 LEU A 263      23.818   0.818 107.640  1.00 31.85           C
ATOM  344  CD2 LEU A 263      26.329   0.882 107.803  1.00 29.98           C
ATOM  345  N   VAL A 264      26.367   1.447 102.422  1.00 24.08           N
ATOM  346  CA  VAL A 264      26.886   0.932 101.182  1.00 25.18           C
ATOM  347  C   VAL A 264      28.396   1.182 101.122  1.00 25.42           C
ATOM  348  O   VAL A 264      29.114   0.240 100.794  1.00 21.59           O
ATOM  349  CB  VAL A 264      26.262   1.632  99.939  1.00 27.61           C
ATOM  350  CG1 VAL A 264      26.819   0.957  98.696  1.00 26.44           C
ATOM  351  CG2 VAL A 264      24.747   1.521 100.000  1.00 27.89           C
ATOM  352  N   HIS A 265      28.890   2.401 101.408  1.00 22.40           N
ATOM  353  CA  HIS A 265      30.327   2.663 101.385  1.00 23.63           C
ATOM  354  C   HIS A 265      31.086   1.980 102.522  1.00 24.49           C
ATOM  355  O   HIS A 265      32.257   1.578 102.407  1.00 23.40           O
ATOM  356  CB  HIS A 265      30.570   4.178 101.348  1.00 25.62           C
ATOM  357  CG  HIS A 265      29.846   4.805 100.204  1.00 27.45           C
ATOM  358  ND1 HIS A 265      30.258   4.664  98.908  1.00 29.66           N
ATOM  359  CD2 HIS A 265      28.724   5.561 100.127  1.00 27.65           C
ATOM  360  CE1 HIS A 265      29.457   5.291  98.079  1.00 27.64           C
ATOM  361  NE2 HIS A 265      28.518   5.847  98.796  1.00 28.52           N
ATOM  362  N   MET A 266      30.488   1.775 103.713  1.00 25.15           N
ATOM  363  CA  MET A 266      31.193   1.100 104.794  1.00 22.96           C
ATOM  364  C   MET A 266      31.572  -0.322 104.351  1.00 21.67           C
ATOM  365  O   MET A 266      32.687  -0.841 104.533  1.00 19.10           O
ATOM  366  CB  MET A 266      30.325   1.052 106.048  1.00 24.53           C
ATOM  367  CG  MET A 266      31.034   0.243 107.182  1.00 26.77           C
ATOM  368  SD  MET A 266      29.992   0.160 108.658  1.00 26.78           S
ATOM  369  CE  MET A 266      29.094  -1.334 108.161  1.00 25.57           C
ATOM  370  N   ILE A 267      30.630  -1.055 103.736  1.00 20.39           N
ATOM  371  CA  ILE A 267      30.910  -2.396 103.269  1.00 21.76           C
ATOM  372  C   ILE A 267      32.099  -2.373 102.312  1.00 21.33           C
ATOM  373  O   ILE A 267      33.030  -3.173 102.407  1.00 22.70           O
ATOM  374  CB  ILE A 267      29.682  -3.087 102.586  1.00 23.17           C
ATOM  375  CG1 ILE A 267      28.612  -3.363 103.653  1.00 22.08           C
ATOM  376  CG2 ILE A 267      30.098  -4.426 102.012  1.00 20.65           C
ATOM  377  CD1 ILE A 267      27.223  -3.488 103.113  1.00 21.71           C
ATOM  378  N   SER A 268      32.124  -1.435 101.363  1.00 23.03           N
ATOM  379  CA  SER A 268      33.208  -1.310 100.407  1.00 23.44           C
ATOM  380  C   SER A 268      34.492  -1.023 101.167  1.00 23.05           C
ATOM  381  O   SER A 268      35.501  -1.674 100.877  1.00 25.33           O
ATOM  382  CB  SER A 268      32.946  -0.193  99.383  1.00 22.70           C
ATOM  383  OG ASER A 268      32.042  -0.683  98.429  0.50 23.47           O
ATOM  384  OG BSER A 268      34.085   0.076  98.617  0.50 21.00           O
ATOM  385  N   TRP A 269      34.452  -0.083 102.108  1.00 19.78           N
ATOM  386  CA  TRP A 269      35.691   0.166 102.848  1.00 21.30           C
ATOM  387  C   TRP A 269      36.275  -1.073 103.501  1.00 19.84           C
ATOM  388  O   TRP A 269      37.483  -1.317 103.432  1.00 17.99           O
ATOM  389  CB  TRP A 269      35.397   1.226 103.919  1.00 23.03           C
ATOM  390  CG  TRP A 269      36.293   1.298 105.112  1.00 21.67           C
ATOM  391  CD1 TRP A 269      37.523   1.907 105.125  1.00 21.65           C
ATOM  392  CD2 TRP A 269      36.075   0.789 106.435  1.00 21.09           C
ATOM  393  NE1 TRP A 269      38.076   1.814 106.398  1.00 19.73           N
```

40

41

```
ATOM  236  O    ALA A 249    11.620  12.639 110.031  1.00 49.24           O
ATOM  238  N    SER A 250    11.662  14.852 110.330  1.00 47.97           N
ATOM  239  CA   SER A 250    12.634  15.122 109.267  1.00 48.27           C
ATOM  240  C    SER A 250    14.047  14.875 109.797  1.00 45.43           C
ATOM  241  O    SER A 250    14.804  14.181 109.068  1.00 44.48           O
ATOM  242  CB   SER A 250    12.329  16.459 108.653  1.00 50.54           C
ATOM  243  OG   SER A 250    13.415  17.273 108.257  1.00 54.83           O
ATOM  244  N    MET A 251    14.426  15.344 110.987  1.00 41.35           N
ATOM  245  CA   MET A 251    15.778  15.042 111.461  1.00 41.24           C
ATOM  246  C    MET A 251    15.982  13.516 111.520  1.00 41.12           C
ATOM  247  O    MET A 251    16.991  13.045 110.953  1.00 42.88           O
ATOM  248  CB   MET A 251    16.150  15.668 112.788  1.00 40.68           C
ATOM  249  CG   MET A 251    17.526  15.290 113.305  1.00 38.74           C
ATOM  250  SD   MET A 251    17.842  15.852 114.986  1.00 40.43           S
ATOM  251  CE   MET A 251    18.291  17.548 114.694  1.00 40.01           C
ATOM  252  N    MET A 252    15.056  12.721 112.038  1.00 36.24           N
ATOM  253  CA   MET A 252    15.247  11.279 112.090  1.00 36.98           C
ATOM  254  C    MET A 252    15.249  10.619 110.722  1.00 37.84           C
ATOM  255  O    MET A 252    15.928   9.602 110.511  1.00 37.78           O
ATOM  256  CB   MET A 252    14.212  10.621 113.015  1.00 35.20           C
ATOM  257  CG   MET A 252    14.357  11.149 114.449  1.00 35.89           C
ATOM  258  SD   MET A 252    16.039  10.997 115.106  1.00 38.18           S
ATOM  259  CE   MET A 252    16.114   9.195 114.997  1.00 34.02           C
ATOM  260  N    MET A 253    14.493  11.186 109.791  1.00 36.46           N
ATOM  261  CA   MET A 253    14.416  10.658 108.433  1.00 37.72           C
ATOM  262  C    MET A 253    15.762  10.927 107.759  1.00 33.34           C
ATOM  263  O    MET A 253    16.278  10.060 107.086  1.00 29.92           O
ATOM  264  CB   MET A 253    13.281  11.294 107.621  1.00 42.37           C
ATOM  265  CG   MET A 253    13.044  10.656 106.259  1.00 47.98           C
ATOM  266  SD   MET A 253    12.447   8.945 106.327  1.00 55.41           S
ATOM  267  CE   MET A 253    11.227   9.121 107.630  1.00 51.19           C
ATOM  268  N    SER A 254    16.326  12.098 108.006  1.00 33.50           N
ATOM  269  CA   SER A 254    17.611  12.474 107.459  1.00 35.90           C
ATOM  270  C    SER A 254    18.763  11.600 107.985  1.00 34.89           C
ATOM  271  O    SER A 254    19.558  11.117 107.170  1.00 37.23           O
ATOM  272  CB   SER A 254    17.995  13.918 107.807  1.00 35.58           C
ATOM  273  OG   SER A 254    17.204  14.792 107.062  1.00 38.19           O
ATOM  274  N    LEU A 255    18.805  11.439 109.290  1.00 32.43           N
ATOM  275  CA   LEU A 255    19.830  10.630 109.933  1.00 32.06           C
ATOM  276  C    LEU A 255    19.804   9.178 109.471  1.00 31.10           C
ATOM  277  O    LEU A 255    20.877   8.656 109.118  1.00 30.25           O
ATOM  278  CB   LEU A 255    19.704  10.706 111.461  1.00 31.81           C
ATOM  279  CG   LEU A 255    20.075  12.091 112.018  1.00 33.79           C
ATOM  280  CD1  LEU A 255    19.836  12.117 113.511  1.00 32.29           C
ATOM  281  CD2  LEU A 255    21.513  12.438 111.650  1.00 33.09           C
ATOM  282  N    THR A 256    18.620   8.576 109.392  1.00 30.23           N
ATOM  283  CA   THR A 256    18.528   7.180 108.930  1.00 30.76           C
ATOM  284  C    THR A 256    18.756   7.061 107.442  1.00 30.31           C
ATOM  285  O    THR A 256    19.397   6.123 106.927  1.00 31.99           O
ATOM  286  CB   THR A 256    17.200   6.566 109.400  1.00 30.86           C
ATOM  287  OG1  THR A 256    16.110   7.311 108.881  1.00 30.03           O
ATOM  288  CG2  THR A 256    17.090   6.699 110.934  1.00 31.49           C
ATOM  289  N    LYS A 257    18.334   8.063 106.679  1.00 30.34           N
ATOM  290  CA   LYS A 257    18.552   7.996 105.222  1.00 29.19           C
ATOM  291  C    LYS A 257    20.051   8.088 104.984  1.00 26.20           C
ATOM  292  O    LYS A 257    20.616   7.359 104.195  1.00 22.90           O
ATOM  293  CB   LYS A 257    17.757   9.110 104.551  1.00 31.56           C
ATOM  294  CG   LYS A 257    18.075   9.373 103.085  1.00 32.91           C
ATOM  298  N    LEU A 258    20.703   9.009 105.705  1.00 26.57           N
ATOM  299  CA   LEU A 258    22.155   9.166 105.585  1.00 24.20           C
ATOM  300  C    LEU A 258    22.880   7.862 105.901  1.00 22.12           C
ATOM  301  O    LEU A 258    23.674   7.315 105.122  1.00 19.95           O
ATOM  302  CB   LEU A 258    22.627  10.328 106.474  1.00 21.87           C
ATOM  303  CG   LEU A 258    24.157  10.514 106.475  1.00 24.51           C
ATOM  304  CD1  LEU A 258    24.725  10.795 105.080  1.00 20.50           C
ATOM  305  CD2  LEU A 258    24.519  11.645 107.439  1.00 23.84           C
ATOM  306  N    ALA A 259    22.552   7.292 107.052  1.00 21.52           N
ATOM  307  CA   ALA A 259    23.155   6.036 107.507  1.00 23.27           C
ATOM  308  C    ALA A 259    23.095   4.968 106.444  1.00 23.02           C
ATOM  309  O    ALA A 259    24.086   4.289 106.152  1.00 23.45           O
ATOM  310  CB   ALA A 259    22.478   5.519 108.794  1.00 19.50           C
ATOM  311  N    ASP A 260    21.898   4.803 105.864  1.00 25.22           N
ATOM  312  CA   ASP A 260    21.724   3.792 104.823  1.00 26.37           C
ATOM  313  C    ASP A 260    22.643   4.073 103.658  1.00 28.40           C
ATOM  314  O    ASP A 260    23.281   3.138 103.182  1.00 30.53           O
ATOM  315  CB   ASP A 260    20.242   3.743 104.427  1.00 30.73           C
ATOM  316  CG   ASP A 260    19.996   2.845 103.236  1.00 33.57           C
```

| ATOM | 124 | CG | PRO A 234 | 34.210 | 6.148 | 104.185 | 1.00 | 27.06 | C |
| ATOM | 125 | CD | PRO A 234 | 35.702 | 5.799 | 104.033 | 1.00 | 27.86 | C |
| ATOM | 126 | N | PRO A 235 | 33.845 | 7.879 | 100.438 | 1.00 | 29.33 | N |
| ATOM | 127 | CA | PRO A 235 | 33.584 | 9.171 | 99.882 | 1.00 | 29.49 | C |
| ATOM | 128 | C | PRO A 235 | 32.763 | 9.999 | 100.838 | 1.00 | 33.17 | C |
| ATOM | 129 | O | PRO A 235 | 32.229 | 9.586 | 101.869 | 1.00 | 30.52 | O |
| ATOM | 130 | CB | PRO A 235 | 32.710 | 8.920 | 98.597 | 1.00 | 30.57 | C |
| ATOM | 131 | CG | PRO A 235 | 32.040 | 7.621 | 98.923 | 1.00 | 30.20 | C |
| ATOM | 132 | CD | PRO A 235 | 33.064 | 6.820 | 99.745 | 1.00 | 30.96 | C |
| ATOM | 133 | N | HIS A 236 | 32.618 | 11.270 | 100.475 | 1.00 | 36.30 | N |
| ATOM | 134 | CA | HIS A 236 | 31.781 | 12.207 | 101.203 | 1.00 | 39.72 | C |
| ATOM | 135 | C | AHIS A 236 | 30.391 | 11.599 | 100.819 | 0.50 | 36.26 | C |
| ATOM | 136 | C | BHIS A 236 | 30.450 | 11.835 | 101.806 | 0.50 | 40.00 | C |
| ATOM | 137 | O | AHIS A 236 | 30.267 | 11.110 | 99.687 | 0.50 | 27.03 | O |
| ATOM | 138 | O | BHIS A 236 | 30.266 | 11.869 | 103.040 | 0.50 | 39.37 | O |
| ATOM | 139 | CB | HIS A 236 | 31.657 | 13.504 | 100.400 | 1.00 | 46.01 | C |
| ATOM | 140 | CG | HIS A 236 | 32.743 | 14.490 | 100.682 | 1.00 | 51.99 | C |
| ATOM | 142 | ND1 | HIS A 236 | 32.693 | 15.283 | 101.822 | 1.00 | 53.72 | N |
| ATOM | 144 | CD2 | HIS A 236 | 33.840 | 14.830 | 99.992 | 1.00 | 51.71 | C |
| ATOM | 146 | CE1 | HIS A 236 | 33.750 | 16.094 | 101.780 | 1.00 | 56.36 | C |
| ATOM | 148 | NE2 | HIS A 236 | 34.440 | 15.842 | 100.680 | 1.00 | 53.60 | N |
| ATOM | 150 | N | AVAL A 237 | 29.432 | 11.671 | 101.701 | 0.50 | 36.73 | N |
| ATOM | 151 | N | BVAL A 237 | 29.445 | 11.515 | 101.042 | 0.50 | 38.83 | N |
| ATOM | 152 | CA | VAL A 237 | 28.086 | 11.164 | 101.381 | 1.00 | 36.84 | C |
| ATOM | 153 | C | AVAL A 237 | 27.162 | 12.332 | 101.718 | 0.50 | 37.09 | C |
| ATOM | 154 | C | BVAL A 237 | 27.206 | 12.364 | 101.725 | 0.50 | 37.30 | C |
| ATOM | 155 | O | AVAL A 237 | 27.194 | 12.984 | 102.751 | 0.50 | 34.40 | O |
| ATOM | 156 | O | BVAL A 237 | 27.222 | 13.027 | 102.741 | 0.50 | 34.44 | O |
| ATOM | 157 | CB | VAL A 237 | 27.801 | 9.933 | 102.226 | 1.00 | 35.46 | C |
| ATOM | 158 | CG1 | VAL A 237 | 26.393 | 9.412 | 101.951 | 1.00 | 32.80 | C |
| ATOM | 160 | CG2 | VAL A 237 | 28.764 | 8.769 | 101.916 | 1.00 | 33.42 | C |
| ATOM | 162 | N | LEU A 238 | 26.317 | 12.594 | 100.752 | 1.00 | 39.18 | N |
| ATOM | 163 | CA | LEU A 238 | 25.312 | 13.628 | 100.749 | 1.00 | 44.36 | C |
| ATOM | 164 | C | LEU A 238 | 23.903 | 13.032 | 100.860 | 1.00 | 47.97 | C |
| ATOM | 165 | O | LEU A 238 | 23.435 | 12.139 | 100.184 | 1.00 | 48.99 | O |
| ATOM | 166 | CB | LEU A 238 | 25.311 | 14.436 | 99.442 | 1.00 | 44.10 | C |
| ATOM | 167 | CG | LEU A 238 | 26.461 | 15.329 | 99.028 | 1.00 | 43.80 | C |
| ATOM | 168 | CD1 | LEU A 238 | 26.209 | 16.019 | 97.677 | 1.00 | 43.53 | C |
| ATOM | 169 | CD2 | LEU A 238 | 26.730 | 16.401 | 100.072 | 1.00 | 43.86 | C |
| ATOM | 170 | N | ILE A 239 | 23.138 | 13.581 | 101.772 | 1.00 | 53.19 | N |
| ATOM | 171 | CA | ILE A 239 | 21.753 | 13.270 | 102.110 | 1.00 | 59.31 | C |
| ATOM | 172 | C | ILE A 239 | 20.901 | 13.619 | 100.912 | 1.00 | 62.00 | C |
| ATOM | 173 | O | ILE A 239 | 20.057 | 12.811 | 100.560 | 1.00 | 63.57 | O |
| ATOM | 174 | CB | ILE A 239 | 21.443 | 14.038 | 103.404 | 1.00 | 60.39 | C |
| ATOM | 175 | CG1 | ILE A 239 | 20.783 | 13.134 | 104.434 | 1.00 | 60.76 | C |
| ATOM | 176 | CG2 | ILE A 239 | 20.657 | 15.329 | 103.252 | 1.00 | 61.25 | C |
| ATOM | 177 | CD1 | ILE A 239 | 19.483 | 12.533 | 104.022 | 1.00 | 62.04 | C |
| ATOM | 178 | N | SER A 240 | 21.150 | 14.748 | 100.254 | 1.00 | 65.62 | N |
| ATOM | 179 | CA | SER A 240 | 20.458 | 15.123 | 99.028 | 1.00 | 70.05 | C |
| ATOM | 180 | C | SER A 240 | 18.956 | 15.194 | 99.221 | 1.00 | 73.01 | C |
| ATOM | 181 | O | SER A 240 | 18.188 | 14.625 | 98.450 | 1.00 | 73.25 | O |
| ATOM | 182 | CB | SER A 240 | 20.845 | 14.056 | 97.998 | 1.00 | 69.92 | C |
| ATOM | 183 | OG | SER A 240 | 21.203 | 14.578 | 96.744 | 1.00 | 71.99 | O |
| ATOM | 184 | N | ARG A 241 | 18.519 | 15.894 | 100.255 | 1.00 | 78.49 | N |
| ATOM | 185 | CA | ARG A 241 | 17.110 | 16.034 | 100.607 | 1.00 | 84.71 | C |
| ATOM | 186 | C | ARG A 241 | 16.390 | 17.017 | 99.699 | 1.00 | 86.76 | C |
| ATOM | 187 | O | ARG A 241 | 16.822 | 18.147 | 99.489 | 1.00 | 86.42 | O |
| ATOM | 188 | CB | ARG A 241 | 17.003 | 16.419 | 102.086 | 1.00 | 87.26 | C |
| ATOM | 189 | CG | ARG A 241 | 17.697 | 17.724 | 102.453 | 1.00 | 89.54 | C |
| ATOM | 190 | CD | ARG A 241 | 18.145 | 17.734 | 103.909 | 1.00 | 91.76 | C |
| ATOM | 191 | NE | ARG A 241 | 17.951 | 19.058 | 104.509 | 1.00 | 93.46 | N |
| ATOM | 192 | CZ | ARG A 241 | 17.561 | 19.224 | 105.772 | 1.00 | 94.36 | C |
| ATOM | 193 | NH1 | ARG A 241 | 17.339 | 18.147 | 106.527 | 1.00 | 96.15 | N |
| ATOM | 194 | NH2 | ARG A 241 | 17.366 | 20.425 | 106.301 | 1.00 | 94.38 | N |
| ATOM | 195 | N | PRO A 242 | 15.274 | 16.567 | 99.137 | 1.00 | 89.53 | N |
| ATOM | 196 | CA | PRO A 242 | 14.470 | 17.282 | 98.168 | 1.00 | 90.60 | C |
| ATOM | 197 | C | PRO A 242 | 13.960 | 18.661 | 98.532 | 1.00 | 91.00 | C |
| ATOM | 198 | O | PRO A 242 | 13.490 | 18.946 | 99.631 | 1.00 | 92.26 | O |
| ATOM | 199 | CB | PRO A 242 | 13.288 | 16.365 | 97.771 | 1.00 | 90.37 | C |
| ATOM | 200 | CG | PRO A 242 | 13.799 | 15.013 | 98.192 | 1.00 | 90.01 | C |
| ATOM | 201 | CD | PRO A 242 | 14.771 | 15.197 | 99.338 | 1.00 | 89.74 | C |
| ATOM | 202 | N | SER A 243 | 14.062 | 19.539 | 97.532 | 1.00 | 92.18 | N |
| ATOM | 203 | CA | SER A 243 | 13.605 | 20.924 | 97.663 | 1.00 | 93.66 | C |
| ATOM | 204 | C | SER A 243 | 12.087 | 20.929 | 97.814 | 1.00 | 93.76 | C |
| ATOM | 205 | O | SER A 243 | 11.452 | 21.711 | 98.508 | 1.00 | 94.18 | O |
| ATOM | 206 | CB | SER A 243 | 14.003 | 21.755 | 96.450 | 1.00 | 93.34 | C |
| ATOM | 235 | C | ALA A 249 | 11.630 | 13.597 | 110.799 | 1.00 | 49.15 | C |

```
ATOM   47  CD   GLN A 224     51.631  -1.507 101.024  1.00 48.60           C
ATOM   48  OE1  GLN A 224     51.597  -2.389 100.131  1.00 49.81           O
ATOM   49  NE2  GLN A 224     51.796  -0.225 100.697  1.00 48.94           N
ATOM   50  N    LEU A 225     50.237  -0.474 105.638  1.00 29.27           N
ATOM   51  CA   LEU A 225     48.869  -0.708 106.109  1.00 24.53           C
ATOM   52  C    LEU A 225     48.123   0.615 106.251  1.00 21.77           C
ATOM   53  O    LEU A 225     46.958   0.727 105.874  1.00 20.93           O
ATOM   54  CB   LEU A 225     48.951  -1.463 107.441  1.00 26.00           C
ATOM   55  CG   LEU A 225     47.648  -1.779 108.184  1.00 29.48           C
ATOM   56  CD1  LEU A 225     46.516  -2.151 107.245  1.00 23.93           C
ATOM   57  CD2  LEU A 225     47.906  -2.929 109.193  1.00 31.19           C
ATOM   58  N    VAL A 226     48.786   1.638 106.795  1.00 19.50           N
ATOM   59  CA   VAL A 226     48.214   2.946 106.987  1.00 21.65           C
ATOM   60  C    VAL A 226     47.917   3.544 105.611  1.00 21.42           C
ATOM   61  O    VAL A 226     46.834   4.072 105.431  1.00 21.96           O
ATOM   62  CB   VAL A 226     49.071   3.886 107.838  1.00 24.06           C
ATOM   63  CG1  VAL A 226     48.523   5.316 107.792  1.00 26.67           C
ATOM   64  CG2  VAL A 226     49.137   3.456 109.312  1.00 22.95           C
ATOM   65  N    LEU A 227     48.823   3.460 104.651  1.00 22.41           N
ATOM   66  CA   LEU A 227     48.582   3.995 103.303  1.00 24.92           C
ATOM   67  C    LEU A 227     47.402   3.300 102.630  1.00 23.98           C
ATOM   68  O    LEU A 227     46.561   3.978 101.997  1.00 23.09           O
ATOM   69  CB   LEU A 227     49.870   3.906 102.452  1.00 24.02           C
ATOM   70  CG   LEU A 227     50.947   4.918 102.905  1.00 25.92           C
ATOM   71  CD1  LEU A 227     52.225   4.721 102.085  1.00 30.09           C
ATOM   72  CD2  LEU A 227     50.513   6.366 102.829  1.00 23.75           C
ATOM   73  N    THR A 228     47.257   1.974 102.762  1.00 21.56           N
ATOM   74  CA   THR A 228     46.083   1.282 102.181  1.00 21.94           C
ATOM   75  C    THR A 228     44.803   1.688 102.882  1.00 22.55           C
ATOM   76  O    THR A 228     43.747   1.853 102.281  1.00 23.26           O
ATOM   77  CB   THR A 228     46.356  -0.235 102.351  1.00 24.02           C
ATOM   78  OG1  THR A 228     47.599  -0.454 101.651  1.00 26.42           O
ATOM   79  CG2  THR A 228     45.322  -1.181 101.820  1.00 17.45           C
ATOM   80  N    LEU A 229     44.840   1.904 104.224  1.00 20.80           N
ATOM   81  CA   LEU A 229     43.654   2.337 104.930  1.00 18.15           C
ATOM   82  C    LEU A 229     43.304   3.714 104.365  1.00 20.91           C
ATOM   83  O    LEU A 229     42.115   3.931 104.123  1.00 17.82           O
ATOM   84  CB   LEU A 229     43.802   2.379 106.461  1.00 16.48           C
ATOM   85  CG   LEU A 229     43.942   0.959 107.089  1.00 19.93           C
ATOM   86  CD1  LEU A 229     44.227   1.082 108.575  1.00 15.20           C
ATOM   87  CD2  LEU A 229     42.706   0.075 106.816  1.00 17.09           C
ATOM   88  N    LEU A 230     44.291   4.606 104.169  1.00 21.48           N
ATOM   89  CA   LEU A 230     43.956   5.922 103.610  1.00 23.11           C
ATOM   90  C    LEU A 230     43.213   5.859 102.281  1.00 23.35           C
ATOM   91  O    LEU A 230     42.179   6.529 102.082  1.00 24.48           O
ATOM   92  CB   LEU A 230     45.269   6.698 103.380  1.00 22.64           C
ATOM   93  CG   LEU A 230     45.105   8.062 102.684  1.00 24.18           C
ATOM   94  CD1  LEU A 230     44.122   8.959 103.441  1.00 24.20           C
ATOM   95  CD2  LEU A 230     46.465   8.750 102.577  1.00 24.07           C
ATOM   96  N    GLU A 231     43.708   5.047 101.341  1.00 20.95           N
ATOM   97  CA   GLU A 231     43.048   4.946 100.048  1.00 23.89           C
ATOM   98  C    GLU A 231     41.708   4.269 100.227  1.00 25.03           C
ATOM   99  O    GLU A 231     40.902   4.502  99.326  1.00 30.32           O
ATOM  100  CB   GLU A 231     43.787   4.122  98.964  1.00 23.14           C
ATOM  101  CG   GLU A 231     45.096   4.756  98.555  1.00 26.17           C
ATOM  102  CD   GLU A 231     44.960   6.121  97.893  1.00 25.40           C
ATOM  103  OE1  GLU A 231     43.911   6.476  97.339  1.00 22.80           O
ATOM  104  OE2  GLU A 231     45.919   6.923  97.861  1.00 26.23           O
ATOM  105  N    ALA A 232     41.464   3.465 101.256  1.00 21.84           N
ATOM  106  CA   ALA A 232     40.155   2.849 101.400  1.00 21.91           C
ATOM  107  C    ALA A 232     39.087   3.767 101.939  1.00 21.07           C
ATOM  108  O    ALA A 232     37.929   3.326 102.082  1.00 21.73           O
ATOM  109  CB   ALA A 232     40.285   1.648 102.382  1.00 26.27           C
ATOM  110  N    GLU A 233     39.369   4.991 102.348  1.00 19.16           N
ATOM  111  CA   GLU A 233     38.335   5.846 102.887  1.00 23.75           C
ATOM  112  C    GLU A 233     37.114   6.020 102.015  1.00 26.18           C
ATOM  113  O    GLU A 233     37.172   6.175 100.810  1.00 26.67           O
ATOM  114  CB   GLU A 233     38.929   7.254 103.175  1.00 23.19           C
ATOM  115  CG   GLU A 233     39.810   7.096 104.425  1.00 25.11           C
ATOM  116  CD   GLU A 233     38.941   7.157 105.679  1.00 26.98           C
ATOM  117  OE1  GLU A 233     38.506   8.251 106.063  1.00 28.59           O
ATOM  118  OE2  GLU A 233     38.660   6.134 106.311  1.00 23.84           O
ATOM  119  N    PRO A 234     35.937   6.001 102.599  1.00 26.09           N
ATOM  120  CA   PRO A 234     34.702   6.179 101.891  1.00 26.36           C
ATOM  121  C    PRO A 234     34.680   7.644 101.435  1.00 28.37           C
ATOM  122  O    PRO A 234     35.315   8.520 102.029  1.00 21.97           O
ATOM  123  CB   PRO A 234     33.515   5.968 102.861  1.00 26.08           C
```

44

| ATOM | 1793 | CA | MET | A | 451 | 23.089 | -5.406 | 101.500 | 1.00 | 43.32 | | C |
|------|------|------|-----|---|-----|--------|--------|---------|------|-------|---|---|
| ATOM | 1794 | C | MET | A | 451 | 24.023 | -6.582 | 101.801 | 1.00 | 43.09 | | C |
| ATOM | 1795 | O | MET | A | 451 | 24.743 | -6.970 | 100.887 | 1.00 | 40.61 | | O |
| ATOM | 1796 | CB | MET | A | 451 | 23.816 | -4.148 | 101.937 | 1.00 | 40.59 | | C |
| ATOM | 1797 | CG | MET | A | 451 | 23.304 | -2.815 | 101.469 | 1.00 | 39.97 | | C |
| ATOM | 1798 | SD | MET | A | 451 | 24.094 | -1.469 | 102.414 | 1.00 | 39.90 | | S |
| ATOM | 1799 | CE | MET | A | 451 | 22.698 | -0.830 | 103.283 | 1.00 | 40.74 | | C |
| ATOM | 1800 | N | LEU | A | 452 | 23.956 | -7.056 | 103.041 | 1.00 | 45.28 | | N |
| ATOM | 1801 | CA | LEU | A | 452 | 24.814 | -8.194 | 103.420 | 1.00 | 50.17 | | C |
| ATOM | 1802 | C | LEU | A | 452 | 24.380 | -9.421 | 102.636 | 1.00 | 54.32 | | C |
| ATOM | 1803 | O | LEU | A | 452 | 25.223 | -10.113 | 102.046 | 1.00 | 54.05 | | O |
| ATOM | 1804 | CB | LEU | A | 452 | 24.806 | -8.343 | 104.934 | 1.00 | 50.06 | | C |
| ATOM | 1805 | CG | LEU | A | 452 | 25.385 | -7.100 | 105.629 | 1.00 | 51.25 | | C |
| ATOM | 1806 | CD1 | LEU | A | 452 | 25.220 | -7.193 | 107.136 | 1.00 | 51.63 | | C |
| ATOM | 1807 | CD2 | LEU | A | 452 | 26.839 | -6.880 | 105.214 | 1.00 | 49.80 | | C |
| ATOM | 1808 | N | ASN | A | 453 | 23.074 | -9.671 | 102.517 | 1.00 | 59.08 | | N |
| ATOM | 1809 | CA | ASN | A | 453 | 22.655 | -10.800 | 101.698 | 1.00 | 65.94 | | C |
| ATOM | 1810 | C | ASN | A | 453 | 23.104 | -10.543 | 100.252 | 1.00 | 67.74 | | C |
| ATOM | 1811 | O | ASN | A | 453 | 23.719 | -11.409 | 99.619 | 1.00 | 64.22 | | O |
| ATOM | 1812 | CB | ASN | A | 453 | 21.153 | -11.075 | 101.751 | 1.00 | 70.37 | | C |
| ATOM | 1813 | CG | ASN | A | 453 | 20.805 | -12.278 | 100.887 | 1.00 | 75.14 | | C |
| ATOM | 1814 | OD1 | ASN | A | 453 | 21.669 | -12.963 | 100.334 | 1.00 | 76.76 | | O |
| ATOM | 1815 | ND2 | ASN | A | 453 | 19.526 | -12.608 | 100.733 | 1.00 | 77.32 | | N |
| ATOM | 1816 | N | ALA | A | 454 | 22.842 | -9.340 | 99.746 | 1.00 | 69.32 | | N |
| ATOM | 1817 | CA | ALA | A | 454 | 23.172 | -8.947 | 98.386 | 1.00 | 71.97 | | C |
| ATOM | 1818 | C | ALA | A | 454 | 24.624 | -9.161 | 97.986 | 1.00 | 74.07 | | C |
| ATOM | 1819 | O | ALA | A | 454 | 24.924 | -9.416 | 96.818 | 1.00 | 73.95 | | O |
| ATOM | 1820 | CB | ALA | A | 454 | 22.806 | -7.492 | 98.126 | 1.00 | 72.94 | | C |
| ATOM | 1821 | N | HIS | A | 455 | 25.527 | -9.042 | 98.941 | 1.00 | 76.80 | | N |
| ATOM | 1822 | CA | HIS | A | 455 | 26.935 | -9.256 | 98.695 | 1.00 | 79.75 | | C |
| ATOM | 1823 | C | HIS | A | 455 | 27.162 | -10.762 | 98.621 | 1.00 | 81.20 | | C |
| ATOM | 1824 | O | HIS | A | 455 | 27.614 | -11.258 | 97.596 | 1.00 | 82.45 | | O |
| ATOM | 1825 | CB | HIS | A | 455 | 27.790 | -8.692 | 99.839 | 1.00 | 80.74 | | C |
| ATOM | 1826 | CG | HIS | A | 455 | 28.114 | -7.268 | 99.467 | 1.00 | 81.86 | | C |
| ATOM | 1827 | ND1 | HIS | A | 455 | 27.199 | -6.234 | 99.567 | 1.00 | 80.97 | | N |
| ATOM | 1828 | CD2 | HIS | A | 455 | 29.261 | -6.739 | 98.982 | 1.00 | 81.25 | | C |
| ATOM | 1829 | CE1 | HIS | A | 455 | 27.786 | -5.132 | 99.160 | 1.00 | 80.66 | | C |
| ATOM | 1830 | NE2 | HIS | A | 455 | 29.033 | -5.395 | 98.800 | 1.00 | 80.86 | | N |
| ATOM | 1831 | N | VAL | A | 456 | 26.755 | -11.424 | 99.712 | 1.00 | 82.57 | | N |
| ATOM | 1832 | CA | VAL | A | 456 | 26.899 | -12.866 | 99.832 | 1.00 | 81.22 | | C |
| ATOM | 1833 | C | VAL | A | 456 | 26.537 | -13.573 | 98.536 | 1.00 | 80.62 | | C |
| ATOM | 1834 | O | VAL | A | 456 | 27.336 | -14.414 | 98.126 | 1.00 | 80.87 | | O |
| ATOM | 1835 | CB | VAL | A | 456 | 26.142 | -13.463 | 101.022 | 1.00 | 81.06 | | C |
| ATOM | 1836 | CG1 | VAL | A | 456 | 26.186 | -14.985 | 100.985 | 1.00 | 82.02 | | C |
| ATOM | 1837 | CG2 | VAL | A | 456 | 26.753 | -12.970 | 102.325 | 1.00 | 82.03 | | C |
| ATOM | 1838 | N | LEU | A | 457 | 25.421 | -13.265 | 97.912 | 1.00 | 80.17 | | N |
| ATOM | 1839 | CA | LEU | A | 457 | 25.017 | -13.894 | 96.668 | 1.00 | 78.46 | | C |
| ATOM | 1840 | C | LEU | A | 457 | 25.914 | -13.444 | 95.528 | 1.00 | 80.89 | | C |
| ATOM | 1841 | O | LEU | A | 457 | 27.132 | -13.745 | 95.673 | 1.00 | 81.66 | | O |
| ATOM | 1842 | CB | LEU | A | 457 | 23.533 | -13.637 | 96.391 | 1.00 | 76.77 | | C |
| ATOM | 1843 | CG | LEU | A | 457 | 22.603 | -14.357 | 97.403 | 1.00 | 76.96 | | C |
| ATOM | 1844 | CD1 | LEU | A | 457 | 21.140 | -13.990 | 97.107 | 1.00 | 75.43 | | C |
| ATOM | 1845 | CD2 | LEU | A | 457 | 22.780 | -15.874 | 97.246 | 1.00 | 74.73 | | C |
| ATOM | 1846 | C1 | GEN | A | 600 | 19.066 | 6.946 | 114.851 | 1.00 | 28.90 | | C |
| ATOM | 1847 | C2 | GEN | A | 600 | 18.787 | 7.338 | 116.178 | 1.00 | 28.74 | | C |
| ATOM | 1848 | O2 | GEN | A | 600 | 17.614 | 6.984 | 116.768 | 1.00 | 30.71 | | O |
| ATOM | 1849 | C3 | GEN | A | 600 | 19.667 | 8.069 | 116.971 | 1.00 | 26.37 | | C |
| ATOM | 1850 | C4 | GEN | A | 600 | 20.885 | 8.440 | 116.411 | 1.00 | 27.82 | | C |
| ATOM | 1851 | O4 | GEN | A | 600 | 21.796 | 9.165 | 117.119 | 1.00 | 27.90 | | O |
| ATOM | 1852 | C5 | GEN | A | 600 | 21.200 | 8.110 | 115.078 | 1.00 | 27.85 | | C |
| ATOM | 1853 | C6 | GEN | A | 600 | 22.452 | 8.550 | 114.458 | 1.00 | 24.59 | | C |
| ATOM | 1854 | O6 | GEN | A | 600 | 23.336 | 9.203 | 114.947 | 1.00 | 22.65 | | O |
| ATOM | 1855 | C7 | GEN | A | 600 | 22.725 | 8.163 | 113.042 | 1.00 | 25.95 | | C |
| ATOM | 1856 | C8 | GEN | A | 600 | 21.766 | 7.426 | 112.431 | 1.00 | 28.52 | | C |
| ATOM | 1857 | O9 | GEN | A | 600 | 20.620 | 7.049 | 113.020 | 1.00 | 30.64 | | O |
| ATOM | 1858 | C10 | GEN | A | 600 | 20.287 | 7.376 | 114.319 | 1.00 | 28.96 | | C |
| ATOM | 1859 | C11 | GEN | A | 600 | 23.964 | 8.445 | 112.265 | 1.00 | 24.81 | | C |
| ATOM | 1860 | C12 | GEN | A | 600 | 25.233 | 8.474 | 112.882 | 1.00 | 21.54 | | C |
| ATOM | 1861 | C13 | GEN | A | 600 | 26.395 | 8.712 | 112.154 | 1.00 | 21.03 | | C |
| ATOM | 1862 | C14 | GEN | A | 600 | 26.323 | 8.914 | 110.770 | 1.00 | 22.70 | | C |
| ATOM | 1863 | O14 | GEN | A | 600 | 27.473 | 9.138 | 110.037 | 1.00 | 23.33 | | O |
| ATOM | 1864 | C15 | GEN | A | 600 | 25.078 | 8.880 | 110.141 | 1.00 | 22.71 | | C |
| ATOM | 1865 | C16 | GEN | A | 600 | 23.898 | 8.649 | 110.870 | 1.00 | 22.04 | | C |
| ATOM | 1866 | OW | WAT | W | 1 | 30.300 | 8.243 | 109.226 | 1.00 | 24.00 | W | O |
| ATOM | 1867 | OW | WAT | W | 2 | 31.923 | 3.768 | 107.118 | 1.00 | 25.37 | W | O |
| ATOM | 1868 | OW | WAT | W | 3 | 34.868 | 3.634 | 106.962 | 1.00 | 23.16 | W | O |
| ATOM | 1869 | OW | WAT | W | 4 | 34.310 | 7.542 | 107.756 | 1.00 | 27.65 | W | O |

46

```
ATOM   1870  OW   WAT W    5      34.623  10.761 107.420  1.00 51.27      W    O
ATOM   1871  OW   WAT W    6      27.728  -0.773 116.443  1.00 28.91      W    O
ATOM   1872  OW   WAT W    7      32.139  18.623 117.543  1.00 20.81      W    O
ATOM   1873  OW   WAT W    8      33.814  -2.391 118.206  1.00 18.99      W    O
ATOM   1874  OW   WAT W    9      30.749   7.627 105.507  1.00 25.20      W    O
ATOM   1875  OW   WAT W   10      31.341  20.242 122.041  1.00 29.52      W    O
ATOM   1876  OW   WAT W   11      35.197  26.818 110.279  1.00 28.55      W    O
ATOM   1877  OW   WAT W   12      43.014   0.699  99.818  1.00 30.89      W    O
ATOM   1878  OW   WAT W   13      40.157  -7.535 102.395  1.00 35.15      W    O
ATOM   1879  OW   WAT W   14      40.040   3.961 106.029  1.00 22.39      W    O
ATOM   1880  OW   WAT W   15      33.301  18.530 120.285  1.00 32.60      W    O
ATOM   1881  OW   WAT W   16      38.138   7.433 127.692  1.00 59.86      W    O
ATOM   1882  OW   WAT W   17      38.617  16.006 110.228  1.00 37.02      W    O
ATOM   1883  OW   WAT W   18      30.802   4.864 104.592  1.00 23.29      W    O
ATOM   1884  OW   WAT W   19      32.175   5.923 109.211  1.00 21.86      W    O
ATOM   1885  OW   WAT W   20      40.045   2.845 108.825  1.00 20.48      W    O
ATOM   1886  OW   WAT W   21      31.810  13.765 104.399  1.00 45.53      W    O
ATOM   1887  OW   WAT W   22      28.739  11.638 105.767  1.00 33.26      W    O
ATOM   1888  OW   WAT W   23      26.076   7.859  98.212  1.00 26.32      W    O
ATOM   1889  OW   WAT W   24      28.987   9.266  97.481  1.00 40.73      W    O
ATOM   1890  OW   WAT W   25      32.542   3.409  97.943  1.00 37.94      W    O
ATOM   1891  OW   WAT W   26      41.488   5.664  96.405  1.00 27.07      W    O
ATOM   1892  OW   WAT W   27      18.903   6.172 102.054  1.00 31.39      W    O
ATOM   1893  OW   WAT W   28      42.694  -2.436  99.214  1.00 57.17      W    O
ATOM   1894  OW   WAT W   29      20.246   0.254 100.414  1.00 73.95      W    O
ATOM   1895  OW   WAT W   30      32.556  -3.497  97.008  1.00 75.30      W    O
ATOM   1896  OW   WAT W   31      42.570  -8.929 100.896  1.00 51.87      W    O
ATOM   1897  OW   WAT W   32      35.906  -1.412 120.194  1.00 33.20      W    O
ATOM   1898  OW   WAT W   33      42.296  11.057 106.956  1.00 33.70      W    O
ATOM   1899  OW   WAT W   34      55.981   1.820 125.082  1.00 45.30      W    O
ATOM   1900  OW   WAT W   35      54.313   3.408 120.612  1.00 33.88      W    O
ATOM   1901  OW   WAT W   36      51.821   2.843 122.217  1.00 28.61      W    O
ATOM   1902  OW   WAT W   37      48.022  11.026 125.057  1.00 37.20      W    O
ATOM   1903  OW   WAT W   38      41.030   8.652 127.426  1.00 33.60      W    O
ATOM   1904  OW   WAT W   39      38.169  -0.431 125.136  0.50 24.25      W    O
ATOM   1905  OW   WAT W   40      21.758  -1.083 121.803  1.00 37.04      W    O
ATOM   1906  OW   WAT W   41      14.988  -1.010 124.768  0.50 19.42      W    O
ATOM   1907  OW   WAT W   42      35.591  -2.856  97.992  1.00 38.15      W    O
ATOM   1908  OW   WAT W   43      26.830 -10.194 114.576  1.00 42.75      W    O
ATOM   1909  OW   WAT W   44      25.193  -1.198 115.003  1.00 45.66      W    O
ATOM   1910  OW   WAT W   45      32.382  10.087 104.560  1.00 49.31      W    O
ATOM   1911  OW   WAT W   46      34.880  13.523 105.049  1.00 57.06      W    O
ATOM   1912  OW   WAT W   47      35.849  19.283 112.078  1.00 32.35      W    O
ATOM   1913  OW   WAT W   48      38.457  19.178 110.470  1.00 47.47      W    O
ATOM   1914  OW   WAT W   49      53.433  11.761 109.442  1.00 38.50      W    O
ATOM   1915  OW   WAT W   50      36.074   2.543  99.936  1.00 50.18      W    O
ATOM   1916  OW   WAT W   51      23.871  16.127 102.601  1.00 41.43      W    O
ATOM   1917  OW   WAT W   52      21.240   0.490 105.686  1.00 50.54      W    O
ATOM   1918  OW   WAT W   53      40.050  22.449 116.644  1.00 55.50      W    O
ATOM   1919  OW   WAT W   54      16.065  15.475 123.259  1.00 45.16      W    O
ATOM   1920  OW   WAT W   55      43.315  16.500 115.918  1.00 51.91      W    O
ATOM   1921  OW   WAT W   56      41.120  14.916 105.440  1.00 46.62      W    O
ATOM   1922  OW   WAT W   57      37.673  -8.848 119.522  1.00 41.08      W    O
ATOM   1923  OW   WAT W   58      50.879  10.310 126.587  1.00 51.15      W    O
ATOM   1924  OW   WAT W   59      34.040   1.099 119.772  1.00 38.40      W    O
ATOM   1926  OW   WAT W   60      22.090   1.501 125.680  1.00 40.94      W    O
ATOM   1927  OW   WAT W   61      51.484  -3.546 111.363  1.00 45.29      W    O
ATOM   1928  OW   WAT W   62      41.193   1.748  97.470  1.00 46.61      W    O
ATOM   1929  OW   WAT W   63      23.028  27.079 118.923  1.00 53.19      W    O
ATOM   1930  OW   WAT W   64      17.518  13.211 125.825  1.00 45.20      W    O
ATOM   1931  OW   WAT W   65      19.216   5.249 124.097  1.00 40.10      W    O
ATOM   1932  OW   WAT W   66      21.712  15.509 127.884  1.00 61.86      W    O
ATOM   1933  OW   WAT W   67      31.631  18.518 125.007  1.00 38.02      W    O
ATOM   1934  OW   WAT W   68      29.996   8.691 124.464  1.00 46.32      W    O
ATOM   1935  OW   WAT W   69      47.557  15.822 123.721  1.00 55.93      W    O
ATOM   1936  OW   WAT W   70      49.003  14.382 118.696  1.00 36.31      W    O
ATOM   1937  OW   WAT W   71      51.156  -8.890 115.021  1.00 55.55      W    O
ATOM   1938  OW   WAT W   72      15.472  -1.569 110.620  1.00 56.86      W    O
ATOM   1939  OW   WAT W   73      28.632  -2.047  98.826  1.00 48.05      W    O
ATOM   1940  OW   WAT W   74      26.629  -1.500 119.449  1.00 45.43      W    O
ATOM   1941  OW   WAT W   75      51.071   9.749 117.409  1.00 52.81      W    O
ATOM   1942  OW   WAT W   76      54.751  -1.975 115.553  1.00 49.77      W    O
ATOM   1943  OW   WAT W   77      53.122  -0.860 126.652  1.00 56.90      W    O
ATOM   1944  OW   WAT W   78      12.755   1.316 114.612  1.00 80.46      W    O
ATOM   1945  OW   WAT W   79      32.412  25.447 116.270  1.00 52.00      W    O
ATOM   1946  OW   WAT W   80      37.245  15.261 101.259  1.00 49.16      W    O
ATOM   1947  OW   WAT W   81      23.445  12.230  96.331  1.00 49.75      W    O   END
```

```
HEADER    NUCLEAR RECEPTOR - ER Beta + RALOXIFENE
REMARK    DATE: 20/1/1998
REMARK    1 Final rebuild/refinement for ERB+ral against Hamburg X11 2.2A
REMARK      data using REFMAC
REMARK                                     COMPND    2 MOLECULE: RAT OESTROGEN RECEPTOR
BETA; COMPND    3 CHAIN: A; COMPND    4 FRAGMENT: LIGAND-BINDING DOMAIN; COMPND    5
SYNONYM: ESTROGEN RECEPTOR, ER-LBD, ER-BETA; COMPND    6 ENGINEERED: YES; COMPND    7
BIOLOGICAL_UNIT: DIMER; COMPND    8 OTHER_DETAILS: LIGAND-BINDING DOMAIN COMPND    9
(DOMAIN E - RESIDUES 211-461) IN COMPLEX WITH THE SELECTIVE COMPND   10 ANTAGONIST
RALOXIFENE
REMARK
REMARK   Overall refinement statistics (REF. CYCLE 9 20/1/98)
REMARK
REMARK    _refine_overall_R_factor               0.23007
REMARK    _refine_ls_number_reflns                 16198
REMARK    _refine_ls_number_reflns_missing           143
REMARK    _refine_free_R_factor                  0.28636
REMARK    _refine_ls_number_reflns_free             1815
REMARK    _refine_ls_number_reflns_free_missing       14
REMARK    _refine_ls_WR_factor                   0.22273
REMARK
REMARK    Correlation_coefficients_Fo_to_Fc      0.91480
REMARK    Free_correlation_coeff_Fo_to_Fc        0.87930
REMARK
REMARK    ****         Precision indication from R values          ****
REMARK
REMARK    Overall_Coordinate_ESU_based_on_R_value(Cruickshanks DPI)   0.25019
REMARK    Overall_Coordinate_ESU_based_on_free_R_value      0.22560
REMARK
REMARK    ****    Precision indication from Maximum Likelihood     ****
REMARK
REMARK    Overall_Coordinate_ESU_based_on_ML     0.14185
REMARK    Overall_Bvalue_ESU_based_on_ML         5.49151
REMARK
REMARK    ***********************************************
REMARK     **** COMMENTS ON THE MODEL AS IS **********
REMARK    ***********************************************
REMARK    7 RESIDUE: SER240 not modelled beyond CB atom
REMARK    7 RESIDUE: SER243 not modelled beyond CB atom
REMARK    7 RESIDUE: MET244 not modelled beyond CB atom
REMARK    7 RESIDUE: PHE246 not modelled beyond CB atom
REMARK    7 RESIDUE: THR247 not modelled beyond CB atom
REMARK    7 RESIDUE: LYS257 not modelled beyond CB atom
REMARK    7 RESIDUE: ASP316 not modelled beyond CB atom
REMARK    7 RESIDUE: GLU328 not modelled beyond CB atom
REMARK    7 RESIDUE: LYS437 not modelled beyond CB atom
REMARK    7 RESIDUE: ASP446 not modelled beyond CB atom
REMARK    7 RESIDUE: LEU447 not modelled beyond CB atom
REMARK    7 RESIDUE: LEU449 not modelled beyond CB atom
REMARK    7 RESIDUE: GLU450 not modelled beyond CB atom
REMARK    7 RESIDUE: MET451 not modelled beyond CB atom
REMARK    8
REMARK    8 RESIDUES MODELLED IN ALTERNATE CONFORMATIONS: GLN224, MET252,
REMARK    8 SER290, LYS382, HIS385, SER420, HIS421. WAT W20, W104
REMARK
REMARK    9 RESIDUES: ARG211 - SER218 (inclusive) have not been modelled
REMARK    9 RESIDUES: CYS438 - TYR445 (inclusive) have not been modelled
REMARK    9 RESIDUES: HIS455 - LYS461 (inclusive) have not been modelled
REMARK
REMARK   10 LOOP BETWEEN H1/2 AND H3 IS INCLUDED BUT CONFIDENCE LEVEL LOW
REMARK   10 FOR CONFORMATION OF RESIDUES 243-247.
REMARK   10 HELIX 12 IS INCLUDED FOR REFERENCE BUT IS HIGHLY MOBILE (see
REMARK   10 temperature factors for this region). CONFORMATION HERE IS
REMARK   10 VISIBLE IN ELECTRON DENSITY MAPS BUT BOTH SIDECHAIN AND
REMARK   10 MAINCHAIN IS POORLY DEFINED. SIDECHAINS THAT HAVE BEEN MODELLED
REMARK   10 ARE HOWEVER VISIBLE. TREAT WITH CAUTION.
REMARK
REMARK   11 NOTE: NOTE: pH OF CRYSTALLISATION IS VERY DIFFERENT FROM THAT
REMARK   11 OF ER-ALPHA + RALOX (pH4.6 VS pH8.5). BEAR THIS IN MIND DURING
REMARK   11 IN COMPARISONS
REMARK
REMARK   12 ONLY ONE MOLECULE IS PRESENT IN CRYSTALLOGRAPHIC ASYMMETRIC UNIT
REMARK   12 CRYSTALLOGRAPHIC DIMER PARTNER CAN BE GENERATED BY APPLYING FOLLOWING
REMARK   12 OPERATION TO THESE COORDINATES
REMARK   12 ROTATION OF (-Y,-X,1/4-Z)
REMARK   12 FRACTIONAL TRANSLATION  (1.0 1.0 0.0)
```

| ATOM | 1153 | C | SER A 366 | 27.497 | 47.437 | 8.737 | 1.00 | 47.42 | C |
| --- | --- | --- | --- | --- | --- | --- | --- | --- | --- |
| ATOM | 1154 | O | SER A 366 | 27.453 | 46.279 | 8.333 | 1.00 | 51.78 | O |
| ATOM | 1155 | CB | SER A 366 | 27.322 | 47.324 | 11.261 | 1.00 | 47.55 | C |
| ATOM | 1156 | OG | SER A 366 | 26.754 | 48.163 | 12.321 | 1.00 | 50.85 | O |
| ATOM | 1157 | N | MET A 367 | 28.240 | 48.331 | 8.098 | 1.00 | 46.78 | N |
| ATOM | 1158 | CA | MET A 367 | 29.001 | 47.883 | 6.925 | 1.00 | 46.42 | C |
| ATOM | 1159 | C | MET A 367 | 30.427 | 47.563 | 7.370 | 1.00 | 47.42 | C |
| ATOM | 1160 | O | MET A 367 | 30.985 | 48.254 | 8.203 | 1.00 | 47.54 | O |
| ATOM | 1161 | CB | MET A 367 | 28.908 | 48.908 | 5.811 | 1.00 | 41.45 | C |
| ATOM | 1162 | CG | MET A 367 | 27.473 | 49.016 | 5.262 | 1.00 | 38.44 | C |
| ATOM | 1163 | SD | MET A 367 | 27.435 | 50.088 | 3.837 | 1.00 | 38.29 | S |
| ATOM | 1164 | CE | MET A 367 | 28.111 | 51.608 | 4.460 | 1.00 | 39.16 | C |
| ATOM | 1165 | N | TYR A 368 | 31.006 | 46.530 | 6.805 | 1.00 | 47.59 | N |
| ATOM | 1166 | CA | TYR A 368 | 32.356 | 46.117 | 7.103 | 1.00 | 51.94 | C |
| ATOM | 1167 | C | TYR A 368 | 33.003 | 45.495 | 5.884 | 1.00 | 51.27 | C |
| ATOM | 1168 | O | TYR A 368 | 32.361 | 44.722 | 5.168 | 1.00 | 51.64 | O |
| ATOM | 1169 | CB | TYR A 368 | 32.283 | 45.042 | 8.216 | 1.00 | 58.29 | C |
| ATOM | 1170 | CG | TYR A 368 | 33.643 | 44.451 | 8.505 | 1.00 | 62.25 | C |
| ATOM | 1171 | CD1 | TYR A 368 | 34.086 | 43.323 | 7.809 | 1.00 | 64.71 | C |
| ATOM | 1172 | CD2 | TYR A 368 | 34.486 | 45.032 | 9.444 | 1.00 | 62.80 | C |
| ATOM | 1173 | CE1 | TYR A 368 | 35.344 | 42.789 | 8.063 | 1.00 | 66.29 | C |
| ATOM | 1174 | CE2 | TYR A 368 | 35.740 | 44.498 | 9.686 | 1.00 | 63.68 | C |
| ATOM | 1175 | CZ | TYR A 368 | 36.161 | 43.387 | 9.000 | 1.00 | 64.65 | C |
| ATOM | 1176 | OH | TYR A 368 | 37.411 | 42.858 | 9.250 | 1.00 | 68.44 | O |
| ATOM | 1177 | N | PRO A 369 | 34.276 | 45.743 | 5.659 | 1.00 | 48.93 | N |
| ATOM | 1178 | CA | PRO A 369 | 35.115 | 46.645 | 6.406 | 1.00 | 46.18 | C |
| ATOM | 1179 | C | PRO A 369 | 34.689 | 48.090 | 6.148 | 1.00 | 44.77 | C |
| ATOM | 1180 | O | PRO A 369 | 33.852 | 48.319 | 5.274 | 1.00 | 45.06 | O |
| ATOM | 1181 | CB | PRO A 369 | 36.540 | 46.486 | 5.845 | 1.00 | 46.31 | C |
| ATOM | 1182 | CG | PRO A 369 | 36.429 | 45.400 | 4.843 | 1.00 | 49.08 | C |
| ATOM | 1183 | CD | PRO A 369 | 34.976 | 45.121 | 4.518 | 1.00 | 48.32 | C |
| ATOM | 1184 | N | LEU A 370 | 35.217 | 49.072 | 6.853 | 1.00 | 42.17 | N |
| ATOM | 1185 | CA | LEU A 370 | 34.890 | 50.469 | 6.736 | 1.00 | 41.64 | C |
| ATOM | 1186 | C | LEU A 370 | 35.734 | 51.287 | 5.776 | 1.00 | 43.45 | C |
| ATOM | 1187 | O | LEU A 370 | 36.943 | 51.078 | 5.617 | 1.00 | 42.86 | O |
| ATOM | 1188 | CB | LEU A 370 | 34.978 | 51.117 | 8.143 | 1.00 | 41.23 | C |
| ATOM | 1189 | CG | LEU A 370 | 33.920 | 50.557 | 9.122 | 1.00 | 45.11 | C |
| ATOM | 1190 | CD1 | LEU A 370 | 34.221 | 50.905 | 10.553 | 1.00 | 45.72 | C |
| ATOM | 1191 | CD2 | LEU A 370 | 32.529 | 51.075 | 8.744 | 1.00 | 47.02 | C |
| ATOM | 1192 | N | ALA A 371 | 35.132 | 52.266 | 5.116 | 1.00 | 42.79 | N |
| ATOM | 1193 | CA | ALA A 371 | 35.858 | 53.113 | 4.171 | 1.00 | 43.14 | C |
| ATOM | 1194 | C | ALA A 371 | 36.524 | 54.200 | 5.027 | 1.00 | 44.80 | C |
| ATOM | 1195 | O | ALA A 371 | 36.542 | 54.048 | 6.246 | 1.00 | 42.86 | O |
| ATOM | 1196 | CB | ALA A 371 | 34.891 | 53.711 | 3.169 | 1.00 | 43.15 | C |
| ATOM | 1197 | N | SER A 372 | 37.032 | 55.272 | 4.433 | 1.00 | 43.82 | N |
| ATOM | 1198 | CA | SER A 372 | 37.608 | 56.278 | 5.302 | 1.00 | 42.99 | C |
| ATOM | 1199 | C | SER A 372 | 36.449 | 56.933 | 6.063 | 1.00 | 45.97 | C |
| ATOM | 1200 | O | SER A 372 | 35.241 | 56.820 | 5.762 | 1.00 | 44.62 | O |
| ATOM | 1201 | CB | SER A 372 | 38.334 | 57.364 | 4.512 | 1.00 | 40.72 | C |
| ATOM | 1202 | OG | SER A 372 | 37.333 | 58.145 | 3.821 | 1.00 | 41.84 | O |
| ATOM | 1203 | N | ALA A 373 | 36.879 | 57.733 | 7.042 | 1.00 | 44.03 | N |
| ATOM | 1204 | CA | ALA A 373 | 35.876 | 58.442 | 7.849 | 1.00 | 50.44 | C |
| ATOM | 1205 | C | ALA A 373 | 35.017 | 59.279 | 6.896 | 1.00 | 50.12 | C |
| ATOM | 1206 | O | ALA A 373 | 33.787 | 59.258 | 7.018 | 1.00 | 48.47 | O |
| ATOM | 1207 | CB | ALA A 373 | 36.572 | 59.196 | 8.980 | 1.00 | 49.63 | C |
| ATOM | 1208 | N | ASN A 374 | 35.600 | 60.001 | 5.957 | 1.00 | 47.72 | N |
| ATOM | 1209 | CA | ASN A 374 | 34.908 | 60.823 | 4.997 | 1.00 | 48.94 | C |
| ATOM | 1210 | C | ASN A 374 | 33.986 | 60.040 | 4.058 | 1.00 | 46.83 | C |
| ATOM | 1211 | O | ASN A 374 | 32.859 | 60.476 | 3.807 | 1.00 | 47.70 | O |
| ATOM | 1212 | CB | ASN A 374 | 35.871 | 61.526 | 4.027 | 1.00 | 53.42 | C |
| ATOM | 1213 | CG | ASN A 374 | 35.732 | 63.013 | 4.218 | 1.00 | 59.73 | C |
| ATOM | 1214 | OD1 | ASN A 374 | 34.740 | 63.623 | 3.803 | 1.00 | 61.32 | O |
| ATOM | 1215 | ND2 | ASN A 374 | 36.774 | 63.543 | 4.867 | 1.00 | 63.63 | N |
| ATOM | 1216 | N | GLN A 375 | 34.472 | 58.932 | 3.537 | 1.00 | 42.74 | N |
| ATOM | 1217 | CA | GLN A 375 | 33.660 | 58.104 | 2.652 | 1.00 | 42.21 | C |
| ATOM | 1218 | C | GLN A 375 | 32.462 | 57.543 | 3.432 | 1.00 | 42.87 | C |
| ATOM | 1219 | O | GLN A 375 | 31.327 | 57.519 | 2.948 | 1.00 | 38.93 | O |
| ATOM | 1220 | CB | GLN A 375 | 34.491 | 56.992 | 2.017 | 1.00 | 40.91 | C |
| ATOM | 1221 | CG | GLN A 375 | 35.604 | 57.603 | 1.109 | 1.00 | 42.11 | C |
| ATOM | 1222 | CD | GLN A 375 | 36.633 | 56.577 | 0.704 | 1.00 | 42.45 | C |
| ATOM | 1223 | OE1 | GLN A 375 | 36.994 | 55.658 | 1.464 | 1.00 | 43.22 | O |
| ATOM | 1224 | NE2 | GLN A 375 | 37.130 | 56.687 | -0.535 | 1.00 | 39.23 | N |
| ATOM | 1225 | N | GLU A 376 | 32.707 | 57.102 | 4.647 | 1.00 | 42.63 | N |
| ATOM | 1226 | CA | GLU A 376 | 31.719 | 56.531 | 5.539 | 1.00 | 44.07 | C |
| ATOM | 1227 | C | GLU A 376 | 30.656 | 57.569 | 5.882 | 1.00 | 43.52 | C |
| ATOM | 1228 | O | GLU A 376 | 29.467 | 57.236 | 5.929 | 1.00 | 43.69 | O |
| ATOM | 1229 | CB | GLU A 376 | 32.310 | 55.932 | 6.821 | 1.00 | 44.25 | C |

| | | | | | | | | | |
|---|---|---|---|---|---|---|---|---|---|
| ATOM | 1076 | CD1 | LEU A 355 | 5.988 | 43.550 | 5.379 | 1.00 | 39.41 | C |
| ATOM | 1077 | CD2 | LEU A 355 | 4.204 | 45.359 | 5.395 | 1.00 | 42.06 | C |
| ATOM | 1078 | N | CYS A 356 | 8.121 | 47.720 | 8.265 | 1.00 | 31.61 | N |
| ATOM | 1079 | CA | CYS A 356 | 9.008 | 48.845 | 8.486 | 1.00 | 32.80 | C |
| ATOM | 1080 | C | CYS A 356 | 10.231 | 48.354 | 9.259 | 1.00 | 34.99 | C |
| ATOM | 1081 | O | CYS A 356 | 11.374 | 48.642 | 8.894 | 1.00 | 35.81 | O |
| ATOM | 1082 | CB | CYS A 356 | 8.259 | 49.933 | 9.245 | 1.00 | 31.61 | C |
| ATOM | 1083 | SG | CYS A 356 | 6.957 | 50.686 | 8.270 | 1.00 | 30.52 | S |
| ATOM | 1084 | N | VAL A 357 | 9.991 | 47.570 | 10.296 | 1.00 | 33.28 | N |
| ATOM | 1085 | CA | VAL A 357 | 11.113 | 47.052 | 11.114 | 1.00 | 34.78 | C |
| ATOM | 1086 | C | VAL A 357 | 12.074 | 46.217 | 10.292 | 1.00 | 33.23 | C |
| ATOM | 1087 | O | VAL A 357 | 13.278 | 46.394 | 10.475 | 1.00 | 35.44 | O |
| ATOM | 1088 | CB | VAL A 357 | 10.612 | 46.210 | 12.312 | 1.00 | 32.96 | C |
| ATOM | 1089 | CG1 | VAL A 357 | 11.718 | 45.437 | 13.026 | 1.00 | 34.31 | C |
| ATOM | 1090 | CG2 | VAL A 357 | 9.914 | 47.199 | 13.269 | 1.00 | 32.22 | C |
| ATOM | 1091 | N | LYS A 358 | 11.585 | 45.349 | 9.404 | 1.00 | 30.86 | N |
| ATOM | 1092 | CA | LYS A 358 | 12.501 | 44.560 | 8.586 | 1.00 | 32.89 | C |
| ATOM | 1093 | C | LYS A 358 | 13.321 | 45.395 | 7.604 | 1.00 | 31.32 | C |
| ATOM | 1094 | O | LYS A 358 | 14.509 | 45.139 | 7.352 | 1.00 | 30.49 | O |
| ATOM | 1095 | CB | LYS A 358 | 11.675 | 43.517 | 7.803 | 1.00 | 32.17 | C |
| ATOM | 1096 | CG | LYS A 358 | 12.538 | 42.456 | 7.152 | 1.00 | 33.53 | C |
| ATOM | 1097 | CD | LYS A 358 | 11.703 | 41.231 | 6.776 | 1.00 | 37.61 | C |
| ATOM | 1098 | CE | LYS A 358 | 10.693 | 41.627 | 5.698 | 1.00 | 37.64 | C |
| ATOM | 1099 | NZ | LYS A 358 | 10.069 | 40.422 | 5.116 | 1.00 | 43.04 | N |
| ATOM | 1100 | N | ALA A 359 | 12.688 | 46.421 | 7.039 | 1.00 | 30.43 | N |
| ATOM | 1101 | CA | ALA A 359 | 13.375 | 47.336 | 6.123 | 1.00 | 30.85 | C |
| ATOM | 1102 | C | ALA A 359 | 14.439 | 48.134 | 6.899 | 1.00 | 32.94 | C |
| ATOM | 1103 | O | ALA A 359 | 15.550 | 48.393 | 6.388 | 1.00 | 33.17 | O |
| ATOM | 1104 | CB | ALA A 359 | 12.358 | 48.257 | 5.459 | 1.00 | 30.43 | C |
| ATOM | 1105 | N | MET A 360 | 14.125 | 48.512 | 8.142 | 1.00 | 31.12 | N |
| ATOM | 1106 | CA | MET A 360 | 15.072 | 49.215 | 8.994 | 1.00 | 34.35 | C |
| ATOM | 1107 | C | MET A 360 | 16.264 | 48.331 | 9.350 | 1.00 | 30.37 | C |
| ATOM | 1108 | O | MET A 360 | 17.401 | 48.827 | 9.424 | 1.00 | 34.78 | O |
| ATOM | 1109 | CB | MET A 360 | 14.442 | 49.666 | 10.330 | 1.00 | 35.15 | C |
| ATOM | 1110 | CG | MET A 360 | 13.532 | 50.870 | 10.204 | 1.00 | 34.29 | C |
| ATOM | 1111 | SD | MET A 360 | 12.723 | 51.201 | 11.791 | 1.00 | 37.14 | S |
| ATOM | 1112 | CE | MET A 360 | 11.589 | 52.493 | 11.308 | 1.00 | 35.95 | C |
| ATOM | 1113 | N | ILE A 361 | 16.081 | 47.041 | 9.520 | 1.00 | 31.26 | N |
| ATOM | 1114 | CA | ILE A 361 | 17.226 | 46.122 | 9.785 | 1.00 | 34.18 | C |
| ATOM | 1115 | C | ILE A 361 | 18.172 | 46.173 | 8.589 | 1.00 | 36.01 | C |
| ATOM | 1116 | O | ILE A 361 | 19.394 | 46.267 | 8.756 | 1.00 | 35.73 | O |
| ATOM | 1117 | CB | ILE A 361 | 16.760 | 44.693 | 10.069 | 1.00 | 33.75 | C |
| ATOM | 1118 | CG1 | ILE A 361 | 16.174 | 44.659 | 11.479 | 1.00 | 33.99 | C |
| ATOM | 1119 | CG2 | ILE A 361 | 17.792 | 43.570 | 9.927 | 1.00 | 34.93 | C |
| ATOM | 1120 | CD1 | ILE A 361 | 15.232 | 43.510 | 11.760 | 1.00 | 34.99 | C |
| ATOM | 1121 | N | LEU A 362 | 17.689 | 46.107 | 7.345 | 1.00 | 35.56 | N |
| ATOM | 1122 | CA | LEU A 362 | 18.573 | 46.171 | 6.190 | 1.00 | 32.71 | C |
| ATOM | 1123 | C | LEU A 362 | 19.306 | 47.510 | 6.153 | 1.00 | 34.02 | C |
| ATOM | 1124 | O | LEU A 362 | 20.524 | 47.551 | 6.006 | 1.00 | 35.91 | O |
| ATOM | 1125 | CB | LEU A 362 | 17.760 | 46.097 | 4.889 | 1.00 | 36.02 | C |
| ATOM | 1126 | CG | LEU A 362 | 18.486 | 46.325 | 3.551 | 1.00 | 38.35 | C |
| ATOM | 1127 | CD1 | LEU A 362 | 19.346 | 45.107 | 3.256 | 1.00 | 35.52 | C |
| ATOM | 1128 | CD2 | LEU A 362 | 17.523 | 46.499 | 2.368 | 1.00 | 40.87 | C |
| ATOM | 1129 | N | LEU A 363 | 18.597 | 48.635 | 6.258 | 1.00 | 32.95 | N |
| ATOM | 1130 | CA | LEU A 363 | 19.231 | 49.928 | 6.125 | 1.00 | 35.19 | C |
| ATOM | 1131 | C | LEU A 363 | 20.076 | 50.377 | 7.302 | 1.00 | 36.97 | C |
| ATOM | 1132 | O | LEU A 363 | 20.900 | 51.242 | 7.014 | 1.00 | 36.49 | O |
| ATOM | 1133 | CB | LEU A 363 | 18.231 | 51.046 | 5.720 | 1.00 | 32.90 | C |
| ATOM | 1134 | CG | LEU A 363 | 17.472 | 50.779 | 4.404 | 1.00 | 34.40 | C |
| ATOM | 1135 | CD1 | LEU A 363 | 16.251 | 51.734 | 4.257 | 1.00 | 31.22 | C |
| ATOM | 1136 | CD2 | LEU A 363 | 18.379 | 51.008 | 3.195 | 1.00 | 28.34 | C |
| ATOM | 1137 | N | ASN A 364 | 19.904 | 49.899 | 8.518 | 1.00 | 35.20 | N |
| ATOM | 1138 | CA | ASN A 364 | 20.629 | 50.238 | 9.702 | 1.00 | 35.90 | C |
| ATOM | 1139 | C | ASN A 364 | 21.748 | 49.207 | 9.928 | 1.00 | 35.81 | C |
| ATOM | 1140 | O | ASN A 364 | 22.421 | 49.174 | 10.939 | 1.00 | 32.93 | O |
| ATOM | 1141 | CB | ASN A 364 | 19.710 | 50.187 | 10.948 | 1.00 | 37.40 | C |
| ATOM | 1142 | CG | ASN A 364 | 20.285 | 50.822 | 12.192 | 1.00 | 37.28 | C |
| ATOM | 1143 | OD1 | ASN A 364 | 20.927 | 51.854 | 12.015 | 1.00 | 36.48 | O |
| ATOM | 1144 | ND2 | ASN A 364 | 20.115 | 50.289 | 13.406 | 1.00 | 33.27 | N |
| ATOM | 1145 | N | SER A 365 | 21.994 | 48.354 | 8.950 | 1.00 | 36.69 | N |
| ATOM | 1146 | CA | SER A 365 | 23.044 | 47.354 | 9.006 | 1.00 | 37.31 | C |
| ATOM | 1147 | C | SER A 365 | 24.410 | 47.987 | 9.141 | 1.00 | 38.98 | C |
| ATOM | 1148 | O | SER A 365 | 24.629 | 49.057 | 8.574 | 1.00 | 37.45 | O |
| ATOM | 1149 | CB | SER A 365 | 23.019 | 46.528 | 7.706 | 1.00 | 41.83 | C |
| ATOM | 1150 | OG | SER A 365 | 23.640 | 45.267 | 7.948 | 1.00 | 45.14 | O |
| ATOM | 1151 | N | SER A 366 | 25.328 | 47.336 | 9.835 | 1.00 | 40.90 | N |
| ATOM | 1152 | CA | SER A 366 | 26.688 | 47.852 | 9.961 | 1.00 | 45.64 | C |

| | | | | | | | | | |
|---|---|---|---|---|---|---|---|---|---|
| ATOM | 999 | O | LEU | A 347 | 1.797 | 45.096 | 20.320 | 1.00 39.14 | O |
| ATOM | 1000 | CB | LEU | A 347 | 4.637 | 44.798 | 21.281 | 1.00 44.38 | C |
| ATOM | 1001 | CG | LEU | A 347 | 5.689 | 45.195 | 22.317 | 1.00 46.33 | C |
| ATOM | 1002 | CD1 | LEU | A 347 | 7.071 | 45.376 | 21.696 | 1.00 42.12 | C |
| ATOM | 1003 | CD2 | LEU | A 347 | 5.205 | 46.440 | 23.052 | 1.00 44.24 | C |
| ATOM | 1004 | N | LYS | A 348 | 1.905 | 42.868 | 20.348 | 1.00 42.11 | N |
| ATOM | 1005 | CA | LYS | A 348 | 0.895 | 42.764 | 19.299 | 1.00 42.40 | C |
| ATOM | 1006 | C | LYS | A 348 | 1.415 | 43.421 | 18.001 | 1.00 40.00 | C |
| ATOM | 1007 | O | LYS | A 348 | 0.731 | 44.163 | 17.329 | 1.00 38.81 | O |
| ATOM | 1008 | CB | LYS | A 348 | -0.414 | 43.424 | 19.715 | 1.00 45.56 | C |
| ATOM | 1009 | CG | LYS | A 348 | -1.138 | 42.641 | 20.809 | 1.00 52.50 | C |
| ATOM | 1010 | CD | LYS | A 348 | -2.221 | 43.453 | 21.495 | 1.00 56.50 | C |
| ATOM | 1011 | CE | LYS | A 348 | -3.043 | 42.529 | 22.407 | 1.00 61.47 | C |
| ATOM | 1012 | NZ | LYS | A 348 | -4.330 | 43.185 | 22.829 | 1.00 63.43 | N |
| ATOM | 1013 | N | LEU | A 349 | 2.632 | 43.134 | 17.612 | 1.00 38.96 | N |
| ATOM | 1014 | CA | LEU | A 349 | 3.209 | 43.678 | 16.387 | 1.00 39.89 | C |
| ATOM | 1015 | C | LEU | A 349 | 2.253 | 43.508 | 15.214 | 1.00 39.52 | C |
| ATOM | 1016 | O | LEU | A 349 | 1.815 | 42.382 | 14.983 | 1.00 40.34 | O |
| ATOM | 1017 | CB | LEU | A 349 | 4.538 | 42.954 | 16.140 | 1.00 36.04 | C |
| ATOM | 1018 | CG | LEU | A 349 | 5.377 | 43.407 | 14.931 | 1.00 36.19 | C |
| ATOM | 1019 | CD1 | LEU | A 349 | 6.005 | 44.785 | 15.205 | 1.00 33.34 | C |
| ATOM | 1020 | CD2 | LEU | A 349 | 6.470 | 42.357 | 14.727 | 1.00 32.07 | C |
| ATOM | 1021 | N | GLN | A 350 | 1.899 | 44.574 | 14.515 | 1.00 38.71 | N |
| ATOM | 1022 | CA | GLN | A 350 | 1.045 | 44.526 | 13.336 | 1.00 39.61 | C |
| ATOM | 1023 | C | GLN | A 350 | 1.912 | 44.298 | 12.104 | 1.00 41.73 | C |
| ATOM | 1024 | O | GLN | A 350 | 3.104 | 44.654 | 12.065 | 1.00 43.13 | O |
| ATOM | 1025 | CB | GLN | A 350 | 0.270 | 45.842 | 13.224 | 1.00 42.30 | C |
| ATOM | 1026 | CG | GLN | A 350 | -0.498 | 46.089 | 14.550 | 1.00 46.55 | C |
| ATOM | 1027 | CD | GLN | A 350 | -1.769 | 45.224 | 14.396 | 1.00 51.79 | C |
| ATOM | 1028 | OE1 | GLN | A 350 | -2.650 | 45.656 | 13.659 | 1.00 55.11 | O |
| ATOM | 1029 | NE2 | GLN | A 350 | -1.798 | 44.061 | 15.023 | 1.00 50.80 | N |
| ATOM | 1030 | N | HIS | A 351 | 1.378 | 43.687 | 11.052 | 1.00 41.17 | N |
| ATOM | 1031 | CA | HIS | A 351 | 2.058 | 43.334 | 9.829 | 1.00 38.37 | C |
| ATOM | 1032 | C | HIS | A 351 | 2.785 | 44.511 | 9.180 | 1.00 36.26 | C |
| ATOM | 1033 | O | HIS | A 351 | 3.939 | 44.384 | 8.799 | 1.00 37.99 | O |
| ATOM | 1034 | CB | HIS | A 351 | 1.039 | 42.738 | 8.813 | 1.00 39.10 | C |
| ATOM | 1035 | CG | HIS | A 351 | 1.798 | 42.107 | 7.687 | 1.00 39.41 | C |
| ATOM | 1036 | ND1 | HIS | A 351 | 1.483 | 42.282 | 6.392 | 1.00 39.89 | N |
| ATOM | 1037 | CD2 | HIS | A 351 | 2.894 | 41.264 | 7.679 | 1.00 39.28 | C |
| ATOM | 1038 | CE1 | HIS | A 351 | 2.279 | 41.623 | 5.569 | 1.00 38.88 | C |
| ATOM | 1039 | NE2 | HIS | A 351 | 3.149 | 41.025 | 6.356 | 1.00 41.95 | N |
| ATOM | 1040 | N | LYS | A 352 | 2.151 | 45.667 | 9.088 | 1.00 33.90 | N |
| ATOM | 1041 | CA | LYS | A 352 | 2.704 | 46.877 | 8.541 | 1.00 35.84 | C |
| ATOM | 1042 | C | LYS | A 352 | 3.864 | 47.377 | 9.441 | 1.00 37.84 | C |
| ATOM | 1043 | O | LYS | A 352 | 4.824 | 47.959 | 8.908 | 1.00 37.21 | O |
| ATOM | 1044 | CB | LYS | A 352 | 1.630 | 47.954 | 8.359 | 1.00 34.99 | C |
| ATOM | 1045 | CG | LYS | A 352 | 0.626 | 47.683 | 7.226 | 1.00 37.49 | C |
| ATOM | 1046 | CD | LYS | A 352 | -0.161 | 48.926 | 6.813 | 1.00 37.62 | C |
| ATOM | 1047 | CE | LYS | A 352 | -1.255 | 49.254 | 7.843 | 1.00 41.74 | C |
| ATOM | 1048 | NZ | LYS | A 352 | -2.120 | 48.027 | 8.013 | 1.00 44.69 | N |
| ATOM | 1049 | N | GLU | A 353 | 3.822 | 47.190 | 10.752 | 1.00 34.39 | N |
| ATOM | 1050 | CA | GLU | A 353 | 4.927 | 47.628 | 11.631 | 1.00 34.62 | C |
| ATOM | 1051 | C | GLU | A 353 | 6.111 | 46.709 | 11.365 | 1.00 34.92 | C |
| ATOM | 1052 | O | GLU | A 353 | 7.258 | 47.133 | 11.191 | 1.00 34.70 | O |
| ATOM | 1053 | CB | GLU | A 353 | 4.567 | 47.584 | 13.134 | 1.00 33.03 | C |
| ATOM | 1054 | CG | GLU | A 353 | 3.314 | 48.446 | 13.393 | 1.00 33.55 | C |
| ATOM | 1055 | CD | GLU | A 353 | 2.808 | 48.272 | 14.823 | 1.00 34.35 | C |
| ATOM | 1056 | OE1 | GLU | A 353 | 2.581 | 47.149 | 15.284 | 1.00 33.01 | O |
| ATOM | 1057 | OE2 | GLU | A 353 | 2.670 | 49.313 | 15.483 | 1.00 34.10 | O |
| ATOM | 1058 | N | TYR | A 354 | 5.793 | 45.422 | 11.288 | 1.00 33.14 | N |
| ATOM | 1059 | CA | TYR | A 354 | 6.814 | 44.431 | 10.980 | 1.00 33.90 | C |
| ATOM | 1060 | C | TYR | A 354 | 7.567 | 44.768 | 9.686 | 1.00 34.91 | C |
| ATOM | 1061 | O | TYR | A 354 | 8.792 | 44.618 | 9.583 | 1.00 35.84 | O |
| ATOM | 1062 | CB | TYR | A 354 | 6.123 | 43.069 | 10.822 | 1.00 33.60 | C |
| ATOM | 1063 | CG | TYR | A 354 | 6.898 | 42.053 | 10.018 | 1.00 36.59 | C |
| ATOM | 1064 | CD1 | TYR | A 354 | 8.063 | 41.529 | 10.539 | 1.00 35.16 | C |
| ATOM | 1065 | CD2 | TYR | A 354 | 6.509 | 41.627 | 8.749 | 1.00 38.31 | C |
| ATOM | 1066 | CE1 | TYR | A 354 | 8.796 | 40.595 | 9.844 | 1.00 36.74 | C |
| ATOM | 1067 | CE2 | TYR | A 354 | 7.231 | 40.692 | 8.028 | 1.00 36.03 | C |
| ATOM | 1068 | CZ | TYR | A 354 | 8.373 | 40.196 | 8.597 | 1.00 39.33 | C |
| ATOM | 1069 | OH | TYR | A 354 | 9.176 | 39.263 | 7.979 | 1.00 44.53 | O |
| ATOM | 1070 | N | LEU | A 355 | 6.881 | 45.198 | 8.642 | 1.00 35.97 | N |
| ATOM | 1071 | CA | LEU | A 355 | 7.467 | 45.545 | 7.355 | 1.00 37.66 | C |
| ATOM | 1072 | C | LEU | A 355 | 8.468 | 46.705 | 7.503 | 1.00 34.57 | C |
| ATOM | 1073 | O | LEU | A 355 | 9.552 | 46.693 | 6.902 | 1.00 33.09 | O |
| ATOM | 1074 | CB | LEU | A 355 | 6.426 | 45.925 | 6.330 | 1.00 37.43 | C |
| ATOM | 1075 | CG | LEU | A 355 | 5.703 | 45.030 | 5.342 | 1.00 43.23 | C |

| ATOM | 922 | CA | LEU A 338 | 11.336 | 32.458 | 21.299 | 1.00 | 47.50 | C |
| --- | --- | --- | --- | --- | --- | --- | --- | --- | --- |
| ATOM | 923 | C | LEU A 338 | 11.030 | 33.645 | 22.183 | 1.00 | 45.56 | C |
| ATOM | 924 | O | LEU A 338 | 9.909 | 34.167 | 22.175 | 1.00 | 47.32 | O |
| ATOM | 925 | CB | LEU A 338 | 11.186 | 31.106 | 21.996 | 1.00 | 49.57 | C |
| ATOM | 926 | CG | LEU A 338 | 11.198 | 29.914 | 21.013 | 1.00 | 51.80 | C |
| ATOM | 927 | CD1 | LEU A 338 | 11.850 | 28.691 | 21.616 | 1.00 | 50.00 | C |
| ATOM | 928 | CD2 | LEU A 338 | 9.771 | 29.595 | 20.568 | 1.00 | 51.29 | C |
| ATOM | 929 | N | ALA A 339 | 11.984 | 34.102 | 22.996 | 1.00 | 43.32 | N |
| ATOM | 930 | CA | ALA A 339 | 11.688 | 35.268 | 23.842 | 1.00 | 44.25 | C |
| ATOM | 931 | C | ALA A 339 | 11.457 | 36.507 | 22.964 | 1.00 | 45.46 | C |
| ATOM | 932 | O | ALA A 339 | 10.444 | 37.200 | 23.141 | 1.00 | 48.57 | O |
| ATOM | 933 | CB | ALA A 339 | 12.895 | 35.481 | 24.738 | 1.00 | 44.91 | C |
| ATOM | 934 | N | THR A 340 | 12.341 | 36.762 | 21.971 | 1.00 | 43.51 | N |
| ATOM | 935 | CA | THR A 340 | 12.098 | 37.944 | 21.117 | 1.00 | 42.19 | C |
| ATOM | 936 | C | THR A 340 | 10.745 | 37.802 | 20.458 | 1.00 | 42.15 | C |
| ATOM | 937 | O | THR A 340 | 9.960 | 38.760 | 20.474 | 1.00 | 41.10 | O |
| ATOM | 938 | CB | THR A 340 | 13.247 | 38.207 | 20.163 | 1.00 | 43.29 | C |
| ATOM | 939 | OG1 | THR A 340 | 14.466 | 38.252 | 20.953 | 1.00 | 44.57 | O |
| ATOM | 940 | CG2 | THR A 340 | 13.093 | 39.527 | 19.436 | 1.00 | 43.25 | C |
| ATOM | 941 | N | THR A 341 | 10.415 | 36.601 | 19.942 | 1.00 | 41.49 | N |
| ATOM | 942 | CA | THR A 341 | 9.093 | 36.360 | 19.371 | 1.00 | 42.29 | C |
| ATOM | 943 | C | THR A 341 | 8.027 | 36.677 | 20.410 | 1.00 | 42.15 | C |
| ATOM | 944 | O | THR A 341 | 7.059 | 37.377 | 20.060 | 1.00 | 44.54 | O |
| ATOM | 945 | CB | THR A 341 | 8.903 | 34.893 | 18.909 | 1.00 | 43.49 | C |
| ATOM | 946 | OG1 | THR A 341 | 9.944 | 34.525 | 18.011 | 1.00 | 44.01 | O |
| ATOM | 947 | CG2 | THR A 341 | 7.535 | 34.705 | 18.277 | 1.00 | 41.81 | C |
| ATOM | 948 | N | SER A 342 | 8.153 | 36.240 | 21.689 | 1.00 | 44.00 | N |
| ATOM | 949 | CA | SER A 342 | 7.116 | 36.616 | 22.674 | 1.00 | 44.23 | C |
| ATOM | 950 | C | SER A 342 | 7.072 | 38.121 | 22.903 | 1.00 | 43.12 | C |
| ATOM | 951 | O | SER A 342 | 6.026 | 38.712 | 23.192 | 1.00 | 44.21 | O |
| ATOM | 952 | CB | SER A 342 | 7.410 | 35.927 | 24.027 | 1.00 | 47.46 | C |
| ATOM | 953 | OG | SER A 342 | 7.563 | 34.513 | 23.833 | 1.00 | 42.91 | O |
| ATOM | 954 | N | ARG A 343 | 8.193 | 38.857 | 22.807 | 1.00 | 44.17 | N |
| ATOM | 955 | CA | ARG A 343 | 8.084 | 40.330 | 23.017 | 1.00 | 44.19 | C |
| ATOM | 956 | C | ARG A 343 | 7.181 | 40.918 | 21.946 | 1.00 | 44.53 | C |
| ATOM | 957 | O | ARG A 343 | 6.302 | 41.740 | 22.203 | 1.00 | 45.99 | O |
| ATOM | 958 | CB | ARG A 343 | 9.453 | 41.002 | 23.053 | 1.00 | 45.32 | C |
| ATOM | 959 | CG | ARG A 343 | 10.356 | 40.409 | 24.114 | 1.00 | 48.29 | C |
| ATOM | 960 | CD | ARG A 343 | 9.912 | 40.890 | 25.500 | 1.00 | 51.27 | C |
| ATOM | 961 | NE | ARG A 343 | 8.959 | 39.968 | 26.129 | 1.00 | 52.61 | N |
| ATOM | 962 | CZ | ARG A 343 | 9.264 | 38.742 | 26.567 | 1.00 | 53.00 | C |
| ATOM | 963 | NH1 | ARG A 343 | 10.484 | 38.232 | 26.465 | 1.00 | 50.96 | N |
| ATOM | 964 | NH2 | ARG A 343 | 8.318 | 38.005 | 27.123 | 1.00 | 50.91 | N |
| ATOM | 965 | N | PHE A 344 | 7.370 | 40.445 | 20.704 | 1.00 | 44.03 | N |
| ATOM | 966 | CA | PHE A 344 | 6.556 | 40.859 | 19.570 | 1.00 | 46.18 | C |
| ATOM | 967 | C | PHE A 344 | 5.090 | 40.490 | 19.781 | 1.00 | 45.15 | C |
| ATOM | 968 | O | PHE A 344 | 4.178 | 41.277 | 19.458 | 1.00 | 40.80 | O |
| ATOM | 969 | CB | PHE A 344 | 7.117 | 40.273 | 18.250 | 1.00 | 45.20 | C |
| ATOM | 970 | CG | PHE A 344 | 8.309 | 41.069 | 17.746 | 1.00 | 48.53 | C |
| ATOM | 971 | CD1 | PHE A 344 | 8.268 | 42.457 | 17.661 | 1.00 | 49.19 | C |
| ATOM | 972 | CD2 | PHE A 344 | 9.466 | 40.439 | 17.345 | 1.00 | 49.29 | C |
| ATOM | 973 | CE1 | PHE A 344 | 9.348 | 43.188 | 17.198 | 1.00 | 50.40 | C |
| ATOM | 974 | CE2 | PHE A 344 | 10.558 | 41.131 | 16.869 | 1.00 | 51.54 | C |
| ATOM | 975 | CZ | PHE A 344 | 10.500 | 42.526 | 16.795 | 1.00 | 52.95 | C |
| ATOM | 976 | N | ARG A 345 | 4.862 | 39.278 | 20.318 | 1.00 | 46.48 | N |
| ATOM | 977 | CA | ARG A 345 | 3.467 | 38.874 | 20.563 | 1.00 | 48.57 | C |
| ATOM | 978 | C | ARG A 345 | 2.914 | 39.764 | 21.665 | 1.00 | 47.67 | C |
| ATOM | 979 | O | ARG A 345 | 1.808 | 40.285 | 21.569 | 1.00 | 47.71 | O |
| ATOM | 980 | CB | ARG A 345 | 3.326 | 37.407 | 20.983 | 1.00 | 51.37 | C |
| ATOM | 981 | CG | ARG A 345 | 1.947 | 37.036 | 21.515 | 1.00 | 52.39 | C |
| ATOM | 982 | CD | ARG A 345 | 1.923 | 35.615 | 22.100 | 1.00 | 53.54 | C |
| ATOM | 983 | NE | ARG A 345 | 2.911 | 34.807 | 21.469 | 1.00 | 56.63 | N |
| ATOM | 984 | CZ | ARG A 345 | 4.003 | 34.164 | 21.817 | 1.00 | 59.69 | C |
| ATOM | 985 | NH1 | ARG A 345 | 4.469 | 34.117 | 23.066 | 1.00 | 61.27 | N |
| ATOM | 986 | NH2 | ARG A 345 | 4.616 | 33.544 | 20.808 | 1.00 | 58.35 | N |
| ATOM | 987 | N | GLU A 346 | 3.720 | 39.980 | 22.703 | 1.00 | 48.19 | N |
| ATOM | 988 | CA | GLU A 346 | 3.236 | 40.850 | 23.786 | 1.00 | 49.25 | C |
| ATOM | 989 | C | GLU A 346 | 2.899 | 42.230 | 23.266 | 1.00 | 50.06 | C |
| ATOM | 990 | O | GLU A 346 | 1.882 | 42.819 | 23.667 | 1.00 | 49.05 | O |
| ATOM | 991 | CB | GLU A 346 | 4.315 | 40.910 | 24.874 | 1.00 | 53.08 | C |
| ATOM | 992 | CG | GLU A 346 | 4.402 | 39.633 | 25.682 | 1.00 | 56.79 | C |
| ATOM | 993 | CD | GLU A 346 | 5.730 | 39.409 | 26.363 | 1.00 | 60.09 | C |
| ATOM | 994 | OE1 | GLU A 346 | 6.592 | 40.308 | 26.413 | 1.00 | 61.61 | O |
| ATOM | 995 | OE2 | GLU A 346 | 5.924 | 38.280 | 26.878 | 1.00 | 61.31 | O |
| ATOM | 996 | N | LEU A 347 | 3.732 | 42.791 | 22.347 | 1.00 | 45.41 | N |
| ATOM | 997 | CA | LEU A 347 | 3.381 | 44.122 | 21.852 | 1.00 | 43.34 | C |
| ATOM | 998 | C | LEU A 347 | 2.288 | 44.058 | 20.799 | 1.00 | 41.20 | C |

```
ATOM   845  CA  GLU A 328      25.062  21.518  19.028  1.00108.98           C
ATOM   846  C   GLU A 328      24.901  22.772  19.867  1.00106.98           C
ATOM   847  O   GLU A 328      25.590  23.765  19.595  1.00107.31           O
ATOM   848  CB  GLU A 328      26.223  21.792  18.036  1.00109.39           C
ATOM   849  N   GLY A 329      24.066  22.770  20.899  1.00104.40           N
ATOM   850  CA  GLY A 329      23.880  23.950  21.736  1.00101.09           C
ATOM   851  C   GLY A 329      23.126  25.037  20.971  1.00 99.06           C
ATOM   852  O   GLY A 329      23.578  26.170  20.829  1.00 98.65           O
ATOM   853  N   ILE A 330      21.950  24.682  20.468  1.00 96.48           N
ATOM   854  CA  ILE A 330      21.116  25.600  19.703  1.00 93.88           C
ATOM   855  C   ILE A 330      19.855  25.955  20.480  1.00 92.39           C
ATOM   856  O   ILE A 330      19.089  26.836  20.074  1.00 91.38           O
ATOM   857  CB  ILE A 330      20.821  24.971  18.331  1.00 93.74           C
ATOM   858  CG1 ILE A 330      20.592  26.020  17.241  1.00 93.90           C
ATOM   859  CG2 ILE A 330      19.621  24.036  18.385  1.00 93.92           C
ATOM   860  CD1 ILE A 330      20.505  25.429  15.845  1.00 93.02           C
ATOM   861  N   LEU A 331      19.633  25.291  21.615  1.00 89.26           N
ATOM   862  CA  LEU A 331      18.462  25.523  22.453  1.00 86.87           C
ATOM   863  C   LEU A 331      18.459  26.899  23.114  1.00 84.60           C
ATOM   864  O   LEU A 331      17.404  27.520  23.260  1.00 84.38           O
ATOM   865  CB  LEU A 331      18.286  24.436  23.533  1.00 86.39           C
ATOM   866  CG  LEU A 331      17.053  24.613  24.430  1.00 86.20           C
ATOM   867  CD1 LEU A 331      15.769  24.261  23.687  1.00 85.81           C
ATOM   868  CD2 LEU A 331      17.135  23.787  25.706  1.00 85.84           C
ATOM   869  N   GLU A 332      19.630  27.391  23.509  1.00 81.60           N
ATOM   870  CA  GLU A 332      19.712  28.717  24.126  1.00 79.93           C
ATOM   871  C   GLU A 332      19.530  29.768  23.028  1.00 76.07           C
ATOM   872  O   GLU A 332      19.034  30.852  23.302  1.00 74.35           O
ATOM   873  CB  GLU A 332      20.998  28.883  24.918  1.00 81.55           C
ATOM   874  CG  GLU A 332      22.217  28.429  24.125  1.00 84.90           C
ATOM   875  CD  GLU A 332      23.380  29.382  24.329  1.00 87.54           C
ATOM   876  OE1 GLU A 332      23.899  29.441  25.469  1.00 87.83           O
ATOM   877  OE2 GLU A 332      23.732  30.045  23.324  1.00 89.23           O
ATOM   878  N   ILE A 333      19.906  29.442  21.789  1.00 72.13           N
ATOM   879  CA  ILE A 333      19.697  30.337  20.667  1.00 68.67           C
ATOM   880  C   ILE A 333      18.198  30.280  20.312  1.00 65.84           C
ATOM   881  O   ILE A 333      17.566  31.290  20.043  1.00 64.75           O
ATOM   882  CB  ILE A 333      20.482  29.984  19.397  1.00 68.17           C
ATOM   883  CG1 ILE A 333      21.960  29.843  19.694  1.00 69.96           C
ATOM   884  CG2 ILE A 333      20.201  31.029  18.316  1.00 69.48           C
ATOM   885  CD1 ILE A 333      22.707  31.096  20.080  1.00 70.73           C
ATOM   886  N   PHE A 334      17.604  29.083  20.365  1.00 63.55           N
ATOM   887  CA  PHE A 334      16.192  28.903  20.089  1.00 62.27           C
ATOM   888  C   PHE A 334      15.393  29.616  21.178  1.00 60.31           C
ATOM   889  O   PHE A 334      14.316  30.116  20.856  1.00 61.28           O
ATOM   890  CB  PHE A 334      15.716  27.467  19.987  1.00 63.25           C
ATOM   891  CG  PHE A 334      15.816  26.741  18.681  1.00 65.00           C
ATOM   892  CD1 PHE A 334      16.686  27.124  17.671  1.00 65.00           C
ATOM   893  CD2 PHE A 334      15.000  25.628  18.461  1.00 65.53           C
ATOM   894  CE1 PHE A 334      16.752  26.423  16.486  1.00 65.69           C
ATOM   895  CE2 PHE A 334      15.062  24.928  17.274  1.00 65.02           C
ATOM   896  CZ  PHE A 334      15.936  25.321  16.283  1.00 64.98           C
ATOM   897  N   ASP A 335      15.903  29.678  22.406  1.00 57.39           N
ATOM   898  CA  ASP A 335      15.188  30.371  23.470  1.00 57.07           C
ATOM   899  C   ASP A 335      15.240  31.882  23.278  1.00 51.87           C
ATOM   900  O   ASP A 335      14.307  32.600  23.608  1.00 48.90           O
ATOM   901  CB  ASP A 335      15.789  30.024  24.838  1.00 61.35           C
ATOM   902  CG  ASP A 335      15.507  28.599  25.271  1.00 65.45           C
ATOM   903  OD1 ASP A 335      14.737  27.842  24.651  1.00 65.48           O
ATOM   904  OD2 ASP A 335      16.125  28.254  26.307  1.00 68.54           O
ATOM   905  N   MET A 336      16.366  32.374  22.755  1.00 50.29           N
ATOM   906  CA  MET A 336      16.495  33.823  22.495  1.00 48.59           C
ATOM   907  C   MET A 336      15.424  34.207  21.470  1.00 46.17           C
ATOM   908  O   MET A 336      14.620  35.139  21.593  1.00 42.53           O
ATOM   909  CB  MET A 336      17.920  34.126  22.053  1.00 50.17           C
ATOM   910  CG  MET A 336      19.041  33.800  23.021  1.00 50.53           C
ATOM   911  SD  MET A 336      20.666  34.415  22.422  1.00 51.85           S
ATOM   912  CE  MET A 336      20.348  36.090  23.059  1.00 53.67           C
ATOM   913  N   LEU A 337      15.336  33.381  20.417  1.00 47.99           N
ATOM   914  CA  LEU A 337      14.363  33.566  19.338  1.00 48.30           C
ATOM   915  C   LEU A 337      12.941  33.514  19.837  1.00 47.83           C
ATOM   916  O   LEU A 337      12.076  34.310  19.437  1.00 44.47           O
ATOM   917  CB  LEU A 337      14.569  32.519  18.229  1.00 48.13           C
ATOM   918  CG  LEU A 337      15.866  32.759  17.442  1.00 49.23           C
ATOM   919  CD1 LEU A 337      16.191  31.550  16.571  1.00 52.60           C
ATOM   920  CD2 LEU A 337      15.794  34.013  16.582  1.00 48.24           C
ATOM   921  N   LEU A 338      12.709  32.567  20.763  1.00 48.65           N
```

53

| ATOM | 768 | CA | VAL A 318 | 7.461 | 23.673 | 12.696 | 1.00 | 80.16 | C |
| ATOM | 769 | C | VAL A 318 | 8.159 | 22.892 | 13.798 | 1.00 | 82.11 | C |
| ATOM | 770 | O | VAL A 318 | 7.822 | 21.757 | 14.119 | 1.00 | 83.64 | O |
| ATOM | 771 | CB | VAL A 318 | 5.945 | 23.608 | 12.971 | 1.00 | 79.31 | C |
| ATOM | 772 | CG1 | VAL A 318 | 5.624 | 24.165 | 14.349 | 1.00 | 78.34 | C |
| ATOM | 773 | CG2 | VAL A 318 | 5.183 | 24.318 | 11.868 | 1.00 | 77.50 | C |
| ATOM | 774 | N | LEU A 319 | 9.163 | 23.536 | 14.377 | 1.00 | 83.74 | N |
| ATOM | 775 | CA | LEU A 319 | 9.953 | 22.927 | 15.434 | 1.00 | 83.81 | C |
| ATOM | 776 | C | LEU A 319 | 9.542 | 23.394 | 16.813 | 1.00 | 85.26 | C |
| ATOM | 777 | O | LEU A 319 | 9.318 | 24.580 | 17.049 | 1.00 | 84.35 | O |
| ATOM | 778 | CB | LEU A 319 | 11.422 | 23.217 | 15.136 | 1.00 | 83.76 | C |
| ATOM | 779 | CG | LEU A 319 | 11.919 | 22.876 | 13.735 | 1.00 | 83.33 | C |
| ATOM | 780 | CD1 | LEU A 319 | 13.439 | 22.921 | 13.694 | 1.00 | 83.01 | C |
| ATOM | 781 | CD2 | LEU A 319 | 11.445 | 21.504 | 13.270 | 1.00 | 84.15 | C |
| ATOM | 782 | N | ASP A 320 | 9.423 | 22.431 | 17.724 | 1.00 | 87.46 | N |
| ATOM | 783 | CA | ASP A 320 | 9.031 | 22.769 | 19.091 | 1.00 | 90.90 | C |
| ATOM | 784 | C | ASP A 320 | 10.301 | 23.174 | 19.829 | 1.00 | 91.49 | C |
| ATOM | 785 | O | ASP A 320 | 11.395 | 22.830 | 19.383 | 1.00 | 90.28 | O |
| ATOM | 786 | CB | ASP A 320 | 8.328 | 21.605 | 19.763 | 1.00 | 93.97 | C |
| ATOM | 787 | CG | ASP A 320 | 7.448 | 22.045 | 20.912 | 1.00 | 96.68 | C |
| ATOM | 788 | OD1 | ASP A 320 | 6.419 | 22.720 | 20.683 | 1.00 | 98.45 | O |
| ATOM | 789 | OD2 | ASP A 320 | 7.780 | 21.715 | 22.072 | 1.00 | 98.12 | O |
| ATOM | 790 | N | ARG A 321 | 10.153 | 23.890 | 20.925 | 1.00 | 93.31 | N |
| ATOM | 791 | CA | ARG A 321 | 11.303 | 24.334 | 21.704 | 1.00 | 96.26 | C |
| ATOM | 792 | C | ARG A 321 | 12.257 | 23.216 | 22.075 | 1.00 | 98.20 | C |
| ATOM | 793 | O | ARG A 321 | 13.469 | 23.368 | 21.862 | 1.00 | 97.82 | O |
| ATOM | 794 | CB | ARG A 321 | 10.758 | 25.081 | 22.923 | 1.00 | 96.61 | C |
| ATOM | 795 | CG | ARG A 321 | 11.784 | 25.936 | 23.643 | 1.00 | 96.93 | C |
| ATOM | 796 | CD | ARG A 321 | 12.066 | 25.326 | 25.008 | 1.00 | 96.52 | C |
| ATOM | 797 | NE | ARG A 321 | 13.363 | 25.799 | 25.477 | 1.00 | 96.62 | N |
| ATOM | 798 | CZ | ARG A 321 | 13.908 | 25.447 | 26.635 | 1.00 | 95.64 | C |
| ATOM | 799 | NH1 | ARG A 321 | 13.265 | 24.615 | 27.431 | 1.00 | 95.75 | N |
| ATOM | 800 | NH2 | ARG A 321 | 15.085 | 25.959 | 26.930 | 1.00 | 94.67 | N |
| ATOM | 801 | N | ASP A 322 | 11.784 | 22.082 | 22.588 | 1.00 | 100.61 | N |
| ATOM | 802 | CA | ASP A 322 | 12.650 | 20.971 | 22.965 | 1.00 | 103.46 | C |
| ATOM | 803 | C | ASP A 322 | 13.280 | 20.207 | 21.816 | 1.00 | 104.37 | C |
| ATOM | 804 | O | ASP A 322 | 14.135 | 19.348 | 22.071 | 1.00 | 104.78 | O |
| ATOM | 805 | CB | ASP A 322 | 11.920 | 20.003 | 23.917 | 1.00 | 104.09 | C |
| ATOM | 806 | CG | ASP A 322 | 11.594 | 20.670 | 25.244 | 1.00 | 105.16 | C |
| ATOM | 807 | OD1 | ASP A 322 | 12.527 | 20.966 | 26.027 | 1.00 | 105.32 | O |
| ATOM | 808 | OD2 | ASP A 322 | 10.398 | 20.918 | 25.537 | 1.00 | 104.85 | O |
| ATOM | 809 | N | GLU A 323 | 12.970 | 20.475 | 20.556 | 1.00 | 105.72 | N |
| ATOM | 810 | CA | GLU A 323 | 13.566 | 19.791 | 19.419 | 1.00 | 107.17 | C |
| ATOM | 811 | C | GLU A 323 | 14.900 | 20.409 | 19.015 | 1.00 | 107.93 | C |
| ATOM | 812 | O | GLU A 323 | 15.606 | 19.949 | 18.115 | 1.00 | 108.25 | O |
| ATOM | 813 | CB | GLU A 323 | 12.626 | 19.784 | 18.220 | 1.00 | 107.77 | C |
| ATOM | 814 | CG | GLU A 323 | 11.430 | 18.853 | 18.339 | 1.00 | 108.61 | C |
| ATOM | 815 | CD | GLU A 323 | 10.591 | 18.931 | 17.075 | 1.00 | 109.60 | C |
| ATOM | 816 | OE1 | GLU A 323 | 11.102 | 18.558 | 15.999 | 1.00 | 109.67 | O |
| ATOM | 817 | OE2 | GLU A 323 | 9.427 | 19.374 | 17.164 | 1.00 | 109.90 | O |
| ATOM | 818 | N | GLY A 324 | 15.292 | 21.473 | 19.707 | 1.00 | 109.07 | N |
| ATOM | 819 | CA | GLY A 324 | 16.550 | 22.162 | 19.494 | 1.00 | 110.28 | C |
| ATOM | 820 | C | GLY A 324 | 17.674 | 21.473 | 20.267 | 1.00 | 111.19 | C |
| ATOM | 821 | O | GLY A 324 | 18.846 | 21.840 | 20.168 | 1.00 | 110.81 | O |
| ATOM | 822 | N | LYS A 325 | 17.351 | 20.435 | 21.036 | 1.00 | 112.32 | N |
| ATOM | 823 | CA | LYS A 325 | 18.313 | 19.665 | 21.806 | 1.00 | 113.24 | C |
| ATOM | 824 | C | LYS A 325 | 19.136 | 18.737 | 20.916 | 1.00 | 113.14 | C |
| ATOM | 825 | O | LYS A 325 | 20.211 | 18.289 | 21.310 | 1.00 | 113.45 | O |
| ATOM | 826 | CB | LYS A 325 | 17.641 | 18.843 | 22.903 | 1.00 | 113.79 | C |
| ATOM | 827 | CG | LYS A 325 | 16.846 | 17.645 | 22.413 | 1.00 | 114.28 | C |
| ATOM | 828 | CD | LYS A 325 | 16.137 | 16.943 | 23.557 | 1.00 | 114.32 | C |
| ATOM | 829 | CE | LYS A 325 | 14.877 | 16.234 | 23.088 | 1.00 | 114.49 | C |
| ATOM | 830 | NZ | LYS A 325 | 13.670 | 16.656 | 23.850 | 1.00 | 113.91 | N |
| ATOM | 831 | N | CYS A 326 | 18.642 | 18.457 | 19.721 | 1.00 | 113.19 | N |
| ATOM | 832 | CA | CYS A 326 | 19.310 | 17.621 | 18.746 | 1.00 | 113.19 | C |
| ATOM | 833 | C | CYS A 326 | 20.603 | 18.259 | 18.248 | 1.00 | 113.13 | C |
| ATOM | 834 | O | CYS A 326 | 21.613 | 17.569 | 18.085 | 1.00 | 114.20 | O |
| ATOM | 835 | CB | CYS A 326 | 18.384 | 17.378 | 17.548 | 1.00 | 113.54 | C |
| ATOM | 836 | SG | CYS A 326 | 16.777 | 16.634 | 17.914 | 1.00 | 113.60 | S |
| ATOM | 837 | N | VAL A 327 | 20.603 | 19.565 | 18.004 | 1.00 | 112.41 | N |
| ATOM | 838 | CA | VAL A 327 | 21.786 | 20.265 | 17.507 | 1.00 | 111.52 | C |
| ATOM | 839 | C | VAL A 327 | 22.685 | 20.838 | 18.593 | 1.00 | 110.83 | C |
| ATOM | 840 | O | VAL A 327 | 22.327 | 21.134 | 19.730 | 1.00 | 109.92 | O |
| ATOM | 841 | CB | VAL A 327 | 21.364 | 21.361 | 16.504 | 1.00 | 111.40 | C |
| ATOM | 842 | CG1 | VAL A 327 | 22.555 | 21.996 | 15.807 | 1.00 | 111.32 | C |
| ATOM | 843 | CG2 | VAL A 327 | 20.419 | 20.774 | 15.462 | 1.00 | 111.47 | C |
| ATOM | 844 | N | GLU A 328 | 23.951 | 21.025 | 18.256 | 1.00 | 109.87 | N |

54

| | | | | | | | | | |
|---|---|---|---|---|---|---|---|---|---|
| ATOM | 691 | ND1 | HIS A 307 | 0.762 | 29.040 | 16.022 | 1.00 | 70.97 | N |
| ATOM | 692 | CD2 | HIS A 307 | 2.187 | 29.766 | 14.529 | 1.00 | 70.42 | C |
| ATOM | 693 | CE1 | HIS A 307 | 0.090 | 29.223 | 14.892 | 1.00 | 72.01 | C |
| ATOM | 694 | NE2 | HIS A 307 | 0.931 | 29.672 | 13.974 | 1.00 | 71.38 | N |
| ATOM | 695 | N | PRO A 308 | 3.116 | 30.264 | 20.480 | 1.00 | 57.70 | N |
| ATOM | 696 | CA | PRO A 308 | 3.946 | 30.147 | 21.665 | 1.00 | 58.21 | C |
| ATOM | 697 | C | PRO A 308 | 4.616 | 28.788 | 21.669 | 1.00 | 59.71 | C |
| ATOM | 698 | O | PRO A 308 | 3.980 | 27.776 | 21.348 | 1.00 | 58.73 | O |
| ATOM | 699 | CB | PRO A 308 | 3.018 | 30.355 | 22.866 | 1.00 | 58.27 | C |
| ATOM | 700 | CG | PRO A 308 | 1.980 | 31.257 | 22.060 | 1.00 | 59.98 | C |
| ATOM | 701 | CD | PRO A 308 | 1.793 | 30.823 | 20.789 | 1.00 | 58.01 | C |
| ATOM | 702 | N | GLY A 309 | 5.901 | 28.755 | 22.003 | 1.00 | 60.77 | N |
| ATOM | 703 | CA | GLY A 309 | 6.659 | 27.530 | 22.060 | 1.00 | 61.54 | C |
| ATOM | 704 | C | GLY A 309 | 7.267 | 26.945 | 20.821 | 1.00 | 61.68 | C |
| ATOM | 705 | O | GLY A 309 | 8.087 | 26.002 | 20.908 | 1.00 | 61.34 | O |
| ATOM | 706 | N | LYS A 310 | 6.901 | 27.411 | 19.620 | 1.00 | 62.76 | N |
| ATOM | 707 | CA | LYS A 310 | 7.511 | 26.811 | 18.426 | 1.00 | 62.51 | C |
| ATOM | 708 | C | LYS A 310 | 8.071 | 27.850 | 17.465 | 1.00 | 59.78 | C |
| ATOM | 709 | O | LYS A 310 | 7.626 | 28.984 | 17.411 | 1.00 | 59.07 | O |
| ATOM | 710 | CB | LYS A 310 | 6.533 | 25.922 | 17.669 | 1.00 | 66.12 | C |
| ATOM | 711 | CG | LYS A 310 | 5.689 | 24.932 | 18.457 | 1.00 | 68.30 | C |
| ATOM | 712 | CD | LYS A 310 | 4.284 | 25.517 | 18.618 | 1.00 | 71.16 | C |
| ATOM | 713 | CE | LYS A 310 | 3.349 | 25.007 | 17.525 | 1.00 | 72.57 | C |
| ATOM | 714 | NZ | LYS A 310 | 2.875 | 26.109 | 16.625 | 1.00 | 73.51 | N |
| ATOM | 715 | N | LEU A 311 | 9.046 | 27.462 | 16.687 | 1.00 | 55.96 | N |
| ATOM | 716 | CA | LEU A 311 | 9.695 | 28.269 | 15.675 | 1.00 | 55.45 | C |
| ATOM | 717 | C | LEU A 311 | 9.171 | 27.766 | 14.320 | 1.00 | 57.81 | C |
| ATOM | 718 | O | LEU A 311 | 9.452 | 26.622 | 13.928 | 1.00 | 56.08 | O |
| ATOM | 719 | CB | LEU A 311 | 11.204 | 28.146 | 15.807 | 1.00 | 52.92 | C |
| ATOM | 720 | CG | LEU A 311 | 11.790 | 28.828 | 17.055 | 1.00 | 53.74 | C |
| ATOM | 721 | CD1 | LEU A 311 | 13.195 | 28.340 | 17.360 | 1.00 | 52.44 | C |
| ATOM | 722 | CD2 | LEU A 311 | 11.770 | 30.340 | 16.872 | 1.00 | 51.24 | C |
| ATOM | 723 | N | ILE A 312 | 8.341 | 28.590 | 13.662 | 1.00 | 56.93 | N |
| ATOM | 724 | CA | ILE A 312 | 7.776 | 28.217 | 12.374 | 1.00 | 54.86 | C |
| ATOM | 725 | C | ILE A 312 | 8.755 | 28.581 | 11.260 | 1.00 | 55.40 | C |
| ATOM | 726 | O | ILE A 312 | 8.658 | 29.669 | 10.657 | 1.00 | 51.19 | O |
| ATOM | 727 | CB | ILE A 312 | 6.444 | 28.947 | 12.143 | 1.00 | 56.20 | C |
| ATOM | 728 | CG1 | ILE A 312 | 5.495 | 28.849 | 13.330 | 1.00 | 58.16 | C |
| ATOM | 729 | CG2 | ILE A 312 | 5.758 | 28.464 | 10.869 | 1.00 | 55.96 | C |
| ATOM | 730 | CD1 | ILE A 312 | 5.033 | 27.452 | 13.668 | 1.00 | 60.14 | C |
| ATOM | 731 | N | PHE A 313 | 9.717 | 27.694 | 10.963 | 1.00 | 54.28 | N |
| ATOM | 732 | CA | PHE A 313 | 10.683 | 28.002 | 9.920 | 1.00 | 56.85 | C |
| ATOM | 733 | C | PHE A 313 | 10.061 | 28.006 | 8.518 | 1.00 | 59.64 | C |
| ATOM | 734 | O | PHE A 313 | 10.600 | 28.636 | 7.615 | 1.00 | 58.55 | O |
| ATOM | 735 | CB | PHE A 313 | 11.896 | 27.086 | 9.958 | 1.00 | 58.15 | C |
| ATOM | 736 | CG | PHE A 313 | 12.808 | 27.286 | 11.133 | 1.00 | 60.15 | C |
| ATOM | 737 | CD1 | PHE A 313 | 12.548 | 26.687 | 12.350 | 1.00 | 60.49 | C |
| ATOM | 738 | CD2 | PHE A 313 | 13.937 | 28.080 | 11.015 | 1.00 | 60.67 | C |
| ATOM | 739 | CE1 | PHE A 313 | 13.388 | 26.866 | 13.433 | 1.00 | 62.09 | C |
| ATOM | 740 | CE2 | PHE A 313 | 14.782 | 28.265 | 12.095 | 1.00 | 60.20 | C |
| ATOM | 741 | CZ | PHE A 313 | 14.515 | 27.665 | 13.306 | 1.00 | 61.50 | C |
| ATOM | 742 | N | ALA A 314 | 8.970 | 27.310 | 8.304 | 1.00 | 61.15 | N |
| ATOM | 743 | CA | ALA A 314 | 8.231 | 27.183 | 7.056 | 1.00 | 64.61 | C |
| ATOM | 744 | C | ALA A 314 | 6.965 | 26.448 | 7.448 | 1.00 | 65.39 | C |
| ATOM | 745 | O | ALA A 314 | 6.924 | 25.759 | 8.467 | 1.00 | 65.72 | O |
| ATOM | 746 | CB | ALA A 314 | 9.028 | 26.531 | 5.948 | 1.00 | 64.60 | C |
| ATOM | 747 | N | PRO A 315 | 5.882 | 26.615 | 6.717 | 1.00 | 68.81 | N |
| ATOM | 748 | CA | PRO A 315 | 4.576 | 26.029 | 7.008 | 1.00 | 69.62 | C |
| ATOM | 749 | C | PRO A 315 | 4.603 | 24.546 | 7.338 | 1.00 | 70.29 | C |
| ATOM | 750 | O | PRO A 315 | 3.834 | 24.103 | 8.202 | 1.00 | 69.97 | O |
| ATOM | 751 | CB | PRO A 315 | 3.651 | 26.366 | 5.831 | 1.00 | 69.24 | C |
| ATOM | 752 | CG | PRO A 315 | 4.382 | 27.489 | 5.163 | 1.00 | 68.39 | C |
| ATOM | 753 | CD | PRO A 315 | 5.851 | 27.444 | 5.509 | 1.00 | 68.85 | C |
| ATOM | 754 | N | ASP A 316 | 5.479 | 23.782 | 6.706 | 1.00 | 71.28 | N |
| ATOM | 755 | CA | ASP A 316 | 5.637 | 22.362 | 6.973 | 1.00 | 74.42 | C |
| ATOM | 756 | C | ASP A 316 | 7.028 | 22.112 | 7.566 | 1.00 | 76.23 | C |
| ATOM | 757 | O | ASP A 316 | 7.772 | 21.234 | 7.125 | 1.00 | 75.63 | O |
| ATOM | 758 | CB | ASP A 316 | 5.471 | 21.529 | 5.706 | 1.00 | 74.92 | C |
| ATOM | 759 | N | LEU A 317 | 7.399 | 22.932 | 8.546 | 1.00 | 76.31 | N |
| ATOM | 760 | CA | LEU A 317 | 8.692 | 22.824 | 9.220 | 1.00 | 76.72 | C |
| ATOM | 761 | C | LEU A 317 | 8.595 | 23.652 | 10.504 | 1.00 | 78.61 | C |
| ATOM | 762 | O | LEU A 317 | 9.172 | 24.717 | 10.694 | 1.00 | 79.19 | O |
| ATOM | 763 | CB | LEU A 317 | 9.864 | 23.204 | 8.342 | 1.00 | 75.44 | C |
| ATOM | 764 | CG | LEU A 317 | 11.275 | 23.141 | 8.920 | 1.00 | 75.65 | C |
| ATOM | 765 | CD1 | LEU A 317 | 11.481 | 21.967 | 9.863 | 1.00 | 76.36 | C |
| ATOM | 766 | CD2 | LEU A 317 | 12.337 | 23.089 | 7.834 | 1.00 | 73.69 | C |
| ATOM | 767 | N | VAL A 318 | 7.781 | 23.125 | 11.403 | 1.00 | 79.39 | N |

```
ATOM    614  O    VAL A 298      10.710  37.876  11.811  1.00 36.08           O
ATOM    615  CB   VAL A 298      13.205  40.076  11.756  1.00 36.27           C
ATOM    616  CG1  VAL A 298      13.174  40.373  10.253  1.00 34.27           C
ATOM    617  CG2  VAL A 298      12.247  41.016  12.455  1.00 36.97           C
ATOM    618  N    GLY A 299      12.036  37.374  10.084  1.00 37.16           N
ATOM    619  CA   GLY A 299      10.888  36.730   9.383  1.00 38.18           C
ATOM    620  C    GLY A 299      10.405  35.503  10.178  1.00 39.56           C
ATOM    621  O    GLY A 299       9.191  35.261  10.343  1.00 39.47           O
ATOM    622  N    LEU A 300      11.339  34.729  10.707  1.00 39.16           N
ATOM    623  CA   LEU A 300      11.050  33.546  11.529  1.00 45.42           C
ATOM    624  C    LEU A 300      10.243  33.965  12.749  1.00 46.91           C
ATOM    625  O    LEU A 300       9.199  33.396  13.078  1.00 49.36           O
ATOM    626  CB   LEU A 300      12.368  32.870  11.944  1.00 45.74           C
ATOM    627  CG   LEU A 300      12.279  31.853  13.080  1.00 47.69           C
ATOM    628  CD1  LEU A 300      11.211  30.791  12.777  1.00 49.37           C
ATOM    629  CD2  LEU A 300      13.604  31.217  13.397  1.00 44.76           C
ATOM    630  N    MET A 301      10.649  35.080  13.378  1.00 46.27           N
ATOM    631  CA   MET A 301       9.922  35.602  14.528  1.00 46.14           C
ATOM    632  C    MET A 301       8.493  35.954  14.163  1.00 43.33           C
ATOM    633  O    MET A 301       7.546  35.597  14.864  1.00 41.41           O
ATOM    634  CB   MET A 301      10.614  36.813  15.162  1.00 47.37           C
ATOM    635  CG   MET A 301      11.923  36.497  15.883  1.00 50.79           C
ATOM    636  SD   MET A 301      12.742  38.065  16.368  1.00 50.42           S
ATOM    637  CE   MET A 301      14.406  37.417  16.532  1.00 52.46           C
ATOM    638  N    TRP A 302       8.317  36.686  13.057  1.00 41.74           N
ATOM    639  CA   TRP A 302       6.980  37.064  12.631  1.00 44.16           C
ATOM    640  C    TRP A 302       6.096  35.840  12.325  1.00 45.90           C
ATOM    641  O    TRP A 302       4.895  35.823  12.598  1.00 46.25           O
ATOM    642  CB   TRP A 302       7.144  37.930  11.363  1.00 42.76           C
ATOM    643  CG   TRP A 302       5.827  38.229  10.739  1.00 40.46           C
ATOM    644  CD1  TRP A 302       5.375  37.769   9.529  1.00 41.62           C
ATOM    645  CD2  TRP A 302       4.773  39.017  11.292  1.00 41.72           C
ATOM    646  NE1  TRP A 302       4.105  38.256   9.283  1.00 41.69           N
ATOM    647  CE2  TRP A 302       3.712  39.027  10.361  1.00 40.72           C
ATOM    648  CE3  TRP A 302       4.619  39.740  12.482  1.00 42.29           C
ATOM    649  CZ2  TRP A 302       2.520  39.718  10.589  1.00 40.08           C
ATOM    650  CZ3  TRP A 302       3.437  40.424  12.699  1.00 39.48           C
ATOM    651  CH2  TRP A 302       2.391  40.423  11.772  1.00 39.01           C
ATOM    652  N    ARG A 303       6.675  34.807  11.729  1.00 46.19           N
ATOM    653  CA   ARG A 303       5.973  33.592  11.353  1.00 49.73           C
ATOM    654  C    ARG A 303       5.512  32.856  12.609  1.00 51.74           C
ATOM    655  O    ARG A 303       4.376  32.398  12.660  1.00 51.29           O
ATOM    656  CB   ARG A 303       6.861  32.698  10.472  1.00 48.54           C
ATOM    657  CG   ARG A 303       6.927  33.207   9.038  1.00 49.45           C
ATOM    658  CD   ARG A 303       7.477  32.195   8.062  1.00 48.31           C
ATOM    659  NE   ARG A 303       8.788  31.646   8.407  1.00 48.38           N
ATOM    660  CZ   ARG A 303       9.969  32.186   8.145  1.00 46.10           C
ATOM    661  NH1  ARG A 303      10.060  33.344   7.521  1.00 44.64           N
ATOM    662  NH2  ARG A 303      11.076  31.568   8.497  1.00 46.26           N
ATOM    663  N    SER A 304       6.382  32.820  13.620  1.00 51.26           N
ATOM    664  CA   SER A 304       6.130  32.199  14.897  1.00 50.78           C
ATOM    665  C    SER A 304       5.333  33.007  15.898  1.00 54.32           C
ATOM    666  O    SER A 304       4.924  32.507  16.964  1.00 57.56           O
ATOM    667  CB   SER A 304       7.484  31.915  15.563  1.00 48.79           C
ATOM    668  OG   SER A 304       8.372  31.337  14.619  1.00 47.35           O
ATOM    669  N    ILE A 305       5.059  34.270  15.614  1.00 56.45           N
ATOM    670  CA   ILE A 305       4.355  35.136  16.527  1.00 56.37           C
ATOM    671  C    ILE A 305       3.124  34.579  17.201  1.00 58.53           C
ATOM    672  O    ILE A 305       2.970  34.735  18.430  1.00 57.39           O
ATOM    673  CB   ILE A 305       4.071  36.486  15.831  1.00 55.53           C
ATOM    674  CG1  ILE A 305       3.908  37.589  16.898  1.00 54.07           C
ATOM    675  CG2  ILE A 305       2.887  36.495  14.895  1.00 54.05           C
ATOM    676  CD1  ILE A 305       4.309  38.944  16.347  1.00 52.04           C
ATOM    677  N    ASP A 306       2.206  33.959  16.472  1.00 59.06           N
ATOM    678  CA   ASP A 306       0.977  33.474  17.100  1.00 61.14           C
ATOM    679  C    ASP A 306       1.062  32.038  17.563  1.00 60.88           C
ATOM    680  O    ASP A 306       0.029  31.405  17.726  1.00 61.93           O
ATOM    681  CB   ASP A 306      -0.165  33.624  16.093  1.00 61.98           C
ATOM    682  CG   ASP A 306      -0.463  35.034  15.655  1.00 64.02           C
ATOM    683  OD1  ASP A 306      -0.629  35.931  16.499  1.00 64.86           O
ATOM    684  OD2  ASP A 306      -0.562  35.286  14.430  1.00 66.19           O
ATOM    685  N    HIS A 307       2.226  31.441  17.751  1.00 60.73           N
ATOM    686  CA   HIS A 307       2.503  30.089  18.151  1.00 60.64           C
ATOM    687  C    HIS A 307       3.517  29.911  19.273  1.00 57.80           C
ATOM    688  O    HIS A 307       4.649  29.433  19.128  1.00 53.94           O
ATOM    689  CB   HIS A 307       3.069  29.277  16.944  1.00 64.28           C
ATOM    690  CG   HIS A 307       2.090  29.361  15.809  1.00 68.58           C
```

| | | | | | | | | | |
|---|---|---|---|---|---|---|---|---|---|
| ATOM | 537 | C | GLU | A | 289 | 26.387 | 40.835 | 5.495 | 1.00 43.47 | C |
| ATOM | 538 | O | GLU | A | 289 | 26.499 | 39.784 | 6.168 | 1.00 44.87 | O |
| ATOM | 539 | CB | GLU | A | 289 | 27.960 | 41.026 | 3.532 | 1.00 47.96 | C |
| ATOM | 540 | CG | GLU | A | 289 | 28.138 | 40.803 | 2.061 | 1.00 54.14 | C |
| ATOM | 541 | CD | GLU | A | 289 | 29.518 | 40.763 | 1.458 | 1.00 58.65 | C |
| ATOM | 542 | OE1 | GLU | A | 289 | 30.377 | 41.619 | 1.754 | 1.00 59.43 | O |
| ATOM | 543 | OE2 | GLU | A | 289 | 29.768 | 39.843 | 0.633 | 1.00 60.88 | O |
| ATOM | 544 | N | SER | A | 290 | 26.122 | 42.001 | 6.096 | 1.00 40.97 | N |
| ATOM | 545 | CA | SER | A | 290 | 25.962 | 41.996 | 7.552 | 1.00 40.61 | C |
| ATOM | 546 | C | SER | A | 290 | 24.549 | 41.821 | 8.076 | 1.00 41.20 | C |
| ATOM | 547 | O | SER | A | 290 | 24.493 | 41.547 | 9.279 | 1.00 41.60 | O |
| ATOM | 548 | CB | SER | A | 290 | 26.511 | 43.278 | 8.170 | 1.00 43.97 | C |
| ATOM | 549 | OG | ASER | A | 290 | 26.091 | 44.481 | 7.584 | 0.50 42.23 | O |
| ATOM | 550 | OG | BSER | A | 290 | 27.884 | 43.382 | 7.751 | 0.50 42.33 | O |
| ATOM | 551 | N | CYS | A | 291 | 23.434 | 41.963 | 7.374 | 1.00 39.07 | N |
| ATOM | 552 | CA | CYS | A | 291 | 22.141 | 41.795 | 8.039 | 1.00 37.55 | C |
| ATOM | 553 | C | CYS | A | 291 | 21.316 | 40.602 | 7.592 | 1.00 36.45 | C |
| ATOM | 554 | O | CYS | A | 291 | 20.221 | 40.422 | 8.168 | 1.00 36.95 | O |
| ATOM | 555 | CB | CYS | A | 291 | 21.286 | 43.060 | 7.769 | 1.00 38.66 | C |
| ATOM | 556 | SG | CYS | A | 291 | 20.641 | 43.014 | 6.079 | 1.00 36.48 | S |
| ATOM | 557 | N | TRP | A | 292 | 21.817 | 39.771 | 6.676 | 1.00 37.96 | N |
| ATOM | 558 | CA | TRP | A | 292 | 21.033 | 38.627 | 6.201 | 1.00 38.97 | C |
| ATOM | 559 | C | TRP | A | 292 | 20.538 | 37.753 | 7.321 | 1.00 39.25 | C |
| ATOM | 560 | O | TRP | A | 292 | 19.345 | 37.400 | 7.315 | 1.00 40.32 | O |
| ATOM | 561 | CB | TRP | A | 292 | 21.754 | 37.876 | 5.059 | 1.00 40.76 | C |
| ATOM | 562 | CG | TRP | A | 292 | 22.998 | 37.129 | 5.436 | 1.00 42.03 | C |
| ATOM | 563 | CD1 | TRP | A | 292 | 24.293 | 37.506 | 5.222 | 1.00 41.85 | C |
| ATOM | 564 | CD2 | TRP | A | 292 | 23.055 | 35.853 | 6.101 | 1.00 42.12 | C |
| ATOM | 565 | NE1 | TRP | A | 292 | 25.137 | 36.571 | 5.739 | 1.00 43.65 | N |
| ATOM | 566 | CE2 | TRP | A | 292 | 24.413 | 35.539 | 6.277 | 1.00 42.67 | C |
| ATOM | 567 | CE3 | TRP | A | 292 | 22.085 | 34.975 | 6.580 | 1.00 41.40 | C |
| ATOM | 568 | CZ2 | TRP | A | 292 | 24.842 | 34.364 | 6.894 | 1.00 43.00 | C |
| ATOM | 569 | CZ3 | TRP | A | 292 | 22.498 | 33.809 | 7.202 | 1.00 44.37 | C |
| ATOM | 570 | CH2 | TRP | A | 292 | 23.872 | 33.510 | 7.348 | 1.00 42.74 | C |
| ATOM | 571 | N | MET | A | 293 | 21.334 | 37.389 | 8.326 | 1.00 37.57 | N |
| ATOM | 572 | CA | MET | A | 293 | 20.810 | 36.548 | 9.415 | 1.00 38.36 | C |
| ATOM | 573 | C | MET | A | 293 | 19.754 | 37.273 | 10.230 | 1.00 37.34 | C |
| ATOM | 574 | O | MET | A | 293 | 18.682 | 36.727 | 10.573 | 1.00 37.07 | O |
| ATOM | 575 | CB | MET | A | 293 | 21.989 | 36.009 | 10.237 | 1.00 40.61 | C |
| ATOM | 576 | CG | MET | A | 293 | 21.583 | 35.126 | 11.386 | 1.00 41.96 | C |
| ATOM | 577 | SD | MET | A | 293 | 20.866 | 33.537 | 10.904 | 1.00 50.19 | S |
| ATOM | 578 | CE | MET | A | 293 | 22.371 | 32.580 | 10.699 | 1.00 48.64 | C |
| ATOM | 579 | N | GLU | A | 294 | 19.945 | 38.556 | 10.541 | 1.00 37.15 | N |
| ATOM | 580 | CA | GLU | A | 294 | 18.913 | 39.330 | 11.246 | 1.00 36.31 | C |
| ATOM | 581 | C | GLU | A | 294 | 17.596 | 39.310 | 10.464 | 1.00 36.16 | C |
| ATOM | 582 | O | GLU | A | 294 | 16.496 | 39.121 | 11.006 | 1.00 37.92 | O |
| ATOM | 583 | CB | GLU | A | 294 | 19.382 | 40.779 | 11.365 | 1.00 35.68 | C |
| ATOM | 584 | CG | GLU | A | 294 | 20.452 | 41.067 | 12.418 | 1.00 37.75 | C |
| ATOM | 585 | CD | GLU | A | 294 | 21.095 | 42.414 | 12.207 | 1.00 41.74 | C |
| ATOM | 586 | OE1 | GLU | A | 294 | 22.041 | 42.537 | 11.410 | 1.00 46.35 | O |
| ATOM | 587 | OE2 | GLU | A | 294 | 20.697 | 43.419 | 12.798 | 1.00 41.49 | O |
| ATOM | 588 | N | VAL | A | 295 | 17.688 | 39.503 | 9.138 | 1.00 35.50 | N |
| ATOM | 589 | CA | VAL | A | 295 | 16.510 | 39.495 | 8.258 | 1.00 36.69 | C |
| ATOM | 590 | C | VAL | A | 295 | 15.848 | 38.142 | 8.328 | 1.00 35.04 | C |
| ATOM | 591 | O | VAL | A | 295 | 14.630 | 38.041 | 8.538 | 1.00 38.03 | O |
| ATOM | 592 | CB | VAL | A | 295 | 16.869 | 39.909 | 6.811 | 1.00 36.71 | C |
| ATOM | 593 | CG1 | VAL | A | 295 | 15.657 | 39.854 | 5.890 | 1.00 34.24 | C |
| ATOM | 594 | CG2 | VAL | A | 295 | 17.381 | 41.354 | 6.900 | 1.00 36.11 | C |
| ATOM | 595 | N | LEU | A | 296 | 16.619 | 37.058 | 8.208 | 1.00 37.21 | N |
| ATOM | 596 | CA | LEU | A | 296 | 16.056 | 35.722 | 8.337 | 1.00 36.70 | C |
| ATOM | 597 | C | LEU | A | 296 | 15.360 | 35.557 | 9.686 | 1.00 37.98 | C |
| ATOM | 598 | O | LEU | A | 296 | 14.229 | 35.056 | 9.744 | 1.00 37.18 | O |
| ATOM | 599 | CB | LEU | A | 296 | 17.163 | 34.652 | 8.284 | 1.00 39.35 | C |
| ATOM | 600 | CG | LEU | A | 296 | 17.785 | 34.403 | 6.899 | 1.00 43.64 | C |
| ATOM | 601 | CD1 | LEU | A | 296 | 18.732 | 33.208 | 7.005 | 1.00 41.72 | C |
| ATOM | 602 | CD2 | LEU | A | 296 | 16.700 | 34.136 | 5.853 | 1.00 41.98 | C |
| ATOM | 603 | N | MET | A | 297 | 16.064 | 35.957 | 10.760 | 1.00 37.13 | N |
| ATOM | 604 | CA | MET | A | 297 | 15.503 | 35.802 | 12.093 | 1.00 37.52 | C |
| ATOM | 605 | C | MET | A | 297 | 14.225 | 36.571 | 12.334 | 1.00 39.06 | C |
| ATOM | 606 | O | MET | A | 297 | 13.303 | 36.040 | 12.969 | 1.00 42.02 | O |
| ATOM | 607 | CB | MET | A | 297 | 16.518 | 36.179 | 13.175 | 1.00 35.57 | C |
| ATOM | 608 | CG | MET | A | 297 | 17.720 | 35.259 | 13.134 | 1.00 38.27 | C |
| ATOM | 609 | SD | MET | A | 297 | 18.983 | 35.548 | 14.354 | 1.00 36.36 | S |
| ATOM | 610 | CE | MET | A | 297 | 20.025 | 34.103 | 14.326 | 1.00 38.99 | C |
| ATOM | 611 | N | VAL | A | 298 | 14.176 | 37.818 | 11.880 | 1.00 38.77 | N |
| ATOM | 612 | CA | VAL | A | 298 | 12.940 | 38.592 | 12.088 | 1.00 37.73 | C |
| ATOM | 613 | C | VAL | A | 298 | 11.821 | 37.931 | 11.287 | 1.00 37.62 | C |

| | | | | | | | | | |
|---|---|---|---|---|---|---|---|---|---|
| ATOM | 460 | CD1 | LEU A 279 | 21.689 | 51.563 | 0.122 | 1.00 | 34.25 | C |
| ATOM | 461 | CD2 | LEU A 279 | 22.526 | 53.938 | -0.054 | 1.00 | 38.09 | C |
| ATOM | 462 | N | SER A 280 | 25.473 | 52.870 | -3.823 | 1.00 | 36.65 | N |
| ATOM | 463 | CA | SER A 280 | 26.504 | 52.255 | -4.656 | 1.00 | 38.45 | C |
| ATOM | 464 | C | SER A 280 | 26.374 | 50.768 | -4.424 | 1.00 | 37.42 | C |
| ATOM | 465 | O | SER A 280 | 25.875 | 50.342 | -3.365 | 1.00 | 37.89 | O |
| ATOM | 466 | CB | SER A 280 | 27.906 | 52.670 | -4.136 | 1.00 | 39.25 | C |
| ATOM | 467 | OG | SER A 280 | 28.087 | 52.021 | -2.843 | 1.00 | 40.86 | O |
| ATOM | 468 | N | LEU A 281 | 26.872 | 49.947 | -5.332 | 1.00 | 38.71 | N |
| ATOM | 469 | CA | LEU A 281 | 26.859 | 48.493 | -5.202 | 1.00 | 37.53 | C |
| ATOM | 470 | C | LEU A 281 | 27.735 | 48.042 | -4.055 | 1.00 | 36.54 | C |
| ATOM | 471 | O | LEU A 281 | 27.486 | 47.029 | -3.368 | 1.00 | 38.38 | O |
| ATOM | 472 | CB | LEU A 281 | 27.274 | 47.915 | -6.545 | 1.00 | 44.15 | C |
| ATOM | 473 | CG | LEU A 281 | 27.364 | 46.401 | -6.696 | 1.00 | 47.62 | C |
| ATOM | 474 | CD1 | LEU A 281 | 26.006 | 45.736 | -6.485 | 1.00 | 49.15 | C |
| ATOM | 475 | CD2 | LEU A 281 | 27.864 | 46.081 | -8.112 | 1.00 | 47.55 | C |
| ATOM | 476 | N | LEU A 282 | 28.774 | 48.806 | -3.718 | 1.00 | 36.66 | N |
| ATOM | 477 | CA | LEU A 282 | 29.661 | 48.466 | -2.585 | 1.00 | 36.24 | C |
| ATOM | 478 | C | LEU A 282 | 28.822 | 48.556 | -1.286 | 1.00 | 37.62 | C |
| ATOM | 479 | O | LEU A 282 | 28.930 | 47.697 | -0.411 | 1.00 | 39.43 | O |
| ATOM | 480 | CB | LEU A 282 | 30.856 | 49.427 | -2.539 | 1.00 | 30.91 | C |
| ATOM | 481 | CG | LEU A 282 | 31.949 | 49.222 | -1.509 | 1.00 | 34.10 | C |
| ATOM | 482 | CD1 | LEU A 282 | 32.537 | 47.791 | -1.551 | 1.00 | 31.84 | C |
| ATOM | 483 | CD2 | LEU A 282 | 33.130 | 50.175 | -1.650 | 1.00 | 30.50 | C |
| ATOM | 484 | N | ASP A 283 | 27.984 | 49.596 | -1.139 | 1.00 | 35.49 | N |
| ATOM | 485 | CA | ASP A 283 | 27.154 | 49.698 | 0.070 | 1.00 | 36.92 | C |
| ATOM | 486 | C | ASP A 283 | 26.125 | 48.592 | 0.102 | 1.00 | 37.83 | C |
| ATOM | 487 | O | ASP A 283 | 25.939 | 47.845 | 1.101 | 1.00 | 40.63 | O |
| ATOM | 488 | CB | ASP A 283 | 26.497 | 51.096 | 0.168 | 1.00 | 34.75 | C |
| ATOM | 489 | CG | ASP A 283 | 27.485 | 52.119 | 0.630 | 1.00 | 37.16 | C |
| ATOM | 490 | OD1 | ASP A 283 | 28.656 | 51.736 | 0.903 | 1.00 | 36.40 | O |
| ATOM | 491 | OD2 | ASP A 283 | 27.227 | 53.332 | 0.749 | 1.00 | 39.42 | O |
| ATOM | 492 | N | GLN A 284 | 25.438 | 48.423 | -1.049 | 1.00 | 38.59 | N |
| ATOM | 493 | CA | GLN A 284 | 24.422 | 47.364 | -1.166 | 1.00 | 35.71 | C |
| ATOM | 494 | C | GLN A 284 | 24.977 | 46.017 | -0.761 | 1.00 | 38.55 | C |
| ATOM | 495 | O | GLN A 284 | 24.369 | 45.290 | 0.048 | 1.00 | 38.62 | O |
| ATOM | 496 | CB | GLN A 284 | 23.825 | 47.295 | -2.578 | 1.00 | 34.45 | C |
| ATOM | 497 | CG | GLN A 284 | 23.136 | 48.566 | -3.042 | 1.00 | 35.83 | C |
| ATOM | 498 | CD | GLN A 284 | 22.604 | 48.438 | -4.491 | 1.00 | 38.09 | C |
| ATOM | 499 | OE1 | GLN A 284 | 22.186 | 47.353 | -4.865 | 1.00 | 37.09 | O |
| ATOM | 500 | NE2 | GLN A 284 | 22.601 | 49.493 | -5.277 | 1.00 | 36.37 | N |
| ATOM | 501 | N | VAL A 285 | 26.154 | 45.633 | -1.288 | 1.00 | 39.52 | N |
| ATOM | 502 | CA | VAL A 285 | 26.759 | 44.345 | -0.902 | 1.00 | 40.26 | C |
| ATOM | 503 | C | VAL A 285 | 27.070 | 44.304 | 0.596 | 1.00 | 39.06 | C |
| ATOM | 504 | O | VAL A 285 | 26.740 | 43.369 | 1.348 | 1.00 | 38.70 | O |
| ATOM | 505 | CB | VAL A 285 | 28.070 | 44.092 | -1.694 | 1.00 | 43.09 | C |
| ATOM | 506 | CG1 | VAL A 285 | 28.881 | 42.917 | -1.175 | 1.00 | 44.33 | C |
| ATOM | 507 | CG2 | VAL A 285 | 27.834 | 43.851 | -3.184 | 1.00 | 43.09 | C |
| ATOM | 508 | N | ARG A 286 | 27.714 | 45.356 | 1.110 | 1.00 | 38.77 | N |
| ATOM | 509 | CA | ARG A 286 | 28.025 | 45.314 | 2.564 | 1.00 | 42.07 | C |
| ATOM | 510 | C | ARG A 286 | 26.784 | 45.287 | 3.431 | 1.00 | 41.71 | C |
| ATOM | 511 | O | ARG A 286 | 26.813 | 44.524 | 4.399 | 1.00 | 42.31 | O |
| ATOM | 512 | CB | ARG A 286 | 28.985 | 46.441 | 2.935 | 1.00 | 43.59 | C |
| ATOM | 513 | CG | ARG A 286 | 30.310 | 46.208 | 2.184 | 1.00 | 42.53 | C |
| ATOM | 514 | CD | ARG A 286 | 31.320 | 47.243 | 2.637 | 1.00 | 42.99 | C |
| ATOM | 515 | NE | ARG A 286 | 30.961 | 48.547 | 2.145 | 1.00 | 40.78 | N |
| ATOM | 516 | CZ | ARG A 286 | 31.147 | 49.694 | 2.759 | 1.00 | 40.76 | C |
| ATOM | 517 | NH1 | ARG A 286 | 31.730 | 49.698 | 3.951 | 1.00 | 43.02 | N |
| ATOM | 518 | NH2 | ARG A 286 | 30.794 | 50.875 | 2.256 | 1.00 | 37.68 | N |
| ATOM | 519 | N | LEU A 287 | 25.711 | 46.009 | 3.092 | 1.00 | 40.54 | N |
| ATOM | 520 | CA | LEU A 287 | 24.521 | 45.931 | 3.936 | 1.00 | 40.36 | C |
| ATOM | 521 | C | LEU A 287 | 23.996 | 44.499 | 3.966 | 1.00 | 40.76 | C |
| ATOM | 522 | O | LEU A 287 | 23.768 | 43.902 | 5.034 | 1.00 | 39.54 | O |
| ATOM | 523 | CB | LEU A 287 | 23.509 | 46.961 | 3.456 | 1.00 | 39.69 | C |
| ATOM | 524 | CG | LEU A 287 | 23.944 | 48.423 | 3.580 | 1.00 | 41.19 | C |
| ATOM | 525 | CD1 | LEU A 287 | 23.041 | 49.358 | 2.778 | 1.00 | 40.75 | C |
| ATOM | 526 | CD2 | LEU A 287 | 23.948 | 48.892 | 5.030 | 1.00 | 38.93 | C |
| ATOM | 527 | N | LEU A 288 | 23.802 | 43.879 | 2.802 | 1.00 | 40.47 | N |
| ATOM | 528 | CA | LEU A 288 | 23.320 | 42.501 | 2.788 | 1.00 | 41.85 | C |
| ATOM | 529 | C | LEU A 288 | 24.254 | 41.526 | 3.475 | 1.00 | 43.67 | C |
| ATOM | 530 | O | LEU A 288 | 23.799 | 40.631 | 4.201 | 1.00 | 45.17 | O |
| ATOM | 531 | CB | LEU A 288 | 22.995 | 42.124 | 1.340 | 1.00 | 41.93 | C |
| ATOM | 532 | CG | LEU A 288 | 21.653 | 42.671 | 0.845 | 1.00 | 41.41 | C |
| ATOM | 533 | CD1 | LEU A 288 | 21.522 | 42.404 | -0.660 | 1.00 | 44.21 | C |
| ATOM | 534 | CD2 | LEU A 288 | 20.497 | 42.020 | 1.587 | 1.00 | 42.57 | C |
| ATOM | 535 | N | GLU A 289 | 25.570 | 41.636 | 3.320 | 1.00 | 44.79 | N |
| ATOM | 536 | CA | GLU A 289 | 26.515 | 40.744 | 3.989 | 1.00 | 45.67 | C |

| ATOM | 383 | CZ3 | TRP A 269 | 15.484 | 42.846 | 3.248 | 1.00 | 39.70 | C |
| --- | --- | --- | --- | --- | --- | --- | --- | --- | --- |
| ATOM | 384 | CH2 | TRP A 269 | 14.685 | 43.628 | 4.102 | 1.00 | 37.90 | C |
| ATOM | 385 | N | ALA A 270 | 15.523 | 43.052 | -1.250 | 1.00 | 31.81 | N |
| ATOM | 386 | CA | ALA A 270 | 16.346 | 44.220 | -0.909 | 1.00 | 34.18 | C |
| ATOM | 387 | C | ALA A 270 | 16.380 | 45.269 | -1.983 | 1.00 | 36.53 | C |
| ATOM | 388 | O | ALA A 270 | 16.322 | 46.495 | -1.758 | 1.00 | 33.30 | O |
| ATOM | 389 | CB | ALA A 270 | 17.780 | 43.726 | -0.590 | 1.00 | 35.00 | C |
| ATOM | 390 | N | LYS A 271 | 16.438 | 44.792 | -3.241 | 1.00 | 38.37 | N |
| ATOM | 391 | CA | LYS A 271 | 16.417 | 45.698 | -4.398 | 1.00 | 41.68 | C |
| ATOM | 392 | C | LYS A 271 | 15.149 | 46.514 | -4.532 | 1.00 | 39.87 | C |
| ATOM | 393 | O | LYS A 271 | 15.202 | 47.577 | -5.161 | 1.00 | 39.07 | O |
| ATOM | 394 | CB | LYS A 271 | 16.653 | 44.897 | -5.690 | 1.00 | 44.50 | C |
| ATOM | 395 | CG | LYS A 271 | 18.011 | 44.199 | -5.546 | 1.00 | 49.34 | C |
| ATOM | 396 | CD | LYS A 271 | 18.583 | 43.777 | -6.858 | 1.00 | 54.64 | C |
| ATOM | 397 | CE | LYS A 271 | 18.307 | 42.317 | -7.174 | 1.00 | 56.61 | C |
| ATOM | 398 | NZ | LYS A 271 | 18.707 | 42.040 | -8.594 | 1.00 | 59.75 | N |
| ATOM | 399 | N | LYS A 272 | 14.054 | 46.123 | -3.926 | 1.00 | 38.15 | N |
| ATOM | 400 | CA | LYS A 272 | 12.802 | 46.866 | -3.970 | 1.00 | 40.36 | C |
| ATOM | 401 | C | LYS A 272 | 12.689 | 47.812 | -2.786 | 1.00 | 39.65 | C |
| ATOM | 402 | O | LYS A 272 | 11.744 | 48.579 | -2.792 | 1.00 | 40.33 | O |
| ATOM | 403 | CB | LYS A 272 | 11.575 | 45.925 | -3.903 | 1.00 | 42.23 | C |
| ATOM | 404 | CG | LYS A 272 | 11.427 | 45.099 | -5.194 | 1.00 | 45.50 | C |
| ATOM | 405 | CD | LYS A 272 | 10.367 | 44.029 | -5.047 | 1.00 | 47.85 | C |
| ATOM | 406 | CE | LYS A 272 | 10.499 | 42.983 | -6.173 | 1.00 | 52.46 | C |
| ATOM | 407 | NZ | LYS A 272 | 9.636 | 41.791 | -5.879 | 1.00 | 53.19 | N |
| ATOM | 408 | N | ILE A 273 | 13.579 | 47.817 | -1.808 | 1.00 | 39.68 | N |
| ATOM | 409 | CA | ILE A 273 | 13.395 | 48.754 | -0.686 | 1.00 | 37.48 | C |
| ATOM | 410 | C | ILE A 273 | 13.707 | 50.142 | -1.191 | 1.00 | 37.29 | C |
| ATOM | 411 | O | ILE A 273 | 14.779 | 50.371 | -1.718 | 1.00 | 38.30 | O |
| ATOM | 412 | CB | ILE A 273 | 14.338 | 48.353 | 0.470 | 1.00 | 36.08 | C |
| ATOM | 413 | CG1 | ILE A 273 | 14.075 | 46.963 | 1.015 | 1.00 | 36.07 | C |
| ATOM | 414 | CG2 | ILE A 273 | 14.334 | 49.454 | 1.507 | 1.00 | 35.73 | C |
| ATOM | 415 | CD1 | ILE A 273 | 12.672 | 46.546 | 1.367 | 1.00 | 40.85 | C |
| ATOM | 416 | N | PRO A 274 | 12.828 | 51.106 | -1.033 | 1.00 | 37.05 | N |
| ATOM | 417 | CA | PRO A 274 | 13.009 | 52.453 | -1.535 | 1.00 | 38.73 | C |
| ATOM | 418 | C | PRO A 274 | 14.362 | 53.010 | -1.155 | 1.00 | 42.91 | C |
| ATOM | 419 | O | PRO A 274 | 14.761 | 53.006 | 0.024 | 1.00 | 45.77 | O |
| ATOM | 420 | CB | PRO A 274 | 11.821 | 53.279 | -0.987 | 1.00 | 37.49 | C |
| ATOM | 421 | CG | PRO A 274 | 10.804 | 52.175 | -0.779 | 1.00 | 34.93 | C |
| ATOM | 422 | CD | PRO A 274 | 11.499 | 50.874 | -0.456 | 1.00 | 34.77 | C |
| ATOM | 423 | N | GLY A 275 | 15.111 | 53.452 | -2.155 | 1.00 | 41.72 | N |
| ATOM | 424 | CA | GLY A 275 | 16.428 | 54.024 | -2.047 | 1.00 | 38.98 | C |
| ATOM | 425 | C | GLY A 275 | 17.543 | 53.003 | -2.123 | 1.00 | 41.38 | C |
| ATOM | 426 | O | GLY A 275 | 18.668 | 53.434 | -2.390 | 1.00 | 42.66 | O |
| ATOM | 427 | N | PHE A 276 | 17.323 | 51.722 | -1.820 | 1.00 | 39.90 | N |
| ATOM | 428 | CA | PHE A 276 | 18.429 | 50.764 | -1.792 | 1.00 | 41.43 | C |
| ATOM | 429 | C | PHE A 276 | 19.292 | 50.707 | -3.056 | 1.00 | 44.46 | C |
| ATOM | 430 | O | PHE A 276 | 20.536 | 50.700 | -3.000 | 1.00 | 43.77 | O |
| ATOM | 431 | CB | PHE A 276 | 17.946 | 49.340 | -1.508 | 1.00 | 37.42 | C |
| ATOM | 432 | CG | PHE A 276 | 18.997 | 48.301 | -1.278 | 1.00 | 35.79 | C |
| ATOM | 433 | CD1 | PHE A 276 | 19.645 | 48.198 | -0.048 | 1.00 | 36.81 | C |
| ATOM | 434 | CD2 | PHE A 276 | 19.355 | 47.395 | -2.257 | 1.00 | 36.92 | C |
| ATOM | 435 | CE1 | PHE A 276 | 20.613 | 47.245 | 0.173 | 1.00 | 36.76 | C |
| ATOM | 436 | CE2 | PHE A 276 | 20.306 | 46.417 | -2.059 | 1.00 | 36.53 | C |
| ATOM | 437 | CZ | PHE A 276 | 20.955 | 46.341 | -0.826 | 1.00 | 38.00 | C |
| ATOM | 438 | N | VAL A 277 | 18.632 | 50.664 | -4.225 | 1.00 | 42.04 | N |
| ATOM | 439 | CA | VAL A 277 | 19.354 | 50.608 | -5.475 | 1.00 | 42.77 | C |
| ATOM | 440 | C | VAL A 277 | 19.947 | 51.956 | -5.818 | 1.00 | 44.00 | C |
| ATOM | 441 | O | VAL A 277 | 20.723 | 51.976 | -6.770 | 1.00 | 44.63 | O |
| ATOM | 442 | CB | VAL A 277 | 18.616 | 49.994 | -6.684 | 1.00 | 43.25 | C |
| ATOM | 443 | CG1 | VAL A 277 | 18.370 | 48.522 | -6.388 | 1.00 | 38.96 | C |
| ATOM | 444 | CG2 | VAL A 277 | 17.383 | 50.763 | -7.078 | 1.00 | 41.18 | C |
| ATOM | 445 | N | GLU A 278 | 19.689 | 53.035 | -5.096 | 1.00 | 43.88 | N |
| ATOM | 446 | CA | GLU A 278 | 20.360 | 54.286 | -5.422 | 1.00 | 46.83 | C |
| ATOM | 447 | C | GLU A 278 | 21.663 | 54.386 | -4.600 | 1.00 | 47.18 | C |
| ATOM | 448 | O | GLU A 278 | 22.367 | 55.394 | -4.635 | 1.00 | 47.93 | O |
| ATOM | 449 | CB | GLU A 278 | 19.470 | 55.485 | -5.182 | 1.00 | 51.80 | C |
| ATOM | 450 | CG | GLU A 278 | 18.800 | 55.942 | -6.490 | 1.00 | 59.49 | C |
| ATOM | 451 | CD | GLU A 278 | 17.526 | 55.186 | -6.780 | 1.00 | 62.57 | C |
| ATOM | 452 | OE1 | GLU A 278 | 17.172 | 54.254 | -6.019 | 1.00 | 64.28 | O |
| ATOM | 453 | OE2 | GLU A 278 | 16.849 | 55.537 | -7.782 | 1.00 | 66.61 | O |
| ATOM | 454 | N | LEU A 279 | 21.971 | 53.372 | -3.812 | 1.00 | 42.25 | N |
| ATOM | 455 | CA | LEU A 279 | 23.191 | 53.287 | -3.039 | 1.00 | 40.99 | C |
| ATOM | 456 | C | LEU A 279 | 24.205 | 52.650 | -4.035 | 1.00 | 40.17 | C |
| ATOM | 457 | O | LEU A 279 | 23.758 | 51.934 | -4.951 | 1.00 | 39.24 | O |
| ATOM | 458 | CB | LEU A 279 | 23.106 | 52.298 | -1.869 | 1.00 | 36.88 | C |
| ATOM | 459 | CG | LEU A 279 | 22.041 | 52.715 | -0.806 | 1.00 | 37.01 | C |

59

| ATOM | 306 | OD1 | ASP | A | 260 | 22.130 | 28.774 | 1.790 | 1.00 | 67.94 | O |
| ATOM | 307 | OD2 | ASP | A | 260 | 21.724 | 26.607 | 1.451 | 1.00 | 70.06 | O |
| ATOM | 308 | N | LYS | A | 261 | 17.331 | 29.146 | 0.059 | 1.00 | 59.16 | N |
| ATOM | 309 | CA | LYS | A | 261 | 16.222 | 29.578 | -0.794 | 1.00 | 59.68 | C |
| ATOM | 310 | C | LYS | A | 261 | 15.804 | 30.994 | -0.392 | 1.00 | 57.97 | C |
| ATOM | 311 | O | LYS | A | 261 | 15.617 | 31.874 | -1.233 | 1.00 | 57.65 | O |
| ATOM | 312 | CB | LYS | A | 261 | 15.040 | 28.631 | -0.609 | 1.00 | 62.21 | C |
| ATOM | 313 | CG | LYS | A | 261 | 15.163 | 27.358 | -1.433 | 1.00 | 66.41 | C |
| ATOM | 314 | CD | LYS | A | 261 | 13.804 | 26.657 | -1.470 | 1.00 | 67.86 | C |
| ATOM | 315 | CE | LYS | A | 261 | 14.022 | 25.173 | -1.143 | 1.00 | 69.37 | C |
| ATOM | 316 | NZ | LYS | A | 261 | 14.411 | 24.434 | -2.382 | 1.00 | 69.71 | N |
| ATOM | 317 | N | GLU | A | 262 | 15.660 | 31.215 | 0.924 | 1.00 | 54.83 | N |
| ATOM | 318 | CA | GLU | A | 262 | 15.270 | 32.523 | 1.452 | 1.00 | 51.25 | C |
| ATOM | 319 | C | GLU | A | 262 | 16.278 | 33.590 | 1.059 | 1.00 | 48.21 | C |
| ATOM | 320 | O | GLU | A | 262 | 15.918 | 34.691 | 0.619 | 1.00 | 47.87 | O |
| ATOM | 321 | CB | GLU | A | 262 | 15.077 | 32.434 | 2.956 | 1.00 | 50.05 | C |
| ATOM | 322 | CG | GLU | A | 262 | 13.967 | 31.506 | 3.402 | 1.00 | 48.44 | C |
| ATOM | 323 | CD | GLU | A | 262 | 13.647 | 31.651 | 4.877 | 1.00 | 48.31 | C |
| ATOM | 324 | OE1 | GLU | A | 262 | 12.878 | 32.581 | 5.197 | 1.00 | 46.93 | O |
| ATOM | 325 | OE2 | GLU | A | 262 | 14.133 | 30.855 | 5.682 | 1.00 | 47.16 | O |
| ATOM | 326 | N | LEU | A | 263 | 17.562 | 33.297 | 1.121 | 1.00 | 47.06 | N |
| ATOM | 327 | CA | LEU | A | 263 | 18.563 | 34.288 | 0.712 | 1.00 | 49.70 | C |
| ATOM | 328 | C | LEU | A | 263 | 18.402 | 34.664 | -0.745 | 1.00 | 51.99 | C |
| ATOM | 329 | O | LEU | A | 263 | 18.630 | 35.833 | -1.108 | 1.00 | 53.85 | O |
| ATOM | 330 | CB | LEU | A | 263 | 19.948 | 33.739 | 1.069 | 1.00 | 51.10 | C |
| ATOM | 331 | CG | LEU | A | 263 | 20.081 | 33.672 | 2.616 | 1.00 | 54.75 | C |
| ATOM | 332 | CD1 | LEU | A | 263 | 21.195 | 32.737 | 3.055 | 1.00 | 56.03 | C |
| ATOM | 333 | CD2 | LEU | A | 263 | 20.265 | 35.086 | 3.150 | 1.00 | 53.20 | C |
| ATOM | 334 | N | VAL | A | 264 | 18.026 | 33.718 | -1.625 | 1.00 | 51.01 | N |
| ATOM | 335 | CA | VAL | A | 264 | 17.834 | 34.098 | -3.025 | 1.00 | 50.17 | C |
| ATOM | 336 | C | VAL | A | 264 | 16.735 | 35.153 | -3.049 | 1.00 | 46.15 | C |
| ATOM | 337 | O | VAL | A | 264 | 16.972 | 36.226 | -3.578 | 1.00 | 48.14 | O |
| ATOM | 338 | CB | VAL | A | 264 | 17.491 | 32.925 | -3.959 | 1.00 | 50.60 | C |
| ATOM | 339 | CG1 | VAL | A | 264 | 17.220 | 33.409 | -5.371 | 1.00 | 49.13 | C |
| ATOM | 340 | CG2 | VAL | A | 264 | 18.651 | 31.920 | -3.969 | 1.00 | 52.64 | C |
| ATOM | 341 | N | HIS | A | 265 | 15.565 | 34.938 | -2.476 | 1.00 | 45.03 | N |
| ATOM | 342 | CA | HIS | A | 265 | 14.518 | 35.949 | -2.479 | 1.00 | 46.90 | C |
| ATOM | 343 | C | HIS | A | 265 | 14.894 | 37.209 | -1.700 | 1.00 | 45.41 | C |
| ATOM | 344 | O | HIS | A | 265 | 14.383 | 38.293 | -2.024 | 1.00 | 43.17 | O |
| ATOM | 345 | CB | HIS | A | 265 | 13.240 | 35.365 | -1.904 | 1.00 | 49.98 | C |
| ATOM | 346 | CG | HIS | A | 265 | 12.767 | 34.102 | -2.537 | 1.00 | 56.36 | C |
| ATOM | 347 | ND1 | HIS | A | 265 | 12.482 | 33.965 | -3.880 | 1.00 | 58.33 | N |
| ATOM | 348 | CD2 | HIS | A | 265 | 12.513 | 32.887 | -1.990 | 1.00 | 57.85 | C |
| ATOM | 349 | CE1 | HIS | A | 265 | 12.082 | 32.736 | -4.132 | 1.00 | 58.28 | C |
| ATOM | 350 | NE2 | HIS | A | 265 | 12.096 | 32.058 | -2.997 | 1.00 | 58.84 | N |
| ATOM | 351 | N | MET | A | 266 | 15.819 | 37.121 | -0.717 | 1.00 | 45.21 | N |
| ATOM | 352 | CA | MET | A | 266 | 16.204 | 38.305 | 0.053 | 1.00 | 42.74 | C |
| ATOM | 353 | C | MET | A | 266 | 16.843 | 39.378 | -0.799 | 1.00 | 41.69 | C |
| ATOM | 354 | O | MET | A | 266 | 16.643 | 40.581 | -0.634 | 1.00 | 43.34 | O |
| ATOM | 355 | CB | MET | A | 266 | 17.191 | 37.976 | 1.192 | 1.00 | 42.31 | C |
| ATOM | 356 | CG | MET | A | 266 | 17.253 | 39.099 | 2.242 | 1.00 | 39.26 | C |
| ATOM | 357 | SD | MET | A | 266 | 18.401 | 38.672 | 3.554 | 1.00 | 38.84 | S |
| ATOM | 358 | CE | MET | A | 266 | 17.447 | 37.416 | 4.368 | 1.00 | 34.86 | C |
| ATOM | 359 | N | ILE | A | 267 | 17.640 | 38.964 | -1.776 | 1.00 | 44.08 | N |
| ATOM | 360 | CA | ILE | A | 267 | 18.307 | 39.948 | -2.635 | 1.00 | 43.36 | C |
| ATOM | 361 | C | ILE | A | 267 | 17.283 | 40.623 | -3.512 | 1.00 | 44.04 | C |
| ATOM | 362 | O | ILE | A | 267 | 17.436 | 41.822 | -3.709 | 1.00 | 43.59 | O |
| ATOM | 363 | CB | ILE | A | 267 | 19.394 | 39.236 | -3.459 | 1.00 | 46.74 | C |
| ATOM | 364 | CG1 | ILE | A | 267 | 20.383 | 38.727 | -2.409 | 1.00 | 47.97 | C |
| ATOM | 365 | CG2 | ILE | A | 267 | 20.025 | 40.129 | -4.520 | 1.00 | 44.97 | C |
| ATOM | 366 | CD1 | ILE | A | 267 | 21.334 | 37.669 | -2.940 | 1.00 | 53.31 | C |
| ATOM | 367 | N | GLY | A | 268 | 16.282 | 39.854 | -3.980 | 1.00 | 43.25 | N |
| ATOM | 368 | CA | GLY | A | 268 | 15.246 | 40.454 | -4.834 | 1.00 | 40.68 | C |
| ATOM | 369 | C | GLY | A | 268 | 14.439 | 41.430 | -3.973 | 1.00 | 40.39 | C |
| ATOM | 370 | O | GLY | A | 268 | 14.108 | 42.535 | -4.401 | 1.00 | 40.14 | O |
| ATOM | 371 | N | TRP | A | 269 | 14.133 | 41.030 | -2.734 | 1.00 | 38.10 | N |
| ATOM | 372 | CA | TRP | A | 269 | 13.397 | 41.937 | -1.847 | 1.00 | 35.69 | C |
| ATOM | 373 | C | TRP | A | 269 | 14.227 | 43.193 | -1.556 | 1.00 | 35.04 | C |
| ATOM | 374 | O | TRP | A | 269 | 13.717 | 44.310 | -1.606 | 1.00 | 35.68 | O |
| ATOM | 375 | CB | TRP | A | 269 | 13.179 | 41.170 | -0.528 | 1.00 | 36.69 | C |
| ATOM | 376 | CG | TRP | A | 269 | 12.847 | 42.031 | 0.651 | 1.00 | 36.18 | C |
| ATOM | 377 | CD1 | TRP | A | 269 | 11.617 | 42.566 | 0.879 | 1.00 | 36.39 | C |
| ATOM | 378 | CD2 | TRP | A | 269 | 13.689 | 42.470 | 1.737 | 1.00 | 36.54 | C |
| ATOM | 379 | NE1 | TRP | A | 269 | 11.632 | 43.290 | 2.057 | 1.00 | 36.97 | N |
| ATOM | 380 | CE2 | TRP | A | 269 | 12.894 | 43.249 | 2.598 | 1.00 | 36.38 | C |
| ATOM | 381 | CE3 | TRP | A | 269 | 15.020 | 42.259 | 2.082 | 1.00 | 36.71 | C |
| ATOM | 382 | CZ2 | TRP | A | 269 | 13.364 | 43.846 | 3.769 | 1.00 | 38.34 | C |

| ATOM | 229 | CA | SER A 250 | 19.116 | 16.340 | 9.046 | 1.00 | 114.27 | C |
|------|-----|-----|-----------|--------|--------|-------|------|--------|---|
| ATOM | 230 | C | SER A 250 | 18.446 | 17.632 | 9.476 | 1.00 | 110.36 | C |
| ATOM | 231 | O | SER A 250 | 17.913 | 18.327 | 8.599 | 1.00 | 109.68 | O |
| ATOM | 232 | CB | SER A 250 | 18.056 | 15.228 | 8.989 | 1.00 | 115.03 | C |
| ATOM | 233 | OG | SER A 250 | 18.452 | 14.229 | 8.062 | 1.00 | 115.87 | O |
| ATOM | 234 | N | MET A 251 | 18.443 | 17.946 | 10.764 | 1.00 | 105.44 | N |
| ATOM | 235 | CA | MET A 251 | 17.806 | 19.184 | 11.208 | 1.00 | 100.10 | C |
| ATOM | 236 | C | MET A 251 | 18.458 | 20.376 | 10.513 | 1.00 | 96.49 | C |
| ATOM | 237 | O | MET A 251 | 17.786 | 21.129 | 9.817 | 1.00 | 95.06 | O |
| ATOM | 238 | CB | MET A 251 | 17.886 | 19.351 | 12.722 | 1.00 | 100.52 | C |
| ATOM | 239 | CG | MET A 251 | 17.419 | 20.709 | 13.215 | 1.00 | 99.86 | C |
| ATOM | 240 | SD | MET A 251 | 16.921 | 20.734 | 14.935 | 1.00 | 98.91 | S |
| ATOM | 241 | CE | MET A 251 | 15.211 | 20.220 | 14.829 | 1.00 | 99.30 | C |
| ATOM | 242 | N | MET A 252 | 19.764 | 20.513 | 10.697 | 1.00 | 92.43 | N |
| ATOM | 243 | CA | MET A 252 | 20.540 | 21.590 | 10.117 | 1.00 | 88.81 | C |
| ATOM | 244 | C | MET A 252 | 20.528 | 21.575 | 8.595 | 1.00 | 88.23 | C |
| ATOM | 245 | O | MET A 252 | 20.488 | 22.635 | 7.958 | 1.00 | 87.46 | O |
| ATOM | 246 | CB | MET A 252 | 21.976 | 21.550 | 10.646 | 1.00 | 87.43 | C |
| ATOM | 247 | CG | AMET A 252 | 22.101 | 21.702 | 12.152 | 0.50 | 87.88 | C |
| ATOM | 248 | CG | BMET A 252 | 22.111 | 22.149 | 12.042 | 0.50 | 88.66 | C |
| ATOM | 249 | SD | AMET A 252 | 21.596 | 23.325 | 12.764 | 0.50 | 85.39 | S |
| ATOM | 250 | SD | BMET A 252 | 21.912 | 23.946 | 12.067 | 0.50 | 86.52 | S |
| ATOM | 251 | CE | AMET A 252 | 20.019 | 22.912 | 13.496 | 0.50 | 85.61 | C |
| ATOM | 252 | CE | BMET A 252 | 23.123 | 24.420 | 10.832 | 0.50 | 85.82 | C |
| ATOM | 253 | N | MET A 253 | 20.555 | 20.391 | 8.002 | 1.00 | 84.61 | N |
| ATOM | 254 | CA | MET A 253 | 20.532 | 20.212 | 6.557 | 1.00 | 81.63 | C |
| ATOM | 255 | C | MET A 253 | 19.290 | 20.865 | 5.962 | 1.00 | 78.06 | C |
| ATOM | 256 | O | MET A 253 | 19.325 | 21.625 | 4.991 | 1.00 | 77.65 | O |
| ATOM | 257 | CB | MET A 253 | 20.595 | 18.714 | 6.236 | 1.00 | 83.32 | C |
| ATOM | 258 | CG | MET A 253 | 21.257 | 18.386 | 4.905 | 1.00 | 85.85 | C |
| ATOM | 259 | SD | MET A 253 | 21.784 | 16.652 | 4.802 | 1.00 | 87.76 | S |
| ATOM | 260 | CE | MET A 253 | 20.194 | 15.850 | 4.572 | 1.00 | 87.58 | C |
| ATOM | 261 | N | SER A 254 | 18.137 | 20.585 | 6.552 | 1.00 | 74.03 | N |
| ATOM | 262 | CA | SER A 254 | 16.868 | 21.160 | 6.134 | 1.00 | 72.45 | C |
| ATOM | 263 | C | SER A 254 | 16.974 | 22.684 | 6.322 | 1.00 | 70.56 | C |
| ATOM | 264 | O | SER A 254 | 16.716 | 23.485 | 5.433 | 1.00 | 70.22 | O |
| ATOM | 265 | CB | SER A 254 | 15.720 | 20.595 | 6.961 | 1.00 | 72.55 | C |
| ATOM | 266 | OG | SER A 254 | 15.623 | 19.184 | 6.862 | 1.00 | 73.73 | O |
| ATOM | 267 | N | LEU A 255 | 17.428 | 23.095 | 7.505 | 1.00 | 68.40 | N |
| ATOM | 268 | CA | LEU A 255 | 17.602 | 24.494 | 7.836 | 1.00 | 66.66 | C |
| ATOM | 269 | C | LEU A 255 | 18.480 | 25.206 | 6.826 | 1.00 | 65.20 | C |
| ATOM | 270 | O | LEU A 255 | 18.098 | 26.295 | 6.399 | 1.00 | 62.91 | O |
| ATOM | 271 | CB | LEU A 255 | 18.137 | 24.665 | 9.268 | 1.00 | 65.91 | C |
| ATOM | 272 | CG | LEU A 255 | 17.133 | 24.123 | 10.285 | 1.00 | 66.73 | C |
| ATOM | 273 | CD1 | LEU A 255 | 17.752 | 23.981 | 11.663 | 1.00 | 68.67 | C |
| ATOM | 274 | CD2 | LEU A 255 | 15.885 | 24.990 | 10.307 | 1.00 | 67.78 | C |
| ATOM | 275 | N | THR A 256 | 19.600 | 24.594 | 6.449 | 1.00 | 65.00 | N |
| ATOM | 276 | CA | THR A 256 | 20.512 | 25.188 | 5.488 | 1.00 | 65.09 | C |
| ATOM | 277 | C | THR A 256 | 19.829 | 25.324 | 4.131 | 1.00 | 66.25 | C |
| ATOM | 278 | O | THR A 256 | 20.046 | 26.339 | 3.472 | 1.00 | 66.66 | O |
| ATOM | 279 | CB | THR A 256 | 21.811 | 24.389 | 5.297 | 1.00 | 65.58 | C |
| ATOM | 280 | OG1 | THR A 256 | 22.676 | 24.514 | 6.435 | 1.00 | 64.87 | O |
| ATOM | 281 | CG2 | THR A 256 | 22.610 | 24.833 | 4.081 | 1.00 | 65.43 | C |
| ATOM | 282 | N | LYS A 257 | 19.026 | 24.341 | 3.722 | 1.00 | 64.72 | N |
| ATOM | 283 | CA | LYS A 257 | 18.391 | 24.461 | 2.416 | 1.00 | 63.90 | C |
| ATOM | 284 | C | LYS A 257 | 17.311 | 25.534 | 2.487 | 1.00 | 61.71 | C |
| ATOM | 285 | O | LYS A 257 | 17.096 | 26.235 | 1.508 | 1.00 | 57.92 | O |
| ATOM | 286 | CB | LYS A 257 | 17.857 | 23.129 | 1.906 | 1.00 | 64.32 | C |
| ATOM | 287 | N | LEU A 258 | 16.653 | 25.664 | 3.635 | 1.00 | 62.10 | N |
| ATOM | 288 | CA | LEU A 258 | 15.622 | 26.710 | 3.745 | 1.00 | 61.64 | C |
| ATOM | 289 | C | LEU A 258 | 16.257 | 28.089 | 3.619 | 1.00 | 60.14 | C |
| ATOM | 290 | O | LEU A 258 | 15.888 | 28.907 | 2.759 | 1.00 | 58.37 | O |
| ATOM | 291 | CB | LEU A 258 | 14.851 | 26.492 | 5.035 | 1.00 | 60.80 | C |
| ATOM | 292 | CG | LEU A 258 | 13.825 | 27.572 | 5.388 | 1.00 | 60.73 | C |
| ATOM | 293 | CD1 | LEU A 258 | 12.723 | 27.726 | 4.345 | 1.00 | 59.77 | C |
| ATOM | 294 | CD2 | LEU A 258 | 13.260 | 27.275 | 6.753 | 1.00 | 59.05 | C |
| ATOM | 295 | N | ALA A 259 | 17.276 | 28.350 | 4.434 | 1.00 | 59.90 | N |
| ATOM | 296 | CA | ALA A 259 | 17.982 | 29.622 | 4.422 | 1.00 | 59.71 | C |
| ATOM | 297 | C | ALA A 259 | 18.407 | 30.024 | 3.024 | 1.00 | 59.96 | C |
| ATOM | 298 | O | ALA A 259 | 18.108 | 31.134 | 2.576 | 1.00 | 57.73 | O |
| ATOM | 299 | CB | ALA A 259 | 19.189 | 29.637 | 5.352 | 1.00 | 59.90 | C |
| ATOM | 300 | N | ASP A 260 | 19.107 | 29.121 | 2.333 | 1.00 | 61.84 | N |
| ATOM | 301 | CA | ASP A 260 | 19.578 | 29.365 | 0.974 | 1.00 | 61.27 | C |
| ATOM | 302 | C | ASP A 260 | 18.483 | 29.803 | 0.023 | 1.00 | 59.30 | C |
| ATOM | 303 | O | ASP A 260 | 18.677 | 30.747 | -0.739 | 1.00 | 58.60 | O |
| ATOM | 304 | CB | ASP A 260 | 20.266 | 28.107 | 0.431 | 1.00 | 64.62 | C |
| ATOM | 305 | CG | ASP A 260 | 21.485 | 27.824 | 1.293 | 1.00 | 67.57 | C |

| ATOM | 152 | O | LEU A 238 | 9.564 | 24.525 | 0.527 | 1.00 | 98.51 | O |
|------|-----|-----|-----------|--------|--------|--------|------|-------|---|
| ATOM | 153 | CB | LEU A 238 | 6.635 | 25.469 | 0.715 | 1.00 | 96.64 | C |
| ATOM | 154 | CG | LEU A 238 | 5.564 | 26.521 | 0.420 | 1.00 | 97.60 | C |
| ATOM | 155 | CD1 | LEU A 238 | 4.440 | 25.902 | -0.411 | 1.00 | 97.92 | C |
| ATOM | 156 | CD2 | LEU A 238 | 5.013 | 27.140 | 1.694 | 1.00 | 97.61 | C |
| ATOM | 157 | N | VAL A 239 | 9.098 | 24.318 | 2.699 | 1.00 | 103.60 | N |
| ATOM | 158 | CA | VAL A 239 | 10.043 | 23.225 | 2.930 | 1.00 | 107.98 | C |
| ATOM | 159 | C | VAL A 239 | 9.266 | 22.264 | 3.831 | 1.00 | 111.72 | C |
| ATOM | 160 | O | VAL A 239 | 8.319 | 22.679 | 4.504 | 1.00 | 111.53 | O |
| ATOM | 161 | CB | VAL A 239 | 11.397 | 23.673 | 3.463 | 1.00 | 107.38 | C |
| ATOM | 162 | CG1 | VAL A 239 | 12.027 | 22.712 | 4.460 | 1.00 | 107.06 | C |
| ATOM | 163 | CG2 | VAL A 239 | 12.389 | 23.852 | 2.310 | 1.00 | 106.87 | C |
| ATOM | 164 | N | SER A 240 | 9.629 | 20.996 | 3.792 | 1.00 | 117.13 | N |
| ATOM | 165 | CA | SER A 240 | 8.959 | 19.986 | 4.600 | 1.00 | 122.16 | C |
| ATOM | 166 | C | SER A 240 | 9.987 | 19.295 | 5.492 | 1.00 | 125.90 | C |
| ATOM | 167 | O | SER A 240 | 11.143 | 19.162 | 5.084 | 1.00 | 126.00 | O |
| ATOM | 168 | CB | SER A 240 | 8.247 | 18.979 | 3.708 | 1.00 | 122.02 | C |
| ATOM | 169 | N | ARG A 241 | 9.563 | 18.886 | 6.687 | 1.00 | 130.90 | N |
| ATOM | 170 | CA | ARG A 241 | 10.506 | 18.197 | 7.568 | 1.00 | 135.89 | C |
| ATOM | 171 | C | ARG A 241 | 10.849 | 16.867 | 6.898 | 1.00 | 138.89 | C |
| ATOM | 172 | O | ARG A 241 | 10.111 | 16.356 | 6.059 | 1.00 | 139.00 | O |
| ATOM | 173 | CB | ARG A 241 | 9.938 | 17.888 | 8.944 | 1.00 | 136.97 | C |
| ATOM | 174 | CG | ARG A 241 | 9.152 | 18.982 | 9.631 | 1.00 | 138.27 | C |
| ATOM | 175 | CD | ARG A 241 | 7.859 | 18.429 | 10.220 | 1.00 | 138.85 | C |
| ATOM | 176 | NE | ARG A 241 | 6.758 | 19.364 | 10.015 | 1.00 | 139.51 | N |
| ATOM | 177 | CZ | ARG A 241 | 6.078 | 19.971 | 10.979 | 1.00 | 139.74 | C |
| ATOM | 178 | NH1 | ARG A 241 | 6.359 | 19.758 | 12.257 | 1.00 | 139.81 | N |
| ATOM | 179 | NH2 | ARG A 241 | 5.097 | 20.800 | 10.644 | 1.00 | 139.77 | N |
| ATOM | 180 | N | PRO A 242 | 11.957 | 16.285 | 7.306 | 1.00 | 141.85 | N |
| ATOM | 181 | CA | PRO A 242 | 12.451 | 15.015 | 6.812 | 1.00 | 144.25 | C |
| ATOM | 182 | C | PRO A 242 | 11.471 | 13.870 | 6.999 | 1.00 | 146.39 | C |
| ATOM | 183 | O | PRO A 242 | 11.473 | 12.916 | 6.210 | 1.00 | 147.06 | O |
| ATOM | 184 | CB | PRO A 242 | 13.792 | 14.739 | 7.520 | 1.00 | 143.96 | C |
| ATOM | 185 | CG | PRO A 242 | 14.139 | 16.091 | 8.080 | 1.00 | 143.34 | C |
| ATOM | 186 | CD | PRO A 242 | 12.860 | 16.866 | 8.307 | 1.00 | 142.65 | C |
| ATOM | 187 | N | SER A 243 | 10.627 | 13.878 | 8.023 | 1.00 | 148.37 | N |
| ATOM | 188 | CA | SER A 243 | 9.617 | 12.882 | 8.319 | 1.00 | 149.86 | C |
| ATOM | 189 | C | SER A 243 | 10.156 | 11.527 | 8.760 | 1.00 | 150.75 | C |
| ATOM | 190 | O | SER A 243 | 9.528 | 10.471 | 8.748 | 1.00 | 150.61 | O |
| ATOM | 191 | CB | SER A 243 | 8.697 | 12.695 | 7.112 | 1.00 | 150.09 | C |
| ATOM | 192 | N | MET A 244 | 11.393 | 11.542 | 9.185 | 1.00 | 151.76 | N |
| ATOM | 193 | CA | MET A 244 | 12.225 | 10.471 | 9.677 | 1.00 | 152.55 | C |
| ATOM | 194 | C | MET A 244 | 13.342 | 11.252 | 10.389 | 1.00 | 153.05 | C |
| ATOM | 195 | O | MET A 244 | 14.402 | 11.547 | 9.856 | 1.00 | 153.19 | O |
| ATOM | 196 | CB | MET A 244 | 12.778 | 9.589 | 8.585 | 1.00 | 152.68 | C |
| ATOM | 197 | N | PRO A 245 | 13.007 | 11.647 | 11.604 | 1.00 | 153.37 | N |
| ATOM | 198 | CA | PRO A 245 | 13.859 | 12.427 | 12.465 | 1.00 | 153.26 | C |
| ATOM | 199 | C | PRO A 245 | 15.310 | 11.979 | 12.484 | 1.00 | 152.52 | C |
| ATOM | 200 | O | PRO A 245 | 15.659 | 10.816 | 12.314 | 1.00 | 152.82 | O |
| ATOM | 201 | CB | PRO A 245 | 13.283 | 12.360 | 13.893 | 1.00 | 153.60 | C |
| ATOM | 202 | CG | PRO A 245 | 11.955 | 11.695 | 13.699 | 1.00 | 153.72 | C |
| ATOM | 203 | CD | PRO A 245 | 11.729 | 11.339 | 12.256 | 1.00 | 153.63 | C |
| ATOM | 204 | N | PHE A 246 | 16.157 | 12.972 | 12.702 | 1.00 | 151.08 | N |
| ATOM | 205 | CA | PHE A 246 | 17.600 | 12.802 | 12.815 | 1.00 | 149.39 | C |
| ATOM | 206 | C | PHE A 246 | 17.975 | 13.730 | 13.977 | 1.00 | 148.07 | C |
| ATOM | 207 | O | PHE A 246 | 17.053 | 14.117 | 14.708 | 1.00 | 147.63 | O |
| ATOM | 208 | CB | PHE A 246 | 18.353 | 13.115 | 11.551 | 1.00 | 149.16 | C |
| ATOM | 209 | N | THR A 247 | 19.244 | 14.061 | 14.135 | 1.00 | 146.46 | N |
| ATOM | 210 | CA | THR A 247 | 19.606 | 14.946 | 15.247 | 1.00 | 144.65 | C |
| ATOM | 211 | C | THR A 247 | 20.323 | 16.177 | 14.707 | 1.00 | 142.63 | C |
| ATOM | 212 | O | THR A 247 | 19.667 | 17.160 | 14.355 | 1.00 | 142.89 | O |
| ATOM | 213 | CB | THR A 247 | 20.433 | 14.201 | 16.281 | 1.00 | 145.17 | C |
| ATOM | 214 | N | GLU A 248 | 21.645 | 16.115 | 14.637 | 1.00 | 139.60 | N |
| ATOM | 215 | CA | GLU A 248 | 22.421 | 17.239 | 14.136 | 1.00 | 136.62 | C |
| ATOM | 216 | C | GLU A 248 | 22.458 | 17.252 | 12.614 | 1.00 | 133.59 | C |
| ATOM | 217 | O | GLU A 248 | 22.435 | 18.313 | 11.997 | 1.00 | 133.60 | O |
| ATOM | 218 | CB | GLU A 248 | 23.845 | 17.170 | 14.694 | 1.00 | 137.43 | C |
| ATOM | 219 | CG | GLU A 248 | 24.070 | 18.056 | 15.905 | 1.00 | 138.23 | C |
| ATOM | 220 | CD | GLU A 248 | 25.518 | 18.459 | 16.075 | 1.00 | 138.84 | C |
| ATOM | 221 | OE1 | GLU A 248 | 26.293 | 18.375 | 15.100 | 1.00 | 139.44 | O |
| ATOM | 222 | OE2 | GLU A 248 | 25.896 | 18.867 | 17.194 | 1.00 | 138.88 | O |
| ATOM | 223 | N | ALA A 249 | 22.508 | 16.072 | 12.015 | 1.00 | 129.47 | N |
| ATOM | 224 | CA | ALA A 249 | 22.580 | 15.921 | 10.575 | 1.00 | 125.50 | C |
| ATOM | 225 | C | ALA A 249 | 21.441 | 16.515 | 9.763 | 1.00 | 122.35 | C |
| ATOM | 226 | O | ALA A 249 | 21.638 | 17.506 | 9.055 | 1.00 | 121.91 | O |
| ATOM | 227 | CB | ALA A 249 | 22.707 | 14.427 | 10.252 | 1.00 | 125.67 | C |
| ATOM | 228 | N | SER A 250 | 20.260 | 15.910 | 9.823 | 1.00 | 118.36 | N |

| ATOM | 75 | CA | THR A 228 | 6.005 | 49.197 | -1.791 | 1.00 | 37.00 | C |
| ATOM | 76 | C | THR A 228 | 6.593 | 48.067 | -0.950 | 1.00 | 36.50 | C |
| ATOM | 77 | O | THR A 228 | 6.968 | 46.997 | -1.441 | 1.00 | 33.45 | O |
| ATOM | 78 | CB | THR A 228 | 7.174 | 50.214 | -1.939 | 1.00 | 41.04 | C |
| ATOM | 79 | OG1 | THR A 228 | 6.646 | 51.310 | -2.677 | 1.00 | 36.07 | O |
| ATOM | 80 | CG2 | THR A 228 | 8.391 | 49.629 | -2.667 | 1.00 | 39.93 | C |
| ATOM | 81 | N | LEU A 229 | 6.690 | 48.256 | 0.380 | 1.00 | 36.26 | N |
| ATOM | 82 | CA | LEU A 229 | 7.203 | 47.175 | 1.231 | 1.00 | 35.39 | C |
| ATOM | 83 | C | LEU A 229 | 6.249 | 45.983 | 1.183 | 1.00 | 36.07 | C |
| ATOM | 84 | O | LEU A 229 | 6.692 | 44.841 | 1.148 | 1.00 | 37.07 | O |
| ATOM | 85 | CB | LEU A 229 | 7.322 | 47.637 | 2.696 | 1.00 | 33.22 | C |
| ATOM | 86 | CG | LEU A 229 | 8.345 | 48.734 | 2.968 | 1.00 | 33.68 | C |
| ATOM | 87 | CD1 | LEU A 229 | 8.394 | 49.035 | 4.479 | 1.00 | 33.77 | C |
| ATOM | 88 | CD2 | LEU A 229 | 9.742 | 48.415 | 2.476 | 1.00 | 33.57 | C |
| ATOM | 89 | N | LEU A 230 | 4.927 | 46.173 | 1.255 | 1.00 | 37.88 | N |
| ATOM | 90 | CA | LEU A 230 | 4.007 | 45.012 | 1.233 | 1.00 | 37.38 | C |
| ATOM | 91 | C | LEU A 230 | 4.203 | 44.283 | -0.097 | 1.00 | 38.15 | C |
| ATOM | 92 | O | LEU A 230 | 4.416 | 43.064 | -0.185 | 1.00 | 37.45 | O |
| ATOM | 93 | CB | LEU A 230 | 2.582 | 45.506 | 1.494 | 1.00 | 36.59 | C |
| ATOM | 94 | CG | LEU A 230 | 1.423 | 44.492 | 1.517 | 1.00 | 37.74 | C |
| ATOM | 95 | CD1 | LEU A 230 | 1.678 | 43.307 | 2.456 | 1.00 | 36.47 | C |
| ATOM | 96 | CD2 | LEU A 230 | 0.112 | 45.158 | 1.943 | 1.00 | 34.60 | C |
| ATOM | 97 | N | GLU A 231 | 4.251 | 45.016 | -1.210 | 1.00 | 38.77 | N |
| ATOM | 98 | CA | GLU A 231 | 4.466 | 44.443 | -2.539 | 1.00 | 41.66 | C |
| ATOM | 99 | C | GLU A 231 | 5.798 | 43.730 | -2.660 | 1.00 | 42.60 | C |
| ATOM | 100 | O | GLU A 231 | 5.961 | 42.720 | -3.371 | 1.00 | 41.88 | O |
| ATOM | 101 | CB | GLU A 231 | 4.337 | 45.556 | -3.605 | 1.00 | 43.10 | C |
| ATOM | 102 | CG | GLU A 231 | 2.883 | 46.040 | -3.784 | 1.00 | 46.97 | C |
| ATOM | 103 | CD | GLU A 231 | 2.689 | 46.720 | -5.128 | 1.00 | 48.35 | C |
| ATOM | 104 | OE1 | GLU A 231 | 3.092 | 47.890 | -5.340 | 1.00 | 50.48 | O |
| ATOM | 105 | OE2 | GLU A 231 | 2.134 | 46.076 | -6.028 | 1.00 | 50.03 | O |
| ATOM | 106 | N | ALA A 232 | 6.841 | 44.237 | -1.976 | 1.00 | 41.94 | N |
| ATOM | 107 | CA | ALA A 232 | 8.148 | 43.583 | -2.048 | 1.00 | 41.11 | C |
| ATOM | 108 | C | ALA A 232 | 8.258 | 42.295 | -1.236 | 1.00 | 40.77 | C |
| ATOM | 109 | O | ALA A 232 | 9.227 | 41.543 | -1.412 | 1.00 | 39.07 | O |
| ATOM | 110 | CB | ALA A 232 | 9.210 | 44.608 | -1.630 | 1.00 | 37.10 | C |
| ATOM | 111 | N | GLU A 233 | 7.358 | 41.964 | -0.337 | 1.00 | 43.97 | N |
| ATOM | 112 | CA | GLU A 233 | 7.455 | 40.746 | 0.463 | 1.00 | 48.49 | C |
| ATOM | 113 | C | GLU A 233 | 7.695 | 39.500 | -0.381 | 1.00 | 54.75 | C |
| ATOM | 114 | O | GLU A 233 | 6.932 | 39.174 | -1.298 | 1.00 | 57.04 | O |
| ATOM | 115 | CB | GLU A 233 | 6.160 | 40.541 | 1.250 | 1.00 | 47.42 | C |
| ATOM | 116 | CG | GLU A 233 | 6.080 | 41.014 | 2.671 | 1.00 | 47.35 | C |
| ATOM | 117 | CD | GLU A 233 | 7.239 | 40.584 | 3.548 | 1.00 | 46.92 | C |
| ATOM | 118 | OE1 | GLU A 233 | 8.252 | 41.294 | 3.577 | 1.00 | 42.48 | O |
| ATOM | 119 | OE2 | GLU A 233 | 7.238 | 39.544 | 4.227 | 1.00 | 48.39 | O |
| ATOM | 120 | N | PRO A 234 | 8.758 | 38.777 | -0.112 | 1.00 | 57.48 | N |
| ATOM | 121 | CA | PRO A 234 | 9.107 | 37.552 | -0.802 | 1.00 | 60.37 | C |
| ATOM | 122 | C | PRO A 234 | 8.032 | 36.490 | -0.604 | 1.00 | 62.02 | C |
| ATOM | 123 | O | PRO A 234 | 7.192 | 36.484 | 0.298 | 1.00 | 59.55 | O |
| ATOM | 124 | CB | PRO A 234 | 10.399 | 36.999 | -0.148 | 1.00 | 60.53 | C |
| ATOM | 125 | CG | PRO A 234 | 10.401 | 37.738 | 1.170 | 1.00 | 61.05 | C |
| ATOM | 126 | CD | PRO A 234 | 9.695 | 39.075 | 0.972 | 1.00 | 58.93 | C |
| ATOM | 127 | N | PRO A 235 | 8.065 | 35.518 | -1.489 | 1.00 | 67.26 | N |
| ATOM | 128 | CA | PRO A 235 | 7.152 | 34.380 | -1.445 | 1.00 | 70.48 | C |
| ATOM | 129 | C | PRO A 235 | 7.535 | 33.515 | -0.242 | 1.00 | 72.12 | C |
| ATOM | 130 | O | PRO A 235 | 8.696 | 33.326 | 0.108 | 1.00 | 70.17 | O |
| ATOM | 131 | CB | PRO A 235 | 7.291 | 33.635 | -2.774 | 1.00 | 70.80 | C |
| ATOM | 132 | CG | PRO A 235 | 8.590 | 34.148 | -3.321 | 1.00 | 70.08 | C |
| ATOM | 133 | CD | PRO A 235 | 9.019 | 35.401 | -2.598 | 1.00 | 68.92 | C |
| ATOM | 134 | N | ASN A 236 | 6.530 | 33.013 | 0.445 | 1.00 | 76.12 | N |
| ATOM | 135 | CA | ASN A 236 | 6.715 | 32.146 | 1.601 | 1.00 | 80.87 | C |
| ATOM | 136 | C | ASN A 236 | 7.377 | 30.860 | 1.107 | 1.00 | 81.79 | C |
| ATOM | 137 | O | ASN A 236 | 6.750 | 30.125 | 0.356 | 1.00 | 81.83 | O |
| ATOM | 138 | CB | ASN A 236 | 5.346 | 31.888 | 2.233 | 1.00 | 83.71 | C |
| ATOM | 139 | CG | ASN A 236 | 4.316 | 32.943 | 1.868 | 1.00 | 86.08 | C |
| ATOM | 140 | OD1 | ASN A 236 | 4.164 | 33.971 | 2.529 | 1.00 | 87.08 | O |
| ATOM | 141 | ND2 | ASN A 236 | 3.578 | 32.701 | 0.783 | 1.00 | 87.57 | N |
| ATOM | 142 | N | VAL A 237 | 8.619 | 30.587 | 1.465 | 1.00 | 83.67 | N |
| ATOM | 143 | CA | VAL A 237 | 9.348 | 29.404 | 1.044 | 1.00 | 85.06 | C |
| ATOM | 144 | C | VAL A 237 | 8.901 | 28.140 | 1.774 | 1.00 | 87.41 | C |
| ATOM | 145 | O | VAL A 237 | 9.022 | 27.965 | 2.978 | 1.00 | 85.24 | O |
| ATOM | 146 | CB | VAL A 237 | 10.866 | 29.596 | 1.203 | 1.00 | 84.25 | C |
| ATOM | 147 | CG1 | VAL A 237 | 11.634 | 28.331 | 0.852 | 1.00 | 83.72 | C |
| ATOM | 148 | CG2 | VAL A 237 | 11.331 | 30.748 | 0.323 | 1.00 | 83.12 | C |
| ATOM | 149 | N | LEU A 238 | 8.354 | 27.211 | 0.996 | 1.00 | 91.27 | N |
| ATOM | 150 | CA | LEU A 238 | 7.853 | 25.952 | 1.503 | 1.00 | 96.02 | C |
| ATOM | 151 | C | LEU A 238 | 8.919 | 24.866 | 1.507 | 1.00 | 99.04 | C |

63

```
REMARK CRYST1    67.550   67.550  148.200  90.00  90.00  90.00  P4122 SCALE1
   0.01480   0.00000   0.00000       0.00000 SCALE2      0.00000   0.01480   0.00000
         0.00000 SCALE3        0.00000   0.00000   0.00675         0.00000
ATOM      1  N   THR A 219      10.962  61.463  -2.130  1.00 91.05           N
ATOM      2  CA  THR A 219      10.095  62.061  -1.075  1.00 89.40           C
ATOM      3  C   THR A 219       8.635  61.669  -1.238  1.00 87.15           C
ATOM      4  O   THR A 219       7.704  62.441  -0.968  1.00 87.81           O
ATOM      5  CB  THR A 219      10.236  63.593  -1.031  1.00 91.18           C
ATOM      6  OG1 THR A 219      10.954  64.032  -2.195  1.00 92.02           O
ATOM      7  CG2 THR A 219      10.977  64.008   0.234  1.00 91.71           C
ATOM      8  N   LEU A 220       8.423  60.419  -1.667  1.00 82.33           N
ATOM      9  CA  LEU A 220       7.054  59.907  -1.835  1.00 76.10           C
ATOM     10  C   LEU A 220       6.419  59.826  -0.449  1.00 70.95           C
ATOM     11  O   LEU A 220       7.061  60.119   0.569  1.00 69.79           O
ATOM     12  CB  LEU A 220       7.075  58.561  -2.544  1.00 77.20           C
ATOM     13  CG  LEU A 220       8.380  57.749  -2.462  1.00 78.14           C
ATOM     14  CD1 LEU A 220       8.329  56.668  -1.377  1.00 77.79           C
ATOM     15  CD2 LEU A 220       8.698  57.122  -3.810  1.00 76.44           C
ATOM     16  N   SER A 221       5.148  59.457  -0.340  1.00 63.04           N
ATOM     17  CA  SER A 221       4.513  59.387   0.966  1.00 54.38           C
ATOM     18  C   SER A 221       4.854  58.130   1.766  1.00 48.85           C
ATOM     19  O   SER A 221       5.276  57.081   1.280  1.00 48.18           O
ATOM     20  CB  SER A 221       3.004  59.379   0.641  1.00 53.50           C
ATOM     21  OG  SER A 221       2.558  58.107   0.154  1.00 51.22           O
ATOM     22  N   PRO A 222       4.567  58.171   3.052  1.00 45.47           N
ATOM     23  CA  PRO A 222       4.684  57.044   3.968  1.00 41.72           C
ATOM     24  C   PRO A 222       3.794  55.903   3.485  1.00 40.52           C
ATOM     25  O   PRO A 222       4.159  54.729   3.554  1.00 35.42           O
ATOM     26  CB  PRO A 222       4.229  57.507   5.344  1.00 43.54           C
ATOM     27  CG  PRO A 222       3.808  58.931   5.137  1.00 44.74           C
ATOM     28  CD  PRO A 222       4.063  59.380   3.736  1.00 45.10           C
ATOM     29  N   GLU A 223       2.611  56.195   2.922  1.00 38.92           N
ATOM     30  CA  GLU A 223       1.722  55.157   2.428  1.00 40.39           C
ATOM     31  C   GLU A 223       2.329  54.552   1.166  1.00 37.19           C
ATOM     32  O   GLU A 223       2.280  53.335   1.002  1.00 37.73           O
ATOM     33  CB  GLU A 223       0.281  55.616   2.158  1.00 45.41           C
ATOM     34  CG  GLU A 223       0.142  57.043   1.674  1.00 52.56           C
ATOM     35  CD  GLU A 223       0.335  58.021   2.824  1.00 55.66           C
ATOM     36  OE1 GLU A 223      -0.550  58.232   3.683  1.00 61.06           O
ATOM     37  OE2 GLU A 223       1.422  58.611   2.888  1.00 57.61           O
ATOM     38  N   GLN A 224       2.974  55.376   0.339  1.00 37.61           N
ATOM     39  CA  GLN A 224       3.637  54.813  -0.849  1.00 39.68           C
ATOM     40  C   GLN A 224       4.705  53.818  -0.359  1.00 38.12           C
ATOM     41  O   GLN A 224       4.742  52.656  -0.716  1.00 38.85           O
ATOM     42  CB  GLN A 224       4.307  55.927  -1.680  1.00 40.53           C
ATOM     43  CG  AGLN A 224      5.191  55.287  -2.740  0.50 40.59           C
ATOM     44  CG  BGLN A 224      3.542  56.294  -2.931  0.50 44.12           C
ATOM     45  CD  AGLN A 224      4.399  54.625  -3.865  0.50 40.29           C
ATOM     46  CD  BGLN A 224      3.686  57.569  -3.709  0.50 44.60           C
ATOM     47  OE1AGLN A 224       4.010  55.384  -4.765  0.50 39.59           O
ATOM     48  OE1BGLN A 224       3.988  57.526  -4.922  0.50 43.51           O
ATOM     49  NE2AGLN A 224       4.215  53.306  -3.789  0.50 34.92           N
ATOM     50  NE2BGLN A 224       3.459  58.760  -3.124  0.50 42.94           N
ATOM     51  N   LEU A 225       5.555  54.271   0.567  1.00 38.18           N
ATOM     52  CA  LEU A 225       6.621  53.447   1.108  1.00 37.94           C
ATOM     53  C   LEU A 225       6.105  52.159   1.703  1.00 33.19           C
ATOM     54  O   LEU A 225       6.661  51.114   1.405  1.00 33.70           O
ATOM     55  CB  LEU A 225       7.475  54.201   2.143  1.00 37.34           C
ATOM     56  CG  LEU A 225       8.853  53.548   2.408  1.00 39.10           C
ATOM     57  CD1 LEU A 225       9.863  54.606   2.824  1.00 38.04           C
ATOM     58  CD2 LEU A 225       8.750  52.471   3.484  1.00 41.09           C
ATOM     59  N   VAL A 226       5.073  52.188   2.524  1.00 32.82           N
ATOM     60  CA  VAL A 226       4.549  50.939   3.110  1.00 33.33           C
ATOM     61  C   VAL A 226       3.951  50.062   2.010  1.00 34.37           C
ATOM     62  O   VAL A 226       4.102  48.816   2.004  1.00 34.43           O
ATOM     63  CB  VAL A 226       3.512  51.266   4.203  1.00 35.51           C
ATOM     64  CG1 VAL A 226       2.898  49.972   4.765  1.00 33.87           C
ATOM     65  CG2 VAL A 226       4.153  52.048   5.340  1.00 31.82           C
ATOM     66  N   LEU A 227       3.265  50.701   1.050  1.00 35.79           N
ATOM     67  CA  LEU A 227       2.669  49.966  -0.088  1.00 33.89           C
ATOM     68  C   LEU A 227       3.781  49.248  -0.818  1.00 32.01           C
ATOM     69  O   LEU A 227       3.726  48.024  -1.031  1.00 33.36           O
ATOM     70  CB  LEU A 227       1.893  50.937  -1.031  1.00 34.02           C
ATOM     71  CG  LEU A 227       1.508  50.304  -2.365  1.00 32.95           C
ATOM     72  CD1 LEU A 227       0.688  49.030  -2.169  1.00 32.15           C
ATOM     73  CD2 LEU A 227       0.758  51.263  -3.274  1.00 34.95           C
ATOM     74  N   THR A 228       4.886  49.923  -1.168  1.00 34.72           N
```

64

```
ATOM     42  OW  WAT W   42       0.203  38.575  24.860  1.00 79.22           O
ATOM     43  OW  WAT W   43      -0.957  45.870   9.762  1.00 56.40           O
ATOM     44  OW  WAT W   44      -1.167  46.539  18.314  1.00 75.63           O
ATOM     45  OW  WAT W   45      -3.681  48.802  14.919  1.00 70.97           O
ATOM     46  OW  WAT W   46      -5.534  45.709  14.509  1.00 77.20           O
ATOM     47  OW  WAT W   47      23.525  51.487   8.185  1.00 41.22           O
ATOM     48  OW  WAT W   48      28.234  49.012  14.677  1.00 60.00           O
ATOM     49  OW  WAT W   49      32.414  58.748   9.445  1.00 48.32           O
ATOM     50  OW  WAT W   50      28.879  60.648  -6.043  1.00 67.65           O
ATOM     51  OW  WAT W   51      27.716  63.712   7.635  1.00 71.29           O
ATOM     52  OW  WAT W   52      26.125  55.590  -6.633  1.00 65.01           O
ATOM     53  OW  WAT W   53      15.783  63.256   6.459  1.00 57.69           O
ATOM     54  OW  WAT W   54      -3.520  55.466  24.296  1.00 66.99           O
ATOM     55  OW  WAT W   55       6.513  58.567  25.480  1.00 47.47           O
ATOM     56  OW  WAT W   56       3.742  46.347  26.888  1.00 70.01           O
ATOM     57  OW  WAT W   57      25.663  39.230  12.893  1.00 67.60           O
ATOM     58  OW  WAT W   58      14.114  37.622   3.727  1.00 52.92           O
ATOM     59  OW  WAT W   59       7.782  57.664   4.312  1.00 33.85           O
ATOM     60  OW  WAT W   60      13.238  35.817   1.470  1.00 48.56           O
ATOM     61  OW  WAT W   61       2.854  39.239   2.517  1.00 64.70           O
ATOM     62  OW  WAT W   62       1.690  37.687   7.131  1.00 66.26           O
ATOM     63  OW  WAT W   63      31.061  53.803   2.883  1.00 38.79           O
ATOM     64  OW  WAT W   64      27.642  51.271   8.717  1.00 65.66           O
ATOM     65  OW  WAT W   65       2.904  57.361  15.614  1.00 38.99           O
ATOM     66  OW  WAT W   66      -2.968  59.627  15.555  1.00 73.13           O
ATOM     67  OW  WAT W   67      -0.394  62.009  24.989  1.00 56.00           O
ATOM     68  OW  WAT W   68      12.254  40.016   3.281  1.00 57.52           O
ATOM     69  OW  WAT W   69       2.180  36.316  11.540  1.00 65.13           O
ATOM     70  OW  WAT W   70       8.146  53.692  -3.250  1.00 60.91           O
ATOM     71  OW  WAT W   71       3.584  50.730  -5.938  1.00 53.43           O
ATOM     72  OW  WAT W   72       6.851  50.376  -5.838  1.00 70.78           O
ATOM     73  OW  WAT W   73       1.670  41.318  -3.595  1.00 82.15           O
ATOM     74  OW  WAT W   74       8.876  27.113  -1.925  1.00 79.21           O
ATOM     75  OW  WAT W   75      24.703  26.427   1.886  1.00 75.28           O
ATOM     76  OW  WAT W   76      14.573  29.994  -3.925  1.00 79.42           O
ATOM     77  OW  WAT W   77      12.138  36.628  -5.761  1.00 81.82           O
ATOM     78  OW  WAT W   78      13.950  42.839  -7.437  1.00 51.87           O
ATOM     79  OW  WAT W   79      21.755  49.826  -8.574  1.00 73.46           O
ATOM     80  OW  WAT W   80      21.744  46.304  -7.446  1.00 60.52           O
ATOM     81  OW  WAT W   81      28.146  54.159   6.849  1.00 56.24           O
ATOM     82  OW  WAT W   82      -2.852  30.954  18.854  1.00 86.76           O
ATOM     83  OW  WAT W   83      19.539  30.533  28.175  1.00 43.52           O
ATOM     84  OW  WAT W   84       7.639  30.685  23.862  1.00 67.16           O
ATOM     85  OW  WAT W   85       9.513  32.990  25.460  1.00 56.82           O
ATOM     86  OW  WAT W   86      -0.970  50.506  13.869  1.00 63.21           O
ATOM     87  OW  WAT W   87      -1.421  48.731  11.261  1.00 56.81           O
ATOM     88  OW  WAT W   88      12.222  62.053   6.702  1.00 50.80           O
ATOM     89  OW  WAT W   89      13.981  61.049   4.378  1.00 44.74           O
ATOM     90  OW  WAT W   90       6.212  62.239  11.395  1.00 62.89           O
ATOM     91  OW  WAT W   91       4.762  60.128   9.510  1.00 50.83           O
ATOM     92  OW  WAT W   92       1.818  60.337  10.991  1.00 63.25           O
ATOM     93  OW  WAT W   93       8.666  60.739   4.471  1.00 54.61           O
ATOM     94  OW  WAT W   94      -0.921  58.445  27.367  1.00 61.74           O
ATOM     95  OW  WAT W   95       4.111  60.729  19.027  1.00 58.38           O
ATOM     96  OW  WAT W   96       8.038  60.969  19.586  1.00 48.56           O
ATOM     97  OW  WAT W   97       5.694  56.938  16.858  1.00 41.80           O
ATOM     98  OW  WAT W   98      16.628  39.394  24.991  1.00 64.89           O
ATOM     99  OW  WAT W   99      23.724  41.484  25.120  1.00 63.42           O
ATOM    100  OW  WAT W  100      31.303  42.308   4.266  1.00 70.42           O
ATOM    101  OW  WAT W  101       9.072  58.261   1.545  1.00 57.56           O
ATOM    102  OW  WAT W  102       9.812  45.335  24.666  1.00 57.55           O
ATOM    103  OW  WAT W  103       7.534  42.857  27.942  1.00 68.85           O
ATOM    104  OW  WAT W  104      32.702  53.825   0.381  0.50 16.36           O
ATOM    105  OW  WAT W  105       5.074  62.162  22.081  1.00 70.18           O
ATOM    106  OW  WAT W  106      14.243  52.867  -5.067  1.00 57.54           O
ATOM    107  OW  WAT W  107       2.131  50.725  26.397  1.00 61.28           O
ATOM    108  OW  WAT W  108       0.398  50.216  21.633  1.00 82.05           O
ATOM    109  OW  WAT W  109       3.903  49.608  22.413  1.00 49.55           O
ATOM    110  OW  WAT W  110      22.868  36.381  25.362  1.00 47.19           O
ATOM    111  OW  WAT W  111      -0.194  38.286  13.278  1.00 85.00           O
ATOM    112  OW  WAT W  112      14.409  47.941  -8.098  1.00 66.08           O
ATOM    113  OW  WAT W  113       0.670  27.072  18.568  1.00 82.17           O
ATOM    114  OW  WAT W  114       9.335  17.831  13.617  1.00 83.46           O
ATOM    115  OW  WAT W  115      28.183  36.643   5.478  1.00 66.14           O
ATOM    116  OW  WAT W  116      28.451  51.280  -7.437  1.00 42.24           O
ATOM    117  OW  WAT W  117       8.472  63.750   6.495  1.00 60.52           O
ATOM    118  OW  WAT W  118       5.118  62.115   6.965  1.00 73.59           O
```

```
ATOM   1769  O   ALA A 454      18.705  42.746 -13.813  1.00199.25           O
ATOM   1770  CB  ALA A 454      19.854  39.794 -12.275  1.00199.21           C
ATOM   1771  C1  RAL A 600      16.929  29.473   8.718  1.00 54.67           C
ATOM   1772  C2  RAL A 600      15.822  30.068   8.110  1.00 52.44           C
ATOM   1773  C3  RAL A 600      15.150  31.088   8.777  1.00 51.99           C
ATOM   1774  O3  RAL A 600      14.053  31.648   8.158  1.00 49.44           O
ATOM   1775  C4  RAL A 600      15.583  31.516  10.051  1.00 51.69           C
ATOM   1776  C5  RAL A 600      16.669  30.932  10.633  1.00 53.63           C
ATOM   1777  S6  RAL A 600      17.402  31.241  12.122  1.00 52.51           S
ATOM   1778  C7  RAL A 600      18.636  30.096  12.016  1.00 56.77           C
ATOM   1779  C8  RAL A 600      19.654  29.880  13.085  1.00 58.40           C
ATOM   1780  C9  RAL A 600      19.266  29.560  14.367  1.00 60.86           C
ATOM   1781  C10 RAL A 600      20.200  29.345  15.388  1.00 61.94           C
ATOM   1782  C11 RAL A 600      21.557  29.456  15.116  1.00 63.07           C
ATOM   1783  O11 RAL A 600      22.475  29.246  16.128  1.00 64.22           O
ATOM   1784  C12 RAL A 600      21.961  29.778  13.826  1.00 62.49           C
ATOM   1785  C13 RAL A 600      21.011  29.984  12.821  1.00 61.33           C
ATOM   1786  C14 RAL A 600      17.365  29.885   9.963  1.00 55.02           C
ATOM   1787  C15 RAL A 600      18.502  29.417  10.772  1.00 56.33           C
ATOM   1788  C16 RAL A 600      19.383  28.393  10.418  1.00 58.38           C
ATOM   1789  O16 RAL A 600      19.271  27.331  11.039  1.00 58.20           O
ATOM   1790  C17 RAL A 600      20.400  28.561   9.379  1.00 58.46           C
ATOM   1791  C18 RAL A 600      21.164  27.475   8.950  1.00 61.08           C
ATOM   1792  C19 RAL A 600      22.154  27.594   7.956  1.00 59.49           C
ATOM   1793  C20 RAL A 600      22.357  28.849   7.398  1.00 61.55           C
ATOM   1794  C21 RAL A 600      21.595  29.928   7.832  1.00 58.80           C
ATOM   1795  C22 RAL A 600      20.632  29.804   8.798  1.00 57.87           C
ATOM   1796  O23 RAL A 600      23.264  29.219   6.416  1.00 63.72           O
ATOM   1797  C24 RAL A 600      23.367  28.414   5.265  1.00 66.12           C
ATOM   1798  C25 RAL A 600      24.720  28.743   4.641  1.00 68.51           C
ATOM   1799  N26 RAL A 600      24.775  29.678   3.510  1.00 70.37           N
ATOM   1800  C27 RAL A 600      26.090  29.507   2.845  1.00 71.55           C
ATOM   1801  C28 RAL A 600      26.261  30.380   1.604  1.00 73.06           C
ATOM   1802  C29 RAL A 600      26.015  31.851   1.942  1.00 73.38           C
ATOM   1803  C30 RAL A 600      24.656  32.000   2.632  1.00 73.29           C
ATOM   1804  C31 RAL A 600      24.593  31.096   3.878  1.00 71.96           C
ATOM      1  OW  WAT W   1      18.459  44.580  14.064  1.00 34.81           O
ATOM      2  OW  WAT W   2      20.897  45.875  11.062  1.00 38.48           O
ATOM      3  OW  WAT W   3       7.352  32.908  21.414  1.00 61.85           O
ATOM      4  OW  WAT W   4      -1.306  42.489  11.584  1.00 50.05           O
ATOM      5  OW  WAT W   5       4.708  38.896   5.395  1.00 54.79           O
ATOM      6  OW  WAT W   6      10.366  45.101   4.801  1.00 32.63           O
ATOM      7  OW  WAT W   7       8.827  43.786   2.572  1.00 34.11           O
ATOM      8  OW  WAT W   8      39.265  56.875   8.715  1.00 73.46           O
ATOM      9  OW  WAT W   9      37.496  52.949   1.085  1.00 43.70           O
ATOM     10  OW  WAT W  10      25.918  54.751  -1.411  1.00 40.49           O
ATOM     11  OW  WAT W  11      14.918  57.862  11.704  1.00 40.15           O
ATOM     12  OW  WAT W  12       2.411  52.193  23.443  1.00 48.13           O
ATOM     13  OW  WAT W  13      11.029  49.327  25.041  1.00 48.33           O
ATOM     14  OW  WAT W  14       4.903  49.408  26.282  1.00 38.28           O
ATOM     15  OW  WAT W  15      15.687  50.086  -4.291  1.00 38.57           O
ATOM     16  OW  WAT W  16      22.800  39.581  10.533  1.00 48.16           O
ATOM     17  OW  WAT W  17       6.945  43.242  24.786  1.00 53.74           O
ATOM     18  OW  WAT W  18      12.845  37.081   6.429  1.00 42.84           O
ATOM     19  OW  WAT W  19      27.688  53.608  13.757  1.00 63.84           O
ATOM     20  OW  WAT W  20      18.355  49.820  17.968  0.50 31.19           O
ATOM     21  OW  WAT W  21       2.607  40.841  -0.288  1.00 62.58           O
ATOM     22  OW  WAT W  22       4.300  37.863  -1.166  1.00 81.61           O
ATOM     23  OW  WAT W  23       0.564  43.739  -5.539  1.00 56.98           O
ATOM     24  OW  WAT W  24       7.198  44.012  -5.988  1.00 66.57           O
ATOM     25  OW  WAT W  25       2.927  42.137  -7.495  1.00 82.08           O
ATOM     26  OW  WAT W  26      10.855  40.251  -3.530  1.00 44.61           O
ATOM     27  OW  WAT W  27       9.506  30.092   5.180  1.00 56.65           O
ATOM     28  OW  WAT W  28      12.822  34.160   7.380  1.00 37.09           O
ATOM     29  OW  WAT W  29       8.049  35.619   6.783  1.00 52.65           O
ATOM     30  OW  WAT W  30      11.004  50.073  -5.077  1.00 51.98           O
ATOM     31  OW  WAT W  31      13.620  54.793   2.245  1.00 42.86           O
ATOM     32  OW  WAT W  32      16.757  56.905  -3.969  1.00 63.10           O
ATOM     33  OW  WAT W  33      24.310  51.875  -7.769  1.00 50.07           O
ATOM     34  OW  WAT W  34      29.350  44.387   5.744  1.00 51.46           O
ATOM     35  OW  WAT W  35      24.703  37.980   8.603  1.00 55.40           O
ATOM     36  OW  WAT W  36      19.474  47.428  13.406  1.00 38.21           O
ATOM     37  OW  WAT W  37       0.001  39.526  17.031  1.00 80.46           O
ATOM     38  OW  WAT W  38       2.727  31.649  10.222  1.00 68.95           O
ATOM     39  OW  WAT W  39       6.911  31.300  18.820  1.00 53.91           O
ATOM     40  OW  WAT W  40       5.919  21.168  16.405  1.00 71.57           O
ATOM     41  OW  WAT W  41       1.859  47.618  23.891  1.00 56.25           O
```

```
ATOM  1692  C   LEU A 434      31.501  28.219  13.460  1.00 97.65           C
ATOM  1693  O   LEU A 434      32.618  27.847  13.098  1.00 96.96           O
ATOM  1694  CB  LEU A 434      31.200  30.537  12.528  1.00 96.46           C
ATOM  1695  CG  LEU A 434      32.541  30.907  13.132  1.00 97.64           C
ATOM  1696  CD1 LEU A 434      33.057  32.198  12.502  1.00 98.24           C
ATOM  1697  CD2 LEU A 434      32.474  31.074  14.647  1.00 98.27           C
ATOM  1698  N   SER A 435      30.982  27.859  14.626  1.00100.42           N
ATOM  1699  CA  SER A 435      31.656  27.006  15.587  1.00103.30           C
ATOM  1700  C   SER A 435      31.361  25.531  15.310  1.00104.85           C
ATOM  1701  O   SER A 435      31.962  24.641  15.915  1.00105.23           O
ATOM  1702  CB  SER A 435      31.233  27.351  17.016  1.00103.36           C
ATOM  1703  OG  SER A 435      30.095  26.599  17.417  1.00103.99           O
ATOM  1704  N   MET A 436      30.433  25.282  14.396  1.00106.55           N
ATOM  1705  CA  MET A 436      30.059  23.914  14.021  1.00108.32           C
ATOM  1706  C   MET A 436      30.392  23.691  12.549  1.00109.61           C
ATOM  1707  O   MET A 436      30.127  22.654  11.936  1.00110.28           O
ATOM  1708  CB  MET A 436      28.614  23.680  14.412  1.00107.63           C
ATOM  1709  CG  MET A 436      27.628  23.161  13.401  1.00107.05           C
ATOM  1710  SD  MET A 436      26.132  24.150  13.282  1.00106.08           S
ATOM  1711  CE  MET A 436      26.472  25.079  11.789  1.00107.05           C
ATOM  1712  N   LYS A 437      31.040  24.699  11.957  1.00110.34           N
ATOM  1713  CA  LYS A 437      31.434  24.658  10.557  1.00110.87           C
ATOM  1714  C   LYS A 437      32.430  25.764  10.229  1.00111.19           C
ATOM  1715  O   LYS A 437      32.781  25.978   9.068  1.00111.50           O
ATOM  1716  CB  LYS A 437      30.196  24.783   9.672  1.00111.10           C
ATOM  1717  N   ASP A 446      29.520  35.385  -2.805  1.00205.63           N
ATOM  1718  CA  ASP A 446      30.350  36.226  -3.661  1.00205.54           C
ATOM  1719  C   ASP A 446      29.717  36.376  -5.041  1.00205.39           C
ATOM  1720  O   ASP A 446      30.354  36.795  -6.004  1.00205.36           O
ATOM  1721  CB  ASP A 446      31.754  35.652  -3.772  1.00205.66           C
ATOM  1722  N   LEU A 447      28.439  36.023  -5.120  1.00205.19           N
ATOM  1723  CA  LEU A 447      27.668  36.116  -6.356  1.00204.85           C
ATOM  1724  C   LEU A 447      26.517  37.100  -6.135  1.00204.43           C
ATOM  1725  O   LEU A 447      25.549  37.193  -6.879  1.00204.27           O
ATOM  1726  CB  LEU A 447      27.148  34.759  -6.787  1.00204.93           C
ATOM  1727  N   LEU A 448      26.657  37.869  -5.060  1.00204.02           N
ATOM  1728  CA  LEU A 448      25.709  38.884  -4.642  1.00203.73           C
ATOM  1729  C   LEU A 448      25.441  39.883  -5.760  1.00203.73           C
ATOM  1730  O   LEU A 448      24.293  40.189  -6.077  1.00203.66           O
ATOM  1731  CB  LEU A 448      26.270  39.621  -3.421  1.00203.55           C
ATOM  1732  CG  LEU A 448      25.378  39.688  -2.181  1.00203.38           C
ATOM  1733  CD1 LEU A 448      25.232  38.307  -1.555  1.00203.47           C
ATOM  1734  CD2 LEU A 448      25.964  40.661  -1.164  1.00203.49           C
ATOM  1735  N   LEU A 449      26.510  40.386  -6.369  1.00203.84           N
ATOM  1736  CA  LEU A 449      26.435  41.341  -7.465  1.00203.89           C
ATOM  1737  C   LEU A 449      25.757  40.743  -8.693  1.00203.81           C
ATOM  1738  O   LEU A 449      25.027  41.432  -9.409  1.00203.96           O
ATOM  1739  CB  LEU A 449      27.828  41.840  -7.829  1.00203.84           C
ATOM  1740  N   GLU A 450      25.970  39.455  -8.939  1.00203.50           N
ATOM  1741  CA  GLU A 450      25.363  38.749 -10.062  1.00203.03           C
ATOM  1742  C   GLU A 450      23.843  38.739  -9.909  1.00202.59           C
ATOM  1743  O   GLU A 450      23.092  38.927 -10.864  1.00202.51           O
ATOM  1744  CB  GLU A 450      25.896  37.327 -10.137  1.00203.15           C
ATOM  1745  N   MET A 451      23.397  38.523  -8.672  1.00201.88           N
ATOM  1746  CA  MET A 451      21.979  38.513  -8.345  1.00201.04           C
ATOM  1747  C   MET A 451      21.485  39.950  -8.195  1.00200.49           C
ATOM  1748  O   MET A 451      20.325  40.235  -8.474  1.00200.32           O
ATOM  1749  CB  MET A 451      21.728  37.721  -7.074  1.00201.04           C
ATOM  1750  N   LEU A 452      22.364  40.848  -7.770  1.00199.92           N
ATOM  1751  CA  LEU A 452      22.034  42.249  -7.585  1.00199.41           C
ATOM  1752  C   LEU A 452      21.838  43.008  -8.889  1.00199.39           C
ATOM  1753  O   LEU A 452      20.833  43.722  -9.020  1.00199.20           O
ATOM  1754  CB  LEU A 452      23.122  42.953  -6.760  1.00199.09           C
ATOM  1755  CG  LEU A 452      22.963  42.909  -5.240  1.00198.83           C
ATOM  1756  CD1 LEU A 452      24.286  43.191  -4.545  1.00198.67           C
ATOM  1757  CD2 LEU A 452      21.906  43.902  -4.782  1.00198.76           C
ATOM  1758  N   ASN A 453      22.746  42.893  -9.849  1.00199.33           N
ATOM  1759  CA  ASN A 453      22.612  43.618 -11.108  1.00199.17           C
ATOM  1760  C   ASN A 453      21.535  43.080 -12.036  1.00199.24           C
ATOM  1761  O   ASN A 453      21.006  43.837 -12.858  1.00199.06           O
ATOM  1762  CB  ASN A 453      23.962  43.665 -11.837  1.00199.01           C
ATOM  1763  CG  ASN A 453      24.831  44.801 -11.330  1.00198.82           C
ATOM  1764  OD1 ASN A 453      24.502  45.974 -11.498  1.00198.60           O
ATOM  1765  ND2 ASN A 453      25.946  44.451 -10.702  1.00198.66           N
ATOM  1766  N   ALA A 454      21.202  41.802 -11.930  1.00199.24           N
ATOM  1767  CA  ALA A 454      20.178  41.196 -12.772  1.00199.21           C
ATOM  1768  C   ALA A 454      18.911  42.046 -12.801  1.00199.22           C
```

67

| ATOM | 1615 | CG | HIS A 424 | 22.747 | 39.895 | 21.816 | 1.00 | 42.86 | C |
| ATOM | 1616 | ND1 | HIS A 424 | 24.105 | 40.104 | 22.065 | 1.00 | 41.64 | N |
| ATOM | 1617 | CD2 | HIS A 424 | 22.324 | 38.939 | 22.682 | 1.00 | 42.72 | C |
| ATOM | 1618 | CE1 | HIS A 424 | 24.490 | 39.296 | 23.026 | 1.00 | 42.18 | C |
| ATOM | 1619 | NE2 | HIS A 424 | 23.423 | 38.594 | 23.421 | 1.00 | 43.81 | N |
| ATOM | 1620 | N | ILE A 425 | 21.033 | 38.444 | 18.797 | 1.00 | 40.66 | N |
| ATOM | 1621 | CA | ILE A 425 | 20.807 | 37.040 | 18.455 | 1.00 | 43.55 | C |
| ATOM | 1622 | C | ILE A 425 | 21.514 | 36.650 | 17.165 | 1.00 | 44.14 | C |
| ATOM | 1623 | O | ILE A 425 | 22.120 | 35.583 | 17.031 | 1.00 | 44.44 | O |
| ATOM | 1624 | CB | ILE A 425 | 19.317 | 36.706 | 18.316 | 1.00 | 47.14 | C |
| ATOM | 1625 | CG1 | ILE A 425 | 18.558 | 37.123 | 19.582 | 1.00 | 49.24 | C |
| ATOM | 1626 | CG2 | ILE A 425 | 19.093 | 35.218 | 18.023 | 1.00 | 47.61 | C |
| ATOM | 1627 | CD1 | ILE A 425 | 17.046 | 37.065 | 19.358 | 1.00 | 52.31 | C |
| ATOM | 1628 | N | SER A 426 | 21.475 | 37.549 | 16.180 | 1.00 | 43.21 | N |
| ATOM | 1629 | CA | SER A 426 | 22.151 | 37.292 | 14.916 | 1.00 | 42.19 | C |
| ATOM | 1630 | C | SER A 426 | 23.638 | 37.020 | 15.145 | 1.00 | 43.97 | C |
| ATOM | 1631 | O | SER A 426 | 24.222 | 36.060 | 14.593 | 1.00 | 42.09 | O |
| ATOM | 1632 | CB | SER A 426 | 22.011 | 38.510 | 13.986 | 1.00 | 38.55 | C |
| ATOM | 1633 | OG | SER A 426 | 22.972 | 38.293 | 12.959 | 1.00 | 39.76 | O |
| ATOM | 1634 | N | ASN A 427 | 24.265 | 37.911 | 15.935 | 1.00 | 44.18 | N |
| ATOM | 1635 | CA | ASN A 427 | 25.684 | 37.761 | 16.240 | 1.00 | 50.97 | C |
| ATOM | 1636 | C | ASN A 427 | 25.920 | 36.393 | 16.915 | 1.00 | 53.06 | C |
| ATOM | 1637 | O | ASN A 427 | 26.885 | 35.702 | 16.615 | 1.00 | 54.88 | O |
| ATOM | 1638 | CB | ASN A 427 | 26.279 | 38.847 | 17.142 | 1.00 | 50.47 | C |
| ATOM | 1639 | CG | ASN A 427 | 26.306 | 40.231 | 16.530 | 1.00 | 52.47 | C |
| ATOM | 1640 | OD1 | ASN A 427 | 26.478 | 40.365 | 15.317 | 1.00 | 54.52 | O |
| ATOM | 1641 | ND2 | ASN A 427 | 26.134 | 41.306 | 17.286 | 1.00 | 49.31 | N |
| ATOM | 1642 | N | LYS A 428 | 25.049 | 35.984 | 17.819 | 1.00 | 54.95 | N |
| ATOM | 1643 | CA | LYS A 428 | 25.198 | 34.701 | 18.496 | 1.00 | 58.69 | C |
| ATOM | 1644 | C | LYS A 428 | 25.022 | 33.546 | 17.525 | 1.00 | 60.19 | C |
| ATOM | 1645 | O | LYS A 428 | 25.836 | 32.625 | 17.471 | 1.00 | 59.96 | O |
| ATOM | 1646 | CB | LYS A 428 | 24.189 | 34.607 | 19.643 | 1.00 | 60.11 | C |
| ATOM | 1647 | CG | LYS A 428 | 24.879 | 34.756 | 20.994 | 1.00 | 63.10 | C |
| ATOM | 1648 | CD | LYS A 428 | 25.119 | 36.211 | 21.332 | 1.00 | 64.92 | C |
| ATOM | 1649 | CE | LYS A 428 | 26.211 | 36.351 | 22.379 | 1.00 | 66.05 | C |
| ATOM | 1650 | NZ | LYS A 428 | 27.344 | 35.431 | 22.075 | 1.00 | 68.40 | N |
| ATOM | 1651 | N | GLY A 429 | 23.952 | 33.607 | 16.733 | 1.00 | 61.48 | N |
| ATOM | 1652 | CA | GLY A 429 | 23.657 | 32.590 | 15.735 | 1.00 | 61.80 | C |
| ATOM | 1653 | C | GLY A 429 | 24.836 | 32.446 | 14.781 | 1.00 | 64.44 | C |
| ATOM | 1654 | O | GLY A 429 | 25.225 | 31.307 | 14.482 | 1.00 | 65.87 | O |
| ATOM | 1655 | N | MET A 430 | 25.412 | 33.556 | 14.326 | 1.00 | 65.35 | N |
| ATOM | 1656 | CA | MET A 430 | 26.533 | 33.472 | 13.402 | 1.00 | 68.85 | C |
| ATOM | 1657 | C | MET A 430 | 27.733 | 32.804 | 14.072 | 1.00 | 73.00 | C |
| ATOM | 1658 | O | MET A 430 | 28.386 | 31.964 | 13.434 | 1.00 | 72.66 | O |
| ATOM | 1659 | CB | MET A 430 | 26.956 | 34.813 | 12.808 | 1.00 | 67.96 | C |
| ATOM | 1660 | CG | MET A 430 | 25.901 | 35.498 | 11.955 | 1.00 | 69.34 | C |
| ATOM | 1661 | SD | MET A 430 | 25.804 | 34.854 | 10.270 | 1.00 | 70.32 | S |
| ATOM | 1662 | CE | MET A 430 | 27.107 | 35.795 | 9.480 | 1.00 | 71.21 | C |
| ATOM | 1663 | N | GLU A 431 | 28.019 | 33.154 | 15.328 | 1.00 | 75.37 | N |
| ATOM | 1664 | CA | GLU A 431 | 29.157 | 32.514 | 15.992 | 1.00 | 79.59 | C |
| ATOM | 1665 | C | GLU A 431 | 28.860 | 31.030 | 16.221 | 1.00 | 80.55 | C |
| ATOM | 1666 | O | GLU A 431 | 29.768 | 30.204 | 16.091 | 1.00 | 79.43 | O |
| ATOM | 1667 | CB | GLU A 431 | 29.577 | 33.275 | 17.227 | 1.00 | 81.22 | C |
| ATOM | 1668 | CG | GLU A 431 | 29.084 | 32.778 | 18.571 | 1.00 | 84.68 | C |
| ATOM | 1669 | CD | GLU A 431 | 29.704 | 33.605 | 19.693 | 1.00 | 86.27 | C |
| ATOM | 1670 | OE1 | GLU A 431 | 29.638 | 34.854 | 19.640 | 1.00 | 87.20 | O |
| ATOM | 1671 | OE2 | GLU A 431 | 30.263 | 32.983 | 20.616 | 1.00 | 87.26 | O |
| ATOM | 1672 | N | HIS A 432 | 27.618 | 30.685 | 16.522 | 1.00 | 81.71 | N |
| ATOM | 1673 | CA | HIS A 432 | 27.209 | 29.308 | 16.732 | 1.00 | 83.67 | C |
| ATOM | 1674 | C | HIS A 432 | 27.311 | 28.500 | 15.439 | 1.00 | 84.91 | C |
| ATOM | 1675 | O | HIS A 432 | 27.806 | 27.371 | 15.436 | 1.00 | 85.05 | O |
| ATOM | 1676 | CB | HIS A 432 | 25.784 | 29.256 | 17.287 | 1.00 | 83.84 | C |
| ATOM | 1677 | CG | HIS A 432 | 25.211 | 27.878 | 17.346 | 1.00 | 85.27 | C |
| ATOM | 1678 | ND1 | HIS A 432 | 24.311 | 27.411 | 16.413 | 1.00 | 85.48 | N |
| ATOM | 1679 | CD2 | HIS A 432 | 25.410 | 26.857 | 18.220 | 1.00 | 85.72 | C |
| ATOM | 1680 | CE1 | HIS A 432 | 23.981 | 26.165 | 16.718 | 1.00 | 86.00 | C |
| ATOM | 1681 | NE2 | HIS A 432 | 24.632 | 25.802 | 17.807 | 1.00 | 84.87 | N |
| ATOM | 1682 | N | LEU A 433 | 26.855 | 29.063 | 14.319 | 1.00 | 85.57 | N |
| ATOM | 1683 | CA | LEU A 433 | 26.942 | 28.357 | 13.052 | 1.00 | 86.43 | C |
| ATOM | 1684 | C | LEU A 433 | 28.416 | 28.129 | 12.704 | 1.00 | 88.82 | C |
| ATOM | 1685 | O | LEU A 433 | 28.808 | 27.031 | 12.302 | 1.00 | 88.33 | O |
| ATOM | 1686 | CB | LEU A 433 | 26.237 | 29.088 | 11.916 | 1.00 | 84.98 | C |
| ATOM | 1687 | CG | LEU A 433 | 24.723 | 29.047 | 11.770 | 1.00 | 83.74 | C |
| ATOM | 1688 | CD1 | LEU A 433 | 24.293 | 29.606 | 10.413 | 1.00 | 83.39 | C |
| ATOM | 1689 | CD2 | LEU A 433 | 24.136 | 27.655 | 11.939 | 1.00 | 83.18 | C |
| ATOM | 1690 | N | LEU A 434 | 29.250 | 29.139 | 12.862 | 1.00 | 91.16 | N |
| ATOM | 1691 | CA | LEU A 434 | 30.667 | 29.106 | 12.552 | 1.00 | 95.49 | C |

| | | | | | | | | | |
|---|---|---|---|---|---|---|---|---|---|
| ATOM | 1538 | N | LEU A 416 | 11.774 | 49.879 | 18.039 | 1.00 | 35.78 | N |
| ATOM | 1539 | CA | LEU A 416 | 13.179 | 50.110 | 17.742 | 1.00 | 35.46 | C |
| ATOM | 1540 | C | LEU A 416 | 14.104 | 49.483 | 18.776 | 1.00 | 37.25 | C |
| ATOM | 1541 | O | LEU A 416 | 15.190 | 49.091 | 18.311 | 1.00 | 36.69 | O |
| ATOM | 1542 | CB | LEU A 416 | 13.523 | 51.598 | 17.622 | 1.00 | 37.36 | C |
| ATOM | 1543 | CG | LEU A 416 | 12.668 | 52.385 | 16.612 | 1.00 | 42.31 | C |
| ATOM | 1544 | CD1 | LEU A 416 | 13.205 | 53.803 | 16.409 | 1.00 | 39.75 | C |
| ATOM | 1545 | CD2 | LEU A 416 | 12.594 | 51.658 | 15.288 | 1.00 | 38.60 | C |
| ATOM | 1546 | N | MET A 417 | 13.785 | 49.358 | 20.048 | 1.00 | 34.02 | N |
| ATOM | 1547 | CA | MET A 417 | 14.722 | 48.728 | 20.991 | 1.00 | 37.09 | C |
| ATOM | 1548 | C | MET A 417 | 14.894 | 47.227 | 20.758 | 1.00 | 38.01 | C |
| ATOM | 1549 | O | MET A 417 | 15.950 | 46.662 | 21.071 | 1.00 | 37.19 | O |
| ATOM | 1550 | CB | MET A 417 | 14.301 | 48.946 | 22.432 | 1.00 | 36.64 | C |
| ATOM | 1551 | CG | MET A 417 | 14.539 | 50.403 | 22.866 | 1.00 | 40.79 | C |
| ATOM | 1552 | SD | MET A 417 | 14.068 | 50.493 | 24.617 | 1.00 | 41.99 | S |
| ATOM | 1553 | CE | MET A 417 | 13.975 | 52.274 | 24.846 | 1.00 | 41.08 | C |
| ATOM | 1554 | N | LEU A 418 | 13.927 | 46.561 | 20.149 | 1.00 | 38.86 | N |
| ATOM | 1555 | CA | LEU A 418 | 14.101 | 45.135 | 19.825 | 1.00 | 40.84 | C |
| ATOM | 1556 | C | LEU A 418 | 15.081 | 45.002 | 18.667 | 1.00 | 41.08 | C |
| ATOM | 1557 | O | LEU A 418 | 15.706 | 43.957 | 18.450 | 1.00 | 44.83 | O |
| ATOM | 1558 | CB | LEU A 418 | 12.762 | 44.479 | 19.557 | 1.00 | 42.44 | C |
| ATOM | 1559 | CG | LEU A 418 | 11.877 | 44.358 | 20.816 | 1.00 | 39.84 | C |
| ATOM | 1560 | CD1 | LEU A 418 | 10.478 | 43.968 | 20.358 | 1.00 | 42.85 | C |
| ATOM | 1561 | CD2 | LEU A 418 | 12.460 | 43.359 | 21.782 | 1.00 | 40.93 | C |
| ATOM | 1562 | N | LEU A 419 | 15.369 | 46.076 | 17.923 | 1.00 | 39.17 | N |
| ATOM | 1563 | CA | LEU A 419 | 16.367 | 45.955 | 16.869 | 1.00 | 39.28 | C |
| ATOM | 1564 | C | LEU A 419 | 17.692 | 45.517 | 17.514 | 1.00 | 37.85 | C |
| ATOM | 1565 | O | LEU A 419 | 18.360 | 44.666 | 16.945 | 1.00 | 37.19 | O |
| ATOM | 1566 | CB | LEU A 419 | 16.599 | 47.209 | 16.052 | 1.00 | 38.65 | C |
| ATOM | 1567 | CG | LEU A 419 | 15.429 | 47.601 | 15.141 | 1.00 | 44.81 | C |
| ATOM | 1568 | CD1 | LEU A 419 | 15.529 | 49.119 | 14.864 | 1.00 | 44.36 | C |
| ATOM | 1569 | CD2 | LEU A 419 | 15.459 | 46.842 | 13.831 | 1.00 | 42.00 | C |
| ATOM | 1570 | N | SER A 420 | 18.056 | 46.036 | 18.679 | 1.00 | 34.13 | N |
| ATOM | 1571 | CA | SER A 420 | 19.326 | 45.656 | 19.275 | 1.00 | 37.43 | C |
| ATOM | 1572 | C | SER A 420 | 19.283 | 44.199 | 19.696 | 1.00 | 38.21 | C |
| ATOM | 1573 | O | SER A 420 | 20.310 | 43.523 | 19.655 | 1.00 | 35.41 | O |
| ATOM | 1574 | CB | SER A 420 | 19.697 | 46.694 | 20.371 | 1.00 | 35.74 | C |
| ATOM | 1575 | OG | ASER A 420 | 18.907 | 46.357 | 21.501 | 0.50 | 36.64 | O |
| ATOM | 1576 | OG | BSER A 420 | 20.058 | 45.938 | 21.516 | 0.50 | 38.11 | O |
| ATOM | 1577 | N | HIS A 421 | 18.116 | 43.680 | 20.080 | 1.00 | 40.53 | N |
| ATOM | 1578 | CA | HIS A 421 | 17.968 | 42.280 | 20.437 | 1.00 | 42.12 | C |
| ATOM | 1579 | C | HIS A 421 | 18.101 | 41.412 | 19.169 | 1.00 | 41.64 | C |
| ATOM | 1580 | O | HIS A 421 | 18.788 | 40.399 | 19.197 | 1.00 | 37.89 | O |
| ATOM | 1581 | CB | HIS A 421 | 16.657 | 42.021 | 21.186 | 1.00 | 43.19 | C |
| ATOM | 1582 | CG | AHIS A 421 | 16.521 | 42.628 | 22.542 | 0.50 | 43.21 | C |
| ATOM | 1583 | CG | BHIS A 421 | 16.667 | 42.716 | 22.519 | 0.50 | 45.26 | C |
| ATOM | 1584 | ND1 | AHIS A 421 | 15.858 | 42.003 | 23.582 | 0.50 | 42.18 | N |
| ATOM | 1585 | ND1 | BHIS A 421 | 17.478 | 42.306 | 23.565 | 0.50 | 45.48 | N |
| ATOM | 1586 | CD2 | AHIS A 421 | 16.951 | 43.813 | 23.057 | 0.50 | 42.52 | C |
| ATOM | 1587 | CD2 | BHIS A 421 | 15.972 | 43.801 | 22.958 | 0.50 | 45.02 | C |
| ATOM | 1588 | CE1 | AHIS A 421 | 15.885 | 42.746 | 24.669 | 0.50 | 40.57 | C |
| ATOM | 1589 | CE1 | BHIS A 421 | 17.269 | 43.104 | 24.599 | 0.50 | 45.11 | C |
| ATOM | 1590 | NE2 | AHIS A 421 | 16.543 | 43.854 | 24.372 | 0.50 | 42.40 | N |
| ATOM | 1591 | NE2 | BHIS A 421 | 16.367 | 44.012 | 24.258 | 0.50 | 45.43 | N |
| ATOM | 1592 | N | VAL A 422 | 17.533 | 41.841 | 18.026 | 1.00 | 40.44 | N |
| ATOM | 1593 | CA | VAL A 422 | 17.673 | 41.050 | 16.812 | 1.00 | 38.14 | C |
| ATOM | 1594 | C | VAL A 422 | 19.143 | 41.011 | 16.403 | 1.00 | 39.28 | C |
| ATOM | 1595 | O | VAL A 422 | 19.627 | 39.965 | 15.979 | 1.00 | 39.27 | O |
| ATOM | 1596 | CB | VAL A 422 | 16.770 | 41.537 | 15.668 | 1.00 | 36.77 | C |
| ATOM | 1597 | CG1 | VAL A 422 | 16.993 | 40.717 | 14.383 | 1.00 | 36.78 | C |
| ATOM | 1598 | CG2 | VAL A 422 | 15.306 | 41.435 | 16.089 | 1.00 | 33.39 | C |
| ATOM | 1599 | N | ARG A 423 | 19.899 | 42.097 | 16.519 | 1.00 | 38.90 | N |
| ATOM | 1600 | CA | ARG A 423 | 21.304 | 42.104 | 16.163 | 1.00 | 38.83 | C |
| ATOM | 1601 | C | ARG A 423 | 22.121 | 41.170 | 17.068 | 1.00 | 40.80 | C |
| ATOM | 1602 | O | ARG A 423 | 23.065 | 40.474 | 16.657 | 1.00 | 39.68 | O |
| ATOM | 1603 | CB | ARG A 423 | 21.820 | 43.550 | 16.286 | 1.00 | 37.40 | C |
| ATOM | 1604 | CG | ARG A 423 | 23.306 | 43.729 | 16.034 | 1.00 | 38.67 | C |
| ATOM | 1605 | CD | ARG A 423 | 23.652 | 43.636 | 14.539 | 1.00 | 42.08 | C |
| ATOM | 1606 | NE | ARG A 423 | 22.952 | 44.738 | 13.837 | 1.00 | 42.42 | N |
| ATOM | 1607 | CZ | ARG A 423 | 23.551 | 45.878 | 13.516 | 1.00 | 45.77 | C |
| ATOM | 1608 | NH1 | ARG A 423 | 24.826 | 46.124 | 13.816 | 1.00 | 45.65 | N |
| ATOM | 1609 | NH2 | ARG A 423 | 22.910 | 46.851 | 12.885 | 1.00 | 46.48 | N |
| ATOM | 1610 | N | HIS A 424 | 21.804 | 41.211 | 18.356 | 1.00 | 39.70 | N |
| ATOM | 1611 | CA | HIS A 424 | 22.484 | 40.378 | 19.350 | 1.00 | 41.35 | C |
| ATOM | 1612 | C | HIS A 424 | 22.264 | 38.906 | 18.988 | 1.00 | 41.61 | C |
| ATOM | 1613 | O | HIS A 424 | 23.261 | 38.207 | 18.861 | 1.00 | 40.86 | O |
| ATOM | 1614 | CB | HIS A 424 | 21.972 | 40.638 | 20.766 | 1.00 | 40.24 | C |

```
ATOM  1461  O    GLN A 406     4.005  57.529  24.138  1.00 43.68           O
ATOM  1462  CB   GLN A 406     2.271  59.705  25.967  1.00 44.35           C
ATOM  1463  CG   GLN A 406     3.099  59.183  27.122  1.00 43.86           C
ATOM  1464  CD   GLN A 406     2.967  57.713  27.446  1.00 44.90           C
ATOM  1465  OE1  GLN A 406     3.893  57.016  27.883  1.00 46.75           O
ATOM  1466  NE2  GLN A 406     1.812  57.107  27.252  1.00 45.13           N
ATOM  1467  N    GLN A 407     1.779  57.318  23.992  1.00 44.89           N
ATOM  1468  CA   GLN A 407     1.804  55.912  23.668  1.00 45.43           C
ATOM  1469  C    GLN A 407     2.424  55.675  22.289  1.00 42.40           C
ATOM  1470  O    GLN A 407     3.045  54.633  22.132  1.00 41.59           O
ATOM  1471  CB   GLN A 407     0.387  55.334  23.771  1.00 48.80           C
ATOM  1472  CG   GLN A 407    -0.074  55.163  25.202  1.00 53.36           C
ATOM  1473  CD   GLN A 407     0.708  54.069  25.905  1.00 58.67           C
ATOM  1474  OE1  GLN A 407     1.650  54.271  26.689  1.00 60.92           O
ATOM  1475  NE2  GLN A 407     0.270  52.858  25.574  1.00 59.89           N
ATOM  1476  N    GLN A 408     2.279  56.565  21.339  1.00 38.86           N
ATOM  1477  CA   GLN A 408     2.868  56.435  20.012  1.00 41.29           C
ATOM  1478  C    GLN A 408     4.393  56.510  20.113  1.00 39.03           C
ATOM  1479  O    GLN A 408     5.023  55.684  19.442  1.00 36.56           O
ATOM  1480  CB   GLN A 408     2.314  57.467  19.032  1.00 40.76           C
ATOM  1481  CG   GLN A 408     0.815  57.226  18.754  1.00 45.62           C
ATOM  1482  CD   GLN A 408     0.280  58.339  17.862  1.00 49.28           C
ATOM  1483  OE1  GLN A 408     1.044  58.839  17.033  1.00 47.66           O
ATOM  1484  NE2  GLN A 408    -0.982  58.740  18.018  1.00 48.31           N
ATOM  1485  N    SER A 409     4.963  57.383  20.939  1.00 37.74           N
ATOM  1486  CA   SER A 409     6.411  57.412  21.070  1.00 40.81           C
ATOM  1487  C    SER A 409     6.926  56.152  21.770  1.00 39.32           C
ATOM  1488  O    SER A 409     7.933  55.564  21.384  1.00 37.82           O
ATOM  1489  CB   SER A 409     6.854  58.588  21.975  1.00 39.72           C
ATOM  1490  OG   SER A 409     6.384  59.701  21.248  1.00 43.43           O
ATOM  1491  N    VAL A 410     6.183  55.780  22.812  1.00 36.74           N
ATOM  1492  CA   VAL A 410     6.587  54.581  23.567  1.00 37.87           C
ATOM  1493  C    VAL A 410     6.582  53.393  22.595  1.00 35.67           C
ATOM  1494  O    VAL A 410     7.537  52.627  22.631  1.00 36.25           O
ATOM  1495  CB   VAL A 410     5.674  54.361  24.795  1.00 36.82           C
ATOM  1496  CG1  VAL A 410     5.523  52.895  25.177  1.00 35.68           C
ATOM  1497  CG2  VAL A 410     6.233  55.185  25.955  1.00 38.34           C
ATOM  1498  N    ARG A 411     5.551  53.256  21.760  1.00 32.89           N
ATOM  1499  CA   ARG A 411     5.481  52.134  20.840  1.00 35.52           C
ATOM  1500  C    ARG A 411     6.607  52.206  19.804  1.00 33.95           C
ATOM  1501  O    ARG A 411     7.227  51.193  19.504  1.00 35.15           O
ATOM  1502  CB   ARG A 411     4.123  52.030  20.123  1.00 35.57           C
ATOM  1503  CG   ARG A 411     4.014  50.722  19.309  1.00 35.64           C
ATOM  1504  CD   ARG A 411     2.561  50.577  18.850  1.00 37.45           C
ATOM  1505  NE   ARG A 411     2.378  49.350  18.078  1.00 37.04           N
ATOM  1506  CZ   ARG A 411     2.211  48.166  18.672  1.00 41.14           C
ATOM  1507  NH1  ARG A 411     2.193  48.062  19.998  1.00 41.12           N
ATOM  1508  NH2  ARG A 411     2.046  47.068  17.949  1.00 40.84           N
ATOM  1509  N    LEU A 412     6.913  53.398  19.320  1.00 32.72           N
ATOM  1510  CA   LEU A 412     7.998  53.557  18.356  1.00 34.33           C
ATOM  1511  C    LEU A 412     9.284  53.043  19.022  1.00 33.23           C
ATOM  1512  O    LEU A 412    10.043  52.254  18.456  1.00 32.20           O
ATOM  1513  CB   LEU A 412     8.156  54.990  17.885  1.00 31.60           C
ATOM  1514  CG   LEU A 412     9.355  55.259  16.961  1.00 34.95           C
ATOM  1515  CD1  LEU A 412     9.197  54.478  15.638  1.00 33.60           C
ATOM  1516  CD2  LEU A 412     9.468  56.753  16.662  1.00 30.88           C
ATOM  1517  N    ALA A 413     9.483  53.476  20.248  1.00 33.04           N
ATOM  1518  CA   ALA A 413    10.661  53.081  21.022  1.00 34.56           C
ATOM  1519  C    ALA A 413    10.641  51.607  21.357  1.00 33.97           C
ATOM  1520  O    ALA A 413    11.701  50.992  21.305  1.00 37.65           O
ATOM  1521  CB   ALA A 413    10.766  53.972  22.281  1.00 30.68           C
ATOM  1522  N    ASN A 414     9.510  50.987  21.687  1.00 34.88           N
ATOM  1523  CA   ASN A 414     9.470  49.572  21.990  1.00 35.92           C
ATOM  1524  C    ASN A 414     9.944  48.750  20.764  1.00 37.60           C
ATOM  1525  O    ASN A 414    10.752  47.826  20.921  1.00 34.80           O
ATOM  1526  CB   ASN A 414     8.079  49.052  22.368  1.00 34.60           C
ATOM  1527  CG   ASN A 414     7.642  49.529  23.747  1.00 40.02           C
ATOM  1528  OD1  ASN A 414     8.371  49.823  24.692  1.00 36.64           O
ATOM  1529  ND2  ASN A 414     6.338  49.663  23.898  1.00 38.38           N
ATOM  1530  N    LEU A 415     9.413  49.114  19.587  1.00 35.05           N
ATOM  1531  CA   LEU A 415     9.821  48.432  18.356  1.00 37.76           C
ATOM  1532  C    LEU A 415    11.289  48.633  18.034  1.00 36.60           C
ATOM  1533  O    LEU A 415    12.000  47.664  17.795  1.00 36.87           O
ATOM  1534  CB   LEU A 415     8.978  48.935  17.157  1.00 35.31           C
ATOM  1535  CG   LEU A 415     7.493  48.543  17.349  1.00 39.45           C
ATOM  1536  CD1  LEU A 415     6.613  49.019  16.209  1.00 37.17           C
ATOM  1537  CD2  LEU A 415     7.393  47.032  17.519  1.00 38.18           C
```

```
ATOM  1384  CG2 VAL A 395     7.160  57.887  13.647  1.00 38.50           C
ATOM  1385  N   TRP A 396     3.611  56.869  10.925  1.00 39.91           N
ATOM  1386  CA  TRP A 396     2.313  56.934  10.270  1.00 39.23           C
ATOM  1387  C   TRP A 396     1.547  55.648  10.524  1.00 38.71           C
ATOM  1388  O   TRP A 396     0.389  55.756  10.912  1.00 38.35           O
ATOM  1389  CB  TRP A 396     2.544  57.205   8.789  1.00 40.27           C
ATOM  1390  CG  TRP A 396     1.297  57.177   7.989  1.00 42.69           C
ATOM  1391  CD1 TRP A 396     0.382  58.190   7.840  1.00 45.17           C
ATOM  1392  CD2 TRP A 396     0.811  56.075   7.233  1.00 45.75           C
ATOM  1393  NE1 TRP A 396    -0.649  57.771   7.024  1.00 45.98           N
ATOM  1394  CE2 TRP A 396    -0.407  56.484   6.639  1.00 46.76           C
ATOM  1395  CE3 TRP A 396     1.300  54.781   7.001  1.00 45.92           C
ATOM  1396  CZ2 TRP A 396    -1.134  55.642   5.811  1.00 47.81           C
ATOM  1397  CZ3 TRP A 396     0.566  53.953   6.194  1.00 49.07           C
ATOM  1398  CH2 TRP A 396    -0.628  54.393   5.613  1.00 49.50           C
ATOM  1399  N   VAL A 397     2.151  54.466  10.381  1.00 35.48           N
ATOM  1400  CA  VAL A 397     1.476  53.224  10.699  1.00 38.01           C
ATOM  1401  C   VAL A 397     1.037  53.228  12.167  1.00 40.73           C
ATOM  1402  O   VAL A 397    -0.110  52.895  12.486  1.00 41.26           O
ATOM  1403  CB  VAL A 397     2.331  51.967  10.435  1.00 37.57           C
ATOM  1404  CG1 VAL A 397     1.682  50.703  11.018  1.00 33.87           C
ATOM  1405  CG2 VAL A 397     2.595  51.771   8.945  1.00 36.09           C
ATOM  1406  N   ILE A 398     1.918  53.681  13.077  1.00 41.75           N
ATOM  1407  CA  ILE A 398     1.553  53.697  14.491  1.00 39.25           C
ATOM  1408  C   ILE A 398     0.423  54.685  14.742  1.00 41.38           C
ATOM  1409  O   ILE A 398    -0.493  54.321  15.489  1.00 40.90           O
ATOM  1410  CB  ILE A 398     2.750  53.962  15.429  1.00 38.21           C
ATOM  1411  CG1 ILE A 398     3.691  52.754  15.369  1.00 36.72           C
ATOM  1412  CG2 ILE A 398     2.260  54.237  16.855  1.00 36.41           C
ATOM  1413  CD1 ILE A 398     5.107  52.980  15.893  1.00 34.21           C
ATOM  1414  N   ALA A 399     0.420  55.865  14.129  1.00 40.32           N
ATOM  1415  CA  ALA A 399    -0.637  56.832  14.341  1.00 43.88           C
ATOM  1416  C   ALA A 399    -1.997  56.310  13.878  1.00 47.83           C
ATOM  1417  O   ALA A 399    -3.000  56.839  14.386  1.00 50.02           O
ATOM  1418  CB  ALA A 399    -0.408  58.180  13.657  1.00 41.67           C
ATOM  1419  N   LYS A 400    -2.108  55.310  13.020  1.00 50.36           N
ATOM  1420  CA  LYS A 400    -3.410  54.799  12.592  1.00 54.38           C
ATOM  1421  C   LYS A 400    -4.107  53.950  13.642  1.00 56.20           C
ATOM  1422  O   LYS A 400    -5.283  53.613  13.473  1.00 58.21           O
ATOM  1423  CB  LYS A 400    -3.267  53.975  11.316  1.00 55.20           C
ATOM  1424  CG  LYS A 400    -2.898  54.822  10.109  1.00 57.06           C
ATOM  1425  CD  LYS A 400    -3.350  54.104   8.832  1.00 61.61           C
ATOM  1426  CE  LYS A 400    -4.771  54.501   8.439  1.00 63.49           C
ATOM  1427  NZ  LYS A 400    -5.394  53.510   7.498  1.00 63.31           N
ATOM  1428  N   SER A 401    -3.442  53.581  14.730  1.00 55.04           N
ATOM  1429  CA  SER A 401    -4.033  52.784  15.788  1.00 52.94           C
ATOM  1430  C   SER A 401    -4.832  53.667  16.742  1.00 54.21           C
ATOM  1431  O   SER A 401    -5.505  53.180  17.649  1.00 57.36           O
ATOM  1432  CB  SER A 401    -2.921  52.068  16.558  1.00 50.25           C
ATOM  1433  OG  SER A 401    -2.374  52.881  17.589  1.00 50.43           O
ATOM  1434  N   GLY A 402    -4.750  54.977  16.647  1.00 53.56           N
ATOM  1435  CA  GLY A 402    -5.464  55.907  17.475  1.00 54.88           C
ATOM  1436  C   GLY A 402    -5.010  56.059  18.910  1.00 56.79           C
ATOM  1437  O   GLY A 402    -5.750  56.672  19.703  1.00 56.06           O
ATOM  1438  N   ILE A 403    -3.837  55.548  19.279  1.00 54.07           N
ATOM  1439  CA  ILE A 403    -3.383  55.680  20.665  1.00 51.64           C
ATOM  1440  C   ILE A 403    -2.913  57.104  20.872  1.00 50.87           C
ATOM  1441  O   ILE A 403    -2.724  57.830  19.885  1.00 51.87           O
ATOM  1442  CB  ILE A 403    -2.270  54.686  21.058  1.00 51.02           C
ATOM  1443  CG1 ILE A 403    -1.032  54.858  20.190  1.00 50.41           C
ATOM  1444  CG2 ILE A 403    -2.822  53.265  20.954  1.00 50.05           C
ATOM  1445  CD1 ILE A 403     0.052  53.803  20.283  1.00 47.12           C
ATOM  1446  N   SER A 404    -2.707  57.484  22.130  1.00 50.79           N
ATOM  1447  CA  SER A 404    -2.246  58.849  22.352  1.00 51.61           C
ATOM  1448  C   SER A 404    -0.812  59.057  21.856  1.00 50.37           C
ATOM  1449  O   SER A 404    -0.013  58.166  21.569  1.00 51.68           O
ATOM  1450  CB  SER A 404    -2.270  59.151  23.859  1.00 51.35           C
ATOM  1451  OG  SER A 404    -1.287  58.302  24.427  1.00 53.81           O
ATOM  1452  N   SER A 405    -0.473  60.323  21.812  1.00 48.22           N
ATOM  1453  CA  SER A 405     0.836  60.801  21.410  1.00 50.40           C
ATOM  1454  C   SER A 405     1.914  60.145  22.281  1.00 48.68           C
ATOM  1455  O   SER A 405     2.863  59.639  21.700  1.00 44.59           O
ATOM  1456  CB  SER A 405     0.826  62.322  21.482  1.00 51.68           C
ATOM  1457  OG  SER A 405     2.151  62.820  21.518  1.00 57.41           O
ATOM  1458  N   GLN A 406     1.767  60.121  23.595  1.00 45.10           N
ATOM  1459  CA  GLN A 406     2.700  59.510  24.522  1.00 45.75           C
ATOM  1460  C   GLN A 406     2.881  58.020  24.206  1.00 45.72           C
```

| | | | | | | | | | |
|---|---|---|---|---|---|---|---|---|---|
| ATOM | 1307 | ND1BHIS | A | 385 | 19.545 | 62.560 | 2.611 | 0.50 43.23 | N |
| ATOM | 1308 | CD2AHIS | A | 385 | 16.443 | 60.868 | 1.673 | 0.50 39.40 | C |
| ATOM | 1309 | CD2BHIS | A | 385 | 18.768 | 62.714 | 4.665 | 0.50 42.54 | C |
| ATOM | 1310 | CE1AHIS | A | 385 | 15.817 | 62.870 | 2.346 | 0.50 39.23 | C |
| ATOM | 1311 | CE1BHIS | A | 385 | 19.880 | 63.752 | 3.060 | 0.50 42.58 | C |
| ATOM | 1312 | NE2AHIS | A | 385 | 15.576 | 61.915 | 1.461 | 0.50 39.22 | N |
| ATOM | 1313 | NE2BHIS | A | 385 | 19.418 | 63.865 | 4.311 | 0.50 44.38 | N |
| ATOM | 1314 | N | LEU A | 386 | 17.384 | 57.511 | 4.077 | 1.00 33.92 | N |
| ATOM | 1315 | CA | LEU A | 386 | 16.512 | 56.399 | 3.795 | 1.00 36.66 | C |
| ATOM | 1316 | C | LEU A | 386 | 15.849 | 55.823 | 5.043 | 1.00 36.42 | C |
| ATOM | 1317 | O | LEU A | 386 | 14.684 | 55.396 | 4.949 | 1.00 35.26 | O |
| ATOM | 1318 | CB | LEU A | 386 | 17.228 | 55.285 | 3.001 | 1.00 34.05 | C |
| ATOM | 1319 | CG | LEU A | 386 | 17.880 | 55.765 | 1.687 | 1.00 37.26 | C |
| ATOM | 1320 | CD1 | LEU A | 386 | 18.466 | 54.555 | 0.945 | 1.00 31.17 | C |
| ATOM | 1321 | CD2 | LEU A | 386 | 16.940 | 56.523 | 0.747 | 1.00 32.03 | C |
| ATOM | 1322 | N | LEU A | 387 | 16.564 | 55.788 | 6.165 | 1.00 34.29 | N |
| ATOM | 1323 | CA | LEU A | 387 | 16.002 | 55.306 | 7.409 | 1.00 33.02 | C |
| ATOM | 1324 | C | LEU A | 387 | 14.941 | 56.308 | 7.863 | 1.00 32.21 | C |
| ATOM | 1325 | O | LEU A | 387 | 13.919 | 55.812 | 8.331 | 1.00 30.98 | O |
| ATOM | 1326 | CB | LEU A | 387 | 17.013 | 55.121 | 8.559 | 1.00 32.77 | C |
| ATOM | 1327 | CG | LEU A | 387 | 17.866 | 53.861 | 8.369 | 1.00 35.04 | C |
| ATOM | 1328 | CD1 | LEU A | 387 | 19.178 | 53.855 | 9.151 | 1.00 32.90 | C |
| ATOM | 1329 | CD2 | LEU A | 387 | 17.013 | 52.639 | 8.779 | 1.00 31.79 | C |
| ATOM | 1330 | N | ASN A | 388 | 15.134 | 57.607 | 7.698 | 1.00 31.81 | N |
| ATOM | 1331 | CA | ASN A | 388 | 14.136 | 58.602 | 8.097 | 1.00 34.53 | C |
| ATOM | 1332 | C | ASN A | 388 | 12.807 | 58.437 | 7.350 | 1.00 35.08 | C |
| ATOM | 1333 | O | ASN A | 388 | 11.728 | 58.635 | 7.924 | 1.00 36.36 | O |
| ATOM | 1334 | CB | ASN A | 388 | 14.644 | 60.045 | 7.932 | 1.00 33.22 | C |
| ATOM | 1335 | CG | ASN A | 388 | 15.757 | 60.461 | 8.846 | 1.00 36.53 | C |
| ATOM | 1336 | OD1 | ASN A | 388 | 16.361 | 61.540 | 8.704 | 1.00 36.01 | O |
| ATOM | 1337 | ND2 | ASN A | 388 | 16.106 | 59.646 | 9.852 | 1.00 29.10 | N |
| ATOM | 1338 | N | ALA A | 389 | 12.833 | 58.069 | 6.074 | 1.00 34.51 | N |
| ATOM | 1339 | CA | ALA A | 389 | 11.657 | 57.810 | 5.273 | 1.00 34.03 | C |
| ATOM | 1340 | C | ALA A | 389 | 11.002 | 56.567 | 5.895 | 1.00 33.05 | C |
| ATOM | 1341 | O | ALA A | 389 | 9.799 | 56.584 | 6.072 | 1.00 32.73 | O |
| ATOM | 1342 | CB | ALA A | 389 | 11.913 | 57.522 | 3.789 | 1.00 33.33 | C |
| ATOM | 1343 | N | VAL A | 390 | 11.741 | 55.515 | 6.264 | 1.00 32.59 | N |
| ATOM | 1344 | CA | VAL A | 390 | 11.083 | 54.367 | 6.900 | 1.00 32.80 | C |
| ATOM | 1345 | C | VAL A | 390 | 10.521 | 54.699 | 8.268 | 1.00 33.85 | C |
| ATOM | 1346 | O | VAL A | 390 | 9.401 | 54.277 | 8.619 | 1.00 34.90 | O |
| ATOM | 1347 | CB | VAL A | 390 | 12.001 | 53.134 | 6.894 | 1.00 33.71 | C |
| ATOM | 1348 | CG1 | VAL A | 390 | 11.183 | 51.960 | 7.402 | 1.00 32.33 | C |
| ATOM | 1349 | CG2 | VAL A | 390 | 12.512 | 52.914 | 5.473 | 1.00 29.92 | C |
| ATOM | 1350 | N | THR A | 391 | 11.187 | 55.514 | 9.072 | 1.00 31.90 | N |
| ATOM | 1351 | CA | THR A | 391 | 10.669 | 55.953 | 10.370 | 1.00 33.37 | C |
| ATOM | 1352 | C | THR A | 391 | 9.363 | 56.713 | 10.191 | 1.00 34.55 | C |
| ATOM | 1353 | O | THR A | 391 | 8.393 | 56.550 | 10.945 | 1.00 30.75 | O |
| ATOM | 1354 | CB | THR A | 391 | 11.668 | 56.905 | 11.096 | 1.00 31.48 | C |
| ATOM | 1355 | OG1 | THR A | 391 | 12.831 | 56.116 | 11.392 | 1.00 32.09 | O |
| ATOM | 1356 | CG2 | THR A | 391 | 11.125 | 57.444 | 12.410 | 1.00 30.51 | C |
| ATOM | 1357 | N | ASP A | 392 | 9.328 | 57.611 | 9.183 | 1.00 35.47 | N |
| ATOM | 1358 | CA | ASP A | 392 | 8.125 | 58.380 | 8.909 | 1.00 36.50 | C |
| ATOM | 1359 | C | ASP A | 392 | 6.970 | 57.410 | 8.614 | 1.00 37.64 | C |
| ATOM | 1360 | O | ASP A | 392 | 5.824 | 57.543 | 9.064 | 1.00 38.15 | O |
| ATOM | 1361 | CB | ASP A | 392 | 8.286 | 59.268 | 7.661 | 1.00 35.87 | C |
| ATOM | 1362 | CG | ASP A | 392 | 9.086 | 60.503 | 7.900 | 1.00 37.41 | C |
| ATOM | 1363 | OD1 | ASP A | 392 | 9.305 | 61.012 | 9.011 | 1.00 36.50 | O |
| ATOM | 1364 | OD2 | ASP A | 392 | 9.627 | 61.107 | 6.963 | 1.00 38.10 | O |
| ATOM | 1365 | N | ALA A | 393 | 7.250 | 56.385 | 7.830 | 1.00 36.66 | N |
| ATOM | 1366 | CA | ALA A | 393 | 6.216 | 55.402 | 7.508 | 1.00 36.42 | C |
| ATOM | 1367 | C | ALA A | 393 | 5.800 | 54.630 | 8.759 | 1.00 36.87 | C |
| ATOM | 1368 | O | ALA A | 393 | 4.621 | 54.335 | 8.911 | 1.00 34.25 | O |
| ATOM | 1369 | CB | ALA A | 393 | 6.740 | 54.442 | 6.454 | 1.00 31.97 | C |
| ATOM | 1370 | N | LEU A | 394 | 6.777 | 54.272 | 9.624 | 1.00 35.71 | N |
| ATOM | 1371 | CA | LEU A | 394 | 6.381 | 53.541 | 10.831 | 1.00 34.54 | C |
| ATOM | 1372 | C | LEU A | 394 | 5.578 | 54.464 | 11.762 | 1.00 35.05 | C |
| ATOM | 1373 | O | LEU A | 394 | 4.576 | 54.073 | 12.347 | 1.00 33.35 | O |
| ATOM | 1374 | CB | LEU A | 394 | 7.610 | 52.924 | 11.486 | 1.00 30.81 | C |
| ATOM | 1375 | CG | LEU A | 394 | 7.391 | 52.138 | 12.780 | 1.00 31.82 | C |
| ATOM | 1376 | CD1 | LEU A | 394 | 6.380 | 50.995 | 12.619 | 1.00 26.49 | C |
| ATOM | 1377 | CD2 | LEU A | 394 | 8.730 | 51.641 | 13.349 | 1.00 28.64 | C |
| ATOM | 1378 | N | VAL A | 395 | 5.938 | 55.736 | 11.895 | 1.00 36.27 | N |
| ATOM | 1379 | CA | VAL A | 395 | 5.208 | 56.695 | 12.726 | 1.00 38.81 | C |
| ATOM | 1380 | C | VAL A | 395 | 3.766 | 56.787 | 12.240 | 1.00 40.14 | C |
| ATOM | 1381 | O | VAL A | 395 | 2.797 | 56.751 | 12.993 | 1.00 36.98 | O |
| ATOM | 1382 | CB | VAL A | 395 | 5.919 | 58.058 | 12.731 | 1.00 40.39 | C |
| ATOM | 1383 | CG1 | VAL A | 395 | 5.102 | 59.227 | 13.269 | 1.00 40.32 | C |

```
ATOM   1230  CG   GLU A 376      32.971  54.577   6.607  1.00 50.94           C
ATOM   1231  CD   GLU A 376      32.097  53.516   5.976  1.00 55.51           C
ATOM   1232  OE1  GLU A 376      30.858  53.682   6.105  1.00 58.47           O
ATOM   1233  OE2  GLU A 376      32.456  52.499   5.332  1.00 53.88           O
ATOM   1234  N    ALA A 377      31.056  58.813   6.070  1.00 43.26           N
ATOM   1235  CA   ALA A 377      30.082  59.847   6.405  1.00 42.38           C
ATOM   1236  C    ALA A 377      29.117  60.045   5.251  1.00 44.61           C
ATOM   1237  O    ALA A 377      27.925  60.252   5.484  1.00 41.28           O
ATOM   1238  CB   ALA A 377      30.743  61.152   6.762  1.00 41.95           C
ATOM   1239  N    GLU A 378      29.618  59.962   4.012  1.00 44.78           N
ATOM   1240  CA   GLU A 378      28.773  60.129   2.844  1.00 42.88           C
ATOM   1241  C    GLU A 378      27.776  58.958   2.809  1.00 40.39           C
ATOM   1242  O    GLU A 378      26.590  59.148   2.551  1.00 38.65           O
ATOM   1243  CB   GLU A 378      29.520  60.114   1.499  1.00 43.14           C
ATOM   1244  CG   GLU A 378      28.585  60.307   0.299  1.00 46.44           C
ATOM   1245  CD   GLU A 378      29.291  60.109  -1.031  1.00 50.22           C
ATOM   1246  OE1  GLU A 378      30.526  60.326  -1.083  1.00 51.06           O
ATOM   1247  OE2  GLU A 378      28.660  59.726  -2.047  1.00 51.88           O
ATOM   1248  N    SER A 379      28.255  57.752   3.071  1.00 36.67           N
ATOM   1249  CA   SER A 379      27.338  56.624   3.076  1.00 41.57           C
ATOM   1250  C    SER A 379      26.262  56.774   4.184  1.00 43.28           C
ATOM   1251  O    SER A 379      25.074  56.452   3.978  1.00 40.65           O
ATOM   1252  CB   SER A 379      28.094  55.320   3.255  1.00 41.84           C
ATOM   1253  OG   SER A 379      28.553  54.834   1.997  1.00 43.70           O
ATOM   1254  N    SER A 380      26.668  57.263   5.340  1.00 43.34           N
ATOM   1255  CA   SER A 380      25.806  57.429   6.494  1.00 48.04           C
ATOM   1256  C    SER A 380      24.714  58.447   6.214  1.00 47.91           C
ATOM   1257  O    SER A 380      23.558  58.243   6.597  1.00 44.74           O
ATOM   1258  CB   SER A 380      26.570  57.880   7.749  1.00 48.54           C
ATOM   1259  OG   SER A 380      27.230  56.770   8.321  1.00 53.33           O
ATOM   1260  N    ARG A 381      25.103  59.567   5.611  1.00 49.17           N
ATOM   1261  CA   ARG A 381      24.111  60.598   5.313  1.00 49.82           C
ATOM   1262  C    ARG A 381      22.963  60.037   4.464  1.00 45.45           C
ATOM   1263  O    ARG A 381      21.786  60.264   4.743  1.00 42.24           O
ATOM   1264  CB   ARG A 381      24.689  61.739   4.486  1.00 53.14           C
ATOM   1265  CG   ARG A 381      25.118  62.933   5.305  1.00 59.05           C
ATOM   1266  CD   ARG A 381      25.773  63.916   4.317  1.00 61.85           C
ATOM   1267  NE   ARG A 381      27.168  63.990   4.640  1.00 64.30           N
ATOM   1268  CZ   ARG A 381      28.344  63.927   4.055  1.00 65.07           C
ATOM   1269  NH1  ARG A 381      28.519  63.745   2.762  1.00 62.50           N
ATOM   1270  NH2  ARG A 381      29.375  64.076   4.894  1.00 65.26           N
ATOM   1271  N    LYS A 382      23.375  59.348   3.414  1.00 42.24           N
ATOM   1272  CA   LYS A 382      22.434  58.717   2.498  1.00 42.94           C
ATOM   1273  C    LYS A 382      21.546  57.699   3.219  1.00 41.01           C
ATOM   1274  O    LYS A 382      20.329  57.736   3.118  1.00 41.60           O
ATOM   1275  CB   LYS A 382      23.186  58.019   1.362  1.00 40.40           C
ATOM   1276  CG  ALYS A 382      22.268  57.482   0.273  0.50 42.30           C
ATOM   1277  CG  BLYS A 382      23.694  58.938   0.269  0.50 43.49           C
ATOM   1278  CD  ALYS A 382      21.286  58.510  -0.258  0.50 42.12           C
ATOM   1279  CD  BLYS A 382      24.697  58.207  -0.623  0.50 44.28           C
ATOM   1280  CE  ALYS A 382      20.228  57.860  -1.136  0.50 43.56           C
ATOM   1281  CE  BLYS A 382      25.135  59.113  -1.771  0.50 45.06           C
ATOM   1282  NZ  ALYS A 382      19.674  58.846  -2.101  0.50 44.08           N
ATOM   1283  NZ  BLYS A 382      25.283  58.316  -3.028  0.50 45.33           N
ATOM   1284  N    LEU A 383      22.177  56.781   3.950  1.00 40.04           N
ATOM   1285  CA   LEU A 383      21.462  55.738   4.681  1.00 40.07           C
ATOM   1286  C    LEU A 383      20.532  56.357   5.718  1.00 38.72           C
ATOM   1287  O    LEU A 383      19.406  55.906   5.911  1.00 39.84           O
ATOM   1288  CB   LEU A 383      22.470  54.767   5.306  1.00 37.64           C
ATOM   1289  CG   LEU A 383      23.053  53.709   4.344  1.00 36.85           C
ATOM   1290  CD1  LEU A 383      24.217  52.949   4.966  1.00 29.72           C
ATOM   1291  CD2  LEU A 383      21.976  52.732   3.908  1.00 32.29           C
ATOM   1292  N    THR A 384      20.940  57.424   6.374  1.00 38.87           N
ATOM   1293  CA   THR A 384      20.118  58.108   7.365  1.00 38.81           C
ATOM   1294  C    THR A 384      18.904  58.707   6.651  1.00 38.95           C
ATOM   1295  O    THR A 384      17.786  58.553   7.161  1.00 36.66           O
ATOM   1296  CB   THR A 384      20.878  59.126   8.203  1.00 39.55           C
ATOM   1297  OG1  THR A 384      21.829  58.430   9.023  1.00 39.66           O
ATOM   1298  CG2  THR A 384      19.971  59.889   9.174  1.00 42.29           C
ATOM   1299  N    HIS A 385      19.064  59.319   5.489  1.00 37.62           N
ATOM   1300  CA   HIS A 385      17.920  59.837   4.746  1.00 36.72           C
ATOM   1301  C    HIS A 385      16.954  58.700   4.436  1.00 34.67           C
ATOM   1302  O    HIS A 385      15.760  58.898   4.563  1.00 36.52           O
ATOM   1303  CB   HIS A 385      18.320  60.483   3.402  1.00 40.92           C
ATOM   1304  CG  AHIS A 385      17.218  61.218   2.724  0.50 39.61           C
ATOM   1305  CG  BHIS A 385      18.841  61.882   3.591  0.50 42.07           C
ATOM   1306  ND1 AHIS A 385      16.807  62.472   3.136  0.50 38.88           N
```

| ATOM | 119 | OW | WAT W 119 | 12.235 | 43.300 | 26.169 | 1.00 | 68.31 | O |
| ATOM | 120 | OW | WAT W 120 | 11.218 | 29.189 | -3.406 | 1.00 | 97.33 | O |

```
HEADER    NUCLEAR RECEPTOR - ER Beta + KB177
REMARK   DATE: 19/2/1998
REMARK    1 Final rebuild/refinement for ERB+177 against in-house 2.7A
REMARK      data using REFMAC
REMARK                                     COMPND    2 MOLECULE: RAT OESTROGEN RECEPTOR
BETA; COMPND    3 CHAIN: A; COMPND    4 FRAGMENT: LIGAND-BINDING DOMAIN; COMPND    5
SYNONYM: ESTROGEN RECEPTOR, ER-LBD, ER-BETA; COMPND    6 ENGINEERED: YES; COMPND    7
BIOLOGICAL_UNIT: DIMER; COMPND    8 OTHER_DETAILS: LIGAND-BINDING DOMAIN COMPND    9
(DOMAIN E - RESIDUES 211-461) IN COMPLEX WITH KB177
REMARK
REMARK  Overall refinement statistics (REF. CYCLE 5 16/2/98)
REMARK
REMARK    _refine_overall_R_factor            0.23186
REMARK    _refine_ls_number_reflns               9115
REMARK
REMARK    _refine_ls_number_reflns_missing         39
REMARK    _refine_free_R_factor               0.31013
REMARK    _refine_ls_number_reflns_free           978
REMARK    _refine_ls_number_reflns_free_missing     5
REMARK    _refine_ls_WR_factor                0.23256
REMARK
REMARK    Correlation_coefficients_Fo_to_Fc   0.90218
REMARK    Free_correlation_coeff_Fo_to_Fc     0.82925
REMARK
REMARK    ****         Precision indication from R values       ****
REMARK
REMARK    Overall_Coordinate_ESU_based_on_R_value(Cruickshanks DPI)   0.65490
REMARK    Overall_Coordinate_ESU_based_on_free_R_value    0.38872
REMARK
REMARK    ****    Precision indication from Maximum Likelihood   ****
REMARK
REMARK    Overall_Coordinate_ESU_based_on_ML    0.23920
REMARK    Overall_Bvalue_ESU_based_on_ML       11.19936
REMARK
REMARK    **********************************************
REMARK    **** COMMENTS ON THE MODEL AS IS **********
REMARK    **********************************************
REMARK    7 RESIDUE: SER240 not modelled beyond CB atom
REMARK    7 RESIDUE: PHE246 not modelled beyond CB atom
REMARK    7 RESIDUE: THR247 not modelled beyond CB atom
REMARK    7 RESIDUE: GLU248 not modelled beyond CB atom
REMARK    7 RESIDUE: MET251 not modelled beyond CB atom
REMARK    7 RESIDUE: LYS257 not modelled beyond CB atom
REMARK    7 RESIDUE: ASP316 not modelled beyond CB atom
REMARK    7 RESIDUE: GLU328 not modelled beyond CB atom
REMARK    7 RESIDUE: LYS437 not modelled beyond CB atom
REMARK    7 RESIDUE: ASP446 not modelled beyond CB atom
REMARK    7 RESIDUE: LEU447 not modelled beyond CB atom
REMARK    7 RESIDUE: LEU449 not modelled beyond CB atom
REMARK    7 RESIDUE: GLU450 not modelled beyond CB atom
REMARK    7 RESIDUE: MET451 not modelled beyond CB atom
REMARK    8
REMARK    8 RESIDUES MODELLED IN ALTERNATE CONFORMATIONS: GLN224,
REMARK    8 SER290, LYS382, SER420, HIS421. WAT W1, W2
REMARK
REMARK    9 RESIDUES: ARG211 - SER218 (inclusive) have not been modelled
REMARK    9 RESIDUES: SER243 - PRO245 (inclusive) have not been modelled
REMARK    9 RESIDUES: CYS438 - TYR445 (inclusive) have not been modelled
REMARK    9 RESIDUES: HIS455 - LYS461 (inclusive) have not been modelled
REMARK
REMARK   10 HELIX 12 IS INCLUDED FOR REFERENCE BUT IS HIGHLY MOBILE (see
REMARK   10 temperature factors for this region). CONFORMATION HERE IS
REMARK   10 VISIBLE IN ELECTRON DENSITY MAPS BUT BOTH SIDECHAIN AND
REMARK   10 MAINCHAIN IS POORLY DEFINED. SIDECHAINS THAT HAVE BEEN MODELLED
REMARK   10 ARE HOWEVER VISIBLE. TREAT WITH CAUTION.
REMARK
REMARK   11 NOTE: NOTE: pH OF CRYSTALLISATION IS VERY DIFFERENT FROM THAT
REMARK   11 OF ER-ALPHA + RALOX (pH4.6 VS pH8.5). BEAR THIS IN MIND DURING
REMARK   11 IN COMPARISONS
REMARK
REMARK   12 ONLY ONE MOLECULE IS PRESENT IN CRYSTALLOGRAPHIC ASYMMETRIC UNIT
REMARK   12 CRYSTALLOGRAPHIC DIMER PARTNER CAN BE GENERATED BY APPLYING FOLLOWING
REMARK   12 OPERATION TO THESE COORDINATES
REMARK   12 ROTATION OF (-Y;-X,1/4-Z)
REMARK   12 FRACTIONAL TRANSLATION  (1.0 1.0 0.0)
REMARK
REMARK   13 CORE OF LIGAND HAS REASONABLY WELL DEFINED ED BUT SIDECHAIN WEAK AFTER
```

| | | | | | | | | | |
|---|---|---|---|---|---|---|---|---|---|
| ATOM | 1610 | N   | LYS | A | 428 | 25.222 | 36.301 | 17.922 | 1.00 68.60 | N |
| ATOM | 1611 | CA  | LYS | A | 428 | 25.452 | 35.009 | 18.564 | 1.00 71.18 | C |
| ATOM | 1612 | C   | LYS | A | 428 | 25.241 | 33.891 | 17.564 | 1.00 73.18 | C |
| ATOM | 1613 | O   | LYS | A | 428 | 25.969 | 32.910 | 17.566 | 1.00 72.60 | O |
| ATOM | 1614 | CB  | LYS | A | 428 | 24.630 | 34.890 | 19.830 | 1.00 72.41 | C |
| ATOM | 1615 | CG  | LYS | A | 428 | 25.452 | 35.026 | 21.100 | 1.00 74.18 | C |
| ATOM | 1616 | CD  | LYS | A | 428 | 25.971 | 36.421 | 21.362 | 1.00 76.13 | C |
| ATOM | 1617 | CE  | LYS | A | 428 | 26.739 | 36.513 | 22.682 | 1.00 77.61 | C |
| ATOM | 1618 | NZ  | LYS | A | 428 | 27.830 | 35.504 | 22.805 | 1.00 77.63 | N |
| ATOM | 1619 | N   | GLY | A | 429 | 24.263 | 34.038 | 16.680 | 1.00 75.60 | N |
| ATOM | 1620 | CA  | GLY | A | 429 | 23.967 | 33.064 | 15.661 | 1.00 78.38 | C |
| ATOM | 1621 | C   | GLY | A | 429 | 25.117 | 32.993 | 14.673 | 1.00 81.42 | C |
| ATOM | 1622 | O   | GLY | A | 429 | 25.398 | 31.883 | 14.226 | 1.00 81.05 | O |
| ATOM | 1623 | N   | MET | A | 430 | 25.756 | 34.109 | 14.337 | 1.00 85.33 | N |
| ATOM | 1624 | CA  | MET | A | 430 | 26.864 | 34.060 | 13.388 | 1.00 90.35 | C |
| ATOM | 1625 | C   | MET | A | 430 | 28.112 | 33.451 | 14.041 | 1.00 94.21 | C |
| ATOM | 1626 | O   | MET | A | 430 | 28.975 | 32.929 | 13.325 | 1.00 94.89 | O |
| ATOM | 1627 | CB  | MET | A | 430 | 27.234 | 35.400 | 12.790 | 1.00 90.24 | C |
| ATOM | 1628 | CG  | MET | A | 430 | 26.284 | 36.092 | 11.850 | 1.00 90.79 | C |
| ATOM | 1629 | SD  | MET | A | 430 | 26.383 | 35.584 | 10.131 | 1.00 90.82 | S |
| ATOM | 1630 | CE  | MET | A | 430 | 28.016 | 36.109 |  9.648 | 1.00 90.38 | C |
| ATOM | 1631 | N   | GLU | A | 431 | 28.219 | 33.523 | 15.369 | 1.00 97.86 | N |
| ATOM | 1632 | CA  | GLU | A | 431 | 29.376 | 32.930 | 16.039 | 1.00101.43 | C |
| ATOM | 1633 | C   | GLU | A | 431 | 29.035 | 31.450 | 16.238 | 1.00103.11 | C |
| ATOM | 1634 | O   | GLU | A | 431 | 29.916 | 30.603 | 16.091 | 1.00102.32 | O |
| ATOM | 1635 | CB  | GLU | A | 431 | 29.820 | 33.699 | 17.255 | 1.00102.66 | C |
| ATOM | 1636 | CG  | GLU | A | 431 | 29.259 | 33.468 | 18.628 | 1.00104.78 | C |
| ATOM | 1637 | CD  | GLU | A | 431 | 29.543 | 34.556 | 19.650 | 1.00106.25 | C |
| ATOM | 1638 | OE1 | GLU | A | 431 | 29.463 | 35.775 | 19.345 | 1.00106.06 | O |
| ATOM | 1639 | OE2 | GLU | A | 431 | 29.857 | 34.217 | 20.824 | 1.00107.06 | O |
| ATOM | 1640 | N   | HIS | A | 432 | 27.770 | 31.137 | 16.501 | 1.00105.37 | N |
| ATOM | 1641 | CA  | HIS | A | 432 | 27.304 | 29.779 | 16.683 | 1.00108.33 | C |
| ATOM | 1642 | C   | HIS | A | 432 | 27.429 | 28.923 | 15.422 | 1.00110.47 | C |
| ATOM | 1643 | O   | HIS | A | 432 | 27.777 | 27.737 | 15.491 | 1.00110.83 | O |
| ATOM | 1644 | CB  | HIS | A | 432 | 25.838 | 29.737 | 17.127 | 1.00108.71 | C |
| ATOM | 1645 | CG  | HIS | A | 432 | 25.334 | 28.347 | 17.344 | 1.00109.30 | C |
| ATOM | 1646 | ND1 | HIS | A | 432 | 24.692 | 27.623 | 16.365 | 1.00109.53 | N |
| ATOM | 1647 | CD2 | HIS | A | 432 | 25.394 | 27.545 | 18.431 | 1.00109.60 | C |
| ATOM | 1648 | CE1 | HIS | A | 432 | 24.370 | 26.432 | 16.848 | 1.00109.74 | C |
| ATOM | 1649 | NE2 | HIS | A | 432 | 24.779 | 26.356 | 18.099 | 1.00109.33 | N |
| ATOM | 1650 | N   | LEU | A | 433 | 27.129 | 29.489 | 14.256 | 1.00112.57 | N |
| ATOM | 1651 | CA  | LEU | A | 433 | 27.242 | 28.692 | 13.041 | 1.00114.79 | C |
| ATOM | 1652 | C   | LEU | A | 433 | 28.715 | 28.402 | 12.777 | 1.00116.67 | C |
| ATOM | 1653 | O   | LEU | A | 433 | 29.132 | 27.264 | 12.572 | 1.00116.51 | O |
| ATOM | 1654 | CB  | LEU | A | 433 | 26.523 | 29.324 | 11.852 | 1.00114.07 | C |
| ATOM | 1655 | CG  | LEU | A | 433 | 24.997 | 29.320 | 11.872 | 1.00113.59 | C |
| ATOM | 1656 | CD1 | LEU | A | 433 | 24.393 | 29.872 | 10.584 | 1.00113.63 | C |
| ATOM | 1657 | CD2 | LEU | A | 433 | 24.443 | 27.936 | 12.142 | 1.00113.26 | C |
| ATOM | 1658 | N   | LEU | A | 434 | 29.548 | 29.416 | 12.808 | 1.00119.49 | N |
| ATOM | 1659 | CA  | LEU | A | 434 | 30.976 | 29.381 | 12.554 | 1.00122.51 | C |
| ATOM | 1660 | C   | LEU | A | 434 | 31.840 | 28.513 | 13.438 | 1.00124.11 | C |
| ATOM | 1661 | O   | LEU | A | 434 | 32.979 | 28.220 | 13.084 | 1.00123.27 | O |
| ATOM | 1662 | CB  | LEU | A | 434 | 31.448 | 30.839 | 12.532 | 1.00123.21 | C |
| ATOM | 1663 | CG  | LEU | A | 434 | 32.855 | 31.221 | 12.942 | 1.00124.00 | C |
| ATOM | 1664 | CD1 | LEU | A | 434 | 33.299 | 32.464 | 12.178 | 1.00124.13 | C |
| ATOM | 1665 | CD2 | LEU | A | 434 | 32.969 | 31.470 | 14.441 | 1.00124.18 | C |
| ATOM | 1666 | N   | SER | A | 435 | 31.360 | 28.062 | 14.582 | 1.00127.27 | N |
| ATOM | 1667 | CA  | SER | A | 435 | 32.064 | 27.202 | 15.517 | 1.00129.70 | C |
| ATOM | 1668 | C   | SER | A | 435 | 31.726 | 25.755 | 15.173 | 1.00131.52 | C |
| ATOM | 1669 | O   | SER | A | 435 | 32.439 | 24.801 | 15.463 | 1.00132.54 | O |
| ATOM | 1670 | CB  | SER | A | 435 | 31.674 | 27.539 | 16.949 | 1.00129.93 | C |
| ATOM | 1671 | OG  | SER | A | 435 | 32.515 | 26.896 | 17.895 | 1.00130.67 | O |
| ATOM | 1672 | N   | MET | A | 436 | 30.603 | 25.595 | 14.491 | 1.00133.06 | N |
| ATOM | 1673 | CA  | MET | A | 436 | 30.048 | 24.341 | 14.004 | 1.00134.16 | C |
| ATOM | 1674 | C   | MET | A | 436 | 30.451 | 24.139 | 12.544 | 1.00134.96 | C |
| ATOM | 1675 | O   | MET | A | 436 | 30.092 | 23.173 | 11.869 | 1.00135.07 | O |
| ATOM | 1676 | CB  | MET | A | 436 | 28.541 | 24.437 | 14.177 | 1.00134.22 | C |
| ATOM | 1677 | CG  | MET | A | 436 | 27.634 | 23.388 | 13.579 | 1.00134.16 | C |
| ATOM | 1678 | SD  | MET | A | 436 | 26.188 | 24.166 | 12.827 | 1.00133.84 | S |
| ATOM | 1679 | CE  | MET | A | 436 | 26.980 | 25.184 | 11.579 | 1.00134.14 | C |
| ATOM | 1680 | N   | LYS | A | 437 | 31.238 | 25.089 | 12.036 | 1.00135.52 | N |
| ATOM | 1681 | CA  | LYS | A | 437 | 31.737 | 25.092 | 10.672 | 1.00136.00 | C |
| ATOM | 1682 | C   | LYS | A | 437 | 33.132 | 25.701 | 10.610 | 1.00136.07 | C |
| ATOM | 1683 | O   | LYS | A | 437 | 33.533 | 26.404 |  9.682 | 1.00135.96 | O |
| ATOM | 1684 | CB  | LYS | A | 437 | 30.775 | 25.840 |  9.739 | 1.00136.07 | C |
| ATOM | 1685 | N   | ASP | A | 446 | 29.320 | 36.184 | -2.701 | 1.00153.93 | N |
| ATOM | 1686 | CA  | ASP | A | 446 | 30.337 | 36.455 | -3.712 | 1.00154.17 | C |

| ATOM | 1533 | O    | LEU A 419  | 18.482 | 44.935 | 16.940 | 1.00 | 42.98 | O |
|------|------|------|------------|--------|--------|--------|------|-------|---|
| ATOM | 1534 | CB   | LEU A 419  | 16.790 | 47.604 | 16.194 | 1.00 | 44.02 | C |
| ATOM | 1535 | CG   | LEU A 419  | 15.628 | 48.007 | 15.279 | 1.00 | 44.32 | C |
| ATOM | 1536 | CD1  | LEU A 419  | 15.737 | 49.466 | 14.883 | 1.00 | 45.21 | C |
| ATOM | 1537 | CD2  | LEU A 419  | 15.559 | 47.108 | 14.065 | 1.00 | 44.41 | C |
| ATOM | 1538 | N    | SER A 420  | 18.240 | 46.217 | 18.732 | 1.00 | 42.70 | N |
| ATOM | 1539 | CA   | SER A 420  | 19.511 | 45.741 | 19.297 | 1.00 | 41.87 | C |
| ATOM | 1540 | C    | SER A 420  | 19.496 | 44.271 | 19.690 | 1.00 | 41.98 | C |
| ATOM | 1541 | O    | SER A 420  | 20.524 | 43.603 | 19.663 | 1.00 | 39.92 | O |
| ATOM | 1542 | CB   | SER A 420  | 19.884 | 46.670 | 20.450 | 1.00 | 39.97 | C |
| ATOM | 1543 | OG ASER A 420 |     | 19.288 | 47.921 | 20.100 | 0.50 | 39.80 | O |
| ATOM | 1544 | OG BSER A 420 |     | 19.310 | 46.282 | 21.680 | 0.50 | 39.45 | O |
| ATOM | 1545 | N    | HIS A 421  | 18.315 | 43.777 | 20.030 | 1.00 | 43.15 | N |
| ATOM | 1546 | CA   | HIS A 421  | 18.069 | 42.398 | 20.411 | 1.00 | 44.37 | C |
| ATOM | 1547 | C    | HIS A 421  | 18.266 | 41.522 | 19.185 | 1.00 | 45.24 | C |
| ATOM | 1548 | O    | HIS A 421  | 18.963 | 40.507 | 19.249 | 1.00 | 44.58 | O |
| ATOM | 1549 | CB   | HIS A 421  | 16.667 | 42.276 | 21.008 | 1.00 | 44.57 | C |
| ATOM | 1550 | CG AHIS A 421 |     | 16.608 | 42.805 | 22.422 | 0.50 | 44.49 | C |
| ATOM | 1551 | CG BHIS A 421 |     | 16.653 | 42.869 | 22.397 | 0.50 | 45.30 | C |
| ATOM | 1552 | ND1AHIS A 421 |     | 15.727 | 42.319 | 23.364 | 0.50 | 43.69 | N |
| ATOM | 1553 | ND1BHIS A 421 |     | 17.083 | 42.153 | 23.493 | 0.50 | 45.27 | N |
| ATOM | 1554 | CD2AHIS A 421 |     | 17.330 | 43.771 | 23.046 | 0.50 | 43.96 | C |
| ATOM | 1555 | CD2BHIS A 421 |     | 16.279 | 44.091 | 22.846 | 0.50 | 44.71 | C |
| ATOM | 1556 | CE1AHIS A 421 |     | 15.911 | 42.958 | 24.496 | 0.50 | 43.88 | C |
| ATOM | 1557 | CE1BHIS A 421 |     | 16.970 | 42.919 | 24.564 | 0.50 | 45.28 | C |
| ATOM | 1558 | NE2AHIS A 421 |     | 16.878 | 43.848 | 24.333 | 0.50 | 43.68 | N |
| ATOM | 1559 | NE2BHIS A 421 |     | 16.492 | 44.090 | 24.193 | 0.50 | 44.87 | N |
| ATOM | 1560 | N    | VAL A 422  | 17.690 | 42.016 | 18.070 | 1.00 | 44.37 | N |
| ATOM | 1561 | CA   | VAL A 422  | 17.856 | 41.310 | 16.818 | 1.00 | 43.04 | C |
| ATOM | 1562 | C    | VAL A 422  | 19.328 | 41.306 | 16.459 | 1.00 | 43.58 | C |
| ATOM | 1563 | O    | VAL A 422  | 19.841 | 40.305 | 15.975 | 1.00 | 44.60 | O |
| ATOM | 1564 | CB   | VAL A 422  | 16.930 | 41.888 | 15.726 | 1.00 | 42.84 | C |
| ATOM | 1565 | CG1  | VAL A 422  | 17.131 | 41.147 | 14.410 | 1.00 | 40.76 | C |
| ATOM | 1566 | CG2  | VAL A 422  | 15.475 | 41.709 | 16.208 | 1.00 | 40.85 | C |
| ATOM | 1567 | N    | ARG A 423  | 20.089 | 42.357 | 16.668 | 1.00 | 44.46 | N |
| ATOM | 1568 | CA   | ARG A 423  | 21.492 | 42.427 | 16.310 | 1.00 | 46.06 | C |
| ATOM | 1569 | C    | ARG A 423  | 22.284 | 41.407 | 17.118 | 1.00 | 47.33 | C |
| ATOM | 1570 | O    | ARG A 423  | 23.073 | 40.627 | 16.577 | 1.00 | 48.33 | O |
| ATOM | 1571 | CB   | ARG A 423  | 22.069 | 43.830 | 16.456 | 1.00 | 46.14 | C |
| ATOM | 1572 | CG   | ARG A 423  | 23.531 | 43.976 | 16.040 | 1.00 | 46.68 | C |
| ATOM | 1573 | CD   | ARG A 423  | 23.752 | 43.925 | 14.543 | 1.00 | 46.41 | C |
| ATOM | 1574 | NE   | ARG A 423  | 23.042 | 45.056 | 13.901 | 1.00 | 47.07 | N |
| ATOM | 1575 | CZ   | ARG A 423  | 23.649 | 46.206 | 13.667 | 1.00 | 48.45 | C |
| ATOM | 1576 | NH1  | ARG A 423  | 24.936 | 46.405 | 13.985 | 1.00 | 49.65 | N |
| ATOM | 1577 | NH2  | ARG A 423  | 23.077 | 47.251 | 13.114 | 1.00 | 49.52 | N |
| ATOM | 1578 | N    | HIS A 424  | 22.033 | 41.443 | 18.411 | 1.00 | 47.85 | N |
| ATOM | 1579 | CA   | HIS A 424  | 22.622 | 40.565 | 19.399 | 1.00 | 46.55 | C |
| ATOM | 1580 | C    | HIS A 424  | 22.440 | 39.116 | 19.004 | 1.00 | 47.10 | C |
| ATOM | 1581 | O    | HIS A 424  | 23.441 | 38.427 | 18.844 | 1.00 | 46.60 | O |
| ATOM | 1582 | CB   | HIS A 424  | 21.933 | 40.799 | 20.746 | 1.00 | 46.49 | C |
| ATOM | 1583 | CG   | HIS A 424  | 22.629 | 40.044 | 21.831 | 1.00 | 48.82 | C |
| ATOM | 1584 | ND1  | HIS A 424  | 23.954 | 40.277 | 22.192 | 1.00 | 48.30 | N |
| ATOM | 1585 | CD2  | HIS A 424  | 22.175 | 39.039 | 22.624 | 1.00 | 48.83 | C |
| ATOM | 1586 | CE1  | HIS A 424  | 24.293 | 39.460 | 23.148 | 1.00 | 47.73 | C |
| ATOM | 1587 | NE2  | HIS A 424  | 23.239 | 38.715 | 23.425 | 1.00 | 49.46 | N |
| ATOM | 1588 | N    | ILE A 425  | 21.208 | 38.654 | 18.781 | 1.00 | 47.61 | N |
| ATOM | 1589 | CA   | ILE A 425  | 20.943 | 37.285 | 18.412 | 1.00 | 47.99 | C |
| ATOM | 1590 | C    | ILE A 425  | 21.600 | 36.922 | 17.094 | 1.00 | 50.47 | C |
| ATOM | 1591 | O    | ILE A 425  | 22.087 | 35.789 | 16.902 | 1.00 | 50.99 | O |
| ATOM | 1592 | CB   | ILE A 425  | 19.467 | 36.972 | 18.347 | 1.00 | 49.62 | C |
| ATOM | 1593 | CG1  | ILE A 425  | 18.731 | 37.410 | 19.623 | 1.00 | 50.69 | C |
| ATOM | 1594 | CG2  | ILE A 425  | 19.176 | 35.494 | 18.077 | 1.00 | 50.48 | C |
| ATOM | 1595 | CD1  | ILE A 425  | 17.218 | 37.482 | 19.320 | 1.00 | 51.50 | C |
| ATOM | 1596 | N    | SER A 426  | 21.666 | 37.859 | 16.152 | 1.00 | 51.72 | N |
| ATOM | 1597 | CA   | SER A 426  | 22.342 | 37.498 | 14.904 | 1.00 | 53.69 | C |
| ATOM | 1598 | C    | SER A 426  | 23.841 | 37.375 | 15.179 | 1.00 | 57.25 | C |
| ATOM | 1599 | O    | SER A 426  | 24.536 | 36.524 | 14.587 | 1.00 | 57.64 | O |
| ATOM | 1600 | CB   | SER A 426  | 21.994 | 38.486 | 13.804 | 1.00 | 51.18 | C |
| ATOM | 1601 | OG   | SER A 426  | 23.139 | 38.691 | 13.000 | 1.00 | 48.41 | O |
| ATOM | 1602 | N    | ASN A 427  | 24.393 | 38.222 | 16.070 | 1.00 | 60.16 | N |
| ATOM | 1603 | CA   | ASN A 427  | 25.833 | 38.077 | 16.318 | 1.00 | 63.82 | C |
| ATOM | 1604 | C    | ASN A 427  | 26.064 | 36.720 | 16.978 | 1.00 | 65.88 | C |
| ATOM | 1605 | O    | ASN A 427  | 27.004 | 36.010 | 16.639 | 1.00 | 65.74 | O |
| ATOM | 1606 | CB   | ASN A 427  | 26.479 | 39.192 | 17.106 | 1.00 | 64.54 | C |
| ATOM | 1607 | CG   | ASN A 427  | 26.647 | 40.527 | 16.420 | 1.00 | 65.82 | C |
| ATOM | 1608 | OD1  | ASN A 427  | 27.262 | 40.602 | 15.350 | 1.00 | 67.73 | O |
| ATOM | 1609 | ND2  | ASN A 427  | 26.158 | 41.642 | 16.956 | 1.00 | 64.69 | N |

| ATOM | 1456 | O | SER A 409 | 8.003 | 55.648 | 21.476 | 1.00 | 44.18 | O |
|------|------|-----|-----------|--------|--------|--------|------|-------|---|
| ATOM | 1457 | CB | SER A 409 | 6.954 | 58.759 | 21.946 | 1.00 | 44.01 | C |
| ATOM | 1458 | OG | SER A 409 | 6.548 | 59.928 | 21.294 | 1.00 | 46.68 | O |
| ATOM | 1459 | N | VAL A 410 | 6.355 | 55.932 | 22.912 | 1.00 | 42.67 | N |
| ATOM | 1460 | CA | VAL A 410 | 6.717 | 54.761 | 23.699 | 1.00 | 41.27 | C |
| ATOM | 1461 | C | VAL A 410 | 6.688 | 53.564 | 22.743 | 1.00 | 41.13 | C |
| ATOM | 1462 | O | VAL A 410 | 7.640 | 52.780 | 22.765 | 1.00 | 40.08 | O |
| ATOM | 1463 | CB | VAL A 410 | 5.830 | 54.594 | 24.955 | 1.00 | 39.77 | C |
| ATOM | 1464 | CG1 | VAL A 410 | 5.703 | 53.167 | 25.424 | 1.00 | 36.26 | C |
| ATOM | 1465 | CG2 | VAL A 410 | 6.451 | 55.372 | 26.114 | 1.00 | 39.76 | C |
| ATOM | 1466 | N | ARG A 411 | 5.647 | 53.466 | 21.894 | 1.00 | 39.14 | N |
| ATOM | 1467 | CA | ARG A 411 | 5.610 | 52.365 | 20.954 | 1.00 | 39.71 | C |
| ATOM | 1468 | C | ARG A 411 | 6.760 | 52.386 | 19.940 | 1.00 | 40.03 | C |
| ATOM | 1469 | O | ARG A 411 | 7.411 | 51.360 | 19.697 | 1.00 | 39.55 | O |
| ATOM | 1470 | CB | ARG A 411 | 4.309 | 52.287 | 20.146 | 1.00 | 39.47 | C |
| ATOM | 1471 | CG | ARG A 411 | 4.188 | 50.944 | 19.403 | 1.00 | 37.69 | C |
| ATOM | 1472 | CD | ARG A 411 | 2.839 | 50.889 | 18.735 | 1.00 | 39.54 | C |
| ATOM | 1473 | NE | ARG A 411 | 2.555 | 49.605 | 18.152 | 1.00 | 41.95 | N |
| ATOM | 1474 | CZ | ARG A 411 | 2.464 | 48.415 | 18.715 | 1.00 | 42.97 | C |
| ATOM | 1475 | NH1 | ARG A 411 | 2.639 | 48.278 | 20.010 | 1.00 | 43.79 | N |
| ATOM | 1476 | NH2 | ARG A 411 | 2.201 | 47.329 | 17.991 | 1.00 | 44.08 | N |
| ATOM | 1477 | N | LEU A 412 | 7.012 | 53.582 | 19.382 | 1.00 | 38.90 | N |
| ATOM | 1478 | CA | LEU A 412 | 8.081 | 53.750 | 18.411 | 1.00 | 37.64 | C |
| ATOM | 1479 | C | LEU A 412 | 9.378 | 53.294 | 19.064 | 1.00 | 37.27 | C |
| ATOM | 1480 | O | LEU A 412 | 10.197 | 52.594 | 18.487 | 1.00 | 37.83 | O |
| ATOM | 1481 | CB | LEU A 412 | 8.215 | 55.199 | 17.940 | 1.00 | 37.75 | C |
| ATOM | 1482 | CG | LEU A 412 | 9.375 | 55.495 | 16.997 | 1.00 | 38.09 | C |
| ATOM | 1483 | CD1 | LEU A 412 | 9.274 | 54.627 | 15.724 | 1.00 | 39.47 | C |
| ATOM | 1484 | CD2 | LEU A 412 | 9.419 | 56.950 | 16.602 | 1.00 | 35.89 | C |
| ATOM | 1485 | N | ALA A 413 | 9.540 | 53.697 | 20.310 | 1.00 | 36.73 | N |
| ATOM | 1486 | CA | ALA A 413 | 10.705 | 53.363 | 21.096 | 1.00 | 38.13 | C |
| ATOM | 1487 | C | ALA A 413 | 10.713 | 51.890 | 21.440 | 1.00 | 38.98 | C |
| ATOM | 1488 | O | ALA A 413 | 11.792 | 51.311 | 21.488 | 1.00 | 39.49 | O |
| ATOM | 1489 | CB | ALA A 413 | 10.764 | 54.309 | 22.289 | 1.00 | 38.89 | C |
| ATOM | 1490 | N | ASN A 414 | 9.590 | 51.232 | 21.689 | 1.00 | 41.37 | N |
| ATOM | 1491 | CA | ASN A 414 | 9.593 | 49.826 | 22.007 | 1.00 | 43.43 | C |
| ATOM | 1492 | C | ASN A 414 | 10.064 | 49.040 | 20.780 | 1.00 | 44.63 | C |
| ATOM | 1493 | O | ASN A 414 | 10.872 | 48.140 | 21.014 | 1.00 | 45.81 | O |
| ATOM | 1494 | CB | ASN A 414 | 8.226 | 49.243 | 22.360 | 1.00 | 45.33 | C |
| ATOM | 1495 | CG | ASN A 414 | 7.761 | 49.779 | 23.707 | 1.00 | 46.02 | C |
| ATOM | 1496 | OD1 | ASN A 414 | 8.601 | 49.831 | 24.604 | 1.00 | 43.63 | O |
| ATOM | 1497 | ND2 | ASN A 414 | 6.483 | 50.153 | 23.702 | 1.00 | 45.50 | N |
| ATOM | 1498 | N | LEU A 415 | 9.570 | 49.360 | 19.583 | 1.00 | 44.11 | N |
| ATOM | 1499 | CA | LEU A 415 | 10.057 | 48.598 | 18.429 | 1.00 | 43.56 | C |
| ATOM | 1500 | C | LEU A 415 | 11.495 | 48.898 | 18.062 | 1.00 | 43.26 | C |
| ATOM | 1501 | O | LEU A 415 | 12.256 | 48.001 | 17.705 | 1.00 | 42.71 | O |
| ATOM | 1502 | CB | LEU A 415 | 9.193 | 48.899 | 17.215 | 1.00 | 44.19 | C |
| ATOM | 1503 | CG | LEU A 415 | 7.693 | 48.675 | 17.518 | 1.00 | 46.24 | C |
| ATOM | 1504 | CD1 | LEU A 415 | 6.857 | 49.428 | 16.488 | 1.00 | 46.21 | C |
| ATOM | 1505 | CD2 | LEU A 415 | 7.381 | 47.200 | 17.586 | 1.00 | 44.21 | C |
| ATOM | 1506 | N | LEU A 416 | 11.938 | 50.165 | 18.149 | 1.00 | 43.28 | N |
| ATOM | 1507 | CA | LEU A 416 | 13.322 | 50.412 | 17.746 | 1.00 | 42.51 | C |
| ATOM | 1508 | C | LEU A 416 | 14.259 | 49.796 | 18.770 | 1.00 | 43.15 | C |
| ATOM | 1509 | O | LEU A 416 | 15.331 | 49.352 | 18.363 | 1.00 | 39.88 | O |
| ATOM | 1510 | CB | LEU A 416 | 13.542 | 51.869 | 17.443 | 1.00 | 43.97 | C |
| ATOM | 1511 | CG | LEU A 416 | 12.656 | 52.515 | 16.385 | 1.00 | 44.95 | C |
| ATOM | 1512 | CD1 | LEU A 416 | 13.147 | 53.914 | 16.058 | 1.00 | 44.15 | C |
| ATOM | 1513 | CD2 | LEU A 416 | 12.619 | 51.648 | 15.134 | 1.00 | 45.82 | C |
| ATOM | 1514 | N | MET A 417 | 13.885 | 49.739 | 20.057 | 1.00 | 42.69 | N |
| ATOM | 1515 | CA | MET A 417 | 14.743 | 49.129 | 21.040 | 1.00 | 43.49 | C |
| ATOM | 1516 | C | MET A 417 | 14.946 | 47.655 | 20.737 | 1.00 | 44.21 | C |
| ATOM | 1517 | O | MET A 417 | 16.043 | 47.168 | 21.013 | 1.00 | 44.52 | O |
| ATOM | 1518 | CB | MET A 417 | 14.214 | 49.334 | 22.442 | 1.00 | 45.12 | C |
| ATOM | 1519 | CG | MET A 417 | 14.735 | 50.678 | 23.024 | 1.00 | 46.68 | C |
| ATOM | 1520 | SD | MET A 417 | 13.984 | 50.802 | 24.640 | 1.00 | 47.00 | S |
| ATOM | 1521 | CE | MET A 417 | 13.994 | 52.511 | 25.094 | 1.00 | 48.43 | C |
| ATOM | 1522 | N | LEU A 418 | 13.985 | 46.963 | 20.133 | 1.00 | 44.60 | N |
| ATOM | 1523 | CA | LEU A 418 | 14.080 | 45.573 | 19.749 | 1.00 | 45.32 | C |
| ATOM | 1524 | C | LEU A 418 | 15.127 | 45.358 | 18.665 | 1.00 | 46.49 | C |
| ATOM | 1525 | O | LEU A 418 | 15.792 | 44.313 | 18.514 | 1.00 | 47.28 | O |
| ATOM | 1526 | CB | LEU A 418 | 12.682 | 45.031 | 19.446 | 1.00 | 46.11 | C |
| ATOM | 1527 | CG | LEU A 418 | 11.838 | 44.704 | 20.695 | 1.00 | 46.02 | C |
| ATOM | 1528 | CD1 | LEU A 418 | 10.439 | 44.216 | 20.405 | 1.00 | 44.85 | C |
| ATOM | 1529 | CD2 | LEU A 418 | 12.510 | 43.688 | 21.605 | 1.00 | 46.18 | C |
| ATOM | 1530 | N | LEU A 419 | 15.474 | 46.380 | 17.886 | 1.00 | 46.30 | N |
| ATOM | 1531 | CA | LEU A 419 | 16.549 | 46.283 | 16.906 | 1.00 | 44.87 | C |
| ATOM | 1532 | C | LEU A 419 | 17.843 | 45.796 | 17.543 | 1.00 | 43.66 | C |

```
ATOM   1379  CG1 ILE A 398       3.678  53.049  15.623  1.00 38.62           C
ATOM   1380  CG2 ILE A 398       2.194  54.537  16.983  1.00 39.96           C
ATOM   1381  CD1 ILE A 398       5.130  53.422  15.705  1.00 36.30           C
ATOM   1382  N   ALA A 399       0.463  56.054  14.165  1.00 47.96           N
ATOM   1383  CA  ALA A 399      -0.545  57.086  14.374  1.00 48.51           C
ATOM   1384  C   ALA A 399      -1.925  56.639  13.948  1.00 51.82           C
ATOM   1385  O   ALA A 399      -2.927  57.205  14.398  1.00 52.57           O
ATOM   1386  CB  ALA A 399      -0.120  58.392  13.699  1.00 45.10           C
ATOM   1387  N   LYS A 400      -2.048  55.623  13.098  1.00 55.88           N
ATOM   1388  CA  LYS A 400      -3.284  55.071  12.602  1.00 58.01           C
ATOM   1389  C   LYS A 400      -4.079  54.325  13.656  1.00 59.28           C
ATOM   1390  O   LYS A 400      -5.302  54.178  13.516  1.00 60.50           O
ATOM   1391  CB  LYS A 400      -3.021  54.180  11.404  1.00 60.00           C
ATOM   1392  CG  LYS A 400      -3.293  54.895  10.086  1.00 62.36           C
ATOM   1393  CD  LYS A 400      -3.308  53.831   8.989  1.00 64.54           C
ATOM   1394  CE  LYS A 400      -3.997  54.306   7.711  1.00 65.36           C
ATOM   1395  NZ  LYS A 400      -5.391  53.785   7.599  1.00 65.91           N
ATOM   1396  N   SER A 401      -3.465  53.928  14.752  1.00 59.43           N
ATOM   1397  CA  SER A 401      -4.146  53.235  15.830  1.00 60.33           C
ATOM   1398  C   SER A 401      -4.805  54.216  16.789  1.00 61.01           C
ATOM   1399  O   SER A 401      -5.426  53.876  17.796  1.00 60.75           O
ATOM   1400  CB  SER A 401      -3.122  52.405  16.610  1.00 60.46           C
ATOM   1401  OG  SER A 401      -2.255  53.144  17.454  1.00 58.12           O
ATOM   1402  N   GLY A 402      -4.610  55.505  16.562  1.00 61.85           N
ATOM   1403  CA  GLY A 402      -5.148  56.537  17.416  1.00 62.65           C
ATOM   1404  C   GLY A 402      -4.770  56.428  18.871  1.00 63.87           C
ATOM   1405  O   GLY A 402      -5.578  56.922  19.682  1.00 65.68           O
ATOM   1406  N   ILE A 403      -3.615  55.881  19.271  1.00 63.54           N
ATOM   1407  CA  ILE A 403      -3.339  55.842  20.726  1.00 61.89           C
ATOM   1408  C   ILE A 403      -2.830  57.239  21.057  1.00 60.50           C
ATOM   1409  O   ILE A 403      -2.679  58.022  20.102  1.00 60.51           O
ATOM   1410  CB  ILE A 403      -2.386  54.734  21.185  1.00 62.21           C
ATOM   1411  CG1 ILE A 403      -0.980  54.973  20.625  1.00 61.84           C
ATOM   1412  CG2 ILE A 403      -2.917  53.371  20.775  1.00 61.24           C
ATOM   1413  CD1 ILE A 403      -0.082  53.772  20.560  1.00 61.44           C
ATOM   1414  N   SER A 404      -2.572  57.541  22.319  1.00 58.80           N
ATOM   1415  CA  SER A 404      -2.124  58.913  22.575  1.00 58.28           C
ATOM   1416  C   SER A 404      -0.722  59.173  22.059  1.00 58.30           C
ATOM   1417  O   SER A 404       0.128  58.292  21.876  1.00 57.78           O
ATOM   1418  CB  SER A 404      -2.244  59.239  24.054  1.00 58.30           C
ATOM   1419  OG  SER A 404      -1.102  58.934  24.816  1.00 59.06           O
ATOM   1420  N   SER A 405      -0.462  60.469  21.884  1.00 57.34           N
ATOM   1421  CA  SER A 405       0.851  60.924  21.426  1.00 56.27           C
ATOM   1422  C   SER A 405       1.949  60.420  22.339  1.00 55.17           C
ATOM   1423  O   SER A 405       3.028  60.016  21.880  1.00 56.67           O
ATOM   1424  CB  SER A 405       0.804  62.436  21.255  1.00 57.15           C
ATOM   1425  OG  SER A 405       1.966  63.069  21.769  1.00 58.45           O
ATOM   1426  N   GLN A 406       1.763  60.369  23.648  1.00 52.35           N
ATOM   1427  CA  GLN A 406       2.751  59.858  24.590  1.00 49.20           C
ATOM   1428  C   GLN A 406       3.000  58.380  24.306  1.00 49.61           C
ATOM   1429  O   GLN A 406       4.141  57.942  24.345  1.00 49.78           O
ATOM   1430  CB  GLN A 406       2.247  60.061  26.006  1.00 46.40           C
ATOM   1431  CG  GLN A 406       3.034  59.544  27.160  1.00 44.43           C
ATOM   1432  CD  GLN A 406       2.862  58.079  27.505  1.00 44.05           C
ATOM   1433  OE1 GLN A 406       3.852  57.407  27.860  1.00 42.77           O
ATOM   1434  NE2 GLN A 406       1.632  57.581  27.394  1.00 43.26           N
ATOM   1435  N   GLN A 407       1.935  57.639  24.035  1.00 49.96           N
ATOM   1436  CA  GLN A 407       1.970  56.234  23.736  1.00 51.67           C
ATOM   1437  C   GLN A 407       2.562  55.957  22.352  1.00 50.98           C
ATOM   1438  O   GLN A 407       3.143  54.889  22.167  1.00 50.76           O
ATOM   1439  CB  GLN A 407       0.583  55.581  23.755  1.00 53.49           C
ATOM   1440  CG  GLN A 407      -0.071  55.228  25.057  1.00 56.33           C
ATOM   1441  CD  GLN A 407       0.846  54.501  26.018  1.00 60.01           C
ATOM   1442  OE1 GLN A 407       1.480  55.144  26.891  1.00 61.67           O
ATOM   1443  NE2 GLN A 407       0.943  53.178  25.871  1.00 60.13           N
ATOM   1444  N   GLN A 408       2.402  56.850  21.390  1.00 49.71           N
ATOM   1445  CA  GLN A 408       2.956  56.649  20.061  1.00 48.67           C
ATOM   1446  C   GLN A 408       4.473  56.754  20.129  1.00 47.51           C
ATOM   1447  O   GLN A 408       5.113  56.023  19.354  1.00 49.76           O
ATOM   1448  CB  GLN A 408       2.331  57.611  19.065  1.00 50.53           C
ATOM   1449  CG  GLN A 408       0.866  57.227  18.762  1.00 52.77           C
ATOM   1450  CD  GLN A 408       0.249  58.341  17.929  1.00 53.74           C
ATOM   1451  OE1 GLN A 408       0.964  58.912  17.106  1.00 55.24           O
ATOM   1452  NE2 GLN A 408      -1.011  58.654  18.159  1.00 54.09           N
ATOM   1453  N   SER A 409       5.088  57.531  20.998  1.00 43.43           N
ATOM   1454  CA  SER A 409       6.532  57.556  21.092  1.00 43.25           C
ATOM   1455  C   SER A 409       7.027  56.304  21.810  1.00 43.83           C
```

| ATOM | 1302 | CB | ASN A 388 | 14.717 | 60.330 | 8.073 | 1.00 | 36.69 | C |
|------|------|------|-----------|--------|--------|--------|------|-------|---|
| ATOM | 1303 | CG | ASN A 388 | 15.842 | 60.678 | 9.021 | 1.00 | 37.75 | C |
| ATOM | 1304 | OD1 | ASN A 388 | 16.312 | 61.824 | 8.908 | 1.00 | 38.50 | O |
| ATOM | 1305 | ND2 | ASN A 388 | 16.278 | 59.805 | 9.914 | 1.00 | 35.13 | N |
| ATOM | 1306 | N | ALA A 389 | 12.911 | 58.459 | 6.151 | 1.00 | 36.54 | N |
| ATOM | 1307 | CA | ALA A 389 | 11.720 | 58.136 | 5.381 | 1.00 | 34.90 | C |
| ATOM | 1308 | C | ALA A 389 | 11.124 | 56.875 | 6.009 | 1.00 | 35.50 | C |
| ATOM | 1309 | O | ALA A 389 | 9.909 | 56.935 | 6.227 | 1.00 | 38.21 | O |
| ATOM | 1310 | CB | ALA A 389 | 12.016 | 57.905 | 3.908 | 1.00 | 30.91 | C |
| ATOM | 1311 | N | VAL A 390 | 11.879 | 55.819 | 6.318 | 1.00 | 34.21 | N |
| ATOM | 1312 | CA | VAL A 390 | 11.247 | 54.661 | 6.909 | 1.00 | 34.38 | C |
| ATOM | 1313 | C | VAL A 390 | 10.738 | 55.040 | 8.292 | 1.00 | 37.08 | C |
| ATOM | 1314 | O | VAL A 390 | 9.584 | 54.675 | 8.559 | 1.00 | 38.35 | O |
| ATOM | 1315 | CB | VAL A 390 | 12.039 | 53.368 | 6.881 | 1.00 | 34.55 | C |
| ATOM | 1316 | CG1 | VAL A 390 | 11.135 | 52.269 | 7.450 | 1.00 | 33.06 | C |
| ATOM | 1317 | CG2 | VAL A 390 | 12.590 | 52.986 | 5.492 | 1.00 | 32.03 | C |
| ATOM | 1318 | N | THR A 391 | 11.411 | 55.838 | 9.122 | 1.00 | 36.39 | N |
| ATOM | 1319 | CA | THR A 391 | 10.813 | 56.209 | 10.385 | 1.00 | 37.07 | C |
| ATOM | 1320 | C | THR A 391 | 9.519 | 57.000 | 10.177 | 1.00 | 40.36 | C |
| ATOM | 1321 | O | THR A 391 | 8.589 | 56.905 | 11.005 | 1.00 | 39.02 | O |
| ATOM | 1322 | CB | THR A 391 | 11.744 | 57.162 | 11.156 | 1.00 | 36.98 | C |
| ATOM | 1323 | OG1 | THR A 391 | 13.021 | 56.510 | 11.305 | 1.00 | 39.44 | O |
| ATOM | 1324 | CG2 | THR A 391 | 11.189 | 57.628 | 12.475 | 1.00 | 32.57 | C |
| ATOM | 1325 | N | ASP A 392 | 9.464 | 57.834 | 9.103 | 1.00 | 41.21 | N |
| ATOM | 1326 | CA | ASP A 392 | 8.256 | 58.623 | 8.910 | 1.00 | 43.49 | C |
| ATOM | 1327 | C | ASP A 392 | 7.092 | 57.670 | 8.577 | 1.00 | 45.40 | C |
| ATOM | 1328 | O | ASP A 392 | 5.937 | 57.880 | 9.013 | 1.00 | 46.20 | O |
| ATOM | 1329 | CB | ASP A 392 | 8.342 | 59.724 | 7.899 | 1.00 | 45.29 | C |
| ATOM | 1330 | CG | ASP A 392 | 9.224 | 60.897 | 8.185 | 1.00 | 47.15 | C |
| ATOM | 1331 | OD1 | ASP A 392 | 9.345 | 61.262 | 9.364 | 1.00 | 48.36 | O |
| ATOM | 1332 | OD2 | ASP A 392 | 9.824 | 61.448 | 7.222 | 1.00 | 49.33 | O |
| ATOM | 1333 | N | ALA A 393 | 7.429 | 56.588 | 7.868 | 1.00 | 43.84 | N |
| ATOM | 1334 | CA | ALA A 393 | 6.353 | 55.658 | 7.567 | 1.00 | 42.95 | C |
| ATOM | 1335 | C | ALA A 393 | 5.890 | 54.937 | 8.800 | 1.00 | 42.88 | C |
| ATOM | 1336 | O | ALA A 393 | 4.711 | 54.697 | 8.939 | 1.00 | 43.35 | O |
| ATOM | 1337 | CB | ALA A 393 | 6.826 | 54.703 | 6.483 | 1.00 | 43.46 | C |
| ATOM | 1338 | N | LEU A 394 | 6.749 | 54.513 | 9.719 | 1.00 | 44.46 | N |
| ATOM | 1339 | CA | LEU A 394 | 6.387 | 53.770 | 10.913 | 1.00 | 42.82 | C |
| ATOM | 1340 | C | LEU A 394 | 5.629 | 54.655 | 11.903 | 1.00 | 44.30 | C |
| ATOM | 1341 | O | LEU A 394 | 4.667 | 54.216 | 12.563 | 1.00 | 44.04 | O |
| ATOM | 1342 | CB | LEU A 394 | 7.622 | 53.144 | 11.529 | 1.00 | 41.39 | C |
| ATOM | 1343 | CG | LEU A 394 | 7.387 | 52.278 | 12.776 | 1.00 | 40.65 | C |
| ATOM | 1344 | CD1 | LEU A 394 | 6.368 | 51.172 | 12.524 | 1.00 | 40.16 | C |
| ATOM | 1345 | CD2 | LEU A 394 | 8.720 | 51.806 | 13.277 | 1.00 | 38.43 | C |
| ATOM | 1346 | N | VAL A 395 | 6.010 | 55.943 | 11.922 | 1.00 | 42.45 | N |
| ATOM | 1347 | CA | VAL A 395 | 5.312 | 56.885 | 12.777 | 1.00 | 41.14 | C |
| ATOM | 1348 | C | VAL A 395 | 3.876 | 56.968 | 12.269 | 1.00 | 43.91 | C |
| ATOM | 1349 | O | VAL A 395 | 2.859 | 56.928 | 12.971 | 1.00 | 45.07 | O |
| ATOM | 1350 | CB | VAL A 395 | 6.035 | 58.225 | 12.884 | 1.00 | 39.73 | C |
| ATOM | 1351 | CG1 | VAL A 395 | 5.145 | 59.340 | 13.389 | 1.00 | 35.52 | C |
| ATOM | 1352 | CG2 | VAL A 395 | 7.272 | 58.161 | 13.812 | 1.00 | 37.48 | C |
| ATOM | 1353 | N | TRP A 396 | 3.739 | 57.005 | 10.947 | 1.00 | 46.53 | N |
| ATOM | 1354 | CA | TRP A 396 | 2.423 | 57.071 | 10.290 | 1.00 | 45.93 | C |
| ATOM | 1355 | C | TRP A 396 | 1.662 | 55.785 | 10.534 | 1.00 | 46.29 | C |
| ATOM | 1356 | O | TRP A 396 | 0.450 | 55.859 | 10.810 | 1.00 | 47.26 | O |
| ATOM | 1357 | CB | TRP A 396 | 2.658 | 57.475 | 8.856 | 1.00 | 46.51 | C |
| ATOM | 1358 | CG | TRP A 396 | 1.431 | 57.387 | 8.016 | 1.00 | 50.02 | C |
| ATOM | 1359 | CD1 | TRP A 396 | 0.471 | 58.329 | 7.781 | 1.00 | 50.50 | C |
| ATOM | 1360 | CD2 | TRP A 396 | 1.028 | 56.216 | 7.282 | 1.00 | 51.20 | C |
| ATOM | 1361 | NE1 | TRP A 396 | -0.500 | 57.833 | 6.961 | 1.00 | 51.18 | N |
| ATOM | 1362 | CE2 | TRP A 396 | -0.185 | 56.533 | 6.642 | 1.00 | 51.40 | C |
| ATOM | 1363 | CE3 | TRP A 396 | 1.593 | 54.945 | 7.142 | 1.00 | 50.54 | C |
| ATOM | 1364 | CZ2 | TRP A 396 | -0.849 | 55.624 | 5.845 | 1.00 | 51.85 | C |
| ATOM | 1365 | CZ3 | TRP A 396 | 0.924 | 54.054 | 6.359 | 1.00 | 52.20 | C |
| ATOM | 1366 | CH2 | TRP A 396 | -0.269 | 54.401 | 5.725 | 1.00 | 52.85 | C |
| ATOM | 1367 | N | VAL A 397 | 2.265 | 54.599 | 10.516 | 1.00 | 43.93 | N |
| ATOM | 1368 | CA | VAL A 397 | 1.491 | 53.399 | 10.805 | 1.00 | 43.84 | C |
| ATOM | 1369 | C | VAL A 397 | 1.008 | 53.422 | 12.252 | 1.00 | 46.31 | C |
| ATOM | 1370 | O | VAL A 397 | -0.164 | 53.132 | 12.566 | 1.00 | 46.82 | O |
| ATOM | 1371 | CB | VAL A 397 | 2.334 | 52.165 | 10.527 | 1.00 | 43.47 | C |
| ATOM | 1372 | CG1 | VAL A 397 | 1.692 | 50.932 | 11.134 | 1.00 | 43.10 | C |
| ATOM | 1373 | CG2 | VAL A 397 | 2.622 | 51.999 | 9.038 | 1.00 | 41.81 | C |
| ATOM | 1374 | N | ILE A 398 | 1.903 | 53.814 | 13.184 | 1.00 | 47.02 | N |
| ATOM | 1375 | CA | ILE A 398 | 1.535 | 53.871 | 14.593 | 1.00 | 45.29 | C |
| ATOM | 1376 | C | ILE A 398 | 0.436 | 54.897 | 14.800 | 1.00 | 47.16 | C |
| ATOM | 1377 | O | ILE A 398 | -0.473 | 54.589 | 15.569 | 1.00 | 49.35 | O |
| ATOM | 1378 | CB | ILE A 398 | 2.694 | 54.203 | 15.566 | 1.00 | 42.40 | C |

| | | | | | | | | | |
|---|---|---|---|---|---|---|---|---|---|
| ATOM | 1225 | CB | SER A 379 | 27.994 | 55.561 | 3.188 | 1.00 | 50.21 | C |
| ATOM | 1226 | OG | SER A 379 | 28.516 | 54.982 | 2.023 | 1.00 | 47.05 | O |
| ATOM | 1227 | N | SER A 380 | 26.643 | 57.676 | 5.267 | 1.00 | 51.74 | N |
| ATOM | 1228 | CA | SER A 380 | 25.820 | 57.885 | 6.426 | 1.00 | 51.78 | C |
| ATOM | 1229 | C | SER A 380 | 24.701 | 58.899 | 6.231 | 1.00 | 52.03 | C |
| ATOM | 1230 | O | SER A 380 | 23.553 | 58.668 | 6.624 | 1.00 | 51.45 | O |
| ATOM | 1231 | CB | SER A 380 | 26.631 | 58.393 | 7.621 | 1.00 | 52.26 | C |
| ATOM | 1232 | OG | SER A 380 | 27.162 | 57.322 | 8.364 | 1.00 | 54.52 | O |
| ATOM | 1233 | N | ARG A 381 | 25.064 | 60.025 | 5.625 | 1.00 | 52.00 | N |
| ATOM | 1234 | CA | ARG A 381 | 24.058 | 61.045 | 5.354 | 1.00 | 53.46 | C |
| ATOM | 1235 | C | ARG A 381 | 22.950 | 60.401 | 4.512 | 1.00 | 51.99 | C |
| ATOM | 1236 | O | ARG A 381 | 21.758 | 60.400 | 4.829 | 1.00 | 51.69 | O |
| ATOM | 1237 | CB | ARG A 381 | 24.703 | 62.219 | 4.619 | 1.00 | 56.60 | C |
| ATOM | 1238 | CG | ARG A 381 | 25.392 | 63.175 | 5.577 | 1.00 | 58.69 | C |
| ATOM | 1239 | CD | ARG A 381 | 25.927 | 64.376 | 4.818 | 1.00 | 62.71 | C |
| ATOM | 1240 | NE | ARG A 381 | 27.396 | 64.390 | 4.835 | 1.00 | 66.61 | N |
| ATOM | 1241 | CZ | ARG A 381 | 28.204 | 64.177 | 3.788 | 1.00 | 66.75 | C |
| ATOM | 1242 | NH1 | ARG A 381 | 27.808 | 63.936 | 2.562 | 1.00 | 65.78 | N |
| ATOM | 1243 | NH2 | ARG A 381 | 29.503 | 64.239 | 4.040 | 1.00 | 67.87 | N |
| ATOM | 1244 | N | LYS A 382 | 23.424 | 59.765 | 3.428 | 1.00 | 49.50 | N |
| ATOM | 1245 | CA | LYS A 382 | 22.527 | 59.053 | 2.547 | 1.00 | 47.01 | C |
| ATOM | 1246 | C | LYS A 382 | 21.695 | 58.041 | 3.320 | 1.00 | 44.04 | C |
| ATOM | 1247 | O | LYS A 382 | 20.492 | 58.185 | 3.306 | 1.00 | 41.67 | O |
| ATOM | 1248 | CB | LYS A 382 | 23.215 | 58.344 | 1.378 | 1.00 | 46.82 | C |
| ATOM | 1249 | CG | ALYS A 382 | 22.522 | 58.553 | 0.052 | 0.50 | 47.42 | C |
| ATOM | 1250 | CG | BLYS A 382 | 23.378 | 59.259 | 0.184 | 0.50 | 47.43 | C |
| ATOM | 1251 | CD | ALYS A 382 | 21.014 | 58.378 | 0.079 | 0.50 | 48.26 | C |
| ATOM | 1252 | CD | BLYS A 382 | 24.280 | 58.635 | -0.868 | 0.50 | 47.98 | C |
| ATOM | 1253 | CE | ALYS A 382 | 20.378 | 58.966 | -1.176 | 0.50 | 49.16 | C |
| ATOM | 1254 | CE | BLYS A 382 | 24.956 | 59.739 | -1.686 | 0.50 | 46.90 | C |
| ATOM | 1255 | NZ | ALYS A 382 | 20.404 | 60.462 | -1.151 | 0.50 | 49.32 | N |
| ATOM | 1256 | NZ | BLYS A 382 | 25.702 | 59.078 | -2.792 | 0.50 | 47.65 | N |
| ATOM | 1257 | N | LEU A 383 | 22.335 | 57.059 | 3.953 | 1.00 | 42.46 | N |
| ATOM | 1258 | CA | LEU A 383 | 21.596 | 56.031 | 4.692 | 1.00 | 41.64 | C |
| ATOM | 1259 | C | LEU A 383 | 20.645 | 56.643 | 5.718 | 1.00 | 42.52 | C |
| ATOM | 1260 | O | LEU A 383 | 19.521 | 56.197 | 5.956 | 1.00 | 40.74 | O |
| ATOM | 1261 | CB | LEU A 383 | 22.614 | 55.071 | 5.320 | 1.00 | 39.33 | C |
| ATOM | 1262 | CG | LEU A 383 | 23.322 | 54.090 | 4.369 | 1.00 | 38.51 | C |
| ATOM | 1263 | CD1 | LEU A 383 | 24.542 | 53.397 | 5.015 | 1.00 | 34.06 | C |
| ATOM | 1264 | CD2 | LEU A 383 | 22.336 | 53.051 | 3.840 | 1.00 | 35.45 | C |
| ATOM | 1265 | N | THR A 384 | 21.083 | 57.727 | 6.377 | 1.00 | 42.09 | N |
| ATOM | 1266 | CA | THR A 384 | 20.274 | 58.384 | 7.373 | 1.00 | 43.36 | C |
| ATOM | 1267 | C | THR A 384 | 18.996 | 58.896 | 6.743 | 1.00 | 43.50 | C |
| ATOM | 1268 | O | THR A 384 | 17.938 | 58.771 | 7.372 | 1.00 | 45.77 | O |
| ATOM | 1269 | CB | THR A 384 | 21.074 | 59.485 | 8.089 | 1.00 | 44.97 | C |
| ATOM | 1270 | OG1 | THR A 384 | 21.837 | 58.852 | 9.125 | 1.00 | 45.31 | O |
| ATOM | 1271 | CG2 | THR A 384 | 20.229 | 60.581 | 8.691 | 1.00 | 44.00 | C |
| ATOM | 1272 | N | HIS A 385 | 19.102 | 59.460 | 5.563 | 1.00 | 42.19 | N |
| ATOM | 1273 | CA | HIS A 385 | 17.979 | 59.979 | 4.798 | 1.00 | 41.16 | C |
| ATOM | 1274 | C | HIS A 385 | 17.036 | 58.842 | 4.453 | 1.00 | 38.55 | C |
| ATOM | 1275 | O | HIS A 385 | 15.836 | 59.018 | 4.571 | 1.00 | 39.41 | O |
| ATOM | 1276 | CB | HIS A 385 | 18.470 | 60.585 | 3.500 | 1.00 | 44.64 | C |
| ATOM | 1277 | CG | HIS A 385 | 17.519 | 61.247 | 2.575 | 1.00 | 48.68 | C |
| ATOM | 1278 | ND1 | HIS A 385 | 16.940 | 62.494 | 2.841 | 1.00 | 49.87 | N |
| ATOM | 1279 | CD2 | HIS A 385 | 17.061 | 60.847 | 1.347 | 1.00 | 49.41 | C |
| ATOM | 1280 | CE1 | HIS A 385 | 16.167 | 62.829 | 1.823 | 1.00 | 50.63 | C |
| ATOM | 1281 | NE2 | HIS A 385 | 16.221 | 61.848 | 0.909 | 1.00 | 51.03 | N |
| ATOM | 1282 | N | LEU A 386 | 17.559 | 57.686 | 4.049 | 1.00 | 36.25 | N |
| ATOM | 1283 | CA | LEU A 386 | 16.663 | 56.584 | 3.793 | 1.00 | 36.07 | C |
| ATOM | 1284 | C | LEU A 386 | 16.050 | 56.119 | 5.108 | 1.00 | 37.34 | C |
| ATOM | 1285 | O | LEU A 386 | 14.853 | 55.784 | 5.090 | 1.00 | 38.83 | O |
| ATOM | 1286 | CB | LEU A 386 | 17.327 | 55.519 | 2.975 | 1.00 | 35.85 | C |
| ATOM | 1287 | CG | LEU A 386 | 17.984 | 56.047 | 1.673 | 1.00 | 38.10 | C |
| ATOM | 1288 | CD1 | LEU A 386 | 18.569 | 54.832 | 0.935 | 1.00 | 36.67 | C |
| ATOM | 1289 | CD2 | LEU A 386 | 17.052 | 56.835 | 0.759 | 1.00 | 33.79 | C |
| ATOM | 1290 | N | LEU A 387 | 16.725 | 56.109 | 6.263 | 1.00 | 37.18 | N |
| ATOM | 1291 | CA | LEU A 387 | 16.071 | 55.677 | 7.483 | 1.00 | 37.43 | C |
| ATOM | 1292 | C | LEU A 387 | 14.981 | 56.648 | 7.924 | 1.00 | 37.49 | C |
| ATOM | 1293 | O | LEU A 387 | 13.939 | 56.169 | 8.390 | 1.00 | 36.07 | O |
| ATOM | 1294 | CB | LEU A 387 | 17.066 | 55.513 | 8.632 | 1.00 | 37.95 | C |
| ATOM | 1295 | CG | LEU A 387 | 17.800 | 54.192 | 8.502 | 1.00 | 39.76 | C |
| ATOM | 1296 | CD1 | LEU A 387 | 19.049 | 54.178 | 9.342 | 1.00 | 39.61 | C |
| ATOM | 1297 | CD2 | LEU A 387 | 16.827 | 53.056 | 8.838 | 1.00 | 38.62 | C |
| ATOM | 1298 | N | ASN A 388 | 15.227 | 57.957 | 7.726 | 1.00 | 36.63 | N |
| ATOM | 1299 | CA | ASN A 388 | 14.209 | 58.920 | 8.151 | 1.00 | 36.65 | C |
| ATOM | 1300 | C | ASN A 388 | 12.886 | 58.656 | 7.457 | 1.00 | 36.83 | C |
| ATOM | 1301 | O | ASN A 388 | 11.818 | 58.569 | 8.085 | 1.00 | 38.42 | O |

| | | | | | | | | | |
|---|---|---|---|---|---|---|---|---|---|
| ATOM | 1148 | CZ | TYR A 368 | 36.402 | 43.666 | 8.977 | 1.00 | 72.61 | C |
| ATOM | 1149 | OH | TYR A 368 | 37.655 | 43.086 | 9.128 | 1.00 | 74.80 | O |
| ATOM | 1150 | N | PRO A 369 | 34.477 | 46.085 | 5.757 | 1.00 | 55.93 | N |
| ATOM | 1151 | CA | PRO A 369 | 35.281 | 46.953 | 6.583 | 1.00 | 53.70 | C |
| ATOM | 1152 | C | PRO A 369 | 34.905 | 48.402 | 6.307 | 1.00 | 54.29 | C |
| ATOM | 1153 | O | PRO A 369 | 34.070 | 48.652 | 5.402 | 1.00 | 56.40 | O |
| ATOM | 1154 | CB | PRO A 369 | 36.725 | 46.693 | 6.177 | 1.00 | 54.89 | C |
| ATOM | 1155 | CG | PRO A 369 | 36.653 | 45.828 | 4.950 | 1.00 | 53.85 | C |
| ATOM | 1156 | CD | PRO A 369 | 35.232 | 45.583 | 4.596 | 1.00 | 54.69 | C |
| ATOM | 1157 | N | LEU A 370 | 35.421 | 49.401 | 7.000 | 1.00 | 51.28 | N |
| ATOM | 1158 | CA | LEU A 370 | 35.095 | 50.802 | 6.884 | 1.00 | 47.42 | C |
| ATOM | 1159 | C | LEU A 370 | 35.933 | 51.618 | 5.928 | 1.00 | 47.66 | C |
| ATOM | 1160 | O | LEU A 370 | 37.108 | 51.378 | 5.669 | 1.00 | 48.71 | O |
| ATOM | 1161 | CB | LEU A 370 | 35.176 | 51.458 | 8.280 | 1.00 | 46.49 | C |
| ATOM | 1162 | CG | LEU A 370 | 34.074 | 51.040 | 9.256 | 1.00 | 45.15 | C |
| ATOM | 1163 | CD1 | LEU A 370 | 34.485 | 51.248 | 10.691 | 1.00 | 44.13 | C |
| ATOM | 1164 | CD2 | LEU A 370 | 32.792 | 51.822 | 9.003 | 1.00 | 45.88 | C |
| ATOM | 1165 | N | ALA A 371 | 35.341 | 52.648 | 5.325 | 1.00 | 45.97 | N |
| ATOM | 1166 | CA | ALA A 371 | 36.039 | 53.474 | 4.355 | 1.00 | 43.92 | C |
| ATOM | 1167 | C | ALA A 371 | 36.758 | 54.561 | 5.134 | 1.00 | 44.40 | C |
| ATOM | 1168 | O | ALA A 371 | 36.858 | 54.374 | 6.329 | 1.00 | 46.64 | O |
| ATOM | 1169 | CB | ALA A 371 | 35.085 | 54.009 | 3.297 | 1.00 | 41.06 | C |
| ATOM | 1170 | N | SER A 372 | 37.236 | 55.634 | 4.544 | 1.00 | 44.28 | N |
| ATOM | 1171 | CA | SER A 372 | 37.883 | 56.667 | 5.296 | 1.00 | 45.75 | C |
| ATOM | 1172 | C | SER A 372 | 36.740 | 57.383 | 6.010 | 1.00 | 50.45 | C |
| ATOM | 1173 | O | SER A 372 | 35.547 | 57.241 | 5.664 | 1.00 | 51.34 | O |
| ATOM | 1174 | CB | SER A 372 | 38.585 | 57.620 | 4.362 | 1.00 | 45.81 | C |
| ATOM | 1175 | OG | SER A 372 | 37.624 | 58.441 | 3.695 | 1.00 | 47.81 | O |
| ATOM | 1176 | N | ALA A 373 | 37.089 | 58.182 | 7.026 | 1.00 | 52.49 | N |
| ATOM | 1177 | CA | ALA A 373 | 36.025 | 58.894 | 7.754 | 1.00 | 53.34 | C |
| ATOM | 1178 | C | ALA A 373 | 35.155 | 59.739 | 6.837 | 1.00 | 54.02 | C |
| ATOM | 1179 | O | ALA A 373 | 33.925 | 59.803 | 6.939 | 1.00 | 54.05 | O |
| ATOM | 1180 | CB | ALA A 373 | 36.620 | 59.625 | 8.946 | 1.00 | 50.72 | C |
| ATOM | 1181 | N | ASN A 374 | 35.742 | 60.442 | 5.891 | 1.00 | 56.57 | N |
| ATOM | 1182 | CA | ASN A 374 | 35.104 | 61.295 | 4.916 | 1.00 | 57.03 | C |
| ATOM | 1183 | C | ASN A 374 | 34.129 | 60.479 | 4.079 | 1.00 | 55.70 | C |
| ATOM | 1184 | O | ASN A 374 | 32.966 | 60.765 | 3.893 | 1.00 | 56.12 | O |
| ATOM | 1185 | CB | ASN A 374 | 36.160 | 61.806 | 3.933 | 1.00 | 60.55 | C |
| ATOM | 1186 | CG | ASN A 374 | 35.978 | 63.308 | 3.908 | 1.00 | 64.92 | C |
| ATOM | 1187 | OD1 | ASN A 374 | 35.054 | 63.780 | 3.257 | 1.00 | 66.39 | O |
| ATOM | 1188 | ND2 | ASN A 374 | 36.863 | 64.010 | 4.625 | 1.00 | 68.15 | N |
| ATOM | 1189 | N | GLN A 375 | 34.665 | 59.380 | 3.578 | 1.00 | 53.86 | N |
| ATOM | 1190 | CA | GLN A 375 | 33.884 | 58.479 | 2.768 | 1.00 | 53.01 | C |
| ATOM | 1191 | C | GLN A 375 | 32.663 | 58.015 | 3.532 | 1.00 | 52.02 | C |
| ATOM | 1192 | O | GLN A 375 | 31.537 | 58.156 | 3.068 | 1.00 | 51.59 | O |
| ATOM | 1193 | CB | GLN A 375 | 34.783 | 57.320 | 2.299 | 1.00 | 53.37 | C |
| ATOM | 1194 | CG | GLN A 375 | 35.641 | 57.792 | 1.122 | 1.00 | 51.99 | C |
| ATOM | 1195 | CD | GLN A 375 | 36.766 | 56.813 | 0.832 | 1.00 | 52.39 | C |
| ATOM | 1196 | OE1 | GLN A 375 | 37.106 | 55.934 | 1.643 | 1.00 | 51.38 | O |
| ATOM | 1197 | NE2 | GLN A 375 | 37.317 | 56.983 | -0.369 | 1.00 | 50.29 | N |
| ATOM | 1198 | N | GLU A 376 | 32.885 | 57.487 | 4.719 | 1.00 | 53.13 | N |
| ATOM | 1199 | CA | GLU A 376 | 31.844 | 56.972 | 5.602 | 1.00 | 52.34 | C |
| ATOM | 1200 | C | GLU A 376 | 30.901 | 58.100 | 5.943 | 1.00 | 50.07 | C |
| ATOM | 1201 | O | GLU A 376 | 29.724 | 57.791 | 6.097 | 1.00 | 50.04 | O |
| ATOM | 1202 | CB | GLU A 376 | 32.392 | 56.260 | 6.823 | 1.00 | 54.56 | C |
| ATOM | 1203 | CG | GLU A 376 | 33.103 | 54.934 | 6.566 | 1.00 | 58.16 | C |
| ATOM | 1204 | CD | GLU A 376 | 32.208 | 53.859 | 5.997 | 1.00 | 60.59 | C |
| ATOM | 1205 | OE1 | GLU A 376 | 30.966 | 54.012 | 6.214 | 1.00 | 63.74 | O |
| ATOM | 1206 | OE2 | GLU A 376 | 32.595 | 52.867 | 5.325 | 1.00 | 60.39 | O |
| ATOM | 1207 | N | ALA A 377 | 31.338 | 59.361 | 5.977 | 1.00 | 48.11 | N |
| ATOM | 1208 | CA | ALA A 377 | 30.337 | 60.397 | 6.277 | 1.00 | 47.85 | C |
| ATOM | 1209 | C | ALA A 377 | 29.371 | 60.439 | 5.106 | 1.00 | 49.32 | C |
| ATOM | 1210 | O | ALA A 377 | 28.151 | 60.522 | 5.278 | 1.00 | 49.74 | O |
| ATOM | 1211 | CB | ALA A 377 | 30.994 | 61.681 | 6.655 | 1.00 | 45.36 | C |
| ATOM | 1212 | N | GLU A 378 | 29.888 | 60.335 | 3.872 | 1.00 | 51.22 | N |
| ATOM | 1213 | CA | GLU A 378 | 29.039 | 60.333 | 2.698 | 1.00 | 52.60 | C |
| ATOM | 1214 | C | GLU A 378 | 27.957 | 59.253 | 2.773 | 1.00 | 52.91 | C |
| ATOM | 1215 | O | GLU A 378 | 26.779 | 59.637 | 2.758 | 1.00 | 54.77 | O |
| ATOM | 1216 | CB | GLU A 378 | 29.773 | 60.210 | 1.371 | 1.00 | 53.27 | C |
| ATOM | 1217 | CG | GLU A 378 | 28.863 | 60.678 | 0.258 | 1.00 | 54.94 | C |
| ATOM | 1218 | CD | GLU A 378 | 29.314 | 60.484 | -1.157 | 1.00 | 57.63 | C |
| ATOM | 1219 | OE1 | GLU A 378 | 30.508 | 60.426 | -1.515 | 1.00 | 58.38 | O |
| ATOM | 1220 | OE2 | GLU A 378 | 28.388 | 60.380 | -2.007 | 1.00 | 59.32 | O |
| ATOM | 1221 | N | SER A 379 | 28.279 | 57.981 | 2.890 | 1.00 | 51.84 | N |
| ATOM | 1222 | CA | SER A 379 | 27.290 | 56.921 | 2.984 | 1.00 | 51.73 | C |
| ATOM | 1223 | C | SER A 379 | 26.280 | 57.086 | 4.134 | 1.00 | 51.86 | C |
| ATOM | 1224 | O | SER A 379 | 25.149 | 56.635 | 3.988 | 1.00 | 50.46 | O |

| | | | | | | | | | |
|---|---|---|---|---|---|---|---|---|---|
| ATOM | 1071 | CE | LYS | A | 358 | 10.682 | 41.677 | 6.060 | 1.00 38.77 | C |
| ATOM | 1072 | NZ | LYS | A | 358 | 10.804 | 41.217 | 4.649 | 1.00 41.29 | N |
| ATOM | 1073 | N | ALA | A | 359 | 12.825 | 46.838 | 7.025 | 1.00 35.17 | N |
| ATOM | 1074 | CA | ALA | A | 359 | 13.580 | 47.730 | 6.132 | 1.00 34.53 | C |
| ATOM | 1075 | C | ALA | A | 359 | 14.608 | 48.467 | 6.982 | 1.00 37.51 | C |
| ATOM | 1076 | O | ALA | A | 359 | 15.686 | 48.737 | 6.440 | 1.00 38.27 | O |
| ATOM | 1077 | CB | ALA | A | 359 | 12.686 | 48.664 | 5.392 | 1.00 34.56 | C |
| ATOM | 1078 | N | MET | A | 360 | 14.293 | 48.755 | 8.275 | 1.00 38.34 | N |
| ATOM | 1079 | CA | MET | A | 360 | 15.287 | 49.427 | 9.093 | 1.00 37.98 | C |
| ATOM | 1080 | C | MET | A | 360 | 16.465 | 48.518 | 9.405 | 1.00 37.79 | C |
| ATOM | 1081 | O | MET | A | 360 | 17.604 | 49.023 | 9.465 | 1.00 36.44 | O |
| ATOM | 1082 | CB | MET | A | 360 | 14.760 | 50.006 | 10.394 | 1.00 38.06 | C |
| ATOM | 1083 | CG | MET | A | 360 | 13.633 | 51.015 | 10.137 | 1.00 37.38 | C |
| ATOM | 1084 | SD | MET | A | 360 | 12.909 | 51.386 | 11.756 | 1.00 37.01 | S |
| ATOM | 1085 | CE | MET | A | 360 | 11.640 | 52.555 | 11.327 | 1.00 35.32 | C |
| ATOM | 1086 | N | ILE | A | 361 | 16.184 | 47.222 | 9.575 | 1.00 39.08 | N |
| ATOM | 1087 | CA | ILE | A | 361 | 17.302 | 46.287 | 9.876 | 1.00 40.97 | C |
| ATOM | 1088 | C | ILE | A | 361 | 18.258 | 46.358 | 8.698 | 1.00 41.09 | C |
| ATOM | 1089 | O | ILE | A | 361 | 19.445 | 46.561 | 8.921 | 1.00 41.53 | O |
| ATOM | 1090 | CB | ILE | A | 361 | 16.834 | 44.888 | 10.221 | 1.00 42.70 | C |
| ATOM | 1091 | CG1 | ILE | A | 361 | 16.186 | 44.849 | 11.605 | 1.00 41.62 | C |
| ATOM | 1092 | CG2 | ILE | A | 361 | 17.925 | 43.821 | 10.149 | 1.00 44.32 | C |
| ATOM | 1093 | CD1 | ILE | A | 361 | 15.125 | 43.768 | 11.729 | 1.00 40.02 | C |
| ATOM | 1094 | N | LEU | A | 362 | 17.800 | 46.323 | 7.449 | 1.00 41.21 | N |
| ATOM | 1095 | CA | LEU | A | 362 | 18.693 | 46.467 | 6.317 | 1.00 39.23 | C |
| ATOM | 1096 | C | LEU | A | 362 | 19.390 | 47.820 | 6.260 | 1.00 40.73 | C |
| ATOM | 1097 | O | LEU | A | 362 | 20.631 | 47.932 | 6.209 | 1.00 40.44 | O |
| ATOM | 1098 | CB | LEU | A | 362 | 17.861 | 46.370 | 5.054 | 1.00 38.38 | C |
| ATOM | 1099 | CG | LEU | A | 362 | 18.614 | 46.548 | 3.725 | 1.00 38.62 | C |
| ATOM | 1100 | CD1 | LEU | A | 362 | 19.703 | 45.505 | 3.585 | 1.00 38.35 | C |
| ATOM | 1101 | CD2 | LEU | A | 362 | 17.584 | 46.492 | 2.608 | 1.00 37.84 | C |
| ATOM | 1102 | N | LEU | A | 363 | 18.600 | 48.910 | 6.214 | 1.00 39.57 | N |
| ATOM | 1103 | CA | LEU | A | 363 | 19.318 | 50.183 | 6.109 | 1.00 39.41 | C |
| ATOM | 1104 | C | LEU | A | 363 | 20.116 | 50.580 | 7.313 | 1.00 41.50 | C |
| ATOM | 1105 | O | LEU | A | 363 | 20.998 | 51.394 | 7.030 | 1.00 44.51 | O |
| ATOM | 1106 | CB | LEU | A | 363 | 18.370 | 51.314 | 5.729 | 1.00 38.44 | C |
| ATOM | 1107 | CG | LEU | A | 363 | 17.659 | 51.037 | 4.384 | 1.00 37.69 | C |
| ATOM | 1108 | CD1 | LEU | A | 363 | 16.353 | 51.826 | 4.403 | 1.00 36.26 | C |
| ATOM | 1109 | CD2 | LEU | A | 363 | 18.595 | 51.436 | 3.244 | 1.00 35.74 | C |
| ATOM | 1110 | N | ASN | A | 364 | 19.932 | 50.142 | 8.553 | 1.00 40.81 | N |
| ATOM | 1111 | CA | ASN | A | 364 | 20.729 | 50.561 | 9.690 | 1.00 38.22 | C |
| ATOM | 1112 | C | ASN | A | 364 | 21.917 | 49.640 | 9.954 | 1.00 38.51 | C |
| ATOM | 1113 | O | ASN | A | 364 | 22.616 | 49.638 | 10.974 | 1.00 37.26 | O |
| ATOM | 1114 | CB | ASN | A | 364 | 19.828 | 50.513 | 10.917 | 1.00 38.24 | C |
| ATOM | 1115 | CG | ASN | A | 364 | 20.383 | 51.061 | 12.197 | 1.00 37.31 | C |
| ATOM | 1116 | OD1 | ASN | A | 364 | 21.116 | 52.045 | 12.082 | 1.00 39.77 | O |
| ATOM | 1117 | ND2 | ASN | A | 364 | 20.116 | 50.527 | 13.386 | 1.00 36.27 | N |
| ATOM | 1118 | N | SER | A | 365 | 22.155 | 48.739 | 9.038 | 1.00 39.53 | N |
| ATOM | 1119 | CA | SER | A | 365 | 23.178 | 47.732 | 8.991 | 1.00 41.35 | C |
| ATOM | 1120 | C | SER | A | 365 | 24.558 | 48.366 | 9.088 | 1.00 42.97 | C |
| ATOM | 1121 | O | SER | A | 365 | 24.767 | 49.435 | 8.574 | 1.00 42.06 | O |
| ATOM | 1122 | CB | SER | A | 365 | 23.099 | 46.959 | 7.668 | 1.00 41.38 | C |
| ATOM | 1123 | OG | SER | A | 365 | 23.869 | 45.773 | 7.764 | 1.00 43.63 | O |
| ATOM | 1124 | N | SER | A | 366 | 25.463 | 47.711 | 9.752 | 1.00 47.44 | N |
| ATOM | 1125 | CA | SER | A | 366 | 26.827 | 48.172 | 9.921 | 1.00 52.33 | C |
| ATOM | 1126 | C | SER | A | 366 | 27.720 | 47.716 | 8.789 | 1.00 53.78 | C |
| ATOM | 1127 | O | SER | A | 366 | 27.921 | 46.506 | 8.718 | 1.00 55.73 | O |
| ATOM | 1128 | CB | SER | A | 366 | 27.390 | 47.539 | 11.215 | 1.00 52.93 | C |
| ATOM | 1129 | OG | SER | A | 366 | 26.637 | 48.165 | 12.280 | 1.00 56.84 | O |
| ATOM | 1130 | N | MET | A | 367 | 28.276 | 48.600 | 7.978 | 1.00 55.08 | N |
| ATOM | 1131 | CA | MET | A | 367 | 29.160 | 48.128 | 6.905 | 1.00 54.03 | C |
| ATOM | 1132 | C | MET | A | 367 | 30.557 | 47.787 | 7.360 | 1.00 54.79 | C |
| ATOM | 1133 | O | MET | A | 367 | 31.114 | 48.488 | 8.190 | 1.00 56.70 | O |
| ATOM | 1134 | CB | MET | A | 367 | 29.152 | 49.170 | 5.798 | 1.00 52.07 | C |
| ATOM | 1135 | CG | MET | A | 367 | 27.726 | 49.313 | 5.235 | 1.00 50.80 | C |
| ATOM | 1136 | SD | MET | A | 367 | 27.679 | 50.553 | 3.956 | 1.00 50.05 | S |
| ATOM | 1137 | CE | MET | A | 367 | 28.605 | 51.920 | 4.656 | 1.00 48.47 | C |
| ATOM | 1138 | N | TYR | A | 368 | 31.140 | 46.719 | 6.845 | 1.00 56.79 | N |
| ATOM | 1139 | CA | TYR | A | 368 | 32.504 | 46.327 | 7.176 | 1.00 59.40 | C |
| ATOM | 1140 | C | TYR | A | 368 | 33.197 | 45.783 | 5.934 | 1.00 58.11 | C |
| ATOM | 1141 | O | TYR | A | 368 | 32.608 | 45.066 | 5.121 | 1.00 57.98 | O |
| ATOM | 1142 | CB | TYR | A | 368 | 32.493 | 45.299 | 8.317 | 1.00 63.90 | C |
| ATOM | 1143 | CG | TYR | A | 368 | 33.868 | 44.745 | 8.598 | 1.00 68.58 | C |
| ATOM | 1144 | CD1 | TYR | A | 368 | 34.278 | 43.618 | 7.870 | 1.00 70.67 | C |
| ATOM | 1145 | CD2 | TYR | A | 368 | 34.757 | 45.314 | 9.514 | 1.00 69.62 | C |
| ATOM | 1146 | CE1 | TYR | A | 368 | 35.543 | 43.077 | 8.068 | 1.00 72.01 | C |
| ATOM | 1147 | CE2 | TYR | A | 368 | 36.021 | 44.777 | 9.701 | 1.00 70.98 | C |

83

| ATOM | 994 | N | GLN | A | 350 | 2.089 | 44.907 | 14.505 | 1.00 | 51.43 | N |
| ATOM | 995 | CA | GLN | A | 350 | 1.224 | 44.919 | 13.339 | 1.00 | 52.06 | C |
| ATOM | 996 | C | GLN | A | 350 | 2.055 | 44.705 | 12.095 | 1.00 | 51.72 | C |
| ATOM | 997 | O | GLN | A | 350 | 3.195 | 45.174 | 12.009 | 1.00 | 53.46 | O |
| ATOM | 998 | CB | GLN | A | 350 | 0.540 | 46.276 | 13.348 | 1.00 | 55.71 | C |
| ATOM | 999 | CG | GLN | A | 350 | -0.399 | 46.532 | 14.524 | 1.00 | 57.85 | C |
| ATOM | 1000 | CD | GLN | A | 350 | -1.588 | 45.587 | 14.380 | 1.00 | 60.79 | C |
| ATOM | 1001 | OE1 | GLN | A | 350 | -2.567 | 46.067 | 13.793 | 1.00 | 63.77 | O |
| ATOM | 1002 | NE2 | GLN | A | 350 | -1.507 | 44.351 | 14.849 | 1.00 | 59.97 | N |
| ATOM | 1003 | N | HIS | A | 351 | 1.583 | 43.982 | 11.099 | 1.00 | 49.25 | N |
| ATOM | 1004 | CA | HIS | A | 351 | 2.203 | 43.674 | 9.845 | 1.00 | 45.44 | C |
| ATOM | 1005 | C | HIS | A | 351 | 2.930 | 44.850 | 9.209 | 1.00 | 45.03 | C |
| ATOM | 1006 | O | HIS | A | 351 | 4.095 | 44.748 | 8.776 | 1.00 | 45.71 | O |
| ATOM | 1007 | CB | HIS | A | 351 | 1.137 | 43.190 | 8.826 | 1.00 | 43.63 | C |
| ATOM | 1008 | CG | HIS | A | 351 | 1.828 | 42.520 | 7.685 | 1.00 | 43.89 | C |
| ATOM | 1009 | ND1 | HIS | A | 351 | 1.547 | 42.780 | 6.367 | 1.00 | 44.22 | N |
| ATOM | 1010 | CD2 | HIS | A | 351 | 2.844 | 41.593 | 7.698 | 1.00 | 42.97 | C |
| ATOM | 1011 | CE1 | HIS | A | 351 | 2.340 | 42.024 | 5.605 | 1.00 | 44.56 | C |
| ATOM | 1012 | NE2 | HIS | A | 351 | 3.131 | 41.308 | 6.390 | 1.00 | 43.15 | N |
| ATOM | 1013 | N | LYS | A | 352 | 2.252 | 45.996 | 9.153 | 1.00 | 42.91 | N |
| ATOM | 1014 | CA | LYS | A | 352 | 2.877 | 47.175 | 8.574 | 1.00 | 43.26 | C |
| ATOM | 1015 | C | LYS | A | 352 | 4.000 | 47.655 | 9.460 | 1.00 | 44.09 | C |
| ATOM | 1016 | O | LYS | A | 352 | 4.948 | 48.251 | 8.931 | 1.00 | 47.74 | O |
| ATOM | 1017 | CB | LYS | A | 352 | 1.875 | 48.270 | 8.215 | 1.00 | 42.67 | C |
| ATOM | 1018 | CG | LYS | A | 352 | 0.862 | 47.760 | 7.175 | 1.00 | 42.26 | C |
| ATOM | 1019 | CD | LYS | A | 352 | 0.006 | 48.876 | 6.634 | 1.00 | 42.12 | C |
| ATOM | 1020 | CE | LYS | A | 352 | -0.947 | 49.498 | 7.635 | 1.00 | 42.32 | C |
| ATOM | 1021 | NZ | LYS | A | 352 | -2.124 | 48.614 | 7.944 | 1.00 | 43.47 | N |
| ATOM | 1022 | N | GLU | A | 353 | 3.965 | 47.438 | 10.756 | 1.00 | 43.71 | N |
| ATOM | 1023 | CA | GLU | A | 353 | 5.001 | 47.863 | 11.680 | 1.00 | 42.91 | C |
| ATOM | 1024 | C | GLU | A | 353 | 6.208 | 46.988 | 11.397 | 1.00 | 42.87 | C |
| ATOM | 1025 | O | GLU | A | 353 | 7.327 | 47.460 | 11.206 | 1.00 | 43.43 | O |
| ATOM | 1026 | CB | GLU | A | 353 | 4.558 | 47.697 | 13.134 | 1.00 | 42.82 | C |
| ATOM | 1027 | CG | GLU | A | 353 | 3.380 | 48.611 | 13.494 | 1.00 | 42.01 | C |
| ATOM | 1028 | CD | GLU | A | 353 | 2.926 | 48.385 | 14.931 | 1.00 | 41.74 | C |
| ATOM | 1029 | OE1 | GLU | A | 353 | 2.887 | 47.217 | 15.385 | 1.00 | 39.84 | O |
| ATOM | 1030 | OE2 | GLU | A | 353 | 2.598 | 49.413 | 15.560 | 1.00 | 42.14 | O |
| ATOM | 1031 | N | TYR | A | 354 | 5.938 | 45.692 | 11.328 | 1.00 | 42.13 | N |
| ATOM | 1032 | CA | TYR | A | 354 | 6.984 | 44.713 | 11.067 | 1.00 | 42.59 | C |
| ATOM | 1033 | C | TYR | A | 354 | 7.694 | 45.052 | 9.757 | 1.00 | 44.80 | C |
| ATOM | 1034 | O | TYR | A | 354 | 8.935 | 44.979 | 9.646 | 1.00 | 44.68 | O |
| ATOM | 1035 | CB | TYR | A | 354 | 6.300 | 43.343 | 11.035 | 1.00 | 42.54 | C |
| ATOM | 1036 | CG | TYR | A | 354 | 7.111 | 42.349 | 10.263 | 1.00 | 42.61 | C |
| ATOM | 1037 | CD1 | TYR | A | 354 | 8.272 | 41.845 | 10.836 | 1.00 | 42.26 | C |
| ATOM | 1038 | CD2 | TYR | A | 354 | 6.758 | 41.948 | 8.978 | 1.00 | 43.31 | C |
| ATOM | 1039 | CE1 | TYR | A | 354 | 9.046 | 40.942 | 10.127 | 1.00 | 42.85 | C |
| ATOM | 1040 | CE2 | TYR | A | 354 | 7.533 | 41.037 | 8.258 | 1.00 | 41.81 | C |
| ATOM | 1041 | CZ | TYR | A | 354 | 8.673 | 40.563 | 8.856 | 1.00 | 42.42 | C |
| ATOM | 1042 | OH | TYR | A | 354 | 9.495 | 39.663 | 8.231 | 1.00 | 45.09 | O |
| ATOM | 1043 | N | LEU | A | 355 | 6.909 | 45.451 | 8.736 | 1.00 | 45.15 | N |
| ATOM | 1044 | CA | LEU | A | 355 | 7.460 | 45.827 | 7.432 | 1.00 | 44.26 | C |
| ATOM | 1045 | C | LEU | A | 355 | 8.451 | 46.980 | 7.579 | 1.00 | 44.09 | C |
| ATOM | 1046 | O | LEU | A | 355 | 9.573 | 46.924 | 7.028 | 1.00 | 44.41 | O |
| ATOM | 1047 | CB | LEU | A | 355 | 6.323 | 46.129 | 6.490 | 1.00 | 43.91 | C |
| ATOM | 1048 | CG | LEU | A | 355 | 5.887 | 45.188 | 5.374 | 1.00 | 43.08 | C |
| ATOM | 1049 | CD1 | LEU | A | 355 | 6.336 | 43.745 | 5.493 | 1.00 | 40.80 | C |
| ATOM | 1050 | CD2 | LEU | A | 355 | 4.355 | 45.273 | 5.321 | 1.00 | 41.35 | C |
| ATOM | 1051 | N | CYS | A | 356 | 8.109 | 48.008 | 8.361 | 1.00 | 41.19 | N |
| ATOM | 1052 | CA | CYS | A | 356 | 9.076 | 49.086 | 8.565 | 1.00 | 40.48 | C |
| ATOM | 1053 | C | CYS | A | 356 | 10.275 | 48.594 | 9.381 | 1.00 | 41.32 | C |
| ATOM | 1054 | O | CYS | A | 356 | 11.443 | 48.999 | 9.134 | 1.00 | 41.20 | O |
| ATOM | 1055 | CB | CYS | A | 356 | 8.398 | 50.262 | 9.236 | 1.00 | 39.76 | C |
| ATOM | 1056 | SG | CYS | A | 356 | 7.066 | 50.987 | 8.262 | 1.00 | 38.30 | S |
| ATOM | 1057 | N | VAL | A | 357 | 10.014 | 47.664 | 10.335 | 1.00 | 39.88 | N |
| ATOM | 1058 | CA | VAL | A | 357 | 11.178 | 47.202 | 11.119 | 1.00 | 40.11 | C |
| ATOM | 1059 | C | VAL | A | 357 | 12.150 | 46.428 | 10.252 | 1.00 | 40.31 | C |
| ATOM | 1060 | O | VAL | A | 357 | 13.362 | 46.584 | 10.442 | 1.00 | 39.07 | O |
| ATOM | 1061 | CB | VAL | A | 357 | 10.751 | 46.493 | 12.413 | 1.00 | 40.08 | C |
| ATOM | 1062 | CG1 | VAL | A | 357 | 11.876 | 45.799 | 13.156 | 1.00 | 39.24 | C |
| ATOM | 1063 | CG2 | VAL | A | 357 | 10.133 | 47.580 | 13.319 | 1.00 | 38.97 | C |
| ATOM | 1064 | N | LYS | A | 358 | 11.666 | 45.652 | 9.262 | 1.00 | 38.75 | N |
| ATOM | 1065 | CA | LYS | A | 358 | 12.609 | 44.899 | 8.436 | 1.00 | 35.91 | C |
| ATOM | 1066 | C | LYS | A | 358 | 13.441 | 45.771 | 7.536 | 1.00 | 34.70 | C |
| ATOM | 1067 | O | LYS | A | 358 | 14.635 | 45.500 | 7.326 | 1.00 | 33.39 | O |
| ATOM | 1068 | CB | LYS | A | 358 | 11.928 | 43.799 | 7.650 | 1.00 | 35.59 | C |
| ATOM | 1069 | CG | LYS | A | 358 | 12.760 | 42.680 | 7.130 | 1.00 | 35.40 | C |
| ATOM | 1070 | CD | LYS | A | 358 | 11.955 | 41.418 | 6.847 | 1.00 | 37.84 | C |

| | | | | | | | | | |
|---|---|---|---|---|---|---|---|---|---|
| ATOM | 917 | O | THR | A 341 | 7.352 | 37.807 | 20.038 | 1.00 51.46 | O |
| ATOM | 918 | CB | THR | A 341 | 8.931 | 35.301 | 18.812 | 1.00 48.67 | C |
| ATOM | 919 | OG1 | THR | A 341 | 9.812 | 34.820 | 17.802 | 1.00 48.53 | O |
| ATOM | 920 | CG2 | THR | A 341 | 7.498 | 35.225 | 18.289 | 1.00 46.02 | C |
| ATOM | 921 | N | SER | A 342 | 8.449 | 36.642 | 21.599 | 1.00 51.25 | N |
| ATOM | 922 | CA | SER | A 342 | 7.441 | 36.974 | 22.616 | 1.00 52.84 | C |
| ATOM | 923 | C | SER | A 342 | 7.195 | 38.447 | 22.876 | 1.00 52.89 | C |
| ATOM | 924 | O | SER | A 342 | 6.045 | 38.855 | 23.107 | 1.00 52.28 | O |
| ATOM | 925 | CB | SER | A 342 | 7.761 | 36.305 | 23.970 | 1.00 52.17 | C |
| ATOM | 926 | OG | SER | A 342 | 7.598 | 34.904 | 23.738 | 1.00 52.55 | O |
| ATOM | 927 | N | ARG | A 343 | 8.260 | 39.243 | 22.810 | 1.00 52.70 | N |
| ATOM | 928 | CA | ARG | A 343 | 8.146 | 40.684 | 23.047 | 1.00 53.62 | C |
| ATOM | 929 | C | ARG | A 343 | 7.261 | 41.270 | 21.961 | 1.00 53.64 | C |
| ATOM | 930 | O | ARG | A 343 | 6.372 | 42.089 | 22.193 | 1.00 52.07 | O |
| ATOM | 931 | CB | ARG | A 343 | 9.561 | 41.270 | 23.117 | 1.00 54.80 | C |
| ATOM | 932 | CG | ARG | A 343 | 10.423 | 40.668 | 24.224 | 1.00 55.65 | C |
| ATOM | 933 | CD | ARG | A 343 | 9.866 | 40.886 | 25.629 | 1.00 56.47 | C |
| ATOM | 934 | NE | ARG | A 343 | 9.052 | 39.816 | 26.187 | 1.00 57.70 | N |
| ATOM | 935 | CZ | ARG | A 343 | 9.448 | 38.700 | 26.804 | 1.00 59.34 | C |
| ATOM | 936 | NH1 | ARG | A 343 | 10.701 | 38.302 | 27.063 | 1.00 58.24 | N |
| ATOM | 937 | NH2 | ARG | A 343 | 8.508 | 37.860 | 27.238 | 1.00 59.49 | N |
| ATOM | 938 | N | PHE | A 344 | 7.503 | 40.739 | 20.750 | 1.00 53.60 | N |
| ATOM | 939 | CA | PHE | A 344 | 6.739 | 41.117 | 19.576 | 1.00 53.90 | C |
| ATOM | 940 | C | PHE | A 344 | 5.291 | 40.711 | 19.800 | 1.00 52.79 | C |
| ATOM | 941 | O | PHE | A 344 | 4.375 | 41.521 | 19.535 | 1.00 52.41 | O |
| ATOM | 942 | CB | PHE | A 344 | 7.285 | 40.535 | 18.263 | 1.00 54.75 | C |
| ATOM | 943 | CG | PHE | A 344 | 8.484 | 41.300 | 17.787 | 1.00 55.40 | C |
| ATOM | 944 | CD1 | PHE | A 344 | 8.525 | 42.693 | 17.870 | 1.00 56.19 | C |
| ATOM | 945 | CD2 | PHE | A 344 | 9.560 | 40.633 | 17.247 | 1.00 55.65 | C |
| ATOM | 946 | CE1 | PHE | A 344 | 9.637 | 43.383 | 17.414 | 1.00 57.27 | C |
| ATOM | 947 | CE2 | PHE | A 344 | 10.677 | 41.316 | 16.803 | 1.00 56.22 | C |
| ATOM | 948 | CZ | PHE | A 344 | 10.715 | 42.695 | 16.880 | 1.00 57.25 | C |
| ATOM | 949 | N | ARG | A 345 | 5.132 | 39.478 | 20.281 | 1.00 51.36 | N |
| ATOM | 950 | CA | ARG | A 345 | 3.756 | 39.049 | 20.563 | 1.00 53.53 | C |
| ATOM | 951 | C | ARG | A 345 | 3.128 | 39.995 | 21.598 | 1.00 54.68 | C |
| ATOM | 952 | O | ARG | A 345 | 2.046 | 40.574 | 21.425 | 1.00 54.49 | O |
| ATOM | 953 | CB | ARG | A 345 | 3.715 | 37.664 | 21.182 | 1.00 53.48 | C |
| ATOM | 954 | CG | ARG | A 345 | 2.314 | 37.214 | 21.532 | 1.00 52.85 | C |
| ATOM | 955 | CD | ARG | A 345 | 2.296 | 35.756 | 21.938 | 1.00 53.78 | C |
| ATOM | 956 | NE | ARG | A 345 | 3.134 | 34.878 | 21.163 | 1.00 54.53 | N |
| ATOM | 957 | CZ | ARG | A 345 | 4.257 | 34.309 | 21.592 | 1.00 56.59 | C |
| ATOM | 958 | NH1 | ARG | A 345 | 4.750 | 34.473 | 22.825 | 1.00 56.53 | N |
| ATOM | 959 | NH2 | ARG | A 345 | 4.872 | 33.536 | 20.690 | 1.00 57.05 | N |
| ATOM | 960 | N | GLU | A 346 | 3.911 | 40.156 | 22.684 | 1.00 54.42 | N |
| ATOM | 961 | CA | GLU | A 346 | 3.445 | 41.019 | 23.753 | 1.00 56.12 | C |
| ATOM | 962 | C | GLU | A 346 | 3.112 | 42.407 | 23.275 | 1.00 54.98 | C |
| ATOM | 963 | O | GLU | A 346 | 2.113 | 42.983 | 23.724 | 1.00 56.11 | O |
| ATOM | 964 | CB | GLU | A 346 | 4.429 | 41.014 | 24.919 | 1.00 59.61 | C |
| ATOM | 965 | CG | GLU | A 346 | 4.567 | 39.679 | 25.633 | 1.00 61.99 | C |
| ATOM | 966 | CD | GLU | A 346 | 5.880 | 39.602 | 26.382 | 1.00 65.48 | C |
| ATOM | 967 | OE1 | GLU | A 346 | 6.650 | 40.571 | 26.508 | 1.00 67.23 | O |
| ATOM | 968 | OE2 | GLU | A 346 | 6.189 | 38.494 | 26.875 | 1.00 67.83 | O |
| ATOM | 969 | N | LEU | A 347 | 3.887 | 43.011 | 22.386 | 1.00 53.49 | N |
| ATOM | 970 | CA | LEU | A 347 | 3.580 | 44.351 | 21.894 | 1.00 51.94 | C |
| ATOM | 971 | C | LEU | A 347 | 2.452 | 44.374 | 20.863 | 1.00 50.97 | C |
| ATOM | 972 | O | LEU | A 347 | 2.058 | 45.446 | 20.375 | 1.00 48.85 | O |
| ATOM | 973 | CB | LEU | A 347 | 4.874 | 44.850 | 21.213 | 1.00 52.98 | C |
| ATOM | 974 | CG | LEU | A 347 | 6.010 | 45.230 | 22.158 | 1.00 53.78 | C |
| ATOM | 975 | CD1 | LEU | A 347 | 7.339 | 45.390 | 21.444 | 1.00 51.76 | C |
| ATOM | 976 | CD2 | LEU | A 347 | 5.639 | 46.491 | 22.936 | 1.00 53.86 | C |
| ATOM | 977 | N | LYS | A 348 | 1.951 | 43.220 | 20.434 | 1.00 49.63 | N |
| ATOM | 978 | CA | LYS | A 348 | 0.934 | 43.178 | 19.420 | 1.00 50.67 | C |
| ATOM | 979 | C | LYS | A 348 | 1.417 | 43.764 | 18.098 | 1.00 49.75 | C |
| ATOM | 980 | O | LYS | A 348 | 0.698 | 44.449 | 17.376 | 1.00 50.63 | O |
| ATOM | 981 | CB | LYS | A 348 | -0.343 | 43.833 | 19.923 | 1.00 53.45 | C |
| ATOM | 982 | CG | LYS | A 348 | -1.131 | 43.095 | 20.995 | 1.00 56.40 | C |
| ATOM | 983 | CD | LYS | A 348 | -2.257 | 43.975 | 21.526 | 1.00 59.70 | C |
| ATOM | 984 | CE | LYS | A 348 | -2.603 | 43.700 | 22.981 | 1.00 63.01 | C |
| ATOM | 985 | NZ | LYS | A 348 | -3.117 | 44.897 | 23.738 | 1.00 65.20 | N |
| ATOM | 986 | N | LEU | A 349 | 2.620 | 43.491 | 17.651 | 1.00 49.51 | N |
| ATOM | 987 | CA | LEU | A 349 | 3.221 | 43.913 | 16.407 | 1.00 49.80 | C |
| ATOM | 988 | C | LEU | A 349 | 2.276 | 43.791 | 15.205 | 1.00 51.39 | C |
| ATOM | 989 | O | LEU | A 349 | 1.729 | 42.731 | 14.892 | 1.00 51.69 | O |
| ATOM | 990 | CB | LEU | A 349 | 4.453 | 43.057 | 16.084 | 1.00 48.40 | C |
| ATOM | 991 | CG | LEU | A 349 | 5.470 | 43.528 | 15.043 | 1.00 46.92 | C |
| ATOM | 992 | CD1 | LEU | A 349 | 5.915 | 44.959 | 15.302 | 1.00 45.40 | C |
| ATOM | 993 | CD2 | LEU | A 349 | 6.682 | 42.592 | 15.018 | 1.00 44.81 | C |

| | | | | | | | | |
|---|---|---|---|---|---|---|---|---|
| ATOM | 840 | CD1 | LEU A 331 | 15.797 | 24.243 | 23.731 | 1.00121.64 | C |
| ATOM | 841 | CD2 | LEU A 331 | 17.439 | 24.142 | 25.609 | 1.00121.79 | C |
| ATOM | 842 | N | GLU A 332 | 19.795 | 27.658 | 23.353 | 1.00114.98 | N |
| ATOM | 843 | CA | GLU A 332 | 19.933 | 28.967 | 24.015 | 1.00111.30 | C |
| ATOM | 844 | C | GLU A 332 | 19.662 | 30.042 | 22.959 | 1.00107.15 | C |
| ATOM | 845 | O | GLU A 332 | 19.050 | 31.056 | 23.278 | 1.00106.22 | O |
| ATOM | 846 | CB | GLU A 332 | 21.229 | 29.118 | 24.775 | 1.00112.13 | C |
| ATOM | 847 | CG | GLU A 332 | 22.503 | 28.926 | 23.963 | 1.00113.26 | C |
| ATOM | 848 | CD | GLU A 332 | 23.638 | 29.733 | 24.589 | 1.00114.15 | C |
| ATOM | 849 | OE1 | GLU A 332 | 24.158 | 29.317 | 25.654 | 1.00113.75 | O |
| ATOM | 850 | OE2 | GLU A 332 | 23.978 | 30.783 | 23.990 | 1.00114.26 | O |
| ATOM | 851 | N | ILE A 333 | 20.052 | 29.806 | 21.711 | 1.00102.09 | N |
| ATOM | 852 | CA | ILE A 333 | 19.787 | 30.708 | 20.603 | 1.00 97.52 | C |
| ATOM | 853 | C | ILE A 333 | 18.312 | 30.662 | 20.185 | 1.00 94.10 | C |
| ATOM | 854 | O | ILE A 333 | 17.714 | 31.654 | 19.778 | 1.00 92.75 | O |
| ATOM | 855 | CB | ILE A 333 | 20.650 | 30.410 | 19.369 | 1.00 97.32 | C |
| ATOM | 856 | CG1 | ILE A 333 | 22.130 | 30.470 | 19.729 | 1.00 97.54 | C |
| ATOM | 857 | CG2 | ILE A 333 | 20.326 | 31.395 | 18.256 | 1.00 96.75 | C |
| ATOM | 858 | CD1 | ILE A 333 | 22.613 | 31.833 | 20.186 | 1.00 97.66 | C |
| ATOM | 859 | N | PHE A 334 | 17.678 | 29.506 | 20.323 | 1.00 90.58 | N |
| ATOM | 860 | CA | PHE A 334 | 16.278 | 29.288 | 20.031 | 1.00 87.22 | C |
| ATOM | 861 | C | PHE A 334 | 15.462 | 30.000 | 21.107 | 1.00 84.28 | C |
| ATOM | 862 | O | PHE A 334 | 14.362 | 30.471 | 20.822 | 1.00 83.44 | O |
| ATOM | 863 | CB | PHE A 334 | 15.863 | 27.827 | 20.043 | 1.00 88.43 | C |
| ATOM | 864 | CG | PHE A 334 | 15.884 | 27.004 | 18.799 | 1.00 89.41 | C |
| ATOM | 865 | CD1 | PHE A 334 | 16.848 | 27.168 | 17.817 | 1.00 89.97 | C |
| ATOM | 866 | CD2 | PHE A 334 | 14.919 | 26.022 | 18.611 | 1.00 89.42 | C |
| ATOM | 867 | CE1 | PHE A 334 | 16.854 | 26.387 | 16.679 | 1.00 90.27 | C |
| ATOM | 868 | CE2 | PHE A 334 | 14.911 | 25.233 | 17.480 | 1.00 89.76 | C |
| ATOM | 869 | CZ | PHE A 334 | 15.878 | 25.419 | 16.510 | 1.00 90.35 | C |
| ATOM | 870 | N | ASP A 335 | 16.006 | 30.062 | 22.328 | 1.00 81.51 | N |
| ATOM | 871 | CA | ASP A 335 | 15.263 | 30.734 | 23.403 | 1.00 79.28 | C |
| ATOM | 872 | C | ASP A 335 | 15.329 | 32.238 | 23.194 | 1.00 75.94 | C |
| ATOM | 873 | O | ASP A 335 | 14.353 | 32.962 | 23.377 | 1.00 75.67 | O |
| ATOM | 874 | CB | ASP A 335 | 15.743 | 30.364 | 24.785 | 1.00 81.57 | C |
| ATOM | 875 | CG | ASP A 335 | 15.450 | 28.915 | 25.160 | 1.00 82.70 | C |
| ATOM | 876 | OD1 | ASP A 335 | 14.680 | 28.218 | 24.478 | 1.00 81.70 | O |
| ATOM | 877 | OD2 | ASP A 335 | 16.072 | 28.560 | 26.189 | 1.00 83.68 | O |
| ATOM | 878 | N | MET A 336 | 16.507 | 32.674 | 22.735 | 1.00 71.28 | N |
| ATOM | 879 | CA | MET A 336 | 16.711 | 34.076 | 22.411 | 1.00 66.62 | C |
| ATOM | 880 | C | MET A 336 | 15.658 | 34.499 | 21.381 | 1.00 63.47 | C |
| ATOM | 881 | O | MET A 336 | 15.045 | 35.557 | 21.470 | 1.00 62.14 | O |
| ATOM | 882 | CB | MET A 336 | 18.133 | 34.302 | 21.896 | 1.00 65.84 | C |
| ATOM | 883 | CG | MET A 336 | 19.193 | 33.947 | 22.909 | 1.00 65.11 | C |
| ATOM | 884 | SD | MET A 336 | 20.844 | 34.558 | 22.534 | 1.00 63.00 | S |
| ATOM | 885 | CE | MET A 336 | 20.542 | 36.260 | 23.001 | 1.00 65.34 | C |
| ATOM | 886 | N | LEU A 337 | 15.468 | 33.637 | 20.390 | 1.00 60.44 | N |
| ATOM | 887 | CA | LEU A 337 | 14.539 | 33.758 | 19.298 | 1.00 57.37 | C |
| ATOM | 888 | C | LEU A 337 | 13.095 | 33.748 | 19.769 | 1.00 55.88 | C |
| ATOM | 889 | O | LEU A 337 | 12.229 | 34.546 | 19.373 | 1.00 54.87 | O |
| ATOM | 890 | CB | LEU A 337 | 14.847 | 32.685 | 18.240 | 1.00 56.57 | C |
| ATOM | 891 | CG | LEU A 337 | 16.089 | 32.997 | 17.389 | 1.00 57.08 | C |
| ATOM | 892 | CD1 | LEU A 337 | 16.456 | 31.846 | 16.464 | 1.00 55.54 | C |
| ATOM | 893 | CD2 | LEU A 337 | 15.930 | 34.278 | 16.569 | 1.00 56.16 | C |
| ATOM | 894 | N | LEU A 338 | 12.794 | 32.838 | 20.684 | 1.00 54.48 | N |
| ATOM | 895 | CA | LEU A 338 | 11.432 | 32.746 | 21.246 | 1.00 51.66 | C |
| ATOM | 896 | C | LEU A 338 | 11.190 | 33.931 | 22.152 | 1.00 49.57 | C |
| ATOM | 897 | O | LEU A 338 | 10.121 | 34.568 | 22.163 | 1.00 48.95 | O |
| ATOM | 898 | CB | LEU A 338 | 11.374 | 31.367 | 21.909 | 1.00 52.81 | C |
| ATOM | 899 | CG | LEU A 338 | 11.275 | 30.200 | 20.902 | 1.00 53.51 | C |
| ATOM | 900 | CD1 | LEU A 338 | 11.746 | 28.890 | 21.504 | 1.00 53.22 | C |
| ATOM | 901 | CD2 | LEU A 338 | 9.844 | 30.038 | 20.411 | 1.00 53.22 | C |
| ATOM | 902 | N | ALA A 339 | 12.199 | 34.320 | 22.940 | 1.00 47.73 | N |
| ATOM | 903 | CA | ALA A 339 | 12.049 | 35.476 | 23.812 | 1.00 48.65 | C |
| ATOM | 904 | C | ALA A 339 | 11.808 | 36.716 | 22.943 | 1.00 51.74 | C |
| ATOM | 905 | O | ALA A 339 | 10.826 | 37.437 | 23.213 | 1.00 54.54 | O |
| ATOM | 906 | CB | ALA A 339 | 13.284 | 35.703 | 24.625 | 1.00 48.56 | C |
| ATOM | 907 | N | THR A 340 | 12.663 | 36.920 | 21.917 | 1.00 49.91 | N |
| ATOM | 908 | CA | THR A 340 | 12.431 | 38.079 | 21.083 | 1.00 49.81 | C |
| ATOM | 909 | C | THR A 340 | 11.094 | 37.964 | 20.399 | 1.00 50.56 | C |
| ATOM | 910 | O | THR A 340 | 10.354 | 38.978 | 20.392 | 1.00 52.15 | O |
| ATOM | 911 | CB | THR A 340 | 13.639 | 38.425 | 20.222 | 1.00 50.92 | C |
| ATOM | 912 | OG1 | THR A 340 | 14.847 | 38.423 | 21.035 | 1.00 50.68 | O |
| ATOM | 913 | CG2 | THR A 340 | 13.452 | 39.816 | 19.650 | 1.00 48.99 | C |
| ATOM | 914 | N | THR A 341 | 10.649 | 36.828 | 19.877 | 1.00 49.93 | N |
| ATOM | 915 | CA | THR A 341 | 9.328 | 36.718 | 19.276 | 1.00 48.92 | C |
| ATOM | 916 | C | THR A 341 | 8.304 | 37.092 | 20.350 | 1.00 50.46 | C |

| ATOM | 763 | N   | ARG A 321  | 10.320 | 24.061 | 20.733 | 1.00 | 117.14 | N |
|------|-----|-----|------------|--------|--------|--------|------|--------|---|
| ATOM | 764 | CA  | ARG A 321  | 11.469 | 24.529 | 21.485 | 1.00 | 120.36 | C |
| ATOM | 765 | C   | ARG A 321  | 12.448 | 23.470 | 21.936 | 1.00 | 123.22 | C |
| ATOM | 766 | O   | ARG A 321  | 13.656 | 23.676 | 21.744 | 1.00 | 122.92 | O |
| ATOM | 767 | CB  | ARG A 321  | 10.972 | 25.378 | 22.658 | 1.00 | 120.03 | C |
| ATOM | 768 | CG  | ARG A 321  | 12.063 | 26.104 | 23.416 | 1.00 | 119.96 | C |
| ATOM | 769 | CD  | ARG A 321  | 12.356 | 25.439 | 24.745 | 1.00 | 119.89 | C |
| ATOM | 770 | NE  | ARG A 321  | 13.672 | 25.795 | 25.260 | 1.00 | 119.83 | N |
| ATOM | 771 | CZ  | ARG A 321  | 14.020 | 25.719 | 26.539 | 1.00 | 119.70 | C |
| ATOM | 772 | NH1 | ARG A 321  | 13.129 | 25.296 | 27.429 | 1.00 | 119.85 | N |
| ATOM | 773 | NH2 | ARG A 321  | 15.241 | 26.070 | 26.899 | 1.00 | 119.28 | N |
| ATOM | 774 | N   | ASP A 322  | 12.017 | 22.345 | 22.496 | 1.00 | 127.16 | N |
| ATOM | 775 | CA  | ASP A 322  | 12.948 | 21.317 | 22.946 | 1.00 | 131.30 | C |
| ATOM | 776 | C   | ASP A 322  | 13.500 | 20.432 | 21.838 | 1.00 | 134.04 | C |
| ATOM | 777 | O   | ASP A 322  | 14.071 | 19.386 | 22.151 | 1.00 | 134.47 | O |
| ATOM | 778 | CB  | ASP A 322  | 12.336 | 20.429 | 24.033 | 1.00 | 131.64 | C |
| ATOM | 779 | CG  | ASP A 322  | 11.849 | 21.146 | 25.272 | 1.00 | 132.07 | C |
| ATOM | 780 | OD1 | ASP A 322  | 12.591 | 21.962 | 25.858 | 1.00 | 131.98 | O |
| ATOM | 781 | OD2 | ASP A 322  | 10.693 | 20.882 | 25.685 | 1.00 | 132.10 | O |
| ATOM | 782 | N   | GLU A 323  | 13.387 | 20.778 | 20.569 | 1.00 | 137.16 | N |
| ATOM | 783 | CA  | GLU A 323  | 13.894 | 20.013 | 19.447 | 1.00 | 140.19 | C |
| ATOM | 784 | C   | GLU A 323  | 15.221 | 20.613 | 18.964 | 1.00 | 141.95 | C |
| ATOM | 785 | O   | GLU A 323  | 15.862 | 20.182 | 18.013 | 1.00 | 141.56 | O |
| ATOM | 786 | CB  | GLU A 323  | 12.924 | 20.005 | 18.275 | 1.00 | 141.05 | C |
| ATOM | 787 | CG  | GLU A 323  | 11.682 | 19.138 | 18.386 | 1.00 | 141.79 | C |
| ATOM | 788 | CD  | GLU A 323  | 10.967 | 19.079 | 17.041 | 1.00 | 142.14 | C |
| ATOM | 789 | OE1 | GLU A 323  | 11.636 | 18.725 | 16.048 | 1.00 | 142.25 | O |
| ATOM | 790 | OE2 | GLU A 323  |  9.761 | 19.388 | 16.978 | 1.00 | 142.27 | O |
| ATOM | 791 | N   | GLY A 324  | 15.634 | 21.663 | 19.670 | 1.00 | 144.14 | N |
| ATOM | 792 | CA  | GLY A 324  | 16.872 | 22.384 | 19.431 | 1.00 | 146.49 | C |
| ATOM | 793 | C   | GLY A 324  | 18.005 | 21.690 | 20.183 | 1.00 | 148.26 | C |
| ATOM | 794 | O   | GLY A 324  | 19.189 | 21.874 | 19.910 | 1.00 | 148.03 | O |
| ATOM | 795 | N   | LYS A 325  | 17.655 | 20.810 | 21.121 | 1.00 | 150.06 | N |
| ATOM | 796 | CA  | LYS A 325  | 18.553 | 20.014 | 21.933 | 1.00 | 151.50 | C |
| ATOM | 797 | C   | LYS A 325  | 19.305 | 18.958 | 21.124 | 1.00 | 151.90 | C |
| ATOM | 798 | O   | LYS A 325  | 20.235 | 18.321 | 21.617 | 1.00 | 151.87 | O |
| ATOM | 799 | CB  | LYS A 325  | 17.802 | 19.278 | 23.052 | 1.00 | 152.24 | C |
| ATOM | 800 | CG  | LYS A 325  | 16.775 | 18.276 | 22.552 | 1.00 | 153.06 | C |
| ATOM | 801 | CD  | LYS A 325  | 16.194 | 17.410 | 23.648 | 1.00 | 153.35 | C |
| ATOM | 802 | CE  | LYS A 325  | 14.987 | 16.600 | 23.213 | 1.00 | 153.27 | C |
| ATOM | 803 | NZ  | LYS A 325  | 13.700 | 17.291 | 23.496 | 1.00 | 153.16 | N |
| ATOM | 804 | N   | CYS A 326  | 18.909 | 18.766 | 19.879 | 1.00 | 152.24 | N |
| ATOM | 805 | CA  | CYS A 326  | 19.487 | 17.854 | 18.931 | 1.00 | 152.47 | C |
| ATOM | 806 | C   | CYS A 326  | 20.610 | 18.500 | 18.136 | 1.00 | 152.22 | C |
| ATOM | 807 | O   | CYS A 326  | 21.210 | 17.819 | 17.302 | 1.00 | 152.70 | O |
| ATOM | 808 | CB  | CYS A 326  | 18.421 | 17.330 | 17.953 | 1.00 | 152.77 | C |
| ATOM | 809 | SG  | CYS A 326  | 17.404 | 16.015 | 18.675 | 1.00 | 153.08 | S |
| ATOM | 810 | N   | VAL A 327  | 20.899 | 19.784 | 18.328 | 1.00 | 151.64 | N |
| ATOM | 811 | CA  | VAL A 327  | 21.982 | 20.434 | 17.589 | 1.00 | 150.68 | C |
| ATOM | 812 | C   | VAL A 327  | 22.959 | 21.077 | 18.579 | 1.00 | 149.23 | C |
| ATOM | 813 | O   | VAL A 327  | 22.668 | 21.341 | 19.745 | 1.00 | 148.88 | O |
| ATOM | 814 | CB  | VAL A 327  | 21.573 | 21.460 | 16.527 | 1.00 | 151.08 | C |
| ATOM | 815 | CG1 | VAL A 327  | 22.628 | 21.501 | 15.418 | 1.00 | 151.22 | C |
| ATOM | 816 | CG2 | VAL A 327  | 20.213 | 21.220 | 15.895 | 1.00 | 151.23 | C |
| ATOM | 817 | N   | GLU A 328  | 24.164 | 21.346 | 18.116 | 1.00 | 147.40 | N |
| ATOM | 818 | CA  | GLU A 328  | 25.290 | 21.912 | 18.821 | 1.00 | 145.42 | C |
| ATOM | 819 | C   | GLU A 328  | 25.110 | 23.163 | 19.655 | 1.00 | 143.42 | C |
| ATOM | 820 | O   | GLU A 328  | 25.699 | 24.199 | 19.329 | 1.00 | 143.34 | O |
| ATOM | 821 | CB  | GLU A 328  | 26.389 | 22.201 | 17.761 | 1.00 | 145.63 | C |
| ATOM | 822 | N   | GLY A 329  | 24.359 | 23.111 | 20.747 | 1.00 | 141.08 | N |
| ATOM | 823 | CA  | GLY A 329  | 24.123 | 24.279 | 21.596 | 1.00 | 137.86 | C |
| ATOM | 824 | C   | GLY A 329  | 23.284 | 25.299 | 20.821 | 1.00 | 135.31 | C |
| ATOM | 825 | O   | GLY A 329  | 23.740 | 26.410 | 20.568 | 1.00 | 134.77 | O |
| ATOM | 826 | N   | ILE A 330  | 22.070 | 24.928 | 20.419 | 1.00 | 132.66 | N |
| ATOM | 827 | CA  | ILE A 330  | 21.230 | 25.851 | 19.656 | 1.00 | 129.65 | C |
| ATOM | 828 | C   | ILE A 330  | 19.926 | 26.159 | 20.368 | 1.00 | 127.64 | C |
| ATOM | 829 | O   | ILE A 330  | 19.086 | 26.889 | 19.844 | 1.00 | 127.46 | O |
| ATOM | 830 | CB  | ILE A 330  | 21.010 | 25.288 | 18.241 | 1.00 | 129.44 | C |
| ATOM | 831 | CG1 | ILE A 330  | 20.836 | 26.426 | 17.231 | 1.00 | 129.19 | C |
| ATOM | 832 | CG2 | ILE A 330  | 19.817 | 24.347 | 18.205 | 1.00 | 129.67 | C |
| ATOM | 833 | CD1 | ILE A 330  | 20.648 | 25.965 | 15.803 | 1.00 | 128.69 | C |
| ATOM | 834 | N   | LEU A 331  | 19.739 | 25.628 | 21.575 | 1.00 | 124.90 | N |
| ATOM | 835 | CA  | LEU A 331  | 18.517 | 25.851 | 22.349 | 1.00 | 121.66 | C |
| ATOM | 836 | C   | LEU A 331  | 18.573 | 27.199 | 23.065 | 1.00 | 118.64 | C |
| ATOM | 837 | O   | LEU A 331  | 17.550 | 27.836 | 23.344 | 1.00 | 117.73 | O |
| ATOM | 838 | CB  | LEU A 331  | 18.257 | 24.677 | 23.300 | 1.00 | 121.71 | C |
| ATOM | 839 | CG  | LEU A 331  | 17.094 | 24.802 | 24.286 | 1.00 | 121.74 | C |

```
ATOM   686  CE   LYS A 310       4.444  23.470  18.734  1.00 75.75           C
ATOM   687  NZ   LYS A 310       4.936  22.070  18.483  1.00 76.20           N
ATOM   688  N    LEU A 311       9.416  27.675  16.634  1.00 68.13           N
ATOM   689  CA   LEU A 311      10.035  28.573  15.681  1.00 66.17           C
ATOM   690  C    LEU A 311       9.556  28.064  14.312  1.00 67.64           C
ATOM   691  O    LEU A 311       9.908  26.983  13.876  1.00 66.77           O
ATOM   692  CB   LEU A 311      11.540  28.569  15.749  1.00 64.62           C
ATOM   693  CG   LEU A 311      12.183  29.153  17.006  1.00 63.23           C
ATOM   694  CD1  LEU A 311      13.682  28.881  16.999  1.00 62.21           C
ATOM   695  CD2  LEU A 311      11.869  30.633  17.105  1.00 63.07           C
ATOM   696  N    ILE A 312       8.709  28.809  13.626  1.00 69.31           N
ATOM   697  CA   ILE A 312       8.132  28.479  12.337  1.00 70.01           C
ATOM   698  C    ILE A 312       9.056  28.851  11.185  1.00 71.05           C
ATOM   699  O    ILE A 312       8.939  29.922  10.569  1.00 69.95           O
ATOM   700  CB   ILE A 312       6.835  29.308  12.211  1.00 70.26           C
ATOM   701  CG1  ILE A 312       6.046  29.331  13.512  1.00 70.16           C
ATOM   702  CG2  ILE A 312       5.991  28.790  11.067  1.00 70.68           C
ATOM   703  CD1  ILE A 312       5.703  27.983  14.081  1.00 70.43           C
ATOM   704  N    PHE A 313      10.017  27.980  10.872  1.00 72.16           N
ATOM   705  CA   PHE A 313      10.967  28.273   9.800  1.00 74.01           C
ATOM   706  C    PHE A 313      10.344  28.356   8.414  1.00 74.20           C
ATOM   707  O    PHE A 313      10.787  29.127   7.577  1.00 73.10           O
ATOM   708  CB   PHE A 313      12.125  27.274   9.794  1.00 74.32           C
ATOM   709  CG   PHE A 313      13.124  27.582  10.868  1.00 75.36           C
ATOM   710  CD1  PHE A 313      12.872  27.208  12.177  1.00 75.71           C
ATOM   711  CD2  PHE A 313      14.307  28.244  10.581  1.00 75.59           C
ATOM   712  CE1  PHE A 313      13.784  27.478  13.179  1.00 75.86           C
ATOM   713  CE2  PHE A 313      15.230  28.517  11.576  1.00 75.23           C
ATOM   714  CZ   PHE A 313      14.965  28.142  12.879  1.00 75.78           C
ATOM   715  N    ALA A 314       9.328  27.559   8.185  1.00 75.64           N
ATOM   716  CA   ALA A 314       8.551  27.460   6.955  1.00 77.12           C
ATOM   717  C    ALA A 314       7.274  26.772   7.408  1.00 78.51           C
ATOM   718  O    ALA A 314       7.264  26.106   8.441  1.00 77.41           O
ATOM   719  CB   ALA A 314       9.337  26.717   5.905  1.00 77.33           C
ATOM   720  N    PRO A 315       6.182  26.923   6.685  1.00 80.78           N
ATOM   721  CA   PRO A 315       4.871  26.373   7.039  1.00 82.05           C
ATOM   722  C    PRO A 315       4.873  24.878   7.288  1.00 83.78           C
ATOM   723  O    PRO A 315       4.145  24.385   8.158  1.00 83.48           O
ATOM   724  CB   PRO A 315       3.867  26.874   6.006  1.00 81.02           C
ATOM   725  CG   PRO A 315       4.633  27.970   5.317  1.00 81.16           C
ATOM   726  CD   PRO A 315       6.126  27.720   5.459  1.00 80.69           C
ATOM   727  N    ASP A 316       5.698  24.103   6.586  1.00 85.94           N
ATOM   728  CA   ASP A 316       5.784  22.669   6.829  1.00 88.15           C
ATOM   729  C    ASP A 316       7.201  22.404   7.341  1.00 89.98           C
ATOM   730  O    ASP A 316       7.961  21.595   6.816  1.00 90.07           O
ATOM   731  CB   ASP A 316       5.453  21.787   5.647  1.00 88.31           C
ATOM   732  N    LEU A 317       7.577  23.138   8.385  1.00 91.53           N
ATOM   733  CA   LEU A 317       8.891  23.012   9.009  1.00 92.39           C
ATOM   734  C    LEU A 317       8.883  23.766  10.335  1.00 93.59           C
ATOM   735  O    LEU A 317       9.583  24.742  10.571  1.00 93.31           O
ATOM   736  CB   LEU A 317      10.003  23.480   8.078  1.00 91.45           C
ATOM   737  CG   LEU A 317      11.419  23.417   8.643  1.00 91.13           C
ATOM   738  CD1  LEU A 317      11.807  22.022   9.072  1.00 90.97           C
ATOM   739  CD2  LEU A 317      12.427  23.930   7.632  1.00 91.61           C
ATOM   740  N    VAL A 318       8.022  23.293  11.226  1.00 95.36           N
ATOM   741  CA   VAL A 318       7.848  23.877  12.543  1.00 97.49           C
ATOM   742  C    VAL A 318       8.568  23.077  13.616  1.00 99.80           C
ATOM   743  O    VAL A 318       8.204  21.942  13.922  1.00100.70           O
ATOM   744  CB   VAL A 318       6.350  23.978  12.880  1.00 96.70           C
ATOM   745  CG1  VAL A 318       6.125  24.531  14.274  1.00 96.63           C
ATOM   746  CG2  VAL A 318       5.655  24.825  11.835  1.00 96.35           C
ATOM   747  N    LEU A 319       9.595  23.675  14.205  1.00102.31           N
ATOM   748  CA   LEU A 319      10.348  23.016  15.262  1.00104.79           C
ATOM   749  C    LEU A 319       9.926  23.527  16.638  1.00106.74           C
ATOM   750  O    LEU A 319       9.941  24.732  16.878  1.00106.56           O
ATOM   751  CB   LEU A 319      11.842  23.215  15.039  1.00104.44           C
ATOM   752  CG   LEU A 319      12.429  22.987  13.655  1.00104.36           C
ATOM   753  CD1  LEU A 319      13.952  22.946  13.728  1.00104.17           C
ATOM   754  CD2  LEU A 319      11.918  21.728  12.981  1.00104.51           C
ATOM   755  N    ASP A 320       9.552  22.618  17.529  1.00109.34           N
ATOM   756  CA   ASP A 320       9.153  22.967  18.884  1.00111.92           C
ATOM   757  C    ASP A 320      10.434  23.376  19.610  1.00114.15           C
ATOM   758  O    ASP A 320      11.526  23.075  19.125  1.00113.74           O
ATOM   759  CB   ASP A 320       8.443  21.821  19.581  1.00112.23           C
ATOM   760  CG   ASP A 320       7.747  22.250  20.858  1.00113.12           C
ATOM   761  OD1  ASP A 320       8.432  22.485  21.884  1.00113.59           O
ATOM   762  OD2  ASP A 320       6.503  22.361  20.850  1.00113.05           O
```

| | | | | | | | | | |
|---|---|---|---|---|---|---|---|---|---|
| ATOM | 609 | SD | MET | A | 301 | 12.894 | 38.198 | 16.514 | 1.00 54.40 | S |
| ATOM | 610 | CE | MET | A | 301 | 14.540 | 37.759 | 15.973 | 1.00 52.91 | C |
| ATOM | 611 | N | TRP | A | 302 | 8.617 | 36.846 | 13.102 | 1.00 51.67 | N |
| ATOM | 612 | CA | TRP | A | 302 | 7.275 | 37.276 | 12.706 | 1.00 51.24 | C |
| ATOM | 613 | C | TRP | A | 302 | 6.367 | 36.112 | 12.334 | 1.00 52.88 | C |
| ATOM | 614 | O | TRP | A | 302 | 5.180 | 36.052 | 12.671 | 1.00 53.69 | O |
| ATOM | 615 | CB | TRP | A | 302 | 7.426 | 38.310 | 11.577 | 1.00 48.53 | C |
| ATOM | 616 | CG | TRP | A | 302 | 6.129 | 38.571 | 10.875 | 1.00 47.07 | C |
| ATOM | 617 | CD1 | TRP | A | 302 | 5.769 | 38.106 | 9.647 | 1.00 46.35 | C |
| ATOM | 618 | CD2 | TRP | A | 302 | 5.023 | 39.335 | 11.361 | 1.00 46.65 | C |
| ATOM | 619 | NE1 | TRP | A | 302 | 4.508 | 38.543 | 9.323 | 1.00 46.67 | N |
| ATOM | 620 | CE2 | TRP | A | 302 | 4.021 | 39.298 | 10.363 | 1.00 46.80 | C |
| ATOM | 621 | CE3 | TRP | A | 302 | 4.778 | 40.051 | 12.540 | 1.00 46.35 | C |
| ATOM | 622 | CZ2 | TRP | A | 302 | 2.789 | 39.940 | 10.510 | 1.00 45.04 | C |
| ATOM | 623 | CZ3 | TRP | A | 302 | 3.559 | 40.689 | 12.690 | 1.00 45.53 | C |
| ATOM | 624 | CH2 | TRP | A | 302 | 2.587 | 40.632 | 11.674 | 1.00 45.30 | C |
| ATOM | 625 | N | ARG | A | 303 | 6.858 | 35.093 | 11.632 | 1.00 53.58 | N |
| ATOM | 626 | CA | ARG | A | 303 | 6.138 | 33.905 | 11.266 | 1.00 54.01 | C |
| ATOM | 627 | C | ARG | A | 303 | 5.816 | 33.098 | 12.532 | 1.00 55.89 | C |
| ATOM | 628 | O | ARG | A | 303 | 4.834 | 32.353 | 12.504 | 1.00 56.73 | O |
| ATOM | 629 | CB | ARG | A | 303 | 6.953 | 32.981 | 10.361 | 1.00 52.74 | C |
| ATOM | 630 | CG | ARG | A | 303 | 7.247 | 33.545 | 8.975 | 1.00 51.62 | C |
| ATOM | 631 | CD | ARG | A | 303 | 7.704 | 32.475 | 8.025 | 1.00 49.57 | C |
| ATOM | 632 | NE | ARG | A | 303 | 9.014 | 31.914 | 8.338 | 1.00 49.57 | N |
| ATOM | 633 | CZ | ARG | A | 303 | 10.164 | 32.525 | 8.029 | 1.00 48.55 | C |
| ATOM | 634 | NH1 | ARG | A | 303 | 10.064 | 33.699 | 7.417 | 1.00 46.81 | N |
| ATOM | 635 | NH2 | ARG | A | 303 | 11.331 | 31.970 | 8.324 | 1.00 47.44 | N |
| ATOM | 636 | N | SER | A | 304 | 6.627 | 33.236 | 13.589 | 1.00 55.42 | N |
| ATOM | 637 | CA | SER | A | 304 | 6.379 | 32.510 | 14.823 | 1.00 55.44 | C |
| ATOM | 638 | C | SER | A | 304 | 5.582 | 33.339 | 15.825 | 1.00 57.09 | C |
| ATOM | 639 | O | SER | A | 304 | 5.267 | 32.831 | 16.919 | 1.00 56.43 | O |
| ATOM | 640 | CB | SER | A | 304 | 7.687 | 32.078 | 15.454 | 1.00 55.06 | C |
| ATOM | 641 | OG | SER | A | 304 | 8.585 | 31.643 | 14.425 | 1.00 57.36 | O |
| ATOM | 642 | N | ILE | A | 305 | 5.243 | 34.583 | 15.463 | 1.00 56.94 | N |
| ATOM | 643 | CA | ILE | A | 305 | 4.509 | 35.404 | 16.409 | 1.00 59.06 | C |
| ATOM | 644 | C | ILE | A | 305 | 3.380 | 34.666 | 17.092 | 1.00 61.72 | C |
| ATOM | 645 | O | ILE | A | 305 | 3.463 | 34.362 | 18.285 | 1.00 61.97 | O |
| ATOM | 646 | CB | ILE | A | 305 | 4.126 | 36.757 | 15.808 | 1.00 58.28 | C |
| ATOM | 647 | CG1 | ILE | A | 305 | 4.017 | 37.800 | 16.943 | 1.00 57.28 | C |
| ATOM | 648 | CG2 | ILE | A | 305 | 2.875 | 36.746 | 14.958 | 1.00 57.42 | C |
| ATOM | 649 | CD1 | ILE | A | 305 | 4.601 | 39.139 | 16.572 | 1.00 55.24 | C |
| ATOM | 650 | N | ASP | A | 306 | 2.304 | 34.296 | 16.430 | 1.00 65.24 | N |
| ATOM | 651 | CA | ASP | A | 306 | 1.179 | 33.607 | 17.032 | 1.00 67.57 | C |
| ATOM | 652 | C | ASP | A | 306 | 1.415 | 32.189 | 17.495 | 1.00 68.52 | C |
| ATOM | 653 | O | ASP | A | 306 | 0.440 | 31.570 | 17.936 | 1.00 69.53 | O |
| ATOM | 654 | CB | ASP | A | 306 | -0.009 | 33.601 | 16.067 | 1.00 68.11 | C |
| ATOM | 655 | CG | ASP | A | 306 | -0.322 | 34.984 | 15.559 | 1.00 69.27 | C |
| ATOM | 656 | OD1 | ASP | A | 306 | -0.424 | 35.885 | 16.407 | 1.00 70.07 | O |
| ATOM | 657 | OD2 | ASP | A | 306 | -0.476 | 35.163 | 14.332 | 1.00 70.61 | O |
| ATOM | 658 | N | HIS | A | 307 | 2.586 | 31.589 | 17.492 | 1.00 69.38 | N |
| ATOM | 659 | CA | HIS | A | 307 | 2.831 | 30.232 | 17.949 | 1.00 69.57 | C |
| ATOM | 660 | C | HIS | A | 307 | 3.793 | 30.064 | 19.115 | 1.00 67.38 | C |
| ATOM | 661 | O | HIS | A | 307 | 4.920 | 29.579 | 18.971 | 1.00 65.13 | O |
| ATOM | 662 | CB | HIS | A | 307 | 3.411 | 29.455 | 16.731 | 1.00 72.37 | C |
| ATOM | 663 | CG | HIS | A | 307 | 2.445 | 29.477 | 15.589 | 1.00 76.40 | C |
| ATOM | 664 | ND1 | HIS | A | 307 | 1.076 | 29.305 | 15.794 | 1.00 77.58 | N |
| ATOM | 665 | CD2 | HIS | A | 307 | 2.605 | 29.661 | 14.259 | 1.00 77.77 | C |
| ATOM | 666 | CE1 | HIS | A | 307 | 0.456 | 29.379 | 14.631 | 1.00 78.22 | C |
| ATOM | 667 | NE2 | HIS | A | 307 | 1.357 | 29.601 | 13.678 | 1.00 78.32 | N |
| ATOM | 668 | N | PRO | A | 308 | 3.391 | 30.422 | 20.314 | 1.00 66.84 | N |
| ATOM | 669 | CA | PRO | A | 308 | 4.195 | 30.330 | 21.526 | 1.00 67.19 | C |
| ATOM | 670 | C | PRO | A | 308 | 4.869 | 28.986 | 21.584 | 1.00 68.49 | C |
| ATOM | 671 | O | PRO | A | 308 | 4.150 | 28.027 | 21.282 | 1.00 70.97 | O |
| ATOM | 672 | CB | PRO | A | 308 | 3.275 | 30.488 | 22.733 | 1.00 65.92 | C |
| ATOM | 673 | CG | PRO | A | 308 | 2.134 | 31.237 | 22.112 | 1.00 66.58 | C |
| ATOM | 674 | CD | PRO | A | 308 | 2.079 | 30.991 | 20.619 | 1.00 66.88 | C |
| ATOM | 675 | N | GLY | A | 309 | 6.143 | 28.910 | 21.896 | 1.00 68.18 | N |
| ATOM | 676 | CA | GLY | A | 309 | 6.849 | 27.662 | 21.962 | 1.00 68.62 | C |
| ATOM | 677 | C | GLY | A | 309 | 7.548 | 27.175 | 20.720 | 1.00 70.18 | C |
| ATOM | 678 | O | GLY | A | 309 | 8.564 | 26.450 | 20.802 | 1.00 70.03 | O |
| ATOM | 679 | N | LYS | A | 310 | 7.070 | 27.508 | 19.516 | 1.00 71.29 | N |
| ATOM | 680 | CA | LYS | A | 310 | 7.762 | 26.977 | 18.325 | 1.00 71.43 | C |
| ATOM | 681 | C | LYS | A | 310 | 8.417 | 28.007 | 17.426 | 1.00 70.05 | C |
| ATOM | 682 | O | LYS | A | 310 | 8.009 | 29.150 | 17.403 | 1.00 70.08 | O |
| ATOM | 683 | CB | LYS | A | 310 | 6.718 | 26.244 | 17.473 | 1.00 72.02 | C |
| ATOM | 684 | CG | LYS | A | 310 | 5.449 | 25.756 | 18.142 | 1.00 73.94 | C |
| ATOM | 685 | CD | LYS | A | 310 | 5.645 | 24.411 | 18.808 | 1.00 75.68 | C |

| | | | | | | | | | |
|---|---|---|---|---|---|---|---|---|---|
| ATOM | 532 | C | TRP | A | 292 | 20.852 | 38.190 | 7.273 | 1.00 45.49 | C |
| ATOM | 533 | O | TRP | A | 292 | 19.673 | 37.873 | 7.194 | 1.00 46.68 | O |
| ATOM | 534 | CB | TRP | A | 292 | 21.968 | 38.222 | 5.036 | 1.00 43.71 | C |
| ATOM | 535 | CG | TRP | A | 292 | 23.186 | 37.485 | 5.468 | 1.00 42.78 | C |
| ATOM | 536 | CD1 | TRP | A | 292 | 24.460 | 37.933 | 5.350 | 1.00 42.31 | C |
| ATOM | 537 | CD2 | TRP | A | 292 | 23.263 | 36.208 | 6.118 | 1.00 42.51 | C |
| ATOM | 538 | NE1 | TRP | A | 292 | 25.325 | 37.013 | 5.871 | 1.00 42.31 | N |
| ATOM | 539 | CE2 | TRP | A | 292 | 24.628 | 35.952 | 6.353 | 1.00 42.81 | C |
| ATOM | 540 | CE3 | TRP | A | 292 | 22.314 | 35.272 | 6.515 | 1.00 41.86 | C |
| ATOM | 541 | CZ2 | TRP | A | 292 | 25.097 | 34.797 | 6.977 | 1.00 43.71 | C |
| ATOM | 542 | CZ3 | TRP | A | 292 | 22.766 | 34.118 | 7.126 | 1.00 44.50 | C |
| ATOM | 543 | CH2 | TRP | A | 292 | 24.135 | 33.887 | 7.361 | 1.00 45.06 | C |
| ATOM | 544 | N | MET | A | 293 | 21.607 | 37.804 | 8.274 | 1.00 49.12 | N |
| ATOM | 545 | CA | MET | A | 293 | 21.069 | 36.952 | 9.349 | 1.00 51.22 | C |
| ATOM | 546 | C | MET | A | 293 | 20.004 | 37.672 | 10.159 | 1.00 50.86 | C |
| ATOM | 547 | O | MET | A | 293 | 19.019 | 37.052 | 10.572 | 1.00 51.07 | O |
| ATOM | 548 | CB | MET | A | 293 | 22.199 | 36.450 | 10.224 | 1.00 54.98 | C |
| ATOM | 549 | CG | MET | A | 293 | 21.769 | 35.663 | 11.460 | 1.00 58.98 | C |
| ATOM | 550 | SD | MET | A | 293 | 21.260 | 34.016 | 10.873 | 1.00 63.75 | S |
| ATOM | 551 | CE | MET | A | 293 | 22.925 | 33.314 | 10.797 | 1.00 62.78 | C |
| ATOM | 552 | N | GLU | A | 294 | 20.138 | 38.983 | 10.407 | 1.00 49.04 | N |
| ATOM | 553 | CA | GLU | A | 294 | 19.113 | 39.706 | 11.158 | 1.00 47.19 | C |
| ATOM | 554 | C | GLU | A | 294 | 17.779 | 39.703 | 10.398 | 1.00 46.05 | C |
| ATOM | 555 | O | GLU | A | 294 | 16.728 | 39.517 | 11.009 | 1.00 43.66 | O |
| ATOM | 556 | CB | GLU | A | 294 | 19.550 | 41.134 | 11.399 | 1.00 47.13 | C |
| ATOM | 557 | CG | GLU | A | 294 | 20.416 | 41.428 | 12.606 | 1.00 45.80 | C |
| ATOM | 558 | CD | GLU | A | 294 | 21.233 | 42.664 | 12.294 | 1.00 46.89 | C |
| ATOM | 559 | OE1 | GLU | A | 294 | 22.300 | 42.531 | 11.650 | 1.00 47.29 | O |
| ATOM | 560 | OE2 | GLU | A | 294 | 20.786 | 43.751 | 12.686 | 1.00 46.16 | O |
| ATOM | 561 | N | VAL | A | 295 | 17.871 | 39.913 | 9.072 | 1.00 44.69 | N |
| ATOM | 562 | CA | VAL | A | 295 | 16.722 | 39.883 | 8.181 | 1.00 43.43 | C |
| ATOM | 563 | C | VAL | A | 295 | 16.095 | 38.491 | 8.259 | 1.00 42.67 | C |
| ATOM | 564 | O | VAL | A | 295 | 14.903 | 38.362 | 8.564 | 1.00 41.91 | O |
| ATOM | 565 | CB | VAL | A | 295 | 17.076 | 40.268 | 6.747 | 1.00 44.04 | C |
| ATOM | 566 | CG1 | VAL | A | 295 | 15.836 | 40.271 | 5.840 | 1.00 45.03 | C |
| ATOM | 567 | CG2 | VAL | A | 295 | 17.664 | 41.663 | 6.697 | 1.00 43.29 | C |
| ATOM | 568 | N | LEU | A | 296 | 16.864 | 37.415 | 8.093 | 1.00 42.68 | N |
| ATOM | 569 | CA | LEU | A | 296 | 16.311 | 36.074 | 8.245 | 1.00 42.85 | C |
| ATOM | 570 | C | LEU | A | 296 | 15.711 | 35.901 | 9.638 | 1.00 43.31 | C |
| ATOM | 571 | O | LEU | A | 296 | 14.572 | 35.409 | 9.690 | 1.00 44.83 | O |
| ATOM | 572 | CB | LEU | A | 296 | 17.277 | 34.935 | 8.046 | 1.00 42.91 | C |
| ATOM | 573 | CG | LEU | A | 296 | 18.014 | 34.733 | 6.738 | 1.00 44.50 | C |
| ATOM | 574 | CD1 | LEU | A | 296 | 18.819 | 33.419 | 6.838 | 1.00 44.47 | C |
| ATOM | 575 | CD2 | LEU | A | 296 | 17.083 | 34.645 | 5.528 | 1.00 44.42 | C |
| ATOM | 576 | N | MET | A | 297 | 16.405 | 36.267 | 10.734 | 1.00 42.85 | N |
| ATOM | 577 | CA | MET | A | 297 | 15.822 | 36.063 | 12.054 | 1.00 41.23 | C |
| ATOM | 578 | C | MET | A | 297 | 14.623 | 36.957 | 12.293 | 1.00 41.44 | C |
| ATOM | 579 | O | MET | A | 297 | 13.733 | 36.510 | 13.011 | 1.00 42.23 | O |
| ATOM | 580 | CB | MET | A | 297 | 16.791 | 36.238 | 13.220 | 1.00 40.85 | C |
| ATOM | 581 | CG | MET | A | 297 | 18.005 | 35.337 | 13.072 | 1.00 40.83 | C |
| ATOM | 582 | SD | MET | A | 297 | 19.318 | 35.740 | 14.225 | 1.00 38.03 | S |
| ATOM | 583 | CE | MET | A | 297 | 20.282 | 34.229 | 14.203 | 1.00 38.34 | C |
| ATOM | 584 | N | VAL | A | 298 | 14.521 | 38.158 | 11.746 | 1.00 42.08 | N |
| ATOM | 585 | CA | VAL | A | 298 | 13.299 | 38.921 | 12.060 | 1.00 44.26 | C |
| ATOM | 586 | C | VAL | A | 298 | 12.123 | 38.291 | 11.310 | 1.00 46.48 | C |
| ATOM | 587 | O | VAL | A | 298 | 10.992 | 38.258 | 11.841 | 1.00 47.53 | O |
| ATOM | 588 | CB | VAL | A | 298 | 13.507 | 40.421 | 11.865 | 1.00 43.43 | C |
| ATOM | 589 | CG1 | VAL | A | 298 | 13.510 | 40.775 | 10.381 | 1.00 43.78 | C |
| ATOM | 590 | CG2 | VAL | A | 298 | 12.465 | 41.207 | 12.624 | 1.00 41.41 | C |
| ATOM | 591 | N | GLY | A | 299 | 12.326 | 37.715 | 10.120 | 1.00 46.10 | N |
| ATOM | 592 | CA | GLY | A | 299 | 11.179 | 37.080 | 9.452 | 1.00 47.54 | C |
| ATOM | 593 | C | GLY | A | 299 | 10.772 | 35.805 | 10.186 | 1.00 47.56 | C |
| ATOM | 594 | O | GLY | A | 299 | 9.580 | 35.534 | 10.360 | 1.00 45.18 | O |
| ATOM | 595 | N | LEU | A | 300 | 11.768 | 35.021 | 10.629 | 1.00 47.92 | N |
| ATOM | 596 | CA | LEU | A | 300 | 11.438 | 33.799 | 11.366 | 1.00 49.21 | C |
| ATOM | 597 | C | LEU | A | 300 | 10.565 | 34.131 | 12.575 | 1.00 51.18 | C |
| ATOM | 598 | O | LEU | A | 300 | 9.551 | 33.523 | 12.910 | 1.00 51.82 | O |
| ATOM | 599 | CB | LEU | A | 300 | 12.718 | 33.158 | 11.907 | 1.00 48.64 | C |
| ATOM | 600 | CG | LEU | A | 300 | 12.497 | 32.160 | 13.037 | 1.00 47.68 | C |
| ATOM | 601 | CD1 | LEU | A | 300 | 11.574 | 31.066 | 12.518 | 1.00 47.78 | C |
| ATOM | 602 | CD2 | LEU | A | 300 | 13.781 | 31.583 | 13.609 | 1.00 46.46 | C |
| ATOM | 603 | N | MET | A | 301 | 11.007 | 35.171 | 13.287 | 1.00 52.30 | N |
| ATOM | 604 | CA | MET | A | 301 | 10.292 | 35.656 | 14.458 | 1.00 52.98 | C |
| ATOM | 605 | C | MET | A | 301 | 8.857 | 36.033 | 14.115 | 1.00 51.64 | C |
| ATOM | 606 | O | MET | A | 301 | 7.934 | 35.593 | 14.775 | 1.00 51.38 | O |
| ATOM | 607 | CB | MET | A | 301 | 11.065 | 36.822 | 15.052 | 1.00 53.60 | C |
| ATOM | 608 | CG | MET | A | 301 | 12.101 | 36.577 | 16.129 | 1.00 53.54 | C |

90

| ATOM | 455 | CD1 | LEU A 282 | 32.657 | 48.312 | -1.786 | 1.00 | 44.59 | C |
| ATOM | 456 | CD2 | LEU A 282 | 33.121 | 50.731 | -1.916 | 1.00 | 45.72 | C |
| ATOM | 457 | N | ASP A 283 | 28.092 | 49.821 | -1.168 | 1.00 | 47.38 | N |
| ATOM | 458 | CA | ASP A 283 | 27.253 | 49.942 | 0.012 | 1.00 | 46.63 | C |
| ATOM | 459 | C | ASP A 283 | 26.136 | 48.899 | -0.019 | 1.00 | 47.13 | C |
| ATOM | 460 | O | ASP A 283 | 25.728 | 48.362 | 1.014 | 1.00 | 47.08 | O |
| ATOM | 461 | CB | ASP A 283 | 26.698 | 51.344 | 0.083 | 1.00 | 46.88 | C |
| ATOM | 462 | CG | ASP A 283 | 27.535 | 52.459 | 0.646 | 1.00 | 46.75 | C |
| ATOM | 463 | OD1 | ASP A 283 | 28.729 | 52.297 | 0.948 | 1.00 | 44.77 | O |
| ATOM | 464 | OD2 | ASP A 283 | 26.952 | 53.563 | 0.794 | 1.00 | 46.35 | O |
| ATOM | 465 | N | GLN A 284 | 25.594 | 48.572 | -1.197 | 1.00 | 47.39 | N |
| ATOM | 466 | CA | GLN A 284 | 24.551 | 47.546 | -1.241 | 1.00 | 48.53 | C |
| ATOM | 467 | C | GLN A 284 | 25.153 | 46.220 | -0.769 | 1.00 | 49.83 | C |
| ATOM | 468 | O | GLN A 284 | 24.629 | 45.575 | 0.140 | 1.00 | 50.25 | O |
| ATOM | 469 | CB | GLN A 284 | 23.970 | 47.464 | -2.640 | 1.00 | 48.29 | C |
| ATOM | 470 | CG | GLN A 284 | 23.322 | 48.752 | -3.081 | 1.00 | 48.21 | C |
| ATOM | 471 | CD | GLN A 284 | 22.905 | 48.730 | -4.540 | 1.00 | 46.43 | C |
| ATOM | 472 | OE1 | GLN A 284 | 22.422 | 47.697 | -4.981 | 1.00 | 47.07 | O |
| ATOM | 473 | NE2 | GLN A 284 | 23.093 | 49.842 | -5.230 | 1.00 | 44.75 | N |
| ATOM | 474 | N | VAL A 285 | 26.282 | 45.783 | -1.331 | 1.00 | 50.15 | N |
| ATOM | 475 | CA | VAL A 285 | 26.889 | 44.530 | -0.858 | 1.00 | 50.69 | C |
| ATOM | 476 | C | VAL A 285 | 27.215 | 44.598 | 0.634 | 1.00 | 50.13 | C |
| ATOM | 477 | O | VAL A 285 | 26.852 | 43.708 | 1.431 | 1.00 | 49.62 | O |
| ATOM | 478 | CB | VAL A 285 | 28.149 | 44.192 | -1.687 | 1.00 | 50.78 | C |
| ATOM | 479 | CG1 | VAL A 285 | 28.943 | 43.038 | -1.137 | 1.00 | 49.30 | C |
| ATOM | 480 | CG2 | VAL A 285 | 27.766 | 43.864 | -3.141 | 1.00 | 50.88 | C |
| ATOM | 481 | N | ARG A 286 | 27.898 | 45.666 | 1.061 | 1.00 | 49.14 | N |
| ATOM | 482 | CA | ARG A 286 | 28.255 | 45.737 | 2.491 | 1.00 | 49.59 | C |
| ATOM | 483 | C | ARG A 286 | 27.025 | 45.645 | 3.379 | 1.00 | 49.70 | C |
| ATOM | 484 | O | ARG A 286 | 27.072 | 44.837 | 4.308 | 1.00 | 50.23 | O |
| ATOM | 485 | CB | ARG A 286 | 29.145 | 46.908 | 2.846 | 1.00 | 48.68 | C |
| ATOM | 486 | CG | ARG A 286 | 30.549 | 46.860 | 2.261 | 1.00 | 46.18 | C |
| ATOM | 487 | CD | ARG A 286 | 31.370 | 48.007 | 2.806 | 1.00 | 45.86 | C |
| ATOM | 488 | NE | ARG A 286 | 30.965 | 49.265 | 2.255 | 1.00 | 46.70 | N |
| ATOM | 489 | CZ | ARG A 286 | 31.160 | 50.466 | 2.773 | 1.00 | 50.29 | C |
| ATOM | 490 | NH1 | ARG A 286 | 31.801 | 50.701 | 3.919 | 1.00 | 51.98 | N |
| ATOM | 491 | NH2 | ARG A 286 | 30.721 | 51.573 | 2.164 | 1.00 | 51.67 | N |
| ATOM | 492 | N | LEU A 287 | 25.947 | 46.369 | 3.114 | 1.00 | 49.20 | N |
| ATOM | 493 | CA | LEU A 287 | 24.746 | 46.236 | 3.932 | 1.00 | 47.94 | C |
| ATOM | 494 | C | LEU A 287 | 24.240 | 44.803 | 3.891 | 1.00 | 50.30 | C |
| ATOM | 495 | O | LEU A 287 | 24.036 | 44.187 | 4.976 | 1.00 | 51.20 | O |
| ATOM | 496 | CB | LEU A 287 | 23.701 | 47.252 | 3.467 | 1.00 | 45.69 | C |
| ATOM | 497 | CG | LEU A 287 | 24.181 | 48.708 | 3.597 | 1.00 | 44.99 | C |
| ATOM | 498 | CD1 | LEU A 287 | 23.319 | 49.687 | 2.849 | 1.00 | 43.27 | C |
| ATOM | 499 | CD2 | LEU A 287 | 24.320 | 49.160 | 5.061 | 1.00 | 43.62 | C |
| ATOM | 500 | N | LEU A 288 | 24.072 | 44.207 | 2.686 | 1.00 | 49.08 | N |
| ATOM | 501 | CA | LEU A 288 | 23.566 | 42.837 | 2.707 | 1.00 | 48.48 | C |
| ATOM | 502 | C | LEU A 288 | 24.501 | 41.897 | 3.436 | 1.00 | 50.21 | C |
| ATOM | 503 | O | LEU A 288 | 23.991 | 41.063 | 4.202 | 1.00 | 50.49 | O |
| ATOM | 504 | CB | LEU A 288 | 23.115 | 42.318 | 1.356 | 1.00 | 47.66 | C |
| ATOM | 505 | CG | LEU A 288 | 21.874 | 42.994 | 0.777 | 1.00 | 47.64 | C |
| ATOM | 506 | CD1 | LEU A 288 | 21.792 | 42.860 | -0.739 | 1.00 | 48.77 | C |
| ATOM | 507 | CD2 | LEU A 288 | 20.608 | 42.453 | 1.399 | 1.00 | 47.71 | C |
| ATOM | 508 | N | GLU A 289 | 25.825 | 41.984 | 3.282 | 1.00 | 51.14 | N |
| ATOM | 509 | CA | GLU A 289 | 26.733 | 41.080 | 3.985 | 1.00 | 50.31 | C |
| ATOM | 510 | C | GLU A 289 | 26.642 | 41.156 | 5.491 | 1.00 | 48.00 | C |
| ATOM | 511 | O | GLU A 289 | 26.828 | 40.158 | 6.194 | 1.00 | 48.82 | O |
| ATOM | 512 | CB | GLU A 289 | 28.160 | 41.362 | 3.530 | 1.00 | 53.82 | C |
| ATOM | 513 | CG | GLU A 289 | 28.344 | 41.233 | 2.016 | 1.00 | 57.89 | C |
| ATOM | 514 | CD | GLU A 289 | 29.808 | 41.329 | 1.615 | 1.00 | 60.40 | C |
| ATOM | 515 | OE1 | GLU A 289 | 30.652 | 41.938 | 2.319 | 1.00 | 62.04 | O |
| ATOM | 516 | OE2 | GLU A 289 | 30.143 | 40.759 | 0.551 | 1.00 | 62.04 | O |
| ATOM | 517 | N | SER A 290 | 26.329 | 42.280 | 6.099 | 1.00 | 45.35 | N |
| ATOM | 518 | CA | SER A 290 | 26.204 | 42.380 | 7.533 | 1.00 | 43.39 | C |
| ATOM | 519 | C | SER A 290 | 24.788 | 42.204 | 8.036 | 1.00 | 43.70 | C |
| ATOM | 520 | O | SER A 290 | 24.662 | 41.779 | 9.177 | 1.00 | 44.34 | O |
| ATOM | 521 | CB | SER A 290 | 26.728 | 43.751 | 7.964 | 1.00 | 43.81 | C |
| ATOM | 522 | OG | ASER A 290 | 25.601 | 44.538 | 8.364 | 0.50 | 43.99 | O |
| ATOM | 523 | OG | BSER A 290 | 27.990 | 43.994 | 7.313 | 0.50 | 42.77 | O |
| ATOM | 524 | N | CYS A 291 | 23.691 | 42.475 | 7.362 | 1.00 | 44.26 | N |
| ATOM | 525 | CA | CYS A 291 | 22.370 | 42.299 | 7.939 | 1.00 | 44.18 | C |
| ATOM | 526 | C | CYS A 291 | 21.587 | 41.076 | 7.488 | 1.00 | 44.83 | C |
| ATOM | 527 | O | CYS A 291 | 20.477 | 40.929 | 8.005 | 1.00 | 44.41 | O |
| ATOM | 528 | CB | CYS A 291 | 21.509 | 43.518 | 7.556 | 1.00 | 44.58 | C |
| ATOM | 529 | SG | CYS A 291 | 20.703 | 43.259 | 5.952 | 1.00 | 45.21 | S |
| ATOM | 530 | N | TRP A 292 | 22.099 | 40.202 | 6.611 | 1.00 | 45.41 | N |
| ATOM | 531 | CA | TRP A 292 | 21.336 | 39.057 | 6.155 | 1.00 | 44.63 | C |

91

| ATOM | 378 | CD  | LYS A 272 | 11.000 | 44.250 | -5.193 | 1.00 | 48.94 | C |
| ATOM | 379 | CE  | LYS A 272 | 10.135 | 43.656 | -6.273 | 1.00 | 49.38 | C |
| ATOM | 380 | NZ  | LYS A 272 |  9.935 | 42.190 | -6.026 | 1.00 | 50.71 | N |
| ATOM | 381 | N   | ILE A 273 | 13.726 | 48.196 | -1.865 | 1.00 | 44.69 | N |
| ATOM | 382 | CA  | ILE A 273 | 13.571 | 49.127 | -0.725 | 1.00 | 43.36 | C |
| ATOM | 383 | C   | ILE A 273 | 13.876 | 50.511 | -1.235 | 1.00 | 42.46 | C |
| ATOM | 384 | O   | ILE A 273 | 14.957 | 50.757 | -1.781 | 1.00 | 43.63 | O |
| ATOM | 385 | CB  | ILE A 273 | 14.506 | 48.798 |  0.456 | 1.00 | 43.15 | C |
| ATOM | 386 | CG1 | ILE A 273 | 14.338 | 47.383 |  0.995 | 1.00 | 43.17 | C |
| ATOM | 387 | CG2 | ILE A 273 | 14.363 | 49.835 |  1.557 | 1.00 | 43.61 | C |
| ATOM | 388 | CD1 | ILE A 273 | 12.919 | 47.036 |  1.427 | 1.00 | 43.42 | C |
| ATOM | 389 | N   | PRO A 274 | 12.962 | 51.438 | -1.086 | 1.00 | 41.73 | N |
| ATOM | 390 | CA  | PRO A 274 | 13.120 | 52.804 | -1.608 | 1.00 | 40.16 | C |
| ATOM | 391 | C   | PRO A 274 | 14.497 | 53.311 | -1.320 | 1.00 | 40.53 | C |
| ATOM | 392 | O   | PRO A 274 | 14.943 | 53.075 | -0.209 | 1.00 | 43.33 | O |
| ATOM | 393 | CB  | PRO A 274 | 11.984 | 53.646 | -1.051 | 1.00 | 38.95 | C |
| ATOM | 394 | CG  | PRO A 274 | 11.036 | 52.595 | -0.556 | 1.00 | 40.88 | C |
| ATOM | 395 | CD  | PRO A 274 | 11.670 | 51.224 | -0.450 | 1.00 | 40.34 | C |
| ATOM | 396 | N   | GLY A 275 | 15.223 | 53.925 | -2.200 | 1.00 | 41.97 | N |
| ATOM | 397 | CA  | GLY A 275 | 16.535 | 54.464 | -2.120 | 1.00 | 43.94 | C |
| ATOM | 398 | C   | GLY A 275 | 17.732 | 53.527 | -2.191 | 1.00 | 46.09 | C |
| ATOM | 399 | O   | GLY A 275 | 18.845 | 53.962 | -2.515 | 1.00 | 44.25 | O |
| ATOM | 400 | N   | PHE A 276 | 17.549 | 52.262 | -1.805 | 1.00 | 47.54 | N |
| ATOM | 401 | CA  | PHE A 276 | 18.639 | 51.296 | -1.735 | 1.00 | 49.37 | C |
| ATOM | 402 | C   | PHE A 276 | 19.434 | 51.195 | -3.029 | 1.00 | 50.70 | C |
| ATOM | 403 | O   | PHE A 276 | 20.648 | 51.437 | -2.953 | 1.00 | 52.28 | O |
| ATOM | 404 | CB  | PHE A 276 | 18.212 | 49.888 | -1.368 | 1.00 | 47.29 | C |
| ATOM | 405 | CG  | PHE A 276 | 19.186 | 48.799 | -1.119 | 1.00 | 46.22 | C |
| ATOM | 406 | CD1 | PHE A 276 | 19.767 | 48.623 |  0.133 | 1.00 | 45.70 | C |
| ATOM | 407 | CD2 | PHE A 276 | 19.513 | 47.872 | -2.112 | 1.00 | 45.72 | C |
| ATOM | 408 | CE1 | PHE A 276 | 20.656 | 47.586 |  0.384 | 1.00 | 43.94 | C |
| ATOM | 409 | CE2 | PHE A 276 | 20.373 | 46.816 | -1.886 | 1.00 | 44.01 | C |
| ATOM | 410 | CZ  | PHE A 276 | 20.955 | 46.684 | -0.621 | 1.00 | 45.03 | C |
| ATOM | 411 | N   | VAL A 277 | 18.770 | 50.917 | -4.155 | 1.00 | 48.33 | N |
| ATOM | 412 | CA  | VAL A 277 | 19.511 | 50.804 | -5.394 | 1.00 | 47.00 | C |
| ATOM | 413 | C   | VAL A 277 | 20.088 | 52.144 | -5.790 | 1.00 | 46.93 | C |
| ATOM | 414 | O   | VAL A 277 | 20.817 | 52.176 | -6.778 | 1.00 | 47.69 | O |
| ATOM | 415 | CB  | VAL A 277 | 18.817 | 50.058 | -6.563 | 1.00 | 46.27 | C |
| ATOM | 416 | CG1 | VAL A 277 | 18.398 | 48.655 | -6.111 | 1.00 | 44.41 | C |
| ATOM | 417 | CG2 | VAL A 277 | 17.677 | 50.800 | -7.241 | 1.00 | 40.22 | C |
| ATOM | 418 | N   | GLU A 278 | 19.873 | 53.238 | -5.119 | 1.00 | 48.17 | N |
| ATOM | 419 | CA  | GLU A 278 | 20.448 | 54.539 | -5.383 | 1.00 | 50.40 | C |
| ATOM | 420 | C   | GLU A 278 | 21.717 | 54.657 | -4.544 | 1.00 | 51.92 | C |
| ATOM | 421 | O   | GLU A 278 | 22.469 | 55.624 | -4.566 | 1.00 | 53.83 | O |
| ATOM | 422 | CB  | GLU A 278 | 19.502 | 55.669 | -5.066 | 1.00 | 53.43 | C |
| ATOM | 423 | CG  | GLU A 278 | 18.478 | 56.006 | -6.111 | 1.00 | 59.85 | C |
| ATOM | 424 | CD  | GLU A 278 | 17.382 | 54.996 | -6.351 | 1.00 | 64.83 | C |
| ATOM | 425 | OE1 | GLU A 278 | 17.158 | 54.042 | -5.555 | 1.00 | 67.58 | O |
| ATOM | 426 | OE2 | GLU A 278 | 16.673 | 55.115 | -7.390 | 1.00 | 67.64 | O |
| ATOM | 427 | N   | LEU A 279 | 22.003 | 53.654 | -3.711 | 1.00 | 52.27 | N |
| ATOM | 428 | CA  | LEU A 279 | 23.203 | 53.573 | -2.914 | 1.00 | 50.91 | C |
| ATOM | 429 | C   | LEU A 279 | 24.235 | 53.007 | -3.909 | 1.00 | 50.11 | C |
| ATOM | 430 | O   | LEU A 279 | 23.838 | 52.300 | -4.837 | 1.00 | 49.19 | O |
| ATOM | 431 | CB  | LEU A 279 | 23.112 | 52.544 | -1.786 | 1.00 | 49.94 | C |
| ATOM | 432 | CG  | LEU A 279 | 22.193 | 52.958 | -0.628 | 1.00 | 50.11 | C |
| ATOM | 433 | CD1 | LEU A 279 | 21.933 | 51.819 |  0.354 | 1.00 | 47.10 | C |
| ATOM | 434 | CD2 | LEU A 279 | 22.809 | 54.181 |  0.056 | 1.00 | 49.76 | C |
| ATOM | 435 | N   | SER A 280 | 25.498 | 53.271 | -3.715 | 1.00 | 48.73 | N |
| ATOM | 436 | CA  | SER A 280 | 26.541 | 52.721 | -4.570 | 1.00 | 47.58 | C |
| ATOM | 437 | C   | SER A 280 | 26.524 | 51.210 | -4.408 | 1.00 | 49.36 | C |
| ATOM | 438 | O   | SER A 280 | 26.035 | 50.687 | -3.386 | 1.00 | 51.69 | O |
| ATOM | 439 | CB  | SER A 280 | 27.851 | 53.290 | -4.014 | 1.00 | 45.91 | C |
| ATOM | 440 | OG  | SER A 280 | 28.243 | 52.362 | -3.009 | 1.00 | 46.77 | O |
| ATOM | 441 | N   | LEU A 281 | 27.055 | 50.413 | -5.313 | 1.00 | 50.11 | N |
| ATOM | 442 | CA  | LEU A 281 | 27.016 | 48.956 | -5.187 | 1.00 | 50.12 | C |
| ATOM | 443 | C   | LEU A 281 | 27.806 | 48.402 | -4.021 | 1.00 | 50.04 | C |
| ATOM | 444 | O   | LEU A 281 | 27.479 | 47.380 | -3.387 | 1.00 | 49.06 | O |
| ATOM | 445 | CB  | LEU A 281 | 27.528 | 48.376 | -6.508 | 1.00 | 52.02 | C |
| ATOM | 446 | CG  | LEU A 281 | 27.086 | 46.940 | -6.747 | 1.00 | 53.97 | C |
| ATOM | 447 | CD1 | LEU A 281 | 25.571 | 46.924 | -6.914 | 1.00 | 54.74 | C |
| ATOM | 448 | CD2 | LEU A 281 | 27.809 | 46.359 | -7.943 | 1.00 | 55.02 | C |
| ATOM | 449 | N   | LEU A 282 | 28.879 | 49.124 | -3.687 | 1.00 | 49.07 | N |
| ATOM | 450 | CA  | LEU A 282 | 29.788 | 48.842 | -2.588 | 1.00 | 47.54 | C |
| ATOM | 451 | C   | LEU A 282 | 29.020 | 48.856 | -1.275 | 1.00 | 47.43 | C |
| ATOM | 452 | O   | LEU A 282 | 29.271 | 48.029 | -0.417 | 1.00 | 47.07 | O |
| ATOM | 453 | CB  | LEU A 282 | 30.856 | 49.934 | -2.494 | 1.00 | 46.39 | C |
| ATOM | 454 | CG  | LEU A 282 | 32.051 | 49.700 | -1.615 | 1.00 | 44.67 | C |

| ATOM | 301 | C | LEU A 263 | 18.505 | 35.232 | -0.847 | 1.00 | 63.69 | C |
| ATOM | 302 | O | LEU A 263 | 18.502 | 36.437 | -1.145 | 1.00 | 64.55 | O |
| ATOM | 303 | CB | LEU A 263 | 20.182 | 34.382 | 0.926 | 1.00 | 64.33 | C |
| ATOM | 304 | CG | LEU A 263 | 20.373 | 34.295 | 2.452 | 1.00 | 66.53 | C |
| ATOM | 305 | CD1 | LEU A 263 | 21.427 | 33.267 | 2.864 | 1.00 | 67.85 | C |
| ATOM | 306 | CD2 | LEU A 263 | 20.774 | 35.666 | 2.985 | 1.00 | 67.33 | C |
| ATOM | 307 | N | VAL A 264 | 18.224 | 34.277 | -1.736 | 1.00 | 62.17 | N |
| ATOM | 308 | CA | VAL A 264 | 17.918 | 34.621 | -3.120 | 1.00 | 60.50 | C |
| ATOM | 309 | C | VAL A 264 | 16.836 | 35.688 | -3.116 | 1.00 | 59.29 | C |
| ATOM | 310 | O | VAL A 264 | 17.073 | 36.787 | -3.649 | 1.00 | 60.22 | O |
| ATOM | 311 | CB | VAL A 264 | 17.468 | 33.407 | -3.962 | 1.00 | 59.97 | C |
| ATOM | 312 | CG1 | VAL A 264 | 17.094 | 33.824 | -5.366 | 1.00 | 57.51 | C |
| ATOM | 313 | CG2 | VAL A 264 | 18.535 | 32.329 | -4.018 | 1.00 | 59.35 | C |
| ATOM | 314 | N | HIS A 265 | 15.678 | 35.417 | -2.520 | 1.00 | 57.73 | N |
| ATOM | 315 | CA | HIS A 265 | 14.636 | 36.440 | -2.488 | 1.00 | 57.56 | C |
| ATOM | 316 | C | HIS A 265 | 14.993 | 37.708 | -1.720 | 1.00 | 56.23 | C |
| ATOM | 317 | O | HIS A 265 | 14.417 | 38.781 | -1.965 | 1.00 | 55.89 | O |
| ATOM | 318 | CB | HIS A 265 | 13.391 | 35.877 | -1.827 | 1.00 | 60.34 | C |
| ATOM | 319 | CG | HIS A 265 | 12.894 | 34.628 | -2.472 | 1.00 | 62.96 | C |
| ATOM | 320 | ND1 | HIS A 265 | 12.057 | 34.623 | -3.570 | 1.00 | 63.91 | N |
| ATOM | 321 | CD2 | HIS A 265 | 13.109 | 33.339 | -2.159 | 1.00 | 64.40 | C |
| ATOM | 322 | CE1 | HIS A 265 | 11.803 | 33.381 | -3.906 | 1.00 | 64.87 | C |
| ATOM | 323 | NE2 | HIS A 265 | 12.410 | 32.574 | -3.068 | 1.00 | 64.71 | N |
| ATOM | 324 | N | MET A 266 | 15.956 | 37.645 | -0.784 | 1.00 | 53.46 | N |
| ATOM | 325 | CA | MET A 266 | 16.327 | 38.825 | -0.021 | 1.00 | 50.61 | C |
| ATOM | 326 | C | MET A 266 | 16.995 | 39.930 | -0.827 | 1.00 | 50.26 | C |
| ATOM | 327 | O | MET A 266 | 16.901 | 41.155 | -0.582 | 1.00 | 48.98 | O |
| ATOM | 328 | CB | MET A 266 | 17.213 | 38.378 | 1.124 | 1.00 | 49.57 | C |
| ATOM | 329 | CG | MET A 266 | 17.290 | 39.441 | 2.210 | 1.00 | 48.57 | C |
| ATOM | 330 | SD | MET A 266 | 18.578 | 38.966 | 3.372 | 1.00 | 46.54 | S |
| ATOM | 331 | CE | MET A 266 | 17.640 | 37.857 | 4.393 | 1.00 | 46.03 | C |
| ATOM | 332 | N | ILE A 267 | 17.726 | 39.467 | -1.851 | 1.00 | 48.23 | N |
| ATOM | 333 | CA | ILE A 267 | 18.415 | 40.393 | -2.739 | 1.00 | 45.69 | C |
| ATOM | 334 | C | ILE A 267 | 17.372 | 41.099 | -3.573 | 1.00 | 45.41 | C |
| ATOM | 335 | O | ILE A 267 | 17.405 | 42.313 | -3.761 | 1.00 | 46.18 | O |
| ATOM | 336 | CB | ILE A 267 | 19.393 | 39.593 | -3.594 | 1.00 | 46.35 | C |
| ATOM | 337 | CG1 | ILE A 267 | 20.255 | 38.785 | -2.604 | 1.00 | 46.89 | C |
| ATOM | 338 | CG2 | ILE A 267 | 20.131 | 40.542 | -4.514 | 1.00 | 45.11 | C |
| ATOM | 339 | CD1 | ILE A 267 | 21.533 | 38.236 | -3.207 | 1.00 | 49.17 | C |
| ATOM | 340 | N | GLY A 268 | 16.372 | 40.342 | -4.011 | 1.00 | 44.57 | N |
| ATOM | 341 | CA | GLY A 268 | 15.304 | 40.910 | -4.821 | 1.00 | 43.42 | C |
| ATOM | 342 | C | GLY A 268 | 14.564 | 41.903 | -3.963 | 1.00 | 44.36 | C |
| ATOM | 343 | O | GLY A 268 | 14.306 | 43.059 | -4.336 | 1.00 | 45.57 | O |
| ATOM | 344 | N | TRP A 269 | 14.262 | 41.404 | -2.757 | 1.00 | 44.49 | N |
| ATOM | 345 | CA | TRP A 269 | 13.577 | 42.294 | -1.810 | 1.00 | 43.20 | C |
| ATOM | 346 | C | TRP A 269 | 14.429 | 43.530 | -1.558 | 1.00 | 42.71 | C |
| ATOM | 347 | O | TRP A 269 | 13.878 | 44.645 | -1.653 | 1.00 | 44.04 | O |
| ATOM | 348 | CB | TRP A 269 | 13.319 | 41.522 | -0.537 | 1.00 | 42.91 | C |
| ATOM | 349 | CG | TRP A 269 | 12.983 | 42.398 | 0.636 | 1.00 | 42.30 | C |
| ATOM | 350 | CD1 | TRP A 269 | 11.752 | 42.938 | 0.841 | 1.00 | 41.58 | C |
| ATOM | 351 | CD2 | TRP A 269 | 13.840 | 42.818 | 1.706 | 1.00 | 40.36 | C |
| ATOM | 352 | NE1 | TRP A 269 | 11.801 | 43.662 | 1.998 | 1.00 | 42.90 | N |
| ATOM | 353 | CE2 | TRP A 269 | 13.059 | 43.614 | 2.559 | 1.00 | 41.90 | C |
| ATOM | 354 | CE3 | TRP A 269 | 15.163 | 42.597 | 2.049 | 1.00 | 39.98 | C |
| ATOM | 355 | CZ2 | TRP A 269 | 13.527 | 44.216 | 3.741 | 1.00 | 39.96 | C |
| ATOM | 356 | CZ3 | TRP A 269 | 15.657 | 43.170 | 3.219 | 1.00 | 41.73 | C |
| ATOM | 357 | CH2 | TRP A 269 | 14.831 | 43.975 | 4.052 | 1.00 | 41.02 | C |
| ATOM | 358 | N | ALA A 270 | 15.710 | 43.390 | -1.256 | 1.00 | 41.84 | N |
| ATOM | 359 | CA | ALA A 270 | 16.554 | 44.545 | -0.947 | 1.00 | 42.09 | C |
| ATOM | 360 | C | ALA A 270 | 16.504 | 45.597 | -2.032 | 1.00 | 43.09 | C |
| ATOM | 361 | O | ALA A 270 | 16.301 | 46.788 | -1.771 | 1.00 | 39.98 | O |
| ATOM | 362 | CB | ALA A 270 | 17.987 | 44.154 | -0.668 | 1.00 | 41.89 | C |
| ATOM | 363 | N | LYS A 271 | 16.660 | 45.091 | -3.265 | 1.00 | 45.16 | N |
| ATOM | 364 | CA | LYS A 271 | 16.600 | 45.919 | -4.460 | 1.00 | 46.22 | C |
| ATOM | 365 | C | LYS A 271 | 15.306 | 46.711 | -4.517 | 1.00 | 45.50 | C |
| ATOM | 366 | O | LYS A 271 | 15.366 | 47.785 | -5.127 | 1.00 | 44.69 | O |
| ATOM | 367 | CB | LYS A 271 | 16.725 | 45.117 | -5.747 | 1.00 | 48.55 | C |
| ATOM | 368 | CG | LYS A 271 | 18.066 | 45.030 | -6.389 | 1.00 | 51.17 | C |
| ATOM | 369 | CD | LYS A 271 | 18.831 | 43.755 | -6.256 | 1.00 | 55.01 | C |
| ATOM | 370 | CE | LYS A 271 | 18.236 | 42.588 | -7.028 | 1.00 | 59.71 | C |
| ATOM | 371 | NZ | LYS A 271 | 18.147 | 42.843 | -8.507 | 1.00 | 63.40 | N |
| ATOM | 372 | N | LYS A 272 | 14.174 | 46.301 | -3.979 | 1.00 | 45.43 | N |
| ATOM | 373 | CA | LYS A 272 | 12.983 | 47.124 | -4.005 | 1.00 | 46.52 | C |
| ATOM | 374 | C | LYS A 272 | 12.833 | 48.104 | -2.833 | 1.00 | 45.83 | C |
| ATOM | 375 | O | LYS A 272 | 11.800 | 48.796 | -2.837 | 1.00 | 44.88 | O |
| ATOM | 376 | CB | LYS A 272 | 11.726 | 46.244 | -3.996 | 1.00 | 47.48 | C |
| ATOM | 377 | CG | LYS A 272 | 11.265 | 45.735 | -5.350 | 1.00 | 48.21 | C |

| | | | | | | | | | |
|---|---|---|---|---|---|---|---|---|---|
| ATOM | 224 | SD | MET | A | 252 | 21.509 | 23.673 | 12.606 | 1.00 108.05 | S |
| ATOM | 225 | CE | MET | A | 252 | 22.411 | 24.918 | 11.684 | 1.00 108.27 | C |
| ATOM | 226 | N | MET | A | 253 | 20.796 | 20.522 | 8.001 | 1.00 104.88 | N |
| ATOM | 227 | CA | MET | A | 253 | 20.741 | 20.260 | 6.577 | 1.00 102.79 | C |
| ATOM | 228 | C | MET | A | 253 | 19.562 | 20.962 | 5.921 | 1.00 100.42 | C |
| ATOM | 229 | O | MET | A | 253 | 19.698 | 21.633 | 4.897 | 1.00 100.39 | O |
| ATOM | 230 | CB | MET | A | 253 | 20.642 | 18.742 | 6.361 | 1.00 103.47 | C |
| ATOM | 231 | CG | MET | A | 253 | 21.612 | 18.226 | 5.308 | 1.00 104.43 | C |
| ATOM | 232 | SD | MET | A | 253 | 22.034 | 16.491 | 5.552 | 1.00 104.64 | S |
| ATOM | 233 | CE | MET | A | 253 | 20.620 | 15.719 | 4.744 | 1.00 104.44 | C |
| ATOM | 234 | N | SER | A | 254 | 18.379 | 20.809 | 6.504 | 1.00 97.50 | N |
| ATOM | 235 | CA | SER | A | 254 | 17.176 | 21.438 | 5.965 | 1.00 94.58 | C |
| ATOM | 236 | C | SER | A | 254 | 17.330 | 22.961 | 6.005 | 1.00 91.40 | C |
| ATOM | 237 | O | SER | A | 254 | 17.280 | 23.674 | 5.001 | 1.00 90.63 | O |
| ATOM | 238 | CB | SER | A | 254 | 15.952 | 20.979 | 6.752 | 1.00 95.10 | C |
| ATOM | 239 | OG | SER | A | 254 | 15.754 | 19.578 | 6.674 | 1.00 95.44 | O |
| ATOM | 240 | N | LEU | A | 255 | 17.586 | 23.454 | 7.202 | 1.00 86.86 | N |
| ATOM | 241 | CA | LEU | A | 255 | 17.760 | 24.844 | 7.544 | 1.00 83.38 | C |
| ATOM | 242 | C | LEU | A | 255 | 18.681 | 25.622 | 6.635 | 1.00 80.72 | C |
| ATOM | 243 | O | LEU | A | 255 | 18.418 | 26.789 | 6.343 | 1.00 79.92 | O |
| ATOM | 244 | CB | LEU | A | 255 | 18.141 | 24.953 | 9.040 | 1.00 83.20 | C |
| ATOM | 245 | CG | LEU | A | 255 | 17.009 | 24.575 | 10.001 | 1.00 81.99 | C |
| ATOM | 246 | CD1 | LEU | A | 255 | 17.418 | 24.677 | 11.447 | 1.00 82.44 | C |
| ATOM | 247 | CD2 | LEU | A | 255 | 15.772 | 25.413 | 9.754 | 1.00 81.52 | C |
| ATOM | 248 | N | THR | A | 256 | 19.754 | 25.042 | 6.145 | 1.00 78.08 | N |
| ATOM | 249 | CA | THR | A | 256 | 20.681 | 25.668 | 5.218 | 1.00 75.33 | C |
| ATOM | 250 | C | THR | A | 256 | 20.025 | 25.689 | 3.838 | 1.00 75.22 | C |
| ATOM | 251 | O | THR | A | 256 | 20.264 | 26.607 | 3.058 | 1.00 75.70 | O |
| ATOM | 252 | CB | THR | A | 256 | 21.973 | 24.846 | 5.081 | 1.00 73.83 | C |
| ATOM | 253 | OG1 | THR | A | 256 | 22.646 | 24.801 | 6.326 | 1.00 73.84 | O |
| ATOM | 254 | CG2 | THR | A | 256 | 22.958 | 25.385 | 4.068 | 1.00 73.67 | C |
| ATOM | 255 | N | LYS | A | 257 | 19.205 | 24.694 | 3.485 | 1.00 74.37 | N |
| ATOM | 256 | CA | LYS | A | 257 | 18.612 | 24.777 | 2.147 | 1.00 74.32 | C |
| ATOM | 257 | C | LYS | A | 257 | 17.591 | 25.914 | 2.185 | 1.00 72.57 | C |
| ATOM | 258 | O | LYS | A | 257 | 17.486 | 26.636 | 1.199 | 1.00 72.18 | O |
| ATOM | 259 | CB | LYS | A | 257 | 18.024 | 23.469 | 1.621 | 1.00 75.98 | C |
| ATOM | 260 | N | LEU | A | 258 | 16.873 | 26.071 | 3.294 | 1.00 70.19 | N |
| ATOM | 261 | CA | LEU | A | 258 | 15.893 | 27.150 | 3.405 | 1.00 68.14 | C |
| ATOM | 262 | C | LEU | A | 258 | 16.538 | 28.539 | 3.318 | 1.00 66.76 | C |
| ATOM | 263 | O | LEU | A | 258 | 16.115 | 29.428 | 2.572 | 1.00 64.64 | O |
| ATOM | 264 | CB | LEU | A | 258 | 15.142 | 26.972 | 4.726 | 1.00 67.06 | C |
| ATOM | 265 | CG | LEU | A | 258 | 14.240 | 28.138 | 5.131 | 1.00 66.56 | C |
| ATOM | 266 | CD1 | LEU | A | 258 | 13.115 | 28.328 | 4.124 | 1.00 65.93 | C |
| ATOM | 267 | CD2 | LEU | A | 258 | 13.723 | 27.947 | 6.543 | 1.00 65.55 | C |
| ATOM | 268 | N | ALA | A | 259 | 17.603 | 28.742 | 4.075 | 1.00 64.85 | N |
| ATOM | 269 | CA | ALA | A | 259 | 18.311 | 30.002 | 4.112 | 1.00 65.98 | C |
| ATOM | 270 | C | ALA | A | 259 | 18.735 | 30.475 | 2.735 | 1.00 67.01 | C |
| ATOM | 271 | O | ALA | A | 259 | 18.519 | 31.644 | 2.387 | 1.00 66.74 | O |
| ATOM | 272 | CB | ALA | A | 259 | 19.457 | 29.939 | 5.106 | 1.00 65.17 | C |
| ATOM | 273 | N | ASP | A | 260 | 19.321 | 29.604 | 1.927 | 1.00 68.15 | N |
| ATOM | 274 | CA | ASP | A | 260 | 19.745 | 29.912 | 0.573 | 1.00 68.91 | C |
| ATOM | 275 | C | ASP | A | 260 | 18.615 | 30.384 | -0.327 | 1.00 67.90 | C |
| ATOM | 276 | O | ASP | A | 260 | 18.735 | 31.366 | -1.057 | 1.00 67.93 | O |
| ATOM | 277 | CB | ASP | A | 260 | 20.245 | 28.622 | -0.100 | 1.00 71.92 | C |
| ATOM | 278 | CG | ASP | A | 260 | 21.371 | 28.048 | 0.731 | 1.00 74.56 | C |
| ATOM | 279 | OD1 | ASP | A | 260 | 21.891 | 28.787 | 1.598 | 1.00 75.72 | O |
| ATOM | 280 | OD2 | ASP | A | 260 | 21.668 | 26.859 | 0.500 | 1.00 76.33 | O |
| ATOM | 281 | N | LYS | A | 261 | 17.505 | 29.639 | -0.255 | 1.00 66.34 | N |
| ATOM | 282 | CA | LYS | A | 261 | 16.359 | 30.036 | -1.054 | 1.00 66.62 | C |
| ATOM | 283 | C | LYS | A | 261 | 15.979 | 31.428 | -0.570 | 1.00 66.01 | C |
| ATOM | 284 | O | LYS | A | 261 | 15.816 | 32.321 | -1.400 | 1.00 66.24 | O |
| ATOM | 285 | CB | LYS | A | 261 | 15.212 | 29.047 | -0.997 | 1.00 68.55 | C |
| ATOM | 286 | CG | LYS | A | 261 | 15.507 | 27.691 | -1.647 | 1.00 70.12 | C |
| ATOM | 287 | CD | LYS | A | 261 | 14.226 | 26.881 | -1.662 | 1.00 72.27 | C |
| ATOM | 288 | CE | LYS | A | 261 | 14.409 | 25.398 | -1.431 | 1.00 73.43 | C |
| ATOM | 289 | NZ | LYS | A | 261 | 14.773 | 24.613 | -2.644 | 1.00 74.53 | N |
| ATOM | 290 | N | GLU | A | 262 | 15.906 | 31.619 | 0.755 | 1.00 64.78 | N |
| ATOM | 291 | CA | GLU | A | 262 | 15.555 | 32.905 | 1.338 | 1.00 62.24 | C |
| ATOM | 292 | C | GLU | A | 262 | 16.538 | 34.015 | 0.995 | 1.00 61.70 | C |
| ATOM | 293 | O | GLU | A | 262 | 16.141 | 35.170 | 0.777 | 1.00 61.36 | O |
| ATOM | 294 | CB | GLU | A | 262 | 15.372 | 32.766 | 2.846 | 1.00 60.45 | C |
| ATOM | 295 | CG | GLU | A | 262 | 14.167 | 31.955 | 3.255 | 1.00 58.90 | C |
| ATOM | 296 | CD | GLU | A | 262 | 13.750 | 32.041 | 4.713 | 1.00 57.93 | C |
| ATOM | 297 | OE1 | GLU | A | 262 | 14.344 | 31.344 | 5.556 | 1.00 56.29 | O |
| ATOM | 298 | OE2 | GLU | A | 262 | 12.804 | 32.811 | 5.021 | 1.00 57.84 | O |
| ATOM | 299 | N | LEU | A | 263 | 17.827 | 33.720 | 0.924 | 1.00 61.72 | N |
| ATOM | 300 | CA | LEU | A | 263 | 18.769 | 34.798 | 0.584 | 1.00 63.30 | C |

94

| | | | | | | | | | |
|---|---|---|---|---|---|---|---|---|---|
| ATOM | 147 | CG1 | VAL | A | 237 | 11.809 | 29.049 | 0.957 | 1.00 102.30 | C |
| ATOM | 148 | CG2 | VAL | A | 237 | 11.242 | 31.284 | 0.075 | 1.00 101.95 | C |
| ATOM | 149 | N | LEU | A | 238 | 8.459 | 27.660 | 1.017 | 1.00 110.08 | N |
| ATOM | 150 | CA | LEU | A | 238 | 8.091 | 26.334 | 1.473 | 1.00 114.45 | C |
| ATOM | 151 | C | LEU | A | 238 | 9.229 | 25.331 | 1.459 | 1.00 117.26 | C |
| ATOM | 152 | O | LEU | A | 238 | 10.062 | 25.181 | 0.580 | 1.00 117.03 | O |
| ATOM | 153 | CB | LEU | A | 238 | 6.899 | 25.818 | 0.650 | 1.00 114.60 | C |
| ATOM | 154 | CG | LEU | A | 238 | 5.736 | 26.807 | 0.536 | 1.00 115.17 | C |
| ATOM | 155 | CD1 | LEU | A | 238 | 4.630 | 26.251 | -0.352 | 1.00 115.64 | C |
| ATOM | 156 | CD2 | LEU | A | 238 | 5.180 | 27.176 | 1.905 | 1.00 115.26 | C |
| ATOM | 157 | N | VAL | A | 239 | 9.291 | 24.582 | 2.544 | 1.00 121.36 | N |
| ATOM | 158 | CA | VAL | A | 239 | 10.256 | 23.524 | 2.820 | 1.00 125.15 | C |
| ATOM | 159 | C | VAL | A | 239 | 9.503 | 22.553 | 3.730 | 1.00 128.25 | C |
| ATOM | 160 | O | VAL | A | 239 | 8.540 | 22.955 | 4.382 | 1.00 127.90 | O |
| ATOM | 161 | CB | VAL | A | 239 | 11.581 | 24.035 | 3.380 | 1.00 124.49 | C |
| ATOM | 162 | CG1 | VAL | A | 239 | 12.268 | 23.080 | 4.338 | 1.00 124.31 | C |
| ATOM | 163 | CG2 | VAL | A | 239 | 12.579 | 24.298 | 2.252 | 1.00 124.17 | C |
| ATOM | 164 | N | SER | A | 240 | 9.901 | 21.291 | 3.723 | 1.00 132.82 | N |
| ATOM | 165 | CA | SER | A | 240 | 9.234 | 20.295 | 4.547 | 1.00 136.78 | C |
| ATOM | 166 | C | SER | A | 240 | 10.210 | 19.608 | 5.497 | 1.00 139.62 | C |
| ATOM | 167 | O | SER | A | 240 | 11.402 | 19.503 | 5.236 | 1.00 139.36 | O |
| ATOM | 168 | CB | SER | A | 240 | 8.504 | 19.244 | 3.707 | 1.00 136.60 | C |
| ATOM | 169 | N | ARG | A | 241 | 9.630 | 19.173 | 6.613 | 1.00 143.53 | N |
| ATOM | 170 | CA | ARG | A | 241 | 10.395 | 18.450 | 7.631 | 1.00 147.25 | C |
| ATOM | 171 | C | ARG | A | 241 | 10.727 | 17.102 | 6.988 | 1.00 149.13 | C |
| ATOM | 172 | O | ARG | A | 241 | 9.894 | 16.515 | 6.293 | 1.00 149.56 | O |
| ATOM | 173 | CB | ARG | A | 241 | 9.570 | 18.246 | 8.890 | 1.00 148.44 | C |
| ATOM | 174 | CG | ARG | A | 241 | 9.475 | 19.412 | 9.855 | 1.00 149.55 | C |
| ATOM | 175 | CD | ARG | A | 241 | 8.210 | 19.360 | 10.706 | 1.00 150.08 | C |
| ATOM | 176 | NE | ARG | A | 241 | 7.081 | 19.934 | 9.996 | 1.00 150.87 | N |
| ATOM | 177 | CZ | ARG | A | 241 | 5.902 | 20.310 | 10.454 | 1.00 150.88 | C |
| ATOM | 178 | NH1 | ARG | A | 241 | 5.601 | 20.188 | 11.739 | 1.00 151.06 | N |
| ATOM | 179 | NH2 | ARG | A | 241 | 5.013 | 20.818 | 9.608 | 1.00 150.87 | N |
| ATOM | 180 | N | PRO | A | 242 | 11.938 | 16.633 | 7.194 | 1.00 150.46 | N |
| ATOM | 181 | CA | PRO | A | 242 | 12.434 | 15.386 | 6.645 | 1.00 151.25 | C |
| ATOM | 182 | C | PRO | A | 242 | 11.581 | 14.175 | 6.987 | 1.00 151.85 | C |
| ATOM | 183 | O | PRO | A | 242 | 10.737 | 13.753 | 6.191 | 1.00 152.41 | O |
| ATOM | 184 | CB | PRO | A | 242 | 13.878 | 15.216 | 7.152 | 1.00 151.21 | C |
| ATOM | 185 | CG | PRO | A | 242 | 14.217 | 16.597 | 7.639 | 1.00 150.97 | C |
| ATOM | 186 | CD | PRO | A | 242 | 12.947 | 17.331 | 7.997 | 1.00 150.65 | C |
| ATOM | 187 | N | PHE | A | 246 | 17.079 | 12.452 | 10.660 | 1.00 114.32 | N |
| ATOM | 188 | CA | PHE | A | 246 | 18.077 | 12.520 | 11.729 | 1.00 114.81 | C |
| ATOM | 189 | C | PHE | A | 246 | 17.756 | 13.674 | 12.674 | 1.00 114.88 | C |
| ATOM | 190 | O | PHE | A | 246 | 16.570 | 13.981 | 12.811 | 1.00 114.64 | O |
| ATOM | 191 | CB | PHE | A | 246 | 19.472 | 12.623 | 11.133 | 1.00 114.69 | C |
| ATOM | 192 | N | THR | A | 247 | 18.761 | 14.290 | 13.282 | 1.00 115.41 | N |
| ATOM | 193 | CA | THR | A | 247 | 18.493 | 15.412 | 14.181 | 1.00 116.17 | C |
| ATOM | 194 | C | THR | A | 247 | 19.590 | 16.462 | 14.061 | 1.00 116.56 | C |
| ATOM | 195 | O | THR | A | 247 | 19.319 | 17.552 | 13.539 | 1.00 116.76 | O |
| ATOM | 196 | CB | THR | A | 247 | 18.270 | 14.928 | 15.600 | 1.00 116.04 | C |
| ATOM | 197 | N | GLU | A | 248 | 20.806 | 16.142 | 14.499 | 1.00 116.60 | N |
| ATOM | 198 | CA | GLU | A | 248 | 21.911 | 17.092 | 14.414 | 1.00 116.54 | C |
| ATOM | 199 | C | GLU | A | 248 | 22.343 | 17.303 | 12.967 | 1.00 116.63 | C |
| ATOM | 200 | O | GLU | A | 248 | 22.755 | 18.415 | 12.628 | 1.00 116.79 | O |
| ATOM | 201 | CB | GLU | A | 248 | 23.083 | 16.647 | 15.268 | 1.00 116.51 | C |
| ATOM | 202 | N | ALA | A | 249 | 22.233 | 16.274 | 12.133 | 1.00 116.41 | N |
| ATOM | 203 | CA | ALA | A | 249 | 22.616 | 16.415 | 10.735 | 1.00 116.15 | C |
| ATOM | 204 | C | ALA | A | 249 | 21.426 | 16.669 | 9.819 | 1.00 115.93 | C |
| ATOM | 205 | O | ALA | A | 249 | 21.622 | 17.233 | 8.737 | 1.00 115.98 | O |
| ATOM | 206 | CB | ALA | A | 249 | 23.350 | 15.159 | 10.274 | 1.00 116.28 | C |
| ATOM | 207 | N | SER | A | 250 | 20.226 | 16.254 | 10.212 | 1.00 115.62 | N |
| ATOM | 208 | CA | SER | A | 250 | 19.062 | 16.449 | 9.341 | 1.00 115.48 | C |
| ATOM | 209 | C | SER | A | 250 | 18.386 | 17.803 | 9.541 | 1.00 114.84 | C |
| ATOM | 210 | O | SER | A | 250 | 17.779 | 18.325 | 8.599 | 1.00 114.71 | O |
| ATOM | 211 | CB | SER | A | 250 | 18.073 | 15.304 | 9.526 | 1.00 115.60 | C |
| ATOM | 212 | OG | SER | A | 250 | 16.952 | 15.332 | 8.670 | 1.00 115.89 | O |
| ATOM | 213 | N | MET | A | 251 | 18.483 | 18.361 | 10.744 | 1.00 113.73 | N |
| ATOM | 214 | CA | MET | A | 251 | 17.867 | 19.649 | 11.031 | 1.00 112.30 | C |
| ATOM | 215 | C | MET | A | 251 | 18.668 | 20.772 | 10.387 | 1.00 110.96 | C |
| ATOM | 216 | O | MET | A | 251 | 18.081 | 21.572 | 9.661 | 1.00 110.59 | O |
| ATOM | 217 | CB | MET | A | 251 | 17.720 | 19.920 | 12.520 | 1.00 112.75 | C |
| ATOM | 218 | N | MET | A | 252 | 19.978 | 20.793 | 10.637 | 1.00 109.18 | N |
| ATOM | 219 | CA | MET | A | 252 | 20.809 | 21.838 | 10.048 | 1.00 107.80 | C |
| ATOM | 220 | C | MET | A | 252 | 20.774 | 21.732 | 8.530 | 1.00 106.90 | C |
| ATOM | 221 | O | MET | A | 252 | 20.692 | 22.749 | 7.835 | 1.00 107.59 | O |
| ATOM | 222 | CB | MET | A | 252 | 22.233 | 21.853 | 10.577 | 1.00 107.79 | C |
| ATOM | 223 | CG | MET | A | 252 | 22.366 | 22.190 | 12.047 | 1.00 108.14 | C |

| ATOM | 70  | CB  | LEU A 227 | 2.167  | 51.249 | -1.057 | 1.00 35.77  | C |
|------|-----|-----|-----------|--------|--------|--------|-------------|---|
| ATOM | 71  | CG  | LEU A 227 | 1.615  | 50.671 | -2.340 | 1.00 36.31  | C |
| ATOM | 72  | CD1 | LEU A 227 | 0.734  | 49.458 | -2.105 | 1.00 37.11  | C |
| ATOM | 73  | CD2 | LEU A 227 | 0.841  | 51.732 | -3.096 | 1.00 38.40  | C |
| ATOM | 74  | N   | THR A 228 | 5.048  | 50.267 | -1.134 | 1.00 37.54  | N |
| ATOM | 75  | CA  | THR A 228 | 6.165  | 49.563 | -1.745 | 1.00 38.84  | C |
| ATOM | 76  | C   | THR A 228 | 6.682  | 48.397 | -0.889 | 1.00 39.39  | C |
| ATOM | 77  | O   | THR A 228 | 6.982  | 47.297 | -1.399 | 1.00 39.81  | O |
| ATOM | 78  | CB  | THR A 228 | 7.352  | 50.503 | -1.976 | 1.00 38.81  | C |
| ATOM | 79  | OG1 | THR A 228 | 6.911  | 51.546 | -2.842 | 1.00 39.99  | O |
| ATOM | 80  | CG2 | THR A 228 | 8.520  | 49.758 | -2.562 | 1.00 37.46  | C |
| ATOM | 81  | N   | LEU A 229 | 6.777  | 48.627 | 0.427  | 1.00 38.22  | N |
| ATOM | 82  | CA  | LEU A 229 | 7.254  | 47.545 | 1.275  | 1.00 38.66  | C |
| ATOM | 83  | C   | LEU A 229 | 6.332  | 46.349 | 1.176  | 1.00 40.19  | C |
| ATOM | 84  | O   | LEU A 229 | 6.797  | 45.235 | 1.075  | 1.00 38.04  | O |
| ATOM | 85  | CB  | LEU A 229 | 7.436  | 48.014 | 2.707  | 1.00 37.55  | C |
| ATOM | 86  | CG  | LEU A 229 | 8.455  | 49.141 | 2.901  | 1.00 35.27  | C |
| ATOM | 87  | CD1 | LEU A 229 | 8.424  | 49.497 | 4.372  | 1.00 37.61  | C |
| ATOM | 88  | CD2 | LEU A 229 | 9.828  | 48.762 | 2.459  | 1.00 34.20  | C |
| ATOM | 89  | N   | LEU A 230 | 5.010  | 46.526 | 1.198  | 1.00 43.71  | N |
| ATOM | 90  | CA  | LEU A 230 | 4.071  | 45.412 | 1.085  | 1.00 43.50  | C |
| ATOM | 91  | C   | LEU A 230 | 4.262  | 44.727 | -0.249 | 1.00 45.71  | C |
| ATOM | 92  | O   | LEU A 230 | 4.338  | 43.482 | -0.345 | 1.00 46.94  | O |
| ATOM | 93  | CB  | LEU A 230 | 2.667  | 45.923 | 1.320  | 1.00 42.73  | C |
| ATOM | 94  | CG  | LEU A 230 | 1.523  | 44.925 | 1.519  | 1.00 43.25  | C |
| ATOM | 95  | CD1 | LEU A 230 | 1.788  | 43.959 | 2.658  | 1.00 42.35  | C |
| ATOM | 96  | CD2 | LEU A 230 | 0.178  | 45.608 | 1.726  | 1.00 41.67  | C |
| ATOM | 97  | N   | GLU A 231 | 4.429  | 45.508 | -1.323 | 1.00 47.68  | N |
| ATOM | 98  | CA  | GLU A 231 | 4.586  | 44.886 | -2.654 | 1.00 48.33  | C |
| ATOM | 99  | C   | GLU A 231 | 5.861  | 44.077 | -2.678 | 1.00 49.74  | C |
| ATOM | 100 | O   | GLU A 231 | 5.828  | 42.958 | -3.224 | 1.00 51.13  | O |
| ATOM | 101 | CB  | GLU A 231 | 4.395  | 45.833 | -3.806 | 1.00 48.26  | C |
| ATOM | 102 | CG  | GLU A 231 | 2.945  | 46.308 | -4.016 | 1.00 51.65  | C |
| ATOM | 103 | CD  | GLU A 231 | 2.783  | 47.236 | -5.211 | 1.00 53.81  | C |
| ATOM | 104 | OE1 | GLU A 231 | 3.242  | 48.404 | -5.310 | 1.00 52.53  | O |
| ATOM | 105 | OE2 | GLU A 231 | 2.141  | 46.779 | -6.195 | 1.00 56.06  | O |
| ATOM | 106 | N   | ALA A 232 | 6.928  | 44.601 | -2.076 | 1.00 50.14  | N |
| ATOM | 107 | CA  | ALA A 232 | 8.193  | 43.867 | -2.060 | 1.00 49.70  | C |
| ATOM | 108 | C   | ALA A 232 | 8.236  | 42.634 | -1.183 | 1.00 50.79  | C |
| ATOM | 109 | O   | ALA A 232 | 9.139  | 41.823 | -1.411 | 1.00 49.87  | O |
| ATOM | 110 | CB  | ALA A 232 | 9.290  | 44.843 | -1.689 | 1.00 48.11  | C |
| ATOM | 111 | N   | GLU A 233 | 7.385  | 42.393 | -0.200 | 1.00 54.03  | N |
| ATOM | 112 | CA  | GLU A 233 | 7.552  | 41.162 | 0.587  | 1.00 59.42  | C |
| ATOM | 113 | C   | GLU A 233 | 7.829  | 39.963 | -0.312 | 1.00 62.84  | C |
| ATOM | 114 | O   | GLU A 233 | 7.132  | 39.726 | -1.303 | 1.00 63.58  | O |
| ATOM | 115 | CB  | GLU A 233 | 6.309  | 40.903 | 1.427  | 1.00 57.95  | C |
| ATOM | 116 | CG  | GLU A 233 | 6.326  | 41.383 | 2.860  | 1.00 57.36  | C |
| ATOM | 117 | CD  | GLU A 233 | 7.488  | 40.805 | 3.635  | 1.00 56.45  | C |
| ATOM | 118 | OE1 | GLU A 233 | 7.496  | 39.614 | 3.994  | 1.00 56.83  | O |
| ATOM | 119 | OE2 | GLU A 233 | 8.438  | 41.544 | 3.887  | 1.00 54.36  | O |
| ATOM | 120 | N   | PRO A 234 | 8.851  | 39.193 | -0.026 | 1.00 66.53  | N |
| ATOM | 121 | CA  | PRO A 234 | 9.243  | 37.996 | -0.740 | 1.00 69.24  | C |
| ATOM | 122 | C   | PRO A 234 | 8.231  | 36.878 | -0.554 | 1.00 72.34  | C |
| ATOM | 123 | O   | PRO A 234 | 7.495  | 36.772 | 0.416  | 1.00 71.56  | O |
| ATOM | 124 | CB  | PRO A 234 | 10.556 | 37.477 | -0.116 | 1.00 68.59  | C |
| ATOM | 125 | CG  | PRO A 234 | 10.438 | 38.059 | 1.264  | 1.00 68.18  | C |
| ATOM | 126 | CD  | PRO A 234 | 9.710  | 39.397 | 1.150  | 1.00 67.91  | C |
| ATOM | 127 | N   | PRO A 235 | 8.186  | 36.002 | -1.521 | 1.00 77.51  | N |
| ATOM | 128 | CA  | PRO A 235 | 7.303  | 34.856 | -1.497 | 1.00 81.98  | C |
| ATOM | 129 | C   | PRO A 235 | 7.638  | 33.978 | -0.286 | 1.00 85.76  | C |
| ATOM | 130 | O   | PRO A 235 | 8.781  | 33.748 | 0.090  | 1.00 84.81  | O |
| ATOM | 131 | CB  | PRO A 235 | 7.518  | 34.069 | -2.796 | 1.00 81.40  | C |
| ATOM | 132 | CG  | PRO A 235 | 8.733  | 34.708 | -3.402 | 1.00 80.43  | C |
| ATOM | 133 | CD  | PRO A 235 | 9.033  | 36.017 | -2.719 | 1.00 79.51  | C |
| ATOM | 134 | N   | ASN A 236 | 6.582  | 33.505 | 0.348  | 1.00 90.27  | N |
| ATOM | 135 | CA  | ASN A 236 | 6.654  | 32.587 | 1.478  | 1.00 95.15  | C |
| ATOM | 136 | C   | ASN A 236 | 7.470  | 31.400 | 0.948  | 1.00 97.35  | C |
| ATOM | 137 | O   | ASN A 236 | 7.093  | 30.888 | -0.115 | 1.00 96.95  | O |
| ATOM | 138 | CB  | ASN A 236 | 5.206  | 32.218 | 1.812  | 1.00 96.93  | C |
| ATOM | 139 | CG  | ASN A 236 | 4.165  | 33.255 | 1.428  | 1.00 98.76  | C |
| ATOM | 140 | OD1 | ASN A 236 | 3.622  | 34.009 | 2.248  | 1.00 99.37  | O |
| ATOM | 141 | ND2 | ASN A 236 | 3.805  | 33.358 | 0.138  | 1.00 99.08  | N |
| ATOM | 142 | N   | VAL A 237 | 8.568  | 30.984 | 1.559  | 1.00100.05  | N |
| ATOM | 143 | CA  | VAL A 237 | 9.392  | 29.888 | 1.050  | 1.00102.98  | C |
| ATOM | 144 | C   | VAL A 237 | 9.139  | 28.547 | 1.725  | 1.00105.66  | C |
| ATOM | 145 | O   | VAL A 237 | 9.550  | 28.270 | 2.839  | 1.00105.19  | O |
| ATOM | 146 | CB  | VAL A 237 | 10.889 | 30.247 | 1.131  | 1.00102.30  | C |

```
REMARK  13 PENDANT ARYL GROUP. AT THIS POINT CANNOT DETERMINE EXACT ORIENTATION OF
REMARK  13 COOEt GROUP. THEREFORE ATOMS C25/C26 (LIGAND NUMBERING SAME AS ERA177)
REMARK  13 ARE NOT INCLUDED IN CURRENT MODEL
REMARK
REMARK   1 ERB+kb177 rebuilt for last time adjusted OSS position
CRYST1   67.900   67.900  148.620  90.00  90.00  90.00 P4122    SCALE1      0.01473
 0.00000    0.00000    0.00000 SCALE2      0.00000    0.01473  0.00000
 0.00000 SCALE3      0.00000    0.00000    0.00673      0.00000
ATOM      1  N   THR A 219      10.820  61.097  -1.302  1.00 92.54           N
ATOM      2  CA  THR A 219       9.929  62.227  -0.893  1.00 92.13           C
ATOM      3  C   THR A 219       8.485  61.795  -1.130  1.00 90.48           C
ATOM      4  O   THR A 219       7.511  62.463  -0.786  1.00 90.82           O
ATOM      5  CB  THR A 219      10.254  63.562  -1.554  1.00 93.59           C
ATOM      6  OG1 THR A 219      11.581  63.510  -2.117  1.00 94.46           O
ATOM      7  CG2 THR A 219      10.215  64.669  -0.500  1.00 93.81           C
ATOM      8  N   LEU A 220       8.388  60.601  -1.729  1.00 87.18           N
ATOM      9  CA  LEU A 220       7.080  59.983  -1.976  1.00 82.62           C
ATOM     10  C   LEU A 220       6.502  59.799  -0.575  1.00 78.23           C
ATOM     11  O   LEU A 220       7.254  59.488   0.345  1.00 77.75           O
ATOM     12  CB  LEU A 220       7.267  58.652  -2.701  1.00 84.09           C
ATOM     13  CG  LEU A 220       8.552  57.868  -2.395  1.00 84.63           C
ATOM     14  CD1 LEU A 220       8.409  56.363  -2.581  1.00 84.15           C
ATOM     15  CD2 LEU A 220       9.706  58.366  -3.255  1.00 84.63           C
ATOM     16  N   SER A 221       5.236  60.002  -0.320  1.00 72.63           N
ATOM     17  CA  SER A 221       4.656  59.849   0.997  1.00 66.40           C
ATOM     18  C   SER A 221       4.922  58.513   1.703  1.00 62.08           C
ATOM     19  O   SER A 221       5.302  57.480   1.167  1.00 59.40           O
ATOM     20  CB  SER A 221       3.126  60.000   0.791  1.00 64.93           C
ATOM     21  OG  SER A 221       2.595  58.750   0.384  1.00 63.73           O
ATOM     22  N   PRO A 222       4.642  58.503   3.007  1.00 58.20           N
ATOM     23  CA  PRO A 222       4.707  57.398   3.913  1.00 55.57           C
ATOM     24  C   PRO A 222       3.842  56.231   3.478  1.00 52.63           C
ATOM     25  O   PRO A 222       4.286  55.113   3.692  1.00 51.47           O
ATOM     26  CB  PRO A 222       4.132  57.845   5.283  1.00 56.87           C
ATOM     27  CG  PRO A 222       4.256  59.336   5.171  1.00 57.17           C
ATOM     28  CD  PRO A 222       4.132  59.698   3.714  1.00 57.92           C
ATOM     29  N   GLU A 223       2.662  56.473   2.914  1.00 50.57           N
ATOM     30  CA  GLU A 223       1.847  55.339   2.479  1.00 49.82           C
ATOM     31  C   GLU A 223       2.448  54.788   1.191  1.00 48.10           C
ATOM     32  O   GLU A 223       2.400  53.584   0.959  1.00 47.36           O
ATOM     33  CB  GLU A 223       0.378  55.697   2.346  1.00 53.41           C
ATOM     34  CG  GLU A 223       0.144  56.965   1.542  1.00 56.58           C
ATOM     35  CD  GLU A 223       0.176  58.207   2.404  1.00 59.50           C
ATOM     36  OE1 GLU A 223       0.629  58.097   3.554  1.00 59.59           O
ATOM     37  OE2 GLU A 223      -0.291  59.261   1.889  1.00 61.50           O
ATOM     38  N   GLN A 224       3.089  55.626   0.357  1.00 46.84           N
ATOM     39  CA  GLN A 224       3.749  55.111  -0.836  1.00 46.59           C
ATOM     40  C   GLN A 224       4.815  54.108  -0.387  1.00 45.37           C
ATOM     41  O   GLN A 224       4.940  52.981  -0.849  1.00 46.54           O
ATOM     42  CB  GLN A 224       4.325  56.212  -1.718  1.00 46.82           C
ATOM     43  CG  AGLN A 224      5.118  55.707  -2.896  0.50 45.96           C
ATOM     44  CG  BGLN A 224      4.054  56.128  -3.207  0.50 47.93           C
ATOM     45  CD  AGLN A 224      4.337  54.961  -3.954  0.50 46.12           C
ATOM     46  CD  BGLN A 224      3.861  57.409  -3.988  0.50 48.90           C
ATOM     47  OE1AGLN A 224       4.195  55.521  -5.050  0.50 47.21           O
ATOM     48  OE1BGLN A 224       4.313  57.547  -5.131  0.50 47.75           O
ATOM     49  NE2AGLN A 224       3.846  53.754  -3.718  0.50 44.02           N
ATOM     50  NE2BGLN A 224       3.178  58.437  -3.465  0.50 49.68           N
ATOM     51  N   LEU A 225       5.614  54.486   0.609  1.00 44.43           N
ATOM     52  CA  LEU A 225       6.665  53.669   1.156  1.00 42.35           C
ATOM     53  C   LEU A 225       6.137  52.355   1.704  1.00 40.60           C
ATOM     54  O   LEU A 225       6.729  51.327   1.374  1.00 39.40           O
ATOM     55  CB  LEU A 225       7.385  54.456   2.258  1.00 43.30           C
ATOM     56  CG  LEU A 225       8.824  53.986   2.536  1.00 44.15           C
ATOM     57  CD1 LEU A 225       9.707  55.160   2.936  1.00 43.63           C
ATOM     58  CD2 LEU A 225       8.802  52.889   3.598  1.00 43.25           C
ATOM     59  N   VAL A 226       5.066  52.393   2.489  1.00 37.99           N
ATOM     60  CA  VAL A 226       4.546  51.174   3.091  1.00 37.72           C
ATOM     61  C   VAL A 226       4.063  50.237   1.985  1.00 40.18           C
ATOM     62  O   VAL A 226       4.371  49.028   1.927  1.00 38.59           O
ATOM     63  CB  VAL A 226       3.501  51.428   4.174  1.00 36.81           C
ATOM     64  CG1 VAL A 226       2.970  50.086   4.656  1.00 36.99           C
ATOM     65  CG2 VAL A 226       4.035  52.199   5.365  1.00 33.59           C
ATOM     66  N   LEU A 227       3.337  50.896   1.055  1.00 40.41           N
ATOM     67  CA  LEU A 227       2.805  50.234  -0.130  1.00 37.58           C
ATOM     68  C   LEU A 227       3.962  49.540  -0.834  1.00 39.03           C
ATOM     69  O   LEU A 227       3.862  48.322  -1.091  1.00 40.14           O
```

| ATOM | 1687 | C   | ASP A 446 | 29.706 | 36.471 | -5.101  | 1.00 154.38 | C |
|------|------|-----|-----------|--------|--------|---------|-------------|---|
| ATOM | 1688 | O   | ASP A 446 | 30.347 | 36.731 | -6.117  | 1.00 154.40 | O |
| ATOM | 1689 | CB  | ASP A 446 | 31.472 | 35.434 | -3.652  | 1.00 154.29 | C |
| ATOM | 1690 | N   | LEU A 447 | 28.412 | 36.173 | -5.125  | 1.00 154.69 | N |
| ATOM | 1691 | CA  | LEU A 447 | 27.598 | 36.154 | -6.338  | 1.00 154.71 | C |
| ATOM | 1692 | C   | LEU A 447 | 26.468 | 37.174 | -6.146  | 1.00 154.73 | C |
| ATOM | 1693 | O   | LEU A 447 | 25.494 | 37.313 | -6.875  | 1.00 154.34 | O |
| ATOM | 1694 | CB  | LEU A 447 | 27.027 | 34.767 | -6.620  | 1.00 154.60 | C |
| ATOM | 1695 | N   | LEU A 448 | 26.639 | 37.940 | -5.072  | 1.00 155.13 | N |
| ATOM | 1696 | CA  | LEU A 448 | 25.734 | 38.981 | -4.638  | 1.00 155.79 | C |
| ATOM | 1697 | C   | LEU A 448 | 25.475 | 39.981 | -5.753  | 1.00 157.01 | C |
| ATOM | 1698 | O   | LEU A 448 | 24.319 | 40.269 | -6.074  | 1.00 156.99 | O |
| ATOM | 1699 | CB  | LEU A 448 | 26.317 | 39.681 | -3.406  | 1.00 155.11 | C |
| ATOM | 1700 | CG  | LEU A 448 | 25.381 | 39.758 | -2.199  | 1.00 154.82 | C |
| ATOM | 1701 | CD1 | LEU A 448 | 25.157 | 38.373 | -1.609  | 1.00 154.88 | C |
| ATOM | 1702 | CD2 | LEU A 448 | 25.929 | 40.714 | -1.153  | 1.00 154.70 | C |
| ATOM | 1703 | N   | LEU A 449 | 26.533 | 40.496 | -6.373  | 1.00 158.72 | N |
| ATOM | 1704 | CA  | LEU A 449 | 26.394 | 41.450 | -7.471  | 1.00 160.71 | C |
| ATOM | 1705 | C   | LEU A 449 | 25.813 | 40.794 | -8.721  | 1.00 162.43 | C |
| ATOM | 1706 | O   | LEU A 449 | 25.201 | 41.458 | -9.568  | 1.00 162.58 | O |
| ATOM | 1707 | CB  | LEU A 449 | 27.719 | 42.159 | -7.741  | 1.00 160.28 | C |
| ATOM | 1708 | N   | GLU A 450 | 25.948 | 39.478 | -8.860  | 1.00 164.37 | N |
| ATOM | 1709 | CA  | GLU A 450 | 25.417 | 38.712 | -9.972  | 1.00 166.20 | C |
| ATOM | 1710 | C   | GLU A 450 | 23.896 | 38.636 | -9.852  | 1.00 167.76 | C |
| ATOM | 1711 | O   | GLU A 450 | 23.177 | 38.618 | -10.851 | 1.00 167.91 | O |
| ATOM | 1712 | CB  | GLU A 450 | 26.011 | 37.303 | -10.005 | 1.00 166.03 | C |
| ATOM | 1713 | N   | MET A 451 | 23.418 | 38.592 | -8.607  | 1.00 169.64 | N |
| ATOM | 1714 | CA  | MET A 451 | 21.979 | 38.548 | -8.352  | 1.00 171.46 | C |
| ATOM | 1715 | C   | MET A 451 | 21.472 | 39.978 | -8.175  | 1.00 172.90 | C |
| ATOM | 1716 | O   | MET A 451 | 20.301 | 40.289 | -8.372  | 1.00 172.88 | O |
| ATOM | 1717 | CB  | MET A 451 | 21.653 | 37.684 | -7.138  | 1.00 171.26 | C |
| ATOM | 1718 | N   | LEU A 452 | 22.376 | 40.884 | -7.812  | 1.00 174.89 | N |
| ATOM | 1719 | CA  | LEU A 452 | 22.055 | 42.282 | -7.599  | 1.00 176.90 | C |
| ATOM | 1720 | C   | LEU A 452 | 21.779 | 43.089 | -8.861  | 1.00 178.35 | C |
| ATOM | 1721 | O   | LEU A 452 | 20.866 | 43.923 | -8.869  | 1.00 178.33 | O |
| ATOM | 1722 | CB  | LEU A 452 | 23.189 | 42.990 | -6.834  | 1.00 176.73 | C |
| ATOM | 1723 | CG  | LEU A 452 | 23.092 | 43.026 | -5.311  | 1.00 176.68 | C |
| ATOM | 1724 | CD1 | LEU A 452 | 24.445 | 43.303 | -4.675  | 1.00 176.61 | C |
| ATOM | 1725 | CD2 | LEU A 452 | 22.103 | 44.084 | -4.840  | 1.00 176.70 | C |
| ATOM | 1726 | N   | ASN A 453 | 22.555 | 42.876 | -9.917  | 1.00 180.11 | N |
| ATOM | 1727 | CA  | ASN A 453 | 22.408 | 43.620 | -11.156 | 1.00 181.66 | C |
| ATOM | 1728 | C   | ASN A 453 | 21.319 | 43.188 | -12.118 | 1.00 182.54 | C |
| ATOM | 1729 | O   | ASN A 453 | 20.989 | 43.973 | -13.025 | 1.00 182.77 | O |
| ATOM | 1730 | CB  | ASN A 453 | 23.760 | 43.641 | -11.892 | 1.00 181.83 | C |
| ATOM | 1731 | CG  | ASN A 453 | 24.762 | 44.577 | -11.245 | 1.00 181.80 | C |
| ATOM | 1732 | OD1 | ASN A 453 | 24.629 | 45.798 | -11.296 | 1.00 181.79 | O |
| ATOM | 1733 | ND2 | ASN A 453 | 25.794 | 44.020 | -10.625 | 1.00 181.62 | N |
| ATOM | 1734 | N   | ALA A 454 | 20.746 | 42.002 | -11.980 | 1.00 183.24 | N |
| ATOM | 1735 | CA  | ALA A 454 | 19.690 | 41.559 | -12.888 | 1.00 183.66 | C |
| ATOM | 1736 | C   | ALA A 454 | 18.651 | 42.653 | -13.111 | 1.00 183.79 | C |
| ATOM | 1737 | O   | ALA A 454 | 17.547 | 42.329 | -13.592 | 1.00 183.88 | O |
| ATOM | 1738 | CB  | ALA A 454 | 19.032 | 40.309 | -12.323 | 1.00 183.78 | C |
| ATOM | 1739 | C1  | OSS A 600 | 17.329 | 30.030 | 8.735   | 1.00  77.90 | C |
| ATOM | 1740 | C2  | OSS A 600 | 16.213 | 30.614 | 8.151   | 1.00  76.92 | C |
| ATOM | 1741 | C3  | OSS A 600 | 15.495 | 31.558 | 8.871   | 1.00  76.96 | C |
| ATOM | 1742 | O3  | OSS A 600 | 14.396 | 32.080 | 8.217   | 1.00  75.35 | O |
| ATOM | 1743 | C4  | OSS A 600 | 15.914 | 31.896 | 10.163  | 1.00  77.41 | C |
| ATOM | 1744 | C5  | OSS A 600 | 17.014 | 31.321 | 10.736  | 1.00  77.88 | C |
| ATOM | 1745 | S6  | OSS A 600 | 17.731 | 31.517 | 12.242  | 1.00  78.78 | S |
| ATOM | 1746 | C7  | OSS A 600 | 19.001 | 30.461 | 12.074  | 1.00  79.95 | C |
| ATOM | 1747 | C8  | OSS A 600 | 20.023 | 30.159 | 13.103  | 1.00  81.29 | C |
| ATOM | 1748 | C9  | OSS A 600 | 19.550 | 29.955 | 14.378  | 1.00  81.89 | C |
| ATOM | 1749 | C10 | OSS A 600 | 20.432 | 29.649 | 15.398  | 1.00  83.18 | C |
| ATOM | 1750 | C11 | OSS A 600 | 21.793 | 29.535 | 15.154  | 1.00  84.40 | C |
| ATOM | 1751 | O11 | OSS A 600 | 22.632 | 29.222 | 16.223  | 1.00  85.21 | O |
| ATOM | 1752 | C12 | OSS A 600 | 22.266 | 29.737 | 13.855  | 1.00  83.41 | C |
| ATOM | 1753 | C13 | OSS A 600 | 21.376 | 30.045 | 12.827  | 1.00  82.27 | C |
| ATOM | 1754 | C14 | OSS A 600 | 17.754 | 30.358 | 10.001  | 1.00  78.62 | C |
| ATOM | 1755 | C15 | OSS A 600 | 18.911 | 29.859 | 10.785  | 1.00  80.23 | C |
| ATOM | 1756 | C16 | OSS A 600 | 19.834 | 28.880 | 10.373  | 1.00  81.59 | C |
| ATOM | 1757 | O16 | OSS A 600 | 19.823 | 27.783 | 10.944  | 1.00  81.23 | O |
| ATOM | 1758 | C17 | OSS A 600 | 20.746 | 29.094 | 9.249   | 1.00  82.70 | C |
| ATOM | 1759 | C18 | OSS A 600 | 21.458 | 28.008 | 8.740   | 1.00  83.44 | C |
| ATOM | 1760 | C19 | OSS A 600 | 22.322 | 28.180 | 7.656   | 1.00  84.77 | C |
| ATOM | 1761 | C20 | OSS A 600 | 22.479 | 29.434 | 7.058   | 1.00  86.19 | C |
| ATOM | 1762 | C21 | OSS A 600 | 21.755 | 30.510 | 7.585   | 1.00  85.38 | C |
| ATOM | 1763 | C22 | OSS A 600 | 20.891 | 30.344 | 8.666   | 1.00  83.65 | C |

```
ATOM   1764  C23 OSS A 600      23.389  29.599   5.909  1.00 87.22           C
ATOM   1765  O23 OSS A 600      24.022  28.692   5.454  1.00 87.74           O
ATOM   1766  O24 OSS A 600      23.546  30.789   5.338  1.00 87.48           O
ATOM      1  OW  WAT W   1      32.893  54.434   0.390  0.50 18.13           O
ATOM      2  OW  WAT W   2      18.556  50.095  17.907  0.50 24.54           O
ATOM      3  OW  WAT W   3       8.917  43.846   2.508  1.00 26.67           O
ATOM      4  OW  WAT W   4      18.603  44.726  14.075  1.00 43.61           O
ATOM      5  OW  WAT W   5      13.038  37.322   5.995  1.00 44.02           O
ATOM      6  OW  WAT W   6      15.723  50.322  -4.462  1.00 43.14           O
ATOM      7  OW  WAT W   7      25.978  55.157  -1.356  1.00 44.05           O
ATOM      8  OW  WAT W   8      37.373  53.135   1.151  1.00 46.74           O
ATOM      9  OW  WAT W   9       4.913  39.207   5.332  1.00 45.98           O
ATOM     10  OW  WAT W  10       4.969  49.627  26.301  1.00 47.70           O
ATOM     11  OW  WAT W  11      10.416  45.167   4.845  1.00 51.05           O
ATOM     12  OW  WAT W  12      31.162  54.425   3.150  1.00 52.31           O
ATOM     13  OW  WAT W  13       0.787  44.327  -5.935  1.00 51.59           O
ATOM     14  OW  WAT W  14       2.070  47.410  23.595  1.00 52.96           O
ATOM     15  OW  WAT W  15       7.214  31.367  18.743  1.00 52.26           O
ATOM     16  OW  WAT W  16      12.958  39.742   3.262  1.00 52.64           O
ATOM     17  OW  WAT W  17      -7.934  58.031   4.149  1.00 53.80           O
ATOM     18  OW  WAT W  18       2.432  52.488  23.424  1.00 53.42           O
ATOM     19  OW  WAT W  19      11.361  49.534  25.396  1.00 54.57           O
ATOM     20  OW  WAT W  20      23.395  39.531  10.286  1.00 57.14           O
ATOM     21  OW  WAT W  21      16.016  24.523  29.470  1.00 57.61           O
ATOM     22  OW  WAT W  22      37.563  48.844   9.107  1.00 60.65           O
ATOM     23  OW  WAT W  23      15.853  63.491   6.434  1.00 60.86           O
ATOM     24  OW  WAT W  24      10.797  40.842  -3.518  1.00 57.68           O
ATOM     25  OW  WAT W  25      27.963  57.600  -1.076  1.00 60.19           O
ATOM     26  OW  WAT W  26      21.009  46.233  11.237  1.00 61.29           O
ATOM     27  OW  WAT W  27       8.025  36.047   6.549  1.00 61.58           O
ATOM     28  OW  WAT W  28      12.965  34.543   7.323  1.00 61.97           O
ATOM     29  OW  WAT W  29      -3.594  49.358  14.940  1.00 62.13           O
ATOM     30  OW  WAT W  30       3.818  49.821  22.474  1.00 61.06           O
ATOM     31  OW  WAT W  31      14.799  39.558  23.671  1.00 62.85           O
ATOM     32  OW  WAT W  32      -1.325  58.081  27.772  1.00 64.47           O
ATOM     33  OW  WAT W  33      14.324  53.084  -5.034  1.00 65.46           O
ATOM     34  OW  WAT W  34       1.697  41.965  -3.960  1.00 64.22           O
ATOM     35  OW  WAT W  35      -1.208  48.714  11.345  1.00 64.03           O
ATOM     36  OW  WAT W  36      -1.225  42.831  11.619  1.00 65.81           O
ATOM     37  OW  WAT W  37      14.480  47.283  -8.123  1.00 68.39           O
ATOM     38  OW  WAT W  38      11.066  54.158  -4.586  1.00 66.06           O
ATOM     39  OW  WAT W  39       3.001  46.792  26.955  1.00 65.51           O
ATOM     40  OW  WAT W  40      28.329  52.693  -7.694  1.00 66.32           O
ATOM     41  OW  WAT W  41      11.161  50.612  -5.172  1.00 65.48           O
ATOM     42  OW  WAT W  42      25.758  40.399  12.943  1.00 67.74           O
ATOM     43  OW  WAT W  43      12.510  63.170   7.146  1.00 66.62           O
ATOM     44  OW  WAT W  44      14.889  57.905  -1.923  1.00 70.25           O
ATOM     45  OW  WAT W  45       1.667  61.169  15.103  1.00 70.15           O
ATOM     46  OW  WAT W  46      15.064  19.369  26.473  1.00 71.29           O
ATOM     47  OW  WAT W  47      -5.228  62.030  23.700  1.00 68.74           O
ATOM     48  OW  WAT W  48      -0.888  45.945   9.604  1.00 69.32           O
ATOM     49  OW  WAT W  49      18.966  63.601   4.708  1.00 68.98           O
ATOM     50  OW  WAT W  50       2.695  32.204  10.244  1.00 71.28           O
ATOM     51  OW  WAT W  51       9.646  58.850   1.489  1.00 75.47           O
ATOM     52  OW  WAT W  52       9.050  27.265  -1.894  1.00 73.41           O
ATOM     53  OW  WAT W  53      -0.591  50.481  14.009  1.00 71.83           O
ATOM     54  OW  WAT W  54      -0.220  39.818  17.339  1.00 73.83           O
ATOM     55  OW  WAT W  55      13.148  60.340  -2.989  1.00 74.69           O
ATOM     56  OW  WAT W  56       9.282  61.232   4.071  1.00 70.67           O
ATOM     57  OW  WAT W  57       4.423  38.881  -1.169  1.00 72.65           O
ATOM     58  OW  WAT W  58      -1.218  39.467  10.023  1.00 73.81           O
ATOM     59  OW  WAT W  59      10.728  30.076  -3.336  1.00 74.94           O
ATOM     60  OW  WAT W  60      14.668  18.708  10.951  1.00 79.94           O
ATOM     61  OW  WAT W  61       7.541  32.758  21.505  1.00 79.01           O
ATOM     62  OW  WAT W  62       7.484  30.917  24.334  1.00 78.34           O
ATOM     63  OW  WAT W  63      -0.656  50.614  18.029  1.00 77.76           O
ATOM     64  OW  WAT W  64      30.021  43.888   4.915  1.00 79.89           O  500
```

```
HEADER    NUCLEAR RECEPTOR
NOCHIR
REMARK    This file is erbici_icent_ref3b_2.pdb
REMARK
TITLE     RAT OESTROGEN RECEPTOR BETA LIGAND-BINDING DOMAIN IN
TITLE    2 COMPLEX WITH PURE ANTIOESTROGEN ICI164,384
COMPND    MOL_ID: 1;
COMPND   2 MOLECULE: ESTROGEN RECEPTOR BETA;
COMPND   3 CHAIN: A;
COMPND   4 FRAGMENT: LIGAND-BINDING DOMAIN;
COMPND   5 SYNONYM: OESTROGEN RECEPTOR, ER-LBD;
COMPND   6 ENGINEERED: YES;
COMPND   7 BIOLOGICAL_UNIT: DIMER;
COMPND   8 OTHER_DETAILS: COMPLEXED WITH THE ANTAGONIST ICI164,384
SOURCE    MOL_ID: 1;
SOURCE   2 ORGANISM_SCIENTIFIC: RATTUS NORVEGICUS;
SOURCE   3 ORGANISM_COMMON: RAT;
SOURCE   4 GENE: OESTROGEN RECEPTOR BETA;
SOURCE   5 EXPRESSION_SYSTEM: ESCHERICHIA COLI;
SOURCE   6 EXPRESSION_SYSTEM_STRAIN: GI724;
SOURCE   7 EXPRESSION_SYSTEM_PLASMID: PLEX
KEYWDS    NUCLEAR RECEPTOR, TRANSCRIPTION FACTOR, OESTROGEN,
KEYWDS   2 ANTAGONIST
EXPDTA    X-RAY DIFFRACTION
AUTHOR    A.C.W.PIKE,A.M.BRZOZOWSKI
JRNL        AUTH   A.C.W.PIKE,A.M.BRZOZOWSKI,R.E.HUBBARD,T.BONN,
JRNL        AUTH 2 A.-G.THORSELL,O.ENGSTROM,J.LJUNGGREN,
JRNL        AUTH 3 J.-A.GUSTAFFSON,M.CARLQUIST
JRNL        TITL   STRUCTURE OF THE LIGAND-BINDING DOMAIN OF OESTROGEN
JRNL        TITL 2 RECEPTOR BETA IN THE PRESENCE OF A PARTIAL AGONIST
JRNL        TITL 3 AND A FULL ANTAGONIST
JRNL        REF    TO BE PUBLISHED
JRNL        REFN                                                  0353
REMARK   2 RESOLUTION. 2.3 ANGSTROMS.
REMARK   3
REMARK   3 REFINEMENT.
REMARK   3   PROGRAM     : REFMAC
REMARK   3   AUTHORS     : MURSHUDOV,VAGIN,DODSON
REMARK   3
REMARK   3  DATA USED IN REFINEMENT.
REMARK   3   RESOLUTION RANGE HIGH (ANGSTROMS) : 2.3
REMARK   3   RESOLUTION RANGE LOW  (ANGSTROMS) : 20
REMARK   3   DATA CUTOFF            (SIGMA(F)) : 0
REMARK   3   COMPLETENESS FOR RANGE        (%) : 98.2
REMARK   3   NUMBER OF REFLECTIONS             : 11915
REMARK   3
REMARK   3  FIT TO DATA USED IN REFINEMENT.
REMARK   3   CROSS-VALIDATION METHOD          : THROUGHOUT
REMARK   3   FREE R VALUE TEST SET SELECTION  : RANDOM
REMARK   3   R VALUE     (WORKING + TEST SET) : NONE
REMARK   3   R VALUE            (WORKING SET) : 0.220
REMARK   3   FREE R VALUE                     : 0.251
REMARK   3   FREE R VALUE TEST SET SIZE   (%) : 5
REMARK   3   FREE R VALUE TEST SET COUNT      : 587
REMARK   3
REMARK   3  NUMBER OF NON-HYDROGEN ATOMS USED IN REFINEMENT.
REMARK   3   PROTEIN ATOMS            : NULL
REMARK   3   NUCLEIC ACID ATOMS       : NULL
REMARK   3   HETEROGEN ATOMS          : NULL
```

```
REMARK   3   SOLVENT ATOMS              : NULL
REMARK   3
REMARK   3   B VALUES.
REMARK   3    FROM WILSON PLOT           (A**2) : 48.5
REMARK   3    MEAN B VALUE      (OVERALL, A**2) : 53.0
REMARK   3    OVERALL ANISOTROPIC B VALUE.
REMARK   3     B11 (A**2) : NULL
REMARK   3     B22 (A**2) : NULL
REMARK   3     B33 (A**2) : NULL
REMARK   3     B12 (A**2) : NULL
REMARK   3     B13 (A**2) : NULL
REMARK   3     B23 (A**2) : NULL
REMARK   3
REMARK   3   ESTIMATED OVERALL COORDINATE ERROR.
REMARK   3    ESU BASED ON R VALUE                         (A):
REMARK   3    0.31611
REMARK   3    ESU BASED ON FREE R VALUE                    (A):
REMARK   3    0.22821
REMARK   3    ESU BASED ON MAXIMUM LIKELIHOOD              (A): NULL
REMARK   3    ESU FOR B VALUES BASED ON MAXIMUM LIKELIHOOD (A**2): NULL
REMARK   3
REMARK   3   RMS DEVIATIONS FROM IDEAL VALUES.
REMARK   3    DISTANCE RESTRAINTS.                 RMS     SIGMA
REMARK   3     BOND LENGTH               (A) : 0.012 ; 0.020
REMARK   3     ANGLE DISTANCE            (A) : 0.035 ; 0.040
REMARK   3     INTRAPLANAR 1-4 DISTANCE  (A) : 0.039 ; 0.050
REMARK   3     H-BOND OR METAL COORDINATION (A) : NULL ; NULL
REMARK   3
REMARK   3     PLANE RESTRAINT           (A) : 0.011 ; 0.02
REMARK   3     CHIRAL-CENTER RESTRAINT  (A**3) : 0.121 ; 0.15
REMARK   3
REMARK   3    NON-BONDED CONTACT RESTRAINTS.
REMARK   3     SINGLE TORSION            (A) : 0.182 ; 0.300
REMARK   3     MULTIPLE TORSION          (A) : 0.184 ; 0.300
REMARK   3     H-BOND (X...Y)            (A) : 0.148 ; 0.30
REMARK   3     H-BOND (X-H...Y)          (A) : NULL  ; NULL
REMARK   3
REMARK   3    CONFORMATIONAL TORSION ANGLE RESTRAINTS.
REMARK   3     SPECIFIED          (DEGREES) : NULL ; NULL
REMARK   3     PLANAR             (DEGREES) :  1.7 ;  7.0
REMARK   3     STAGGERED          (DEGREES) : 17.7 ; 15.0
REMARK   3     TRANSVERSE         (DEGREES) : 35.0 ; 20.0
REMARK   3
REMARK   3    ISOTROPIC THERMAL FACTOR RESTRAINTS.    RMS    SIGMA
REMARK   3     MAIN-CHAIN BOND         (A**2) : 1.839 ; 2.000
REMARK   3     MAIN-CHAIN ANGLE        (A**2) : 2.928 ; 3.000
REMARK   3     SIDE-CHAIN BOND         (A**2) : 2.075 ; 2.000
REMARK   3     SIDE-CHAIN ANGLE        (A**2) : 3.301 ; 3.000
REMARK   3
REMARK   3   OTHER REFINEMENT REMARKS: BULK SOLVENT CORRECTION
REMARK   3   CALCULATED IN XPLOR V3.843 WAS USED THROUGHOUT
REMARK   3   REFINEMENT
REMARK   6
REMARK   6 THE C-TERMINAL HELIX (H12) IS NOT VISIBLE IN
REMARK   6 THE ELECTRON DENSITY MAPS.
REMARK   6
REMARK   6 PCMBS molecule covalently bound (PMB) to Cys289
REMARK   6
REMARK 200
REMARK 200 EXPERIMENTAL DETAILS
REMARK 200  EXPERIMENT TYPE              : X-RAY DIFFRACTION
```

```
REMARK 200   DATE OF DATA COLLECTION        : 23-FEB-1999
REMARK 200   TEMPERATURE           (KELVIN) : 100
REMARK 200   PH                             : 8.5
REMARK 200   NUMBER OF CRYSTALS USED        : 1
REMARK 200
REMARK 200   SYNCHROTRON              (Y/N) : Y
REMARK 200   RADIATION SOURCE               : ESRF
REMARK 200   BEAMLINE                       : ID14-4
REMARK 200   X-RAY GENERATOR MODEL          : NULL
REMARK 200   MONOCHROMATIC OR LAUE    (M/L) : M
REMARK 200   WAVELENGTH OR RANGE        (A) : 0.9464
REMARK 200   MONOCHROMATOR                  : NULL
REMARK 200   OPTICS                         : NULL
REMARK 200
REMARK 200   DETECTOR TYPE                  : CCD
REMARK 200   DETECTOR MANUFACTURER          : ADSC QUANTUM4
REMARK 200   INTENSITY-INTEGRATION SOFTWARE : DENZO
REMARK 200   DATA SCALING SOFTWARE          : SCALEPACK
REMARK 200
REMARK 200   NUMBER OF UNIQUE REFLECTIONS   : 12201
REMARK 200   RESOLUTION RANGE HIGH      (A) : 2.3
REMARK 200   RESOLUTION RANGE LOW       (A) : 20
REMARK 200   REJECTION CRITERIA  (SIGMA(I)) : -3.0
REMARK 200
REMARK 200 OVERALL.
REMARK 200   COMPLETENESS FOR RANGE     (%) : 98.2
REMARK 200   DATA REDUNDANCY                : 4
REMARK 200   R MERGE                    (I) : NULL
REMARK 200   R SYM                      (I) : 0.060
REMARK 200   <I/SIGMA(I)> FOR THE DATA SET  : 14.4
REMARK 200
REMARK 200 IN THE HIGHEST RESOLUTION SHELL.
REMARK 200   HIGHEST RESOLUTION SHELL, RANGE HIGH (A) : 2.30
REMARK 200   HIGHEST RESOLUTION SHELL, RANGE LOW  (A) : 2.34
REMARK 200   COMPLETENESS FOR SHELL     (%) : 98.6
REMARK 200   DATA REDUNDANCY IN SHELL       : 4
REMARK 200   R MERGE FOR SHELL          (I) : NULL
REMARK 200   R SYM FOR SHELL            (I) : 0.326
REMARK 200   <I/SIGMA(I)> FOR SHELL         : 2
REMARK 200
REMARK 200 DIFFRACTION PROTOCOL: NULL
REMARK 200 METHOD USED TO DETERMINE THE STRUCTURE: MOLECULAR
REMARK 200      REPLACEMENT
REMARK 200 SOFTWARE USED: AMORE (CCP4)
REMARK 200
REMARK 200 REMARK: NULL
REMARK 280
REMARK 280 CRYSTAL
REMARK 280 SOLVENT CONTENT, VS  (%): 45
REMARK 280 MATTHEWS COEFFICIENT, VM (ANGSTROMS**3/DA): 2.25
REMARK 280
REMARK 280 CRYSTALLIZATION CONDITIONS:
REMARK 280 7.0% (W/V) PEG 2000 MME,
REMARK 280 0.0035M NICKEL CHLORIDE, 0.035M TRIS-HCL, PH 8.5
REMARK 300
REMARK 300 BIOMOLECULE
REMARK 300 HOMODIMER
REMARK 350
REMARK 350 GENERATING THE BIOMOLECULE
REMARK 350 COORDINATES FOR A COMPLETE MULTIMER REPRESENTING THE KNOWN
REMARK 350 BIOLOGICALLY SIGNIFICANT OLIGOMERIZATION STATE OF THE
```

```
REMARK 350 MOLECULE CAN BE GENERATED BY APPLYING BIOMT TRANSFORMATIONS
REMARK 350 GIVEN BELOW.  BOTH NON-CRYSTALLOGRAPHIC AND
REMARK 350 CRYSTALLOGRAPHIC OPERATIONS ARE GIVEN.
REMARK 350
REMARK 350 APPLY THE FOLLOWING TO CHAINS: A
REMARK 350    BIOMT1   1  1.000000  0.000000  0.000000        0.00000
REMARK 350    BIOMT2   1  0.000000 -1.000000  0.000000        0.00000
REMARK 350    BIOMT3   1  0.000000  0.000000 -1.000000       53.17000
REMARK 350 APPLY THE FOLLOWING TO CHAINS:
REMARK 465
REMARK 465 MISSING RESIDUES
REMARK 465 Residues truncated at CB: M242,K255,E326,S363,S378,R379,K380,K435
REMARK 465 Residues truncated (other): K269(CD)
REMARK 465 Missing residues:N-terminal to L218,S364-S377,C-terminal to K435
REMARK 465 Alt. confs: Q222,D258,R343,Q405,NI801
REMARK 465 2 putative nickel ions
REMARK 465 46 solvent molecules
REMARK
CRYST1   60.380   82.670  106.340  90.00  90.00  90.00 I212121
SCALE1      0.01656  0.00000  0.00000        0.00000
SCALE2      0.00000  0.01210  0.00000        0.00000
SCALE3      0.00000  0.00000  0.00940        0.00000
ATOM      1  N   LEU A 218      27.404  19.380  36.226  1.00 62.13      A    N
ATOM      2  CA  LEU A 218      27.370  18.272  37.241  1.00 60.83      A    C
ATOM      3  C   LEU A 218      27.960  16.960  36.780  1.00 59.40      A    C
ATOM      4  O   LEU A 218      27.664  16.499  35.676  1.00 58.63      A    O
ATOM      5  CB  LEU A 218      25.918  18.061  37.644  1.00 62.14      A    C
ATOM      6  CG  LEU A 218      25.601  17.636  39.069  1.00 62.34      A    C
ATOM      7  CD1 LEU A 218      26.124  18.616  40.114  1.00 61.15      A    C
ATOM      8  CD2 LEU A 218      24.081  17.484  39.180  1.00 61.57      A    C
ATOM      9  N   SER A 219      28.822  16.341  37.584  1.00 59.22      A    N
ATOM     10  CA  SER A 219      29.420  15.068  37.191  1.00 59.26      A    C
ATOM     11  C   SER A 219      28.432  13.917  37.463  1.00 58.81      A    C
ATOM     12  O   SER A 219      27.567  14.024  38.319  1.00 56.26      A    O
ATOM     13  CB  SER A 219      30.697  14.835  37.996  1.00 58.80      A    C
ATOM     14  OG  SER A 219      30.416  14.385  39.322  1.00 57.78      A    O
ATOM     15  N   PRO A 220      28.604  12.823  36.767  1.00 59.71      A    N
ATOM     16  CA  PRO A 220      27.797  11.625  36.899  1.00 59.85      A    C
ATOM     17  C   PRO A 220      27.676  11.260  38.367  1.00 60.75      A    C
ATOM     18  O   PRO A 220      26.571  11.071  38.889  1.00 60.47      A    O
ATOM     19  CB  PRO A 220      28.519  10.510  36.148  1.00 60.33      A    C
ATOM     20  CG  PRO A 220      29.383  11.306  35.200  1.00 60.67      A    C
ATOM     21  CD  PRO A 220      29.655  12.679  35.748  1.00 59.29      A    C
ATOM     22  N   GLU A 221      28.824  11.183  39.026  1.00 60.07      A    N
ATOM     23  CA  GLU A 221      28.882  10.861  40.445  1.00 59.23      A    C
ATOM     24  C   GLU A 221      28.036  11.873  41.213  1.00 55.99      A    C
ATOM     25  O   GLU A 221      27.265  11.486  42.085  1.00 55.41      A    O
ATOM     26  CB  GLU A 221      30.302  10.929  41.004  1.00 62.54      A    C
ATOM     27  CG  GLU A 221      30.380  10.684  42.503  1.00 65.97      A    C
ATOM     28  CD  GLU A 221      31.811  10.692  43.017  1.00 68.64      A    C
ATOM     29  OE1 GLU A 221      32.453  11.774  42.910  1.00 69.95      A    O
ATOM     30  OE2 GLU A 221      32.281   9.646  43.518  1.00 68.75      A    O
ATOM     31  N   GLN A 222      28.169  13.135  40.862  1.00 52.52      A    N
ATOM     32  CA  GLN A 222      27.366  14.138  41.565  1.00 53.12      A    C
ATOM     33  CB  GLN A 222      27.881  15.571  41.388  1.00 55.08      A    C
ATOM     34  CG AGLN A 222      28.636  16.073  42.620  0.50 54.86      A    C
ATOM     35  CG BGLN A 222      29.080  15.893  42.270  0.50 55.52      A    C
ATOM     36  CD AGLN A 222      27.714  16.677  43.667  0.50 55.72      A    C
ATOM     37  CD BGLN A 222      29.939  17.052  41.831  0.50 57.59      A    C
ATOM     38  OE1AGLN A 222      27.868  16.479  44.876  0.50 55.59      A    O
ATOM     39  OE1BGLN A 222      30.233  17.241  40.650  0.50 57.39      A    O
```

| ATOM | 40 | NE2A | GLN | A | 222 | 26.715 | 17.443 | 43.237 | 0.50 | 55.64 | A | N |
|------|-----|------|-----|---|-----|--------|--------|--------|------|-------|---|---|
| ATOM | 41 | NE2B | GLN | A | 222 | 30.415 | 17.924 | 42.725 | 0.50 | 57.79 | A | N |
| ATOM | 42 | C | GLN | A | 222 | 25.886 | 14.005 | 41.245 | 1.00 | 51.70 | A | C |
| ATOM | 43 | O | GLN | A | 222 | 25.077 | 14.288 | 42.131 | 1.00 | 51.22 | A | O |
| ATOM | 44 | N | LEU | A | 223 | 25.549 | 13.559 | 40.046 | 1.00 | 49.37 | A | N |
| ATOM | 45 | CA | LEU | A | 223 | 24.166 | 13.374 | 39.679 | 1.00 | 48.67 | A | C |
| ATOM | 46 | C | LEU | A | 223 | 23.604 | 12.253 | 40.554 | 1.00 | 46.26 | A | C |
| ATOM | 47 | O | LEU | A | 223 | 22.552 | 12.397 | 41.120 | 1.00 | 45.67 | A | O |
| ATOM | 48 | CB | LEU | A | 223 | 23.972 | 13.113 | 38.180 | 1.00 | 49.12 | A | C |
| ATOM | 49 | CG | LEU | A | 223 | 22.520 | 12.906 | 37.717 | 1.00 | 48.61 | A | C |
| ATOM | 50 | CD1 | LEU | A | 223 | 21.543 | 13.865 | 38.376 | 1.00 | 46.99 | A | C |
| ATOM | 51 | CD2 | LEU | A | 223 | 22.402 | 13.074 | 36.197 | 1.00 | 47.31 | A | C |
| ATOM | 52 | N | VAL | A | 224 | 24.307 | 11.152 | 40.708 | 1.00 | 44.46 | A | N |
| ATOM | 53 | CA | VAL | A | 224 | 23.895 | 10.053 | 41.512 | 1.00 | 44.17 | A | C |
| ATOM | 54 | C | VAL | A | 224 | 23.677 | 10.435 | 42.974 | 1.00 | 46.54 | A | C |
| ATOM | 55 | O | VAL | A | 224 | 22.678 | 10.096 | 43.624 | 1.00 | 43.30 | A | O |
| ATOM | 56 | CB | VAL | A | 224 | 24.900 | 8.913 | 41.360 | 1.00 | 44.32 | A | C |
| ATOM | 57 | CG1 | VAL | A | 224 | 24.523 | 7.747 | 42.281 | 1.00 | 46.12 | A | C |
| ATOM | 58 | CG2 | VAL | A | 224 | 24.901 | 8.400 | 39.923 | 1.00 | 43.95 | A | C |
| ATOM | 59 | N | LEU | A | 225 | 24.606 | 11.174 | 43.537 | 1.00 | 48.01 | A | N |
| ATOM | 60 | CA | LEU | A | 225 | 24.565 | 11.623 | 44.921 | 1.00 | 48.91 | A | C |
| ATOM | 61 | C | LEU | A | 225 | 23.325 | 12.459 | 45.162 | 1.00 | 48.83 | A | C |
| ATOM | 62 | O | LEU | A | 225 | 22.704 | 12.285 | 46.219 | 1.00 | 46.16 | A | O |
| ATOM | 63 | CB | LEU | A | 225 | 25.892 | 12.328 | 45.214 | 1.00 | 54.27 | A | C |
| ATOM | 64 | CG | LEU | A | 225 | 26.227 | 12.877 | 46.591 | 1.00 | 57.12 | A | C |
| ATOM | 65 | CD1 | LEU | A | 225 | 26.111 | 11.836 | 47.707 | 1.00 | 57.30 | A | C |
| ATOM | 66 | CD2 | LEU | A | 225 | 27.654 | 13.430 | 46.590 | 1.00 | 58.26 | A | C |
| ATOM | 67 | N | THR | A | 226 | 22.903 | 13.321 | 44.241 | 1.00 | 48.19 | A | N |
| ATOM | 68 | CA | THR | A | 226 | 21.716 | 14.129 | 44.448 | 1.00 | 48.15 | A | C |
| ATOM | 69 | C | THR | A | 226 | 20.468 | 13.249 | 44.314 | 1.00 | 45.93 | A | C |
| ATOM | 70 | O | THR | A | 226 | 19.473 | 13.497 | 44.984 | 1.00 | 42.81 | A | O |
| ATOM | 71 | CB | THR | A | 226 | 21.601 | 15.302 | 43.451 | 1.00 | 51.33 | A | C |
| ATOM | 72 | OG1 | THR | A | 226 | 21.269 | 14.716 | 42.181 | 1.00 | 56.23 | A | O |
| ATOM | 73 | CG2 | THR | A | 226 | 22.939 | 15.965 | 43.249 | 1.00 | 52.20 | A | C |
| ATOM | 74 | N | LEU | A | 227 | 20.520 | 12.234 | 43.465 | 1.00 | 44.45 | A | N |
| ATOM | 75 | CA | LEU | A | 227 | 19.358 | 11.341 | 43.329 | 1.00 | 45.51 | A | C |
| ATOM | 76 | C | LEU | A | 227 | 19.201 | 10.587 | 44.668 | 1.00 | 46.83 | A | C |
| ATOM | 77 | O | LEU | A | 227 | 18.085 | 10.430 | 45.155 | 1.00 | 47.02 | A | O |
| ATOM | 78 | CB | LEU | A | 227 | 19.492 | 10.334 | 42.184 | 1.00 | 43.03 | A | C |
| ATOM | 79 | CG | LEU | A | 227 | 19.356 | 10.953 | 40.778 | 1.00 | 44.35 | A | C |
| ATOM | 80 | CD1 | LEU | A | 227 | 19.675 | 9.941 | 39.689 | 1.00 | 42.44 | A | C |
| ATOM | 81 | CD2 | LEU | A | 227 | 17.958 | 11.521 | 40.577 | 1.00 | 42.02 | A | C |
| ATOM | 82 | N | LEU | A | 228 | 20.320 | 10.144 | 45.205 | 1.00 | 46.52 | A | N |
| ATOM | 83 | CA | LEU | A | 228 | 20.390 | 9.414 | 46.438 | 1.00 | 49.82 | A | C |
| ATOM | 84 | C | LEU | A | 228 | 19.745 | 10.258 | 47.535 | 1.00 | 52.21 | A | C |
| ATOM | 85 | O | LEU | A | 228 | 18.872 | 9.795 | 48.260 | 1.00 | 52.05 | A | O |
| ATOM | 86 | CB | LEU | A | 228 | 21.815 | 9.027 | 46.828 | 1.00 | 48.41 | A | C |
| ATOM | 87 | CG | LEU | A | 228 | 21.911 | 8.119 | 48.057 | 1.00 | 51.06 | A | C |
| ATOM | 88 | CD1 | LEU | A | 228 | 21.155 | 6.808 | 47.881 | 1.00 | 50.35 | A | C |
| ATOM | 89 | CD2 | LEU | A | 228 | 23.367 | 7.819 | 48.425 | 1.00 | 49.34 | A | C |
| ATOM | 90 | N | GLU | A | 229 | 20.138 | 11.515 | 47.631 | 1.00 | 53.66 | A | N |
| ATOM | 91 | CA | GLU | A | 229 | 19.565 | 12.367 | 48.659 | 1.00 | 56.51 | A | C |
| ATOM | 92 | C | GLU | A | 229 | 18.153 | 12.765 | 48.280 | 1.00 | 53.19 | A | C |
| ATOM | 93 | O | GLU | A | 229 | 17.455 | 13.265 | 49.170 | 1.00 | 51.80 | A | O |
| ATOM | 94 | CB | GLU | A | 229 | 20.412 | 13.618 | 48.880 | 1.00 | 62.59 | A | C |
| ATOM | 95 | CG | GLU | A | 229 | 21.804 | 13.284 | 49.437 | 1.00 | 70.06 | A | C |
| ATOM | 96 | CD | GLU | A | 229 | 22.525 | 14.585 | 49.737 | 1.00 | 74.96 | A | C |
| ATOM | 97 | OE1 | GLU | A | 229 | 22.014 | 15.648 | 49.303 | 1.00 | 77.65 | A | O |
| ATOM | 98 | OE2 | GLU | A | 229 | 23.578 | 14.543 | 50.393 | 1.00 | 78.30 | A | O |
| ATOM | 99 | N | ALA | A | 230 | 17.762 | 12.556 | 47.014 | 1.00 | 48.78 | A | N |
| ATOM | 100 | CA | ALA | A | 230 | 16.372 | 12.962 | 46.743 | 1.00 | 46.40 | A | C |

104

| | | | | | | | | | | | |
|---|---|---|---|---|---|---|---|---|---|---|---|
| ATOM | 101 | C | ALA | A | 230 | 15.386 | 11.855 | 47.110 | 1.00 43.86 | A | C |
| ATOM | 102 | O | ALA | A | 230 | 14.181 | 12.096 | 47.083 | 1.00 42.73 | A | O |
| ATOM | 103 | CB | ALA | A | 230 | 16.142 | 13.481 | 45.330 | 1.00 45.75 | A | C |
| ATOM | 104 | N | GLU | A | 231 | 15.805 | 10.665 | 47.483 | 1.00 43.54 | A | N |
| ATOM | 105 | CA | GLU | A | 231 | 14.806 | 9.629 | 47.802 | 1.00 44.39 | A | C |
| ATOM | 106 | C | GLU | A | 231 | 13.768 | 10.183 | 48.748 | 1.00 46.23 | A | C |
| ATOM | 107 | O | GLU | A | 231 | 14.042 | 10.876 | 49.733 | 1.00 47.20 | A | O |
| ATOM | 108 | CB | GLU | A | 231 | 15.519 | 8.384 | 48.342 | 1.00 43.73 | A | C |
| ATOM | 109 | CG | GLU | A | 231 | 16.215 | 7.678 | 47.155 | 1.00 42.64 | A | C |
| ATOM | 110 | CD | GLU | A | 231 | 15.158 | 7.092 | 46.238 | 1.00 42.13 | A | C |
| ATOM | 111 | OE1 | GLU | A | 231 | 14.590 | 6.049 | 46.599 | 1.00 41.88 | A | O |
| ATOM | 112 | OE2 | GLU | A | 231 | 14.877 | 7.683 | 45.164 | 1.00 40.85 | A | O |
| ATOM | 113 | N | PRO | A | 232 | 12.522 | 9.893 | 48.467 | 1.00 46.42 | A | N |
| ATOM | 114 | CA | PRO | A | 232 | 11.412 | 10.326 | 49.294 | 1.00 46.00 | A | C |
| ATOM | 115 | C | PRO | A | 232 | 11.478 | 9.621 | 50.642 | 1.00 46.94 | A | C |
| ATOM | 116 | O | PRO | A | 232 | 11.993 | 8.524 | 50.795 | 1.00 44.77 | A | O |
| ATOM | 117 | CB | PRO | A | 232 | 10.150 | 9.888 | 48.555 | 1.00 45.35 | A | C |
| ATOM | 118 | CG | PRO | A | 232 | 10.692 | 8.759 | 47.716 | 1.00 47.13 | A | C |
| ATOM | 119 | CD | PRO | A | 232 | 12.120 | 9.048 | 47.334 | 1.00 46.44 | A | C |
| ATOM | 120 | N | PRO | A | 233 | 10.945 | 10.232 | 51.679 | 1.00 46.78 | A | N |
| ATOM | 121 | CA | PRO | A | 233 | 10.872 | 9.647 | 52.992 | 1.00 45.80 | A | C |
| ATOM | 122 | C | PRO | A | 233 | 9.859 | 8.492 | 52.916 | 1.00 45.40 | A | C |
| ATOM | 123 | O | PRO | A | 233 | 9.023 | 8.477 | 51.998 | 1.00 43.73 | A | O |
| ATOM | 124 | CB | PRO | A | 233 | 10.289 | 10.749 | 53.921 | 1.00 48.18 | A | C |
| ATOM | 125 | CG | PRO | A | 233 | 9.597 | 11.637 | 52.922 | 1.00 50.03 | A | C |
| ATOM | 126 | CD | PRO | A | 233 | 10.289 | 11.548 | 51.568 | 1.00 48.99 | A | C |
| ATOM | 127 | N | ASN | A | 234 | 9.847 | 7.560 | 53.836 | 1.00 42.69 | A | N |
| ATOM | 128 | CA | ASN | A | 234 | 8.866 | 6.481 | 53.803 | 1.00 43.87 | A | C |
| ATOM | 129 | C | ASN | A | 234 | 7.611 | 7.094 | 54.423 | 1.00 47.44 | A | C |
| ATOM | 130 | O | ASN | A | 234 | 7.683 | 8.157 | 55.032 | 1.00 46.24 | A | O |
| ATOM | 131 | CB | ASN | A | 234 | 9.248 | 5.281 | 54.681 | 1.00 43.93 | A | C |
| ATOM | 132 | CG | ASN | A | 234 | 10.285 | 4.462 | 53.913 | 1.00 42.60 | A | C |
| ATOM | 133 | OD1 | ASN | A | 234 | 9.912 | 3.886 | 52.891 | 1.00 41.25 | A | O |
| ATOM | 134 | ND2 | ASN | A | 234 | 11.463 | 4.470 | 54.433 | 1.00 40.39 | A | N |
| ATOM | 135 | N | VAL | A | 235 | 6.557 | 6.354 | 54.209 | 1.00 50.26 | A | N |
| ATOM | 136 | CA | VAL | A | 235 | 5.223 | 6.731 | 54.647 | 1.00 51.64 | A | C |
| ATOM | 137 | C | VAL | A | 235 | 4.767 | 5.970 | 55.882 | 1.00 53.20 | A | C |
| ATOM | 138 | O | VAL | A | 235 | 5.021 | 4.786 | 56.056 | 1.00 53.60 | A | O |
| ATOM | 139 | CB | VAL | A | 235 | 4.332 | 6.386 | 53.436 | 1.00 51.12 | A | C |
| ATOM | 140 | CG1 | VAL | A | 235 | 2.856 | 6.424 | 53.753 | 1.00 51.81 | A | C |
| ATOM | 141 | CG2 | VAL | A | 235 | 4.611 | 7.425 | 52.370 | 1.00 50.88 | A | C |
| ATOM | 142 | N | LEU | A | 236 | 4.056 | 6.650 | 56.760 | 1.00 55.52 | A | N |
| ATOM | 143 | CA | LEU | A | 236 | 3.538 | 6.111 | 57.989 | 1.00 59.12 | A | C |
| ATOM | 144 | C | LEU | A | 236 | 2.248 | 5.332 | 57.735 | 1.00 60.58 | A | C |
| ATOM | 145 | O | LEU | A | 236 | 1.200 | 5.942 | 57.542 | 1.00 60.40 | A | O |
| ATOM | 146 | CB | LEU | A | 236 | 3.232 | 7.255 | 58.973 | 1.00 58.92 | A | C |
| ATOM | 147 | CG | LEU | A | 236 | 2.973 | 6.769 | 60.404 | 1.00 59.58 | A | C |
| ATOM | 148 | CD1 | LEU | A | 236 | 4.222 | 6.075 | 60.948 | 1.00 60.88 | A | C |
| ATOM | 149 | CD2 | LEU | A | 236 | 2.560 | 7.948 | 61.270 | 1.00 59.76 | A | C |
| ATOM | 150 | N | VAL | A | 237 | 2.325 | 4.012 | 57.704 | 1.00 62.81 | A | N |
| ATOM | 151 | CA | VAL | A | 237 | 1.145 | 3.203 | 57.514 | 1.00 66.09 | A | C |
| ATOM | 152 | C | VAL | A | 237 | 1.259 | 1.933 | 58.377 | 1.00 69.65 | A | C |
| ATOM | 153 | O | VAL | A | 237 | 2.221 | 1.661 | 59.097 | 1.00 70.38 | A | O |
| ATOM | 154 | CB | VAL | A | 237 | 0.728 | 2.692 | 56.130 | 1.00 64.70 | A | C |
| ATOM | 155 | CG1 | VAL | A | 237 | 0.147 | 3.820 | 55.305 | 1.00 64.59 | A | C |
| ATOM | 156 | CG2 | VAL | A | 237 | 1.890 | 1.968 | 55.494 | 1.00 64.58 | A | C |
| ATOM | 157 | N | SER | A | 238 | 0.175 | 1.161 | 58.244 | 1.00 72.55 | A | N |
| ATOM | 158 | CA | SER | A | 238 | 0.125 | -0.078 | 58.993 | 1.00 75.38 | A | C |
| ATOM | 159 | C | SER | A | 238 | -1.023 | -0.974 | 58.553 | 1.00 76.77 | A | C |
| ATOM | 160 | O | SER | A | 238 | -2.039 | -0.558 | 57.999 | 1.00 75.92 | A | O |
| ATOM | 161 | CB | SER | A | 238 | 0.013 | 0.275 | 60.487 | 1.00 75.88 | A | C |

| ATOM | 162 | OG | SER A 238 | 0.075 | -0.964 | 61.181 | 1.00 | 77.78 | A | O |
| ATOM | 163 | N | ARG A 239 | -0.815 | -2.254 | 58.841 | 1.00 | 77.92 | A | N |
| ATOM | 164 | CA | ARG A 239 | -1.751 | -3.308 | 58.565 | 1.00 | 79.17 | A | C |
| ATOM | 165 | C | ARG A 239 | -2.804 | -3.266 | 59.668 | 1.00 | 82.33 | A | C |
| ATOM | 166 | O | ARG A 239 | -2.454 | -3.113 | 60.829 | 1.00 | 82.48 | A | O |
| ATOM | 167 | CB | ARG A 239 | -1.115 | -4.700 | 58.667 | 1.00 | 76.91 | A | C |
| ATOM | 168 | CG | ARG A 239 | -0.093 | -5.029 | 57.602 | 1.00 | 74.57 | A | C |
| ATOM | 169 | CD | ARG A 239 | 0.510 | -6.406 | 57.819 | 1.00 | 73.23 | A | C |
| ATOM | 170 | NE | ARG A 239 | -0.377 | -7.503 | 57.536 | 1.00 | 71.82 | A | N |
| ATOM | 171 | CZ | ARG A 239 | -0.510 | -8.434 | 56.623 | 1.00 | 70.25 | A | C |
| ATOM | 172 | NH1 | ARG A 239 | 0.290 | -8.621 | 55.595 | 1.00 | 68.65 | A | N |
| ATOM | 173 | NH2 | ARG A 239 | -1.545 | -9.273 | 56.760 | 1.00 | 70.63 | A | N |
| ATOM | 174 | N | PRO A 240 | -4.040 | -3.409 | 59.273 | 1.00 | 85.96 | A | N |
| ATOM | 175 | CA | PRO A 240 | -5.147 | -3.460 | 60.233 | 1.00 | 87.75 | A | C |
| ATOM | 176 | C | PRO A 240 | -4.872 | -4.755 | 60.992 | 1.00 | 89.77 | A | C |
| ATOM | 177 | O | PRO A 240 | -4.385 | -5.696 | 60.343 | 1.00 | 90.23 | A | O |
| ATOM | 178 | CB | PRO A 240 | -6.435 | -3.501 | 59.423 | 1.00 | 87.65 | A | C |
| ATOM | 179 | CG | PRO A 240 | -5.956 | -3.278 | 58.013 | 1.00 | 87.27 | A | C |
| ATOM | 180 | CD | PRO A 240 | -4.480 | -3.609 | 57.895 | 1.00 | 86.35 | A | C |
| ATOM | 181 | N | SER A 241 | -5.110 | -4.827 | 62.293 | 1.00 | 91.61 | A | N |
| ATOM | 182 | CA | SER A 241 | -4.832 | -6.068 | 63.013 | 1.00 | 92.34 | A | C |
| ATOM | 183 | C | SER A 241 | -5.571 | -7.287 | 62.466 | 1.00 | 92.40 | A | C |
| ATOM | 184 | O | SER A 241 | -4.902 | -8.318 | 62.326 | 1.00 | 93.86 | A | O |
| ATOM | 185 | CB | SER A 241 | -5.171 | -5.936 | 64.501 | 1.00 | 92.79 | A | C |
| ATOM | 186 | OG | SER A 241 | -4.605 | -4.783 | 65.085 | 1.00 | 92.22 | A | O |
| ATOM | 187 | N | MET A 242 | -6.866 | -7.204 | 62.190 | 1.00 | 91.14 | A | N |
| ATOM | 188 | CA | MET A 242 | -7.615 | -8.359 | 61.700 | 1.00 | 89.72 | A | C |
| ATOM | 189 | C | MET A 242 | -7.214 | -8.695 | 60.272 | 1.00 | 88.33 | A | C |
| ATOM | 190 | O | MET A 242 | -6.630 | -7.864 | 59.589 | 1.00 | 88.12 | A | O |
| ATOM | 191 | CB | MET A 242 | -9.115 | -8.110 | 61.816 | 1.00 | 90.08 | A | C |
| ATOM | 192 | N | PRO A 243 | -7.517 | -9.895 | 59.827 | 1.00 | 86.26 | A | N |
| ATOM | 193 | CA | PRO A 243 | -7.243 | -10.383 | 58.494 | 1.00 | 83.09 | A | C |
| ATOM | 194 | C | PRO A 243 | -7.829 | -9.443 | 57.451 | 1.00 | 78.86 | A | C |
| ATOM | 195 | O | PRO A 243 | -8.945 | -8.947 | 57.585 | 1.00 | 78.45 | A | O |
| ATOM | 196 | CB | PRO A 243 | -7.909 | -11.767 | 58.341 | 1.00 | 84.67 | A | C |
| ATOM | 197 | CG | PRO A 243 | -8.773 | -11.828 | 59.574 | 1.00 | 86.42 | A | C |
| ATOM | 198 | CD | PRO A 243 | -8.242 | -10.886 | 60.635 | 1.00 | 86.33 | A | C |
| ATOM | 199 | N | PHE A 244 | -7.080 | -9.185 | 56.397 | 1.00 | 73.43 | A | N |
| ATOM | 200 | CA | PHE A 244 | -7.535 | -8.298 | 55.344 | 1.00 | 67.87 | A | C |
| ATOM | 201 | C | PHE A 244 | -8.822 | -8.747 | 54.670 | 1.00 | 64.69 | A | C |
| ATOM | 202 | O | PHE A 244 | -9.084 | -9.926 | 54.547 | 1.00 | 63.41 | A | O |
| ATOM | 203 | CB | PHE A 244 | -6.469 | -8.187 | 54.245 | 1.00 | 65.58 | A | C |
| ATOM | 204 | CG | PHE A 244 | -5.398 | -7.160 | 54.419 | 1.00 | 64.57 | A | C |
| ATOM | 205 | CD1 | PHE A 244 | -5.760 | -5.817 | 54.458 | 1.00 | 63.55 | A | C |
| ATOM | 206 | CD2 | PHE A 244 | -4.043 | -7.474 | 54.515 | 1.00 | 63.31 | A | C |
| ATOM | 207 | CE1 | PHE A 244 | -4.829 | -4.813 | 54.602 | 1.00 | 62.01 | A | C |
| ATOM | 208 | CE2 | PHE A 244 | -3.083 | -6.483 | 54.665 | 1.00 | 61.48 | A | C |
| ATOM | 209 | CZ | PHE A 244 | -3.485 | -5.152 | 54.706 | 1.00 | 62.58 | A | C |
| ATOM | 210 | N | THR A 245 | -9.585 | -7.761 | 54.193 | 1.00 | 61.41 | A | N |
| ATOM | 211 | CA | THR A 245 | -10.786 | -7.973 | 53.420 | 1.00 | 58.43 | A | C |
| ATOM | 212 | C | THR A 245 | -10.568 | -7.154 | 52.132 | 1.00 | 58.19 | A | C |
| ATOM | 213 | O | THR A 245 | -9.712 | -6.256 | 52.127 | 1.00 | 56.82 | A | O |
| ATOM | 214 | CB | THR A 245 | -12.094 | -7.467 | 54.051 | 1.00 | 58.77 | A | C |
| ATOM | 215 | OG1 | THR A 245 | -12.103 | -6.024 | 54.187 | 1.00 | 56.75 | A | O |
| ATOM | 216 | CG2 | THR A 245 | -12.290 | -8.088 | 55.429 | 1.00 | 58.35 | A | C |
| ATOM | 217 | N | GLU A 246 | -11.339 | -7.395 | 51.099 | 1.00 | 57.94 | A | N |
| ATOM | 218 | CA | GLU A 246 | -11.223 | -6.620 | 49.875 | 1.00 | 61.05 | A | C |
| ATOM | 219 | C | GLU A 246 | -11.250 | -5.125 | 50.195 | 1.00 | 59.76 | A | C |
| ATOM | 220 | O | GLU A 246 | -10.475 | -4.353 | 49.609 | 1.00 | 60.77 | A | O |
| ATOM | 221 | CB | GLU A 246 | -12.327 | -6.992 | 48.904 | 1.00 | 64.20 | A | C |
| ATOM | 222 | CG | GLU A 246 | -12.226 | -6.478 | 47.472 | 1.00 | 69.17 | A | C |

| | | | | | | | | | | |
|---|---|---|---|---|---|---|---|---|---|---|
| ATOM | 223 | CD | GLU | A | 246 | -12.670 | -7.555 | 46.496 | 1.00 72.05 | A | C |
| ATOM | 224 | OE1 | GLU | A | 246 | -12.810 | -8.728 | 46.914 | 1.00 74.48 | A | O |
| ATOM | 225 | OE2 | GLU | A | 246 | -12.890 | -7.301 | 45.299 | 1.00 73.61 | A | O |
| ATOM | 226 | N | ALA | A | 247 | -12.098 | -4.722 | 51.135 | 1.00 57.27 | A | N |
| ATOM | 227 | CA | ALA | A | 247 | -12.203 | -3.313 | 51.460 | 1.00 55.84 | A | C |
| ATOM | 228 | C | ALA | A | 247 | -10.986 | -2.783 | 52.193 | 1.00 53.22 | A | C |
| ATOM | 229 | O | ALA | A | 247 | -10.546 | -1.709 | 51.857 | 1.00 53.01 | A | O |
| ATOM | 230 | CB | ALA | A | 247 | -13.403 | -2.920 | 52.355 | 1.00 53.95 | A | C |
| ATOM | 231 | N | SER | A | 248 | -10.547 | -3.511 | 53.204 | 1.00 52.69 | A | N |
| ATOM | 232 | CA | SER | A | 248 | -9.416 | -2.960 | 53.960 | 1.00 53.88 | A | C |
| ATOM | 233 | C | SER | A | 248 | -8.121 | -3.068 | 53.141 | 1.00 51.07 | A | C |
| ATOM | 234 | O | SER | A | 248 | -7.304 | -2.169 | 53.297 | 1.00 49.50 | A | O |
| ATOM | 235 | CB | SER | A | 248 | -9.404 | -3.691 | 55.294 | 1.00 53.41 | A | C |
| ATOM | 236 | OG | SER | A | 248 | -9.189 | -5.077 | 55.023 | 1.00 55.96 | A | O |
| ATOM | 237 | N | MET | A | 249 | -7.931 | -4.073 | 52.303 | 1.00 50.16 | A | N |
| ATOM | 238 | CA | MET | A | 249 | -6.702 | -4.095 | 51.505 | 1.00 52.40 | A | C |
| ATOM | 239 | C | MET | A | 249 | -6.732 | -2.926 | 50.513 | 1.00 52.14 | A | C |
| ATOM | 240 | O | MET | A | 249 | -5.712 | -2.215 | 50.450 | 1.00 52.43 | A | O |
| ATOM | 241 | CB | MET | A | 249 | -6.416 | -5.365 | 50.733 | 1.00 51.02 | A | C |
| ATOM | 242 | CG | MET | A | 249 | -5.171 | -5.381 | 49.838 | 1.00 49.42 | A | C |
| ATOM | 243 | SD | MET | A | 249 | -4.788 | -7.044 | 49.237 | 1.00 47.83 | A | S |
| ATOM | 244 | CE | MET | A | 249 | -4.477 | -7.842 | 50.812 | 1.00 49.00 | A | C |
| ATOM | 245 | N | MET | A | 250 | -7.819 | -2.717 | 49.790 | 1.00 51.74 | A | N |
| ATOM | 246 | CA | MET | A | 250 | -7.817 | -1.591 | 48.848 | 1.00 53.85 | A | C |
| ATOM | 247 | C | MET | A | 250 | -7.755 | -0.249 | 49.556 | 1.00 53.17 | A | C |
| ATOM | 248 | O | MET | A | 250 | -7.200 | 0.712 | 49.018 | 1.00 54.04 | A | O |
| ATOM | 249 | CB | MET | A | 250 | -9.042 | -1.650 | 47.907 | 1.00 54.06 | A | C |
| ATOM | 250 | CG | MET | A | 250 | -8.747 | -2.709 | 46.838 | 1.00 55.30 | A | C |
| ATOM | 251 | SD | MET | A | 250 | -7.429 | -2.174 | 45.724 | 1.00 55.22 | A | S |
| ATOM | 252 | CE | MET | A | 250 | -7.209 | -3.724 | 44.934 | 1.00 54.98 | A | C |
| ATOM | 253 | N | MET | A | 251 | -8.310 | -0.196 | 50.760 | 1.00 53.01 | A | N |
| ATOM | 254 | CA | MET | A | 251 | -8.251 | 1.052 | 51.531 | 1.00 54.37 | A | C |
| ATOM | 255 | C | MET | A | 251 | -6.767 | 1.337 | 51.838 | 1.00 51.22 | A | C |
| ATOM | 256 | O | MET | A | 251 | -6.252 | 2.417 | 51.565 | 1.00 47.50 | A | O |
| ATOM | 257 | CB | MET | A | 251 | -9.151 | 1.015 | 52.776 | 1.00 57.10 | A | C |
| ATOM | 258 | CG | MET | A | 251 | -9.079 | 2.290 | 53.610 | 1.00 64.59 | A | C |
| ATOM | 259 | SD | MET | A | 251 | -9.949 | 2.287 | 55.207 | 1.00 71.04 | A | S |
| ATOM | 260 | CE | MET | A | 251 | -9.618 | 3.984 | 55.722 | 1.00 70.25 | A | C |
| ATOM | 261 | N | SER | A | 252 | -6.010 | 0.379 | 52.372 | 1.00 50.16 | A | N |
| ATOM | 262 | CA | SER | A | 252 | -4.599 | 0.518 | 52.688 | 1.00 50.55 | A | C |
| ATOM | 263 | C | SER | A | 252 | -3.710 | 0.888 | 51.498 | 1.00 47.53 | A | C |
| ATOM | 264 | O | SER | A | 252 | -2.898 | 1.803 | 51.582 | 1.00 46.68 | A | O |
| ATOM | 265 | CB | SER | A | 252 | -4.050 | -0.831 | 53.240 | 1.00 51.58 | A | C |
| ATOM | 266 | OG | SER | A | 252 | -4.664 | -0.937 | 54.515 | 1.00 54.79 | A | O |
| ATOM | 267 | N | LEU | A | 253 | -3.886 | 0.170 | 50.395 | 1.00 45.80 | A | N |
| ATOM | 268 | CA | LEU | A | 253 | -3.077 | 0.454 | 49.198 | 1.00 44.49 | A | C |
| ATOM | 269 | C | LEU | A | 253 | -3.327 | 1.865 | 48.705 | 1.00 43.20 | A | C |
| ATOM | 270 | O | LEU | A | 253 | -2.435 | 2.667 | 48.410 | 1.00 39.83 | A | O |
| ATOM | 271 | CB | LEU | A | 253 | -3.396 | -0.663 | 48.197 | 1.00 43.88 | A | C |
| ATOM | 272 | CG | LEU | A | 253 | -2.821 | -2.032 | 48.669 | 1.00 44.17 | A | C |
| ATOM | 273 | CD1 | LEU | A | 253 | -3.030 | -3.107 | 47.618 | 1.00 42.95 | A | C |
| ATOM | 274 | CD2 | LEU | A | 253 | -1.332 | -1.857 | 48.943 | 1.00 45.37 | A | C |
| ATOM | 275 | N | THR | A | 254 | -4.609 | 2.206 | 48.646 | 1.00 43.66 | A | N |
| ATOM | 276 | CA | THR | A | 254 | -5.020 | 3.558 | 48.196 | 1.00 45.27 | A | C |
| ATOM | 277 | C | THR | A | 254 | -4.478 | 4.608 | 49.121 | 1.00 43.75 | A | C |
| ATOM | 278 | O | THR | A | 254 | -3.864 | 5.566 | 48.638 | 1.00 45.76 | A | O |
| ATOM | 279 | CB | THR | A | 254 | -6.573 | 3.560 | 48.149 | 1.00 47.80 | A | C |
| ATOM | 280 | OG1 | THR | A | 254 | -6.936 | 2.863 | 46.951 | 1.00 50.37 | A | O |
| ATOM | 281 | CG2 | THR | A | 254 | -7.088 | 4.969 | 48.134 | 1.00 49.70 | A | C |
| ATOM | 282 | N | LYS | A | 255 | -4.595 | 4.523 | 50.450 | 1.00 42.36 | A | N |
| ATOM | 283 | CA | LYS | A | 255 | -4.023 | 5.577 | 51.291 | 1.00 44.27 | A | C |

107

| | | | | | | | | | | | |
|---|---|---|---|---|---|---|---|---|---|---|---|
| ATOM | 284 | C | LYS | A | 255 | -2.507 | 5.675 | 51.095 | 1.00 | 41.85 | A C |
| ATOM | 285 | O | LYS | A | 255 | -1.937 | 6.756 | 51.026 | 1.00 | 42.85 | A O |
| ATOM | 286 | CB | LYS | A | 255 | -4.239 | 5.375 | 52.802 | 1.00 | 44.97 | A C |
| ATOM | 287 | N | LEU | A | 256 | -1.865 | 4.527 | 51.034 | 1.00 | 41.69 | A N |
| ATOM | 288 | CA | LEU | A | 256 | -0.405 | 4.496 | 50.815 | 1.00 | 41.59 | A C |
| ATOM | 289 | C | LEU | A | 256 | -0.043 | 5.259 | 49.542 | 1.00 | 39.37 | A C |
| ATOM | 290 | O | LEU | A | 256 | 0.803 | 6.127 | 49.545 | 1.00 | 37.07 | A O |
| ATOM | 291 | CB | LEU | A | 256 | 0.020 | 3.009 | 50.650 | 1.00 | 39.85 | A C |
| ATOM | 292 | CG | LEU | A | 256 | 1.443 | 2.848 | 50.104 | 1.00 | 41.32 | A C |
| ATOM | 293 | CD1 | LEU | A | 256 | 2.471 | 3.443 | 51.039 | 1.00 | 41.12 | A C |
| ATOM | 294 | CD2 | LEU | A | 256 | 1.769 | 1.387 | 49.828 | 1.00 | 41.30 | A C |
| ATOM | 295 | N | ALA | A | 257 | -0.715 | 4.891 | 48.430 | 1.00 | 39.56 | A N |
| ATOM | 296 | CA | ALA | A | 257 | -0.338 | 5.573 | 47.172 | 1.00 | 40.19 | A C |
| ATOM | 297 | C | ALA | A | 257 | -0.534 | 7.064 | 47.275 | 1.00 | 39.85 | A C |
| ATOM | 298 | O | ALA | A | 257 | 0.251 | 7.837 | 46.741 | 1.00 | 39.94 | A O |
| ATOM | 299 | CB | ALA | A | 257 | -1.081 | 5.024 | 45.950 | 1.00 | 36.76 | A C |
| ATOM | 300 | N | ASP | A | 258 | -1.593 | 7.455 | 47.970 | 1.00 | 43.26 | A N |
| ATOM | 301 | CA | ASP | A | 258 | -1.832 | 8.914 | 48.036 | 1.00 | 44.80 | A C |
| ATOM | 302 | C | ASP | A | 258 | -0.664 | 9.624 | 48.654 | 1.00 | 45.18 | A C |
| ATOM | 303 | O | ASP | A | 258 | -0.236 | 10.641 | 48.114 | 1.00 | 47.81 | A O |
| ATOM | 304 | CB | ASP | A | 258 | -3.075 | 9.176 | 48.892 | 1.00 | 47.80 | A C |
| ATOM | 305 | CG A | ASP | A | 258 | -4.323 | 9.073 | 48.033 | 0.50 | 46.88 | A C |
| ATOM | 306 | CG B | ASP | A | 258 | -3.530 | 10.605 | 48.797 | 0.50 | 50.12 | A C |
| ATOM | 307 | OD1A | ASP | A | 258 | -5.413 | 8.911 | 48.622 | 0.50 | 46.11 | A O |
| ATOM | 308 | OD1B | ASP | A | 258 | -2.929 | 11.429 | 48.073 | 0.50 | 53.81 | A O |
| ATOM | 309 | OD2A | ASP | A | 258 | -4.150 | 9.154 | 46.795 | 0.50 | 45.45 | A O |
| ATOM | 310 | OD2B | ASP | A | 258 | -4.524 | 10.964 | 49.446 | 0.50 | 50.93 | A O |
| ATOM | 311 | N | LYS | A | 259 | -0.193 | 9.090 | 49.768 | 1.00 | 44.84 | A N |
| ATOM | 312 | CA | LYS | A | 259 | 0.965 | 9.736 | 50.400 | 1.00 | 47.23 | A C |
| ATOM | 313 | C | LYS | A | 259 | 2.200 | 9.560 | 49.535 | 1.00 | 45.75 | A C |
| ATOM | 314 | O | LYS | A | 259 | 2.984 | 10.510 | 49.425 | 1.00 | 44.52 | A O |
| ATOM | 315 | CB | LYS | A | 259 | 1.124 | 9.146 | 51.807 | 1.00 | 52.11 | A C |
| ATOM | 316 | CG | LYS | A | 259 | -0.242 | 9.069 | 52.502 | 1.00 | 58.56 | A C |
| ATOM | 317 | CD | LYS | A | 259 | -0.111 | 8.696 | 53.972 | 1.00 | 62.17 | A C |
| ATOM | 318 | CE | LYS | A | 259 | -1.479 | 8.230 | 54.495 | 1.00 | 63.77 | A C |
| ATOM | 319 | NZ | LYS | A | 259 | -1.201 | 7.449 | 55.745 | 1.00 | 65.81 | A N |
| ATOM | 320 | N | GLU | A | 260 | 2.357 | 8.384 | 48.868 | 1.00 | 43.47 | A N |
| ATOM | 321 | CA | GLU | A | 260 | 3.574 | 8.301 | 48.022 | 1.00 | 41.95 | A C |
| ATOM | 322 | C | GLU | A | 260 | 3.484 | 9.292 | 46.861 | 1.00 | 40.94 | A C |
| ATOM | 323 | O | GLU | A | 260 | 4.554 | 9.797 | 46.496 | 1.00 | 40.26 | A O |
| ATOM | 324 | CB | GLU | A | 260 | 3.859 | 6.913 | 47.468 | 1.00 | 40.17 | A C |
| ATOM | 325 | CG | GLU | A | 260 | 3.985 | 5.837 | 48.523 | 1.00 | 37.98 | A C |
| ATOM | 326 | CD | GLU | A | 260 | 4.276 | 4.514 | 47.839 | 1.00 | 37.85 | A C |
| ATOM | 327 | OE1 | GLU | A | 260 | 5.474 | 4.252 | 47.650 | 1.00 | 36.95 | A O |
| ATOM | 328 | OE2 | GLU | A | 260 | 3.373 | 3.731 | 47.514 | 1.00 | 38.12 | A O |
| ATOM | 329 | N | LEU | A | 261 | 2.281 | 9.524 | 46.358 | 1.00 | 39.79 | A N |
| ATOM | 330 | CA | LEU | A | 261 | 2.144 | 10.449 | 45.224 | 1.00 | 42.24 | A C |
| ATOM | 331 | C | LEU | A | 261 | 2.546 | 11.865 | 45.616 | 1.00 | 43.48 | A C |
| ATOM | 332 | O | LEU | A | 261 | 3.155 | 12.559 | 44.804 | 1.00 | 41.65 | A O |
| ATOM | 333 | CB | LEU | A | 261 | 0.763 | 10.310 | 44.572 | 1.00 | 43.31 | A C |
| ATOM | 334 | CG | LEU | A | 261 | 0.578 | 9.005 | 43.808 | 1.00 | 44.09 | A C |
| ATOM | 335 | CD1 | LEU | A | 261 | -0.791 | 8.777 | 43.201 | 1.00 | 45.11 | A C |
| ATOM | 336 | CD2 | LEU | A | 261 | 1.578 | 8.999 | 42.659 | 1.00 | 45.62 | A C |
| ATOM | 337 | N | VAL | A | 262 | 2.342 | 12.287 | 46.874 | 1.00 | 43.28 | A N |
| ATOM | 338 | CA | VAL | A | 262 | 2.737 | 13.604 | 47.330 | 1.00 | 42.28 | A C |
| ATOM | 339 | C | VAL | A | 262 | 4.269 | 13.685 | 47.341 | 1.00 | 45.44 | A C |
| ATOM | 340 | O | VAL | A | 262 | 4.914 | 14.638 | 46.871 | 1.00 | 45.55 | A O |
| ATOM | 341 | CB | VAL | A | 262 | 2.217 | 13.863 | 48.769 | 1.00 | 44.61 | A C |
| ATOM | 342 | CG1 | VAL | A | 262 | 2.904 | 15.054 | 49.472 | 1.00 | 39.58 | A C |
| ATOM | 343 | CG2 | VAL | A | 262 | 0.687 | 13.958 | 48.716 | 1.00 | 42.22 | A C |
| ATOM | 344 | N | HIS | A | 263 | 4.879 | 12.651 | 47.937 | 1.00 | 45.28 | A N |

| ATOM | 345 | CA  | HIS | A | 263 | 6.342  | 12.616 | 47.986 | 1.00 | 45.58 | A | C |
| ATOM | 346 | C   | HIS | A | 263 | 6.935  | 12.471 | 46.577 | 1.00 | 45.24 | A | C |
| ATOM | 347 | O   | HIS | A | 263 | 8.056  | 12.966 | 46.395 | 1.00 | 44.73 | A | O |
| ATOM | 348 | CB  | HIS | A | 263 | 6.836  | 11.440 | 48.809 | 1.00 | 46.27 | A | C |
| ATOM | 349 | CG  | HIS | A | 263 | 6.458  | 11.540 | 50.252 | 1.00 | 50.50 | A | C |
| ATOM | 350 | ND1 | HIS | A | 263 | 6.292  | 10.496 | 51.135 | 1.00 | 50.62 | A | N |
| ATOM | 351 | CD2 | HIS | A | 263 | 6.197  | 12.665 | 50.950 | 1.00 | 50.02 | A | C |
| ATOM | 352 | CE1 | HIS | A | 263 | 5.968  | 10.952 | 52.332 | 1.00 | 50.17 | A | C |
| ATOM | 353 | NE2 | HIS | A | 263 | 5.902  | 12.273 | 52.217 | 1.00 | 54.47 | A | N |
| ATOM | 354 | N   | MET | A | 264 | 6.241  | 11.787 | 45.685 | 1.00 | 42.02 | A | N |
| ATOM | 355 | CA  | MET | A | 264 | 6.824  | 11.652 | 44.343 | 1.00 | 42.62 | A | C |
| ATOM | 356 | C   | MET | A | 264 | 7.014  | 13.030 | 43.722 | 1.00 | 43.82 | A | C |
| ATOM | 357 | O   | MET | A | 264 | 8.086  | 13.296 | 43.127 | 1.00 | 46.33 | A | O |
| ATOM | 358 | CB  | MET | A | 264 | 5.922  | 10.765 | 43.458 | 1.00 | 39.88 | A | C |
| ATOM | 359 | CG  | MET | A | 264 | 6.559  | 10.508 | 42.106 | 1.00 | 36.83 | A | C |
| ATOM | 360 | SD  | MET | A | 264 | 5.530  | 9.613  | 40.970 | 1.00 | 36.52 | A | S |
| ATOM | 361 | CE  | MET | A | 264 | 5.027  | 8.174  | 41.835 | 1.00 | 30.85 | A | C |
| ATOM | 362 | N   | ILE | A | 265 | 6.027  | 13.912 | 43.867 | 1.00 | 43.54 | A | N |
| ATOM | 363 | CA  | ILE | A | 265 | 6.139  | 15.259 | 43.283 | 1.00 | 45.13 | A | C |
| ATOM | 364 | C   | ILE | A | 265 | 7.355  | 15.988 | 43.835 | 1.00 | 47.10 | A | C |
| ATOM | 365 | O   | ILE | A | 265 | 8.153  | 16.598 | 43.078 | 1.00 | 47.90 | A | O |
| ATOM | 366 | CB  | ILE | A | 265 | 4.807  | 15.981 | 43.536 | 1.00 | 48.87 | A | C |
| ATOM | 367 | CG1 | ILE | A | 265 | 3.688  | 15.382 | 42.650 | 1.00 | 49.16 | A | C |
| ATOM | 368 | CG2 | ILE | A | 265 | 4.820  | 17.497 | 43.355 | 1.00 | 47.29 | A | C |
| ATOM | 369 | CD1 | ILE | A | 265 | 2.307  | 15.867 | 43.086 | 1.00 | 51.30 | A | C |
| ATOM | 370 | N   | GLY | A | 266 | 7.616  | 15.912 | 45.147 | 1.00 | 44.93 | A | N |
| ATOM | 371 | CA  | GLY | A | 266 | 8.783  | 16.609 | 45.686 | 1.00 | 46.37 | A | C |
| ATOM | 372 | C   | GLY | A | 266 | 10.074 | 15.956 | 45.205 | 1.00 | 48.04 | A | C |
| ATOM | 373 | O   | GLY | A | 266 | 11.128 | 16.584 | 45.021 | 1.00 | 46.75 | A | O |
| ATOM | 374 | N   | TRP | A | 267 | 9.978  | 14.622 | 44.980 | 1.00 | 46.60 | A | N |
| ATOM | 375 | CA  | TRP | A | 267 | 11.207 | 13.949 | 44.515 | 1.00 | 44.16 | A | C |
| ATOM | 376 | C   | TRP | A | 267 | 11.591 | 14.443 | 43.126 | 1.00 | 42.73 | A | C |
| ATOM | 377 | O   | TRP | A | 267 | 12.737 | 14.746 | 42.898 | 1.00 | 40.61 | A | O |
| ATOM | 378 | CB  | TRP | A | 267 | 10.980 | 12.446 | 44.463 | 1.00 | 43.65 | A | C |
| ATOM | 379 | CG  | TRP | A | 267 | 11.858 | 11.669 | 43.534 | 1.00 | 43.07 | A | C |
| ATOM | 380 | CD1 | TRP | A | 267 | 13.165 | 11.296 | 43.761 | 1.00 | 40.80 | A | C |
| ATOM | 381 | CD2 | TRP | A | 267 | 11.492 | 11.152 | 42.246 | 1.00 | 41.18 | A | C |
| ATOM | 382 | NE1 | TRP | A | 267 | 13.620 | 10.582 | 42.689 | 1.00 | 40.80 | A | N |
| ATOM | 383 | CE2 | TRP | A | 267 | 12.625 | 10.480 | 41.750 | 1.00 | 41.89 | A | C |
| ATOM | 384 | CE3 | TRP | A | 267 | 10.333 | 11.178 | 41.479 | 1.00 | 39.33 | A | C |
| ATOM | 385 | CZ2 | TRP | A | 267 | 12.639 | 9.837  | 40.505 | 1.00 | 40.92 | A | C |
| ATOM | 386 | CZ3 | TRP | A | 267 | 10.343 | 10.547 | 40.260 | 1.00 | 39.84 | A | C |
| ATOM | 387 | CH2 | TRP | A | 267 | 11.480 | 9.867  | 39.767 | 1.00 | 39.22 | A | C |
| ATOM | 388 | N   | ALA | A | 268 | 10.609 | 14.450 | 42.233 | 1.00 | 42.56 | A | N |
| ATOM | 389 | CA  | ALA | A | 268 | 10.902 | 14.863 | 40.866 | 1.00 | 44.92 | A | C |
| ATOM | 390 | C   | ALA | A | 268 | 11.430 | 16.287 | 40.893 | 1.00 | 49.13 | A | C |
| ATOM | 391 | O   | ALA | A | 268 | 12.365 | 16.568 | 40.131 | 1.00 | 50.44 | A | O |
| ATOM | 392 | CB  | ALA | A | 268 | 9.675  | 14.732 | 39.984 | 1.00 | 42.30 | A | C |
| ATOM | 393 | N   | LYS | A | 269 | 10.885 | 17.125 | 41.780 | 1.00 | 53.15 | A | N |
| ATOM | 394 | CA  | LYS | A | 269 | 11.398 | 18.510 | 41.817 | 1.00 | 57.36 | A | C |
| ATOM | 395 | C   | LYS | A | 269 | 12.855 | 18.570 | 42.239 | 1.00 | 58.02 | A | C |
| ATOM | 396 | O   | LYS | A | 269 | 13.498 | 19.571 | 41.883 | 1.00 | 58.80 | A | O |
| ATOM | 397 | CB  | LYS | A | 269 | 10.493 | 19.472 | 42.601 | 1.00 | 58.62 | A | C |
| ATOM | 398 | CG  | LYS | A | 269 | 9.251  | 19.757 | 41.737 | 1.00 | 60.26 | A | C |
| ATOM | 399 | CD  | LYS | A | 269 | 8.477  | 20.970 | 42.187 | 1.00 | 61.12 | A | C |
| ATOM | 402 | N   | LYS | A | 270 | 13.357 | 17.536 | 42.920 | 1.00 | 57.68 | A | N |
| ATOM | 403 | CA  | LYS | A | 270 | 14.767 | 17.533 | 43.304 | 1.00 | 57.55 | A | C |
| ATOM | 404 | C   | LYS | A | 270 | 15.653 | 16.984 | 42.183 | 1.00 | 57.12 | A | C |
| ATOM | 405 | O   | LYS | A | 270 | 16.879 | 16.996 | 42.311 | 1.00 | 57.60 | A | O |
| ATOM | 406 | CB  | LYS | A | 270 | 15.038 | 16.761 | 44.584 | 1.00 | 57.50 | A | C |
| ATOM | 407 | CG  | LYS | A | 270 | 14.304 | 17.218 | 45.826 | 1.00 | 59.57 | A | C |

109

| | | | | | | | | | | | |
|---|---|---|---|---|---|---|---|---|---|---|---|
| ATOM | 408 | CD | LYS | A | 270 | 14.949 | 16.661 | 47.081 | 1.00 61.00 | A | C |
| ATOM | 409 | CE | LYS | A | 270 | 14.461 | 17.343 | 48.357 | 1.00 62.53 | A | C |
| ATOM | 410 | NZ | LYS | A | 270 | 13.310 | 16.608 | 48.964 | 1.00 62.41 | A | N |
| ATOM | 411 | N | ILE | A | 271 | 15.108 | 16.497 | 41.070 | 1.00 56.67 | A | N |
| ATOM | 412 | CA | ILE | A | 271 | 15.970 | 15.971 | 39.999 | 1.00 55.42 | A | C |
| ATOM | 413 | C | ILE | A | 271 | 16.565 | 17.226 | 39.364 | 1.00 57.45 | A | C |
| ATOM | 414 | O | ILE | A | 271 | 15.868 | 18.179 | 39.060 | 1.00 57.01 | A | O |
| ATOM | 415 | CB | ILE | A | 271 | 15.274 | 15.049 | 39.003 | 1.00 53.35 | A | C |
| ATOM | 416 | CG1 | ILE | A | 271 | 14.854 | 13.716 | 39.680 | 1.00 51.49 | A | C |
| ATOM | 417 | CG2 | ILE | A | 271 | 16.200 | 14.728 | 37.831 | 1.00 52.07 | A | C |
| ATOM | 418 | CD1 | ILE | A | 271 | 13.807 | 12.943 | 38.924 | 1.00 47.48 | A | C |
| ATOM | 419 | N | PRO | A | 272 | 17.861 | 17.286 | 39.201 | 1.00 59.30 | A | N |
| ATOM | 420 | CA | PRO | A | 272 | 18.570 | 18.422 | 38.639 | 1.00 60.35 | A | C |
| ATOM | 421 | C | PRO | A | 272 | 18.078 | 18.751 | 37.232 | 1.00 60.55 | A | C |
| ATOM | 422 | O | PRO | A | 272 | 18.224 | 17.956 | 36.310 | 1.00 59.75 | A | O |
| ATOM | 423 | CB | PRO | A | 272 | 20.073 | 18.071 | 38.640 | 1.00 60.45 | A | C |
| ATOM | 424 | CG | PRO | A | 272 | 20.121 | 16.812 | 39.453 | 1.00 60.45 | A | C |
| ATOM | 425 | CD | PRO | A | 272 | 18.762 | 16.169 | 39.538 | 1.00 59.79 | A | C |
| ATOM | 426 | N | GLY | A | 273 | 17.462 | 19.917 | 37.066 | 1.00 59.68 | A | N |
| ATOM | 427 | CA | GLY | A | 273 | 16.928 | 20.392 | 35.822 | 1.00 58.56 | A | C |
| ATOM | 428 | C | GLY | A | 273 | 15.428 | 20.206 | 35.667 | 1.00 59.45 | A | C |
| ATOM | 429 | O | GLY | A | 273 | 14.814 | 20.764 | 34.740 | 1.00 59.32 | A | O |
| ATOM | 430 | N | PHE | A | 274 | 14.779 | 19.429 | 36.543 | 1.00 57.86 | A | N |
| ATOM | 431 | CA | PHE | A | 274 | 13.350 | 19.196 | 36.381 | 1.00 56.27 | A | C |
| ATOM | 432 | C | PHE | A | 274 | 12.520 | 20.472 | 36.549 | 1.00 57.01 | A | C |
| ATOM | 433 | O | PHE | A | 274 | 11.608 | 20.634 | 35.725 | 1.00 55.31 | A | O |
| ATOM | 434 | CB | PHE | A | 274 | 12.860 | 18.084 | 37.281 | 1.00 52.95 | A | C |
| ATOM | 435 | CG | PHE | A | 274 | 11.442 | 17.608 | 37.068 | 1.00 51.41 | A | C |
| ATOM | 436 | CD1 | PHE | A | 274 | 10.370 | 18.154 | 37.723 | 1.00 50.09 | A | C |
| ATOM | 437 | CD2 | PHE | A | 274 | 11.205 | 16.567 | 36.196 | 1.00 50.40 | A | C |
| ATOM | 438 | CE1 | PHE | A | 274 | 9.082 | 17.709 | 37.555 | 1.00 49.07 | A | C |
| ATOM | 439 | CE2 | PHE | A | 274 | 9.931 | 16.099 | 35.993 | 1.00 50.84 | A | C |
| ATOM | 440 | CZ | PHE | A | 274 | 8.862 | 16.664 | 36.674 | 1.00 50.66 | A | C |
| ATOM | 441 | N | VAL | A | 275 | 12.830 | 21.301 | 37.541 | 1.00 58.85 | A | N |
| ATOM | 442 | CA | VAL | A | 275 | 12.056 | 22.528 | 37.753 | 1.00 62.19 | A | C |
| ATOM | 443 | C | VAL | A | 275 | 12.268 | 23.576 | 36.670 | 1.00 63.04 | A | C |
| ATOM | 444 | O | VAL | A | 275 | 11.457 | 24.469 | 36.493 | 1.00 62.74 | A | O |
| ATOM | 445 | CB | VAL | A | 275 | 12.273 | 23.146 | 39.155 | 1.00 61.63 | A | C |
| ATOM | 446 | CG1 | VAL | A | 275 | 11.616 | 22.228 | 40.184 | 1.00 58.99 | A | C |
| ATOM | 447 | CG2 | VAL | A | 275 | 13.758 | 23.342 | 39.417 | 1.00 61.30 | A | C |
| ATOM | 448 | N | GLU | A | 276 | 13.323 | 23.471 | 35.882 | 1.00 65.82 | A | N |
| ATOM | 449 | CA | GLU | A | 276 | 13.609 | 24.398 | 34.788 | 1.00 67.70 | A | C |
| ATOM | 450 | C | GLU | A | 276 | 12.782 | 24.020 | 33.547 | 1.00 66.49 | A | C |
| ATOM | 451 | O | GLU | A | 276 | 12.712 | 24.765 | 32.561 | 1.00 64.84 | A | O |
| ATOM | 452 | CB | GLU | A | 276 | 15.098 | 24.450 | 34.443 | 1.00 69.90 | A | C |
| ATOM | 453 | CG | GLU | A | 276 | 16.097 | 24.749 | 35.524 | 1.00 73.34 | A | C |
| ATOM | 454 | CD | GLU | A | 276 | 17.517 | 24.246 | 35.320 | 1.00 76.12 | A | C |
| ATOM | 455 | OE1 | GLU | A | 276 | 17.917 | 23.731 | 34.247 | 1.00 76.39 | A | O |
| ATOM | 456 | OE2 | GLU | A | 276 | 18.302 | 24.366 | 36.308 | 1.00 77.16 | A | O |
| ATOM | 457 | N | LEU | A | 277 | 12.141 | 22.847 | 33.572 | 1.00 64.25 | A | N |
| ATOM | 458 | CA | LEU | A | 277 | 11.284 | 22.400 | 32.471 | 1.00 61.35 | A | C |
| ATOM | 459 | C | LEU | A | 277 | 9.995 | 23.214 | 32.588 | 1.00 58.48 | A | C |
| ATOM | 460 | O | LEU | A | 277 | 9.710 | 23.677 | 33.690 | 1.00 57.15 | A | O |
| ATOM | 461 | CB | LEU | A | 277 | 10.843 | 20.939 | 32.554 | 1.00 61.20 | A | C |
| ATOM | 462 | CG | LEU | A | 277 | 11.821 | 19.791 | 32.344 | 1.00 62.57 | A | C |
| ATOM | 463 | CD1 | LEU | A | 277 | 11.248 | 18.425 | 32.733 | 1.00 61.96 | A | C |
| ATOM | 464 | CD2 | LEU | A | 277 | 12.290 | 19.649 | 30.901 | 1.00 61.91 | A | C |
| ATOM | 465 | N | SER | A | 278 | 9.223 | 23.331 | 31.535 | 1.00 57.27 | A | N |
| ATOM | 466 | CA | SER | A | 278 | 7.961 | 24.069 | 31.634 | 1.00 57.81 | A | C |
| ATOM | 467 | C | SER | A | 278 | 7.000 | 23.347 | 32.582 | 1.00 56.67 | A | C |
| ATOM | 468 | O | SER | A | 278 | 7.012 | 22.110 | 32.648 | 1.00 58.11 | A | O |

110

| ATOM | 469 | CB | SER A 278 | 7.311 | 24.255 | 30.263 | 1.00 | 56.81 | A | C |
| --- | --- | --- | --- | --- | --- | --- | --- | --- | --- | --- |
| ATOM | 470 | OG | SER A 278 | 6.946 | 22.978 | 29.769 | 1.00 | 59.53 | A | O |
| ATOM | 471 | N | LEU A 279 | 6.174 | 24.083 | 33.304 | 1.00 | 53.88 | A | N |
| ATOM | 472 | CA | LEU A 279 | 5.241 | 23.516 | 34.251 | 1.00 | 53.47 | A | C |
| ATOM | 473 | C | LEU A 279 | 4.416 | 22.427 | 33.571 | 1.00 | 53.40 | A | C |
| ATOM | 474 | O | LEU A 279 | 4.247 | 21.349 | 34.137 | 1.00 | 52.33 | A | O |
| ATOM | 475 | CB | LEU A 279 | 4.397 | 24.626 | 34.887 | 1.00 | 53.23 | A | C |
| ATOM | 476 | CG | LEU A 279 | 3.573 | 24.231 | 36.126 | 1.00 | 53.18 | A | C |
| ATOM | 477 | CD1 | LEU A 279 | 4.465 | 23.601 | 37.179 | 1.00 | 51.32 | A | C |
| ATOM | 478 | CD2 | LEU A 279 | 2.883 | 25.468 | 36.700 | 1.00 | 55.18 | A | C |
| ATOM | 479 | N | LEU A 280 | 3.937 | 22.698 | 32.361 | 1.00 | 52.22 | A | N |
| ATOM | 480 | CA | LEU A 280 | 3.172 | 21.756 | 31.574 | 1.00 | 54.28 | A | C |
| ATOM | 481 | C | LEU A 280 | 3.913 | 20.436 | 31.348 | 1.00 | 53.12 | A | C |
| ATOM | 482 | O | LEU A 280 | 3.340 | 19.367 | 31.531 | 1.00 | 53.06 | A | O |
| ATOM | 483 | CB | LEU A 280 | 2.728 | 22.301 | 30.212 | 1.00 | 55.56 | A | C |
| ATOM | 484 | CG | LEU A 280 | 1.584 | 23.323 | 30.251 | 1.00 | 59.33 | A | C |
| ATOM | 485 | CD1 | LEU A 280 | 1.078 | 23.716 | 28.853 | 1.00 | 58.86 | A | C |
| ATOM | 486 | CD2 | LEU A 280 | 0.413 | 22.815 | 31.078 | 1.00 | 58.59 | A | C |
| ATOM | 487 | N | ASP A 281 | 5.167 | 20.465 | 30.951 | 1.00 | 52.44 | A | N |
| ATOM | 488 | CA | ASP A 281 | 5.938 | 19.236 | 30.751 | 1.00 | 52.85 | A | C |
| ATOM | 489 | C | ASP A 281 | 6.117 | 18.488 | 32.082 | 1.00 | 50.64 | A | C |
| ATOM | 490 | O | ASP A 281 | 6.102 | 17.266 | 32.111 | 1.00 | 48.12 | A | O |
| ATOM | 491 | CB | ASP A 281 | 7.294 | 19.586 | 30.144 | 1.00 | 55.89 | A | C |
| ATOM | 492 | CG | ASP A 281 | 7.224 | 19.972 | 28.683 | 1.00 | 59.12 | A | C |
| ATOM | 493 | OD1 | ASP A 281 | 6.121 | 20.063 | 28.087 | 1.00 | 61.18 | A | O |
| ATOM | 494 | OD2 | ASP A 281 | 8.322 | 20.201 | 28.123 | 1.00 | 60.68 | A | O |
| ATOM | 495 | N | GLN A 282 | 6.281 | 19.247 | 33.167 | 1.00 | 48.03 | A | N |
| ATOM | 496 | CA | GLN A 282 | 6.453 | 18.687 | 34.484 | 1.00 | 46.51 | A | C |
| ATOM | 497 | C | GLN A 282 | 5.243 | 17.837 | 34.852 | 1.00 | 45.43 | A | C |
| ATOM | 498 | O | GLN A 282 | 5.355 | 16.667 | 35.238 | 1.00 | 43.02 | A | O |
| ATOM | 499 | CB | GLN A 282 | 6.702 | 19.730 | 35.583 | 1.00 | 46.57 | A | C |
| ATOM | 500 | CG | GLN A 282 | 8.107 | 20.353 | 35.481 | 1.00 | 47.92 | A | C |
| ATOM | 501 | CD | GLN A 282 | 8.321 | 21.443 | 36.509 | 1.00 | 49.11 | A | C |
| ATOM | 502 | OE1 | GLN A 282 | 8.118 | 21.176 | 37.704 | 1.00 | 49.50 | A | O |
| ATOM | 503 | NE2 | GLN A 282 | 8.704 | 22.662 | 36.150 | 1.00 | 47.66 | A | N |
| ATOM | 504 | N | VAL A 283 | 4.088 | 18.461 | 34.724 | 1.00 | 45.46 | A | N |
| ATOM | 505 | CA | VAL A 283 | 2.837 | 17.794 | 35.039 | 1.00 | 44.88 | A | C |
| ATOM | 506 | C | VAL A 283 | 2.634 | 16.638 | 34.084 | 1.00 | 46.75 | A | C |
| ATOM | 507 | O | VAL A 283 | 2.180 | 15.578 | 34.550 | 1.00 | 45.83 | A | O |
| ATOM | 508 | CB | VAL A 283 | 1.589 | 18.704 | 34.986 | 1.00 | 44.01 | A | C |
| ATOM | 509 | CG1 | VAL A 283 | 0.305 | 17.920 | 35.194 | 1.00 | 42.88 | A | C |
| ATOM | 510 | CG2 | VAL A 283 | 1.739 | 19.765 | 36.064 | 1.00 | 44.13 | A | C |
| ATOM | 511 | N | ARG A 284 | 2.956 | 16.879 | 32.810 | 1.00 | 48.36 | A | N |
| ATOM | 512 | CA | ARG A 284 | 2.773 | 15.796 | 31.844 | 1.00 | 52.28 | A | C |
| ATOM | 513 | C | ARG A 284 | 3.574 | 14.549 | 32.252 | 1.00 | 50.71 | A | C |
| ATOM | 514 | O | ARG A 284 | 2.976 | 13.469 | 32.306 | 1.00 | 50.31 | A | O |
| ATOM | 515 | CB | ARG A 284 | 3.241 | 16.287 | 30.463 | 1.00 | 56.33 | A | C |
| ATOM | 516 | CG | ARG A 284 | 2.566 | 15.654 | 29.290 | 1.00 | 61.32 | A | C |
| ATOM | 517 | CD | ARG A 284 | 2.617 | 16.467 | 28.027 | 1.00 | 66.68 | A | C |
| ATOM | 518 | NE | ARG A 284 | 3.046 | 17.855 | 28.073 | 1.00 | 69.89 | A | N |
| ATOM | 519 | CZ | ARG A 284 | 2.461 | 18.849 | 27.403 | 1.00 | 72.20 | A | C |
| ATOM | 520 | NH1 | ARG A 284 | 1.392 | 18.602 | 26.648 | 1.00 | 71.79 | A | N |
| ATOM | 521 | NH2 | ARG A 284 | 2.899 | 20.112 | 27.457 | 1.00 | 73.24 | A | N |
| ATOM | 522 | N | LEU A 285 | 4.858 | 14.668 | 32.554 | 1.00 | 47.13 | A | N |
| ATOM | 523 | CA | LEU A 285 | 5.635 | 13.470 | 32.911 | 1.00 | 48.55 | A | C |
| ATOM | 524 | C | LEU A 285 | 5.149 | 12.694 | 34.135 | 1.00 | 48.84 | A | C |
| ATOM | 525 | O | LEU A 285 | 4.996 | 11.472 | 34.152 | 1.00 | 44.97 | A | O |
| ATOM | 526 | CB | LEU A 285 | 7.110 | 13.842 | 33.075 | 1.00 | 48.08 | A | C |
| ATOM | 527 | CG | LEU A 285 | 7.732 | 14.469 | 31.823 | 1.00 | 49.95 | A | C |
| ATOM | 528 | CD1 | LEU A 285 | 9.186 | 14.812 | 32.036 | 1.00 | 48.24 | A | C |
| ATOM | 529 | CD2 | LEU A 285 | 7.587 | 13.511 | 30.634 | 1.00 | 49.03 | A | C |

| ATOM | 530 | N   | LEU A 286 | 4.846  | 13.418 | 35.214 | 1.00 | 48.76 | A | N |
|------|-----|-----|-----------|--------|--------|--------|------|-------|---|---|
| ATOM | 531 | CA  | LEU A 286 | 4.370  | 12.796 | 36.441 | 1.00 | 48.40 | A | C |
| ATOM | 532 | C   | LEU A 286 | 3.055  | 12.098 | 36.175 | 1.00 | 48.45 | A | C |
| ATOM | 533 | O   | LEU A 286 | 2.762  | 11.003 | 36.668 | 1.00 | 49.67 | A | O |
| ATOM | 534 | CB  | LEU A 286 | 4.222  | 13.858 | 37.521 | 1.00 | 47.87 | A | C |
| ATOM | 535 | CG  | LEU A 286 | 5.555  | 14.211 | 38.180 | 1.00 | 49.39 | A | C |
| ATOM | 536 | CD1 | LEU A 286 | 5.526  | 15.561 | 38.888 | 1.00 | 50.62 | A | C |
| ATOM | 537 | CD2 | LEU A 286 | 5.918  | 13.100 | 39.132 | 1.00 | 48.77 | A | C |
| ATOM | 538 | N   | GLU A 287 | 2.235  | 12.735 | 35.356 | 1.00 | 48.11 | A | N |
| ATOM | 539 | CA  | GLU A 287 | 0.926  | 12.166 | 35.066 | 1.00 | 49.36 | A | C |
| ATOM | 540 | C   | GLU A 287 | 0.930  | 10.911 | 34.212 | 1.00 | 47.60 | A | C |
| ATOM | 541 | O   | GLU A 287 | 0.063  | 10.039 | 34.353 | 1.00 | 49.27 | A | O |
| ATOM | 542 | CB  | GLU A 287 | 0.048  | 13.180 | 34.305 | 1.00 | 50.33 | A | C |
| ATOM | 543 | CG  | GLU A 287 | -1.389 | 12.708 | 34.318 | 1.00 | 53.26 | A | C |
| ATOM | 544 | CD  | GLU A 287 | -2.323 | 13.620 | 33.525 | 1.00 | 55.74 | A | C |
| ATOM | 545 | OE1 | GLU A 287 | -1.809 | 14.486 | 32.780 | 1.00 | 55.11 | A | O |
| ATOM | 546 | OE2 | GLU A 287 | -3.552 | 13.417 | 33.669 | 1.00 | 53.80 | A | O |
| ATOM | 547 | N   | SER A 288 | 1.844  | 10.820 | 33.255 | 1.00 | 44.86 | A | N |
| ATOM | 548 | CA  | SER A 288 | 1.844  | 9.649  | 32.419 | 1.00 | 44.99 | A | C |
| ATOM | 549 | C   | SER A 288 | 2.631  | 8.460  | 32.963 | 1.00 | 42.97 | A | C |
| ATOM | 550 | O   | SER A 288 | 2.358  | 7.361  | 32.490 | 1.00 | 42.14 | A | O |
| ATOM | 551 | CB  | SER A 288 | 2.464  | 10.023 | 31.041 | 1.00 | 46.50 | A | C |
| ATOM | 552 | OG  | SER A 288 | 3.876  | 10.043 | 31.271 | 1.00 | 51.88 | A | O |
| ATOM | 553 | N   | CYS A 289 | 3.589  | 8.575  | 33.841 | 1.00 | 39.75 | A | N |
| ATOM | 554 | CA  | CYS A 289 | 4.386  | 7.441  | 34.281 | 1.00 | 40.36 | A | C |
| ATOM | 555 | C   | CYS A 289 | 4.371  | 7.269  | 35.829 | 1.00 | 37.86 | A | C |
| ATOM | 556 | O   | CYS A 289 | 5.187  | 6.527  | 36.387 | 1.00 | 35.56 | A | O |
| ATOM | 557 | CB  | CYS A 289 | 5.826  | 7.622  | 33.766 | 1.00 | 40.83 | A | C |
| ATOM | 558 | SG  | CYS A 289 | 6.133  | 8.172  | 32.047 | 1.00 | 49.03 | A | S |
| ATOM | 559 | N   | TRP A 290 | 3.428  | 7.802  | 36.573 | 1.00 | 36.00 | A | N |
| ATOM | 560 | CA  | TRP A 290 | 3.416  | 7.676  | 38.038 | 1.00 | 37.61 | A | C |
| ATOM | 561 | C   | TRP A 290 | 3.257  | 6.246  | 38.539 | 1.00 | 38.90 | A | C |
| ATOM | 562 | O   | TRP A 290 | 3.908  | 5.874  | 39.517 | 1.00 | 39.54 | A | O |
| ATOM | 563 | CB  | TRP A 290 | 2.393  | 8.579  | 38.744 | 1.00 | 38.05 | A | C |
| ATOM | 564 | CG  | TRP A 290 | 0.980  | 8.324  | 38.392 | 1.00 | 39.28 | A | C |
| ATOM | 565 | CD1 | TRP A 290 | 0.241  | 8.982  | 37.462 | 1.00 | 40.73 | A | C |
| ATOM | 566 | CD2 | TRP A 290 | 0.109  | 7.325  | 38.939 | 1.00 | 41.64 | A | C |
| ATOM | 567 | NE1 | TRP A 290 | -1.028 | 8.482  | 37.399 | 1.00 | 41.73 | A | N |
| ATOM | 568 | CE2 | TRP A 290 | -1.140 | 7.455  | 38.295 | 1.00 | 42.50 | A | C |
| ATOM | 569 | CE3 | TRP A 290 | 0.255  | 6.353  | 39.936 | 1.00 | 41.05 | A | C |
| ATOM | 570 | CZ2 | TRP A 290 | -2.226 | 6.656  | 38.626 | 1.00 | 43.71 | A | C |
| ATOM | 571 | CZ3 | TRP A 290 | -0.797 | 5.543  | 40.247 | 1.00 | 41.33 | A | C |
| ATOM | 572 | CH2 | TRP A 290 | -2.020 | 5.701  | 39.604 | 1.00 | 44.45 | A | C |
| ATOM | 573 | N   | MET A 291 | 2.422  | 5.420  | 37.908 | 1.00 | 37.11 | A | N |
| ATOM | 574 | CA  | MET A 291 | 2.277  | 4.043  | 38.362 | 1.00 | 37.68 | A | C |
| ATOM | 575 | C   | MET A 291 | 3.566  | 3.269  | 38.154 | 1.00 | 36.78 | A | C |
| ATOM | 576 | O   | MET A 291 | 3.936  | 2.391  | 38.939 | 1.00 | 41.22 | A | O |
| ATOM | 577 | CB  | MET A 291 | 1.092  | 3.355  | 37.681 | 1.00 | 36.00 | A | C |
| ATOM | 578 | CG  | MET A 291 | 0.857  | 1.899  | 38.048 | 1.00 | 35.92 | A | C |
| ATOM | 579 | SD  | MET A 291 | 0.533  | 1.713  | 39.830 | 1.00 | 38.45 | A | S |
| ATOM | 580 | CE  | MET A 291 | -1.251 | 1.556  | 39.737 | 1.00 | 39.34 | A | C |
| ATOM | 581 | N   | GLU A 292 | 4.329  | 3.613  | 37.143 | 1.00 | 38.96 | A | N |
| ATOM | 582 | CA  | GLU A 292 | 5.604  | 2.930  | 36.859 | 1.00 | 38.23 | A | C |
| ATOM | 583 | C   | GLU A 292 | 6.629  | 3.283  | 37.932 | 1.00 | 33.45 | A | C |
| ATOM | 584 | O   | GLU A 292 | 7.366  | 2.465  | 38.401 | 1.00 | 33.90 | A | O |
| ATOM | 585 | CB  | GLU A 292 | 6.157  | 3.309  | 35.492 | 1.00 | 39.45 | A | C |
| ATOM | 586 | CG  | GLU A 292 | 5.637  | 2.440  | 34.355 | 1.00 | 44.86 | A | C |
| ATOM | 587 | CD  | GLU A 292 | 5.743  | 3.120  | 33.020 | 1.00 | 48.51 | A | C |
| ATOM | 588 | OE1 | GLU A 292 | 6.750  | 3.689  | 32.569 | 1.00 | 51.98 | A | O |
| ATOM | 589 | OE2 | GLU A 292 | 4.766  | 3.154  | 32.248 | 1.00 | 53.11 | A | O |
| ATOM | 590 | N   | VAL A 293 | 6.775  | 4.541  | 38.280 | 1.00 | 32.48 | A | N |

```
ATOM   591  CA   VAL A 293       7.687   5.001  39.311  1.00 34.51      A    C
ATOM   592  C    VAL A 293       7.298   4.320  40.622  1.00 33.20      A    C
ATOM   593  O    VAL A 293       8.178   3.909  41.327  1.00 34.86      A    O
ATOM   594  CB   VAL A 293       7.555   6.524  39.499  1.00 37.22      A    C
ATOM   595  CG1  VAL A 293       8.355   7.071  40.691  1.00 35.34      A    C
ATOM   596  CG2  VAL A 293       7.891   7.164  38.167  1.00 34.93      A    C
ATOM   597  N    LEU A 294       5.995   4.163  40.911  1.00 35.07      A    N
ATOM   598  CA   LEU A 294       5.602   3.484  42.149  1.00 37.21      A    C
ATOM   599  C    LEU A 294       5.995   1.992  42.117  1.00 36.51      A    C
ATOM   600  O    LEU A 294       6.472   1.538  43.148  1.00 35.18      A    O
ATOM   601  CB   LEU A 294       4.078   3.433  42.462  1.00 33.37      A    C
ATOM   602  CG   LEU A 294       3.414   4.760  42.770  1.00 36.82      A    C
ATOM   603  CD1  LEU A 294       1.888   4.609  42.888  1.00 35.23      A    C
ATOM   604  CD2  LEU A 294       3.955   5.399  44.072  1.00 36.97      A    C
ATOM   605  N    MET A 295       5.740   1.330  40.997  1.00 34.85      A    N
ATOM   606  CA   MET A 295       6.043  -0.095  40.930  1.00 37.73      A    C
ATOM   607  C    MET A 295       7.528  -0.426  41.027  1.00 38.26      A    C
ATOM   608  O    MET A 295       7.929  -1.371  41.736  1.00 39.35      A    O
ATOM   609  CB   MET A 295       5.459  -0.664  39.616  1.00 37.32      A    C
ATOM   610  CG   MET A 295       3.926  -0.793  39.712  1.00 36.39      A    C
ATOM   611  SD   MET A 295       3.308  -1.404  38.125  1.00 36.52      A    S
ATOM   612  CE   MET A 295       1.695  -2.009  38.564  1.00 36.42      A    C
ATOM   613  N    VAL A 296       8.334   0.393  40.362  1.00 36.30      A    N
ATOM   614  CA   VAL A 296       9.768   0.093  40.422  1.00 37.01      A    C
ATOM   615  C    VAL A 296      10.262   0.314  41.856  1.00 37.68      A    C
ATOM   616  O    VAL A 296      11.235  -0.324  42.241  1.00 38.12      A    O
ATOM   617  CB   VAL A 296      10.593   0.872  39.414  1.00 33.68      A    C
ATOM   618  CG1  VAL A 296      10.656   2.343  39.734  1.00 35.13      A    C
ATOM   619  CG2  VAL A 296      12.036   0.387  39.362  1.00 36.00      A    C
ATOM   620  N    GLY A 297       9.641   1.223  42.594  1.00 38.05      A    N
ATOM   621  CA   GLY A 297      10.106   1.461  44.001  1.00 36.57      A    C
ATOM   622  C    GLY A 297       9.731   0.257  44.842  1.00 35.43      A    C
ATOM   623  O    GLY A 297      10.461  -0.209  45.712  1.00 38.65      A    O
ATOM   624  N    LEU A 298       8.551  -0.288  44.562  1.00 36.63      A    N
ATOM   625  CA   LEU A 298       8.013  -1.467  45.220  1.00 36.38      A    C
ATOM   626  C    LEU A 298       8.901  -2.668  44.888  1.00 37.98      A    C
ATOM   627  O    LEU A 298       9.104  -3.482  45.770  1.00 37.21      A    O
ATOM   628  CB   LEU A 298       6.598  -1.807  44.712  1.00 34.59      A    C
ATOM   629  CG   LEU A 298       6.040  -3.168  45.127  1.00 35.88      A    C
ATOM   630  CD1  LEU A 298       5.873  -3.350  46.638  1.00 35.42      A    C
ATOM   631  CD2  LEU A 298       4.753  -3.492  44.376  1.00 34.06      A    C
ATOM   632  N    MET A 299       9.381  -2.728  43.641  1.00 38.28      A    N
ATOM   633  CA   MET A 299      10.210  -3.860  43.279  1.00 39.29      A    C
ATOM   634  C    MET A 299      11.562  -3.810  44.001  1.00 39.00      A    C
ATOM   635  O    MET A 299      12.027  -4.855  44.449  1.00 36.16      A    O
ATOM   636  CB   MET A 299      10.462  -3.967  41.761  1.00 38.63      A    C
ATOM   637  CG   MET A 299       9.133  -4.165  41.010  1.00 38.86      A    C
ATOM   638  SD   MET A 299       9.463  -4.224  39.218  1.00 40.39      A    S
ATOM   639  CE   MET A 299       7.864  -4.697  38.633  1.00 39.89      A    C
ATOM   640  N    TRP A 300      12.159  -2.620  44.027  1.00 39.82      A    N
ATOM   641  CA   TRP A 300      13.410  -2.404  44.678  1.00 39.31      A    C
ATOM   642  C    TRP A 300      13.150  -2.813  46.145  1.00 39.63      A    C
ATOM   643  O    TRP A 300      13.896  -3.623  46.682  1.00 38.21      A    O
ATOM   644  CB   TRP A 300      13.913  -0.918  44.687  1.00 40.77      A    C
ATOM   645  CG   TRP A 300      15.038  -0.802  45.702  1.00 44.28      A    C
ATOM   646  CD1  TRP A 300      15.009  -0.187  46.916  1.00 44.94      A    C
ATOM   647  CD2  TRP A 300      16.356  -1.366  45.590  1.00 45.46      A    C
ATOM   648  NE1  TRP A 300      16.221  -0.313  47.565  1.00 46.42      A    N
ATOM   649  CE2  TRP A 300      17.068  -1.043  46.770  1.00 46.83      A    C
ATOM   650  CE3  TRP A 300      17.004  -2.124  44.620  1.00 45.56      A    C
ATOM   651  CZ2  TRP A 300      18.389  -1.445  47.014  1.00 45.92      A    C
```

| | | | | | | | | | | |
|---|---|---|---|---|---|---|---|---|---|---|
| ATOM | 652 | CZ3 | TRP | A | 300 | 18.305 | -2.512 | 44.857 | 1.00 45.89 | A | C |
| ATOM | 653 | CH2 | TRP | A | 300 | 18.986 | -2.182 | 46.027 | 1.00 45.50 | A | C |
| ATOM | 654 | N | ARG | A | 301 | 12.082 | -2.263 | 46.747 | 1.00 38.18 | A | N |
| ATOM | 655 | CA | ARG | A | 301 | 11.930 | -2.635 | 48.172 | 1.00 39.48 | A | C |
| ATOM | 656 | C | ARG | A | 301 | 11.711 | -4.137 | 48.339 | 1.00 39.80 | A | C |
| ATOM | 657 | O | ARG | A | 301 | 12.007 | -4.624 | 49.435 | 1.00 38.55 | A | O |
| ATOM | 658 | CB | ARG | A | 301 | 10.753 | -1.893 | 48.837 | 1.00 36.92 | A | C |
| ATOM | 659 | CG | ARG | A | 301 | 10.935 | -0.377 | 48.957 | 1.00 35.98 | A | C |
| ATOM | 660 | CD | ARG | A | 301 | 9.702 | 0.220 | 49.618 | 1.00 37.26 | A | C |
| ATOM | 661 | NE | ARG | A | 301 | 8.384 | 0.051 | 49.017 | 1.00 33.59 | A | N |
| ATOM | 662 | CZ | ARG | A | 301 | 7.953 | 0.844 | 48.013 | 1.00 33.64 | A | C |
| ATOM | 663 | NH1 | ARG | A | 301 | 8.716 | 1.834 | 47.503 | 1.00 30.33 | A | N |
| ATOM | 664 | NH2 | ARG | A | 301 | 6.732 | 0.591 | 47.561 | 1.00 29.13 | A | N |
| ATOM | 665 | N | SER | A | 302 | 11.198 | -4.861 | 47.347 | 1.00 37.38 | A | N |
| ATOM | 666 | CA | SER | A | 302 | 10.924 | -6.272 | 47.690 | 1.00 41.01 | A | C |
| ATOM | 667 | C | SER | A | 302 | 11.962 | -7.236 | 47.151 | 1.00 42.15 | A | C |
| ATOM | 668 | O | SER | A | 302 | 11.739 | -8.448 | 47.159 | 1.00 42.05 | A | O |
| ATOM | 669 | CB | SER | A | 302 | 9.562 | -6.622 | 47.016 | 1.00 40.60 | A | C |
| ATOM | 670 | OG | SER | A | 302 | 8.538 | -5.691 | 47.410 | 1.00 43.17 | A | O |
| ATOM | 671 | N | ILE | A | 303 | 13.041 | -6.663 | 46.633 | 1.00 42.71 | A | N |
| ATOM | 672 | CA | ILE | A | 303 | 14.020 | -7.469 | 45.925 | 1.00 46.27 | A | C |
| ATOM | 673 | C | ILE | A | 303 | 14.602 | -8.648 | 46.641 | 1.00 48.05 | A | C |
| ATOM | 674 | O | ILE | A | 303 | 14.716 | -9.737 | 46.041 | 1.00 48.26 | A | O |
| ATOM | 675 | CB | ILE | A | 303 | 15.056 | -6.552 | 45.246 | 1.00 46.35 | A | C |
| ATOM | 676 | CG1 | ILE | A | 303 | 15.323 | -7.164 | 43.865 | 1.00 44.61 | A | C |
| ATOM | 677 | CG2 | ILE | A | 303 | 16.267 | -6.351 | 46.113 | 1.00 45.59 | A | C |
| ATOM | 678 | CD1 | ILE | A | 303 | 16.444 | -6.397 | 43.160 | 1.00 44.74 | A | C |
| ATOM | 679 | N | ASP | A | 304 | 14.927 | -8.472 | 47.900 | 1.00 48.69 | A | N |
| ATOM | 680 | CA | ASP | A | 304 | 15.495 | -9.550 | 48.689 | 1.00 54.75 | A | C |
| ATOM | 681 | C | ASP | A | 304 | 14.464 | -10.368 | 49.461 | 1.00 55.28 | A | C |
| ATOM | 682 | O | ASP | A | 304 | 14.873 | -11.038 | 50.410 | 1.00 52.51 | A | O |
| ATOM | 683 | CB | ASP | A | 304 | 16.502 | -8.844 | 49.639 | 1.00 58.08 | A | C |
| ATOM | 684 | CG | ASP | A | 304 | 17.717 | -8.299 | 48.903 | 1.00 61.45 | A | C |
| ATOM | 685 | OD1 | ASP | A | 304 | 18.247 | -9.005 | 47.997 | 1.00 63.08 | A | O |
| ATOM | 686 | OD2 | ASP | A | 304 | 18.223 | -7.183 | 49.159 | 1.00 62.92 | A | O |
| ATOM | 687 | N | HIS | A | 305 | 13.169 | -10.343 | 49.158 | 1.00 56.35 | A | N |
| ATOM | 688 | CA | HIS | A | 305 | 12.137 | -11.053 | 49.858 | 1.00 57.08 | A | C |
| ATOM | 689 | C | HIS | A | 305 | 11.123 | -11.803 | 49.015 | 1.00 59.27 | A | C |
| ATOM | 690 | O | HIS | A | 305 | 9.969 | -11.428 | 48.789 | 1.00 58.80 | A | O |
| ATOM | 691 | CB | HIS | A | 305 | 11.293 | -10.103 | 50.745 | 1.00 57.98 | A | C |
| ATOM | 692 | CG | HIS | A | 305 | 12.181 | -9.325 | 51.659 | 1.00 58.80 | A | C |
| ATOM | 693 | ND1 | HIS | A | 305 | 12.684 | -9.853 | 52.827 | 1.00 59.71 | A | N |
| ATOM | 694 | CD2 | HIS | A | 305 | 12.678 | -8.080 | 51.606 | 1.00 57.55 | A | C |
| ATOM | 695 | CE1 | HIS | A | 305 | 13.441 | -8.968 | 53.451 | 1.00 58.11 | A | C |
| ATOM | 696 | NE2 | HIS | A | 305 | 13.473 | -7.862 | 52.723 | 1.00 58.41 | A | N |
| ATOM | 697 | N | PRO | A | 306 | 11.539 | -12.957 | 48.550 | 1.00 60.83 | A | N |
| ATOM | 698 | CA | PRO | A | 306 | 10.758 | -13.891 | 47.764 | 1.00 61.28 | A | C |
| ATOM | 699 | C | PRO | A | 306 | 9.353 | -14.113 | 48.299 | 1.00 60.85 | A | C |
| ATOM | 700 | O | PRO | A | 306 | 9.094 | -14.319 | 49.495 | 1.00 59.86 | A | O |
| ATOM | 701 | CB | PRO | A | 306 | 11.591 | -15.205 | 47.805 | 1.00 61.90 | A | C |
| ATOM | 702 | CG | PRO | A | 306 | 12.990 | -14.591 | 47.824 | 1.00 61.31 | A | C |
| ATOM | 703 | CD | PRO | A | 306 | 12.911 | -13.452 | 48.814 | 1.00 61.21 | A | C |
| ATOM | 704 | N | GLY | A | 307 | 8.376 | -14.053 | 47.392 | 1.00 60.03 | A | N |
| ATOM | 705 | CA | GLY | A | 307 | 6.976 | -14.213 | 47.742 | 1.00 60.17 | A | C |
| ATOM | 706 | C | GLY | A | 307 | 6.366 | -13.085 | 48.575 | 1.00 60.77 | A | C |
| ATOM | 707 | O | GLY | A | 307 | 5.242 | -13.239 | 49.096 | 1.00 60.48 | A | O |
| ATOM | 708 | N | LYS | A | 308 | 7.027 | -11.936 | 48.699 | 1.00 59.61 | A | N |
| ATOM | 709 | CA | LYS | A | 308 | 6.485 | -10.830 | 49.487 | 1.00 58.56 | A | C |
| ATOM | 710 | C | LYS | A | 308 | 6.579 | -9.475 | 48.809 | 1.00 54.93 | A | C |
| ATOM | 711 | O | LYS | A | 308 | 7.577 | -9.141 | 48.153 | 1.00 53.10 | A | O |
| ATOM | 712 | CB | LYS | A | 308 | 7.183 | -10.743 | 50.855 | 1.00 61.89 | A | C |

| | | | | | | | | | | |
|---|---|---|---|---|---|---|---|---|---|---|
| ATOM | 713 | CG | LYS | A | 308 | 6.898 | -11.973 | 51.736 | 1.00 65.21 | A C |
| ATOM | 714 | CD | LYS | A | 308 | 7.855 | -11.933 | 52.934 | 1.00 69.16 | A C |
| ATOM | 715 | CE | LYS | A | 308 | 8.010 | -13.314 | 53.574 | 1.00 69.88 | A C |
| ATOM | 716 | NZ | LYS | A | 308 | 6.692 | -13.747 | 54.149 | 1.00 70.43 | A N |
| ATOM | 717 | N | LEU | A | 309 | 5.517 | -8.674 | 48.993 | 1.00 51.08 | A N |
| ATOM | 718 | CA | LEU | A | 309 | 5.574 | -7.343 | 48.358 | 1.00 47.08 | A C |
| ATOM | 719 | C | LEU | A | 309 | 5.744 | -6.330 | 49.477 | 1.00 46.70 | A C |
| ATOM | 720 | O | LEU | A | 309 | 4.905 | -6.264 | 50.385 | 1.00 47.98 | A O |
| ATOM | 721 | CB | LEU | A | 309 | 4.397 | -7.154 | 47.459 | 1.00 45.50 | A C |
| ATOM | 722 | CG | LEU | A | 309 | 4.299 | -7.981 | 46.173 | 1.00 43.57 | A C |
| ATOM | 723 | CD1 | LEU | A | 309 | 2.997 | -7.691 | 45.445 | 1.00 41.69 | A C |
| ATOM | 724 | CD2 | LEU | A | 309 | 5.484 | -7.659 | 45.269 | 1.00 43.78 | A C |
| ATOM | 725 | N | ILE | A | 310 | 6.866 | -5.615 | 49.477 | 1.00 41.81 | A N |
| ATOM | 726 | CA | ILE | A | 310 | 7.083 | -4.626 | 50.520 | 1.00 40.87 | A C |
| ATOM | 727 | C | ILE | A | 310 | 6.491 | -3.267 | 50.148 | 1.00 38.35 | A C |
| ATOM | 728 | O | ILE | A | 310 | 7.171 | -2.311 | 49.788 | 1.00 36.96 | A O |
| ATOM | 729 | CB | ILE | A | 310 | 8.589 | -4.487 | 50.862 | 1.00 40.92 | A C |
| ATOM | 730 | CG1 | ILE | A | 310 | 9.230 | -5.865 | 50.993 | 1.00 44.70 | A C |
| ATOM | 731 | CG2 | ILE | A | 310 | 8.871 | -3.685 | 52.103 | 1.00 40.33 | A C |
| ATOM | 732 | CD1 | ILE | A | 310 | 8.989 | -6.719 | 52.205 | 1.00 43.29 | A C |
| ATOM | 733 | N | PHE | A | 311 | 5.168 | -3.110 | 50.207 | 1.00 37.28 | A N |
| ATOM | 734 | CA | PHE | A | 311 | 4.487 | -1.842 | 49.939 | 1.00 32.81 | A C |
| ATOM | 735 | C | PHE | A | 311 | 5.000 | -0.748 | 50.833 | 1.00 34.66 | A C |
| ATOM | 736 | O | PHE | A | 311 | 5.110 | 0.344 | 50.293 | 1.00 38.10 | A O |
| ATOM | 737 | CB | PHE | A | 311 | 2.966 | -2.034 | 50.083 | 1.00 33.58 | A C |
| ATOM | 738 | CG | PHE | A | 311 | 2.400 | -2.691 | 48.829 | 1.00 32.15 | A C |
| ATOM | 739 | CD1 | PHE | A | 311 | 2.190 | -1.948 | 47.678 | 1.00 30.57 | A C |
| ATOM | 740 | CD2 | PHE | A | 311 | 2.141 | -4.036 | 48.825 | 1.00 32.47 | A C |
| ATOM | 741 | CE1 | PHE | A | 311 | 1.715 | -2.574 | 46.546 | 1.00 32.08 | A C |
| ATOM | 742 | CE2 | PHE | A | 311 | 1.625 | -4.670 | 47.715 | 1.00 35.26 | A C |
| ATOM | 743 | CZ | PHE | A | 311 | 1.396 | -3.919 | 46.541 | 1.00 33.88 | A C |
| ATOM | 744 | N | ALA | A | 312 | 5.361 | -0.912 | 52.104 | 1.00 35.30 | A N |
| ATOM | 745 | CA | ALA | A | 312 | 5.872 | 0.118 | 52.965 | 1.00 36.27 | A C |
| ATOM | 746 | C | ALA | A | 312 | 6.517 | -0.618 | 54.135 | 1.00 35.88 | A C |
| ATOM | 747 | O | ALA | A | 312 | 6.260 | -1.808 | 54.305 | 1.00 33.18 | A O |
| ATOM | 748 | CB | ALA | A | 312 | 4.837 | 1.209 | 53.357 | 1.00 33.47 | A C |
| ATOM | 749 | N | PRO | A | 313 | 7.429 | -0.008 | 54.843 | 1.00 37.68 | A N |
| ATOM | 750 | CA | PRO | A | 313 | 8.149 | -0.623 | 55.953 | 1.00 41.31 | A C |
| ATOM | 751 | C | PRO | A | 313 | 7.232 | -1.468 | 56.836 | 1.00 39.88 | A C |
| ATOM | 752 | O | PRO | A | 313 | 7.647 | -2.567 | 57.190 | 1.00 39.31 | A O |
| ATOM | 753 | CB | PRO | A | 313 | 8.797 | 0.531 | 56.762 | 1.00 40.49 | A C |
| ATOM | 754 | CG | PRO | A | 313 | 9.129 | 1.403 | 55.537 | 1.00 39.81 | A C |
| ATOM | 755 | CD | PRO | A | 313 | 7.862 | 1.379 | 54.704 | 1.00 38.84 | A C |
| ATOM | 756 | N | ASP | A | 314 | 6.075 | -0.966 | 57.177 | 1.00 40.10 | A N |
| ATOM | 757 | CA | ASP | A | 314 | 5.175 | -1.769 | 58.031 | 1.00 42.87 | A C |
| ATOM | 758 | C | ASP | A | 314 | 3.911 | -2.203 | 57.295 | 1.00 43.62 | A C |
| ATOM | 759 | O | ASP | A | 314 | 2.836 | -2.388 | 57.929 | 1.00 41.94 | A O |
| ATOM | 760 | CB | ASP | A | 314 | 4.804 | -0.964 | 59.281 | 1.00 43.07 | A C |
| ATOM | 761 | CG | ASP | A | 314 | 5.931 | -0.785 | 60.259 | 1.00 44.66 | A C |
| ATOM | 762 | OD1 | ASP | A | 314 | 6.905 | -1.579 | 60.269 | 1.00 44.33 | A O |
| ATOM | 763 | OD2 | ASP | A | 314 | 5.836 | 0.198 | 61.050 | 1.00 46.70 | A O |
| ATOM | 764 | N | LEU | A | 315 | 4.039 | -2.345 | 55.971 | 1.00 41.74 | A N |
| ATOM | 765 | CA | LEU | A | 315 | 2.934 | -2.775 | 55.121 | 1.00 44.64 | A C |
| ATOM | 766 | C | LEU | A | 315 | 3.496 | -3.779 | 54.113 | 1.00 45.12 | A C |
| ATOM | 767 | O | LEU | A | 315 | 3.660 | -3.527 | 52.925 | 1.00 43.82 | A O |
| ATOM | 768 | CB | LEU | A | 315 | 2.291 | -1.586 | 54.411 | 1.00 45.37 | A C |
| ATOM | 769 | CG | LEU | A | 315 | 1.031 | -1.851 | 53.594 | 1.00 48.20 | A C |
| ATOM | 770 | CD1 | LEU | A | 315 | -0.035 | -2.579 | 54.410 | 1.00 47.99 | A C |
| ATOM | 771 | CD2 | LEU | A | 315 | 0.409 | -0.534 | 53.078 | 1.00 49.44 | A C |
| ATOM | 772 | N | VAL | A | 316 | 3.894 | -4.900 | 54.657 | 1.00 46.28 | A N |
| ATOM | 773 | CA | VAL | A | 316 | 4.455 | -6.065 | 54.023 | 1.00 48.06 | A C |

| | | | | | | | | | | |
|---|---|---|---|---|---|---|---|---|---|---|
| ATOM | 774 | C | VAL | A | 316 | 3.379 | -7.113 | 53.754 | 1.00 49.26 | A C |
| ATOM | 775 | O | VAL | A | 316 | 2.846 | -7.642 | 54.719 | 1.00 50.44 | A O |
| ATOM | 776 | CB | VAL | A | 316 | 5.502 | -6.722 | 54.953 | 1.00 47.68 | A C |
| ATOM | 777 | CG1 | VAL | A | 316 | 5.952 | -8.052 | 54.373 | 1.00 48.14 | A C |
| ATOM | 778 | CG2 | VAL | A | 316 | 6.678 | -5.763 | 55.104 | 1.00 47.60 | A C |
| ATOM | 779 | N | LEU | A | 317 | 3.052 | -7.414 | 52.518 | 1.00 48.97 | A N |
| ATOM | 780 | CA | LEU | A | 317 | 2.044 | -8.351 | 52.165 | 1.00 48.79 | A C |
| ATOM | 781 | C | LEU | A | 317 | 2.562 | -9.680 | 51.619 | 1.00 51.99 | A C |
| ATOM | 782 | O | LEU | A | 317 | 3.401 | -9.687 | 50.719 | 1.00 50.71 | A O |
| ATOM | 783 | CB | LEU | A | 317 | 1.164 | -7.755 | 51.053 | 1.00 48.14 | A C |
| ATOM | 784 | CG | LEU | A | 317 | 0.301 | -6.513 | 51.289 | 1.00 47.70 | A C |
| ATOM | 785 | CD1 | LEU | A | 317 | -0.874 | -6.423 | 50.325 | 1.00 45.28 | A C |
| ATOM | 786 | CD2 | LEU | A | 317 | -0.226 | -6.388 | 52.700 | 1.00 46.15 | A C |
| ATOM | 787 | N | ASP | A | 318 | 2.006 | -10.794 | 52.141 | 1.00 53.65 | A N |
| ATOM | 788 | CA | ASP | A | 318 | 2.408 | -12.096 | 51.609 | 1.00 55.93 | A C |
| ATOM | 789 | C | ASP | A | 318 | 1.738 | -12.253 | 50.236 | 1.00 54.49 | A C |
| ATOM | 790 | O | ASP | A | 318 | 0.638 | -11.730 | 50.027 | 1.00 51.03 | A O |
| ATOM | 791 | CB | ASP | A | 318 | 2.015 | -13.301 | 52.443 | 1.00 59.66 | A C |
| ATOM | 792 | CG | ASP | A | 318 | 2.907 | -13.653 | 53.614 | 1.00 62.31 | A C |
| ATOM | 793 | OD1 | ASP | A | 318 | 4.141 | -13.527 | 53.555 | 1.00 62.89 | A O |
| ATOM | 794 | OD2 | ASP | A | 318 | 2.354 | -14.070 | 54.670 | 1.00 63.45 | A O |
| ATOM | 795 | N | ARG | A | 319 | 2.401 | -12.960 | 49.331 | 1.00 54.17 | A N |
| ATOM | 796 | CA | ARG | A | 319 | 1.841 | -13.193 | 48.003 | 1.00 55.69 | A C |
| ATOM | 797 | C | ARG | A | 319 | 0.406 | -13.703 | 48.091 | 1.00 58.10 | A C |
| ATOM | 798 | O | ARG | A | 319 | -0.493 | -13.150 | 47.455 | 1.00 57.56 | A O |
| ATOM | 799 | CB | ARG | A | 319 | 2.720 | -14.195 | 47.259 | 1.00 56.23 | A C |
| ATOM | 800 | CG | ARG | A | 319 | 2.223 | -14.564 | 45.887 | 1.00 58.04 | A C |
| ATOM | 801 | CD | ARG | A | 319 | 1.312 | -15.779 | 45.893 | 1.00 59.54 | A C |
| ATOM | 802 | NE | ARG | A | 319 | 1.055 | -16.152 | 44.501 | 1.00 63.73 | A N |
| ATOM | 803 | CZ | ARG | A | 319 | 0.017 | -16.896 | 44.109 | 1.00 65.28 | A C |
| ATOM | 804 | NH1 | ARG | A | 319 | -0.869 | -17.335 | 45.001 | 1.00 65.33 | A N |
| ATOM | 805 | NH2 | ARG | A | 319 | -0.111 | -17.172 | 42.814 | 1.00 65.79 | A N |
| ATOM | 806 | N | ASP | A | 320 | 0.205 | -14.760 | 48.876 | 1.00 59.47 | A N |
| ATOM | 807 | CA | ASP | A | 320 | -1.101 | -15.379 | 49.053 | 1.00 62.44 | A C |
| ATOM | 808 | C | ASP | A | 320 | -2.158 | -14.389 | 49.516 | 1.00 62.19 | A C |
| ATOM | 809 | O | ASP | A | 320 | -3.358 | -14.626 | 49.320 | 1.00 62.20 | A O |
| ATOM | 810 | CB | ASP | A | 320 | -1.032 | -16.620 | 49.968 | 1.00 63.64 | A C |
| ATOM | 811 | CG | ASP | A | 320 | -0.288 | -17.793 | 49.332 | 1.00 65.03 | A C |
| ATOM | 812 | OD1 | ASP | A | 320 | -0.408 | -17.992 | 48.106 | 1.00 64.51 | A O |
| ATOM | 813 | OD2 | ASP | A | 320 | 0.453 | -18.539 | 50.009 | 1.00 66.49 | A O |
| ATOM | 814 | N | GLU | A | 321 | -1.789 | -13.262 | 50.120 | 1.00 61.91 | A N |
| ATOM | 815 | CA | GLU | A | 321 | -2.835 | -12.326 | 50.565 | 1.00 62.51 | A C |
| ATOM | 816 | C | GLU | A | 321 | -3.549 | -11.691 | 49.379 | 1.00 62.23 | A C |
| ATOM | 817 | O | GLU | A | 321 | -4.594 | -11.063 | 49.487 | 1.00 60.56 | A O |
| ATOM | 818 | CB | GLU | A | 321 | -2.289 | -11.313 | 51.552 | 1.00 61.43 | A C |
| ATOM | 819 | CG | GLU | A | 321 | -1.827 | -11.945 | 52.846 | 1.00 60.32 | A C |
| ATOM | 820 | CD | GLU | A | 321 | -1.285 | -10.911 | 53.815 | 1.00 60.60 | A C |
| ATOM | 821 | OE1 | GLU | A | 321 | -0.141 | -10.453 | 53.650 | 1.00 59.71 | A O |
| ATOM | 822 | OE2 | GLU | A | 321 | -2.106 | -10.621 | 54.714 | 1.00 60.02 | A O |
| ATOM | 823 | N | GLY | A | 322 | -2.992 | -11.891 | 48.190 | 1.00 63.95 | A N |
| ATOM | 824 | CA | GLY | A | 322 | -3.572 | -11.368 | 46.967 | 1.00 66.46 | A C |
| ATOM | 825 | C | GLY | A | 322 | -4.986 | -11.886 | 46.734 | 1.00 68.46 | A C |
| ATOM | 826 | O | GLY | A | 322 | -5.825 | -11.212 | 46.123 | 1.00 68.14 | A O |
| ATOM | 827 | N | LYS | A | 323 | -5.288 | -13.088 | 47.219 | 1.00 69.56 | A N |
| ATOM | 828 | CA | LYS | A | 323 | -6.640 | -13.599 | 46.991 | 1.00 71.63 | A C |
| ATOM | 829 | C | LYS | A | 323 | -7.664 | -12.789 | 47.774 | 1.00 70.97 | A C |
| ATOM | 830 | O | LYS | A | 323 | -8.858 | -13.025 | 47.580 | 1.00 70.04 | A O |
| ATOM | 831 | CB | LYS | A | 323 | -6.798 | -15.075 | 47.308 | 1.00 73.09 | A C |
| ATOM | 832 | CG | LYS | A | 323 | -6.112 | -15.530 | 48.574 | 1.00 74.28 | A C |
| ATOM | 833 | CD | LYS | A | 323 | -5.676 | -16.988 | 48.478 | 1.00 76.15 | A C |
| ATOM | 834 | CE | LYS | A | 323 | -4.897 | -17.363 | 47.231 | 1.00 75.25 | A C |

116

| ATOM | 835 | NZ | LYS A 323 | -4.268 | -18.707 | 47.321 | 1.00 | 74.43 | A | N |
| ATOM | 836 | N | CYS A 324 | -7.187 | -11.862 | 48.598 | 1.00 | 70.12 | A | N |
| ATOM | 837 | CA | CYS A 324 | -8.128 | -11.057 | 49.370 | 1.00 | 69.23 | A | C |
| ATOM | 838 | C | CYS A 324 | -8.844 | -10.059 | 48.467 | 1.00 | 68.18 | A | C |
| ATOM | 839 | O | CYS A 324 | -9.835 | -9.477 | 48.903 | 1.00 | 68.77 | A | O |
| ATOM | 840 | CB | CYS A 324 | -7.420 | -10.366 | 50.528 | 1.00 | 70.28 | A | C |
| ATOM | 841 | SG | CYS A 324 | -6.625 | -11.382 | 51.796 | 1.00 | 69.61 | A | S |
| ATOM | 842 | N | VAL A 325 | -8.397 | -9.822 | 47.244 | 1.00 | 65.73 | A | N |
| ATOM | 843 | CA | VAL A 325 | -9.015 | -8.870 | 46.332 | 1.00 | 63.42 | A | C |
| ATOM | 844 | C | VAL A 325 | -9.186 | -9.490 | 44.957 | 1.00 | 62.65 | A | C |
| ATOM | 845 | O | VAL A 325 | -8.253 | -10.130 | 44.463 | 1.00 | 62.56 | A | O |
| ATOM | 846 | CB | VAL A 325 | -8.153 | -7.602 | 46.150 | 1.00 | 63.26 | A | C |
| ATOM | 847 | CG1 | VAL A 325 | -8.711 | -6.693 | 45.071 | 1.00 | 60.94 | A | C |
| ATOM | 848 | CG2 | VAL A 325 | -7.989 | -6.850 | 47.463 | 1.00 | 62.68 | A | C |
| ATOM | 849 | N | GLU A 326 | -10.331 | -9.302 | 44.319 | 1.00 | 61.17 | A | N |
| ATOM | 850 | CA | GLU A 326 | -10.532 | -9.914 | 43.008 | 1.00 | 59.92 | A | C |
| ATOM | 851 | C | GLU A 326 | -9.621 | -9.351 | 41.927 | 1.00 | 58.21 | A | C |
| ATOM | 852 | O | GLU A 326 | -9.625 | -8.167 | 41.632 | 1.00 | 54.99 | A | O |
| ATOM | 853 | CB | GLU A 326 | -11.998 | -9.813 | 42.534 | 1.00 | 59.51 | A | C |
| ATOM | 854 | N | GLY A 327 | -8.862 | -10.243 | 41.303 | 1.00 | 57.77 | A | N |
| ATOM | 855 | CA | GLY A 327 | -7.944 | -9.924 | 40.240 | 1.00 | 58.10 | A | C |
| ATOM | 856 | C | GLY A 327 | -6.610 | -9.309 | 40.647 | 1.00 | 58.15 | A | C |
| ATOM | 857 | O | GLY A 327 | -5.825 | -8.908 | 39.761 | 1.00 | 58.00 | A | O |
| ATOM | 858 | N | ILE A 328 | -6.332 | -9.203 | 41.941 | 1.00 | 56.29 | A | N |
| ATOM | 859 | CA | ILE A 328 | -5.051 | -8.589 | 42.342 | 1.00 | 56.20 | A | C |
| ATOM | 860 | C | ILE A 328 | -3.950 | -9.633 | 42.359 | 1.00 | 56.41 | A | C |
| ATOM | 861 | O | ILE A 328 | -2.772 | -9.365 | 42.117 | 1.00 | 53.07 | A | O |
| ATOM | 862 | CB | ILE A 328 | -5.209 | -7.806 | 43.638 | 1.00 | 55.57 | A | C |
| ATOM | 863 | CG1 | ILE A 328 | -4.236 | -6.625 | 43.731 | 1.00 | 54.75 | A | C |
| ATOM | 864 | CG2 | ILE A 328 | -5.070 | -8.681 | 44.882 | 1.00 | 53.12 | A | C |
| ATOM | 865 | CD1 | ILE A 328 | -4.666 | -5.620 | 44.786 | 1.00 | 52.04 | A | C |
| ATOM | 866 | N | LEU A 329 | -4.346 | -10.871 | 42.595 | 1.00 | 59.22 | A | N |
| ATOM | 867 | CA | LEU A 329 | -3.410 | -12.006 | 42.623 | 1.00 | 62.03 | A | C |
| ATOM | 868 | C | LEU A 329 | -2.495 | -12.023 | 41.406 | 1.00 | 60.40 | A | C |
| ATOM | 869 | O | LEU A 329 | -1.264 | -12.070 | 41.571 | 1.00 | 59.40 | A | O |
| ATOM | 870 | CB | LEU A 329 | -4.190 | -13.294 | 42.823 | 1.00 | 64.46 | A | C |
| ATOM | 871 | CG | LEU A 329 | -3.547 | -14.642 | 43.046 | 1.00 | 67.18 | A | C |
| ATOM | 872 | CD1 | LEU A 329 | -4.147 | -15.272 | 44.299 | 1.00 | 68.39 | A | C |
| ATOM | 873 | CD2 | LEU A 329 | -3.800 | -15.639 | 41.895 | 1.00 | 68.75 | A | C |
| ATOM | 874 | N | GLU A 330 | -3.052 | -11.942 | 40.200 | 1.00 | 59.84 | A | N |
| ATOM | 875 | CA | GLU A 330 | -2.194 | -11.986 | 39.016 | 1.00 | 59.81 | A | C |
| ATOM | 876 | C | GLU A 330 | -1.247 | -10.787 | 38.915 | 1.00 | 56.71 | A | C |
| ATOM | 877 | O | GLU A 330 | -0.102 | -10.960 | 38.468 | 1.00 | 56.53 | A | O |
| ATOM | 878 | CB | GLU A 330 | -3.013 | -12.220 | 37.769 | 1.00 | 63.25 | A | C |
| ATOM | 879 | CG | GLU A 330 | -3.681 | -11.080 | 37.043 | 1.00 | 68.16 | A | C |
| ATOM | 880 | CD | GLU A 330 | -3.946 | -11.441 | 35.585 | 1.00 | 73.23 | A | C |
| ATOM | 881 | OE1 | GLU A 330 | -3.399 | -12.484 | 35.118 | 1.00 | 74.76 | A | O |
| ATOM | 882 | OE2 | GLU A 330 | -4.681 | -10.725 | 34.853 | 1.00 | 74.51 | A | O |
| ATOM | 883 | N | ILE A 331 | -1.700 | -9.591 | 39.307 | 1.00 | 51.33 | A | N |
| ATOM | 884 | CA | ILE A 331 | -0.916 | -8.387 | 39.302 | 1.00 | 47.88 | A | C |
| ATOM | 885 | C | ILE A 331 | 0.196 | -8.585 | 40.349 | 1.00 | 46.53 | A | C |
| ATOM | 886 | O | ILE A 331 | 1.352 | -8.314 | 40.059 | 1.00 | 45.63 | A | O |
| ATOM | 887 | CB | ILE A 331 | -1.705 | -7.107 | 39.662 | 1.00 | 46.86 | A | C |
| ATOM | 888 | CG1 | ILE A 331 | -2.949 | -6.932 | 38.811 | 1.00 | 46.20 | A | C |
| ATOM | 889 | CG2 | ILE A 331 | -0.798 | -5.887 | 39.645 | 1.00 | 42.47 | A | C |
| ATOM | 890 | CD1 | ILE A 331 | -2.794 | -6.782 | 37.322 | 1.00 | 45.54 | A | C |
| ATOM | 891 | N | PHE A 332 | -0.133 | -9.096 | 41.543 | 1.00 | 45.92 | A | N |
| ATOM | 892 | CA | PHE A 332 | 0.912 | -9.332 | 42.535 | 1.00 | 47.78 | A | C |
| ATOM | 893 | C | PHE A 332 | 1.988 | -10.239 | 41.923 | 1.00 | 48.86 | A | C |
| ATOM | 894 | O | PHE A 332 | 3.189 | -9.952 | 41.959 | 1.00 | 46.82 | A | O |
| ATOM | 895 | CB | PHE A 332 | 0.314 | -9.937 | 43.791 | 1.00 | 47.95 | A | C |

```
ATOM    896  CG   PHE A 332      -0.296   -8.976   44.778  1.00 47.95      A    C
ATOM    897  CD1  PHE A 332      -0.493   -7.648   44.501  1.00 45.39      A    C
ATOM    898  CD2  PHE A 332      -0.678   -9.434   46.035  1.00 48.60      A    C
ATOM    899  CE1  PHE A 332      -1.040   -6.806   45.416  1.00 46.17      A    C
ATOM    900  CE2  PHE A 332      -1.242   -8.587   46.964  1.00 49.11      A    C
ATOM    901  CZ   PHE A 332      -1.423   -7.247   46.674  1.00 47.33      A    C
ATOM    902  N    ASP A 333       1.520  -11.330   41.284  1.00 50.08      A    N
ATOM    903  CA   ASP A 333       2.414  -12.295   40.652  1.00 49.39      A    C
ATOM    904  C    ASP A 333       3.284  -11.661   39.575  1.00 46.61      A    C
ATOM    905  O    ASP A 333       4.413  -12.094   39.490  1.00 43.34      A    O
ATOM    906  CB   ASP A 333       1.736  -13.531   40.037  1.00 51.48      A    C
ATOM    907  CG   ASP A 333       1.286  -14.576   41.039  1.00 55.61      A    C
ATOM    908  OD1  ASP A 333       1.858  -14.708   42.155  1.00 55.76      A    O
ATOM    909  OD2  ASP A 333       0.278  -15.284   40.707  1.00 57.93      A    O
ATOM    910  N    MET A 334       2.748  -10.770   38.759  1.00 47.53      A    N
ATOM    911  CA   MET A 334       3.576  -10.122   37.735  1.00 47.26      A    C
ATOM    912  C    MET A 334       4.615   -9.239   38.471  1.00 46.01      A    C
ATOM    913  O    MET A 334       5.782   -9.248   38.062  1.00 43.94      A    O
ATOM    914  CB   MET A 334       2.751   -9.303   36.773  1.00 48.48      A    C
ATOM    915  CG   MET A 334       1.876  -10.161   35.837  1.00 52.66      A    C
ATOM    916  SD   MET A 334       0.803   -9.098   34.845  1.00 54.89      A    S
ATOM    917  CE   MET A 334       2.011   -8.395   33.741  1.00 56.18      A    C
ATOM    918  N    LEU A 335       4.200   -8.542   39.537  1.00 42.98      A    N
ATOM    919  CA   LEU A 335       5.195   -7.741   40.263  1.00 43.93      A    C
ATOM    920  C    LEU A 335       6.276   -8.646   40.861  1.00 42.60      A    C
ATOM    921  O    LEU A 335       7.472   -8.294   40.757  1.00 43.69      A    O
ATOM    922  CB   LEU A 335       4.594   -6.903   41.407  1.00 41.90      A    C
ATOM    923  CG   LEU A 335       3.508   -5.950   40.907  1.00 43.06      A    C
ATOM    924  CD1  LEU A 335       2.635   -5.469   42.075  1.00 43.60      A    C
ATOM    925  CD2  LEU A 335       4.171   -4.765   40.208  1.00 42.39      A    C
ATOM    926  N    LEU A 336       5.889   -9.764   41.461  1.00 42.49      A    N
ATOM    927  CA   LEU A 336       6.893  -10.643   42.052  1.00 44.45      A    C
ATOM    928  C    LEU A 336       7.851  -11.222   41.011  1.00 45.83      A    C
ATOM    929  O    LEU A 336       9.066  -11.317   41.265  1.00 46.60      A    O
ATOM    930  CB   LEU A 336       6.241  -11.742   42.889  1.00 44.32      A    C
ATOM    931  CG   LEU A 336       5.622  -11.283   44.222  1.00 43.66      A    C
ATOM    932  CD1  LEU A 336       4.569  -12.296   44.716  1.00 41.79      A    C
ATOM    933  CD2  LEU A 336       6.694  -11.113   45.274  1.00 42.22      A    C
ATOM    934  N    ALA A 337       7.367  -11.581   39.825  1.00 46.10      A    N
ATOM    935  CA   ALA A 337       8.218  -12.139   38.779  1.00 45.89      A    C
ATOM    936  C    ALA A 337       9.260  -11.111   38.324  1.00 44.78      A    C
ATOM    937  O    ALA A 337      10.440  -11.474   38.272  1.00 44.40      A    O
ATOM    938  CB   ALA A 337       7.408  -12.611   37.572  1.00 44.57      A    C
ATOM    939  N    THR A 338       8.794   -9.899   37.997  1.00 44.13      A    N
ATOM    940  CA   THR A 338       9.731   -8.873   37.541  1.00 43.52      A    C
ATOM    941  C    THR A 338      10.734   -8.571   38.648  1.00 42.89      A    C
ATOM    942  O    THR A 338      11.914   -8.389   38.332  1.00 43.24      A    O
ATOM    943  CB   THR A 338       9.037   -7.626   37.009  1.00 41.91      A    C
ATOM    944  OG1  THR A 338       8.323   -8.080   35.848  1.00 44.69      A    O
ATOM    945  CG2  THR A 338      10.046   -6.581   36.562  1.00 41.71      A    C
ATOM    946  N    THR A 339      10.275   -8.565   39.894  1.00 42.10      A    N
ATOM    947  CA   THR A 339      11.166   -8.338   41.015  1.00 43.58      A    C
ATOM    948  C    THR A 339      12.203   -9.456   40.998  1.00 43.02      A    C
ATOM    949  O    THR A 339      13.387   -9.158   41.052  1.00 43.08      A    O
ATOM    950  CB   THR A 339      10.474   -8.238   42.379  1.00 45.04      A    C
ATOM    951  OG1  THR A 339       9.515   -7.164   42.396  1.00 45.72      A    O
ATOM    952  CG2  THR A 339      11.513   -7.993   43.469  1.00 46.09      A    C
ATOM    953  N    SER A 340      11.849  -10.707   40.886  1.00 43.69      A    N
ATOM    954  CA   SER A 340      12.809  -11.784   40.823  1.00 47.18      A    C
ATOM    955  C    SER A 340      13.799  -11.562   39.681  1.00 46.41      A    C
ATOM    956  O    SER A 340      14.941  -11.933   39.933  1.00 46.37      A    O
```

| | | | | | | | | | | |
|---|---|---|---|---|---|---|---|---|---|---|
| ATOM | 957 | CB | SER | A | 340 | 12.223 | -13.193 | 40.582 | 1.00 49.11 | A | C |
| ATOM | 958 | OG | SER | A | 340 | 11.073 | -13.369 | 41.397 | 1.00 51.58 | A | O |
| ATOM | 959 | N | ARG | A | 341 | 13.393 | -11.040 | 38.539 | 1.00 46.77 | A | N |
| ATOM | 960 | CA | ARG | A | 341 | 14.364 | -10.831 | 37.455 | 1.00 49.81 | A | C |
| ATOM | 961 | C | ARG | A | 341 | 15.417 | -9.787 | 37.884 | 1.00 49.55 | A | C |
| ATOM | 962 | O | ARG | A | 341 | 16.624 | -9.937 | 37.652 | 1.00 47.71 | A | O |
| ATOM | 963 | CB | ARG | A | 341 | 13.669 | -10.396 | 36.201 | 1.00 52.68 | A | C |
| ATOM | 964 | CG | ARG | A | 341 | 13.188 | -11.259 | 35.104 | 1.00 61.97 | A | C |
| ATOM | 965 | CD | ARG | A | 341 | 13.346 | -12.766 | 35.291 | 1.00 69.42 | A | C |
| ATOM | 966 | NE | ARG | A | 341 | 12.186 | -13.225 | 36.036 | 1.00 74.59 | A | N |
| ATOM | 967 | CZ | ARG | A | 341 | 11.717 | -14.450 | 36.202 | 1.00 76.76 | A | C |
| ATOM | 968 | NH1 | ARG | A | 341 | 12.337 | -15.487 | 35.645 | 1.00 79.02 | A | N |
| ATOM | 969 | NH2 | ARG | A | 341 | 10.612 | -14.630 | 36.926 | 1.00 77.51 | A | N |
| ATOM | 970 | N | PHE | A | 342 | 14.936 | -8.732 | 38.558 | 1.00 48.39 | A | N |
| ATOM | 971 | CA | PHE | A | 342 | 15.853 | -7.697 | 39.039 | 1.00 48.05 | A | C |
| ATOM | 972 | C | PHE | A | 342 | 16.776 | -8.341 | 40.072 | 1.00 48.62 | A | C |
| ATOM | 973 | O | PHE | A | 342 | 17.948 | -7.931 | 40.104 | 1.00 49.02 | A | O |
| ATOM | 974 | CB | PHE | A | 342 | 15.119 | -6.494 | 39.631 | 1.00 46.01 | A | C |
| ATOM | 975 | CG | PHE | A | 342 | 14.695 | -5.456 | 38.604 | 1.00 43.63 | A | C |
| ATOM | 976 | CD1 | PHE | A | 342 | 15.635 | -4.787 | 37.832 | 1.00 41.66 | A | C |
| ATOM | 977 | CD2 | PHE | A | 342 | 13.379 | -5.120 | 38.451 | 1.00 42.24 | A | C |
| ATOM | 978 | CE1 | PHE | A | 342 | 15.270 | -3.854 | 36.908 | 1.00 40.71 | A | C |
| ATOM | 979 | CE2 | PHE | A | 342 | 12.976 | -4.167 | 37.537 | 1.00 41.62 | A | C |
| ATOM | 980 | CZ | PHE | A | 342 | 13.916 | -3.532 | 36.754 | 1.00 41.89 | A | C |
| ATOM | 981 | N | ARG | A | 343 | 16.285 | -9.283 | 40.851 | 1.00 47.59 | A | N |
| ATOM | 982 | CA | ARG | A | 343 | 17.159 | -9.903 | 41.848 | 1.00 51.93 | A | C |
| ATOM | 983 | CB | ARG | A | 343 | 16.346 | -10.736 | 42.834 | 1.00 53.15 | A | C |
| ATOM | 984 | CG | AARG | A | 343 | 17.196 | -11.554 | 43.802 | 0.50 54.28 | A | C |
| ATOM | 985 | CG | BARG | A | 343 | 17.113 | -11.308 | 44.010 | 0.50 54.07 | A | C |
| ATOM | 986 | CD | AARG | A | 343 | 16.383 | -12.754 | 44.313 | 0.50 56.33 | A | C |
| ATOM | 987 | CD | BARG | A | 343 | 16.466 | -12.595 | 44.527 | 0.50 56.33 | A | C |
| ATOM | 988 | NE | AARG | A | 343 | 15.129 | -12.288 | 44.835 | 0.50 58.00 | A | N |
| ATOM | 989 | NE | BARG | A | 343 | 16.508 | -12.612 | 45.982 | 0.50 58.39 | A | N |
| ATOM | 990 | CZ | AARG | A | 343 | 13.846 | -12.382 | 44.635 | 0.50 59.28 | A | C |
| ATOM | 991 | CZ | BARG | A | 343 | 16.674 | -13.595 | 46.834 | 0.50 58.93 | A | C |
| ATOM | 992 | NH1 | AARG | A | 343 | 13.334 | -13.166 | 43.694 | 0.50 59.80 | A | N |
| ATOM | 993 | NH1 | BARG | A | 343 | 16.856 | -14.833 | 46.401 | 0.50 60.20 | A | N |
| ATOM | 994 | NH2 | AARG | A | 343 | 13.014 | -11.690 | 45.416 | 0.50 58.96 | A | N |
| ATOM | 995 | NH2 | BARG | A | 343 | 16.680 | -13.375 | 48.145 | 0.50 59.88 | A | N |
| ATOM | 996 | C | ARG | A | 343 | 18.244 | -10.757 | 41.169 | 1.00 52.19 | A | C |
| ATOM | 997 | O | ARG | A | 343 | 19.435 | -10.697 | 41.439 | 1.00 48.94 | A | O |
| ATOM | 998 | N | GLU | A | 344 | 17.842 | -11.551 | 40.198 | 1.00 54.30 | A | N |
| ATOM | 999 | CA | GLU | A | 344 | 18.775 | -12.378 | 39.450 | 1.00 57.15 | A | C |
| ATOM | 1000 | C | GLU | A | 344 | 19.848 | -11.511 | 38.793 | 1.00 55.47 | A | C |
| ATOM | 1001 | O | GLU | A | 344 | 20.976 | -11.969 | 38.656 | 1.00 54.75 | A | O |
| ATOM | 1002 | CB | GLU | A | 344 | 18.093 | -13.174 | 38.339 | 1.00 59.94 | A | C |
| ATOM | 1003 | CG | GLU | A | 344 | 17.012 | -14.102 | 38.851 | 1.00 65.48 | A | C |
| ATOM | 1004 | CD | GLU | A | 344 | 16.138 | -14.643 | 37.721 | 1.00 68.83 | A | C |
| ATOM | 1005 | OE1 | GLU | A | 344 | 16.344 | -14.343 | 36.519 | 1.00 69.29 | A | O |
| ATOM | 1006 | OE2 | GLU | A | 344 | 15.229 | -15.390 | 38.166 | 1.00 70.67 | A | O |
| ATOM | 1007 | N | LEU | A | 345 | 19.459 | -10.313 | 38.391 | 1.00 53.01 | A | N |
| ATOM | 1008 | CA | LEU | A | 345 | 20.395 | -9.424 | 37.701 | 1.00 51.89 | A | C |
| ATOM | 1009 | C | LEU | A | 345 | 21.329 | -8.717 | 38.662 | 1.00 48.40 | A | C |
| ATOM | 1010 | O | LEU | A | 345 | 22.254 | -8.008 | 38.314 | 1.00 46.92 | A | O |
| ATOM | 1011 | CB | LEU | A | 345 | 19.510 | -8.393 | 36.990 | 1.00 54.46 | A | C |
| ATOM | 1012 | CG | LEU | A | 345 | 20.113 | -7.641 | 35.828 | 1.00 57.62 | A | C |
| ATOM | 1013 | CD1 | LEU | A | 345 | 20.653 | -8.660 | 34.811 | 1.00 57.72 | A | C |
| ATOM | 1014 | CD2 | LEU | A | 345 | 19.057 | -6.737 | 35.206 | 1.00 58.43 | A | C |
| ATOM | 1015 | N | LYS | A | 346 | 21.048 | -8.914 | 39.942 | 1.00 47.86 | A | N |
| ATOM | 1016 | CA | LYS | A | 346 | 21.744 | -8.342 | 41.066 | 1.00 45.63 | A | C |
| ATOM | 1017 | C | LYS | A | 346 | 21.732 | -6.832 | 40.935 | 1.00 42.38 | A | C |

| | | | | | | | | | | |
|---|---|---|---|---|---|---|---|---|---|---|
| ATOM | 1018 | O | LYS | A | 346 | 22.733 | -6.159 | 41.035 | 1.00 42.26 | A | O |
| ATOM | 1019 | CB | LYS | A | 346 | 23.179 | -8.850 | 41.247 | 1.00 50.10 | A | C |
| ATOM | 1020 | CG | LYS | A | 346 | 23.255 | -10.201 | 41.956 | 1.00 52.84 | A | C |
| ATOM | 1021 | CD | LYS | A | 346 | 24.662 | -10.778 | 41.925 | 1.00 54.64 | A | C |
| ATOM | 1022 | CE | LYS | A | 346 | 24.586 | -12.304 | 41.978 | 1.00 57.83 | A | C |
| ATOM | 1023 | NZ | LYS | A | 346 | 25.916 | -12.837 | 41.548 | 1.00 61.21 | A | N |
| ATOM | 1024 | N | LEU | A | 347 | 20.537 | -6.289 | 40.702 | 1.00 41.30 | A | N |
| ATOM | 1025 | CA | LEU | A | 347 | 20.387 | -4.850 | 40.592 | 1.00 37.22 | A | C |
| ATOM | 1026 | C | LEU | A | 347 | 20.898 | -4.182 | 41.862 | 1.00 35.57 | A | C |
| ATOM | 1027 | O | LEU | A | 347 | 20.523 | -4.568 | 42.983 | 1.00 32.73 | A | O |
| ATOM | 1028 | CB | LEU | A | 347 | 18.899 | -4.519 | 40.487 | 1.00 36.71 | A | C |
| ATOM | 1029 | CG | LEU | A | 347 | 18.560 | -3.003 | 40.327 | 1.00 36.91 | A | C |
| ATOM | 1030 | CD1 | LEU | A | 347 | 18.764 | -2.530 | 38.895 | 1.00 34.87 | A | C |
| ATOM | 1031 | CD2 | LEU | A | 347 | 17.083 | -2.870 | 40.737 | 1.00 35.78 | A | C |
| ATOM | 1032 | N | GLN | A | 348 | 21.702 | -3.166 | 41.648 | 1.00 37.45 | A | N |
| ATOM | 1033 | CA | GLN | A | 348 | 22.271 | -2.313 | 42.653 | 1.00 39.66 | A | C |
| ATOM | 1034 | C | GLN | A | 348 | 21.337 | -1.105 | 42.925 | 1.00 41.49 | A | C |
| ATOM | 1035 | O | GLN | A | 348 | 20.630 | -0.595 | 42.040 | 1.00 39.59 | A | O |
| ATOM | 1036 | CB | GLN | A | 348 | 23.652 | -1.817 | 42.195 | 1.00 40.52 | A | C |
| ATOM | 1037 | CG | GLN | A | 348 | 24.612 | -3.007 | 41.964 | 1.00 43.66 | A | C |
| ATOM | 1038 | CD | GLN | A | 348 | 24.893 | -3.795 | 43.241 | 1.00 46.76 | A | C |
| ATOM | 1039 | OE1 | GLN | A | 348 | 25.650 | -3.331 | 44.127 | 1.00 50.75 | A | O |
| ATOM | 1040 | NE2 | GLN | A | 348 | 24.304 | -4.972 | 43.399 | 1.00 43.13 | A | N |
| ATOM | 1041 | N | HIS | A | 349 | 21.434 | -0.640 | 44.184 | 1.00 40.09 | A | N |
| ATOM | 1042 | CA | HIS | A | 349 | 20.642 | 0.488 | 44.606 | 1.00 39.82 | A | C |
| ATOM | 1043 | C | HIS | A | 349 | 21.061 | 1.690 | 43.780 | 1.00 37.60 | A | C |
| ATOM | 1044 | O | HIS | A | 349 | 20.151 | 2.455 | 43.466 | 1.00 33.22 | A | O |
| ATOM | 1045 | CB | HIS | A | 349 | 20.782 | 0.829 | 46.086 | 1.00 41.53 | A | C |
| ATOM | 1046 | CG | HIS | A | 349 | 20.000 | 1.965 | 46.630 | 1.00 43.53 | A | C |
| ATOM | 1047 | ND1 | HIS | A | 349 | 20.552 | 3.156 | 47.030 | 1.00 44.73 | A | N |
| ATOM | 1048 | CD2 | HIS | A | 349 | 18.669 | 2.096 | 46.887 | 1.00 45.46 | A | C |
| ATOM | 1049 | CE1 | HIS | A | 349 | 19.601 | 3.957 | 47.507 | 1.00 45.22 | A | C |
| ATOM | 1050 | NE2 | HIS | A | 349 | 18.424 | 3.345 | 47.422 | 1.00 45.80 | A | N |
| ATOM | 1051 | N | LYS | A | 350 | 22.335 | 1.819 | 43.447 | 1.00 36.77 | A | N |
| ATOM | 1052 | CA | LYS | A | 350 | 22.672 | 3.034 | 42.667 | 1.00 39.32 | A | C |
| ATOM | 1053 | C | LYS | A | 350 | 22.165 | 2.986 | 41.220 | 1.00 41.17 | A | C |
| ATOM | 1054 | O | LYS | A | 350 | 22.035 | 4.054 | 40.574 | 1.00 39.92 | A | O |
| ATOM | 1055 | CB | LYS | A | 350 | 24.156 | 3.315 | 42.692 | 1.00 41.59 | A | C |
| ATOM | 1056 | CG | LYS | A | 350 | 25.183 | 2.252 | 42.439 | 1.00 47.25 | A | C |
| ATOM | 1057 | CD | LYS | A | 350 | 26.611 | 2.781 | 42.664 | 1.00 50.83 | A | C |
| ATOM | 1058 | CE | LYS | A | 350 | 27.141 | 2.473 | 44.060 | 1.00 51.07 | A | C |
| ATOM | 1059 | NZ | LYS | A | 350 | 27.120 | 1.007 | 44.378 | 1.00 49.33 | A | N |
| ATOM | 1060 | N | GLU | A | 351 | 21.965 | 1.762 | 40.714 | 1.00 39.43 | A | N |
| ATOM | 1061 | CA | GLU | A | 351 | 21.471 | 1.675 | 39.329 | 1.00 40.32 | A | C |
| ATOM | 1062 | C | GLU | A | 351 | 19.954 | 1.890 | 39.428 | 1.00 40.75 | A | C |
| ATOM | 1063 | O | GLU | A | 351 | 19.360 | 2.404 | 38.512 | 1.00 38.48 | A | O |
| ATOM | 1064 | CB | GLU | A | 351 | 21.689 | 0.292 | 38.707 | 1.00 38.85 | A | C |
| ATOM | 1065 | CG | GLU | A | 351 | 23.132 | -0.207 | 38.767 | 1.00 40.46 | A | C |
| ATOM | 1066 | CD | GLU | A | 351 | 23.322 | -1.677 | 38.539 | 1.00 41.05 | A | C |
| ATOM | 1067 | OE1 | GLU | A | 351 | 22.670 | -2.590 | 39.093 | 1.00 40.35 | A | O |
| ATOM | 1068 | OE2 | GLU | A | 351 | 24.198 | -1.994 | 37.716 | 1.00 43.77 | A | O |
| ATOM | 1069 | N | TYR | A | 352 | 19.416 | 1.468 | 40.601 | 1.00 40.66 | A | N |
| ATOM | 1070 | CA | TYR | A | 352 | 17.960 | 1.647 | 40.725 | 1.00 41.10 | A | C |
| ATOM | 1071 | C | TYR | A | 352 | 17.639 | 3.137 | 40.681 | 1.00 40.02 | A | C |
| ATOM | 1072 | O | TYR | A | 352 | 16.650 | 3.541 | 40.073 | 1.00 39.10 | A | O |
| ATOM | 1073 | CB | TYR | A | 352 | 17.449 | 0.996 | 41.993 | 1.00 42.41 | A | C |
| ATOM | 1074 | CG | TYR | A | 352 | 16.299 | 1.710 | 42.666 | 1.00 43.76 | A | C |
| ATOM | 1075 | CD1 | TYR | A | 352 | 15.008 | 1.438 | 42.247 | 1.00 45.76 | A | C |
| ATOM | 1076 | CD2 | TYR | A | 352 | 16.476 | 2.633 | 43.669 | 1.00 43.83 | A | C |
| ATOM | 1077 | CE1 | TYR | A | 352 | 13.929 | 2.067 | 42.837 | 1.00 46.50 | A | C |
| ATOM | 1078 | CE2 | TYR | A | 352 | 15.422 | 3.278 | 44.276 | 1.00 45.10 | A | C |

120

| | | | | | | | | | | | |
|---|---|---|---|---|---|---|---|---|---|---|---|
| ATOM | 1079 | CZ | TYR | A | 352 | 14.153 | 2.974 | 43.848 | 1.00 | 46.97 | A | C |
| ATOM | 1080 | OH | TYR | A | 352 | 13.083 | 3.616 | 44.434 | 1.00 | 48.24 | A | O |
| ATOM | 1081 | N | LEU | A | 353 | 18.465 | 3.945 | 41.329 | 1.00 | 40.12 | A | N |
| ATOM | 1082 | CA | LEU | A | 353 | 18.190 | 5.382 | 41.270 | 1.00 | 43.49 | A | C |
| ATOM | 1083 | C | LEU | A | 353 | 18.208 | 5.934 | 39.831 | 1.00 | 42.77 | A | C |
| ATOM | 1084 | O | LEU | A | 353 | 17.379 | 6.812 | 39.530 | 1.00 | 41.29 | A | O |
| ATOM | 1085 | CB | LEU | A | 353 | 19.219 | 6.179 | 42.079 | 1.00 | 40.83 | A | C |
| ATOM | 1086 | CG | LEU | A | 353 | 19.197 | 5.819 | 43.579 | 1.00 | 43.29 | A | C |
| ATOM | 1087 | CD1 | LEU | A | 353 | 20.586 | 6.185 | 44.097 | 1.00 | 42.26 | A | C |
| ATOM | 1088 | CD2 | LEU | A | 353 | 18.086 | 6.558 | 44.342 | 1.00 | 41.49 | A | C |
| ATOM | 1089 | N | CYS | A | 354 | 19.157 | 5.522 | 39.003 | 1.00 | 39.98 | A | N |
| ATOM | 1090 | CA | CYS | A | 354 | 19.136 | 6.148 | 37.650 | 1.00 | 40.76 | A | C |
| ATOM | 1091 | C | CYS | A | 354 | 17.944 | 5.644 | 36.835 | 1.00 | 39.68 | A | C |
| ATOM | 1092 | O | CYS | A | 354 | 17.312 | 6.365 | 36.082 | 1.00 | 41.17 | A | O |
| ATOM | 1093 | CB | CYS | A | 354 | 20.427 | 5.829 | 36.900 | 1.00 | 38.29 | A | C |
| ATOM | 1094 | SG | CYS | A | 354 | 21.937 | 6.196 | 37.824 | 1.00 | 39.33 | A | S |
| ATOM | 1095 | N | VAL | A | 355 | 17.629 | 4.369 | 36.945 | 1.00 | 38.60 | A | N |
| ATOM | 1096 | CA | VAL | A | 355 | 16.574 | 3.694 | 36.183 | 1.00 | 40.63 | A | C |
| ATOM | 1097 | C | VAL | A | 355 | 15.230 | 4.323 | 36.535 | 1.00 | 41.22 | A | C |
| ATOM | 1098 | O | VAL | A | 355 | 14.339 | 4.571 | 35.731 | 1.00 | 41.16 | A | O |
| ATOM | 1099 | CB | VAL | A | 355 | 16.738 | 2.198 | 36.534 | 1.00 | 40.76 | A | C |
| ATOM | 1100 | CG1 | VAL | A | 355 | 15.519 | 1.379 | 36.565 | 1.00 | 39.10 | A | C |
| ATOM | 1101 | CG2 | VAL | A | 355 | 17.756 | 1.536 | 35.552 | 1.00 | 43.62 | A | C |
| ATOM | 1102 | N | LYS | A | 356 | 15.011 | 4.628 | 37.807 | 1.00 | 40.60 | A | N |
| ATOM | 1103 | CA | LYS | A | 356 | 13.808 | 5.269 | 38.260 | 1.00 | 41.20 | A | C |
| ATOM | 1104 | C | LYS | A | 356 | 13.682 | 6.663 | 37.603 | 1.00 | 38.77 | A | C |
| ATOM | 1105 | O | LYS | A | 356 | 12.586 | 7.011 | 37.162 | 1.00 | 35.42 | A | O |
| ATOM | 1106 | CB | LYS | A | 356 | 13.786 | 5.468 | 39.780 | 1.00 | 41.41 | A | C |
| ATOM | 1107 | CG | LYS | A | 356 | 12.447 | 6.009 | 40.244 | 1.00 | 44.11 | A | C |
| ATOM | 1108 | CD | LYS | A | 356 | 12.162 | 5.811 | 41.725 | 1.00 | 47.68 | A | C |
| ATOM | 1109 | CE | LYS | A | 356 | 13.392 | 5.938 | 42.607 | 1.00 | 50.57 | A | C |
| ATOM | 1110 | NZ | LYS | A | 356 | 13.071 | 6.546 | 43.926 | 1.00 | 51.82 | A | N |
| ATOM | 1111 | N | ALA | A | 357 | 14.752 | 7.440 | 37.620 | 1.00 | 36.54 | A | N |
| ATOM | 1112 | CA | ALA | A | 357 | 14.698 | 8.762 | 37.020 | 1.00 | 38.55 | A | C |
| ATOM | 1113 | C | ALA | A | 357 | 14.520 | 8.654 | 35.494 | 1.00 | 40.03 | A | C |
| ATOM | 1114 | O | ALA | A | 357 | 13.799 | 9.485 | 34.934 | 1.00 | 39.45 | A | O |
| ATOM | 1115 | CB | ALA | A | 357 | 15.909 | 9.554 | 37.461 | 1.00 | 38.77 | A | C |
| ATOM | 1116 | N | MET | A | 358 | 15.020 | 7.648 | 34.803 | 1.00 | 42.47 | A | N |
| ATOM | 1117 | CA | MET | A | 358 | 14.832 | 7.474 | 33.363 | 1.00 | 46.31 | A | C |
| ATOM | 1118 | C | MET | A | 358 | 13.366 | 7.127 | 33.040 | 1.00 | 48.76 | A | C |
| ATOM | 1119 | O | MET | A | 358 | 12.844 | 7.505 | 31.975 | 1.00 | 46.01 | A | O |
| ATOM | 1120 | CB | MET | A | 358 | 15.703 | 6.375 | 32.740 | 1.00 | 45.80 | A | C |
| ATOM | 1121 | CG | MET | A | 358 | 17.151 | 6.560 | 33.034 | 1.00 | 50.30 | A | C |
| ATOM | 1122 | SD | MET | A | 358 | 18.360 | 5.308 | 32.551 | 1.00 | 51.39 | A | S |
| ATOM | 1123 | CE | MET | A | 358 | 18.210 | 5.397 | 30.766 | 1.00 | 52.40 | A | C |
| ATOM | 1124 | N | ILE | A | 359 | 12.716 | 6.402 | 33.975 | 1.00 | 47.44 | A | N |
| ATOM | 1125 | CA | ILE | A | 359 | 11.312 | 6.109 | 33.686 | 1.00 | 49.67 | A | C |
| ATOM | 1126 | C | ILE | A | 359 | 10.543 | 7.434 | 33.635 | 1.00 | 49.65 | A | C |
| ATOM | 1127 | O | ILE | A | 359 | 9.792 | 7.652 | 32.702 | 1.00 | 49.36 | A | O |
| ATOM | 1128 | CB | ILE | A | 359 | 10.644 | 5.186 | 34.726 | 1.00 | 50.16 | A | C |
| ATOM | 1129 | CG1 | ILE | A | 359 | 11.097 | 3.749 | 34.528 | 1.00 | 48.55 | A | C |
| ATOM | 1130 | CG2 | ILE | A | 359 | 9.121 | 5.259 | 34.598 | 1.00 | 51.05 | A | C |
| ATOM | 1131 | CD1 | ILE | A | 359 | 11.071 | 2.959 | 35.824 | 1.00 | 50.24 | A | C |
| ATOM | 1132 | N | LEU | A | 360 | 10.706 | 8.317 | 34.612 | 1.00 | 50.88 | A | N |
| ATOM | 1133 | CA | LEU | A | 360 | 10.013 | 9.595 | 34.636 | 1.00 | 50.30 | A | C |
| ATOM | 1134 | C | LEU | A | 360 | 10.295 | 10.458 | 33.409 | 1.00 | 51.54 | A | C |
| ATOM | 1135 | O | LEU | A | 360 | 9.349 | 11.170 | 33.040 | 1.00 | 53.76 | A | O |
| ATOM | 1136 | CB | LEU | A | 360 | 10.410 | 10.433 | 35.861 | 1.00 | 49.51 | A | C |
| ATOM | 1137 | CG | LEU | A | 360 | 9.701 | 11.756 | 36.096 | 1.00 | 51.04 | A | C |
| ATOM | 1138 | CD1 | LEU | A | 360 | 8.231 | 11.587 | 36.463 | 1.00 | 50.22 | A | C |
| ATOM | 1139 | CD2 | LEU | A | 360 | 10.337 | 12.567 | 37.231 | 1.00 | 51.54 | A | C |

| | | | | | | | | | | |
|---|---|---|---|---|---|---|---|---|---|---|
| ATOM | 1140 | N | LEU | A | 361 | 11.480 | 10.436 | 32.839 | 1.00 49.46 | A N |
| ATOM | 1141 | CA | LEU | A | 361 | 11.882 | 11.263 | 31.759 | 1.00 51.71 | A C |
| ATOM | 1142 | C | LEU | A | 361 | 11.868 | 10.731 | 30.332 | 1.00 54.92 | A C |
| ATOM | 1143 | O | LEU | A | 361 | 11.966 | 11.613 | 29.458 | 1.00 57.24 | A O |
| ATOM | 1144 | CB | LEU | A | 361 | 13.353 | 11.707 | 31.962 | 1.00 48.70 | A C |
| ATOM | 1145 | CG | LEU | A | 361 | 13.763 | 12.369 | 33.259 | 1.00 49.58 | A C |
| ATOM | 1146 | CD1 | LEU | A | 361 | 15.285 | 12.521 | 33.321 | 1.00 48.58 | A C |
| ATOM | 1147 | CD2 | LEU | A | 361 | 13.079 | 13.737 | 33.436 | 1.00 48.54 | A C |
| ATOM | 1148 | N | ASN | A | 362 | 11.867 | 9.445 | 30.055 | 1.00 55.48 | A N |
| ATOM | 1149 | CA | ASN | A | 362 | 11.888 | 8.951 | 28.698 | 1.00 57.20 | A C |
| ATOM | 1150 | C | ASN | A | 362 | 10.443 | 9.064 | 28.245 | 1.00 59.17 | A C |
| ATOM | 1151 | O | ASN | A | 362 | 9.756 | 8.095 | 28.595 | 1.00 59.55 | A O |
| ATOM | 1152 | CB | ASN | A | 362 | 12.378 | 7.499 | 28.614 | 1.00 57.60 | A C |
| ATOM | 1153 | CG | ASN | A | 362 | 12.484 | 6.960 | 27.198 | 1.00 59.16 | A C |
| ATOM | 1154 | OD1 | ASN | A | 362 | 12.542 | 7.696 | 26.196 | 1.00 57.47 | A O |
| ATOM | 1155 | ND2 | ASN | A | 362 | 12.524 | 5.631 | 27.001 | 1.00 57.78 | A N |
| ATOM | 1156 | N | SER | A | 363 | 10.010 | 10.149 | 27.611 | 1.00 60.55 | A N |
| ATOM | 1157 | CA | SER | A | 363 | 8.599 | 10.200 | 27.184 | 1.00 62.18 | A C |
| ATOM | 1158 | C | SER | A | 363 | 8.487 | 10.172 | 25.647 | 1.00 63.61 | A C |
| ATOM | 1159 | O | SER | A | 363 | 9.322 | 10.829 | 24.974 | 1.00 64.80 | A O |
| ATOM | 1160 | CB | SER | A | 363 | 7.804 | 11.401 | 27.673 | 1.00 62.53 | A C |
| ATOM | 1161 | N | SER | A | 378 | 11.436 | 19.431 | 24.654 | 1.00 88.36 | A N |
| ATOM | 1162 | CA | SER | A | 378 | 12.110 | 18.247 | 24.128 | 1.00 90.01 | A C |
| ATOM | 1163 | C | SER | A | 378 | 13.603 | 18.446 | 24.392 | 1.00 88.95 | A C |
| ATOM | 1164 | O | SER | A | 378 | 14.375 | 17.567 | 24.740 | 1.00 88.96 | A O |
| ATOM | 1165 | CB | SER | A | 378 | 11.837 | 18.053 | 22.647 | 1.00 88.81 | A C |
| ATOM | 1166 | N | ARG | A | 379 | 13.978 | 19.711 | 24.220 | 1.00 86.69 | A N |
| ATOM | 1167 | CA | ARG | A | 379 | 15.347 | 20.166 | 24.369 | 1.00 84.45 | A C |
| ATOM | 1168 | C | ARG | A | 379 | 15.949 | 20.055 | 25.757 | 1.00 81.60 | A C |
| ATOM | 1169 | O | ARG | A | 379 | 16.930 | 19.302 | 25.820 | 1.00 81.23 | A O |
| ATOM | 1170 | CB | ARG | A | 379 | 15.499 | 21.592 | 23.839 | 1.00 84.39 | A C |
| ATOM | 1171 | N | LYS | A | 380 | 15.477 | 20.752 | 26.784 | 1.00 77.75 | A N |
| ATOM | 1172 | CA | LYS | A | 380 | 16.116 | 20.591 | 28.091 | 1.00 75.94 | A C |
| ATOM | 1173 | C | LYS | A | 380 | 15.788 | 19.203 | 28.664 | 1.00 73.90 | A C |
| ATOM | 1174 | O | LYS | A | 380 | 16.469 | 18.725 | 29.571 | 1.00 74.22 | A O |
| ATOM | 1175 | CB | LYS | A | 380 | 15.788 | 21.696 | 29.073 | 1.00 76.20 | A C |
| ATOM | 1176 | N | LEU | A | 381 | 14.780 | 18.562 | 28.092 | 1.00 70.15 | A N |
| ATOM | 1177 | CA | LEU | A | 381 | 14.362 | 17.249 | 28.536 | 1.00 69.08 | A C |
| ATOM | 1178 | C | LEU | A | 381 | 15.369 | 16.200 | 28.062 | 1.00 67.30 | A C |
| ATOM | 1179 | O | LEU | A | 381 | 15.834 | 15.335 | 28.806 | 1.00 67.30 | A O |
| ATOM | 1180 | CB | LEU | A | 381 | 12.932 | 16.932 | 28.083 | 1.00 67.96 | A C |
| ATOM | 1181 | CG | LEU | A | 381 | 12.460 | 15.521 | 28.456 | 1.00 68.65 | A C |
| ATOM | 1182 | CD1 | LEU | A | 381 | 12.391 | 15.382 | 29.978 | 1.00 67.87 | A C |
| ATOM | 1183 | CD2 | LEU | A | 381 | 11.136 | 15.173 | 27.793 | 1.00 68.21 | A C |
| ATOM | 1184 | N | THR | A | 382 | 15.732 | 16.303 | 26.795 | 1.00 64.61 | A N |
| ATOM | 1185 | CA | THR | A | 382 | 16.688 | 15.430 | 26.162 | 1.00 62.26 | A C |
| ATOM | 1186 | C | THR | A | 382 | 18.007 | 15.574 | 26.902 | 1.00 59.46 | A C |
| ATOM | 1187 | O | THR | A | 382 | 18.733 | 14.590 | 27.042 | 1.00 58.58 | A O |
| ATOM | 1188 | CB | THR | A | 382 | 16.881 | 15.755 | 24.673 | 1.00 63.42 | A C |
| ATOM | 1189 | OG1 | THR | A | 382 | 15.663 | 15.359 | 24.021 | 1.00 63.89 | A O |
| ATOM | 1190 | CG2 | THR | A | 382 | 18.019 | 14.975 | 24.012 | 1.00 63.40 | A C |
| ATOM | 1191 | N | HIS | A | 383 | 18.236 | 16.805 | 27.345 | 1.00 58.01 | A N |
| ATOM | 1192 | CA | HIS | A | 383 | 19.500 | 17.067 | 28.052 | 1.00 58.71 | A C |
| ATOM | 1193 | C | HIS | A | 383 | 19.489 | 16.295 | 29.380 | 1.00 55.18 | A C |
| ATOM | 1194 | O | HIS | A | 383 | 20.411 | 15.602 | 29.777 | 1.00 51.65 | A O |
| ATOM | 1195 | CB | HIS | A | 383 | 19.721 | 18.571 | 28.270 | 1.00 61.54 | A C |
| ATOM | 1196 | CG | HIS | A | 383 | 21.158 | 18.960 | 28.459 | 1.00 65.96 | A C |
| ATOM | 1197 | ND1 | HIS | A | 383 | 22.059 | 19.149 | 27.412 | 1.00 67.16 | A N |
| ATOM | 1198 | CD2 | HIS | A | 383 | 21.845 | 19.177 | 29.611 | 1.00 67.70 | A C |
| ATOM | 1199 | CE1 | HIS | A | 383 | 23.235 | 19.470 | 27.928 | 1.00 69.43 | A C |
| ATOM | 1200 | NE2 | HIS | A | 383 | 23.134 | 19.491 | 29.266 | 1.00 68.86 | A N |

| ATOM | 1201 | N   | LEU A 384 | 18.362 | 16.430 | 30.067 | 1.00 | 52.85 | A | N |
|------|------|-----|-----------|--------|--------|--------|------|-------|---|---|
| ATOM | 1202 | CA  | LEU A 384 | 18.171 | 15.761 | 31.349 | 1.00 | 52.85 | A | C |
| ATOM | 1203 | C   | LEU A 384 | 18.280 | 14.244 | 31.251 | 1.00 | 50.45 | A | C |
| ATOM | 1204 | O   | LEU A 384 | 18.931 | 13.630 | 32.083 | 1.00 | 45.70 | A | O |
| ATOM | 1205 | CB  | LEU A 384 | 16.765 | 16.087 | 31.841 | 1.00 | 54.39 | A | C |
| ATOM | 1206 | CG  | LEU A 384 | 16.673 | 16.650 | 33.250 | 1.00 | 57.19 | A | C |
| ATOM | 1207 | CD1 | LEU A 384 | 15.257 | 17.195 | 33.457 | 1.00 | 58.67 | A | C |
| ATOM | 1208 | CD2 | LEU A 384 | 17.057 | 15.634 | 34.315 | 1.00 | 58.80 | A | C |
| ATOM | 1209 | N   | LEU A 385 | 17.663 | 13.677 | 30.207 | 1.00 | 50.91 | A | N |
| ATOM | 1210 | CA  | LEU A 385 | 17.698 | 12.223 | 30.027 | 1.00 | 51.75 | A | C |
| ATOM | 1211 | C   | LEU A 385 | 19.127 | 11.753 | 29.754 | 1.00 | 51.17 | A | C |
| ATOM | 1212 | O   | LEU A 385 | 19.564 | 10.730 | 30.299 | 1.00 | 51.28 | A | O |
| ATOM | 1213 | CB  | LEU A 385 | 16.818 | 11.764 | 28.876 | 1.00 | 52.65 | A | C |
| ATOM | 1214 | CG  | LEU A 385 | 16.025 | 10.472 | 28.961 | 1.00 | 54.31 | A | C |
| ATOM | 1215 | CD1 | LEU A 385 | 15.698 | 9.938  | 27.567 | 1.00 | 52.04 | A | C |
| ATOM | 1216 | CD2 | LEU A 385 | 16.651 | 9.346  | 29.772 | 1.00 | 53.79 | A | C |
| ATOM | 1217 | N   | ASN A 386 | 19.814 | 12.542 | 28.929 | 1.00 | 50.43 | A | N |
| ATOM | 1218 | CA  | ASN A 386 | 21.206 | 12.202 | 28.609 | 1.00 | 52.20 | A | C |
| ATOM | 1219 | C   | ASN A 386 | 22.057 | 12.140 | 29.873 | 1.00 | 48.98 | A | C |
| ATOM | 1220 | O   | ASN A 386 | 22.881 | 11.255 | 30.113 | 1.00 | 47.40 | A | O |
| ATOM | 1221 | CB  | ASN A 386 | 21.746 | 13.185 | 27.569 | 1.00 | 57.21 | A | C |
| ATOM | 1222 | CG  | ASN A 386 | 21.213 | 12.943 | 26.160 | 1.00 | 61.05 | A | C |
| ATOM | 1223 | OD1 | ASN A 386 | 21.195 | 13.853 | 25.319 | 1.00 | 63.89 | A | O |
| ATOM | 1224 | ND2 | ASN A 386 | 20.772 | 11.726 | 25.822 | 1.00 | 62.65 | A | N |
| ATOM | 1225 | N   | ALA A 387 | 21.840 | 13.116 | 30.752 | 1.00 | 47.84 | A | N |
| ATOM | 1226 | CA  | ALA A 387 | 22.589 | 13.219 | 32.023 | 1.00 | 47.03 | A | C |
| ATOM | 1227 | C   | ALA A 387 | 22.367 | 11.989 | 32.910 | 1.00 | 44.04 | A | C |
| ATOM | 1228 | O   | ALA A 387 | 23.249 | 11.426 | 33.522 | 1.00 | 41.70 | A | O |
| ATOM | 1229 | CB  | ALA A 387 | 22.159 | 14.550 | 32.680 | 1.00 | 44.56 | A | C |
| ATOM | 1230 | N   | VAL A 388 | 21.133 | 11.501 | 32.978 | 1.00 | 45.00 | A | N |
| ATOM | 1231 | CA  | VAL A 388 | 20.763 | 10.328 | 33.750 | 1.00 | 44.63 | A | C |
| ATOM | 1232 | C   | VAL A 388 | 21.385 | 9.092  | 33.107 | 1.00 | 44.29 | A | C |
| ATOM | 1233 | O   | VAL A 388 | 21.939 | 8.236  | 33.814 | 1.00 | 43.88 | A | O |
| ATOM | 1234 | CB  | VAL A 388 | 19.249 | 10.209 | 34.012 | 1.00 | 44.45 | A | C |
| ATOM | 1235 | CG1 | VAL A 388 | 19.009 | 8.896  | 34.761 | 1.00 | 42.74 | A | C |
| ATOM | 1236 | CG2 | VAL A 388 | 18.753 | 11.353 | 34.903 | 1.00 | 42.43 | A | C |
| ATOM | 1237 | N   | THR A 389 | 21.322 | 9.052  | 31.770 | 1.00 | 41.82 | A | N |
| ATOM | 1238 | CA  | THR A 389 | 21.918 | 7.923  | 31.066 | 1.00 | 41.69 | A | C |
| ATOM | 1239 | C   | THR A 389 | 23.416 | 7.872  | 31.309 | 1.00 | 43.66 | A | C |
| ATOM | 1240 | O   | THR A 389 | 23.953 | 6.776  | 31.513 | 1.00 | 45.11 | A | O |
| ATOM | 1241 | CB  | THR A 389 | 21.687 | 8.030  | 29.512 | 1.00 | 41.00 | A | C |
| ATOM | 1242 | OG1 | THR A 389 | 20.299 | 8.067  | 29.175 | 1.00 | 40.80 | A | O |
| ATOM | 1243 | CG2 | THR A 389 | 22.257 | 6.774  | 28.895 | 1.00 | 39.46 | A | C |
| ATOM | 1244 | N   | ASP A 390 | 24.106 | 9.040  | 31.258 | 1.00 | 46.12 | A | N |
| ATOM | 1245 | CA  | ASP A 390 | 25.547 | 9.038  | 31.524 | 1.00 | 47.16 | A | C |
| ATOM | 1246 | C   | ASP A 390 | 25.740 | 8.636  | 32.986 | 1.00 | 45.17 | A | C |
| ATOM | 1247 | O   | ASP A 390 | 26.681 | 7.946  | 33.381 | 1.00 | 45.74 | A | O |
| ATOM | 1248 | CB  | ASP A 390 | 26.228 | 10.395 | 31.337 | 1.00 | 50.94 | A | C |
| ATOM | 1249 | CG  | ASP A 390 | 26.309 | 11.003 | 29.971 | 1.00 | 51.74 | A | C |
| ATOM | 1250 | OD1 | ASP A 390 | 26.443 | 10.269 | 28.957 | 1.00 | 54.82 | A | O |
| ATOM | 1251 | OD2 | ASP A 390 | 26.235 | 12.237 | 29.825 | 1.00 | 51.48 | A | O |
| ATOM | 1252 | N   | ALA A 391 | 24.800 | 9.017  | 33.847 | 1.00 | 44.20 | A | N |
| ATOM | 1253 | CA  | ALA A 391 | 24.988 | 8.579  | 35.257 | 1.00 | 43.29 | A | C |
| ATOM | 1254 | C   | ALA A 391 | 24.784 | 7.073  | 35.308 | 1.00 | 44.41 | A | C |
| ATOM | 1255 | O   | ALA A 391 | 25.585 | 6.437  | 36.023 | 1.00 | 43.74 | A | O |
| ATOM | 1256 | CB  | ALA A 391 | 24.163 | 9.404  | 36.190 | 1.00 | 42.30 | A | C |
| ATOM | 1257 | N   | LEU A 392 | 23.840 | 6.483  | 34.522 | 1.00 | 43.94 | A | N |
| ATOM | 1258 | CA  | LEU A 392 | 23.736 | 5.000  | 34.667 | 1.00 | 43.30 | A | C |
| ATOM | 1259 | C   | LEU A 392 | 24.989 | 4.291  | 34.166 | 1.00 | 44.20 | A | C |
| ATOM | 1260 | O   | LEU A 392 | 25.450 | 3.312  | 34.760 | 1.00 | 41.64 | A | O |
| ATOM | 1261 | CB  | LEU A 392 | 22.477 | 4.399  | 34.064 | 1.00 | 39.84 | A | C |

| | | | | | | | | | | |
|---|---|---|---|---|---|---|---|---|---|---|
| ATOM | 1262 | CG | LEU A 392 | 22.295 | 2.885 | 33.976 | 1.00 | 38.96 | A | C |
| ATOM | 1263 | CD1 | LEU A 392 | 22.167 | 2.186 | 35.346 | 1.00 | 36.68 | A | C |
| ATOM | 1264 | CD2 | LEU A 392 | 20.998 | 2.580 | 33.228 | 1.00 | 39.89 | A | C |
| ATOM | 1265 | N | VAL A 393 | 25.492 | 4.764 | 33.022 | 1.00 | 46.47 | A | N |
| ATOM | 1266 | CA | VAL A 393 | 26.697 | 4.191 | 32.439 | 1.00 | 47.97 | A | C |
| ATOM | 1267 | C | VAL A 393 | 27.881 | 4.322 | 33.409 | 1.00 | 48.62 | A | C |
| ATOM | 1268 | O | VAL A 393 | 28.689 | 3.396 | 33.568 | 1.00 | 50.13 | A | O |
| ATOM | 1269 | CB | VAL A 393 | 27.010 | 4.986 | 31.112 | 1.00 | 48.79 | A | C |
| ATOM | 1270 | CG1 | VAL A 393 | 28.438 | 4.727 | 30.637 | 1.00 | 45.59 | A | C |
| ATOM | 1271 | CG2 | VAL A 393 | 25.978 | 4.656 | 30.048 | 1.00 | 45.90 | A | C |
| ATOM | 1272 | N | TRP A 394 | 28.042 | 5.435 | 34.097 | 1.00 | 49.05 | A | N |
| ATOM | 1273 | CA | TRP A 394 | 29.140 | 5.599 | 35.060 | 1.00 | 52.14 | A | C |
| ATOM | 1274 | C | TRP A 394 | 28.980 | 4.576 | 36.183 | 1.00 | 52.89 | A | C |
| ATOM | 1275 | O | TRP A 394 | 29.924 | 3.924 | 36.640 | 1.00 | 52.65 | A | O |
| ATOM | 1276 | CB | TRP A 394 | 29.184 | 7.042 | 35.575 | 1.00 | 54.90 | A | C |
| ATOM | 1277 | CG | TRP A 394 | 30.170 | 7.280 | 36.665 | 1.00 | 58.63 | A | C |
| ATOM | 1278 | CD1 | TRP A 394 | 31.501 | 7.599 | 36.454 | 1.00 | 59.77 | A | C |
| ATOM | 1279 | CD2 | TRP A 394 | 29.981 | 7.235 | 38.075 | 1.00 | 59.31 | A | C |
| ATOM | 1280 | NE1 | TRP A 394 | 32.128 | 7.743 | 37.668 | 1.00 | 60.80 | A | N |
| ATOM | 1281 | CE2 | TRP A 394 | 31.227 | 7.527 | 38.678 | 1.00 | 60.71 | A | C |
| ATOM | 1282 | CE3 | TRP A 394 | 28.887 | 6.981 | 38.904 | 1.00 | 61.00 | A | C |
| ATOM | 1283 | CZ2 | TRP A 394 | 31.406 | 7.583 | 40.058 | 1.00 | 61.27 | A | C |
| ATOM | 1284 | CZ3 | TRP A 394 | 29.070 | 7.026 | 40.279 | 1.00 | 61.83 | A | C |
| ATOM | 1285 | CH2 | TRP A 394 | 30.319 | 7.325 | 40.849 | 1.00 | 61.01 | A | C |
| ATOM | 1286 | N | VAL A 395 | 27.755 | 4.382 | 36.675 | 1.00 | 50.16 | A | N |
| ATOM | 1287 | CA | VAL A 395 | 27.567 | 3.403 | 37.726 | 1.00 | 50.33 | A | C |
| ATOM | 1288 | C | VAL A 395 | 27.917 | 2.020 | 37.234 | 1.00 | 50.84 | A | C |
| ATOM | 1289 | O | VAL A 395 | 28.520 | 1.228 | 37.997 | 1.00 | 52.76 | A | O |
| ATOM | 1290 | CB | VAL A 395 | 26.128 | 3.373 | 38.277 | 1.00 | 50.15 | A | C |
| ATOM | 1291 | CG1 | VAL A 395 | 25.984 | 2.217 | 39.248 | 1.00 | 49.44 | A | C |
| ATOM | 1292 | CG2 | VAL A 395 | 25.720 | 4.673 | 38.943 | 1.00 | 48.73 | A | C |
| ATOM | 1293 | N | ILE A 396 | 27.555 | 1.702 | 35.990 | 1.00 | 49.65 | A | N |
| ATOM | 1294 | CA | ILE A 396 | 27.907 | 0.327 | 35.557 | 1.00 | 50.03 | A | C |
| ATOM | 1295 | C | ILE A 396 | 29.434 | 0.223 | 35.362 | 1.00 | 52.37 | A | C |
| ATOM | 1296 | O | ILE A 396 | 30.032 | -0.835 | 35.598 | 1.00 | 50.11 | A | O |
| ATOM | 1297 | CB | ILE A 396 | 27.075 | 0.016 | 34.316 | 1.00 | 48.84 | A | C |
| ATOM | 1298 | CG1 | ILE A 396 | 25.567 | -0.123 | 34.650 | 1.00 | 47.82 | A | C |
| ATOM | 1299 | CG2 | ILE A 396 | 27.605 | -1.197 | 33.559 | 1.00 | 46.76 | A | C |
| ATOM | 1300 | CD1 | ILE A 396 | 24.677 | -0.052 | 33.408 | 1.00 | 46.03 | A | C |
| ATOM | 1301 | N | ALA A 397 | 30.115 | 1.282 | 34.931 | 1.00 | 54.97 | A | N |
| ATOM | 1302 | CA | ALA A 397 | 31.569 | 1.189 | 34.734 | 1.00 | 61.24 | A | C |
| ATOM | 1303 | C | ALA A 397 | 32.247 | 0.822 | 36.059 | 1.00 | 64.50 | A | C |
| ATOM | 1304 | O | ALA A 397 | 33.115 | -0.059 | 36.104 | 1.00 | 66.29 | A | O |
| ATOM | 1305 | CB | ALA A 397 | 32.167 | 2.449 | 34.148 | 1.00 | 59.15 | A | C |
| ATOM | 1306 | N | LYS A 398 | 31.835 | 1.423 | 37.165 | 1.00 | 67.39 | A | N |
| ATOM | 1307 | CA | LYS A 398 | 32.407 | 1.137 | 38.469 | 1.00 | 69.36 | A | C |
| ATOM | 1308 | C | LYS A 398 | 32.186 | -0.287 | 38.961 | 1.00 | 68.55 | A | C |
| ATOM | 1309 | O | LYS A 398 | 32.653 | -0.586 | 40.068 | 1.00 | 70.54 | A | O |
| ATOM | 1310 | CB | LYS A 398 | 31.829 | 2.091 | 39.526 | 1.00 | 72.34 | A | C |
| ATOM | 1311 | CG | LYS A 398 | 31.675 | 3.538 | 39.124 | 1.00 | 74.49 | A | C |
| ATOM | 1312 | CD | LYS A 398 | 32.944 | 4.351 | 39.270 | 1.00 | 77.06 | A | C |
| ATOM | 1313 | CE | LYS A 398 | 33.390 | 4.470 | 40.727 | 1.00 | 78.45 | A | C |
| ATOM | 1314 | NZ | LYS A 398 | 34.842 | 4.852 | 40.738 | 1.00 | 79.35 | A | N |
| ATOM | 1315 | N | SER A 399 | 31.495 | -1.153 | 38.245 | 1.00 | 66.51 | A | N |
| ATOM | 1316 | CA | SER A 399 | 31.289 | -2.519 | 38.698 | 1.00 | 65.00 | A | C |
| ATOM | 1317 | C | SER A 399 | 32.472 | -3.397 | 38.289 | 1.00 | 65.24 | A | C |
| ATOM | 1318 | O | SER A 399 | 32.651 | -4.550 | 38.686 | 1.00 | 65.72 | A | O |
| ATOM | 1319 | CB | SER A 399 | 30.025 | -3.100 | 38.049 | 1.00 | 63.83 | A | C |
| ATOM | 1320 | OG | SER A 399 | 30.225 | -3.000 | 36.643 | 1.00 | 63.31 | A | O |
| ATOM | 1321 | N | GLY A 400 | 33.322 | -2.881 | 37.417 | 1.00 | 65.10 | A | N |
| ATOM | 1322 | CA | GLY A 400 | 34.488 | -3.506 | 36.891 | 1.00 | 66.50 | A | C |

```
ATOM   1323  C    GLY A 400      34.387  -4.584  35.835  1.00 66.89      A    C
ATOM   1324  O    GLY A 400      35.428  -5.150  35.459  1.00 66.55      A    O
ATOM   1325  N    ILE A 401      33.202  -4.919  35.331  1.00 64.97      A    N
ATOM   1326  CA   ILE A 401      33.135  -5.969  34.294  1.00 62.12      A    C
ATOM   1327  C    ILE A 401      33.739  -5.436  33.011  1.00 61.47      A    C
ATOM   1328  O    ILE A 401      34.102  -4.249  32.970  1.00 60.50      A    O
ATOM   1329  CB   ILE A 401      31.659  -6.369  34.175  1.00 61.26      A    C
ATOM   1330  CG1  ILE A 401      30.765  -5.191  33.744  1.00 59.31      A    C
ATOM   1331  CG2  ILE A 401      31.251  -6.915  35.541  1.00 59.59      A    C
ATOM   1332  CD1  ILE A 401      29.272  -5.493  33.889  1.00 58.00      A    C
ATOM   1333  N    SER A 402      33.861  -6.240  31.969  1.00 62.03      A    N
ATOM   1334  CA   SER A 402      34.403  -5.789  30.697  1.00 64.98      A    C
ATOM   1335  C    SER A 402      33.454  -4.824  29.968  1.00 67.43      A    C
ATOM   1336  O    SER A 402      32.263  -4.681  30.265  1.00 67.88      A    O
ATOM   1337  CB   SER A 402      34.615  -6.950  29.719  1.00 65.05      A    C
ATOM   1338  OG   SER A 402      33.395  -7.304  29.096  1.00 64.34      A    O
ATOM   1339  N    SER A 403      34.031  -4.160  28.973  1.00 68.55      A    N
ATOM   1340  CA   SER A 403      33.339  -3.190  28.169  1.00 69.23      A    C
ATOM   1341  C    SER A 403      32.085  -3.810  27.540  1.00 71.10      A    C
ATOM   1342  O    SER A 403      31.070  -3.096  27.552  1.00 71.03      A    O
ATOM   1343  CB   SER A 403      34.245  -2.702  27.038  1.00 68.60      A    C
ATOM   1344  OG   SER A 403      34.099  -1.332  26.794  1.00 68.74      A    O
ATOM   1345  N    GLN A 404      32.263  -5.034  27.020  1.00 68.62      A    N
ATOM   1346  CA   GLN A 404      31.115  -5.653  26.368  1.00 68.48      A    C
ATOM   1347  C    GLN A 404      30.080  -5.995  27.430  1.00 68.66      A    C
ATOM   1348  O    GLN A 404      28.885  -5.782  27.176  1.00 67.93      A    O
ATOM   1349  CB   GLN A 404      31.597  -6.763  25.453  1.00 69.53      A    C
ATOM   1350  CG   GLN A 404      30.554  -7.619  24.755  1.00 70.31      A    C
ATOM   1351  CD   GLN A 404      30.022  -8.711  25.668  1.00 70.62      A    C
ATOM   1352  OE1  GLN A 404      30.580  -8.897  26.757  1.00 71.02      A    O
ATOM   1353  NE2  GLN A 404      28.983  -9.384  25.191  1.00 70.12      A    N
ATOM   1354  N    GLN A 405      30.498  -6.495  28.600  1.00 67.42      A    N
ATOM   1355  CA   GLN A 405      29.533  -6.859  29.620  1.00 65.45      A    C
ATOM   1356  CB   GLN A 405      30.075  -7.757  30.730  1.00 66.70      A    C
ATOM   1357  CG  AGLN A 405      29.983  -9.247  30.478  0.50 66.81      A    C
ATOM   1358  CG  BGLN A 405      30.875  -8.935  30.202  0.50 67.92      A    C
ATOM   1359  CD  AGLN A 405      28.718  -9.789  29.853  0.50 66.59      A    C
ATOM   1360  CD  BGLN A 405      31.670  -9.625  31.293  0.50 67.95      A    C
ATOM   1361  OE1 AGLN A 405      27.660  -9.984  30.464  0.50 66.08      A    O
ATOM   1362  OE1 BGLN A 405      32.644  -9.103  31.838  0.50 67.91      A    O
ATOM   1363  NE2 AGLN A 405      28.780 -10.079  28.544  0.50 66.61      A    N
ATOM   1364  NE2 BGLN A 405      31.222 -10.836  31.608  0.50 68.58      A    N
ATOM   1365  C    GLN A 405      28.830  -5.636  30.222  1.00 62.91      A    C
ATOM   1366  O    GLN A 405      27.768  -5.804  30.798  1.00 59.77      A    O
ATOM   1367  N    GLN A 406      29.435  -4.472  30.082  1.00 61.57      A    N
ATOM   1368  CA   GLN A 406      28.851  -3.229  30.557  1.00 59.26      A    C
ATOM   1369  C    GLN A 406      27.732  -2.823  29.577  1.00 58.40      A    C
ATOM   1370  O    GLN A 406      26.642  -2.422  30.000  1.00 55.67      A    O
ATOM   1371  CB   GLN A 406      29.851  -2.101  30.633  1.00 60.49      A    C
ATOM   1372  CG   GLN A 406      30.585  -2.049  31.959  1.00 62.28      A    C
ATOM   1373  CD   GLN A 406      31.796  -1.156  31.842  1.00 63.20      A    C
ATOM   1374  OE1  GLN A 406      31.647  -0.010  31.427  1.00 63.71      A    O
ATOM   1375  NE2  GLN A 406      32.915  -1.786  32.207  1.00 64.44      A    N
ATOM   1376  N    SER A 407      28.012  -2.938  28.272  1.00 55.06      A    N
ATOM   1377  CA   SER A 407      26.943  -2.639  27.317  1.00 54.01      A    C
ATOM   1378  C    SER A 407      25.792  -3.633  27.590  1.00 52.42      A    C
ATOM   1379  O    SER A 407      24.651  -3.180  27.749  1.00 52.41      A    O
ATOM   1380  CB   SER A 407      27.402  -2.766  25.864  1.00 52.16      A    C
ATOM   1381  OG   SER A 407      28.116  -1.600  25.480  1.00 50.49      A    O
ATOM   1382  N    VAL A 408      26.077  -4.931  27.633  1.00 49.30      A    N
ATOM   1383  CA   VAL A 408      25.044  -5.920  27.850  1.00 49.30      A    C
```

| ATOM | 1384 | C | VAL | A | 408 | 24.189 | -5.631 | 29.090 | 1.00 | 51.69 | A | C |
|------|------|------|------|---|-----|--------|--------|--------|------|-------|---|---|
| ATOM | 1385 | O | VAL | A | 408 | 22.957 | -5.855 | 29.099 | 1.00 | 51.03 | A | O |
| ATOM | 1386 | CB | VAL | A | 408 | 25.579 | -7.363 | 27.880 | 1.00 | 48.38 | A | C |
| ATOM | 1387 | CG1 | VAL | A | 408 | 24.617 | -8.411 | 28.441 | 1.00 | 47.17 | A | C |
| ATOM | 1388 | CG2 | VAL | A | 408 | 25.924 | -7.808 | 26.444 | 1.00 | 46.83 | A | C |
| ATOM | 1389 | N | ARG | A | 409 | 24.874 | -5.210 | 30.160 | 1.00 | 49.10 | A | N |
| ATOM | 1390 | CA | ARG | A | 409 | 24.158 | -4.955 | 31.392 | 1.00 | 48.22 | A | C |
| ATOM | 1391 | C | ARG | A | 409 | 23.204 | -3.775 | 31.182 | 1.00 | 47.83 | A | C |
| ATOM | 1392 | O | ARG | A | 409 | 22.103 | -3.804 | 31.698 | 1.00 | 48.13 | A | O |
| ATOM | 1393 | CB | ARG | A | 409 | 25.119 | -4.681 | 32.569 | 1.00 | 47.13 | A | C |
| ATOM | 1394 | CG | ARG | A | 409 | 24.389 | -4.746 | 33.896 | 1.00 | 45.00 | A | C |
| ATOM | 1395 | CD | ARG | A | 409 | 25.281 | -4.444 | 35.081 | 1.00 | 43.96 | A | C |
| ATOM | 1396 | NE | ARG | A | 409 | 24.601 | -4.503 | 36.345 | 1.00 | 43.74 | A | N |
| ATOM | 1397 | CZ | ARG | A | 409 | 23.996 | -5.497 | 36.965 | 1.00 | 43.16 | A | C |
| ATOM | 1398 | NH1 | ARG | A | 409 | 23.950 | -6.722 | 36.486 | 1.00 | 42.31 | A | N |
| ATOM | 1399 | NH2 | ARG | A | 409 | 23.407 | -5.361 | 38.170 | 1.00 | 42.88 | A | N |
| ATOM | 1400 | N | LEU | A | 410 | 23.621 | -2.787 | 30.425 | 1.00 | 47.27 | A | N |
| ATOM | 1401 | CA | LEU | A | 410 | 22.818 | -1.619 | 30.159 | 1.00 | 50.84 | A | C |
| ATOM | 1402 | C | LEU | A | 410 | 21.535 | -2.038 | 29.431 | 1.00 | 53.32 | A | C |
| ATOM | 1403 | O | LEU | A | 410 | 20.409 | -1.737 | 29.850 | 1.00 | 53.71 | A | O |
| ATOM | 1404 | CB | LEU | A | 410 | 23.667 | -0.576 | 29.452 | 1.00 | 50.49 | A | C |
| ATOM | 1405 | CG | LEU | A | 410 | 22.988 | 0.773 | 29.261 | 1.00 | 51.23 | A | C |
| ATOM | 1406 | CD1 | LEU | A | 410 | 22.320 | 1.186 | 30.570 | 1.00 | 52.94 | A | C |
| ATOM | 1407 | CD2 | LEU | A | 410 | 23.896 | 1.870 | 28.787 | 1.00 | 50.94 | A | C |
| ATOM | 1408 | N | ALA | A | 411 | 21.720 | -2.801 | 28.361 | 1.00 | 52.82 | A | N |
| ATOM | 1409 | CA | ALA | A | 411 | 20.642 | -3.326 | 27.559 | 1.00 | 52.07 | A | C |
| ATOM | 1410 | C | ALA | A | 411 | 19.717 | -4.143 | 28.460 | 1.00 | 51.89 | A | C |
| ATOM | 1411 | O | ALA | A | 411 | 18.497 | -4.007 | 28.293 | 1.00 | 51.87 | A | O |
| ATOM | 1412 | CB | ALA | A | 411 | 21.129 | -4.243 | 26.430 | 1.00 | 50.64 | A | C |
| ATOM | 1413 | N | ASN | A | 412 | 20.218 | -4.956 | 29.368 | 1.00 | 51.36 | A | N |
| ATOM | 1414 | CA | ASN | A | 412 | 19.327 | -5.755 | 30.215 | 1.00 | 51.53 | A | C |
| ATOM | 1415 | C | ASN | A | 412 | 18.546 | -4.873 | 31.192 | 1.00 | 51.05 | A | C |
| ATOM | 1416 | O | ASN | A | 412 | 17.345 | -5.135 | 31.411 | 1.00 | 48.95 | A | O |
| ATOM | 1417 | CB | ASN | A | 412 | 20.022 | -6.895 | 30.933 | 1.00 | 55.28 | A | C |
| ATOM | 1418 | CG | ASN | A | 412 | 20.491 | -8.027 | 30.030 | 1.00 | 58.87 | A | C |
| ATOM | 1419 | OD1 | ASN | A | 412 | 19.744 | -8.891 | 29.566 | 1.00 | 61.80 | A | O |
| ATOM | 1420 | ND2 | ASN | A | 412 | 21.773 | -8.105 | 29.713 | 1.00 | 58.69 | A | N |
| ATOM | 1421 | N | LEU | A | 413 | 19.178 | -3.840 | 31.763 | 1.00 | 49.71 | A | N |
| ATOM | 1422 | CA | LEU | A | 413 | 18.422 | -2.987 | 32.697 | 1.00 | 49.18 | A | C |
| ATOM | 1423 | C | LEU | A | 413 | 17.286 | -2.292 | 31.933 | 1.00 | 50.80 | A | C |
| ATOM | 1424 | O | LEU | A | 413 | 16.156 | -2.449 | 32.376 | 1.00 | 49.65 | A | O |
| ATOM | 1425 | CB | LEU | A | 413 | 19.312 | -2.006 | 33.417 | 1.00 | 45.43 | A | C |
| ATOM | 1426 | CG | LEU | A | 413 | 20.276 | -2.639 | 34.439 | 1.00 | 45.28 | A | C |
| ATOM | 1427 | CD1 | LEU | A | 413 | 21.339 | -1.634 | 34.827 | 1.00 | 43.59 | A | C |
| ATOM | 1428 | CD2 | LEU | A | 413 | 19.559 | -3.179 | 35.670 | 1.00 | 41.24 | A | C |
| ATOM | 1429 | N | LEU | A | 414 | 17.546 | -1.608 | 30.828 | 1.00 | 51.48 | A | N |
| ATOM | 1430 | CA | LEU | A | 414 | 16.540 | -0.945 | 30.036 | 1.00 | 52.29 | A | C |
| ATOM | 1431 | C | LEU | A | 414 | 15.438 | -1.847 | 29.534 | 1.00 | 53.42 | A | C |
| ATOM | 1432 | O | LEU | A | 414 | 14.263 | -1.448 | 29.549 | 1.00 | 53.50 | A | O |
| ATOM | 1433 | CB | LEU | A | 414 | 17.205 | -0.206 | 28.885 | 1.00 | 52.80 | A | C |
| ATOM | 1434 | CG | LEU | A | 414 | 18.170 | 0.865 | 29.391 | 1.00 | 54.42 | A | C |
| ATOM | 1435 | CD1 | LEU | A | 414 | 18.811 | 1.577 | 28.213 | 1.00 | 55.76 | A | C |
| ATOM | 1436 | CD2 | LEU | A | 414 | 17.545 | 1.905 | 30.302 | 1.00 | 54.83 | A | C |
| ATOM | 1437 | N | MET | A | 415 | 15.738 | -3.084 | 29.154 | 1.00 | 54.00 | A | N |
| ATOM | 1438 | CA | MET | A | 415 | 14.666 | -3.969 | 28.689 | 1.00 | 53.40 | A | C |
| ATOM | 1439 | C | MET | A | 415 | 13.767 | -4.368 | 29.831 | 1.00 | 52.15 | A | C |
| ATOM | 1440 | O | MET | A | 415 | 12.616 | -4.736 | 29.613 | 1.00 | 52.52 | A | O |
| ATOM | 1441 | CB | MET | A | 415 | 15.267 | -5.143 | 27.902 | 1.00 | 54.44 | A | C |
| ATOM | 1442 | CG | MET | A | 415 | 15.719 | -4.644 | 26.505 | 1.00 | 54.60 | A | C |
| ATOM | 1443 | SD | MET | A | 415 | 16.186 | -6.007 | 25.413 | 1.00 | 55.69 | A | S |
| ATOM | 1444 | CE | MET | A | 415 | 17.803 | -6.467 | 26.000 | 1.00 | 52.29 | A | C |

| | | | | | | | | | | |
|---|---|---|---|---|---|---|---|---|---|---|
| ATOM | 1445 | N | LEU | A | 416 | 14.241 | -4.311 | 31.066 | 1.00 53.11 | A N |
| ATOM | 1446 | CA | LEU | A | 416 | 13.412 | -4.641 | 32.216 | 1.00 52.22 | A C |
| ATOM | 1447 | C | LEU | A | 416 | 12.395 | -3.516 | 32.459 | 1.00 52.80 | A C |
| ATOM | 1448 | O | LEU | A | 416 | 11.261 | -3.806 | 32.895 | 1.00 53.25 | A O |
| ATOM | 1449 | CB | LEU | A | 416 | 14.199 | -4.992 | 33.458 | 1.00 51.11 | A C |
| ATOM | 1450 | CG | LEU | A | 416 | 14.759 | -6.420 | 33.517 | 1.00 50.68 | A C |
| ATOM | 1451 | CD1 | LEU | A | 416 | 15.279 | -6.730 | 34.912 | 1.00 50.23 | A C |
| ATOM | 1452 | CD2 | LEU | A | 416 | 13.722 | -7.463 | 33.143 | 1.00 50.40 | A C |
| ATOM | 1453 | N | LEU | A | 417 | 12.764 | -2.273 | 32.161 | 1.00 50.86 | A N |
| ATOM | 1454 | CA | LEU | A | 417 | 11.811 | -1.181 | 32.353 | 1.00 50.85 | A C |
| ATOM | 1455 | C | LEU | A | 417 | 10.575 | -1.301 | 31.464 | 1.00 52.09 | A C |
| ATOM | 1456 | O | LEU | A | 417 | 9.545 | -0.666 | 31.759 | 1.00 53.16 | A O |
| ATOM | 1457 | CB | LEU | A | 417 | 12.452 | 0.173 | 31.964 | 1.00 49.56 | A C |
| ATOM | 1458 | CG | LEU | A | 417 | 13.645 | 0.506 | 32.849 | 1.00 51.27 | A C |
| ATOM | 1459 | CD1 | LEU | A | 417 | 14.129 | 1.907 | 32.505 | 1.00 50.57 | A C |
| ATOM | 1460 | CD2 | LEU | A | 417 | 13.235 | 0.356 | 34.311 | 1.00 49.72 | A C |
| ATOM | 1461 | N | SER | A | 418 | 10.731 | -2.017 | 30.334 | 1.00 48.22 | A N |
| ATOM | 1462 | CA | SER | A | 418 | 9.554 | -2.128 | 29.472 | 1.00 47.45 | A C |
| ATOM | 1463 | C | SER | A | 418 | 8.640 | -3.166 | 30.144 | 1.00 46.25 | A C |
| ATOM | 1464 | O | SER | A | 418 | 7.418 | -3.138 | 29.931 | 1.00 47.63 | A O |
| ATOM | 1465 | CB | SER | A | 418 | 9.902 | -2.425 | 28.008 | 1.00 46.06 | A C |
| ATOM | 1466 | OG | SER | A | 418 | 10.209 | -3.822 | 27.964 | 1.00 46.04 | A O |
| ATOM | 1467 | N | HIS | A | 419 | 9.157 | -4.049 | 30.985 | 1.00 45.57 | A N |
| ATOM | 1468 | CA | HIS | A | 419 | 8.269 | -4.970 | 31.670 | 1.00 47.07 | A C |
| ATOM | 1469 | C | HIS | A | 419 | 7.493 | -4.120 | 32.703 | 1.00 47.28 | A C |
| ATOM | 1470 | O | HIS | A | 419 | 6.310 | -4.377 | 32.882 | 1.00 46.07 | A O |
| ATOM | 1471 | CB | HIS | A | 419 | 8.861 | -6.151 | 32.395 | 1.00 50.51 | A C |
| ATOM | 1472 | CG | HIS | A | 419 | 9.645 | -7.087 | 31.526 | 1.00 55.42 | A C |
| ATOM | 1473 | ND1 | HIS | A | 419 | 10.078 | -6.754 | 30.248 | 1.00 55.67 | A N |
| ATOM | 1474 | CD2 | HIS | A | 419 | 10.114 | -8.334 | 31.771 | 1.00 57.06 | A C |
| ATOM | 1475 | CE1 | HIS | A | 419 | 10.755 | -7.743 | 29.723 | 1.00 56.57 | A C |
| ATOM | 1476 | NE2 | HIS | A | 419 | 10.797 | -8.710 | 30.623 | 1.00 58.33 | A N |
| ATOM | 1477 | N | VAL | A | 420 | 8.146 | -3.183 | 33.391 | 1.00 46.11 | A N |
| ATOM | 1478 | CA | VAL | A | 420 | 7.462 | -2.365 | 34.379 | 1.00 43.59 | A C |
| ATOM | 1479 | C | VAL | A | 420 | 6.322 | -1.658 | 33.634 | 1.00 44.09 | A C |
| ATOM | 1480 | O | VAL | A | 420 | 5.219 | -1.632 | 34.141 | 1.00 40.35 | A O |
| ATOM | 1481 | CB | VAL | A | 420 | 8.402 | -1.339 | 35.030 | 1.00 44.34 | A C |
| ATOM | 1482 | CG1 | VAL | A | 420 | 7.664 | -0.373 | 35.927 | 1.00 42.60 | A C |
| ATOM | 1483 | CG2 | VAL | A | 420 | 9.544 | -2.014 | 35.807 | 1.00 44.44 | A C |
| ATOM | 1484 | N | ARG | A | 421 | 6.551 | -1.112 | 32.441 | 1.00 43.76 | A N |
| ATOM | 1485 | CA | ARG | A | 421 | 5.515 | -0.448 | 31.673 | 1.00 44.37 | A C |
| ATOM | 1486 | C | ARG | A | 421 | 4.266 | -1.310 | 31.493 | 1.00 45.34 | A C |
| ATOM | 1487 | O | ARG | A | 421 | 3.101 | -0.942 | 31.739 | 1.00 43.42 | A O |
| ATOM | 1488 | CB | ARG | A | 421 | 6.105 | 0.009 | 30.332 | 1.00 46.01 | A C |
| ATOM | 1489 | CG | ARG | A | 421 | 5.048 | 0.580 | 29.386 | 1.00 46.02 | A C |
| ATOM | 1490 | CD | ARG | A | 421 | 5.513 | 1.845 | 28.722 | 1.00 45.60 | A C |
| ATOM | 1491 | NE | ARG | A | 421 | 6.013 | 2.809 | 29.689 | 1.00 46.59 | A N |
| ATOM | 1492 | CZ | ARG | A | 421 | 6.765 | 3.854 | 29.379 | 1.00 42.81 | A C |
| ATOM | 1493 | NH1 | ARG | A | 421 | 7.025 | 3.990 | 28.107 | 1.00 44.03 | A N |
| ATOM | 1494 | NH2 | ARG | A | 421 | 7.152 | 4.649 | 30.332 | 1.00 40.75 | A N |
| ATOM | 1495 | N | HIS | A | 422 | 4.493 | -2.549 | 31.085 | 1.00 46.49 | A N |
| ATOM | 1496 | CA | HIS | A | 422 | 3.431 | -3.529 | 30.876 | 1.00 46.67 | A C |
| ATOM | 1497 | C | HIS | A | 422 | 2.670 | -3.788 | 32.173 | 1.00 46.60 | A C |
| ATOM | 1498 | O | HIS | A | 422 | 1.420 | -3.752 | 32.195 | 1.00 47.53 | A O |
| ATOM | 1499 | CB | HIS | A | 422 | 4.082 | -4.805 | 30.296 | 1.00 45.59 | A C |
| ATOM | 1500 | CG | HIS | A | 422 | 3.068 | -5.894 | 30.200 | 1.00 46.95 | A C |
| ATOM | 1501 | ND1 | HIS | A | 422 | 2.060 | -5.865 | 29.288 | 1.00 46.74 | A N |
| ATOM | 1502 | CD2 | HIS | A | 422 | 2.870 | -7.042 | 30.913 | 1.00 49.41 | A C |
| ATOM | 1503 | CE1 | HIS | A | 422 | 1.264 | -6.915 | 29.411 | 1.00 46.77 | A C |
| ATOM | 1504 | NE2 | HIS | A | 422 | 1.756 | -7.638 | 30.394 | 1.00 49.01 | A N |
| ATOM | 1505 | N | ILE | A | 423 | 3.329 | -4.062 | 33.287 | 1.00 44.37 | A N |

| | | | | | | | | | | | |
|---|---|---|---|---|---|---|---|---|---|---|---|
| ATOM | 1506 | CA | ILE | A | 423 | 2.612 | -4.312 | 34.554 | 1.00 | 44.34 | A | C |
| ATOM | 1507 | C | ILE | A | 423 | 1.864 | -3.059 | 34.976 | 1.00 | 43.86 | A | C |
| ATOM | 1508 | O | ILE | A | 423 | 0.786 | -3.230 | 35.495 | 1.00 | 43.20 | A | O |
| ATOM | 1509 | CB | ILE | A | 423 | 3.492 | -4.795 | 35.704 | 1.00 | 45.02 | A | C |
| ATOM | 1510 | CG1 | ILE | A | 423 | 4.250 | -6.032 | 35.187 | 1.00 | 45.75 | A | C |
| ATOM | 1511 | CG2 | ILE | A | 423 | 2.744 | -5.199 | 36.975 | 1.00 | 44.05 | A | C |
| ATOM | 1512 | CD1 | ILE | A | 423 | 5.355 | -6.455 | 36.136 | 1.00 | 46.73 | A | C |
| ATOM | 1513 | N | SER | A | 424 | 2.387 | -1.859 | 34.733 | 1.00 | 42.83 | A | N |
| ATOM | 1514 | CA | SER | A | 424 | 1.670 | -0.652 | 35.105 | 1.00 | 41.86 | A | C |
| ATOM | 1515 | C | SER | A | 424 | 0.354 | -0.560 | 34.298 | 1.00 | 43.78 | A | C |
| ATOM | 1516 | O | SER | A | 424 | -0.695 | -0.191 | 34.830 | 1.00 | 41.50 | A | O |
| ATOM | 1517 | CB | SER | A | 424 | 2.539 | 0.568 | 34.863 | 1.00 | 39.72 | A | C |
| ATOM | 1518 | OG | SER | A | 424 | 1.733 | 1.741 | 34.978 | 1.00 | 41.15 | A | O |
| ATOM | 1519 | N | ASN | A | 425 | 0.392 | -0.877 | 32.999 | 1.00 | 43.32 | A | N |
| ATOM | 1520 | CA | ASN | A | 425 | -0.805 | -0.846 | 32.194 | 1.00 | 45.05 | A | C |
| ATOM | 1521 | C | ASN | A | 425 | -1.802 | -1.818 | 32.817 | 1.00 | 44.39 | A | C |
| ATOM | 1522 | O | ASN | A | 425 | -2.933 | -1.400 | 33.043 | 1.00 | 45.53 | A | O |
| ATOM | 1523 | CB | ASN | A | 425 | -0.621 | -1.195 | 30.703 | 1.00 | 45.32 | A | C |
| ATOM | 1524 | CG | ASN | A | 425 | 0.090 | -0.071 | 30.009 | 1.00 | 47.89 | A | C |
| ATOM | 1525 | OD1 | ASN | A | 425 | 0.078 | 1.066 | 30.468 | 1.00 | 48.65 | A | O |
| ATOM | 1526 | ND2 | ASN | A | 425 | 0.762 | -0.255 | 28.875 | 1.00 | 51.02 | A | N |
| ATOM | 1527 | N | LYS | A | 426 | -1.453 | -3.048 | 33.111 | 1.00 | 45.43 | A | N |
| ATOM | 1528 | CA | LYS | A | 426 | -2.430 | -3.956 | 33.695 | 1.00 | 48.39 | A | C |
| ATOM | 1529 | C | LYS | A | 426 | -2.934 | -3.527 | 35.081 | 1.00 | 48.85 | A | C |
| ATOM | 1530 | O | LYS | A | 426 | -4.108 | -3.784 | 35.409 | 1.00 | 48.12 | A | O |
| ATOM | 1531 | CB | LYS | A | 426 | -1.854 | -5.376 | 33.859 | 1.00 | 50.56 | A | C |
| ATOM | 1532 | CG | LYS | A | 426 | -1.219 | -5.910 | 32.590 | 1.00 | 54.51 | A | C |
| ATOM | 1533 | CD | LYS | A | 426 | -2.311 | -6.474 | 31.661 | 1.00 | 57.70 | A | C |
| ATOM | 1534 | CE | LYS | A | 426 | -2.006 | -5.945 | 30.251 | 1.00 | 59.52 | A | C |
| ATOM | 1535 | NZ | LYS | A | 426 | -2.251 | -4.450 | 30.162 | 1.00 | 59.39 | A | N |
| ATOM | 1536 | N | GLY | A | 427 | -2.053 | -2.958 | 35.891 | 1.00 | 46.73 | A | N |
| ATOM | 1537 | CA | GLY | A | 427 | -2.477 | -2.546 | 37.234 | 1.00 | 48.19 | A | C |
| ATOM | 1538 | C | GLY | A | 427 | -3.528 | -1.437 | 37.091 | 1.00 | 49.03 | A | C |
| ATOM | 1539 | O | GLY | A | 427 | -4.507 | -1.408 | 37.840 | 1.00 | 46.69 | A | O |
| ATOM | 1540 | N | MET | A | 428 | -3.309 | -0.555 | 36.124 | 1.00 | 50.22 | A | N |
| ATOM | 1541 | CA | MET | A | 428 | -4.234 | 0.539 | 35.877 | 1.00 | 54.06 | A | C |
| ATOM | 1542 | C | MET | A | 428 | -5.618 | 0.007 | 35.472 | 1.00 | 56.42 | A | C |
| ATOM | 1543 | O | MET | A | 428 | -6.638 | 0.327 | 36.085 | 1.00 | 55.80 | A | O |
| ATOM | 1544 | CB | MET | A | 428 | -3.797 | 1.495 | 34.780 | 1.00 | 52.87 | A | C |
| ATOM | 1545 | CG | MET | A | 428 | -2.552 | 2.291 | 35.045 | 1.00 | 52.10 | A | C |
| ATOM | 1546 | SD | MET | A | 428 | -2.766 | 3.342 | 36.504 | 1.00 | 52.54 | A | S |
| ATOM | 1547 | CE | MET | A | 428 | -3.945 | 4.532 | 35.742 | 1.00 | 49.94 | A | C |
| ATOM | 1548 | N | GLU | A | 429 | -5.631 | -0.816 | 34.442 | 1.00 | 59.40 | A | N |
| ATOM | 1549 | CA | GLU | A | 429 | -6.921 | -1.375 | 34.008 | 1.00 | 62.37 | A | C |
| ATOM | 1550 | C | GLU | A | 429 | -7.559 | -2.077 | 35.210 | 1.00 | 62.27 | A | C |
| ATOM | 1551 | O | GLU | A | 429 | -8.782 | -1.963 | 35.406 | 1.00 | 61.13 | A | O |
| ATOM | 1552 | CB | GLU | A | 429 | -6.821 | -2.223 | 32.778 | 1.00 | 64.78 | A | C |
| ATOM | 1553 | CG | GLU | A | 429 | -6.317 | -3.628 | 32.847 | 1.00 | 70.69 | A | C |
| ATOM | 1554 | CD | GLU | A | 429 | -6.216 | -4.360 | 31.516 | 1.00 | 72.83 | A | C |
| ATOM | 1555 | OE1 | GLU | A | 429 | -5.384 | -4.019 | 30.641 | 1.00 | 73.91 | A | O |
| ATOM | 1556 | OE2 | GLU | A | 429 | -7.014 | -5.316 | 31.367 | 1.00 | 74.71 | A | O |
| ATOM | 1557 | N | HIS | A | 430 | -6.753 | -2.770 | 36.004 | 1.00 | 61.01 | A | N |
| ATOM | 1558 | CA | HIS | A | 430 | -7.291 | -3.452 | 37.180 | 1.00 | 61.90 | A | C |
| ATOM | 1559 | C | HIS | A | 430 | -7.976 | -2.441 | 38.108 | 1.00 | 64.17 | A | C |
| ATOM | 1560 | O | HIS | A | 430 | -8.984 | -2.699 | 38.765 | 1.00 | 62.46 | A | O |
| ATOM | 1561 | CB | HIS | A | 430 | -6.213 | -4.214 | 37.959 | 1.00 | 58.81 | A | C |
| ATOM | 1562 | CG | HIS | A | 430 | -6.773 | -4.951 | 39.131 | 1.00 | 58.88 | A | C |
| ATOM | 1563 | ND1 | HIS | A | 430 | -6.272 | -4.848 | 40.421 | 1.00 | 57.32 | A | N |
| ATOM | 1564 | CD2 | HIS | A | 430 | -7.845 | -5.812 | 39.192 | 1.00 | 57.45 | A | C |
| ATOM | 1565 | CE1 | HIS | A | 430 | -6.996 | -5.617 | 41.218 | 1.00 | 57.54 | A | C |
| ATOM | 1566 | NE2 | HIS | A | 430 | -7.953 | -6.205 | 40.502 | 1.00 | 56.75 | A | N |

128

```
ATOM   1567  N   LEU A 431      -7.410  -1.237  38.183  1.00 67.23      A  N
ATOM   1568  CA  LEU A 431      -7.988  -0.190  39.008  1.00 70.21      A  C
ATOM   1569  C   LEU A 431      -9.287   0.351  38.399  1.00 72.74      A  C
ATOM   1570  O   LEU A 431     -10.253   0.541  39.129  1.00 71.65      A  O
ATOM   1571  CB  LEU A 431      -7.047   1.000  39.161  1.00 70.40      A  C
ATOM   1572  CG  LEU A 431      -6.166   1.070  40.403  1.00 70.70      A  C
ATOM   1573  CD1 LEU A 431      -4.944   1.954  40.174  1.00 70.05      A  C
ATOM   1574  CD2 LEU A 431      -6.955   1.597  41.595  1.00 69.76      A  C
ATOM   1575  N   LEU A 432      -9.265   0.611  37.105  1.00 76.70      A  N
ATOM   1576  CA  LEU A 432     -10.410   1.172  36.400  1.00 81.81      A  C
ATOM   1577  C   LEU A 432     -11.616   0.272  36.624  1.00 84.38      A  C
ATOM   1578  O   LEU A 432     -12.580   0.717  37.240  1.00 84.65      A  O
ATOM   1579  CB  LEU A 432     -10.183   1.341  34.897  1.00 83.09      A  C
ATOM   1580  CG  LEU A 432     -10.575   2.690  34.251  1.00 84.25      A  C
ATOM   1581  CD1 LEU A 432     -10.520   2.547  32.703  1.00 84.60      A  C
ATOM   1582  CD2 LEU A 432     -12.054   3.030  34.556  1.00 84.81      A  C
ATOM   1583  N   SER A 433     -11.533  -0.964  36.163  1.00 87.80      A  N
ATOM   1584  CA  SER A 433     -12.626  -1.915  36.317  1.00 90.24      A  C
ATOM   1585  C   SER A 433     -13.149  -1.959  37.748  1.00 91.95      A  C
ATOM   1586  O   SER A 433     -14.339  -2.104  38.017  1.00 92.17      A  O
ATOM   1587  CB  SER A 433     -12.143  -3.316  35.918  1.00 90.29      A  C
ATOM   1588  OG  SER A 433     -11.356  -3.877  36.961  1.00 89.72      A  O
ATOM   1589  N   MET A 434     -12.250  -1.832  38.703  1.00 93.91      A  N
ATOM   1590  CA  MET A 434     -12.547  -1.863  40.124  1.00 96.41      A  C
ATOM   1591  C   MET A 434     -13.339  -0.675  40.652  1.00 98.33      A  C
ATOM   1592  O   MET A 434     -14.479  -0.781  41.116  1.00 98.63      A  O
ATOM   1593  CB  MET A 434     -11.197  -1.922  40.826  1.00 95.96      A  C
ATOM   1594  CG  MET A 434     -11.143  -2.069  42.323  1.00 95.44      A  C
ATOM   1595  SD  MET A 434      -9.870  -3.294  42.749  1.00 95.35      A  S
ATOM   1596  CE  MET A 434     -10.661  -4.773  42.104  1.00 94.22      A  C
ATOM   1597  N   LYS A 435     -12.708   0.497  40.610  1.00 99.71      A  N
ATOM   1598  CA  LYS A 435     -13.320   1.734  41.088  1.00100.32      A  C
ATOM   1599  C   LYS A 435     -14.074   2.411  39.944  1.00100.66      A  C
ATOM   1600  O   LYS A 435     -14.784   1.692  39.203  1.00100.32      A  O
ATOM   1601  CB  LYS A 435     -12.255   2.663  41.660  1.00 99.90      A  C
ATOM   1613  C1  ICI A 600       2.290  -0.107  43.331  1.00 44.82      A  C
ATOM   1614  C2  ICI A 600       3.329   0.475  44.056  1.00 43.64      A  C
ATOM   1615  C3  ICI A 600       3.079   1.140  45.237  1.00 43.67      A  C
ATOM   1616  O3  ICI A 600       4.069   1.766  45.986  1.00 44.02      A  O
ATOM   1617  C4  ICI A 600       1.785   1.196  45.675  1.00 44.28      A  C
ATOM   1618  C5  ICI A 600       0.720   0.605  44.987  1.00 45.45      A  C
ATOM   1619  C6  ICI A 600      -0.665   0.733  45.608  1.00 44.73      A  C
ATOM   1620  C7  ICI A 600      -1.760   0.351  44.599  1.00 47.10      A  C
ATOM   1621  C8  ICI A 600      -1.393  -0.928  43.809  1.00 44.76      A  C
ATOM   1622  C9  ICI A 600      -0.160  -0.603  42.934  1.00 42.89      A  C
ATOM   1623  C10 ICI A 600       0.960  -0.063  43.778  1.00 42.86      A  C
ATOM   1624  C11 ICI A 600       0.246  -1.870  42.135  1.00 43.69      A  C
ATOM   1625  C12 ICI A 600      -0.875  -2.386  41.198  1.00 43.57      A  C
ATOM   1626  C13 ICI A 600      -2.151  -2.561  42.042  1.00 43.84      A  C
ATOM   1627  C14 ICI A 600      -2.514  -1.251  42.785  1.00 44.08      A  C
ATOM   1628  C15 ICI A 600      -3.858  -1.688  43.438  1.00 45.36      A  C
ATOM   1629  C16 ICI A 600      -4.537  -2.509  42.322  1.00 44.19      A  C
ATOM   1630  C17 ICI A 600      -3.459  -2.728  41.237  1.00 42.78      A  C
ATOM   1631  C18 ICI A 600      -1.884  -3.682  43.043  1.00 38.94      A  C
ATOM   1632  O17 ICI A 600      -3.506  -4.046  40.780  1.00 39.40      A  O
ATOM   1633  C19 ICI A 600      -1.882   1.512  43.570  1.00 48.05      A  C
ATOM   1634  C20 ICI A 600      -2.793   2.563  44.231  1.00 51.04      A  C
ATOM   1635  C21 ICI A 600      -3.073   3.656  43.214  1.00 53.06      A  C
ATOM   1636  C22 ICI A 600      -3.879   4.740  43.914  1.00 56.06      A  C
ATOM   1637  C23 ICI A 600      -5.188   4.959  43.138  1.00 58.53      A  C
ATOM   1638  C24 ICI A 600      -5.304   6.487  43.029  1.00 61.08      A  C
```

```
ATOM   1639  C25  ICI A 600      -4.622    7.003   41.760  1.00 63.08       A    C
ATOM   1640  C26  ICI A 600      -4.065    8.416   42.045  1.00 64.72       A    C
ATOM   1641  C27  ICI A 600      -3.977    9.195   40.732  1.00 63.90       A    C
ATOM   1642  C28  ICI A 600      -2.677   10.036   40.733  1.00 64.89       A    C
ATOM   1643  C29  ICI A 600      -2.885   11.007   39.546  1.00 65.68       A    C
ATOM   1644  O29  ICI A 600      -3.856   10.733   38.844  1.00 67.10       A    O
ATOM   1645  N29  ICI A 600      -2.017   12.029   39.398  1.00 63.65       A    N
ATOM   1646  C30  ICI A 600      -2.237   12.929   38.279  1.00 62.90       A    C
ATOM   1647  C31  ICI A 600      -0.901   12.215   40.327  1.00 63.16       A    C
ATOM   1648  C32  ICI A 600       0.417   12.100   39.576  1.00 62.36       A    C
ATOM   1649  C33  ICI A 600       1.514   12.832   40.345  1.00 64.26       A    C
ATOM   1650  C34  ICI A 600       2.197   11.974   41.424  1.00 63.80       A    C
ATOM   1602  C1   PMB A 700       3.312    4.857   27.410  1.00 61.26       A    C
ATOM   1603  C2   PMB A 700       4.016    5.635   28.326  1.00 59.18       A    C
ATOM   1604  C3   PMB A 700       3.769    5.398   29.678  1.00 58.95       A    C
ATOM   1605  C4   PMB A 700       2.862    4.453   30.103  1.00 58.63       A    C
ATOM   1606  C5   PMB A 700       2.171    3.704   29.148  1.00 60.78       A    C
ATOM   1607  C6   PMB A 700       2.393    3.907   27.807  1.00 61.69       A    C
ATOM   1608  S1   PMB A 700       1.601    3.019   26.521  1.00 62.54       A    S
ATOM   1609  O1   PMB A 700       0.840    1.816   27.092  1.00 61.19       A    O
ATOM   1610  O2   PMB A 700       2.797    2.484   25.858  1.00 62.51       A    O
ATOM   1611  O3   PMB A 700       0.684    3.875   25.910  1.00 62.46       A    O
ATOM   1612  HG   PMB A 700       4.824    6.528   31.020  1.00 56.38       A   HG
ATOM   1651  NI   IUM A 800       5.509   13.811   53.632  1.00 62.96       A   NI
ATOM   1688  NI   IUM A 801      14.952   -6.385   52.295  0.50 56.59       A   NI
ATOM   1652  OW   WAT W   1      16.175    9.381   43.686  1.00 36.68       W    O
ATOM   1653  OW   WAT W   2       5.238    1.724   57.009  1.00 49.33       W    O
ATOM   1654  OW   WAT W   3      18.394    8.222   50.305  1.00 42.47       W    O
ATOM   1655  OW   WAT W   4       7.165    4.118   52.496  1.00 44.02       W    O
ATOM   1656  OW   WAT W   5       5.787   10.226   55.519  1.00 42.43       W    O
ATOM   1657  OW   WAT W   6       7.197    8.414   46.444  1.00 36.84       W    O
ATOM   1658  OW   WAT W   7       8.265    7.764   44.139  1.00 39.16       W    O
ATOM   1659  OW   WAT W   8      10.779    8.267   43.783  1.00 46.68       W    O
ATOM   1660  OW   WAT W   9       7.466    6.038   48.061  1.00 41.90       W    O
ATOM   1661  OW   WAT W  10       9.586   13.834   48.465  1.00 52.85       W    O
ATOM   1662  OW   WAT W  11      15.866    8.681   41.004  1.00 45.28       W    O
ATOM   1663  OW   WAT W  12      11.116  -11.832   53.674  1.00 51.33       W    O
ATOM   1664  OW   WAT W  13       8.875  -14.288   44.767  1.00 49.56       W    O
ATOM   1665  OW   WAT W  14      23.617  -11.423   37.747  1.00 62.59       W    O
ATOM   1666  OW   WAT W  15      24.591   19.569   31.408  1.00 60.35       W    O
ATOM   1667  OW   WAT W  16       0.686   -9.737   31.157  1.00 53.54       W    O
ATOM   1668  OW   WAT W  17      29.084   -1.273   21.760  1.00 45.99       W    O
ATOM   1669  OW   WAT W  18      31.163   -2.164   23.953  1.00 58.99       W    O
ATOM   1670  OW   WAT W  19       6.816    3.152   45.474  1.00 37.50       W    O
ATOM   1671  OW   WAT W  20       7.050    7.948   49.853  1.00 51.13       W    O
ATOM   1672  OW   WAT W  21      11.661    2.697   47.225  1.00 49.48       W    O
ATOM   1673  OW   WAT W  22      -8.508   -6.170   57.938  1.00 54.72       W    O
ATOM   1674  OW   WAT W  23      15.237  -14.562   41.801  1.00 60.79       W    O
ATOM   1675  OW   WAT W  24      15.622   12.442   23.880  1.00 58.22       W    O
ATOM   1676  OW   WAT W  25      27.134   13.601   32.008  1.00 50.96       W    O
ATOM   1677  OW   WAT W  26      -2.547    9.604   35.399  1.00 56.71       W    O
ATOM   1678  OW   WAT W  27       6.271    2.760   50.118  1.00 45.90       W    O
ATOM   1679  OW   WAT W  28       9.603   -9.943   46.193  1.00 46.48       W    O
ATOM   1680  OW   WAT W  29       8.440    5.016   43.935  1.00 41.96       W    O
ATOM   1681  OW   WAT W  30      25.628   12.534   34.429  1.00 51.00       W    O
ATOM   1682  OW   WAT W  31      31.734    6.724   44.182  1.00 61.55       W    O
ATOM   1683  OW   WAT W  32      10.984   17.384   50.114  1.00 67.85       W    O
ATOM   1684  OW   WAT W  33      17.179    0.762   50.197  1.00 50.48       W    O
ATOM   1685  OW   WAT W  34      15.929    4.463   48.490  1.00 57.30       W    O
ATOM   1686  OW   WAT W  35      27.181   -0.447   23.324  1.00 46.73       W    O
ATOM   1687  OW   WAT W  36      14.033   13.971   50.437  1.00 60.52       W    O
```

130

```
ATOM   1689  OW   WAT W   37      10.021    4.916  49.431  1.00 63.92      W    O
ATOM   1690  OW   WAT W   38      12.279    5.773  56.547  1.00 55.04      W    O
ATOM   1691  OW   WAT W   39       0.804    6.266  35.468  1.00 47.05      W    O
ATOM   1692  OW   WAT W   40      31.625   11.381  38.154  1.00 58.13      W    O
ATOM   1693  OW   WAT W   41      34.501   10.913  44.470  1.00 66.80      W    O
ATOM   1694  OW   WAT W   42       6.057   17.009  47.920  1.00 53.35      W    O
ATOM   1695  OW   WAT W   43       3.819   25.148  31.273  1.00 50.79      W    O
ATOM   1696  OW   WAT W   44       6.560   15.956  27.986  1.00 66.09      W    O
ATOM   1697  OW   WAT W   45      10.134   -3.625  56.477  1.00 51.95      W    O
ATOM   1699  OW   WAT W   46       0.630    2.469  32.675  1.00 50.12      W    O
END
```

```
HEADER    NUCLEAR RECEPTOR
REMARK    This file is e2cia_ref5_1.pdb
TITLE     RAT OESTROGEN RECEPTOR BETA LIGAND-BINDING DOMAIN IN
TITLE    2 COMPLEX WITH 17b-OESTRADIOL
COMPND    MOL_ID: 1;
COMPND   2 MOLECULE: OESTROGEN RECEPTOR BETA;
COMPND   3 CHAIN: A;
COMPND   4 FRAGMENT: LIGAND-BINDING DOMAIN;
COMPND   5 SYNONYM: OESTROGEN RECEPTOR, ER-LBD;
COMPND   6 ENGINEERED: YES;
COMPND   7 BIOLOGICAL_UNIT: HOMODIMER;
COMPND   8 MOL_ID: 2;
COMPND   9 MOLECULE: COACTIVATOR INDEPENDENT OF AF2;
COMPND  10 CHAIN: B;
COMPND  11 FRAGMENT: NUCLEAR RECEPTOR BOX;
COMPND  12 SYNONYM: CIA;
COMPND  13 OTHER_DETAILS: COMPLEXED WITH OESTRADIOL,
COMPND  14 CARBOXYMETHYL GROUP
SOURCE    MOL_ID: 1;
SOURCE   2 ORGANISM_SCIENTIFIC: RATTUS NORVEGICUS;
SOURCE   3 ORGANISM_COMMON: NORWAY RAT;
SOURCE   4 STRAIN: GI724;
SOURCE   5 PLASMID: PLEX;
SOURCE   6 GENE: OESTROGEN RECEPTOR BETA;
SOURCE   7 EXPRESSION_SYSTEM: ESCHERICHIA COLI;
SOURCE   8 EXPRESSION_SYSTEM_STRAIN: GI724;
SOURCE   9 EXPRESSION_SYSTEM_PLASMID: PLEX
SOURCE   9 MOL_ID: 2
KEYWDS    NUCLEAR RECEPTOR, TRANSCRIPTION FACTOR, OESTROGEN,
KEYWDS   2 AGONIST, COACTIVATOR
EXPDTA    X-RAY DIFFRACTION
AUTHOR    A.C.W.PIKE,A.M.BRZOZOWSKI,M.CARLQUIST
REMARK    2
REMARK    2 RESOLUTION. 2.1  ANGSTROMS.
REMARK    3
REMARK    3 REFINEMENT.
REMARK    3   PROGRAM     : REFMAC 5.0
REMARK    3
REMARK    3    REFINEMENT TARGET : MAXIMUM LIKELIHOOD
REMARK    3
REMARK    3  DATA USED IN REFINEMENT.
REMARK    3   RESOLUTION RANGE HIGH (ANGSTROMS) :   2.10
REMARK    3   RESOLUTION RANGE LOW  (ANGSTROMS) :  40.00
REMARK    3   DATA CUTOFF            (SIGMA(F)) : NONE
REMARK    3   COMPLETENESS FOR RANGE        (%) :  99.80
REMARK    3   NUMBER OF REFLECTIONS             :  19671
REMARK    3
REMARK    3  FIT TO DATA USED IN REFINEMENT.
REMARK    3   CROSS-VALIDATION METHOD           : THROUGHOUT
REMARK    3   FREE R VALUE TEST SET SELECTION   : RANDOM
REMARK    3   R VALUE     (WORKING + TEST SET) : 0.20565
REMARK    3   R VALUE              (WORKING SET) : 0.20398
REMARK    3   FREE R VALUE                      : 0.23848
REMARK    3   FREE R VALUE TEST SET SIZE    (%) : 5.1
REMARK    3   FREE R VALUE TEST SET COUNT       : 1056
REMARK    3
REMARK    3  FIT IN THE HIGHEST RESOLUTION BIN.
```

132

```
REMARK   3    TOTAL NUMBER OF BINS USED              :     20
REMARK   3    BIN RESOLUTION RANGE HIGH              :   2.100
REMARK   3    BIN RESOLUTION RANGE LOW               :   2.154
REMARK   3    REFLECTION IN BIN     (WORKING SET) :    1410
REMARK   3    BIN R VALUE           (WORKING SET) :   0.218
REMARK   3    BIN FREE R VALUE SET COUNT             :      70
REMARK   3    BIN FREE R VALUE                       :   0.271
REMARK   3
REMARK   3  NUMBER OF NON-HYDROGEN ATOMS USED IN REFINEMENT.
REMARK   3    ALL ATOMS               :     1997
REMARK   3
REMARK   3  B VALUES.
REMARK   3    FROM WILSON PLOT          (A**2) :  37.60
REMARK   3    MEAN B VALUE      (OVERALL, A**2) :  32.169
REMARK   3    OVERALL ANISOTROPIC B VALUE.
REMARK   3     B11 (A**2) :      1.19
REMARK   3     B22 (A**2) :      1.19
REMARK   3     B33 (A**2) :     -2.38
REMARK   3     B12 (A**2) :      0.00
REMARK   3     B13 (A**2) :      0.00
REMARK   3     B23 (A**2) :      0.00
REMARK   3
REMARK   3  ESTIMATED OVERALL COORDINATE ERROR.
REMARK   3    ESU BASED ON R VALUE                     (A):   0.180
REMARK   3    ESU BASED ON FREE R VALUE                (A):   0.162
REMARK   3    ESU BASED ON MAXIMUM LIKELIHOOD          (A):   0.126
REMARK   3    ESU FOR B VALUES BASED ON MAXIMUM LIKELIHOOD (A**2):   4.619
REMARK   3
REMARK   3 CORRELATION COEFFICIENTS.
REMARK   3    CORRELATION COEFFICIENT FO-FC      :   0.950
REMARK   3    CORRELATION COEFFICIENT FO-FC FREE :   0.927
REMARK   3
REMARK   3  RMS DEVIATIONS FROM IDEAL VALUES        COUNT    RMS    WEIGHT
REMARK   3   BOND LENGTHS REFINED ATOMS       (A):  1954 ; 0.012 ; 0.022
REMARK   3   BOND ANGLES REFINED ATOMS  (DEGREES):  2637 ; 1.363 ; 2.006
REMARK   3   TORSION ANGLES, PERIOD 1   (DEGREES):   236 ; 3.449 ; 3.000
REMARK   3   TORSION ANGLES, PERIOD 3   (DEGREES):   398 ;14.150 ;15.000
REMARK   3   CHIRAL-CENTER RESTRAINTS       (A**3):   321 ; 0.095 ; 0.200
REMARK   3   GENERAL PLANES REFINED ATOMS     (A):  1353 ; 0.005 ; 0.020
REMARK   3   NON-BONDED CONTACTS REFINED ATOMS (A):  953 ; 0.230 ; 0.300
REMARK   3   H-BOND (X...Y) REFINED ATOMS     (A):    98 ; 0.164 ; 0.500
REMARK   3   SYMMETRY VDW REFINED ATOMS       (A):    38 ; 0.155 ; 0.300
REMARK   3   SYMMETRY H-BOND REFINED ATOMS    (A):     5 ; 0.083 ; 0.500
REMARK   3
REMARK   3  ISOTROPIC THERMAL FACTOR RESTRAINTS.    COUNT    RMS    WEIGHT
REMARK   3   MAIN-CHAIN BOND REFINED ATOMS  (A**2): 1200 ; 0.736 ; 1.500
REMARK   3   MAIN-CHAIN ANGLE REFINED ATOMS (A**2): 1938 ; 1.320 ; 2.000
REMARK   3   SIDE-CHAIN BOND REFINED ATOMS  (A**2):  754 ; 2.045 ; 3.000
REMARK   3   SIDE-CHAIN ANGLE REFINED ATOMS (A**2):  699 ; 3.348 ; 4.500
REMARK   3
REMARK   3  NCS RESTRAINTS STATISTICS
REMARK   3   NUMBER OF NCS GROUPS : NULL
REMARK   3
REMARK   3
REMARK   3  TLS DETAILS
REMARK   3   NUMBER OF TLS GROUPS  :    2
REMARK   3
REMARK   3   TLS GROUP :     1
REMARK   3    NUMBER OF COMPONENTS GROUP :    2
REMARK   3    COMPONENTS        C SSSEQI   TO  C SSSEQI
REMARK   3    RESIDUE RANGE :    A    217          A    453
```

```
REMARK   3       RESIDUE RANGE :   A   600        A   600
REMARK   3       ORIGIN FOR THE GROUP (A):   51.2177   41.0431   76.6166
REMARK   3       T TENSOR
REMARK   3         T11:    0.0161 T22:    0.0914
REMARK   3         T33:    0.0629 T12:   -0.0364
REMARK   3         T13:   -0.0108 T23:    0.0020
REMARK   3       L TENSOR
REMARK   3         L11:    2.5491 L22:    1.6048
REMARK   3         L33:    2.9366 L12:    0.0258
REMARK   3         L13:    0.0043 L23:   -0.4989
REMARK   3       S TENSOR
REMARK   3         S11:   -0.0196 S12:   -0.0562 S13:   -0.3230
REMARK   3         S21:   -0.0493 S22:    0.0571 S23:    0.1700
REMARK   3         S31:    0.3174 S32:   -0.2621 S33:   -0.0375
REMARK   3
REMARK   3    TLS GROUP :     2
REMARK   3     NUMBER OF COMPONENTS GROUP :    1
REMARK   3     COMPONENTS         C SSSEQI     TO    C SSSEQI
REMARK   3     RESIDUE RANGE :   B     5        B    15
REMARK   3     ORIGIN FOR THE GROUP (A):   37.6560   42.6768   91.8264
REMARK   3       T TENSOR
REMARK   3         T11:    0.0678 T22:    0.7165
REMARK   3         T33:    0.2475 T12:    0.0355
REMARK   3         T13:    0.1043 T23:    0.1654
REMARK   3       L TENSOR
REMARK   3         L11:   22.5821 L22:   51.5960
REMARK   3         L33:   21.5397 L12:    3.5110
REMARK   3         L13:    1.5532 L23:    4.2243
REMARK   3       S TENSOR
REMARK   3         S11:   -0.2183 S12:   -2.6042 S13:   -0.9330
REMARK   3         S21:    2.4880 S22:    0.1297 S23:    0.9965
REMARK   3         S31:    1.0177 S32:    0.1440 S33:    0.0886
REMARK   3
REMARK   3
REMARK   3  BULK SOLVENT MODELLING.
REMARK   3   METHOD USED : BABINET MODEL WITH MASK
REMARK   3   PARAMETERS FOR MASK CALCULATION
REMARK   3   VDW PROBE RADIUS    :   1.40
REMARK   3   ION PROBE RADIUS    :   0.80
REMARK   3   SHRINKAGE RADIUS    :   0.80
REMARK   3
REMARK   3  OTHER REFINEMENT REMARKS: NULL
REMARK   3
REMARK   6
REMARK   6  Sidechains missing for R239,K255,R379,K398,K437,
REMARK   6  Multiple confs for R284,M334,R341,M365,M415,M428,C436,W1
LINK             ARG A 239                 MET A 242                   gap
LINK             LEU A 368                 ALA A 375                   gap
CRYST1   62.550   62.550  171.700  90.00  90.00  90.00 P 41 2 2
SCALE1      0.015987  0.000000  0.000000        0.00000
SCALE2      0.000000  0.015987  0.000000        0.00000
SCALE3      0.000000  0.000000  0.005824        0.00000
ATOM      1  N   THR A 217      49.328  65.582  84.409  1.00 50.05           A N
ATOM      2  CA  THR A 217      50.454  65.255  83.477  1.00 49.58           A C
ATOM      3  C   THR A 217      51.815  65.114  84.183  1.00 48.30           A C
ATOM      4  O   THR A 217      52.301  66.039  84.846  1.00 48.58           A O
ATOM      5  CB  THR A 217      50.532  66.313  82.349  1.00 50.25           A C
ATOM      6  OG1 THR A 217      49.425  66.133  81.456  1.00 51.96           A O
ATOM      7  CG2 THR A 217      51.739  66.066  81.450  1.00 50.75           A C
ATOM      8  N   LEU A 218      52.421  63.943  84.028  1.00 46.15           A N
ATOM      9  CA  LEU A 218      53.727  63.674  84.592  1.00 43.49           A C
```

| ATOM | 10 | C   | LEU A 218 | 54.724 | 63.932 | 83.500 | 1.00 | 41.99 | A | C |
| ATOM | 11 | O   | LEU A 218 | 54.362 | 64.030 | 82.333 | 1.00 | 41.22 | A | O |
| ATOM | 12 | CB  | LEU A 218 | 53.814 | 62.205 | 84.986 | 1.00 | 43.57 | A | C |
| ATOM | 13 | CG  | LEU A 218 | 52.778 | 61.724 | 86.003 | 1.00 | 43.42 | A | C |
| ATOM | 14 | CD1 | LEU A 218 | 52.627 | 60.213 | 85.959 | 1.00 | 45.37 | A | C |
| ATOM | 15 | CD2 | LEU A 218 | 53.149 | 62.175 | 87.401 | 1.00 | 42.57 | A | C |
| ATOM | 16 | N   | SER A 219 | 55.987 | 64.051 | 83.856 | 1.00 | 40.30 | A | N |
| ATOM | 17 | CA  | SER A 219 | 56.993 | 64.094 | 82.820 | 1.00 | 39.47 | A | C |
| ATOM | 18 | C   | SER A 219 | 57.080 | 62.675 | 82.213 | 1.00 | 38.64 | A | C |
| ATOM | 19 | O   | SER A 219 | 56.541 | 61.714 | 82.779 | 1.00 | 37.10 | A | O |
| ATOM | 20 | CB  | SER A 219 | 58.340 | 64.499 | 83.413 | 1.00 | 39.82 | A | C |
| ATOM | 21 | OG  | SER A 219 | 58.840 | 63.482 | 84.260 | 1.00 | 40.24 | A | O |
| ATOM | 22 | N   | PRO A 220 | 57.725 | 62.540 | 81.058 | 1.00 | 38.17 | A | N |
| ATOM | 23 | CA  | PRO A 220 | 57.905 | 61.210 | 80.464 | 1.00 | 37.78 | A | C |
| ATOM | 24 | C   | PRO A 220 | 58.728 | 60.349 | 81.406 | 1.00 | 37.11 | A | C |
| ATOM | 25 | O   | PRO A 220 | 58.406 | 59.170 | 81.598 | 1.00 | 36.38 | A | O |
| ATOM | 26 | CB  | PRO A 220 | 58.668 | 61.486 | 79.166 | 1.00 | 38.01 | A | C |
| ATOM | 27 | CG  | PRO A 220 | 58.389 | 62.957 | 78.881 | 1.00 | 39.76 | A | C |
| ATOM | 28 | CD  | PRO A 220 | 58.325 | 63.613 | 80.242 | 1.00 | 38.52 | A | C |
| ATOM | 29 | N   | GLU A 221 | 59.752 | 60.914 | 82.031 | 1.00 | 35.88 | A | N |
| ATOM | 30 | CA  | GLU A 221 | 60.486 | 60.065 | 82.943 | 1.00 | 35.77 | A | C |
| ATOM | 31 | C   | GLU A 221 | 59.670 | 59.680 | 84.172 | 1.00 | 34.13 | A | C |
| ATOM | 32 | O   | GLU A 221 | 59.796 | 58.574 | 84.660 | 1.00 | 33.07 | A | O |
| ATOM | 33 | CB  | GLU A 221 | 61.893 | 60.575 | 83.316 | 1.00 | 36.49 | A | C |
| ATOM | 34 | CG  | GLU A 221 | 62.019 | 62.011 | 83.717 | 1.00 | 41.04 | A | C |
| ATOM | 35 | CD  | GLU A 221 | 62.436 | 62.864 | 82.537 | 1.00 | 46.78 | A | C |
| ATOM | 36 | OE1 | GLU A 221 | 63.651 | 63.195 | 82.420 | 1.00 | 48.62 | A | O |
| ATOM | 37 | OE2 | GLU A 221 | 61.550 | 63.181 | 81.721 | 1.00 | 47.20 | A | O |
| ATOM | 38 | N   | GLN A 222 | 58.843 | 60.586 | 84.680 | 1.00 | 32.80 | A | N |
| ATOM | 39 | CA  | GLN A 222 | 57.997 | 60.234 | 85.815 | 1.00 | 31.83 | A | C |
| ATOM | 40 | C   | GLN A 222 | 57.044 | 59.099 | 85.411 | 1.00 | 30.39 | A | C |
| ATOM | 41 | O   | GLN A 222 | 56.813 | 58.149 | 86.162 | 1.00 | 29.10 | A | O |
| ATOM | 42 | CB  | GLN A 222 | 57.218 | 61.462 | 86.334 | 1.00 | 32.05 | A | C |
| ATOM | 43 | CG  | GLN A 222 | 58.141 | 62.466 | 87.026 | 1.00 | 34.61 | A | C |
| ATOM | 44 | CD  | GLN A 222 | 57.497 | 63.821 | 87.329 | 1.00 | 37.70 | A | C |
| ATOM | 45 | OE1 | GLN A 222 | 56.447 | 64.179 | 86.782 | 1.00 | 37.66 | A | O |
| ATOM | 46 | NE2 | GLN A 222 | 58.140 | 64.576 | 88.204 | 1.00 | 38.45 | A | N |
| ATOM | 47 | N   | LEU A 223 | 56.511 | 59.194 | 84.205 | 1.00 | 29.24 | A | N |
| ATOM | 48 | CA  | LEU A 223 | 55.583 | 58.179 | 83.725 | 1.00 | 29.40 | A | C |
| ATOM | 49 | C   | LEU A 223 | 56.250 | 56.809 | 83.629 | 1.00 | 28.49 | A | C |
| ATOM | 50 | O   | LEU A 223 | 55.725 | 55.802 | 84.115 | 1.00 | 28.47 | A | O |
| ATOM | 51 | CB  | LEU A 223 | 55.012 | 58.585 | 82.376 | 1.00 | 29.10 | A | C |
| ATOM | 52 | CG  | LEU A 223 | 54.047 | 57.592 | 81.747 | 1.00 | 31.79 | A | C |
| ATOM | 53 | CD1 | LEU A 223 | 53.032 | 57.172 | 82.813 | 1.00 | 34.05 | A | C |
| ATOM | 54 | CD2 | LEU A 223 | 53.340 | 58.234 | 80.514 | 1.00 | 33.39 | A | C |
| ATOM | 55 | N   | VAL A 224 | 57.420 | 56.772 | 83.018 | 1.00 | 28.14 | A | N |
| ATOM | 56 | CA  | VAL A 224 | 58.115 | 55.493 | 82.863 | 1.00 | 28.37 | A | C |
| ATOM | 57 | C   | VAL A 224 | 58.413 | 54.877 | 84.252 | 1.00 | 27.04 | A | C |
| ATOM | 58 | O   | VAL A 224 | 58.252 | 53.697 | 84.453 | 1.00 | 26.15 | A | O |
| ATOM | 59 | CB  | VAL A 224 | 59.408 | 55.659 | 82.028 | 1.00 | 28.61 | A | C |
| ATOM | 60 | CG1 | VAL A 224 | 60.202 | 54.370 | 82.034 | 1.00 | 28.15 | A | C |
| ATOM | 61 | CG2 | VAL A 224 | 59.044 | 56.058 | 80.581 | 1.00 | 30.01 | A | C |
| ATOM | 62 | N   | LEU A 225 | 58.814 | 55.696 | 85.203 | 1.00 | 26.61 | A | N |
| ATOM | 63 | CA  | LEU A 225 | 59.086 | 55.220 | 86.558 | 1.00 | 27.32 | A | C |
| ATOM | 64 | C   | LEU A 225 | 57.811 | 54.679 | 87.226 | 1.00 | 27.45 | A | C |
| ATOM | 65 | O   | LEU A 225 | 57.873 | 53.742 | 88.008 | 1.00 | 26.14 | A | O |
| ATOM | 66 | CB  | LEU A 225 | 59.702 | 56.329 | 87.422 | 1.00 | 28.11 | A | C |
| ATOM | 67 | CG  | LEU A 225 | 61.214 | 56.627 | 87.294 | 1.00 | 30.12 | A | C |
| ATOM | 68 | CD1 | LEU A 225 | 61.600 | 57.740 | 88.260 | 1.00 | 32.50 | A | C |
| ATOM | 69 | CD2 | LEU A 225 | 62.072 | 55.420 | 87.558 | 1.00 | 26.67 | A | C |
| ATOM | 70 | N   | THR A 226 | 56.660 | 55.292 | 86.940 | 1.00 | 27.59 | A | N |

| ATOM | 71  | CA  | THR A 226 | 55.398 | 54.777 | 87.472 | 1.00 | 27.77 | A | C |
| ATOM | 72  | C   | THR A 226 | 55.099 | 53.412 | 86.832 | 1.00 | 27.14 | A | C |
| ATOM | 73  | O   | THR A 226 | 54.622 | 52.517 | 87.495 | 1.00 | 26.62 | A | O |
| ATOM | 74  | CB  | THR A 226 | 54.253 | 55.775 | 87.187 | 1.00 | 28.67 | A | C |
| ATOM | 75  | OG1 | THR A 226 | 54.564 | 57.003 | 87.855 | 1.00 | 28.43 | A | O |
| ATOM | 76  | CG2 | THR A 226 | 52.941 | 55.329 | 87.859 | 1.00 | 30.03 | A | C |
| ATOM | 77  | N   | LEU A 227 | 55.413 | 53.240 | 85.552 | 1.00 | 26.63 | A | N |
| ATOM | 78  | CA  | LEU A 227 | 55.166 | 51.962 | 84.887 | 1.00 | 26.70 | A | C |
| ATOM | 79  | C   | LEU A 227 | 56.060 | 50.876 | 85.485 | 1.00 | 26.88 | A | C |
| ATOM | 80  | O   | LEU A 227 | 55.642 | 49.736 | 85.678 | 1.00 | 27.39 | A | O |
| ATOM | 81  | CB  | LEU A 227 | 55.419 | 52.070 | 83.368 | 1.00 | 26.49 | A | C |
| ATOM | 82  | CG  | LEU A 227 | 54.523 | 53.039 | 82.601 | 1.00 | 27.13 | A | C |
| ATOM | 83  | CD1 | LEU A 227 | 54.791 | 52.947 | 81.128 | 1.00 | 26.80 | A | C |
| ATOM | 84  | CD2 | LEU A 227 | 53.049 | 52.733 | 82.907 | 1.00 | 26.58 | A | C |
| ATOM | 85  | N   | LEU A 228 | 57.313 | 51.222 | 85.735 | 1.00 | 26.41 | A | N |
| ATOM | 86  | CA  | LEU A 228 | 58.234 | 50.296 | 86.402 | 1.00 | 26.40 | A | C |
| ATOM | 87  | C   | LEU A 228 | 57.650 | 49.829 | 87.747 | 1.00 | 26.62 | A | C |
| ATOM | 88  | O   | LEU A 228 | 57.598 | 48.636 | 88.039 | 1.00 | 26.30 | A | O |
| ATOM | 89  | CB  | LEU A 228 | 59.573 | 51.007 | 86.722 | 1.00 | 25.42 | A | C |
| ATOM | 90  | CG  | LEU A 228 | 60.514 | 50.106 | 87.549 | 1.00 | 25.88 | A | C |
| ATOM | 91  | CD1 | LEU A 228 | 60.821 | 48.768 | 86.843 | 1.00 | 25.26 | A | C |
| ATOM | 92  | CD2 | LEU A 228 | 61.831 | 50.842 | 87.894 | 1.00 | 28.22 | A | C |
| ATOM | 93  | N   | GLU A 229 | 57.244 | 50.767 | 88.582 | 1.00 | 25.57 | A | N |
| ATOM | 94  | CA  | GLU A 229 | 56.773 | 50.363 | 89.913 | 1.00 | 28.01 | A | C |
| ATOM | 95  | C   | GLU A 229 | 55.442 | 49.598 | 89.854 | 1.00 | 28.37 | A | C |
| ATOM | 96  | O   | GLU A 229 | 55.062 | 48.900 | 90.804 | 1.00 | 29.07 | A | O |
| ATOM | 97  | CB  | GLU A 229 | 56.678 | 51.565 | 90.861 | 1.00 | 27.47 | A | C |
| ATOM | 98  | CG  | GLU A 229 | 56.790 | 51.173 | 92.332 | 1.00 | 31.46 | A | C |
| ATOM | 99  | CD  | GLU A 229 | 58.107 | 50.425 | 92.633 | 1.00 | 31.78 | A | C |
| ATOM | 100 | OE1 | GLU A 229 | 59.195 | 51.027 | 92.485 | 1.00 | 28.21 | A | O |
| ATOM | 101 | OE2 | GLU A 229 | 58.048 | 49.237 | 93.031 | 1.00 | 30.15 | A | O |
| ATOM | 102 | N   | ALA A 230 | 54.748 | 49.724 | 88.733 | 1.00 | 27.76 | A | N |
| ATOM | 103 | CA  | ALA A 230 | 53.486 | 49.011 | 88.547 | 1.00 | 28.55 | A | C |
| ATOM | 104 | C   | ALA A 230 | 53.662 | 47.508 | 88.234 | 1.00 | 28.66 | A | C |
| ATOM | 105 | O   | ALA A 230 | 52.714 | 46.751 | 88.310 | 1.00 | 28.18 | A | O |
| ATOM | 106 | CB  | ALA A 230 | 52.665 | 49.695 | 87.443 | 1.00 | 27.25 | A | C |
| ATOM | 107 | N   | GLU A 231 | 54.871 | 47.095 | 87.873 | 1.00 | 28.40 | A | N |
| ATOM | 108 | CA  | GLU A 231 | 55.104 | 45.732 | 87.425 | 1.00 | 29.31 | A | C |
| ATOM | 109 | C   | GLU A 231 | 54.551 | 44.692 | 88.396 | 1.00 | 29.76 | A | C |
| ATOM | 110 | O   | GLU A 231 | 54.757 | 44.781 | 89.597 | 1.00 | 29.54 | A | O |
| ATOM | 111 | CB  | GLU A 231 | 56.619 | 45.471 | 87.191 | 1.00 | 29.28 | A | C |
| ATOM | 112 | CG  | GLU A 231 | 57.152 | 46.065 | 85.886 | 1.00 | 29.56 | A | C |
| ATOM | 113 | CD  | GLU A 231 | 56.716 | 45.242 | 84.708 | 1.00 | 33.27 | A | C |
| ATOM | 114 | OE1 | GLU A 231 | 57.375 | 44.212 | 84.466 | 1.00 | 32.92 | A | O |
| ATOM | 115 | OE2 | GLU A 231 | 55.705 | 45.608 | 84.044 | 1.00 | 30.85 | A | O |
| ATOM | 116 | N   | PRO A 232 | 53.933 | 43.656 | 87.854 | 1.00 | 30.40 | A | N |
| ATOM | 117 | CA  | PRO A 232 | 53.293 | 42.618 | 88.683 | 1.00 | 30.85 | A | C |
| ATOM | 118 | C   | PRO A 232 | 54.333 | 41.703 | 89.318 | 1.00 | 31.23 | A | C |
| ATOM | 119 | O   | PRO A 232 | 55.414 | 41.619 | 88.798 | 1.00 | 30.01 | A | O |
| ATOM | 120 | CB  | PRO A 232 | 52.508 | 41.779 | 87.678 | 1.00 | 30.50 | A | C |
| ATOM | 121 | CG  | PRO A 232 | 52.927 | 42.207 | 86.314 | 1.00 | 31.42 | A | C |
| ATOM | 122 | CD  | PRO A 232 | 53.838 | 43.397 | 86.403 | 1.00 | 30.37 | A | C |
| ATOM | 123 | N   | PRO A 233 | 53.992 | 41.002 | 90.394 | 1.00 | 32.33 | A | N |
| ATOM | 124 | CA  | PRO A 233 | 54.911 | 40.012 | 90.961 | 1.00 | 32.72 | A | C |
| ATOM | 125 | C   | PRO A 233 | 55.047 | 38.869 | 89.965 | 1.00 | 33.35 | A | C |
| ATOM | 126 | O   | PRO A 233 | 54.152 | 38.674 | 89.144 | 1.00 | 33.19 | A | O |
| ATOM | 127 | CB  | PRO A 233 | 54.161 | 39.478 | 92.181 | 1.00 | 33.52 | A | C |
| ATOM | 128 | CG  | PRO A 233 | 52.989 | 40.342 | 92.389 | 1.00 | 33.71 | A | C |
| ATOM | 129 | CD  | PRO A 233 | 52.714 | 41.080 | 91.121 | 1.00 | 32.10 | A | C |
| ATOM | 130 | N   | ASN A 234 | 56.139 | 38.126 | 90.026 | 1.00 | 32.67 | A | N |
| ATOM | 131 | CA  | ASN A 234 | 56.252 | 36.944 | 89.198 | 1.00 | 33.40 | A | C |

| | | | | | | | | | | |
|---|---|---|---|---|---|---|---|---|---|---|
| ATOM | 132 | C | ASN | A | 234 | 55.484 | 35.766 | 89.818 | 1.00 33.29 | A C |
| ATOM | 133 | O | ASN | A | 234 | 55.253 | 35.740 | 91.012 | 1.00 31.27 | A O |
| ATOM | 134 | CB | ASN | A | 234 | 57.707 | 36.596 | 88.999 | 1.00 33.87 | A C |
| ATOM | 135 | CG | ASN | A | 234 | 58.427 | 37.686 | 88.246 | 1.00 35.30 | A C |
| ATOM | 136 | OD1 | ASN | A | 234 | 57.830 | 38.305 | 87.378 | 1.00 35.97 | A O |
| ATOM | 137 | ND2 | ASN | A | 234 | 59.685 | 37.961 | 88.602 | 1.00 35.15 | A N |
| ATOM | 138 | N | VAL | A | 235 | 55.109 | 34.817 | 88.970 | 1.00 33.53 | A N |
| ATOM | 139 | CA | VAL | A | 235 | 54.322 | 33.666 | 89.344 | 1.00 35.06 | A C |
| ATOM | 140 | C | VAL | A | 235 | 55.063 | 32.396 | 89.018 | 1.00 35.16 | A C |
| ATOM | 141 | O | VAL | A | 235 | 55.799 | 32.339 | 88.042 | 1.00 34.87 | A O |
| ATOM | 142 | CB | VAL | A | 235 | 53.025 | 33.598 | 88.507 | 1.00 35.44 | A C |
| ATOM | 143 | CG1 | VAL | A | 235 | 52.265 | 32.333 | 88.847 | 1.00 36.24 | A C |
| ATOM | 144 | CG2 | VAL | A | 235 | 52.170 | 34.826 | 88.743 | 1.00 36.92 | A C |
| ATOM | 145 | N | LEU | A | 236 | 54.849 | 31.385 | 89.841 | 1.00 35.41 | A N |
| ATOM | 146 | CA | LEU | A | 236 | 55.399 | 30.063 | 89.625 | 1.00 37.91 | A C |
| ATOM | 147 | C | LEU | A | 236 | 54.253 | 29.103 | 89.374 | 1.00 39.58 | A C |
| ATOM | 148 | O | LEU | A | 236 | 53.248 | 29.119 | 90.094 | 1.00 39.11 | A O |
| ATOM | 149 | CB | LEU | A | 236 | 56.124 | 29.580 | 90.867 | 1.00 37.57 | A C |
| ATOM | 150 | CG | LEU | A | 236 | 57.481 | 30.191 | 91.151 | 1.00 38.20 | A C |
| ATOM | 151 | CD1 | LEU | A | 236 | 58.059 | 29.559 | 92.398 | 1.00 36.80 | A C |
| ATOM | 152 | CD2 | LEU | A | 236 | 58.384 | 29.950 | 89.959 | 1.00 39.57 | A C |
| ATOM | 153 | N | VAL | A | 237 | 54.398 | 28.263 | 88.362 | 1.00 41.95 | A N |
| ATOM | 154 | CA | VAL | A | 237 | 53.365 | 27.278 | 88.077 | 1.00 44.60 | A C |
| ATOM | 155 | C | VAL | A | 237 | 53.328 | 26.229 | 89.176 | 1.00 46.06 | A C |
| ATOM | 156 | O | VAL | A | 237 | 52.455 | 26.269 | 90.039 | 1.00 46.54 | A O |
| ATOM | 157 | CB | VAL | A | 237 | 53.572 | 26.597 | 86.727 | 1.00 44.58 | A C |
| ATOM | 158 | CG1 | VAL | A | 237 | 52.393 | 25.708 | 86.414 | 1.00 45.40 | A C |
| ATOM | 159 | CG2 | VAL | A | 237 | 53.738 | 27.636 | 85.650 | 1.00 45.07 | A C |
| ATOM | 160 | N | SER | A | 238 | 54.273 | 25.295 | 89.166 | 1.00 48.00 | A N |
| ATOM | 161 | CA | SER | A | 238 | 54.258 | 24.249 | 90.192 | 1.00 49.68 | A C |
| ATOM | 162 | C | SER | A | 238 | 55.108 | 23.016 | 89.890 | 1.00 50.98 | A C |
| ATOM | 163 | O | SER | A | 238 | 56.247 | 22.910 | 90.351 | 1.00 51.68 | A O |
| ATOM | 164 | CB | SER | A | 238 | 52.819 | 23.805 | 90.479 | 1.00 49.88 | A C |
| ATOM | 165 | OG | SER | A | 238 | 52.790 | 22.696 | 91.366 | 1.00 48.90 | A O |
| ATOM | 166 | N | ARG | A | 239 | 54.541 | 22.068 | 89.144 | 1.00 52.19 | A N |
| ATOM | 167 | CA | ARG | A | 239 | 55.231 | 20.798 | 88.868 | 1.00 52.75 | A C |
| ATOM | 168 | C | ARG | A | 239 | 54.850 | 20.180 | 87.519 | 1.00 53.12 | A C |
| ATOM | 169 | O | ARG | A | 239 | 55.568 | 20.333 | 86.525 | 1.00 53.28 | A O |
| ATOM | 170 | CB | ARG | A | 239 | 54.961 | 19.789 | 89.992 | 1.00 52.92 | A C |
| ATOM | 177 | N | MET | A | 242 | 55.966 | 14.613 | 85.933 | 1.00 42.79 | A N |
| ATOM | 178 | CA | MET | A | 242 | 56.374 | 13.676 | 84.890 | 1.00 42.66 | A C |
| ATOM | 179 | C | MET | A | 242 | 56.449 | 14.379 | 83.529 | 1.00 42.27 | A C |
| ATOM | 180 | O | MET | A | 242 | 56.238 | 15.593 | 83.455 | 1.00 42.30 | A O |
| ATOM | 181 | CB | MET | A | 242 | 55.414 | 12.494 | 84.842 | 1.00 42.97 | A C |
| ATOM | 182 | N | PRO | A | 243 | 56.775 | 13.632 | 82.467 | 1.00 41.67 | A N |
| ATOM | 183 | CA | PRO | A | 243 | 56.846 | 14.206 | 81.114 | 1.00 40.88 | A C |
| ATOM | 184 | C | PRO | A | 243 | 55.492 | 14.756 | 80.675 | 1.00 39.97 | A C |
| ATOM | 185 | O | PRO | A | 243 | 54.448 | 14.203 | 81.035 | 1.00 40.09 | A O |
| ATOM | 186 | CB | PRO | A | 243 | 57.236 | 13.011 | 80.231 | 1.00 41.05 | A C |
| ATOM | 187 | CG | PRO | A | 243 | 57.800 | 11.974 | 81.167 | 1.00 41.48 | A C |
| ATOM | 188 | CD | PRO | A | 243 | 57.114 | 12.195 | 82.484 | 1.00 41.63 | A C |
| ATOM | 189 | N | PHE | A | 244 | 55.520 | 15.831 | 79.897 | 1.00 38.69 | A N |
| ATOM | 190 | CA | PHE | A | 244 | 54.309 | 16.492 | 79.427 | 1.00 37.49 | A C |
| ATOM | 191 | C | PHE | A | 244 | 53.396 | 15.634 | 78.546 | 1.00 36.55 | A C |
| ATOM | 192 | O | PHE | A | 244 | 53.859 | 14.812 | 77.760 | 1.00 36.45 | A O |
| ATOM | 193 | CB | PHE | A | 244 | 54.694 | 17.738 | 78.631 | 1.00 37.86 | A C |
| ATOM | 194 | CG | PHE | A | 244 | 55.034 | 18.930 | 79.482 | 1.00 38.00 | A C |
| ATOM | 195 | CD1 | PHE | A | 244 | 54.090 | 19.488 | 80.326 | 1.00 38.36 | A C |
| ATOM | 196 | CD2 | PHE | A | 244 | 56.295 | 19.498 | 79.427 | 1.00 38.11 | A C |
| ATOM | 197 | CE1 | PHE | A | 244 | 54.399 | 20.589 | 81.107 | 1.00 38.30 | A C |
| ATOM | 198 | CE2 | PHE | A | 244 | 56.609 | 20.598 | 80.206 | 1.00 37.68 | A C |

| | | | | | | | | | | |
|---|---|---|---|---|---|---|---|---|---|---|
| ATOM | 199 | CZ | PHE A 244 | 55.661 | 21.141 | 81.048 | 1.00 | 37.74 | A | C |
| ATOM | 200 | N | THR A 245 | 52.092 | 15.830 | 78.706 | 1.00 | 35.10 | A | N |
| ATOM | 201 | CA | THR A 245 | 51.089 | 15.268 | 77.815 | 1.00 | 33.73 | A | C |
| ATOM | 202 | C | THR A 245 | 50.326 | 16.480 | 77.310 | 1.00 | 33.32 | A | C |
| ATOM | 203 | O | THR A 245 | 50.466 | 17.573 | 77.863 | 1.00 | 32.67 | A | O |
| ATOM | 204 | CB | THR A 245 | 50.093 | 14.422 | 78.573 | 1.00 | 33.72 | A | C |
| ATOM | 205 | OG1 | THR A 245 | 49.601 | 15.187 | 79.677 | 1.00 | 32.06 | A | O |
| ATOM | 206 | CG2 | THR A 245 | 50.760 | 13.174 | 79.214 | 1.00 | 33.47 | A | C |
| ATOM | 207 | N | GLU A 246 | 49.498 | 16.292 | 76.290 | 1.00 | 32.60 | A | N |
| ATOM | 208 | CA | GLU A 246 | 48.680 | 17.387 | 75.797 | 1.00 | 32.65 | A | C |
| ATOM | 209 | C | GLU A 246 | 47.924 | 18.002 | 76.969 | 1.00 | 32.03 | A | C |
| ATOM | 210 | O | GLU A 246 | 47.874 | 19.227 | 77.125 | 1.00 | 31.28 | A | O |
| ATOM | 211 | CB | GLU A 246 | 47.698 | 16.905 | 74.730 | 1.00 | 32.87 | A | C |
| ATOM | 212 | CG | GLU A 246 | 46.794 | 18.007 | 74.200 | 1.00 | 33.81 | A | C |
| ATOM | 213 | CD | GLU A 246 | 46.018 | 17.576 | 72.975 | 1.00 | 35.20 | A | C |
| ATOM | 214 | OE1 | GLU A 246 | 45.045 | 16.799 | 73.113 | 1.00 | 36.37 | A | O |
| ATOM | 215 | OE2 | GLU A 246 | 46.392 | 18.014 | 71.872 | 1.00 | 36.51 | A | O |
| ATOM | 216 | N | ALA A 247 | 47.361 | 17.131 | 77.801 | 1.00 | 31.16 | A | N |
| ATOM | 217 | CA | ALA A 247 | 46.594 | 17.550 | 78.967 | 1.00 | 30.87 | A | C |
| ATOM | 218 | C | ALA A 247 | 47.411 | 18.310 | 80.020 | 1.00 | 30.54 | A | C |
| ATOM | 219 | O | ALA A 247 | 47.005 | 19.381 | 80.460 | 1.00 | 30.27 | A | O |
| ATOM | 220 | CB | ALA A 247 | 45.915 | 16.356 | 79.602 | 1.00 | 30.84 | A | C |
| ATOM | 221 | N | SER A 248 | 48.543 | 17.757 | 80.440 | 1.00 | 30.16 | A | N |
| ATOM | 222 | CA | SER A 248 | 49.315 | 18.402 | 81.498 | 1.00 | 30.11 | A | C |
| ATOM | 223 | C | SER A 248 | 49.976 | 19.704 | 81.059 | 1.00 | 29.84 | A | C |
| ATOM | 224 | O | SER A 248 | 50.092 | 20.638 | 81.853 | 1.00 | 30.09 | A | O |
| ATOM | 225 | CB | SER A 248 | 50.309 | 17.431 | 82.161 | 1.00 | 29.92 | A | C |
| ATOM | 226 | OG | SER A 248 | 51.361 | 17.048 | 81.295 | 1.00 | 29.93 | A | O |
| ATOM | 227 | N | MET A 249 | 50.387 | 19.797 | 79.799 | 1.00 | 29.63 | A | N |
| ATOM | 228 | CA | MET A 249 | 50.959 | 21.054 | 79.333 | 1.00 | 29.78 | A | C |
| ATOM | 229 | C | MET A 249 | 49.891 | 22.148 | 79.352 | 1.00 | 29.26 | A | C |
| ATOM | 230 | O | MET A 249 | 50.107 | 23.218 | 79.918 | 1.00 | 29.20 | A | O |
| ATOM | 231 | CB | MET A 249 | 51.600 | 20.937 | 77.952 | 1.00 | 29.75 | A | C |
| ATOM | 232 | CG | MET A 249 | 52.253 | 22.234 | 77.529 | 1.00 | 32.29 | A | C |
| ATOM | 233 | SD | MET A 249 | 53.373 | 22.139 | 76.117 | 1.00 | 35.32 | A | S |
| ATOM | 234 | CE | MET A 249 | 54.461 | 20.869 | 76.679 | 1.00 | 34.31 | A | C |
| ATOM | 235 | N | MET A 250 | 48.729 | 21.873 | 78.767 | 1.00 | 28.66 | A | N |
| ATOM | 236 | CA | MET A 250 | 47.658 | 22.864 | 78.770 | 1.00 | 28.34 | A | C |
| ATOM | 237 | C | MET A 250 | 47.288 | 23.234 | 80.206 | 1.00 | 28.27 | A | C |
| ATOM | 238 | O | MET A 250 | 46.983 | 24.390 | 80.506 | 1.00 | 27.84 | A | O |
| ATOM | 239 | CB | MET A 250 | 46.427 | 22.366 | 78.008 | 1.00 | 28.13 | A | C |
| ATOM | 240 | CG | MET A 250 | 46.603 | 22.336 | 76.508 | 1.00 | 26.95 | A | C |
| ATOM | 241 | SD | MET A 250 | 47.085 | 23.936 | 75.873 | 1.00 | 28.38 | A | S |
| ATOM | 242 | CE | MET A 250 | 45.743 | 24.950 | 76.447 | 1.00 | 27.55 | A | C |
| ATOM | 243 | N | MET A 251 | 47.320 | 22.237 | 81.089 | 1.00 | 27.87 | A | N |
| ATOM | 244 | CA | MET A 251 | 47.023 | 22.445 | 82.502 | 1.00 | 27.69 | A | C |
| ATOM | 245 | C | MET A 251 | 47.996 | 23.444 | 83.123 | 1.00 | 26.70 | A | C |
| ATOM | 246 | O | MET A 251 | 47.578 | 24.428 | 83.733 | 1.00 | 26.69 | A | O |
| ATOM | 247 | CB | MET A 251 | 47.063 | 21.115 | 83.262 | 1.00 | 28.01 | A | C |
| ATOM | 248 | CG | MET A 251 | 46.682 | 21.204 | 84.731 | 1.00 | 30.75 | A | C |
| ATOM | 249 | SD | MET A 251 | 46.462 | 19.543 | 85.491 | 1.00 | 37.84 | A | S |
| ATOM | 250 | CE | MET A 251 | 45.112 | 18.855 | 84.488 | 1.00 | 36.61 | A | C |
| ATOM | 251 | N | SER A 252 | 49.295 | 23.209 | 82.966 | 1.00 | 25.84 | A | N |
| ATOM | 252 | CA | SER A 252 | 50.267 | 24.154 | 83.520 | 1.00 | 24.99 | A | C |
| ATOM | 253 | C | SER A 252 | 50.124 | 25.543 | 82.904 | 1.00 | 24.95 | A | C |
| ATOM | 254 | O | SER A 252 | 50.175 | 26.543 | 83.613 | 1.00 | 24.38 | A | O |
| ATOM | 255 | CB | SER A 252 | 51.699 | 23.649 | 83.356 | 1.00 | 24.79 | A | C |
| ATOM | 256 | OG | SER A 252 | 51.836 | 22.358 | 83.906 | 1.00 | 23.60 | A | O |
| ATOM | 257 | N | LEU A 253 | 49.930 | 25.614 | 81.591 | 1.00 | 24.93 | A | N |
| ATOM | 258 | CA | LEU A 253 | 49.818 | 26.921 | 80.944 | 1.00 | 25.00 | A | C |
| ATOM | 259 | C | LEU A 253 | 48.554 | 27.684 | 81.341 | 1.00 | 25.00 | A | C |

| | | | | | | | | | | |
|---|---|---|---|---|---|---|---|---|---|---|
| ATOM | 260 | O | LEU A 253 | 48.586 | 28.891 | 81.482 | 1.00 | 25.12 | A | O |
| ATOM | 261 | CB | LEU A 253 | 49.887 | 26.780 | 79.425 | 1.00 | 24.94 | A | C |
| ATOM | 262 | CG | LEU A 253 | 51.194 | 26.276 | 78.830 | 1.00 | 25.22 | A | C |
| ATOM | 263 | CD1 | LEU A 253 | 50.997 | 25.975 | 77.355 | 1.00 | 25.77 | A | C |
| ATOM | 264 | CD2 | LEU A 253 | 52.307 | 27.310 | 79.037 | 1.00 | 25.40 | A | C |
| ATOM | 265 | N | THR A 254 | 47.428 | 26.993 | 81.481 | 1.00 | 25.40 | A | N |
| ATOM | 266 | CA | THR A 254 | 46.204 | 27.697 | 81.840 | 1.00 | 25.53 | A | C |
| ATOM | 267 | C | THR A 254 | 46.243 | 28.109 | 83.299 | 1.00 | 26.05 | A | C |
| ATOM | 268 | O | THR A 254 | 45.773 | 29.196 | 83.650 | 1.00 | 26.19 | A | O |
| ATOM | 269 | CB | THR A 254 | 44.922 | 26.892 | 81.498 | 1.00 | 25.20 | A | C |
| ATOM | 270 | OG1 | THR A 254 | 45.037 | 25.547 | 81.979 | 1.00 | 25.99 | A | O |
| ATOM | 271 | CG2 | THR A 254 | 44.788 | 26.735 | 79.977 | 1.00 | 25.08 | A | C |
| ATOM | 272 | N | LYS A 255 | 46.819 | 27.255 | 84.141 | 1.00 | 25.96 | A | N |
| ATOM | 273 | CA | LYS A 255 | 46.991 | 27.595 | 85.543 | 1.00 | 26.78 | A | C |
| ATOM | 274 | C | LYS A 255 | 47.827 | 28.852 | 85.666 | 1.00 | 27.19 | A | C |
| ATOM | 275 | O | LYS A 255 | 47.510 | 29.754 | 86.442 | 1.00 | 27.14 | A | O |
| ATOM | 276 | CB | LYS A 255 | 47.698 | 26.473 | 86.299 | 1.00 | 27.30 | A | C |
| ATOM | 281 | N | LEU A 256 | 48.898 | 28.901 | 84.885 | 1.00 | 27.30 | A | N |
| ATOM | 282 | CA | LEU A 256 | 49.795 | 30.033 | 84.902 | 1.00 | 28.12 | A | C |
| ATOM | 283 | C | LEU A 256 | 49.044 | 31.276 | 84.441 | 1.00 | 28.09 | A | C |
| ATOM | 284 | O | LEU A 256 | 49.096 | 32.329 | 85.092 | 1.00 | 27.59 | A | O |
| ATOM | 285 | CB | LEU A 256 | 51.010 | 29.773 | 83.994 | 1.00 | 27.97 | A | C |
| ATOM | 286 | CG | LEU A 256 | 52.021 | 30.917 | 83.813 | 1.00 | 29.55 | A | C |
| ATOM | 287 | CD1 | LEU A 256 | 52.652 | 31.351 | 85.123 | 1.00 | 28.22 | A | C |
| ATOM | 288 | CD2 | LEU A 256 | 53.103 | 30.476 | 82.846 | 1.00 | 30.01 | A | C |
| ATOM | 289 | N | ALA A 257 | 48.327 | 31.153 | 83.326 | 1.00 | 28.19 | A | N |
| ATOM | 290 | CA | ALA A 257 | 47.631 | 32.317 | 82.780 | 1.00 | 28.25 | A | C |
| ATOM | 291 | C | ALA A 257 | 46.652 | 32.919 | 83.799 | 1.00 | 28.18 | A | C |
| ATOM | 292 | O | ALA A 257 | 46.570 | 34.137 | 83.980 | 1.00 | 27.66 | A | O |
| ATOM | 293 | CB | ALA A 257 | 46.901 | 31.944 | 81.498 | 1.00 | 28.46 | A | C |
| ATOM | 294 | N | ASP A 258 | 45.920 | 32.052 | 84.471 | 1.00 | 27.72 | A | N |
| ATOM | 295 | CA | ASP A 258 | 44.943 | 32.485 | 85.461 | 1.00 | 28.45 | A | C |
| ATOM | 296 | C | ASP A 258 | 45.576 | 33.247 | 86.631 | 1.00 | 28.53 | A | C |
| ATOM | 297 | O | ASP A 258 | 45.029 | 34.251 | 87.079 | 1.00 | 29.47 | A | O |
| ATOM | 298 | CB | ASP A 258 | 44.158 | 31.284 | 85.980 | 1.00 | 28.73 | A | C |
| ATOM | 299 | CG | ASP A 258 | 43.165 | 31.664 | 87.042 | 1.00 | 30.52 | A | C |
| ATOM | 300 | OD1 | ASP A 258 | 42.113 | 32.253 | 86.690 | 1.00 | 29.61 | A | O |
| ATOM | 301 | OD2 | ASP A 258 | 43.366 | 31.427 | 88.255 | 1.00 | 32.63 | A | O |
| ATOM | 302 | N | LYS A 259 | 46.703 | 32.769 | 87.146 | 1.00 | 27.43 | A | N |
| ATOM | 303 | CA | LYS A 259 | 47.380 | 33.483 | 88.215 | 1.00 | 27.73 | A | C |
| ATOM | 304 | C | LYS A 259 | 47.880 | 34.845 | 87.715 | 1.00 | 26.94 | A | C |
| ATOM | 305 | O | LYS A 259 | 47.808 | 35.841 | 88.423 | 1.00 | 26.18 | A | O |
| ATOM | 306 | CB | LYS A 259 | 48.564 | 32.678 | 88.764 | 1.00 | 27.79 | A | C |
| ATOM | 307 | CG | LYS A 259 | 48.160 | 31.500 | 89.662 | 1.00 | 30.25 | A | C |
| ATOM | 308 | CD | LYS A 259 | 49.421 | 30.735 | 90.102 | 1.00 | 32.97 | A | C |
| ATOM | 309 | CE | LYS A 259 | 49.116 | 29.548 | 91.027 | 1.00 | 35.95 | A | C |
| ATOM | 310 | NZ | LYS A 259 | 50.373 | 28.804 | 91.379 | 1.00 | 35.53 | A | N |
| ATOM | 311 | N | GLU A 260 | 48.390 | 34.883 | 86.493 | 1.00 | 26.86 | A | N |
| ATOM | 312 | CA | GLU A 260 | 48.879 | 36.136 | 85.954 | 1.00 | 27.21 | A | C |
| ATOM | 313 | C | GLU A 260 | 47.767 | 37.145 | 85.768 | 1.00 | 26.43 | A | C |
| ATOM | 314 | O | GLU A 260 | 47.947 | 38.326 | 86.002 | 1.00 | 26.54 | A | O |
| ATOM | 315 | CB | GLU A 260 | 49.629 | 35.917 | 84.645 | 1.00 | 27.28 | A | C |
| ATOM | 316 | CG | GLU A 260 | 50.986 | 35.261 | 84.825 | 1.00 | 28.62 | A | C |
| ATOM | 317 | CD | GLU A 260 | 51.702 | 35.153 | 83.499 | 1.00 | 31.21 | A | C |
| ATOM | 318 | OE1 | GLU A 260 | 51.434 | 34.184 | 82.776 | 1.00 | 32.45 | A | O |
| ATOM | 319 | OE2 | GLU A 260 | 52.499 | 36.053 | 83.169 | 1.00 | 31.59 | A | O |
| ATOM | 320 | N | LEU A 261 | 46.609 | 36.665 | 85.352 | 1.00 | 26.10 | A | N |
| ATOM | 321 | CA | LEU A 261 | 45.461 | 37.524 | 85.134 | 1.00 | 26.12 | A | C |
| ATOM | 322 | C | LEU A 261 | 45.126 | 38.290 | 86.399 | 1.00 | 25.75 | A | C |
| ATOM | 323 | O | LEU A 261 | 44.807 | 39.482 | 86.343 | 1.00 | 24.92 | A | O |
| ATOM | 324 | CB | LEU A 261 | 44.258 | 36.682 | 84.671 | 1.00 | 25.98 | A | C |

| | | | | | | | | | | | |
|---|---|---|---|---|---|---|---|---|---|---|---|
| ATOM | 325 | CG | LEU | A | 261 | 44.305 | 36.446 | 83.172 | 1.00 | 28.10 | A | C |
| ATOM | 326 | CD1 | LEU | A | 261 | 43.155 | 35.504 | 82.730 | 1.00 | 29.47 | A | C |
| ATOM | 327 | CD2 | LEU | A | 261 | 44.196 | 37.783 | 82.429 | 1.00 | 29.65 | A | C |
| ATOM | 328 | N | VAL | A | 262 | 45.208 | 37.607 | 87.539 | 1.00 | 25.82 | A | N |
| ATOM | 329 | CA | VAL | A | 262 | 44.914 | 38.239 | 88.812 | 1.00 | 26.62 | A | C |
| ATOM | 330 | C | VAL | A | 262 | 45.830 | 39.434 | 89.004 | 1.00 | 26.57 | A | C |
| ATOM | 331 | O | VAL | A | 262 | 45.368 | 40.528 | 89.301 | 1.00 | 26.34 | A | O |
| ATOM | 332 | CB | VAL | A | 262 | 45.064 | 37.273 | 89.998 | 1.00 | 27.22 | A | C |
| ATOM | 333 | CG1 | VAL | A | 262 | 44.995 | 38.047 | 91.333 | 1.00 | 28.40 | A | C |
| ATOM | 334 | CG2 | VAL | A | 262 | 43.975 | 36.187 | 89.972 | 1.00 | 27.87 | A | C |
| ATOM | 335 | N | HIS | A | 263 | 47.126 | 39.245 | 88.775 | 1.00 | 26.60 | A | N |
| ATOM | 336 | CA | HIS | A | 263 | 48.091 | 40.330 | 88.961 | 1.00 | 27.04 | A | C |
| ATOM | 337 | C | HIS | A | 263 | 47.982 | 41.378 | 87.874 | 1.00 | 26.94 | A | C |
| ATOM | 338 | O | HIS | A | 263 | 48.291 | 42.551 | 88.093 | 1.00 | 26.40 | A | O |
| ATOM | 339 | CB | HIS | A | 263 | 49.524 | 39.791 | 89.044 | 1.00 | 27.39 | A | C |
| ATOM | 340 | CG | HIS | A | 263 | 49.759 | 38.929 | 90.248 | 1.00 | 28.07 | A | C |
| ATOM | 341 | ND1 | HIS | A | 263 | 49.438 | 39.340 | 91.525 | 1.00 | 28.29 | A | N |
| ATOM | 342 | CD2 | HIS | A | 263 | 50.237 | 37.667 | 90.364 | 1.00 | 27.92 | A | C |
| ATOM | 343 | CE1 | HIS | A | 263 | 49.733 | 38.371 | 92.378 | 1.00 | 31.73 | A | C |
| ATOM | 344 | NE2 | HIS | A | 263 | 50.215 | 37.345 | 91.696 | 1.00 | 28.39 | A | N |
| ATOM | 345 | N | MET | A | 264 | 47.519 | 40.955 | 86.707 | 1.00 | 26.99 | A | N |
| ATOM | 346 | CA | MET | A | 264 | 47.383 | 41.877 | 85.605 | 1.00 | 28.09 | A | C |
| ATOM | 347 | C | MET | A | 264 | 46.379 | 42.975 | 85.965 | 1.00 | 27.82 | A | C |
| ATOM | 348 | O | MET | A | 264 | 46.593 | 44.134 | 85.636 | 1.00 | 27.62 | A | O |
| ATOM | 349 | CB | MET | A | 264 | 46.961 | 41.149 | 84.329 | 1.00 | 28.26 | A | C |
| ATOM | 350 | CG | MET | A | 264 | 46.928 | 42.070 | 83.123 | 1.00 | 30.34 | A | C |
| ATOM | 351 | SD | MET | A | 264 | 46.277 | 41.349 | 81.647 | 1.00 | 29.23 | A | S |
| ATOM | 352 | CE | MET | A | 264 | 47.372 | 39.937 | 81.477 | 1.00 | 27.01 | A | C |
| ATOM | 353 | N | ILE | A | 265 | 45.304 | 42.616 | 86.666 | 1.00 | 27.33 | A | N |
| ATOM | 354 | CA | ILE | A | 265 | 44.305 | 43.605 | 87.039 | 1.00 | 27.44 | A | C |
| ATOM | 355 | C | ILE | A | 265 | 44.924 | 44.614 | 87.983 | 1.00 | 26.93 | A | C |
| ATOM | 356 | O | ILE | A | 265 | 44.720 | 45.813 | 87.826 | 1.00 | 26.29 | A | O |
| ATOM | 357 | CB | ILE | A | 265 | 43.048 | 42.946 | 87.709 | 1.00 | 28.05 | A | C |
| ATOM | 358 | CG1 | ILE | A | 265 | 42.534 | 41.791 | 86.869 | 1.00 | 28.06 | A | C |
| ATOM | 359 | CG2 | ILE | A | 265 | 41.904 | 43.979 | 87.901 | 1.00 | 27.68 | A | C |
| ATOM | 360 | CD1 | ILE | A | 265 | 42.106 | 42.186 | 85.527 | 1.00 | 31.88 | A | C |
| ATOM | 361 | N | GLY | A | 266 | 45.694 | 44.135 | 88.959 | 1.00 | 26.91 | A | N |
| ATOM | 362 | CA | GLY | A | 266 | 46.334 | 45.046 | 89.909 | 1.00 | 27.13 | A | C |
| ATOM | 363 | C | GLY | A | 266 | 47.336 | 45.959 | 89.180 | 1.00 | 26.76 | A | C |
| ATOM | 364 | O | GLY | A | 266 | 47.493 | 47.127 | 89.505 | 1.00 | 26.31 | A | O |
| ATOM | 365 | N | TRP | A | 267 | 48.003 | 45.420 | 88.175 | 1.00 | 26.65 | A | N |
| ATOM | 366 | CA | TRP | A | 267 | 48.963 | 46.212 | 87.397 | 1.00 | 26.19 | A | C |
| ATOM | 367 | C | TRP | A | 267 | 48.245 | 47.328 | 86.646 | 1.00 | 26.72 | A | C |
| ATOM | 368 | O | TRP | A | 267 | 48.641 | 48.492 | 86.731 | 1.00 | 25.48 | A | O |
| ATOM | 369 | CB | TRP | A | 267 | 49.705 | 45.309 | 86.430 | 1.00 | 26.15 | A | C |
| ATOM | 370 | CG | TRP | A | 267 | 50.372 | 45.995 | 85.266 | 1.00 | 25.86 | A | C |
| ATOM | 371 | CD1 | TRP | A | 267 | 51.570 | 46.658 | 85.282 | 1.00 | 27.39 | A | C |
| ATOM | 372 | CD2 | TRP | A | 267 | 49.906 | 46.041 | 83.913 | 1.00 | 28.27 | A | C |
| ATOM | 373 | NE1 | TRP | A | 267 | 51.865 | 47.141 | 84.033 | 1.00 | 26.86 | A | N |
| ATOM | 374 | CE2 | TRP | A | 267 | 50.872 | 46.760 | 83.161 | 1.00 | 28.73 | A | C |
| ATOM | 375 | CE3 | TRP | A | 267 | 48.751 | 45.566 | 83.256 | 1.00 | 25.69 | A | C |
| ATOM | 376 | CZ2 | TRP | A | 267 | 50.727 | 47.019 | 81.799 | 1.00 | 28.63 | A | C |
| ATOM | 377 | CZ3 | TRP | A | 267 | 48.618 | 45.797 | 81.890 | 1.00 | 26.84 | A | C |
| ATOM | 378 | CH2 | TRP | A | 267 | 49.601 | 46.529 | 81.167 | 1.00 | 28.52 | A | C |
| ATOM | 379 | N | ALA | A | 268 | 47.164 | 46.976 | 85.944 | 1.00 | 26.35 | A | N |
| ATOM | 380 | CA | ALA | A | 268 | 46.408 | 47.978 | 85.192 | 1.00 | 26.93 | A | C |
| ATOM | 381 | C | ALA | A | 268 | 46.001 | 49.130 | 86.124 | 1.00 | 27.32 | A | C |
| ATOM | 382 | O | ALA | A | 268 | 46.099 | 50.303 | 85.759 | 1.00 | 26.96 | A | O |
| ATOM | 383 | CB | ALA | A | 268 | 45.146 | 47.347 | 84.525 | 1.00 | 26.88 | A | C |
| ATOM | 384 | N | LYS | A | 269 | 45.573 | 48.783 | 87.328 | 1.00 | 27.54 | A | N |
| ATOM | 385 | CA | LYS | A | 269 | 45.138 | 49.772 | 88.311 | 1.00 | 29.49 | A | C |

| | | | | | | | | | | |
|---|---|---|---|---|---|---|---|---|---|---|
| ATOM | 386 | C | LYS | A | 269 | 46.211 | 50.773 | 88.734 | 1.00 30.25 | A C |
| ATOM | 387 | O | LYS | A | 269 | 45.897 | 51.880 | 89.179 | 1.00 29.08 | A O |
| ATOM | 388 | CB | LYS | A | 269 | 44.498 | 49.084 | 89.520 | 1.00 28.89 | A C |
| ATOM | 389 | CG | LYS | A | 269 | 43.098 | 48.552 | 89.175 | 1.00 30.16 | A C |
| ATOM | 390 | CD | LYS | A | 269 | 42.526 | 47.681 | 90.286 | 1.00 29.66 | A C |
| ATOM | 391 | CE | LYS | A | 269 | 42.216 | 48.504 | 91.517 | 1.00 29.48 | A C |
| ATOM | 392 | NZ | LYS | A | 269 | 41.540 | 47.654 | 92.534 | 1.00 28.73 | A N |
| ATOM | 393 | N | LYS | A | 270 | 47.469 | 50.392 | 88.530 | 1.00 31.80 | A N |
| ATOM | 394 | CA | LYS | A | 270 | 48.595 | 51.257 | 88.855 | 1.00 33.66 | A C |
| ATOM | 395 | C | LYS | A | 270 | 49.032 | 52.134 | 87.672 | 1.00 34.20 | A C |
| ATOM | 396 | O | LYS | A | 270 | 49.912 | 52.982 | 87.827 | 1.00 35.33 | A O |
| ATOM | 397 | CB | LYS | A | 270 | 49.771 | 50.420 | 89.376 | 1.00 33.55 | A C |
| ATOM | 398 | CG | LYS | A | 270 | 49.462 | 49.743 | 90.711 | 1.00 35.25 | A C |
| ATOM | 399 | CD | LYS | A | 270 | 50.604 | 48.885 | 91.202 | 1.00 38.44 | A C |
| ATOM | 400 | CE | LYS | A | 270 | 50.188 | 48.062 | 92.440 | 1.00 40.86 | A C |
| ATOM | 401 | NZ | LYS | A | 270 | 51.189 | 46.992 | 92.772 | 1.00 38.83 | A N |
| ATOM | 402 | N | ILE | A | 271 | 48.440 | 51.946 | 86.498 | 1.00 34.01 | A N |
| ATOM | 403 | CA | ILE | A | 271 | 48.806 | 52.788 | 85.358 | 1.00 34.31 | A C |
| ATOM | 404 | C | ILE | A | 271 | 48.089 | 54.097 | 85.591 | 1.00 35.02 | A C |
| ATOM | 405 | O | ILE | A | 271 | 46.880 | 54.115 | 85.777 | 1.00 34.17 | A O |
| ATOM | 406 | CB | ILE | A | 271 | 48.360 | 52.176 | 84.054 | 1.00 34.43 | A C |
| ATOM | 407 | CG1 | ILE | A | 271 | 48.924 | 50.756 | 83.917 | 1.00 35.51 | A C |
| ATOM | 408 | CG2 | ILE | A | 271 | 48.787 | 53.057 | 82.882 | 1.00 34.47 | A C |
| ATOM | 409 | CD1 | ILE | A | 271 | 50.399 | 50.685 | 84.049 | 1.00 38.10 | A C |
| ATOM | 410 | N | PRO | A | 272 | 48.816 | 55.207 | 85.559 | 1.00 35.43 | A N |
| ATOM | 411 | CA | PRO | A | 272 | 48.220 | 56.486 | 85.952 | 1.00 35.42 | A C |
| ATOM | 412 | C | PRO | A | 272 | 47.019 | 56.810 | 85.068 | 1.00 34.11 | A C |
| ATOM | 413 | O | PRO | A | 272 | 47.079 | 56.723 | 83.834 | 1.00 34.35 | A O |
| ATOM | 414 | CB | PRO | A | 272 | 49.349 | 57.495 | 85.735 | 1.00 36.42 | A C |
| ATOM | 415 | CG | PRO | A | 272 | 50.629 | 56.665 | 85.638 | 1.00 37.09 | A C |
| ATOM | 416 | CD | PRO | A | 272 | 50.192 | 55.344 | 85.050 | 1.00 36.24 | A C |
| ATOM | 417 | N | GLY | A | 273 | 45.917 | 57.146 | 85.711 | 1.00 33.23 | A N |
| ATOM | 418 | CA | GLY | A | 273 | 44.703 | 57.483 | 84.997 | 1.00 31.62 | A C |
| ATOM | 419 | C | GLY | A | 273 | 43.752 | 56.312 | 84.808 | 1.00 30.95 | A C |
| ATOM | 420 | O | GLY | A | 273 | 42.550 | 56.514 | 84.712 | 1.00 30.18 | A O |
| ATOM | 421 | N | PHE | A | 274 | 44.275 | 55.088 | 84.766 | 1.00 29.88 | A N |
| ATOM | 422 | CA | PHE | A | 274 | 43.425 | 53.946 | 84.462 | 1.00 29.19 | A C |
| ATOM | 423 | C | PHE | A | 274 | 42.167 | 53.921 | 85.325 | 1.00 28.54 | A C |
| ATOM | 424 | O | PHE | A | 274 | 41.086 | 53.714 | 84.807 | 1.00 27.83 | A O |
| ATOM | 425 | CB | PHE | A | 274 | 44.170 | 52.606 | 84.572 | 1.00 28.12 | A C |
| ATOM | 426 | CG | PHE | A | 274 | 43.372 | 51.425 | 84.076 | 1.00 28.25 | A C |
| ATOM | 427 | CD1 | PHE | A | 274 | 43.303 | 51.139 | 82.716 | 1.00 28.96 | A C |
| ATOM | 428 | CD2 | PHE | A | 274 | 42.680 | 50.601 | 84.963 | 1.00 27.12 | A C |
| ATOM | 429 | CE1 | PHE | A | 274 | 42.568 | 50.047 | 82.244 | 1.00 27.71 | A C |
| ATOM | 430 | CE2 | PHE | A | 274 | 41.936 | 49.516 | 84.493 | 1.00 25.62 | A C |
| ATOM | 431 | CZ | PHE | A | 274 | 41.897 | 49.240 | 83.128 | 1.00 24.36 | A C |
| ATOM | 432 | N | VAL | A | 275 | 42.303 | 54.136 | 86.630 | 1.00 29.13 | A N |
| ATOM | 433 | CA | VAL | A | 275 | 41.140 | 54.058 | 87.505 | 1.00 30.21 | A C |
| ATOM | 434 | C | VAL | A | 275 | 40.181 | 55.247 | 87.420 | 1.00 29.77 | A C |
| ATOM | 435 | O | VAL | A | 275 | 39.084 | 55.186 | 87.964 | 1.00 29.57 | A O |
| ATOM | 436 | CB | VAL | A | 275 | 41.493 | 53.726 | 88.977 | 1.00 30.91 | A C |
| ATOM | 437 | CG1 | VAL | A | 275 | 42.174 | 52.369 | 89.052 | 1.00 31.78 | A C |
| ATOM | 438 | CG2 | VAL | A | 275 | 42.356 | 54.810 | 89.599 | 1.00 32.10 | A C |
| ATOM | 439 | N | GLU | A | 276 | 40.586 | 56.309 | 86.723 | 1.00 29.22 | A N |
| ATOM | 440 | CA | GLU | A | 276 | 39.706 | 57.458 | 86.479 | 1.00 29.45 | A C |
| ATOM | 441 | C | GLU | A | 276 | 38.800 | 57.207 | 85.251 | 1.00 27.61 | A C |
| ATOM | 442 | O | GLU | A | 276 | 37.874 | 57.964 | 84.985 | 1.00 27.03 | A O |
| ATOM | 443 | CB | GLU | A | 276 | 40.531 | 58.728 | 86.256 | 1.00 30.38 | A C |
| ATOM | 444 | CG | GLU | A | 276 | 41.130 | 59.363 | 87.511 | 1.00 37.25 | A C |
| ATOM | 445 | CD | GLU | A | 276 | 42.366 | 60.212 | 87.203 | 1.00 45.26 | A C |
| ATOM | 446 | OE1 | GLU | A | 276 | 42.263 | 61.169 | 86.388 | 1.00 48.96 | A O |

| ATOM | 447 | OE2 | GLU | A | 276 | 43.455 | 59.918 | 87.760 | 1.00 | 47.90 | A | O |
|------|-----|-----|-----|---|-----|--------|--------|--------|------|-------|---|---|
| ATOM | 448 | N   | LEU | A | 277 | 39.098 | 56.168 | 84.476 | 1.00 | 25.79 | A | N |
| ATOM | 449 | CA  | LEU | A | 277 | 38.235 | 55.809 | 83.339 | 1.00 | 24.19 | A | C |
| ATOM | 450 | C   | LEU | A | 277 | 36.927 | 55.220 | 83.876 | 1.00 | 23.30 | A | C |
| ATOM | 451 | O   | LEU | A | 277 | 36.935 | 54.678 | 84.977 | 1.00 | 21.56 | A | O |
| ATOM | 452 | CB  | LEU | A | 277 | 38.910 | 54.732 | 82.501 | 1.00 | 23.48 | A | C |
| ATOM | 453 | CG  | LEU | A | 277 | 40.256 | 55.191 | 81.893 | 1.00 | 23.63 | A | C |
| ATOM | 454 | CD1 | LEU | A | 277 | 40.926 | 54.064 | 81.159 | 1.00 | 25.09 | A | C |
| ATOM | 455 | CD2 | LEU | A | 277 | 40.056 | 56.398 | 80.947 | 1.00 | 25.32 | A | C |
| ATOM | 456 | N   | SER | A | 278 | 35.841 | 55.278 | 83.097 | 1.00 | 21.64 | A | N |
| ATOM | 457 | CA  | SER | A | 278 | 34.600 | 54.623 | 83.534 | 1.00 | 22.58 | A | C |
| ATOM | 458 | C   | SER | A | 278 | 34.904 | 53.148 | 83.760 | 1.00 | 22.31 | A | C |
| ATOM | 459 | O   | SER | A | 278 | 35.780 | 52.565 | 83.108 | 1.00 | 20.32 | A | O |
| ATOM | 460 | CB  | SER | A | 278 | 33.514 | 54.703 | 82.467 | 1.00 | 22.69 | A | C |
| ATOM | 461 | OG  | SER | A | 278 | 33.845 | 53.825 | 81.389 | 1.00 | 23.88 | A | O |
| ATOM | 462 | N   | LEU | A | 279 | 34.157 | 52.543 | 84.665 | 1.00 | 22.00 | A | N |
| ATOM | 463 | CA  | LEU | A | 279 | 34.362 | 51.132 | 84.972 | 1.00 | 22.61 | A | C |
| ATOM | 464 | C   | LEU | A | 279 | 34.158 | 50.262 | 83.729 | 1.00 | 22.31 | A | C |
| ATOM | 465 | O   | LEU | A | 279 | 34.871 | 49.280 | 83.518 | 1.00 | 21.58 | A | O |
| ATOM | 466 | CB  | LEU | A | 279 | 33.385 | 50.710 | 86.076 | 1.00 | 22.22 | A | C |
| ATOM | 467 | CG  | LEU | A | 279 | 33.481 | 49.266 | 86.548 | 1.00 | 23.67 | A | C |
| ATOM | 468 | CD1 | LEU | A | 279 | 34.881 | 48.983 | 87.088 | 1.00 | 25.92 | A | C |
| ATOM | 469 | CD2 | LEU | A | 279 | 32.409 | 49.007 | 87.628 | 1.00 | 25.76 | A | C |
| ATOM | 470 | N   | LEU | A | 280 | 33.199 | 50.633 | 82.896 | 1.00 | 21.94 | A | N |
| ATOM | 471 | CA  | LEU | A | 280 | 32.941 | 49.882 | 81.674 | 1.00 | 23.32 | A | C |
| ATOM | 472 | C   | LEU | A | 280 | 34.182 | 49.897 | 80.765 | 1.00 | 23.59 | A | C |
| ATOM | 473 | O   | LEU | A | 280 | 34.577 | 48.856 | 80.218 | 1.00 | 24.13 | A | O |
| ATOM | 474 | CB  | LEU | A | 280 | 31.711 | 50.431 | 80.949 | 1.00 | 23.05 | A | C |
| ATOM | 475 | CG  | LEU | A | 280 | 31.249 | 49.631 | 79.722 | 1.00 | 24.38 | A | C |
| ATOM | 476 | CD1 | LEU | A | 280 | 30.968 | 48.173 | 80.112 | 1.00 | 24.17 | A | C |
| ATOM | 477 | CD2 | LEU | A | 280 | 29.985 | 50.268 | 79.109 | 1.00 | 23.40 | A | C |
| ATOM | 478 | N   | ASP | A | 281 | 34.812 | 51.061 | 80.621 | 1.00 | 23.89 | A | N |
| ATOM | 479 | CA  | ASP | A | 281 | 36.071 | 51.142 | 79.857 | 1.00 | 25.43 | A | C |
| ATOM | 480 | C   | ASP | A | 281 | 37.149 | 50.289 | 80.498 | 1.00 | 25.26 | A | C |
| ATOM | 481 | O   | ASP | A | 281 | 37.916 | 49.592 | 79.807 | 1.00 | 25.73 | A | O |
| ATOM | 482 | CB  | ASP | A | 281 | 36.567 | 52.584 | 79.716 | 1.00 | 25.28 | A | C |
| ATOM | 483 | CG  | ASP | A | 281 | 35.817 | 53.352 | 78.632 | 1.00 | 28.71 | A | C |
| ATOM | 484 | OD1 | ASP | A | 281 | 35.145 | 52.697 | 77.815 | 1.00 | 31.28 | A | O |
| ATOM | 485 | OD2 | ASP | A | 281 | 35.815 | 54.596 | 78.518 | 1.00 | 30.50 | A | O |
| ATOM | 486 | N   | GLN | A | 282 | 37.232 | 50.312 | 81.824 | 1.00 | 25.06 | A | N |
| ATOM | 487 | CA  | GLN | A | 282 | 38.309 | 49.523 | 82.434 | 1.00 | 25.06 | A | C |
| ATOM | 488 | C   | GLN | A | 282 | 38.096 | 48.069 | 82.082 | 1.00 | 24.69 | A | C |
| ATOM | 489 | O   | GLN | A | 282 | 39.029 | 47.382 | 81.650 | 1.00 | 23.92 | A | O |
| ATOM | 490 | CB  | GLN | A | 282 | 38.374 | 49.700 | 83.945 | 1.00 | 24.81 | A | C |
| ATOM | 491 | CG  | GLN | A | 282 | 38.667 | 51.125 | 84.374 | 1.00 | 23.64 | A | C |
| ATOM | 492 | CD  | GLN | A | 282 | 38.590 | 51.291 | 85.884 | 1.00 | 24.54 | A | C |
| ATOM | 493 | OE1 | GLN | A | 282 | 39.148 | 50.484 | 86.620 | 1.00 | 25.02 | A | O |
| ATOM | 494 | NE2 | GLN | A | 282 | 37.925 | 52.346 | 86.338 | 1.00 | 21.15 | A | N |
| ATOM | 495 | N   | VAL | A | 283 | 36.857 | 47.615 | 82.258 | 1.00 | 23.51 | A | N |
| ATOM | 496 | CA  | VAL | A | 283 | 36.505 | 46.252 | 81.919 | 1.00 | 24.24 | A | C |
| ATOM | 497 | C   | VAL | A | 283 | 36.780 | 45.919 | 80.443 | 1.00 | 24.25 | A | C |
| ATOM | 498 | O   | VAL | A | 283 | 37.396 | 44.903 | 80.148 | 1.00 | 24.24 | A | O |
| ATOM | 499 | CB  | VAL | A | 283 | 35.013 | 45.953 | 82.229 | 1.00 | 24.24 | A | C |
| ATOM | 500 | CG1 | VAL | A | 283 | 34.586 | 44.622 | 81.604 | 1.00 | 23.31 | A | C |
| ATOM | 501 | CG2 | VAL | A | 283 | 34.803 | 45.932 | 83.735 | 1.00 | 24.71 | A | C |
| ATOM | 502 | N   | ARG | A | 284 | 36.345 | 46.773 | 79.525 | 1.00 | 24.03 | A | N |
| ATOM | 503 | CA  | ARG | A | 284 | 36.527 | 46.452 | 78.110 | 1.00 | 24.41 | A | C |
| ATOM | 504 | CB  | ARG | A | 284 | 35.646 | 47.310 | 77.205 | 1.00 | 24.29 | A | C |
| ATOM | 505 | CG  | AARG| A | 284 | 34.197 | 46.864 | 77.284 | 0.50 | 25.09 | A | C |
| ATOM | 506 | CG  | BARG| A | 284 | 34.115 | 47.074 | 77.332 | 0.50 | 24.28 | A | C |
| ATOM | 507 | CD  | AARG| A | 284 | 33.253 | 47.612 | 76.408 | 0.50 | 24.47 | A | C |

| ATOM | 508 | CD B | ARG A | 284 | 33.618 | 45.680 | 76.912 | 0.50 | 23.30 | A | C |
| ATOM | 509 | NE A | ARG A | 284 | 31.907 | 47.063 | 76.523 | 0.50 | 26.39 | A | N |
| ATOM | 510 | NE B | ARG A | 284 | 32.151 | 45.582 | 76.937 | 0.50 | 21.87 | A | N |
| ATOM | 511 | CZ A | ARG A | 284 | 30.818 | 47.739 | 76.220 | 0.50 | 25.78 | A | C |
| ATOM | 512 | CZ B | ARG A | 284 | 31.462 | 44.609 | 77.522 | 0.50 | 21.24 | A | C |
| ATOM | 513 | NH1A | ARG A | 284 | 30.925 | 48.991 | 75.794 | 0.50 | 26.11 | A | N |
| ATOM | 514 | NH1B | ARG A | 284 | 32.089 | 43.632 | 78.166 | 0.50 | 18.46 | A | N |
| ATOM | 515 | NH2A | ARG A | 284 | 29.628 | 47.172 | 76.352 | 0.50 | 26.66 | A | N |
| ATOM | 516 | NH2B | ARG A | 284 | 30.124 | 44.625 | 77.482 | 0.50 | 20.42 | A | N |
| ATOM | 517 | C | ARG A | 284 | 37.994 | 46.475 | 77.658 | 1.00 | 24.67 | A | C |
| ATOM | 518 | O | ARG A | 284 | 38.399 | 45.681 | 76.820 | 1.00 | 23.19 | A | O |
| ATOM | 519 | N | LEU A | 285 | 38.781 | 47.390 | 78.208 | 1.00 | 24.63 | A | N |
| ATOM | 520 | CA | LEU A | 285 | 40.195 | 47.418 | 77.858 | 1.00 | 25.61 | A | C |
| ATOM | 521 | C | LEU A | 285 | 40.847 | 46.084 | 78.252 | 1.00 | 26.08 | A | C |
| ATOM | 522 | O | LEU A | 285 | 41.629 | 45.513 | 77.492 | 1.00 | 26.66 | A | O |
| ATOM | 523 | CB | LEU A | 285 | 40.911 | 48.600 | 78.550 | 1.00 | 25.20 | A | C |
| ATOM | 524 | CG | LEU A | 285 | 40.504 | 49.984 | 78.012 | 1.00 | 27.58 | A | C |
| ATOM | 525 | CD1 | LEU A | 285 | 41.086 | 51.094 | 78.891 | 1.00 | 28.11 | A | C |
| ATOM | 526 | CD2 | LEU A | 285 | 40.909 | 50.172 | 76.532 | 1.00 | 24.04 | A | C |
| ATOM | 527 | N | LEU A | 286 | 40.562 | 45.604 | 79.462 | 1.00 | 26.80 | A | N |
| ATOM | 528 | CA | LEU A | 286 | 41.168 | 44.351 | 79.931 | 1.00 | 27.14 | A | C |
| ATOM | 529 | C | LEU A | 286 | 40.644 | 43.136 | 79.169 | 1.00 | 26.74 | A | C |
| ATOM | 530 | O | LEU A | 286 | 41.429 | 42.275 | 78.803 | 1.00 | 26.81 | A | O |
| ATOM | 531 | CB | LEU A | 286 | 41.009 | 44.161 | 81.452 | 1.00 | 27.30 | A | C |
| ATOM | 532 | CG | LEU A | 286 | 41.936 | 45.070 | 82.256 | 1.00 | 28.49 | A | C |
| ATOM | 533 | CD1 | LEU A | 286 | 41.422 | 45.277 | 83.683 | 1.00 | 28.29 | A | C |
| ATOM | 534 | CD2 | LEU A | 286 | 43.416 | 44.581 | 82.215 | 1.00 | 27.58 | A | C |
| ATOM | 535 | N | GLU A | 287 | 39.334 | 43.070 | 78.929 | 1.00 | 26.36 | A | N |
| ATOM | 536 | CA | GLU A | 287 | 38.772 | 41.982 | 78.138 | 1.00 | 27.20 | A | C |
| ATOM | 537 | C | GLU A | 287 | 39.432 | 41.961 | 76.748 | 1.00 | 27.55 | A | C |
| ATOM | 538 | O | GLU A | 287 | 39.724 | 40.906 | 76.207 | 1.00 | 26.85 | A | O |
| ATOM | 539 | CB | GLU A | 287 | 37.243 | 42.119 | 77.982 | 1.00 | 27.27 | A | C |
| ATOM | 540 | CG | GLU A | 287 | 36.452 | 42.002 | 79.285 | 1.00 | 27.09 | A | C |
| ATOM | 541 | CD | GLU A | 287 | 34.930 | 42.031 | 79.083 | 1.00 | 29.11 | A | C |
| ATOM | 542 | OE1 | GLU A | 287 | 34.433 | 42.614 | 78.093 | 1.00 | 27.57 | A | O |
| ATOM | 543 | OE2 | GLU A | 287 | 34.225 | 41.451 | 79.927 | 1.00 | 29.41 | A | O |
| ATOM | 544 | N | SER A | 288 | 39.698 | 43.137 | 76.199 | 1.00 | 27.57 | A | N |
| ATOM | 545 | CA | SER A | 288 | 40.285 | 43.219 | 74.865 | 1.00 | 28.75 | A | C |
| ATOM | 546 | C | SER A | 288 | 41.771 | 42.849 | 74.767 | 1.00 | 28.32 | A | C |
| ATOM | 547 | O | SER A | 288 | 42.179 | 42.229 | 73.793 | 1.00 | 28.96 | A | O |
| ATOM | 548 | CB | SER A | 288 | 40.085 | 44.614 | 74.267 | 1.00 | 28.31 | A | C |
| ATOM | 549 | OG | SER A | 288 | 40.843 | 44.739 | 73.075 | 1.00 | 30.22 | A | O |
| ATOM | 550 | N | CYS A | 289 | 42.576 | 43.207 | 75.760 | 1.00 | 27.49 | A | N |
| ATOM | 551 | CA | CYS A | 289 | 44.009 | 43.055 | 75.596 | 1.00 | 27.55 | A | C |
| ATOM | 552 | C | CYS A | 289 | 44.707 | 42.000 | 76.431 | 1.00 | 27.73 | A | C |
| ATOM | 553 | O | CYS A | 289 | 45.931 | 41.822 | 76.289 | 1.00 | 28.03 | A | O |
| ATOM | 554 | CB | CYS A | 289 | 44.693 | 44.378 | 75.951 | 1.00 | 27.05 | A | C |
| ATOM | 555 | SG | CYS A | 289 | 44.817 | 44.655 | 77.739 | 1.00 | 29.39 | A | S |
| ATOM | 556 | N | TRP A | 290 | 43.986 | 41.345 | 77.335 | 1.00 | 27.09 | A | N |
| ATOM | 557 | CA | TRP A | 290 | 44.672 | 40.480 | 78.299 | 1.00 | 27.14 | A | C |
| ATOM | 558 | C | TRP A | 290 | 45.622 | 39.446 | 77.712 | 1.00 | 27.05 | A | C |
| ATOM | 559 | O | TRP A | 290 | 46.685 | 39.210 | 78.265 | 1.00 | 27.42 | A | O |
| ATOM | 560 | CB | TRP A | 290 | 43.695 | 39.843 | 79.279 | 1.00 | 27.22 | A | C |
| ATOM | 561 | CG | TRP A | 290 | 42.771 | 38.888 | 78.653 | 1.00 | 28.82 | A | C |
| ATOM | 562 | CD1 | TRP A | 290 | 41.540 | 39.158 | 78.111 | 1.00 | 29.48 | A | C |
| ATOM | 563 | CD2 | TRP A | 290 | 42.982 | 37.489 | 78.505 | 1.00 | 29.36 | A | C |
| ATOM | 564 | NE1 | TRP A | 290 | 40.980 | 38.001 | 77.631 | 1.00 | 30.09 | A | N |
| ATOM | 565 | CE2 | TRP A | 290 | 41.836 | 36.956 | 77.869 | 1.00 | 30.81 | A | C |
| ATOM | 566 | CE3 | TRP A | 290 | 44.015 | 36.615 | 78.873 | 1.00 | 30.70 | A | C |
| ATOM | 567 | CZ2 | TRP A | 290 | 41.690 | 35.587 | 77.594 | 1.00 | 30.32 | A | C |
| ATOM | 568 | CZ3 | TRP A | 290 | 43.869 | 35.236 | 78.588 | 1.00 | 30.61 | A | C |

```
ATOM   569  CH2 TRP A 290      42.718  34.750  77.950  1.00 29.86      A    C
ATOM   570  N   MET A 291      45.248  38.836  76.596  1.00 27.11      A    N
ATOM   571  CA  MET A 291      46.099  37.828  75.983  1.00 28.18      A    C
ATOM   572  C   MET A 291      47.349  38.458  75.351  1.00 27.66      A    C
ATOM   573  O   MET A 291      48.425  37.880  75.418  1.00 27.75      A    O
ATOM   574  CB  MET A 291      45.313  37.002  74.961  1.00 28.64      A    C
ATOM   575  CG  MET A 291      46.153  35.978  74.243  1.00 31.80      A    C
ATOM   576  SD  MET A 291      46.542  34.583  75.328  1.00 37.74      A    S
ATOM   577  CE  MET A 291      44.964  33.685  75.253  1.00 35.39      A    C
ATOM   578  N   GLU A 292      47.206  39.648  74.777  1.00 27.46      A    N
ATOM   579  CA  GLU A 292      48.345  40.395  74.237  1.00 28.67      A    C
ATOM   580  C   GLU A 292      49.338  40.753  75.335  1.00 28.14      A    C
ATOM   581  O   GLU A 292      50.539  40.639  75.142  1.00 28.06      A    O
ATOM   582  CB  GLU A 292      47.897  41.685  73.538  1.00 28.95      A    C
ATOM   583  CG  GLU A 292      47.089  41.431  72.270  1.00 31.56      A    C
ATOM   584  CD  GLU A 292      46.200  42.612  71.923  1.00 35.38      A    C
ATOM   585  OE1 GLU A 292      46.699  43.653  71.466  1.00 33.39      A    O
ATOM   586  OE2 GLU A 292      44.984  42.505  72.130  1.00 38.48      A    O
ATOM   587  N   VAL A 293      48.828  41.184  76.484  1.00 27.82      A    N
ATOM   588  CA  VAL A 293      49.673  41.492  77.635  1.00 28.34      A    C
ATOM   589  C   VAL A 293      50.401  40.235  78.154  1.00 28.64      A    C
ATOM   590  O   VAL A 293      51.599  40.293  78.471  1.00 28.42      A    O
ATOM   591  CB  VAL A 293      48.849  42.154  78.760  1.00 29.70      A    C
ATOM   592  CG1 VAL A 293      49.705  42.409  80.019  1.00 28.00      A    C
ATOM   593  CG2 VAL A 293      48.231  43.473  78.250  1.00 29.82      A    C
ATOM   594  N   LEU A 294      49.702  39.098  78.248  1.00 27.57      A    N
ATOM   595  CA  LEU A 294      50.374  37.861  78.680  1.00 27.15      A    C
ATOM   596  C   LEU A 294      51.542  37.542  77.729  1.00 27.25      A    C
ATOM   597  O   LEU A 294      52.656  37.203  78.170  1.00 27.06      A    O
ATOM   598  CB  LEU A 294      49.399  36.675  78.686  1.00 26.72      A    C
ATOM   599  CG  LEU A 294      48.403  36.603  79.860  1.00 27.64      A    C
ATOM   600  CD1 LEU A 294      47.549  35.339  79.787  1.00 29.42      A    C
ATOM   601  CD2 LEU A 294      49.134  36.674  81.209  1.00 27.35      A    C
ATOM   602  N   MET A 295      51.264  37.672  76.433  1.00 26.51      A    N
ATOM   603  CA  MET A 295      52.201  37.321  75.376  1.00 27.10      A    C
ATOM   604  C   MET A 295      53.397  38.250  75.325  1.00 27.66      A    C
ATOM   605  O   MET A 295      54.511  37.758  75.168  1.00 27.08      A    O
ATOM   606  CB  MET A 295      51.521  37.289  74.014  1.00 26.77      A    C
ATOM   607  CG  MET A 295      50.632  36.057  73.824  1.00 27.23      A    C
ATOM   608  SD  MET A 295      49.689  36.010  72.278  1.00 27.18      A    S
ATOM   609  CE  MET A 295      49.195  34.256  72.362  1.00 23.74      A    C
ATOM   610  N   VAL A 296      53.179  39.567  75.457  1.00 27.66      A    N
ATOM   611  CA  VAL A 296      54.309  40.485  75.403  1.00 29.07      A    C
ATOM   612  C   VAL A 296      55.166  40.272  76.656  1.00 29.19      A    C
ATOM   613  O   VAL A 296      56.387  40.379  76.584  1.00 30.33      A    O
ATOM   614  CB  VAL A 296      53.908  41.961  75.174  1.00 30.30      A    C
ATOM   615  CG1 VAL A 296      53.375  42.590  76.474  1.00 28.44      A    C
ATOM   616  CG2 VAL A 296      55.119  42.783  74.610  1.00 31.42      A    C
ATOM   617  N   GLY A 297      54.531  39.937  77.784  1.00 28.20      A    N
ATOM   618  CA  GLY A 297      55.263  39.557  78.985  1.00 28.00      A    C
ATOM   619  C   GLY A 297      56.168  38.347  78.716  1.00 27.88      A    C
ATOM   620  O   GLY A 297      57.362  38.337  79.053  1.00 26.75      A    O
ATOM   621  N   LEU A 298      55.596  37.316  78.099  1.00 27.33      A    N
ATOM   622  CA  LEU A 298      56.335  36.106  77.709  1.00 26.93      A    C
ATOM   623  C   LEU A 298      57.519  36.432  76.788  1.00 27.23      A    C
ATOM   624  O   LEU A 298      58.635  35.972  77.007  1.00 27.64      A    O
ATOM   625  CB  LEU A 298      55.390  35.165  76.980  1.00 26.56      A    C
ATOM   626  CG  LEU A 298      56.014  33.923  76.352  1.00 27.45      A    C
ATOM   627  CD1 LEU A 298      56.636  33.067  77.429  1.00 26.87      A    C
ATOM   628  CD2 LEU A 298      54.959  33.145  75.581  1.00 27.45      A    C
ATOM   629  N   MET A 299      57.281  37.227  75.754  1.00 27.38      A    N
```

| | | | | | | | | | | | |
|---|---|---|---|---|---|---|---|---|---|---|---|
| ATOM | 630 | CA  | MET | A | 299 | 58.365 | 37.618 | 74.842 | 1.00 | 28.41 | A C |
| ATOM | 631 | C   | MET | A | 299 | 59.516 | 38.323 | 75.576 | 1.00 | 28.13 | A C |
| ATOM | 632 | O   | MET | A | 299 | 60.699 | 38.032 | 75.331 | 1.00 | 26.75 | A O |
| ATOM | 633 | CB  | MET | A | 299 | 57.820 | 38.533 | 73.735 | 1.00 | 28.52 | A C |
| ATOM | 634 | CG  | MET | A | 299 | 56.833 | 37.808 | 72.769 | 1.00 | 32.00 | A C |
| ATOM | 635 | SD  | MET | A | 299 | 56.029 | 38.966 | 71.655 | 1.00 | 38.54 | A S |
| ATOM | 636 | CE  | MET | A | 299 | 54.722 | 37.909 | 70.873 | 1.00 | 37.79 | A C |
| ATOM | 637 | N   | TRP | A | 300 | 59.164 | 39.275 | 76.439 | 1.00 | 28.01 | A N |
| ATOM | 638 | CA  | TRP | A | 300 | 60.170 | 39.997 | 77.216 | 1.00 | 29.36 | A C |
| ATOM | 639 | C   | TRP | A | 300 | 60.975 | 39.044 | 78.096 | 1.00 | 28.58 | A C |
| ATOM | 640 | O   | TRP | A | 300 | 62.211 | 39.127 | 78.160 | 1.00 | 27.80 | A O |
| ATOM | 641 | CB  | TRP | A | 300 | 59.514 | 41.081 | 78.091 | 1.00 | 29.12 | A C |
| ATOM | 642 | CG  | TRP | A | 300 | 60.500 | 41.931 | 78.866 | 1.00 | 31.92 | A C |
| ATOM | 643 | CD1 | TRP | A | 300 | 60.544 | 42.088 | 80.226 | 1.00 | 33.24 | A C |
| ATOM | 644 | CD2 | TRP | A | 300 | 61.554 | 42.755 | 78.338 | 1.00 | 30.23 | A C |
| ATOM | 645 | NE1 | TRP | A | 300 | 61.555 | 42.946 | 80.567 | 1.00 | 30.43 | A N |
| ATOM | 646 | CE2 | TRP | A | 300 | 62.192 | 43.375 | 79.436 | 1.00 | 31.85 | A C |
| ATOM | 647 | CE3 | TRP | A | 300 | 62.013 | 43.047 | 77.051 | 1.00 | 30.75 | A C |
| ATOM | 648 | CZ2 | TRP | A | 300 | 63.300 | 44.243 | 79.293 | 1.00 | 31.61 | A C |
| ATOM | 649 | CZ3 | TRP | A | 300 | 63.113 | 43.925 | 76.899 | 1.00 | 32.57 | A C |
| ATOM | 650 | CH2 | TRP | A | 300 | 63.739 | 44.508 | 78.018 | 1.00 | 31.60 | A C |
| ATOM | 651 | N   | ARG | A | 301 | 60.295 | 38.142 | 78.793 | 1.00 | 27.29 | A N |
| ATOM | 652 | CA  | ARG | A | 301 | 61.022 | 37.146 | 79.597 | 1.00 | 27.36 | A C |
| ATOM | 653 | C   | ARG | A | 301 | 61.914 | 36.230 | 78.751 | 1.00 | 27.07 | A C |
| ATOM | 654 | O   | ARG | A | 301 | 62.902 | 35.656 | 79.243 | 1.00 | 26.53 | A O |
| ATOM | 655 | CB  | ARG | A | 301 | 60.042 | 36.259 | 80.375 | 1.00 | 28.01 | A C |
| ATOM | 656 | CG  | ARG | A | 301 | 59.178 | 36.985 | 81.418 | 1.00 | 27.70 | A C |
| ATOM | 657 | CD  | ARG | A | 301 | 58.447 | 36.026 | 82.381 | 1.00 | 26.65 | A C |
| ATOM | 658 | NE  | ARG | A | 301 | 57.398 | 35.231 | 81.736 | 1.00 | 26.47 | A N |
| ATOM | 659 | CZ  | ARG | A | 301 | 56.183 | 35.666 | 81.410 | 1.00 | 29.81 | A C |
| ATOM | 660 | NH1 | ARG | A | 301 | 55.811 | 36.940 | 81.645 | 1.00 | 27.68 | A N |
| ATOM | 661 | NH2 | ARG | A | 301 | 55.321 | 34.816 | 80.846 | 1.00 | 28.58 | A N |
| ATOM | 662 | N   | SER | A | 302 | 61.570 | 36.081 | 77.478 | 1.00 | 26.78 | A N |
| ATOM | 663 | CA  | SER | A | 302 | 62.277 | 35.104 | 76.640 | 1.00 | 27.46 | A C |
| ATOM | 664 | C   | SER | A | 302 | 63.309 | 35.754 | 75.719 | 1.00 | 27.53 | A C |
| ATOM | 665 | O   | SER | A | 302 | 64.053 | 35.059 | 75.032 | 1.00 | 26.57 | A O |
| ATOM | 666 | CB  | SER | A | 302 | 61.239 | 34.313 | 75.790 | 1.00 | 27.11 | A C |
| ATOM | 667 | OG  | SER | A | 302 | 60.261 | 33.639 | 76.606 | 1.00 | 26.55 | A O |
| ATOM | 668 | N   | ILE | A | 303 | 63.361 | 37.087 | 75.730 | 1.00 | 28.26 | A N |
| ATOM | 669 | CA  | ILE | A | 303 | 64.114 | 37.830 | 74.722 | 1.00 | 29.06 | A C |
| ATOM | 670 | C   | ILE | A | 303 | 65.596 | 37.465 | 74.608 | 1.00 | 30.64 | A C |
| ATOM | 671 | O   | ILE | A | 303 | 66.170 | 37.535 | 73.515 | 1.00 | 31.11 | A O |
| ATOM | 672 | CB  | ILE | A | 303 | 63.904 | 39.362 | 74.895 | 1.00 | 29.07 | A C |
| ATOM | 673 | CG1 | ILE | A | 303 | 64.296 | 40.133 | 73.623 | 1.00 | 29.79 | A C |
| ATOM | 674 | CG2 | ILE | A | 303 | 64.685 | 39.915 | 76.113 | 1.00 | 29.04 | A C |
| ATOM | 675 | CD1 | ILE | A | 303 | 64.021 | 41.659 | 73.754 | 1.00 | 29.27 | A C |
| ATOM | 676 | N   | ASP | A | 304 | 66.225 | 37.078 | 75.704 | 1.00 | 31.38 | A N |
| ATOM | 677 | CA  | ASP | A | 304 | 67.635 | 36.724 | 75.583 | 1.00 | 33.42 | A C |
| ATOM | 678 | C   | ASP | A | 304 | 67.890 | 35.234 | 75.551 | 1.00 | 34.12 | A C |
| ATOM | 679 | O   | ASP | A | 304 | 68.983 | 34.788 | 75.919 | 1.00 | 33.58 | A O |
| ATOM | 680 | CB  | ASP | A | 304 | 68.469 | 37.348 | 76.680 | 1.00 | 33.39 | A C |
| ATOM | 681 | CG  | ASP | A | 304 | 68.456 | 38.855 | 76.616 | 1.00 | 35.72 | A C |
| ATOM | 682 | OD1 | ASP | A | 304 | 68.715 | 39.413 | 75.516 | 1.00 | 38.30 | A O |
| ATOM | 683 | OD2 | ASP | A | 304 | 68.173 | 39.542 | 77.614 | 1.00 | 31.85 | A O |
| ATOM | 684 | N   | HIS | A | 305 | 66.900 | 34.465 | 75.091 | 1.00 | 34.18 | A N |
| ATOM | 685 | CA  | HIS | A | 305 | 67.099 | 33.019 | 74.994 | 1.00 | 34.25 | A C |
| ATOM | 686 | C   | HIS | A | 305 | 66.487 | 32.403 | 73.750 | 1.00 | 33.00 | A C |
| ATOM | 687 | O   | HIS | A | 305 | 65.381 | 31.853 | 73.793 | 1.00 | 32.40 | A O |
| ATOM | 688 | CB  | HIS | A | 305 | 66.581 | 32.360 | 76.252 | 1.00 | 34.63 | A C |
| ATOM | 689 | CG  | HIS | A | 305 | 67.344 | 32.767 | 77.463 | 1.00 | 38.44 | A C |
| ATOM | 690 | ND1 | HIS | A | 305 | 68.667 | 32.416 | 77.653 | 1.00 | 44.08 | A N |

145

| ATOM | 691 | CD2 | HIS | A | 305 | 66.998 | 33.533 | 78.519 | 1.00 | 41.31 | A | C |
| ATOM | 692 | CE1 | HIS | A | 305 | 69.092 | 32.935 | 78.790 | 1.00 | 46.11 | A | C |
| ATOM | 693 | NE2 | HIS | A | 305 | 68.099 | 33.616 | 79.335 | 1.00 | 44.76 | A | N |
| ATOM | 694 | N | PRO | A | 306 | 67.233 | 32.514 | 72.652 | 1.00 | 31.68 | A | N |
| ATOM | 695 | CA | PRO | A | 306 | 66.809 | 32.008 | 71.352 | 1.00 | 30.82 | A | C |
| ATOM | 696 | C | PRO | A | 306 | 66.292 | 30.590 | 71.496 | 1.00 | 29.93 | A | C |
| ATOM | 697 | O | PRO | A | 306 | 66.927 | 29.783 | 72.169 | 1.00 | 28.90 | A | O |
| ATOM | 698 | CB | PRO | A | 306 | 68.119 | 31.999 | 70.545 | 1.00 | 31.37 | A | C |
| ATOM | 699 | CG | PRO | A | 306 | 68.928 | 33.104 | 71.140 | 1.00 | 31.59 | A | C |
| ATOM | 700 | CD | PRO | A | 306 | 68.566 | 33.143 | 72.600 | 1.00 | 31.82 | A | C |
| ATOM | 701 | N | GLY | A | 307 | 65.137 | 30.304 | 70.905 | 1.00 | 29.38 | A | N |
| ATOM | 702 | CA | GLY | A | 307 | 64.589 | 28.952 | 70.921 | 1.00 | 28.63 | A | C |
| ATOM | 703 | C | GLY | A | 307 | 63.872 | 28.529 | 72.192 | 1.00 | 28.27 | A | C |
| ATOM | 704 | O | GLY | A | 307 | 63.437 | 27.389 | 72.313 | 1.00 | 28.37 | A | O |
| ATOM | 705 | N | LYS | A | 308 | 63.752 | 29.426 | 73.159 | 1.00 | 27.65 | A | N |
| ATOM | 706 | CA | LYS | A | 308 | 63.087 | 29.046 | 74.390 | 1.00 | 27.48 | A | C |
| ATOM | 707 | C | LYS | A | 308 | 61.979 | 29.999 | 74.746 | 1.00 | 26.73 | A | C |
| ATOM | 708 | O | LYS | A | 308 | 62.064 | 31.181 | 74.466 | 1.00 | 26.87 | A | O |
| ATOM | 709 | CB | LYS | A | 308 | 64.085 | 28.967 | 75.541 | 1.00 | 27.63 | A | C |
| ATOM | 710 | CG | LYS | A | 308 | 64.989 | 27.750 | 75.449 | 1.00 | 30.10 | A | C |
| ATOM | 711 | CD | LYS | A | 308 | 66.139 | 27.811 | 76.451 | 1.00 | 33.37 | A | C |
| ATOM | 712 | CE | LYS | A | 308 | 67.243 | 26.781 | 76.120 | 1.00 | 33.25 | A | C |
| ATOM | 713 | NZ | LYS | A | 308 | 66.930 | 25.449 | 76.696 | 1.00 | 35.96 | A | N |
| ATOM | 714 | N | LEU | A | 309 | 60.926 | 29.481 | 75.354 | 1.00 | 26.09 | A | N |
| ATOM | 715 | CA | LEU | A | 309 | 59.868 | 30.356 | 75.851 | 1.00 | 26.11 | A | C |
| ATOM | 716 | C | LEU | A | 309 | 59.896 | 30.248 | 77.373 | 1.00 | 26.01 | A | C |
| ATOM | 717 | O | LEU | A | 309 | 59.707 | 29.171 | 77.928 | 1.00 | 24.60 | A | O |
| ATOM | 718 | CB | LEU | A | 309 | 58.492 | 29.992 | 75.266 | 1.00 | 25.76 | A | C |
| ATOM | 719 | CG | LEU | A | 309 | 58.295 | 30.320 | 73.773 | 1.00 | 25.43 | A | C |
| ATOM | 720 | CD1 | LEU | A | 309 | 56.988 | 29.726 | 73.231 | 1.00 | 24.90 | A | C |
| ATOM | 721 | CD2 | LEU | A | 309 | 58.326 | 31.839 | 73.538 | 1.00 | 26.62 | A | C |
| ATOM | 722 | N | ILE | A | 310 | 60.233 | 31.348 | 78.042 | 1.00 | 26.27 | A | N |
| ATOM | 723 | CA | ILE | A | 310 | 60.304 | 31.329 | 79.496 | 1.00 | 26.70 | A | C |
| ATOM | 724 | C | ILE | A | 310 | 58.929 | 31.703 | 80.025 | 1.00 | 26.88 | A | C |
| ATOM | 725 | O | ILE | A | 310 | 58.662 | 32.887 | 80.308 | 1.00 | 26.69 | A | O |
| ATOM | 726 | CB | ILE | A | 310 | 61.418 | 32.292 | 80.029 | 1.00 | 27.33 | A | C |
| ATOM | 727 | CG1 | ILE | A | 310 | 62.822 | 31.740 | 79.750 | 1.00 | 29.43 | A | C |
| ATOM | 728 | CG2 | ILE | A | 310 | 61.393 | 32.379 | 81.546 | 1.00 | 26.37 | A | C |
| ATOM | 729 | CD1 | ILE | A | 310 | 62.998 | 31.199 | 78.406 | 1.00 | 33.08 | A | C |
| ATOM | 730 | N | PHE | A | 311 | 58.035 | 30.722 | 80.131 | 1.00 | 26.69 | A | N |
| ATOM | 731 | CA | PHE | A | 311 | 56.672 | 31.017 | 80.600 | 1.00 | 27.38 | A | C |
| ATOM | 732 | C | PHE | A | 311 | 56.688 | 31.489 | 82.046 | 1.00 | 28.08 | A | C |
| ATOM | 733 | O | PHE | A | 311 | 55.968 | 32.425 | 82.422 | 1.00 | 27.93 | A | O |
| ATOM | 734 | CB | PHE | A | 311 | 55.730 | 29.831 | 80.417 | 1.00 | 27.68 | A | C |
| ATOM | 735 | CG | PHE | A | 311 | 55.203 | 29.700 | 79.023 | 1.00 | 27.46 | A | C |
| ATOM | 736 | CD1 | PHE | A | 311 | 54.042 | 30.352 | 78.649 | 1.00 | 25.34 | A | C |
| ATOM | 737 | CD2 | PHE | A | 311 | 55.885 | 28.935 | 78.079 | 1.00 | 27.88 | A | C |
| ATOM | 738 | CE1 | PHE | A | 311 | 53.561 | 30.246 | 77.361 | 1.00 | 25.56 | A | C |
| ATOM | 739 | CE2 | PHE | A | 311 | 55.400 | 28.815 | 76.786 | 1.00 | 26.22 | A | C |
| ATOM | 740 | CZ | PHE | A | 311 | 54.236 | 29.467 | 76.436 | 1.00 | 27.11 | A | C |
| ATOM | 741 | N | ALA | A | 312 | 57.558 | 30.869 | 82.828 | 1.00 | 28.08 | A | N |
| ATOM | 742 | CA | ALA | A | 312 | 57.754 | 31.226 | 84.220 | 1.00 | 29.19 | A | C |
| ATOM | 743 | C | ALA | A | 312 | 58.982 | 30.484 | 84.720 | 1.00 | 30.25 | A | C |
| ATOM | 744 | O | ALA | A | 312 | 59.437 | 29.530 | 84.098 | 1.00 | 30.35 | A | O |
| ATOM | 745 | CB | ALA | A | 312 | 56.530 | 30.805 | 85.048 | 1.00 | 28.45 | A | C |
| ATOM | 746 | N | PRO | A | 313 | 59.509 | 30.891 | 85.861 | 1.00 | 31.36 | A | N |
| ATOM | 747 | CA | PRO | A | 313 | 60.592 | 30.135 | 86.467 | 1.00 | 32.52 | A | C |
| ATOM | 748 | C | PRO | A | 313 | 60.071 | 28.717 | 86.662 | 1.00 | 33.13 | A | C |
| ATOM | 749 | O | PRO | A | 313 | 58.959 | 28.525 | 87.149 | 1.00 | 33.71 | A | O |
| ATOM | 750 | CB | PRO | A | 313 | 60.774 | 30.821 | 87.820 | 1.00 | 32.81 | A | C |
| ATOM | 751 | CG | PRO | A | 313 | 60.289 | 32.211 | 87.598 | 1.00 | 33.40 | A | C |

| ATOM | 752 | CD  | PRO | A | 313 | 59.134 | 32.079 | 86.643 | 1.00 | 31.39 | A | C |
| ATOM | 753 | N   | ASP | A | 314 | 60.839 | 27.725 | 86.259 | 1.00 | 33.54 | A | N |
| ATOM | 754 | CA  | ASP | A | 314 | 60.385 | 26.336 | 86.413 | 1.00 | 33.61 | A | C |
| ATOM | 755 | C   | ASP | A | 314 | 59.328 | 25.940 | 85.351 | 1.00 | 32.94 | A | C |
| ATOM | 756 | O   | ASP | A | 314 | 58.675 | 24.890 | 85.464 | 1.00 | 32.47 | A | O |
| ATOM | 757 | CB  | ASP | A | 314 | 59.874 | 26.081 | 87.844 | 1.00 | 34.61 | A | C |
| ATOM | 758 | CG  | ASP | A | 314 | 60.644 | 24.949 | 88.570 | 1.00 | 36.71 | A | C |
| ATOM | 759 | OD1 | ASP | A | 314 | 61.693 | 24.492 | 88.051 | 1.00 | 39.93 | A | O |
| ATOM | 760 | OD2 | ASP | A | 314 | 60.283 | 24.457 | 89.678 | 1.00 | 39.07 | A | O |
| ATOM | 761 | N   | LEU | A | 315 | 59.131 | 26.799 | 84.350 | 1.00 | 31.31 | A | N |
| ATOM | 762 | CA  | LEU | A | 315 | 58.310 | 26.450 | 83.188 | 1.00 | 30.32 | A | C |
| ATOM | 763 | C   | LEU | A | 315 | 58.925 | 27.095 | 81.952 | 1.00 | 29.66 | A | C |
| ATOM | 764 | O   | LEU | A | 315 | 58.432 | 28.095 | 81.423 | 1.00 | 27.68 | A | O |
| ATOM | 765 | CB  | LEU | A | 315 | 56.842 | 26.852 | 83.329 | 1.00 | 30.26 | A | C |
| ATOM | 766 | CG  | LEU | A | 315 | 55.994 | 26.195 | 82.227 | 1.00 | 30.80 | A | C |
| ATOM | 767 | CD1 | LEU | A | 315 | 56.136 | 24.672 | 82.278 | 1.00 | 31.91 | A | C |
| ATOM | 768 | CD2 | LEU | A | 315 | 54.529 | 26.577 | 82.299 | 1.00 | 29.40 | A | C |
| ATOM | 769 | N   | VAL | A | 316 | 60.042 | 26.520 | 81.536 | 1.00 | 29.07 | A | N |
| ATOM | 770 | CA  | VAL | A | 316 | 60.785 | 26.979 | 80.385 | 1.00 | 29.34 | A | C |
| ATOM | 771 | C   | VAL | A | 316 | 60.603 | 25.931 | 79.299 | 1.00 | 29.63 | A | C |
| ATOM | 772 | O   | VAL | A | 316 | 60.957 | 24.767 | 79.496 | 1.00 | 27.75 | A | O |
| ATOM | 773 | CB  | VAL | A | 316 | 62.266 | 27.028 | 80.746 | 1.00 | 29.56 | A | C |
| ATOM | 774 | CG1 | VAL | A | 316 | 63.091 | 27.477 | 79.551 | 1.00 | 29.98 | A | C |
| ATOM | 775 | CG2 | VAL | A | 316 | 62.467 | 27.929 | 81.960 | 1.00 | 29.81 | A | C |
| ATOM | 776 | N   | LEU | A | 317 | 60.066 | 26.334 | 78.153 | 1.00 | 29.96 | A | N |
| ATOM | 777 | CA  | LEU | A | 317 | 59.797 | 25.358 | 77.093 | 1.00 | 30.60 | A | C |
| ATOM | 778 | C   | LEU | A | 317 | 60.640 | 25.562 | 75.838 | 1.00 | 31.00 | A | C |
| ATOM | 779 | O   | LEU | A | 317 | 60.754 | 26.677 | 75.325 | 1.00 | 30.84 | A | O |
| ATOM | 780 | CB  | LEU | A | 317 | 58.318 | 25.372 | 76.721 | 1.00 | 30.19 | A | C |
| ATOM | 781 | CG  | LEU | A | 317 | 57.374 | 24.972 | 77.855 | 1.00 | 30.68 | A | C |
| ATOM | 782 | CD1 | LEU | A | 317 | 55.929 | 25.132 | 77.440 | 1.00 | 29.83 | A | C |
| ATOM | 783 | CD2 | LEU | A | 317 | 57.645 | 23.549 | 78.306 | 1.00 | 30.23 | A | C |
| ATOM | 784 | N   | ASP | A | 318 | 61.242 | 24.474 | 75.366 | 1.00 | 31.40 | A | N |
| ATOM | 785 | CA  | ASP | A | 318 | 62.002 | 24.498 | 74.125 | 1.00 | 32.17 | A | C |
| ATOM | 786 | C   | ASP | A | 318 | 60.977 | 24.564 | 73.012 | 1.00 | 31.68 | A | C |
| ATOM | 787 | O   | ASP | A | 318 | 59.841 | 24.107 | 73.171 | 1.00 | 31.42 | A | O |
| ATOM | 788 | CB  | ASP | A | 318 | 62.812 | 23.201 | 73.943 | 1.00 | 32.70 | A | C |
| ATOM | 789 | CG  | ASP | A | 318 | 64.137 | 23.204 | 74.710 | 1.00 | 35.61 | A | C |
| ATOM | 790 | OD1 | ASP | A | 318 | 64.808 | 24.264 | 74.769 | 1.00 | 37.29 | A | O |
| ATOM | 791 | OD2 | ASP | A | 318 | 64.601 | 22.167 | 75.262 | 1.00 | 38.87 | A | O |
| ATOM | 792 | N   | ARG | A | 319 | 61.373 | 25.127 | 71.882 | 1.00 | 31.26 | A | N |
| ATOM | 793 | CA  | ARG | A | 319 | 60.476 | 25.221 | 70.744 | 1.00 | 31.15 | A | C |
| ATOM | 794 | C   | ARG | A | 319 | 59.847 | 23.860 | 70.384 | 1.00 | 31.47 | A | C |
| ATOM | 795 | O   | ARG | A | 319 | 58.653 | 23.783 | 70.102 | 1.00 | 31.51 | A | O |
| ATOM | 796 | CB  | ARG | A | 319 | 61.206 | 25.844 | 69.548 | 1.00 | 30.95 | A | C |
| ATOM | 797 | CG  | ARG | A | 319 | 60.356 | 25.974 | 68.284 | 1.00 | 29.95 | A | C |
| ATOM | 798 | CD  | ARG | A | 319 | 60.385 | 24.735 | 67.363 | 1.00 | 28.07 | A | C |
| ATOM | 799 | NE  | ARG | A | 319 | 59.589 | 24.965 | 66.158 | 1.00 | 25.63 | A | N |
| ATOM | 800 | CZ  | ARG | A | 319 | 59.336 | 24.049 | 65.232 | 1.00 | 26.41 | A | C |
| ATOM | 801 | NH1 | ARG | A | 319 | 59.841 | 22.828 | 65.344 | 1.00 | 23.07 | A | N |
| ATOM | 802 | NH2 | ARG | A | 319 | 58.586 | 24.361 | 64.178 | 1.00 | 24.29 | A | N |
| ATOM | 803 | N   | ASP | A | 320 | 60.632 | 22.786 | 70.431 | 1.00 | 31.59 | A | N |
| ATOM | 804 | CA  | ASP | A | 320 | 60.122 | 21.462 | 70.072 | 1.00 | 32.09 | A | C |
| ATOM | 805 | C   | ASP | A | 320 | 59.035 | 20.939 | 71.008 | 1.00 | 32.49 | A | C |
| ATOM | 806 | O   | ASP | A | 320 | 58.275 | 20.036 | 70.647 | 1.00 | 31.67 | A | O |
| ATOM | 807 | CB  | ASP | A | 320 | 61.257 | 20.422 | 69.971 | 1.00 | 32.16 | A | C |
| ATOM | 808 | CG  | ASP | A | 320 | 62.096 | 20.581 | 68.707 | 1.00 | 32.03 | A | C |
| ATOM | 809 | OD1 | ASP | A | 320 | 61.697 | 21.347 | 67.799 | 1.00 | 30.77 | A | O |
| ATOM | 810 | OD2 | ASP | A | 320 | 63.176 | 19.977 | 68.535 | 1.00 | 31.43 | A | O |
| ATOM | 811 | N   | GLU | A | 321 | 58.960 | 21.494 | 72.212 | 1.00 | 32.92 | A | N |
| ATOM | 812 | CA  | GLU | A | 321 | 57.954 | 21.029 | 73.161 | 1.00 | 33.69 | A | C |

| | | | | | | | | | | |
|---|---|---|---|---|---|---|---|---|---|---|
| ATOM | 813 | C | GLU | A | 321 | 56.535 | 21.431 | 72.757 | 1.00 33.51 | A C |
| ATOM | 814 | O | GLU | A | 321 | 55.555 | 20.965 | 73.339 | 1.00 33.71 | A O |
| ATOM | 815 | CB | GLU | A | 321 | 58.302 | 21.441 | 74.590 | 1.00 33.76 | A C |
| ATOM | 816 | CG | GLU | A | 321 | 59.484 | 20.639 | 75.123 | 1.00 35.52 | A C |
| ATOM | 817 | CD | GLU | A | 321 | 59.897 | 21.046 | 76.522 | 1.00 37.12 | A C |
| ATOM | 818 | OE1 | GLU | A | 321 | 60.563 | 22.094 | 76.668 | 1.00 37.00 | A O |
| ATOM | 819 | OE2 | GLU | A | 321 | 59.554 | 20.310 | 77.470 | 1.00 37.53 | A O |
| ATOM | 820 | N | GLY | A | 322 | 56.423 | 22.265 | 71.732 | 1.00 33.23 | A N |
| ATOM | 821 | CA | GLY | A | 322 | 55.118 | 22.606 | 71.210 | 1.00 33.37 | A C |
| ATOM | 822 | C | GLY | A | 322 | 54.472 | 21.406 | 70.531 | 1.00 33.77 | A C |
| ATOM | 823 | O | GLY | A | 322 | 53.268 | 21.386 | 70.316 | 1.00 33.27 | A O |
| ATOM | 824 | N | LYS | A | 323 | 55.262 | 20.386 | 70.212 | 1.00 34.20 | A N |
| ATOM | 825 | CA | LYS | A | 323 | 54.712 | 19.202 | 69.551 | 1.00 35.27 | A C |
| ATOM | 826 | C | LYS | A | 323 | 53.769 | 18.414 | 70.465 | 1.00 35.37 | A C |
| ATOM | 827 | O | LYS | A | 323 | 53.001 | 17.575 | 70.002 | 1.00 35.15 | A O |
| ATOM | 828 | CB | LYS | A | 323 | 55.831 | 18.303 | 68.999 | 1.00 35.27 | A C |
| ATOM | 829 | CG | LYS | A | 323 | 56.683 | 19.005 | 67.940 | 1.00 36.62 | A C |
| ATOM | 830 | CD | LYS | A | 323 | 57.764 | 18.117 | 67.329 | 1.00 37.43 | A C |
| ATOM | 831 | CE | LYS | A | 323 | 58.597 | 18.923 | 66.331 | 1.00 37.79 | A C |
| ATOM | 832 | NZ | LYS | A | 323 | 59.724 | 18.153 | 65.725 | 1.00 37.97 | A N |
| ATOM | 833 | N | CYS | A | 324 | 53.817 | 18.714 | 71.759 | 1.00 35.78 | A N |
| ATOM | 834 | CA | CYS | A | 324 | 52.995 | 18.018 | 72.749 | 1.00 36.21 | A C |
| ATOM | 835 | C | CYS | A | 324 | 51.516 | 18.384 | 72.687 | 1.00 35.25 | A C |
| ATOM | 836 | O | CYS | A | 324 | 50.668 | 17.586 | 73.057 | 1.00 35.08 | A O |
| ATOM | 837 | CB | CYS | A | 324 | 53.506 | 18.301 | 74.162 | 1.00 36.73 | A C |
| ATOM | 838 | SG | CYS | A | 324 | 55.153 | 17.658 | 74.538 | 1.00 40.83 | A S |
| ATOM | 839 | N | VAL | A | 325 | 51.206 | 19.591 | 72.233 | 1.00 34.06 | A N |
| ATOM | 840 | CA | VAL | A | 325 | 49.820 | 20.020 | 72.182 | 1.00 33.34 | A C |
| ATOM | 841 | C | VAL | A | 325 | 49.384 | 20.291 | 70.752 | 1.00 33.26 | A C |
| ATOM | 842 | O | VAL | A | 325 | 50.032 | 21.063 | 70.043 | 1.00 32.82 | A O |
| ATOM | 843 | CB | VAL | A | 325 | 49.623 | 21.304 | 72.988 | 1.00 33.42 | A C |
| ATOM | 844 | CG1 | VAL | A | 325 | 48.158 | 21.709 | 72.996 | 1.00 33.24 | A C |
| ATOM | 845 | CG2 | VAL | A | 325 | 50.157 | 21.138 | 74.399 | 1.00 32.82 | A C |
| ATOM | 846 | N | GLU | A | 326 | 48.288 | 19.670 | 70.323 | 1.00 32.70 | A N |
| ATOM | 847 | CA | GLU | A | 326 | 47.814 | 19.892 | 68.962 | 1.00 32.96 | A C |
| ATOM | 848 | C | GLU | A | 326 | 47.632 | 21.386 | 68.703 | 1.00 32.36 | A C |
| ATOM | 849 | O | GLU | A | 326 | 46.993 | 22.082 | 69.488 | 1.00 32.09 | A O |
| ATOM | 850 | CB | GLU | A | 326 | 46.500 | 19.143 | 68.680 | 1.00 33.12 | A C |
| ATOM | 851 | CG | GLU | A | 326 | 45.952 | 19.362 | 67.269 | 1.00 35.15 | A C |
| ATOM | 852 | CD | GLU | A | 326 | 44.756 | 18.473 | 66.917 | 1.00 38.31 | A C |
| ATOM | 853 | OE1 | GLU | A | 326 | 44.906 | 17.228 | 66.869 | 1.00 39.89 | A O |
| ATOM | 854 | OE2 | GLU | A | 326 | 43.656 | 19.016 | 66.666 | 1.00 39.66 | A O |
| ATOM | 855 | N | GLY | A | 327 | 48.226 | 21.867 | 67.615 | 1.00 31.97 | A N |
| ATOM | 856 | CA | GLY | A | 327 | 48.056 | 23.241 | 67.168 | 1.00 31.63 | A C |
| ATOM | 857 | C | GLY | A | 327 | 48.850 | 24.333 | 67.857 | 1.00 31.32 | A C |
| ATOM | 858 | O | GLY | A | 327 | 48.908 | 25.466 | 67.359 | 1.00 31.59 | A O |
| ATOM | 859 | N | ILE | A | 328 | 49.478 | 24.021 | 68.985 | 1.00 30.43 | A N |
| ATOM | 860 | CA | ILE | A | 328 | 50.197 | 25.055 | 69.712 | 1.00 29.58 | A C |
| ATOM | 861 | C | ILE | A | 328 | 51.580 | 25.364 | 69.123 | 1.00 29.47 | A C |
| ATOM | 862 | O | ILE | A | 328 | 52.127 | 26.445 | 69.370 | 1.00 28.69 | A O |
| ATOM | 863 | CB | ILE | A | 328 | 50.303 | 24.697 | 71.220 | 1.00 29.56 | A C |
| ATOM | 864 | CG1 | ILE | A | 328 | 50.308 | 25.963 | 72.082 | 1.00 29.26 | A C |
| ATOM | 865 | CG2 | ILE | A | 328 | 51.529 | 23.852 | 71.492 | 1.00 28.78 | A C |
| ATOM | 866 | CD1 | ILE | A | 328 | 50.277 | 25.667 | 73.584 | 1.00 28.68 | A C |
| ATOM | 867 | N | LEU | A | 329 | 52.146 | 24.430 | 68.351 | 1.00 28.81 | A N |
| ATOM | 868 | CA | LEU | A | 329 | 53.479 | 24.638 | 67.773 | 1.00 28.74 | A C |
| ATOM | 869 | C | LEU | A | 329 | 53.534 | 25.867 | 66.871 | 1.00 29.17 | A C |
| ATOM | 870 | O | LEU | A | 329 | 54.482 | 26.656 | 66.935 | 1.00 28.68 | A O |
| ATOM | 871 | CB | LEU | A | 329 | 53.964 | 23.405 | 67.008 | 1.00 29.05 | A C |
| ATOM | 872 | CG | LEU | A | 329 | 55.358 | 23.533 | 66.389 | 1.00 28.42 | A C |
| ATOM | 873 | CD1 | LEU | A | 329 | 56.419 | 23.762 | 67.460 | 1.00 27.20 | A C |

| | | | | | | | | | | |
|---|---|---|---|---|---|---|---|---|---|---|
| ATOM | 874 | CD2 | LEU | A | 329 | 55.670 | 22.285 | 65.575 | 1.00 28.42 | A C |
| ATOM | 875 | N | GLU | A | 330 | 52.504 | 26.040 | 66.054 | 1.00 29.23 | A N |
| ATOM | 876 | CA | GLU | A | 330 | 52.411 | 27.182 | 65.156 | 1.00 30.37 | A C |
| ATOM | 877 | C | GLU | A | 330 | 52.476 | 28.467 | 65.965 | 1.00 29.80 | A C |
| ATOM | 878 | O | GLU | A | 330 | 53.175 | 29.409 | 65.610 | 1.00 30.08 | A O |
| ATOM | 879 | CB | GLU | A | 330 | 51.098 | 27.107 | 64.374 | 1.00 31.25 | A C |
| ATOM | 880 | CG | GLU | A | 330 | 50.840 | 28.242 | 63.391 | 1.00 34.72 | A C |
| ATOM | 881 | CD | GLU | A | 330 | 49.766 | 27.871 | 62.357 | 1.00 39.95 | A C |
| ATOM | 882 | OE1 | GLU | A | 330 | 49.405 | 26.671 | 62.253 | 1.00 40.05 | A O |
| ATOM | 883 | OE2 | GLU | A | 330 | 49.280 | 28.775 | 61.641 | 1.00 42.39 | A O |
| ATOM | 884 | N | ILE | A | 331 | 51.755 | 28.481 | 67.079 | 1.00 29.23 | A N |
| ATOM | 885 | CA | ILE | A | 331 | 51.718 | 29.627 | 67.976 | 1.00 28.70 | A C |
| ATOM | 886 | C | ILE | A | 331 | 53.061 | 29.868 | 68.677 | 1.00 27.73 | A C |
| ATOM | 887 | O | ILE | A | 331 | 53.527 | 31.002 | 68.761 | 1.00 26.35 | A O |
| ATOM | 888 | CB | ILE | A | 331 | 50.556 | 29.461 | 68.972 | 1.00 29.22 | A C |
| ATOM | 889 | CG1 | ILE | A | 331 | 49.239 | 29.422 | 68.187 | 1.00 30.54 | A C |
| ATOM | 890 | CG2 | ILE | A | 331 | 50.530 | 30.579 | 69.982 | 1.00 28.78 | A C |
| ATOM | 891 | CD1 | ILE | A | 331 | 48.013 | 29.288 | 69.040 | 1.00 32.86 | A C |
| ATOM | 892 | N | PHE | A | 332 | 53.691 | 28.798 | 69.150 | 1.00 27.39 | A N |
| ATOM | 893 | CA | PHE | A | 332 | 55.019 | 28.922 | 69.746 | 1.00 26.98 | A C |
| ATOM | 894 | C | PHE | A | 332 | 55.947 | 29.560 | 68.710 | 1.00 26.53 | A C |
| ATOM | 895 | O | PHE | A | 332 | 56.708 | 30.463 | 69.035 | 1.00 25.70 | A O |
| ATOM | 896 | CB | PHE | A | 332 | 55.578 | 27.555 | 70.158 | 1.00 26.75 | A C |
| ATOM | 897 | CG | PHE | A | 332 | 55.113 | 27.070 | 71.509 | 1.00 27.41 | A C |
| ATOM | 898 | CD1 | PHE | A | 332 | 54.003 | 27.621 | 72.130 | 1.00 26.35 | A C |
| ATOM | 899 | CD2 | PHE | A | 332 | 55.794 | 26.040 | 72.156 | 1.00 27.58 | A C |
| ATOM | 900 | CE1 | PHE | A | 332 | 53.572 | 27.146 | 73.367 | 1.00 26.18 | A C |
| ATOM | 901 | CE2 | PHE | A | 332 | 55.370 | 25.569 | 73.395 | 1.00 26.28 | A C |
| ATOM | 902 | CZ | PHE | A | 332 | 54.258 | 26.134 | 73.999 | 1.00 26.52 | A C |
| ATOM | 903 | N | ASP | A | 333 | 55.861 | 29.115 | 67.452 | 1.00 26.44 | A N |
| ATOM | 904 | CA | ASP | A | 333 | 56.768 | 29.644 | 66.431 | 1.00 27.13 | A C |
| ATOM | 905 | C | ASP | A | 333 | 56.527 | 31.112 | 66.195 | 1.00 27.21 | A C |
| ATOM | 906 | O | ASP | A | 333 | 57.459 | 31.868 | 65.943 | 1.00 27.51 | A O |
| ATOM | 907 | CB | ASP | A | 333 | 56.657 | 28.885 | 65.111 | 1.00 27.51 | A C |
| ATOM | 908 | CG | ASP | A | 333 | 57.410 | 27.579 | 65.133 | 1.00 27.53 | A C |
| ATOM | 909 | OD1 | ASP | A | 333 | 58.347 | 27.436 | 65.952 | 1.00 27.70 | A O |
| ATOM | 910 | OD2 | ASP | A | 333 | 57.129 | 26.646 | 64.369 | 1.00 26.65 | A O |
| ATOM | 911 | N | MET | A | 334 | 55.269 | 31.521 | 66.248 | 1.00 26.99 | A N |
| ATOM | 912 | CA | MET | A | 334 | 54.958 | 32.932 | 66.068 | 1.00 26.99 | A C |
| ATOM | 913 | CB | MET | A | 334 | 53.449 | 33.156 | 65.873 | 1.00 26.54 | A C |
| ATOM | 914 | CG AMET | | A | 334 | 52.929 | 32.747 | 64.500 | 0.50 27.97 | A C |
| ATOM | 915 | CG BMET | | A | 334 | 52.840 | 32.336 | 64.728 | 0.50 27.22 | A C |
| ATOM | 916 | SD AMET | | A | 334 | 51.165 | 33.142 | 64.361 | 0.50 29.80 | A S |
| ATOM | 917 | SD BMET | | A | 334 | 51.025 | 32.255 | 64.849 | 0.50 26.74 | A S |
| ATOM | 918 | CE AMET | | A | 334 | 50.750 | 32.244 | 62.915 | 0.50 27.50 | A C |
| ATOM | 919 | CE BMET | | A | 334 | 50.640 | 33.980 | 64.710 | 0.50 26.20 | A C |
| ATOM | 920 | C | MET | A | 334 | 55.484 | 33.735 | 67.250 | 1.00 26.73 | A C |
| ATOM | 921 | O | MET | A | 334 | 56.042 | 34.807 | 67.058 | 1.00 26.84 | A O |
| ATOM | 922 | N | LEU | A | 335 | 55.290 | 33.232 | 68.466 | 1.00 26.33 | A N |
| ATOM | 923 | CA | LEU | A | 335 | 55.790 | 33.909 | 69.669 | 1.00 26.89 | A C |
| ATOM | 924 | C | LEU | A | 335 | 57.316 | 34.029 | 69.628 | 1.00 26.97 | A C |
| ATOM | 925 | O | LEU | A | 335 | 57.872 | 35.095 | 69.932 | 1.00 26.45 | A O |
| ATOM | 926 | CB | LEU | A | 335 | 55.351 | 33.159 | 70.932 | 1.00 26.91 | A C |
| ATOM | 927 | CG | LEU | A | 335 | 53.845 | 33.221 | 71.231 | 1.00 27.43 | A C |
| ATOM | 928 | CD1 | LEU | A | 335 | 53.490 | 32.199 | 72.319 | 1.00 26.45 | A C |
| ATOM | 929 | CD2 | LEU | A | 335 | 53.458 | 34.660 | 71.637 | 1.00 25.61 | A C |
| ATOM | 930 | N | LEU | A | 336 | 57.977 | 32.952 | 69.201 | 1.00 26.15 | A N |
| ATOM | 931 | CA | LEU | A | 336 | 59.436 | 32.951 | 69.075 | 1.00 27.42 | A C |
| ATOM | 932 | C | LEU | A | 336 | 59.951 | 33.900 | 67.982 | 1.00 27.67 | A C |
| ATOM | 933 | O | LEU | A | 336 | 60.944 | 34.592 | 68.181 | 1.00 27.34 | A O |
| ATOM | 934 | CB | LEU | A | 336 | 59.969 | 31.535 | 68.850 | 1.00 26.08 | A C |

| ATOM | 935 | CG   | LEU  A 336 | 59.944 | 30.648 | 70.103 | 1.00 | 26.75 | A | C |
|------|-----|------|------------|--------|--------|--------|------|-------|---|---|
| ATOM | 936 | CD1  | LEU  A 336 | 59.911 | 29.143 | 69.719 | 1.00 | 24.48 | A | C |
| ATOM | 937 | CD2  | LEU  A 336 | 61.112 | 30.944 | 71.079 | 1.00 | 27.12 | A | C |
| ATOM | 938 | N    | ALA  A 337 | 59.294 | 33.904 | 66.819 | 1.00 | 28.27 | A | N |
| ATOM | 939 | CA   | ALA  A 337 | 59.703 | 34.827 | 65.754 | 1.00 | 28.70 | A | C |
| ATOM | 940 | C    | ALA  A 337 | 59.533 | 36.279 | 66.210 | 1.00 | 29.05 | A | C |
| ATOM | 941 | O    | ALA  A 337 | 60.400 | 37.103 | 65.951 | 1.00 | 29.49 | A | O |
| ATOM | 942 | CB   | ALA  A 337 | 58.949 | 34.564 | 64.434 | 1.00 | 28.34 | A | C |
| ATOM | 943 | N    | THR  A 338 | 58.428 | 36.590 | 66.888 | 1.00 | 27.78 | A | N |
| ATOM | 944 | CA   | THR  A 338 | 58.235 | 37.940 | 67.374 | 1.00 | 28.43 | A | C |
| ATOM | 945 | C    | THR  A 338 | 59.275 | 38.305 | 68.448 | 1.00 | 28.39 | A | C |
| ATOM | 946 | O    | THR  A 338 | 59.814 | 39.429 | 68.469 | 1.00 | 27.81 | A | O |
| ATOM | 947 | CB   | THR  A 338 | 56.783 | 38.129 | 67.894 | 1.00 | 29.16 | A | C |
| ATOM | 948 | OG1  | THR  A 338 | 55.864 | 37.801 | 66.843 | 1.00 | 28.50 | A | O |
| ATOM | 949 | CG2  | THR  A 338 | 56.510 | 39.586 | 68.165 | 1.00 | 29.02 | A | C |
| ATOM | 950 | N    | THR  A 339 | 59.535 | 37.372 | 69.349 | 1.00 | 26.75 | A | N |
| ATOM | 951 | CA   | THR  A 339 | 60.557 | 37.593 | 70.347 | 1.00 | 28.06 | A | C |
| ATOM | 952 | C    | THR  A 339 | 61.884 | 37.864 | 69.639 | 1.00 | 28.16 | A | C |
| ATOM | 953 | O    | THR  A 339 | 62.632 | 38.756 | 70.037 | 1.00 | 27.85 | A | O |
| ATOM | 954 | CB   | THR  A 339 | 60.723 | 36.367 | 71.232 | 1.00 | 28.20 | A | C |
| ATOM | 955 | OG1  | THR  A 339 | 59.490 | 36.115 | 71.906 | 1.00 | 27.10 | A | O |
| ATOM | 956 | CG2  | THR  A 339 | 61.738 | 36.648 | 72.364 | 1.00 | 28.63 | A | C |
| ATOM | 957 | N    | SER  A 340 | 62.175 | 37.090 | 68.598 | 1.00 | 28.03 | A | N |
| ATOM | 958 | CA   | SER  A 340 | 63.407 | 37.309 | 67.845 | 1.00 | 29.01 | A | C |
| ATOM | 959 | C    | SER  A 340 | 63.494 | 38.719 | 67.227 | 1.00 | 28.90 | A | C |
| ATOM | 960 | O    | SER  A 340 | 64.590 | 39.270 | 67.152 | 1.00 | 27.46 | A | O |
| ATOM | 961 | CB   | SER  A 340 | 63.620 | 36.244 | 66.761 | 1.00 | 28.95 | A | C |
| ATOM | 962 | OG   | SER  A 340 | 63.830 | 34.983 | 67.373 | 1.00 | 31.80 | A | O |
| ATOM | 963 | N    | ARG  A 341 | 62.377 | 39.268 | 66.743 | 1.00 | 28.63 | A | N |
| ATOM | 964 | CA   | ARG  A 341 | 62.424 | 40.635 | 66.218 | 1.00 | 29.62 | A | C |
| ATOM | 965 | CB   | ARG  A 341 | 61.138 | 41.067 | 65.472 | 1.00 | 29.80 | A | C |
| ATOM | 966 | CG   | AARG A 341 | 60.549 | 40.010 | 64.502 | 0.50 | 30.78 | A | C |
| ATOM | 967 | CG   | BARG A 341 | 61.128 | 40.750 | 63.998 | 0.50 | 33.01 | A | C |
| ATOM | 968 | CD   | AARG A 341 | 61.234 | 39.913 | 63.116 | 0.50 | 31.93 | A | C |
| ATOM | 969 | CD   | BARG A 341 | 62.153 | 41.523 | 63.192 | 0.50 | 35.92 | A | C |
| ATOM | 970 | NE   | AARG A 341 | 62.515 | 39.210 | 63.188 | 0.50 | 33.09 | A | N |
| ATOM | 971 | NE   | BARG A 341 | 61.758 | 42.911 | 62.977 | 0.50 | 38.09 | A | N |
| ATOM | 972 | CZ   | AARG A 341 | 62.648 | 37.887 | 63.266 | 0.50 | 33.71 | A | C |
| ATOM | 973 | CZ   | BARG A 341 | 62.604 | 43.927 | 62.949 | 0.50 | 37.85 | A | C |
| ATOM | 974 | NH1  | AARG A 341 | 61.576 | 37.099 | 63.270 | 0.50 | 30.99 | A | N |
| ATOM | 975 | NH1  | BARG A 341 | 63.900 | 43.718 | 63.140 | 0.50 | 38.39 | A | N |
| ATOM | 976 | NH2  | AARG A 341 | 63.864 | 37.350 | 63.338 | 0.50 | 32.61 | A | N |
| ATOM | 977 | NH2  | BARG A 341 | 62.155 | 45.152 | 62.727 | 0.50 | 38.48 | A | N |
| ATOM | 978 | C    | ARG  A 341 | 62.744 | 41.633 | 67.348 | 1.00 | 29.13 | A | C |
| ATOM | 979 | O    | ARG  A 341 | 63.537 | 42.571 | 67.145 | 1.00 | 29.07 | A | O |
| ATOM | 980 | N    | PHE  A 342 | 62.142 | 41.447 | 68.520 | 1.00 | 28.28 | A | N |
| ATOM | 981 | CA   | PHE  A 342 | 62.441 | 42.335 | 69.660 | 1.00 | 29.23 | A | C |
| ATOM | 982 | C    | PHE  A 342 | 63.925 | 42.241 | 70.047 | 1.00 | 28.74 | A | C |
| ATOM | 983 | O    | PHE  A 342 | 64.567 | 43.254 | 70.323 | 1.00 | 28.32 | A | O |
| ATOM | 984 | CB   | PHE  A 342 | 61.515 | 42.057 | 70.867 | 1.00 | 29.77 | A | C |
| ATOM | 985 | CG   | PHE  A 342 | 60.096 | 42.589 | 70.686 | 1.00 | 31.14 | A | C |
| ATOM | 986 | CD1  | PHE  A 342 | 59.877 | 43.922 | 70.398 | 1.00 | 32.79 | A | C |
| ATOM | 987 | CD2  | PHE  A 342 | 59.004 | 41.757 | 70.811 | 1.00 | 32.81 | A | C |
| ATOM | 988 | CE1  | PHE  A 342 | 58.584 | 44.417 | 70.256 | 1.00 | 35.92 | A | C |
| ATOM | 989 | CE2  | PHE  A 342 | 57.706 | 42.238 | 70.649 | 1.00 | 35.83 | A | C |
| ATOM | 990 | CZ   | PHE  A 342 | 57.494 | 43.566 | 70.362 | 1.00 | 34.64 | A | C |
| ATOM | 991 | N    | ARG  A 343 | 64.471 | 41.032 | 70.025 | 1.00 | 28.38 | A | N |
| ATOM | 992 | CA   | ARG  A 343 | 65.877 | 40.849 | 70.333 | 1.00 | 29.40 | A | C |
| ATOM | 993 | C    | ARG  A 343 | 66.732 | 41.576 | 69.290 | 1.00 | 29.35 | A | C |
| ATOM | 994 | O    | ARG  A 343 | 67.640 | 42.289 | 69.653 | 1.00 | 28.43 | A | O |
| ATOM | 995 | CB   | ARG  A 343 | 66.263 | 39.364 | 70.384 | 1.00 | 29.37 | A | C |

150

| | | | | | | | | | | |
|---|---|---|---|---|---|---|---|---|---|---|
| ATOM | 996 | CG | ARG | A | 343 | 67.791 | 39.093 | 70.635 | 1.00 30.77 | A C |
| ATOM | 997 | CD | ARG | A | 343 | 68.202 | 37.621 | 70.352 | 1.00 32.66 | A C |
| ATOM | 998 | NE | ARG | A | 343 | 67.181 | 36.796 | 70.944 | 1.00 35.00 | A N |
| ATOM | 999 | CZ | ARG | A | 343 | 66.384 | 35.963 | 70.297 | 1.00 33.98 | A C |
| ATOM | 1000 | NH1 | ARG | A | 343 | 66.540 | 35.712 | 68.999 | 1.00 32.92 | A N |
| ATOM | 1001 | NH2 | ARG | A | 343 | 65.435 | 35.362 | 70.992 | 1.00 34.62 | A N |
| ATOM | 1002 | N | GLU | A | 344 | 66.441 | 41.392 | 68.006 | 1.00 29.80 | A N |
| ATOM | 1003 | CA | GLU | A | 344 | 67.221 | 42.063 | 66.954 | 1.00 31.37 | A C |
| ATOM | 1004 | C | GLU | A | 344 | 67.160 | 43.582 | 67.104 | 1.00 30.73 | A C |
| ATOM | 1005 | O | GLU | A | 344 | 68.142 | 44.270 | 66.837 | 1.00 29.40 | A O |
| ATOM | 1006 | CB | GLU | A | 344 | 66.691 | 41.711 | 65.555 | 1.00 31.66 | A C |
| ATOM | 1007 | CG | GLU | A | 344 | 66.933 | 40.270 | 65.138 | 1.00 38.32 | A C |
| ATOM | 1008 | CD | GLU | A | 344 | 66.000 | 39.823 | 64.014 | 1.00 45.80 | A C |
| ATOM | 1009 | OE1 | GLU | A | 344 | 65.410 | 40.719 | 63.327 | 1.00 46.84 | A O |
| ATOM | 1010 | OE2 | GLU | A | 344 | 65.853 | 38.575 | 63.839 | 1.00 47.06 | A O |
| ATOM | 1011 | N | LEU | A | 345 | 65.989 | 44.091 | 67.510 | 1.00 29.56 | A N |
| ATOM | 1012 | CA | LEU | A | 345 | 65.801 | 45.516 | 67.717 | 1.00 30.20 | A C |
| ATOM | 1013 | C | LEU | A | 345 | 66.477 | 45.974 | 68.986 | 1.00 29.21 | A C |
| ATOM | 1014 | O | LEU | A | 345 | 66.647 | 47.176 | 69.203 | 1.00 29.00 | A O |
| ATOM | 1015 | CB | LEU | A | 345 | 64.293 | 45.868 | 67.809 | 1.00 30.68 | A C |
| ATOM | 1016 | CG | LEU | A | 345 | 63.566 | 45.822 | 66.459 | 1.00 32.26 | A C |
| ATOM | 1017 | CD1 | LEU | A | 345 | 62.058 | 45.885 | 66.640 | 1.00 33.47 | A C |
| ATOM | 1018 | CD2 | LEU | A | 345 | 64.066 | 47.003 | 65.594 | 1.00 36.39 | A C |
| ATOM | 1019 | N | LYS | A | 346 | 66.879 | 45.028 | 69.820 | 1.00 28.37 | A N |
| ATOM | 1020 | CA | LYS | A | 346 | 67.419 | 45.363 | 71.146 | 1.00 29.79 | A C |
| ATOM | 1021 | C | LYS | A | 346 | 66.424 | 46.196 | 71.976 | 1.00 28.79 | A C |
| ATOM | 1022 | O | LYS | A | 346 | 66.745 | 47.291 | 72.493 | 1.00 28.85 | A O |
| ATOM | 1023 | CB | LYS | A | 346 | 68.791 | 46.060 | 71.084 | 1.00 29.67 | A C |
| ATOM | 1024 | CG | LYS | A | 346 | 69.932 | 45.164 | 70.558 | 1.00 34.69 | A C |
| ATOM | 1025 | CD | LYS | A | 346 | 71.201 | 45.996 | 70.265 | 1.00 38.98 | A C |
| ATOM | 1026 | CE | LYS | A | 346 | 72.397 | 45.117 | 69.886 | 1.00 43.56 | A C |
| ATOM | 1027 | NZ | LYS | A | 346 | 72.344 | 44.640 | 68.472 | 1.00 45.51 | A N |
| ATOM | 1028 | N | LEU | A | 347 | 65.230 | 45.654 | 72.128 | 1.00 28.22 | A N |
| ATOM | 1029 | CA | LEU | A | 347 | 64.176 | 46.318 | 72.886 | 1.00 27.59 | A C |
| ATOM | 1030 | C | LEU | A | 347 | 64.701 | 46.723 | 74.244 | 1.00 27.53 | A C |
| ATOM | 1031 | O | LEU | A | 347 | 65.299 | 45.912 | 74.937 | 1.00 26.72 | A O |
| ATOM | 1032 | CB | LEU | A | 347 | 62.989 | 45.360 | 73.065 | 1.00 27.05 | A C |
| ATOM | 1033 | CG | LEU | A | 347 | 61.729 | 45.949 | 73.711 | 1.00 27.35 | A C |
| ATOM | 1034 | CD1 | LEU | A | 347 | 61.171 | 47.071 | 72.794 | 1.00 28.64 | A C |
| ATOM | 1035 | CD2 | LEU | A | 347 | 60.715 | 44.787 | 73.906 | 1.00 27.50 | A C |
| ATOM | 1036 | N | GLN | A | 348 | 64.477 | 47.966 | 74.653 | 1.00 28.00 | A N |
| ATOM | 1037 | CA | GLN | A | 348 | 65.001 | 48.414 | 75.961 | 1.00 29.07 | A C |
| ATOM | 1038 | C | GLN | A | 348 | 63.986 | 48.196 | 77.069 | 1.00 28.60 | A C |
| ATOM | 1039 | O | GLN | A | 348 | 62.791 | 48.050 | 76.794 | 1.00 26.86 | A O |
| ATOM | 1040 | CB | GLN | A | 348 | 65.352 | 49.905 | 75.930 | 1.00 29.68 | A C |
| ATOM | 1041 | CG | GLN | A | 348 | 66.360 | 50.296 | 74.869 | 1.00 33.66 | A C |
| ATOM | 1042 | CD | GLN | A | 348 | 67.773 | 49.863 | 75.199 | 1.00 41.21 | A C |
| ATOM | 1043 | OE1 | GLN | A | 348 | 68.223 | 48.771 | 74.785 | 1.00 45.96 | A O |
| ATOM | 1044 | NE2 | GLN | A | 348 | 68.485 | 50.699 | 75.949 | 1.00 42.97 | A N |
| ATOM | 1045 | N | HIS | A | 349 | 64.458 | 48.208 | 78.316 | 1.00 28.17 | A N |
| ATOM | 1046 | CA | HIS | A | 349 | 63.565 | 48.077 | 79.460 | 1.00 29.45 | A C |
| ATOM | 1047 | C | HIS | A | 349 | 62.490 | 49.166 | 79.415 | 1.00 29.42 | A C |
| ATOM | 1048 | O | HIS | A | 349 | 61.295 | 48.890 | 79.614 | 1.00 28.15 | A O |
| ATOM | 1049 | CB | HIS | A | 349 | 64.330 | 48.202 | 80.778 | 1.00 29.61 | A C |
| ATOM | 1050 | CG | HIS | A | 349 | 65.136 | 46.991 | 81.132 | 1.00 31.28 | A C |
| ATOM | 1051 | ND1 | HIS | A | 349 | 64.698 | 46.042 | 82.031 | 1.00 32.84 | A N |
| ATOM | 1052 | CD2 | HIS | A | 349 | 66.356 | 46.578 | 80.718 | 1.00 31.70 | A C |
| ATOM | 1053 | CE1 | HIS | A | 349 | 65.603 | 45.085 | 82.138 | 1.00 29.15 | A C |
| ATOM | 1054 | NE2 | HIS | A | 349 | 66.621 | 45.392 | 81.358 | 1.00 30.72 | A N |
| ATOM | 1055 | N | LYS | A | 350 | 62.926 | 50.400 | 79.179 | 1.00 28.24 | A N |
| ATOM | 1056 | CA | LYS | A | 350 | 62.006 | 51.525 | 79.148 | 1.00 28.95 | A C |

| ATOM | 1057 | C   | LYS A 350 | 60.955 | 51.401 | 78.031 | 1.00 | 29.33 | A | C |
| ATOM | 1058 | O   | LYS A 350 | 59.786 | 51.748 | 78.238 | 1.00 | 29.02 | A | O |
| ATOM | 1059 | CB  | LYS A 350 | 62.773 | 52.844 | 79.075 | 1.00 | 29.18 | A | C |
| ATOM | 1060 | CG  | LYS A 350 | 63.507 | 53.160 | 80.389 | 1.00 | 29.67 | A | C |
| ATOM | 1061 | CD  | LYS A 350 | 64.044 | 54.580 | 80.447 | 1.00 | 33.34 | A | C |
| ATOM | 1062 | CE  | LYS A 350 | 64.981 | 54.934 | 79.278 | 1.00 | 34.81 | A | C |
| ATOM | 1063 | NZ  | LYS A 350 | 66.130 | 53.995 | 79.116 | 1.00 | 34.41 | A | N |
| ATOM | 1064 | N   | GLU A 351 | 61.378 | 50.889 | 76.870 | 1.00 | 29.12 | A | N |
| ATOM | 1065 | CA  | GLU A 351 | 60.480 | 50.708 | 75.736 | 1.00 | 28.94 | A | C |
| ATOM | 1066 | C   | GLU A 351 | 59.468 | 49.603 | 76.031 | 1.00 | 28.32 | A | C |
| ATOM | 1067 | O   | GLU A 351 | 58.281 | 49.716 | 75.720 | 1.00 | 26.62 | A | O |
| ATOM | 1068 | CB  | GLU A 351 | 61.248 | 50.390 | 74.439 | 1.00 | 28.40 | A | C |
| ATOM | 1069 | CG  | GLU A 351 | 62.170 | 51.505 | 73.953 | 1.00 | 30.45 | A | C |
| ATOM | 1070 | CD  | GLU A 351 | 63.087 | 51.058 | 72.800 | 1.00 | 30.35 | A | C |
| ATOM | 1071 | OE1 | GLU A 351 | 63.546 | 49.896 | 72.806 | 1.00 | 25.57 | A | O |
| ATOM | 1072 | OE2 | GLU A 351 | 63.314 | 51.853 | 71.867 | 1.00 | 28.90 | A | O |
| ATOM | 1073 | N   | TYR A 352 | 59.949 | 48.521 | 76.629 | 1.00 | 28.37 | A | N |
| ATOM | 1074 | CA  | TYR A 352 | 59.057 | 47.418 | 76.978 | 1.00 | 28.33 | A | C |
| ATOM | 1075 | C   | TYR A 352 | 57.944 | 47.910 | 77.886 | 1.00 | 28.11 | A | C |
| ATOM | 1076 | O   | TYR A 352 | 56.798 | 47.554 | 77.721 | 1.00 | 27.78 | A | O |
| ATOM | 1077 | CB  | TYR A 352 | 59.833 | 46.303 | 77.679 | 1.00 | 28.10 | A | C |
| ATOM | 1078 | CG  | TYR A 352 | 58.920 | 45.312 | 78.403 | 1.00 | 29.32 | A | C |
| ATOM | 1079 | CD1 | TYR A 352 | 58.167 | 44.360 | 77.699 | 1.00 | 30.62 | A | C |
| ATOM | 1080 | CD2 | TYR A 352 | 58.791 | 45.347 | 79.791 | 1.00 | 31.95 | A | C |
| ATOM | 1081 | CE1 | TYR A 352 | 57.296 | 43.473 | 78.380 | 1.00 | 30.77 | A | C |
| ATOM | 1082 | CE2 | TYR A 352 | 57.969 | 44.456 | 80.467 | 1.00 | 33.86 | A | C |
| ATOM | 1083 | CZ  | TYR A 352 | 57.213 | 43.536 | 79.750 | 1.00 | 33.20 | A | C |
| ATOM | 1084 | OH  | TYR A 352 | 56.424 | 42.651 | 80.440 | 1.00 | 35.79 | A | O |
| ATOM | 1085 | N   | LEU A 353 | 58.306 | 48.692 | 78.896 | 1.00 | 28.10 | A | N |
| ATOM | 1086 | CA  | LEU A 353 | 57.312 | 49.199 | 79.814 | 1.00 | 28.36 | A | C |
| ATOM | 1087 | C   | LEU A 353 | 56.258 | 50.028 | 79.071 | 1.00 | 29.30 | A | C |
| ATOM | 1088 | O   | LEU A 353 | 55.056 | 49.890 | 79.341 | 1.00 | 29.77 | A | O |
| ATOM | 1089 | CB  | LEU A 353 | 57.979 | 50.025 | 80.899 | 1.00 | 27.63 | A | C |
| ATOM | 1090 | CG  | LEU A 353 | 58.834 | 49.258 | 81.929 | 1.00 | 29.15 | A | C |
| ATOM | 1091 | CD1 | LEU A 353 | 59.558 | 50.234 | 82.817 | 1.00 | 28.74 | A | C |
| ATOM | 1092 | CD2 | LEU A 353 | 57.991 | 48.245 | 82.769 | 1.00 | 28.67 | A | C |
| ATOM | 1093 | N   | CYS A 354 | 56.712 | 50.903 | 78.167 | 1.00 | 28.58 | A | N |
| ATOM | 1094 | CA  | CYS A 354 | 55.793 | 51.764 | 77.423 | 1.00 | 29.64 | A | C |
| ATOM | 1095 | C   | CYS A 354 | 54.877 | 50.963 | 76.528 | 1.00 | 29.92 | A | C |
| ATOM | 1096 | O   | CYS A 354 | 53.679 | 51.182 | 76.478 | 1.00 | 29.94 | A | O |
| ATOM | 1097 | CB  | CYS A 354 | 56.560 | 52.780 | 76.561 | 1.00 | 28.39 | A | C |
| ATOM | 1098 | SG  | CYS A 354 | 57.392 | 54.071 | 77.554 | 1.00 | 29.41 | A | S |
| ATOM | 1099 | N   | VAL A 355 | 55.462 | 50.023 | 75.821 | 1.00 | 29.83 | A | N |
| ATOM | 1100 | CA  | VAL A 355 | 54.727 | 49.210 | 74.868 | 1.00 | 31.36 | A | C |
| ATOM | 1101 | C   | VAL A 355 | 53.634 | 48.340 | 75.544 | 1.00 | 30.64 | A | C |
| ATOM | 1102 | O   | VAL A 355 | 52.523 | 48.222 | 75.025 | 1.00 | 30.15 | A | O |
| ATOM | 1103 | CB  | VAL A 355 | 55.809 | 48.448 | 74.083 | 1.00 | 32.51 | A | C |
| ATOM | 1104 | CG1 | VAL A 355 | 55.540 | 47.029 | 73.918 | 1.00 | 36.03 | A | C |
| ATOM | 1105 | CG2 | VAL A 355 | 56.214 | 49.249 | 72.818 | 1.00 | 32.47 | A | C |
| ATOM | 1106 | N   | LYS A 356 | 53.931 | 47.772 | 76.712 | 1.00 | 29.82 | A | N |
| ATOM | 1107 | CA  | LYS A 356 | 52.943 | 46.966 | 77.439 | 1.00 | 30.26 | A | C |
| ATOM | 1108 | C   | LYS A 356 | 51.797 | 47.886 | 77.892 | 1.00 | 29.71 | A | C |
| ATOM | 1109 | O   | LYS A 356 | 50.628 | 47.547 | 77.715 | 1.00 | 29.49 | A | O |
| ATOM | 1110 | CB  | LYS A 356 | 53.600 | 46.223 | 78.620 | 1.00 | 30.20 | A | C |
| ATOM | 1111 | CG  | LYS A 356 | 52.708 | 45.171 | 79.276 | 1.00 | 32.60 | A | C |
| ATOM | 1112 | CD  | LYS A 356 | 53.469 | 44.215 | 80.206 | 1.00 | 33.15 | A | C |
| ATOM | 1113 | CE  | LYS A 356 | 54.034 | 44.908 | 81.414 | 1.00 | 31.71 | A | C |
| ATOM | 1114 | NZ  | LYS A 356 | 54.303 | 43.917 | 82.555 | 1.00 | 30.92 | A | N |
| ATOM | 1115 | N   | ALA A 357 | 52.128 | 49.087 | 78.374 | 1.00 | 28.18 | A | N |
| ATOM | 1116 | CA  | ALA A 357 | 51.091 | 50.042 | 78.739 | 1.00 | 29.08 | A | C |
| ATOM | 1117 | C   | ALA A 357 | 50.270 | 50.508 | 77.511 | 1.00 | 29.20 | A | C |

| | | | | | | | | | | |
|---|---|---|---|---|---|---|---|---|---|---|
| ATOM | 1118 | O | ALA A 357 | 49.061 | 50.662 | 77.589 | 1.00 | 28.47 | A | O |
| ATOM | 1119 | CB | ALA A 357 | 51.685 | 51.264 | 79.513 | 1.00 | 28.44 | A | C |
| ATOM | 1120 | N | MET A 358 | 50.924 | 50.693 | 76.368 | 1.00 | 28.49 | A | N |
| ATOM | 1121 | CA | MET A 358 | 50.189 | 51.118 | 75.179 | 1.00 | 29.61 | A | C |
| ATOM | 1122 | C | MET A 358 | 49.193 | 50.038 | 74.742 | 1.00 | 29.10 | A | C |
| ATOM | 1123 | O | MET A 358 | 48.093 | 50.345 | 74.290 | 1.00 | 28.35 | A | O |
| ATOM | 1124 | CB | MET A 358 | 51.147 | 51.451 | 74.043 | 1.00 | 29.40 | A | C |
| ATOM | 1125 | CG | MET A 358 | 51.982 | 52.662 | 74.380 | 1.00 | 31.87 | A | C |
| ATOM | 1126 | SD | MET A 358 | 53.331 | 52.992 | 73.231 | 1.00 | 36.22 | A | S |
| ATOM | 1127 | CE | MET A 358 | 52.441 | 53.193 | 71.709 | 1.00 | 32.29 | A | C |
| ATOM | 1128 | N | ILE A 359 | 49.598 | 48.783 | 74.859 | 1.00 | 29.07 | A | N |
| ATOM | 1129 | CA | ILE A 359 | 48.712 | 47.690 | 74.517 | 1.00 | 30.18 | A | C |
| ATOM | 1130 | C | ILE A 359 | 47.435 | 47.765 | 75.394 | 1.00 | 30.35 | A | C |
| ATOM | 1131 | O | ILE A 359 | 46.316 | 47.677 | 74.885 | 1.00 | 29.05 | A | O |
| ATOM | 1132 | CB | ILE A 359 | 49.397 | 46.352 | 74.769 | 1.00 | 30.86 | A | C |
| ATOM | 1133 | CG1 | ILE A 359 | 50.433 | 46.052 | 73.672 | 1.00 | 31.86 | A | C |
| ATOM | 1134 | CG2 | ILE A 359 | 48.352 | 45.194 | 74.777 | 1.00 | 31.67 | A | C |
| ATOM | 1135 | CD1 | ILE A 359 | 51.341 | 44.879 | 74.039 | 1.00 | 32.79 | A | C |
| ATOM | 1136 | N | LEU A 360 | 47.612 | 47.946 | 76.699 | 1.00 | 29.58 | A | N |
| ATOM | 1137 | CA | LEU A 360 | 46.460 | 48.063 | 77.599 | 1.00 | 30.72 | A | C |
| ATOM | 1138 | C | LEU A 360 | 45.554 | 49.229 | 77.196 | 1.00 | 30.69 | A | C |
| ATOM | 1139 | O | LEU A 360 | 44.348 | 49.097 | 77.186 | 1.00 | 30.37 | A | O |
| ATOM | 1140 | CB | LEU A 360 | 46.908 | 48.268 | 79.062 | 1.00 | 30.41 | A | C |
| ATOM | 1141 | CG | LEU A 360 | 45.773 | 48.631 | 80.057 | 1.00 | 32.06 | A | C |
| ATOM | 1142 | CD1 | LEU A 360 | 44.902 | 47.398 | 80.425 | 1.00 | 31.50 | A | C |
| ATOM | 1143 | CD2 | LEU A 360 | 46.351 | 49.231 | 81.336 | 1.00 | 33.41 | A | C |
| ATOM | 1144 | N | LEU A 361 | 46.155 | 50.374 | 76.883 | 1.00 | 30.49 | A | N |
| ATOM | 1145 | CA | LEU A 361 | 45.412 | 51.603 | 76.637 | 1.00 | 30.53 | A | C |
| ATOM | 1146 | C | LEU A 361 | 44.868 | 51.665 | 75.209 | 1.00 | 31.22 | A | C |
| ATOM | 1147 | O | LEU A 361 | 44.428 | 52.708 | 74.730 | 1.00 | 28.43 | A | O |
| ATOM | 1148 | CB | LEU A 361 | 46.271 | 52.834 | 76.989 | 1.00 | 30.65 | A | C |
| ATOM | 1149 | CG | LEU A 361 | 46.646 | 52.892 | 78.491 | 1.00 | 31.35 | A | C |
| ATOM | 1150 | CD1 | LEU A 361 | 47.765 | 53.891 | 78.797 | 1.00 | 32.21 | A | C |
| ATOM | 1151 | CD2 | LEU A 361 | 45.408 | 53.160 | 79.400 | 1.00 | 30.42 | A | C |
| ATOM | 1152 | N | ASN A 362 | 44.936 | 50.529 | 74.532 | 1.00 | 31.58 | A | N |
| ATOM | 1153 | CA | ASN A 362 | 44.271 | 50.392 | 73.259 | 1.00 | 33.73 | A | C |
| ATOM | 1154 | C | ASN A 362 | 44.928 | 51.125 | 72.116 | 1.00 | 33.90 | A | C |
| ATOM | 1155 | O | ASN A 362 | 44.244 | 51.706 | 71.287 | 1.00 | 33.14 | A | O |
| ATOM | 1156 | CB | ASN A 362 | 42.793 | 50.818 | 73.370 | 1.00 | 33.66 | A | C |
| ATOM | 1157 | CG | ASN A 362 | 41.964 | 50.247 | 72.270 | 1.00 | 35.32 | A | C |
| ATOM | 1158 | OD1 | ASN A 362 | 42.327 | 49.226 | 71.703 | 1.00 | 38.21 | A | O |
| ATOM | 1159 | ND2 | ASN A 362 | 40.852 | 50.897 | 71.938 | 1.00 | 36.02 | A | N |
| ATOM | 1160 | N | SER A 363 | 46.252 | 51.071 | 72.066 | 1.00 | 34.71 | A | N |
| ATOM | 1161 | CA | SER A 363 | 46.985 | 51.590 | 70.916 | 1.00 | 36.13 | A | C |
| ATOM | 1162 | C | SER A 363 | 46.414 | 50.971 | 69.634 | 1.00 | 35.70 | A | C |
| ATOM | 1163 | O | SER A 363 | 46.424 | 51.585 | 68.578 | 1.00 | 36.22 | A | O |
| ATOM | 1164 | CB | SER A 363 | 48.492 | 51.276 | 71.050 | 1.00 | 36.04 | A | C |
| ATOM | 1165 | OG | SER A 363 | 49.240 | 51.655 | 69.879 | 1.00 | 38.18 | A | O |
| ATOM | 1166 | N | SER A 364 | 45.868 | 49.766 | 69.754 | 1.00 | 35.85 | A | N |
| ATOM | 1167 | CA | SER A 364 | 45.305 | 49.042 | 68.614 | 1.00 | 36.13 | A | C |
| ATOM | 1168 | C | SER A 364 | 43.992 | 49.698 | 68.124 | 1.00 | 35.79 | A | C |
| ATOM | 1169 | O | SER A 364 | 43.546 | 49.496 | 66.991 | 1.00 | 34.28 | A | O |
| ATOM | 1170 | CB | SER A 364 | 45.074 | 47.570 | 69.029 | 1.00 | 36.46 | A | C |
| ATOM | 1171 | OG | SER A 364 | 44.277 | 46.876 | 68.092 | 1.00 | 36.61 | A | O |
| ATOM | 1172 | N | MET A 365 | 43.375 | 50.486 | 69.002 | 1.00 | 35.83 | A | N |
| ATOM | 1173 | CA | MET A 365 | 42.135 | 51.201 | 68.664 | 1.00 | 36.12 | A | C |
| ATOM | 1174 | CB | MET A 365 | 42.328 | 52.169 | 67.476 | 1.00 | 35.91 | A | C |
| ATOM | 1175 | CG | AMET A 365 | 43.498 | 53.134 | 67.647 | 0.50 | 37.74 | A | C |
| ATOM | 1176 | CG | BMET A 365 | 43.439 | 53.197 | 67.686 | 0.50 | 35.18 | A | C |
| ATOM | 1177 | SD | AMET A 365 | 43.108 | 54.822 | 67.121 | 0.50 | 41.23 | A | S |
| ATOM | 1178 | SD | BMET A 365 | 43.193 | 54.230 | 69.152 | 0.50 | 32.77 | A | S |

| ATOM | 1179 | CE A | MET | A | 365 | 42.095 | 55.345 | 68.465 | 0.50 | 39.12 | A | C |
|------|------|------|-----|---|-----|--------|--------|--------|------|-------|---|---|
| ATOM | 1180 | CE B | MET | A | 365 | 44.405 | 55.623 | 68.827 | 0.50 | 30.85 | A | C |
| ATOM | 1181 | C    | MET | A | 365 | 40.964 | 50.261 | 68.404 | 1.00 | 36.29 | A | C |
| ATOM | 1182 | O    | MET | A | 365 | 40.149 | 50.492 | 67.510 | 1.00 | 35.06 | A | O |
| ATOM | 1183 | N    | TYR | A | 366 | 40.890 | 49.188 | 69.178 | 1.00 | 37.10 | A | N |
| ATOM | 1184 | CA   | TYR | A | 366 | 39.706 | 48.341 | 69.083 | 1.00 | 38.62 | A | C |
| ATOM | 1185 | C    | TYR | A | 366 | 38.502 | 49.191 | 69.533 | 1.00 | 38.89 | A | C |
| ATOM | 1186 | O    | TYR | A | 366 | 38.586 | 49.899 | 70.526 | 1.00 | 37.87 | A | O |
| ATOM | 1187 | CB   | TYR | A | 366 | 39.866 | 47.107 | 69.974 | 1.00 | 38.71 | A | C |
| ATOM | 1188 | CG   | TYR | A | 366 | 38.695 | 46.147 | 69.895 | 1.00 | 41.59 | A | C |
| ATOM | 1189 | CD1  | TYR | A | 366 | 38.534 | 45.305 | 68.798 | 1.00 | 43.83 | A | C |
| ATOM | 1190 | CD2  | TYR | A | 366 | 37.746 | 46.092 | 70.910 | 1.00 | 43.21 | A | C |
| ATOM | 1191 | CE1  | TYR | A | 366 | 37.450 | 44.416 | 68.720 | 1.00 | 45.33 | A | C |
| ATOM | 1192 | CE2  | TYR | A | 366 | 36.665 | 45.213 | 70.848 | 1.00 | 45.27 | A | C |
| ATOM | 1193 | CZ   | TYR | A | 366 | 36.527 | 44.380 | 69.758 | 1.00 | 46.56 | A | C |
| ATOM | 1194 | OH   | TYR | A | 366 | 35.460 | 43.520 | 69.699 | 1.00 | 49.98 | A | O |
| ATOM | 1195 | N    | PRO | A | 367 | 37.385 | 49.133 | 68.813 | 1.00 | 40.07 | A | N |
| ATOM | 1196 | CA   | PRO | A | 367 | 36.212 | 49.927 | 69.194 | 1.00 | 41.22 | A | C |
| ATOM | 1197 | C    | PRO | A | 367 | 35.640 | 49.371 | 70.498 | 1.00 | 42.30 | A | C |
| ATOM | 1198 | O    | PRO | A | 367 | 35.134 | 48.247 | 70.485 | 1.00 | 43.10 | A | O |
| ATOM | 1199 | CB   | PRO | A | 367 | 35.206 | 49.669 | 68.053 | 1.00 | 41.35 | A | C |
| ATOM | 1200 | CG   | PRO | A | 367 | 35.979 | 48.967 | 66.954 | 1.00 | 40.74 | A | C |
| ATOM | 1201 | CD   | PRO | A | 367 | 37.139 | 48.294 | 67.629 | 1.00 | 40.47 | A | C |
| ATOM | 1202 | N    | LEU | A | 368 | 35.736 | 50.104 | 71.600 | 1.00 | 42.89 | A | N |
| ATOM | 1203 | CA   | LEU | A | 368 | 35.144 | 49.630 | 72.853 | 1.00 | 43.84 | A | C |
| ATOM | 1204 | C    | LEU | A | 368 | 33.617 | 49.717 | 72.789 | 1.00 | 44.56 | A | C |
| ATOM | 1205 | O    | LEU | A | 368 | 32.907 | 48.763 | 73.135 | 1.00 | 45.70 | A | O |
| ATOM | 1206 | CB   | LEU | A | 368 | 35.648 | 50.445 | 74.050 | 1.00 | 44.03 | A | C |
| ATOM | 1207 | CG   | LEU | A | 368 | 37.129 | 50.360 | 74.451 | 1.00 | 43.89 | A | C |
| ATOM | 1208 | CD1  | LEU | A | 368 | 37.722 | 48.994 | 74.132 | 1.00 | 41.41 | A | C |
| ATOM | 1209 | CD2  | LEU | A | 368 | 37.901 | 51.467 | 73.786 | 1.00 | 45.47 | A | C |
| ATOM | 1210 | N    | ALA | A | 375 | 31.526 | 60.242 | 77.352 | 1.00 | 41.77 | A | N |
| ATOM | 1211 | CA   | ALA | A | 375 | 32.456 | 61.100 | 76.622 | 1.00 | 41.37 | A | C |
| ATOM | 1212 | C    | ALA | A | 375 | 33.700 | 61.373 | 77.458 | 1.00 | 40.76 | A | C |
| ATOM | 1213 | O    | ALA | A | 375 | 34.809 | 61.306 | 76.941 | 1.00 | 40.90 | A | O |
| ATOM | 1214 | CB   | ALA | A | 375 | 31.784 | 62.407 | 76.225 | 1.00 | 41.74 | A | C |
| ATOM | 1215 | N    | GLU | A | 376 | 33.503 | 61.687 | 78.739 | 1.00 | 39.80 | A | N |
| ATOM | 1216 | CA   | GLU | A | 376 | 34.602 | 61.945 | 79.664 | 1.00 | 39.68 | A | C |
| ATOM | 1217 | C    | GLU | A | 376 | 35.667 | 60.860 | 79.597 | 1.00 | 38.26 | A | C |
| ATOM | 1218 | O    | GLU | A | 376 | 36.855 | 61.147 | 79.482 | 1.00 | 37.89 | A | O |
| ATOM | 1219 | CB   | GLU | A | 376 | 34.101 | 61.939 | 81.103 | 1.00 | 40.17 | A | C |
| ATOM | 1220 | CG   | GLU | A | 376 | 33.639 | 63.270 | 81.651 | 1.00 | 43.76 | A | C |
| ATOM | 1221 | CD   | GLU | A | 376 | 32.825 | 63.092 | 82.920 | 1.00 | 46.28 | A | C |
| ATOM | 1222 | OE1  | GLU | A | 376 | 33.304 | 62.375 | 83.835 | 1.00 | 47.69 | A | O |
| ATOM | 1223 | OE2  | GLU | A | 376 | 31.710 | 63.655 | 82.993 | 1.00 | 46.53 | A | O |
| ATOM | 1224 | N    | SER | A | 377 | 35.219 | 59.617 | 79.711 | 1.00 | 36.95 | A | N |
| ATOM | 1225 | CA   | SER | A | 377 | 36.118 | 58.475 | 79.766 | 1.00 | 36.39 | A | C |
| ATOM | 1226 | C    | SER | A | 377 | 36.918 | 58.346 | 78.473 | 1.00 | 35.83 | A | C |
| ATOM | 1227 | O    | SER | A | 377 | 38.121 | 58.124 | 78.505 | 1.00 | 35.02 | A | O |
| ATOM | 1228 | CB   | SER | A | 377 | 35.333 | 57.191 | 80.074 | 1.00 | 36.29 | A | C |
| ATOM | 1229 | OG   | SER | A | 377 | 36.204 | 56.139 | 80.477 | 1.00 | 35.35 | A | O |
| ATOM | 1230 | N    | SER | A | 378 | 36.243 | 58.511 | 77.342 | 1.00 | 35.99 | A | N |
| ATOM | 1231 | CA   | SER | A | 378 | 36.889 | 58.421 | 76.036 | 1.00 | 36.59 | A | C |
| ATOM | 1232 | C    | SER | A | 378 | 37.971 | 59.474 | 75.879 | 1.00 | 36.00 | A | C |
| ATOM | 1233 | O    | SER | A | 378 | 39.054 | 59.187 | 75.389 | 1.00 | 35.26 | A | O |
| ATOM | 1234 | CB   | SER | A | 378 | 35.860 | 58.614 | 74.922 | 1.00 | 37.33 | A | C |
| ATOM | 1235 | OG   | SER | A | 378 | 35.274 | 57.377 | 74.566 | 1.00 | 39.42 | A | O |
| ATOM | 1236 | N    | ARG | A | 379 | 37.667 | 60.704 | 76.275 | 1.00 | 35.31 | A | N |
| ATOM | 1237 | CA   | ARG | A | 379 | 38.641 | 61.777 | 76.139 | 1.00 | 35.02 | A | C |
| ATOM | 1238 | C    | ARG | A | 379 | 39.821 | 61.487 | 77.039 | 1.00 | 34.41 | A | C |
| ATOM | 1239 | O    | ARG | A | 379 | 40.986 | 61.643 | 76.641 | 1.00 | 34.34 | A | O |

| ATOM | 1240 | CB | ARG A 379 | 38.018 | 63.125 | 76.495 | 1.00 | 35.65 | A | C |
|------|------|-----|-----------|--------|--------|--------|------|-------|---|---|
| ATOM | 1241 | CG | ARG A 379 | 38.886 | 64.318 | 76.111 | 1.00 | 37.59 | A | C |
| ATOM | 1247 | N | LYS A 380 | 39.516 | 61.039 | 78.249 | 1.00 | 33.01 | A | N |
| ATOM | 1248 | CA | LYS A 380 | 40.541 | 60.692 | 79.213 | 1.00 | 33.20 | A | C |
| ATOM | 1249 | C | LYS A 380 | 41.459 | 59.593 | 78.668 | 1.00 | 32.38 | A | C |
| ATOM | 1250 | O | LYS A 380 | 42.676 | 59.721 | 78.721 | 1.00 | 31.83 | A | O |
| ATOM | 1251 | CB | LYS A 380 | 39.892 | 60.229 | 80.506 | 1.00 | 33.50 | A | C |
| ATOM | 1252 | CG | LYS A 380 | 40.838 | 60.072 | 81.671 | 1.00 | 36.94 | A | C |
| ATOM | 1253 | CD | LYS A 380 | 39.977 | 59.938 | 82.936 | 1.00 | 42.02 | A | C |
| ATOM | 1254 | CE | LYS A 380 | 38.762 | 60.843 | 82.829 | 1.00 | 43.90 | A | C |
| ATOM | 1255 | NZ | LYS A 380 | 37.475 | 60.191 | 83.256 | 1.00 | 45.90 | A | N |
| ATOM | 1256 | N | LEU A 381 | 40.863 | 58.527 | 78.132 | 1.00 | 31.16 | A | N |
| ATOM | 1257 | CA | LEU A 381 | 41.633 | 57.423 | 77.573 | 1.00 | 30.86 | A | C |
| ATOM | 1258 | C | LEU A 381 | 42.613 | 57.939 | 76.506 | 1.00 | 30.50 | A | C |
| ATOM | 1259 | O | LEU A 381 | 43.773 | 57.581 | 76.482 | 1.00 | 28.38 | A | O |
| ATOM | 1260 | CB | LEU A 381 | 40.696 | 56.374 | 76.963 | 1.00 | 30.51 | A | C |
| ATOM | 1261 | CG | LEU A 381 | 41.427 | 55.204 | 76.280 | 1.00 | 32.20 | A | C |
| ATOM | 1262 | CD1 | LEU A 381 | 42.411 | 54.578 | 77.230 | 1.00 | 29.77 | A | C |
| ATOM | 1263 | CD2 | LEU A 381 | 40.439 | 54.164 | 75.752 | 1.00 | 32.46 | A | C |
| ATOM | 1264 | N | THR A 382 | 42.121 | 58.789 | 75.618 | 1.00 | 30.52 | A | N |
| ATOM | 1265 | CA | THR A 382 | 42.966 | 59.338 | 74.561 | 1.00 | 30.80 | A | C |
| ATOM | 1266 | C | THR A 382 | 44.177 | 60.037 | 75.157 | 1.00 | 30.95 | A | C |
| ATOM | 1267 | O | THR A 382 | 45.316 | 59.807 | 74.739 | 1.00 | 30.85 | A | O |
| ATOM | 1268 | CB | THR A 382 | 42.139 | 60.304 | 73.716 | 1.00 | 31.19 | A | C |
| ATOM | 1269 | OG1 | THR A 382 | 41.149 | 59.543 | 73.024 | 1.00 | 30.61 | A | O |
| ATOM | 1270 | CG2 | THR A 382 | 42.995 | 60.921 | 72.591 | 1.00 | 32.48 | A | C |
| ATOM | 1271 | N | HIS A 383 | 43.925 | 60.877 | 76.152 | 1.00 | 30.72 | A | N |
| ATOM | 1272 | CA | HIS A 383 | 44.987 | 61.563 | 76.863 | 1.00 | 31.53 | A | C |
| ATOM | 1273 | C | HIS A 383 | 46.001 | 60.577 | 77.464 | 1.00 | 30.08 | A | C |
| ATOM | 1274 | O | HIS A 383 | 47.211 | 60.805 | 77.378 | 1.00 | 28.92 | A | O |
| ATOM | 1275 | CB | HIS A 383 | 44.381 | 62.421 | 77.977 | 1.00 | 32.84 | A | C |
| ATOM | 1276 | CG | HIS A 383 | 45.370 | 63.299 | 78.670 | 1.00 | 38.98 | A | C |
| ATOM | 1277 | ND1 | HIS A 383 | 45.671 | 64.571 | 78.227 | 1.00 | 43.43 | A | N |
| ATOM | 1278 | CD2 | HIS A 383 | 46.117 | 63.100 | 79.786 | 1.00 | 44.56 | A | C |
| ATOM | 1279 | CE1 | HIS A 383 | 46.566 | 65.114 | 79.039 | 1.00 | 46.22 | A | C |
| ATOM | 1280 | NE2 | HIS A 383 | 46.854 | 64.242 | 79.993 | 1.00 | 45.71 | A | N |
| ATOM | 1281 | N | LEU A 384 | 45.516 | 59.491 | 78.067 | 1.00 | 28.83 | A | N |
| ATOM | 1282 | CA | LEU A 384 | 46.429 | 58.518 | 78.679 | 1.00 | 29.80 | A | C |
| ATOM | 1283 | C | LEU A 384 | 47.286 | 57.811 | 77.636 | 1.00 | 29.24 | A | C |
| ATOM | 1284 | O | LEU A 384 | 48.495 | 57.638 | 77.812 | 1.00 | 28.63 | A | O |
| ATOM | 1285 | CB | LEU A 384 | 45.691 | 57.482 | 79.542 | 1.00 | 29.77 | A | C |
| ATOM | 1286 | CG | LEU A 384 | 44.795 | 58.037 | 80.663 | 1.00 | 33.52 | A | C |
| ATOM | 1287 | CD1 | LEU A 384 | 44.115 | 56.886 | 81.427 | 1.00 | 35.12 | A | C |
| ATOM | 1288 | CD2 | LEU A 384 | 45.570 | 58.996 | 81.642 | 1.00 | 32.55 | A | C |
| ATOM | 1289 | N | LEU A 385 | 46.660 | 57.384 | 76.551 | 1.00 | 28.89 | A | N |
| ATOM | 1290 | CA | LEU A 385 | 47.411 | 56.718 | 75.497 | 1.00 | 28.99 | A | C |
| ATOM | 1291 | C | LEU A 385 | 48.421 | 57.716 | 74.880 | 1.00 | 29.09 | A | C |
| ATOM | 1292 | O | LEU A 385 | 49.589 | 57.357 | 74.631 | 1.00 | 29.31 | A | O |
| ATOM | 1293 | CB | LEU A 385 | 46.465 | 56.148 | 74.421 | 1.00 | 28.95 | A | C |
| ATOM | 1294 | CG | LEU A 385 | 47.205 | 55.547 | 73.212 | 1.00 | 29.34 | A | C |
| ATOM | 1295 | CD1 | LEU A 385 | 48.119 | 54.387 | 73.684 | 1.00 | 27.74 | A | C |
| ATOM | 1296 | CD2 | LEU A 385 | 46.188 | 55.062 | 72.223 | 1.00 | 31.61 | A | C |
| ATOM | 1297 | N | ASN A 386 | 47.993 | 58.965 | 74.672 | 1.00 | 28.32 | A | N |
| ATOM | 1298 | CA | ASN A 386 | 48.896 | 59.961 | 74.084 | 1.00 | 29.16 | A | C |
| ATOM | 1299 | C | ASN A 386 | 50.134 | 60.158 | 74.986 | 1.00 | 29.05 | A | C |
| ATOM | 1300 | O | ASN A 386 | 51.245 | 60.313 | 74.498 | 1.00 | 29.30 | A | O |
| ATOM | 1301 | CB | ASN A 386 | 48.207 | 61.325 | 73.847 | 1.00 | 28.35 | A | C |
| ATOM | 1302 | CG | ASN A 386 | 47.217 | 61.309 | 72.657 | 1.00 | 30.05 | A | C |
| ATOM | 1303 | OD1 | ASN A 386 | 46.453 | 62.256 | 72.459 | 1.00 | 30.63 | A | O |
| ATOM | 1304 | ND2 | ASN A 386 | 47.209 | 60.237 | 71.906 | 1.00 | 24.98 | A | N |
| ATOM | 1305 | N | ALA A 387 | 49.919 | 60.151 | 76.300 | 1.00 | 28.57 | A | N |

| | | | | | | | | | | | |
|---|---|---|---|---|---|---|---|---|---|---|---|
| ATOM | 1306 | CA | ALA | A | 387 | 50.990 | 60.343 | 77.262 | 1.00 | 28.78 | A C |
| ATOM | 1307 | C | ALA | A | 387 | 52.008 | 59.186 | 77.201 | 1.00 | 28.62 | A C |
| ATOM | 1308 | O | ALA | A | 387 | 53.208 | 59.411 | 77.231 | 1.00 | 28.32 | A O |
| ATOM | 1309 | CB | ALA | A | 387 | 50.421 | 60.510 | 78.694 | 1.00 | 28.94 | A C |
| ATOM | 1310 | N | VAL | A | 388 | 51.526 | 57.953 | 77.140 | 1.00 | 28.07 | A N |
| ATOM | 1311 | CA | VAL | A | 388 | 52.441 | 56.835 | 77.056 | 1.00 | 28.55 | A C |
| ATOM | 1312 | C | VAL | A | 388 | 53.149 | 56.836 | 75.704 | 1.00 | 28.42 | A C |
| ATOM | 1313 | O | VAL | A | 388 | 54.329 | 56.529 | 75.621 | 1.00 | 28.38 | A O |
| ATOM | 1314 | CB | VAL | A | 388 | 51.763 | 55.486 | 77.342 | 1.00 | 29.27 | A C |
| ATOM | 1315 | CG1 | VAL | A | 388 | 52.821 | 54.394 | 77.369 | 1.00 | 31.25 | A C |
| ATOM | 1316 | CG2 | VAL | A | 388 | 50.992 | 55.531 | 78.703 | 1.00 | 29.00 | A C |
| ATOM | 1317 | N | THR | A | 389 | 52.442 | 57.220 | 74.651 | 1.00 | 28.23 | A N |
| ATOM | 1318 | CA | THR | A | 389 | 53.092 | 57.318 | 73.338 | 1.00 | 28.59 | A C |
| ATOM | 1319 | C | THR | A | 389 | 54.193 | 58.373 | 73.364 | 1.00 | 28.04 | A C |
| ATOM | 1320 | O | THR | A | 389 | 55.261 | 58.145 | 72.833 | 1.00 | 28.16 | A O |
| ATOM | 1321 | CB | THR | A | 389 | 52.066 | 57.641 | 72.263 | 1.00 | 28.29 | A C |
| ATOM | 1322 | OG1 | THR | A | 389 | 51.113 | 56.575 | 72.225 | 1.00 | 29.28 | A O |
| ATOM | 1323 | CG2 | THR | A | 389 | 52.725 | 57.614 | 70.865 | 1.00 | 29.34 | A C |
| ATOM | 1324 | N | ASP | A | 390 | 53.918 | 59.522 | 73.991 | 1.00 | 27.29 | A N |
| ATOM | 1325 | CA | ASP | A | 390 | 54.908 | 60.582 | 74.123 | 1.00 | 26.97 | A C |
| ATOM | 1326 | C | ASP | A | 390 | 56.102 | 60.018 | 74.887 | 1.00 | 26.49 | A C |
| ATOM | 1327 | O | ASP | A | 390 | 57.239 | 60.284 | 74.548 | 1.00 | 25.54 | A O |
| ATOM | 1328 | CB | ASP | A | 390 | 54.336 | 61.776 | 74.914 | 1.00 | 27.56 | A C |
| ATOM | 1329 | CG | ASP | A | 390 | 53.482 | 62.700 | 74.055 | 1.00 | 29.58 | A C |
| ATOM | 1330 | OD1 | ASP | A | 390 | 53.499 | 62.579 | 72.805 | 1.00 | 29.94 | A O |
| ATOM | 1331 | OD2 | ASP | A | 390 | 52.777 | 63.588 | 74.546 | 1.00 | 31.60 | A O |
| ATOM | 1332 | N | ALA | A | 391 | 55.848 | 59.241 | 75.932 | 1.00 | 26.44 | A N |
| ATOM | 1333 | CA | ALA | A | 391 | 56.978 | 58.687 | 76.684 | 1.00 | 27.26 | A C |
| ATOM | 1334 | C | ALA | A | 391 | 57.845 | 57.734 | 75.844 | 1.00 | 27.00 | A C |
| ATOM | 1335 | O | ALA | A | 391 | 59.074 | 57.790 | 75.901 | 1.00 | 27.26 | A O |
| ATOM | 1336 | CB | ALA | A | 391 | 56.506 | 58.029 | 77.997 | 1.00 | 27.87 | A C |
| ATOM | 1337 | N | LEU | A | 392 | 57.216 | 56.909 | 75.021 | 1.00 | 26.63 | A N |
| ATOM | 1338 | CA | LEU | A | 392 | 57.975 | 56.004 | 74.156 | 1.00 | 27.00 | A C |
| ATOM | 1339 | C | LEU | A | 392 | 58.807 | 56.825 | 73.149 | 1.00 | 26.78 | A C |
| ATOM | 1340 | O | LEU | A | 392 | 59.998 | 56.542 | 72.915 | 1.00 | 25.92 | A O |
| ATOM | 1341 | CB | LEU | A | 392 | 57.047 | 55.013 | 73.436 | 1.00 | 27.30 | A C |
| ATOM | 1342 | CG | LEU | A | 392 | 57.713 | 54.103 | 72.393 | 1.00 | 28.95 | A C |
| ATOM | 1343 | CD1 | LEU | A | 392 | 58.763 | 53.168 | 73.017 | 1.00 | 30.33 | A C |
| ATOM | 1344 | CD2 | LEU | A | 392 | 56.662 | 53.292 | 71.658 | 1.00 | 27.80 | A C |
| ATOM | 1345 | N | VAL | A | 393 | 58.201 | 57.885 | 72.617 | 1.00 | 25.43 | A N |
| ATOM | 1346 | CA | VAL | A | 393 | 58.927 | 58.741 | 71.695 | 1.00 | 25.55 | A C |
| ATOM | 1347 | C | VAL | A | 393 | 60.151 | 59.343 | 72.402 | 1.00 | 25.51 | A C |
| ATOM | 1348 | O | VAL | A | 393 | 61.251 | 59.383 | 71.864 | 1.00 | 24.34 | A O |
| ATOM | 1349 | CB | VAL | A | 393 | 57.999 | 59.841 | 71.075 | 1.00 | 24.46 | A C |
| ATOM | 1350 | CG1 | VAL | A | 393 | 58.829 | 60.907 | 70.386 | 1.00 | 25.10 | A C |
| ATOM | 1351 | CG2 | VAL | A | 393 | 56.992 | 59.179 | 70.100 | 1.00 | 24.53 | A C |
| ATOM | 1352 | N | TRP | A | 394 | 59.942 | 59.809 | 73.619 | 1.00 | 26.11 | A N |
| ATOM | 1353 | CA | TRP | A | 394 | 61.032 | 60.381 | 74.422 | 1.00 | 27.18 | A C |
| ATOM | 1354 | C | TRP | A | 394 | 62.133 | 59.328 | 74.682 | 1.00 | 26.30 | A C |
| ATOM | 1355 | O | TRP | A | 394 | 63.315 | 59.603 | 74.558 | 1.00 | 25.13 | A O |
| ATOM | 1356 | CB | TRP | A | 394 | 60.439 | 60.902 | 75.734 | 1.00 | 27.70 | A C |
| ATOM | 1357 | CG | TRP | A | 394 | 61.415 | 61.371 | 76.740 | 1.00 | 31.53 | A C |
| ATOM | 1358 | CD1 | TRP | A | 394 | 61.958 | 62.621 | 76.844 | 1.00 | 33.68 | A C |
| ATOM | 1359 | CD2 | TRP | A | 394 | 61.962 | 60.600 | 77.807 | 1.00 | 34.46 | A C |
| ATOM | 1360 | NE1 | TRP | A | 394 | 62.807 | 62.672 | 77.922 | 1.00 | 35.68 | A N |
| ATOM | 1361 | CE2 | TRP | A | 394 | 62.824 | 61.439 | 78.533 | 1.00 | 37.26 | A C |
| ATOM | 1362 | CE3 | TRP | A | 394 | 61.778 | 59.282 | 78.247 | 1.00 | 36.12 | A C |
| ATOM | 1363 | CZ2 | TRP | A | 394 | 63.525 | 60.999 | 79.669 | 1.00 | 38.69 | A C |
| ATOM | 1364 | CZ3 | TRP | A | 394 | 62.466 | 58.843 | 79.364 | 1.00 | 39.16 | A C |
| ATOM | 1365 | CH2 | TRP | A | 394 | 63.340 | 59.701 | 80.062 | 1.00 | 40.35 | A C |
| ATOM | 1366 | N | VAL | A | 395 | 61.733 | 58.109 | 75.011 | 1.00 | 27.04 | A N |

156

| | | | | | | | | | | | |
|---|---|---|---|---|---|---|---|---|---|---|---|
| ATOM | 1367 | CA | VAL | A | 395 | 62.713 | 57.047 | 75.246 | 1.00 | 27.91 | A | C |
| ATOM | 1368 | C | VAL | A | 395 | 63.523 | 56.823 | 73.993 | 1.00 | 27.56 | A | C |
| ATOM | 1369 | O | VAL | A | 395 | 64.744 | 56.745 | 74.013 | 1.00 | 27.74 | A | O |
| ATOM | 1370 | CB | VAL | A | 395 | 62.026 | 55.704 | 75.646 | 1.00 | 29.04 | A | C |
| ATOM | 1371 | CG1 | VAL | A | 395 | 63.047 | 54.553 | 75.550 | 1.00 | 29.87 | A | C |
| ATOM | 1372 | CG2 | VAL | A | 395 | 61.450 | 55.801 | 77.044 | 1.00 | 28.31 | A | C |
| ATOM | 1373 | N | ILE | A | 396 | 62.844 | 56.774 | 72.863 | 1.00 | 28.02 | A | N |
| ATOM | 1374 | CA | ILE | A | 396 | 63.552 | 56.548 | 71.617 | 1.00 | 28.19 | A | C |
| ATOM | 1375 | C | ILE | A | 396 | 64.507 | 57.689 | 71.297 | 1.00 | 28.58 | A | C |
| ATOM | 1376 | O | ILE | A | 396 | 65.626 | 57.456 | 70.854 | 1.00 | 28.16 | A | O |
| ATOM | 1377 | CB | ILE | A | 396 | 62.550 | 56.260 | 70.475 | 1.00 | 28.30 | A | C |
| ATOM | 1378 | CG1 | ILE | A | 396 | 61.938 | 54.873 | 70.722 | 1.00 | 28.85 | A | C |
| ATOM | 1379 | CG2 | ILE | A | 396 | 63.250 | 56.270 | 69.133 | 1.00 | 24.56 | A | C |
| ATOM | 1380 | CD1 | ILE | A | 396 | 60.791 | 54.524 | 69.757 | 1.00 | 31.52 | A | C |
| ATOM | 1381 | N | ALA | A | 397 | 64.080 | 58.920 | 71.524 | 1.00 | 28.64 | A | N |
| ATOM | 1382 | CA | ALA | A | 397 | 64.967 | 60.064 | 71.263 | 1.00 | 30.75 | A | C |
| ATOM | 1383 | C | ALA | A | 397 | 66.261 | 60.028 | 72.102 | 1.00 | 31.51 | A | C |
| ATOM | 1384 | O | ALA | A | 397 | 67.263 | 60.599 | 71.711 | 1.00 | 31.37 | A | O |
| ATOM | 1385 | CB | ALA | A | 397 | 64.215 | 61.416 | 71.500 | 1.00 | 30.16 | A | C |
| ATOM | 1386 | N | LYS | A | 398 | 66.239 | 59.366 | 73.254 | 1.00 | 32.78 | A | N |
| ATOM | 1387 | CA | LYS | A | 398 | 67.432 | 59.345 | 74.120 | 1.00 | 34.96 | A | C |
| ATOM | 1388 | C | LYS | A | 398 | 68.483 | 58.451 | 73.545 | 1.00 | 35.89 | A | C |
| ATOM | 1389 | O | LYS | A | 398 | 69.650 | 58.554 | 73.902 | 1.00 | 35.22 | A | O |
| ATOM | 1390 | CB | LYS | A | 398 | 67.119 | 58.821 | 75.520 | 1.00 | 35.38 | A | C |
| ATOM | 1391 | CG | LYS | A | 398 | 66.261 | 59.740 | 76.340 | 1.00 | 37.31 | A | C |
| ATOM | 1392 | CD | LYS | A | 398 | 66.911 | 61.124 | 76.471 | 1.00 | 42.24 | A | C |
| ATOM | 1395 | N | SER | A | 399 | 68.057 | 57.554 | 72.662 | 1.00 | 36.62 | A | N |
| ATOM | 1396 | CA | SER | A | 399 | 68.970 | 56.604 | 72.071 | 1.00 | 37.67 | A | C |
| ATOM | 1397 | C | SER | A | 399 | 69.999 | 57.336 | 71.241 | 1.00 | 38.14 | A | C |
| ATOM | 1398 | O | SER | A | 399 | 71.069 | 56.805 | 70.958 | 1.00 | 39.47 | A | O |
| ATOM | 1399 | CB | SER | A | 399 | 68.199 | 55.596 | 71.213 | 1.00 | 37.93 | A | C |
| ATOM | 1400 | OG | SER | A | 399 | 67.985 | 56.119 | 69.909 | 1.00 | 38.18 | A | O |
| ATOM | 1401 | N | GLY | A | 400 | 69.669 | 58.558 | 70.825 | 1.00 | 37.91 | A | N |
| ATOM | 1402 | CA | GLY | A | 400 | 70.599 | 59.376 | 70.074 | 1.00 | 36.76 | A | C |
| ATOM | 1403 | C | GLY | A | 400 | 70.706 | 59.068 | 68.592 | 1.00 | 36.45 | A | C |
| ATOM | 1404 | O | GLY | A | 400 | 71.419 | 59.763 | 67.875 | 1.00 | 35.84 | A | O |
| ATOM | 1405 | N | ILE | A | 401 | 69.993 | 58.050 | 68.112 | 1.00 | 35.05 | A | N |
| ATOM | 1406 | CA | ILE | A | 401 | 70.079 | 57.705 | 66.700 | 1.00 | 33.66 | A | C |
| ATOM | 1407 | C | ILE | A | 401 | 69.391 | 58.787 | 65.878 | 1.00 | 32.60 | A | C |
| ATOM | 1408 | O | ILE | A | 401 | 68.710 | 59.628 | 66.434 | 1.00 | 32.47 | A | O |
| ATOM | 1409 | CB | ILE | A | 401 | 69.470 | 56.308 | 66.434 | 1.00 | 34.14 | A | C |
| ATOM | 1410 | CG1 | ILE | A | 401 | 67.943 | 56.355 | 66.503 | 1.00 | 33.08 | A | C |
| ATOM | 1411 | CG2 | ILE | A | 401 | 70.059 | 55.272 | 67.412 | 1.00 | 33.76 | A | C |
| ATOM | 1412 | CD1 | ILE | A | 401 | 67.269 | 54.975 | 66.519 | 1.00 | 33.75 | A | C |
| ATOM | 1413 | N | SER | A | 402 | 69.565 | 58.761 | 64.565 | 1.00 | 31.28 | A | N |
| ATOM | 1414 | CA | SER | A | 402 | 69.001 | 59.783 | 63.695 | 1.00 | 30.79 | A | C |
| ATOM | 1415 | C | SER | A | 402 | 67.480 | 59.898 | 63.769 | 1.00 | 30.19 | A | C |
| ATOM | 1416 | O | SER | A | 402 | 66.778 | 58.941 | 64.132 | 1.00 | 30.10 | A | O |
| ATOM | 1417 | CB | SER | A | 402 | 69.412 | 59.527 | 62.247 | 1.00 | 31.51 | A | C |
| ATOM | 1418 | OG | SER | A | 402 | 68.544 | 58.593 | 61.630 | 1.00 | 31.79 | A | O |
| ATOM | 1419 | N | SER | A | 403 | 66.973 | 61.075 | 63.434 | 1.00 | 28.55 | A | N |
| ATOM | 1420 | CA | SER | A | 403 | 65.543 | 61.306 | 63.462 | 1.00 | 28.56 | A | C |
| ATOM | 1421 | C | SER | A | 403 | 64.808 | 60.301 | 62.534 | 1.00 | 27.36 | A | C |
| ATOM | 1422 | O | SER | A | 403 | 63.748 | 59.811 | 62.879 | 1.00 | 25.78 | A | O |
| ATOM | 1423 | CB | SER | A | 403 | 65.235 | 62.748 | 63.070 | 1.00 | 28.88 | A | C |
| ATOM | 1424 | OG | SER | A | 403 | 63.841 | 62.987 | 63.162 | 1.00 | 33.71 | A | O |
| ATOM | 1425 | N | GLN | A | 404 | 65.387 | 60.022 | 61.365 | 1.00 | 26.30 | A | N |
| ATOM | 1426 | CA | GLN | A | 404 | 64.832 | 59.035 | 60.434 | 1.00 | 26.80 | A | C |
| ATOM | 1427 | C | GLN | A | 404 | 64.755 | 57.651 | 61.076 | 1.00 | 25.79 | A | C |
| ATOM | 1428 | O | GLN | A | 404 | 63.744 | 56.977 | 60.980 | 1.00 | 25.02 | A | O |
| ATOM | 1429 | CB | GLN | A | 404 | 65.661 | 58.981 | 59.144 | 1.00 | 26.82 | A | C |

| | | | | | | | | | | |
|---|---|---|---|---|---|---|---|---|---|---|
| ATOM | 1430 | CG | GLN | A | 404 | 64.948 | 58.329 | 57.927 | 1.00 28.83 | A | C |
| ATOM | 1431 | CD | GLN | A | 404 | 65.031 | 56.791 | 57.932 | 1.00 30.28 | A | C |
| ATOM | 1432 | OE1 | GLN | A | 404 | 65.826 | 56.220 | 58.668 | 1.00 28.00 | A | O |
| ATOM | 1433 | NE2 | GLN | A | 404 | 64.210 | 56.134 | 57.096 | 1.00 31.19 | A | N |
| ATOM | 1434 | N | GLN | A | 405 | 65.811 | 57.251 | 61.774 | 1.00 25.61 | A | N |
| ATOM | 1435 | CA | GLN | A | 405 | 65.857 | 55.927 | 62.404 | 1.00 26.39 | A | C |
| ATOM | 1436 | C | GLN | A | 405 | 64.928 | 55.839 | 63.630 | 1.00 25.56 | A | C |
| ATOM | 1437 | O | GLN | A | 405 | 64.382 | 54.779 | 63.945 | 1.00 24.42 | A | O |
| ATOM | 1438 | CB | GLN | A | 405 | 67.312 | 55.550 | 62.765 | 1.00 27.23 | A | C |
| ATOM | 1439 | CG | GLN | A | 405 | 68.232 | 55.434 | 61.546 | 1.00 31.65 | A | C |
| ATOM | 1440 | CD | GLN | A | 405 | 69.740 | 55.310 | 61.886 | 1.00 39.14 | A | C |
| ATOM | 1441 | OE1 | GLN | A | 405 | 70.493 | 54.673 | 61.134 | 1.00 42.78 | A | O |
| ATOM | 1442 | NE2 | GLN | A | 405 | 70.182 | 55.954 | 62.973 | 1.00 41.00 | A | N |
| ATOM | 1443 | N | GLN | A | 406 | 64.741 | 56.959 | 64.313 | 1.00 24.67 | A | N |
| ATOM | 1444 | CA | GLN | A | 406 | 63.837 | 56.978 | 65.449 | 1.00 25.27 | A | C |
| ATOM | 1445 | C | GLN | A | 406 | 62.402 | 56.727 | 64.965 | 1.00 24.78 | A | C |
| ATOM | 1446 | O | GLN | A | 406 | 61.622 | 56.069 | 65.645 | 1.00 24.89 | A | O |
| ATOM | 1447 | CB | GLN | A | 406 | 63.911 | 58.318 | 66.171 | 1.00 25.25 | A | C |
| ATOM | 1448 | CG | GLN | A | 406 | 65.243 | 58.574 | 66.924 | 1.00 26.85 | A | C |
| ATOM | 1449 | CD | GLN | A | 406 | 65.225 | 59.913 | 67.654 | 1.00 32.30 | A | C |
| ATOM | 1450 | OE1 | GLN | A | 406 | 64.186 | 60.308 | 68.211 | 1.00 34.47 | A | O |
| ATOM | 1451 | NE2 | GLN | A | 406 | 66.362 | 60.611 | 67.655 | 1.00 27.41 | A | N |
| ATOM | 1452 | N | SER | A | 407 | 62.061 | 57.298 | 63.820 | 1.00 24.47 | A | N |
| ATOM | 1453 | CA | SER | A | 407 | 60.739 | 57.130 | 63.233 | 1.00 25.09 | A | C |
| ATOM | 1454 | C | SER | A | 407 | 60.567 | 55.674 | 62.784 | 1.00 25.21 | A | C |
| ATOM | 1455 | O | SER | A | 407 | 59.538 | 55.044 | 63.049 | 1.00 23.90 | A | O |
| ATOM | 1456 | CB | SER | A | 407 | 60.574 | 58.066 | 62.029 | 1.00 24.99 | A | C |
| ATOM | 1457 | OG | SER | A | 407 | 60.430 | 59.410 | 62.461 | 1.00 24.27 | A | O |
| ATOM | 1458 | N | VAL | A | 408 | 61.588 | 55.129 | 62.130 | 1.00 25.19 | A | N |
| ATOM | 1459 | CA | VAL | A | 408 | 61.478 | 53.769 | 61.641 | 1.00 25.99 | A | C |
| ATOM | 1460 | C | VAL | A | 408 | 61.380 | 52.834 | 62.843 | 1.00 26.47 | A | C |
| ATOM | 1461 | O | VAL | A | 408 | 60.579 | 51.903 | 62.839 | 1.00 25.85 | A | O |
| ATOM | 1462 | CB | VAL | A | 408 | 62.666 | 53.383 | 60.728 | 1.00 27.56 | A | C |
| ATOM | 1463 | CG1 | VAL | A | 408 | 62.666 | 51.865 | 60.386 | 1.00 27.68 | A | C |
| ATOM | 1464 | CG2 | VAL | A | 408 | 62.625 | 54.211 | 59.468 | 1.00 26.92 | A | C |
| ATOM | 1465 | N | ARG | A | 409 | 62.159 | 53.101 | 63.889 | 1.00 25.86 | A | N |
| ATOM | 1466 | CA | ARG | A | 409 | 62.098 | 52.247 | 65.070 | 1.00 26.42 | A | C |
| ATOM | 1467 | C | ARG | A | 409 | 60.674 | 52.270 | 65.691 | 1.00 26.79 | A | C |
| ATOM | 1468 | O | ARG | A | 409 | 60.142 | 51.234 | 66.076 | 1.00 25.76 | A | O |
| ATOM | 1469 | CB | ARG | A | 409 | 63.149 | 52.636 | 66.111 | 1.00 26.12 | A | C |
| ATOM | 1470 | CG | ARG | A | 409 | 63.201 | 51.724 | 67.325 | 1.00 26.64 | A | C |
| ATOM | 1471 | CD | ARG | A | 409 | 64.165 | 52.202 | 68.416 | 1.00 28.10 | A | C |
| ATOM | 1472 | NE | ARG | A | 409 | 64.263 | 51.253 | 69.524 | 1.00 27.07 | A | N |
| ATOM | 1473 | CZ | ARG | A | 409 | 64.934 | 50.102 | 69.444 | 1.00 29.26 | A | C |
| ATOM | 1474 | NH1 | ARG | A | 409 | 65.545 | 49.747 | 68.306 | 1.00 26.06 | A | N |
| ATOM | 1475 | NH2 | ARG | A | 409 | 65.004 | 49.296 | 70.496 | 1.00 28.04 | A | N |
| ATOM | 1476 | N | LEU | A | 410 | 60.085 | 53.458 | 65.803 | 1.00 26.24 | A | N |
| ATOM | 1477 | CA | LEU | A | 410 | 58.733 | 53.574 | 66.328 | 1.00 27.01 | A | C |
| ATOM | 1478 | C | LEU | A | 410 | 57.735 | 52.824 | 65.441 | 1.00 26.55 | A | C |
| ATOM | 1479 | O | LEU | A | 410 | 56.877 | 52.094 | 65.937 | 1.00 26.17 | A | O |
| ATOM | 1480 | CB | LEU | A | 410 | 58.333 | 55.050 | 66.418 | 1.00 27.19 | A | C |
| ATOM | 1481 | CG | LEU | A | 410 | 56.893 | 55.360 | 66.815 | 1.00 29.04 | A | C |
| ATOM | 1482 | CD1 | LEU | A | 410 | 56.588 | 54.749 | 68.186 | 1.00 27.92 | A | C |
| ATOM | 1483 | CD2 | LEU | A | 410 | 56.594 | 56.895 | 66.778 | 1.00 27.24 | A | C |
| ATOM | 1484 | N | ALA | A | 411 | 57.849 | 52.994 | 64.127 | 1.00 26.23 | A | N |
| ATOM | 1485 | CA | ALA | A | 411 | 56.964 | 52.283 | 63.209 | 1.00 26.94 | A | C |
| ATOM | 1486 | C | ALA | A | 411 | 57.116 | 50.765 | 63.418 | 1.00 26.80 | A | C |
| ATOM | 1487 | O | ALA | A | 411 | 56.120 | 50.048 | 63.473 | 1.00 25.42 | A | O |
| ATOM | 1488 | CB | ALA | A | 411 | 57.268 | 52.650 | 61.741 | 1.00 26.66 | A | C |
| ATOM | 1489 | N | ASN | A | 412 | 58.355 | 50.295 | 63.520 | 1.00 25.81 | A | N |
| ATOM | 1490 | CA | ASN | A | 412 | 58.609 | 48.852 | 63.682 | 1.00 27.59 | A | C |

| | | | | | | | | | | |
|---|---|---|---|---|---|---|---|---|---|---|
| ATOM | 1491 | C | ASN | A | 412 | 57.982 | 48.311 | 64.987 | 1.00 27.18 | A C |
| ATOM | 1492 | O | ASN | A | 412 | 57.373 | 47.246 | 65.003 | 1.00 26.23 | A O |
| ATOM | 1493 | CB | ASN | A | 412 | 60.120 | 48.526 | 63.641 | 1.00 26.72 | A C |
| ATOM | 1494 | CG | ASN | A | 412 | 60.769 | 48.740 | 62.223 | 1.00 30.38 | A C |
| ATOM | 1495 | OD1 | ASN | A | 412 | 60.092 | 48.792 | 61.217 | 1.00 33.17 | A O |
| ATOM | 1496 | ND2 | ASN | A | 412 | 62.088 | 48.886 | 62.190 | 1.00 29.33 | A N |
| ATOM | 1497 | N | LEU | A | 413 | 58.135 | 49.045 | 66.085 | 1.00 26.82 | A N |
| ATOM | 1498 | CA | LEU | A | 413 | 57.551 | 48.602 | 67.352 | 1.00 27.93 | A C |
| ATOM | 1499 | C | LEU | A | 413 | 56.032 | 48.548 | 67.263 | 1.00 28.39 | A C |
| ATOM | 1500 | O | LEU | A | 413 | 55.407 | 47.610 | 67.767 | 1.00 27.02 | A O |
| ATOM | 1501 | CB | LEU | A | 413 | 57.935 | 49.523 | 68.496 | 1.00 27.49 | A C |
| ATOM | 1502 | CG | LEU | A | 413 | 59.434 | 49.504 | 68.775 | 1.00 30.10 | A C |
| ATOM | 1503 | CD1 | LEU | A | 413 | 59.732 | 50.551 | 69.810 | 1.00 28.77 | A C |
| ATOM | 1504 | CD2 | LEU | A | 413 | 59.841 | 48.110 | 69.282 | 1.00 29.06 | A C |
| ATOM | 1505 | N | LEU | A | 414 | 55.439 | 49.564 | 66.642 | 1.00 28.10 | A N |
| ATOM | 1506 | CA | LEU | A | 414 | 53.973 | 49.590 | 66.520 | 1.00 29.11 | A C |
| ATOM | 1507 | C | LEU | A | 414 | 53.460 | 48.461 | 65.614 | 1.00 28.83 | A C |
| ATOM | 1508 | O | LEU | A | 414 | 52.396 | 47.872 | 65.871 | 1.00 28.10 | A O |
| ATOM | 1509 | CB | LEU | A | 414 | 53.461 | 50.946 | 66.015 | 1.00 28.71 | A C |
| ATOM | 1510 | CG | LEU | A | 414 | 53.646 | 52.109 | 67.016 | 1.00 30.80 | A C |
| ATOM | 1511 | CD1 | LEU | A | 414 | 53.162 | 53.464 | 66.427 | 1.00 28.20 | A C |
| ATOM | 1512 | CD2 | LEU | A | 414 | 52.886 | 51.815 | 68.305 | 1.00 31.63 | A C |
| ATOM | 1513 | N | MET | A | 415 | 54.190 | 48.172 | 64.544 | 1.00 27.43 | A N |
| ATOM | 1514 | CA | MET | A | 415 | 53.753 | 47.093 | 63.664 | 1.00 28.64 | A C |
| ATOM | 1515 | CB | MET | A | 415 | 54.513 | 47.097 | 62.339 | 1.00 28.82 | A C |
| ATOM | 1516 | CG A | MET | A | 415 | 53.993 | 48.220 | 61.392 | 0.50 29.72 | A C |
| ATOM | 1517 | CG B | MET | A | 415 | 54.430 | 48.377 | 61.537 | 0.50 29.88 | A C |
| ATOM | 1518 | SD A | MET | A | 415 | 54.779 | 48.302 | 59.751 | 0.50 31.65 | A S |
| ATOM | 1519 | SD B | MET | A | 415 | 55.635 | 48.413 | 60.155 | 0.50 31.04 | A S |
| ATOM | 1520 | CE A | MET | A | 415 | 56.557 | 48.293 | 60.278 | 0.50 28.59 | A C |
| ATOM | 1521 | CE B | MET | A | 415 | 54.902 | 49.825 | 59.227 | 0.50 28.20 | A C |
| ATOM | 1522 | C | MET | A | 415 | 53.890 | 45.742 | 64.425 | 1.00 28.59 | A C |
| ATOM | 1523 | O | MET | A | 415 | 53.091 | 44.831 | 64.249 | 1.00 27.92 | A O |
| ATOM | 1524 | N | LEU | A | 416 | 54.896 | 45.634 | 65.269 | 1.00 28.06 | A N |
| ATOM | 1525 | CA | LEU | A | 416 | 55.040 | 44.435 | 66.111 | 1.00 29.80 | A C |
| ATOM | 1526 | C | LEU | A | 416 | 53.872 | 44.257 | 67.116 | 1.00 30.04 | A C |
| ATOM | 1527 | O | LEU | A | 416 | 53.397 | 43.136 | 67.296 | 1.00 30.00 | A O |
| ATOM | 1528 | CB | LEU | A | 416 | 56.398 | 44.400 | 66.820 | 1.00 29.53 | A C |
| ATOM | 1529 | CG | LEU | A | 416 | 57.596 | 44.068 | 65.892 | 1.00 30.74 | A C |
| ATOM | 1530 | CD1 | LEU | A | 416 | 58.936 | 44.370 | 66.564 | 1.00 31.36 | A C |
| ATOM | 1531 | CD2 | LEU | A | 416 | 57.588 | 42.594 | 65.408 | 1.00 31.18 | A C |
| ATOM | 1532 | N | LEU | A | 417 | 53.407 | 45.348 | 67.735 | 1.00 29.18 | A N |
| ATOM | 1533 | CA | LEU | A | 417 | 52.238 | 45.300 | 68.609 | 1.00 29.72 | A C |
| ATOM | 1534 | C | LEU | A | 417 | 51.049 | 44.796 | 67.796 | 1.00 29.66 | A C |
| ATOM | 1535 | O | LEU | A | 417 | 50.245 | 43.986 | 68.273 | 1.00 27.54 | A O |
| ATOM | 1536 | CB | LEU | A | 417 | 51.903 | 46.670 | 69.222 | 1.00 29.49 | A C |
| ATOM | 1537 | CG | LEU | A | 417 | 53.028 | 47.263 | 70.099 | 1.00 33.08 | A C |
| ATOM | 1538 | CD1 | LEU | A | 417 | 52.528 | 48.457 | 70.945 | 1.00 34.82 | A C |
| ATOM | 1539 | CD2 | LEU | A | 417 | 53.618 | 46.214 | 71.008 | 1.00 33.08 | A C |
| ATOM | 1540 | N | SER | A | 418 | 50.963 | 45.243 | 66.544 | 1.00 28.38 | A N |
| ATOM | 1541 | CA | SER | A | 418 | 49.852 | 44.820 | 65.708 | 1.00 29.07 | A C |
| ATOM | 1542 | C | SER | A | 418 | 49.958 | 43.301 | 65.475 | 1.00 29.11 | A C |
| ATOM | 1543 | O | SER | A | 418 | 48.979 | 42.575 | 65.527 | 1.00 27.08 | A O |
| ATOM | 1544 | CB | SER | A | 418 | 49.831 | 45.583 | 64.387 | 1.00 28.51 | A C |
| ATOM | 1545 | OG | SER | A | 418 | 48.659 | 45.229 | 63.679 | 1.00 29.77 | A O |
| ATOM | 1546 | N | HIS | A | 419 | 51.178 | 42.828 | 65.287 | 1.00 29.10 | A N |
| ATOM | 1547 | CA | HIS | A | 419 | 51.384 | 41.408 | 65.117 | 1.00 29.97 | A C |
| ATOM | 1548 | C | HIS | A | 419 | 51.021 | 40.640 | 66.391 | 1.00 29.37 | A C |
| ATOM | 1549 | O | HIS | A | 419 | 50.481 | 39.540 | 66.334 | 1.00 28.54 | A O |
| ATOM | 1550 | CB | HIS | A | 419 | 52.841 | 41.115 | 64.806 | 1.00 30.09 | A C |
| ATOM | 1551 | CG | HIS | A | 419 | 53.067 | 39.704 | 64.401 | 1.00 33.09 | A C |

| | | | | | | | | | | |
|---|---|---|---|---|---|---|---|---|---|---|
| ATOM | 1552 | ND1 | HIS | A | 419 | 52.379 | 39.125 | 63.356 | 1.00 34.04 | A | N |
| ATOM | 1553 | CD2 | HIS | A | 419 | 53.861 | 38.737 | 64.915 | 1.00 33.54 | A | C |
| ATOM | 1554 | CE1 | HIS | A | 419 | 52.773 | 37.870 | 63.221 | 1.00 36.77 | A | C |
| ATOM | 1555 | NE2 | HIS | A | 419 | 53.673 | 37.612 | 64.153 | 1.00 34.31 | A | N |
| ATOM | 1556 | N | VAL | A | 420 | 51.331 | 41.219 | 67.539 | 1.00 28.34 | A | N |
| ATOM | 1557 | CA | VAL | A | 420 | 51.034 | 40.530 | 68.787 | 1.00 28.89 | A | C |
| ATOM | 1558 | C | VAL | A | 420 | 49.504 | 40.348 | 68.901 | 1.00 28.25 | A | C |
| ATOM | 1559 | O | VAL | A | 420 | 49.023 | 39.308 | 69.355 | 1.00 27.68 | A | O |
| ATOM | 1560 | CB | VAL | A | 420 | 51.633 | 41.251 | 69.998 | 1.00 28.42 | A | C |
| ATOM | 1561 | CG1 | VAL | A | 420 | 51.094 | 40.690 | 71.318 | 1.00 30.57 | A | C |
| ATOM | 1562 | CG2 | VAL | A | 420 | 53.177 | 41.168 | 69.992 | 1.00 30.49 | A | C |
| ATOM | 1563 | N | ARG | A | 421 | 48.755 | 41.348 | 68.461 | 1.00 27.77 | A | N |
| ATOM | 1564 | CA | ARG | A | 421 | 47.296 | 41.278 | 68.468 | 1.00 29.34 | A | C |
| ATOM | 1565 | C | ARG | A | 421 | 46.805 | 40.091 | 67.646 | 1.00 29.54 | A | C |
| ATOM | 1566 | O | ARG | A | 421 | 45.884 | 39.350 | 68.038 | 1.00 28.88 | A | O |
| ATOM | 1567 | CB | ARG | A | 421 | 46.704 | 42.581 | 67.922 | 1.00 29.69 | A | C |
| ATOM | 1568 | CG | ARG | A | 421 | 45.182 | 42.548 | 67.675 | 1.00 32.30 | A | C |
| ATOM | 1569 | CD | ARG | A | 421 | 44.391 | 42.856 | 68.910 | 1.00 35.34 | A | C |
| ATOM | 1570 | NE | ARG | A | 421 | 42.943 | 42.820 | 68.705 | 1.00 38.32 | A | N |
| ATOM | 1571 | CZ | ARG | A | 421 | 42.082 | 43.052 | 69.690 | 1.00 39.14 | A | C |
| ATOM | 1572 | NH1 | ARG | A | 421 | 42.546 | 43.335 | 70.917 | 1.00 37.30 | A | N |
| ATOM | 1573 | NH2 | ARG | A | 421 | 40.776 | 43.007 | 69.457 | 1.00 37.14 | A | N |
| ATOM | 1574 | N | HIS | A | 422 | 47.426 | 39.888 | 66.497 | 1.00 29.42 | A | N |
| ATOM | 1575 | CA | HIS | A | 422 | 47.004 | 38.788 | 65.647 | 1.00 30.01 | A | C |
| ATOM | 1576 | C | HIS | A | 422 | 47.340 | 37.462 | 66.342 | 1.00 29.16 | A | C |
| ATOM | 1577 | O | HIS | A | 422 | 46.519 | 36.558 | 66.344 | 1.00 27.98 | A | O |
| ATOM | 1578 | CB | HIS | A | 422 | 47.651 | 38.900 | 64.261 | 1.00 30.69 | A | C |
| ATOM | 1579 | CG | HIS | A | 422 | 47.133 | 40.049 | 63.443 | 1.00 35.16 | A | C |
| ATOM | 1580 | ND1 | HIS | A | 422 | 45.838 | 40.101 | 62.961 | 1.00 37.40 | A | N |
| ATOM | 1581 | CD2 | HIS | A | 422 | 47.740 | 41.183 | 63.010 | 1.00 36.41 | A | C |
| ATOM | 1582 | CE1 | HIS | A | 422 | 45.671 | 41.220 | 62.276 | 1.00 38.15 | A | C |
| ATOM | 1583 | NE2 | HIS | A | 422 | 46.809 | 41.894 | 62.291 | 1.00 37.52 | A | N |
| ATOM | 1584 | N | ILE | A | 423 | 48.529 | 37.353 | 66.943 | 1.00 28.64 | A | N |
| ATOM | 1585 | CA | ILE | A | 423 | 48.901 | 36.119 | 67.653 | 1.00 29.05 | A | C |
| ATOM | 1586 | C | ILE | A | 423 | 47.906 | 35.850 | 68.800 | 1.00 29.01 | A | C |
| ATOM | 1587 | O | ILE | A | 423 | 47.483 | 34.721 | 69.025 | 1.00 28.51 | A | O |
| ATOM | 1588 | CB | ILE | A | 423 | 50.350 | 36.156 | 68.207 | 1.00 28.72 | A | C |
| ATOM | 1589 | CG1 | ILE | A | 423 | 51.378 | 36.444 | 67.109 | 1.00 28.92 | A | C |
| ATOM | 1590 | CG2 | ILE | A | 423 | 50.710 | 34.817 | 68.864 | 1.00 27.47 | A | C |
| ATOM | 1591 | CD1 | ILE | A | 423 | 52.817 | 36.661 | 67.688 | 1.00 28.87 | A | C |
| ATOM | 1592 | N | SER | A | 424 | 47.527 | 36.917 | 69.488 | 1.00 28.69 | A | N |
| ATOM | 1593 | CA | SER | A | 424 | 46.546 | 36.851 | 70.556 | 1.00 29.98 | A | C |
| ATOM | 1594 | C | SER | A | 424 | 45.234 | 36.242 | 70.039 | 1.00 29.62 | A | C |
| ATOM | 1595 | O | SER | A | 424 | 44.672 | 35.359 | 70.679 | 1.00 29.85 | A | O |
| ATOM | 1596 | CB | SER | A | 424 | 46.316 | 38.252 | 71.147 | 1.00 29.48 | A | C |
| ATOM | 1597 | OG | SER | A | 424 | 45.129 | 38.304 | 71.938 | 1.00 33.89 | A | O |
| ATOM | 1598 | N | ASN | A | 425 | 44.750 | 36.699 | 68.887 | 1.00 29.42 | A | N |
| ATOM | 1599 | CA | ASN | A | 425 | 43.532 | 36.113 | 68.302 | 1.00 30.26 | A | C |
| ATOM | 1600 | C | ASN | A | 425 | 43.678 | 34.602 | 68.058 | 1.00 29.89 | A | C |
| ATOM | 1601 | O | ASN | A | 425 | 42.749 | 33.829 | 68.283 | 1.00 28.84 | A | O |
| ATOM | 1602 | CB | ASN | A | 425 | 43.128 | 36.818 | 66.985 | 1.00 30.57 | A | C |
| ATOM | 1603 | CG | ASN | A | 425 | 42.643 | 38.252 | 67.199 | 1.00 33.51 | A | C |
| ATOM | 1604 | OD1 | ASN | A | 425 | 42.240 | 38.629 | 68.308 | 1.00 37.41 | A | O |
| ATOM | 1605 | ND2 | ASN | A | 425 | 42.703 | 39.066 | 66.142 | 1.00 33.12 | A | N |
| ATOM | 1606 | N | LYS | A | 426 | 44.848 | 34.195 | 67.580 | 1.00 29.75 | A | N |
| ATOM | 1607 | CA | LYS | A | 426 | 45.133 | 32.790 | 67.326 | 1.00 30.14 | A | C |
| ATOM | 1608 | C | LYS | A | 426 | 45.130 | 32.021 | 68.651 | 1.00 29.50 | A | C |
| ATOM | 1609 | O | LYS | A | 426 | 44.623 | 30.918 | 68.747 | 1.00 28.62 | A | O |
| ATOM | 1610 | CB | LYS | A | 426 | 46.504 | 32.646 | 66.665 | 1.00 30.22 | A | C |
| ATOM | 1611 | CG | LYS | A | 426 | 46.482 | 31.977 | 65.314 | 1.00 36.32 | A | C |
| ATOM | 1612 | CD | LYS | A | 426 | 46.094 | 32.999 | 64.254 | 1.00 40.32 | A | C |

| ATOM | 1613 | CE | LYS A 426 | 45.451 | 32.352 | 63.038 | 1.00 43.73 | A | C |
|------|------|------|-----------|--------|--------|--------|------------|---|---|
| ATOM | 1614 | NZ | LYS A 426 | 44.777 | 33.378 | 62.166 | 1.00 43.68 | A | N |
| ATOM | 1615 | N | GLY A 427 | 45.716 | 32.627 | 69.675 | 1.00 29.48 | A | N |
| ATOM | 1616 | CA | GLY A 427 | 45.786 | 32.005 | 70.980 | 1.00 29.35 | A | C |
| ATOM | 1617 | C | GLY A 427 | 44.411 | 31.825 | 71.583 | 1.00 29.80 | A | C |
| ATOM | 1618 | O | GLY A 427 | 44.112 | 30.778 | 72.173 | 1.00 29.46 | A | O |
| ATOM | 1619 | N | MET A 428 | 43.572 | 32.848 | 71.453 | 1.00 30.15 | A | N |
| ATOM | 1620 | CA | MET A 428 | 42.221 | 32.768 | 71.995 | 1.00 31.32 | A | C |
| ATOM | 1621 | CB | MET A 428 | 41.469 | 34.093 | 71.886 | 1.00 31.58 | A | C |
| ATOM | 1622 | CG AMET | A 428 | 42.007 | 35.175 | 72.808 | 0.50 33.12 | A | C |
| ATOM | 1623 | CG BMET | A 428 | 41.231 | 34.689 | 73.280 | 0.50 34.27 | A | C |
| ATOM | 1624 | SD AMET | A 428 | 41.406 | 34.904 | 74.483 | 0.50 35.41 | A | S |
| ATOM | 1625 | SD BMET | A 428 | 41.721 | 36.411 | 73.514 | 0.50 36.37 | A | S |
| ATOM | 1626 | CE AMET | A 428 | 39.773 | 35.449 | 74.339 | 0.50 34.03 | A | C |
| ATOM | 1627 | CE BMET | A 428 | 40.110 | 37.160 | 73.794 | 0.50 37.85 | A | C |
| ATOM | 1628 | C | MET A 428 | 41.462 | 31.667 | 71.322 | 1.00 30.57 | A | C |
| ATOM | 1629 | O | MET A 428 | 40.829 | 30.852 | 71.975 | 1.00 30.62 | A | O |
| ATOM | 1630 | N | GLU A 429 | 41.557 | 31.645 | 70.006 | 1.00 30.56 | A | N |
| ATOM | 1631 | CA | GLU A 429 | 40.897 | 30.636 | 69.197 | 1.00 31.20 | A | C |
| ATOM | 1632 | C | GLU A 429 | 41.341 | 29.252 | 69.660 | 1.00 30.65 | A | C |
| ATOM | 1633 | O | GLU A 429 | 40.517 | 28.359 | 69.832 | 1.00 29.65 | A | O |
| ATOM | 1634 | CB | GLU A 429 | 41.223 | 30.890 | 67.720 | 1.00 31.25 | A | C |
| ATOM | 1635 | CG | GLU A 429 | 40.922 | 29.772 | 66.742 | 1.00 34.53 | A | C |
| ATOM | 1636 | CD | GLU A 429 | 41.092 | 30.236 | 65.299 | 1.00 37.67 | A | C |
| ATOM | 1637 | OE1 | GLU A 429 | 42.103 | 30.923 | 64.991 | 1.00 40.07 | A | O |
| ATOM | 1638 | OE2 | GLU A 429 | 40.207 | 29.938 | 64.479 | 1.00 38.30 | A | O |
| ATOM | 1639 | N | HIS A 430 | 42.643 | 29.099 | 69.901 | 1.00 30.04 | A | N |
| ATOM | 1640 | CA | HIS A 430 | 43.207 | 27.814 | 70.311 | 1.00 30.05 | A | C |
| ATOM | 1641 | C | HIS A 430 | 42.731 | 27.365 | 71.699 | 1.00 29.71 | A | C |
| ATOM | 1642 | O | HIS A 430 | 42.403 | 26.201 | 71.919 | 1.00 29.74 | A | O |
| ATOM | 1643 | CB | HIS A 430 | 44.740 | 27.876 | 70.284 | 1.00 30.25 | A | C |
| ATOM | 1644 | CG | HIS A 430 | 45.394 | 26.580 | 70.645 | 1.00 30.44 | A | C |
| ATOM | 1645 | ND1 | HIS A 430 | 45.764 | 26.267 | 71.935 | 1.00 28.41 | A | N |
| ATOM | 1646 | CD2 | HIS A 430 | 45.723 | 25.505 | 69.886 | 1.00 29.60 | A | C |
| ATOM | 1647 | CE1 | HIS A 430 | 46.306 | 25.062 | 71.955 | 1.00 29.48 | A | C |
| ATOM | 1648 | NE2 | HIS A 430 | 46.293 | 24.579 | 70.725 | 1.00 29.57 | A | N |
| ATOM | 1649 | N | LEU A 431 | 42.690 | 28.296 | 72.631 | 1.00 29.37 | A | N |
| ATOM | 1650 | CA | LEU A 431 | 42.256 | 27.999 | 73.978 | 1.00 29.97 | A | C |
| ATOM | 1651 | C | LEU A 431 | 40.783 | 27.612 | 73.950 | 1.00 30.63 | A | C |
| ATOM | 1652 | O | LEU A 431 | 40.382 | 26.603 | 74.536 | 1.00 29.73 | A | O |
| ATOM | 1653 | CB | LEU A 431 | 42.509 | 29.190 | 74.902 | 1.00 30.00 | A | C |
| ATOM | 1654 | CG | LEU A 431 | 42.069 | 28.984 | 76.350 | 1.00 30.37 | A | C |
| ATOM | 1655 | CD1 | LEU A 431 | 42.660 | 27.697 | 76.907 | 1.00 29.63 | A | C |
| ATOM | 1656 | CD2 | LEU A 431 | 42.464 | 30.164 | 77.191 | 1.00 29.44 | A | C |
| ATOM | 1657 | N | LEU A 432 | 39.974 | 28.396 | 73.248 | 1.00 31.15 | A | N |
| ATOM | 1658 | CA | LEU A 432 | 38.560 | 28.043 | 73.129 | 1.00 31.98 | A | C |
| ATOM | 1659 | C | LEU A 432 | 38.404 | 26.641 | 72.574 | 1.00 31.62 | A | C |
| ATOM | 1660 | O | LEU A 432 | 37.582 | 25.855 | 73.055 | 1.00 31.43 | A | O |
| ATOM | 1661 | CB | LEU A 432 | 37.803 | 29.045 | 72.268 | 1.00 32.42 | A | C |
| ATOM | 1662 | CG | LEU A 432 | 37.483 | 30.273 | 73.117 | 1.00 34.95 | A | C |
| ATOM | 1663 | CD1 | LEU A 432 | 37.254 | 31.512 | 72.248 | 1.00 38.78 | A | C |
| ATOM | 1664 | CD2 | LEU A 432 | 36.280 | 29.992 | 74.022 | 1.00 38.04 | A | C |
| ATOM | 1665 | N | SER A 433 | 39.199 | 26.314 | 71.569 | 1.00 31.34 | A | N |
| ATOM | 1666 | CA | SER A 433 | 39.124 | 24.972 | 71.013 | 1.00 31.35 | A | C |
| ATOM | 1667 | C | SER A 433 | 39.450 | 23.920 | 72.076 | 1.00 31.49 | A | C |
| ATOM | 1668 | O | SER A 433 | 38.684 | 22.973 | 72.276 | 1.00 31.68 | A | O |
| ATOM | 1669 | CB | SER A 433 | 40.042 | 24.823 | 69.801 | 1.00 31.34 | A | C |
| ATOM | 1670 | OG | SER A 433 | 39.936 | 23.516 | 69.255 | 1.00 29.98 | A | O |
| ATOM | 1671 | N | MET A 434 | 40.580 | 24.091 | 72.755 | 1.00 31.63 | A | N |
| ATOM | 1672 | CA | MET A 434 | 41.007 | 23.175 | 73.804 | 1.00 32.22 | A | C |
| ATOM | 1673 | C | MET A 434 | 39.921 | 22.959 | 74.862 | 1.00 32.66 | A | C |

| | | | | | | | | | | |
|---|---|---|---|---|---|---|---|---|---|---|
| ATOM | 1674 | O | MET | A | 434 | 39.643 | 21.828 | 75.250 | 1.00 32.48 | A | O |
| ATOM | 1675 | CB | MET | A | 434 | 42.306 | 23.654 | 74.452 | 1.00 32.39 | A | C |
| ATOM | 1676 | CG | MET | A | 434 | 43.521 | 23.513 | 73.548 | 1.00 33.38 | A | C |
| ATOM | 1677 | SD | MET | A | 434 | 43.888 | 21.796 | 73.181 | 1.00 35.23 | A | S |
| ATOM | 1678 | CE | MET | A | 434 | 43.880 | 21.787 | 71.413 | 1.00 35.36 | A | C |
| ATOM | 1679 | N | LYS | A | 435 | 39.308 | 24.047 | 75.318 | 1.00 33.04 | A | N |
| ATOM | 1680 | CA | LYS | A | 435 | 38.232 | 23.962 | 76.299 | 1.00 33.74 | A | C |
| ATOM | 1681 | C | LYS | A | 435 | 37.055 | 23.157 | 75.753 | 1.00 33.89 | A | C |
| ATOM | 1682 | O | LYS | A | 435 | 36.599 | 22.203 | 76.381 | 1.00 33.90 | A | O |
| ATOM | 1683 | CB | LYS | A | 435 | 37.762 | 25.361 | 76.680 | 1.00 33.83 | A | C |
| ATOM | 1684 | CG | LYS | A | 435 | 36.476 | 25.403 | 77.498 | 1.00 35.13 | A | C |
| ATOM | 1685 | CD | LYS | A | 435 | 35.974 | 26.849 | 77.581 | 1.00 36.97 | A | C |
| ATOM | 1686 | CE | LYS | A | 435 | 34.950 | 27.061 | 78.691 | 1.00 38.07 | A | C |
| ATOM | 1687 | NZ | LYS | A | 435 | 33.608 | 26.481 | 78.377 | 1.00 37.23 | A | N |
| ATOM | 1688 | N | CYS | A | 436 | 36.576 | 23.551 | 74.579 | 1.00 35.17 | A | N |
| ATOM | 1689 | CA | CYS | A | 436 | 35.435 | 22.904 | 73.934 | 1.00 34.69 | A | C |
| ATOM | 1690 | CB | CYS | A | 436 | 35.120 | 23.585 | 72.599 | 1.00 34.82 | A | C |
| ATOM | 1691 | SG | ACYS | A | 436 | 33.487 | 23.229 | 71.927 | 0.50 33.85 | A | S |
| ATOM | 1692 | SG | BCYS | A | 436 | 34.236 | 25.158 | 72.738 | 0.50 35.54 | A | S |
| ATOM | 1693 | C | CYS | A | 436 | 35.669 | 21.416 | 73.716 | 1.00 35.00 | A | C |
| ATOM | 1694 | O | CYS | A | 436 | 34.762 | 20.607 | 73.919 | 1.00 35.31 | A | O |
| ATOM | 1695 | N | LYS | A | 437 | 36.881 | 21.053 | 73.307 | 1.00 35.17 | A | N |
| ATOM | 1696 | CA | LYS | A | 437 | 37.222 | 19.650 | 73.093 | 1.00 35.33 | A | C |
| ATOM | 1697 | C | LYS | A | 437 | 37.480 | 18.925 | 74.412 | 1.00 35.43 | A | C |
| ATOM | 1698 | O | LYS | A | 437 | 37.832 | 17.744 | 74.422 | 1.00 35.27 | A | O |
| ATOM | 1699 | CB | LYS | A | 437 | 38.437 | 19.516 | 72.174 | 1.00 35.31 | A | C |
| ATOM | 1700 | CG | LYS | A | 437 | 38.120 | 19.630 | 70.690 | 1.00 35.66 | A | C |
| ATOM | 1701 | CD | LYS | A | 437 | 39.388 | 19.810 | 69.854 | 1.00 35.62 | A | C |
| ATOM | 1704 | N | ASN | A | 438 | 37.306 | 19.639 | 75.521 | 1.00 35.68 | A | N |
| ATOM | 1705 | CA | ASN | A | 438 | 37.510 | 19.070 | 76.854 | 1.00 36.15 | A | C |
| ATOM | 1706 | C | ASN | A | 438 | 38.931 | 18.581 | 77.096 | 1.00 36.07 | A | C |
| ATOM | 1707 | O | ASN | A | 438 | 39.170 | 17.667 | 77.894 | 1.00 35.64 | A | O |
| ATOM | 1708 | CB | ASN | A | 438 | 36.507 | 17.954 | 77.136 | 1.00 36.55 | A | C |
| ATOM | 1709 | CG | ASN | A | 438 | 35.219 | 18.478 | 77.715 | 1.00 37.74 | A | C |
| ATOM | 1710 | OD1 | ASN | A | 438 | 34.134 | 18.152 | 77.237 | 1.00 39.59 | A | O |
| ATOM | 1711 | ND2 | ASN | A | 438 | 35.331 | 19.304 | 78.754 | 1.00 38.91 | A | N |
| ATOM | 1712 | N | VAL | A | 439 | 39.872 | 19.197 | 76.396 | 1.00 35.65 | A | N |
| ATOM | 1713 | CA | VAL | A | 439 | 41.265 | 18.844 | 76.566 | 1.00 35.83 | A | C |
| ATOM | 1714 | C | VAL | A | 439 | 41.737 | 19.383 | 77.910 | 1.00 35.47 | A | C |
| ATOM | 1715 | O | VAL | A | 439 | 42.531 | 18.753 | 78.605 | 1.00 35.32 | A | O |
| ATOM | 1716 | CB | VAL | A | 439 | 42.115 | 19.396 | 75.411 | 1.00 35.87 | A | C |
| ATOM | 1717 | CG1 | VAL | A | 439 | 43.576 | 19.480 | 75.802 | 1.00 36.48 | A | C |
| ATOM | 1718 | CG2 | VAL | A | 439 | 41.930 | 18.523 | 74.177 | 1.00 36.22 | A | C |
| ATOM | 1719 | N | VAL | A | 440 | 41.212 | 20.544 | 78.282 | 1.00 35.17 | A | N |
| ATOM | 1720 | CA | VAL | A | 440 | 41.572 | 21.180 | 79.535 | 1.00 35.22 | A | C |
| ATOM | 1721 | C | VAL | A | 440 | 40.386 | 21.953 | 80.070 | 1.00 35.27 | A | C |
| ATOM | 1722 | O | VAL | A | 440 | 39.672 | 22.612 | 79.312 | 1.00 35.15 | A | O |
| ATOM | 1723 | CB | VAL | A | 440 | 42.757 | 22.177 | 79.356 | 1.00 35.42 | A | C |
| ATOM | 1724 | CG1 | VAL | A | 440 | 42.330 | 23.384 | 78.529 | 1.00 34.79 | A | C |
| ATOM | 1725 | CG2 | VAL | A | 440 | 43.271 | 22.641 | 80.705 | 1.00 35.49 | A | C |
| ATOM | 1726 | N | PRO | A | 441 | 40.167 | 21.861 | 81.376 | 1.00 35.38 | A | N |
| ATOM | 1727 | CA | PRO | A | 441 | 39.106 | 22.625 | 82.032 | 1.00 35.36 | A | C |
| ATOM | 1728 | C | PRO | A | 441 | 39.533 | 24.092 | 82.086 | 1.00 35.22 | A | C |
| ATOM | 1729 | O | PRO | A | 441 | 40.733 | 24.359 | 82.128 | 1.00 35.14 | A | O |
| ATOM | 1730 | CB | PRO | A | 441 | 39.085 | 22.046 | 83.449 | 1.00 35.38 | A | C |
| ATOM | 1731 | CG | PRO | A | 441 | 39.919 | 20.814 | 83.398 | 1.00 35.70 | A | C |
| ATOM | 1732 | CD | PRO | A | 441 | 40.917 | 21.021 | 82.322 | 1.00 35.43 | A | C |
| ATOM | 1733 | N | VAL | A | 442 | 38.590 | 25.026 | 82.044 | 1.00 34.92 | A | N |
| ATOM | 1734 | CA | VAL | A | 442 | 38.941 | 26.439 | 82.159 | 1.00 34.73 | A | C |
| ATOM | 1735 | C | VAL | A | 442 | 38.112 | 27.066 | 83.268 | 1.00 34.82 | A | C |
| ATOM | 1736 | O | VAL | A | 442 | 36.887 | 27.130 | 83.175 | 1.00 34.56 | A | O |

| | | | | | | | | | | |
|---|---|---|---|---|---|---|---|---|---|---|
| ATOM | 1737 | CB | VAL | A | 442 | 38.773 | 27.220 | 80.841 | 1.00 34.67 | A C |
| ATOM | 1738 | CG1 | VAL | A | 442 | 39.117 | 28.687 | 81.064 | 1.00 35.17 | A C |
| ATOM | 1739 | CG2 | VAL | A | 442 | 39.662 | 26.641 | 79.752 | 1.00 33.20 | A C |
| ATOM | 1740 | N | TYR | A | 443 | 38.790 | 27.529 | 84.314 | 1.00 34.91 | A N |
| ATOM | 1741 | CA | TYR | A | 443 | 38.105 | 28.028 | 85.504 | 1.00 35.03 | A C |
| ATOM | 1742 | C | TYR | A | 443 | 38.336 | 29.499 | 85.856 | 1.00 34.67 | A C |
| ATOM | 1743 | O | TYR | A | 443 | 39.313 | 30.126 | 85.425 | 1.00 33.28 | A O |
| ATOM | 1744 | CB | TYR | A | 443 | 38.532 | 27.211 | 86.725 | 1.00 35.53 | A C |
| ATOM | 1745 | CG | TYR | A | 443 | 38.300 | 25.717 | 86.626 | 1.00 37.74 | A C |
| ATOM | 1746 | CD1 | TYR | A | 443 | 37.015 | 25.183 | 86.645 | 1.00 38.75 | A C |
| ATOM | 1747 | CD2 | TYR | A | 443 | 39.375 | 24.837 | 86.547 | 1.00 39.51 | A C |
| ATOM | 1748 | CE1 | TYR | A | 443 | 36.806 | 23.808 | 86.567 | 1.00 39.15 | A C |
| ATOM | 1749 | CE2 | TYR | A | 443 | 39.177 | 23.469 | 86.470 | 1.00 38.47 | A C |
| ATOM | 1750 | CZ | TYR | A | 443 | 37.896 | 22.962 | 86.477 | 1.00 39.40 | A C |
| ATOM | 1751 | OH | TYR | A | 443 | 37.720 | 21.599 | 86.401 | 1.00 39.46 | A O |
| ATOM | 1752 | N | ASP | A | 444 | 37.399 | 30.015 | 86.653 | 1.00 33.89 | A N |
| ATOM | 1753 | CA | ASP | A | 444 | 37.497 | 31.317 | 87.301 | 1.00 33.95 | A C |
| ATOM | 1754 | C | ASP | A | 444 | 37.855 | 32.511 | 86.406 | 1.00 33.58 | A C |
| ATOM | 1755 | O | ASP | A | 444 | 37.233 | 32.735 | 85.364 | 1.00 33.29 | A O |
| ATOM | 1756 | CB | ASP | A | 444 | 38.462 | 31.220 | 88.487 | 1.00 33.70 | A C |
| ATOM | 1757 | CG | ASP | A | 444 | 38.138 | 30.041 | 89.410 | 1.00 34.59 | A C |
| ATOM | 1758 | OD1 | ASP | A | 444 | 36.949 | 29.846 | 89.743 | 1.00 32.57 | A O |
| ATOM | 1759 | OD2 | ASP | A | 444 | 39.007 | 29.252 | 89.836 | 1.00 33.64 | A O |
| ATOM | 1760 | N | LEU | A | 445 | 38.873 | 33.265 | 86.809 | 1.00 33.60 | A N |
| ATOM | 1761 | CA | LEU | A | 445 | 39.210 | 34.479 | 86.092 | 1.00 33.29 | A C |
| ATOM | 1762 | C | LEU | A | 445 | 39.542 | 34.228 | 84.622 | 1.00 33.12 | A C |
| ATOM | 1763 | O | LEU | A | 445 | 39.096 | 34.981 | 83.749 | 1.00 32.64 | A O |
| ATOM | 1764 | CB | LEU | A | 445 | 40.317 | 35.250 | 86.805 | 1.00 33.60 | A C |
| ATOM | 1765 | CG | LEU | A | 445 | 40.621 | 36.628 | 86.227 | 1.00 34.01 | A C |
| ATOM | 1766 | CD1 | LEU | A | 445 | 39.359 | 37.484 | 86.136 | 1.00 34.29 | A C |
| ATOM | 1767 | CD2 | LEU | A | 445 | 41.687 | 37.322 | 87.054 | 1.00 35.37 | A C |
| ATOM | 1768 | N | LEU | A | 446 | 40.319 | 33.184 | 84.339 | 1.00 33.04 | A N |
| ATOM | 1769 | CA | LEU | A | 446 | 40.650 | 32.873 | 82.949 | 1.00 33.11 | A C |
| ATOM | 1770 | C | LEU | A | 446 | 39.357 | 32.557 | 82.195 | 1.00 33.48 | A C |
| ATOM | 1771 | O | LEU | A | 446 | 39.146 | 33.009 | 81.065 | 1.00 32.75 | A O |
| ATOM | 1772 | CB | LEU | A | 446 | 41.607 | 31.688 | 82.846 | 1.00 33.28 | A C |
| ATOM | 1773 | CG | LEU | A | 446 | 41.988 | 31.311 | 81.404 | 1.00 33.18 | A C |
| ATOM | 1774 | CD1 | LEU | A | 446 | 42.788 | 32.450 | 80.723 | 1.00 31.41 | A C |
| ATOM | 1775 | CD2 | LEU | A | 446 | 42.754 | 29.997 | 81.333 | 1.00 31.90 | A C |
| ATOM | 1776 | N | LEU | A | 447 | 38.479 | 31.804 | 82.836 | 1.00 34.01 | A N |
| ATOM | 1777 | CA | LEU | A | 447 | 37.211 | 31.468 | 82.199 | 1.00 35.27 | A C |
| ATOM | 1778 | C | LEU | A | 447 | 36.449 | 32.749 | 81.914 | 1.00 35.84 | A C |
| ATOM | 1779 | O | LEU | A | 447 | 35.978 | 32.954 | 80.796 | 1.00 35.45 | A O |
| ATOM | 1780 | CB | LEU | A | 447 | 36.377 | 30.512 | 83.059 | 1.00 34.81 | A C |
| ATOM | 1781 | CG | LEU | A | 447 | 34.986 | 30.157 | 82.504 | 1.00 35.76 | A C |
| ATOM | 1782 | CD1 | LEU | A | 447 | 35.100 | 29.448 | 81.167 | 1.00 35.60 | A C |
| ATOM | 1783 | CD2 | LEU | A | 447 | 34.198 | 29.306 | 83.490 | 1.00 35.42 | A C |
| ATOM | 1784 | N | GLU | A | 448 | 36.349 | 33.615 | 82.919 | 1.00 37.04 | A N |
| ATOM | 1785 | CA | GLU | A | 448 | 35.650 | 34.884 | 82.748 | 1.00 38.86 | A C |
| ATOM | 1786 | C | GLU | A | 448 | 36.234 | 35.676 | 81.566 | 1.00 39.74 | A C |
| ATOM | 1787 | O | GLU | A | 448 | 35.495 | 36.144 | 80.700 | 1.00 39.77 | A O |
| ATOM | 1788 | CB | GLU | A | 448 | 35.674 | 35.708 | 84.044 | 1.00 38.93 | A C |
| ATOM | 1789 | CG | GLU | A | 448 | 34.904 | 37.028 | 83.983 | 1.00 40.58 | A C |
| ATOM | 1790 | CD | GLU | A | 448 | 34.788 | 37.712 | 85.340 | 1.00 43.55 | A C |
| ATOM | 1791 | OE1 | GLU | A | 448 | 35.519 | 37.314 | 86.272 | 1.00 46.19 | A O |
| ATOM | 1792 | OE2 | GLU | A | 448 | 33.963 | 38.643 | 85.495 | 1.00 44.50 | A O |
| ATOM | 1793 | N | MET | A | 449 | 37.558 | 35.792 | 81.515 | 1.00 40.43 | A N |
| ATOM | 1794 | CA | MET | A | 449 | 38.218 | 36.539 | 80.445 | 1.00 41.54 | A C |
| ATOM | 1795 | C | MET | A | 449 | 38.052 | 35.885 | 79.069 | 1.00 42.72 | A C |
| ATOM | 1796 | O | MET | A | 449 | 37.924 | 36.572 | 78.052 | 1.00 42.21 | A O |
| ATOM | 1797 | CB | MET | A | 449 | 39.704 | 36.736 | 80.755 | 1.00 41.05 | A C |

163

| | | | | | | | | | | | |
|---|---|---|---|---|---|---|---|---|---|---|---|
| ATOM | 1798 | CG | MET | A | 449 | 39.938 | 37.467 | 82.045 | 1.00 | 40.99 | A | C |
| ATOM | 1799 | SD | MET | A | 449 | 39.029 | 39.001 | 82.091 | 1.00 | 42.70 | A | S |
| ATOM | 1800 | CE | MET | A | 449 | 40.197 | 40.085 | 81.325 | 1.00 | 42.04 | A | C |
| ATOM | 1801 | N | LEU | A | 450 | 38.064 | 34.557 | 79.046 | 1.00 | 44.02 | A | N |
| ATOM | 1802 | CA | LEU | A | 450 | 37.918 | 33.820 | 77.800 | 1.00 | 45.48 | A | C |
| ATOM | 1803 | C | LEU | A | 450 | 36.511 | 33.967 | 77.228 | 1.00 | 46.81 | A | C |
| ATOM | 1804 | O | LEU | A | 450 | 36.330 | 34.139 | 76.023 | 1.00 | 47.09 | A | O |
| ATOM | 1805 | CB | LEU | A | 450 | 38.226 | 32.346 | 78.032 | 1.00 | 45.35 | A | C |
| ATOM | 1806 | CG | LEU | A | 450 | 38.153 | 31.482 | 76.783 | 1.00 | 45.41 | A | C |
| ATOM | 1807 | CD1 | LEU | A | 450 | 39.034 | 32.066 | 75.694 | 1.00 | 43.98 | A | C |
| ATOM | 1808 | CD2 | LEU | A | 450 | 38.555 | 30.059 | 77.107 | 1.00 | 46.02 | A | C |
| ATOM | 1809 | N | ASN | A | 451 | 35.514 | 33.895 | 78.099 | 1.00 | 48.26 | A | N |
| ATOM | 1810 | CA | ASN | A | 451 | 34.130 | 34.024 | 77.669 | 1.00 | 50.08 | A | C |
| ATOM | 1811 | C | ASN | A | 451 | 33.875 | 35.333 | 76.928 | 1.00 | 51.32 | A | C |
| ATOM | 1812 | O | ASN | A | 451 | 33.154 | 35.361 | 75.936 | 1.00 | 51.75 | A | O |
| ATOM | 1813 | CB | ASN | A | 451 | 33.181 | 33.888 | 78.861 | 1.00 | 49.66 | A | C |
| ATOM | 1814 | CG | ASN | A | 451 | 33.006 | 32.442 | 79.306 | 1.00 | 50.02 | A | C |
| ATOM | 1815 | OD1 | ASN | A | 451 | 33.311 | 31.509 | 78.560 | 1.00 | 49.24 | A | O |
| ATOM | 1816 | ND2 | ASN | A | 451 | 32.514 | 32.252 | 80.529 | 1.00 | 49.24 | A | N |
| ATOM | 1817 | N | ALA | A | 452 | 34.484 | 36.414 | 77.398 | 1.00 | 52.68 | A | N |
| ATOM | 1818 | CA | ALA | A | 452 | 34.284 | 37.722 | 76.786 | 1.00 | 54.29 | A | C |
| ATOM | 1819 | C | ALA | A | 452 | 34.612 | 37.732 | 75.290 | 1.00 | 55.51 | A | C |
| ATOM | 1820 | O | ALA | A | 452 | 34.237 | 38.657 | 74.566 | 1.00 | 55.84 | A | O |
| ATOM | 1821 | CB | ALA | A | 452 | 35.098 | 38.781 | 77.523 | 1.00 | 54.27 | A | C |
| ATOM | 1822 | N | HIS | A | 453 | 35.331 | 36.715 | 74.832 | 1.00 | 56.69 | A | N |
| ATOM | 1823 | CA | HIS | A | 453 | 35.630 | 36.592 | 73.413 | 1.00 | 57.94 | A | C |
| ATOM | 1824 | C | HIS | A | 453 | 34.446 | 35.941 | 72.698 | 1.00 | 57.74 | A | C |
| ATOM | 1825 | O | HIS | A | 453 | 33.790 | 36.573 | 71.877 | 1.00 | 57.92 | A | O |
| ATOM | 1826 | CB | HIS | A | 453 | 36.875 | 35.739 | 73.208 | 1.00 | 58.43 | A | C |
| ATOM | 1827 | CG | HIS | A | 453 | 37.661 | 36.103 | 71.989 | 1.00 | 61.17 | A | C |
| ATOM | 1828 | ND1 | HIS | A | 453 | 38.219 | 37.352 | 71.810 | 1.00 | 63.60 | A | N |
| ATOM | 1829 | CD2 | HIS | A | 453 | 37.999 | 35.379 | 70.895 | 1.00 | 63.43 | A | C |
| ATOM | 1830 | CE1 | HIS | A | 453 | 38.861 | 37.384 | 70.655 | 1.00 | 64.96 | A | C |
| ATOM | 1831 | NE2 | HIS | A | 453 | 38.745 | 36.199 | 70.081 | 1.00 | 65.17 | A | N |
| ATOM | 1832 | O17 | EST | A | 600 | 45.651 | 27.897 | 74.439 | 1.00 | 29.62 | A | O |
| ATOM | 1833 | C17 | EST | A | 600 | 47.040 | 28.260 | 74.386 | 1.00 | 30.78 | A | C |
| ATOM | 1834 | C16 | EST | A | 600 | 47.422 | 28.932 | 73.054 | 1.00 | 30.17 | A | C |
| ATOM | 1835 | C13 | EST | A | 600 | 47.400 | 29.307 | 75.425 | 1.00 | 30.99 | A | C |
| ATOM | 1836 | C12 | EST | A | 600 | 47.610 | 28.811 | 76.856 | 1.00 | 31.46 | A | C |
| ATOM | 1837 | C18 | EST | A | 600 | 46.347 | 30.416 | 75.365 | 1.00 | 29.45 | A | C |
| ATOM | 1838 | C14 | EST | A | 600 | 48.716 | 29.829 | 74.888 | 1.00 | 30.69 | A | C |
| ATOM | 1839 | C15 | EST | A | 600 | 48.448 | 30.025 | 73.406 | 1.00 | 32.39 | A | C |
| ATOM | 1840 | C8 | EST | A | 600 | 49.261 | 30.999 | 75.697 | 1.00 | 31.06 | A | C |
| ATOM | 1841 | C7 | EST | A | 600 | 50.561 | 31.540 | 75.111 | 1.00 | 29.56 | A | C |
| ATOM | 1842 | C9 | EST | A | 600 | 49.554 | 30.453 | 77.094 | 1.00 | 30.40 | A | C |
| ATOM | 1843 | C11 | EST | A | 600 | 48.256 | 29.935 | 77.705 | 1.00 | 30.19 | A | C |
| ATOM | 1844 | C10 | EST | A | 600 | 50.264 | 31.473 | 77.948 | 1.00 | 30.26 | A | C |
| ATOM | 1845 | C5 | EST | A | 600 | 50.958 | 32.626 | 77.340 | 1.00 | 29.59 | A | C |
| ATOM | 1846 | C6 | EST | A | 600 | 50.950 | 32.825 | 75.833 | 1.00 | 29.03 | A | C |
| ATOM | 1847 | C4 | EST | A | 600 | 51.605 | 33.558 | 78.169 | 1.00 | 30.85 | A | C |
| ATOM | 1848 | C3 | EST | A | 600 | 51.621 | 33.393 | 79.555 | 1.00 | 30.24 | A | C |
| ATOM | 1849 | O3 | EST | A | 600 | 52.252 | 34.297 | 80.363 | 1.00 | 28.61 | A | O |
| ATOM | 1850 | C2 | EST | A | 600 | 50.974 | 32.293 | 80.131 | 1.00 | 31.02 | A | C |
| ATOM | 1851 | C1 | EST | A | 600 | 50.311 | 31.355 | 79.338 | 1.00 | 31.08 | A | C |
| ATOM | 1852 | O2 | EDO | A | 700 | 56.992 | 39.355 | 82.550 | 1.00 | 39.75 | A | O |
| ATOM | 1853 | C2 | EDO | A | 700 | 58.161 | 40.149 | 82.473 | 1.00 | 39.35 | A | C |
| ATOM | 1854 | C1 | EDO | A | 700 | 58.058 | 41.350 | 83.414 | 1.00 | 40.26 | A | C |
| ATOM | 1855 | O1 | EDO | A | 700 | 57.074 | 42.266 | 82.941 | 1.00 | 35.65 | A | O |
| ATOM | 1856 | O2 | EDO | A | 701 | 53.179 | 37.647 | 85.091 | 1.00 | 52.07 | A | O |
| ATOM | 1857 | C2 | EDO | A | 701 | 53.740 | 38.761 | 84.434 | 1.00 | 54.52 | A | C |
| ATOM | 1858 | C1 | EDO | A | 701 | 54.939 | 39.298 | 85.187 | 1.00 | 55.96 | A | C |

164

| ATOM | 1859 | O1  | EDO | A | 701 | 56.042 | 38.417 | 85.088 | 1.00 | 58.19 | A | O |
|------|------|-----|-----|---|-----|--------|--------|--------|------|-------|---|---|
| ATOM | 1860 | O2  | BCT | A | 710 | 54.885 | 34.461 | 84.368 | 1.00 | 67.48 | A | O |
| ATOM | 1861 | C   | BCT | A | 710 | 55.620 | 34.904 | 85.369 | 1.00 | 67.59 | A | C |
| ATOM | 1862 | O1  | BCT | A | 710 | 56.861 | 34.509 | 85.503 | 1.00 | 67.26 | A | O |
| ATOM | 1863 | O3  | BCT | A | 710 | 55.123 | 35.750 | 86.243 | 1.00 | 67.23 | A | O |
| ATOM | 1864 | N   | ILE | B | 5   | 38.382 | 32.460 | 92.377 | 1.00 | 36.63 | B | N |
| ATOM | 1865 | CA  | ILE | B | 5   | 37.448 | 32.894 | 93.452 | 1.00 | 36.56 | B | C |
| ATOM | 1866 | C   | ILE | B | 5   | 36.977 | 34.324 | 93.213 | 1.00 | 36.47 | B | C |
| ATOM | 1867 | O   | ILE | B | 5   | 35.809 | 34.649 | 93.429 | 1.00 | 36.56 | B | O |
| ATOM | 1868 | CB  | ILE | B | 5   | 38.113 | 32.770 | 94.815 | 1.00 | 36.68 | B | C |
| ATOM | 1869 | N   | GLN | B | 6   | 37.888 | 35.176 | 92.759 | 1.00 | 36.12 | B | N |
| ATOM | 1870 | CA  | GLN | B | 6   | 37.547 | 36.569 | 92.516 | 1.00 | 35.78 | B | C |
| ATOM | 1871 | C   | GLN | B | 6   | 37.324 | 36.857 | 91.033 | 1.00 | 34.93 | B | C |
| ATOM | 1872 | O   | GLN | B | 6   | 37.975 | 36.278 | 90.163 | 1.00 | 34.71 | B | O |
| ATOM | 1873 | CB  | GLN | B | 6   | 38.590 | 37.507 | 93.125 | 1.00 | 36.10 | B | C |
| ATOM | 1874 | CG  | GLN | B | 6   | 38.408 | 37.712 | 94.627 | 1.00 | 38.19 | B | C |
| ATOM | 1875 | CD  | GLN | B | 6   | 39.071 | 38.979 | 95.137 | 1.00 | 40.40 | B | C |
| ATOM | 1876 | OE1 | GLN | B | 6   | 38.393 | 39.964 | 95.457 | 1.00 | 40.76 | B | O |
| ATOM | 1877 | NE2 | GLN | B | 6   | 40.397 | 38.959 | 95.218 | 1.00 | 41.40 | B | N |
| ATOM | 1878 | N   | SER | B | 7   | 36.380 | 37.750 | 90.767 | 1.00 | 33.70 | B | N |
| ATOM | 1879 | CA  | SER | B | 7   | 35.979 | 38.076 | 89.414 | 1.00 | 32.32 | B | C |
| ATOM | 1880 | C   | SER | B | 7   | 36.638 | 39.366 | 88.951 | 1.00 | 31.52 | B | C |
| ATOM | 1881 | O   | SER | B | 7   | 37.225 | 40.093 | 89.746 | 1.00 | 31.36 | B | O |
| ATOM | 1882 | CB  | SER | B | 7   | 34.463 | 38.252 | 89.370 | 1.00 | 32.42 | B | C |
| ATOM | 1883 | OG  | SER | B | 7   | 34.126 | 39.478 | 89.983 | 1.00 | 31.19 | B | O |
| ATOM | 1884 | N   | LEU | B | 8   | 36.504 | 39.656 | 87.664 | 1.00 | 30.60 | B | N |
| ATOM | 1885 | CA  | LEU | B | 8   | 37.116 | 40.843 | 87.066 | 1.00 | 30.26 | B | C |
| ATOM | 1886 | C   | LEU | B | 8   | 36.685 | 42.118 | 87.781 | 1.00 | 30.52 | B | C |
| ATOM | 1887 | O   | LEU | B | 8   | 37.512 | 42.920 | 88.222 | 1.00 | 30.06 | B | O |
| ATOM | 1888 | CB  | LEU | B | 8   | 36.742 | 40.930 | 85.583 | 1.00 | 29.44 | B | C |
| ATOM | 1889 | CG  | LEU | B | 8   | 37.332 | 42.130 | 84.848 | 1.00 | 29.41 | B | C |
| ATOM | 1890 | CD1 | LEU | B | 8   | 38.846 | 42.214 | 85.092 | 1.00 | 25.73 | B | C |
| ATOM | 1891 | CD2 | LEU | B | 8   | 37.002 | 42.091 | 83.361 | 1.00 | 26.86 | B | C |
| ATOM | 1892 | N   | ILE | B | 9   | 35.380 | 42.296 | 87.894 | 1.00 | 30.51 | B | N |
| ATOM | 1893 | CA  | ILE | B | 9   | 34.824 | 43.486 | 88.508 | 1.00 | 31.24 | B | C |
| ATOM | 1894 | C   | ILE | B | 9   | 35.215 | 43.633 | 89.985 | 1.00 | 30.69 | B | C |
| ATOM | 1895 | O   | ILE | B | 9   | 35.519 | 44.728 | 90.440 | 1.00 | 30.84 | B | O |
| ATOM | 1896 | CB  | ILE | B | 9   | 33.315 | 43.483 | 88.346 | 1.00 | 31.62 | B | C |
| ATOM | 1897 | CG1 | ILE | B | 9   | 32.780 | 44.906 | 88.369 | 1.00 | 33.62 | B | C |
| ATOM | 1898 | CG2 | ILE | B | 9   | 32.678 | 42.631 | 89.407 | 1.00 | 32.77 | B | C |
| ATOM | 1899 | CD1 | ILE | B | 9   | 33.091 | 45.657 | 87.098 | 1.00 | 36.80 | B | C |
| ATOM | 1900 | N   | ASN | B | 10  | 35.221 | 42.537 | 90.732 | 1.00 | 29.57 | B | N |
| ATOM | 1901 | CA  | ASN | B | 10  | 35.594 | 42.635 | 92.134 | 1.00 | 28.86 | B | C |
| ATOM | 1902 | C   | ASN | B | 10  | 37.075 | 43.030 | 92.262 | 1.00 | 27.90 | B | C |
| ATOM | 1903 | O   | ASN | B | 10  | 37.443 | 43.849 | 93.100 | 1.00 | 26.39 | B | O |
| ATOM | 1904 | CB  | ASN | B | 10  | 35.278 | 41.333 | 92.873 | 1.00 | 28.85 | B | C |
| ATOM | 1905 | CG  | ASN | B | 10  | 33.782 | 41.186 | 93.190 | 1.00 | 30.17 | B | C |
| ATOM | 1906 | OD1 | ASN | B | 10  | 33.098 | 42.167 | 93.494 | 1.00 | 30.40 | B | O |
| ATOM | 1907 | ND2 | ASN | B | 10  | 33.281 | 39.957 | 93.136 | 1.00 | 30.07 | B | N |
| ATOM | 1908 | N   | LEU | B | 11  | 37.908 | 42.462 | 91.396 | 1.00 | 27.32 | B | N |
| ATOM | 1909 | CA  | LEU | B | 11  | 39.329 | 42.798 | 91.381 | 1.00 | 27.19 | B | C |
| ATOM | 1910 | C   | LEU | B | 11  | 39.533 | 44.274 | 91.029 | 1.00 | 27.01 | B | C |
| ATOM | 1911 | O   | LEU | B | 11  | 40.383 | 44.944 | 91.615 | 1.00 | 25.61 | B | O |
| ATOM | 1912 | CB  | LEU | B | 11  | 40.091 | 41.876 | 90.432 | 1.00 | 27.22 | B | C |
| ATOM | 1913 | CG  | LEU | B | 11  | 40.384 | 40.490 | 91.027 | 1.00 | 26.93 | B | C |
| ATOM | 1914 | CD1 | LEU | B | 11  | 40.868 | 39.514 | 89.969 | 1.00 | 26.35 | B | C |
| ATOM | 1915 | CD2 | LEU | B | 11  | 41.388 | 40.568 | 92.172 | 1.00 | 28.12 | B | C |
| ATOM | 1916 | N   | LEU | B | 12  | 38.702 | 44.787 | 90.119 | 1.00 | 27.14 | B | N |
| ATOM | 1917 | CA  | LEU | B | 12  | 38.802 | 46.179 | 89.685 | 1.00 | 27.76 | B | C |
| ATOM | 1918 | C   | LEU | B | 12  | 38.312 | 47.147 | 90.755 | 1.00 | 28.20 | B | C |
| ATOM | 1919 | O   | LEU | B | 12  | 38.941 | 48.186 | 91.014 | 1.00 | 26.95 | B | O |

165

| | | | | | | | | | | | |
|---|---|---|---|---|---|---|---|---|---|---|---|
| ATOM | 1920 | CB | LEU | B | 12 | 38.029 | 46.424 | 88.383 | 1.00 27.19 | B | C |
| ATOM | 1921 | CG | LEU | B | 12 | 38.744 | 46.095 | 87.069 | 1.00 27.38 | B | C |
| ATOM | 1922 | CD1 | LEU | B | 12 | 37.755 | 46.214 | 85.900 | 1.00 24.89 | B | C |
| ATOM | 1923 | CD2 | LEU | B | 12 | 39.989 | 46.978 | 86.839 | 1.00 24.41 | B | C |
| ATOM | 1924 | N | ALA | B | 13 | 37.217 | 46.785 | 91.402 | 1.00 29.02 | B | N |
| ATOM | 1925 | CA | ALA | B | 13 | 36.600 | 47.674 | 92.376 | 1.00 31.10 | B | C |
| ATOM | 1926 | C | ALA | B | 13 | 37.298 | 47.838 | 93.723 | 1.00 32.78 | B | C |
| ATOM | 1927 | O | ALA | B | 13 | 37.425 | 48.953 | 94.231 | 1.00 33.15 | B | O |
| ATOM | 1928 | CB | ALA | B | 13 | 35.128 | 47.253 | 92.615 | 1.00 31.11 | B | C |
| ATOM | 1929 | N | ASP | B | 14 | 37.748 | 46.735 | 94.305 | 1.00 34.82 | B | N |
| ATOM | 1930 | CA | ASP | B | 14 | 38.165 | 46.751 | 95.715 | 1.00 36.76 | B | C |
| ATOM | 1931 | C | ASP | B | 14 | 39.552 | 47.279 | 96.095 | 1.00 37.45 | B | C |
| ATOM | 1932 | O | ASP | B | 14 | 40.303 | 47.785 | 95.260 | 1.00 37.96 | B | O |
| ATOM | 1933 | CB | ASP | B | 14 | 37.943 | 45.365 | 96.327 | 1.00 37.11 | B | C |
| ATOM | 1934 | CG | ASP | B | 14 | 36.528 | 44.861 | 96.116 | 1.00 38.31 | B | C |
| ATOM | 1935 | OD1 | ASP | B | 14 | 35.576 | 45.582 | 96.500 | 1.00 39.99 | B | O |
| ATOM | 1936 | OD2 | ASP | B | 14 | 36.271 | 43.764 | 95.574 | 1.00 39.18 | B | O |
| ATOM | 1937 | N | ASN | B | 15 | 39.861 | 47.161 | 97.384 | 1.00 38.38 | B | N |
| ATOM | 1938 | CA | ASN | B | 15 | 41.130 | 47.623 | 97.943 | 1.00 39.06 | B | C |
| ATOM | 1939 | C | ASN | B | 15 | 41.329 | 49.129 | 97.769 | 1.00 39.09 | B | C |
| ATOM | 1940 | O | ASN | B | 15 | 41.125 | 49.903 | 98.706 | 1.00 39.10 | B | O |
| ATOM | 1941 | CB | ASN | B | 15 | 42.302 | 46.843 | 97.338 | 1.00 39.34 | B | C |
| ATOM | 1942 | CG | ASN | B | 15 | 43.640 | 47.227 | 97.944 | 1.00 40.27 | B | C |
| ATOM | 1943 | OD1 | ASN | B | 15 | 43.730 | 48.127 | 98.784 | 1.00 41.21 | B | O |
| ATOM | 1944 | ND2 | ASN | B | 15 | 44.693 | 46.538 | 97.520 | 1.00 41.36 | B | N |
| ATOM | 1987 | O | HOH | W | 1 | 61.479 | 61.483 | 64.385 | 0.50 37.67 | W | O |
| ATOM | 1946 | O | HOH | W | 2 | 54.494 | 48.012 | 84.000 | 1.00 27.84 | W | O |
| ATOM | 1951 | O | HOH | W | 3 | 53.074 | 37.231 | 80.906 | 1.00 30.51 | W | O |
| ATOM | 1947 | O | HOH | W | 4 | 53.679 | 48.818 | 81.458 | 1.00 31.24 | W | O |
| ATOM | 1986 | O | HOH | W | 5 | 58.043 | 60.173 | 61.536 | 1.00 33.53 | W | O |
| ATOM | 1954 | O | HOH | W | 6 | 50.445 | 39.783 | 85.480 | 1.00 34.10 | W | O |
| ATOM | 1981 | O | HOH | W | 7 | 61.770 | 59.284 | 69.057 | 1.00 34.93 | W | O |
| ATOM | 1953 | O | HOH | W | 8 | 50.563 | 40.958 | 83.201 | 1.00 35.24 | W | O |
| ATOM | 1952 | O | HOH | W | 9 | 52.277 | 39.887 | 81.089 | 1.00 35.97 | W | O |
| ATOM | 1961 | O | HOH | W | 10 | 42.909 | 47.381 | 75.576 | 1.00 36.48 | W | O |
| ATOM | 1980 | O | HOH | W | 11 | 57.887 | 62.709 | 73.492 | 1.00 36.56 | W | O |
| ATOM | 1967 | O | HOH | W | 12 | 67.233 | 38.709 | 79.486 | 1.00 37.76 | W | O |
| ATOM | 1994 | O | HOH | W | 13 | 51.191 | 45.518 | 90.317 | 1.00 38.43 | W | O |
| ATOM | 1965 | O | HOH | W | 14 | 48.441 | 47.159 | 70.517 | 1.00 38.47 | W | O |
| ATOM | 1968 | O | HOH | W | 15 | 62.859 | 33.301 | 72.729 | 1.00 38.90 | W | O |
| ATOM | 2014 | O | HOH | W | 16 | 64.125 | 40.045 | 79.987 | 1.00 39.34 | W | O |
| ATOM | 1997 | O | HOH | W | 17 | 50.022 | 43.389 | 90.187 | 1.00 39.39 | W | O |
| ATOM | 1962 | O | HOH | W | 18 | 44.355 | 40.325 | 73.629 | 1.00 40.33 | W | O |
| ATOM | 1963 | O | HOH | W | 19 | 46.157 | 47.928 | 72.061 | 1.00 40.61 | W | O |
| ATOM | 1988 | O | HOH | W | 20 | 64.159 | 49.693 | 63.631 | 1.00 40.69 | W | O |
| ATOM | 1985 | O | HOH | W | 21 | 62.112 | 61.410 | 60.933 | 1.00 40.80 | W | O |
| ATOM | 1945 | O | HOH | W | 22 | 54.573 | 61.253 | 78.642 | 1.00 40.87 | W | O |
| ATOM | 1957 | O | HOH | W | 23 | 54.413 | 41.286 | 82.405 | 1.00 40.96 | W | O |
| ATOM | 1956 | O | HOH | W | 24 | 51.708 | 43.591 | 83.376 | 1.00 41.26 | W | O |
| ATOM | 1995 | O | HOH | W | 25 | 60.663 | 63.285 | 72.931 | 1.00 41.73 | W | O |
| ATOM | 1996 | O | HOH | W | 26 | 53.247 | 48.857 | 93.338 | 1.00 42.20 | W | O |
| ATOM | 1959 | O | HOH | W | 27 | 45.071 | 53.980 | 87.614 | 1.00 42.26 | W | O |
| ATOM | 1948 | O | HOH | W | 28 | 56.098 | 47.900 | 93.993 | 1.00 42.38 | W | O |
| ATOM | 1979 | O | HOH | W | 29 | 51.392 | 61.341 | 71.841 | 1.00 42.69 | W | O |
| ATOM | 1974 | O | HOH | W | 30 | 68.327 | 49.452 | 71.426 | 1.00 42.94 | W | O |
| ATOM | 1984 | O | HOH | W | 31 | 67.355 | 61.909 | 60.076 | 1.00 44.81 | W | O |
| ATOM | 1998 | O | HOH | W | 32 | 53.121 | 52.452 | 89.847 | 1.00 44.92 | W | O |
| ATOM | 1969 | O | HOH | W | 33 | 63.386 | 33.829 | 70.231 | 1.00 45.41 | W | O |
| ATOM | 1960 | O | HOH | W | 34 | 39.134 | 50.419 | 89.209 | 1.00 45.43 | W | O |
| ATOM | 1950 | O | HOH | W | 35 | 45.561 | 29.315 | 88.566 | 1.00 45.87 | W | O |
| ATOM | 2003 | O | HOH | W | 36 | 47.742 | 35.107 | 91.424 | 1.00 45.94 | W | O |

166

```
ATOM   1955  O   HOH W  37     52.052  38.139  87.017  1.00 45.98      W   O
ATOM   2006  O   HOH W  38     46.475  47.665  92.245  1.00 46.04      W   O
ATOM   1992  O   HOH W  39     43.641  38.668  63.320  1.00 47.74      W   O
ATOM   1964  O   HOH W  40     42.766  46.817  72.962  1.00 47.81      W   O
ATOM   2005  O   HOH W  41     46.240  50.099  93.264  1.00 48.10      W   O
ATOM   1966  O   HOH W  42     65.345  36.989  78.589  1.00 48.42      W   O
ATOM   1975  O   HOH W  43     69.189  49.216  68.695  1.00 48.81      W   O
ATOM   1999  O   HOH W  44     53.020  51.289  92.261  1.00 49.23      W   O
ATOM   1977  O   HOH W  45     67.361  44.120  74.399  1.00 49.71      W   O
ATOM   1949  O   HOH W  46     56.701  43.205  90.947  1.00 49.79      W   O
ATOM   2007  O   HOH W  47     44.183  46.387  93.072  1.00 50.03      W   O
ATOM   1970  O   HOH W  48     64.000  31.958  68.566  1.00 50.33      W   O
ATOM   2002  O   HOH W  49     53.096  31.886  92.382  1.00 50.87      W   O
ATOM   1958  O   HOH W  50     49.370  42.049  92.453  1.00 50.97      W   O
ATOM   1976  O   HOH W  51     65.513  53.098  71.947  1.00 51.95      W   O
ATOM   1978  O   HOH W  52     49.507  60.661  70.220  1.00 52.20      W   O
ATOM   2000  O   HOH W  53     50.614  52.470  92.939  1.00 52.55      W   O
ATOM   2016  O   HOH W  54     59.718  35.326  85.982  1.00 52.94      W   O
ATOM   2004  O   HOH W  55     47.073  36.280  93.709  1.00 53.67      W   O
ATOM   1982  O   HOH W  56     67.357  53.225  69.538  1.00 53.72      W   O
ATOM   2011  O   HOH W  57     68.849  46.943  66.812  1.00 54.68      W   O
ATOM   1990  O   HOH W  58     55.367  35.583  63.854  1.00 55.39      W   O
ATOM   1989  O   HOH W  59     65.323  52.422  63.397  1.00 55.44      W   O
ATOM   2012  O   HOH W  60     38.225  27.983  68.891  1.00 55.68      W   O
ATOM   1983  O   HOH W  61     68.811  51.668  68.056  1.00 56.25      W   O
ATOM   1991  O   HOH W  62     42.075  41.950  66.506  1.00 56.36      W   O
ATOM   2009  O   HOH W  63     64.406  23.865  88.680  1.00 58.46      W   O
ATOM   1973  O   HOH W  64     63.619  22.869  70.237  1.00 58.76      W   O
ATOM   2001  O   HOH W  65     59.224  42.888  86.228  1.00 59.81      W   O
ATOM   2008  O   HOH W  66     45.036  45.627  71.357  1.00 60.43      W   O
ATOM   2010  O   HOH W  67     56.310  31.738  62.530  1.00 60.46      W   O
ATOM   1972  O   HOH W  68     65.403  25.082  71.526  1.00 61.93      W   O
ATOM   1993  O   HOH W  69     42.865  39.021  70.693  1.00 63.16      W   O
ATOM   1971  O   HOH W  70     56.839  27.754  87.764  1.00 64.38      W   O
ATOM   2015  O   HOH W  71     67.205  53.047  76.493  1.00 64.38      W   O
ATOM   2013  O   HOH W  72     40.783  49.967  94.016  1.00 69.30      W   O
END
```

```
HEADER    RAT ERb-LBD
COMPND    16alpha-17alpha-epiestrol (KB0032) complex (EPI)
REMARK
REMARK    EPI exhibits 'flipped' binding mode (C18 directed towards
REMARK    alpha face of cavity). A-ring interactions maintained; D-ring
REMARK    prot-lig interactions confined to 16aOH with His430. Possible
REMARK    interaction between 17aOH and mc carbonyl Gly427 (bifurc H-bond)?
REMARK    Molecule A exhibits H12 in 'agonist' position
REMARK    Molecule B exhibits H12 in quasi antagonist position. Reasons
REMARK    for different orientations due to xtal packing effects and
REMARK    possible influence of coordinated Ni++ ion.
REMARK
REMARK    Data collected by ACWP / AMB (York) at ESRF station 14.4 Feb2000
REMARK    Structure refined with REFMAC v5.0.11
REMARK    TLS 2-body followed by restrained atomic refinement using ML
REMARK
REMARK    TLS    Chain A
REMARK    RANGE  'A 217.' 'A 450.' ALL
REMARK    ORIGIN    6.547   1.153   36.077
REMARK    T      0.1149  0.1082  0.1410 -0.0311 -0.0185 -0.1123
REMARK    L      4.2036  2.0450  5.5544  0.3867 -2.4101  0.3165
REMARK    S     -0.0567 -0.1822  0.3375 -0.1013  0.1489 -0.0005  0.0367 -0.6453
REMARK
REMARK    TLS    Chain B
REMARK    RANGE  'B 217.' 'B 453.' ALL
REMARK    ORIGIN    9.925  -6.026   8.553
REMARK    T      0.1105  0.0488  0.1380 -0.0268  0.0482  0.0148
REMARK    L      3.3765  1.4169  4.6698 -0.1170  1.1518  0.5564
REMARK    S     -0.0480  0.0233 -0.1725 -0.1382  0.1092  0.0075  0.2660 -0.2595
REMARK
REMARK    Refinement statistics:
REMARK    Resolution limits                    =     28.000   2.800
REMARK    Number of used reflections           =     12099
REMARK    Percentage observed                  =     99.7412
REMARK    Percentage of free reflections       =      4.8671
REMARK    Overall R factor                     =      0.2493
REMARK    Free R factor                        =      0.2811
REMARK    Overall weighted R factor            =      0.2595
REMARK    Free weighted R factor               =      0.3000
REMARK    Overall correlation coefficient      =      0.9215
REMARK    Free correlation coefficient         =      0.9154
REMARK    Cruickshanks DPI for coordinate error=      0.0000
REMARK    DPI based on free R facotr           =      0.4311
REMARK    Overall figure of merit              =      0.7466
REMARK    ML based su of positional parameters =      0.3629
REMARK    ML based su of thermal parameters    =     17.9138
REMARK    Rmsd bonds:0.012 Rmsd angles:1.55deg
REMARK    ----------------------------------------------------------------
REMARK    Atomic B-factors are given after removal of TLS contribution.
REMARK    Note Wilson B for data:70.6
REMARK
REMARK    Some sidechains modelled as ALA and others truncated due to incomplete
REMARK    electron density
REMARK
LINK          NE2  HIS A 263         1.945   NI    NI A   1           HIS-NI
LINK          NE2  HIS A 305         1.945   NI    NI A   2           HIS-NI
LINK          NI    NI A   1         2.100   CL    CL A   3           NI-CL
LINK          NI    NI A   1         2.100   CL    CL A   4           NI-CL
LINK          NE2  HIS B 263         1.945   NI    NI B   1           HIS-NI
```

168

```
LINK            ALA A 365       .           ALA A 379               gap
LINK            MET B 365       .           ALA B 379               gap
LINK            LYS B 435       .           ALA B 440               gap
CRYST1    55.200   84.620  105.940   90.00   90.00   90.00 P 21 21 21
SCALE1      0.018120  0.000000  0.000000        0.000000
SCALE2      0.000000  0.011820  0.000000        0.000000
SCALE3      0.000000  0.000000  0.009440        0.000000
ATOM       1  N   ALA A 217      17.771  24.866  29.138  1.00 50.76           N
ATOM       2  CA  ALA A 217      18.826  23.893  28.710  1.00 50.73           C
ATOM       3  CB  ALA A 217      19.833  24.579  27.791  1.00 50.80           C
ATOM       4  C   ALA A 217      19.535  23.260  29.911  1.00 50.65           C
ATOM       5  O   ALA A 217      20.410  23.873  30.522  1.00 50.65           O
ATOM       6  N   LEU A 218      19.140  22.035  30.251  1.00 50.50           N
ATOM       7  CA  LEU A 218      19.728  21.307  31.380  1.00 50.27           C
ATOM       8  CB  LEU A 218      18.656  20.509  32.124  1.00 50.38           C
ATOM       9  CG  LEU A 218      17.495  21.320  32.702  1.00 50.82           C
ATOM      10  CD1 LEU A 218      16.541  20.397  33.447  1.00 51.11           C
ATOM      11  CD2 LEU A 218      17.996  22.430  33.622  1.00 51.30           C
ATOM      12  C   LEU A 218      20.870  20.381  30.945  1.00 49.93           C
ATOM      13  O   LEU A 218      21.287  20.385  29.794  1.00 50.09           O
ATOM      14  N   SER A 219      21.385  19.587  31.866  1.00 49.42           N
ATOM      15  CA  SER A 219      22.482  18.701  31.519  1.00 48.92           C
ATOM      16  CB  SER A 219      23.797  19.223  32.112  1.00 48.84           C
ATOM      17  OG  SER A 219      23.923  18.919  33.488  1.00 48.80           O
ATOM      18  C   SER A 219      22.155  17.277  31.983  1.00 48.60           C
ATOM      19  O   SER A 219      21.168  17.063  32.679  1.00 48.61           O
ATOM      20  N   PRO A 220      22.970  16.304  31.597  1.00 48.22           N
ATOM      21  CA  PRO A 220      22.707  14.909  31.953  1.00 47.85           C
ATOM      22  CB  PRO A 220      23.893  14.164  31.341  1.00 47.89           C
ATOM      23  CG  PRO A 220      24.365  15.064  30.238  1.00 48.11           C
ATOM      24  CD  PRO A 220      24.200  16.452  30.801  1.00 48.25           C
ATOM      25  C   PRO A 220      22.657  14.719  33.459  1.00 47.46           C
ATOM      26  O   PRO A 220      21.670  14.186  33.959  1.00 47.38           O
ATOM      27  N   GLU A 221      23.688  15.153  34.176  1.00 47.04           N
ATOM      28  CA  GLU A 221      23.682  15.008  35.630  1.00 46.78           C
ATOM      29  CB  GLU A 221      24.971  15.523  36.258  1.00 46.98           C
ATOM      30  CG  GLU A 221      25.513  16.786  35.610  1.00 48.60           C
ATOM      31  CD  GLU A 221      26.620  16.487  34.602  1.00 50.51           C
ATOM      32  OE1 GLU A 221      27.793  16.394  35.044  1.00 51.18           O
ATOM      33  OE2 GLU A 221      26.320  16.334  33.379  1.00 50.83           O
ATOM      34  C   GLU A 221      22.501  15.745  36.220  1.00 46.13           C
ATOM      35  O   GLU A 221      21.816  15.230  37.108  1.00 46.13           O
ATOM      36  N   GLN A 222      22.249  16.946  35.708  1.00 45.36           N
ATOM      37  CA  GLN A 222      21.133  17.745  36.200  1.00 44.59           C
ATOM      38  CB  GLN A 222      21.195  19.176  35.639  1.00 44.71           C
ATOM      43  C   GLN A 222      19.781  17.077  35.897  1.00 43.90           C
ATOM      44  O   GLN A 222      18.877  17.094  36.727  1.00 43.68           O
ATOM      45  N   LEU A 223      19.658  16.490  34.707  1.00 43.14           N
ATOM      46  CA  LEU A 223      18.435  15.807  34.312  1.00 42.44           C
ATOM      47  CB  LEU A 223      18.518  15.348  32.855  1.00 42.36           C
ATOM      48  CG  LEU A 223      17.170  14.996  32.221  1.00 42.05           C
ATOM      49  CD1 LEU A 223      16.118  15.943  32.720  1.00 42.04           C
ATOM      50  CD2 LEU A 223      17.213  15.019  30.713  1.00 41.75           C
ATOM      51  C   LEU A 223      18.155  14.630  35.256  1.00 42.03           C
ATOM      52  O   LEU A 223      17.035  14.440  35.725  1.00 41.72           O
ATOM      53  N   VAL A 224      19.196  13.867  35.552  1.00 41.55           N
ATOM      54  CA  VAL A 224      19.078  12.735  36.448  1.00 41.19           C
ATOM      55  CB  VAL A 224      20.395  11.918  36.485  1.00 41.33           C
ATOM      56  CG1 VAL A 224      20.350  10.809  37.527  1.00 40.65           C
ATOM      57  CG2 VAL A 224      20.687  11.332  35.109  1.00 41.17           C
ATOM      58  C   VAL A 224      18.726  13.238  37.831  1.00 41.05           C
```

| | | | | | | | | | |
|---|---|---|---|---|---|---|---|---|---|
| ATOM | 59 | O | VAL | A 224 | 17.879 | 12.670 | 38.525 | 1.00 40.73 | O |
| ATOM | 60 | N | LEU | A 225 | 19.377 | 14.325 | 38.227 | 1.00 41.03 | N |
| ATOM | 61 | CA | LEU | A 225 | 19.123 | 14.922 | 39.529 | 1.00 40.90 | C |
| ATOM | 62 | CB | LEU | A 225 | 20.019 | 16.113 | 39.727 | 1.00 41.07 | C |
| ATOM | 63 | CG | LEU | A 225 | 20.737 | 16.011 | 41.059 | 1.00 41.53 | C |
| ATOM | 64 | CD1 | LEU | A 225 | 22.095 | 15.505 | 40.840 | 1.00 42.03 | C |
| ATOM | 65 | CD2 | LEU | A 225 | 20.913 | 17.339 | 41.606 | 1.00 42.03 | C |
| ATOM | 66 | C | LEU | A 225 | 17.669 | 15.351 | 39.616 | 1.00 40.75 | C |
| ATOM | 67 | O | LEU | A 225 | 16.971 | 15.088 | 40.598 | 1.00 40.61 | O |
| ATOM | 68 | N | THR | A 226 | 17.208 | 16.006 | 38.566 | 1.00 40.65 | N |
| ATOM | 69 | CA | THR | A 226 | 15.828 | 16.426 | 38.510 | 1.00 40.67 | C |
| ATOM | 70 | CB | THR | A 226 | 15.576 | 17.167 | 37.210 | 1.00 40.63 | C |
| ATOM | 71 | OG1 | THR | A 226 | 16.529 | 18.229 | 37.072 | 1.00 40.72 | O |
| ATOM | 72 | CG2 | THR | A 226 | 14.243 | 17.864 | 37.266 | 1.00 40.56 | C |
| ATOM | 73 | C | THR | A 226 | 14.893 | 15.224 | 38.587 | 1.00 40.79 | C |
| ATOM | 74 | O | THR | A 226 | 13.886 | 15.264 | 39.297 | 1.00 40.88 | O |
| ATOM | 75 | N | LEU | A 227 | 15.226 | 14.155 | 37.858 | 1.00 40.72 | N |
| ATOM | 76 | CA | LEU | A 227 | 14.367 | 12.978 | 37.824 | 1.00 40.63 | C |
| ATOM | 77 | CB | LEU | A 227 | 14.804 | 12.003 | 36.734 | 1.00 40.44 | C |
| ATOM | 78 | CG | LEU | A 227 | 14.593 | 12.332 | 35.263 | 1.00 40.14 | C |
| ATOM | 79 | CD1 | LEU | A 227 | 15.174 | 11.196 | 34.422 | 1.00 39.64 | C |
| ATOM | 80 | CD2 | LEU | A 227 | 13.123 | 12.586 | 34.935 | 1.00 39.54 | C |
| ATOM | 81 | C | LEU | A 227 | 14.304 | 12.239 | 39.164 | 1.00 40.77 | C |
| ATOM | 82 | O | LEU | A 227 | 13.303 | 11.630 | 39.503 | 1.00 40.62 | O |
| ATOM | 83 | N | LEU | A 228 | 15.393 | 12.259 | 39.907 | 1.00 41.06 | N |
| ATOM | 84 | CA | LEU | A 228 | 15.418 | 11.572 | 41.175 | 1.00 41.34 | C |
| ATOM | 85 | CB | LEU | A 228 | 16.858 | 11.447 | 41.642 | 1.00 41.38 | C |
| ATOM | 86 | CG | LEU | A 228 | 17.204 | 11.536 | 43.118 | 1.00 41.72 | C |
| ATOM | 87 | CD1 | LEU | A 228 | 16.127 | 10.871 | 43.938 | 1.00 42.53 | C |
| ATOM | 88 | CD2 | LEU | A 228 | 18.552 | 10.888 | 43.339 | 1.00 41.57 | C |
| ATOM | 89 | C | LEU | A 228 | 14.544 | 12.366 | 42.132 | 1.00 41.66 | C |
| ATOM | 90 | O | LEU | A 228 | 13.670 | 11.820 | 42.787 | 1.00 41.74 | O |
| ATOM | 91 | N | GLU | A 229 | 14.758 | 13.667 | 42.195 | 1.00 42.00 | N |
| ATOM | 92 | CA | GLU | A 229 | 13.902 | 14.507 | 43.005 | 1.00 42.37 | C |
| ATOM | 93 | CB | GLU | A 229 | 14.295 | 15.930 | 42.802 | 1.00 42.51 | C |
| ATOM | 94 | CG | AGLU | A 229 | 15.717 | 16.083 | 43.202 | 0.50 42.63 | C |
| ATOM | 95 | CG | BGLU | A 229 | 15.738 | 16.239 | 43.213 | 0.50 43.02 | C |
| ATOM | 96 | CD | AGLU | A 229 | 16.058 | 17.462 | 43.109 | 0.50 42.81 | C |
| ATOM | 97 | CD | BGLU | A 229 | 16.127 | 15.647 | 44.565 | 0.50 43.76 | C |
| ATOM | 98 | OE1 | AGLU | A 229 | 15.376 | 18.011 | 42.278 | 0.50 42.81 | O |
| ATOM | 99 | OE1 | BGLU | A 229 | 15.381 | 14.791 | 45.089 | 0.50 44.36 | O |
| ATOM | 100 | OE2 | AGLU | A 229 | 16.914 | 17.953 | 43.844 | 0.50 43.02 | O |
| ATOM | 101 | OE2 | BGLU | A 229 | 17.188 | 16.029 | 45.111 | 0.50 43.83 | O |
| ATOM | 102 | C | GLU | A 229 | 12.438 | 14.359 | 42.696 | 1.00 42.47 | C |
| ATOM | 103 | O | GLU | A 229 | 11.623 | 14.417 | 43.598 | 1.00 42.38 | O |
| ATOM | 104 | N | ALA | A 230 | 12.102 | 14.151 | 41.427 | 1.00 42.65 | N |
| ATOM | 105 | CA | ALA | A 230 | 10.708 | 13.982 | 41.039 | 1.00 42.84 | C |
| ATOM | 106 | CB | ALA | A 230 | 10.568 | 14.086 | 39.537 | 1.00 42.69 | C |
| ATOM | 107 | C | ALA | A 230 | 10.072 | 12.680 | 41.526 | 1.00 43.06 | C |
| ATOM | 108 | O | ALA | A 230 | 8.860 | 12.518 | 41.439 | 1.00 42.95 | O |
| ATOM | 109 | N | GLU | A 231 | 10.874 | 11.753 | 42.031 | 1.00 43.51 | N |
| ATOM | 110 | CA | GLU | A 231 | 10.341 | 10.464 | 42.456 | 1.00 44.16 | C |
| ATOM | 111 | CB | GLU | A 231 | 11.427 | 9.607 | 43.102 | 1.00 44.13 | C |
| ATOM | 112 | CG | GLU | A 231 | 12.259 | 8.770 | 42.148 | 1.00 44.69 | C |
| ATOM | 113 | CD | GLU | A 231 | 11.432 | 7.777 | 41.345 | 1.00 45.77 | C |
| ATOM | 114 | OE1 | GLU | A 231 | 10.981 | 6.724 | 41.765 | 1.00 45.58 | O |
| ATOM | 115 | OE2 | GLU | A 231 | 11.194 | 8.026 | 40.215 | 1.00 46.15 | O |
| ATOM | 116 | C | GLU | A 231 | 9.166 | 10.596 | 43.417 | 1.00 44.64 | C |
| ATOM | 117 | O | GLU | A 231 | 9.225 | 11.346 | 44.396 | 1.00 44.85 | O |
| ATOM | 118 | N | PRO | A 232 | 8.096 | 9.867 | 43.145 | 1.00 45.10 | N |
| ATOM | 119 | CA | PRO | A 232 | 6.927 | 9.862 | 44.025 | 1.00 45.69 | C |

170

| | | | | | | | | | | |
|---|---|---|---|---|---|---|---|---|---|---|
| ATOM | 120 | CB | PRO | A | 232 | 5.949 | 8.898 | 43.340 | 1.00 45.50 | C |
| ATOM | 121 | CG | PRO | A | 232 | 6.581 | 8.406 | 42.154 | 1.00 45.17 | C |
| ATOM | 122 | CD | PRO | A | 232 | 7.936 | 8.990 | 41.986 | 1.00 45.12 | C |
| ATOM | 123 | C | PRO | A | 232 | 7.250 | 9.256 | 45.389 | 1.00 46.39 | C |
| ATOM | 124 | O | PRO | A | 232 | 8.093 | 8.365 | 45.495 | 1.00 46.42 | O |
| ATOM | 125 | N | PRO | A | 233 | 6.550 | 9.701 | 46.420 | 1.00 47.01 | N |
| ATOM | 126 | CA | PRO | A | 233 | 6.702 | 9.095 | 47.734 | 1.00 47.57 | C |
| ATOM | 127 | CB | PRO | A | 233 | 5.808 | 9.943 | 48.635 | 1.00 47.58 | C |
| ATOM | 128 | CG | PRO | A | 233 | 5.146 | 10.936 | 47.787 | 1.00 47.42 | C |
| ATOM | 129 | CD | PRO | A | 233 | 5.541 | 10.767 | 46.383 | 1.00 47.08 | C |
| ATOM | 130 | C | PRO | A | 233 | 6.098 | 7.709 | 47.674 | 1.00 48.20 | C |
| ATOM | 131 | O | PRO | A | 233 | 5.487 | 7.333 | 46.675 | 1.00 48.25 | O |
| ATOM | 132 | N | ASN | A | 234 | 6.254 | 6.955 | 48.743 | 1.00 48.97 | N |
| ATOM | 133 | CA | ASN | A | 234 | 5.604 | 5.674 | 48.819 | 1.00 49.88 | C |
| ATOM | 134 | CB | ASN | A | 234 | 6.339 | 4.769 | 49.784 | 1.00 49.82 | C |
| ATOM | 135 | CG | ASN | A | 234 | 7.673 | 4.341 | 49.256 | 1.00 49.70 | C |
| ATOM | 136 | OD1 | ASN | A | 234 | 7.766 | 3.760 | 48.177 | 1.00 49.28 | O |
| ATOM | 137 | ND2 | ASN | A | 234 | 8.721 | 4.626 | 50.011 | 1.00 49.82 | N |
| ATOM | 138 | C | ASN | A | 234 | 4.178 | 5.856 | 49.279 | 1.00 50.63 | C |
| ATOM | 139 | O | ASN | A | 234 | 3.825 | 6.857 | 49.891 | 1.00 50.72 | O |
| ATOM | 140 | N | VAL | A | 235 | 3.345 | 4.883 | 48.971 | 1.00 51.69 | N |
| ATOM | 141 | CA | VAL | A | 235 | 1.964 | 4.940 | 49.394 | 1.00 52.71 | C |
| ATOM | 142 | CB | VAL | A | 235 | 1.050 | 4.588 | 48.235 | 1.00 52.61 | C |
| ATOM | 143 | CG1 | VAL | A | 235 | -0.129 | 3.798 | 48.721 | 1.00 52.97 | C |
| ATOM | 144 | CG2 | VAL | A | 235 | 0.614 | 5.862 | 47.531 | 1.00 52.70 | C |
| ATOM | 145 | C | VAL | A | 235 | 1.757 | 4.009 | 50.579 | 1.00 53.42 | C |
| ATOM | 146 | O | VAL | A | 235 | 2.306 | 2.918 | 50.613 | 1.00 53.51 | O |
| ATOM | 147 | N | LEU | A | 236 | 1.006 | 4.447 | 51.576 | 1.00 54.43 | N |
| ATOM | 148 | CA | LEU | A | 236 | 0.794 | 3.602 | 52.737 | 1.00 55.49 | C |
| ATOM | 149 | CB | LEU | A | 236 | 0.428 | 4.442 | 53.957 | 1.00 55.50 | C |
| ATOM | 153 | C | LEU | A | 236 | -0.295 | 2.582 | 52.447 | 1.00 56.32 | C |
| ATOM | 154 | O | LEU | A | 236 | -1.468 | 2.924 | 52.347 | 1.00 56.42 | O |
| ATOM | 155 | N | VAL | A | 237 | 0.101 | 1.330 | 52.289 | 1.00 57.41 | N |
| ATOM | 156 | CA | VAL | A | 237 | -0.849 | 0.261 | 52.020 | 1.00 58.56 | C |
| ATOM | 157 | CB | VAL | A | 237 | -1.055 | 0.028 | 50.524 | 1.00 58.52 | C |
| ATOM | 158 | CG1 | VAL | A | 237 | -1.516 | -1.407 | 50.287 | 1.00 58.77 | C |
| ATOM | 159 | CG2 | VAL | A | 237 | -2.069 | 1.007 | 49.956 | 1.00 58.73 | C |
| ATOM | 160 | C | VAL | A | 237 | -0.369 | -1.048 | 52.620 | 1.00 59.29 | C |
| ATOM | 161 | O | VAL | A | 237 | 0.717 | -1.528 | 52.293 | 1.00 59.49 | O |
| ATOM | 162 | N | SER | A | 238 | -1.188 | -1.634 | 53.483 | 1.00 60.16 | N |
| ATOM | 163 | CA | SER | A | 238 | -0.816 | -2.880 | 54.137 | 1.00 60.96 | C |
| ATOM | 164 | CB | SER | A | 238 | -0.776 | -2.701 | 55.657 | 1.00 61.04 | C |
| ATOM | 165 | OG | SER | A | 238 | -1.951 | -2.066 | 56.132 | 1.00 61.23 | O |
| ATOM | 166 | C | SER | A | 238 | -1.720 | -4.045 | 53.758 | 1.00 61.39 | C |
| ATOM | 167 | O | SER | A | 238 | -2.826 | -3.869 | 53.251 | 1.00 61.55 | O |
| ATOM | 168 | N | ARG | A | 239 | -1.230 | -5.240 | 54.031 | 1.00 61.90 | N |
| ATOM | 169 | CA | ARG | A | 239 | -1.919 | -6.466 | 53.682 | 1.00 62.44 | C |
| ATOM | 170 | CB | ARG | A | 239 | -0.845 | -7.557 | 53.547 | 1.00 62.57 | C |
| ATOM | 171 | CG | ARG | A | 239 | -1.197 | -8.841 | 54.101 | 1.00 63.53 | C |
| ATOM | 172 | CD | ARG | A | 239 | -0.419 | -10.045 | 53.647 | 1.00 65.23 | C |
| ATOM | 173 | NE | ARG | A | 239 | 0.885 | -9.969 | 53.023 | 1.00 66.21 | N |
| ATOM | 174 | CZ | ARG | A | 239 | 1.161 | -10.722 | 51.991 | 1.00 67.24 | C |
| ATOM | 175 | NH1 | ARG | A | 239 | 0.222 | -11.438 | 51.548 | 1.00 67.62 | N |
| ATOM | 176 | NH2 | ARG | A | 239 | 2.303 | -10.784 | 51.366 | 1.00 67.82 | N |
| ATOM | 177 | C | ARG | A | 239 | -3.046 | -6.782 | 54.691 | 1.00 62.52 | C |
| ATOM | 178 | O | ARG | A | 239 | -2.869 | -6.579 | 55.889 | 1.00 62.51 | O |
| ATOM | 179 | N | PRO | A | 240 | -4.221 | -7.205 | 54.211 | 1.00 62.70 | N |
| ATOM | 180 | CA | PRO | A | 240 | -5.351 | -7.533 | 55.102 | 1.00 62.76 | C |
| ATOM | 181 | CB | PRO | A | 240 | -6.445 | -8.004 | 54.138 | 1.00 62.77 | C |
| ATOM | 182 | CG | PRO | A | 240 | -6.090 | -7.408 | 52.821 | 1.00 62.73 | C |
| ATOM | 183 | CD | PRO | A | 240 | -4.572 | -7.391 | 52.792 | 1.00 62.75 | C |

171

| | | | | | | | | | | |
|---|---|---|---|---|---|---|---|---|---|---|
| ATOM | 184 | C | PRO | A | 240 | -4.993 | -8.645 | 56.086 | 1.00 62.84 | C |
| ATOM | 185 | O | PRO | A | 240 | -4.204 | -9.530 | 55.751 | 1.00 62.83 | O |
| ATOM | 186 | N | SER | A | 241 | -5.570 | -8.591 | 57.283 | 1.00 62.96 | N |
| ATOM | 187 | CA | SER | A | 241 | -5.244 | -9.539 | 58.350 | 1.00 63.09 | C |
| ATOM | 188 | CB | SER | A | 241 | -6.033 | -9.205 | 59.619 | 1.00 63.13 | C |
| ATOM | 189 | OG | SER | A | 241 | -6.001 | -7.810 | 59.877 | 1.00 63.16 | O |
| ATOM | 190 | C | SER | A | 241 | -5.440 | -11.005 | 57.955 | 1.00 63.12 | C |
| ATOM | 191 | O | SER | A | 241 | -4.473 | -11.769 | 57.878 | 1.00 63.16 | O |
| ATOM | 192 | N | MET | A | 242 | -6.686 | -11.399 | 57.711 | 1.00 63.11 | N |
| ATOM | 193 | CA | MET | A | 242 | -6.975 | -12.768 | 57.291 | 1.00 63.11 | C |
| ATOM | 194 | CB | MET | A | 242 | -8.487 | -12.986 | 57.174 | 1.00 63.23 | C |
| ATOM | 195 | CG | MET | A | 242 | -9.273 | -11.729 | 56.829 | 1.00 63.71 | C |
| ATOM | 196 | SD | MET | A | 242 | -9.844 | -11.717 | 55.109 | 1.00 64.70 | S |
| ATOM | 197 | CE | MET | A | 242 | -9.356 | -10.036 | 54.594 | 1.00 64.11 | C |
| ATOM | 198 | C | MET | A | 242 | -6.282 | -13.047 | 55.959 | 1.00 62.92 | C |
| ATOM | 199 | O | MET | A | 242 | -5.792 | -12.127 | 55.319 | 1.00 62.95 | O |
| ATOM | 200 | N | PRO | A | 243 | -6.232 | -14.307 | 55.540 | 1.00 62.77 | N |
| ATOM | 201 | CA | PRO | A | 243 | -5.566 | -14.666 | 54.281 | 1.00 62.58 | C |
| ATOM | 202 | CB | PRO | A | 243 | -5.812 | -16.170 | 54.164 | 1.00 62.60 | C |
| ATOM | 203 | CG | PRO | A | 243 | -6.126 | -16.624 | 55.558 | 1.00 62.75 | C |
| ATOM | 204 | CD | PRO | A | 243 | -6.807 | -15.476 | 56.228 | 1.00 62.77 | C |
| ATOM | 205 | C | PRO | A | 243 | -6.174 | -13.943 | 53.082 | 1.00 62.37 | C |
| ATOM | 206 | O | PRO | A | 243 | -7.175 | -13.232 | 53.217 | 1.00 62.34 | O |
| ATOM | 207 | N | PHE | A | 244 | -5.582 | -14.138 | 51.911 | 1.00 62.07 | N |
| ATOM | 208 | CA | PHE | A | 244 | -6.043 | -13.429 | 50.731 | 1.00 61.79 | C |
| ATOM | 209 | CB | PHE | A | 244 | -4.890 | -13.132 | 49.777 | 1.00 61.81 | C |
| ATOM | 210 | CG | PHE | A | 244 | -4.529 | -11.681 | 49.728 | 1.00 61.88 | C |
| ATOM | 211 | CD1 | PHE | A | 244 | -5.463 | -10.750 | 49.316 | 1.00 61.87 | C |
| ATOM | 212 | CE1 | PHE | A | 244 | -5.155 | -9.412 | 49.284 | 1.00 61.79 | C |
| ATOM | 213 | CZ | PHE | A | 244 | -3.901 | -8.982 | 49.669 | 1.00 61.88 | C |
| ATOM | 214 | CE2 | PHE | A | 244 | -2.960 | -9.895 | 50.090 | 1.00 61.86 | C |
| ATOM | 215 | CD2 | PHE | A | 244 | -3.276 | -11.239 | 50.121 | 1.00 61.89 | C |
| ATOM | 216 | C | PHE | A | 244 | -7.182 | -14.087 | 49.992 | 1.00 61.61 | C |
| ATOM | 217 | O | PHE | A | 244 | -7.409 | -15.291 | 50.111 | 1.00 61.65 | O |
| ATOM | 218 | N | THR | A | 245 | -7.900 | -13.275 | 49.228 | 1.00 61.34 | N |
| ATOM | 219 | CA | THR | A | 245 | -9.016 | -13.755 | 48.441 | 1.00 61.10 | C |
| ATOM | 220 | CB | THR | A | 245 | -10.331 | -13.358 | 49.095 | 1.00 61.08 | C |
| ATOM | 221 | OG1 | THR | A | 245 | -10.252 | -13.598 | 50.501 | 1.00 61.08 | O |
| ATOM | 222 | CG2 | THR | A | 245 | -11.453 | -14.279 | 48.631 | 1.00 61.19 | C |
| ATOM | 223 | C | THR | A | 245 | -8.951 | -13.110 | 47.085 | 1.00 60.93 | C |
| ATOM | 224 | O | THR | A | 245 | -7.958 | -12.486 | 46.730 | 1.00 61.00 | O |
| ATOM | 225 | N | GLU | A | 246 | -10.033 | -13.229 | 46.337 | 1.00 60.68 | N |
| ATOM | 226 | CA | GLU | A | 246 | -10.077 | -12.641 | 45.018 | 1.00 60.46 | C |
| ATOM | 227 | CB | GLU | A | 246 | -11.084 | -13.373 | 44.163 | 1.00 60.60 | C |
| ATOM | 228 | CG | GLU | A | 246 | -10.461 | -13.938 | 42.907 | 1.00 61.43 | C |
| ATOM | 229 | CD | GLU | A | 246 | -11.366 | -13.800 | 41.706 | 1.00 62.60 | C |
| ATOM | 230 | OE1 | GLU | A | 246 | -12.203 | -12.875 | 41.711 | 1.00 63.26 | O |
| ATOM | 231 | OE2 | GLU | A | 246 | -11.242 | -14.609 | 40.759 | 1.00 62.99 | O |
| ATOM | 232 | C | GLU | A | 246 | -10.419 | -11.158 | 45.071 | 1.00 60.05 | C |
| ATOM | 233 | O | GLU | A | 246 | -9.769 | -10.336 | 44.435 | 1.00 60.04 | O |
| ATOM | 234 | N | ALA | A | 247 | -11.444 | -10.818 | 45.836 | 1.00 59.55 | N |
| ATOM | 235 | CA | ALA | A | 247 | -11.861 | -9.433 | 45.964 | 1.00 59.01 | C |
| ATOM | 236 | CB | ALA | A | 247 | -13.294 | -9.364 | 46.481 | 1.00 59.10 | C |
| ATOM | 237 | C | ALA | A | 247 | -10.925 | -8.685 | 46.896 | 1.00 58.58 | C |
| ATOM | 238 | O | ALA | A | 247 | -10.828 | -7.462 | 46.839 | 1.00 58.55 | O |
| ATOM | 239 | N | SER | A | 248 | -10.248 | -9.428 | 47.762 | 1.00 58.00 | N |
| ATOM | 240 | CA | SER | A | 248 | -9.324 | -8.835 | 48.707 | 1.00 57.42 | C |
| ATOM | 241 | CB | SER | A | 248 | -8.963 | -9.850 | 49.790 | 1.00 57.43 | C |
| ATOM | 242 | OG | SER | A | 248 | -8.419 | -9.211 | 50.923 | 1.00 57.66 | O |
| ATOM | 243 | C | SER | A | 248 | -8.078 | -8.372 | 47.961 | 1.00 56.92 | C |
| ATOM | 244 | O | SER | A | 248 | -7.627 | -7.244 | 48.130 | 1.00 56.92 | O |

| ATOM | 245 | N   | MET A 249 | -7.538  | -9.248  | 47.121 | 1.00 | 56.27 | N |
| ATOM | 246 | CA  | MET A 249 | -6.350  | -8.925  | 46.351 | 1.00 | 55.60 | C |
| ATOM | 247 | CB  | MET A 249 | -5.788  | -10.165 | 45.657 | 1.00 | 55.55 | C |
| ATOM | 248 | CG  | MET A 249 | -4.363  | -10.006 | 45.171 | 1.00 | 55.15 | C |
| ATOM | 249 | SD  | MET A 249 | -3.560  | -11.569 | 44.774 | 1.00 | 54.31 | S |
| ATOM | 250 | CE  | MET A 249 | -3.017  | -12.116 | 46.364 | 1.00 | 54.42 | C |
| ATOM | 251 | C   | MET A 249 | -6.641  | -7.814  | 45.351 | 1.00 | 55.22 | C |
| ATOM | 252 | O   | MET A 249 | -5.937  | -6.808  | 45.322 | 1.00 | 55.34 | O |
| ATOM | 253 | N   | MET A 250 | -7.684  | -7.979  | 44.548 | 1.00 | 54.63 | N |
| ATOM | 254 | CA  | MET A 250 | -8.043  | -6.962  | 43.560 | 1.00 | 54.08 | C |
| ATOM | 255 | CB  | MET A 250 | -9.327  | -7.330  | 42.806 | 1.00 | 54.05 | C |
| ATOM | 256 | CG  | MET A 250 | -9.130  | -8.081  | 41.481 | 1.00 | 53.92 | C |
| ATOM | 257 | SD  | MET A 250 | -7.802  | -7.466  | 40.389 | 1.00 | 53.56 | S |
| ATOM | 258 | CE  | MET A 250 | -6.531  | -8.591  | 40.783 | 1.00 | 53.43 | C |
| ATOM | 259 | C   | MET A 250 | -8.190  | -5.577  | 44.182 | 1.00 | 53.73 | C |
| ATOM | 260 | O   | MET A 250 | -7.615  | -4.610  | 43.688 | 1.00 | 53.82 | O |
| ATOM | 261 | N   | MET A 251 | -8.960  | -5.478  | 45.261 | 1.00 | 53.17 | N |
| ATOM | 262 | CA  | MET A 251 | -9.167  | -4.199  | 45.930 | 1.00 | 52.59 | C |
| ATOM | 263 | CB  | MET A 251 | -10.057 | -4.362  | 47.164 | 1.00 | 52.75 | C |
| ATOM | 264 | CG  | MET A 251 | -11.550 | -4.321  | 46.891 | 1.00 | 53.23 | C |
| ATOM | 265 | SD  | MET A 251 | -12.466 | -4.406  | 48.441 | 1.00 | 54.36 | S |
| ATOM | 266 | CE  | MET A 251 | -14.180 | -4.604  | 47.848 | 1.00 | 54.39 | C |
| ATOM | 267 | C   | MET A 251 | -7.850  | -3.576  | 46.347 | 1.00 | 52.01 | C |
| ATOM | 268 | O   | MET A 251 | -7.649  | -2.375  | 46.189 | 1.00 | 51.97 | O |
| ATOM | 269 | N   | SER A 252 | -6.966  | -4.398  | 46.897 | 1.00 | 51.27 | N |
| ATOM | 270 | CA  | SER A 252 | -5.653  | -3.946  | 47.330 | 1.00 | 50.59 | C |
| ATOM | 271 | CB  | SER A 252 | -4.850  | -5.129  | 47.854 | 1.00 | 50.67 | C |
| ATOM | 272 | OG  | SER A 252 | -4.989  | -5.261  | 49.250 | 1.00 | 50.67 | O |
| ATOM | 273 | C   | SER A 252 | -4.874  | -3.311  | 46.181 | 1.00 | 50.04 | C |
| ATOM | 274 | O   | SER A 252 | -4.367  | -2.188  | 46.297 | 1.00 | 49.94 | O |
| ATOM | 275 | N   | LEU A 253 | -4.787  | -4.046  | 45.075 | 1.00 | 49.16 | N |
| ATOM | 276 | CA  | LEU A 253 | -4.034  | -3.600  | 43.920 | 1.00 | 48.32 | C |
| ATOM | 277 | CB  | LEU A 253 | -3.865  | -4.743  | 42.927 | 1.00 | 48.35 | C |
| ATOM | 278 | CG  | LEU A 253 | -3.194  | -5.980  | 43.518 | 1.00 | 48.14 | C |
| ATOM | 279 | CD1 | LEU A 253 | -3.090  | -7.066  | 42.477 | 1.00 | 47.74 | C |
| ATOM | 280 | CD2 | LEU A 253 | -1.816  | -5.610  | 44.082 | 1.00 | 48.04 | C |
| ATOM | 281 | C   | LEU A 253 | -4.680  | -2.407  | 43.257 | 1.00 | 47.77 | C |
| ATOM | 282 | O   | LEU A 253 | -4.005  | -1.431  | 42.939 | 1.00 | 47.55 | O |
| ATOM | 283 | N   | THR A 254 | -5.989  | -2.489  | 43.046 | 1.00 | 47.15 | N |
| ATOM | 284 | CA  | THR A 254 | -6.714  | -1.392  | 42.421 | 1.00 | 46.60 | C |
| ATOM | 285 | CB  | THR A 254 | -8.194  | -1.736  | 42.223 | 1.00 | 46.75 | C |
| ATOM | 286 | OG1 | THR A 254 | -8.452  | -3.057  | 42.703 | 1.00 | 46.94 | O |
| ATOM | 287 | CG2 | THR A 254 | -8.512  | -1.855  | 40.756 | 1.00 | 46.77 | C |
| ATOM | 288 | C   | THR A 254 | -6.608  | -0.129  | 43.247 | 1.00 | 46.08 | C |
| ATOM | 289 | O   | THR A 254 | -6.490  |  0.965  | 42.707 | 1.00 | 46.09 | O |
| ATOM | 290 | N   | LYS A 255 | -6.663  | -0.270  | 44.562 | 1.00 | 45.36 | N |
| ATOM | 291 | CA  | LYS A 255 | -6.536  |  0.897  | 45.414 | 1.00 | 44.76 | C |
| ATOM | 292 | CB  | LYS A 255 | -6.954  |  0.581  | 46.852 | 1.00 | 44.95 | C |
| ATOM | 293 | CG  | LYS A 255 | -6.974  |  1.796  | 47.771 | 1.00 | 45.62 | C |
| ATOM | 294 | CD  | LYS A 255 | -7.348  |  1.432  | 49.203 | 1.00 | 47.26 | C |
| ATOM | 295 | CE  | LYS A 255 | -6.322  |  0.501  | 49.832 | 1.00 | 48.80 | C |
| ATOM | 296 | NZ  | LYS A 255 | -6.589  | -0.950  | 49.555 | 1.00 | 50.21 | N |
| ATOM | 297 | C   | LYS A 255 | -5.105  |  1.433  | 45.363 | 1.00 | 44.06 | C |
| ATOM | 298 | O   | LYS A 255 | -4.884  |  2.636  | 45.345 | 1.00 | 43.83 | O |
| ATOM | 299 | N   | LEU A 256 | -4.136  |  0.532  | 45.334 | 1.00 | 43.31 | N |
| ATOM | 300 | CA  | LEU A 256 | -2.755  |  0.950  | 45.241 | 1.00 | 42.74 | C |
| ATOM | 301 | CB  | LEU A 256 | -1.824  | -0.250  | 45.346 | 1.00 | 42.65 | C |
| ATOM | 302 | CG  | LEU A 256 | -0.382  | -0.009  | 44.917 | 1.00 | 42.50 | C |
| ATOM | 303 | CD1 | LEU A 256 |  0.376  |  0.828  | 45.927 | 1.00 | 42.32 | C |
| ATOM | 304 | CD2 | LEU A 256 |  0.284  | -1.336  | 44.743 | 1.00 | 42.76 | C |
| ATOM | 305 | C   | LEU A 256 | -2.537  |  1.690  | 43.928 | 1.00 | 42.40 | C |

173

| | | | | | | | | | |
|---|---|---|---|---|---|---|---|---|---|
| ATOM | 306 | O | LEU A 256 | -1.941 | 2.772 | 43.903 | 1.00 | 42.24 | O |
| ATOM | 307 | N | ALA A 257 | -3.045 | 1.114 | 42.841 | 1.00 | 41.98 | N |
| ATOM | 308 | CA | ALA A 257 | -2.912 | 1.713 | 41.516 | 1.00 | 41.57 | C |
| ATOM | 309 | CB | ALA A 257 | -3.707 | 0.931 | 40.509 | 1.00 | 41.55 | C |
| ATOM | 310 | C | ALA A 257 | -3.399 | 3.140 | 41.545 | 1.00 | 41.36 | C |
| ATOM | 311 | O | ALA A 257 | -2.774 | 4.055 | 41.000 | 1.00 | 41.16 | O |
| ATOM | 312 | N | ASP A 258 | -4.532 | 3.317 | 42.201 | 1.00 | 41.14 | N |
| ATOM | 313 | CA | ASP A 258 | -5.153 | 4.610 | 42.290 | 1.00 | 41.01 | C |
| ATOM | 314 | CB | ASP A 258 | -6.487 | 4.465 | 42.992 | 1.00 | 41.14 | C |
| ATOM | 315 | CG | ASP A 258 | -7.492 | 5.464 | 42.506 | 1.00 | 41.46 | C |
| ATOM | 316 | OD1 | ASP A 258 | -7.510 | 5.740 | 41.290 | 1.00 | 42.06 | O |
| ATOM | 317 | OD2 | ASP A 258 | -8.292 | 6.035 | 43.260 | 1.00 | 41.54 | O |
| ATOM | 318 | C | ASP A 258 | -4.273 | 5.616 | 43.022 | 1.00 | 40.85 | C |
| ATOM | 319 | O | ASP A 258 | -3.993 | 6.699 | 42.515 | 1.00 | 40.84 | O |
| ATOM | 320 | N | LYS A 259 | -3.850 | 5.267 | 44.229 | 1.00 | 40.70 | N |
| ATOM | 321 | CA | LYS A 259 | -2.971 | 6.147 | 44.979 | 1.00 | 40.53 | C |
| ATOM | 322 | CB | LYS A 259 | -2.544 | 5.539 | 46.318 | 1.00 | 40.58 | C |
| ATOM | 323 | CG | LYS A 259 | -3.638 | 4.910 | 47.145 | 1.00 | 41.09 | C |
| ATOM | 324 | CD | LYS A 259 | -4.382 | 5.798 | 48.079 | 1.00 | 42.29 | C |
| ATOM | 325 | CE | LYS A 259 | -4.033 | 5.755 | 49.572 | 1.00 | 42.97 | C |
| ATOM | 326 | NZ | LYS A 259 | -4.410 | 4.550 | 50.376 | 1.00 | 43.71 | N |
| ATOM | 327 | C | LYS A 259 | -1.747 | 6.446 | 44.125 | 1.00 | 40.30 | C |
| ATOM | 328 | O | LYS A 259 | -1.342 | 7.596 | 43.999 | 1.00 | 40.14 | O |
| ATOM | 329 | N | GLU A 260 | -1.171 | 5.407 | 43.517 | 1.00 | 40.18 | N |
| ATOM | 330 | CA | GLU A 260 | -0.002 | 5.585 | 42.653 | 1.00 | 39.87 | C |
| ATOM | 331 | CB | GLU A 260 | 0.530 | 4.250 | 42.217 | 1.00 | 39.73 | C |
| ATOM | 332 | CG | GLU A 260 | 1.047 | 3.431 | 43.364 | 1.00 | 39.84 | C |
| ATOM | 333 | CD | GLU A 260 | 2.133 | 2.509 | 42.913 | 1.00 | 40.22 | C |
| ATOM | 334 | OE1 | GLU A 260 | 3.232 | 2.911 | 42.736 | 1.00 | 41.01 | O |
| ATOM | 335 | OE2 | GLU A 260 | 1.937 | 1.371 | 42.657 | 1.00 | 40.08 | O |
| ATOM | 336 | C | GLU A 260 | -0.289 | 6.438 | 41.423 | 1.00 | 39.77 | C |
| ATOM | 337 | O | GLU A 260 | 0.580 | 7.169 | 40.953 | 1.00 | 39.65 | O |
| ATOM | 338 | N | LEU A 261 | -1.506 | 6.341 | 40.896 | 1.00 | 39.65 | N |
| ATOM | 339 | CA | LEU A 261 | -1.880 | 7.179 | 39.766 | 1.00 | 39.54 | C |
| ATOM | 340 | CB | LEU A 261 | -3.261 | 6.831 | 39.250 | 1.00 | 39.53 | C |
| ATOM | 341 | CG | LEU A 261 | -3.179 | 5.824 | 38.108 | 1.00 | 39.71 | C |
| ATOM | 342 | CD1 | LEU A 261 | -4.544 | 5.636 | 37.515 | 1.00 | 39.68 | C |
| ATOM | 343 | CD2 | LEU A 261 | -2.194 | 6.302 | 37.049 | 1.00 | 39.62 | C |
| ATOM | 344 | C | LEU A 261 | -1.803 | 8.656 | 40.098 | 1.00 | 39.45 | C |
| ATOM | 345 | O | LEU A 261 | -1.211 | 9.429 | 39.349 | 1.00 | 39.59 | O |
| ATOM | 346 | N | VAL A 262 | -2.398 | 9.054 | 41.214 | 1.00 | 39.26 | N |
| ATOM | 347 | CA | VAL A 262 | -2.353 | 10.452 | 41.604 | 1.00 | 39.12 | C |
| ATOM | 348 | CB | VAL A 262 | -3.033 | 10.687 | 42.985 | 1.00 | 39.04 | C |
| ATOM | 349 | CG1 | VAL A 262 | -2.605 | 12.015 | 43.591 | 1.00 | 38.57 | C |
| ATOM | 350 | CG2 | VAL A 262 | -4.534 | 10.608 | 42.863 | 1.00 | 38.69 | C |
| ATOM | 351 | C | VAL A 262 | -0.895 | 10.876 | 41.671 | 1.00 | 39.23 | C |
| ATOM | 352 | O | VAL A 262 | -0.502 | 11.901 | 41.134 | 1.00 | 39.12 | O |
| ATOM | 353 | N | HIS A 263 | -0.084 | 10.047 | 42.307 | 1.00 | 39.38 | N |
| ATOM | 354 | CA | HIS A 263 | 1.300 | 10.388 | 42.522 | 1.00 | 39.75 | C |
| ATOM | 355 | CB | HIS A 263 | 1.959 | 9.370 | 43.455 | 1.00 | 40.40 | C |
| ATOM | 356 | CG | HIS A 263 | 1.665 | 9.611 | 44.902 | 1.00 | 43.81 | C |
| ATOM | 357 | ND1 | HIS A 263 | 1.750 | 8.622 | 45.858 | 1.00 | 46.77 | N |
| ATOM | 358 | CE1 | HIS A 263 | 1.423 | 9.121 | 47.037 | 1.00 | 48.91 | C |
| ATOM | 359 | NE2 | HIS A 263 | 1.133 | 10.402 | 46.882 | 1.00 | 53.65 | N |
| ATOM | 360 | CD2 | HIS A 263 | 1.277 | 10.733 | 45.556 | 1.00 | 47.38 | C |
| ATOM | 361 | C | HIS A 263 | 2.056 | 10.542 | 41.218 | 1.00 | 39.01 | C |
| ATOM | 362 | O | HIS A 263 | 2.927 | 11.403 | 41.097 | 1.00 | 38.93 | O |
| ATOM | 363 | N | MET A 264 | 1.701 | 9.716 | 40.241 | 1.00 | 38.30 | N |
| ATOM | 364 | CA | MET A 264 | 2.351 | 9.725 | 38.943 | 1.00 | 37.52 | C |
| ATOM | 365 | CB | MET A 264 | 1.826 | 8.584 | 38.090 | 1.00 | 37.50 | C |
| ATOM | 366 | CG | MET A 264 | 2.597 | 8.377 | 36.809 | 1.00 | 36.94 | C |

| ATOM | 367 | SD | MET | A | 264 | 1.728 | 7.294 | 35.704 | 1.00 | 36.25 | S |
|------|-----|-----|-----|---|-----|-------|-------|--------|------|-------|---|
| ATOM | 368 | CE | MET | A | 264 | 1.766 | 5.726 | 36.683 | 1.00 | 36.21 | C |
| ATOM | 369 | C | MET | A | 264 | 2.115 | 11.031 | 38.214 | 1.00 | 37.18 | C |
| ATOM | 370 | O | MET | A | 264 | 3.022 | 11.567 | 37.578 | 1.00 | 37.13 | O |
| ATOM | 371 | N | ILE | A | 265 | 0.890 | 11.538 | 38.286 | 1.00 | 36.57 | N |
| ATOM | 372 | CA | ILE | A | 265 | 0.598 | 12.804 | 37.649 | 1.00 | 36.12 | C |
| ATOM | 373 | CB | ILE | A | 265 | -0.872 | 13.205 | 37.881 | 1.00 | 36.18 | C |
| ATOM | 374 | CG1 | ILE | A | 265 | -1.777 | 12.329 | 37.014 | 1.00 | 36.18 | C |
| ATOM | 375 | CD1 | ILE | A | 265 | -3.227 | 12.655 | 37.132 | 1.00 | 36.07 | C |
| ATOM | 376 | CG2 | ILE | A | 265 | -1.100 | 14.680 | 37.573 | 1.00 | 35.81 | C |
| ATOM | 377 | C | ILE | A | 265 | 1.543 | 13.806 | 38.253 | 1.00 | 35.83 | C |
| ATOM | 378 | O | ILE | A | 265 | 2.172 | 14.583 | 37.553 | 1.00 | 35.59 | O |
| ATOM | 379 | N | GLY | A | 266 | 1.662 | 13.751 | 39.571 | 1.00 | 35.64 | N |
| ATOM | 380 | CA | GLY | A | 266 | 2.556 | 14.637 | 40.271 | 1.00 | 35.57 | C |
| ATOM | 381 | C | GLY | A | 266 | 3.909 | 14.509 | 39.619 | 1.00 | 35.63 | C |
| ATOM | 382 | O | GLY | A | 266 | 4.558 | 15.512 | 39.287 | 1.00 | 35.73 | O |
| ATOM | 383 | N | TRP | A | 267 | 4.312 | 13.261 | 39.397 | 1.00 | 35.47 | N |
| ATOM | 384 | CA | TRP | A | 267 | 5.609 | 12.948 | 38.825 | 1.00 | 35.34 | C |
| ATOM | 385 | CB | TRP | A | 267 | 5.805 | 11.434 | 38.832 | 1.00 | 35.02 | C |
| ATOM | 386 | CG | TRP | A | 267 | 6.963 | 10.955 | 38.029 | 1.00 | 33.77 | C |
| ATOM | 387 | CD1 | TRP | A | 267 | 8.273 | 11.080 | 38.337 | 1.00 | 32.65 | C |
| ATOM | 388 | NE1 | TRP | A | 267 | 9.047 | 10.512 | 37.357 | 1.00 | 31.98 | N |
| ATOM | 389 | CE2 | TRP | A | 267 | 8.232 | 9.989 | 36.390 | 1.00 | 32.03 | C |
| ATOM | 390 | CD2 | TRP | A | 267 | 6.907 | 10.255 | 36.779 | 1.00 | 32.45 | C |
| ATOM | 391 | CE3 | TRP | A | 267 | 5.865 | 9.819 | 35.948 | 1.00 | 31.64 | C |
| ATOM | 392 | CZ3 | TRP | A | 267 | 6.177 | 9.148 | 34.784 | 1.00 | 31.38 | C |
| ATOM | 393 | CH2 | TRP | A | 267 | 7.506 | 8.902 | 34.424 | 1.00 | 31.30 | C |
| ATOM | 394 | CZ2 | TRP | A | 267 | 8.547 | 9.302 | 35.212 | 1.00 | 31.23 | C |
| ATOM | 395 | C | TRP | A | 267 | 5.849 | 13.543 | 37.441 | 1.00 | 35.77 | C |
| ATOM | 396 | O | TRP | A | 267 | 6.875 | 14.163 | 37.202 | 1.00 | 35.56 | O |
| ATOM | 397 | N | ALA | A | 268 | 4.900 | 13.362 | 36.534 | 1.00 | 36.58 | N |
| ATOM | 398 | CA | ALA | A | 268 | 5.045 | 13.872 | 35.169 | 1.00 | 37.48 | C |
| ATOM | 399 | CB | ALA | A | 268 | 3.829 | 13.534 | 34.326 | 1.00 | 37.33 | C |
| ATOM | 400 | C | ALA | A | 268 | 5.281 | 15.361 | 35.170 | 1.00 | 38.18 | C |
| ATOM | 401 | O | ALA | A | 268 | 6.147 | 15.849 | 34.457 | 1.00 | 38.14 | O |
| ATOM | 402 | N | LYS | A | 269 | 4.507 | 16.068 | 35.991 | 1.00 | 39.27 | N |
| ATOM | 403 | CA | LYS | A | 269 | 4.598 | 17.521 | 36.128 | 1.00 | 40.28 | C |
| ATOM | 404 | CB | LYS | A | 269 | 3.625 | 18.026 | 37.195 | 1.00 | 40.24 | C |
| ATOM | 409 | C | LYS | A | 269 | 6.005 | 18.014 | 36.452 | 1.00 | 41.02 | C |
| ATOM | 410 | O | LYS | A | 269 | 6.314 | 19.178 | 36.207 | 1.00 | 41.19 | O |
| ATOM | 411 | N | LYS | A | 270 | 6.852 | 17.147 | 36.999 | 1.00 | 41.89 | N |
| ATOM | 412 | CA | LYS | A | 270 | 8.213 | 17.543 | 37.330 | 1.00 | 42.89 | C |
| ATOM | 413 | CB | LYS | A | 270 | 8.652 | 16.961 | 38.668 | 1.00 | 42.92 | C |
| ATOM | 414 | CG | LYS | A | 270 | 7.928 | 17.514 | 39.857 | 1.00 | 43.35 | C |
| ATOM | 415 | CD | LYS | A | 270 | 8.146 | 16.643 | 41.066 | 1.00 | 44.07 | C |
| ATOM | 416 | CE | LYS | A | 270 | 7.418 | 17.220 | 42.263 | 1.00 | 45.34 | C |
| ATOM | 417 | NZ | LYS | A | 270 | 6.859 | 16.151 | 43.148 | 1.00 | 46.44 | N |
| ATOM | 418 | C | LYS | A | 270 | 9.232 | 17.151 | 36.269 | 1.00 | 43.60 | C |
| ATOM | 419 | O | LYS | A | 270 | 10.415 | 17.441 | 36.418 | 1.00 | 43.78 | O |
| ATOM | 420 | N | ILE | A | 271 | 8.807 | 16.478 | 35.211 | 1.00 | 44.42 | N |
| ATOM | 421 | CA | ILE | A | 271 | 9.753 | 16.162 | 34.153 | 1.00 | 45.28 | C |
| ATOM | 422 | CB | ILE | A | 271 | 9.335 | 14.906 | 33.427 | 1.00 | 45.23 | C |
| ATOM | 423 | CG1 | ILE | A | 271 | 9.103 | 13.809 | 34.469 | 1.00 | 45.16 | C |
| ATOM | 424 | CD1 | ILE | A | 271 | 8.922 | 12.466 | 33.905 | 1.00 | 44.88 | C |
| ATOM | 425 | CG2 | ILE | A | 271 | 10.399 | 14.505 | 32.428 | 1.00 | 45.02 | C |
| ATOM | 426 | C | ILE | A | 271 | 9.862 | 17.366 | 33.233 | 1.00 | 46.14 | C |
| ATOM | 427 | O | ILE | A | 271 | 8.936 | 17.698 | 32.491 | 1.00 | 46.24 | O |
| ATOM | 428 | N | PRO | A | 272 | 11.019 | 18.008 | 33.277 | 1.00 | 47.00 | N |
| ATOM | 429 | CA | PRO | A | 272 | 11.210 | 19.311 | 32.635 | 1.00 | 47.70 | C |
| ATOM | 430 | CB | PRO | A | 272 | 12.732 | 19.478 | 32.637 | 1.00 | 47.68 | C |
| ATOM | 431 | CG | PRO | A | 272 | 13.185 | 18.687 | 33.799 | 1.00 | 47.43 | C |

| ATOM | 432 | CD  | PRO A 272 | 12.259 | 17.494 | 33.881 | 1.00 47.04 | C |
| ATOM | 433 | C   | PRO A 272 | 10.663 | 19.352 | 31.215 | 1.00 48.39 | C |
| ATOM | 434 | O   | PRO A 272 | 11.137 | 18.611 | 30.369 | 1.00 48.36 | O |
| ATOM | 435 | N   | GLY A 273 | 9.677  | 20.208 | 30.970 | 1.00 49.22 | N |
| ATOM | 436 | CA  | GLY A 273 | 9.103  | 20.338 | 29.645 | 1.00 50.26 | C |
| ATOM | 437 | C   | GLY A 273 | 7.727  | 19.722 | 29.553 | 1.00 51.00 | C |
| ATOM | 438 | O   | GLY A 273 | 6.916  | 20.106 | 28.717 | 1.00 50.99 | O |
| ATOM | 439 | N   | PHE A 274 | 7.455  | 18.763 | 30.424 | 1.00 51.82 | N |
| ATOM | 440 | CA  | PHE A 274 | 6.161  | 18.105 | 30.402 | 1.00 52.67 | C |
| ATOM | 441 | CB  | PHE A 274 | 6.080  | 16.997 | 31.451 | 1.00 52.52 | C |
| ATOM | 442 | CG  | PHE A 274 | 4.825  | 16.185 | 31.365 | 1.00 52.19 | C |
| ATOM | 443 | CD1 | PHE A 274 | 4.737  | 15.110 | 30.500 | 1.00 51.74 | C |
| ATOM | 444 | CE1 | PHE A 274 | 3.586  | 14.371 | 30.413 | 1.00 51.25 | C |
| ATOM | 445 | CZ  | PHE A 274 | 2.507  | 14.699 | 31.186 | 1.00 51.20 | C |
| ATOM | 446 | CE2 | PHE A 274 | 2.576  | 15.769 | 32.042 | 1.00 51.51 | C |
| ATOM | 447 | CD2 | PHE A 274 | 3.726  | 16.508 | 32.130 | 1.00 51.79 | C |
| ATOM | 448 | C   | PHE A 274 | 5.002  | 19.090 | 30.558 | 1.00 53.41 | C |
| ATOM | 449 | O   | PHE A 274 | 3.937  | 18.877 | 29.987 | 1.00 53.42 | O |
| ATOM | 450 | N   | VAL A 275 | 5.201  | 20.157 | 31.328 | 1.00 54.42 | N |
| ATOM | 451 | CA  | VAL A 275 | 4.146  | 21.162 | 31.490 | 1.00 55.49 | C |
| ATOM | 452 | CB  | VAL A 275 | 4.293  | 22.018 | 32.774 | 1.00 55.42 | C |
| ATOM | 453 | CG1 | VAL A 275 | 3.541  | 21.384 | 33.922 | 1.00 55.51 | C |
| ATOM | 454 | CG2 | VAL A 275 | 5.753  | 22.251 | 33.128 | 1.00 55.50 | C |
| ATOM | 455 | C   | VAL A 275 | 4.079  | 22.074 | 30.271 | 1.00 56.23 | C |
| ATOM | 456 | O   | VAL A 275 | 3.003  | 22.534 | 29.876 | 1.00 56.25 | O |
| ATOM | 457 | N   | GLU A 276 | 5.248  | 22.327 | 29.691 | 1.00 57.18 | N |
| ATOM | 458 | CA  | GLU A 276 | 5.385  | 23.112 | 28.474 | 1.00 58.10 | C |
| ATOM | 459 | CB  | GLU A 276 | 6.871  | 23.326 | 28.184 | 1.00 58.21 | C |
| ATOM | 460 | CG  | GLU A 276 | 7.379  | 24.654 | 28.660 | 1.00 59.10 | C |
| ATOM | 461 | CD  | GLU A 276 | 8.642  | 24.671 | 29.486 | 1.00 60.04 | C |
| ATOM | 462 | OE1 | GLU A 276 | 8.501  | 24.626 | 30.719 | 1.00 60.47 | O |
| ATOM | 463 | OE2 | GLU A 276 | 9.747  | 24.842 | 28.921 | 1.00 60.38 | O |
| ATOM | 464 | C   | GLU A 276 | 4.759  | 22.341 | 27.328 | 1.00 58.51 | C |
| ATOM | 465 | O   | GLU A 276 | 5.103  | 22.545 | 26.166 | 1.00 58.59 | O |
| ATOM | 466 | N   | LEU A 277 | 3.851  | 21.436 | 27.666 | 1.00 59.04 | N |
| ATOM | 467 | CA  | LEU A 277 | 3.198  | 20.618 | 26.664 | 1.00 59.55 | C |
| ATOM | 468 | CB  | LEU A 277 | 3.345  | 19.139 | 27.000 | 1.00 59.60 | C |
| ATOM | 469 | CG  | LEU A 277 | 4.537  | 18.343 | 26.479 | 1.00 59.92 | C |
| ATOM | 470 | CD1 | LEU A 277 | 4.232  | 16.856 | 26.577 | 1.00 60.09 | C |
| ATOM | 471 | CD2 | LEU A 277 | 4.839  | 18.719 | 25.052 | 1.00 60.28 | C |
| ATOM | 472 | C   | LEU A 277 | 1.718  | 20.914 | 26.510 | 1.00 59.85 | C |
| ATOM | 473 | O   | LEU A 277 | 1.058  | 21.426 | 27.414 | 1.00 59.94 | O |
| ATOM | 474 | N   | SER A 278 | 1.213  | 20.565 | 25.337 | 1.00 60.20 | N |
| ATOM | 475 | CA  | SER A 278 | -0.199 | 20.638 | 25.043 | 1.00 60.47 | C |
| ATOM | 476 | CB  | SER A 278 | -0.419 | 20.339 | 23.560 | 1.00 60.49 | C |
| ATOM | 477 | OG  | SER A 278 | 0.639  | 19.542 | 23.042 | 1.00 60.52 | O |
| ATOM | 478 | C   | SER A 278 | -0.908 | 19.599 | 25.908 | 1.00 60.64 | C |
| ATOM | 479 | O   | SER A 278 | -0.511 | 18.434 | 25.950 | 1.00 60.67 | O |
| ATOM | 480 | N   | LEU A 279 | -1.947 | 20.028 | 26.613 | 1.00 60.83 | N |
| ATOM | 481 | CA  | LEU A 279 | -2.709 | 19.122 | 27.454 | 1.00 60.97 | C |
| ATOM | 482 | CB  | LEU A 279 | -3.840 | 19.862 | 28.163 | 1.00 61.08 | C |
| ATOM | 483 | CG  | LEU A 279 | -3.391 | 20.655 | 29.393 | 1.00 61.45 | C |
| ATOM | 484 | CD1 | LEU A 279 | -2.808 | 22.008 | 28.989 | 1.00 61.59 | C |
| ATOM | 485 | CD2 | LEU A 279 | -4.538 | 20.828 | 30.381 | 1.00 61.82 | C |
| ATOM | 486 | C   | LEU A 279 | -3.248 | 17.942 | 26.656 | 1.00 60.94 | C |
| ATOM | 487 | O   | LEU A 279 | -3.424 | 16.853 | 27.199 | 1.00 60.99 | O |
| ATOM | 488 | N   | LEU A 280 | -3.518 | 18.158 | 25.372 | 1.00 60.87 | N |
| ATOM | 489 | CA  | LEU A 280 | -3.938 | 17.063 | 24.511 | 1.00 60.77 | C |
| ATOM | 490 | CB  | LEU A 280 | -4.042 | 17.513 | 23.049 | 1.00 60.89 | C |
| ATOM | 491 | CG  | LEU A 280 | -4.082 | 16.404 | 21.985 | 1.00 61.13 | C |
| ATOM | 492 | CD1 | LEU A 280 | -5.371 | 15.598 | 22.077 | 1.00 61.36 | C |

| | | | | | | | | | |
|---|---|---|---|---|---|---|---|---|---|
| ATOM | 493 | CD2 | LEU A 280 | -3.909 | 16.976 | 20.580 | 1.00 | 61.34 | C |
| ATOM | 494 | C | LEU A 280 | -2.887 | 15.972 | 24.654 | 1.00 | 60.54 | C |
| ATOM | 495 | O | LEU A 280 | -3.208 | 14.807 | 24.873 | 1.00 | 60.55 | O |
| ATOM | 496 | N | ASP A 281 | -1.624 | 16.369 | 24.561 | 1.00 | 60.22 | N |
| ATOM | 497 | CA | ASP A 281 | -0.518 | 15.426 | 24.692 | 1.00 | 59.95 | C |
| ATOM | 498 | CB | ASP A 281 | 0.772 | 16.014 | 24.110 | 1.00 | 60.12 | C |
| ATOM | 499 | CG | ASP A 281 | 0.755 | 16.063 | 22.588 | 1.00 | 60.54 | C |
| ATOM | 500 | OD1 | ASP A 281 | -0.265 | 15.656 | 21.992 | 1.00 | 61.18 | O |
| ATOM | 501 | OD2 | ASP A 281 | 1.706 | 16.495 | 21.902 | 1.00 | 60.94 | O |
| ATOM | 502 | C | ASP A 281 | -0.305 | 14.960 | 26.133 | 1.00 | 59.54 | C |
| ATOM | 503 | O | ASP A 281 | -0.187 | 13.758 | 26.392 | 1.00 | 59.49 | O |
| ATOM | 504 | N | GLN A 282 | -0.258 | 15.904 | 27.068 | 1.00 | 58.97 | N |
| ATOM | 505 | CA | GLN A 282 | -0.085 | 15.557 | 28.474 | 1.00 | 58.37 | C |
| ATOM | 506 | CB | GLN A 282 | -0.300 | 16.772 | 29.365 | 1.00 | 58.47 | C |
| ATOM | 507 | CG | GLN A 282 | 0.916 | 17.672 | 29.478 | 1.00 | 58.83 | C |
| ATOM | 508 | CD | GLN A 282 | 0.722 | 18.780 | 30.497 | 1.00 | 59.39 | C |
| ATOM | 509 | OE1 | GLN A 282 | -0.031 | 18.622 | 31.457 | 1.00 | 59.72 | O |
| ATOM | 510 | NE2 | GLN A 282 | 1.395 | 19.901 | 30.289 | 1.00 | 59.60 | N |
| ATOM | 511 | C | GLN A 282 | -1.009 | 14.422 | 28.904 | 1.00 | 57.84 | C |
| ATOM | 512 | O | GLN A 282 | -0.564 | 13.447 | 29.512 | 1.00 | 57.89 | O |
| ATOM | 513 | N | VAL A 283 | -2.293 | 14.541 | 28.588 | 1.00 | 57.05 | N |
| ATOM | 514 | CA | VAL A 283 | -3.240 | 13.491 | 28.933 | 1.00 | 56.30 | C |
| ATOM | 515 | CB | VAL A 283 | -4.698 | 13.920 | 28.652 | 1.00 | 56.45 | C |
| ATOM | 516 | CG1 | VAL A 283 | -5.641 | 12.717 | 28.736 | 1.00 | 56.48 | C |
| ATOM | 517 | CG2 | VAL A 283 | -5.136 | 15.031 | 29.605 | 1.00 | 56.47 | C |
| ATOM | 518 | C | VAL A 283 | -2.956 | 12.226 | 28.133 | 1.00 | 55.65 | C |
| ATOM | 519 | O | VAL A 283 | -2.980 | 11.118 | 28.667 | 1.00 | 55.64 | O |
| ATOM | 520 | N | ARG A 284 | -2.677 | 12.400 | 26.846 | 1.00 | 54.75 | N |
| ATOM | 521 | CA | ARG A 284 | -2.461 | 11.266 | 25.953 | 1.00 | 53.82 | C |
| ATOM | 522 | CB | ARG A 284 | -2.288 | 11.754 | 24.509 | 1.00 | 53.88 | C |
| ATOM | 529 | C | ARG A 284 | -1.286 | 10.375 | 26.380 | 1.00 | 53.08 | C |
| ATOM | 530 | O | ARG A 284 | -1.377 | 9.146 | 26.362 | 1.00 | 52.93 | O |
| ATOM | 531 | N | LEU A 285 | -0.186 | 10.999 | 26.773 | 1.00 | 52.14 | N |
| ATOM | 532 | CA | LEU A 285 | 0.994 | 10.250 | 27.172 | 1.00 | 51.24 | C |
| ATOM | 533 | CB | LEU A 285 | 2.173 | 11.193 | 27.376 | 1.00 | 51.29 | C |
| ATOM | 534 | CG | LEU A 285 | 2.657 | 11.711 | 26.023 | 1.00 | 51.48 | C |
| ATOM | 535 | CD1 | LEU A 285 | 3.412 | 13.022 | 26.165 | 1.00 | 51.35 | C |
| ATOM | 536 | CD2 | LEU A 285 | 3.487 | 10.635 | 25.313 | 1.00 | 51.68 | C |
| ATOM | 537 | C | LEU A 285 | 0.722 | 9.457 | 28.429 | 1.00 | 50.46 | C |
| ATOM | 538 | O | LEU A 285 | 1.044 | 8.274 | 28.520 | 1.00 | 50.43 | O |
| ATOM | 539 | N | LEU A 286 | 0.105 | 10.115 | 29.395 | 1.00 | 49.46 | N |
| ATOM | 540 | CA | LEU A 286 | -0.230 | 9.460 | 30.646 | 1.00 | 48.52 | C |
| ATOM | 541 | CB | LEU A 286 | -0.749 | 10.487 | 31.652 | 1.00 | 48.52 | C |
| ATOM | 542 | CG | LEU A 286 | 0.382 | 11.228 | 32.356 | 1.00 | 48.48 | C |
| ATOM | 543 | CD1 | LEU A 286 | -0.103 | 12.537 | 32.953 | 1.00 | 48.51 | C |
| ATOM | 544 | CD2 | LEU A 286 | 1.019 | 10.318 | 33.414 | 1.00 | 48.47 | C |
| ATOM | 545 | C | LEU A 286 | -1.244 | 8.338 | 30.442 | 1.00 | 47.81 | C |
| ATOM | 546 | O | LEU A 286 | -1.271 | 7.370 | 31.204 | 1.00 | 47.71 | O |
| ATOM | 547 | N | GLU A 287 | -2.072 | 8.470 | 29.409 | 1.00 | 46.83 | N |
| ATOM | 548 | CA | GLU A 287 | -3.093 | 7.477 | 29.133 | 1.00 | 45.86 | C |
| ATOM | 549 | CB | GLU A 287 | -4.109 | 8.018 | 28.133 | 1.00 | 45.97 | C |
| ATOM | 550 | CG | GLU A 287 | -5.119 | 8.983 | 28.723 | 1.00 | 46.14 | C |
| ATOM | 554 | C | GLU A 287 | -2.538 | 6.142 | 28.633 | 1.00 | 45.13 | C |
| ATOM | 555 | O | GLU A 287 | -3.092 | 5.088 | 28.930 | 1.00 | 45.01 | O |
| ATOM | 556 | N | SER A 288 | -1.452 | 6.166 | 27.875 | 1.00 | 44.20 | N |
| ATOM | 557 | CA | SER A 288 | -0.925 | 4.903 | 27.369 | 1.00 | 43.33 | C |
| ATOM | 558 | CB | SER A 288 | -0.470 | 5.038 | 25.928 | 1.00 | 43.41 | C |
| ATOM | 559 | OG | SER A 288 | 0.556 | 6.000 | 25.847 | 1.00 | 43.40 | O |
| ATOM | 560 | C | SER A 288 | 0.228 | 4.329 | 28.166 | 1.00 | 42.68 | C |
| ATOM | 561 | O | SER A 288 | 0.505 | 3.141 | 28.067 | 1.00 | 42.77 | O |
| ATOM | 562 | N | CYS A 289 | 0.910 | 5.142 | 28.958 | 1.00 | 41.63 | N |

| | | | | | | | | | | |
|---|---|---|---|---|---|---|---|---|---|---|
| ATOM | 563 | CA | CYS | A | 289 | 2.060 | 4.607 | 29.656 | 1.00 40.59 | C |
| ATOM | 564 | CB | CYS | A | 289 | 3.245 | 5.567 | 29.519 | 1.00 40.59 | C |
| ATOM | 565 | SG | CYS | A | 289 | 3.116 | 7.057 | 30.509 | 1.00 41.13 | S |
| ATOM | 566 | C | CYS | A | 289 | 1.811 | 4.257 | 31.122 | 1.00 39.80 | C |
| ATOM | 567 | O | CYS | A | 289 | 2.633 | 3.578 | 31.754 | 1.00 39.62 | O |
| ATOM | 568 | N | TRP | A | 290 | 0.677 | 4.680 | 31.663 | 1.00 38.85 | N |
| ATOM | 569 | CA | TRP | A | 290 | 0.493 | 4.548 | 33.107 | 1.00 38.03 | C |
| ATOM | 570 | CB | TRP | A | 290 | -0.856 | 5.103 | 33.616 | 1.00 37.86 | C |
| ATOM | 571 | CG | TRP | A | 290 | -2.055 | 4.311 | 33.273 | 1.00 36.72 | C |
| ATOM | 572 | CD1 | TRP | A | 290 | -2.888 | 4.516 | 32.216 | 1.00 36.49 | C |
| ATOM | 573 | NE1 | TRP | A | 290 | -3.896 | 3.583 | 32.217 | 1.00 36.08 | N |
| ATOM | 574 | CE2 | TRP | A | 290 | -3.730 | 2.757 | 33.295 | 1.00 35.83 | C |
| ATOM | 575 | CD2 | TRP | A | 290 | -2.577 | 3.190 | 33.981 | 1.00 35.61 | C |
| ATOM | 576 | CE3 | TRP | A | 290 | -2.192 | 2.503 | 35.129 | 1.00 35.35 | C |
| ATOM | 577 | CZ3 | TRP | A | 290 | -2.949 | 1.427 | 35.548 | 1.00 35.25 | C |
| ATOM | 578 | CH2 | TRP | A | 290 | -4.089 | 1.026 | 34.845 | 1.00 35.26 | C |
| ATOM | 579 | CZ2 | TRP | A | 290 | -4.493 | 1.674 | 33.718 | 1.00 35.35 | C |
| ATOM | 580 | C | TRP | A | 290 | 0.789 | 3.164 | 33.639 | 1.00 37.76 | C |
| ATOM | 581 | O | TRP | A | 290 | 1.484 | 3.037 | 34.639 | 1.00 37.79 | O |
| ATOM | 582 | N | MET | A | 291 | 0.283 | 2.126 | 32.979 | 1.00 37.31 | N |
| ATOM | 583 | CA | MET | A | 291 | 0.552 | 0.762 | 33.424 | 1.00 36.85 | C |
| ATOM | 584 | CB | MET | A | 291 | -0.342 | -0.236 | 32.701 | 1.00 36.93 | C |
| ATOM | 585 | CG | MET | A | 291 | -0.177 | -1.661 | 33.187 | 1.00 37.15 | C |
| ATOM | 586 | SD | MET | A | 291 | -0.613 | -1.767 | 34.928 | 1.00 38.56 | S |
| ATOM | 587 | CE | MET | A | 291 | -2.375 | -2.138 | 34.815 | 1.00 37.95 | C |
| ATOM | 588 | C | MET | A | 291 | 2.025 | 0.376 | 33.258 | 1.00 36.56 | C |
| ATOM | 589 | O | MET | A | 291 | 2.570 | -0.351 | 34.081 | 1.00 36.46 | O |
| ATOM | 590 | N | GLU | A | 292 | 2.666 | 0.865 | 32.199 | 1.00 36.23 | N |
| ATOM | 591 | CA | GLU | A | 292 | 4.076 | 0.584 | 31.973 | 1.00 35.92 | C |
| ATOM | 592 | CB | GLU | A | 292 | 4.550 | 1.148 | 30.627 | 1.00 36.04 | C |
| ATOM | 593 | CG | GLU | A | 292 | 4.260 | 0.237 | 29.449 | 1.00 37.37 | C |
| ATOM | 594 | CD | GLU | A | 292 | 4.574 | 0.876 | 28.106 | 1.00 39.35 | C |
| ATOM | 595 | OE1 | GLU | A | 292 | 5.759 | 0.858 | 27.690 | 1.00 40.33 | O |
| ATOM | 596 | OE2 | GLU | A | 292 | 3.633 | 1.388 | 27.447 | 1.00 40.22 | O |
| ATOM | 597 | C | GLU | A | 292 | 4.865 | 1.201 | 33.107 | 1.00 35.39 | C |
| ATOM | 598 | O | GLU | A | 292 | 5.735 | 0.554 | 33.694 | 1.00 35.36 | O |
| ATOM | 599 | N | VAL | A | 293 | 4.541 | 2.454 | 33.412 | 1.00 34.60 | N |
| ATOM | 600 | CA | VAL | A | 293 | 5.208 | 3.181 | 34.479 | 1.00 33.93 | C |
| ATOM | 601 | CB | VAL | A | 293 | 4.717 | 4.660 | 34.562 | 1.00 33.94 | C |
| ATOM | 602 | CG1 | VAL | A | 293 | 5.303 | 5.353 | 35.740 | 1.00 33.75 | C |
| ATOM | 603 | CG2 | VAL | A | 293 | 5.094 | 5.428 | 33.295 | 1.00 33.93 | C |
| ATOM | 604 | C | VAL | A | 293 | 5.034 | 2.451 | 35.802 | 1.00 33.43 | C |
| ATOM | 605 | O | VAL | A | 293 | 5.998 | 2.206 | 36.520 | 1.00 33.30 | O |
| ATOM | 606 | N | LEU | A | 294 | 3.807 | 2.073 | 36.112 | 1.00 32.99 | N |
| ATOM | 607 | CA | LEU | A | 294 | 3.550 | 1.333 | 37.338 | 1.00 32.66 | C |
| ATOM | 608 | CB | LEU | A | 294 | 2.075 | 0.951 | 37.468 | 1.00 32.60 | C |
| ATOM | 609 | CG | LEU | A | 294 | 1.081 | 2.055 | 37.822 | 1.00 32.67 | C |
| ATOM | 610 | CD1 | LEU | A | 294 | -0.253 | 1.457 | 38.196 | 1.00 32.37 | C |
| ATOM | 611 | CD2 | LEU | A | 294 | 1.617 | 2.942 | 38.952 | 1.00 32.18 | C |
| ATOM | 612 | C | LEU | A | 294 | 4.383 | 0.064 | 37.368 | 1.00 32.46 | C |
| ATOM | 613 | O | LEU | A | 294 | 4.977 | -0.286 | 38.391 | 1.00 32.44 | O |
| ATOM | 614 | N | MET | A | 295 | 4.444 | -0.619 | 36.232 | 1.00 32.07 | N |
| ATOM | 615 | CA | MET | A | 295 | 5.135 | -1.898 | 36.169 | 1.00 31.52 | C |
| ATOM | 616 | CB | MET | A | 295 | 4.771 | -2.636 | 34.885 | 1.00 31.36 | C |
| ATOM | 617 | CG | MET | A | 295 | 3.398 | -3.292 | 34.948 | 1.00 30.46 | C |
| ATOM | 618 | SD | MET | A | 295 | 2.925 | -4.184 | 33.467 | 1.00 27.92 | S |
| ATOM | 619 | CE | MET | A | 295 | 1.494 | -5.075 | 34.127 | 1.00 28.00 | C |
| ATOM | 620 | C | MET | A | 295 | 6.627 | -1.793 | 36.297 | 1.00 31.45 | C |
| ATOM | 621 | O | MET | A | 295 | 7.259 | -2.599 | 36.974 | 1.00 31.44 | O |
| ATOM | 622 | N | VAL | A | 296 | 7.208 | -0.802 | 35.642 | 1.00 31.48 | N |
| ATOM | 623 | CA | VAL | A | 296 | 8.658 | -0.691 | 35.649 | 1.00 31.38 | C |

| | | | | | | | | | |
|---|---|---|---|---|---|---|---|---|---|
| ATOM | 624 | CB | VAL | A | 296 | 9.174 | 0.313 | 34.624 | 1.00 31.38 | C |
| ATOM | 625 | CG1 | VAL | A | 296 | 8.954 | 1.736 | 35.116 | 1.00 31.58 | C |
| ATOM | 626 | CG2 | VAL | A | 296 | 10.630 | 0.081 | 34.393 | 1.00 31.51 | C |
| ATOM | 627 | C | VAL | A | 296 | 9.075 | -0.321 | 37.061 | 1.00 31.27 | C |
| ATOM | 628 | O | VAL | A | 296 | 10.115 | -0.756 | 37.560 | 1.00 31.32 | O |
| ATOM | 629 | N | GLY | A | 297 | 8.245 | 0.458 | 37.727 | 1.00 30.95 | N |
| ATOM | 630 | CA | GLY | A | 297 | 8.534 | 0.769 | 39.102 | 1.00 30.87 | C |
| ATOM | 631 | C | GLY | A | 297 | 8.437 | -0.496 | 39.916 | 1.00 30.83 | C |
| ATOM | 632 | O | GLY | A | 297 | 9.281 | -0.790 | 40.752 | 1.00 30.85 | O |
| ATOM | 633 | N | LEU | A | 298 | 7.385 | -1.259 | 39.685 | 1.00 31.12 | N |
| ATOM | 634 | CA | LEU | A | 298 | 7.235 | -2.527 | 40.383 | 1.00 31.29 | C |
| ATOM | 635 | CB | LEU | A | 298 | 5.964 | -3.226 | 39.943 | 1.00 31.13 | C |
| ATOM | 636 | CG | LEU | A | 298 | 5.902 | -4.716 | 40.262 | 1.00 31.27 | C |
| ATOM | 637 | CD1 | LEU | A | 298 | 5.982 | -4.942 | 41.776 | 1.00 30.91 | C |
| ATOM | 638 | CD2 | LEU | A | 298 | 4.637 | -5.357 | 39.664 | 1.00 30.82 | C |
| ATOM | 639 | C | LEU | A | 298 | 8.483 | -3.409 | 40.145 | 1.00 31.52 | C |
| ATOM | 640 | O | LEU | A | 298 | 9.087 | -3.944 | 41.091 | 1.00 31.48 | O |
| ATOM | 641 | N | MET | A | 299 | 8.900 | -3.527 | 38.892 | 1.00 31.72 | N |
| ATOM | 642 | CA | MET | A | 299 | 10.103 | -4.295 | 38.615 | 1.00 32.13 | C |
| ATOM | 643 | CB | MET | A | 299 | 10.383 | -4.313 | 37.118 | 1.00 32.22 | C |
| ATOM | 644 | CG | MET | A | 299 | 9.447 | -5.252 | 36.375 | 1.00 32.40 | C |
| ATOM | 645 | SD | MET | A | 299 | 9.510 | -5.012 | 34.610 | 1.00 32.60 | S |
| ATOM | 646 | CE | MET | A | 299 | 8.080 | -5.859 | 34.180 | 1.00 32.23 | C |
| ATOM | 647 | C | MET | A | 299 | 11.316 | -3.757 | 39.371 | 1.00 32.27 | C |
| ATOM | 648 | O | MET | A | 299 | 12.052 | -4.512 | 39.999 | 1.00 32.34 | O |
| ATOM | 649 | N | TRP | A | 300 | 11.529 | -2.447 | 39.312 | 1.00 32.41 | N |
| ATOM | 650 | CA | TRP | A | 300 | 12.666 | -1.883 | 39.995 | 1.00 32.42 | C |
| ATOM | 651 | CB | TRP | A | 300 | 12.699 | -0.375 | 39.860 | 1.00 32.18 | C |
| ATOM | 652 | CG | TRP | A | 300 | 13.660 | 0.182 | 40.819 | 1.00 31.21 | C |
| ATOM | 653 | CD1 | TRP | A | 300 | 13.371 | 0.922 | 41.915 | 1.00 30.41 | C |
| ATOM | 654 | NE1 | TRP | A | 300 | 14.524 | 1.247 | 42.584 | 1.00 30.20 | N |
| ATOM | 655 | CE2 | TRP | A | 300 | 15.588 | 0.682 | 41.934 | 1.00 30.17 | C |
| ATOM | 656 | CD2 | TRP | A | 300 | 15.076 | 0.002 | 40.812 | 1.00 30.04 | C |
| ATOM | 657 | CE3 | TRP | A | 300 | 15.967 | -0.655 | 39.966 | 1.00 29.66 | C |
| ATOM | 658 | CZ3 | TRP | A | 300 | 17.326 | -0.611 | 40.259 | 1.00 29.76 | C |
| ATOM | 659 | CH2 | TRP | A | 300 | 17.803 | 0.079 | 41.388 | 1.00 29.79 | C |
| ATOM | 660 | CZ2 | TRP | A | 300 | 16.948 | 0.722 | 42.238 | 1.00 29.74 | C |
| ATOM | 661 | C | TRP | A | 300 | 12.639 | -2.239 | 41.464 | 1.00 32.86 | C |
| ATOM | 662 | O | TRP | A | 300 | 13.617 | -2.730 | 42.013 | 1.00 32.79 | O |
| ATOM | 663 | N | ARG | A | 301 | 11.511 | -1.971 | 42.111 | 1.00 33.51 | N |
| ATOM | 664 | CA | ARG | A | 301 | 11.396 | -2.241 | 43.547 | 1.00 34.01 | C |
| ATOM | 665 | CB | ARG | A | 301 | 10.022 | -1.837 | 44.075 | 1.00 33.71 | C |
| ATOM | 666 | CG | ARG | A | 301 | 9.778 | -0.374 | 44.095 | 1.00 32.93 | C |
| ATOM | 667 | CD | ARG | A | 301 | 8.537 | 0.041 | 44.847 | 1.00 30.84 | C |
| ATOM | 668 | NE | ARG | A | 301 | 7.365 | -0.603 | 44.309 | 1.00 29.91 | N |
| ATOM | 669 | CZ | ARG | A | 301 | 6.704 | -0.173 | 43.248 | 1.00 29.85 | C |
| ATOM | 670 | NH1 | ARG | A | 301 | 7.096 | 0.894 | 42.586 | 1.00 29.53 | N |
| ATOM | 671 | NH2 | ARG | A | 301 | 5.646 | -0.825 | 42.833 | 1.00 30.39 | N |
| ATOM | 672 | C | ARG | A | 301 | 11.636 | -3.711 | 43.876 | 1.00 34.60 | C |
| ATOM | 673 | O | ARG | A | 301 | 12.092 | -4.029 | 44.961 | 1.00 34.56 | O |
| ATOM | 674 | N | SER | A | 302 | 11.324 | -4.597 | 42.936 | 1.00 35.40 | N |
| ATOM | 675 | CA | SER | A | 302 | 11.413 | -6.040 | 43.182 | 1.00 36.19 | C |
| ATOM | 676 | CB | SER | A | 302 | 10.272 | -6.759 | 42.457 | 1.00 36.08 | C |
| ATOM | 677 | OG | SER | A | 302 | 9.024 | -6.263 | 42.880 | 1.00 36.03 | O |
| ATOM | 678 | C | SER | A | 302 | 12.746 | -6.689 | 42.796 | 1.00 36.77 | C |
| ATOM | 679 | O | SER | A | 302 | 13.010 | -7.823 | 43.148 | 1.00 36.77 | O |
| ATOM | 680 | N | ILE | A | 303 | 13.583 | -5.950 | 42.091 | 1.00 37.62 | N |
| ATOM | 681 | CA | ILE | A | 303 | 14.846 | -6.458 | 41.572 | 1.00 38.65 | C |
| ATOM | 682 | CB | ILE | A | 303 | 15.663 | -5.292 | 41.018 | 1.00 38.76 | C |
| ATOM | 683 | CG1 | ILE | A | 303 | 16.382 | -5.719 | 39.748 | 1.00 39.33 | C |
| ATOM | 684 | CD1 | ILE | A | 303 | 17.264 | -4.633 | 39.191 | 1.00 40.69 | C |

| | | | | | | | | | |
|---|---|---|---|---|---|---|---|---|---|
| ATOM | 685 | CG2 | ILE | A | 303 | 16.668 | -4.805 | 42.045 | 1.00 38.73 | C |
| ATOM | 686 | C | ILE | A | 303 | 15.746 | -7.358 | 42.458 | 1.00 39.24 | C |
| ATOM | 687 | O | ILE | A | 303 | 16.276 | -8.359 | 41.981 | 1.00 39.30 | O |
| ATOM | 688 | N | ASP | A | 304 | 15.937 | -7.017 | 43.723 | 1.00 39.94 | N |
| ATOM | 689 | CA | ASP | A | 304 | 16.825 | -7.815 | 44.564 | 1.00 40.77 | C |
| ATOM | 690 | CB | ASP | A | 304 | 17.825 | -6.916 | 45.327 | 1.00 40.94 | C |
| ATOM | 691 | CG | ASP | A | 304 | 18.749 | -6.097 | 44.391 | 1.00 41.97 | C |
| ATOM | 692 | OD1 | ASP | A | 304 | 18.914 | -6.480 | 43.198 | 1.00 42.76 | O |
| ATOM | 693 | OD2 | ASP | A | 304 | 19.349 | -5.045 | 44.767 | 1.00 42.80 | O |
| ATOM | 694 | C | ASP | A | 304 | 16.043 | -8.703 | 45.544 | 1.00 41.08 | C |
| ATOM | 695 | O | ASP | A | 304 | 16.509 | -8.997 | 46.649 | 1.00 41.05 | O |
| ATOM | 696 | N | HIS | A | 305 | 14.857 | -9.142 | 45.138 | 1.00 41.51 | N |
| ATOM | 697 | CA | HIS | A | 305 | 13.995 | -9.921 | 46.034 | 1.00 41.90 | C |
| ATOM | 698 | CB | HIS | A | 305 | 13.007 | -9.008 | 46.764 | 1.00 42.20 | C |
| ATOM | 699 | CG | HIS | A | 305 | 13.654 | -7.852 | 47.449 | 1.00 43.86 | C |
| ATOM | 700 | ND1 | HIS | A | 305 | 14.334 | -7.978 | 48.640 | 1.00 45.55 | N |
| ATOM | 701 | CE1 | HIS | A | 305 | 14.807 | -6.800 | 48.996 | 1.00 46.58 | C |
| ATOM | 702 | NE2 | HIS | A | 305 | 14.471 | -5.924 | 48.068 | 1.00 49.84 | N |
| ATOM | 703 | CD2 | HIS | A | 305 | 13.750 | -6.553 | 47.093 | 1.00 45.67 | C |
| ATOM | 704 | C | HIS | A | 305 | 13.229 | -10.986 | 45.272 | 1.00 41.72 | C |
| ATOM | 705 | O | HIS | A | 305 | 12.018 | -10.908 | 45.092 | 1.00 41.70 | O |
| ATOM | 706 | N | PRO | A | 306 | 13.959 | -11.994 | 44.836 | 1.00 41.64 | N |
| ATOM | 707 | CA | PRO | A | 306 | 13.408 | -13.098 | 44.047 | 1.00 41.45 | C |
| ATOM | 708 | CB | PRO | A | 306 | 14.508 | -14.166 | 44.130 | 1.00 41.47 | C |
| ATOM | 709 | CG | PRO | A | 306 | 15.530 | -13.621 | 45.105 | 1.00 41.63 | C |
| ATOM | 710 | CD | PRO | A | 306 | 15.408 | -12.132 | 45.048 | 1.00 41.74 | C |
| ATOM | 711 | C | PRO | A | 306 | 12.095 | -13.671 | 44.557 | 1.00 41.24 | C |
| ATOM | 712 | O | PRO | A | 306 | 11.785 | -13.623 | 45.744 | 1.00 41.21 | O |
| ATOM | 713 | N | GLY | A | 307 | 11.336 | -14.236 | 43.627 | 1.00 41.02 | N |
| ATOM | 714 | CA | GLY | A | 307 | 10.078 | -14.877 | 43.940 | 1.00 40.64 | C |
| ATOM | 715 | C | GLY | A | 307 | 9.032 | -13.943 | 44.499 | 1.00 40.41 | C |
| ATOM | 716 | O | GLY | A | 307 | 7.885 | -14.353 | 44.704 | 1.00 40.39 | O |
| ATOM | 717 | N | LYS | A | 308 | 9.416 | -12.688 | 44.728 | 1.00 40.08 | N |
| ATOM | 718 | CA | LYS | A | 308 | 8.515 | -11.715 | 45.351 | 1.00 39.80 | C |
| ATOM | 719 | CB | LYS | A | 308 | 9.006 | -11.402 | 46.767 | 1.00 39.89 | C |
| ATOM | 720 | CG | LYS | A | 308 | 9.202 | -12.686 | 47.601 | 1.00 40.16 | C |
| ATOM | 721 | CD | LYS | A | 308 | 9.016 | -12.469 | 49.081 | 1.00 40.66 | C |
| ATOM | 722 | CE | LYS | A | 308 | 9.536 | -13.655 | 49.853 | 1.00 41.55 | C |
| ATOM | 723 | NZ | LYS | A | 308 | 9.755 | -13.318 | 51.292 | 1.00 42.39 | N |
| ATOM | 724 | C | LYS | A | 308 | 8.308 | -10.437 | 44.541 | 1.00 39.51 | C |
| ATOM | 725 | O | LYS | A | 308 | 9.140 | -10.075 | 43.712 | 1.00 39.59 | O |
| ATOM | 726 | N | LEU | A | 309 | 7.181 | -9.769 | 44.755 | 1.00 39.09 | N |
| ATOM | 727 | CA | LEU | A | 309 | 6.915 | -8.505 | 44.070 | 1.00 38.73 | C |
| ATOM | 728 | CB | LEU | A | 309 | 5.763 | -8.629 | 43.068 | 1.00 38.68 | C |
| ATOM | 729 | CG | LEU | A | 309 | 5.995 | -9.469 | 41.792 | 1.00 38.90 | C |
| ATOM | 730 | CD1 | LEU | A | 309 | 4.746 | -9.628 | 40.925 | 1.00 38.74 | C |
| ATOM | 731 | CD2 | LEU | A | 309 | 7.100 | -8.880 | 40.959 | 1.00 38.81 | C |
| ATOM | 732 | C | LEU | A | 309 | 6.625 | -7.417 | 45.096 | 1.00 38.60 | C |
| ATOM | 733 | O | LEU | A | 309 | 5.587 | -7.413 | 45.729 | 1.00 38.48 | O |
| ATOM | 734 | N | ILE | A | 310 | 7.564 | -6.504 | 45.284 | 1.00 38.51 | N |
| ATOM | 735 | CA | ILE | A | 310 | 7.346 | -5.421 | 46.216 | 1.00 38.47 | C |
| ATOM | 736 | CB | ILE | A | 310 | 8.682 | -4.746 | 46.607 | 1.00 38.51 | C |
| ATOM | 737 | CG1 | ILE | A | 310 | 9.738 | -5.794 | 46.968 | 1.00 38.32 | C |
| ATOM | 738 | CD1 | ILE | A | 310 | 9.174 | -6.996 | 47.652 | 1.00 38.02 | C |
| ATOM | 739 | CG2 | ILE | A | 310 | 8.475 | -3.793 | 47.763 | 1.00 38.19 | C |
| ATOM | 740 | C | ILE | A | 310 | 6.388 | -4.396 | 45.619 | 1.00 38.59 | C |
| ATOM | 741 | O | ILE | A | 310 | 6.820 | -3.384 | 45.058 | 1.00 38.63 | O |
| ATOM | 742 | N | PHE | A | 311 | 5.088 | -4.657 | 45.729 | 1.00 38.59 | N |
| ATOM | 743 | CA | PHE | A | 311 | 4.095 | -3.708 | 45.231 | 1.00 38.64 | C |
| ATOM | 744 | CB | PHE | A | 311 | 2.685 | -4.281 | 45.331 | 1.00 38.48 | C |
| ATOM | 745 | CG | PHE | A | 311 | 2.287 | -5.083 | 44.129 | 1.00 38.51 | C |

180

| ATOM | 746 | CD1 | PHE | A | 311 | 1.739 | -4.462 | 43.030 | 1.00 | 38.54 | C |
| --- | --- | --- | --- | --- | --- | --- | --- | --- | --- | --- | --- |
| ATOM | 747 | CE1 | PHE | A | 311 | 1.381 | -5.176 | 41.930 | 1.00 | 39.04 | C |
| ATOM | 748 | CZ | PHE | A | 311 | 1.581 | -6.546 | 41.902 | 1.00 | 39.21 | C |
| ATOM | 749 | CE2 | PHE | A | 311 | 2.133 | -7.185 | 42.994 | 1.00 | 38.74 | C |
| ATOM | 750 | CD2 | PHE | A | 311 | 2.482 | -6.453 | 44.092 | 1.00 | 38.79 | C |
| ATOM | 751 | C | PHE | A | 311 | 4.214 | -2.374 | 45.959 | 1.00 | 38.67 | C |
| ATOM | 752 | O | PHE | A | 311 | 4.202 | -1.315 | 45.338 | 1.00 | 38.52 | O |
| ATOM | 753 | N | ALA | A | 312 | 4.347 | -2.458 | 47.280 | 1.00 | 38.82 | N |
| ATOM | 754 | CA | ALA | A | 312 | 4.514 | -1.302 | 48.148 | 1.00 | 39.05 | C |
| ATOM | 755 | CB | ALA | A | 312 | 3.180 | -0.731 | 48.533 | 1.00 | 38.79 | C |
| ATOM | 756 | C | ALA | A | 312 | 5.319 | -1.753 | 49.377 | 1.00 | 39.35 | C |
| ATOM | 757 | O | ALA | A | 312 | 5.469 | -2.935 | 49.600 | 1.00 | 39.26 | O |
| ATOM | 758 | N | PRO | A | 313 | 5.895 | -0.834 | 50.139 | 1.00 | 39.78 | N |
| ATOM | 759 | CA | PRO | A | 313 | 6.709 | -1.231 | 51.280 | 1.00 | 40.18 | C |
| ATOM | 760 | CB | PRO | A | 313 | 6.895 | 0.080 | 52.026 | 1.00 | 40.06 | C |
| ATOM | 761 | CG | PRO | A | 313 | 6.963 | 1.056 | 50.942 | 1.00 | 39.91 | C |
| ATOM | 762 | CD | PRO | A | 313 | 5.901 | 0.630 | 49.967 | 1.00 | 39.83 | C |
| ATOM | 763 | C | PRO | A | 313 | 6.077 | -2.292 | 52.169 | 1.00 | 40.60 | C |
| ATOM | 764 | O | PRO | A | 313 | 6.778 | -3.209 | 52.589 | 1.00 | 40.74 | O |
| ATOM | 765 | N | ASP | A | 314 | 4.793 | -2.192 | 52.465 | 1.00 | 40.95 | N |
| ATOM | 766 | CA | ASP | A | 314 | 4.200 | -3.193 | 53.336 | 1.00 | 41.27 | C |
| ATOM | 767 | CB | ASP | A | 314 | 3.557 | -2.537 | 54.568 | 1.00 | 41.12 | C |
| ATOM | 768 | CG | ASP | A | 314 | 4.588 | -2.130 | 55.633 | 1.00 | 40.31 | C |
| ATOM | 769 | OD1 | ASP | A | 314 | 5.661 | -2.767 | 55.702 | 1.00 | 39.47 | O |
| ATOM | 770 | OD2 | ASP | A | 314 | 4.407 | -1.193 | 56.441 | 1.00 | 38.61 | O |
| ATOM | 771 | C | ASP | A | 314 | 3.199 | -4.045 | 52.581 | 1.00 | 41.82 | C |
| ATOM | 772 | O | ASP | A | 314 | 2.352 | -4.686 | 53.175 | 1.00 | 41.87 | O |
| ATOM | 773 | N | LEU | A | 315 | 3.301 | -4.031 | 51.261 | 1.00 | 42.57 | N |
| ATOM | 774 | CA | LEU | A | 315 | 2.435 | -4.813 | 50.414 | 1.00 | 43.36 | C |
| ATOM | 775 | CB | LEU | A | 315 | 1.529 | -3.902 | 49.596 | 1.00 | 43.24 | C |
| ATOM | 776 | CG | LEU | A | 315 | 0.494 | -4.571 | 48.674 | 1.00 | 43.09 | C |
| ATOM | 777 | CD1 | LEU | A | 315 | -0.307 | -5.632 | 49.416 | 1.00 | 42.51 | C |
| ATOM | 778 | CD2 | LEU | A | 315 | -0.421 | -3.524 | 48.031 | 1.00 | 42.72 | C |
| ATOM | 779 | C | LEU | A | 315 | 3.333 | -5.628 | 49.514 | 1.00 | 44.09 | C |
| ATOM | 780 | O | LEU | A | 315 | 3.589 | -5.264 | 48.378 | 1.00 | 44.14 | O |
| ATOM | 781 | N | VAL | A | 316 | 3.830 | -6.730 | 50.047 | 1.00 | 45.19 | N |
| ATOM | 782 | CA | VAL | A | 316 | 4.736 | -7.600 | 49.323 | 1.00 | 46.32 | C |
| ATOM | 783 | CB | VAL | A | 316 | 6.025 | -7.806 | 50.120 | 1.00 | 46.26 | C |
| ATOM | 784 | CG1 | VAL | A | 316 | 6.779 | -9.039 | 49.623 | 1.00 | 46.15 | C |
| ATOM | 785 | CG2 | VAL | A | 316 | 6.887 | -6.555 | 50.079 | 1.00 | 46.00 | C |
| ATOM | 786 | C | VAL | A | 316 | 4.103 | -8.965 | 49.097 | 1.00 | 47.33 | C |
| ATOM | 787 | O | VAL | A | 316 | 3.752 | -9.653 | 50.046 | 1.00 | 47.35 | O |
| ATOM | 788 | N | LEU | A | 317 | 3.971 | -9.369 | 47.842 | 1.00 | 48.64 | N |
| ATOM | 789 | CA | LEU | A | 317 | 3.324 | -10.631 | 47.553 | 1.00 | 49.92 | C |
| ATOM | 790 | CB | LEU | A | 317 | 2.292 | -10.463 | 46.438 | 1.00 | 49.86 | C |
| ATOM | 791 | CG | LEU | A | 317 | 1.238 | -9.369 | 46.624 | 1.00 | 50.07 | C |
| ATOM | 792 | CD1 | LEU | A | 317 | -0.050 | -9.761 | 45.918 | 1.00 | 49.94 | C |
| ATOM | 793 | CD2 | LEU | A | 317 | 0.970 | -9.106 | 48.095 | 1.00 | 49.86 | C |
| ATOM | 794 | C | LEU | A | 317 | 4.301 | -11.716 | 47.171 | 1.00 | 50.91 | C |
| ATOM | 795 | O | LEU | A | 317 | 5.460 | -11.448 | 46.852 | 1.00 | 50.98 | O |
| ATOM | 796 | N | ASP | A | 318 | 3.799 | -12.948 | 47.214 | 1.00 | 52.26 | N |
| ATOM | 797 | CA | ASP | A | 318 | 4.524 | -14.140 | 46.794 | 1.00 | 53.50 | C |
| ATOM | 798 | CB | ASP | A | 318 | 4.210 | -15.287 | 47.745 | 1.00 | 53.56 | C |
| ATOM | 799 | CG | ASP | A | 318 | 5.260 | -15.472 | 48.812 | 1.00 | 54.03 | C |
| ATOM | 800 | OD1 | ASP | A | 318 | 6.352 | -14.885 | 48.694 | 1.00 | 54.36 | O |
| ATOM | 801 | OD2 | ASP | A | 318 | 5.083 | -16.205 | 49.809 | 1.00 | 54.87 | O |
| ATOM | 802 | C | ASP | A | 318 | 4.042 | -14.551 | 45.412 | 1.00 | 54.24 | C |
| ATOM | 803 | O | ASP | A | 318 | 2.909 | -14.259 | 45.049 | 1.00 | 54.29 | O |
| ATOM | 804 | N | ARG | A | 319 | 4.882 | -15.240 | 44.646 | 1.00 | 55.29 | N |
| ATOM | 805 | CA | ARG | A | 319 | 4.437 | -15.726 | 43.350 | 1.00 | 56.30 | C |
| ATOM | 806 | CB | ARG | A | 319 | 5.476 | -16.615 | 42.681 | 1.00 | 56.34 | C |

| | | | | | | | | | |
|---|---|---|---|---|---|---|---|---|---|
| ATOM | 807 | CG | ARG | A | 319 | 4.990 | -17.083 | 41.326 | 1.00 56.84 | C |
| ATOM | 808 | CD | ARG | A | 319 | 5.495 | -18.425 | 40.871 | 1.00 57.76 | C |
| ATOM | 809 | NE | ARG | A | 319 | 4.754 | -18.844 | 39.687 | 1.00 58.64 | N |
| ATOM | 810 | CZ | ARG | A | 319 | 4.443 | -20.099 | 39.405 | 1.00 58.88 | C |
| ATOM | 811 | NH1 | ARG | A | 319 | 4.825 | -21.073 | 40.218 | 1.00 59.13 | N |
| ATOM | 812 | NH2 | ARG | A | 319 | 3.756 | -20.380 | 38.306 | 1.00 58.88 | N |
| ATOM | 813 | C | ARG | A | 319 | 3.179 | -16.544 | 43.551 | 1.00 56.95 | C |
| ATOM | 814 | O | ARG | A | 319 | 2.147 | -16.271 | 42.948 | 1.00 56.98 | O |
| ATOM | 815 | N | ASP | A | 320 | 3.274 | -17.541 | 44.423 | 1.00 57.83 | N |
| ATOM | 816 | CA | ASP | A | 320 | 2.156 | -18.428 | 44.702 | 1.00 58.78 | C |
| ATOM | 817 | CB | ASP | A | 320 | 2.514 | -19.385 | 45.844 | 1.00 58.89 | C |
| ATOM | 818 | CG | ASP | A | 320 | 3.433 | -20.519 | 45.395 | 1.00 59.37 | C |
| ATOM | 819 | OD1 | ASP | A | 320 | 3.454 | -20.826 | 44.182 | 1.00 59.96 | O |
| ATOM | 820 | OD2 | ASP | A | 320 | 4.167 | -21.165 | 46.178 | 1.00 59.69 | O |
| ATOM | 821 | C | ASP | A | 320 | 0.853 | -17.687 | 45.013 | 1.00 59.26 | C |
| ATOM | 822 | O | ASP | A | 320 | -0.231 | -18.104 | 44.597 | 1.00 59.28 | O |
| ATOM | 823 | N | GLU | A | 321 | 0.966 | -16.573 | 45.723 | 1.00 59.95 | N |
| ATOM | 824 | CA | GLU | A | 321 | -0.209 | -15.815 | 46.139 | 1.00 60.60 | C |
| ATOM | 825 | CB | GLU | A | 321 | 0.199 | -14.608 | 46.973 | 1.00 60.65 | C |
| ATOM | 826 | CG | GLU | A | 321 | 0.872 | -14.969 | 48.284 | 1.00 61.19 | C |
| ATOM | 827 | CD | GLU | A | 321 | 0.992 | -13.776 | 49.216 | 1.00 61.94 | C |
| ATOM | 828 | OE1 | GLU | A | 321 | -0.024 | -13.430 | 49.862 | 1.00 62.06 | O |
| ATOM | 829 | OE2 | GLU | A | 321 | 2.094 | -13.179 | 49.297 | 1.00 62.06 | O |
| ATOM | 830 | C | GLU | A | 321 | -1.067 | -15.363 | 44.978 | 1.00 60.89 | C |
| ATOM | 831 | O | GLU | A | 321 | -2.186 | -14.903 | 45.172 | 1.00 60.92 | O |
| ATOM | 832 | N | GLY | A | 322 | -0.537 | -15.486 | 43.772 | 1.00 61.28 | N |
| ATOM | 833 | CA | GLY | A | 322 | -1.292 | -15.124 | 42.593 | 1.00 61.82 | C |
| ATOM | 834 | C | GLY | A | 322 | -2.365 | -16.156 | 42.312 | 1.00 62.17 | C |
| ATOM | 835 | O | GLY | A | 322 | -3.327 | -15.886 | 41.594 | 1.00 62.23 | O |
| ATOM | 836 | N | LYS | A | 323 | -2.200 | -17.347 | 42.878 | 1.00 62.47 | N |
| ATOM | 837 | CA | LYS | A | 323 | -3.186 | -18.402 | 42.701 | 1.00 62.87 | C |
| ATOM | 838 | CB | LYS | A | 323 | -2.849 | -19.606 | 43.585 | 1.00 62.96 | C |
| ATOM | 839 | CG | LYS | A | 323 | -1.621 | -20.397 | 43.139 | 1.00 63.17 | C |
| ATOM | 840 | CD | LYS | A | 323 | -1.298 | -21.547 | 44.095 | 1.00 63.39 | C |
| ATOM | 841 | CE | LYS | A | 323 | 0.119 | -22.058 | 43.861 | 1.00 63.52 | C |
| ATOM | 842 | NZ | LYS | A | 323 | 0.479 | -23.204 | 44.738 | 1.00 63.74 | N |
| ATOM | 843 | C | LYS | A | 323 | -4.589 | -17.893 | 43.033 | 1.00 63.03 | C |
| ATOM | 844 | O | LYS | A | 323 | -5.581 | -18.342 | 42.459 | 1.00 63.10 | O |
| ATOM | 845 | N | CYS | A | 324 | -4.652 | -16.937 | 43.953 | 1.00 63.17 | N |
| ATOM | 846 | CA | CYS | A | 324 | -5.911 | -16.367 | 44.428 | 1.00 63.29 | C |
| ATOM | 847 | CB | CYS | A | 324 | -5.633 | -15.282 | 45.469 | 1.00 63.34 | C |
| ATOM | 848 | SG | CYS | A | 324 | -4.940 | -15.894 | 47.024 | 1.00 63.93 | S |
| ATOM | 849 | C | CYS | A | 324 | -6.853 | -15.807 | 43.360 | 1.00 63.20 | C |
| ATOM | 850 | O | CYS | A | 324 | -8.052 | -16.083 | 43.386 | 1.00 63.28 | O |
| ATOM | 851 | N | VAL | A | 325 | -6.322 | -15.013 | 42.437 | 1.00 63.01 | N |
| ATOM | 852 | CA | VAL | A | 325 | -7.152 | -14.392 | 41.413 | 1.00 62.80 | C |
| ATOM | 853 | CB | VAL | A | 325 | -6.770 | -12.923 | 41.203 | 1.00 62.85 | C |
| ATOM | 854 | CG1 | VAL | A | 325 | -7.951 | -12.142 | 40.672 | 1.00 62.99 | C |
| ATOM | 855 | CG2 | VAL | A | 325 | -6.287 | -12.315 | 42.505 | 1.00 63.02 | C |
| ATOM | 856 | C | VAL | A | 325 | -6.999 | -15.116 | 40.095 | 1.00 62.52 | C |
| ATOM | 857 | O | VAL | A | 325 | -5.901 | -15.539 | 39.746 | 1.00 62.63 | O |
| ATOM | 858 | N | GLU | A | 326 | -8.094 | -15.247 | 39.356 | 1.00 62.09 | N |
| ATOM | 859 | CA | GLU | A | 326 | -8.062 | -15.959 | 38.083 | 1.00 61.62 | C |
| ATOM | 860 | CB | GLU | A | 326 | -9.470 | -16.079 | 37.488 | 1.00 61.76 | C |
| ATOM | 865 | C | GLU | A | 326 | -7.106 | -15.340 | 37.063 | 1.00 61.16 | C |
| ATOM | 866 | O | GLU | A | 326 | -7.295 | -14.204 | 36.630 | 1.00 61.10 | O |
| ATOM | 867 | N | GLY | A | 327 | -6.077 | -16.104 | 36.703 | 1.00 60.56 | N |
| ATOM | 868 | CA | GLY | A | 327 | -5.115 | -15.711 | 35.691 | 1.00 59.79 | C |
| ATOM | 869 | C | GLY | A | 327 | -4.287 | -14.492 | 36.036 | 1.00 59.24 | C |
| ATOM | 870 | O | GLY | A | 327 | -4.136 | -13.584 | 35.218 | 1.00 59.18 | O |
| ATOM | 871 | N | ILE | A | 328 | -3.757 | -14.459 | 37.252 | 1.00 58.58 | N |

| | | | | | | | | | |
|---|---|---|---|---|---|---|---|---|---|
| ATOM | 872 | CA | ILE | A | 328 | -2.914 | -13.352 | 37.658 | 1.00 57.87 | C |
| ATOM | 873 | CB | ILE | A | 328 | -3.414 | -12.732 | 38.971 | 1.00 57.97 | C |
| ATOM | 874 | CG1 | ILE | A | 328 | -3.613 | -11.229 | 38.813 | 1.00 58.04 | C |
| ATOM | 875 | CD1 | ILE | A | 328 | -3.672 | -10.495 | 40.129 | 1.00 58.01 | C |
| ATOM | 876 | CG2 | ILE | A | 328 | -2.455 | -13.021 | 40.114 | 1.00 58.04 | C |
| ATOM | 877 | C | ILE | A | 328 | -1.515 | -13.910 | 37.816 | 1.00 57.23 | C |
| ATOM | 878 | O | ILE | A | 328 | -0.535 | -13.180 | 37.763 | 1.00 57.15 | O |
| ATOM | 879 | N | LEU | A | 329 | -1.437 | -15.223 | 37.984 | 1.00 56.46 | N |
| ATOM | 880 | CA | LEU | A | 329 | -0.161 | -15.896 | 38.125 | 1.00 55.69 | C |
| ATOM | 881 | CB | LEU | A | 329 | -0.351 | -17.375 | 38.477 | 1.00 55.87 | C |
| ATOM | 882 | CG | LEU | A | 329 | 0.922 | -18.231 | 38.461 | 1.00 56.12 | C |
| ATOM | 883 | CD1 | LEU | A | 329 | 2.094 | -17.443 | 39.013 | 1.00 56.66 | C |
| ATOM | 884 | CD2 | LEU | A | 329 | 0.745 | -19.522 | 39.227 | 1.00 56.27 | C |
| ATOM | 885 | C | LEU | A | 329 | 0.674 | -15.756 | 36.863 | 1.00 55.01 | C |
| ATOM | 886 | O | LEU | A | 329 | 1.889 | -15.643 | 36.944 | 1.00 54.94 | O |
| ATOM | 887 | N | GLU | A | 330 | 0.045 | -15.752 | 35.694 | 1.00 54.17 | N |
| ATOM | 888 | CA | GLU | A | 330 | 0.843 | -15.641 | 34.478 | 1.00 53.44 | C |
| ATOM | 889 | CB | GLU | A | 330 | 0.141 | -16.201 | 33.214 | 1.00 53.71 | C |
| ATOM | 890 | CG | GLU | A | 330 | -0.855 | -15.296 | 32.499 | 1.00 54.79 | C |
| ATOM | 891 | CD | GLU | A | 330 | -1.348 | -15.889 | 31.179 | 1.00 56.08 | C |
| ATOM | 892 | OE1 | GLU | A | 330 | -1.434 | -17.135 | 31.061 | 1.00 56.23 | O |
| ATOM | 893 | OE2 | GLU | A | 330 | -1.649 | -15.101 | 30.251 | 1.00 56.93 | O |
| ATOM | 894 | C | GLU | A | 330 | 1.373 | -14.218 | 34.338 | 1.00 52.52 | C |
| ATOM | 895 | O | GLU | A | 330 | 2.484 | -14.001 | 33.848 | 1.00 52.43 | O |
| ATOM | 896 | N | ILE | A | 331 | 0.593 | -13.256 | 34.816 | 1.00 51.36 | N |
| ATOM | 897 | CA | ILE | A | 331 | 1.044 | -11.878 | 34.845 | 1.00 50.09 | C |
| ATOM | 898 | CB | ILE | A | 331 | -0.105 | -10.920 | 35.181 | 1.00 50.16 | C |
| ATOM | 899 | CG1 | ILE | A | 331 | -1.302 | -11.147 | 34.250 | 1.00 50.05 | C |
| ATOM | 900 | CD1 | ILE | A | 331 | -1.428 | -10.100 | 33.159 | 1.00 50.07 | C |
| ATOM | 901 | CG2 | ILE | A | 331 | 0.361 | -9.476 | 35.064 | 1.00 49.76 | C |
| ATOM | 902 | C | ILE | A | 331 | 2.143 | -11.783 | 35.894 | 1.00 49.25 | C |
| ATOM | 903 | O | ILE | A | 331 | 3.231 | -11.285 | 35.619 | 1.00 49.19 | O |
| ATOM | 904 | N | PHE | A | 332 | 1.875 | -12.276 | 37.095 | 1.00 48.11 | N |
| ATOM | 905 | CA | PHE | A | 332 | 2.898 | -12.251 | 38.131 | 1.00 47.16 | C |
| ATOM | 906 | CB | PHE | A | 332 | 2.502 | -13.077 | 39.349 | 1.00 47.06 | C |
| ATOM | 907 | CG | PHE | A | 332 | 1.709 | -12.325 | 40.382 | 1.00 46.77 | C |
| ATOM | 908 | CD1 | PHE | A | 332 | 0.847 | -11.299 | 40.027 | 1.00 46.45 | C |
| ATOM | 909 | CE1 | PHE | A | 332 | 0.108 | -10.640 | 40.985 | 1.00 46.20 | C |
| ATOM | 910 | CZ | PHE | A | 332 | 0.228 | -10.996 | 42.313 | 1.00 46.14 | C |
| ATOM | 911 | CE2 | PHE | A | 332 | 1.080 | -12.010 | 42.675 | 1.00 46.09 | C |
| ATOM | 912 | CD2 | PHE | A | 332 | 1.812 | -12.669 | 41.716 | 1.00 46.40 | C |
| ATOM | 913 | C | PHE | A | 332 | 4.208 | -12.800 | 37.592 | 1.00 46.60 | C |
| ATOM | 914 | O | PHE | A | 332 | 5.268 | -12.228 | 37.847 | 1.00 46.50 | O |
| ATOM | 915 | N | ASP | A | 333 | 4.128 | -13.905 | 36.844 | 1.00 45.83 | N |
| ATOM | 916 | CA | ASP | A | 333 | 5.320 | -14.567 | 36.319 | 1.00 45.02 | C |
| ATOM | 917 | CB | ASP | A | 333 | 5.001 | -15.972 | 35.830 | 1.00 45.24 | C |
| ATOM | 918 | CG | ASP | A | 333 | 5.062 | -17.009 | 36.951 | 1.00 45.64 | C |
| ATOM | 919 | OD1 | ASP | A | 333 | 5.880 | -16.841 | 37.885 | 1.00 46.05 | O |
| ATOM | 920 | OD2 | ASP | A | 333 | 4.332 | -18.025 | 36.978 | 1.00 45.75 | O |
| ATOM | 921 | C | ASP | A | 333 | 6.026 | -13.776 | 35.234 | 1.00 44.34 | C |
| ATOM | 922 | O | ASP | A | 333 | 7.246 | -13.777 | 35.162 | 1.00 44.37 | O |
| ATOM | 923 | N | MET | A | 334 | 5.263 | -13.113 | 34.379 | 1.00 43.40 | N |
| ATOM | 924 | CA | MET | A | 334 | 5.856 | -12.260 | 33.372 | 1.00 42.43 | C |
| ATOM | 925 | CB | MET | A | 334 | 4.775 | -11.688 | 32.457 | 1.00 42.46 | C |
| ATOM | 926 | CG | MET | A | 334 | 4.205 | -12.698 | 31.473 | 1.00 42.55 | C |
| ATOM | 927 | SD | MET | A | 334 | 2.685 | -12.149 | 30.682 | 1.00 42.41 | S |
| ATOM | 928 | CE | MET | A | 334 | 3.300 | -10.994 | 29.568 | 1.00 42.60 | C |
| ATOM | 929 | C | MET | A | 334 | 6.603 | -11.144 | 34.091 | 1.00 41.80 | C |
| ATOM | 930 | O | MET | A | 334 | 7.755 | -10.828 | 33.761 | 1.00 41.69 | O |
| ATOM | 931 | N | LEU | A | 335 | 5.944 | -10.555 | 35.087 | 1.00 40.95 | N |
| ATOM | 932 | CA | LEU | A | 335 | 6.557 | -9.491 | 35.866 | 1.00 40.00 | C |

| ATOM | 933 | CB | LEU A 335 | 5.572 | -8.904 | 36.878 | 1.00 | 39.86 | C |
| --- | --- | --- | --- | --- | --- | --- | --- | --- | --- |
| ATOM | 934 | CG | LEU A 335 | 4.409 | -8.071 | 36.329 | 1.00 | 39.40 | C |
| ATOM | 935 | CD1 | LEU A 335 | 3.267 | -7.930 | 37.319 | 1.00 | 38.22 | C |
| ATOM | 936 | CD2 | LEU A 335 | 4.886 | -6.720 | 35.873 | 1.00 | 39.34 | C |
| ATOM | 937 | C | LEU A 335 | 7.826 | -9.993 | 36.561 | 1.00 | 39.60 | C |
| ATOM | 938 | O | LEU A 335 | 8.807 | -9.263 | 36.655 | 1.00 | 39.50 | O |
| ATOM | 939 | N | LEU A 336 | 7.837 | -11.243 | 37.015 | 1.00 | 39.02 | N |
| ATOM | 940 | CA | LEU A 336 | 9.011 | -11.732 | 37.722 | 1.00 | 38.65 | C |
| ATOM | 941 | CB | LEU A 336 | 8.665 | -12.909 | 38.604 | 1.00 | 38.50 | C |
| ATOM | 942 | CG | LEU A 336 | 7.839 | -12.550 | 39.834 | 1.00 | 38.83 | C |
| ATOM | 943 | CD1 | LEU A 336 | 7.027 | -13.770 | 40.311 | 1.00 | 38.80 | C |
| ATOM | 944 | CD2 | LEU A 336 | 8.704 | -11.954 | 40.963 | 1.00 | 38.73 | C |
| ATOM | 945 | C | LEU A 336 | 10.141 | -12.105 | 36.791 | 1.00 | 38.46 | C |
| ATOM | 946 | O | LEU A 336 | 11.314 | -11.957 | 37.124 | 1.00 | 38.35 | O |
| ATOM | 947 | N | ALA A 337 | 9.785 | -12.596 | 35.620 | 1.00 | 38.29 | N |
| ATOM | 948 | CA | ALA A 337 | 10.789 | -12.991 | 34.664 | 1.00 | 38.10 | C |
| ATOM | 949 | CB | ALA A 337 | 10.145 | -13.684 | 33.467 | 1.00 | 37.95 | C |
| ATOM | 950 | C | ALA A 337 | 11.528 | -11.727 | 34.244 | 1.00 | 37.98 | C |
| ATOM | 951 | O | ALA A 337 | 12.755 | -11.663 | 34.265 | 1.00 | 38.11 | O |
| ATOM | 952 | N | THR A 338 | 10.783 | -10.712 | 33.866 | 1.00 | 37.70 | N |
| ATOM | 953 | CA | THR A 338 | 11.431 | -9.507 | 33.444 | 1.00 | 37.72 | C |
| ATOM | 954 | CB | THR A 338 | 10.383 | -8.524 | 32.931 | 1.00 | 37.83 | C |
| ATOM | 955 | OG1 | THR A 338 | 9.703 | -9.128 | 31.817 | 1.00 | 37.69 | O |
| ATOM | 956 | CG2 | THR A 338 | 11.050 | -7.238 | 32.356 | 1.00 | 37.19 | C |
| ATOM | 957 | C | THR A 338 | 12.271 | -8.915 | 34.585 | 1.00 | 37.82 | C |
| ATOM | 958 | O | THR A 338 | 13.410 | -8.474 | 34.376 | 1.00 | 37.84 | O |
| ATOM | 959 | N | THR A 339 | 11.723 | -8.904 | 35.796 | 1.00 | 37.69 | N |
| ATOM | 960 | CA | THR A 339 | 12.497 | -8.407 | 36.919 | 1.00 | 37.55 | C |
| ATOM | 961 | CB | THR A 339 | 11.752 | -8.643 | 38.237 | 1.00 | 37.54 | C |
| ATOM | 962 | OG1 | THR A 339 | 10.529 | -7.909 | 38.207 | 1.00 | 37.70 | O |
| ATOM | 963 | CG2 | THR A 339 | 12.487 | -8.009 | 39.409 | 1.00 | 37.19 | C |
| ATOM | 964 | C | THR A 339 | 13.855 | -9.099 | 36.915 | 1.00 | 37.56 | C |
| ATOM | 965 | O | THR A 339 | 14.886 | -8.463 | 37.092 | 1.00 | 37.57 | O |
| ATOM | 966 | N | SER A 340 | 13.859 | -10.399 | 36.664 | 1.00 | 37.62 | N |
| ATOM | 967 | CA | SER A 340 | 15.095 | -11.164 | 36.672 | 1.00 | 37.79 | C |
| ATOM | 968 | CB | SER A 340 | 14.798 | -12.651 | 36.631 | 1.00 | 37.83 | C |
| ATOM | 969 | OG | SER A 340 | 14.396 | -13.086 | 37.911 | 1.00 | 38.05 | O |
| ATOM | 970 | C | SER A 340 | 16.076 | -10.793 | 35.567 | 1.00 | 37.98 | C |
| ATOM | 971 | O | SER A 340 | 17.292 | -10.848 | 35.767 | 1.00 | 37.84 | O |
| ATOM | 972 | N | ARG A 341 | 15.568 | -10.444 | 34.392 | 1.00 | 38.21 | N |
| ATOM | 973 | CA | ARG A 341 | 16.464 | -10.019 | 33.338 | 1.00 | 38.54 | C |
| ATOM | 974 | CB | ARG A 341 | 15.698 | -9.725 | 32.053 | 1.00 | 38.78 | C |
| ATOM | 975 | CG | ARG A 341 | 14.874 | -10.895 | 31.540 | 1.00 | 40.08 | C |
| ATOM | 976 | CD | ARG A 341 | 15.690 | -12.070 | 31.052 | 1.00 | 42.16 | C |
| ATOM | 977 | NE | ARG A 341 | 16.185 | -12.886 | 32.157 | 1.00 | 44.40 | N |
| ATOM | 978 | CZ | ARG A 341 | 15.527 | -13.934 | 32.662 | 1.00 | 45.74 | C |
| ATOM | 979 | NH1 | ARG A 341 | 14.343 | -14.290 | 32.146 | 1.00 | 46.18 | N |
| ATOM | 980 | NH2 | ARG A 341 | 16.056 | -14.633 | 33.673 | 1.00 | 45.77 | N |
| ATOM | 981 | C | ARG A 341 | 17.122 | -8.767 | 33.867 | 1.00 | 38.36 | C |
| ATOM | 982 | O | ARG A 341 | 18.348 | -8.606 | 33.805 | 1.00 | 38.27 | O |
| ATOM | 983 | N | PHE A 342 | 16.295 | -7.903 | 34.435 | 1.00 | 38.26 | N |
| ATOM | 984 | CA | PHE A 342 | 16.783 | -6.666 | 35.000 | 1.00 | 38.27 | C |
| ATOM | 985 | CB | PHE A 342 | 15.635 | -5.796 | 35.511 | 1.00 | 38.33 | C |
| ATOM | 986 | CG | PHE A 342 | 15.015 | -4.941 | 34.447 | 1.00 | 38.66 | C |
| ATOM | 987 | CD1 | PHE A 342 | 15.790 | -4.098 | 33.690 | 1.00 | 39.13 | C |
| ATOM | 988 | CE1 | PHE A 342 | 15.223 | -3.313 | 32.705 | 1.00 | 39.57 | C |
| ATOM | 989 | CZ | PHE A 342 | 13.859 | -3.359 | 32.476 | 1.00 | 39.35 | C |
| ATOM | 990 | CE2 | PHE A 342 | 13.081 | -4.183 | 33.219 | 1.00 | 39.05 | C |
| ATOM | 991 | CD2 | PHE A 342 | 13.659 | -4.987 | 34.194 | 1.00 | 39.25 | C |
| ATOM | 992 | C | PHE A 342 | 17.815 | -6.935 | 36.076 | 1.00 | 38.17 | C |
| ATOM | 993 | O | PHE A 342 | 18.840 | -6.260 | 36.128 | 1.00 | 38.21 | O |

184

| | | | | | | | | | |
|---|---|---|---|---|---|---|---|---|---|
| ATOM | 994 | N | ARG | A | 343 | 17.569 | -7.921 | 36.928 | 1.00 38.08 | N |
| ATOM | 995 | CA | ARG | A | 343 | 18.577 | -8.261 | 37.929 | 1.00 38.17 | C |
| ATOM | 996 | CB | ARG | A | 343 | 18.106 | -9.365 | 38.858 | 1.00 38.12 | C |
| ATOM | 997 | CG | ARG | A | 343 | 19.072 | -9.665 | 40.004 | 1.00 38.71 | C |
| ATOM | 998 | CD | ARG | A | 343 | 18.590 | -10.786 | 40.891 | 1.00 40.20 | C |
| ATOM | 999 | NE | ARG | A | 343 | 17.133 | -10.730 | 40.903 | 1.00 42.14 | N |
| ATOM | 1000 | CZ | ARG | A | 343 | 16.328 | -11.669 | 40.418 | 1.00 42.55 | C |
| ATOM | 1001 | NH1 | ARG | A | 343 | 16.848 | -12.787 | 39.895 | 1.00 42.28 | N |
| ATOM | 1002 | NH2 | ARG | A | 343 | 15.003 | -11.479 | 40.471 | 1.00 42.19 | N |
| ATOM | 1003 | C | ARG | A | 343 | 19.851 | -8.697 | 37.242 | 1.00 38.08 | C |
| ATOM | 1004 | O | ARG | A | 343 | 20.928 | -8.258 | 37.577 | 1.00 37.97 | O |
| ATOM | 1005 | N | GLU | A | 344 | 19.714 | -9.557 | 36.253 | 1.00 38.30 | N |
| ATOM | 1006 | CA | GLU | A | 344 | 20.882 | -10.060 | 35.569 | 1.00 38.44 | C |
| ATOM | 1007 | CB | GLU | A | 344 | 20.500 | -11.157 | 34.646 | 1.00 38.54 | C |
| ATOM | 1008 | CG | GLU | A | 344 | 20.179 | -12.314 | 35.537 | 1.00 39.76 | C |
| ATOM | 1009 | CD | GLU | A | 344 | 19.237 | -13.153 | 34.879 | 1.00 41.45 | C |
| ATOM | 1010 | OE1 | GLU | A | 344 | 19.235 | -12.824 | 33.719 | 1.00 41.45 | O |
| ATOM | 1011 | OE2 | GLU | A | 344 | 18.557 | -14.033 | 35.470 | 1.00 41.90 | O |
| ATOM | 1012 | C | GLU | A | 344 | 21.633 | -8.987 | 34.861 | 1.00 38.22 | C |
| ATOM | 1013 | O | GLU | A | 344 | 22.853 | -9.067 | 34.725 | 1.00 38.15 | O |
| ATOM | 1014 | N | LEU | A | 345 | 20.922 | -7.958 | 34.436 | 1.00 37.91 | N |
| ATOM | 1015 | CA | LEU | A | 345 | 21.608 | -6.895 | 33.743 | 1.00 37.70 | C |
| ATOM | 1016 | CB | LEU | A | 345 | 20.656 | -6.168 | 32.840 | 1.00 37.85 | C |
| ATOM | 1017 | CG | LEU | A | 345 | 21.286 | -5.894 | 31.489 | 1.00 38.43 | C |
| ATOM | 1018 | CD1 | LEU | A | 345 | 20.591 | -6.743 | 30.479 | 1.00 39.20 | C |
| ATOM | 1019 | CD2 | LEU | A | 345 | 21.092 | -4.438 | 31.147 | 1.00 39.63 | C |
| ATOM | 1020 | C | LEU | A | 345 | 22.204 | -5.907 | 34.718 | 1.00 37.53 | C |
| ATOM | 1021 | O | LEU | A | 345 | 22.897 | -4.991 | 34.303 | 1.00 37.46 | O |
| ATOM | 1022 | N | LYS | A | 346 | 21.916 | -6.096 | 36.007 | 1.00 37.31 | N |
| ATOM | 1023 | CA | LYS | A | 346 | 22.383 | -5.219 | 37.075 | 1.00 37.05 | C |
| ATOM | 1024 | CB | LYS | A | 346 | 23.895 | -5.299 | 37.234 | 1.00 37.11 | C |
| ATOM | 1025 | CG | LYS | A | 346 | 24.340 | -6.487 | 38.076 | 1.00 37.75 | C |
| ATOM | 1026 | CD | LYS | A | 346 | 25.855 | -6.623 | 38.109 | 1.00 38.64 | C |
| ATOM | 1027 | CE | LYS | A | 346 | 26.271 | -7.931 | 38.751 | 1.00 39.39 | C |
| ATOM | 1028 | NZ | LYS | A | 346 | 27.712 | -7.917 | 39.173 | 1.00 40.04 | N |
| ATOM | 1029 | C | LYS | A | 346 | 21.933 | -3.775 | 36.926 | 1.00 36.83 | C |
| ATOM | 1030 | O | LYS | A | 346 | 22.683 | -2.844 | 37.182 | 1.00 36.85 | O |
| ATOM | 1031 | N | LEU | A | 347 | 20.686 | -3.597 | 36.532 | 1.00 36.62 | N |
| ATOM | 1032 | CA | LEU | A | 347 | 20.106 | -2.269 | 36.364 | 1.00 36.41 | C |
| ATOM | 1033 | CB | LEU | A | 347 | 18.603 | -2.408 | 36.154 | 1.00 36.35 | C |
| ATOM | 1034 | CG | LEU | A | 347 | 17.814 | -1.121 | 36.024 | 1.00 36.42 | C |
| ATOM | 1035 | CD1 | LEU | A | 347 | 17.996 | -0.619 | 34.623 | 1.00 36.26 | C |
| ATOM | 1036 | CD2 | LEU | A | 347 | 16.339 | -1.383 | 36.334 | 1.00 36.30 | C |
| ATOM | 1037 | C | LEU | A | 347 | 20.344 | -1.354 | 37.554 | 1.00 36.25 | C |
| ATOM | 1038 | O | LEU | A | 347 | 19.917 | -1.649 | 38.665 | 1.00 36.41 | O |
| ATOM | 1039 | N | GLN | A | 348 | 21.000 | -0.231 | 37.312 | 1.00 36.02 | N |
| ATOM | 1040 | CA | GLN | A | 348 | 21.250 | 0.743 | 38.347 | 1.00 35.88 | C |
| ATOM | 1041 | CB | GLN | A | 348 | 22.481 | 1.557 | 37.998 | 1.00 36.00 | C |
| ATOM | 1042 | CG | GLN | A | 348 | 23.784 | 0.772 | 38.003 | 1.00 37.10 | C |
| ATOM | 1043 | CD | GLN | A | 348 | 24.078 | 0.110 | 39.344 | 1.00 38.63 | C |
| ATOM | 1044 | OE1 | GLN | A | 348 | 24.672 | 0.729 | 40.246 | 1.00 39.15 | O |
| ATOM | 1045 | NE2 | GLN | A | 348 | 23.675 | -1.154 | 39.477 | 1.00 38.82 | N |
| ATOM | 1046 | C | GLN | A | 348 | 20.040 | 1.667 | 38.532 | 1.00 35.73 | C |
| ATOM | 1047 | O | GLN | A | 348 | 19.150 | 1.747 | 37.679 | 1.00 35.94 | O |
| ATOM | 1048 | N | HIS | A | 349 | 20.008 | 2.367 | 39.657 | 1.00 35.28 | N |
| ATOM | 1049 | CA | HIS | A | 349 | 18.910 | 3.254 | 39.985 | 1.00 34.77 | C |
| ATOM | 1050 | CB | HIS | A | 349 | 19.087 | 3.733 | 41.419 | 1.00 34.77 | C |
| ATOM | 1051 | CG | HIS | A | 349 | 17.997 | 4.626 | 41.904 | 1.00 34.89 | C |
| ATOM | 1052 | ND1 | HIS | A | 349 | 18.248 | 5.880 | 42.417 | 1.00 34.87 | N |
| ATOM | 1053 | CE1 | HIS | A | 349 | 17.103 | 6.439 | 42.770 | 1.00 34.70 | C |
| ATOM | 1054 | NE2 | HIS | A | 349 | 16.126 | 5.585 | 42.532 | 1.00 33.93 | N |

```
ATOM   1055  CD2 HIS A 349      16.659   4.440  41.992  1.00 34.54           C
ATOM   1056  C   HIS A 349      18.835   4.418  39.003  1.00 34.45           C
ATOM   1057  O   HIS A 349      17.768   4.754  38.520  1.00 34.42           O
ATOM   1058  N   LYS A 350      19.978   5.014  38.694  1.00 34.14           N
ATOM   1059  CA  LYS A 350      20.045   6.121  37.750  1.00 33.82           C
ATOM   1060  CB  LYS A 350      21.487   6.621  37.609  1.00 33.81           C
ATOM   1061  CG  LYS A 350      21.978   7.364  38.840  1.00 34.50           C
ATOM   1062  CD  LYS A 350      23.433   7.781  38.755  1.00 35.54           C
ATOM   1063  CE  LYS A 350      24.341   6.574  38.644  1.00 37.02           C
ATOM   1064  NZ  LYS A 350      24.167   5.659  39.805  1.00 38.25           N
ATOM   1065  C   LYS A 350      19.490   5.668  36.397  1.00 33.61           C
ATOM   1066  O   LYS A 350      18.825   6.439  35.693  1.00 33.40           O
ATOM   1067  N   GLU A 351      19.749   4.409  36.048  1.00 33.25           N
ATOM   1068  CA  GLU A 351      19.297   3.889  34.774  1.00 33.07           C
ATOM   1069  CB  GLU A 351      19.964   2.536  34.457  1.00 33.19           C
ATOM   1070  CG  GLU A 351      21.458   2.593  34.203  1.00 33.00           C
ATOM   1071  CD  GLU A 351      22.089   1.228  33.962  1.00 33.28           C
ATOM   1072  OE1 GLU A 351      21.661   0.206  34.542  1.00 32.64           O
ATOM   1073  OE2 GLU A 351      23.047   1.180  33.176  1.00 34.29           O
ATOM   1074  C   GLU A 351      17.788   3.750  34.838  1.00 32.96           C
ATOM   1075  O   GLU A 351      17.084   4.167  33.939  1.00 33.04           O
ATOM   1076  N   TYR A 352      17.293   3.154  35.914  1.00 32.84           N
ATOM   1077  CA  TYR A 352      15.864   3.049  36.130  1.00 32.65           C
ATOM   1078  CB  TYR A 352      15.595   2.367  37.467  1.00 32.85           C
ATOM   1079  CG  TYR A 352      14.321   2.789  38.134  1.00 32.80           C
ATOM   1080  CD1 TYR A 352      13.100   2.331  37.684  1.00 32.99           C
ATOM   1081  CE1 TYR A 352      11.918   2.732  38.310  1.00 33.99           C
ATOM   1082  CZ  TYR A 352      11.988   3.593  39.405  1.00 34.33           C
ATOM   1083  OH  TYR A 352      10.857   4.034  40.040  1.00 35.66           O
ATOM   1084  CE2 TYR A 352      13.200   4.060  39.858  1.00 33.34           C
ATOM   1085  CD2 TYR A 352      14.348   3.655  39.231  1.00 33.11           C
ATOM   1086  C   TYR A 352      15.149   4.420  36.055  1.00 32.46           C
ATOM   1087  O   TYR A 352      14.063   4.505  35.471  1.00 32.49           O
ATOM   1088  N   LEU A 353      15.734   5.485  36.618  1.00 31.84           N
ATOM   1089  CA  LEU A 353      15.094   6.785  36.504  1.00 31.41           C
ATOM   1090  CB  LEU A 353      15.811   7.859  37.327  1.00 31.45           C
ATOM   1091  CG  LEU A 353      15.985   7.742  38.845  1.00 31.01           C
ATOM   1092  CD1 LEU A 353      17.093   8.682  39.326  1.00 30.07           C
ATOM   1093  CD2 LEU A 353      14.692   7.952  39.577  1.00 30.25           C
ATOM   1094  C   LEU A 353      14.938   7.263  35.045  1.00 31.39           C
ATOM   1095  O   LEU A 353      13.881   7.797  34.681  1.00 31.29           O
ATOM   1096  N   CYS A 354      15.975   7.106  34.223  1.00 31.27           N
ATOM   1097  CA  CYS A 354      15.908   7.575  32.843  1.00 31.30           C
ATOM   1098  CB  CYS A 354      17.282   7.536  32.184  1.00 31.22           C
ATOM   1099  SG  CYS A 354      18.499   8.658  32.901  1.00 29.80           S
ATOM   1100  C   CYS A 354      14.921   6.740  32.034  1.00 31.71           C
ATOM   1101  O   CYS A 354      14.100   7.254  31.262  1.00 31.63           O
ATOM   1102  N   VAL A 355      15.004   5.437  32.233  1.00 32.17           N
ATOM   1103  CA  VAL A 355      14.162   4.492  31.526  1.00 32.53           C
ATOM   1104  CB  VAL A 355      14.557   3.052  31.920  1.00 32.53           C
ATOM   1105  CG1 VAL A 355      13.359   2.140  32.009  1.00 32.78           C
ATOM   1106  CG2 VAL A 355      15.573   2.527  30.958  1.00 32.06           C
ATOM   1107  C   VAL A 355      12.693   4.769  31.800  1.00 32.77           C
ATOM   1108  O   VAL A 355      11.863   4.675  30.903  1.00 32.61           O
ATOM   1109  N   LYS A 356      12.381   5.135  33.038  1.00 33.28           N
ATOM   1110  CA  LYS A 356      11.006   5.448  33.423  1.00 33.82           C
ATOM   1111  CB  LYS A 356      10.903   5.632  34.926  1.00 33.99           C
ATOM   1112  CG  LYS A 356       9.488   5.812  35.459  1.00 34.98           C
ATOM   1113  CD  LYS A 356       9.364   5.243  36.896  1.00 36.68           C
ATOM   1114  CE  LYS A 356      10.011   6.145  37.926  1.00 37.13           C
ATOM   1115  NZ  LYS A 356       8.971   6.919  38.651  1.00 38.55           N
```

```
ATOM   1116  C    LYS A 356      10.487   6.681  32.708  1.00 33.98           C
ATOM   1117  O    LYS A 356       9.378   6.670  32.217  1.00 33.75           O
ATOM   1118  N    ALA A 357      11.303   7.731  32.635  1.00 34.53           N
ATOM   1119  CA   ALA A 357      10.930   8.961  31.931  1.00 35.09           C
ATOM   1120  CB   ALA A 357      11.926  10.081  32.223  1.00 34.92           C
ATOM   1121  C    ALA A 357      10.855   8.652  30.436  1.00 35.48           C
ATOM   1122  O    ALA A 357       9.989   9.140  29.708  1.00 35.43           O
ATOM   1123  N    MET A 358      11.765   7.803  29.997  1.00 36.18           N
ATOM   1124  CA   MET A 358      11.754   7.305  28.637  1.00 36.94           C
ATOM   1125  CB   MET A 358      12.923   6.339  28.450  1.00 36.99           C
ATOM   1126  CG   MET A 358      13.387   6.179  27.028  1.00 37.44           C
ATOM   1127  SD   MET A 358      15.129   5.728  26.984  1.00 38.11           S
ATOM   1128  CE   MET A 358      15.769   6.765  28.121  1.00 36.64           C
ATOM   1129  C    MET A 358      10.424   6.630  28.289  1.00 37.32           C
ATOM   1130  O    MET A 358       9.862   6.893  27.250  1.00 37.38           O
ATOM   1131  N    ILE A 359       9.900   5.772  29.153  1.00 38.10           N
ATOM   1132  CA   ILE A 359       8.637   5.105  28.822  1.00 38.96           C
ATOM   1133  CB   ILE A 359       8.221   4.086  29.886  1.00 38.93           C
ATOM   1134  CG1  ILE A 359       8.985   2.778  29.688  1.00 38.62           C
ATOM   1135  CD1  ILE A 359       9.141   2.006  30.952  1.00 38.65           C
ATOM   1136  CG2  ILE A 359       6.743   3.782  29.770  1.00 38.87           C
ATOM   1137  C    ILE A 359       7.518   6.083  28.589  1.00 39.69           C
ATOM   1138  O    ILE A 359       6.794   5.975  27.618  1.00 39.81           O
ATOM   1139  N    LEU A 360       7.383   7.036  29.500  1.00 40.87           N
ATOM   1140  CA   LEU A 360       6.388   8.096  29.400  1.00 41.82           C
ATOM   1141  CB   LEU A 360       6.530   9.061  30.584  1.00 41.76           C
ATOM   1142  CG   LEU A 360       5.700  10.354  30.496  1.00 41.76           C
ATOM   1143  CD1  LEU A 360       4.241  10.111  30.821  1.00 41.24           C
ATOM   1144  CD2  LEU A 360       6.269  11.431  31.410  1.00 41.56           C
ATOM   1145  C    LEU A 360       6.493   8.881  28.097  1.00 42.56           C
ATOM   1146  O    LEU A 360       5.512   9.048  27.407  1.00 42.58           O
ATOM   1147  N    LEU A 361       7.687   9.346  27.758  1.00 43.59           N
ATOM   1148  CA   LEU A 361       7.854  10.179  26.583  1.00 44.67           C
ATOM   1149  CB   LEU A 361       9.138  11.008  26.676  1.00 44.58           C
ATOM   1150  CG   LEU A 361       9.268  11.921  27.898  1.00 44.56           C
ATOM   1151  CD1  LEU A 361      10.549  12.707  27.875  1.00 43.89           C
ATOM   1152  CD2  LEU A 361       8.065  12.844  28.000  1.00 44.80           C
ATOM   1153  C    LEU A 361       7.837   9.411  25.279  1.00 45.65           C
ATOM   1154  O    LEU A 361       7.735  10.009  24.217  1.00 46.02           O
ATOM   1155  N    ASN A 362       7.939   8.094  25.331  1.00 46.73           N
ATOM   1156  CA   ASN A 362       7.932   7.324  24.098  1.00 47.85           C
ATOM   1157  CB   ASN A 362       9.123   6.352  24.073  1.00 47.89           C
ATOM   1158  CG   ASN A 362       9.121   5.439  22.838  1.00 48.48           C
ATOM   1159  OD1  ASN A 362       9.157   5.906  21.694  1.00 48.75           O
ATOM   1160  ND2  ASN A 362       9.060   4.132  23.074  1.00 48.91           N
ATOM   1161  C    ASN A 362       6.604   6.589  23.882  1.00 48.47           C
ATOM   1162  O    ASN A 362       6.554   5.565  23.213  1.00 48.77           O
ATOM   1163  N    SER A 363       5.530   7.129  24.442  1.00 49.14           N
ATOM   1164  CA   SER A 363       4.217   6.483  24.420  1.00 49.91           C
ATOM   1165  CB   SER A 363       3.412   6.943  25.635  1.00 49.97           C
ATOM   1166  OG   SER A 363       2.895   5.834  26.348  1.00 50.59           O
ATOM   1167  C    SER A 363       3.399   6.742  23.149  1.00 50.33           C
ATOM   1168  O    SER A 363       3.246   7.896  22.719  1.00 50.43           O
ATOM   1169  N    SER A 364       2.848   5.675  22.568  1.00 50.75           N
ATOM   1170  CA   SER A 364       2.065   5.819  21.337  1.00 51.16           C
ATOM   1171  CB   SER A 364       2.585   4.883  20.234  1.00 51.18           C
ATOM   1172  OG   SER A 364       1.844   3.677  20.175  1.00 50.97           O
ATOM   1173  C    SER A 364       0.550   5.632  21.528  1.00 51.43           C
ATOM   1174  O    SER A 364       0.081   4.512  21.764  1.00 51.54           O
ATOM   1175  N    ALA A 365      -0.200   6.735  21.417  1.00 51.64           N
ATOM   1176  CA   ALA A 365      -1.664   6.720  21.511  1.00 51.71           C
```

| | | | | | | | | | |
|---|---|---|---|---|---|---|---|---|---|
| ATOM | 1177 | CB | ALA | A | 365 | -2.117 | 6.383 | 22.924 | 1.00 51.69 | C |
| ATOM | 1178 | C | ALA | A | 365 | -2.270 | 8.051 | 21.062 | 1.00 51.80 | C |
| ATOM | 1179 | O | ALA | A | 365 | -3.424 | 8.111 | 20.609 | 1.00 51.85 | O |
| ATOM | 1180 | N | ALA | A | 379 | 6.912 | 18.301 | 18.375 | 1.00 57.07 | N |
| ATOM | 1181 | CA | ALA | A | 379 | 8.353 | 18.530 | 18.415 | 1.00 57.00 | C |
| ATOM | 1182 | CB | ALA | A | 379 | 8.717 | 19.805 | 17.652 | 1.00 56.99 | C |
| ATOM | 1183 | C | ALA | A | 379 | 8.864 | 18.597 | 19.853 | 1.00 56.94 | C |
| ATOM | 1184 | O | ALA | A | 379 | 10.025 | 18.293 | 20.121 | 1.00 56.99 | O |
| ATOM | 1185 | N | ALA | A | 380 | 7.997 | 18.993 | 20.776 | 1.00 56.82 | N |
| ATOM | 1186 | CA | ALA | A | 380 | 8.391 | 19.095 | 22.171 | 1.00 56.74 | C |
| ATOM | 1187 | CB | ALA | A | 380 | 7.278 | 19.722 | 22.994 | 1.00 56.76 | C |
| ATOM | 1188 | C | ALA | A | 380 | 8.776 | 17.720 | 22.716 | 1.00 56.65 | C |
| ATOM | 1189 | O | ALA | A | 380 | 9.827 | 17.564 | 23.340 | 1.00 56.69 | O |
| ATOM | 1190 | N | LEU | A | 381 | 7.927 | 16.727 | 22.465 | 1.00 56.47 | N |
| ATOM | 1191 | CA | LEU | A | 381 | 8.183 | 15.366 | 22.922 | 1.00 56.30 | C |
| ATOM | 1192 | CB | LEU | A | 381 | 7.076 | 14.433 | 22.449 | 1.00 56.31 | C |
| ATOM | 1193 | CG | LEU | A | 381 | 5.886 | 14.366 | 23.388 | 1.00 56.65 | C |
| ATOM | 1194 | CD1 | LEU | A | 381 | 4.823 | 13.448 | 22.817 | 1.00 56.97 | C |
| ATOM | 1195 | CD2 | LEU | A | 381 | 6.357 | 13.884 | 24.754 | 1.00 56.95 | C |
| ATOM | 1196 | C | LEU | A | 381 | 9.504 | 14.862 | 22.388 | 1.00 56.11 | C |
| ATOM | 1197 | O | LEU | A | 381 | 10.340 | 14.333 | 23.120 | 1.00 56.16 | O |
| ATOM | 1198 | N | THR | A | 382 | 9.686 | 15.033 | 21.092 | 1.00 55.87 | N |
| ATOM | 1199 | CA | THR | A | 382 | 10.890 | 14.566 | 20.445 | 1.00 55.63 | C |
| ATOM | 1200 | CB | THR | A | 382 | 10.836 | 14.897 | 18.952 | 1.00 55.62 | C |
| ATOM | 1201 | OG1 | THR | A | 382 | 10.362 | 13.749 | 18.240 | 1.00 55.70 | O |
| ATOM | 1202 | CG2 | THR | A | 382 | 12.237 | 15.086 | 18.398 | 1.00 55.74 | C |
| ATOM | 1203 | C | THR | A | 382 | 12.140 | 15.153 | 21.081 | 1.00 55.40 | C |
| ATOM | 1204 | O | THR | A | 382 | 13.146 | 14.458 | 21.274 | 1.00 55.38 | O |
| ATOM | 1205 | N | HIS | A | 383 | 12.069 | 16.431 | 21.423 | 1.00 55.06 | N |
| ATOM | 1206 | CA | HIS | A | 383 | 13.222 | 17.104 | 21.982 | 1.00 54.77 | C |
| ATOM | 1207 | CB | HIS | A | 383 | 12.995 | 18.605 | 22.012 | 1.00 55.04 | C |
| ATOM | 1208 | CG | HIS | A | 383 | 14.255 | 19.386 | 22.189 | 1.00 55.96 | C |
| ATOM | 1209 | ND1 | HIS | A | 383 | 15.231 | 19.443 | 21.216 | 1.00 56.86 | N |
| ATOM | 1210 | CE1 | HIS | A | 383 | 16.231 | 20.192 | 21.645 | 1.00 57.24 | C |
| ATOM | 1211 | NE2 | HIS | A | 383 | 15.941 | 20.620 | 22.863 | 1.00 57.23 | N |
| ATOM | 1212 | CD2 | HIS | A | 383 | 14.712 | 20.123 | 23.229 | 1.00 56.65 | C |
| ATOM | 1213 | C | HIS | A | 383 | 13.553 | 16.618 | 23.382 | 1.00 54.22 | C |
| ATOM | 1214 | O | HIS | A | 383 | 14.715 | 16.562 | 23.778 | 1.00 54.22 | O |
| ATOM | 1215 | N | LEU | A | 384 | 12.527 | 16.271 | 24.137 | 1.00 53.50 | N |
| ATOM | 1216 | CA | LEU | A | 384 | 12.736 | 15.819 | 25.493 | 1.00 52.83 | C |
| ATOM | 1217 | CB | LEU | A | 384 | 11.450 | 15.935 | 26.274 | 1.00 53.04 | C |
| ATOM | 1218 | CG | LEU | A | 384 | 11.371 | 17.234 | 27.065 | 1.00 53.51 | C |
| ATOM | 1219 | CD1 | LEU | A | 384 | 10.224 | 17.113 | 28.055 | 1.00 53.82 | C |
| ATOM | 1220 | CD2 | LEU | A | 384 | 12.703 | 17.485 | 27.785 | 1.00 54.24 | C |
| ATOM | 1221 | C | LEU | A | 384 | 13.243 | 14.399 | 25.564 | 1.00 52.15 | C |
| ATOM | 1222 | O | LEU | A | 384 | 14.049 | 14.059 | 26.430 | 1.00 52.16 | O |
| ATOM | 1223 | N | LEU | A | 385 | 12.752 | 13.565 | 24.662 | 1.00 51.16 | N |
| ATOM | 1224 | CA | LEU | A | 385 | 13.210 | 12.207 | 24.595 | 1.00 50.19 | C |
| ATOM | 1225 | CB | LEU | A | 385 | 12.556 | 11.511 | 23.411 | 1.00 50.36 | C |
| ATOM | 1226 | CG | LEU | A | 385 | 11.741 | 10.254 | 23.713 | 1.00 50.37 | C |
| ATOM | 1227 | CD1 | LEU | A | 385 | 11.533 | 9.473 | 22.423 | 1.00 50.29 | C |
| ATOM | 1228 | CD2 | LEU | A | 385 | 12.402 | 9.381 | 24.774 | 1.00 50.08 | C |
| ATOM | 1229 | C | LEU | A | 385 | 14.714 | 12.271 | 24.392 | 1.00 49.48 | C |
| ATOM | 1230 | O | LEU | A | 385 | 15.476 | 11.561 | 25.044 | 1.00 49.40 | O |
| ATOM | 1231 | N | ASN | A | 386 | 15.143 | 13.148 | 23.495 | 1.00 48.54 | N |
| ATOM | 1232 | CA | ASN | A | 386 | 16.561 | 13.267 | 23.212 | 1.00 47.73 | C |
| ATOM | 1233 | CB | ASN | A | 386 | 16.823 | 14.367 | 22.183 | 1.00 47.72 | C |
| ATOM | 1234 | CG | ASN | A | 386 | 16.356 | 13.980 | 20.784 | 1.00 47.71 | C |
| ATOM | 1235 | OD1 | ASN | A | 386 | 16.561 | 12.922 | 20.332 | 1.00 47.14 | O |
| ATOM | 1236 | ND2 | ASN | A | 386 | 15.743 | 14.854 | 20.124 | 1.00 47.64 | N |
| ATOM | 1237 | C | ASN | A | 386 | 17.352 | 13.506 | 24.484 | 1.00 47.10 | C |

| | | | | | | | | | |
|---|---|---|---|---|---|---|---|---|---|
| ATOM | 1238 | O | ASN | A 386 | 18.398 | 12.902 | 24.701 | 1.00 47.11 | O |
| ATOM | 1239 | N | ALA | A 387 | 16.831 | 14.376 | 25.337 | 1.00 46.25 | N |
| ATOM | 1240 | CA | ALA | A 387 | 17.503 | 14.721 | 26.577 | 1.00 45.41 | C |
| ATOM | 1241 | CB | ALA | A 387 | 16.838 | 15.917 | 27.216 | 1.00 45.46 | C |
| ATOM | 1242 | C | ALA | A 387 | 17.532 | 13.550 | 27.545 | 1.00 44.83 | C |
| ATOM | 1243 | O | ALA | A 387 | 18.563 | 13.269 | 28.160 | 1.00 44.76 | O |
| ATOM | 1244 | N | VAL | A 388 | 16.401 | 12.870 | 27.693 | 1.00 43.98 | N |
| ATOM | 1245 | CA | VAL | A 388 | 16.386 | 11.703 | 28.536 | 1.00 43.17 | C |
| ATOM | 1246 | CB | VAL | A 388 | 14.980 | 11.204 | 28.774 | 1.00 43.07 | C |
| ATOM | 1247 | CG1 | VAL | A 388 | 14.992 | 10.193 | 29.874 | 1.00 43.14 | C |
| ATOM | 1248 | CG2 | VAL | A 388 | 14.107 | 12.328 | 29.182 | 1.00 42.93 | C |
| ATOM | 1249 | C | VAL | A 388 | 17.275 | 10.639 | 27.878 | 1.00 42.79 | C |
| ATOM | 1250 | O | VAL | A 388 | 18.057 | 9.975 | 28.538 | 1.00 42.61 | O |
| ATOM | 1251 | N | THR | A 389 | 17.189 | 10.500 | 26.564 | 1.00 42.37 | N |
| ATOM | 1252 | CA | THR | A 389 | 18.041 | 9.537 | 25.885 | 1.00 42.06 | C |
| ATOM | 1253 | CB | THR | A 389 | 17.698 | 9.462 | 24.398 | 1.00 42.13 | C |
| ATOM | 1254 | OG1 | THR | A 389 | 16.329 | 9.066 | 24.250 | 1.00 42.30 | O |
| ATOM | 1255 | CG2 | THR | A 389 | 18.464 | 8.333 | 23.732 | 1.00 41.99 | C |
| ATOM | 1256 | C | THR | A 389 | 19.524 | 9.859 | 26.098 | 1.00 41.83 | C |
| ATOM | 1257 | O | THR | A 389 | 20.339 | 8.958 | 26.292 | 1.00 41.88 | O |
| ATOM | 1258 | N | ASP | A 390 | 19.879 | 11.141 | 26.069 | 1.00 41.43 | N |
| ATOM | 1259 | CA | ASP | A 390 | 21.252 | 11.529 | 26.337 | 1.00 40.98 | C |
| ATOM | 1260 | CB | ASP | A 390 | 21.477 | 13.017 | 26.101 | 1.00 41.01 | C |
| ATOM | 1261 | CG | ASP | A 390 | 21.399 | 13.406 | 24.653 | 1.00 41.13 | C |
| ATOM | 1262 | OD1 | ASP | A 390 | 21.804 | 12.615 | 23.791 | 1.00 42.07 | O |
| ATOM | 1263 | OD2 | ASP | A 390 | 20.957 | 14.508 | 24.278 | 1.00 41.39 | O |
| ATOM | 1264 | C | ASP | A 390 | 21.557 | 11.225 | 27.797 | 1.00 40.66 | C |
| ATOM | 1265 | O | ASP | A 390 | 22.681 | 10.854 | 28.149 | 1.00 40.60 | O |
| ATOM | 1266 | N | ALA | A 391 | 20.555 | 11.396 | 28.654 | 1.00 40.15 | N |
| ATOM | 1267 | CA | ALA | A 391 | 20.754 | 11.159 | 30.080 | 1.00 39.72 | C |
| ATOM | 1268 | CB | ALA | A 391 | 19.527 | 11.562 | 30.871 | 1.00 39.60 | C |
| ATOM | 1269 | C | ALA | A 391 | 21.118 | 9.704 | 30.341 | 1.00 39.54 | C |
| ATOM | 1270 | O | ALA | A 391 | 22.021 | 9.412 | 31.133 | 1.00 39.33 | O |
| ATOM | 1271 | N | LEU | A 392 | 20.425 | 8.795 | 29.653 | 1.00 39.33 | N |
| ATOM | 1272 | CA | LEU | A 392 | 20.675 | 7.375 | 29.824 | 1.00 39.07 | C |
| ATOM | 1273 | CB | LEU | A 392 | 19.610 | 6.532 | 29.131 | 1.00 38.96 | C |
| ATOM | 1274 | CG | LEU | A 392 | 19.835 | 5.018 | 29.091 | 1.00 38.54 | C |
| ATOM | 1275 | CD1 | LEU | A 392 | 19.982 | 4.466 | 30.473 | 1.00 38.36 | C |
| ATOM | 1276 | CD2 | LEU | A 392 | 18.704 | 4.323 | 28.358 | 1.00 37.97 | C |
| ATOM | 1277 | C | LEU | A 392 | 22.041 | 7.063 | 29.270 | 1.00 39.08 | C |
| ATOM | 1278 | O | LEU | A 392 | 22.796 | 6.286 | 29.856 | 1.00 39.06 | O |
| ATOM | 1279 | N | VAL | A 393 | 22.364 | 7.690 | 28.148 | 1.00 39.03 | N |
| ATOM | 1280 | CA | VAL | A 393 | 23.649 | 7.465 | 27.519 | 1.00 39.03 | C |
| ATOM | 1281 | CB | VAL | A 393 | 23.719 | 8.149 | 26.148 | 1.00 39.09 | C |
| ATOM | 1282 | CG1 | VAL | A 393 | 25.156 | 8.225 | 25.640 | 1.00 38.90 | C |
| ATOM | 1283 | CG2 | VAL | A 393 | 22.827 | 7.413 | 25.151 | 1.00 38.80 | C |
| ATOM | 1284 | C | VAL | A 393 | 24.767 | 7.925 | 28.440 | 1.00 39.16 | C |
| ATOM | 1285 | O | VAL | A 393 | 25.775 | 7.235 | 28.583 | 1.00 39.16 | O |
| ATOM | 1286 | N | TRP | A 394 | 24.566 | 9.071 | 29.090 | 1.00 39.34 | N |
| ATOM | 1287 | CA | TRP | A 394 | 25.557 | 9.636 | 30.008 | 1.00 39.51 | C |
| ATOM | 1288 | CB | TRP | A 394 | 25.159 | 11.050 | 30.456 | 1.00 39.57 | C |
| ATOM | 1289 | CG | TRP | A 394 | 26.091 | 11.647 | 31.498 | 1.00 39.42 | C |
| ATOM | 1290 | CD1 | TRP | A 394 | 27.306 | 12.231 | 31.275 | 1.00 39.39 | C |
| ATOM | 1291 | NE1 | TRP | A 394 | 27.862 | 12.644 | 32.460 | 1.00 39.08 | N |
| ATOM | 1292 | CE2 | TRP | A 394 | 27.009 | 12.330 | 33.481 | 1.00 39.25 | C |
| ATOM | 1293 | CD2 | TRP | A 394 | 25.882 | 11.704 | 32.912 | 1.00 39.12 | C |
| ATOM | 1294 | CE3 | TRP | A 394 | 24.855 | 11.293 | 33.758 | 1.00 38.67 | C |
| ATOM | 1295 | CZ3 | TRP | A 394 | 24.981 | 11.514 | 35.115 | 1.00 38.88 | C |
| ATOM | 1296 | CH2 | TRP | A 394 | 26.105 | 12.132 | 35.649 | 1.00 39.11 | C |
| ATOM | 1297 | CZ2 | TRP | A 394 | 27.130 | 12.554 | 34.850 | 1.00 39.41 | C |
| ATOM | 1298 | C | TRP | A 394 | 25.745 | 8.758 | 31.228 | 1.00 39.65 | C |

| ATOM | 1299 | O   | TRP A 394 | 26.867 | 8.512  | 31.658 | 1.00 | 39.49 | O |
| ATOM | 1300 | N   | VAL A 395 | 24.636 | 8.307  | 31.799 | 1.00 | 40.00 | N |
| ATOM | 1301 | CA  | VAL A 395 | 24.705 | 7.419  | 32.947 | 1.00 | 40.29 | C |
| ATOM | 1302 | CB  | VAL A 395 | 23.311 | 6.951  | 33.418 | 1.00 | 40.38 | C |
| ATOM | 1303 | CG1 | VAL A 395 | 23.406 | 5.621  | 34.142 | 1.00 | 40.24 | C |
| ATOM | 1304 | CG2 | VAL A 395 | 22.650 | 8.001  | 34.321 | 1.00 | 40.33 | C |
| ATOM | 1305 | C   | VAL A 395 | 25.545 | 6.211  | 32.573 | 1.00 | 40.56 | C |
| ATOM | 1306 | O   | VAL A 395 | 26.576 | 5.954  | 33.204 | 1.00 | 40.71 | O |
| ATOM | 1307 | N   | ILE A 396 | 25.132 | 5.491  | 31.529 | 1.00 | 40.70 | N |
| ATOM | 1308 | CA  | ILE A 396 | 25.857 | 4.298  | 31.107 | 1.00 | 40.92 | C |
| ATOM | 1309 | CB  | ILE A 396 | 25.222 | 3.659  | 29.836 | 1.00 | 40.89 | C |
| ATOM | 1310 | CG1 | ILE A 396 | 23.829 | 3.131  | 30.159 | 1.00 | 40.62 | C |
| ATOM | 1311 | CD1 | ILE A 396 | 23.100 | 2.630  | 28.977 | 1.00 | 40.07 | C |
| ATOM | 1312 | CG2 | ILE A 396 | 26.089 | 2.527  | 29.287 | 1.00 | 40.34 | C |
| ATOM | 1313 | C   | ILE A 396 | 27.340 | 4.578  | 30.914 | 1.00 | 41.27 | C |
| ATOM | 1314 | O   | ILE A 396 | 28.176 | 3.803  | 31.363 | 1.00 | 41.25 | O |
| ATOM | 1315 | N   | ALA A 397 | 27.669 | 5.695  | 30.276 | 1.00 | 41.79 | N |
| ATOM | 1316 | CA  | ALA A 397 | 29.077 | 6.036  | 30.030 | 1.00 | 42.45 | C |
| ATOM | 1317 | CB  | ALA A 397 | 29.188 | 7.224  | 29.078 | 1.00 | 42.32 | C |
| ATOM | 1318 | C   | ALA A 397 | 29.869 | 6.292  | 31.320 | 1.00 | 42.87 | C |
| ATOM | 1319 | O   | ALA A 397 | 31.081 | 6.122  | 31.362 | 1.00 | 42.91 | O |
| ATOM | 1320 | N   | LYS A 398 | 29.181 | 6.689  | 32.380 | 1.00 | 43.44 | N |
| ATOM | 1321 | CA  | LYS A 398 | 29.870 | 6.936  | 33.636 | 1.00 | 43.99 | C |
| ATOM | 1322 | CB  | LYS A 398 | 28.995 | 7.752  | 34.597 | 1.00 | 44.01 | C |
| ATOM | 1327 | C   | LYS A 398 | 30.320 | 5.637  | 34.297 | 1.00 | 44.25 | C |
| ATOM | 1328 | O   | LYS A 398 | 31.182 | 5.647  | 35.161 | 1.00 | 44.35 | O |
| ATOM | 1329 | N   | SER A 399 | 29.746 | 4.516  | 33.884 | 1.00 | 44.57 | N |
| ATOM | 1330 | CA  | SER A 399 | 30.078 | 3.242  | 34.503 | 1.00 | 44.84 | C |
| ATOM | 1331 | CB  | SER A 399 | 29.034 | 2.200  | 34.169 | 1.00 | 44.82 | C |
| ATOM | 1332 | OG  | SER A 399 | 29.313 | 1.649  | 32.899 | 1.00 | 45.29 | O |
| ATOM | 1333 | C   | SER A 399 | 31.452 | 2.720  | 34.091 | 1.00 | 44.99 | C |
| ATOM | 1334 | O   | SER A 399 | 31.921 | 1.718  | 34.624 | 1.00 | 45.07 | O |
| ATOM | 1335 | N   | GLY A 400 | 32.090 | 3.371  | 33.129 | 1.00 | 45.10 | N |
| ATOM | 1336 | CA  | GLY A 400 | 33.447 | 2.993  | 32.770 | 1.00 | 45.24 | C |
| ATOM | 1337 | C   | GLY A 400 | 33.676 | 1.894  | 31.745 | 1.00 | 45.38 | C |
| ATOM | 1338 | O   | GLY A 400 | 34.775 | 1.802  | 31.194 | 1.00 | 45.46 | O |
| ATOM | 1339 | N   | ILE A 401 | 32.677 | 1.054  | 31.479 | 1.00 | 45.40 | N |
| ATOM | 1340 | CA  | ILE A 401 | 32.853 | 0.012  | 30.472 | 1.00 | 45.37 | C |
| ATOM | 1341 | CB  | ILE A 401 | 31.611 | -0.880 | 30.374 | 1.00 | 45.40 | C |
| ATOM | 1342 | CG1 | ILE A 401 | 30.415 | -0.082 | 29.846 | 1.00 | 45.50 | C |
| ATOM | 1343 | CD1 | ILE A 401 | 29.128 | -0.891 | 29.735 | 1.00 | 45.38 | C |
| ATOM | 1344 | CG2 | ILE A 401 | 31.309 | -1.518 | 31.722 | 1.00 | 45.33 | C |
| ATOM | 1345 | C   | ILE A 401 | 33.161 | 0.660  | 29.127 | 1.00 | 45.39 | C |
| ATOM | 1346 | O   | ILE A 401 | 32.927 | 1.851  | 28.943 | 1.00 | 45.31 | O |
| ATOM | 1347 | N   | SER A 402 | 33.681 | -0.115 | 28.183 | 1.00 | 45.40 | N |
| ATOM | 1348 | CA  | SER A 402 | 34.053 | 0.451  | 26.896 | 1.00 | 45.49 | C |
| ATOM | 1349 | CB  | SER A 402 | 34.890 | -0.538 | 26.108 | 1.00 | 45.55 | C |
| ATOM | 1350 | OG  | SER A 402 | 34.053 | -1.354 | 25.314 | 1.00 | 45.69 | O |
| ATOM | 1351 | C   | SER A 402 | 32.872 | 0.859  | 26.028 | 1.00 | 45.58 | C |
| ATOM | 1352 | O   | SER A 402 | 31.718 | 0.539  | 26.319 | 1.00 | 45.67 | O |
| ATOM | 1353 | N   | SER A 403 | 33.191 | 1.552  | 24.940 | 1.00 | 45.62 | N |
| ATOM | 1354 | CA  | SER A 403 | 32.213 | 1.990  | 23.948 | 1.00 | 45.60 | C |
| ATOM | 1355 | CB  | SER A 403 | 32.933 | 2.563  | 22.727 | 1.00 | 45.69 | C |
| ATOM | 1356 | OG  | SER A 403 | 32.801 | 3.966  | 22.679 | 1.00 | 46.10 | O |
| ATOM | 1357 | C   | SER A 403 | 31.296 | 0.882  | 23.461 | 1.00 | 45.42 | C |
| ATOM | 1358 | O   | SER A 403 | 30.078 | 0.988  | 23.540 | 1.00 | 45.60 | O |
| ATOM | 1359 | N   | GLN A 404 | 31.883 | -0.174 | 22.921 | 1.00 | 45.10 | N |
| ATOM | 1360 | CA  | GLN A 404 | 31.079 | -1.261 | 22.410 | 1.00 | 44.76 | C |
| ATOM | 1361 | CB  | GLN A 404 | 31.965 | -2.374 | 21.838 | 1.00 | 44.74 | C |
| ATOM | 1362 | CG  | GLN A 404 | 31.280 | -3.235 | 20.792 | 1.00 | 44.70 | C |
| ATOM | 1363 | CD  | GLN A 404 | 30.609 | -4.452 | 21.402 | 1.00 | 44.98 | C |

190

| | | | | | | | | | |
|---|---|---|---|---|---|---|---|---|---|
| ATOM | 1364 | OE1 | GLN A 404 | 30.992 | -4.902 | 22.483 | 1.00 | 45.17 | O |
| ATOM | 1365 | NE2 | GLN A 404 | 29.613 | -4.989 | 20.713 | 1.00 | 44.84 | N |
| ATOM | 1366 | C | GLN A 404 | 30.135 | -1.754 | 23.511 | 1.00 | 44.50 | C |
| ATOM | 1367 | O | GLN A 404 | 28.930 | -1.827 | 23.297 | 1.00 | 44.47 | O |
| ATOM | 1368 | N | GLN A 405 | 30.676 | -2.047 | 24.692 | 1.00 | 44.12 | N |
| ATOM | 1369 | CA | GLN A 405 | 29.852 | -2.507 | 25.809 | 1.00 | 43.84 | C |
| ATOM | 1370 | CB | GLN A 405 | 30.716 | -2.843 | 27.039 | 1.00 | 44.06 | C |
| ATOM | 1371 | CG | GLN A 405 | 31.426 | -4.216 | 26.987 | 1.00 | 45.41 | C |
| ATOM | 1372 | CD | GLN A 405 | 30.499 | -5.383 | 26.569 | 1.00 | 47.19 | C |
| ATOM | 1373 | OE1 | GLN A 405 | 29.858 | -6.021 | 27.421 | 1.00 | 47.73 | O |
| ATOM | 1374 | NE2 | GLN A 405 | 30.440 | -5.663 | 25.258 | 1.00 | 47.50 | N |
| ATOM | 1375 | C | GLN A 405 | 28.739 | -1.511 | 26.178 | 1.00 | 43.20 | C |
| ATOM | 1376 | O | GLN A 405 | 27.644 | -1.913 | 26.567 | 1.00 | 43.00 | O |
| ATOM | 1377 | N | GLN A 406 | 29.028 | -0.218 | 26.057 | 1.00 | 42.53 | N |
| ATOM | 1378 | CA | GLN A 406 | 28.047 | 0.816 | 26.369 | 1.00 | 41.95 | C |
| ATOM | 1379 | CB | GLN A 406 | 28.651 | 2.208 | 26.229 | 1.00 | 42.05 | C |
| ATOM | 1380 | CG | GLN A 406 | 29.345 | 2.726 | 27.466 | 1.00 | 42.21 | C |
| ATOM | 1381 | CD | GLN A 406 | 30.092 | 4.011 | 27.195 | 1.00 | 42.55 | C |
| ATOM | 1382 | OE1 | GLN A 406 | 29.523 | 4.956 | 26.656 | 1.00 | 42.58 | O |
| ATOM | 1383 | NE2 | GLN A 406 | 31.368 | 4.047 | 27.551 | 1.00 | 42.72 | N |
| ATOM | 1384 | C | GLN A 406 | 26.866 | 0.708 | 25.438 | 1.00 | 41.45 | C |
| ATOM | 1385 | O | GLN A 406 | 25.718 | 0.823 | 25.852 | 1.00 | 41.38 | O |
| ATOM | 1386 | N | SER A 407 | 27.156 | 0.500 | 24.163 | 1.00 | 40.84 | N |
| ATOM | 1387 | CA | SER A 407 | 26.106 | 0.345 | 23.181 | 1.00 | 40.17 | C |
| ATOM | 1388 | CB | SER A 407 | 26.677 | 0.419 | 21.777 | 1.00 | 40.21 | C |
| ATOM | 1389 | OG | SER A 407 | 26.980 | 1.762 | 21.440 | 1.00 | 40.30 | O |
| ATOM | 1390 | C | SER A 407 | 25.325 | -0.944 | 23.395 | 1.00 | 39.72 | C |
| ATOM | 1391 | O | SER A 407 | 24.108 | -0.949 | 23.263 | 1.00 | 39.95 | O |
| ATOM | 1392 | N | VAL A 408 | 25.997 | -2.034 | 23.738 | 1.00 | 38.98 | N |
| ATOM | 1393 | CA | VAL A 408 | 25.268 | -3.263 | 23.973 | 1.00 | 38.39 | C |
| ATOM | 1394 | CB | VAL A 408 | 26.188 | -4.483 | 24.171 | 1.00 | 38.35 | C |
| ATOM | 1395 | CG1 | VAL A 408 | 25.417 | -5.657 | 24.748 | 1.00 | 38.12 | C |
| ATOM | 1396 | CG2 | VAL A 408 | 26.808 | -4.875 | 22.866 | 1.00 | 38.27 | C |
| ATOM | 1397 | C | VAL A 408 | 24.334 | -3.067 | 25.156 | 1.00 | 38.13 | C |
| ATOM | 1398 | O | VAL A 408 | 23.151 | -3.399 | 25.060 | 1.00 | 38.08 | O |
| ATOM | 1399 | N | ARG A 409 | 24.855 | -2.503 | 26.248 | 1.00 | 37.79 | N |
| ATOM | 1400 | CA | ARG A 409 | 24.047 | -2.244 | 27.450 | 1.00 | 37.43 | C |
| ATOM | 1401 | CB | ARG A 409 | 24.824 | -1.456 | 28.514 | 1.00 | 37.18 | C |
| ATOM | 1402 | CG | ARG A 409 | 24.162 | -1.500 | 29.864 | 1.00 | 36.33 | C |
| ATOM | 1403 | CD | ARG A 409 | 25.011 | -1.033 | 31.020 | 1.00 | 35.01 | C |
| ATOM | 1404 | NE | ARG A 409 | 24.214 | -0.990 | 32.240 | 1.00 | 34.27 | N |
| ATOM | 1405 | CZ | ARG A 409 | 23.786 | -2.060 | 32.904 | 1.00 | 33.83 | C |
| ATOM | 1406 | NH1 | ARG A 409 | 24.090 | -3.279 | 32.480 | 1.00 | 33.23 | N |
| ATOM | 1407 | NH2 | ARG A 409 | 23.046 | -1.906 | 33.996 | 1.00 | 33.57 | N |
| ATOM | 1408 | C | ARG A 409 | 22.777 | -1.502 | 27.060 | 1.00 | 37.45 | C |
| ATOM | 1409 | O | ARG A 409 | 21.655 | -1.981 | 27.311 | 1.00 | 37.28 | O |
| ATOM | 1410 | N | LEU A 410 | 22.966 | -0.345 | 26.426 | 1.00 | 37.47 | N |
| ATOM | 1411 | CA | LEU A 410 | 21.847 | 0.460 | 25.935 | 1.00 | 37.53 | C |
| ATOM | 1412 | CB | LEU A 410 | 22.350 | 1.541 | 24.984 | 1.00 | 37.34 | C |
| ATOM | 1413 | CG | LEU A 410 | 21.251 | 2.488 | 24.519 | 1.00 | 37.02 | C |
| ATOM | 1414 | CD1 | LEU A 410 | 20.376 | 2.858 | 25.682 | 1.00 | 36.70 | C |
| ATOM | 1415 | CD2 | LEU A 410 | 21.840 | 3.730 | 23.886 | 1.00 | 36.85 | C |
| ATOM | 1416 | C | LEU A 410 | 20.814 | -0.411 | 25.214 | 1.00 | 37.69 | C |
| ATOM | 1417 | O | LEU A 410 | 19.601 | -0.331 | 25.481 | 1.00 | 37.53 | O |
| ATOM | 1418 | N | ALA A 411 | 21.311 | -1.251 | 24.313 | 1.00 | 37.77 | N |
| ATOM | 1419 | CA | ALA A 411 | 20.442 | -2.091 | 23.523 | 1.00 | 38.14 | C |
| ATOM | 1420 | CB | ALA A 411 | 21.239 | -2.799 | 22.446 | 1.00 | 38.11 | C |
| ATOM | 1421 | C | ALA A 411 | 19.650 | -3.083 | 24.373 | 1.00 | 38.42 | C |
| ATOM | 1422 | O | ALA A 411 | 18.459 | -3.256 | 24.163 | 1.00 | 38.31 | O |
| ATOM | 1423 | N | ASN A 412 | 20.317 | -3.734 | 25.323 | 1.00 | 38.93 | N |
| ATOM | 1424 | CA | ASN A 412 | 19.657 | -4.677 | 26.222 | 1.00 | 39.31 | C |

| ATOM | 1425 | CB | ASN A 412 | 20.662 | -5.377 | 27.121 | 1.00 | 39.30 | C |
|---|---|---|---|---|---|---|---|---|---|
| ATOM | 1426 | CG | ASN A 412 | 21.601 | -6.249 | 26.345 | 1.00 | 39.70 | C |
| ATOM | 1427 | OD1 | ASN A 412 | 21.243 | -6.805 | 25.319 | 1.00 | 40.03 | O |
| ATOM | 1428 | ND2 | ASN A 412 | 22.824 | -6.358 | 26.819 | 1.00 | 40.68 | N |
| ATOM | 1429 | C | ASN A 412 | 18.595 | -4.011 | 27.066 | 1.00 | 39.63 | C |
| ATOM | 1430 | O | ASN A 412 | 17.487 | -4.534 | 27.182 | 1.00 | 39.75 | O |
| ATOM | 1431 | N | LEU A 413 | 18.926 | -2.866 | 27.659 | 1.00 | 39.97 | N |
| ATOM | 1432 | CA | LEU A 413 | 17.937 | -2.123 | 28.421 | 1.00 | 40.30 | C |
| ATOM | 1433 | CB | LEU A 413 | 18.544 | -0.850 | 29.006 | 1.00 | 40.23 | C |
| ATOM | 1434 | CG | LEU A 413 | 19.626 | -1.040 | 30.061 | 1.00 | 39.77 | C |
| ATOM | 1435 | CD1 | LEU A 413 | 20.106 | 0.305 | 30.500 | 1.00 | 39.53 | C |
| ATOM | 1436 | CD2 | LEU A 413 | 19.100 | -1.822 | 31.234 | 1.00 | 39.50 | C |
| ATOM | 1437 | C | LEU A 413 | 16.714 | -1.814 | 27.548 | 1.00 | 40.71 | C |
| ATOM | 1438 | O | LEU A 413 | 15.602 | -2.191 | 27.891 | 1.00 | 40.75 | O |
| ATOM | 1439 | N | LEU A 414 | 16.908 | -1.156 | 26.411 | 1.00 | 41.27 | N |
| ATOM | 1440 | CA | LEU A 414 | 15.769 | -0.845 | 25.543 | 1.00 | 42.03 | C |
| ATOM | 1441 | CB | LEU A 414 | 16.204 | -0.005 | 24.345 | 1.00 | 41.97 | C |
| ATOM | 1442 | CG | LEU A 414 | 16.833 | 1.331 | 24.748 | 1.00 | 42.12 | C |
| ATOM | 1443 | CD1 | LEU A 414 | 17.480 | 2.000 | 23.560 | 1.00 | 42.32 | C |
| ATOM | 1444 | CD2 | LEU A 414 | 15.805 | 2.249 | 25.377 | 1.00 | 42.19 | C |
| ATOM | 1445 | C | LEU A 414 | 14.953 | -2.066 | 25.091 | 1.00 | 42.61 | C |
| ATOM | 1446 | O | LEU A 414 | 13.730 | -1.994 | 25.003 | 1.00 | 42.61 | O |
| ATOM | 1447 | N | MET A 415 | 15.612 | -3.190 | 24.811 | 1.00 | 43.46 | N |
| ATOM | 1448 | CA | MET A 415 | 14.880 | -4.390 | 24.401 | 1.00 | 44.30 | C |
| ATOM | 1449 | CB | MET A 415 | 15.812 | -5.486 | 23.898 | 1.00 | 44.24 | C |
| ATOM | 1450 | CG | MET A 415 | 16.527 | -5.125 | 22.603 | 1.00 | 44.48 | C |
| ATOM | 1451 | SD | MET A 415 | 17.395 | -6.508 | 21.838 | 1.00 | 44.69 | S |
| ATOM | 1452 | CE | MET A 415 | 18.920 | -5.806 | 21.526 | 1.00 | 44.81 | C |
| ATOM | 1453 | C | MET A 415 | 13.957 | -4.902 | 25.506 | 1.00 | 44.92 | C |
| ATOM | 1454 | O | MET A 415 | 12.843 | -5.331 | 25.240 | 1.00 | 44.96 | O |
| ATOM | 1455 | N | LEU A 416 | 14.417 | -4.851 | 26.746 | 1.00 | 45.75 | N |
| ATOM | 1456 | CA | LEU A 416 | 13.549 | -5.193 | 27.864 | 1.00 | 46.54 | C |
| ATOM | 1457 | CB | LEU A 416 | 14.303 | -5.135 | 29.192 | 1.00 | 46.47 | C |
| ATOM | 1458 | CG | LEU A 416 | 15.599 | -5.928 | 29.358 | 1.00 | 46.39 | C |
| ATOM | 1459 | CD1 | LEU A 416 | 15.720 | -6.433 | 30.787 | 1.00 | 46.27 | C |
| ATOM | 1460 | CD2 | LEU A 416 | 15.660 | -7.079 | 28.408 | 1.00 | 46.69 | C |
| ATOM | 1461 | C | LEU A 416 | 12.334 | -4.250 | 27.934 | 1.00 | 47.14 | C |
| ATOM | 1462 | O | LEU A 416 | 11.231 | -4.684 | 28.277 | 1.00 | 47.55 | O |
| ATOM | 1463 | N | LEU A 417 | 12.507 | -2.972 | 27.616 | 1.00 | 47.58 | N |
| ATOM | 1464 | CA | LEU A 417 | 11.358 | -2.075 | 27.664 | 1.00 | 48.15 | C |
| ATOM | 1465 | CB | LEU A 417 | 11.729 | -0.653 | 27.258 | 1.00 | 48.21 | C |
| ATOM | 1466 | CG | LEU A 417 | 12.529 | 0.146 | 28.280 | 1.00 | 48.63 | C |
| ATOM | 1467 | CD1 | LEU A 417 | 12.201 | 1.622 | 28.079 | 1.00 | 49.12 | C |
| ATOM | 1468 | CD2 | LEU A 417 | 12.215 | -0.302 | 29.712 | 1.00 | 48.49 | C |
| ATOM | 1469 | C | LEU A 417 | 10.194 | -2.562 | 26.800 | 1.00 | 48.46 | C |
| ATOM | 1470 | O | LEU A 417 | 9.035 | -2.212 | 27.063 | 1.00 | 48.68 | O |
| ATOM | 1471 | N | SER A 418 | 10.496 | -3.357 | 25.770 | 1.00 | 48.67 | N |
| ATOM | 1472 | CA | SER A 418 | 9.459 | -3.864 | 24.868 | 1.00 | 48.82 | C |
| ATOM | 1473 | CB | SER A 418 | 10.080 | -4.504 | 23.636 | 1.00 | 48.83 | C |
| ATOM | 1474 | OG | SER A 418 | 11.182 | -3.751 | 23.179 | 1.00 | 49.42 | O |
| ATOM | 1475 | C | SER A 418 | 8.603 | -4.883 | 25.587 | 1.00 | 48.86 | C |
| ATOM | 1476 | O | SER A 418 | 7.383 | -4.933 | 25.424 | 1.00 | 48.76 | O |
| ATOM | 1477 | N | HIS A 419 | 9.263 | -5.698 | 26.392 | 1.00 | 48.99 | N |
| ATOM | 1478 | CA | HIS A 419 | 8.577 | -6.697 | 27.174 | 1.00 | 49.27 | C |
| ATOM | 1479 | CB | HIS A 419 | 9.599 | -7.579 | 27.864 | 1.00 | 49.31 | C |
| ATOM | 1480 | CG | HIS A 419 | 10.649 | -8.085 | 26.931 | 1.00 | 49.87 | C |
| ATOM | 1481 | ND1 | HIS A 419 | 11.529 | -9.088 | 27.265 | 1.00 | 50.25 | N |
| ATOM | 1482 | CE1 | HIS A 419 | 12.331 | -9.322 | 26.243 | 1.00 | 50.19 | C |
| ATOM | 1483 | NE2 | HIS A 419 | 11.998 | -8.515 | 25.254 | 1.00 | 50.09 | N |
| ATOM | 1484 | CD2 | HIS A 419 | 10.940 | -7.740 | 25.654 | 1.00 | 50.24 | C |
| ATOM | 1485 | C | HIS A 419 | 7.667 | -6.025 | 28.171 | 1.00 | 49.34 | C |

| | | | | | | | | | |
|---|---|---|---|---|---|---|---|---|---|
| ATOM | 1486 | O | HIS | A | 419 | 6.598 | -6.530 | 28.473 | 1.00 49.25 | O |
| ATOM | 1487 | N | VAL | A | 420 | 8.088 | -4.874 | 28.679 | 1.00 49.52 | N |
| ATOM | 1488 | CA | VAL | A | 420 | 7.259 | -4.169 | 29.631 | 1.00 49.72 | C |
| ATOM | 1489 | CB | VAL | A | 420 | 7.977 | -2.959 | 30.214 | 1.00 49.78 | C |
| ATOM | 1490 | CG1 | VAL | A | 420 | 6.975 | -1.943 | 30.728 | 1.00 49.65 | C |
| ATOM | 1491 | CG2 | VAL | A | 420 | 8.905 | -3.415 | 31.329 | 1.00 49.78 | C |
| ATOM | 1492 | C | VAL | A | 420 | 5.988 | -3.763 | 28.925 | 1.00 49.85 | C |
| ATOM | 1493 | O | VAL | A | 420 | 4.895 | -4.099 | 29.363 | 1.00 49.89 | O |
| ATOM | 1494 | N | ARG | A | 421 | 6.149 | -3.063 | 27.811 | 1.00 50.02 | N |
| ATOM | 1495 | CA | ARG | A | 421 | 5.031 | -2.659 | 26.975 | 1.00 50.20 | C |
| ATOM | 1496 | CB | ARG | A | 421 | 5.564 | -2.199 | 25.618 | 1.00 50.40 | C |
| ATOM | 1497 | CG | ARG | A | 421 | 4.540 | -2.119 | 24.515 | 1.00 51.39 | C |
| ATOM | 1498 | CD | ARG | A | 421 | 3.551 | -1.021 | 24.703 | 1.00 53.57 | C |
| ATOM | 1499 | NE | ARG | A | 421 | 4.212 | 0.191 | 25.162 | 1.00 55.72 | N |
| ATOM | 1500 | CZ | ARG | A | 421 | 4.313 | 1.302 | 24.446 | 1.00 57.02 | C |
| ATOM | 1501 | NH1 | ARG | A | 421 | 3.786 | 1.355 | 23.228 | 1.00 57.57 | N |
| ATOM | 1502 | NH2 | ARG | A | 421 | 4.935 | 2.362 | 24.952 | 1.00 57.70 | N |
| ATOM | 1503 | C | ARG | A | 421 | 4.088 | -3.838 | 26.795 | 1.00 50.01 | C |
| ATOM | 1504 | O | ARG | A | 421 | 2.871 | -3.707 | 26.840 | 1.00 50.01 | O |
| ATOM | 1505 | N | HIS | A | 422 | 4.661 | -5.010 | 26.609 | 1.00 49.93 | N |
| ATOM | 1506 | CA | HIS | A | 422 | 3.844 | -6.182 | 26.380 | 1.00 49.78 | C |
| ATOM | 1507 | CB | HIS | A | 422 | 4.704 | -7.374 | 25.977 | 1.00 49.81 | C |
| ATOM | 1508 | CG | HIS | A | 422 | 3.913 | -8.584 | 25.624 | 1.00 49.76 | C |
| ATOM | 1509 | ND1 | HIS | A | 422 | 3.085 | -8.630 | 24.523 | 1.00 50.13 | N |
| ATOM | 1510 | CE1 | HIS | A | 422 | 2.503 | -9.814 | 24.465 | 1.00 50.09 | C |
| ATOM | 1511 | NE2 | HIS | A | 422 | 2.922 | -10.535 | 25.491 | 1.00 50.15 | N |
| ATOM | 1512 | CD2 | HIS | A | 422 | 3.808 | -9.789 | 26.230 | 1.00 49.73 | C |
| ATOM | 1513 | C | HIS | A | 422 | 3.025 | -6.508 | 27.605 | 1.00 49.68 | C |
| ATOM | 1514 | O | HIS | A | 422 | 1.810 | -6.522 | 27.532 | 1.00 49.69 | O |
| ATOM | 1515 | N | ILE | A | 423 | 3.695 | -6.750 | 28.729 | 1.00 49.66 | N |
| ATOM | 1516 | CA | ILE | A | 423 | 3.028 | -7.109 | 29.981 | 1.00 49.65 | C |
| ATOM | 1517 | CB | ILE | A | 423 | 4.047 | -7.256 | 31.101 | 1.00 49.51 | C |
| ATOM | 1518 | CG1 | ILE | A | 423 | 5.159 | -8.199 | 30.682 | 1.00 49.30 | C |
| ATOM | 1519 | CD1 | ILE | A | 423 | 6.305 | -8.232 | 31.668 | 1.00 48.84 | C |
| ATOM | 1520 | CG2 | ILE | A | 423 | 3.382 | -7.741 | 32.375 | 1.00 49.23 | C |
| ATOM | 1521 | C | ILE | A | 423 | 1.981 | -6.095 | 30.409 | 1.00 49.89 | C |
| ATOM | 1522 | O | ILE | A | 423 | 1.011 | -6.436 | 31.060 | 1.00 49.69 | O |
| ATOM | 1523 | N | SER | A | 424 | 2.198 | -4.841 | 30.058 | 1.00 50.37 | N |
| ATOM | 1524 | CA | SER | A | 424 | 1.245 | -3.805 | 30.372 | 1.00 50.98 | C |
| ATOM | 1525 | CB | SER | A | 424 | 1.791 | -2.451 | 29.937 | 1.00 50.98 | C |
| ATOM | 1526 | OG | SER | A | 424 | 0.780 | -1.461 | 29.948 | 1.00 51.46 | O |
| ATOM | 1527 | C | SER | A | 424 | -0.093 | -4.103 | 29.701 | 1.00 51.37 | C |
| ATOM | 1528 | O | SER | A | 424 | -1.142 | -4.063 | 30.345 | 1.00 51.39 | O |
| ATOM | 1529 | N | ASN | A | 425 | -0.058 | -4.422 | 28.413 | 1.00 52.00 | N |
| ATOM | 1530 | CA | ASN | A | 425 | -1.285 | -4.764 | 27.698 | 1.00 52.58 | C |
| ATOM | 1531 | CB | ASN | A | 425 | -1.001 | -5.102 | 26.238 | 1.00 52.48 | C |
| ATOM | 1532 | CG | ASN | A | 425 | -0.488 | -3.906 | 25.448 | 1.00 52.28 | C |
| ATOM | 1533 | OD1 | ASN | A | 425 | -0.821 | -2.759 | 25.738 | 1.00 52.36 | O |
| ATOM | 1534 | ND2 | ASN | A | 425 | 0.320 | -4.176 | 24.441 | 1.00 51.51 | N |
| ATOM | 1535 | C | ASN | A | 425 | -2.044 | -5.900 | 28.375 | 1.00 53.11 | C |
| ATOM | 1536 | O | ASN | A | 425 | -3.246 | -5.794 | 28.607 | 1.00 53.18 | O |
| ATOM | 1537 | N | LYS | A | 426 | -1.347 | -6.980 | 28.707 | 1.00 53.82 | N |
| ATOM | 1538 | CA | LYS | A | 426 | -1.992 | -8.103 | 29.384 | 1.00 54.61 | C |
| ATOM | 1539 | CB | LYS | A | 426 | -1.022 | -9.275 | 29.561 | 1.00 54.52 | C |
| ATOM | 1544 | C | LYS | A | 426 | -2.595 | -7.684 | 30.730 | 1.00 55.22 | C |
| ATOM | 1545 | O | LYS | A | 426 | -3.603 | -8.231 | 31.159 | 1.00 55.28 | O |
| ATOM | 1546 | N | GLY | A | 427 | -1.986 | -6.699 | 31.381 | 1.00 56.00 | N |
| ATOM | 1547 | CA | GLY | A | 427 | -2.467 | -6.232 | 32.664 | 1.00 57.03 | C |
| ATOM | 1548 | C | GLY | A | 427 | -3.665 | -5.336 | 32.483 | 1.00 57.85 | C |
| ATOM | 1549 | O | GLY | A | 427 | -4.612 | -5.366 | 33.270 | 1.00 57.78 | O |
| ATOM | 1550 | N | MET | A | 428 | -3.607 | -4.525 | 31.436 | 1.00 58.74 | N |

| ATOM | 1551 | CA | MET | A | 428 | -4.705 | -3.652 | 31.092 | 1.00 | 59.76 | C |
|------|------|-----|-----|---|-----|--------|--------|--------|------|-------|---|
| ATOM | 1552 | CB | MET | A | 428 | -4.389 | -2.917 | 29.801 | 1.00 | 59.63 | C |
| ATOM | 1553 | CG | MET | A | 428 | -3.448 | -1.764 | 29.945 | 1.00 | 59.57 | C |
| ATOM | 1554 | SD | MET | A | 428 | -4.319 | -0.355 | 30.552 | 1.00 | 59.45 | S |
| ATOM | 1555 | CE | MET | A | 428 | -3.546 | 0.895 | 29.600 | 1.00 | 59.62 | C |
| ATOM | 1556 | C | MET | A | 428 | -5.924 | -4.506 | 30.856 | 1.00 | 60.58 | C |
| ATOM | 1557 | O | MET | A | 428 | -6.970 | -4.319 | 31.469 | 1.00 | 60.76 | O |
| ATOM | 1558 | N | GLU | A | 429 | -5.781 | -5.461 | 29.952 | 1.00 | 61.67 | N |
| ATOM | 1559 | CA | GLU | A | 429 | -6.906 | -6.299 | 29.587 | 1.00 | 62.69 | C |
| ATOM | 1560 | CB | GLU | A | 429 | -6.625 | -7.117 | 28.314 | 1.00 | 62.71 | C |
| ATOM | 1561 | CG | GLU | A | 429 | -5.972 | -8.475 | 28.518 | 1.00 | 63.06 | C |
| ATOM | 1562 | CD | GLU | A | 429 | -5.637 | -9.153 | 27.197 | 1.00 | 63.43 | C |
| ATOM | 1563 | OE1 | GLU | A | 429 | -4.614 | -8.791 | 26.573 | 1.00 | 63.33 | O |
| ATOM | 1564 | OE2 | GLU | A | 429 | -6.404 | -10.045 | 26.775 | 1.00 | 63.61 | O |
| ATOM | 1565 | C | GLU | A | 429 | -7.314 | -7.169 | 30.755 | 1.00 | 63.32 | C |
| ATOM | 1566 | O | GLU | A | 429 | -8.451 | -7.617 | 30.824 | 1.00 | 63.45 | O |
| ATOM | 1567 | N | HIS | A | 430 | -6.402 | -7.393 | 31.691 | 1.00 | 64.16 | N |
| ATOM | 1568 | CA | HIS | A | 430 | -6.769 | -8.184 | 32.852 | 1.00 | 65.06 | C |
| ATOM | 1569 | CB | HIS | A | 430 | -5.558 | -8.693 | 33.618 | 1.00 | 65.03 | C |
| ATOM | 1570 | CG | HIS | A | 430 | -5.921 | -9.583 | 34.763 | 1.00 | 65.12 | C |
| ATOM | 1571 | ND1 | HIS | A | 430 | -6.308 | -9.093 | 35.991 | 1.00 | 65.14 | N |
| ATOM | 1572 | CE1 | HIS | A | 430 | -6.574 | -10.102 | 36.800 | 1.00 | 65.22 | C |
| ATOM | 1573 | NE2 | HIS | A | 430 | -6.391 | -11.229 | 36.135 | 1.00 | 65.13 | N |
| ATOM | 1574 | CD2 | HIS | A | 430 | -5.986 | -10.932 | 34.858 | 1.00 | 65.12 | C |
| ATOM | 1575 | C | HIS | A | 430 | -7.650 | -7.366 | 33.775 | 1.00 | 65.67 | C |
| ATOM | 1576 | O | HIS | A | 430 | -8.628 | -7.869 | 34.318 | 1.00 | 65.76 | O |
| ATOM | 1577 | N | LEU | A | 431 | -7.295 | -6.097 | 33.934 | 1.00 | 66.45 | N |
| ATOM | 1578 | CA | LEU | A | 431 | -8.045 | -5.186 | 34.783 | 1.00 | 67.17 | C |
| ATOM | 1579 | CB | LEU | A | 431 | -7.264 | -3.884 | 34.973 | 1.00 | 67.19 | C |
| ATOM | 1580 | CG | LEU | A | 431 | -6.923 | -3.530 | 36.419 | 1.00 | 67.23 | C |
| ATOM | 1581 | CD1 | LEU | A | 431 | -5.631 | -2.748 | 36.477 | 1.00 | 67.46 | C |
| ATOM | 1582 | CD2 | LEU | A | 431 | -8.045 | -2.756 | 37.058 | 1.00 | 67.52 | C |
| ATOM | 1583 | C | LEU | A | 431 | -9.421 | -4.919 | 34.183 | 1.00 | 67.62 | C |
| ATOM | 1584 | O | LEU | A | 431 | -10.412 | -4.827 | 34.897 | 1.00 | 67.73 | O |
| ATOM | 1585 | N | LEU | A | 432 | -9.486 | -4.805 | 32.867 | 1.00 | 68.22 | N |
| ATOM | 1586 | CA | LEU | A | 432 | -10.765 | -4.589 | 32.210 | 1.00 | 68.83 | C |
| ATOM | 1587 | CB | LEU | A | 432 | -10.552 | -4.173 | 30.751 | 1.00 | 68.96 | C |
| ATOM | 1588 | CG | LEU | A | 432 | -10.704 | -2.682 | 30.432 | 1.00 | 69.26 | C |
| ATOM | 1589 | CD1 | LEU | A | 432 | -9.813 | -2.245 | 29.272 | 1.00 | 69.44 | C |
| ATOM | 1590 | CD2 | LEU | A | 432 | -12.169 | -2.369 | 30.143 | 1.00 | 69.57 | C |
| ATOM | 1591 | C | LEU | A | 432 | -11.635 | -5.842 | 32.284 | 1.00 | 69.08 | C |
| ATOM | 1592 | O | LEU | A | 432 | -12.859 | -5.759 | 32.334 | 1.00 | 69.13 | O |
| ATOM | 1593 | N | SER | A | 433 | -10.990 | -7.002 | 32.298 | 1.00 | 69.40 | N |
| ATOM | 1594 | CA | SER | A | 433 | -11.696 | -8.272 | 32.350 | 1.00 | 69.71 | C |
| ATOM | 1595 | CB | SER | A | 433 | -10.705 | -9.434 | 32.298 | 1.00 | 69.81 | C |
| ATOM | 1596 | OG | SER | A | 433 | -11.118 | -10.487 | 33.153 | 1.00 | 70.01 | O |
| ATOM | 1597 | C | SER | A | 433 | -12.554 | -8.397 | 33.597 | 1.00 | 69.79 | C |
| ATOM | 1598 | O | SER | A | 433 | -13.564 | -9.094 | 33.591 | 1.00 | 69.88 | O |
| ATOM | 1599 | N | MET | A | 434 | -12.127 | -7.748 | 34.678 | 1.00 | 69.81 | N |
| ATOM | 1600 | CA | MET | A | 434 | -12.885 | -7.743 | 35.926 | 1.00 | 69.85 | C |
| ATOM | 1601 | CB | MET | A | 434 | -11.963 | -7.837 | 37.136 | 1.00 | 69.92 | C |
| ATOM | 1602 | CG | MET | A | 434 | -12.069 | -9.166 | 37.856 | 1.00 | 70.06 | C |
| ATOM | 1603 | SD | MET | A | 434 | -10.453 | -9.689 | 38.370 | 1.00 | 70.45 | S |
| ATOM | 1604 | CE | MET | A | 434 | -9.543 | -9.055 | 37.071 | 1.00 | 70.16 | C |
| ATOM | 1605 | C | MET | A | 434 | -13.775 | -6.510 | 36.023 | 1.00 | 69.80 | C |
| ATOM | 1606 | O | MET | A | 434 | -14.848 | -6.548 | 36.636 | 1.00 | 69.86 | O |
| ATOM | 1607 | N | LYS | A | 435 | -13.332 | -5.418 | 35.409 | 1.00 | 69.62 | N |
| ATOM | 1608 | CA | LYS | A | 435 | -14.116 | -4.195 | 35.412 | 1.00 | 69.44 | C |
| ATOM | 1609 | CB | LYS | A | 435 | -13.392 | -3.090 | 34.658 | 1.00 | 69.47 | C |
| ATOM | 1610 | CG | LYS | A | 435 | -14.040 | -1.736 | 34.818 | 1.00 | 69.53 | C |
| ATOM | 1611 | CD | LYS | A | 435 | -13.482 | -0.739 | 33.823 | 1.00 | 69.77 | C |

| | | | | | | | | | |
|---|---|---|---|---|---|---|---|---|---|
| ATOM | 1612 | CE | LYS | A | 435 | -14.579 | 0.199 | 33.349 | 1.00 69.79 | C |
| ATOM | 1613 | NZ | LYS | A | 435 | -14.055 | 1.323 | 32.527 | 1.00 69.90 | N |
| ATOM | 1614 | C | LYS | A | 435 | -15.496 | -4.439 | 34.810 | 1.00 69.28 | C |
| ATOM | 1615 | O | LYS | A | 435 | -16.507 | -4.156 | 35.447 | 1.00 69.28 | O |
| ATOM | 1616 | N | CYS | A | 436 | -15.538 | -4.974 | 33.593 | 1.00 69.10 | N |
| ATOM | 1617 | CA | CYS | A | 436 | -16.813 | -5.292 | 32.949 | 1.00 68.96 | C |
| ATOM | 1618 | CB | CYS | A | 436 | -16.620 | -5.644 | 31.468 | 1.00 68.98 | C |
| ATOM | 1619 | SG | CYS | A | 436 | -16.018 | -4.285 | 30.437 | 1.00 69.13 | S |
| ATOM | 1620 | C | CYS | A | 436 | -17.518 | -6.440 | 33.676 | 1.00 68.79 | C |
| ATOM | 1621 | O | CYS | A | 436 | -18.685 | -6.740 | 33.403 | 1.00 68.78 | O |
| ATOM | 1622 | N | ALA | A | 437 | -16.800 | -7.082 | 34.595 | 1.00 68.53 | N |
| ATOM | 1623 | CA | ALA | A | 437 | -17.359 | -8.178 | 35.379 | 1.00 68.28 | C |
| ATOM | 1624 | CB | ALA | A | 437 | -16.371 | -9.326 | 35.480 | 1.00 68.26 | C |
| ATOM | 1625 | C | ALA | A | 437 | -17.746 | -7.688 | 36.767 | 1.00 68.08 | C |
| ATOM | 1626 | O | ALA | A | 437 | -18.468 | -8.371 | 37.490 | 1.00 68.08 | O |
| ATOM | 1627 | N | ASN | A | 438 | -17.243 | -6.509 | 37.132 | 1.00 67.81 | N |
| ATOM | 1628 | CA | ASN | A | 438 | -17.558 | -5.878 | 38.415 | 1.00 67.51 | C |
| ATOM | 1629 | CB | ASN | A | 438 | -19.077 | -5.782 | 38.608 | 1.00 67.57 | C |
| ATOM | 1630 | CG | ASN | A | 438 | -19.689 | -4.606 | 37.868 | 1.00 67.62 | C |
| ATOM | 1631 | OD1 | ASN | A | 438 | -19.692 | -3.482 | 38.368 | 1.00 67.66 | O |
| ATOM | 1632 | ND2 | ASN | A | 438 | -20.216 | -4.862 | 36.674 | 1.00 67.69 | N |
| ATOM | 1633 | C | ASN | A | 438 | -16.923 | -6.542 | 39.637 | 1.00 67.23 | C |
| ATOM | 1634 | O | ASN | A | 438 | -17.588 | -7.262 | 40.377 | 1.00 67.22 | O |
| ATOM | 1635 | N | VAL | A | 439 | -15.635 | -6.292 | 39.846 | 1.00 66.90 | N |
| ATOM | 1636 | CA | VAL | A | 439 | -14.913 | -6.846 | 40.992 | 1.00 66.53 | C |
| ATOM | 1637 | CB | VAL | A | 439 | -14.054 | -8.062 | 40.591 | 1.00 66.58 | C |
| ATOM | 1638 | CG1 | VAL | A | 439 | -12.879 | -8.229 | 41.532 | 1.00 66.54 | C |
| ATOM | 1639 | CG2 | VAL | A | 439 | -14.899 | -9.328 | 40.558 | 1.00 66.63 | C |
| ATOM | 1640 | C | VAL | A | 439 | -14.020 | -5.763 | 41.578 | 1.00 66.21 | C |
| ATOM | 1641 | O | VAL | A | 439 | -13.798 | -5.702 | 42.790 | 1.00 66.14 | O |
| ATOM | 1642 | N | VAL | A | 440 | -13.518 | -4.912 | 40.688 | 1.00 65.80 | N |
| ATOM | 1643 | CA | VAL | A | 440 | -12.669 | -3.783 | 41.046 | 1.00 65.42 | C |
| ATOM | 1644 | CB | VAL | A | 440 | -11.849 | -3.330 | 39.827 | 1.00 65.44 | C |
| ATOM | 1645 | CG1 | VAL | A | 440 | -10.925 | -4.447 | 39.381 | 1.00 65.45 | C |
| ATOM | 1646 | CG2 | VAL | A | 440 | -12.773 | -2.956 | 38.685 | 1.00 65.57 | C |
| ATOM | 1647 | C | VAL | A | 440 | -13.538 | -2.626 | 41.533 | 1.00 65.07 | C |
| ATOM | 1648 | O | VAL | A | 440 | -14.526 | -2.274 | 40.887 | 1.00 65.00 | O |
| ATOM | 1649 | N | PRO | A | 441 | -13.172 | -2.034 | 42.668 | 1.00 64.70 | N |
| ATOM | 1650 | CA | PRO | A | 441 | -13.953 | -0.936 | 43.241 | 1.00 64.39 | C |
| ATOM | 1651 | CB | PRO | A | 441 | -13.138 | -0.495 | 44.461 | 1.00 64.40 | C |
| ATOM | 1652 | CG | PRO | A | 441 | -12.186 | -1.585 | 44.741 | 1.00 64.61 | C |
| ATOM | 1653 | CD | PRO | A | 441 | -11.983 | -2.360 | 43.469 | 1.00 64.77 | C |
| ATOM | 1654 | C | PRO | A | 441 | -14.085 | 0.225 | 42.267 | 1.00 64.05 | C |
| ATOM | 1655 | O | PRO | A | 441 | -13.655 | 0.141 | 41.116 | 1.00 64.04 | O |
| ATOM | 1656 | N | VAL | A | 442 | -14.686 | 1.307 | 42.746 | 1.00 63.66 | N |
| ATOM | 1657 | CA | VAL | A | 442 | -14.914 | 2.491 | 41.935 | 1.00 63.17 | C |
| ATOM | 1658 | CB | VAL | A | 442 | -16.383 | 2.991 | 42.076 | 1.00 63.22 | C |
| ATOM | 1659 | CG1 | VAL | A | 442 | -16.636 | 3.560 | 43.465 | 1.00 63.08 | C |
| ATOM | 1660 | CG2 | VAL | A | 442 | -16.717 | 4.018 | 41.008 | 1.00 63.29 | C |
| ATOM | 1661 | C | VAL | A | 442 | -13.928 | 3.579 | 42.342 | 1.00 62.79 | C |
| ATOM | 1662 | O | VAL | A | 442 | -14.310 | 4.610 | 42.901 | 1.00 62.73 | O |
| ATOM | 1663 | N | TYR | A | 443 | -12.647 | 3.326 | 42.092 | 1.00 62.35 | N |
| ATOM | 1664 | CA | TYR | A | 443 | -11.617 | 4.322 | 42.366 | 1.00 61.83 | C |
| ATOM | 1665 | CB | TYR | A | 443 | -10.249 | 3.673 | 42.554 | 1.00 61.76 | C |
| ATOM | 1666 | CG | TYR | A | 443 | -10.201 | 2.977 | 43.886 | 1.00 61.49 | C |
| ATOM | 1667 | CD1 | TYR | A | 443 | -10.228 | 3.709 | 45.067 | 1.00 61.19 | C |
| ATOM | 1668 | CE1 | TYR | A | 443 | -10.217 | 3.088 | 46.289 | 1.00 60.98 | C |
| ATOM | 1669 | CZ | TYR | A | 443 | -10.202 | 1.713 | 46.349 | 1.00 60.98 | C |
| ATOM | 1670 | OH | TYR | A | 443 | -10.190 | 1.083 | 47.569 | 1.00 61.01 | O |
| ATOM | 1671 | CE2 | TYR | A | 443 | -10.196 | 0.963 | 45.195 | 1.00 61.02 | C |
| ATOM | 1672 | CD2 | TYR | A | 443 | -10.205 | 1.595 | 43.971 | 1.00 61.21 | C |

195

| | | | | | | | | | |
|---|---|---|---|---|---|---|---|---|---|
| ATOM | 1673 | C | TYR | A | 443 | -11.647 | 5.352 | 41.258 | 1.00 61.55 | C |
| ATOM | 1674 | O | TYR | A | 443 | -11.115 | 5.149 | 40.175 | 1.00 61.46 | O |
| ATOM | 1675 | N | ASP | A | 444 | -12.330 | 6.447 | 41.553 | 1.00 61.25 | N |
| ATOM | 1676 | CA | ASP | A | 444 | -12.570 | 7.534 | 40.615 | 1.00 60.98 | C |
| ATOM | 1677 | CB | ASP | A | 444 | -13.058 | 8.761 | 41.388 | 1.00 61.05 | C |
| ATOM | 1678 | CG | ASP | A | 444 | -12.670 | 8.703 | 42.856 | 1.00 61.24 | C |
| ATOM | 1679 | OD1 | ASP | A | 444 | -11.448 | 8.667 | 43.147 | 1.00 61.05 | O |
| ATOM | 1680 | OD2 | ASP | A | 444 | -13.519 | 8.657 | 43.779 | 1.00 61.48 | O |
| ATOM | 1681 | C | ASP | A | 444 | -11.401 | 7.883 | 39.687 | 1.00 60.66 | C |
| ATOM | 1682 | O | ASP | A | 444 | -11.600 | 8.102 | 38.494 | 1.00 60.61 | O |
| ATOM | 1683 | N | LEU | A | 445 | -10.186 | 7.943 | 40.211 | 1.00 60.32 | N |
| ATOM | 1684 | CA | LEU | A | 445 | -9.065 | 8.313 | 39.356 | 1.00 59.95 | C |
| ATOM | 1685 | CB | LEU | A | 445 | -7.885 | 8.813 | 40.174 | 1.00 59.93 | C |
| ATOM | 1686 | CG | LEU | A | 445 | -6.737 | 9.283 | 39.285 | 1.00 59.75 | C |
| ATOM | 1687 | CD1 | LEU | A | 445 | -7.246 | 10.276 | 38.266 | 1.00 59.74 | C |
| ATOM | 1688 | CD2 | LEU | A | 445 | -5.637 | 9.897 | 40.107 | 1.00 59.63 | C |
| ATOM | 1689 | C | LEU | A | 445 | -8.623 | 7.176 | 38.445 | 1.00 59.78 | C |
| ATOM | 1690 | O | LEU | A | 445 | -8.232 | 7.403 | 37.300 | 1.00 59.67 | O |
| ATOM | 1691 | N | LEU | A | 446 | -8.670 | 5.955 | 38.965 | 1.00 59.57 | N |
| ATOM | 1692 | CA | LEU | A | 446 | -8.344 | 4.783 | 38.171 | 1.00 59.39 | C |
| ATOM | 1693 | CB | LEU | A | 446 | -8.325 | 3.520 | 39.036 | 1.00 59.35 | C |
| ATOM | 1694 | CG | LEU | A | 446 | -7.905 | 2.226 | 38.331 | 1.00 59.26 | C |
| ATOM | 1695 | CD1 | LEU | A | 446 | -6.554 | 2.398 | 37.683 | 1.00 59.27 | C |
| ATOM | 1696 | CD2 | LEU | A | 446 | -7.876 | 1.053 | 39.285 | 1.00 58.95 | C |
| ATOM | 1697 | C | LEU | A | 446 | -9.330 | 4.623 | 37.012 | 1.00 59.36 | C |
| ATOM | 1698 | O | LEU | A | 446 | -8.930 | 4.190 | 35.929 | 1.00 59.39 | O |
| ATOM | 1699 | N | LEU | A | 447 | -10.598 | 4.988 | 37.233 | 1.00 59.23 | N |
| ATOM | 1700 | CA | LEU | A | 447 | -11.649 | 4.848 | 36.211 | 1.00 59.20 | C |
| ATOM | 1701 | CB | LEU | A | 447 | -13.047 | 4.926 | 36.830 | 1.00 59.21 | C |
| ATOM | 1702 | CG | LEU | A | 447 | -13.414 | 3.821 | 37.817 | 1.00 59.17 | C |
| ATOM | 1703 | CD1 | LEU | A | 447 | -14.814 | 4.057 | 38.361 | 1.00 58.87 | C |
| ATOM | 1704 | CD2 | LEU | A | 447 | -13.288 | 2.448 | 37.164 | 1.00 58.99 | C |
| ATOM | 1705 | C | LEU | A | 447 | -11.559 | 5.843 | 35.061 | 1.00 59.16 | C |
| ATOM | 1706 | O | LEU | A | 447 | -11.845 | 5.500 | 33.920 | 1.00 59.14 | O |
| ATOM | 1707 | N | GLU | A | 448 | -11.187 | 7.081 | 35.365 | 1.00 59.17 | N |
| ATOM | 1708 | CA | GLU | A | 448 | -11.022 | 8.092 | 34.331 | 1.00 59.18 | C |
| ATOM | 1709 | CB | GLU | A | 448 | -10.686 | 9.449 | 34.944 | 1.00 59.18 | C |
| ATOM | 1710 | CG AGLU | A | 448 | -11.899 | 10.320 | 35.203 | 0.50 59.12 | C |
| ATOM | 1711 | CG BGLU | A | 448 | -11.849 | 10.119 | 35.652 | 0.50 59.23 | C |
| ATOM | 1712 | CD AGLU | A | 448 | -12.740 | 10.509 | 33.957 | 0.50 59.05 | C |
| ATOM | 1713 | CD BGLU | A | 448 | -11.546 | 11.558 | 36.012 | 0.50 59.32 | C |
| ATOM | 1714 | OE1AGLU | A | 448 | -12.175 | 10.871 | 32.904 | 0.50 58.95 | O |
| ATOM | 1715 | OE1BGLU | A | 448 | -10.349 | 11.919 | 36.020 | 0.50 59.41 | O |
| ATOM | 1716 | OE2AGLU | A | 448 | -13.966 | 10.288 | 34.027 | 0.50 59.03 | O |
| ATOM | 1717 | OE2BGLU | A | 448 | -12.497 | 12.325 | 36.282 | 0.50 59.18 | O |
| ATOM | 1718 | C | GLU | A | 448 | -9.941 | 7.686 | 33.338 | 1.00 59.21 | C |
| ATOM | 1719 | O | GLU | A | 448 | -10.053 | 7.973 | 32.144 | 1.00 59.22 | O |
| ATOM | 1720 | N | MET | A | 449 | -8.897 | 7.025 | 33.841 | 1.00 59.21 | N |
| ATOM | 1721 | CA | MET | A | 449 | -7.803 | 6.539 | 33.004 | 1.00 59.24 | C |
| ATOM | 1722 | CB | MET | A | 449 | -6.641 | 6.038 | 33.859 | 1.00 59.27 | C |
| ATOM | 1723 | CG | MET | A | 449 | -5.708 | 7.123 | 34.358 | 1.00 59.28 | C |
| ATOM | 1724 | SD | MET | A | 449 | -4.725 | 7.856 | 33.060 | 1.00 59.23 | S |
| ATOM | 1725 | CE | MET | A | 449 | -5.874 | 9.032 | 32.382 | 1.00 59.64 | C |
| ATOM | 1726 | C | MET | A | 449 | -8.257 | 5.421 | 32.077 | 1.00 59.28 | C |
| ATOM | 1727 | O | MET | A | 449 | -7.996 | 5.458 | 30.875 | 1.00 59.34 | O |
| ATOM | 1728 | N | LEU | A | 450 | -8.920 | 4.417 | 32.643 | 1.00 59.23 | N |
| ATOM | 1729 | CA | LEU | A | 450 | -9.453 | 3.317 | 31.852 | 1.00 59.17 | C |
| ATOM | 1730 | CB | LEU | A | 450 | -10.053 | 2.250 | 32.764 | 1.00 59.17 | C |
| ATOM | 1731 | CG | LEU | A | 450 | -9.056 | 1.592 | 33.714 | 1.00 59.17 | C |
| ATOM | 1732 | CD1 | LEU | A | 450 | -9.744 | 0.544 | 34.562 | 1.00 59.35 | C |
| ATOM | 1733 | CD2 | LEU | A | 450 | -7.922 | 0.977 | 32.929 | 1.00 59.19 | C |

196

| | | | | | | | | | |
|---|---|---|---|---|---|---|---|---|---|
| ATOM | 1734 | C | LEU | A | 450 | -10.513 | 3.835 | 30.892 | 1.00 59.13 | C |
| ATOM | 1735 | O | LEU | A | 450 | -10.349 | 3.766 | 29.679 | 1.00 59.13 | O |
| ATOM | 1736 | NI | NI | A | 1 | 0.352 | 10.986 | 48.566 | 1.00 71.09 | NI |
| ATOM | 1737 | NI | NI | A | 2 | 15.120 | -4.357 | 48.923 | 1.00 65.65 | NI |
| ATOM | 1738 | CL | CL | A | 3 | 1.333 | 12.786 | 48.185 | 1.00 75.38 | CL |
| ATOM | 1739 | CL | CL | A | 4 | -1.391 | 10.487 | 47.487 | 1.00 78.17 | CL |
| ATOM | 1740 | O16 | EPI | A | 600 | -5.284 | -6.327 | 36.854 | 1.00 73.79 | O |
| ATOM | 1741 | C16 | EPI | A | 600 | -4.312 | -6.795 | 37.762 | 1.00 72.07 | C |
| ATOM | 1742 | C17 | EPI | A | 600 | -3.056 | -7.238 | 37.012 | 1.00 71.76 | C |
| ATOM | 1743 | O17 | EPI | A | 600 | -3.097 | -6.768 | 35.683 | 1.00 70.69 | O |
| ATOM | 1744 | C13 | EPI | A | 600 | -1.927 | -6.539 | 37.740 | 1.00 71.07 | C |
| ATOM | 1745 | C12 | EPI | A | 600 | -0.677 | -6.262 | 36.932 | 1.00 70.13 | C |
| ATOM | 1746 | C18 | EPI | A | 600 | -1.575 | -7.353 | 38.977 | 1.00 70.62 | C |
| ATOM | 1747 | C14 | EPI | A | 600 | -2.568 | -5.228 | 38.113 | 1.00 70.81 | C |
| ATOM | 1748 | C15 | EPI | A | 600 | -3.912 | -5.638 | 38.672 | 1.00 71.43 | C |
| ATOM | 1749 | C8 | EPI | A | 600 | -1.665 | -4.437 | 39.027 | 1.00 70.65 | C |
| ATOM | 1750 | C7 | EPI | A | 600 | -2.349 | -3.165 | 39.505 | 1.00 70.31 | C |
| ATOM | 1751 | C9 | EPI | A | 600 | -0.410 | -4.117 | 38.234 | 1.00 70.20 | C |
| ATOM | 1752 | C11 | EPI | A | 600 | 0.262 | -5.403 | 37.765 | 1.00 69.79 | C |
| ATOM | 1753 | C10 | EPI | A | 600 | 0.509 | -3.277 | 39.107 | 1.00 69.84 | C |
| ATOM | 1754 | C5 | EPI | A | 600 | -0.059 | -2.436 | 40.230 | 1.00 68.90 | C |
| ATOM | 1755 | C6 | EPI | A | 600 | -1.533 | -2.454 | 40.574 | 1.00 68.85 | C |
| ATOM | 1756 | C4 | EPI | A | 600 | 0.836 | -1.541 | 40.934 | 1.00 68.79 | C |
| ATOM | 1757 | C3 | EPI | A | 600 | 2.174 | -1.466 | 40.579 | 1.00 67.65 | C |
| ATOM | 1758 | O3 | EPI | A | 600 | 2.982 | -0.612 | 41.272 | 1.00 65.19 | O |
| ATOM | 1759 | C2 | EPI | A | 600 | 2.692 | -2.240 | 39.550 | 1.00 68.05 | C |
| ATOM | 1760 | C1 | EPI | A | 600 | 1.924 | -3.131 | 38.810 | 1.00 68.65 | C |
| ATOM | 1761 | N | ALA | B | 217 | 34.796 | -17.379 | 13.021 | 1.00 52.03 | N |
| ATOM | 1762 | CA | ALA | B | 217 | 33.482 | -18.011 | 12.723 | 1.00 51.98 | C |
| ATOM | 1763 | CB | ALA | B | 217 | 32.815 | -18.478 | 14.013 | 1.00 52.04 | C |
| ATOM | 1764 | C | ALA | B | 217 | 32.550 | -17.085 | 11.930 | 1.00 51.90 | C |
| ATOM | 1765 | O | ALA | B | 217 | 31.937 | -17.514 | 10.945 | 1.00 52.04 | O |
| ATOM | 1766 | N | LEU | B | 218 | 32.447 | -15.823 | 12.347 | 1.00 51.65 | N |
| ATOM | 1767 | CA | LEU | B | 218 | 31.554 | -14.866 | 11.668 | 1.00 51.36 | C |
| ATOM | 1768 | CB | LEU | B | 218 | 30.155 | -15.468 | 11.533 | 1.00 51.38 | C |
| ATOM | 1769 | CG | LEU | B | 218 | 28.999 | -14.497 | 11.377 | 1.00 51.71 | C |
| ATOM | 1770 | CD1 | LEU | B | 218 | 28.616 | -14.407 | 9.916 | 1.00 52.03 | C |
| ATOM | 1771 | CD2 | LEU | B | 218 | 27.809 | -14.949 | 12.234 | 1.00 52.18 | C |
| ATOM | 1772 | C | LEU | B | 218 | 31.496 | -13.496 | 12.384 | 1.00 50.98 | C |
| ATOM | 1773 | O | LEU | B | 218 | 31.202 | -13.408 | 13.579 | 1.00 51.10 | O |
| ATOM | 1774 | N | SER | B | 219 | 31.768 | -12.427 | 11.648 | 1.00 50.35 | N |
| ATOM | 1775 | CA | SER | B | 219 | 31.833 | -11.097 | 12.247 | 1.00 49.65 | C |
| ATOM | 1776 | CB | SER | B | 219 | 33.148 | -10.425 | 11.834 | 1.00 49.71 | C |
| ATOM | 1777 | OG | SER | B | 219 | 33.129 | -10.080 | 10.454 | 1.00 49.20 | O |
| ATOM | 1778 | C | SER | B | 219 | 30.677 | -10.208 | 11.819 | 1.00 49.15 | C |
| ATOM | 1779 | O | SER | B | 219 | 29.803 | -10.627 | 11.061 | 1.00 49.19 | O |
| ATOM | 1780 | N | PRO | B | 220 | 30.697 | -8.966 | 12.283 | 1.00 48.59 | N |
| ATOM | 1781 | CA | PRO | B | 220 | 29.665 | -7.987 | 11.928 | 1.00 48.23 | C |
| ATOM | 1782 | CB | PRO | B | 220 | 30.105 | -6.729 | 12.685 | 1.00 48.31 | C |
| ATOM | 1783 | CG | PRO | B | 220 | 30.976 | -7.245 | 13.792 | 1.00 48.28 | C |
| ATOM | 1784 | CD | PRO | B | 220 | 31.705 | -8.404 | 13.195 | 1.00 48.50 | C |
| ATOM | 1785 | C | PRO | B | 220 | 29.633 | -7.712 | 10.439 | 1.00 47.84 | C |
| ATOM | 1786 | O | PRO | B | 220 | 28.562 | -7.679 | 9.848 | 1.00 47.83 | O |
| ATOM | 1787 | N | GLU | B | 221 | 30.797 | -7.522 | 9.837 | 1.00 47.46 | N |
| ATOM | 1788 | CA | GLU | B | 221 | 30.873 | -7.284 | 8.402 | 1.00 47.14 | C |
| ATOM | 1789 | CB | GLU | B | 221 | 32.310 | -7.003 | 8.005 | 1.00 47.37 | C |
| ATOM | 1790 | CG | GLU | B | 221 | 32.510 | -6.619 | 6.564 | 1.00 48.56 | C |
| ATOM | 1791 | CD | GLU | B | 221 | 33.955 | -6.796 | 6.153 | 1.00 51.00 | C |
| ATOM | 1792 | OE1 | GLU | B | 221 | 34.411 | -7.966 | 6.064 | 1.00 51.76 | O |
| ATOM | 1793 | OE2 | GLU | B | 221 | 34.646 | -5.769 | 5.933 | 1.00 52.21 | O |
| ATOM | 1794 | C | GLU | B | 221 | 30.330 | -8.483 | 7.623 | 1.00 46.54 | C |

197

| | | | | | | | | | | |
|---|---|---|---|---|---|---|---|---|---|---|
| ATOM | 1795 | O | | GLU | B | 221 | 29.540 | -8.328 | 6.692 | 1.00 46.47 | O |
| ATOM | 1796 | N | | GLN | B | 222 | 30.743 | -9.678 | 8.022 | 1.00 45.83 | N |
| ATOM | 1797 | CA | | GLN | B | 222 | 30.277 | -10.902 | 7.379 | 1.00 45.22 | C |
| ATOM | 1798 | CB | | GLN | B | 222 | 31.149 | -12.096 | 7.795 | 1.00 45.38 | C |
| ATOM | 1799 | CG | | GLN | B | 222 | 30.558 | -13.467 | 7.437 | 1.00 45.92 | C |
| ATOM | 1800 | CD | | GLN | B | 222 | 30.819 | -13.909 | 5.990 | 1.00 46.62 | C |
| ATOM | 1801 | OE1 | | GLN | B | 222 | 30.294 | -13.323 | 5.032 | 1.00 46.77 | O |
| ATOM | 1802 | NE2 | | GLN | B | 222 | 31.611 | -14.961 | 5.837 | 1.00 46.83 | N |
| ATOM | 1803 | C | | GLN | B | 222 | 28.808 | -11.179 | 7.683 | 1.00 44.51 | C |
| ATOM | 1804 | O | | GLN | B | 222 | 28.088 | -11.733 | 6.860 | 1.00 44.39 | O |
| ATOM | 1805 | N | | LEU | B | 223 | 28.369 | -10.793 | 8.872 | 1.00 43.75 | N |
| ATOM | 1806 | CA | | LEU | B | 223 | 26.976 | -10.970 | 9.251 | 1.00 42.98 | C |
| ATOM | 1807 | CB | | LEU | B | 223 | 26.783 | -10.614 | 10.719 | 1.00 42.89 | C |
| ATOM | 1808 | CG | | LEU | B | 223 | 25.476 | -11.105 | 11.339 | 1.00 42.73 | C |
| ATOM | 1809 | CD1 | | LEU | B | 223 | 25.049 | -12.429 | 10.731 | 1.00 42.49 | C |
| ATOM | 1810 | CD2 | | LEU | B | 223 | 25.582 | -11.209 | 12.852 | 1.00 42.11 | C |
| ATOM | 1811 | C | | LEU | B | 223 | 26.073 | -10.122 | 8.367 | 1.00 42.49 | C |
| ATOM | 1812 | O | | LEU | B | 223 | 25.067 | -10.596 | 7.865 | 1.00 42.48 | O |
| ATOM | 1813 | N | | VAL | B | 224 | 26.451 | -8.868 | 8.168 | 1.00 41.93 | N |
| ATOM | 1814 | CA | | VAL | B | 224 | 25.677 | -7.962 | 7.331 | 1.00 41.35 | C |
| ATOM | 1815 | CB | | VAL | B | 224 | 26.300 | -6.527 | 7.334 | 1.00 41.35 | C |
| ATOM | 1816 | CG1 | | VAL | B | 224 | 25.626 | -5.619 | 6.334 | 1.00 40.88 | C |
| ATOM | 1817 | CG2 | | VAL | B | 224 | 26.231 | -5.925 | 8.717 | 1.00 40.84 | C |
| ATOM | 1818 | C | | VAL | B | 224 | 25.638 | -8.541 | 5.932 | 1.00 41.09 | C |
| ATOM | 1819 | O | | VAL | B | 224 | 24.597 | -8.610 | 5.308 | 1.00 40.84 | O |
| ATOM | 1820 | N | | LEU | B | 225 | 26.796 | -8.982 | 5.462 | 1.00 41.02 | N |
| ATOM | 1821 | CA | | LEU | B | 225 | 26.934 | -9.554 | 4.135 | 1.00 40.98 | C |
| ATOM | 1822 | CB | | LEU | B | 225 | 28.369 | -10.012 | 3.925 | 1.00 41.07 | C |
| ATOM | 1823 | CG | | LEU | B | 225 | 28.980 | -9.685 | 2.572 | 1.00 41.44 | C |
| ATOM | 1824 | CD1 | | LEU | B | 225 | 28.741 | -8.293 | 2.238 | 1.00 41.72 | C |
| ATOM | 1825 | CD2 | | LEU | B | 225 | 30.417 | -9.863 | 2.608 | 1.00 41.55 | C |
| ATOM | 1826 | C | | LEU | B | 225 | 25.969 | -10.722 | 4.002 | 1.00 40.86 | C |
| ATOM | 1827 | O | | LEU | B | 225 | 25.174 | -10.795 | 3.076 | 1.00 40.89 | O |
| ATOM | 1828 | N | | THR | B | 226 | 26.021 | -11.628 | 4.959 | 1.00 40.86 | N |
| ATOM | 1829 | CA | | THR | B | 226 | 25.108 | -12.748 | 4.979 | 1.00 40.90 | C |
| ATOM | 1830 | CB | | THR | B | 226 | 25.333 | -13.541 | 6.229 | 1.00 40.88 | C |
| ATOM | 1831 | OG1 | | THR | B | 226 | 26.724 | -13.839 | 6.347 | 1.00 41.21 | O |
| ATOM | 1832 | CG2 | | THR | B | 226 | 24.689 | -14.879 | 6.097 | 1.00 41.02 | C |
| ATOM | 1833 | C | | THR | B | 226 | 23.662 | -12.274 | 4.974 | 1.00 40.94 | C |
| ATOM | 1834 | O | | THR | B | 226 | 22.825 | -12.811 | 4.249 | 1.00 41.13 | O |
| ATOM | 1835 | N | | LEU | B | 227 | 23.355 | -11.269 | 5.781 | 1.00 40.75 | N |
| ATOM | 1836 | CA | | LEU | B | 227 | 21.992 | -10.803 | 5.826 | 1.00 40.75 | C |
| ATOM | 1837 | CB | | LEU | B | 227 | 21.797 | -9.779 | 6.945 | 1.00 40.67 | C |
| ATOM | 1838 | CG | | LEU | B | 227 | 21.846 | -10.243 | 8.406 | 1.00 40.24 | C |
| ATOM | 1839 | CD1 | | LEU | B | 227 | 21.716 | -9.020 | 9.325 | 1.00 39.63 | C |
| ATOM | 1840 | CD2 | | LEU | B | 227 | 20.783 | -11.316 | 8.734 | 1.00 39.31 | C |
| ATOM | 1841 | C | | LEU | B | 227 | 21.531 | -10.233 | 4.490 | 1.00 40.84 | C |
| ATOM | 1842 | O | | LEU | B | 227 | 20.400 | -10.442 | 4.090 | 1.00 40.85 | O |
| ATOM | 1843 | N | | LEU | B | 228 | 22.400 | -9.502 | 3.812 | 1.00 41.11 | N |
| ATOM | 1844 | CA | | LEU | B | 228 | 22.035 | -8.897 | 2.537 | 1.00 41.47 | C |
| ATOM | 1845 | CB | | LEU | B | 228 | 23.153 | -7.972 | 2.069 | 1.00 41.57 | C |
| ATOM | 1846 | CG | | LEU | B | 228 | 23.377 | -7.723 | 0.588 | 1.00 41.74 | C |
| ATOM | 1847 | CD1 | | LEU | B | 228 | 22.058 | -7.740 | -0.157 | 1.00 42.26 | C |
| ATOM | 1848 | CD2 | | LEU | B | 228 | 24.062 | -6.391 | 0.426 | 1.00 41.89 | C |
| ATOM | 1849 | C | | LEU | B | 228 | 21.760 | -10.020 | 1.551 | 1.00 41.56 | C |
| ATOM | 1850 | O | | LEU | B | 228 | 20.714 | -10.060 | 0.908 | 1.00 41.43 | O |
| ATOM | 1851 | N | | GLU | B | 229 | 22.711 | -10.939 | 1.469 | 1.00 41.80 | N |
| ATOM | 1852 | CA | | GLU | B | 229 | 22.570 | -12.176 | 0.710 | 1.00 42.16 | C |
| ATOM | 1853 | CB | | GLU | B | 229 | 23.649 | -13.168 | 1.182 | 1.00 42.16 | C |
| ATOM | 1854 | CG | A | GLU | B | 229 | 24.946 | -12.910 | 0.400 | 0.50 42.62 | C |
| ATOM | 1855 | CG | B | GLU | B | 229 | 25.068 | -12.691 | 1.080 | 0.50 42.57 | C |

| | | | | | | | | | | |
|---|---|---|---|---|---|---|---|---|---|---|
| ATOM | 1856 | CD | AGLU | B | 229 | 26.197 | -13.614 | 0.922 | 0.50 43.04 | C |
| ATOM | 1857 | CD | BGLU | B | 229 | 25.305 | -12.634 | -0.321 | 0.50 43.04 | C |
| ATOM | 1858 | OE1 | AGLU | B | 229 | 26.141 | -14.237 | 1.996 | 0.50 43.44 | O |
| ATOM | 1859 | OE1 | BGLU | B | 229 | 24.390 | -13.218 | -0.855 | 0.50 43.05 | O |
| ATOM | 1860 | OE2 | AGLU | B | 229 | 27.255 | -13.540 | 0.251 | 0.50 43.19 | O |
| ATOM | 1861 | OE2 | BGLU | B | 229 | 26.251 | -12.039 | -0.844 | 0.50 43.44 | O |
| ATOM | 1862 | C | GLU | B | 229 | 21.201 | -12.832 | 0.880 | 1.00 42.23 | C |
| ATOM | 1863 | O | GLU | B | 229 | 20.579 | -13.276 | -0.081 | 1.00 42.20 | O |
| ATOM | 1864 | N | ALA | B | 230 | 20.732 | -12.881 | 2.120 | 1.00 42.42 | N |
| ATOM | 1865 | CA | ALA | B | 230 | 19.480 | -13.547 | 2.444 | 1.00 42.55 | C |
| ATOM | 1866 | CB | ALA | B | 230 | 19.417 | -13.840 | 3.927 | 1.00 42.44 | C |
| ATOM | 1867 | C | ALA | B | 230 | 18.230 | -12.803 | 2.018 | 1.00 42.73 | C |
| ATOM | 1868 | O | ALA | B | 230 | 17.136 | -13.335 | 2.090 | 1.00 42.67 | O |
| ATOM | 1869 | N | GLU | B | 231 | 18.369 | -11.577 | 1.563 | 1.00 43.28 | N |
| ATOM | 1870 | CA | GLU | B | 231 | 17.178 | -10.828 | 1.191 | 1.00 43.99 | C |
| ATOM | 1871 | CB | GLU | B | 231 | 17.553 | -9.438 | 0.680 | 1.00 43.88 | C |
| ATOM | 1872 | CG | GLU | B | 231 | 17.789 | -8.439 | 1.792 | 1.00 44.45 | C |
| ATOM | 1873 | CD | GLU | B | 231 | 16.488 | -7.999 | 2.436 | 1.00 45.78 | C |
| ATOM | 1874 | OE1 | GLU | B | 231 | 16.003 | -8.537 | 3.395 | 1.00 46.10 | O |
| ATOM | 1875 | OE2 | GLU | B | 231 | 15.866 | -7.088 | 1.994 | 1.00 46.04 | O |
| ATOM | 1876 | C | GLU | B | 231 | 16.290 | -11.562 | 0.188 | 1.00 44.43 | C |
| ATOM | 1877 | O | GLU | B | 231 | 16.761 | -12.039 | -0.839 | 1.00 44.37 | O |
| ATOM | 1878 | N | PRO | B | 232 | 14.994 | -11.631 | 0.482 | 1.00 45.03 | N |
| ATOM | 1879 | CA | PRO | B | 232 | 14.024 | -12.250 | -0.432 | 1.00 45.45 | C |
| ATOM | 1880 | CB | PRO | B | 232 | 12.675 | -12.038 | 0.263 | 1.00 45.20 | C |
| ATOM | 1881 | CG | PRO | B | 232 | 12.921 | -11.441 | 1.534 | 1.00 44.88 | C |
| ATOM | 1882 | CD | PRO | B | 232 | 14.361 | -11.092 | 1.693 | 1.00 45.00 | C |
| ATOM | 1883 | C | PRO | B | 232 | 13.961 | -11.492 | -1.741 | 1.00 46.05 | C |
| ATOM | 1884 | O | PRO | B | 232 | 14.234 | -10.298 | -1.770 | 1.00 46.03 | O |
| ATOM | 1885 | N | PRO | B | 233 | 13.580 | -12.173 | -2.808 | 1.00 46.72 | N |
| ATOM | 1886 | CA | PRO | B | 233 | 13.330 | -11.511 | -4.084 | 1.00 47.29 | C |
| ATOM | 1887 | CB | PRO | B | 233 | 13.116 | -12.668 | -5.050 | 1.00 47.36 | C |
| ATOM | 1888 | CG | PRO | B | 233 | 13.422 | -13.901 | -4.311 | 1.00 47.02 | C |
| ATOM | 1889 | CD | PRO | B | 233 | 13.350 | -13.622 | -2.867 | 1.00 46.74 | C |
| ATOM | 1890 | C | PRO | B | 233 | 12.020 | -10.766 | -3.977 | 1.00 47.98 | C |
| ATOM | 1891 | O | PRO | B | 233 | 11.283 | -10.878 | -2.987 | 1.00 47.92 | O |
| ATOM | 1892 | N | ASN | B | 234 | 11.718 | -10.006 | -5.009 | 1.00 48.85 | N |
| ATOM | 1893 | CA | ASN | B | 234 | 10.465 | -9.305 | -5.047 | 1.00 49.76 | C |
| ATOM | 1894 | CB | ASN | B | 234 | 10.567 | -8.120 | -5.980 | 1.00 49.63 | C |
| ATOM | 1895 | CG | ASN | B | 234 | 11.401 | -7.040 | -5.404 | 1.00 49.73 | C |
| ATOM | 1896 | OD1 | ASN | B | 234 | 11.205 | -6.667 | -4.248 | 1.00 50.14 | O |
| ATOM | 1897 | ND2 | ASN | B | 234 | 12.356 | -6.536 | -6.176 | 1.00 49.41 | N |
| ATOM | 1898 | C | ASN | B | 234 | 9.415 | -10.266 | -5.522 | 1.00 50.47 | C |
| ATOM | 1899 | O | ASN | B | 234 | 9.714 | -11.265 | -6.140 | 1.00 50.42 | O |
| ATOM | 1900 | N | VAL | B | 235 | 8.176 | -9.974 | -5.196 | 1.00 51.61 | N |
| ATOM | 1901 | CA | VAL | B | 235 | 7.077 | -10.789 | -5.644 | 1.00 52.62 | C |
| ATOM | 1902 | CB | VAL | B | 235 | 6.131 | -11.033 | -4.475 | 1.00 52.56 | C |
| ATOM | 1903 | CG1 | VAL | B | 235 | 4.695 | -11.025 | -4.927 | 1.00 52.83 | C |
| ATOM | 1904 | CG2 | VAL | B | 235 | 6.496 | -12.337 | -3.797 | 1.00 52.67 | C |
| ATOM | 1905 | C | VAL | B | 235 | 6.373 | -10.081 | -6.801 | 1.00 53.42 | C |
| ATOM | 1906 | O | VAL | B | 235 | 6.236 | -8.859 | -6.801 | 1.00 53.57 | O |
| ATOM | 1907 | N | LEU | B | 236 | 5.962 | -10.829 | -7.813 | 1.00 54.45 | N |
| ATOM | 1908 | CA | LEU | B | 236 | 5.279 | -10.212 | -8.944 | 1.00 55.53 | C |
| ATOM | 1909 | CB | LEU | B | 236 | 5.411 | -11.081 | -10.198 | 1.00 55.44 | C |
| ATOM | 1913 | C | LEU | B | 236 | 3.808 | -9.994 | -8.620 | 1.00 56.32 | C |
| ATOM | 1914 | O | LEU | B | 236 | 3.052 | -10.957 | -8.550 | 1.00 56.36 | O |
| ATOM | 1915 | N | VAL | B | 237 | 3.410 | -8.739 | -8.417 | 1.00 57.35 | N |
| ATOM | 1916 | CA | VAL | B | 237 | 2.034 | -8.410 | -8.095 | 1.00 58.49 | C |
| ATOM | 1917 | CB | VAL | B | 237 | 1.792 | -8.390 | -6.596 | 1.00 58.43 | C |
| ATOM | 1918 | CG1 | VAL | B | 237 | 0.629 | -7.476 | -6.284 | 1.00 58.87 | C |
| ATOM | 1919 | CG2 | VAL | B | 237 | 1.488 | -9.785 | -6.082 | 1.00 58.81 | C |

| | | | | | | | | | |
|---|---|---|---|---|---|---|---|---|---|
| ATOM | 1920 | C | VAL | B | 237 | 1.673 | -7.036 | -8.595 | 1.00 59.27 | C |
| ATOM | 1921 | O | VAL | B | 237 | 2.263 | -6.045 | -8.170 | 1.00 59.59 | O |
| ATOM | 1922 | N | SER | B | 238 | 0.677 | -6.958 | -9.466 | 1.00 60.16 | N |
| ATOM | 1923 | CA | SER | B | 238 | 0.285 | -5.670 | -10.008 | 1.00 60.99 | C |
| ATOM | 1924 | CB | SER | B | 238 | 0.441 | -5.647 | -11.537 | 1.00 61.05 | C |
| ATOM | 1925 | OG | SER | B | 238 | -0.057 | -6.840 | -12.121 | 1.00 61.45 | O |
| ATOM | 1926 | C | SER | B | 238 | -1.115 | -5.250 | -9.599 | 1.00 61.41 | C |
| ATOM | 1927 | O | SER | B | 238 | -1.893 | -6.028 | -9.069 | 1.00 61.55 | O |
| ATOM | 1928 | N | ARG | B | 239 | -1.411 | -3.998 | -9.886 | 1.00 61.97 | N |
| ATOM | 1929 | CA | ARG | B | 239 | -2.652 | -3.358 | -9.531 | 1.00 62.48 | C |
| ATOM | 1930 | CB | ARG | B | 239 | -2.350 | -1.896 | -9.634 | 1.00 62.67 | C |
| ATOM | 1931 | CG | ARG | B | 239 | -3.335 | -0.983 | -9.138 | 1.00 63.73 | C |
| ATOM | 1932 | CD | ARG | B | 239 | -2.636 | 0.271 | -8.916 | 1.00 65.26 | C |
| ATOM | 1933 | NE | ARG | B | 239 | -3.004 | 0.892 | -7.688 | 1.00 66.57 | N |
| ATOM | 1934 | CZ | ARG | B | 239 | -2.839 | 2.154 | -7.504 | 1.00 67.58 | C |
| ATOM | 1935 | NH1 | ARG | B | 239 | -2.337 | 2.822 | -8.453 | 1.00 68.02 | N |
| ATOM | 1936 | NH2 | ARG | B | 239 | -3.157 | 2.779 | -6.418 | 1.00 68.14 | N |
| ATOM | 1937 | C | ARG | B | 239 | -3.803 | -3.717 | -10.466 | 1.00 62.47 | C |
| ATOM | 1938 | O | ARG | B | 239 | -3.630 | -3.769 | -11.677 | 1.00 62.52 | O |
| ATOM | 1956 | N | PRO | B | 243 | -9.045 | 1.362 | -10.476 | 1.00 60.60 | N |
| ATOM | 1957 | CA | PRO | B | 243 | -8.815 | 1.589 | -9.048 | 1.00 60.62 | C |
| ATOM | 1958 | CB | PRO | B | 243 | -9.763 | 2.744 | -8.715 | 1.00 60.59 | C |
| ATOM | 1959 | CG | PRO | B | 243 | -10.476 | 3.083 | -9.988 | 1.00 60.56 | C |
| ATOM | 1960 | CD | PRO | B | 243 | -10.346 | 1.896 | -10.899 | 1.00 60.60 | C |
| ATOM | 1961 | C | PRO | B | 243 | -9.235 | 0.387 | -8.228 | 1.00 60.63 | C |
| ATOM | 1962 | O | PRO | B | 243 | -9.561 | -0.657 | -8.788 | 1.00 60.73 | O |
| ATOM | 1963 | N | PHE | B | 244 | -9.286 | 0.556 | -6.914 | 1.00 60.57 | N |
| ATOM | 1964 | CA | PHE | B | 244 | -9.580 | -0.561 | -6.032 | 1.00 60.53 | C |
| ATOM | 1965 | CB | PHE | B | 244 | -8.526 | -0.657 | -4.923 | 1.00 60.62 | C |
| ATOM | 1966 | CG | PHE | B | 244 | -7.272 | -1.354 | -5.339 | 1.00 60.69 | C |
| ATOM | 1967 | CD1 | PHE | B | 244 | -7.282 | -2.705 | -5.623 | 1.00 60.91 | C |
| ATOM | 1968 | CE1 | PHE | B | 244 | -6.124 | -3.355 | -6.008 | 1.00 61.19 | C |
| ATOM | 1969 | CZ | PHE | B | 244 | -4.935 | -2.649 | -6.115 | 1.00 61.11 | C |
| ATOM | 1970 | CE2 | PHE | B | 244 | -4.913 | -1.293 | -5.832 | 1.00 61.00 | C |
| ATOM | 1971 | CD2 | PHE | B | 244 | -6.078 | -0.655 | -5.447 | 1.00 60.99 | C |
| ATOM | 1972 | C | PHE | B | 244 | -10.964 | -0.599 | -5.406 | 1.00 60.41 | C |
| ATOM | 1973 | O | PHE | B | 244 | -11.625 | 0.423 | -5.214 | 1.00 60.33 | O |
| ATOM | 1974 | N | THR | B | 245 | -11.354 | -1.823 | -5.077 | 1.00 60.34 | N |
| ATOM | 1975 | CA | THR | B | 245 | -12.599 | -2.155 | -4.407 | 1.00 60.31 | C |
| ATOM | 1976 | CB | THR | B | 245 | -13.228 | -3.351 | -5.133 | 1.00 60.29 | C |
| ATOM | 1977 | OG1 | THR | B | 245 | -13.817 | -2.909 | -6.362 | 1.00 60.07 | O |
| ATOM | 1978 | CG2 | THR | B | 245 | -14.388 | -3.920 | -4.347 | 1.00 60.46 | C |
| ATOM | 1979 | C | THR | B | 245 | -12.207 | -2.554 | -2.990 | 1.00 60.29 | C |
| ATOM | 1980 | O | THR | B | 245 | -11.036 | -2.443 | -2.636 | 1.00 60.37 | O |
| ATOM | 1981 | N | GLU | B | 246 | -13.156 | -3.003 | -2.171 | 1.00 60.25 | N |
| ATOM | 1982 | CA | GLU | B | 246 | -12.819 | -3.482 | -0.837 | 1.00 60.23 | C |
| ATOM | 1983 | CB | GLU | B | 246 | -14.054 | -3.524 | 0.064 | 1.00 60.42 | C |
| ATOM | 1984 | CG | GLU | B | 246 | -13.930 | -2.708 | 1.341 | 1.00 61.37 | C |
| ATOM | 1985 | CD | GLU | B | 246 | -14.728 | -3.297 | 2.490 | 1.00 62.71 | C |
| ATOM | 1986 | OE1 | GLU | B | 246 | -15.062 | -4.503 | 2.425 | 1.00 63.38 | O |
| ATOM | 1987 | OE2 | GLU | B | 246 | -15.018 | -2.562 | 3.462 | 1.00 63.23 | O |
| ATOM | 1988 | C | GLU | B | 246 | -12.221 | -4.884 | -0.965 | 1.00 59.89 | C |
| ATOM | 1989 | O | GLU | B | 246 | -11.168 | -5.183 | -0.402 | 1.00 59.96 | O |
| ATOM | 1990 | N | ALA | B | 247 | -12.896 | -5.739 | -1.725 | 1.00 59.44 | N |
| ATOM | 1991 | CA | ALA | B | 247 | -12.439 | -7.110 | -1.927 | 1.00 58.90 | C |
| ATOM | 1992 | CB | ALA | B | 247 | -13.560 | -7.972 | -2.490 | 1.00 58.96 | C |
| ATOM | 1993 | C | ALA | B | 247 | -11.230 | -7.129 | -2.852 | 1.00 58.45 | C |
| ATOM | 1994 | O | ALA | B | 247 | -10.425 | -8.051 | -2.814 | 1.00 58.44 | O |
| ATOM | 1995 | N | SER | B | 248 | -11.114 | -6.101 | -3.683 | 1.00 57.84 | N |
| ATOM | 1996 | CA | SER | B | 248 | -9.992 | -5.968 | -4.601 | 1.00 57.18 | C |
| ATOM | 1997 | CB | SER | B | 248 | -10.285 | -4.873 | -5.615 | 1.00 57.17 | C |

200

| | | | | | | | | | | |
|---|---|---|---|---|---|---|---|---|---|---|
| ATOM | 1998 | OG | SER | B | 248 | -9.613 | -5.116 | -6.826 | 1.00 57.13 | O |
| ATOM | 1999 | C | SER | B | 248 | -8.710 | -5.639 | -3.825 | 1.00 56.77 | C |
| ATOM | 2000 | O | SER | B | 248 | -7.660 | -6.259 | -4.027 | 1.00 56.70 | O |
| ATOM | 2001 | N | MET | B | 249 | -8.800 | -4.668 | -2.924 | 1.00 56.12 | N |
| ATOM | 2002 | CA | MET | B | 249 | -7.649 | -4.299 | -2.122 | 1.00 55.40 | C |
| ATOM | 2003 | CB | MET | B | 249 | -7.908 | -2.996 | -1.363 | 1.00 55.40 | C |
| ATOM | 2004 | CG | MET | B | 249 | -6.651 | -2.356 | -0.808 | 1.00 54.97 | C |
| ATOM | 2005 | SD | MET | B | 249 | -6.864 | -0.665 | -0.271 | 1.00 53.98 | S |
| ATOM | 2006 | CE | MET | B | 249 | -6.736 | 0.210 | -1.829 | 1.00 54.50 | C |
| ATOM | 2007 | C | MET | B | 249 | -7.252 | -5.432 | -1.176 | 1.00 55.00 | C |
| ATOM | 2008 | O | MET | B | 249 | -6.101 | -5.856 | -1.177 | 1.00 54.95 | O |
| ATOM | 2009 | N | MET | B | 250 | -8.200 | -5.934 | -0.386 | 1.00 54.44 | N |
| ATOM | 2010 | CA | MET | B | 250 | -7.906 | -7.017 | 0.553 | 1.00 53.89 | C |
| ATOM | 2011 | CB | MET | B | 250 | -9.157 | -7.483 | 1.304 | 1.00 53.91 | C |
| ATOM | 2012 | CG | MET | B | 250 | -9.386 | -6.834 | 2.675 | 1.00 53.63 | C |
| ATOM | 2013 | SD | MET | B | 250 | -7.907 | -6.626 | 3.722 | 1.00 52.67 | S |
| ATOM | 2014 | CE | MET | B | 250 | -7.585 | -4.964 | 3.455 | 1.00 52.60 | C |
| ATOM | 2015 | C | MET | B | 250 | -7.243 | -8.206 | -0.125 | 1.00 53.55 | C |
| ATOM | 2016 | O | MET | B | 250 | -6.217 | -8.688 | 0.350 | 1.00 53.52 | O |
| ATOM | 2017 | N | MET | B | 251 | -7.821 | -8.671 | -1.232 | 1.00 53.06 | N |
| ATOM | 2018 | CA | MET | B | 251 | -7.258 | -9.803 | -1.971 | 1.00 52.62 | C |
| ATOM | 2019 | CB | MET | B | 251 | -8.091 | -10.132 | -3.210 | 1.00 52.79 | C |
| ATOM | 2020 | CG | MET | B | 251 | -9.291 | -11.035 | -2.962 | 1.00 53.40 | C |
| ATOM | 2021 | SD | MET | B | 251 | -10.038 | -11.519 | -4.534 | 1.00 54.71 | S |
| ATOM | 2022 | CE | MET | B | 251 | -11.599 | -12.246 | -3.951 | 1.00 54.66 | C |
| ATOM | 2023 | C | MET | B | 251 | -5.824 | -9.521 | -2.393 | 1.00 52.13 | C |
| ATOM | 2024 | O | MET | B | 251 | -4.950 | -10.372 | -2.263 | 1.00 52.11 | O |
| ATOM | 2025 | N | SER | B | 252 | -5.588 | -8.322 | -2.912 | 1.00 51.45 | N |
| ATOM | 2026 | CA | SER | B | 252 | -4.246 | -7.925 | -3.304 | 1.00 50.72 | C |
| ATOM | 2027 | CB | SER | B | 252 | -4.231 | -6.465 | -3.746 | 1.00 50.79 | C |
| ATOM | 2028 | OG | SER | B | 252 | -4.461 | -6.342 | -5.129 | 1.00 50.90 | O |
| ATOM | 2029 | C | SER | B | 252 | -3.271 | -8.079 | -2.150 | 1.00 50.15 | C |
| ATOM | 2030 | O | SER | B | 252 | -2.238 | -8.736 | -2.277 | 1.00 50.13 | O |
| ATOM | 2031 | N | LEU | B | 253 | -3.602 | -7.456 | -1.026 | 1.00 49.30 | N |
| ATOM | 2032 | CA | LEU | B | 253 | -2.713 | -7.458 | 0.125 | 1.00 48.54 | C |
| ATOM | 2033 | CB | LEU | B | 253 | -3.205 | -6.467 | 1.187 | 1.00 48.57 | C |
| ATOM | 2034 | CG | LEU | B | 253 | -3.407 | -5.046 | 0.676 | 1.00 48.10 | C |
| ATOM | 2035 | CD1 | LEU | B | 253 | -3.894 | -4.150 | 1.769 | 1.00 47.71 | C |
| ATOM | 2036 | CD2 | LEU | B | 253 | -2.116 | -4.539 | 0.109 | 1.00 48.17 | C |
| ATOM | 2037 | C | LEU | B | 253 | -2.544 | -8.848 | 0.721 | 1.00 47.97 | C |
| ATOM | 2038 | O | LEU | B | 253 | -1.430 | -9.278 | 0.996 | 1.00 47.91 | O |
| ATOM | 2039 | N | THR | B | 254 | -3.653 | -9.549 | 0.904 | 1.00 47.20 | N |
| ATOM | 2040 | CA | THR | B | 254 | -3.608 | -10.889 | 1.454 | 1.00 46.53 | C |
| ATOM | 2041 | CB | THR | B | 254 | -5.022 | -11.480 | 1.580 | 1.00 46.62 | C |
| ATOM | 2042 | OG1 | THR | B | 254 | -5.985 | -10.423 | 1.611 | 1.00 46.98 | O |
| ATOM | 2043 | CG2 | THR | B | 254 | -5.200 | -12.145 | 2.923 | 1.00 46.58 | C |
| ATOM | 2044 | C | THR | B | 254 | -2.789 | -11.796 | 0.571 | 1.00 45.93 | C |
| ATOM | 2045 | O | THR | B | 254 | -2.064 | -12.640 | 1.052 | 1.00 46.03 | O |
| ATOM | 2046 | N | LYS | B | 255 | -2.918 | -11.651 | -0.734 | 1.00 45.25 | N |
| ATOM | 2047 | CA | LYS | B | 255 | -2.163 | -12.510 | -1.627 | 1.00 44.62 | C |
| ATOM | 2048 | CB | LYS | B | 255 | -2.729 | -12.459 | -3.046 | 1.00 44.76 | C |
| ATOM | 2049 | CG | LYS | B | 255 | -2.027 | -13.391 | -4.036 | 1.00 45.22 | C |
| ATOM | 2050 | CD | LYS | B | 255 | -2.558 | -13.192 | -5.455 | 1.00 46.21 | C |
| ATOM | 2053 | C | LYS | B | 255 | -0.680 | -12.127 | -1.593 | 1.00 44.02 | C |
| ATOM | 2054 | O | LYS | B | 255 | 0.199 | -12.981 | -1.602 | 1.00 43.81 | O |
| ATOM | 2055 | N | LEU | B | 256 | -0.405 | -10.833 | -1.543 | 1.00 43.33 | N |
| ATOM | 2056 | CA | LEU | B | 256 | 0.963 | -10.389 | -1.420 | 1.00 42.72 | C |
| ATOM | 2057 | CB | LEU | B | 256 | 1.031 | -8.872 | -1.465 | 1.00 42.73 | C |
| ATOM | 2058 | CG | LEU | B | 256 | 2.342 | -8.221 | -1.038 | 1.00 42.56 | C |
| ATOM | 2059 | CD1 | LEU | B | 256 | 3.414 | -8.428 | -2.066 | 1.00 41.92 | C |
| ATOM | 2060 | CD2 | LEU | B | 256 | 2.101 | -6.743 | -0.801 | 1.00 42.69 | C |

201

| | | | | | | | | | | |
|---|---|---|---|---|---|---|---|---|---|---|
| ATOM | 2061 | C | LEU | B | 256 | 1.542 | -10.924 | -0.112 | 1.00 42.36 | C |
| ATOM | 2062 | O | LEU | B | 256 | 2.650 | -11.451 | -0.089 | 1.00 42.29 | O |
| ATOM | 2063 | N | ALA | B | 257 | 0.782 | -10.812 | 0.973 | 1.00 41.83 | N |
| ATOM | 2064 | CA | ALA | B | 257 | 1.236 | -11.305 | 2.266 | 1.00 41.48 | C |
| ATOM | 2065 | CB | ALA | B | 257 | 0.147 | -11.156 | 3.295 | 1.00 41.28 | C |
| ATOM | 2066 | C | ALA | B | 257 | 1.675 | -12.755 | 2.179 | 1.00 41.31 | C |
| ATOM | 2067 | O | ALA | B | 257 | 2.725 | -13.158 | 2.684 | 1.00 41.13 | O |
| ATOM | 2068 | N | ASP | B | 258 | 0.840 | -13.540 | 1.530 | 1.00 41.28 | N |
| ATOM | 2069 | CA | ASP | B | 258 | 1.092 | -14.945 | 1.352 | 1.00 41.31 | C |
| ATOM | 2070 | CB | ASP | B | 258 | -0.016 | -15.528 | 0.507 | 1.00 41.44 | C |
| ATOM | 2071 | CG | ASP | B | 258 | -0.719 | -16.674 | 1.183 | 1.00 42.14 | C |
| ATOM | 2072 | OD1 | ASP | B | 258 | -0.647 | -16.758 | 2.430 | 1.00 42.68 | O |
| ATOM | 2073 | OD2 | ASP | B | 258 | -1.377 | -17.540 | 0.552 | 1.00 42.59 | O |
| ATOM | 2074 | C | ASP | B | 258 | 2.411 | -15.153 | 0.631 | 1.00 41.25 | C |
| ATOM | 2075 | O | ASP | B | 258 | 3.305 | -15.838 | 1.128 | 1.00 41.29 | O |
| ATOM | 2076 | N | LYS | B | 259 | 2.531 | -14.562 | -0.551 | 1.00 41.10 | N |
| ATOM | 2077 | CA | LYS | B | 259 | 3.745 | -14.709 | -1.330 | 1.00 40.90 | C |
| ATOM | 2078 | CB | LYS | B | 259 | 3.630 | -13.934 | -2.629 | 1.00 41.01 | C |
| ATOM | 2079 | CG | LYS | B | 259 | 2.806 | -14.746 | -3.568 | 1.00 41.43 | C |
| ATOM | 2080 | CD | LYS | B | 259 | 2.236 | -14.022 | -4.671 | 1.00 42.64 | C |
| ATOM | 2081 | CE | LYS | B | 259 | 2.186 | -14.826 | -5.948 | 1.00 43.67 | C |
| ATOM | 2082 | NZ | LYS | B | 259 | 1.680 | -13.909 | -7.011 | 1.00 44.39 | N |
| ATOM | 2083 | C | LYS | B | 259 | 4.946 | -14.320 | -0.507 | 1.00 40.64 | C |
| ATOM | 2084 | O | LYS | B | 259 | 5.929 | -15.058 | -0.431 | 1.00 40.69 | O |
| ATOM | 2085 | N | GLU | B | 260 | 4.851 | -13.181 | 0.154 | 1.00 40.36 | N |
| ATOM | 2086 | CA | GLU | B | 260 | 5.942 | -12.724 | 0.994 | 1.00 40.03 | C |
| ATOM | 2087 | CB | GLU | B | 260 | 5.683 | -11.321 | 1.483 | 1.00 39.89 | C |
| ATOM | 2088 | CG | GLU | B | 260 | 5.664 | -10.309 | 0.376 | 1.00 39.72 | C |
| ATOM | 2089 | CD | GLU | B | 260 | 5.902 | -8.923 | 0.915 | 1.00 40.10 | C |
| ATOM | 2090 | OE1 | GLU | B | 260 | 5.013 | -8.245 | 1.345 | 1.00 40.37 | O |
| ATOM | 2091 | OE2 | GLU | B | 260 | 6.993 | -8.459 | 0.973 | 1.00 39.62 | O |
| ATOM | 2092 | C | GLU | B | 260 | 6.189 | -13.636 | 2.182 | 1.00 39.94 | C |
| ATOM | 2093 | O | GLU | B | 260 | 7.310 | -13.725 | 2.653 | 1.00 39.93 | O |
| ATOM | 2094 | N | LEU | B | 261 | 5.147 | -14.290 | 2.684 | 1.00 39.87 | N |
| ATOM | 2095 | CA | LEU | B | 261 | 5.329 | -15.231 | 3.782 | 1.00 39.82 | C |
| ATOM | 2096 | CB | LEU | B | 261 | 3.989 | -15.751 | 4.268 | 1.00 39.86 | C |
| ATOM | 2097 | CG | LEU | B | 261 | 3.468 | -14.985 | 5.469 | 1.00 39.97 | C |
| ATOM | 2098 | CD1 | LEU | B | 261 | 2.232 | -15.672 | 5.965 | 1.00 40.44 | C |
| ATOM | 2099 | CD2 | LEU | B | 261 | 4.514 | -14.955 | 6.564 | 1.00 40.20 | C |
| ATOM | 2100 | C | LEU | B | 261 | 6.231 | -16.407 | 3.375 | 1.00 39.74 | C |
| ATOM | 2101 | O | LEU | B | 261 | 7.190 | -16.741 | 4.080 | 1.00 39.70 | O |
| ATOM | 2102 | N | VAL | B | 262 | 5.927 | -17.033 | 2.241 | 1.00 39.50 | N |
| ATOM | 2103 | CA | VAL | B | 262 | 6.759 | -18.126 | 1.765 | 1.00 39.37 | C |
| ATOM | 2104 | CB | VAL | B | 262 | 6.347 | -18.628 | 0.353 | 1.00 39.34 | C |
| ATOM | 2105 | CG1 | VAL | B | 262 | 7.464 | -19.457 | -0.281 | 1.00 38.76 | C |
| ATOM | 2106 | CG2 | VAL | B | 262 | 5.043 | -19.408 | 0.414 | 1.00 38.99 | C |
| ATOM | 2107 | C | VAL | B | 262 | 8.186 | -17.645 | 1.689 | 1.00 39.46 | C |
| ATOM | 2108 | O | VAL | B | 262 | 9.102 | -18.333 | 2.122 | 1.00 39.41 | O |
| ATOM | 2109 | N | HIS | B | 263 | 8.368 | -16.451 | 1.143 | 1.00 39.54 | N |
| ATOM | 2110 | CA | HIS | B | 263 | 9.708 | -15.921 | 0.952 | 1.00 39.86 | C |
| ATOM | 2111 | CB | HIS | B | 263 | 9.677 | -14.688 | 0.059 | 1.00 40.51 | C |
| ATOM | 2112 | CG | HIS | B | 263 | 9.574 | -15.005 | -1.402 | 1.00 44.00 | C |
| ATOM | 2113 | ND1 | HIS | B | 263 | 9.028 | -14.131 | -2.317 | 1.00 46.92 | N |
| ATOM | 2114 | CE1 | HIS | B | 263 | 9.077 | -14.668 | -3.521 | 1.00 48.94 | C |
| ATOM | 2115 | NE2 | HIS | B | 263 | 9.624 | -15.867 | -3.422 | 1.00 54.30 | N |
| ATOM | 2116 | CD2 | HIS | B | 263 | 9.945 | -16.100 | -2.107 | 1.00 47.31 | C |
| ATOM | 2117 | C | HIS | B | 263 | 10.421 | -15.638 | 2.267 | 1.00 39.12 | C |
| ATOM | 2118 | O | HIS | B | 263 | 11.629 | -15.805 | 2.375 | 1.00 39.17 | O |
| ATOM | 2119 | N | MET | B | 264 | 9.668 | -15.226 | 3.274 | 1.00 38.30 | N |
| ATOM | 2120 | CA | MET | B | 264 | 10.246 | -14.920 | 4.561 | 1.00 37.44 | C |
| ATOM | 2121 | CB | MET | B | 264 | 9.191 | -14.279 | 5.452 | 1.00 37.29 | C |

202

| | | | | | | | | | | |
|---|---|---|---|---|---|---|---|---|---|---|
| ATOM | 2122 | CG | MET | B | 264 | 9.728 | -13.721 | 6.751 | 1.00 36.86 | C |
| ATOM | 2123 | SD | MET | B | 264 | 8.418 | -13.238 | 7.909 | 1.00 36.42 | S |
| ATOM | 2124 | CE | MET | B | 264 | 7.444 | -12.191 | 6.904 | 1.00 35.19 | C |
| ATOM | 2125 | C | MET | B | 264 | 10.815 | -16.188 | 5.205 | 1.00 37.18 | C |
| ATOM | 2126 | O | MET | B | 264 | 11.912 | -16.176 | 5.769 | 1.00 37.10 | O |
| ATOM | 2127 | N | ILE | B | 265 | 10.068 | -17.283 | 5.141 | 1.00 36.67 | N |
| ATOM | 2128 | CA | ILE | B | 265 | 10.574 | -18.524 | 5.689 | 1.00 36.34 | C |
| ATOM | 2129 | CB | ILE | B | 265 | 9.604 | -19.673 | 5.405 | 1.00 36.40 | C |
| ATOM | 2130 | CG1 | ILE | B | 265 | 8.347 | -19.499 | 6.256 | 1.00 36.24 | C |
| ATOM | 2131 | CD1 | ILE | B | 265 | 7.348 | -20.580 | 6.086 | 1.00 35.71 | C |
| ATOM | 2132 | CG2 | ILE | B | 265 | 10.267 | -21.021 | 5.678 | 1.00 36.22 | C |
| ATOM | 2133 | C | ILE | B | 265 | 11.922 | -18.783 | 5.041 | 1.00 36.16 | C |
| ATOM | 2134 | O | ILE | B | 265 | 12.897 | -19.125 | 5.719 | 1.00 36.01 | O |
| ATOM | 2135 | N | GLY | B | 266 | 11.967 | -18.578 | 3.727 | 1.00 35.91 | N |
| ATOM | 2136 | CA | GLY | B | 266 | 13.188 | -18.721 | 2.971 | 1.00 35.78 | C |
| ATOM | 2137 | C | GLY | B | 266 | 14.249 | -17.915 | 3.664 | 1.00 35.73 | C |
| ATOM | 2138 | O | GLY | B | 266 | 15.304 | -18.416 | 4.029 | 1.00 35.82 | O |
| ATOM | 2139 | N | TRP | B | 267 | 13.924 | -16.663 | 3.906 | 1.00 35.75 | N |
| ATOM | 2140 | CA | TRP | B | 267 | 14.821 | -15.717 | 4.550 | 1.00 35.67 | C |
| ATOM | 2141 | CB | TRP | B | 267 | 14.108 | -14.378 | 4.658 | 1.00 35.28 | C |
| ATOM | 2142 | CG | TRP | B | 267 | 14.781 | -13.395 | 5.527 | 1.00 34.07 | C |
| ATOM | 2143 | CD1 | TRP | B | 267 | 15.919 | -12.722 | 5.253 | 1.00 32.85 | C |
| ATOM | 2144 | NE1 | TRP | B | 267 | 16.232 | -11.880 | 6.287 | 1.00 32.15 | N |
| ATOM | 2145 | CE2 | TRP | B | 267 | 15.274 | -11.985 | 7.253 | 1.00 32.24 | C |
| ATOM | 2146 | CD2 | TRP | B | 267 | 14.338 | -12.936 | 6.809 | 1.00 32.78 | C |
| ATOM | 2147 | CE3 | TRP | B | 267 | 13.241 | -13.234 | 7.629 | 1.00 31.95 | C |
| ATOM | 2148 | CZ3 | TRP | B | 267 | 13.121 | -12.590 | 8.826 | 1.00 31.94 | C |
| ATOM | 2149 | CH2 | TRP | B | 267 | 14.078 | -11.644 | 9.242 | 1.00 32.14 | C |
| ATOM | 2150 | CZ2 | TRP | B | 267 | 15.157 | -11.332 | 8.468 | 1.00 32.06 | C |
| ATOM | 2151 | C | TRP | B | 267 | 15.342 | -16.166 | 5.912 | 1.00 36.24 | C |
| ATOM | 2152 | O | TRP | B | 267 | 16.545 | -16.202 | 6.132 | 1.00 36.09 | O |
| ATOM | 2153 | N | ALA | B | 268 | 14.449 | -16.523 | 6.829 | 1.00 37.17 | N |
| ATOM | 2154 | CA | ALA | B | 268 | 14.885 | -16.949 | 8.173 | 1.00 38.02 | C |
| ATOM | 2155 | CB | ALA | B | 268 | 13.696 | -17.370 | 9.042 | 1.00 37.73 | C |
| ATOM | 2156 | C | ALA | B | 268 | 15.915 | -18.073 | 8.093 | 1.00 38.71 | C |
| ATOM | 2157 | O | ALA | B | 268 | 16.898 | -18.065 | 8.836 | 1.00 38.73 | O |
| ATOM | 2158 | N | LYS | B | 269 | 15.690 | -19.021 | 7.184 | 1.00 39.56 | N |
| ATOM | 2159 | CA | LYS | B | 269 | 16.586 | -20.156 | 7.028 | 1.00 40.56 | C |
| ATOM | 2160 | CB | LYS | B | 269 | 16.105 | -21.086 | 5.919 | 1.00 40.63 | C |
| ATOM | 2161 | CG | LYS | B | 269 | 14.611 | -21.303 | 5.897 | 1.00 40.98 | C |
| ATOM | 2162 | CD | LYS | B | 269 | 14.187 | -22.480 | 6.741 | 1.00 40.64 | C |
| ATOM | 2163 | CE | LYS | B | 269 | 13.991 | -23.699 | 5.884 | 1.00 41.05 | C |
| ATOM | 2164 | NZ | LYS | B | 269 | 13.267 | -24.781 | 6.630 | 1.00 41.45 | N |
| ATOM | 2165 | C | LYS | B | 269 | 18.008 | -19.739 | 6.717 | 1.00 41.19 | C |
| ATOM | 2166 | O | LYS | B | 269 | 18.936 | -20.500 | 6.953 | 1.00 41.38 | O |
| ATOM | 2167 | N | LYS | B | 270 | 18.192 | -18.545 | 6.181 | 1.00 42.00 | N |
| ATOM | 2168 | CA | LYS | B | 270 | 19.539 | -18.096 | 5.892 | 1.00 42.87 | C |
| ATOM | 2169 | CB | LYS | B | 270 | 19.579 | -17.313 | 4.598 | 1.00 42.92 | C |
| ATOM | 2170 | CG | LYS | B | 270 | 19.251 | -18.126 | 3.392 | 1.00 43.06 | C |
| ATOM | 2171 | CD | LYS | B | 270 | 18.959 | -17.236 | 2.223 | 1.00 43.93 | C |
| ATOM | 2172 | CE | LYS | B | 270 | 18.657 | -18.073 | 1.000 | 1.00 45.18 | C |
| ATOM | 2173 | NZ | LYS | B | 270 | 17.599 | -17.469 | 0.143 | 1.00 46.57 | N |
| ATOM | 2174 | C | LYS | B | 270 | 20.151 | -17.254 | 6.997 | 1.00 43.53 | C |
| ATOM | 2175 | O | LYS | B | 270 | 21.263 | -16.782 | 6.852 | 1.00 43.69 | O |
| ATOM | 2176 | N | ILE | B | 271 | 19.445 | -17.037 | 8.094 | 1.00 44.39 | N |
| ATOM | 2177 | CA | ILE | B | 271 | 20.057 | -16.269 | 9.162 | 1.00 45.24 | C |
| ATOM | 2178 | CB | ILE | B | 271 | 19.014 | -15.491 | 9.948 | 1.00 45.16 | C |
| ATOM | 2179 | CG1 | ILE | B | 271 | 18.143 | -14.718 | 8.954 | 1.00 44.78 | C |
| ATOM | 2180 | CD1 | ILE | B | 271 | 17.317 | -13.664 | 9.569 | 1.00 45.08 | C |
| ATOM | 2181 | CG2 | ILE | B | 271 | 19.700 | -14.585 | 10.965 | 1.00 44.91 | C |
| ATOM | 2182 | C | ILE | B | 271 | 20.850 | -17.243 | 10.006 | 1.00 46.06 | C |

203

| | | | | | | | | | | |
|---|---|---|---|---|---|---|---|---|---|---|
| ATOM | 2183 | O | ILE | B | 271 | 20.289 | -18.110 | 10.668 | 1.00 46.20 | O |
| ATOM | 2184 | N | PRO | B | 272 | 22.166 | -17.092 | 9.968 | 1.00 46.84 | N |
| ATOM | 2185 | CA | PRO | B | 272 | 23.086 | -18.069 | 10.557 | 1.00 47.44 | C |
| ATOM | 2186 | CB | PRO | B | 272 | 24.411 | -17.317 | 10.585 | 1.00 47.43 | C |
| ATOM | 2187 | CG | PRO | B | 272 | 24.297 | -16.340 | 9.468 | 1.00 47.24 | C |
| ATOM | 2188 | CD | PRO | B | 272 | 22.866 | -15.923 | 9.405 | 1.00 46.89 | C |
| ATOM | 2189 | C | PRO | B | 272 | 22.695 | -18.497 | 11.959 | 1.00 48.09 | C |
| ATOM | 2190 | O | PRO | B | 272 | 22.728 | -17.696 | 12.870 | 1.00 48.18 | O |
| ATOM | 2191 | N | GLY | B | 273 | 22.329 | -19.757 | 12.123 | 1.00 48.90 | N |
| ATOM | 2192 | CA | GLY | B | 273 | 21.962 | -20.274 | 13.425 | 1.00 49.95 | C |
| ATOM | 2193 | C | GLY | B | 273 | 20.487 | -20.586 | 13.508 | 1.00 50.69 | C |
| ATOM | 2194 | O | GLY | B | 273 | 20.062 | -21.443 | 14.284 | 1.00 50.57 | O |
| ATOM | 2195 | N | PHE | B | 274 | 19.700 | -19.898 | 12.690 | 1.00 51.53 | N |
| ATOM | 2196 | CA | PHE | B | 274 | 18.258 | -20.073 | 12.740 | 1.00 52.43 | C |
| ATOM | 2197 | CB | PHE | B | 274 | 17.537 | -19.127 | 11.778 | 1.00 52.27 | C |
| ATOM | 2198 | CG | PHE | B | 274 | 16.042 | -19.183 | 11.885 | 1.00 51.77 | C |
| ATOM | 2199 | CD1 | PHE | B | 274 | 15.372 | -18.433 | 12.831 | 1.00 51.13 | C |
| ATOM | 2200 | CE1 | PHE | B | 274 | 14.001 | -18.489 | 12.923 | 1.00 50.69 | C |
| ATOM | 2201 | CZ | PHE | B | 274 | 13.287 | -19.290 | 12.072 | 1.00 50.68 | C |
| ATOM | 2202 | CE2 | PHE | B | 274 | 13.940 | -20.046 | 11.131 | 1.00 50.87 | C |
| ATOM | 2203 | CD2 | PHE | B | 274 | 15.307 | -19.991 | 11.038 | 1.00 51.24 | C |
| ATOM | 2204 | C | PHE | B | 274 | 17.861 | -21.522 | 12.513 | 1.00 53.22 | C |
| ATOM | 2205 | O | PHE | B | 274 | 16.880 | -21.985 | 13.078 | 1.00 53.27 | O |
| ATOM | 2206 | N | VAL | B | 275 | 18.617 | -22.241 | 11.693 | 1.00 54.28 | N |
| ATOM | 2207 | CA | VAL | B | 275 | 18.339 | -23.665 | 11.495 | 1.00 55.37 | C |
| ATOM | 2208 | CB | VAL | B | 275 | 18.905 | -24.230 | 10.170 | 1.00 55.34 | C |
| ATOM | 2209 | CG1 | VAL | B | 275 | 17.900 | -24.081 | 9.037 | 1.00 55.31 | C |
| ATOM | 2210 | CG2 | VAL | B | 275 | 20.239 | -23.594 | 9.831 | 1.00 55.70 | C |
| ATOM | 2211 | C | VAL | B | 275 | 18.851 | -24.525 | 12.654 | 1.00 56.09 | C |
| ATOM | 2212 | O | VAL | B | 275 | 18.222 | -25.527 | 12.996 | 1.00 56.10 | O |
| ATOM | 2213 | N | GLU | B | 276 | 19.987 | -24.157 | 13.251 | 1.00 57.03 | N |
| ATOM | 2214 | CA | GLU | B | 276 | 20.479 | -24.911 | 14.404 | 1.00 57.97 | C |
| ATOM | 2215 | CB | GLU | B | 276 | 21.939 | -24.591 | 14.774 | 1.00 58.07 | C |
| ATOM | 2216 | CG | GLU | B | 276 | 22.614 | -23.627 | 13.844 | 1.00 59.15 | C |
| ATOM | 2217 | CD | GLU | B | 276 | 24.005 | -23.968 | 13.364 | 1.00 60.21 | C |
| ATOM | 2218 | OE1 | GLU | B | 276 | 24.073 | -24.633 | 12.316 | 1.00 60.56 | O |
| ATOM | 2219 | OE2 | GLU | B | 276 | 25.007 | -23.482 | 13.951 | 1.00 60.63 | O |
| ATOM | 2220 | C | GLU | B | 276 | 19.557 | -24.625 | 15.581 | 1.00 58.35 | C |
| ATOM | 2221 | O | GLU | B | 276 | 19.973 | -24.670 | 16.734 | 1.00 58.50 | O |
| ATOM | 2222 | N | LEU | B | 277 | 18.299 | -24.326 | 15.279 | 1.00 58.85 | N |
| ATOM | 2223 | CA | LEU | B | 277 | 17.316 | -24.028 | 16.310 | 1.00 59.33 | C |
| ATOM | 2224 | CB | LEU | B | 277 | 16.613 | -22.698 | 16.045 | 1.00 59.37 | C |
| ATOM | 2225 | CG | LEU | B | 277 | 17.114 | -21.399 | 16.656 | 1.00 59.59 | C |
| ATOM | 2226 | CD1 | LEU | B | 277 | 15.978 | -20.393 | 16.663 | 1.00 59.84 | C |
| ATOM | 2227 | CD2 | LEU | B | 277 | 17.594 | -21.636 | 18.056 | 1.00 60.01 | C |
| ATOM | 2228 | C | LEU | B | 277 | 16.254 | -25.097 | 16.414 | 1.00 59.59 | C |
| ATOM | 2229 | O | LEU | B | 277 | 15.976 | -25.825 | 15.468 | 1.00 59.60 | O |
| ATOM | 2230 | N | SER | B | 278 | 15.658 | -25.164 | 17.592 | 1.00 59.99 | N |
| ATOM | 2231 | CA | SER | B | 278 | 14.559 | -26.059 | 17.865 | 1.00 60.28 | C |
| ATOM | 2232 | CB | SER | B | 278 | 14.235 | -26.006 | 19.354 | 1.00 60.29 | C |
| ATOM | 2233 | OG | SER | B | 278 | 14.710 | -24.797 | 19.935 | 1.00 60.46 | O |
| ATOM | 2234 | C | SER | B | 278 | 13.369 | -25.586 | 17.052 | 1.00 60.49 | C |
| ATOM | 2235 | O | SER | B | 278 | 13.007 | -24.412 | 17.090 | 1.00 60.53 | O |
| ATOM | 2236 | N | LEU | B | 279 | 12.763 | -26.494 | 16.302 | 1.00 60.72 | N |
| ATOM | 2237 | CA | LEU | B | 279 | 11.613 | -26.130 | 15.490 | 1.00 60.89 | C |
| ATOM | 2238 | CB | LEU | B | 279 | 11.084 | -27.334 | 14.712 | 1.00 61.01 | C |
| ATOM | 2239 | CG | LEU | B | 279 | 11.891 | -27.650 | 13.450 | 1.00 61.49 | C |
| ATOM | 2240 | CD1 | LEU | B | 279 | 13.169 | -28.431 | 13.777 | 1.00 61.89 | C |
| ATOM | 2241 | CD2 | LEU | B | 279 | 11.044 | -28.418 | 12.449 | 1.00 62.01 | C |
| ATOM | 2242 | C | LEU | B | 279 | 10.516 | -25.497 | 16.337 | 1.00 60.82 | C |
| ATOM | 2243 | O | LEU | B | 279 | 9.761 | -24.661 | 15.853 | 1.00 60.84 | O |

204

| ATOM | 2244 | N   | LEU B 280 | 10.427 | -25.898 | 17.601 | 1.00 | 60.77 | N |
| ATOM | 2245 | CA  | LEU B 280 | 9.456  | -25.297 | 18.505 | 1.00 | 60.62 | C |
| ATOM | 2246 | CB  | LEU B 280 | 9.653  | -25.783 | 19.945 | 1.00 | 60.75 | C |
| ATOM | 2247 | CG  | LEU B 280 | 8.993  | -24.944 | 21.048 | 1.00 | 60.88 | C |
| ATOM | 2248 | CD1 | LEU B 280 | 7.476  | -25.008 | 20.956 | 1.00 | 61.14 | C |
| ATOM | 2249 | CD2 | LEU B 280 | 9.467  | -25.367 | 22.434 | 1.00 | 60.97 | C |
| ATOM | 2250 | C   | LEU B 280 | 9.678  | -23.804 | 18.426 | 1.00 | 60.40 | C |
| ATOM | 2251 | O   | LEU B 280 | 8.739  | -23.030 | 18.237 | 1.00 | 60.43 | O |
| ATOM | 2252 | N   | ASP B 281 | 10.941 | -23.412 | 18.540 | 1.00 | 60.07 | N |
| ATOM | 2253 | CA  | ASP B 281 | 11.322 | -22.007 | 18.464 | 1.00 | 59.68 | C |
| ATOM | 2254 | CB  | ASP B 281 | 12.730 | -21.818 | 19.026 | 1.00 | 59.87 | C |
| ATOM | 2255 | CG  | ASP B 281 | 12.776 | -21.992 | 20.529 | 1.00 | 60.22 | C |
| ATOM | 2256 | OD1 | ASP B 281 | 11.719 | -22.316 | 21.112 | 1.00 | 60.82 | O |
| ATOM | 2257 | OD2 | ASP B 281 | 13.813 | -21.820 | 21.206 | 1.00 | 60.59 | O |
| ATOM | 2258 | C   | ASP B 281 | 11.193 | -21.423 | 17.052 | 1.00 | 59.14 | C |
| ATOM | 2259 | O   | ASP B 281 | 10.566 | -20.393 | 16.864 | 1.00 | 59.04 | O |
| ATOM | 2260 | N   | GLN B 282 | 11.775 | -22.088 | 16.063 | 1.00 | 58.58 | N |
| ATOM | 2261 | CA  | GLN B 282 | 11.683 | -21.619 | 14.681 | 1.00 | 57.99 | C |
| ATOM | 2262 | CB  | GLN B 282 | 12.191 | -22.669 | 13.696 | 1.00 | 58.08 | C |
| ATOM | 2263 | CG  | GLN B 282 | 13.694 | -22.724 | 13.579 | 1.00 | 58.48 | C |
| ATOM | 2264 | CD  | GLN B 282 | 14.153 | -23.679 | 12.499 | 1.00 | 59.19 | C |
| ATOM | 2265 | OE1 | GLN B 282 | 13.425 | -23.932 | 11.538 | 1.00 | 59.26 | O |
| ATOM | 2266 | NE2 | GLN B 282 | 15.362 | -24.212 | 12.650 | 1.00 | 59.63 | N |
| ATOM | 2267 | C   | GLN B 282 | 10.270 | -21.201 | 14.306 | 1.00 | 57.42 | C |
| ATOM | 2268 | O   | GLN B 282 | 10.063 | -20.121 | 13.776 | 1.00 | 57.41 | O |
| ATOM | 2269 | N   | VAL B 283 | 9.294  | -22.056 | 14.571 | 1.00 | 56.71 | N |
| ATOM | 2270 | CA  | VAL B 283 | 7.912  | -21.720 | 14.259 | 1.00 | 55.96 | C |
| ATOM | 2271 | CB  | VAL B 283 | 6.966  | -22.915 | 14.471 | 1.00 | 56.05 | C |
| ATOM | 2272 | CG1 | VAL B 283 | 5.522  | -22.461 | 14.398 | 1.00 | 56.05 | C |
| ATOM | 2273 | CG2 | VAL B 283 | 7.233  | -24.011 | 13.455 | 1.00 | 56.09 | C |
| ATOM | 2274 | C   | VAL B 283 | 7.428  | -20.580 | 15.142 | 1.00 | 55.34 | C |
| ATOM | 2275 | O   | VAL B 283 | 6.769  | -19.654 | 14.685 | 1.00 | 55.24 | O |
| ATOM | 2276 | N   | ARG B 284 | 7.770  | -20.653 | 16.417 | 1.00 | 54.54 | N |
| ATOM | 2277 | CA  | ARG B 284 | 7.312  | -19.670 | 17.387 | 1.00 | 53.71 | C |
| ATOM | 2278 | CB  | ARG B 284 | 7.775  | -20.096 | 18.779 | 1.00 | 53.91 | C |
| ATOM | 2279 | CG  | ARG B 284 | 7.341  | -19.205 | 19.907 | 1.00 | 54.61 | C |
| ATOM | 2280 | CD  | ARG B 284 | 8.152  | -19.420 | 21.165 | 1.00 | 55.69 | C |
| ATOM | 2281 | NE  | ARG B 284 | 8.612  | -18.156 | 21.739 | 1.00 | 56.69 | N |
| ATOM | 2282 | CZ  | ARG B 284 | 9.883  | -17.896 | 22.059 | 1.00 | 57.06 | C |
| ATOM | 2283 | NH1 | ARG B 284 | 10.824 | -18.816 | 21.860 | 1.00 | 56.83 | N |
| ATOM | 2284 | NH2 | ARG B 284 | 10.217 | -16.716 | 22.578 | 1.00 | 57.16 | N |
| ATOM | 2285 | C   | ARG B 284 | 7.761  | -18.248 | 17.066 | 1.00 | 52.80 | C |
| ATOM | 2286 | O   | ARG B 284 | 6.989  | -17.306 | 17.190 | 1.00 | 52.61 | O |
| ATOM | 2287 | N   | LEU B 285 | 9.011  | -18.107 | 16.643 | 1.00 | 51.84 | N |
| ATOM | 2288 | CA  | LEU B 285 | 9.573  | -16.808 | 16.315 | 1.00 | 50.81 | C |
| ATOM | 2289 | CB  | LEU B 285 | 11.077 | -16.943 | 16.080 | 1.00 | 50.83 | C |
| ATOM | 2293 | C   | LEU B 285 | 8.871  | -16.206 | 15.104 | 1.00 | 50.05 | C |
| ATOM | 2294 | O   | LEU B 285 | 8.437  | -15.058 | 15.131 | 1.00 | 49.88 | O |
| ATOM | 2295 | N   | LEU B 286 | 8.749  | -17.006 | 14.051 | 1.00 | 49.15 | N |
| ATOM | 2296 | CA  | LEU B 286 | 8.081  | -16.583 | 12.832 | 1.00 | 48.27 | C |
| ATOM | 2297 | CB  | LEU B 286 | 8.228  | -17.650 | 11.747 | 1.00 | 48.28 | C |
| ATOM | 2298 | CG  | LEU B 286 | 9.561  | -17.617 | 11.004 | 1.00 | 48.48 | C |
| ATOM | 2299 | CD1 | LEU B 286 | 9.896  | -18.955 | 10.347 | 1.00 | 48.28 | C |
| ATOM | 2300 | CD2 | LEU B 286 | 9.564  | -16.475 | 9.982  | 1.00 | 48.72 | C |
| ATOM | 2301 | C   | LEU B 286 | 6.610  | -16.289 | 13.067 | 1.00 | 47.62 | C |
| ATOM | 2302 | O   | LEU B 286 | 5.995  | -15.552 | 12.303 | 1.00 | 47.62 | O |
| ATOM | 2303 | N   | GLU B 287 | 6.049  | -16.869 | 14.122 | 1.00 | 46.74 | N |
| ATOM | 2304 | CA  | GLU B 287 | 4.629  | -16.716 | 14.412 | 1.00 | 45.87 | C |
| ATOM | 2305 | CB  | GLU B 287 | 4.159  | -17.772 | 15.400 | 1.00 | 46.02 | C |
| ATOM | 2306 | CG  | GLU B 287 | 3.543  | -19.014 | 14.792 | 1.00 | 46.55 | C |
| ATOM | 2307 | CD  | GLU B 287 | 2.634  | -19.687 | 15.798 | 1.00 | 47.59 | C |

205

| ATOM | 2308 | OE1 | GLU | B | 287 | 2.389 | -19.076 | 16.864 | 1.00 | 48.36 | O |
| ATOM | 2309 | OE2 | GLU | B | 287 | 2.167 | -20.820 | 15.545 | 1.00 | 48.01 | O |
| ATOM | 2310 | C | GLU | B | 287 | 4.309 | -15.354 | 14.978 | 1.00 | 45.07 | C |
| ATOM | 2311 | O | GLU | B | 287 | 3.249 | -14.804 | 14.716 | 1.00 | 45.04 | O |
| ATOM | 2312 | N | SER | B | 288 | 5.217 | -14.800 | 15.764 | 1.00 | 44.04 | N |
| ATOM | 2313 | CA | SER | B | 288 | 4.951 | -13.498 | 16.340 | 1.00 | 43.12 | C |
| ATOM | 2314 | CB | SER | B | 288 | 5.416 | -13.454 | 17.779 | 1.00 | 43.18 | C |
| ATOM | 2315 | OG | SER | B | 288 | 6.801 | -13.641 | 17.826 | 1.00 | 43.47 | O |
| ATOM | 2316 | C | SER | B | 288 | 5.553 | -12.329 | 15.576 | 1.00 | 42.38 | C |
| ATOM | 2317 | O | SER | B | 288 | 5.065 | -11.210 | 15.694 | 1.00 | 42.54 | O |
| ATOM | 2318 | N | CYS | B | 289 | 6.588 | -12.558 | 14.781 | 1.00 | 41.21 | N |
| ATOM | 2319 | CA | CYS | B | 289 | 7.201 | -11.432 | 14.092 | 1.00 | 40.03 | C |
| ATOM | 2320 | CB | CYS | B | 289 | 8.716 | -11.542 | 14.162 | 1.00 | 40.02 | C |
| ATOM | 2321 | SG | CYS | B | 289 | 9.389 | -12.764 | 13.036 | 1.00 | 39.42 | S |
| ATOM | 2322 | C | CYS | B | 289 | 6.783 | -11.238 | 12.639 | 1.00 | 39.36 | C |
| ATOM | 2323 | O | CYS | B | 289 | 7.096 | -10.220 | 12.042 | 1.00 | 39.17 | O |
| ATOM | 2324 | N | TRP | B | 290 | 6.068 | -12.192 | 12.057 | 1.00 | 38.53 | N |
| ATOM | 2325 | CA | TRP | B | 290 | 5.820 | -12.090 | 10.625 | 1.00 | 37.64 | C |
| ATOM | 2326 | CB | TRP | B | 290 | 5.003 | -13.266 | 10.073 | 1.00 | 37.44 | C |
| ATOM | 2327 | CG | TRP | B | 290 | 3.573 | -13.288 | 10.459 | 1.00 | 36.55 | C |
| ATOM | 2328 | CD1 | TRP | B | 290 | 3.034 | -13.906 | 11.537 | 1.00 | 35.87 | C |
| ATOM | 2329 | NE1 | TRP | B | 290 | 1.677 | -13.720 | 11.561 | 1.00 | 35.29 | N |
| ATOM | 2330 | CE2 | TRP | B | 290 | 1.315 | -12.979 | 10.472 | 1.00 | 35.22 | C |
| ATOM | 2331 | CD2 | TRP | B | 290 | 2.485 | -12.692 | 9.755 | 1.00 | 35.48 | C |
| ATOM | 2332 | CE3 | TRP | B | 290 | 2.380 | -11.940 | 8.588 | 1.00 | 35.10 | C |
| ATOM | 2333 | CZ3 | TRP | B | 290 | 1.146 | -11.504 | 8.187 | 1.00 | 34.85 | C |
| ATOM | 2334 | CH2 | TRP | B | 290 | 0.004 | -11.803 | 8.920 | 1.00 | 35.20 | C |
| ATOM | 2335 | CZ2 | TRP | B | 290 | 0.065 | -12.542 | 10.066 | 1.00 | 35.16 | C |
| ATOM | 2336 | C | TRP | B | 290 | 5.268 | -10.733 | 10.209 | 1.00 | 37.30 | C |
| ATOM | 2337 | O | TRP | B | 290 | 5.781 | -10.121 | 9.280 | 1.00 | 37.21 | O |
| ATOM | 2338 | N | MET | B | 291 | 4.254 | -10.240 | 10.906 | 1.00 | 36.90 | N |
| ATOM | 2339 | CA | MET | B | 291 | 3.693 | -8.948 | 10.527 | 1.00 | 36.63 | C |
| ATOM | 2340 | CB | MET | B | 291 | 2.356 | -8.685 | 11.216 | 1.00 | 36.59 | C |
| ATOM | 2341 | CG | MET | B | 291 | 1.734 | -7.370 | 10.796 | 1.00 | 36.68 | C |
| ATOM | 2342 | SD | MET | B | 291 | 1.294 | -7.370 | 9.052 | 1.00 | 37.60 | S |
| ATOM | 2343 | CE | MET | B | 291 | -0.386 | -8.094 | 9.180 | 1.00 | 37.23 | C |
| ATOM | 2344 | C | MET | B | 291 | 4.679 | -7.789 | 10.746 | 1.00 | 36.34 | C |
| ATOM | 2345 | O | MET | B | 291 | 4.691 | -6.833 | 9.989 | 1.00 | 36.40 | O |
| ATOM | 2346 | N | GLU | B | 292 | 5.508 | -7.884 | 11.772 | 1.00 | 35.99 | N |
| ATOM | 2347 | CA | GLU | B | 292 | 6.502 | -6.859 | 12.027 | 1.00 | 35.87 | C |
| ATOM | 2348 | CB | GLU | B | 292 | 7.211 | -7.092 | 13.364 | 1.00 | 35.93 | C |
| ATOM | 2349 | CG | GLU | B | 292 | 6.416 | -6.594 | 14.557 | 1.00 | 37.54 | C |
| ATOM | 2350 | CD | GLU | B | 292 | 7.001 | -7.004 | 15.907 | 1.00 | 39.99 | C |
| ATOM | 2351 | OE1 | GLU | B | 292 | 7.934 | -6.308 | 16.403 | 1.00 | 41.58 | O |
| ATOM | 2352 | OE2 | GLU | B | 292 | 6.524 | -8.010 | 16.493 | 1.00 | 40.09 | O |
| ATOM | 2353 | C | GLU | B | 292 | 7.505 | -6.824 | 10.884 | 1.00 | 35.36 | C |
| ATOM | 2354 | O | GLU | B | 292 | 7.843 | -5.753 | 10.369 | 1.00 | 35.41 | O |
| ATOM | 2355 | N | VAL | B | 293 | 7.964 | -8.003 | 10.487 | 1.00 | 34.76 | N |
| ATOM | 2356 | CA | VAL | B | 293 | 8.921 | -8.143 | 9.400 | 1.00 | 34.18 | C |
| ATOM | 2357 | CB | VAL | B | 293 | 9.378 | -9.609 | 9.245 | 1.00 | 34.20 | C |
| ATOM | 2358 | CG1 | VAL | B | 293 | 10.176 | -9.803 | 8.009 | 1.00 | 33.76 | C |
| ATOM | 2359 | CG2 | VAL | B | 293 | 10.192 | -10.043 | 10.480 | 1.00 | 34.25 | C |
| ATOM | 2360 | C | VAL | B | 293 | 8.300 | -7.615 | 8.115 | 1.00 | 33.95 | C |
| ATOM | 2361 | O | VAL | B | 293 | 8.917 | -6.802 | 7.406 | 1.00 | 33.96 | O |
| ATOM | 2362 | N | LEU | B | 294 | 7.073 | -8.036 | 7.821 | 1.00 | 33.38 | N |
| ATOM | 2363 | CA | LEU | B | 294 | 6.408 | -7.534 | 6.625 | 1.00 | 32.97 | C |
| ATOM | 2364 | CB | LEU | B | 294 | 4.975 | -8.061 | 6.518 | 1.00 | 33.00 | C |
| ATOM | 2365 | CG | LEU | B | 294 | 4.781 | -9.501 | 6.054 | 1.00 | 32.92 | C |
| ATOM | 2366 | CD1 | LEU | B | 294 | 3.369 | -9.703 | 5.634 | 1.00 | 32.96 | C |
| ATOM | 2367 | CD2 | LEU | B | 294 | 5.722 | -9.851 | 4.890 | 1.00 | 32.92 | C |
| ATOM | 2368 | C | LEU | B | 294 | 6.367 | -6.019 | 6.682 | 1.00 | 32.69 | C |

| | | | | | | | | | |
|---|---|---|---|---|---|---|---|---|---|
| ATOM | 2369 | O | LEU | B | 294 | 6.694 | -5.336 | 5.709 | 1.00 32.70 | O |
| ATOM | 2370 | N | MET | B | 295 | 5.975 | -5.496 | 7.838 | 1.00 32.12 | N |
| ATOM | 2371 | CA | MET | B | 295 | 5.836 | -4.057 | 8.011 | 1.00 31.62 | C |
| ATOM | 2372 | CB | MET | B | 295 | 5.126 | -3.760 | 9.326 | 1.00 31.45 | C |
| ATOM | 2373 | CG | MET | B | 295 | 3.641 | -3.962 | 9.204 | 1.00 30.48 | C |
| ATOM | 2374 | SD | MET | B | 295 | 2.783 | -3.702 | 10.709 | 1.00 28.52 | S |
| ATOM | 2375 | CE | MET | B | 295 | 1.079 | -3.660 | 10.092 | 1.00 28.62 | C |
| ATOM | 2376 | C | MET | B | 295 | 7.118 | -3.249 | 7.920 | 1.00 31.53 | C |
| ATOM | 2377 | O | MET | B | 295 | 7.128 | -2.157 | 7.345 | 1.00 31.46 | O |
| ATOM | 2378 | N | VAL | B | 296 | 8.192 | -3.774 | 8.502 | 1.00 31.47 | N |
| ATOM | 2379 | CA | VAL | B | 296 | 9.460 | -3.050 | 8.506 | 1.00 31.37 | C |
| ATOM | 2380 | CB | VAL | B | 296 | 10.510 | -3.673 | 9.473 | 1.00 31.42 | C |
| ATOM | 2381 | CG1 | VAL | B | 296 | 11.125 | -4.889 | 8.842 | 1.00 31.48 | C |
| ATOM | 2382 | CG2 | VAL | B | 296 | 11.616 | -2.677 | 9.776 | 1.00 31.32 | C |
| ATOM | 2383 | C | VAL | B | 296 | 9.976 | -2.996 | 7.075 | 1.00 31.10 | C |
| ATOM | 2384 | O | VAL | B | 296 | 10.495 | -1.989 | 6.627 | 1.00 31.03 | O |
| ATOM | 2385 | N | GLY | B | 297 | 9.788 | -4.073 | 6.339 | 1.00 31.01 | N |
| ATOM | 2386 | CA | GLY | B | 297 | 10.185 | -4.070 | 4.946 | 1.00 30.85 | C |
| ATOM | 2387 | C | GLY | B | 297 | 9.336 | -3.063 | 4.200 | 1.00 30.88 | C |
| ATOM | 2388 | O | GLY | B | 297 | 9.826 | -2.303 | 3.367 | 1.00 30.80 | O |
| ATOM | 2389 | N | LEU | B | 298 | 8.042 | -3.047 | 4.491 | 1.00 31.00 | N |
| ATOM | 2390 | CA | LEU | B | 298 | 7.179 | -2.079 | 3.842 | 1.00 31.12 | C |
| ATOM | 2391 | CB | LEU | B | 298 | 5.730 | -2.250 | 4.288 | 1.00 31.05 | C |
| ATOM | 2392 | CG | LEU | B | 298 | 4.823 | -1.041 | 4.009 | 1.00 30.91 | C |
| ATOM | 2393 | CD1 | LEU | B | 298 | 4.751 | -0.688 | 2.523 | 1.00 29.73 | C |
| ATOM | 2394 | CD2 | LEU | B | 298 | 3.439 | -1.292 | 4.577 | 1.00 30.52 | C |
| ATOM | 2395 | C | LEU | B | 298 | 7.705 | -0.665 | 4.127 | 1.00 31.29 | C |
| ATOM | 2396 | O | LEU | B | 298 | 7.887 | 0.127 | 3.207 | 1.00 31.40 | O |
| ATOM | 2397 | N | MET | B | 299 | 7.988 | -0.365 | 5.389 | 1.00 31.36 | N |
| ATOM | 2398 | CA | MET | B | 299 | 8.546 | 0.930 | 5.736 | 1.00 31.57 | C |
| ATOM | 2399 | CB | MET | B | 299 | 8.761 | 1.012 | 7.227 | 1.00 31.62 | C |
| ATOM | 2400 | CG | MET | B | 299 | 7.473 | 1.140 | 7.960 | 1.00 31.61 | C |
| ATOM | 2401 | SD | MET | B | 299 | 7.718 | 0.929 | 9.654 | 1.00 31.72 | S |
| ATOM | 2402 | CE | MET | B | 299 | 6.009 | 0.909 | 10.148 | 1.00 31.29 | C |
| ATOM | 2403 | C | MET | B | 299 | 9.843 | 1.247 | 5.006 | 1.00 31.69 | C |
| ATOM | 2404 | O | MET | B | 299 | 9.999 | 2.325 | 4.437 | 1.00 31.51 | O |
| ATOM | 2405 | N | TRP | B | 300 | 10.773 | 0.301 | 5.014 | 1.00 31.99 | N |
| ATOM | 2406 | CA | TRP | B | 300 | 12.040 | 0.516 | 4.344 | 1.00 32.22 | C |
| ATOM | 2407 | CB | TRP | B | 300 | 12.947 | -0.706 | 4.443 | 1.00 32.11 | C |
| ATOM | 2408 | CG | TRP | B | 300 | 14.068 | -0.586 | 3.432 | 1.00 31.52 | C |
| ATOM | 2409 | CD1 | TRP | B | 300 | 14.221 | -1.308 | 2.299 | 1.00 30.60 | C |
| ATOM | 2410 | NE1 | TRP | B | 300 | 15.334 | -0.883 | 1.617 | 1.00 30.73 | N |
| ATOM | 2411 | CE2 | TRP | B | 300 | 15.908 | 0.156 | 2.292 | 1.00 30.19 | C |
| ATOM | 2412 | CD2 | TRP | B | 300 | 15.135 | 0.375 | 3.442 | 1.00 30.25 | C |
| ATOM | 2413 | CE3 | TRP | B | 300 | 15.513 | 1.395 | 4.313 | 1.00 29.84 | C |
| ATOM | 2414 | CZ3 | TRP | B | 300 | 16.638 | 2.143 | 4.026 | 1.00 29.35 | C |
| ATOM | 2415 | CH2 | TRP | B | 300 | 17.395 | 1.899 | 2.870 | 1.00 29.50 | C |
| ATOM | 2416 | CZ2 | TRP | B | 300 | 17.043 | 0.912 | 1.988 | 1.00 29.78 | C |
| ATOM | 2417 | C | TRP | B | 300 | 11.855 | 0.876 | 2.870 | 1.00 32.67 | C |
| ATOM | 2418 | O | TRP | B | 300 | 12.434 | 1.836 | 2.408 | 1.00 32.72 | O |
| ATOM | 2419 | N | ARG | B | 301 | 11.081 | 0.075 | 2.137 | 1.00 33.26 | N |
| ATOM | 2420 | CA | ARG | B | 301 | 10.786 | 0.320 | 0.722 | 1.00 33.55 | C |
| ATOM | 2421 | CB | ARG | B | 301 | 9.910 | -0.804 | 0.129 | 1.00 33.40 | C |
| ATOM | 2422 | CG | ARG | B | 301 | 10.539 | -2.200 | 0.018 | 1.00 32.14 | C |
| ATOM | 2423 | CD | ARG | B | 301 | 9.725 | -3.209 | -0.734 | 1.00 29.70 | C |
| ATOM | 2424 | NE | ARG | B | 301 | 8.392 | -3.346 | -0.175 | 1.00 29.92 | N |
| ATOM | 2425 | CZ | ARG | B | 301 | 8.047 | -4.141 | 0.855 | 1.00 29.72 | C |
| ATOM | 2426 | NH1 | ARG | B | 301 | 8.923 | -4.911 | 1.478 | 1.00 28.60 | N |
| ATOM | 2427 | NH2 | ARG | B | 301 | 6.791 | -4.167 | 1.263 | 1.00 29.72 | N |
| ATOM | 2428 | C | ARG | B | 301 | 10.049 | 1.639 | 0.505 | 1.00 34.24 | C |
| ATOM | 2429 | O | ARG | B | 301 | 10.104 | 2.197 | -0.573 | 1.00 34.34 | O |

207

| | | | | | | | | | | |
|---|---|---|---|---|---|---|---|---|---|---|
| ATOM | 2430 | N | SER | B | 302 | 9.345 | 2.139 | 1.513 | 1.00 35.13 | N |
| ATOM | 2431 | CA | SER | B | 302 | 8.537 | 3.349 | 1.333 | 1.00 35.97 | C |
| ATOM | 2432 | CB | SER | B | 302 | 7.190 | 3.194 | 2.045 | 1.00 35.92 | C |
| ATOM | 2433 | OG | SER | B | 302 | 6.414 | 2.153 | 1.477 | 1.00 36.09 | O |
| ATOM | 2434 | C | SER | B | 302 | 9.202 | 4.623 | 1.828 | 1.00 36.61 | C |
| ATOM | 2435 | O | SER | B | 302 | 8.657 | 5.708 | 1.689 | 1.00 36.66 | O |
| ATOM | 2436 | N | ILE | B | 303 | 10.387 | 4.482 | 2.392 | 1.00 37.47 | N |
| ATOM | 2437 | CA | ILE | B | 303 | 11.105 | 5.583 | 3.017 | 1.00 38.39 | C |
| ATOM | 2438 | CB | ILE | B | 303 | 12.432 | 5.060 | 3.510 | 1.00 38.36 | C |
| ATOM | 2439 | CG1 | ILE | B | 303 | 12.766 | 5.642 | 4.855 | 1.00 38.89 | C |
| ATOM | 2440 | CD1 | ILE | B | 303 | 14.157 | 5.264 | 5.280 | 1.00 40.50 | C |
| ATOM | 2441 | CG2 | ILE | B | 303 | 13.522 | 5.369 | 2.530 | 1.00 38.54 | C |
| ATOM | 2442 | C | ILE | B | 303 | 11.317 | 6.875 | 2.211 | 1.00 39.02 | C |
| ATOM | 2443 | O | ILE | B | 303 | 11.148 | 7.960 | 2.754 | 1.00 39.26 | O |
| ATOM | 2444 | N | ASP | B | 304 | 11.691 | 6.787 | 0.944 | 1.00 39.67 | N |
| ATOM | 2445 | CA | ASP | B | 304 | 11.940 | 7.997 | 0.149 | 1.00 40.48 | C |
| ATOM | 2446 | CB | ASP | B | 304 | 13.247 | 7.821 | -0.664 | 1.00 40.76 | C |
| ATOM | 2447 | CG | ASP | B | 304 | 14.495 | 7.612 | 0.216 | 1.00 41.48 | C |
| ATOM | 2448 | OD1 | ASP | B | 304 | 14.476 | 8.032 | 1.389 | 1.00 42.64 | O |
| ATOM | 2449 | OD2 | ASP | B | 304 | 15.548 | 7.053 | -0.194 | 1.00 42.10 | O |
| ATOM | 2450 | C | ASP | B | 304 | 10.766 | 8.328 | -0.825 | 1.00 40.77 | C |
| ATOM | 2451 | O | ASP | B | 304 | 10.978 | 8.861 | -1.922 | 1.00 40.59 | O |
| ATOM | 2452 | N | HIS | B | 305 | 9.538 | 7.986 | -0.438 | 1.00 41.12 | N |
| ATOM | 2453 | CA | HIS | B | 305 | 8.384 | 8.144 | -1.327 | 1.00 41.48 | C |
| ATOM | 2454 | CB | HIS | B | 305 | 8.114 | 6.841 | -2.115 | 1.00 41.66 | C |
| ATOM | 2455 | CG | HIS | B | 305 | 9.301 | 6.317 | -2.857 | 1.00 42.63 | C |
| ATOM | 2456 | ND1 | HIS | B | 305 | 9.741 | 6.870 | -4.039 | 1.00 44.23 | N |
| ATOM | 2457 | CE1 | HIS | B | 305 | 10.800 | 6.208 | -4.466 | 1.00 44.69 | C |
| ATOM | 2458 | NE2 | HIS | B | 305 | 11.068 | 5.249 | -3.598 | 1.00 45.03 | N |
| ATOM | 2459 | CD2 | HIS | B | 305 | 10.146 | 5.299 | -2.582 | 1.00 43.78 | C |
| ATOM | 2460 | C | HIS | B | 305 | 7.132 | 8.563 | -0.548 | 1.00 41.38 | C |
| ATOM | 2461 | O | HIS | B | 305 | 6.147 | 7.841 | -0.445 | 1.00 41.38 | O |
| ATOM | 2462 | N | PRO | B | 306 | 7.179 | 9.769 | -0.031 | 1.00 41.42 | N |
| ATOM | 2463 | CA | PRO | B | 306 | 6.112 | 10.346 | 0.803 | 1.00 41.33 | C |
| ATOM | 2464 | CB | PRO | B | 306 | 6.372 | 11.850 | 0.722 | 1.00 41.31 | C |
| ATOM | 2465 | CG | PRO | B | 306 | 7.738 | 12.018 | 0.150 | 1.00 41.52 | C |
| ATOM | 2466 | CD | PRO | B | 306 | 8.300 | 10.688 | -0.242 | 1.00 41.55 | C |
| ATOM | 2467 | C | PRO | B | 306 | 4.692 | 10.122 | 0.324 | 1.00 41.13 | C |
| ATOM | 2468 | O | PRO | B | 306 | 4.423 | 10.101 | -0.879 | 1.00 41.23 | O |
| ATOM | 2469 | N | GLY | B | 307 | 3.783 | 10.023 | 1.287 | 1.00 40.80 | N |
| ATOM | 2470 | CA | GLY | B | 307 | 2.376 | 9.835 | 1.012 | 1.00 40.44 | C |
| ATOM | 2471 | C | GLY | B | 307 | 2.054 | 8.507 | 0.360 | 1.00 40.22 | C |
| ATOM | 2472 | O | GLY | B | 307 | 0.877 | 8.183 | 0.174 | 1.00 40.17 | O |
| ATOM | 2473 | N | LYS | B | 308 | 3.090 | 7.728 | 0.047 | 1.00 39.91 | N |
| ATOM | 2474 | CA | LYS | B | 308 | 2.920 | 6.466 | -0.661 | 1.00 39.68 | C |
| ATOM | 2475 | CB | LYS | B | 308 | 3.554 | 6.584 | -2.052 | 1.00 39.77 | C |
| ATOM | 2480 | C | LYS | B | 308 | 3.472 | 5.239 | 0.094 | 1.00 39.46 | C |
| ATOM | 2481 | O | LYS | B | 308 | 4.391 | 5.356 | 0.896 | 1.00 39.53 | O |
| ATOM | 2482 | N | LEU | B | 309 | 2.888 | 4.065 | -0.140 | 1.00 39.08 | N |
| ATOM | 2483 | CA | LEU | B | 309 | 3.400 | 2.830 | 0.457 | 1.00 38.76 | C |
| ATOM | 2484 | CB | LEU | B | 309 | 2.381 | 2.209 | 1.412 | 1.00 38.67 | C |
| ATOM | 2485 | CG | LEU | B | 309 | 2.118 | 2.956 | 2.729 | 1.00 38.89 | C |
| ATOM | 2486 | CD1 | LEU | B | 309 | 1.045 | 2.314 | 3.574 | 1.00 38.87 | C |
| ATOM | 2487 | CD2 | LEU | B | 309 | 3.382 | 3.084 | 3.553 | 1.00 38.90 | C |
| ATOM | 2488 | C | LEU | B | 309 | 3.780 | 1.837 | -0.648 | 1.00 38.66 | C |
| ATOM | 2489 | O | LEU | B | 309 | 2.901 | 1.316 | -1.337 | 1.00 38.63 | O |
| ATOM | 2490 | N | ILE | B | 310 | 5.080 | 1.604 | -0.843 | 1.00 38.41 | N |
| ATOM | 2491 | CA | ILE | B | 310 | 5.530 | 0.661 | -1.854 | 1.00 38.34 | C |
| ATOM | 2492 | CB | ILE | B | 310 | 7.019 | 0.915 | -2.241 | 1.00 38.48 | C |
| ATOM | 2493 | CG1 | ILE | B | 310 | 7.281 | 2.392 | -2.505 | 1.00 37.94 | C |
| ATOM | 2494 | CD1 | ILE | B | 310 | 6.122 | 3.079 | -3.098 | 1.00 37.51 | C |

208

| ATOM | 2495 | CG2 | ILE | B | 310 | 7.425 | 0.073 | -3.460 | 1.00 | 38.19 | C |
| ATOM | 2496 | C | ILE | B | 310 | 5.357 | -0.780 | -1.351 | 1.00 | 38.45 | C |
| ATOM | 2497 | O | ILE | B | 310 | 6.310 | -1.399 | -0.876 | 1.00 | 38.22 | O |
| ATOM | 2498 | N | PHE | B | 311 | 4.136 | -1.305 | -1.439 | 1.00 | 38.59 | N |
| ATOM | 2499 | CA | PHE | B | 311 | 3.864 | -2.679 | -1.007 | 1.00 | 38.80 | C |
| ATOM | 2500 | CB | PHE | B | 311 | 2.377 | -3.014 | -1.110 | 1.00 | 38.82 | C |
| ATOM | 2501 | CG | PHE | B | 311 | 1.602 | -2.634 | 0.114 | 1.00 | 38.85 | C |
| ATOM | 2502 | CD1 | PHE | B | 311 | 1.617 | -3.453 | 1.220 | 1.00 | 38.62 | C |
| ATOM | 2503 | CE1 | PHE | B | 311 | 0.940 | -3.116 | 2.348 | 1.00 | 39.08 | C |
| ATOM | 2504 | CZ | PHE | B | 311 | 0.235 | -1.934 | 2.403 | 1.00 | 39.07 | C |
| ATOM | 2505 | CE2 | PHE | B | 311 | 0.210 | -1.096 | 1.305 | 1.00 | 38.93 | C |
| ATOM | 2506 | CD2 | PHE | B | 311 | 0.892 | -1.445 | 0.170 | 1.00 | 38.86 | C |
| ATOM | 2507 | C | PHE | B | 311 | 4.713 | -3.665 | -1.796 | 1.00 | 38.95 | C |
| ATOM | 2508 | O | PHE | B | 311 | 5.288 | -4.597 | -1.226 | 1.00 | 38.97 | O |
| ATOM | 2509 | N | ALA | B | 312 | 4.779 | -3.442 | -3.105 | 1.00 | 38.97 | N |
| ATOM | 2510 | CA | ALA | B | 312 | 5.641 | -4.199 | -3.992 | 1.00 | 39.15 | C |
| ATOM | 2511 | CB | ALA | B | 312 | 4.950 | -5.473 | -4.447 | 1.00 | 38.97 | C |
| ATOM | 2512 | C | ALA | B | 312 | 6.035 | -3.277 | -5.177 | 1.00 | 39.49 | C |
| ATOM | 2513 | O | ALA | B | 312 | 5.486 | -2.196 | -5.340 | 1.00 | 39.32 | O |
| ATOM | 2514 | N | PRO | B | 313 | 7.030 | -3.650 | -5.961 | 1.00 | 39.90 | N |
| ATOM | 2515 | CA | PRO | B | 313 | 7.412 | -2.845 | -7.122 | 1.00 | 40.35 | C |
| ATOM | 2516 | CB | PRO | B | 313 | 8.290 | -3.803 | -7.924 | 1.00 | 40.28 | C |
| ATOM | 2517 | CG | PRO | B | 313 | 8.964 | -4.597 | -6.875 | 1.00 | 40.09 | C |
| ATOM | 2518 | CD | PRO | B | 313 | 7.929 | -4.800 | -5.778 | 1.00 | 39.93 | C |
| ATOM | 2519 | C | PRO | B | 313 | 6.260 | -2.311 | -7.987 | 1.00 | 40.81 | C |
| ATOM | 2520 | O | PRO | B | 313 | 6.308 | -1.147 | -8.400 | 1.00 | 40.92 | O |
| ATOM | 2521 | N | ASP | B | 314 | 5.257 | -3.130 | -8.278 | 1.00 | 41.17 | N |
| ATOM | 2522 | CA | ASP | B | 314 | 4.163 | -2.643 | -9.109 | 1.00 | 41.49 | C |
| ATOM | 2523 | CB | ASP | B | 314 | 4.014 | -3.495 | -10.368 | 1.00 | 41.19 | C |
| ATOM | 2524 | CG | ASP | B | 314 | 5.037 | -3.152 | -11.421 | 1.00 | 40.32 | C |
| ATOM | 2525 | OD1 | ASP | B | 314 | 5.533 | -2.007 | -11.401 | 1.00 | 39.45 | O |
| ATOM | 2526 | OD2 | ASP | B | 314 | 5.400 | -3.963 | -12.300 | 1.00 | 38.85 | O |
| ATOM | 2527 | C | ASP | B | 314 | 2.845 | -2.560 | -8.343 | 1.00 | 42.10 | C |
| ATOM | 2528 | O | ASP | B | 314 | 1.766 | -2.500 | -8.936 | 1.00 | 42.15 | O |
| ATOM | 2529 | N | LEU | B | 315 | 2.947 | -2.570 | -7.021 | 1.00 | 42.77 | N |
| ATOM | 2530 | CA | LEU | B | 315 | 1.792 | -2.467 | -6.161 | 1.00 | 43.49 | C |
| ATOM | 2531 | CB | LEU | B | 315 | 1.589 | -3.779 | -5.423 | 1.00 | 43.32 | C |
| ATOM | 2532 | CG | LEU | B | 315 | 0.377 | -3.880 | -4.492 | 1.00 | 43.16 | C |
| ATOM | 2533 | CD1 | LEU | B | 315 | -0.896 | -3.435 | -5.175 | 1.00 | 42.62 | C |
| ATOM | 2534 | CD2 | LEU | B | 315 | 0.247 | -5.290 | -3.952 | 1.00 | 42.76 | C |
| ATOM | 2535 | C | LEU | B | 315 | 2.043 | -1.321 | -5.190 | 1.00 | 44.24 | C |
| ATOM | 2536 | O | LEU | B | 315 | 2.446 | -1.543 | -4.063 | 1.00 | 44.34 | O |
| ATOM | 2537 | N | VAL | B | 316 | 1.823 | -0.095 | -5.653 | 1.00 | 45.24 | N |
| ATOM | 2538 | CA | VAL | B | 316 | 2.091 | 1.104 | -4.875 | 1.00 | 46.24 | C |
| ATOM | 2539 | CB | VAL | B | 316 | 3.001 | 2.063 | -5.660 | 1.00 | 46.09 | C |
| ATOM | 2540 | CG1 | VAL | B | 316 | 2.933 | 3.474 | -5.089 | 1.00 | 45.80 | C |
| ATOM | 2541 | CG2 | VAL | B | 316 | 4.416 | 1.538 | -5.701 | 1.00 | 45.87 | C |
| ATOM | 2542 | C | VAL | B | 316 | 0.793 | 1.830 | -4.569 | 1.00 | 47.25 | C |
| ATOM | 2543 | O | VAL | B | 316 | 0.044 | 2.193 | -5.481 | 1.00 | 47.20 | O |
| ATOM | 2544 | N | LEU | B | 317 | 0.518 | 2.055 | -3.288 | 1.00 | 48.51 | N |
| ATOM | 2545 | CA | LEU | B | 317 | -0.741 | 2.697 | -2.932 | 1.00 | 49.82 | C |
| ATOM | 2546 | CB | LEU | B | 317 | -1.507 | 1.888 | -1.898 | 1.00 | 49.70 | C |
| ATOM | 2547 | CG | LEU | B | 317 | -1.727 | 0.403 | -2.161 | 1.00 | 49.89 | C |
| ATOM | 2548 | CD1 | LEU | B | 317 | -3.012 | -0.028 | -1.495 | 1.00 | 50.06 | C |
| ATOM | 2549 | CD2 | LEU | B | 317 | -1.775 | 0.086 | -3.642 | 1.00 | 50.00 | C |
| ATOM | 2550 | C | LEU | B | 317 | -0.594 | 4.126 | -2.448 | 1.00 | 50.80 | C |
| ATOM | 2551 | O | LEU | B | 317 | 0.485 | 4.565 | -2.066 | 1.00 | 50.94 | O |
| ATOM | 2552 | N | ASP | B | 318 | -1.706 | 4.845 | -2.489 | 1.00 | 52.07 | N |
| ATOM | 2553 | CA | ASP | B | 318 | -1.779 | 6.220 | -2.030 | 1.00 | 53.32 | C |
| ATOM | 2554 | CB | ASP | B | 318 | -2.709 | 7.012 | -2.935 | 1.00 | 53.42 | C |
| ATOM | 2555 | CG | ASP | B | 318 | -1.974 | 7.913 | -3.896 | 1.00 | 53.89 | C |

209

```
ATOM   2556  OD1 ASP B 318      -0.770   8.169  -3.686  1.00 53.72           O
ATOM   2557  OD2 ASP B 318      -2.543   8.428  -4.891  1.00 54.84           O
ATOM   2558  C   ASP B 318      -2.405   6.202  -0.661  1.00 54.07           C
ATOM   2559  O   ASP B 318      -3.167   5.297  -0.347  1.00 54.13           O
ATOM   2560  N   ARG B 319      -2.106   7.205   0.156  1.00 55.17           N
ATOM   2561  CA  ARG B 319      -2.740   7.280   1.463  1.00 56.20           C
ATOM   2562  CB  ARG B 319      -2.398   8.563   2.201  1.00 56.21           C
ATOM   2563  CG  ARG B 319      -3.059   8.569   3.554  1.00 56.69           C
ATOM   2564  CD  ARG B 319      -3.413   9.917   4.100  1.00 57.76           C
ATOM   2565  NE  ARG B 319      -4.268   9.776   5.273  1.00 58.43           N
ATOM   2566  CZ  ARG B 319      -5.207  10.640   5.620  1.00 58.70           C
ATOM   2567  NH1 ARG B 319      -5.411  11.723   4.887  1.00 58.86           N
ATOM   2568  NH2 ARG B 319      -5.940  10.423   6.703  1.00 58.79           N
ATOM   2569  C   ARG B 319      -4.239   7.235   1.281  1.00 56.81           C
ATOM   2570  O   ARG B 319      -4.914   6.398   1.866  1.00 56.82           O
ATOM   2571  N   ASP B 320      -4.748   8.142   0.453  1.00 57.71           N
ATOM   2572  CA  ASP B 320      -6.179   8.249   0.204  1.00 58.61           C
ATOM   2573  CB  ASP B 320      -6.463   9.292  -0.878  1.00 58.66           C
ATOM   2574  CG  ASP B 320      -6.383  10.709  -0.355  1.00 59.06           C
ATOM   2575  OD1 ASP B 320      -6.509  10.895   0.872  1.00 59.34           O
ATOM   2576  OD2 ASP B 320      -6.202  11.701  -1.094  1.00 59.57           O
ATOM   2577  C   ASP B 320      -6.813   6.918  -0.175  1.00 59.16           C
ATOM   2578  O   ASP B 320      -7.938   6.625   0.230  1.00 59.23           O
ATOM   2579  N   GLU B 321      -6.090   6.107  -0.940  1.00 59.86           N
ATOM   2580  CA  GLU B 321      -6.623   4.822  -1.397  1.00 60.56           C
ATOM   2581  CB  GLU B 321      -5.623   4.105  -2.295  1.00 60.55           C
ATOM   2582  CG  GLU B 321      -5.317   4.866  -3.566  1.00 61.01           C
ATOM   2583  CD  GLU B 321      -4.550   4.035  -4.563  1.00 61.41           C
ATOM   2584  OE1 GLU B 321      -5.199   3.262  -5.302  1.00 61.39           O
ATOM   2585  OE2 GLU B 321      -3.303   4.160  -4.606  1.00 61.63           O
ATOM   2586  C   GLU B 321      -7.052   3.897  -0.268  1.00 60.92           C
ATOM   2587  O   GLU B 321      -7.720   2.896  -0.498  1.00 61.03           O
ATOM   2588  N   GLY B 322      -6.659   4.229   0.952  1.00 61.35           N
ATOM   2589  CA  GLY B 322      -7.052   3.438   2.099  1.00 61.89           C
ATOM   2590  C   GLY B 322      -8.518   3.659   2.420  1.00 62.29           C
ATOM   2591  O   GLY B 322      -9.136   2.872   3.135  1.00 62.36           O
ATOM   2592  N   LYS B 323      -9.080   4.740   1.891  1.00 62.57           N
ATOM   2593  CA  LYS B 323     -10.483   5.036   2.117  1.00 62.80           C
ATOM   2594  CB  LYS B 323     -10.907   6.273   1.324  1.00 62.79           C
ATOM   2599  C   LYS B 323     -11.324   3.831   1.712  1.00 62.95           C
ATOM   2600  O   LYS B 323     -12.389   3.588   2.278  1.00 63.02           O
ATOM   2601  N   CYS B 324     -10.822   3.061   0.752  1.00 63.05           N
ATOM   2602  CA  CYS B 324     -11.551   1.913   0.209  1.00 63.18           C
ATOM   2603  CB  CYS B 324     -10.744   1.249  -0.908  1.00 63.19           C
ATOM   2604  SG  CYS B 324     -10.570   2.278  -2.377  1.00 63.35           S
ATOM   2605  C   CYS B 324     -11.999   0.854   1.221  1.00 63.13           C
ATOM   2606  O   CYS B 324     -13.137   0.390   1.172  1.00 63.24           O
ATOM   2607  N   VAL B 325     -11.109   0.465   2.124  1.00 62.96           N
ATOM   2608  CA  VAL B 325     -11.429  -0.573   3.093  1.00 62.77           C
ATOM   2609  CB  VAL B 325     -10.290  -1.594   3.217  1.00 62.82           C
ATOM   2610  CG1 VAL B 325     -10.826  -2.939   3.650  1.00 62.91           C
ATOM   2611  CG2 VAL B 325      -9.571  -1.739   1.895  1.00 62.99           C
ATOM   2612  C   VAL B 325     -11.712   0.039   4.453  1.00 62.54           C
ATOM   2613  O   VAL B 325     -11.090   1.024   4.843  1.00 62.57           O
ATOM   2614  N   GLU B 326     -12.654  -0.548   5.176  1.00 62.23           N
ATOM   2615  CA  GLU B 326     -13.037  -0.008   6.467  1.00 61.85           C
ATOM   2616  CB  GLU B 326     -14.269  -0.736   7.023  1.00 62.01           C
ATOM   2617  CG  GLU B 326     -15.284   0.216   7.635  1.00 62.42           C
ATOM   2618  CD  GLU B 326     -14.904   1.661   7.371  1.00 63.06           C
ATOM   2619  OE1 GLU B 326     -15.076   2.131   6.221  1.00 63.42           O
ATOM   2620  OE2 GLU B 326     -14.403   2.317   8.312  1.00 63.22           O
```

210

| ATOM | 2621 | C | GLU B 326 | -11.861 | -0.021 | 7.439 | 1.00 | 61.37 | C |
| ATOM | 2622 | O | GLU B 326 | -11.239 | -1.057 | 7.659 | 1.00 | 61.29 | O |
| ATOM | 2623 | N | GLY B 327 | -11.547 | 1.154 | 7.978 | 1.00 | 60.83 | N |
| ATOM | 2624 | CA | GLY B 327 | -10.468 | 1.320 | 8.939 | 1.00 | 60.05 | C |
| ATOM | 2625 | C | GLY B 327 | -9.090 | 0.834 | 8.515 | 1.00 | 59.46 | C |
| ATOM | 2626 | O | GLY B 327 | -8.423 | 0.121 | 9.262 | 1.00 | 59.41 | O |
| ATOM | 2627 | N | ILE B 328 | -8.655 | 1.213 | 7.320 | 1.00 | 58.78 | N |
| ATOM | 2628 | CA | ILE B 328 | -7.338 | 0.820 | 6.864 | 1.00 | 58.06 | C |
| ATOM | 2629 | CB | ILE B 328 | -7.415 | 0.093 | 5.512 | 1.00 | 58.14 | C |
| ATOM | 2630 | CG1 | ILE B 328 | -6.726 | -1.270 | 5.596 | 1.00 | 58.23 | C |
| ATOM | 2631 | CD1 | ILE B 328 | -6.373 | -1.849 | 4.257 | 1.00 | 57.96 | C |
| ATOM | 2632 | CG2 | ILE B 328 | -6.805 | 0.928 | 4.404 | 1.00 | 58.30 | C |
| ATOM | 2633 | C | ILE B 328 | -6.524 | 2.091 | 6.756 | 1.00 | 57.47 | C |
| ATOM | 2634 | O | ILE B 328 | -5.295 | 2.065 | 6.730 | 1.00 | 57.49 | O |
| ATOM | 2635 | N | LEU B 329 | -7.227 | 3.214 | 6.723 | 1.00 | 56.68 | N |
| ATOM | 2636 | CA | LEU B 329 | -6.568 | 4.500 | 6.625 | 1.00 | 55.90 | C |
| ATOM | 2637 | CB | LEU B 329 | -7.577 | 5.627 | 6.344 | 1.00 | 56.04 | C |
| ATOM | 2638 | CG | LEU B 329 | -6.999 | 7.051 | 6.381 | 1.00 | 56.40 | C |
| ATOM | 2639 | CD1 | LEU B 329 | -5.580 | 7.099 | 5.790 | 1.00 | 56.80 | C |
| ATOM | 2640 | CD2 | LEU B 329 | -7.901 | 8.043 | 5.678 | 1.00 | 56.55 | C |
| ATOM | 2641 | C | LEU B 329 | -5.763 | 4.790 | 7.877 | 1.00 | 55.14 | C |
| ATOM | 2642 | O | LEU B 329 | -4.692 | 5.375 | 7.793 | 1.00 | 55.12 | O |
| ATOM | 2643 | N | GLU B 330 | -6.261 | 4.378 | 9.039 | 1.00 | 54.22 | N |
| ATOM | 2644 | CA | GLU B 330 | -5.527 | 4.664 | 10.264 | 1.00 | 53.34 | C |
| ATOM | 2645 | CB | GLU B 330 | -6.406 | 4.633 | 11.527 | 1.00 | 53.53 | C |
| ATOM | 2646 | CG | GLU B 330 | -6.690 | 3.283 | 12.168 | 1.00 | 54.50 | C |
| ATOM | 2647 | CD | GLU B 330 | -7.418 | 3.422 | 13.513 | 1.00 | 55.94 | C |
| ATOM | 2648 | OE1 | GLU B 330 | -8.179 | 4.403 | 13.709 | 1.00 | 56.07 | O |
| ATOM | 2649 | OE2 | GLU B 330 | -7.231 | 2.548 | 14.390 | 1.00 | 56.68 | O |
| ATOM | 2650 | C | GLU B 330 | -4.275 | 3.797 | 10.345 | 1.00 | 52.43 | C |
| ATOM | 2651 | O | GLU B 330 | -3.241 | 4.227 | 10.862 | 1.00 | 52.33 | O |
| ATOM | 2652 | N | ILE B 331 | -4.361 | 2.593 | 9.791 | 1.00 | 51.17 | N |
| ATOM | 2653 | CA | ILE B 331 | -3.201 | 1.733 | 9.705 | 1.00 | 49.97 | C |
| ATOM | 2654 | CB | ILE B 331 | -3.598 | 0.319 | 9.300 | 1.00 | 50.00 | C |
| ATOM | 2655 | CG1 | ILE B 331 | -4.665 | -0.220 | 10.240 | 1.00 | 49.85 | C |
| ATOM | 2656 | CD1 | ILE B 331 | -4.127 | -1.151 | 11.291 | 1.00 | 49.72 | C |
| ATOM | 2657 | CG2 | ILE B 331 | -2.389 | -0.604 | 9.315 | 1.00 | 49.74 | C |
| ATOM | 2658 | C | ILE B 331 | -2.239 | 2.328 | 8.684 | 1.00 | 49.21 | C |
| ATOM | 2659 | O | ILE B 331 | -1.058 | 2.514 | 8.975 | 1.00 | 49.10 | O |
| ATOM | 2660 | N | PHE B 332 | -2.742 | 2.633 | 7.493 | 1.00 | 48.15 | N |
| ATOM | 2661 | CA | PHE B 332 | -1.917 | 3.244 | 6.468 | 1.00 | 47.19 | C |
| ATOM | 2662 | CB | PHE B 332 | -2.773 | 3.756 | 5.309 | 1.00 | 47.19 | C |
| ATOM | 2663 | CG | PHE B 332 | -2.994 | 2.761 | 4.200 | 1.00 | 46.74 | C |
| ATOM | 2664 | CD1 | PHE B 332 | -3.064 | 1.414 | 4.452 | 1.00 | 46.83 | C |
| ATOM | 2665 | CE1 | PHE B 332 | -3.291 | 0.517 | 3.427 | 1.00 | 46.51 | C |
| ATOM | 2666 | CZ | PHE B 332 | -3.452 | 0.967 | 2.142 | 1.00 | 46.21 | C |
| ATOM | 2667 | CE2 | PHE B 332 | -3.375 | 2.301 | 1.878 | 1.00 | 46.00 | C |
| ATOM | 2668 | CD2 | PHE B 332 | -3.154 | 3.192 | 2.899 | 1.00 | 46.29 | C |
| ATOM | 2669 | C | PHE B 332 | -1.172 | 4.433 | 7.078 | 1.00 | 46.67 | C |
| ATOM | 2670 | O | PHE B 332 | 0.017 | 4.624 | 6.834 | 1.00 | 46.63 | O |
| ATOM | 2671 | N | ASP B 333 | -1.871 | 5.232 | 7.878 | 1.00 | 45.90 | N |
| ATOM | 2672 | CA | ASP B 333 | -1.260 | 6.429 | 8.454 | 1.00 | 45.22 | C |
| ATOM | 2673 | CB | ASP B 333 | -2.319 | 7.383 | 9.000 | 1.00 | 45.38 | C |
| ATOM | 2674 | CG | ASP B 333 | -2.853 | 8.316 | 7.933 | 1.00 | 45.83 | C |
| ATOM | 2675 | OD1 | ASP B 333 | -2.068 | 8.684 | 7.017 | 1.00 | 46.45 | O |
| ATOM | 2676 | OD2 | ASP B 333 | -4.031 | 8.731 | 7.929 | 1.00 | 46.09 | O |
| ATOM | 2677 | C | ASP B 333 | -0.190 | 6.140 | 9.505 | 1.00 | 44.53 | C |
| ATOM | 2678 | O | ASP B 333 | 0.835 | 6.819 | 9.566 | 1.00 | 44.52 | O |
| ATOM | 2679 | N | MET B 334 | -0.435 | 5.139 | 10.340 | 1.00 | 43.53 | N |
| ATOM | 2680 | CA | MET B 334 | 0.558 | 4.728 | 11.304 | 1.00 | 42.45 | C |
| ATOM | 2681 | CB | MET B 334 | 0.008 | 3.600 | 12.173 | 1.00 | 42.43 | C |

211

| | | | | | | | | | | |
|---|---|---|---|---|---|---|---|---|---|---|
| ATOM | 2682 | CG | MET | B | 334 | -1.060 | 4.037 | 13.165 | 1.00 42.50 | C |
| ATOM | 2683 | SD | MET | B | 334 | -2.001 | 2.692 | 13.923 | 1.00 42.05 | S |
| ATOM | 2684 | CE | MET | B | 334 | -0.808 | 2.102 | 15.021 | 1.00 42.43 | C |
| ATOM | 2685 | C | MET | B | 334 | 1.782 | 4.272 | 10.506 | 1.00 41.89 | C |
| ATOM | 2686 | O | MET | B | 334 | 2.918 | 4.657 | 10.797 | 1.00 41.87 | O |
| ATOM | 2687 | N | LEU | B | 335 | 1.550 | 3.465 | 9.477 | 1.00 40.91 | N |
| ATOM | 2688 | CA | LEU | B | 335 | 2.651 | 3.007 | 8.668 | 1.00 39.99 | C |
| ATOM | 2689 | CB | LEU | B | 335 | 2.192 | 1.999 | 7.608 | 1.00 39.98 | C |
| ATOM | 2690 | CG | LEU | B | 335 | 1.682 | 0.633 | 8.094 | 1.00 39.33 | C |
| ATOM | 2691 | CD1 | LEU | B | 335 | 0.857 | -0.041 | 7.043 | 1.00 38.07 | C |
| ATOM | 2692 | CD2 | LEU | B | 335 | 2.828 | -0.256 | 8.521 | 1.00 39.24 | C |
| ATOM | 2693 | C | LEU | B | 335 | 3.395 | 4.178 | 8.038 | 1.00 39.56 | C |
| ATOM | 2694 | O | LEU | B | 335 | 4.616 | 4.154 | 7.958 | 1.00 39.55 | O |
| ATOM | 2695 | N | LEU | B | 336 | 2.683 | 5.214 | 7.616 | 1.00 38.96 | N |
| ATOM | 2696 | CA | LEU | B | 336 | 3.362 | 6.339 | 6.982 | 1.00 38.45 | C |
| ATOM | 2697 | CB | LEU | B | 336 | 2.403 | 7.133 | 6.121 | 1.00 38.34 | C |
| ATOM | 2698 | CG | LEU | B | 336 | 1.895 | 6.427 | 4.871 | 1.00 38.49 | C |
| ATOM | 2699 | CD1 | LEU | B | 336 | 0.554 | 7.011 | 4.468 | 1.00 38.53 | C |
| ATOM | 2700 | CD2 | LEU | B | 336 | 2.906 | 6.475 | 3.705 | 1.00 38.48 | C |
| ATOM | 2701 | C | LEU | B | 336 | 4.062 | 7.252 | 7.975 | 1.00 38.14 | C |
| ATOM | 2702 | O | LEU | B | 336 | 5.110 | 7.804 | 7.690 | 1.00 38.04 | O |
| ATOM | 2703 | N | ALA | B | 337 | 3.481 | 7.413 | 9.148 | 1.00 37.95 | N |
| ATOM | 2704 | CA | ALA | B | 337 | 4.101 | 8.232 | 10.174 | 1.00 37.86 | C |
| ATOM | 2705 | CB | ALA | B | 337 | 3.209 | 8.323 | 11.389 | 1.00 37.68 | C |
| ATOM | 2706 | C | ALA | B | 337 | 5.452 | 7.634 | 10.548 | 1.00 37.81 | C |
| ATOM | 2707 | O | ALA | B | 337 | 6.475 | 8.310 | 10.565 | 1.00 37.89 | O |
| ATOM | 2708 | N | THR | B | 338 | 5.458 | 6.352 | 10.843 | 1.00 37.75 | N |
| ATOM | 2709 | CA | THR | B | 338 | 6.695 | 5.712 | 11.207 | 1.00 37.74 | C |
| ATOM | 2710 | CB | THR | B | 338 | 6.406 | 4.292 | 11.674 | 1.00 37.80 | C |
| ATOM | 2711 | OG1 | THR | B | 338 | 5.524 | 4.372 | 12.797 | 1.00 37.83 | O |
| ATOM | 2712 | CG2 | THR | B | 338 | 7.660 | 3.643 | 12.245 | 1.00 37.57 | C |
| ATOM | 2713 | C | THR | B | 338 | 7.701 | 5.754 | 10.053 | 1.00 37.64 | C |
| ATOM | 2714 | O | THR | B | 338 | 8.883 | 6.048 | 10.268 | 1.00 37.66 | O |
| ATOM | 2715 | N | THR | B | 339 | 7.242 | 5.474 | 8.839 | 1.00 37.41 | N |
| ATOM | 2716 | CA | THR | B | 339 | 8.131 | 5.560 | 7.693 | 1.00 37.39 | C |
| ATOM | 2717 | CB | THR | B | 339 | 7.356 | 5.414 | 6.362 | 1.00 37.33 | C |
| ATOM | 2718 | OG1 | THR | B | 339 | 6.825 | 4.094 | 6.278 | 1.00 37.19 | O |
| ATOM | 2719 | CG2 | THR | B | 339 | 8.283 | 5.471 | 5.165 | 1.00 36.91 | C |
| ATOM | 2720 | C | THR | B | 339 | 8.831 | 6.899 | 7.752 | 1.00 37.49 | C |
| ATOM | 2721 | O | THR | B | 339 | 10.030 | 6.986 | 7.517 | 1.00 37.46 | O |
| ATOM | 2722 | N | SER | B | 340 | 8.083 | 7.938 | 8.103 | 1.00 37.63 | N |
| ATOM | 2723 | CA | SER | B | 340 | 8.647 | 9.275 | 8.167 | 1.00 37.96 | C |
| ATOM | 2724 | CB | SER | B | 340 | 7.548 | 10.319 | 8.275 | 1.00 37.94 | C |
| ATOM | 2725 | OG | SER | B | 340 | 6.961 | 10.466 | 7.007 | 1.00 38.34 | O |
| ATOM | 2726 | C | SER | B | 340 | 9.710 | 9.477 | 9.246 | 1.00 38.11 | C |
| ATOM | 2727 | O | SER | B | 340 | 10.721 | 10.148 | 9.000 | 1.00 38.20 | O |
| ATOM | 2728 | N | ARG | B | 341 | 9.487 | 8.931 | 10.436 | 1.00 38.23 | N |
| ATOM | 2729 | CA | ARG | B | 341 | 10.510 | 9.029 | 11.455 | 1.00 38.55 | C |
| ATOM | 2730 | CB | ARG | B | 341 | 10.083 | 8.337 | 12.733 | 1.00 38.75 | C |
| ATOM | 2731 | CG | ARG | B | 341 | 8.696 | 8.730 | 13.221 | 1.00 40.11 | C |
| ATOM | 2732 | CD | ARG | B | 341 | 8.621 | 10.119 | 13.847 | 1.00 42.62 | C |
| ATOM | 2733 | NE | ARG | B | 341 | 8.610 | 11.177 | 12.834 | 1.00 44.37 | N |
| ATOM | 2734 | CZ | ARG | B | 341 | 7.506 | 11.739 | 12.368 | 1.00 45.14 | C |
| ATOM | 2735 | NH1 | ARG | B | 341 | 6.324 | 11.344 | 12.833 | 1.00 45.54 | N |
| ATOM | 2736 | NH2 | ARG | B | 341 | 7.582 | 12.686 | 11.440 | 1.00 45.43 | N |
| ATOM | 2737 | C | ARG | B | 341 | 11.747 | 8.363 | 10.878 | 1.00 38.46 | C |
| ATOM | 2738 | O | ARG | B | 341 | 12.846 | 8.896 | 10.982 | 1.00 38.51 | O |
| ATOM | 2739 | N | PHE | B | 342 | 11.566 | 7.211 | 10.241 | 1.00 38.34 | N |
| ATOM | 2740 | CA | PHE | B | 342 | 12.693 | 6.527 | 9.632 | 1.00 38.35 | C |
| ATOM | 2741 | CB | PHE | B | 342 | 12.281 | 5.181 | 9.036 | 1.00 38.46 | C |
| ATOM | 2742 | CG | PHE | B | 342 | 12.270 | 4.064 | 10.029 | 1.00 38.69 | C |

| | | | | | | | | | |
|---|---|---|---|---|---|---|---|---|---|
| ATOM | 2743 | CD1 | PHE | B | 342 | 13.426 | 3.728 | 10.710 | 1.00 39.19 | C |
| ATOM | 2744 | CE1 | PHE | B | 342 | 13.425 | 2.705 | 11.649 | 1.00 39.58 | C |
| ATOM | 2745 | CZ | PHE | B | 342 | 12.250 | 1.991 | 11.900 | 1.00 39.35 | C |
| ATOM | 2746 | CE2 | PHE | B | 342 | 11.093 | 2.316 | 11.218 | 1.00 39.04 | C |
| ATOM | 2747 | CD2 | PHE | B | 342 | 11.106 | 3.350 | 10.290 | 1.00 39.06 | C |
| ATOM | 2748 | C | PHE | B | 342 | 13.379 | 7.404 | 8.592 | 1.00 38.30 | C |
| ATOM | 2749 | O | PHE | B | 342 | 14.608 | 7.433 | 8.526 | 1.00 38.30 | O |
| ATOM | 2750 | N | ARG | B | 343 | 12.602 | 8.113 | 7.775 | 1.00 38.24 | N |
| ATOM | 2751 | CA | ARG | B | 343 | 13.192 | 9.040 | 6.812 | 1.00 38.35 | C |
| ATOM | 2752 | CB | ARG | B | 343 | 12.131 | 9.697 | 5.945 | 1.00 38.43 | C |
| ATOM | 2753 | CG | ARG | B | 343 | 12.724 | 10.587 | 4.863 | 1.00 39.27 | C |
| ATOM | 2754 | CD | ARG | B | 343 | 11.674 | 11.220 | 4.001 | 1.00 40.89 | C |
| ATOM | 2755 | NE | ARG | B | 343 | 10.530 | 10.313 | 3.969 | 1.00 42.52 | N |
| ATOM | 2756 | CZ | ARG | B | 343 | 9.338 | 10.583 | 4.492 | 1.00 43.12 | C |
| ATOM | 2757 | NH1 | ARG | B | 343 | 9.113 | 11.770 | 5.082 | 1.00 42.88 | N |
| ATOM | 2758 | NH2 | ARG | B | 343 | 8.371 | 9.665 | 4.410 | 1.00 42.74 | N |
| ATOM | 2759 | C | ARG | B | 343 | 13.964 | 10.138 | 7.539 | 1.00 38.23 | C |
| ATOM | 2760 | O | ARG | B | 343 | 15.101 | 10.457 | 7.193 | 1.00 38.05 | O |
| ATOM | 2761 | N | GLU | B | 344 | 13.324 | 10.718 | 8.551 | 1.00 38.19 | N |
| ATOM | 2762 | CA | GLU | B | 344 | 13.964 | 11.736 | 9.355 | 1.00 38.26 | C |
| ATOM | 2763 | CB | GLU | B | 344 | 13.083 | 12.185 | 10.547 | 1.00 38.42 | C |
| ATOM | 2764 | CG A | GLU | B | 344 | 12.023 | 13.186 | 10.095 | 0.50 38.74 | C |
| ATOM | 2765 | CG B | GLU | B | 344 | 11.741 | 12.884 | 10.378 | 0.50 39.29 | C |
| ATOM | 2766 | CD A | GLU | B | 344 | 10.691 | 12.999 | 10.801 | 0.50 39.22 | C |
| ATOM | 2767 | CD B | GLU | B | 344 | 11.626 | 13.426 | 9.075 | 1.00 40.46 | C |
| ATOM | 2768 | OE1A | GLU | B | 344 | 10.704 | 12.599 | 11.980 | 0.50 39.32 | O |
| ATOM | 2769 | OE1B | GLU | B | 344 | 12.729 | 13.579 | 8.671 | 0.50 40.73 | O |
| ATOM | 2770 | OE2A | GLU | B | 344 | 9.631 | 13.244 | 10.183 | 0.50 39.34 | O |
| ATOM | 2771 | OE2B | GLU | B | 344 | 10.540 | 13.632 | 8.502 | 0.50 41.12 | O |
| ATOM | 2772 | C | GLU | B | 344 | 15.269 | 11.198 | 9.926 | 1.00 37.98 | C |
| ATOM | 2773 | O | GLU | B | 344 | 16.245 | 11.925 | 10.054 | 1.00 38.05 | O |
| ATOM | 2774 | N | LEU | B | 345 | 15.284 | 9.929 | 10.303 | 1.00 37.68 | N |
| ATOM | 2775 | CA | LEU | B | 345 | 16.464 | 9.383 | 10.938 | 1.00 37.53 | C |
| ATOM | 2776 | CB | LEU | B | 345 | 16.096 | 8.182 | 11.785 | 1.00 37.69 | C |
| ATOM | 2777 | CG | LEU | B | 345 | 16.779 | 8.257 | 13.141 | 1.00 38.50 | C |
| ATOM | 2778 | CD1 | LEU | B | 345 | 15.725 | 8.465 | 14.213 | 1.00 39.02 | C |
| ATOM | 2779 | CD2 | LEU | B | 345 | 17.566 | 6.985 | 13.397 | 1.00 39.50 | C |
| ATOM | 2780 | C | LEU | B | 345 | 17.526 | 8.976 | 9.940 | 1.00 37.25 | C |
| ATOM | 2781 | O | LEU | B | 345 | 18.639 | 8.601 | 10.328 | 1.00 36.97 | O |
| ATOM | 2782 | N | LYS | B | 346 | 17.159 | 9.041 | 8.660 | 1.00 37.02 | N |
| ATOM | 2783 | CA | LYS | B | 346 | 18.033 | 8.670 | 7.553 | 1.00 36.96 | C |
| ATOM | 2784 | CB | LYS | B | 346 | 19.222 | 9.634 | 7.415 | 1.00 37.10 | C |
| ATOM | 2785 | CG | LYS | B | 346 | 18.886 | 10.920 | 6.675 | 1.00 37.46 | C |
| ATOM | 2786 | CD | LYS | B | 346 | 20.015 | 11.913 | 6.718 | 1.00 38.29 | C |
| ATOM | 2787 | CE | LYS | B | 346 | 19.609 | 13.232 | 6.063 | 1.00 38.89 | C |
| ATOM | 2788 | NZ | LYS | B | 346 | 20.796 | 14.105 | 5.743 | 1.00 39.35 | N |
| ATOM | 2789 | C | LYS | B | 346 | 18.512 | 7.227 | 7.647 | 1.00 36.78 | C |
| ATOM | 2790 | O | LYS | B | 346 | 19.694 | 6.922 | 7.455 | 1.00 36.74 | O |
| ATOM | 2791 | N | LEU | B | 347 | 17.572 | 6.340 | 7.912 | 1.00 36.44 | N |
| ATOM | 2792 | CA | LEU | B | 347 | 17.883 | 4.938 | 8.061 | 1.00 36.22 | C |
| ATOM | 2793 | CB | LEU | B | 347 | 16.586 | 4.173 | 8.262 | 1.00 36.18 | C |
| ATOM | 2794 | CG | LEU | B | 347 | 16.672 | 2.661 | 8.337 | 1.00 36.09 | C |
| ATOM | 2795 | CD1 | LEU | B | 347 | 17.103 | 2.291 | 9.729 | 1.00 35.98 | C |
| ATOM | 2796 | CD2 | LEU | B | 347 | 15.322 | 2.057 | 7.986 | 1.00 35.61 | C |
| ATOM | 2797 | C | LEU | B | 347 | 18.645 | 4.377 | 6.861 | 1.00 36.13 | C |
| ATOM | 2798 | O | LEU | B | 347 | 18.182 | 4.462 | 5.734 | 1.00 36.18 | O |
| ATOM | 2799 | N | GLN | B | 348 | 19.818 | 3.803 | 7.102 | 1.00 35.92 | N |
| ATOM | 2800 | CA | GLN | B | 348 | 20.573 | 3.186 | 6.024 | 1.00 35.81 | C |
| ATOM | 2801 | CB | GLN | B | 348 | 22.061 | 3.230 | 6.327 | 1.00 35.80 | C |
| ATOM | 2802 | CG | GLN | B | 348 | 22.648 | 4.621 | 6.380 | 1.00 36.84 | C |
| ATOM | 2803 | CD | GLN | B | 348 | 22.493 | 5.386 | 5.078 | 1.00 38.13 | C |

213

| | | | | | | | | | | |
|---|---|---|---|---|---|---|---|---|---|---|
| ATOM | 2804 | OE1 | GLN | B | 348 | 23.382 | 5.356 | 4.225 | 1.00 38.66 | O |
| ATOM | 2805 | NE2 | GLN | B | 348 | 21.370 | 6.089 | 4.927 | 1.00 38.93 | N |
| ATOM | 2806 | C | GLN | B | 348 | 20.103 | 1.736 | 5.763 | 1.00 35.58 | C |
| ATOM | 2807 | O | GLN | B | 348 | 19.436 | 1.121 | 6.592 | 1.00 35.46 | O |
| ATOM | 2808 | N | HIS | B | 349 | 20.470 | 1.202 | 4.604 | 1.00 35.28 | N |
| ATOM | 2809 | CA | HIS | B | 349 | 20.074 | -0.127 | 4.193 | 1.00 34.88 | C |
| ATOM | 2810 | CB | HIS | B | 349 | 20.482 | -0.329 | 2.746 | 1.00 34.88 | C |
| ATOM | 2811 | CG | HIS | B | 349 | 20.096 | -1.655 | 2.191 | 1.00 35.23 | C |
| ATOM | 2812 | ND1 | HIS | B | 349 | 21.024 | -2.543 | 1.688 | 1.00 35.49 | N |
| ATOM | 2813 | CE1 | HIS | B | 349 | 20.398 | -3.633 | 1.274 | 1.00 35.67 | C |
| ATOM | 2814 | NE2 | HIS | B | 349 | 19.100 | -3.474 | 1.471 | 1.00 35.07 | N |
| ATOM | 2815 | CD2 | HIS | B | 349 | 18.884 | -2.241 | 2.038 | 1.00 35.10 | C |
| ATOM | 2816 | C | HIS | B | 349 | 20.699 | -1.176 | 5.112 | 1.00 34.77 | C |
| ATOM | 2817 | O | HIS | B | 349 | 20.024 | -2.122 | 5.574 | 1.00 34.96 | O |
| ATOM | 2818 | N | LYS | B | 350 | 21.974 | -0.990 | 5.415 | 1.00 34.32 | N |
| ATOM | 2819 | CA | LYS | B | 350 | 22.668 | -1.882 | 6.319 | 1.00 34.03 | C |
| ATOM | 2820 | CB | LYS | B | 350 | 24.124 | -1.446 | 6.480 | 1.00 34.05 | C |
| ATOM | 2821 | CG | LYS | B | 350 | 24.934 | -1.683 | 5.222 | 1.00 34.78 | C |
| ATOM | 2822 | CD | LYS | B | 350 | 26.365 | -1.211 | 5.327 | 1.00 35.80 | C |
| ATOM | 2823 | CE | LYS | B | 350 | 26.429 | 0.302 | 5.438 | 1.00 36.71 | C |
| ATOM | 2824 | NZ | LYS | B | 350 | 25.720 | 0.996 | 4.333 | 1.00 37.44 | N |
| ATOM | 2825 | C | LYS | B | 350 | 21.951 | -1.906 | 7.659 | 1.00 33.75 | C |
| ATOM | 2826 | O | LYS | B | 350 | 21.827 | -2.957 | 8.294 | 1.00 33.67 | O |
| ATOM | 2827 | N | GLU | B | 351 | 21.464 | -0.745 | 8.080 | 1.00 33.42 | N |
| ATOM | 2828 | CA | GLU | B | 351 | 20.779 | -0.646 | 9.367 | 1.00 33.27 | C |
| ATOM | 2829 | CB | GLU | B | 351 | 20.547 | 0.823 | 9.770 | 1.00 33.31 | C |
| ATOM | 2830 | CG | GLU | B | 351 | 21.818 | 1.613 | 10.095 | 1.00 33.05 | C |
| ATOM | 2831 | CD | GLU | B | 351 | 21.555 | 3.096 | 10.344 | 1.00 33.30 | C |
| ATOM | 2832 | OE1 | GLU | B | 351 | 20.679 | 3.681 | 9.686 | 1.00 32.96 | O |
| ATOM | 2833 | OE2 | GLU | B | 351 | 22.232 | 3.699 | 11.200 | 1.00 33.91 | O |
| ATOM | 2834 | C | GLU | B | 351 | 19.471 | -1.418 | 9.287 | 1.00 33.13 | C |
| ATOM | 2835 | O | GLU | B | 351 | 19.152 | -2.243 | 10.148 | 1.00 32.99 | O |
| ATOM | 2836 | N | TYR | B | 352 | 18.732 | -1.165 | 8.216 | 1.00 33.00 | N |
| ATOM | 2837 | CA | TYR | B | 352 | 17.512 | -1.892 | 7.947 | 1.00 32.80 | C |
| ATOM | 2838 | CB | TYR | B | 352 | 16.946 | -1.454 | 6.614 | 1.00 32.90 | C |
| ATOM | 2839 | CG | TYR | B | 352 | 16.112 | -2.493 | 5.945 | 1.00 33.16 | C |
| ATOM | 2840 | CD1 | TYR | B | 352 | 14.877 | -2.847 | 6.442 | 1.00 32.82 | C |
| ATOM | 2841 | CE1 | TYR | B | 352 | 14.125 | -3.820 | 5.808 | 1.00 33.82 | C |
| ATOM | 2842 | CZ | TYR | B | 352 | 14.620 | -4.429 | 4.663 | 1.00 34.06 | C |
| ATOM | 2843 | OH | TYR | B | 352 | 13.894 | -5.403 | 4.008 | 1.00 35.25 | O |
| ATOM | 2844 | CE2 | TYR | B | 352 | 15.846 | -4.084 | 4.163 | 1.00 33.08 | C |
| ATOM | 2845 | CD2 | TYR | B | 352 | 16.577 | -3.128 | 4.795 | 1.00 33.30 | C |
| ATOM | 2846 | C | TYR | B | 352 | 17.724 | -3.415 | 7.971 | 1.00 32.68 | C |
| ATOM | 2847 | O | TYR | B | 352 | 16.869 | -4.153 | 8.498 | 1.00 32.61 | O |
| ATOM | 2848 | N | LEU | B | 353 | 18.845 | -3.901 | 7.430 | 1.00 32.19 | N |
| ATOM | 2849 | CA | LEU | B | 353 | 19.069 | -5.349 | 7.454 | 1.00 31.89 | C |
| ATOM | 2850 | CB | LEU | B | 353 | 20.281 | -5.749 | 6.610 | 1.00 31.76 | C |
| ATOM | 2851 | CG | LEU | B | 353 | 20.329 | -5.557 | 5.092 | 1.00 31.59 | C |
| ATOM | 2852 | CD1 | LEU | B | 353 | 21.756 | -5.761 | 4.605 | 1.00 31.10 | C |
| ATOM | 2853 | CD2 | LEU | B | 353 | 19.337 | -6.424 | 4.319 | 1.00 30.77 | C |
| ATOM | 2854 | C | LEU | B | 353 | 19.238 | -5.908 | 8.890 | 1.00 31.97 | C |
| ATOM | 2855 | O | LEU | B | 353 | 18.710 | -6.980 | 9.225 | 1.00 32.03 | O |
| ATOM | 2856 | N | CYS | B | 354 | 19.980 | -5.200 | 9.735 | 1.00 31.87 | N |
| ATOM | 2857 | CA | CYS | B | 354 | 20.200 | -5.671 | 11.092 | 1.00 31.83 | C |
| ATOM | 2858 | CB | CYS | B | 354 | 21.269 | -4.827 | 11.789 | 1.00 31.71 | C |
| ATOM | 2859 | SG | CYS | B | 354 | 22.942 | -4.989 | 11.132 | 1.00 29.51 | S |
| ATOM | 2860 | C | CYS | B | 354 | 18.898 | -5.624 | 11.889 | 1.00 32.38 | C |
| ATOM | 2861 | O | CYS | B | 354 | 18.490 | -6.601 | 12.533 | 1.00 32.48 | O |
| ATOM | 2862 | N | VAL | B | 355 | 18.247 | -4.471 | 11.833 | 1.00 32.83 | N |
| ATOM | 2863 | CA | VAL | B | 355 | 16.980 | -4.264 | 12.519 | 1.00 33.10 | C |
| ATOM | 2864 | CB | VAL | B | 355 | 16.413 | -2.884 | 12.151 | 1.00 33.02 | C |

214

| | | | | | | | | | | |
|---|---|---|---|---|---|---|---|---|---|---|
| ATOM | 2865 | CG1 | VAL | B | 355 | 14.906 | -2.907 | 12.074 | 1.00 32.83 | C |
| ATOM | 2866 | CG2 | VAL | B | 355 | 16.906 | -1.856 | 13.117 | 1.00 32.94 | C |
| ATOM | 2867 | C | VAL | B | 355 | 15.970 | -5.358 | 12.169 | 1.00 33.41 | C |
| ATOM | 2868 | O | VAL | B | 355 | 15.252 | -5.854 | 13.038 | 1.00 33.24 | O |
| ATOM | 2869 | N | LYS | B | 356 | 15.917 | -5.743 | 10.897 | 1.00 33.81 | N |
| ATOM | 2870 | CA | LYS | B | 356 | 14.952 | -6.762 | 10.479 | 1.00 34.38 | C |
| ATOM | 2871 | CB | LYS | B | 356 | 14.923 | -6.854 | 8.953 | 1.00 34.54 | C |
| ATOM | 2872 | CG | LYS | B | 356 | 13.919 | -7.821 | 8.347 | 1.00 35.27 | C |
| ATOM | 2873 | CD | LYS | B | 356 | 13.490 | -7.316 | 6.969 | 1.00 36.27 | C |
| ATOM | 2874 | CE | LYS | B | 356 | 14.443 | -7.731 | 5.865 | 1.00 37.32 | C |
| ATOM | 2875 | NZ | LYS | B | 356 | 14.041 | -9.057 | 5.236 | 1.00 39.28 | N |
| ATOM | 2876 | C | LYS | B | 356 | 15.255 | -8.112 | 11.162 | 1.00 34.53 | C |
| ATOM | 2877 | O | LYS | B | 356 | 14.367 | -8.749 | 11.699 | 1.00 34.23 | O |
| ATOM | 2878 | N | ALA | B | 357 | 16.527 | -8.512 | 11.165 | 1.00 34.98 | N |
| ATOM | 2879 | CA | ALA | B | 357 | 16.967 | -9.750 | 11.821 | 1.00 35.40 | C |
| ATOM | 2880 | CB | ALA | B | 357 | 18.422 | -9.994 | 11.552 | 1.00 35.10 | C |
| ATOM | 2881 | C | ALA | B | 357 | 16.725 | -9.641 | 13.316 | 1.00 35.89 | C |
| ATOM | 2882 | O | ALA | B | 357 | 16.361 | -10.612 | 13.988 | 1.00 35.85 | O |
| ATOM | 2883 | N | MET | B | 358 | 16.932 | -8.440 | 13.828 | 1.00 36.57 | N |
| ATOM | 2884 | CA | MET | B | 358 | 16.656 | -8.147 | 15.214 | 1.00 37.28 | C |
| ATOM | 2885 | CB | MET | B | 358 | 17.066 | -6.710 | 15.532 | 1.00 37.32 | C |
| ATOM | 2886 | CG | MET | B | 358 | 17.265 | -6.372 | 16.991 | 1.00 37.12 | C |
| ATOM | 2887 | SD | MET | B | 358 | 18.399 | -4.966 | 17.189 | 1.00 37.34 | S |
| ATOM | 2888 | CE | MET | B | 358 | 19.579 | -5.327 | 15.989 | 1.00 36.54 | C |
| ATOM | 2889 | C | MET | B | 358 | 15.171 | -8.358 | 15.513 | 1.00 37.92 | C |
| ATOM | 2890 | O | MET | B | 358 | 14.844 | -8.954 | 16.519 | 1.00 38.19 | O |
| ATOM | 2891 | N | ILE | B | 359 | 14.251 | -7.911 | 14.664 | 1.00 38.58 | N |
| ATOM | 2892 | CA | ILE | B | 359 | 12.844 | -8.097 | 15.038 | 1.00 39.33 | C |
| ATOM | 2893 | CB | ILE | B | 359 | 11.874 | -7.460 | 14.021 | 1.00 39.21 | C |
| ATOM | 2894 | CG1 | ILE | B | 359 | 11.801 | -5.951 | 14.210 | 1.00 38.68 | C |
| ATOM | 2895 | CD1 | ILE | B | 359 | 11.554 | -5.227 | 12.955 | 1.00 37.55 | C |
| ATOM | 2896 | CG2 | ILE | B | 359 | 10.496 | -8.050 | 14.199 | 1.00 39.13 | C |
| ATOM | 2897 | C | ILE | B | 359 | 12.523 | -9.581 | 15.195 | 1.00 40.12 | C |
| ATOM | 2898 | O | ILE | B | 359 | 11.892 | -10.006 | 16.153 | 1.00 40.28 | O |
| ATOM | 2899 | N | LEU | B | 360 | 12.968 | -10.367 | 14.232 | 1.00 41.14 | N |
| ATOM | 2900 | CA | LEU | B | 360 | 12.749 | -11.792 | 14.242 | 1.00 42.04 | C |
| ATOM | 2901 | CB | LEU | B | 360 | 13.395 | -12.425 | 13.006 | 1.00 41.84 | C |
| ATOM | 2902 | CG | LEU | B | 360 | 13.490 | -13.957 | 12.998 | 1.00 41.98 | C |
| ATOM | 2903 | CD1 | LEU | B | 360 | 12.160 | -14.618 | 12.640 | 1.00 42.06 | C |
| ATOM | 2904 | CD2 | LEU | B | 360 | 14.572 | -14.436 | 12.063 | 1.00 41.44 | C |
| ATOM | 2905 | C | LEU | B | 360 | 13.285 | -12.447 | 15.513 | 1.00 42.91 | C |
| ATOM | 2906 | O | LEU | B | 360 | 12.588 | -13.221 | 16.148 | 1.00 42.98 | O |
| ATOM | 2907 | N | LEU | B | 361 | 14.510 | -12.122 | 15.900 | 1.00 43.98 | N |
| ATOM | 2908 | CA | LEU | B | 361 | 15.128 | -12.803 | 17.027 | 1.00 45.15 | C |
| ATOM | 2909 | CB | LEU | B | 361 | 16.660 | -12.748 | 16.918 | 1.00 45.03 | C |
| ATOM | 2910 | CG | LEU | B | 361 | 17.265 | -13.381 | 15.657 | 1.00 45.01 | C |
| ATOM | 2911 | CD1 | LEU | B | 361 | 18.769 | -13.237 | 15.631 | 1.00 44.51 | C |
| ATOM | 2912 | CD2 | LEU | B | 361 | 16.838 | -14.837 | 15.505 | 1.00 44.46 | C |
| ATOM | 2913 | C | LEU | B | 361 | 14.698 | -12.291 | 18.382 | 1.00 46.18 | C |
| ATOM | 2914 | O | LEU | B | 361 | 14.977 | -12.913 | 19.404 | 1.00 46.38 | O |
| ATOM | 2915 | N | ASN | B | 362 | 14.025 | -11.156 | 18.413 | 1.00 47.56 | N |
| ATOM | 2916 | CA | ASN | B | 362 | 13.639 | -10.570 | 19.693 | 1.00 48.92 | C |
| ATOM | 2917 | CB | ASN | B | 362 | 14.103 | -9.101 | 19.763 | 1.00 48.89 | C |
| ATOM | 2918 | CG | ASN | B | 362 | 13.556 | -8.368 | 20.986 | 1.00 49.59 | C |
| ATOM | 2919 | OD1 | ASN | B | 362 | 13.791 | -8.777 | 22.139 | 1.00 50.10 | O |
| ATOM | 2920 | ND2 | ASN | B | 362 | 12.799 | -7.294 | 20.742 | 1.00 49.89 | N |
| ATOM | 2921 | C | ASN | B | 362 | 12.141 | -10.676 | 19.965 | 1.00 49.79 | C |
| ATOM | 2922 | O | ASN | B | 362 | 11.532 | -9.746 | 20.451 | 1.00 50.00 | O |
| ATOM | 2923 | N | SER | B | 363 | 11.543 | -11.819 | 19.679 | 1.00 51.14 | N |
| ATOM | 2924 | CA | SER | B | 363 | 10.095 | -11.954 | 19.862 | 1.00 52.35 | C |
| ATOM | 2925 | CB | SER | B | 363 | 9.564 | -13.202 | 19.147 | 1.00 52.35 | C |

215

| ATOM | 2926 | OG | SER | B | 363 | 9.656 | -13.041 | 17.724 | 1.00 | 52.22 | O |
| ATOM | 2927 | C | SER | B | 363 | 9.695 | -11.933 | 21.335 | 1.00 | 53.13 | C |
| ATOM | 2928 | O | SER | B | 363 | 9.958 | -12.898 | 22.068 | 1.00 | 53.44 | O |
| ATOM | 2929 | N | SER | B | 364 | 9.066 | -10.825 | 21.748 | 1.00 | 53.95 | N |
| ATOM | 2930 | CA | SER | B | 364 | 8.664 | -10.593 | 23.148 | 1.00 | 54.71 | C |
| ATOM | 2931 | CB | SER | B | 364 | 7.351 | -9.781 | 23.245 | 1.00 | 54.78 | C |
| ATOM | 2932 | OG | SER | B | 364 | 7.565 | -8.396 | 22.964 | 1.00 | 55.29 | O |
| ATOM | 2933 | C | SER | B | 364 | 8.574 | -11.854 | 24.000 | 1.00 | 54.98 | C |
| ATOM | 2934 | O | SER | B | 364 | 7.652 | -12.665 | 23.848 | 1.00 | 55.10 | O |
| ATOM | 2935 | N | MET | B | 365 | 9.570 | -12.015 | 24.867 | 1.00 | 55.38 | N |
| ATOM | 2936 | CA | MET | B | 365 | 9.628 | -13.113 | 25.831 | 1.00 | 55.71 | C |
| ATOM | 2937 | CB | MET | B | 365 | 8.411 | -13.055 | 26.756 | 1.00 | 55.73 | C |
| ATOM | 2938 | CG | MET | B | 365 | 8.774 | -13.039 | 28.225 | 1.00 | 56.19 | C |
| ATOM | 2939 | SD | MET | B | 365 | 7.346 | -12.763 | 29.281 | 1.00 | 56.93 | S |
| ATOM | 2940 | CE | MET | B | 365 | 6.296 | -14.214 | 28.832 | 1.00 | 56.35 | C |
| ATOM | 2941 | C | MET | B | 365 | 9.749 | -14.489 | 25.173 | 1.00 | 55.83 | C |
| ATOM | 2942 | O | MET | B | 365 | 9.124 | -15.463 | 25.615 | 1.00 | 55.90 | O |
| ATOM | 2943 | N | ALA | B | 379 | 19.312 | -20.106 | 24.704 | 1.00 | 56.37 | N |
| ATOM | 2944 | CA | ALA | B | 379 | 20.747 | -20.143 | 24.440 | 1.00 | 56.39 | C |
| ATOM | 2945 | CB | ALA | B | 379 | 21.314 | -21.527 | 24.712 | 1.00 | 56.41 | C |
| ATOM | 2946 | C | ALA | B | 379 | 20.988 | -19.733 | 23.002 | 1.00 | 56.41 | C |
| ATOM | 2947 | O | ALA | B | 379 | 21.459 | -18.631 | 22.742 | 1.00 | 56.60 | O |
| ATOM | 2948 | N | ALA | B | 380 | 20.638 | -20.608 | 22.066 | 1.00 | 56.37 | N |
| ATOM | 2949 | CA | ALA | B | 380 | 20.806 | -20.325 | 20.640 | 1.00 | 56.21 | C |
| ATOM | 2950 | CB | ALA | B | 380 | 20.071 | -21.360 | 19.807 | 1.00 | 56.31 | C |
| ATOM | 2951 | C | ALA | B | 380 | 20.334 | -18.926 | 20.274 | 1.00 | 56.08 | C |
| ATOM | 2952 | O | ALA | B | 380 | 21.065 | -18.186 | 19.631 | 1.00 | 56.10 | O |
| ATOM | 2953 | N | LEU | B | 381 | 19.120 | -18.577 | 20.702 | 1.00 | 55.95 | N |
| ATOM | 2954 | CA | LEU | B | 381 | 18.501 | -17.279 | 20.409 | 1.00 | 55.78 | C |
| ATOM | 2955 | CB | LEU | B | 381 | 17.064 | -17.248 | 20.927 | 1.00 | 55.80 | C |
| ATOM | 2956 | CG | LEU | B | 381 | 15.994 | -17.655 | 19.928 | 1.00 | 55.69 | C |
| ATOM | 2957 | CD1 | LEU | B | 381 | 14.615 | -17.420 | 20.526 | 1.00 | 55.81 | C |
| ATOM | 2958 | CD2 | LEU | B | 381 | 16.187 | -16.836 | 18.676 | 1.00 | 55.48 | C |
| ATOM | 2959 | C | LEU | B | 381 | 19.267 | -16.089 | 20.966 | 1.00 | 55.68 | C |
| ATOM | 2960 | O | LEU | B | 381 | 19.647 | -15.191 | 20.227 | 1.00 | 55.73 | O |
| ATOM | 2961 | N | THR | B | 382 | 19.480 | -16.082 | 22.274 | 1.00 | 55.58 | N |
| ATOM | 2962 | CA | THR | B | 382 | 20.196 | -15.000 | 22.941 | 1.00 | 55.46 | C |
| ATOM | 2963 | CB | THR | B | 382 | 20.385 | -15.332 | 24.449 | 1.00 | 55.48 | C |
| ATOM | 2964 | OG1 | THR | B | 382 | 19.397 | -14.636 | 25.219 | 1.00 | 55.66 | O |
| ATOM | 2965 | CG2 | THR | B | 382 | 21.671 | -14.736 | 24.969 | 1.00 | 55.37 | C |
| ATOM | 2966 | C | THR | B | 382 | 21.545 | -14.723 | 22.295 | 1.00 | 55.25 | C |
| ATOM | 2967 | O | THR | B | 382 | 21.971 | -13.571 | 22.147 | 1.00 | 55.30 | O |
| ATOM | 2968 | N | HIS | B | 383 | 22.215 | -15.787 | 21.894 | 1.00 | 54.94 | N |
| ATOM | 2969 | CA | HIS | B | 383 | 23.539 | -15.630 | 21.343 | 1.00 | 54.70 | C |
| ATOM | 2970 | CB | HIS | B | 383 | 24.229 | -16.975 | 21.218 | 1.00 | 54.89 | C |
| ATOM | 2971 | CG | HIS | B | 383 | 25.705 | -16.851 | 21.046 | 1.00 | 55.85 | C |
| ATOM | 2972 | ND1 | HIS | B | 383 | 26.532 | -16.392 | 22.052 | 1.00 | 56.77 | N |
| ATOM | 2973 | CE1 | HIS | B | 383 | 27.777 | -16.363 | 21.614 | 1.00 | 56.97 | C |
| ATOM | 2974 | NE2 | HIS | B | 383 | 27.785 | -16.770 | 20.356 | 1.00 | 57.09 | N |
| ATOM | 2975 | CD2 | HIS | B | 383 | 26.501 | -17.076 | 19.975 | 1.00 | 56.50 | C |
| ATOM | 2976 | C | HIS | B | 383 | 23.531 | -14.929 | 19.990 | 1.00 | 54.23 | C |
| ATOM | 2977 | O | HIS | B | 383 | 24.444 | -14.169 | 19.651 | 1.00 | 54.21 | O |
| ATOM | 2978 | N | LEU | B | 384 | 22.493 | -15.195 | 19.214 | 1.00 | 53.51 | N |
| ATOM | 2979 | CA | LEU | B | 384 | 22.377 | -14.604 | 17.901 | 1.00 | 52.77 | C |
| ATOM | 2980 | CB | LEU | B | 384 | 21.370 | -15.380 | 17.079 | 1.00 | 52.94 | C |
| ATOM | 2981 | CG | LEU | B | 384 | 22.029 | -16.362 | 16.131 | 1.00 | 53.45 | C |
| ATOM | 2982 | CD1 | LEU | B | 384 | 20.976 | -16.866 | 15.170 | 1.00 | 53.67 | C |
| ATOM | 2983 | CD2 | LEU | B | 384 | 23.170 | -15.667 | 15.387 | 1.00 | 53.95 | C |
| ATOM | 2984 | C | LEU | B | 384 | 21.977 | -13.140 | 17.956 | 1.00 | 52.04 | C |
| ATOM | 2985 | O | LEU | B | 384 | 22.435 | -12.334 | 17.145 | 1.00 | 51.95 | O |
| ATOM | 2986 | N | LEU | B | 385 | 21.100 | -12.810 | 18.899 | 1.00 | 51.02 | N |

216

| | | | | | | | | | | |
|---|---|---|---|---|---|---|---|---|---|---|
| ATOM | 2987 | CA | LEU | B | 385 | 20.695 | -11.432 | 19.100 | 1.00 50.04 | C |
| ATOM | 2988 | CB | LEU | B | 385 | 19.784 | -11.306 | 20.312 | 1.00 50.09 | C |
| ATOM | 2989 | CG | LEU | B | 385 | 18.373 | -10.824 | 20.057 | 1.00 49.79 | C |
| ATOM | 2990 | CD1 | LEU | B | 385 | 17.782 | -10.425 | 21.368 | 1.00 49.56 | C |
| ATOM | 2991 | CD2 | LEU | B | 385 | 18.393 | -9.645 | 19.104 | 1.00 49.66 | C |
| ATOM | 2992 | C | LEU | B | 385 | 21.944 | -10.616 | 19.325 | 1.00 49.37 | C |
| ATOM | 2993 | O | LEU | B | 385 | 22.099 | -9.531 | 18.764 | 1.00 49.29 | O |
| ATOM | 2994 | N | ASN | B | 386 | 22.841 | -11.156 | 20.143 | 1.00 48.40 | N |
| ATOM | 2995 | CA | ASN | B | 386 | 24.082 | -10.477 | 20.428 | 1.00 47.54 | C |
| ATOM | 2996 | CB | ASN | B | 386 | 24.938 | -11.302 | 21.380 | 1.00 47.70 | C |
| ATOM | 2997 | CG | ASN | B | 386 | 24.343 | -11.400 | 22.756 | 1.00 47.44 | C |
| ATOM | 2998 | OD1 | ASN | B | 386 | 24.514 | -12.327 | 23.428 | 1.00 47.51 | O |
| ATOM | 2999 | ND2 | ASN | B | 386 | 23.659 | -10.440 | 23.151 | 1.00 47.24 | N |
| ATOM | 3000 | C | ASN | B | 386 | 24.856 | -10.176 | 19.159 | 1.00 46.86 | C |
| ATOM | 3001 | O | ASN | B | 386 | 25.386 | -9.086 | 18.992 | 1.00 46.82 | O |
| ATOM | 3002 | N | ALA | B | 387 | 24.917 | -11.147 | 18.261 | 1.00 46.02 | N |
| ATOM | 3003 | CA | ALA | B | 387 | 25.666 | -10.975 | 17.032 | 1.00 45.19 | C |
| ATOM | 3004 | CB | ALA | B | 387 | 25.850 | -12.306 | 16.339 | 1.00 45.18 | C |
| ATOM | 3005 | C | ALA | B | 387 | 24.985 | -9.957 | 16.128 | 1.00 44.62 | C |
| ATOM | 3006 | O | ALA | B | 387 | 25.629 | -9.080 | 15.582 | 1.00 44.54 | O |
| ATOM | 3007 | N | VAL | B | 388 | 23.673 | -10.056 | 15.983 | 1.00 44.02 | N |
| ATOM | 3008 | CA | VAL | B | 388 | 22.960 | -9.056 | 15.203 | 1.00 43.39 | C |
| ATOM | 3009 | CB | VAL | B | 388 | 21.494 | -9.435 | 14.963 | 1.00 43.34 | C |
| ATOM | 3010 | CG1 | VAL | B | 388 | 20.865 | -8.488 | 13.970 | 1.00 43.27 | C |
| ATOM | 3011 | CG2 | VAL | B | 388 | 21.421 | -10.842 | 14.413 | 1.00 43.32 | C |
| ATOM | 3012 | C | VAL | B | 388 | 23.085 | -7.705 | 15.894 | 1.00 42.93 | C |
| ATOM | 3013 | O | VAL | B | 388 | 23.328 | -6.700 | 15.245 | 1.00 42.72 | O |
| ATOM | 3014 | N | THR | B | 389 | 22.953 | -7.693 | 17.218 | 1.00 42.49 | N |
| ATOM | 3015 | CA | THR | B | 389 | 23.094 | -6.460 | 17.971 | 1.00 42.16 | C |
| ATOM | 3016 | CB | THR | B | 389 | 22.799 | -6.690 | 19.442 | 1.00 42.18 | C |
| ATOM | 3017 | OG1 | THR | B | 389 | 21.430 | -7.067 | 19.596 | 1.00 42.08 | O |
| ATOM | 3018 | CG2 | THR | B | 389 | 22.879 | -5.385 | 20.217 | 1.00 42.21 | C |
| ATOM | 3019 | C | THR | B | 389 | 24.487 | -5.862 | 17.781 | 1.00 42.09 | C |
| ATOM | 3020 | O | THR | B | 389 | 24.636 | -4.643 | 17.635 | 1.00 42.19 | O |
| ATOM | 3021 | N | ASP | B | 390 | 25.512 | -6.709 | 17.760 | 1.00 41.78 | N |
| ATOM | 3022 | CA | ASP | B | 390 | 26.847 | -6.214 | 17.513 | 1.00 41.49 | C |
| ATOM | 3023 | CB | ASP | B | 390 | 27.896 | -7.312 | 17.676 | 1.00 41.62 | C |
| ATOM | 3024 | CG | ASP | B | 390 | 28.098 | -7.727 | 19.119 | 1.00 42.03 | C |
| ATOM | 3025 | OD1 | ASP | B | 390 | 27.886 | -6.891 | 20.040 | 1.00 42.63 | O |
| ATOM | 3026 | OD2 | ASP | B | 390 | 28.471 | -8.885 | 19.424 | 1.00 42.44 | O |
| ATOM | 3027 | C | ASP | B | 390 | 26.880 | -5.708 | 16.087 | 1.00 41.25 | C |
| ATOM | 3028 | O | ASP | B | 390 | 27.512 | -4.688 | 15.801 | 1.00 41.47 | O |
| ATOM | 3029 | N | ALA | B | 391 | 26.197 | -6.418 | 15.192 | 1.00 40.70 | N |
| ATOM | 3030 | CA | ALA | B | 391 | 26.200 | -6.050 | 13.783 | 1.00 40.25 | C |
| ATOM | 3031 | CB | ALA | B | 391 | 25.411 | -7.077 | 12.947 | 1.00 40.07 | C |
| ATOM | 3032 | C | ALA | B | 391 | 25.660 | -4.625 | 13.599 | 1.00 39.97 | C |
| ATOM | 3033 | O | ALA | B | 391 | 26.253 | -3.819 | 12.897 | 1.00 39.93 | O |
| ATOM | 3034 | N | LEU | B | 392 | 24.554 | -4.315 | 14.261 | 1.00 39.63 | N |
| ATOM | 3035 | CA | LEU | B | 392 | 23.967 | -2.992 | 14.150 | 1.00 39.40 | C |
| ATOM | 3036 | CB | LEU | B | 392 | 22.603 | -2.928 | 14.846 | 1.00 39.27 | C |
| ATOM | 3037 | CG | LEU | B | 392 | 21.966 | -1.550 | 14.990 | 1.00 38.72 | C |
| ATOM | 3038 | CD1 | LEU | B | 392 | 21.727 | -0.959 | 13.630 | 1.00 38.28 | C |
| ATOM | 3039 | CD2 | LEU | B | 392 | 20.658 | -1.634 | 15.787 | 1.00 38.22 | C |
| ATOM | 3040 | C | LEU | B | 392 | 24.905 | -1.979 | 14.753 | 1.00 39.36 | C |
| ATOM | 3041 | O | LEU | B | 392 | 25.041 | -0.876 | 14.229 | 1.00 39.26 | O |
| ATOM | 3042 | N | VAL | B | 393 | 25.560 | -2.363 | 15.847 | 1.00 39.30 | N |
| ATOM | 3043 | CA | VAL | B | 393 | 26.482 | -1.458 | 16.523 | 1.00 39.25 | C |
| ATOM | 3044 | CB | VAL | B | 393 | 26.962 | -2.024 | 17.874 | 1.00 39.17 | C |
| ATOM | 3045 | CG1 | VAL | B | 393 | 28.188 | -1.276 | 18.369 | 1.00 38.85 | C |
| ATOM | 3046 | CG2 | VAL | B | 393 | 25.852 | -1.947 | 18.900 | 1.00 38.94 | C |
| ATOM | 3047 | C | VAL | B | 393 | 27.661 | -1.147 | 15.611 | 1.00 39.45 | C |

| | | | | | | | | | |
|---|---|---|---|---|---|---|---|---|---|
| ATOM | 3048 | O | VAL | B | 393 | 28.097 | 0.008 | 15.524 | 1.00 39.45 | O |
| ATOM | 3049 | N | TRP | B | 394 | 28.144 | -2.174 | 14.907 | 1.00 39.56 | N |
| ATOM | 3050 | CA | TRP | B | 394 | 29.271 | -2.025 | 14.005 | 1.00 39.71 | C |
| ATOM | 3051 | CB | TRP | B | 394 | 29.724 | -3.381 | 13.449 | 1.00 39.83 | C |
| ATOM | 3052 | CG | TRP | B | 394 | 30.822 | -3.273 | 12.414 | 1.00 39.57 | C |
| ATOM | 3053 | CD1 | TRP | B | 394 | 32.145 | -3.034 | 12.643 | 1.00 39.44 | C |
| ATOM | 3054 | NE1 | TRP | B | 394 | 32.830 | -2.999 | 11.451 | 1.00 39.77 | N |
| ATOM | 3055 | CE2 | TRP | B | 394 | 31.950 | -3.206 | 10.423 | 1.00 39.45 | C |
| ATOM | 3056 | CD2 | TRP | B | 394 | 30.676 | -3.383 | 10.994 | 1.00 39.31 | C |
| ATOM | 3057 | CE3 | TRP | B | 394 | 29.597 | -3.614 | 10.144 | 1.00 39.13 | C |
| ATOM | 3058 | CZ3 | TRP | B | 394 | 29.818 | -3.657 | 8.777 | 1.00 39.28 | C |
| ATOM | 3059 | CH2 | TRP | B | 394 | 31.092 | -3.482 | 8.245 | 1.00 39.40 | C |
| ATOM | 3060 | CZ2 | TRP | B | 394 | 32.171 | -3.257 | 9.048 | 1.00 39.50 | C |
| ATOM | 3061 | C | TRP | B | 394 | 28.899 | -1.114 | 12.866 | 1.00 39.84 | C |
| ATOM | 3062 | O | TRP | B | 394 | 29.649 | -0.199 | 12.528 | 1.00 39.89 | O |
| ATOM | 3063 | N | VAL | B | 395 | 27.744 | -1.371 | 12.268 | 1.00 40.00 | N |
| ATOM | 3064 | CA | VAL | B | 395 | 27.265 | -0.541 | 11.174 | 1.00 40.30 | C |
| ATOM | 3065 | CB | VAL | B | 395 | 25.852 | -0.958 | 10.703 | 1.00 40.31 | C |
| ATOM | 3066 | CG1 | VAL | B | 395 | 25.121 | 0.221 | 10.094 | 1.00 40.60 | C |
| ATOM | 3067 | CG2 | VAL | B | 395 | 25.929 | -2.098 | 9.705 | 1.00 40.19 | C |
| ATOM | 3068 | C | VAL | B | 395 | 27.264 | 0.923 | 11.599 | 1.00 40.49 | C |
| ATOM | 3069 | O | VAL | B | 395 | 27.923 | 1.749 | 10.982 | 1.00 40.57 | O |
| ATOM | 3070 | N | ILE | B | 396 | 26.554 | 1.233 | 12.677 | 1.00 40.72 | N |
| ATOM | 3071 | CA | ILE | B | 396 | 26.456 | 2.606 | 13.159 | 1.00 40.99 | C |
| ATOM | 3072 | CB | ILE | B | 396 | 25.560 | 2.682 | 14.425 | 1.00 40.89 | C |
| ATOM | 3073 | CG1 | ILE | B | 396 | 24.118 | 2.328 | 14.061 | 1.00 40.56 | C |
| ATOM | 3074 | CD1 | ILE | B | 396 | 23.188 | 2.262 | 15.227 | 1.00 40.46 | C |
| ATOM | 3075 | CG2 | ILE | B | 396 | 25.606 | 4.065 | 15.043 | 1.00 40.50 | C |
| ATOM | 3076 | C | ILE | B | 396 | 27.817 | 3.250 | 13.400 | 1.00 41.37 | C |
| ATOM | 3077 | O | ILE | B | 396 | 28.029 | 4.418 | 13.082 | 1.00 41.34 | O |
| ATOM | 3078 | N | ALA | B | 397 | 28.750 | 2.486 | 13.946 | 1.00 41.95 | N |
| ATOM | 3079 | CA | ALA | B | 397 | 30.081 | 3.024 | 14.213 | 1.00 42.47 | C |
| ATOM | 3080 | CB | ALA | B | 397 | 30.869 | 2.087 | 15.117 | 1.00 42.44 | C |
| ATOM | 3081 | C | ALA | B | 397 | 30.851 | 3.297 | 12.925 | 1.00 42.86 | C |
| ATOM | 3082 | O | ALA | B | 397 | 31.753 | 4.128 | 12.903 | 1.00 42.91 | O |
| ATOM | 3083 | N | LYS | B | 398 | 30.495 | 2.603 | 11.847 | 1.00 43.37 | N |
| ATOM | 3084 | CA | LYS | B | 398 | 31.185 | 2.800 | 10.575 | 1.00 43.87 | C |
| ATOM | 3085 | CB | LYS | B | 398 | 30.921 | 1.624 | 9.625 | 1.00 43.98 | C |
| ATOM | 3086 | CG | LYS | B | 398 | 32.090 | 1.266 | 8.706 | 1.00 44.27 | C |
| ATOM | 3090 | C | LYS | B | 398 | 30.793 | 4.128 | 9.923 | 1.00 44.07 | C |
| ATOM | 3091 | O | LYS | B | 398 | 31.444 | 4.577 | 8.980 | 1.00 44.01 | O |
| ATOM | 3092 | N | SER | B | 399 | 29.738 | 4.755 | 10.441 | 1.00 44.36 | N |
| ATOM | 3093 | CA | SER | B | 399 | 29.254 | 6.019 | 9.898 | 1.00 44.72 | C |
| ATOM | 3094 | CB | SER | B | 399 | 27.818 | 6.261 | 10.328 | 1.00 44.82 | C |
| ATOM | 3095 | OG | SER | B | 399 | 27.800 | 6.787 | 11.648 | 1.00 45.01 | O |
| ATOM | 3096 | C | SER | B | 399 | 30.091 | 7.219 | 10.330 | 1.00 44.84 | C |
| ATOM | 3097 | O | SER | B | 399 | 29.898 | 8.319 | 9.824 | 1.00 44.85 | O |
| ATOM | 3098 | N | GLY | B | 400 | 30.978 | 7.025 | 11.298 | 1.00 44.94 | N |
| ATOM | 3099 | CA | GLY | B | 400 | 31.869 | 8.094 | 11.706 | 1.00 45.15 | C |
| ATOM | 3100 | C | GLY | B | 400 | 31.448 | 9.079 | 12.784 | 1.00 45.24 | C |
| ATOM | 3101 | O | GLY | B | 400 | 32.305 | 9.760 | 13.347 | 1.00 45.31 | O |
| ATOM | 3102 | N | ILE | B | 401 | 30.154 | 9.182 | 13.070 | 1.00 45.29 | N |
| ATOM | 3103 | CA | ILE | B | 401 | 29.704 | 10.083 | 14.127 | 1.00 45.22 | C |
| ATOM | 3104 | CB | ILE | B | 401 | 28.167 | 10.089 | 14.237 | 1.00 45.22 | C |
| ATOM | 3105 | CG1 | ILE | B | 401 | 27.662 | 8.717 | 14.687 | 1.00 45.24 | C |
| ATOM | 3106 | CD1 | ILE | B | 401 | 26.152 | 8.616 | 14.768 | 1.00 45.13 | C |
| ATOM | 3107 | CG2 | ILE | B | 401 | 27.529 | 10.519 | 12.922 | 1.00 44.86 | C |
| ATOM | 3108 | C | ILE | B | 401 | 30.336 | 9.641 | 15.441 | 1.00 45.22 | C |
| ATOM | 3109 | O | ILE | B | 401 | 30.787 | 8.512 | 15.559 | 1.00 45.20 | O |
| ATOM | 3110 | N | SER | B | 402 | 30.371 | 10.529 | 16.425 | 1.00 45.28 | N |
| ATOM | 3111 | CA | SER | B | 402 | 30.996 | 10.223 | 17.706 | 1.00 45.32 | C |

| | | | | | | | | | |
|---|---|---|---|---|---|---|---|---|---|
| ATOM | 3112 | CB | SER | B | 402 | 31.110 | 11.491 | 18.540 | 1.00 45.36 | C |
| ATOM | 3113 | OG | SER | B | 402 | 29.947 | 11.668 | 19.327 | 1.00 45.30 | O |
| ATOM | 3114 | C | SER | B | 402 | 30.258 | 9.177 | 18.537 | 1.00 45.38 | C |
| ATOM | 3115 | O | SER | B | 402 | 29.108 | 8.827 | 18.257 | 1.00 45.46 | O |
| ATOM | 3116 | N | SER | B | 403 | 30.933 | 8.707 | 19.580 | 1.00 45.32 | N |
| ATOM | 3117 | CA | SER | B | 403 | 30.376 | 7.744 | 20.522 | 1.00 45.29 | C |
| ATOM | 3118 | CB | SER | B | 403 | 31.301 | 7.607 | 21.720 | 1.00 45.37 | C |
| ATOM | 3119 | OG | SER | B | 403 | 32.148 | 6.494 | 21.554 | 1.00 45.98 | O |
| ATOM | 3120 | C | SER | B | 403 | 28.994 | 8.096 | 21.050 | 1.00 45.06 | C |
| ATOM | 3121 | O | SER | B | 403 | 28.078 | 7.283 | 21.006 | 1.00 45.15 | O |
| ATOM | 3122 | N | GLN | B | 404 | 28.857 | 9.299 | 21.585 | 1.00 44.72 | N |
| ATOM | 3123 | CA | GLN | B | 404 | 27.598 | 9.702 | 22.163 | 1.00 44.38 | C |
| ATOM | 3124 | CB | GLN | B | 404 | 27.711 | 11.092 | 22.784 | 1.00 44.32 | C |
| ATOM | 3125 | CG | GLN | B | 404 | 26.711 | 11.376 | 23.874 | 1.00 44.35 | C |
| ATOM | 3126 | CD | GLN | B | 404 | 25.466 | 12.037 | 23.341 | 1.00 44.49 | C |
| ATOM | 3127 | OE1 | GLN | B | 404 | 25.519 | 12.707 | 22.315 | 1.00 44.45 | O |
| ATOM | 3128 | NE2 | GLN | B | 404 | 24.345 | 11.860 | 24.033 | 1.00 44.51 | N |
| ATOM | 3129 | C | GLN | B | 404 | 26.517 | 9.640 | 21.094 | 1.00 44.22 | C |
| ATOM | 3130 | O | GLN | B | 404 | 25.440 | 9.077 | 21.319 | 1.00 44.16 | O |
| ATOM | 3131 | N | GLN | B | 405 | 26.810 | 10.193 | 19.921 | 1.00 43.93 | N |
| ATOM | 3132 | CA | GLN | B | 405 | 25.848 | 10.169 | 18.821 | 1.00 43.62 | C |
| ATOM | 3133 | CB | GLN | B | 405 | 26.345 | 11.000 | 17.636 | 1.00 43.78 | C |
| ATOM | 3134 | CG | GLN | B | 405 | 26.118 | 12.504 | 17.780 | 1.00 45.18 | C |
| ATOM | 3135 | CD | GLN | B | 405 | 24.694 | 12.857 | 18.256 | 1.00 46.95 | C |
| ATOM | 3136 | OE1 | GLN | B | 405 | 23.786 | 13.076 | 17.435 | 1.00 47.54 | O |
| ATOM | 3137 | NE2 | GLN | B | 405 | 24.503 | 12.923 | 19.583 | 1.00 47.21 | N |
| ATOM | 3138 | C | GLN | B | 405 | 25.521 | 8.738 | 18.372 | 1.00 43.03 | C |
| ATOM | 3139 | O | GLN | B | 405 | 24.410 | 8.454 | 17.931 | 1.00 42.81 | O |
| ATOM | 3140 | N | GLN | B | 406 | 26.495 | 7.843 | 18.484 | 1.00 42.39 | N |
| ATOM | 3141 | CA | GLN | B | 406 | 26.287 | 6.467 | 18.087 | 1.00 41.81 | C |
| ATOM | 3142 | CB | GLN | B | 406 | 27.584 | 5.676 | 18.184 | 1.00 41.92 | C |
| ATOM | 3143 | CG | GLN | B | 406 | 28.435 | 5.699 | 16.935 | 1.00 42.28 | C |
| ATOM | 3144 | CD | GLN | B | 406 | 29.814 | 5.119 | 17.184 | 1.00 42.83 | C |
| ATOM | 3145 | OE1 | GLN | B | 406 | 29.940 | 4.012 | 17.700 | 1.00 43.31 | O |
| ATOM | 3146 | NE2 | GLN | B | 406 | 30.847 | 5.870 | 16.838 | 1.00 42.80 | N |
| ATOM | 3147 | C | GLN | B | 406 | 25.243 | 5.840 | 18.983 | 1.00 41.32 | C |
| ATOM | 3148 | O | GLN | B | 406 | 24.348 | 5.137 | 18.515 | 1.00 41.14 | O |
| ATOM | 3149 | N | SER | B | 407 | 25.371 | 6.102 | 20.281 | 1.00 40.72 | N |
| ATOM | 3150 | CA | SER | B | 407 | 24.434 | 5.577 | 21.264 | 1.00 40.04 | C |
| ATOM | 3151 | CB | SER | B | 407 | 24.980 | 5.754 | 22.683 | 1.00 40.10 | C |
| ATOM | 3152 | OG | SER | B | 407 | 26.006 | 4.811 | 22.943 | 1.00 39.93 | O |
| ATOM | 3153 | C | SER | B | 407 | 23.043 | 6.193 | 21.106 | 1.00 39.53 | C |
| ATOM | 3154 | O | SER | B | 407 | 22.033 | 5.508 | 21.245 | 1.00 39.64 | O |
| ATOM | 3155 | N | VAL | B | 408 | 22.977 | 7.476 | 20.796 | 1.00 38.78 | N |
| ATOM | 3156 | CA | VAL | B | 408 | 21.684 | 8.084 | 20.589 | 1.00 38.13 | C |
| ATOM | 3157 | CB | VAL | B | 408 | 21.773 | 9.627 | 20.461 | 1.00 38.07 | C |
| ATOM | 3158 | CG1 | VAL | B | 408 | 20.494 | 10.216 | 19.908 | 1.00 37.92 | C |
| ATOM | 3159 | CG2 | VAL | B | 408 | 22.033 | 10.227 | 21.804 | 1.00 37.97 | C |
| ATOM | 3160 | C | VAL | B | 408 | 21.012 | 7.430 | 19.388 | 1.00 37.87 | C |
| ATOM | 3161 | O | VAL | B | 408 | 19.849 | 7.020 | 19.474 | 1.00 37.83 | O |
| ATOM | 3162 | N | ARG | B | 409 | 21.746 | 7.315 | 18.281 | 1.00 37.49 | N |
| ATOM | 3163 | CA | ARG | B | 409 | 21.210 | 6.702 | 17.066 | 1.00 37.11 | C |
| ATOM | 3164 | CB | ARG | B | 409 | 22.270 | 6.605 | 15.963 | 1.00 37.02 | C |
| ATOM | 3165 | CG | ARG | B | 409 | 21.691 | 6.237 | 14.612 | 1.00 36.13 | C |
| ATOM | 3166 | CD | ARG | B | 409 | 22.671 | 6.284 | 13.478 | 1.00 35.01 | C |
| ATOM | 3167 | NE | ARG | B | 409 | 22.040 | 5.968 | 12.202 | 1.00 33.99 | N |
| ATOM | 3168 | CZ | ARG | B | 409 | 21.136 | 6.733 | 11.606 | 1.00 33.54 | C |
| ATOM | 3169 | NH1 | ARG | B | 409 | 20.742 | 7.863 | 12.157 | 1.00 33.01 | N |
| ATOM | 3170 | NH2 | ARG | B | 409 | 20.601 | 6.357 | 10.459 | 1.00 33.88 | N |
| ATOM | 3171 | C | ARG | B | 409 | 20.636 | 5.323 | 17.374 | 1.00 37.10 | C |
| ATOM | 3172 | O | ARG | B | 409 | 19.488 | 5.028 | 17.041 | 1.00 36.89 | O |

219

| | | | | | | | | | | |
|---|---|---|---|---|---|---|---|---|---|---|
| ATOM | 3173 | N | LEU | B | 410 | 21.440 | 4.489 | 18.027 | 1.00 37.11 | N |
| ATOM | 3174 | CA | LEU | B | 410 | 20.999 | 3.161 | 18.419 | 1.00 37.16 | C |
| ATOM | 3175 | CB | LEU | B | 410 | 22.018 | 2.505 | 19.335 | 1.00 37.04 | C |
| ATOM | 3176 | CG | LEU | B | 410 | 21.686 | 1.080 | 19.733 | 1.00 36.65 | C |
| ATOM | 3177 | CD1 | LEU | B | 410 | 21.188 | 0.339 | 18.527 | 1.00 36.70 | C |
| ATOM | 3178 | CD2 | LEU | B | 410 | 22.911 | 0.406 | 20.286 | 1.00 36.76 | C |
| ATOM | 3179 | C | LEU | B | 410 | 19.669 | 3.249 | 19.138 | 1.00 37.35 | C |
| ATOM | 3180 | O | LEU | B | 410 | 18.724 | 2.538 | 18.807 | 1.00 37.31 | O |
| ATOM | 3181 | N | ALA | B | 411 | 19.600 | 4.138 | 20.117 | 1.00 37.60 | N |
| ATOM | 3182 | CA | ALA | B | 411 | 18.395 | 4.301 | 20.909 | 1.00 37.92 | C |
| ATOM | 3183 | CB | ALA | B | 411 | 18.643 | 5.293 | 22.031 | 1.00 37.95 | C |
| ATOM | 3184 | C | ALA | B | 411 | 17.194 | 4.721 | 20.071 | 1.00 38.19 | C |
| ATOM | 3185 | O | ALA | B | 411 | 16.107 | 4.190 | 20.242 | 1.00 38.19 | O |
| ATOM | 3186 | N | ASN | B | 412 | 17.384 | 5.669 | 19.163 | 1.00 38.58 | N |
| ATOM | 3187 | CA | ASN | B | 412 | 16.290 | 6.101 | 18.308 | 1.00 39.09 | C |
| ATOM | 3188 | CB | ASN | B | 412 | 16.694 | 7.289 | 17.460 | 1.00 39.13 | C |
| ATOM | 3189 | CG | ASN | B | 412 | 16.898 | 8.526 | 18.287 | 1.00 39.33 | C |
| ATOM | 3190 | OD1 | ASN | B | 412 | 16.085 | 8.828 | 19.146 | 1.00 39.65 | O |
| ATOM | 3191 | ND2 | ASN | B | 412 | 17.996 | 9.233 | 18.056 | 1.00 39.54 | N |
| ATOM | 3192 | C | ASN | B | 412 | 15.777 | 5.000 | 17.429 | 1.00 39.45 | C |
| ATOM | 3193 | O | ASN | B | 412 | 14.571 | 4.816 | 17.304 | 1.00 39.53 | O |
| ATOM | 3194 | N | LEU | B | 413 | 16.688 | 4.277 | 16.796 | 1.00 40.00 | N |
| ATOM | 3195 | CA | LEU | B | 413 | 16.299 | 3.136 | 15.989 | 1.00 40.51 | C |
| ATOM | 3196 | CB | LEU | B | 413 | 17.530 | 2.459 | 15.405 | 1.00 40.39 | C |
| ATOM | 3197 | CG | LEU | B | 413 | 18.268 | 3.188 | 14.290 | 1.00 40.10 | C |
| ATOM | 3198 | CD1 | LEU | B | 413 | 19.457 | 2.373 | 13.872 | 1.00 39.75 | C |
| ATOM | 3199 | CD2 | LEU | B | 413 | 17.360 | 3.450 | 13.123 | 1.00 39.82 | C |
| ATOM | 3200 | C | LEU | B | 413 | 15.482 | 2.140 | 16.835 | 1.00 41.12 | C |
| ATOM | 3201 | O | LEU | B | 413 | 14.336 | 1.819 | 16.506 | 1.00 41.36 | O |
| ATOM | 3202 | N | LEU | B | 414 | 16.043 | 1.655 | 17.934 | 1.00 41.74 | N |
| ATOM | 3203 | CA | LEU | B | 414 | 15.296 | 0.712 | 18.759 | 1.00 42.46 | C |
| ATOM | 3204 | CB | LEU | B | 414 | 16.143 | 0.208 | 19.921 | 1.00 42.34 | C |
| ATOM | 3205 | CG | LEU | B | 414 | 17.395 | -0.540 | 19.457 | 1.00 42.23 | C |
| ATOM | 3206 | CD1 | LEU | B | 414 | 18.358 | -0.798 | 20.606 | 1.00 42.09 | C |
| ATOM | 3207 | CD2 | LEU | B | 414 | 17.002 | -1.829 | 18.809 | 1.00 42.13 | C |
| ATOM | 3208 | C | LEU | B | 414 | 13.920 | 1.227 | 19.230 | 1.00 43.09 | C |
| ATOM | 3209 | O | LEU | B | 414 | 12.933 | 0.489 | 19.204 | 1.00 43.27 | O |
| ATOM | 3210 | N | MET | B | 415 | 13.824 | 2.483 | 19.644 | 1.00 43.87 | N |
| ATOM | 3211 | CA | MET | B | 415 | 12.514 | 3.003 | 20.051 | 1.00 44.63 | C |
| ATOM | 3212 | CB | MET | B | 415 | 12.618 | 4.416 | 20.619 | 1.00 44.50 | C |
| ATOM | 3213 | CG | MET | B | 415 | 13.449 | 4.503 | 21.897 | 1.00 44.69 | C |
| ATOM | 3214 | SD | MET | B | 415 | 13.318 | 6.086 | 22.731 | 1.00 44.41 | S |
| ATOM | 3215 | CE | MET | B | 415 | 15.036 | 6.407 | 22.985 | 1.00 45.20 | C |
| ATOM | 3216 | C | MET | B | 415 | 11.484 | 2.937 | 18.907 | 1.00 45.26 | C |
| ATOM | 3217 | O | MET | B | 415 | 10.294 | 2.689 | 19.138 | 1.00 45.48 | O |
| ATOM | 3218 | N | LEU | B | 416 | 11.931 | 3.135 | 17.672 | 1.00 45.82 | N |
| ATOM | 3219 | CA | LEU | B | 416 | 11.008 | 3.049 | 16.564 | 1.00 46.50 | C |
| ATOM | 3220 | CB | LEU | B | 416 | 11.667 | 3.521 | 15.280 | 1.00 46.46 | C |
| ATOM | 3221 | CG | LEU | B | 416 | 12.223 | 4.935 | 15.166 | 1.00 46.51 | C |
| ATOM | 3222 | CD1 | LEU | B | 416 | 12.015 | 5.463 | 13.753 | 1.00 46.30 | C |
| ATOM | 3223 | CD2 | LEU | B | 416 | 11.598 | 5.885 | 16.153 | 1.00 47.32 | C |
| ATOM | 3224 | C | LEU | B | 416 | 10.520 | 1.614 | 16.380 | 1.00 47.06 | C |
| ATOM | 3225 | O | LEU | B | 416 | 9.425 | 1.366 | 15.875 | 1.00 47.23 | O |
| ATOM | 3226 | N | LEU | B | 417 | 11.337 | 0.652 | 16.767 | 1.00 47.64 | N |
| ATOM | 3227 | CA | LEU | B | 417 | 10.918 | -0.728 | 16.615 | 1.00 48.14 | C |
| ATOM | 3228 | CB | LEU | B | 417 | 12.054 | -1.686 | 16.967 | 1.00 48.20 | C |
| ATOM | 3229 | CG | LEU | B | 417 | 13.152 | -1.805 | 15.917 | 1.00 48.46 | C |
| ATOM | 3230 | CD1 | LEU | B | 417 | 13.748 | -3.195 | 16.044 | 1.00 48.90 | C |
| ATOM | 3231 | CD2 | LEU | B | 417 | 12.611 | -1.577 | 14.495 | 1.00 48.40 | C |
| ATOM | 3232 | C | LEU | B | 417 | 9.683 | -1.019 | 17.465 | 1.00 48.46 | C |
| ATOM | 3233 | O | LEU | B | 417 | 8.875 | -1.893 | 17.129 | 1.00 48.65 | O |

220

| | | | | | | | | | |
|---|---|---|---|---|---|---|---|---|---|
| ATOM | 3234 | N | SER B 418 | 9.523 | -0.290 | 18.563 | 1.00 | 48.65 | N |
| ATOM | 3235 | CA | SER B 418 | 8.384 | -0.539 | 19.440 | 1.00 | 48.87 | C |
| ATOM | 3236 | CB | SER B 418 | 8.500 | 0.271 | 20.732 | 1.00 | 48.92 | C |
| ATOM | 3237 | OG | SER B 418 | 9.848 | 0.399 | 21.145 | 1.00 | 49.71 | O |
| ATOM | 3238 | C | SER B 418 | 7.106 | -0.147 | 18.725 | 1.00 | 48.88 | C |
| ATOM | 3239 | O | SER B 418 | 6.057 | -0.779 | 18.893 | 1.00 | 48.90 | O |
| ATOM | 3240 | N | HIS B 419 | 7.211 | 0.920 | 17.944 | 1.00 | 48.87 | N |
| ATOM | 3241 | CA | HIS B 419 | 6.107 | 1.451 | 17.176 | 1.00 | 49.03 | C |
| ATOM | 3242 | CB | HIS B 419 | 6.548 | 2.741 | 16.495 | 1.00 | 49.10 | C |
| ATOM | 3243 | CG | HIS B 419 | 6.935 | 3.799 | 17.469 | 1.00 | 49.66 | C |
| ATOM | 3244 | ND1 | HIS B 419 | 6.577 | 5.118 | 17.320 | 1.00 | 49.90 | N |
| ATOM | 3245 | CE1 | HIS B 419 | 7.027 | 5.808 | 18.354 | 1.00 | 50.39 | C |
| ATOM | 3246 | NE2 | HIS B 419 | 7.651 | 4.981 | 19.174 | 1.00 | 50.37 | N |
| ATOM | 3247 | CD2 | HIS B 419 | 7.604 | 3.717 | 18.644 | 1.00 | 50.23 | C |
| ATOM | 3248 | C | HIS B 419 | 5.686 | 0.430 | 16.157 | 1.00 | 49.11 | C |
| ATOM | 3249 | O | HIS B 419 | 4.505 | 0.262 | 15.876 | 1.00 | 49.06 | O |
| ATOM | 3250 | N | VAL B 420 | 6.667 | -0.265 | 15.607 | 1.00 | 49.17 | N |
| ATOM | 3251 | CA | VAL B 420 | 6.368 | -1.276 | 14.628 | 1.00 | 49.33 | C |
| ATOM | 3252 | CB | VAL B 420 | 7.644 | -1.820 | 13.991 | 1.00 | 49.31 | C |
| ATOM | 3253 | CG1 | VAL B 420 | 7.402 | -3.208 | 13.412 | 1.00 | 49.07 | C |
| ATOM | 3254 | CG2 | VAL B 420 | 8.126 | -0.856 | 12.936 | 1.00 | 49.02 | C |
| ATOM | 3255 | C | VAL B 420 | 5.576 | -2.384 | 15.302 | 1.00 | 49.51 | C |
| ATOM | 3256 | O | VAL B 420 | 4.500 | -2.768 | 14.843 | 1.00 | 49.43 | O |
| ATOM | 3257 | N | ARG B 421 | 6.122 | -2.884 | 16.402 | 1.00 | 49.72 | N |
| ATOM | 3258 | CA | ARG B 421 | 5.458 | -3.887 | 17.215 | 1.00 | 49.96 | C |
| ATOM | 3259 | CB | ARG B 421 | 6.178 | -3.980 | 18.551 | 1.00 | 50.29 | C |
| ATOM | 3260 | CG | ARG B 421 | 5.434 | -4.726 | 19.621 | 1.00 | 51.25 | C |
| ATOM | 3261 | CD | ARG B 421 | 5.409 | -6.178 | 19.360 | 1.00 | 53.76 | C |
| ATOM | 3262 | NE | ARG B 421 | 6.701 | -6.666 | 18.883 | 1.00 | 55.74 | N |
| ATOM | 3263 | CZ | ARG B 421 | 7.365 | -7.641 | 19.481 | 1.00 | 57.17 | C |
| ATOM | 3264 | NH1 | ARG B 421 | 6.849 | -8.207 | 20.579 | 1.00 | 57.71 | N |
| ATOM | 3265 | NH2 | ARG B 421 | 8.529 | -8.057 | 18.988 | 1.00 | 57.50 | N |
| ATOM | 3266 | C | ARG B 421 | 4.009 | -3.468 | 17.440 | 1.00 | 49.82 | C |
| ATOM | 3267 | O | ARG B 421 | 3.085 | -4.277 | 17.367 | 1.00 | 49.84 | O |
| ATOM | 3268 | N | HIS B 422 | 3.802 | -2.191 | 17.703 | 1.00 | 49.63 | N |
| ATOM | 3269 | CA | HIS B 422 | 2.459 | -1.718 | 17.940 | 1.00 | 49.51 | C |
| ATOM | 3270 | CB | HIS B 422 | 2.481 | -0.268 | 18.397 | 1.00 | 49.52 | C |
| ATOM | 3271 | CG | HIS B 422 | 1.136 | 0.248 | 18.777 | 1.00 | 49.43 | C |
| ATOM | 3272 | ND1 | HIS B 422 | 0.458 | -0.208 | 19.886 | 1.00 | 49.63 | N |
| ATOM | 3273 | CE1 | HIS B 422 | -0.706 | 0.408 | 19.970 | 1.00 | 49.74 | C |
| ATOM | 3274 | NE2 | HIS B 422 | -0.814 | 1.238 | 18.948 | 1.00 | 49.69 | N |
| ATOM | 3275 | CD2 | HIS B 422 | 0.326 | 1.156 | 18.185 | 1.00 | 49.44 | C |
| ATOM | 3276 | C | HIS B 422 | 1.555 | -1.868 | 16.717 | 1.00 | 49.50 | C |
| ATOM | 3277 | O | HIS B 422 | 0.523 | -2.526 | 16.788 | 1.00 | 49.50 | O |
| ATOM | 3278 | N | ILE B 423 | 1.948 | -1.250 | 15.605 | 1.00 | 49.46 | N |
| ATOM | 3279 | CA | ILE B 423 | 1.181 | -1.276 | 14.369 | 1.00 | 49.43 | C |
| ATOM | 3280 | CB | ILE B 423 | 1.923 | -0.510 | 13.285 | 1.00 | 49.38 | C |
| ATOM | 3281 | CG1 | ILE B 423 | 2.324 | 0.867 | 13.795 | 1.00 | 49.04 | C |
| ATOM | 3282 | CD1 | ILE B 423 | 3.197 | 1.634 | 12.851 | 1.00 | 48.54 | C |
| ATOM | 3283 | CG2 | ILE B 423 | 1.070 | -0.418 | 12.028 | 1.00 | 49.21 | C |
| ATOM | 3284 | C | ILE B 423 | 0.904 | -2.679 | 13.858 | 1.00 | 49.67 | C |
| ATOM | 3285 | O | ILE B 423 | -0.095 | -2.912 | 13.206 | 1.00 | 49.47 | O |
| ATOM | 3286 | N | SER B 424 | 1.815 | -3.602 | 14.127 | 1.00 | 50.11 | N |
| ATOM | 3287 | CA | SER B 424 | 1.631 | -4.986 | 13.739 | 1.00 | 50.62 | C |
| ATOM | 3288 | CB | SER B 424 | 2.885 | -5.783 | 14.057 | 1.00 | 50.54 | C |
| ATOM | 3289 | OG | SER B 424 | 2.624 | -7.169 | 14.051 | 1.00 | 50.73 | O |
| ATOM | 3290 | C | SER B 424 | 0.406 | -5.599 | 14.428 | 1.00 | 51.10 | C |
| ATOM | 3291 | O | SER B 424 | -0.362 | -6.327 | 13.804 | 1.00 | 51.09 | O |
| ATOM | 3292 | N | ASN B 425 | 0.225 | -5.310 | 15.715 | 1.00 | 51.74 | N |
| ATOM | 3293 | CA | ASN B 425 | -0.947 | -5.782 | 16.431 | 1.00 | 52.35 | C |
| ATOM | 3294 | CB | ASN B 425 | -0.891 | -5.395 | 17.910 | 1.00 | 52.25 | C |

221

| | | | | | | | | | |
|---|---|---|---|---|---|---|---|---|---|
| ATOM | 3295 | CG | ASN | B | 425 | 0.193 | -6.143 | 18.676 | 1.00 52.12 | C |
| ATOM | 3296 | OD1 | ASN | B | 425 | 0.553 | -7.268 | 18.333 | 1.00 52.25 | O |
| ATOM | 3297 | ND2 | ASN | B | 425 | 0.715 | -5.518 | 19.720 | 1.00 51.45 | N |
| ATOM | 3298 | C | ASN | B | 425 | -2.221 | -5.245 | 15.785 | 1.00 52.97 | C |
| ATOM | 3299 | O | ASN | B | 425 | -3.151 | -6.000 | 15.501 | 1.00 53.05 | O |
| ATOM | 3300 | N | LYS | B | 426 | -2.272 | -3.944 | 15.539 | 1.00 53.70 | N |
| ATOM | 3301 | CA | LYS | B | 426 | -3.450 | -3.380 | 14.905 | 1.00 54.55 | C |
| ATOM | 3302 | CB | LYS | B | 426 | -3.321 | -1.863 | 14.741 | 1.00 54.60 | C |
| ATOM | 3303 | CG | LYS | B | 426 | -4.088 | -1.037 | 15.774 | 1.00 54.88 | C |
| ATOM | 3304 | CD | LYS | B | 426 | -3.350 | -0.949 | 17.112 | 1.00 55.70 | C |
| ATOM | 3305 | CE | LYS | B | 426 | -4.227 | -0.303 | 18.216 | 1.00 56.01 | C |
| ATOM | 3306 | NZ | LYS | B | 426 | -5.456 | -1.083 | 18.581 | 1.00 55.37 | N |
| ATOM | 3307 | C | LYS | B | 426 | -3.733 | -4.053 | 13.563 | 1.00 55.12 | C |
| ATOM | 3308 | O | LYS | B | 426 | -4.886 | -4.284 | 13.210 | 1.00 55.16 | O |
| ATOM | 3309 | N | GLY | B | 427 | -2.676 | -4.375 | 12.825 | 1.00 55.89 | N |
| ATOM | 3310 | CA | GLY | B | 427 | -2.811 | -5.007 | 11.525 | 1.00 56.92 | C |
| ATOM | 3311 | C | GLY | B | 427 | -3.280 | -6.440 | 11.625 | 1.00 57.75 | C |
| ATOM | 3312 | O | GLY | B | 427 | -4.120 | -6.894 | 10.851 | 1.00 57.71 | O |
| ATOM | 3313 | N | MET | B | 428 | -2.708 | -7.161 | 12.578 | 1.00 58.69 | N |
| ATOM | 3314 | CA | MET | B | 428 | -3.124 | -8.514 | 12.874 | 1.00 59.69 | C |
| ATOM | 3315 | CB | MET | B | 428 | -2.435 | -8.986 | 14.148 | 1.00 59.65 | C |
| ATOM | 3316 | CG | MET | B | 428 | -0.983 | -9.350 | 14.014 | 1.00 59.58 | C |
| ATOM | 3317 | SD | MET | B | 428 | -0.846 | -10.982 | 13.365 | 1.00 59.04 | S |
| ATOM | 3318 | CE | MET | B | 428 | 0.459 | -11.552 | 14.302 | 1.00 59.03 | C |
| ATOM | 3319 | C | MET | B | 428 | -4.621 | -8.508 | 13.140 | 1.00 60.53 | C |
| ATOM | 3320 | O | MET | B | 428 | -5.387 | -9.214 | 12.486 | 1.00 60.60 | O |
| ATOM | 3321 | N | GLU | B | 429 | -5.036 | -7.702 | 14.115 | 1.00 61.57 | N |
| ATOM | 3322 | CA | GLU | B | 429 | -6.430 | -7.678 | 14.512 | 1.00 62.60 | C |
| ATOM | 3323 | CB | GLU | B | 429 | -6.655 | -6.918 | 15.837 | 1.00 62.62 | C |
| ATOM | 3324 | CG | GLU | B | 429 | -6.995 | -5.440 | 15.710 | 1.00 62.98 | C |
| ATOM | 3325 | CD | GLU | B | 429 | -7.014 | -4.725 | 17.050 | 1.00 63.26 | C |
| ATOM | 3326 | OE1 | GLU | B | 429 | -5.925 | -4.461 | 17.616 | 1.00 63.34 | O |
| ATOM | 3327 | OE2 | GLU | B | 429 | -8.120 | -4.420 | 17.534 | 1.00 63.49 | O |
| ATOM | 3328 | C | GLU | B | 429 | -7.271 | -7.134 | 13.377 | 1.00 63.28 | C |
| ATOM | 3329 | O | GLU | B | 429 | -8.466 | -7.423 | 13.300 | 1.00 63.40 | O |
| ATOM | 3330 | N | HIS | B | 430 | -6.661 | -6.369 | 12.478 | 1.00 64.12 | N |
| ATOM | 3331 | CA | HIS | B | 430 | -7.438 | -5.889 | 11.354 | 1.00 65.01 | C |
| ATOM | 3332 | CB | HIS | B | 430 | -6.794 | -4.724 | 10.629 | 1.00 64.96 | C |
| ATOM | 3333 | CG | HIS | B | 430 | -7.653 | -4.188 | 9.528 | 1.00 65.18 | C |
| ATOM | 3334 | ND1 | HIS | B | 430 | -7.654 | -4.724 | 8.259 | 1.00 65.23 | N |
| ATOM | 3335 | CE1 | HIS | B | 430 | -8.521 | -4.069 | 7.509 | 1.00 65.20 | C |
| ATOM | 3336 | NE2 | HIS | B | 430 | -9.098 | -3.142 | 8.252 | 1.00 65.08 | N |
| ATOM | 3337 | CD2 | HIS | B | 430 | -8.582 | -3.204 | 9.522 | 1.00 65.21 | C |
| ATOM | 3338 | C | HIS | B | 430 | -7.685 | -7.018 | 10.374 | 1.00 65.64 | C |
| ATOM | 3339 | O | HIS | B | 430 | -8.761 | -7.124 | 9.795 | 1.00 65.76 | O |
| ATOM | 3340 | N | LEU | B | 431 | -6.678 | -7.858 | 10.188 | 1.00 66.46 | N |
| ATOM | 3341 | CA | LEU | B | 431 | -6.802 | -8.995 | 9.290 | 1.00 67.29 | C |
| ATOM | 3342 | CB | LEU | B | 431 | -5.435 | -9.629 | 9.035 | 1.00 67.31 | C |
| ATOM | 3343 | CG | LEU | B | 431 | -4.934 | -9.562 | 7.595 | 1.00 67.42 | C |
| ATOM | 3344 | CD1 | LEU | B | 431 | -3.435 | -9.446 | 7.544 | 1.00 67.51 | C |
| ATOM | 3345 | CD2 | LEU | B | 431 | -5.394 | -10.783 | 6.838 | 1.00 67.83 | C |
| ATOM | 3346 | C | LEU | B | 431 | -7.778 | -10.015 | 9.861 | 1.00 67.86 | C |
| ATOM | 3347 | O | LEU | B | 431 | -8.569 | -10.613 | 9.131 | 1.00 68.03 | O |
| ATOM | 3348 | N | LEU | B | 432 | -7.729 | -10.207 | 11.173 | 1.00 68.49 | N |
| ATOM | 3349 | CA | LEU | B | 432 | -8.648 | -11.126 | 11.833 | 1.00 69.11 | C |
| ATOM | 3350 | CB | LEU | B | 432 | -8.206 | -11.407 | 13.266 | 1.00 69.16 | C |
| ATOM | 3351 | CG | LEU | B | 432 | -7.478 | -12.733 | 13.485 | 1.00 69.46 | C |
| ATOM | 3352 | CD1 | LEU | B | 432 | -6.500 | -12.642 | 14.654 | 1.00 69.63 | C |
| ATOM | 3353 | CD2 | LEU | B | 432 | -8.493 | -13.865 | 13.693 | 1.00 69.73 | C |
| ATOM | 3354 | C | LEU | B | 432 | -10.067 | -10.586 | 11.827 | 1.00 69.45 | C |
| ATOM | 3355 | O | LEU | B | 432 | -11.024 | -11.351 | 11.762 | 1.00 69.55 | O |

| | | | | | | | | | |
|---|---|---|---|---|---|---|---|---|---|
| ATOM | 3356 | N | SER | B | 433 | -10.192 | -9.264 | 11.894 | 1.00 69.92 | N |
| ATOM | 3357 | CA | SER | B | 433 | -11.492 | -8.594 | 11.901 | 1.00 70.36 | C |
| ATOM | 3358 | CB | SER | B | 433 | -11.306 | -7.078 | 11.917 | 1.00 70.39 | C |
| ATOM | 3359 | OG | SER | B | 433 | -12.131 | -6.456 | 10.947 | 1.00 70.48 | O |
| ATOM | 3360 | C | SER | B | 433 | -12.290 | -8.967 | 10.683 | 1.00 70.61 | C |
| ATOM | 3361 | O | SER | B | 433 | -13.522 | -8.918 | 10.670 | 1.00 70.67 | O |
| ATOM | 3362 | N | MET | B | 434 | -11.575 | -9.348 | 9.648 | 1.00 70.93 | N |
| ATOM | 3363 | CA | MET | B | 434 | -12.242 | -9.696 | 8.427 | 1.00 71.30 | C |
| ATOM | 3364 | CB | MET | B | 434 | -11.444 | -9.139 | 7.249 | 1.00 71.35 | C |
| ATOM | 3365 | CG | MET | B | 434 | -11.058 | -7.653 | 7.417 | 1.00 71.64 | C |
| ATOM | 3366 | SD | MET | B | 434 | -12.368 | -6.437 | 7.036 | 1.00 72.20 | S |
| ATOM | 3367 | CE | MET | B | 434 | -12.881 | -7.002 | 5.381 | 1.00 72.23 | C |
| ATOM | 3368 | C | MET | B | 434 | -12.399 | -11.207 | 8.355 | 1.00 71.46 | C |
| ATOM | 3369 | O | MET | B | 434 | -13.293 | -11.718 | 7.679 | 1.00 71.48 | O |
| ATOM | 3370 | N | LYS | B | 435 | -11.547 | -11.922 | 9.085 | 1.00 71.63 | N |
| ATOM | 3371 | CA | LYS | B | 435 | -11.575 | -13.384 | 9.060 | 1.00 71.71 | C |
| ATOM | 3372 | CB | LYS | B | 435 | -10.158 | -13.946 | 8.901 | 1.00 71.71 | C |
| ATOM | 3377 | C | LYS | B | 435 | -12.250 | -13.984 | 10.290 | 1.00 71.71 | C |
| ATOM | 3378 | O | LYS | B | 435 | -12.608 | -15.162 | 10.294 | 1.00 71.74 | O |
| ATOM | 3379 | N | ALA | B | 440 | -4.800 | -17.520 | 4.635 | 1.00 79.09 | N |
| ATOM | 3380 | CA | ALA | B | 440 | -4.322 | -18.757 | 5.237 | 1.00 79.10 | C |
| ATOM | 3381 | CB | ALA | B | 440 | -2.990 | -19.159 | 4.617 | 1.00 79.12 | C |
| ATOM | 3382 | C | ALA | B | 440 | -4.150 | -18.594 | 6.735 | 1.00 79.08 | C |
| ATOM | 3383 | O | ALA | B | 440 | -3.662 | -17.554 | 7.178 | 1.00 79.15 | O |
| ATOM | 3384 | N | PRO | B | 441 | -4.649 | -19.564 | 7.506 | 1.00 79.02 | N |
| ATOM | 3385 | CA | PRO | B | 441 | -4.266 | -19.719 | 8.919 | 1.00 78.93 | C |
| ATOM | 3386 | CB | PRO | B | 441 | -5.007 | -20.985 | 9.371 | 1.00 78.95 | C |
| ATOM | 3387 | CG | PRO | B | 441 | -5.936 | -21.379 | 8.266 | 1.00 79.02 | C |
| ATOM | 3388 | CD | PRO | B | 441 | -5.711 | -20.494 | 7.088 | 1.00 79.00 | C |
| ATOM | 3389 | C | PRO | B | 441 | -2.752 | -19.983 | 8.964 | 1.00 78.86 | C |
| ATOM | 3390 | O | PRO | B | 441 | -2.315 | -21.133 | 8.909 | 1.00 78.85 | O |
| ATOM | 3391 | N | ALA | B | 442 | -1.969 | -18.912 | 9.055 | 1.00 78.76 | N |
| ATOM | 3392 | CA | ALA | B | 442 | -0.502 | -18.950 | 9.003 | 1.00 78.64 | C |
| ATOM | 3393 | CB | ALA | B | 442 | 0.046 | -17.537 | 9.161 | 1.00 78.66 | C |
| ATOM | 3394 | C | ALA | B | 442 | 0.218 | -19.869 | 9.981 | 1.00 78.55 | C |
| ATOM | 3395 | O | ALA | B | 442 | 1.297 | -20.369 | 9.671 | 1.00 78.58 | O |
| ATOM | 3396 | N | ALA | B | 443 | -0.354 | -20.045 | 11.169 | 1.00 78.43 | N |
| ATOM | 3397 | CA | ALA | B | 443 | 0.251 | -20.851 | 12.230 | 1.00 78.24 | C |
| ATOM | 3398 | CB | ALA | B | 443 | -0.735 | -21.021 | 13.392 | 1.00 78.25 | C |
| ATOM | 3399 | C | ALA | B | 443 | 0.707 | -22.215 | 11.731 | 1.00 78.09 | C |
| ATOM | 3400 | O | ALA | B | 443 | 1.907 | -22.515 | 11.688 | 1.00 78.05 | O |
| ATOM | 3401 | N | ALA | B | 444 | -0.271 | -23.038 | 11.366 | 1.00 77.87 | N |
| ATOM | 3402 | CA | ALA | B | 444 | -0.017 | -24.383 | 10.877 | 1.00 77.62 | C |
| ATOM | 3403 | CB | ALA | B | 444 | -1.340 | -25.088 | 10.569 | 1.00 77.64 | C |
| ATOM | 3404 | C | ALA | B | 444 | 0.871 | -24.362 | 9.638 | 1.00 77.41 | C |
| ATOM | 3405 | O | ALA | B | 444 | 1.864 | -25.093 | 9.554 | 1.00 77.40 | O |
| ATOM | 3406 | N | ALA | B | 445 | 0.512 | -23.508 | 8.685 | 1.00 77.09 | N |
| ATOM | 3407 | CA | ALA | B | 445 | 1.219 | -23.430 | 7.412 | 1.00 76.77 | C |
| ATOM | 3408 | CB | ALA | B | 445 | 0.544 | -22.412 | 6.497 | 1.00 76.82 | C |
| ATOM | 3409 | C | ALA | B | 445 | 2.705 | -23.109 | 7.565 | 1.00 76.49 | C |
| ATOM | 3410 | O | ALA | B | 445 | 3.503 | -23.358 | 6.662 | 1.00 76.45 | O |
| ATOM | 3411 | N | LEU | B | 446 | 3.075 | -22.555 | 8.711 | 1.00 76.13 | N |
| ATOM | 3412 | CA | LEU | B | 446 | 4.460 | -22.189 | 8.948 | 1.00 75.75 | C |
| ATOM | 3413 | CB | LEU | B | 446 | 4.563 | -21.252 | 10.146 | 1.00 75.71 | C |
| ATOM | 3414 | CG | LEU | B | 446 | 3.987 | -19.861 | 9.888 | 1.00 75.44 | C |
| ATOM | 3415 | CD1 | LEU | B | 446 | 4.225 | -18.932 | 11.062 | 1.00 75.06 | C |
| ATOM | 3416 | CD2 | LEU | B | 446 | 4.599 | -19.296 | 8.637 | 1.00 75.40 | C |
| ATOM | 3417 | C | LEU | B | 446 | 5.348 | -23.409 | 9.136 | 1.00 75.62 | C |
| ATOM | 3418 | O | LEU | B | 446 | 6.458 | -23.459 | 8.611 | 1.00 75.51 | O |
| ATOM | 3419 | N | LEU | B | 447 | 4.851 | -24.397 | 9.874 | 1.00 75.47 | N |
| ATOM | 3420 | CA | LEU | B | 447 | 5.607 | -25.618 | 10.116 | 1.00 75.33 | C |

223

| | | | | | | | | | | |
|---|---|---|---|---|---|---|---|---|---|---|
| ATOM | 3421 | CB | LEU | B | 447 | 5.010 | -26.416 | 11.276 | 1.00 75.36 | C |
| ATOM | 3422 | CG | LEU | B | 447 | 5.762 | -27.697 | 11.654 | 1.00 75.23 | C |
| ATOM | 3423 | CD1 | LEU | B | 447 | 7.178 | -27.397 | 12.111 | 1.00 75.39 | C |
| ATOM | 3424 | CD2 | LEU | B | 447 | 5.020 | -28.418 | 12.735 | 1.00 75.07 | C |
| ATOM | 3425 | C | LEU | B | 447 | 5.647 | -26.479 | 8.866 | 1.00 75.24 | C |
| ATOM | 3426 | O | LEU | B | 447 | 6.687 | -27.033 | 8.521 | 1.00 75.27 | O |
| ATOM | 3427 | N | ALA | B | 448 | 4.507 | -26.602 | 8.198 | 1.00 75.11 | N |
| ATOM | 3428 | CA | ALA | B | 448 | 4.445 | -27.353 | 6.952 | 1.00 75.01 | C |
| ATOM | 3429 | CB | ALA | B | 448 | 3.118 | -27.109 | 6.257 | 1.00 74.98 | C |
| ATOM | 3430 | C | ALA | B | 448 | 5.594 | -26.909 | 6.059 | 1.00 74.95 | C |
| ATOM | 3431 | O | ALA | B | 448 | 6.392 | -27.725 | 5.594 | 1.00 74.95 | O |
| ATOM | 3432 | N | MET | B | 449 | 5.678 | -25.601 | 5.839 | 1.00 74.86 | N |
| ATOM | 3433 | CA | MET | B | 449 | 6.724 | -25.029 | 5.013 | 1.00 74.76 | C |
| ATOM | 3434 | CB | MET | B | 449 | 6.377 | -23.592 | 4.644 | 1.00 74.72 | C |
| ATOM | 3435 | CG | MET | B | 449 | 5.160 | -23.493 | 3.746 | 1.00 74.58 | C |
| ATOM | 3436 | SD | MET | B | 449 | 4.845 | -21.846 | 3.121 | 1.00 74.43 | S |
| ATOM | 3437 | CE | MET | B | 449 | 3.501 | -22.180 | 1.992 | 1.00 74.60 | C |
| ATOM | 3438 | C | MET | B | 449 | 8.074 | -25.111 | 5.707 | 1.00 74.77 | C |
| ATOM | 3439 | O | MET | B | 449 | 9.112 | -25.245 | 5.056 | 1.00 74.79 | O |
| ATOM | 3440 | N | LEU | B | 450 | 8.062 | -25.032 | 7.032 | 1.00 74.75 | N |
| ATOM | 3441 | CA | LEU | B | 450 | 9.294 | -25.164 | 7.792 | 1.00 74.75 | C |
| ATOM | 3442 | CB | LEU | B | 450 | 9.080 | -24.754 | 9.246 | 1.00 74.71 | C |
| ATOM | 3443 | CG | LEU | B | 450 | 9.175 | -23.258 | 9.552 | 1.00 74.45 | C |
| ATOM | 3444 | CD1 | LEU | B | 450 | 8.876 | -22.982 | 11.001 | 1.00 74.16 | C |
| ATOM | 3445 | CD2 | LEU | B | 450 | 10.550 | -22.748 | 9.213 | 1.00 74.35 | C |
| ATOM | 3446 | C | LEU | B | 450 | 9.808 | -26.599 | 7.708 | 1.00 74.88 | C |
| ATOM | 3447 | O | LEU | B | 450 | 10.986 | -26.829 | 7.439 | 1.00 74.89 | O |
| ATOM | 3448 | N | ASN | B | 451 | 8.912 | -27.559 | 7.927 | 1.00 75.04 | N |
| ATOM | 3449 | CA | ASN | B | 451 | 9.250 | -28.976 | 7.877 | 1.00 75.15 | C |
| ATOM | 3450 | CB | ASN | B | 451 | 8.085 | -29.816 | 8.404 | 1.00 75.18 | C |
| ATOM | 3451 | CG | ASN | B | 451 | 8.510 | -31.215 | 8.814 | 1.00 75.28 | C |
| ATOM | 3452 | OD1 | ASN | B | 451 | 9.696 | -31.533 | 8.824 | 1.00 75.56 | O |
| ATOM | 3453 | ND2 | ASN | B | 451 | 7.543 | -32.054 | 9.161 | 1.00 75.22 | N |
| ATOM | 3454 | C | ASN | B | 451 | 9.594 | -29.409 | 6.459 | 1.00 75.25 | C |
| ATOM | 3455 | O | ASN | B | 451 | 10.410 | -30.308 | 6.250 | 1.00 75.24 | O |
| ATOM | 3456 | N | ALA | B | 452 | 8.961 | -28.763 | 5.484 | 1.00 75.36 | N |
| ATOM | 3457 | CA | ALA | B | 452 | 9.197 | -29.084 | 4.085 | 1.00 75.46 | C |
| ATOM | 3458 | CB | ALA | B | 452 | 8.132 | -28.452 | 3.203 | 1.00 75.45 | C |
| ATOM | 3459 | C | ALA | B | 452 | 10.587 | -28.627 | 3.658 | 1.00 75.55 | C |
| ATOM | 3460 | O | ALA | B | 452 | 11.349 | -29.399 | 3.067 | 1.00 75.57 | O |
| ATOM | 3461 | N | ALA | B | 453 | 10.915 | -27.376 | 3.973 | 1.00 75.61 | N |
| ATOM | 3462 | CA | ALA | B | 453 | 12.202 | -26.800 | 3.596 | 1.00 75.66 | C |
| ATOM | 3463 | CB | ALA | B | 453 | 12.283 | -25.342 | 4.032 | 1.00 75.68 | C |
| ATOM | 3464 | C | ALA | B | 453 | 13.377 | -27.602 | 4.152 | 1.00 75.68 | C |
| ATOM | 3465 | O | ALA | B | 453 | 14.171 | -28.157 | 3.391 | 1.00 75.67 | O |
| ATOM | 3466 | NI | NI | B | 1 | 9.781 | -17.276 | -4.788 | 1.00 74.65 | NI |
| ATOM | 3467 | O16 | EPI | B | 600 | -5.033 | -6.346 | 7.235 | 1.00 53.42 | O |
| ATOM | 3468 | C16 | EPI | B | 600 | -4.549 | -5.323 | 6.401 | 1.00 54.55 | C |
| ATOM | 3469 | C17 | EPI | B | 600 | -3.741 | -4.326 | 7.243 | 1.00 54.42 | C |
| ATOM | 3470 | O17 | EPI | B | 600 | -3.602 | -4.819 | 8.557 | 1.00 53.24 | O |
| ATOM | 3471 | C13 | EPI | B | 600 | -2.412 | -4.208 | 6.514 | 1.00 52.81 | C |
| ATOM | 3472 | C12 | EPI | B | 600 | -1.194 | -3.867 | 7.334 | 1.00 52.17 | C |
| ATOM | 3473 | C18 | EPI | B | 600 | -2.573 | -3.176 | 5.414 | 1.00 51.95 | C |
| ATOM | 3474 | C14 | EPI | B | 600 | -2.250 | -5.593 | 5.930 | 1.00 52.64 | C |
| ATOM | 3475 | C15 | EPI | B | 600 | -3.618 | -5.921 | 5.354 | 1.00 52.94 | C |
| ATOM | 3476 | C8 | EPI | B | 600 | -1.077 | -5.664 | 4.978 | 1.00 51.48 | C |
| ATOM | 3477 | C7 | EPI | B | 600 | -1.029 | -7.031 | 4.311 | 1.00 51.66 | C |
| ATOM | 3478 | C9 | EPI | B | 600 | 0.151 | -5.398 | 5.823 | 1.00 51.19 | C |
| ATOM | 3479 | C11 | EPI | B | 600 | 0.046 | -4.003 | 6.446 | 1.00 52.04 | C |
| ATOM | 3480 | C10 | EPI | B | 600 | 1.388 | -5.585 | 4.963 | 1.00 50.93 | C |
| ATOM | 3481 | C5 | EPI | B | 600 | 1.339 | -6.395 | 3.695 | 1.00 51.47 | C |

224

```
ATOM   3482  C6  EPI B 600       0.103  -7.184   3.296  1.00 52.22           C
ATOM   3483  C4  EPI B 600       2.568  -6.553   2.948  1.00 52.22           C
ATOM   3484  C3  EPI B 600       3.741  -5.947   3.382  1.00 50.93           C
ATOM   3485  O3  EPI B 600       4.881  -6.093   2.642  1.00 48.88           O
ATOM   3486  C2  EPI B 600       3.774  -5.183   4.529  1.00 49.47           C
ATOM   3487  C1  EPI B 600       2.656  -4.993   5.321  1.00 50.91           C
ATOM   3488  O   HOH W   1       4.761   1.505  40.680  1.00 49.72           O
ATOM   3489  O   HOH W   2       6.148   3.723  39.380  1.00 58.58           O
ATOM   3490  O   HOH W   3      15.447  -2.388  44.145  1.00 47.96           O
ATOM   3491  O   HOH W   4      11.664  10.014  38.798  1.00 44.30           O
ATOM   3492  O   HOH W   5      11.644   8.725  36.082  1.00 55.78           O
ATOM   3493  O   HOH W   6       3.626   6.314  45.241  1.00 62.85           O
ATOM   3494  O   HOH W   7      26.709   5.674  26.685  1.00 64.47           O
ATOM   3495  O   HOH W   8       7.886  -6.875   3.610  1.00 69.77           O
ATOM   3496  O   HOH W   9       9.987  -8.358   5.148  1.00 55.62           O
ATOM   3497  O   HOH W  10      14.067   3.798  -1.612  1.00 79.33           O
ATOM   3498  O   HOH W  11      13.763  -9.999  -7.172  1.00 43.49           O
ATOM   3499  O   HOH W  12       9.513 -13.984  -6.647  1.00 71.81           O
ATOM   3500  O   HOH W  13      24.913   7.946   4.380  1.00 48.86           O
ATOM   3501  O   HOH W  14       3.905  -9.536  13.943  1.00 51.37           O
ATOM   3502  O   HOH W  15      15.204  -6.618  -2.290  1.00 58.68           O
ATOM   3503  O   HOH W  16      16.598  -4.998   0.002  1.00 58.17           O
ATOM   3504  O   HOH W  17       6.236   6.337   2.476  1.00 53.20           O
END
```

5RR101!.DOC\10706\27\269245.01

What is claimed is:

1. A crystal of ERβ ligand binding domain of SEQ ID NO:2 complexed with N-(n-butyl)-11-[3,17β-dihydroxyestra-1,3,5(10)-trien-7α-yl]N-methylundecanamide, said crystal belonging to the space group $I2_12_12_1$ and having unit cell dimensions a=59.37 Å, b=81.4 Å, c=520.97 Å, and containing five ligand binding domain monomers per asymmetric unit.

2. The crystal of claim 1, wherein said crystal has a resolution determined by X-ray crystallography of less than 2.5 Å.

3. A process of preparing the crystal of claim 1, comprising the steps of:

providing ERβ ligand binding domain of SEQ ID NO:2 complexed with N-(n-butyl)-11-[3,17β- dihydroxyestra-1,3,5(10)-trien-7α-yl]N-methylundecanamide, and growing one or more of said crystals by hanging drop vapor diffusion at 18° C. from a solution comprising equal volumes of ERβ ligand binding domain complexed with N-(n-butyl)-11-[3,17β-dihydroxyestra-1,3,5(10)-trien-7α-yl]N-methylundecanamide (10 mg/ml) and resevoir solution, said resevoir solution comprising 7% (w/v) polyethylene glycol 2000 monomethyl ether, 3.5 mM nickel chloride, and 10% (v/v) dioxane in 35 mM Tris-HCl, pH 8.5.

4. A crystal of ERβ ligand binding domain of SEQ ID NO:2 complexed with estradiol and a peptide comprising the amino acid sequence of SEQ ID NO:3, said crystal belonging to the space group P4122 and having the unit cell dimensions a=62.55 Å, b=62.55 Å, c=171.70 Å.

5. The crystal of claim 4, wherein said crystal has a resolution determined by X-ray crystallography of less than 2.5 Å.

6. A process of preparing the crystal of claim 4, comprising the steps of:

providing ERβ ligand binding domain of SEQ ID NO:2 complexed with estradiol and a peptide comprising the amino acid sequence of SEQ ID NO:3, and growing one or more of said crystals by hanging drop vapor diffusion at 18° C. from a solution comprising equal volumes of ERβ ligand binding domain complexed with estradiol and a peptide comprising the amino acid sequence of SEQ ID NO:3, said ERβ ligand binding domain and said peptide present in a 1:5 molar ratio, and resevoir solution, said resevoir solution comprising 0.5–0.605 dilution of 10% (w/v) polyethylene glycol 8000, 10% (w/v) polyethylene glycol 1000, and 0.2 M lithium sulphate, and 100 mM Tris-HCl, pH 8.0.

7. A crystal of ERβ ligand binding domain SEQ ID NO:2 complexed with 17-epiestriol and a peptide comprising the amino acid sequence of SEQ ID NO:3, said crystal belonging to the space group P4122 and having the unit cell dimensions a=62.64 Å, b=62.64 Å, c=171.64 Å.

8. The crystal of claim 7, wherein said crystal has a resolution determined by X-ray crystallography of less than 2.0 Å.

9. A process of preparing the crystal of claim 7, comprising the steps of:

providing ERβ ligand binding domain of SEQ ID NO:2 complexed with 2-(4-hydroxyphenyl)-6-hydroxybenzo-β-thienyl-3-yl (4-carboxyphenyl) methanone and a peptide comprising the amino acid sequence of SEQ ID NO:3, and growing one or more of said crystals by hanging drop vapor diffusion at 18° C. from a solution comprising equal volumes of ERβ ligand binding domain complexed with 2-(4-hydroxyphenyl)-6-hydroxybenzo-β-thienyl-3-yl (4-carboxyphenyl)methanone and a peptide comprising the amino acid sequence of SEQ ID NO:3, said ERβ ligand binding domain and said peptide present in a 1:5 molar ratio, and resevoir solution, said resevoir solution comprising 0.5–0.605 dilution of 10% (w/v) polyethylene glycol 8000, 10% (w/v) polyethylene glycol 1000, and 0.2 M lithium sulphate, and 100 mM Tris-HCl, pH 8.0.

* * * * *

UNITED STATES PATENT AND TRADEMARK OFFICE
CERTIFICATE OF CORRECTION

PATENT NO. : 6,476,196 B1
DATED : November 5, 2002
INVENTOR(S) : Jan Ljunggren et al.

It is certified that error appears in the above-identified patent and that said Letters Patent is hereby corrected as shown below:

<u>Title page</u>,
Item [73], Assignee, name "Kara Bio AB" should read -- Karo Bio AB --

<u>Column 426</u>,
Lines 14-16 and 21-22, the phrase
"2-(4-hydroxyphenyl)-6-hydroxybenzo-β-thienyl-3-y1-(4-carboxyphenyl) methanone"
should read -- 17-epiestriol --.

Signed and Sealed this

Seventeenth Day of February, 2004

JON W. DUDAS
*Acting Director of the United States Patent and Trademark Office*

SEQUENCE LISTING

<160> NUMBER OF SEQ ID NOS: 4

<210> SEQ ID NO 1
<211> LENGTH: 229
<212> TYPE: PRT
<213> ORGANISM: Human

<400> SEQUENCE: 1

Asp Ala Leu Ser Glu Glu Gln Leu Val Leu Thr Leu Leu Glu Ala Glu
1               5                   10                  15

Pro Pro His Val Leu Ile Ser Arg Pro Ser Ala Ser Met Met Met Ser
            20                  25                  30

Leu Thr Lys Leu Ala Asp Leu Glu Leu Val His Met Ile Ser Trp Ala
        35                  40                  45

Lys Lys Ile Pro Gly Phe Val Glu Leu Ser Leu Phe Asp Gln Val Arg
    50                  55                  60

Leu Leu Glu Ser Cys Trp Met Glu Val Leu Met Met Gly Leu Met Trp
65                  70                  75                  80

Arg Ser Ile Asp His Pro Gly Lys Leu Ile Phe Ala Pro Asp Leu Val
                85                  90                  95

Leu Asp Arg Asp Glu Gly Lys Cys Val Glu Gly Ile Leu Glu Ile Phe
            100                 105                 110

Asp Met Leu Leu Ala Thr Thr Ser Arg Phe Arg Glu Leu Lys Leu Gln
        115                 120                 125

His Lys Glu Tyr Leu Cys Val Lys Ala Met Ile Leu Leu Asn Ser Ser
    130                 135                 140

Met Tyr Pro Leu Val Asp Ser Ser Arg Lys Leu Ala His Leu Leu Asn
145                 150                 155                 160

Ala Val Thr Asp Ala Leu Val Trp Val Ile Ala Lys Ser Gly Ile Ser
                165                 170                 175

Ser Gln Gln Gln Ser Met Arg Leu Ala Asn Leu Leu Met Leu Leu Ser
            180                 185                 190

His Val Arg His Ala Ser Asn Lys Gly Met Glu His Leu Leu Met Met
        195                 200                 205

Lys Cys Lys Asn Val Val Pro Val Tyr Asp Leu Leu Leu Glu Met Leu
    210                 215                 220

Asn Ala His Val Leu
225

<210> SEQ ID NO 2
<211> LENGTH: 228
<212> TYPE: PRT
<213> ORGANISM: RAT

<400> SEQUENCE: 2

Thr Leu Ser Pro Glu Gln Leu Val Leu Thr Leu Leu Glu Ala Glu Pro
1               5                   10                  15

Pro Asn Val Leu Val Ser Arg Pro Ser Met Pro Phe Thr Glu Ala Ser
            20                  25                  30

Met Met Met Ser Leu Thr Lys Leu Ala Asp Lys Glu Leu Val His Met
        35                  40                  45

Ile Gly Trp Ala Lys Lys Ile Pro Gly Phe Val Glu Leu Ser Leu Leu
    50                  55                  60

Asp Gln Val Arg Leu Leu Glu Ser Cys Trp Met Glu Val Leu Met Val
65                  70                  75                  80

```
Gly Leu Met Trp Arg Ser Ile Asp His Pro Gly Lys Leu Ile Phe Ala
                85                  90                  95

Pro Asp Leu Val Leu Asp Arg Asp Glu Gly Lys Cys Val Glu Gly Ile
            100                 105                 110

Leu Glu Ile Phe Asp Met Leu Leu Ala Thr Thr Ser Arg Phe Arg Glu
        115                 120                 125

Leu Lys Leu Gln His Lys Glu Tyr Leu Cys Val Lys Ala Met Ile Leu
    130                 135                 140

Leu Asn Ser Ser Met Tyr Pro Leu Ala Ser Ala Asn Gln Glu Ala Glu
145                 150                 155                 160

Ser Ser Arg Lys Leu Thr His Leu Leu Asn Ala Val Thr Asp Ala Leu
                165                 170                 175

Val Trp Val Ile Ala Lys Ser Gly Ile Ser Ser Gln Gln Gln Ser Val
                180                 185                 190

Arg Leu Ala Asn Leu Leu Met Leu Leu Ser His Val Arg His Ile Ser
            195                 200                 205

Asn Lys Gly Met Glu His Leu Leu Ser Met Lys Asp Leu Leu Leu Glu
        210                 215                 220

Met Leu Asn Ala
225

<210> SEQ ID NO 3
<211> LENGTH: 17
<212> TYPE: PRT
<213> ORGANISM: Artificial Sequence
<220> FEATURE:
<223> OTHER INFORMATION: LXXLL coactivator peptide derived from the
      coactivator independent of AF2 function (CIA)
      described in Sauve, F. et al. Mol. Cell Biol.
      21:343-353 (2001).

<400> SEQUENCE: 3

His Pro Pro Ala Ile Gln Ser Leu Ile Asn Leu Leu Ala Asp Asn Arg
1               5                   10                  15

Tyr

<210> SEQ ID NO 4
<211> LENGTH: 5
<212> TYPE: PRT
<213> ORGANISM: Artificial Sequence
<220> FEATURE:
<221> NAME/KEY: VARIANT
<222> LOCATION: (1)...(5)
<223> OTHER INFORMATION: Xaa = Any Amino Acid
<220> FEATURE:
<223> OTHER INFORMATION: LXXLL coactivator peptide derived from the
      coactivator independent of AF2 function (CIA)
      described in Sauve, F. et al. Mol. Cell Biol.
      21:343-353 (2001).

<400> SEQUENCE: 4

Leu Xaa Xaa Leu Leu
1               5
```